(12) United States Patent
Duncton et al.

(10) Patent No.: US 12,319,652 B2
(45) Date of Patent: Jun. 3, 2025

(54) SALTS AND SOLID FORMS OF (R)-1-(5-METHOXY-1H-INDOL-1-YL)-N,N-DIMETHYLPROPAN-2-AMINE

(71) Applicant: Terran Biosciences Inc., New York, NY (US)

(72) Inventors: Matthew Duncton, San Bruno, CA (US); Samuel Clark, New York, NY (US)

(73) Assignee: Terran Biosciences Inc., Miami Beach, FL (US)

( * ) Notice: Subject to any disclaimer, the term of this patent is extended or adjusted under 35 U.S.C. 154(b) by 21 days.

(21) Appl. No.: 18/177,408

(22) Filed: Mar. 2, 2023

(65) Prior Publication Data

US 2024/0034718 A1    Feb. 1, 2024

Related U.S. Application Data

(63) Continuation of application No. 17/988,753, filed on Nov. 16, 2022, now abandoned.

(60) Provisional application No. 63/319,735, filed on Mar. 14, 2022, provisional application No. 63/316,924, filed on Mar. 4, 2022, provisional application No. 63/310,977, filed on Feb. 16, 2022, provisional application No. 63/280,084, filed on Nov. 16, 2021, provisional application No. 63/280,085, filed on Nov. 16, 2021.

(51) Int. Cl.
*C07D 209/08* (2006.01)

(52) U.S. Cl.
CPC ........ *C07D 209/08* (2013.01); *C07B 2200/13* (2013.01)

(58) Field of Classification Search
CPC .......................... C07D 209/08; C07B 2200/13
See application file for complete search history.

(56) References Cited

U.S. PATENT DOCUMENTS

| | | |
|---|---|---|
| 2023/0159456 A1 | 5/2023 | Duncton et al. |
| 2024/0002337 A1 | 1/2024 | Duncton et al. |

FOREIGN PATENT DOCUMENTS

| | | |
|---|---|---|
| WO | WO-2015049616 A1 | 4/2015 |
| WO | WO-2020176597 A1 | 9/2020 |
| WO | WO-2021252692 A1 | 12/2021 |
| WO | WO-2023077127 A2 | 5/2023 |
| WO | WO-2023091974 A2 | 5/2023 |

OTHER PUBLICATIONS

Arnt et al. "Facilitation of 8-OHDPAT-induced forepaw treading of rats by the 5-HT2 agonist DOI", European Journal of Pharmacology, (1989); 161(1):45-51.

Canal et al. "Head-twitch response in rodents induced by the hallucinogen 2, 5-dimethoxy-4-iodoamphetamine: a comprehensive history, a re-evaluation of mechanisms, and its utility as a model", Drug Testing and Analysis, (2012); 4(7-8):556-576.

Darmani et al. "Do functional relationships exist between 5-HT1A and 5-HT2 receptors?" Pharmacology Biochemistry and Behavior, (1990); 36(4):901-906.

Dong et al. "Psychedelic-inspired drug discovery using an engineered biosensor", Cell, (2021); 184(10):2779-2792.

Fitzgerald et al. "Possible role of valvular serotonin 5-HT2B receptors in the cardiopathy associated with fenfluramine", Molecular Pharmacology, (2000); 57(1):75-81.

Keller et al. "'Permanent' Alteration of Behavior in Mice by Chemical and Psychological Means", Science, (1956); 124(3225):723-724.

Kennett et al. "SB 242084, a selective and brain penetrant 5-HT2C receptor antagonist", Neuropharmacology, (1997); 36(4-5):609-620.

Kennett et al. "In vivo properties of SB 200646A, a 5-HT2C/2B receptor antagonist", British Journal of Pharmacology, (1994); 111(3):797-802.

Rothman et al. "Evidence for possible involvement of 5-HT2B receptors in the cardiac valvulopathy associated with fenfluramine and other serotonergic medications", Circulation, (2000); 102(23):2836-2841.

Al-Muhammed et al. "In-vivo studies on dexamethasone sodium phosphate liposomes", Journal of microencapsulation, Jan. 1, 1996;13(3):293-305.

Byrn et al. "Pharmaceutical solids: a strategic approach to regulatory considerations", Pharmaceutical Research, (Jul. 1995); 12:945-954.

Chonn et al. "Recent advances in liposomal drug-delivery systems", Current Opinion in Biotechnology, (Jan. 1, 1995); 6(6):698-708.

Eyles JE, et al. "Oral delivery and fate of poly (lactic acid) microsphere-encapsulated interferon in rats", Journal of pharmacy and pharmacology, (Jul. 1997); 49(7):669-774.

Gao, Z.H., et al., "Controlled release of a contraceptive steroids from biodegradable and injectable gel formulations: in vitro evaluation," Pharm Res., (Jun. 1995);12(6):857-863.

Haleblian et al. "Pharmaceutical applications of polymorphism", Journal of Pharmaceutical Sciences, (Aug. 1969); 58(8):911-929.

Minto et al. "Pharmacokinetics and pharmacodynamics of nandrolone esters in oil vehicle: effects of ester, injection site and injection volume", Journal of pharmacology and experimental therapeutics, (Apr. 1, 1997); 281(1):93-102.

Ostro, M. et al., "Use of liposomes as injectable-drug delivery systems," American J. Hosp. Pharm., Aug. 1989, vol. 46, No. 8, pp. 1576-1588.

Panduranga RK. "Recent developments of collagen-based materials for medical applications and drug delivery systems". Journal of Biomaterials Science, Polymer Edition. (Jan. 1, 1996); 7(7):623-645.

(Continued)

*Primary Examiner* — Laura L Stockton
(74) *Attorney, Agent, or Firm* — COOLEY LLP; Heidi A. Erlacher; Eric A. Owens

(57) ABSTRACT

The present disclosure is directed to salt and solid forms of (R)-1-(5-METHOXY-1H-INDOL-1-YL)-N,N-DIMETHYLPROPAN-2-AMINE and methods of treating neurological disorder and/or a psychiatric disorder in a subject in need thereof.

30 Claims, 403 Drawing Sheets

(56) References Cited

OTHER PUBLICATIONS

Rohatagi, S., et al., "Pharmacokinetic and pharmacodynamic evaluation of triamcinolone acetonide after intravenous, oral, and inhaled administration", The Journal of Clinical Pharmacology, (Dec. 1995); 35(12):1187-1193.
Tjwa, M.K.T., "Budesonide inhaled via Turbuhaler: a more effective treatment for asthma than beclomethasone dipropionate via Rotahaler", Annals of Allergy, Asthma & Immunology: official publication of the American College of Allergy, Asthma, & Immunology, (Aug. 1, 1995); 75(2):107-111.
Berge et al., "Pharmaceutical salts," Journal of pharmaceutical sciences, (Jan. 1977); 66(1):1-19.
Gould, "Salt selection for basic drugs," International Journal of Pharmaceutics (Nov. 1986); 33, pp. 201-217.
Stahl et al., Handbook of Pharmaceutical Salts: Properties, Selection, and Use, International Union of Pure and Applied Chemistry (IUPAC), Wiley-VCH, pp. 330-350 (2008), 24 pages.

Compound 1 Monofumarate
MW: 348.399
$C_{18}H_{24}N_2O_5$

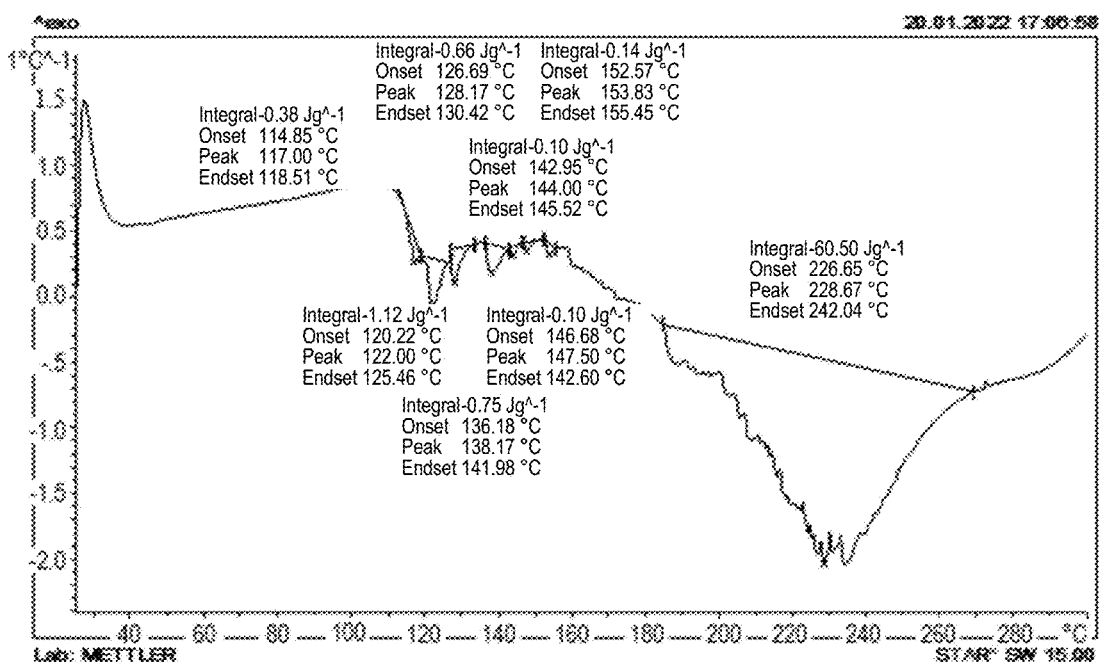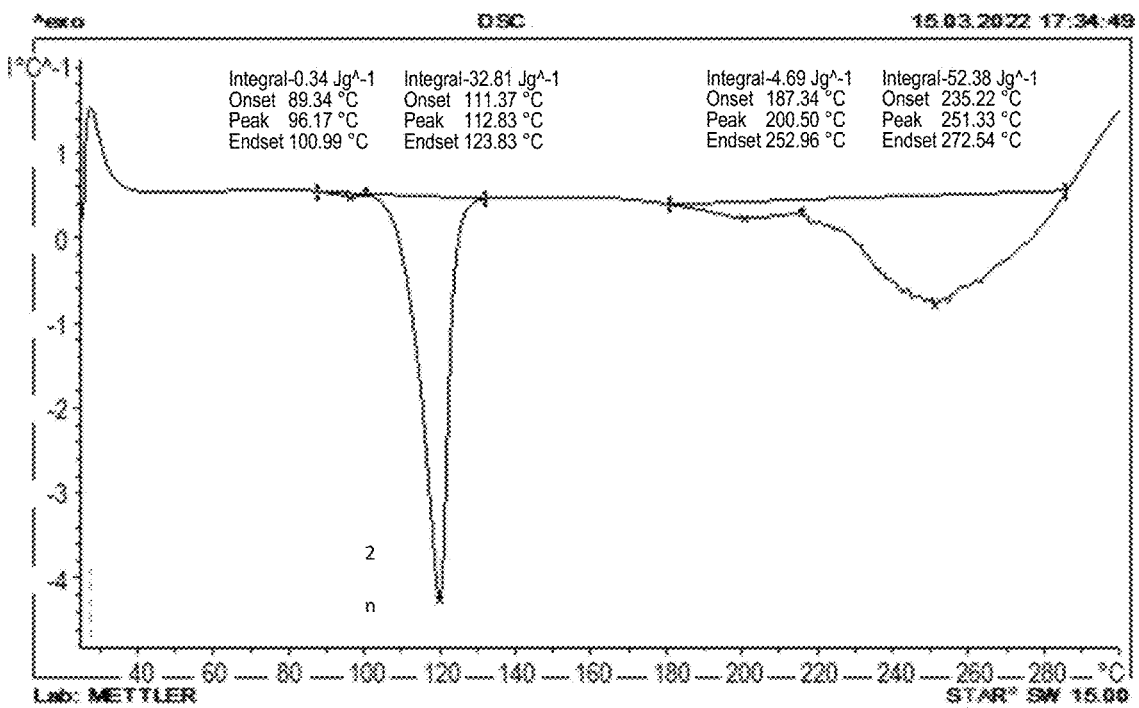
FIG. 20, Continued

| | | |
|---|---|---|
| Instrument Name | HPLC 5/2 | |
| Sequence Acquired Date | 2022-02-25 14:55:09+00:00 | |
| Sequence Name | HPLC 5-2-2022-02-25 14-55-06+00:-00 | |„

| | |
|---|---|
| Injection Acq Method Name | METCR2616 Stage 2 IPC.amx |
| Injection Volume | 5.000 |

Signal: VWD1A, Wavelength=212 nm

| RT [min] | Peak Relative Ret Time | Type | Width [min] | Area | Height | Area% | Compound Name |
|---|---|---|---|---|---|---|---|
| 11.407 | | BB | 0.4972 | 357.6487 | 58.4261 | 1.2116 | |
| 11.860 | | BV | 0.2067 | 21.3227 | 2.8583 | 0.0722 | |
| 12.048 | | VB | 0.2381 | 45.6466 | 8.2620 | 0.1546 | |
| 12.297 | | BV | 0.9137 | 27139.6879 | 2236.2150 | 91.9433 | |
| 12.193 | | VB | 0.2317 | 33.1726 | 6.7395 | 0.1124 | |
| 13.684 | | BB | 0.4708 | 574.1726 | 96.6362 | 1.9452 | |
| 14.199 | | BV | 0.2387 | 30.2427 | 4.9964 | 0.1025 | |
| 14.411 | | VB | 0.2979 | 797.0432 | 132.9137 | 2.7002 | |
| 14.645 | | BV | 0.1768 | 87.4443 | 19.0001 | 0.2962 | |
| 14.834 | | VB | 0.2331 | 134.1064 | 27.3751 | 0.4543 | |
| 15.706 | | BB | 0.2621 | 48.7512 | 10.2185 | 0.1652 | |
| 16.804 | | BB | 0.2881 | 21.4093 | 2.9527 | 0.0725 | |
| 16.662 | | VB | 0.3192 | 66.1421 | 11.2990 | 0.2241 | |
| 16.884 | | BV | 0.1986 | 50.5813 | 9.6356 | 0.1714 | |
| 17.016 | | MM m | 0.1468 | 9.7635 | 1.7402 | 0.0331 | |
| 17.208 | | MM m | 0.1827 | 6.3332 | 1.1471 | 0.0215 | |
| 17.431 | | BV | 0.1671 | 26.5334 | 5.1882 | 0.0899 | |
| 17.500 | | VB | 0.1193 | 19.1044 | 4.4590 | 0.0647 | |
| 17.665 | | BB | 0.2035 | 26.4752 | 5.8984 | 0.0897 | |
| 18.020 | | MM m | 0.2096 | 22.2831 | 5.9861 | 0.0755 | |
| | | | Sum | 29517.8668 | | | |

| | | | | | | |
|---|---|---|---|---|---|---|
| Instrument Name | HPLC 5/2 | | | Injection Acq Method Name | METCR2616 Stage 2 IPC.amx | |
| Sequence Acquired Date | 2022-02-24 16:51:27+00:00 | | | | | |
| Sequence Name | SingleSample | | | Injection Volume | 5.000 | |

Signal: VWD1A, Wavelength=212 nm

| RT [min] | Peak Relative Ret Time | Type | Width [min] | Area | Height | Area% | Compound Name |
|---|---|---|---|---|---|---|---|
| 11.430 | | MM m | 0.2779 | 147.4565 | 34.5597 | 1.0727 | |
| 11.893 | | MM m | 0.1779 | 8.7192 | 1.8161 | 0.0634 | |
| 12.076 | | MM m | 0.2057 | 20.1348 | 4.4367 | 0.1465 | |
| 12.387 | | MM m | 0.6726 | 12627.6296 | 1529.2393 | 91.8621 | |
| 13.205 | | MM m | 0.1612 | 11.2401 | 2.8993 | 0.0818 | |
| 13.694 | | MM m | 0.3113 | 247.1474 | 50.5601 | 1.7979 | |
| 14.203 | | MM m | 0.2168 | 38.5273 | 6.8324 | 0.2803 | |
| 14.412 | | MM m | 0.2223 | 390.6831 | 84.8176 | 2.8421 | |
| 14.648 | | MM m | 0.1779 | 44.1621 | 9.6498 | 0.3213 | |
| 14.832 | | MM m | 0.2890 | 65.3854 | 13.2826 | 0.4757 | |
| 15.699 | | MM m | 0.1779 | 18.0045 | 4.0547 | 0.1310 | |
| 16.652 | | MM m | 0.2223 | 21.7140 | 4.4244 | 0.1580 | |
| 16.884 | | MM m | 0.2335 | 50.1329 | 10.9151 | 0.3647 | |
| 17.423 | | MM m | 0.1065 | 7.7346 | 2.0485 | 0.0563 | |
| 17.507 | | MM m | 0.1477 | 11.9103 | 2.2691 | 0.0866 | |
| 17.667 | | MM m | 0.1786 | 5.4661 | 1.2454 | 0.0398 | |
| 18.023 | | MM m | 0.1614 | 18.1394 | 4.1732 | 0.1320 | |
| 18.187 | | MM m | 0.1168 | 4.1456 | 1.3097 | 0.0302 | |
| 18.271 | | MM m | 0.1271 | 7.9526 | 1.7893 | 0.579 | |
| | | | Sum | 13746.2855 | | | |

| | | | | | | |
|---|---|---|---|---|---|---|
| Instrument Name | HPLC 5/2 | | | Injection Acq Method Name | METCR2616 Stage 2 IPC.amx | |
| Sequence Acquired Date | 2022-02-24 17:02:40+00:00 | | | | | |
| Sequence Name | SingleSample | | | Injection Volume | 5.000 | |

Signal: VWD1A, wavelength=212 nm

| RT [min] Peak Relative Ret Time | Type | Width [min] | Area | Height | Area% | Compound Name |
|---|---|---|---|---|---|---|
| 11.407 | MM m | 0.2853 | 338.2689 | 79.6217 | 1.1715 | |
| 12.047 | MM m | 0.1970 | 46.3743 | 11.2913 | 0.1606 | |
| 12.293 | MM m | 0.7024 | 26440.5202 | 2226.4722 | 91.5667 | |
| 13.199 | MM m | 0.1970 | 30.6511 | 7.2978 | 0.1061 | |
| 13.685 | MM m | 0.3683 | 561.8296 | 114.1165 | 1.9457 | |
| 14.186 | MM m | 0.2398 | 115.8409 | 21.0448 | 0.4012 | |
| 14.404 | MM m | 0.2655 | 862.0602 | 184.4186 | 2.9854 | |
| 14.647 | MM m | 0.1713 | 98.8267 | 22.2289 | 0.3422 | |
| 14.833 | MM m | 0.2741 | 150.6637 | 30.5977 | 0.5218 | |
| 15.701 | MM m | 0.2227 | 41.4091 | 8.9737 | 0.1434 | |
| 16.654 | MM m | 0.3255 | 60.3672 | 10.3986 | 0.2091 | |
| 16.883 | MM m | 0.2313 | 128.8750 | 28.5778 | 0.4463 | |
| | | Sum | 28875.6867 | | | |

| | | |
|---|---|---|
| Instrument Name | HPLC 5/2 | |
| Sequence Acquired Date | 2022-02-25 14:55:09+00:00 | |
| Sequence Name | HPLC 5-2-2022-02-25 14-55-06+00-00 | |
| Injection Acq Method Name | METCR2616 Stage 2 IPC.amx | |
| Injection Volume | 5.000 | |

Signal: VWD1A, Wavelength=212 nm

| RT [min] | Peak Relative Ret Time | Type | Width [min] | Area | Height | Area% | Compound Name |
|---|---|---|---|---|---|---|---|
| 11.419 | | VB | 0.5061 | 268.079 | 41.1261 | 1.2010 | |
| 11.876 | | BV | 0.2048 | 15.8744 | 2.2762 | 0.0711 | |
| 12.064 | | VB | 0.2401 | 31.9020 | 5.6417 | 0.1429 | |
| 12.344 | | BV | 0.8996 | 20360.0587 | 1979.0565 | 91.2089 | |
| 13.204 | | VB | 0.4277 | 29.8695 | 5.0301 | 0.1338 | |
| 13.693 | | BB | 0.4800 | 446.6227 | 76.2830 | 2.0008 | |
| 14.206 | | BV | 0.2253 | 19.3013 | 3.3758 | 0.0865 | |
| 14.414 | | VB | 0.3013 | 725.1109 | 125.0223 | 3.2483 | |
| 14.651 | | BV | 0.1707 | 63.1657 | 13.5434 | 0.2830 | |
| 14.838 | | VB | 0.3923 | 105.5805 | 20.1859 | 0.4730 | |
| 15.709 | | BB | 0.2923 | 34.7000 | 7.3148 | 0.1554 | |
| 16.086 | | BB | 0.4877 | 19.8590 | 2.3674 | 0.0890 | |
| 16.664 | | BB | 0.3238 | 44.5398 | 7.6852 | 0.1995 | |
| 16.882 | | BV | 0.1965 | 38.9253 | 7.4064 | 0.1744 | |
| 17.428 | | BV | 0.2906 | 44.5064 | 5.0787 | 0.1994 | |
| 17.674 | | VB | 0.2361 | 26.8609 | 5.1309 | 0.1203 | |
| 18.026 | | BM m | 0.1863 | 21.4191 | 4.5987 | 0.0960 | |
| 18.195 | | MM m | 0.2947 | 26.0495 | 3.9639 | 0.1167 | |
| | | | Sum | 22322.4439 | | | |

| | | | | | | |
|---|---|---|---|---|---|---|
| Instrument Name | HPLC 5/2 | | Injection Acq Method Name | METCR2616 Stage 2 IPC.amx | | |
| Sequence Acquired Date | 2022-02-24 16:57:02+00:00 | | Injection Volume | 5.000 | | |
| Sequence Name | SingleSample | | | | | |

Signal: VWD1A, Wavelength=212 nm

| RT [min] | Peak Relative Ret Time | Type | Width [min] | Area | Height | Area% | Compound Name |
|---|---|---|---|---|---|---|---|
| 11.413 | | ..lM m | 0.3114 | 260.2660 | 42.7067 | 1.1295 | |
| 12.053 | | MM m | 0.2188 | 31.3946 | 6.1993 | 0.1363 | |
| 12.327 | | MM m | 0.5891 | 21183.6120 | 2025.2398 | 91.9353 | |
| 13.189 | | MM m | 0.2020 | 24.5955 | 5.0767 | 0.1067 | |
| 13.681 | | MM m | 0.3619 | 462.5643 | 79.7748 | 2.0075 | |
| 14.406 | | MM m | 0.4292 | 758.1813 | 126.7501 | 3.2905 | |
| 14.638 | | MM m | 0.1683 | 67.4836 | 14.5943 | 0.2929 | |
| 14.825 | | MM m | 0.2861 | 111.9056 | 21.7387 | 0.4857 | |
| 15.695 | | MM m | 0.2188 | 33.9665 | 7.3116 | 0.1474 | |
| 16.650 | | MM m | 0.2693 | 44.6008 | 7.8895 | 0.1936 | |
| 16.886 | | MM m | 0.3198 | 63.2980 | 11.6403 | 0.2747 | |
| | | Sum | | 23041.8682 | | | |

| | | | | | | |
|---|---|---|---|---|---|---|
| Instrument Name | HPLC 5/2 | | Injection Acq Method Name | METCR2616 Stage 2 IPC.amx | | |
| Sequence Acquired Date | 2022-02-24 16:51:47+00:00 | | Injection Volume | 5.000 | | |
| Sequence Name | SingleSample | | | | | |

Signal: VWD1A, Wavelength=212 nm

| RT [min] | Peak Relative Ret Time | Type | Width [min] | Area | Height | Area% | Compound Name |
|---|---|---|---|---|---|---|---|
| 11.414 | | ..IM m | 0.3150 | 229.5772 | 54.0445 | 1.1066 | |
| 11.875 | | MM m | 0.1944 | 12.6006 | 2.6367 | 0.0607 | |
| 12.061 | | MM m | 0.1877 | 34.7055 | 7.8756 | 0.1673 | |
| 12.340 | | MM m | 0.6970 | 18857.7590 | 1921.0820 | 90.8979 | |
| 13.197 | | MM m | 0.2011 | 20.8499 | 4.9573 | 0.1005 | |
| 13.686 | | MM m | 0.3016 | 409.8823 | 84.0590 | 1.9757 | |
| 14.197 | | MM m | 0.2748 | 63.3245 | 11.3649 | 0.3052 | |
| 14.407 | | MM m | 0.2614 | 691.1885 | 148.4319 | 3.3317 | |
| 14.644 | | MM m | 0.1474 | 65.6935 | 14.9986 | 0.3167 | |
| 14.829 | | MM m | 0.3753 | 106.1409 | 21.3831 | 0.5116 | |
| 15.698 | | MM m | 0.1877 | 26.4950 | 6.0746 | 0.1277 | |
| 16.087 | | MM m | 0.2547 | 16.6153 | 2.4385 | 0.0801 | |
| 16.651 | | MM m | 0.2763 | 42.2008 | 7.1889 | 0.2034 | |
| 16.885 | | MM m | 0.2190 | 81.2776 | 17.9423 | 0.3918 | |
| 17.426 | | MM m | 0.1608 | 20.0035 | 3.7667 | 0.0964 | |
| 17.506 | | MM m | 0.1065 | 10.9115 | 2.8555 | 0.0526 | |
| 17.658 | | MM m | 0.1460 | 7.8404 | 1.9947 | 0.0378 | |
| 18.017 | | MM m | 0.1909 | 29.1291 | 6.5660 | 0.1404 | |
| 18.180 | | MM m | 0.1151 | 9.4876 | 2.2887 | 0.0457 | |
| 18.266 | | MM m | 0.1572 | 10.3983 | 2.7291 | 0.0501 | |
| | | Sum | | 20746.0810 | | | |

| Instrument Name | HPLC 5/2 | Injection Acq Method Name | METCR2616 Stage 2 IPC.amx |
|---|---|---|---|
| Sequence Acquired Date | 2022-02-24 17:03:08+00:00 | Injection Volume | 5.000 |
| Sequence Name | SingleSample | | |

Signal: VWD1A, Wavelength=212 nm

| RT [min] | Peak Relative Ret Time | Type | Width [min] | Area | Height | Area% | Compound Name |
|---|---|---|---|---|---|---|---|
| 11.418 | | MM m | 0.2912 | 238.9664 | 57.2707 | 1.1005 | |
| 12.062 | | MM m | 0.1713 | 38.8464 | 9.0629 | 0.1789 | |
| 12.336 | | MM m | 0.6338 | 19825.5172 | 1974.7019 | 91.2982 | |
| 13.199 | | MM m | 0.2741 | 22.2087 | 5.3396 | 0.1023 | |
| 13.687 | | MM m | 0.3683 | 438.6696 | 89.7384 | 2.0201 | |
| 14.192 | | MM m | 0.2741 | 73.7348 | 13.0456 | 0.3396 | |
| 14.407 | | MM m | 0.2398 | 724.1000 | 156.5275 | 3.3345 | |
| 14.647 | | MM m | 0.1799 | 74.5324 | 16.2986 | 0.3432 | |
| 14.833 | | MM m | 0.3683 | 115.2924 | 22.6382 | 0.5309 | |
| 15.705 | | MM m | 0.2655 | 31.3608 | 6.6848 | 0.1444 | |
| 16.659 | | MM m | 0.1970 | 33.0024 | 6.6152 | 0.1520 | |
| 16.892 | | MM m | 0.2484 | 98.9017 | 22.8162 | 0.4555 | |
| | | | Sum | 21715.1328 | | | |

| Signal | | | |
|---|---|---|---|
| DAD1C, Sig=225,4 Ref=off | | | |
| RT (min) | Area | Area% | MS Base Peak |
| 3.834 | 9.9924 | 0.0557 | |
| 3.989 | 17847.2686 | 99.5064 | 233.0 |
| 4.470 | 43.9368 | 0.2450 | |
| DAD1D, Sig=240,4 Ref=off | | | |
| RT (min) | Area | Area% | MS Base Peak |
| 4.889 | 34.6084 | 0.1930 | |
| Sum | 17935.8062 | | 233.0 |
| DAD1E, Sig=254,4 Ref=off | | | |
| RT (min) | Area | Area% | MS Base Peak |
| 3.989 | 2892.5071 | 99.3813 | 233.0 |
| 4.469 | 18.0067 | 0.6187 | |
| Sum | 2910.5137 | | |
| DAD1F, Sig=272,4 Ref=off | | | |
| RT (min) | Area | Area% | MS Base Peak |
| 3.989 | 3289.8123 | 100.0000 | 233.0 |
| Sum | 3289.8123 | | |
| | | | MS Base Peak |
| RT (min) | Area | Area% | 233.0 |
| 3.989 | 6499.7424 | 100.0000 | |
| Sum | 6499.7424 | | |
| MS1 + TIC Scan ESI Frag=135V | | | |
| RT (min) | Area | Area% | MS Base Peak |
| 3.984 | 21811803.2633 | 96.6491 | 233.0 |
| 10.170 | 417513.0792 | 1.8500 | 284.1 |
| 11.145 | 338708.0601 | 1.5008 | 130.1 |
| Sum | 22568024.4026 | | |

FIG. 187 (Cont'd)

Signal: VWD1A, Wavelength=254 nm

| RT [min] | Peak Type | Width [min] | Area | Height | Area% | Compound Name |
|---|---|---|---|---|---|---|
| | Relative Ret Time | | | | | |
| 11.767 | MM m | 0.2523 | 2.3063 | 0.3856 | 0.0145 | |
| 12.545 | MM m | 0.1165 | 2.5490 | 0.7021 | 0.0160 | |
| 13.055 | MM m | 0.2198 | 1.9700 | 0.4175 | 0.0124 | |
| 13.200 | MM m | 1.1584 | 15871.8397 | 840.0912 | 99.5966 | |
| 15.831 | MM m | 0.2360 | 2.3222 | 0.3787 | 0.0146 | |
| 16.098 | MM m | 0.5128 | 16.8675 | 1.2330 | 0.1058 | |
| 16.597 | MM m | 0.3270 | 25.7949 | 4.1847 | 0.1619 | |
| 17.125 | MM m | 0.3744 | 4.8210 | 0.6671 | 0.0303 | |
| 17.443 | MM m | 0.2523 | 1.7622 | 0.3519 | 0.0111 | |
| 18.220 | MM m | 0.2849 | 5.8862 | 0.9483 | 0.0369 | |
| Sum | | | 15936.1190 | | | |

FIG. 194 (Cont'd)

Signal: VWD1A,Wavelength=254 nm

| RT [min] Peak Relative Ret Time | Type | Width [min] | Area | Height | Area% | Compound Name |
|---|---|---|---|---|---|---|
| 13.032 | MM m | 0.1736 | 4.1032 | 0.9447 | 0.0347 | |
| 13.541 | MM m | 0.3074 | 7.5352 | 1.2021 | 0.0637 | |
| 13.722 | MM m | 0.9837 | 11734.3664 | 738.3225 | 99.2171 | |
| 15.033 | MM m | 0.5280 | 33.6448 | 2.1473 | 0.2845 | |
| 15.565 | MM m | 0.2712 | 16.0932 | 3.1116 | 0.1361 | |
| 16.072 | MM m | 0.1230 | 2.0105 | 0.4554 | 0.0170 | |
| 16.204 | MM m | 0.1555 | 3.4913 | 0.7985 | 0.0295 | |
| 16.365 | MM m | 0.1989 | 9.0695 | 2.0806 | 0.0767 | |
| 17.206 | MM m | 0.2061 | 4.0514 | 0.7950 | 0.0343 | |
| 18.382 | MM m | 0.3660 | 12.5884 | 2.0070 | 0.1064 | |
| | | Sum | 11826.9539 | | | |

FIG. 203 (Cont'd)

Signal: VWD1A, Wavelength=254 nm

| RT [min] | Peak Relative Ret Time | Type | Width [min] | Area | Height | Area% | Compound Name |
|---|---|---|---|---|---|---|---|
| 13.819 | | MM m | 0.7476 | 7191.1796 | 556.8431 | 99.6371 | |
| 15.033 | | MM m | 0.1523 | 2.3290 | 0.4824 | 0.0323 | |
| 16.061 | | MM m | 0.2081 | 2.5118 | 0.4356 | 0.0348 | |
| 16.359 | | MM m | 0.1784 | 7.4474 | 1.5266 | 0.1032 | |
| 16.500 | | MM m | 0.1368 | 1.2879 | 0.2597 | 0.0178 | |
| 17.201 | | MM m | 0.3211 | 4.2242 | 0.7285 | 0.0585 | |
| 17.652 | | MM m | 0.2141 | 0.9671 | 0.1934 | 0.0134 | |
| 18.390 | | MM m | 0.2795 | 7.4218 | 1.2903 | 0.1028 | |
| | | | Sum | 7217.3688 | | | |

FIG. 212 (Cont'd)

Signal: VWD1A, Wavelength=212 nm

| RT [min] | Peak Relative Ret Time | Type | Width [min] | Area | Height | Area% | Compound Name |
|---|---|---|---|---|---|---|---|
| 11.404 | | VB | 0.5135 | 212.5121 | 32.8501 | 1.4533 | |
| 11.866 | | BV | 0.2037 | 12.7813 | 1.9320 | 0.0874 | |
| 12.057 | | VV | 0.2561 | 11.8186 | 1.9092 | 0.0808 | |
| 12.368 | | VV | 0.8771 | 13721.6677 | 1608.0160 | 93.8358 | |
| 13.176 | | VB | 0.2133 | 20.0926 | 4.0733 | 0.1374 | |
| 13.678 | | BB | 0.5803 | 336.0242 | 58.6136 | 2.2979 | |
| 14.425 | | BV | 0.3024 | 40.7582 | 5.5758 | 0.2787 | |
| 14.634 | | VV | 0.1814 | 56.0136 | 12.0610 | 0.3830 | |
| 14.825 | | VB | 0.2490 | 79.9526 | 16.8366 | 0.5468 | |
| 15.701 | | BB | 0.2397 | 23.9460 | 5.3194 | 0.1638 | |
| 16.651 | | VB | 0.3553 | 29.5576 | 5.9011 | 0.2021 | |
| 17.418 | | VV | 0.2329 | 17.1502 | 3.2728 | 0.1173 | |
| 17.647 | | VB | 0.3410 | 38.1637 | 7.2885 | 0.2610 | |
| 18.170 | | VB | 0.2618 | 22.6169 | 4.7468 | 0.1547 | |

Sum 14623.0556

FIG. 342 (Cont'd)

SALTS AND SOLID FORMS OF (R)-1-(5-METHOXY-1H-INDOL-1-YL)-N,N-DIMETHYLPROPAN-2-AMINE

CROSS-REFERENCES TO RELATED APPLICATIONS

This application is a continuation of U.S. patent application Ser. No. 17/988,753, filed on Nov. 16, 2022, which claims priority to, and the benefit of, U.S. Provisional Application No. 63/280,084 filed Nov. 16, 2021; U.S. Provisional Application No. 63/310,977, filed Feb. 16, 2022; U.S. Provisional Application No. 63/316,924, filed Mar. 4, 2022; U.S. Provisional Application No. 63/280,085, filed Nov. 16, 2021, and U.S. Provisional Application No. 63/319,735, filed Mar. 14, 2022 all of which are incorporated herein by reference in their entirety.

BACKGROUND OF THE INVENTION

The development of (R)-1-(5-methoxy-1H-indol-1-yl)-N,N-dimethylpropan-2-amine is limited by difficulties in formulating (R)-1-(5-methoxy-1H-indol-1-yl)-N,N-dimethylpropan-2-amine, e.g., salt and solid forms of (R)-1-(5-methoxy-1H-indol-1-yl)-N,N-dimethylpropan-2-amine including solid forms of (R)-1-(5-methoxy-1H-indol-1-yl)-N,N-dimethylpropan-2-amine fumarate. Accordingly, the present disclosure addresses this unmet need.

SUMMARY

In one aspect, this disclosure provides an (R)-1-(5-methoxy-1H-indol-1-yl)-N,N-dimethylpropan-2-amine (compound 1) salt. In one aspect, this disclosure provides a polymorphic form of a (R)-1-(5-methoxy-1H-indol-1-yl)-N,N-dimethylpropan-2-amine (compound 1) salt.

Disclosed herein are novel forms of (R)-1-(5-methoxy-1H-indol-1-yl)-N,N-dimethylpropan-2-amine fumarate, including solid forms of (R)-1-(5-methoxy-1H-indol-1-yl)-N,N-dimethylpropan-2-amine fumarate, and hemifumarate forms of (R)-1-(5-methoxy-1H-indol-1-yl)-N,N-dimethylpropan-2-amine. The solid form of (R)-1-(5-methoxy-1H-indol-1-yl)-N,N-dimethylpropan-2-amine fumarate, e.g., monofumarate or hemifumarate may have at least one improved property compared to other forms of (R)-1-(5-methoxy-1H-indol-1-yl)-N,N-dimethylpropan-2-amine, such as (R)-1-(5-methoxy-1H-indol-1-yl)-N,N-dimethylpropan-2-amine fumarate.

Also disclosed herein is a solid form of (R)-1-(5-methoxy-1H-indol-1-yl)-N,N-dimethylpropan-2-amine fumarate that is made by the method described in Example 1. The solid form of (R)-1-(5-methoxy-1H-indol-1-yl)-N,N-dimethylpropan-2-amine fumarate made by the disclosed method may have at least one improved property compared to a known form of (R)-1-(5-methoxy-1H-indol-1-yl)-N,N-dimethylpropan-2-amine fumarate. In one embodiment, the (R)-1-(5-methoxy-1H-indol-1-yl)-N,N-dimethylpropan-2-amine fumarate solid form disclosed herein is a crystalline form that has an improved property relative to amorphous (R)-1-(5-methoxy-1H-indol-1-yl)-N,N-dimethylpropan-2-amine fumarate. In one embodiment a crystalline form disclosed herein is a polymorph of (R)-1-(5-methoxy-1H-indol-1-yl)-N,N-dimethylpropan-2-amine fumarate. In certain embodiments, a disclosed polymorph of (R)-1-(5-methoxy-1H-indol-1-yl)-N,N-dimethylpropan-2-amine fumarate has an improved property over one or more other solid forms of (R)-1-(5-methoxy-1H-indol-1-yl)-N,N-dimethylpropan-2-amine fumarate.

In some embodiments, the at least one improved property of the solid form of (R)-1-(5-methoxy-1H-indol-1-yl)-N,N-dimethylpropan-2-amine fumarate disclosed herein may comprise a physical property, chemical property, pharmacokinetic property, or a combination thereof. In some embodiments, the at least one improved property comprises a melting point, glass transition temperature, flowability, thermal stability, shelf life, stability against polymorphic transition, hygroscopic properties, solubility in water and/or organic solvents, reactivity, compatibility with excipients and/or delivery vehicles, bioavailability, absorption, distribution, metabolism, excretion, toxicity including cytotoxicity, dissolution rate, half-life, or a combination thereof, that is improved compared to an amorphous sample of (R)-1-(5-methoxy-1H-indol-1-yl)-N,N-dimethylpropan-2-amine fumarate.

In some embodiments, the solid form of (R)-1-(5-methoxy-1H-indol-1-yl)-NN-dimethylpropan-2-amine fumarate may be a solvate, such as a hydrate.

Also disclosed herein are embodiments, of a pharmaceutical composition, comprising a solid form of and/or a previously known crystalline form of (R)-1-(5-methoxy-1H-indol-1-yl)-N,N-dimethylpropan-2-amine fumarate, and a pharmaceutically acceptable excipient.

A method for administering the solid form of and/or a previously known crystalline form of and/or a previously known crystalline form of and/or a previously known crystalline form of and/or a previously known crystalline form of and/or a previously known crystalline form of (R)-1-(5-methoxy-1H-indol-1-yl)-N,N-dimethylpropan-2-amine fumarate also is disclosed herein. In some embodiments, the method comprises administering to a subject an effective amount of a solid form of (R)-1-(5-methoxy-1H-indol-1-yl)-N,N-dimethylpropan-2-amine fumarate, or a pharmaceutical composition thereof. In some embodiments, the subject is suffering from a neurological disease or a psychiatric disorder, or both, such as a neurodegenerative disorder. The neurological disorder or psychiatric disorder, or both, may comprise depression, addiction, anxiety, or a post-traumatic stress disorder, and/or the neurological disorder or psychiatric disorder, or both, may comprise treatment resistant depression, suicidal ideation, major depressive disorder, bipolar disorder, schizophrenia, or substance use disorder. In some embodiments, the neurological disorder or psychiatric disorder, or both, comprises stroke, traumatic brain injury, or a combination thereof.

In some embodiments, administering the solid form of (R)-1-(5-methoxy-1H-indol-1-yl)-N,N-dimethylpropan-2-amine fumarate comprises oral, intravenous, parenteral, or topical administration. In certain embodiments, oral administration is used, but in other particular embodiments, administration is by injection, inhalation, intraocular, intravaginal, intrarectal or transdermal routes.

In some embodiments, the salt is crystalline. In some embodiments, the salt is amorphous. In some embodiments, the salt is an acid addition salt. In some embodiments, the salt is a 4:1 compound 1:acid salt. In some embodiments, the salt is a 3:1 compound 1:acid salt. In some embodiments, the salt is a 2:1 compound 1:acid salt. In some embodiments, the salt is a 1:1 compound 1:acid salt. In some embodiments, the salt is a 1:2 compound 1:acid salt. In some embodiments, the salt is a 1:3 compound 1:acid salt. In some embodiments, the salt is a 1:4 compound 1:acid salt.

In some embodiments, the salt is a fumarate or hemifumarate salt. In some embodiments, the compound 1 salt is a crystalline compound 1 monofumarate Form A salt. In some embodiments, the compound 1 salt is a compound 1 monofumarate salt that is a crystalline polymorphic form characterized by XRPD signals at two signals or more, or three signals selected from the group consisting of 22.4°2θ, 15.9°2θ, and 19.5°2θ (±0.2°2θ; ±0.1°2θ; or ±0.0°2θ; Cu Kα1 radiation). In some embodiments, the compound 1 monofumarate salt is a crystalline polymorphic form characterized by XRPD signals at 22.4°2θ, 15.9°2θ, and 19.5°2θ. In some embodiments, the compound 1 monofumarate salt is a crystalline polymorphic form characterized by an XRPD pattern substantially similar to that shown in FIG. 157. In some embodiments, the compound 1 monofumarate salt is a crystalline polymorphic form characterized by a DSC diagram having a melting signal at about 118.2° C. In some embodiments, the compound 1 monofumarate salt is a crystalline polymorphic form characterized by a DSC profile substantially similar to that shown in FIG. 159. In some embodiments, the compound 1 monofumarate salt is a crystalline polymorph characterized by a TGA diagram having an onset at about 207.9° C. In some embodiments, the compound 1 monofumarate salt is a crystalline polymorph characterized by a TGA diagram substantially similar to that shown in FIG. 158.

In some embodiments, the compound 1 monofumarate salt is a crystalline compound 1 fumarate Form B salt. In some embodiments, the compound 1 monofumarate salt is a crystalline polymorph characterized by XRPD signals at two signals or more, or three signals selected from 17.6°2θ, 19.4°2θ, and 23.5°2θ (±0.2°2θ; ±0.1°2θ; or ±0.0°2θ; Cu Kα1 radiation). In some embodiments, the compound 1 monofumarate salt is a crystalline polymorph characterized by XRPD signals at 17.6°2θ, 19.4°2θ, and 23.5°2θ (±0.2°2θ; ±0.1°2θ; or ±0.0°2θ; Cu Kα1 radiation). In some embodiments, the compound 1 monofumarate salt is a crystalline polymorph characterized by XRPD signals at 16.7°2θ, 17.6°2θ, 19.4°2θ, 23.5°2θ, and 24.7°2θ (±0.2°2θ; ±0.1°2θ; or ±0.0°2θ; Cu Kα1 radiation). In some embodiments, the compound 1 monofumarate salt is a crystalline polymorph characterized by any combination of the XRPD signals contained in Table 32. In some embodiments, the compound 1 monofumarate salt is a crystalline polymorph characterized by an XRPD pattern substantially similar to that shown in FIG. 5. In some embodiments, the compound 1 monofumarate salt is a crystalline polymorph characterized by a DSC diagram having an melting signal at about 66.2° C. In some embodiments, the compound 1 monofumarate salt is a crystalline polymorph characterized by a TGA diagram having an onset at about 208.4° C.

In some embodiments, the compound 1 salt is a crystalline compound 1 fumarate Pattern 3a salt. In some embodiments, the compound 1 fumarate salt is a crystalline polymorph characterized by XRPD signals at two signals or more, or three signals selected from the group consisting of 24.0°2θ, 19.8°2θ, and 18.1°2θ (±0.2°2θ; ±0.1°2θ; or ±0.0°2θ; Cu Kα1 radiation). In some embodiments, the compound 1 fumarate salt is a crystalline polymorph characterized by XRPD signals at 24.0°2θ, 19.8°2θ, and 18.1°2θ (±0.2°2θ; ±0.1°2θ; or ±0.0°2θ; Cu Kα1 radiation). In some embodiments, the compound 1 fumarate salt is a crystalline polymorph characterized by XRPD signals at 18.1°2θ, 19.8°2θ, 19.9°2θ, 23.6°2θ, and 24.0°2θ (±0.2°2θ; ±0.1°2θ; or ±0.0°2θ; Cu Kα1 radiation). In some embodiments, the compound 1 fumarate salt is a crystalline polymorph characterized by XRPD signals at 9.5°2θ, 11.9°2θ, 14.1°2θ, 15.1°2θ, 16.8°2θ, 17.6°2θ, 18.1°2θ, 19.0°2θ, 19.8°2θ, 19.9°2θ, 23.6°2θ, 24.0°2θ, 25.7°2θ, 28.3°2θ, 30.0°2θ, and 31.7°2θ (±0.2°2θ; ±0.1°2θ; or ±0.0°2θ; Cu Kα1 radiation). In some embodiments, the compound 1 fumarate salt is a crystalline polymorph characterized by any combination of the XRPD signals contained in Table 36. In some embodiments, the compound 1 fumarate salt is a crystalline polymorph characterized by an XRPD pattern substantially similar to that shown in FIG. 70.

In some embodiments, the compound 1 hemi-fumarate salt is a crystalline polymorph characterized by XRPD signals at two signals or more, or three signals selected from the group consisting of 15.8°2θ, 20.9°2θ, and 26.9°2θ (±0.2°2θ; ±0.1°2θ; or ±0.0°2θ; Cu Kα1 radiation).

In some embodiments, the compound 1 hemi-fumarate salt is a crystalline polymorph characterized by XRPD signals at 15.8°2θ, 20.9°2θ, and 26.9°2θ (±0.2°2θ; ±0.1°2θ; or ±0.0°2θ; Cu Kα1 radiation). In some embodiments, the compound 1 hemi-fumarate salt is a crystalline polymorph characterized by XRPD signals at 15.1°2θ, 15.8°2θ, 19.2°2θ, 20.9°2θ, and 26.9°2θ (±0.2°2θ; ±0.1°2θ; or ±0.0°2θ; Cu Kα1 radiation). In some embodiments, the compound 1 hemi-fumarate salt is a crystalline polymorph characterized by XRPD signals at 11.5°2θ, 13.3°2θ, 13.5°2θ, 15.1°2θ, 15.8°2θ, 18.8°2θ, 19.2°2θ, 20.9°2θ, 21.4°2θ, 22.4°2θ, 23.1°2θ, 24.0°2θ, 24.7°2θ, 26.9°2θ, 28.2°2θ (±0.2°2θ; ±0.1°2θ; or ±0.0°2θ; Cu Kα1 radiation). In some embodiments, the compound 1 hemi-fumarate salt is a crystalline polymorph characterized by any combination of the XRPD signals contained in Table 35. In some embodiments, the compound 1 hemi-fumarate salt is a crystalline polymorph characterized by an XRPD pattern substantially similar to that shown in FIG. 7. In some embodiments, the compound 1 hemi-fumarate salt is a crystalline polymorph characterized by DSC having a melting signal at about 97.2° C. In some embodiments, the compound 1 hemi-fumarate salt is a crystalline polymorph characterized by DSC profile substantially similar to that shown in FIG. 60. In some embodiments, the compound 1 hemi-fumarate salt is a crystalline polymorph characterized by a TGA diagram having an onset at about 246.4° C. In some embodiments, the compound 1 hemi-fumarate salt is a crystalline polymorph characterized by a TGA diagram substantially similar to that shown in FIG. 59.

In some embodiments, the compound 1 salt is a crystalline compound 1 hemi-fumarate Form I salt. In some embodiments, the compound 1 hemi-fumarate salt is a crystalline polymorph characterized by XRPD signals at two signals or more, or three signals selected from the group consisting of 15.9°2θ, 21.0°2θ, and 19.4°2θ (±0.2°2θ; ±0.1°2θ; or ±0.0°2θ; Cu Kα1 radiation). In some embodiments, the compound 1 hemi-fumarate salt is a crystalline polymorph characterized by XRPD signals at 15.9°2θ, 21.0°2θ, and 19.4°2θ (±0.2°2θ; ±0.1°2θ; or ±0.0° 2θ; Cu Kα1 radiation). In some embodiments, the compound 1 hemi-fumarate salt is a crystalline polymorph characterized by XRPD signals at 15.2°2θ, 15.9°2θ, 19.4°2θ, 21.0°2θ, and 27.1°2θ (±0.2°2θ; ±0.1°2θ; or ±0.0°2θ; Cu Kα1 radiation). In some embodiments, the compound 1 hemi-fumarate salt is a crystalline polymorph characterized by XRPD signals at 11.7°2θ, 13.4°2θ, 13.7°2θ, 15.2°2θ, 15.9°2θ, 18.9°2θ, 19.4°2θ, 21.0°2θ, 21.6°2θ, 22.5°2θ, 23.2°2θ, and 27.1°2θ (±0.2°2θ; ±0.1°2θ; or ±0.0°2θ; Cu Kα1 radiation). In some embodiments, the compound 1 hemi-fumarate salt is a crystalline polymorph characterized by any combination of the XRPD signals contained in Table 33. In some embodiments, the compound 1 hemi-fumarate salt is a crystalline polymorph characterized by DSC having a melting signal at about 91.5° C. In some embodiments, the compound 1 hemi-fumarate salt is a crystalline polymorph characterized A TGA diagram having an onset at about 246.4° C.

In some embodiments, the compound 1 salt is a crystalline compound 1 fumarate Pattern 5 salt. In some embodiments, wherein the compound 1 fumarate salt is a crystalline polymorph characterized by XRPD signals at two signals or more, or three signals selected from the group consisting of 7.9°2θ, 21.6°2θ, and 20.2°2θ (±0.2°2θ; ±0.1°2θ; or ±0.0°2θ; Cu Kα1 radiation). In some embodiments, the compound 1 fumarate salt is a crystalline polymorph characterized by XRPD signals at 7.9°2θ, 21.6°2θ, and 20.2°2θ (±0.2°2θ; ±0.1°2θ; or ±0.0°2θ; Cu Kα1 radiation). In some embodiments, the compound 1 fumarate salt is a crystalline polymorph characterized by XRPD signals at 7.9°2θ, 15.7°2θ, 20.2°2θ, 21.6°2θ, and 23.7°2θ (±0.2°2θ; ±0.1°2θ; or ±0.0°2θ; Cu Kα1 radiation). In some embodiments, the compound 1 fumarate salt is a crystalline polymorph characterized by any combination of the XRPD signals contained in Table 38. In some embodiments, the compound 1 fumarate salt is a crystalline polymorph characterized by an XRPD pattern substantially similar to that shown in FIG. 1.

In some embodiments, the compound 1 salt is a crystalline compound 1 fumarate Pattern 6 salt. In some embodiments, the compound 1 fumarate salt is a crystalline polymorph characterized by XRPD signals at two signals or more, or three signals selected from the group consisting of 19.3°2θ, 8.2°2θ, and 20.2°2θ (±0.2°2θ; ±0.1°2θ; or ±0.0°2θ; Cu Kα1 radiation). In some embodiments, the compound 1 fumarate salt is a crystalline polymorph characterized by XRPD signals at 19.3°2θ, 8.2°2θ, and 20.2°2θ (±0.2°2θ; ±0.1°2θ; or ±0.0°2θ; Cu Kα1 radiation). In some embodiments, the compound 1 fumarate salt is a crystalline polymorph characterized by XRPD signals at 8.2°2θ, 19.3°2θ, 20.2°2θ, 21.7°2θ, and 23.2°2θ (±0.2°2θ; ±0.1°2θ; or ±0.0°2θ; Cu Kα1 radiation). In some embodiments, the compound 1 fumarate salt is a crystalline polymorph characterized by XRPD signals at 8.2°2θ, 12.3°2θ, 13.4°2θ, 13.9°2θ, 14.9°2θ, 16.7°2θ, 17.2°2θ, 18.4°2θ, 19.3°2θ, 20.2°2θ, 20.9°2θ, 21.7°2θ, 22.4°2θ, 23.2°2θ, 23.8°2θ, 24.4°2θ, 25.1°2θ, 26.1°2θ, 27.6°2θ, 29.1°2θ, and 29.8°2θ (±0.2°2θ; ±0.1°2θ; or ±0.0°2θ; Cu Kα1 radiation). In some embodiments, the compound 1 fumarate salt is a crystalline polymorph characterized by any combination of the XRPD signals contained in Table 39. In some embodiments, the compound 1 fumarate salt is a crystalline polymorph characterized by an XRPD pattern substantially similar to that shown in FIG. 71.

In some embodiments, the compound 1 salt is a compound 1 HCl salt. In some embodiments, the compound 1 HCl salt is a crystalline HCl salt. In some embodiments, the compound 1 HCl salt is a crystalline HCl Form A salt. In some embodiments, the compound 1 HCl salt is a crystalline HCl Form B salt.

In some embodiments, the compound 1 HCl salt is a crystalline polymorph characterized by XRPD signals at two signals or more, or three signals selected from the group consisting of 18.1°2θ, 24.9°2θ, and 21.7°2θ (±0.2°2θ; ±0.1°2θ; or ±0.0°2θ; Cu Kα1 radiation). In some embodiments, the compound 1 HCl salt is a crystalline polymorph characterized by XRPD signals at 18.1°2θ, 24.9°2θ, and 21.7°2θ (±0.2°2θ; ±0.1°2θ; or ±0.0°2θ; Cu Kα1 radiation). In some embodiments, the compound 1 HCl salt is a crystalline polymorph characterized by XRPD signals at 17.8°2θ, 18.1°2θ, 21.7°2θ, 24.9°2θ, and 29.0°2θ (±0.2°2θ; ±0.1°2θ; or ±0.0°2θ; Cu Kα1 radiation). In some embodiments, the compound 1 HCl salt is a crystalline polymorph characterized by XRPD signals at 6.4°2θ, 12.4°2θ, 13.6°2θ, 15.3°2θ, 17.6°2θ, 17.8°2θ, 18.1°2θ, 18.7°2θ, 20.0°2θ, 20.5°2θ, 21.7°2θ, 23.1°2θ, 24.9°2θ, 25.5°2θ, 25.9°2θ, 27.4°2θ, 29.0°2θ, 30.1°2θ, and 30.3°2θ (±0.2°2θ; ±0.1°2θ; or ±0.0°2θ; Cu Kα1 radiation). In some embodiments, the compound 1 HCl salt is a crystalline polymorph characterized by any combination of the XRPD signals contained in Table 41. In some embodiments, the compound 1 HCl salt is a crystalline polymorph characterized by an XRPD pattern that is substantially similar to that shown in FIG. 167. In some embodiments, the compound 1 HCl salt is a crystalline polymorph characterized by a DSC curve having a melting signal at about 229.8° C. In some embodiments, the compound 1 HCl salt is a crystalline polymorph characterized by a DSC curve that is substantially similar to that shown in FIG. 190. In some embodiments, the compound 1 HCl salt is a crystalline polymorph characterized by a TGA diagram having an onset at about 243.3° C. In some embodiments, wherein the compound 1 HCl salt is a crystalline polymorph characterized by a TGA diagram that is substantially similar to that shown in FIG. 195.

In some embodiments, the compound 1 salt is a maleate salt. In some embodiments, the maleate salt is a crystalline maleate salt, the compound 1 maleate salt is a crystalline polymorph characterized by XRPD signals at two signals or more, or three signals selected from the group consisting of 23.7°2θ, 21.6°2θ, and 26.0°2θ (±0.2°2θ; ±0.1°2θ; or ±0.0°2θ; Cu Kα1 radiation). In some embodiments, the compound 1 maleate salt is a crystalline polymorph characterized by XRPD signals at 23.7°2θ, 21.6°2θ, and 26.0°2θ (±0.2°2θ; ±0.1°2θ; or ±0.0°2θ; Cu Kα1 radiation). In some embodiments, the compound 1 maleate salt is a crystalline polymorph characterized by XRPD signals at 19.2°2θ, 21.6°2θ, 23.7°2θ, 26.0°2θ, and 26.5°2θ (±0.2°2θ; ±0.1°2θ; or ±0.0°2θ; Cu Kα1 radiation). In some embodiments, the compound 1 maleate salt is a crystalline polymorph characterized by XRPD signals at 9.4°2θ, 10.9°2θ, 11.8°2θ, 16.9°2θ, 18.6°2θ, 19.2°2θ, 20.9°2θ, 21.6°2θ, 22.2°2θ, 23.7°2θ, 25.0°2θ, 26.0°2θ, and 26.5°2θ (±0.2°2θ; ±0.1°2θ; or ±0.0°2θ; Cu Kα1 radiation). In some embodiments, the compound 1 maleate salt is a crystalline polymorph characterized by any combination of the XRPD signals contained in Table 43. In some embodiments, the compound 1 maleate salt is a crystalline polymorph characterized by an XRPD pattern that is substantially similar to that shown in FIG. 205. In some embodiments, the compound 1 maleate salt is a crystalline polymorph characterized by a DSC curve having a melting signal at about 60.2° C. In some embodiments, the compound 1 maleate salt is a crystalline polymorph characterized by a DSC that is substantially similar to FIG. 199. In some embodiments, compound 1 maleate salt is a crystalline polymorph characterized by a TGA curve having an onset at about 200.0° C. In some embodiments, the compound 1 maleate salt is a crystalline polymorph characterized by a TGA curve that is substantially similar to that shown in FIG. 223.

In some embodiments, the compound 1 salt is a benzoate salt. In some embodiments, the benzoate salt is a crystalline benzoate salt. In some embodiments, the compound 1 benzoate salt is a crystalline polymorph characterized by XRPD signals at two signals or more, or three signals selected from the group consisting of 17.5°2θ, 14.5°2θ, and 18.6°2θ (±0.2°2θ; ±0.1°2θ; or ±0.0° 2θ; Cu Kα1 radiation). In some embodiments, the compound 1 benzoate salt is a crystalline polymorph characterized by XRPD signals at 17.5°2θ, 14.5°2θ, and 18.6°2θ (±0.2°2θ; ±0.1°2θ; or ±0.0°2θ; Cu Kα1 radiation). In some embodiments, the compound 1 benzoate salt is a crystalline polymorph characterized by XRPD signals at 13.8°2θ, 14.5°2θ, 17.5°2θ, 18.6°2θ, and 19.2°2θ (±0.2°2θ; ±0.1°2θ; or ±0.0°2θ; Cu Kα1 radiation).

In some embodiments, the compound 1 benzoate salt is a crystalline polymorph characterized by XRPD signals at 7.8°2θ, 12.5°2θ, 13.8°2θ, 14.5°2θ, 15.5°2θ, 17.5°2θ, 18.6°2θ, 19.2°2θ, 19.7°2θ, 20.6°2θ, 23.7°2θ, 25.2°2θ, and 25.3°2θ (±0.2°2θ; ±0.1°2θ, or ±0.0°2θ; Cu Kα1 radiation). In some embodiments, the compound 1 benzoate salt is a crystalline polymorph characterized by any combination of the XRPD signals contained in Table 45. In some embodiments, the compound 1 benzoate salt is a crystalline polymorph characterized by an XRPD pattern that is substantially similar to that shown in FIG. 214. In some embodiments, the compound 1 benzoate salt is a crystalline polymorph characterized by an XRPD pattern that is substantially similar to that shown in FIG. 214. In some embodiments, the compound 1 benzoate salt is a crystalline polymorph characterized by a DSC curve having a melting signal at about 101.0° C. In some embodiments, wherein the compound 1 benzoate salt is a crystalline polymorph characterized by a DSC that is substantially similar to FIG. 208. In some embodiments, the compound 1 benzoate salt is a crystalline polymorph characterized by a TGA curve having an onset at about 102.2° C. In some embodiments, the compound 1 benzoate salt is a crystalline polymorph characterized by a TGA curve that is substantially similar to that shown in FIG. 213.

In some embodiments, the compound 1 salt is a tosylate salt. In some embodiments, the tosylate salt is a crystalline tosylate salt. In some embodiments, the compound 1 tosylate salt is a crystalline polymorph characterized by XRPD signals at two signals or more, or three signals selected from the group consisting of 19.8°2θ, 19.5°2θ, and 25.5°2θ (±0.2°2θ; ±0.1°2θ; or ±0.0°2θ; Cu Kα1 radiation). In some embodiments, the compound 1 tosylate salt is a crystalline polymorph characterized by XRPD signals at 19.8°2θ, 19.5°2θ, and 25.5°2θ (±0.2°2θ; ±0.1°2θ; or ±0.0°2θ; Cu Kα1 radiation). In some embodiments, the compound 1 tosylate salt is a crystalline polymorph characterized by XRPD signals at 14.5°2θ, 15.3°2θ, 19.5°2θ, 19.8°2θ, and 25.5°2θ (±0.2°2θ; ±0.1°2θ; or ±0.0°2θ; Cu Kα1 radiation). In some embodiments, the compound 1 tosylate salt is a crystalline polymorph characterized by XRPD signals at 10.3°2θ, 14.5°2θ, 15.3°2θ, 16.3°2θ, 16.5°2θ, 18.2°2θ, 19.5°2θ, 19.8°2θ, 20.6°2θ, 20.7°2θ, 22.9°2θ, 23.3°2θ, 25.5°2θ, 26.0°2θ, 26.2°2θ, 26.6°2θ, 29.4°2θ, and 30.3°2θ (±0.2°2θ; ±0.1°2θ; or ±0.0°2θ; Cu Kα1 radiation). In some embodiments, the compound 1 tosylate salt is a crystalline polymorph characterized by any combination of the XRPD signals contained in Table 113. In some embodiments the compound 1 tosylate salt is a crystalline polymorph characterized by an XRPD pattern that is substantially similar to that shown in FIG. 170. In some embodiments, the compound 1 tosylate salt is a crystalline polymorph characterized by a DSC curve having a melting signal at about 137.7° C. In some embodiments, the compound 1 tosylate salt is a crystalline polymorph characterized by a DSC that is substantially similar to FIG. 234. In some embodiments, the compound 1 tosylate salt is a crystalline polymorph characterized by a TGA curve having a TGA curve that is substantially similar to that shown in FIG. 235. In some embodiments, the compound 1 tosylate salt is a crystalline polymorph characterized by a TGA curve as shown in FIG. 235.

In some embodiments, the compound 1 salt is a tartrate salt. In some embodiments, the tartrate salt is a crystalline tartrate salt. In some embodiments, the compound 1 tartrate salt is a crystalline polymorph characterized by XRPD signals at two signals or more, or three signals selected from the group consisting of 4.3°2θ, 17.5°2θ, and 19.3°2θ (±0.2°2θ; ±0.1°2θ; or ±0.0°2θ; Cu Kα1 radiation). In some embodiments, the compound 1 tartrate salt is a crystalline polymorph characterized by XRPD signals at 4.3°2θ, 17.5°2θ, and 19.3°2θ (±0.2°2θ; ±0.1°2θ; or ±0.0°2θ; Cu Kα1 radiation). In some embodiments, the compound 1 tartrate salt is a crystalline polymorph characterized by XRPD signals at 4.3°2θ, 14.5°2θ, 17.5°2θ, 19.3°2θ, and 20.1°2θ (±0.2°2θ; ±0.1°2θ; or ±0.0°2θ; Cu Kα1 radiation). In some embodiments, the compound 1 tartrate salt is a crystalline polymorph characterized by XRPD signals at 4.3°2θ, 8.7°2θ, 13.1°2θ, 14.5°2θ, 16.2°2θ, 16.9°2θ, 17.5°2θ, 18.7°2θ, 19.3°2θ, 20.1°2θ, 21.0°2θ, 21.8°2θ, 23.3°2θ, 23.7°2θ, 24.8°2θ, 26.8°2θ, 27.5°2θ, 28.0°2θ, 29.1°2θ, 29.2°2θ, 29.7°2θ, 30.8°2θ, 31.8°2θ, 33.3°2θ, 35.0°2θ, 36.1°2θ, 37.6°2θ, and 38.9°2θ (±0.2°2θ; ±0.1°2θ; or ±0.0°2θ; Cu Kα1 radiation). In some embodiments, the compound 1 tartrate salt is a crystalline polymorph characterized by an XRPD pattern that is substantially similar to that shown in FIG. 171. In some embodiments, the compound 1 tartrate salt is a crystalline polymorph characterized by an XRPD pattern that is substantially similar to that shown in FIG. 171. In some embodiments, the compound 1 tartrate salt is a crystalline polymorph characterized by a DSC curve having a melting signal at about 115.5° C. In some embodiments, the compound 1 tartrate salt is a crystalline polymorph characterized by a DSC that is substantially similar to FIG. 238. In some embodiments, the compound 1 tartrate salt is a crystalline polymorph characterized by a TGA curve that is substantially similar to that shown in FIG. 239. In some embodiments, the compound 1 tartrate salt is a crystalline polymorph characterized by a TGA curve as shown in FIG. 239.

In some embodiments, the compound 1 salt is a HBr salt. In some embodiments, the HBr salt is a crystalline HBr salt. In some embodiments, the compound 1 HBr salt is a crystalline polymorph characterized by XRPD signals at two signals or more, or three signals selected from the group consisting of 21.6°2θ, 18.1°2θ, and 12.2°2θ (±0.2°2θ; ±0.1°2θ; or ±0.0°2θ; Cu Kα1 radiation). In some embodiments, the compound 1 HBr salt is a crystalline polymorph characterized by XRPD signals at 21.6°2θ, 18.1°2θ, and 12.2°2θ (±0.2°2θ; ±0.1°2θ; or ±0.0°2θ; Cu Kα1 radiation). In some embodiments, the compound 1 HBr salt is a crystalline polymorph characterized by XRPD signals at 12.2°2θ, 18.1°2θ, 21.6°2θ, 24.4°2θ, and 28.5°2θ (±0.2°2θ; ±0.1°2θ; or ±0.0°2θ; Cu Kα1 radiation). In some embodiments, the compound 1 HBr salt is a crystalline polymorph characterized by XRPD signals at 6.5°2θ, 12.2°2θ, 13.0°2θ, 14.2°2θ, 17.5°2θ, 18.1°2θ, 18.4°2θ, 19.8°2θ, 20.6°2θ, 21.6°2θ, 22.9°2θ, 23.3°2θ, 23.7°2θ, 24.4°2θ, 25.5°2θ, 26.1°2θ, 26.8°2θ, 27.0°2θ, 27.5°2θ, 28.4°2θ, 28.5°2θ, 29.6°2θ, 30.1°2θ, 33.3°2θ, and 34.9°2θ (±0.2°2θ; ±0.1°2θ; or ±0.0°2θ; Cu Kα1 radiation). In some embodiments, the compound 1 HBr salt is a crystalline polymorph characterized by an XRPD pattern that is substantially similar to that shown in FIG. 172. In some embodiments, the compound 1 HBr salt is a crystalline polymorph characterized by an XRPD pattern that is substantially similar to that shown in FIG. 172. In some embodiments, the compound 1 HBr salt is a crystalline polymorph characterized by a DSC curve having a melting signal at about 194.8° C. In some embodiments, the compound 1 HBr salt is a crystalline polymorph characterized by a DSC that is substantially similar to FIG. 241. IN some embodiments, the compound 1 HBr salt is a crystalline polymorph characterized by a TGA curve having an onset at about 253.7. In some embodiments, the compound 1 HBr salt is a crystalline polymorph characterized by a TGA curve that is substantially similar to that shown in FIG. 242.

In some embodiments, the compound 1 salt is a galactarate salt. In some embodiments, the galactarate salt is a crystalline galactarate salt. In some embodiments, the compound 1 galactarate salt is a crystalline polymorph characterized by XRPD signals at two signals or more, or three signals selected from the group consisting of 19.6°2θ, 5.2°2θ, and 15.9°2θ (±0.2°2θ; ±0.1°2θ; or ±0.0°2θ; Cu Kα1 radiation). In some embodiments, the compound 1 galactarate salt is a crystalline polymorph characterized by XRPD signals at 19.6°2θ, 5.2°2θ, and 15.9°2θ (±0.2° 2θ; ±0.1°2θ; or ±0.0°2θ; Cu Kα1 radiation). In some embodiments, the compound 1 galactarate salt is a crystalline polymorph characterized by XRPD signals at 5.2°2θ, 15.9°2θ, 17.9°2θ, 19.6° 2θ, and 30.7°2θ (±0.2°2θ; ±0.1°2θ; or ±0.0°2θ, Cu Kα1 radiation). In some embodiments, the compound 1 galactarate salt is a crystalline polymorph characterized by XRPD signals at 5.2°2θ, 12.1°2θ, 13.0°2θ, 15.9°2θ, 16.4°2θ, 17.9°2θ, 19.6°2θ, 20.4°2θ, 21.5°2θ, 22.4°2θ, 24.9°2θ, 25.2°2θ, 26.7°2θ, 30.7°2θ, 34.4°2θ, 34.8°2θ, and 37.6°2θ (±0.2°2θ; ±0.1°2θ; or ±0.0°2θ; Cu Kα1 radiation). In some embodiments, wherein the compound 1 galactarate salt is a crystalline polymorph characterized by any combination of the XRPD signals contained in Table 49. In some embodiments, the compound 1 galactarate salt is a crystalline polymorph characterized by an XRPD pattern that is substantially similar to that shown in FIG. 173. In some embodiments, the compound 1 galactarate salt is a crystalline polymorph characterized by a DSC curve having a melting signal at about 167.5° C. In some embodiments, the compound 1 galactarate salt is a crystalline polymorph characterized by a DSC that is substantially similar to FIG. 245.

In some embodiments, the compound 1 salt is a succinate salt. In some embodiments, the succinate salt is a crystalline succinate salt. In some embodiments, the compound 1 succinate salt is a crystalline polymorph characterized by XRPD signals at two signals or more, or three signals selected from the group consisting of 18.2°2θ, 19.3°2θ, and 22.0°2θ (±0.2°2θ; ±0.1°2θ, or ±0.0°2θ; Cu Kα1 radiation). In some embodiments, compound 1 succinate salt is a crystalline polymorph characterized by XRPD signals at 18.2°2θ, 19.3°2θ, and 22.0°2θ (±0.2°2θ; ±0.1°2θ; or ±0.0°2θ; Cu Kα1 radiation). In some embodiments, compound 1 succinate salt is a crystalline polymorph characterized by XRPD signals at 18.2°2θ, 19.3°2θ, 20.0°2θ, 22.0°2θ, and 26.1°2θ (±0.2°2θ; ±0.1°2θ; or ±0.0°2θ; Cu Kα1 radiation). In some embodiments, compound 1 succinate salt is a crystalline polymorph characterized by XRPD signals at 12.7°2θ, 13.9°2θ, 17.3°2θ, 17.7°2θ, 18.2°2θ, 19.3°2θ, 20.0°2θ, 21.2°2θ, 21.3°2θ, 22.0°2θ, 23.7°2θ, 24.1°2θ, 24.7°2θ, 25.5°2θ, 26.1°2θ, 27.5°2θ, 28.2°2θ, and 31.4°2θ (±0.2°2θ; ±0.1°2θ; or ±0.0°2θ; Cu Kα1 radiation). In some embodiments, the compound 1 succinate salt is a crystalline polymorph characterized by any combination of the XRPD signals contained in Table 50. In some embodiments, the compound 1 succinate salt is a crystalline polymorph characterized by an XRPD pattern that is substantially similar to that shown in FIG. 174. In some embodiments, the compound 1 succinate salt is a crystalline polymorph characterized by a DSC curve having a melting signal at about 89.8° C. In some embodiments, the compound 1 succinate salt is a crystalline polymorph characterized by a DSC that is substantially similar to FIG. 248.

In some embodiments, the compound 1 salt is a succinate salt. In some embodiments, the succinate salt is a crystalline succinate salt. In some embodiments, the compound 1 citrate salt is a crystalline polymorph characterized by XRPD signals at two signals or more, or three signals selected from the group consisting of 23.9°2θ, 18.2°2θ, and 26.2°2θ (±0.2°2θ; ±0.1°2θ; or ±0.0° 2θ; Cu Kα1 radiation). In some embodiments, the compound 1 citrate salt is a crystalline polymorph characterized by XRPD signals at 23.9°2θ, 18.2°2θ, and 26.2°2θ (±0.2°2θ; ±0.1°2θ; or ±0.0°2θ; Cu Kα1 radiation). In some embodiments, the compound 1 citrate salt is a crystalline polymorph characterized by XRPD signals 18.0°2θ, 18.2°2θ, 19.6°2θ, 23.9°2θ, and 26.2°2θ (±0.2°2θ; ±0.1°2θ; or ±0.0°2θ; Cu Kα1 radiation). In some embodiments, the compound 1 citrate salt is a crystalline polymorph characterized by XRPD signals 14.2°2θ, 14.4°2θ, 18.0°2θ, 18.2°2θ, 19.6°2θ, 23.9°2θ, 26.1°2θ, 26.2°2θ, 27.6°2θ, 28.9°2θ, 31.1°2θ, 31.4°2θ, 33.7°2θ, 36.2°2θ, 37.0°2θ, and 37.6°2θ (±0.2°2θ; ±0.1°2θ; or ±0.0°2θ; Cu Kα1 radiation). In some embodiments, the compound 1 citrate salt is a crystalline polymorph characterized by any combination of the XRPD signals contained in Table 51. In some embodiments, the compound 1 citrate salt is a crystalline polymorph characterized by an XRPD pattern that is substantially similar to that shown in FIG. 257. In some embodiments, the compound 1 citrate salt is a crystalline polymorph characterized by a DSC curve having a melting signal at about 182.8° C. In some embodiments, the compound 1 citrate salt is a crystalline polymorph characterized by a DSC that is substantially similar to FIG. 258.

In some embodiments, the compound 1 salt is a malate salt. In some embodiments, the malate salt is a crystalline malate salt. In some embodiments, the compound 1 malate salt is a crystalline polymorph characterized by XRPD signals at two signals or more, or three signals selected from the group consisting of 19.3°2θ, 24.4°2θ, and 29.4°2θ (±0.2°2θ; ±0.1°2θ; or ±0.0°2θ; Cu Kα1 radiation). In some embodiments, the compound 1 malate salt is a crystalline polymorph characterized by XRPD signals at 19.3°2θ, 24.4°2θ, and 29.4°2θ (±0.2°2θ; ±0.1°2θ; or ±0.0°2θ; Cu Kα1 radiation). In some embodiments, the compound 1 malate salt is a crystalline polymorph characterized by XRPD signals at 19.3°2θ, 21.0°2θ, 24.4°2θ, 29.4°2θ, and 37.7°2θ (±0.2°2θ; ±0.1°2θ; or ±0.0°2θ; Cu Kα1 radiation). In some embodiments, the compound 1 malate salt is a crystalline polymorph characterized by XRPD signals at 7.5°2θ, 19.3°2θ, 20.9°2θ, 21.0°2θ, 22.3°2θ, 24.4°2θ, 27.7°2θ, 29.4°2θ, 29.7°2θ, 30.2°2θ, 34.1°2θ, 37.0°2θ, and 37.7°2θ (±0.2°2θ; ±0.1°2θ; or ±0.0°2θ; Cu Kα1 radiation). In some embodiments, the compound 1 malate salt is a crystalline polymorph characterized by any combination of the XRPD signals contained in Table 52. In some embodiments, the compound 1 malate salt is a crystalline polymorph characterized by an XRPD pattern that is substantially similar to that shown in FIG. 261. In some embodiments, the compound 1 malate salt is a crystalline polymorph characterized by a DSC curve having a melting signal at about 193.5° C. In some embodiments, the compound 1 malate salt is a crystalline polymorph characterized by a DSC that is substantially similar to FIG. 262.

In some embodiments, the compound 1 salt is a glucuronate salt. In some embodiments, the glucuronate salt is a crystalline glucuronate salt. In some embodiments, the glucuronate salt is a crystalline polymorph characterized by XRPD signals at two signals or more, or three signals selected from the group consisting of 20.0°2θ, 20.5°2θ, and 22.5°2θ (±0.2°2θ; ±0.1°2θ, or ±0.0°2θ; Cu Kα1 radiation). In some embodiments, the glucuronate salt is a crystalline polymorph characterized by XRPD signals at 20.0°2θ, 20.5°2θ, and 22.5°2θ (±0.2°2θ; ±0.1°2θ; or ±0.0°2θ; Cu Kα1 radiation). In some embodiments, the glucuronate salt is a crystalline polymorph characterized by XRPD signals at 17.7°2θ, 20.0°2θ, 20.5°2θ, 22.5°2θ, and 24.4°2θ (±0.2°2θ; ±0.1°2θ; or ±0.0°2θ; Cu Kα1 radiation). In some embodiments, the glucuronate salt is a crystalline polymorph characterized by XRPD signals at 15.1°2θ, 17.7°2θ, 20.0°2θ, 20.5°2θ, 22.5°2θ, 24.4°2θ, 25.5°2θ, 26.1°2θ, 30.6°2θ, and 35.5°2θ (±0.2°2θ; ±0.1°2θ; or ±0.0°2θ; Cu Kα1 radiation). In some embodiments, the compound 1 glucuronate salt is a crystalline polymorph characterized by any combination of the XRPD signals contained in Table 53. In some embodiments, the compound 1 glucuronate salt of any one of claims 108 to 110, wherein compound 1 glucuronate salt is a crystalline polymorph characterized by an XRPD pattern that is substantially similar to that shown in FIG. 259. In some embodiments, the compound 1 glucuronate salt is a crystalline polymorph characterized by a DSC curve having a melting signal at about 131.83° C. In some embodiments, the compound 1 glucuronate salt is a crystalline polymorph characterized by a DSC that is substantially similar to FIG. 260.

In some embodiments, the compound 1 salt is an ascorbate salt. In some embodiments, the ascorbate salt is a crystalline ascorbate salt. In some embodiments, compound 1 ascorbate salt is a crystalline polymorph characterized by XRPD signals at two signals or more, or three signals selected from the group consisting of 19.3°2θ, 24.4°2θ, and 29.4°2θ (±0.2°2θ; ±0.1°2θ; or ±0.0° 2θ; Cu Kα1 radiation). In some embodiments, the compound 1 ascorbate salt is a crystalline polymorph characterized by XRPD signals at 34.8°2θ, 10.5°2θ, and 19.9°2θ (±0.2°2θ; ±0.1°2θ; or ±0.0°2θ; Cu Kα1 radiation). In some embodiments, the compound 1 ascorbate salt is a crystalline polymorph characterized by XRPD signals at 10.5°2θ, 19.9°2θ, 28.1°2θ, 30.1°2θ, and 34.8°2θ (±0.2°2θ; ±0.1°2θ; or ±0.0°2θ. Cu Kα1 radiation). In some embodiments, the compound 1 ascorbate salt is a crystalline polymorph characterized by XRPD signals at 10.5°2θ, 16.1°2θ, 17.5°2θ, 19.9°2θ, 21.1°2θ, 25.3°2θ, 28.1°2θ, 30.1°2θ, and 34.8°2θ (±0.2°2θ; ±0.1°2θ; or ±0.0°2θ; Cu Kα1 radiation). In some embodiments, the compound 1 ascorbate salt is a crystalline polymorph characterized by any combination of the XRPD signals contained in Table 54. In some embodiments, the compound 1 ascorbate salt is a crystalline polymorph characterized by an XRPD pattern that is substantially similar to that shown in FIG. 265. In some embodiments, the compound 1 ascorbate salt is a crystalline polymorph characterized by a DSC curve having a melting signal at about 157° C. In some embodiments, the compound 1 ascorbate salt is a crystalline polymorph characterized by a DSC that is substantially similar to FIG. 266.

In some embodiments, the compound 1 salt is a sulfate salt. In some embodiments, the sulfate salt is a crystalline sulfate salt.

In some embodiments, the compound 1 salt is a mesylate salt. In some embodiments, the mesylate salt is a crystalline mesylate salt.

In some embodiments, the compound 1 salt is an esylate salt. In some embodiments, the esylate salt is a crystalline esylate salt.

In some embodiments, the compound 1 salt is a phosphate salt. In some embodiments, the phosphate salt is a crystalline phosphate salt.

In some embodiments, the compound 1 salt is an edisylate salt. In some embodiments, the edisylate salt is a crystalline edisylate salt. In some embodiments, the compound 1 salt is a fumarate salt that is a crystalline polymorphic form characterized by XRPD signals at 14.0°2θ, 15.9°2θ, and 22.3°2θ (±0.2°2θ; ±0.1°2θ; or ±0.0°2θ; Cu Kα1 radiation). In some embodiments, the compound 1 fumarate salt is a crystalline polymorphic form characterized by XRPD signals at 14.0°2θ, 15.9°2θ, 19.4°2θ, 21.3°2θ, and 22.3°2θ (±0.2°2θ; ±0.1°2θ; or ±0.0°2θ; Cu Kα1 radiation). In some embodiments, the compound 1 fumarate salt is a crystalline polymorphic form characterized by XRPD signals at 13.4°2θ, 14.0°2θ, 15.9°2θ, 18.9°2θ, 19.2°2θ, 19.4°2θ, 20.8°2θ, 21.3°2θ, 21.5°2θ, and 22.3°2θ (±0.2°2θ; ±0.1°2θ; or ±0.0°2θ; Cu Kα1 radiation). In some embodiments, the compound 1 fumarate salt is a crystalline polymorphic form characterized by XRPD signals at 10.1°2θ, 13.4°2θ, 14.0°2θ, 15.6°2θ, 15.9°2θ, 18.4°2θ, 18.9°2θ, 19.2°2θ, 19.4°2θ, 20.8°2θ, 21.3°2θ, 21.5°2θ, 22.3°2θ, 23.2°2θ, 24.4°2θ, 25.0°2θ, 28.1°2θ, and 29.1° 2θ (±0.2°2θ; ±0.1°2θ; or ±0.0°2θ; Cu Kα1 radiation). In some embodiments, the compound 1 fumarate salt is a crystalline polymorphic form characterized by any combination of the XRPD signals in Table 6. In some embodiments, the compound 1 fumarate salt is a crystalline polymorphic form characterized by the XRPD signals in Table 6 (±0.2°2θ; ±0.1°2θ; or ±0.0°2θ; Cu Kα1 radiation). In some embodiments, the compound 1 fumarate salt is a crystalline polymorphic form characterized by an XRPD pattern substantially similar to that shown in FIG. 8. In some embodiments, the compound 1 fumarate salt is a crystalline polymorphic form characterized by a DSC diagram having melting signals at about 116.8° C. and 241.3° C. In some embodiments, the compound 1 fumarate salt is a crystalline polymorphic form characterized by a DSC profile substantially similar to that shown in FIG. 86. In some embodiments, the compound 1 fumarate salt is a crystalline polymorph characterized by a TGA diagram having an onset at about 210.71° C. In some embodiments, the compound 1 fumarate salt is a crystalline polymorph characterized by a TGA diagram substantially similar to that shown in FIG. 81.

In some embodiments, the compound 1 HCl salt is a crystalline polymorph characterized by XRPD signals at two signals or more, or three signals selected from the group consisting of 18.2°2θ, 25.0°2θ, and 26.0°2θ (±0.2°2θ; ±0.1°2θ; or ±0.0°2θ; Cu Kα1 radiation). In some embodiments, the compound 1 HCl salt is a crystalline polymorph characterized by XRPD signals at 18.2°2θ, 25.0°2θ, and 26.0°2θ (±0.2°2θ; ±0.1°2θ; or ±0.0°2θ; Cu Kα1 radiation). In some embodiments, the compound 1 HCl salt is a crystalline polymorph characterized by XRPD signals at 12.9°2θ, 18.2°2θ, 21.9°2θ, 25.0°2θ, and 26.0°2θ (±0.2°2θ; ±0.1°2θ; or ±0.0°2θ; Cu Kα1 radiation). In some embodiments, the compound 1 HCl salt is a crystalline polymorph characterized by XRPD signals at 6.4°2θ, 6.5°2θ, 12.5°2θ, 12.9°2θ, 17.8°2θ, 18.0°2θ, 18.2°2θ, 18.8°2θ, 20.1°2θ, 20.6°2θ, 21.9°2θ, 23.2°2θ, 25.0°2θ, 25.6°2θ, 26.0°2θ, 27.6°2θ, 28.6°2θ, 29.1°2θ, 32.4°2θ, 34.6°2θ, and 37.8 (±0.2°2θ; ±0.1°2θ; or ±0.0°2θ; Cu Kα1 radiation). In some embodiments, the compound 1 HCl salt is a crystalline polymorph characterized by any combination of the XRPD signals contained in Table 124. In some embodiments, the compound 1 HCl salt is a crystalline polymorph characterized by an XRPD pattern that is substantially similar to that shown in FIG. 365.

In some embodiments, the compound 1 salt is an adipate salt. In some embodiments, the adipate salt is a crystalline adipate salt.

In some embodiments, the present disclosure provides a pharmaceutical composition comprising any of the compound 1 salts disclosed herein and a pharmaceutically acceptable excipient.

In some embodiments, the present disclosure provides method of treating a brain disorder, a neurological disorder and/or a psychiatric disorder in a subject in need, comprising administering to the subject any of the compound 1 salts disclosed herein or any of the pharmaceutical compositions disclosed herein.

The foregoing and other objects, features, and advantages of the invention will become more apparent from the following detailed description, which proceeds with reference to the accompanying figures.

BRIEF DESCRIPTION OF THE DRAWINGS

FIG. 121 shows a $^1$H NMR spectrum of crystalline compound 1 monofumarate, spectrum was acquired in DMSO-d$_6$ and calibrated to the non-deuterated solvent residual at 2.50 ppm. IPA content, 0.2% w/w.

FIG. 122 shows a $^1$H NMR spectrum of crystalline compound 1 monofumarate, spectrum was acquired in DMSO-d$_6$ and calibrated to the non-deuterated solvent residual at 2.50 ppm. MEK content, 2.3% w/w.

FIG. 123 shows a $^1$H NMR spectrum of crystalline compound 1 monofumarate, spectrum was acquired in DMSO-d$_6$ and calibrated to the non-deuterated solvent residual at 2.50 ppm. 2-MeTHF content, 0.2% w/w.

FIG. 124 shows a $^1$H NMR spectrum of crystalline compound 1 monofumarate, spectrum was acquired in DMSO-d$_6$ and calibrated to the non-deuterated solvent residual at 2.50 ppm. n-Butanol content, 0.5% w/w.

FIG. 125 shows a $^1$H NMR spectrum of crystalline compound 1 fumarate, spectrum was acquired in DMSO-d$_6$ and calibrated to the non-deuterated solvent residual at 2.50 ppm. MIBK content, 0.3% w/w.

FIG. 126 shows a XRPD profile of crystalline compound 1 monofumarate (Pattern #1, Form A).

FIG. 127 shows a XRPD profile of crystalline compound 1 monofumarate fumarate (Pattern #1, Form A).

FIG. 128 shows a XRPD profile of crystalline compound 1 monofumarate (Pattern #1, Form A).

FIG. 129 shows a XRPD profile of crystalline compound 1 monofumarate (Pattern #1, Form A).

FIG. 130 shows a XRPD profile of crystalline compound 1 monofumarate (Pattern #1, Form A).

FIG. 131 shows an XRPD profile of crystalline compound 1 monofumarate (Pattern #1, Form A).

FIG. 132 shows an XRPD profile of crystalline compound 1 monofumarate (Pattern #1, Form A).

Figure 133:
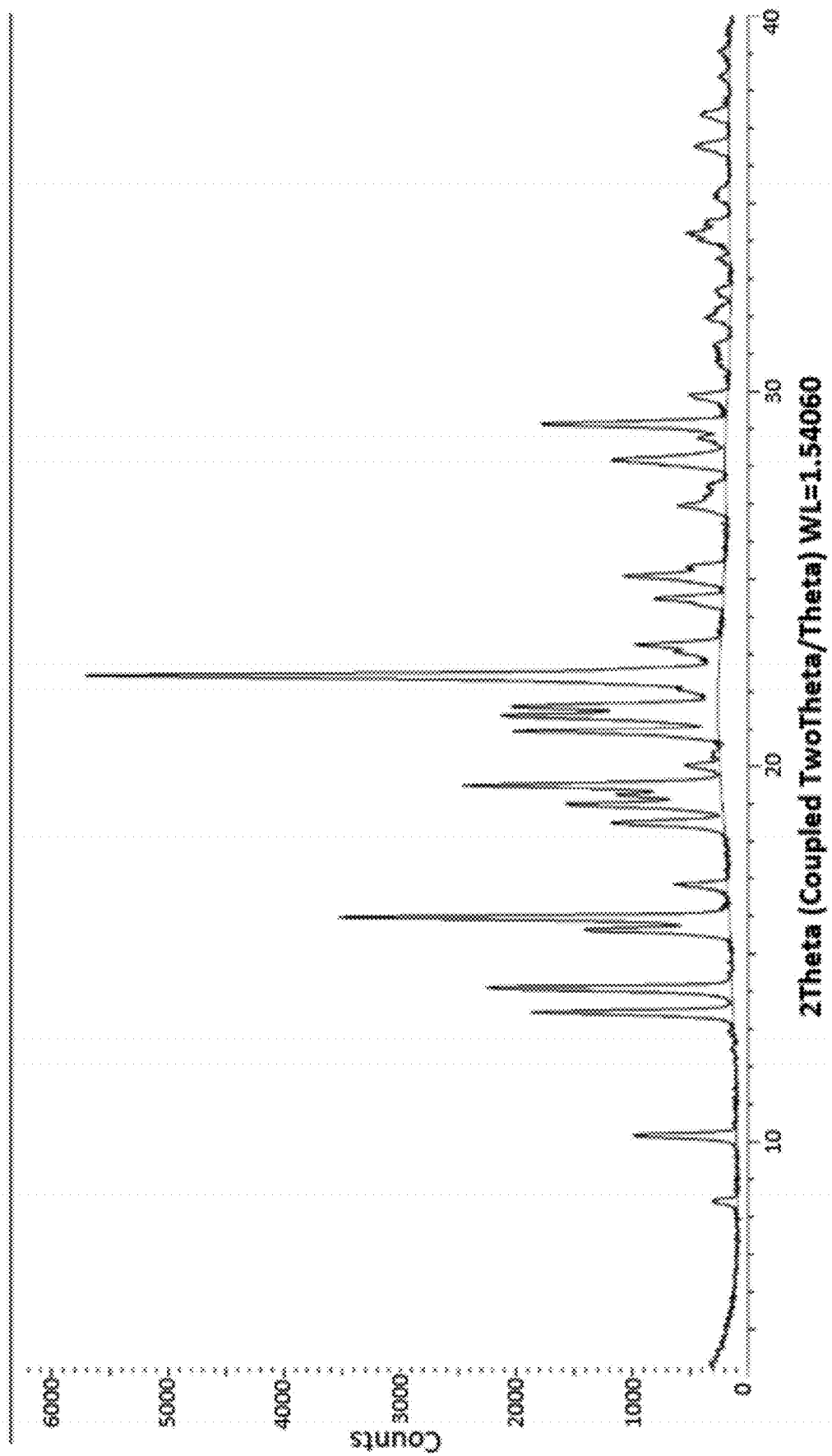

FIG. 133 shows an XRPD profile of crystalline compound 1 monofumarate (Pattern #1, Form A).

Figure 134:
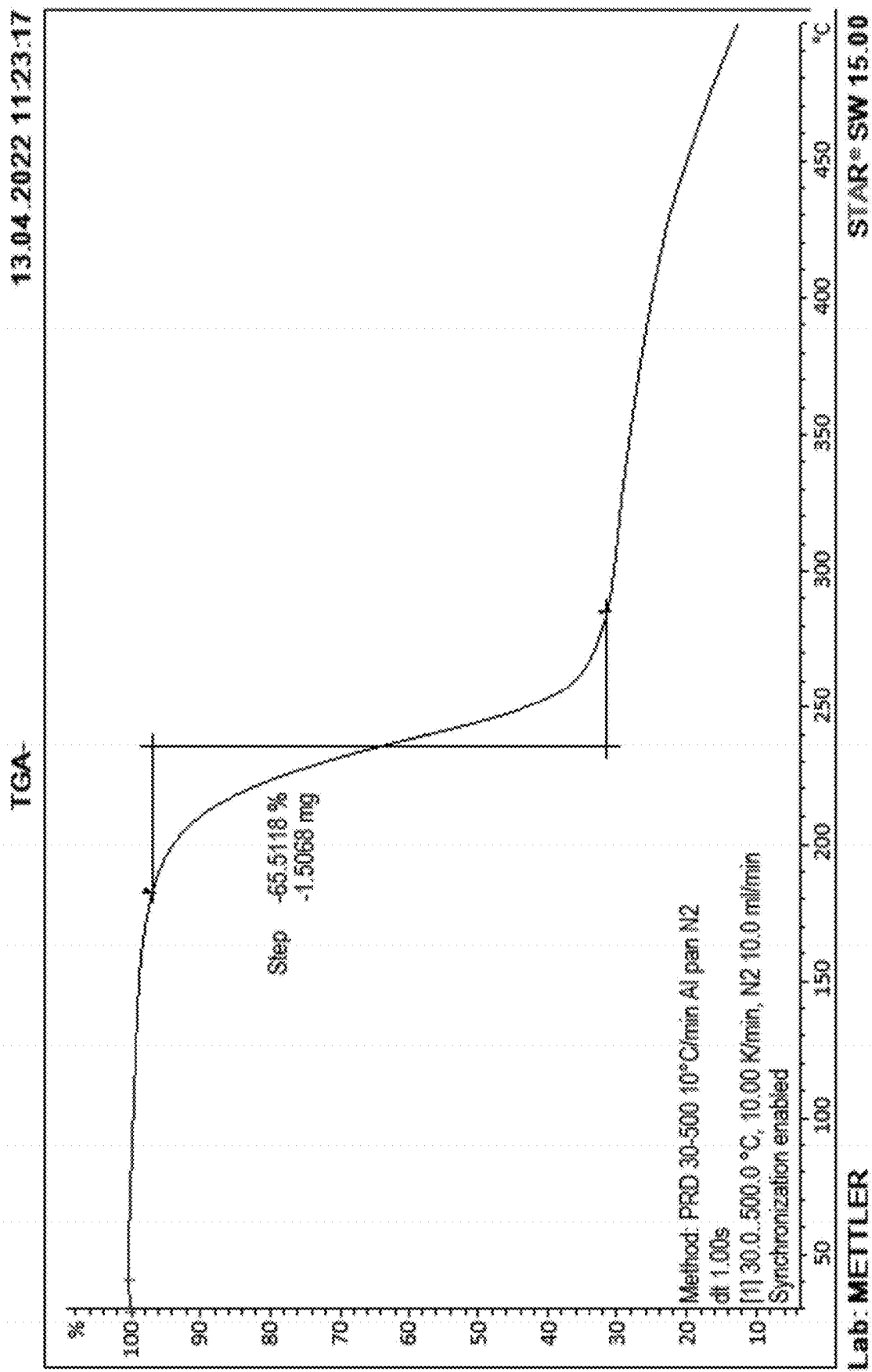

FIG. 134 shows a TGA thermogram of crystalline compound 1 monofumarate, analysis was acquired at a ramp rate of +10° C./minute.

Figure 135:
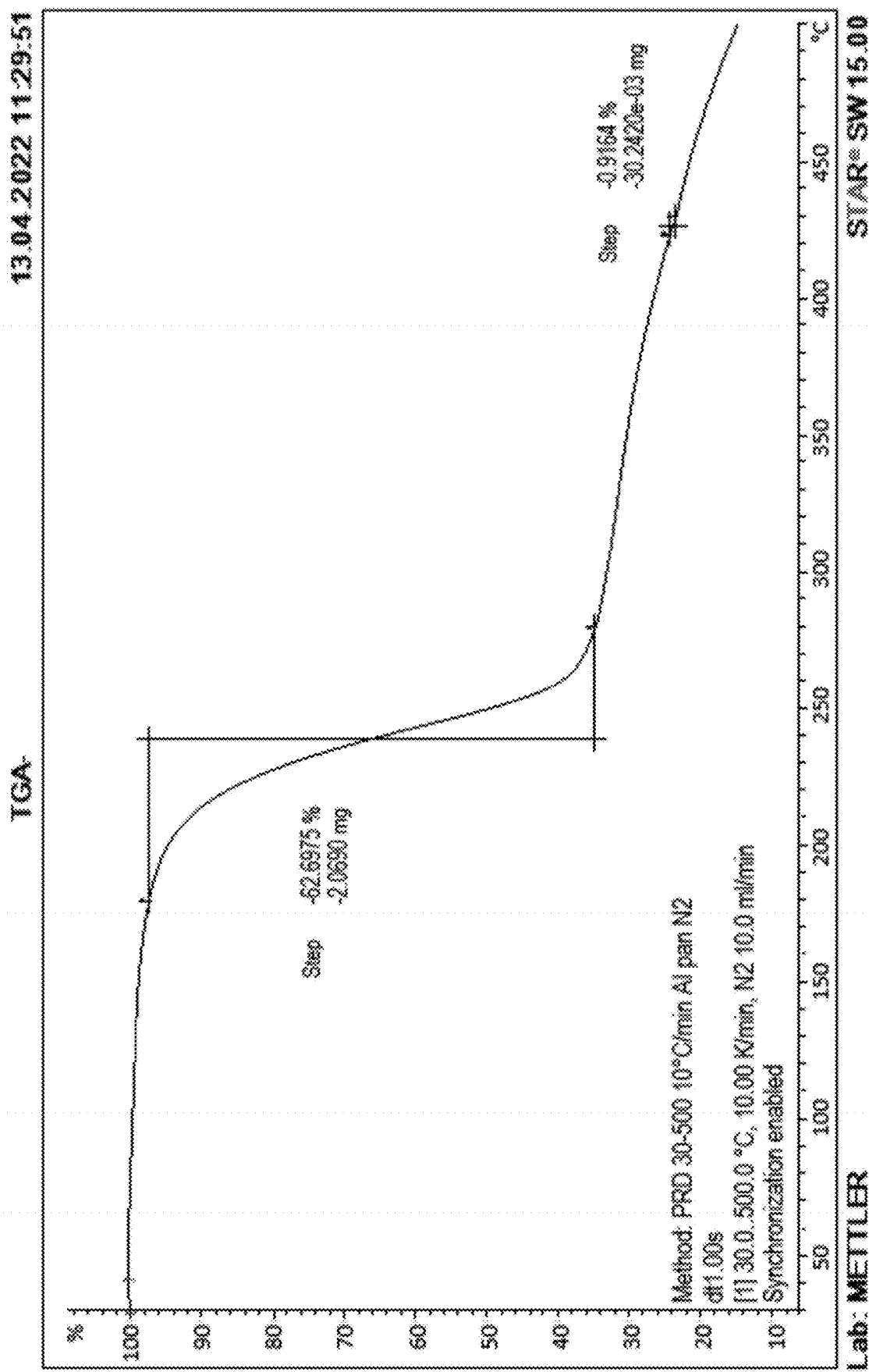

FIG. 135 shows a TGA thermogram of crystalline compound 1 monofumarate, analysis was acquired at a ramp rate of +10° C./minute.

Figure 136:
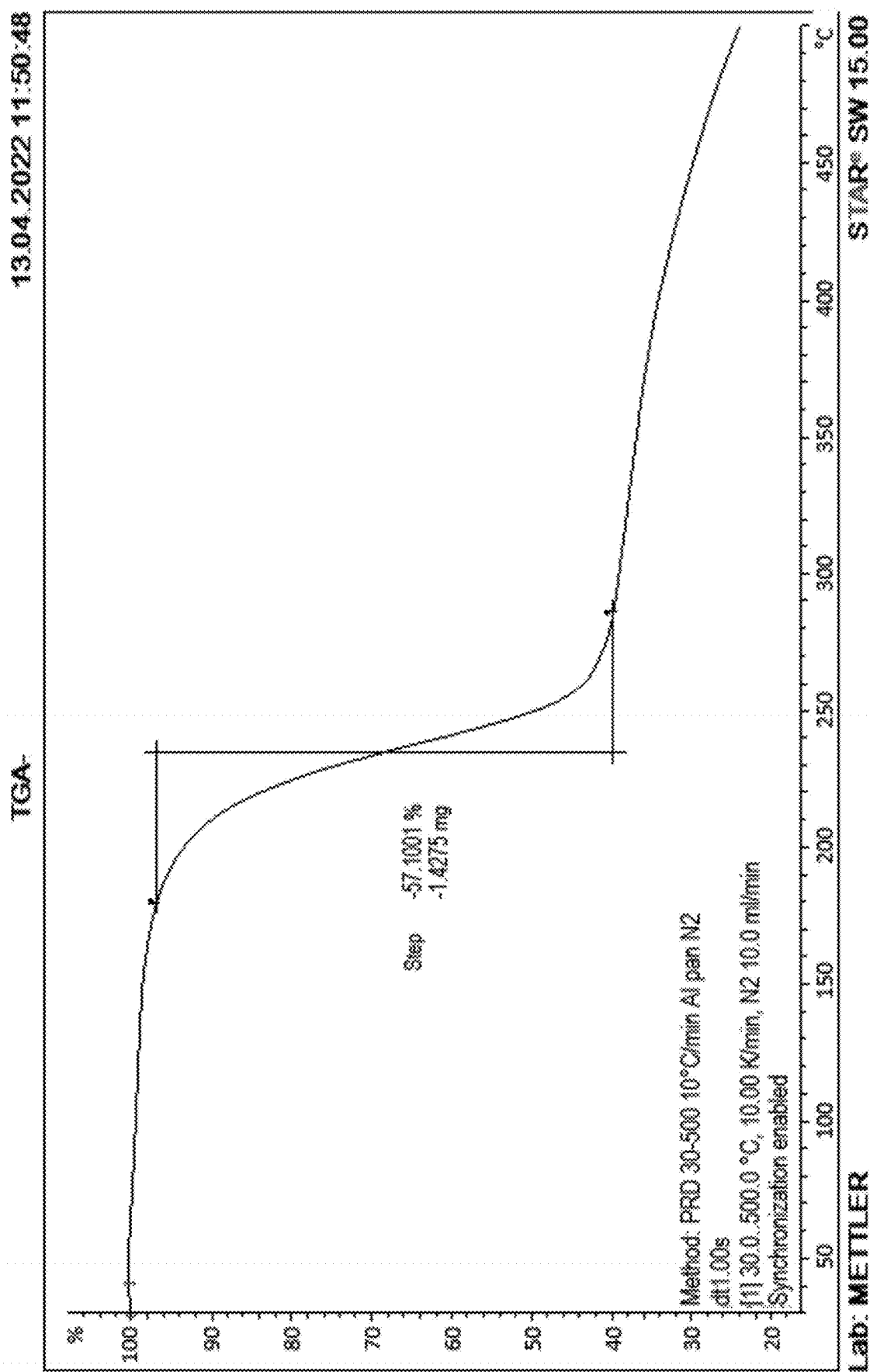

FIG. 136 shows a TGA thermogram of crystalline compound 1 monofumarate, analysis was acquired at a ramp rate of +10° C./minute.

Figure 137:
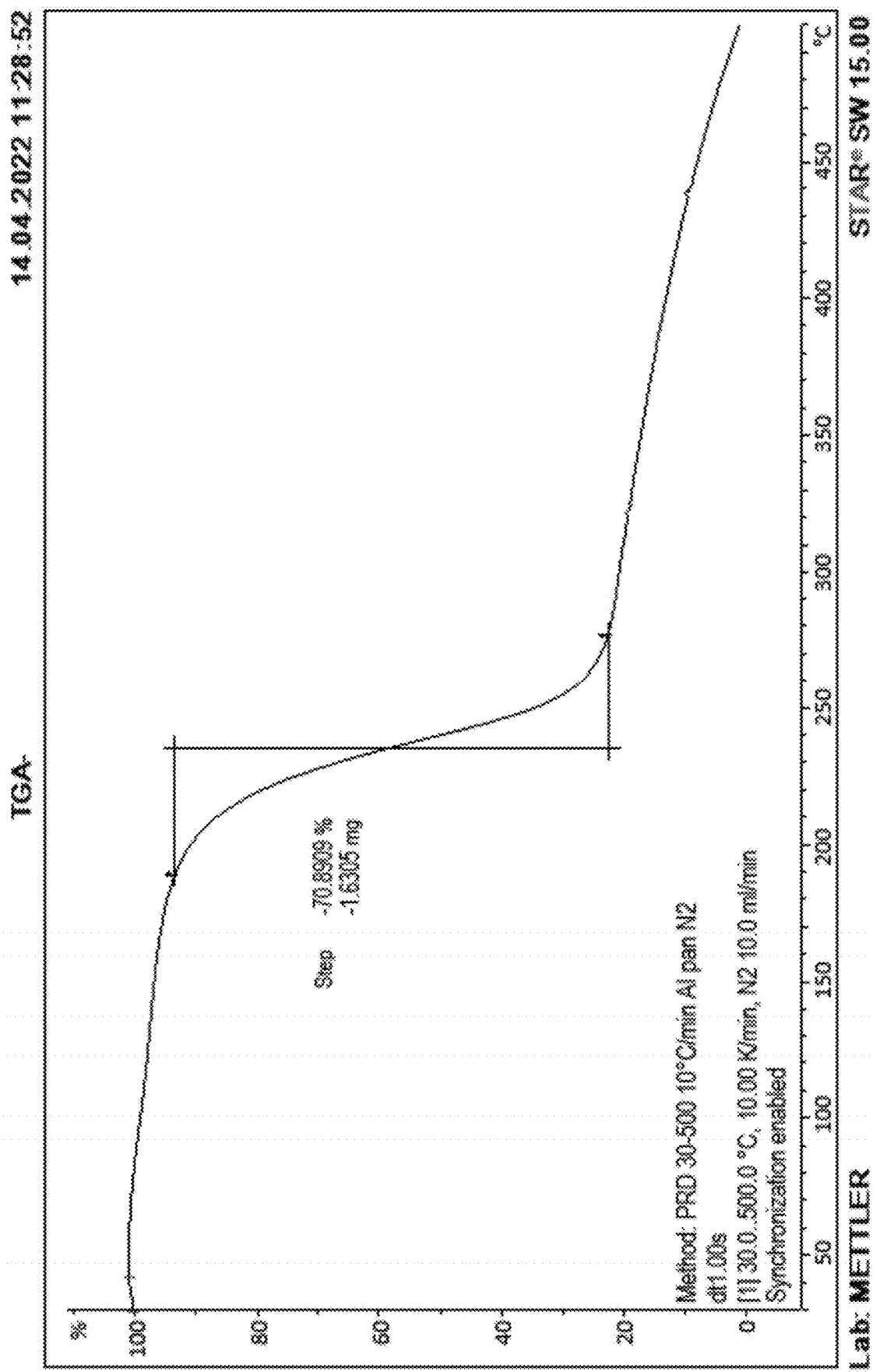

FIG. 137 shows a TGA thermogram of crystalline compound 1 monofumarate, analysis was acquired at a ramp rate of +10° C./minute.

Figure 138:
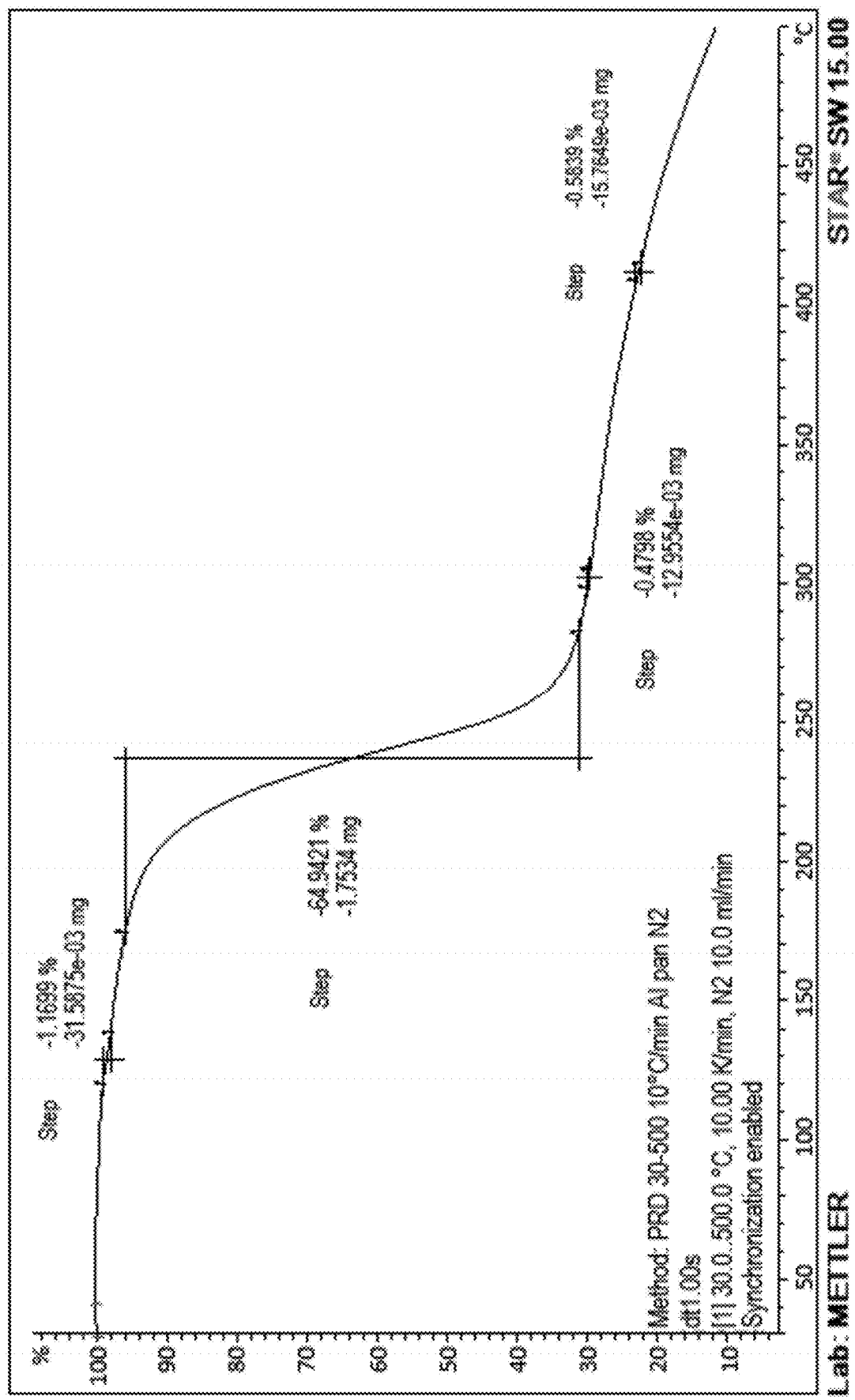

FIG. 138 shows a TGA thermogram of crystalline compound 1 monofumarate, analysis was acquired at a ramp rate of +10° C./minute.

Figure 139:
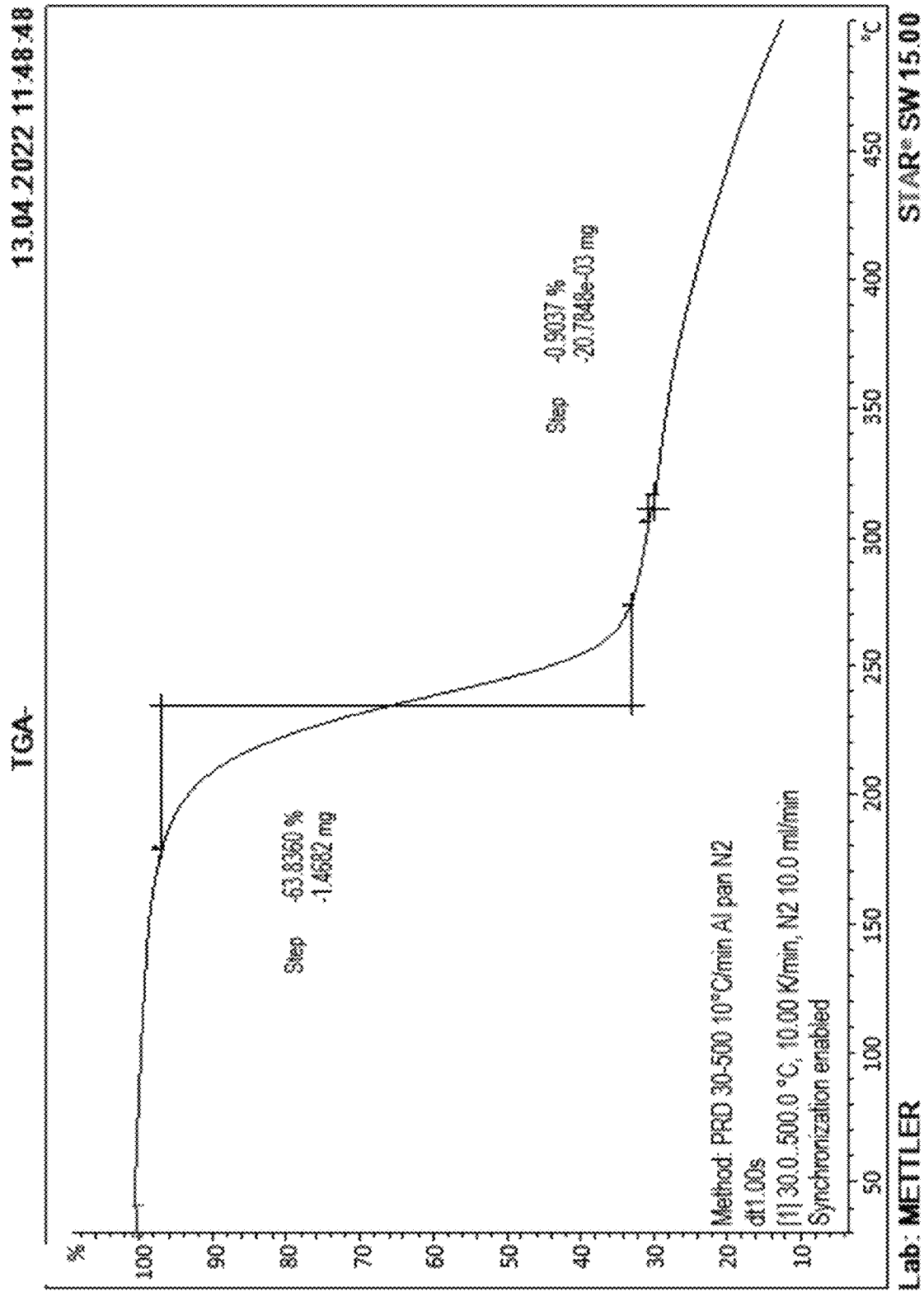

FIG. 139 shows a TGA thermogram of crystalline compound 1 monofumarate, analysis was acquired at a ramp rate of +10° C./minute.

Figure 140:
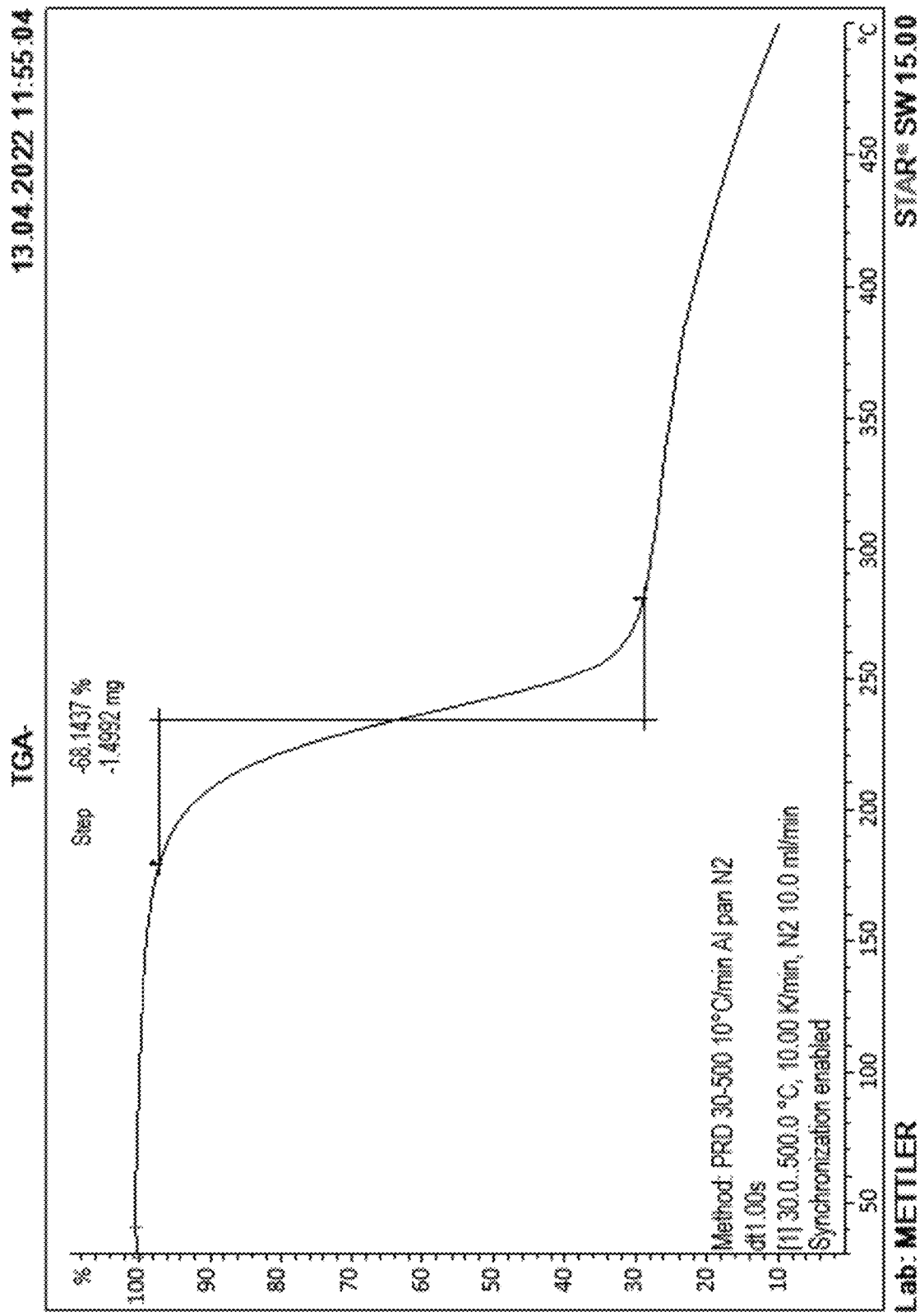

FIG. 140 shows a TGA thermogram of crystalline compound 1 monofumarate, analysis was acquired at a ramp rate of +10° C./minute.

Figure 141:
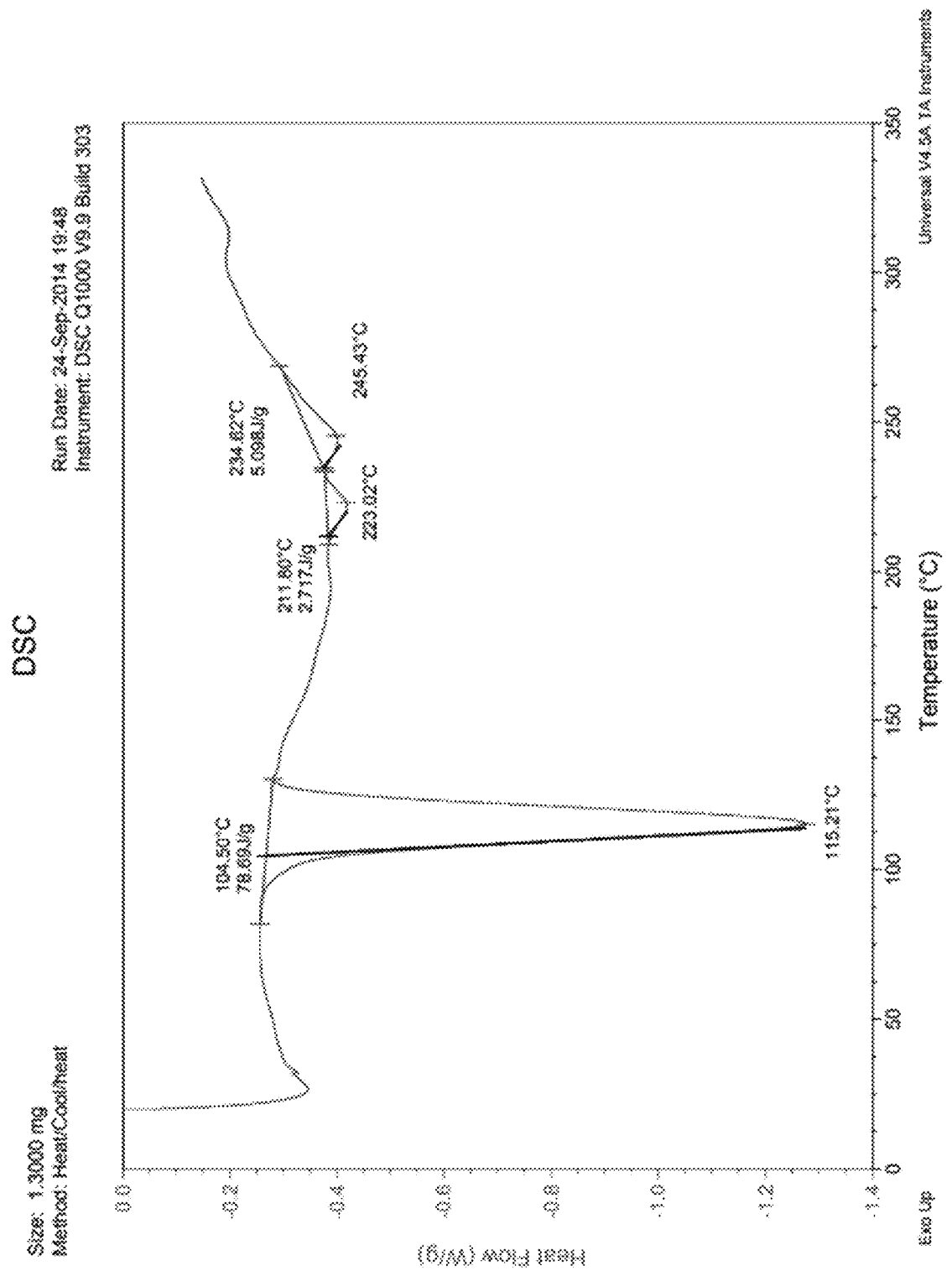

FIG. 141 shows a DSC profile of crystalline compound 1 monofumarate, analysis was acquired at a ramp rate of +10° C./minute.

Figure 142:
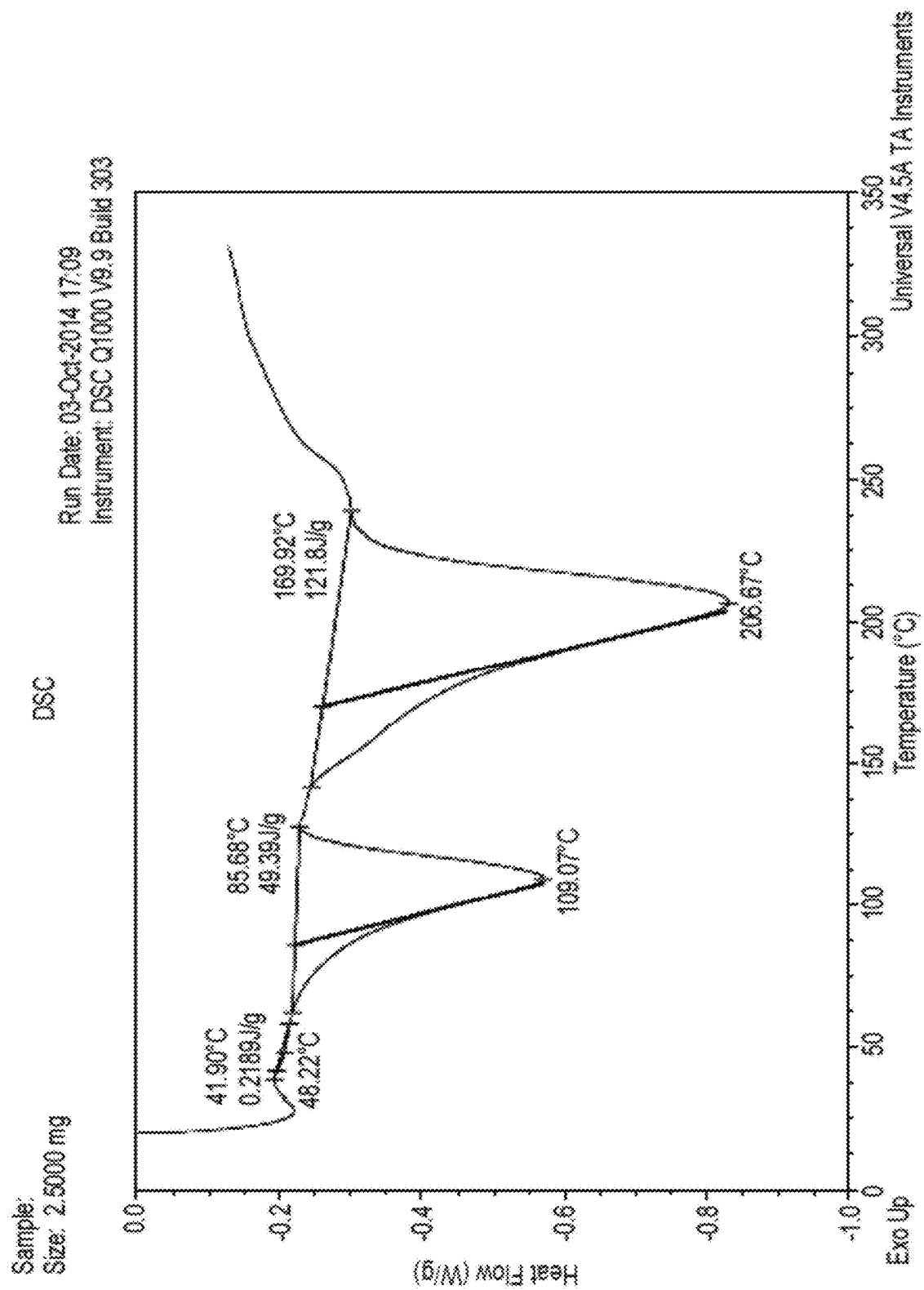

FIG. 142 shows a DSC profile of crystalline compound 1 monofumarate, analysis was acquired at a ramp rate of +10° C./minute.

Figure 143:
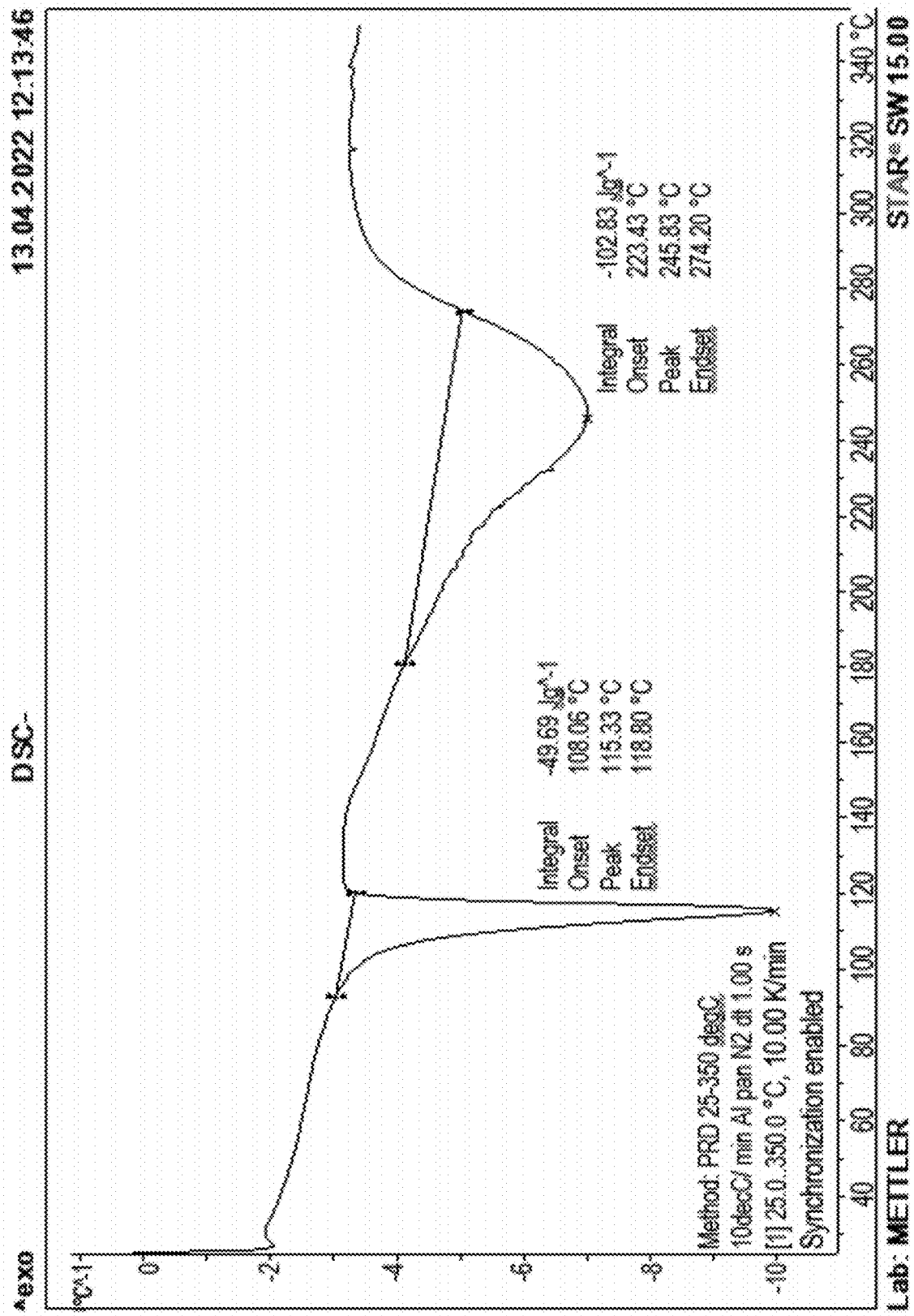

FIG. 143 shows a DSC profile of crystalline compound 1 monofumarate, analysis was acquired at a ramp rate of +10° C./minute.

Figure 144:
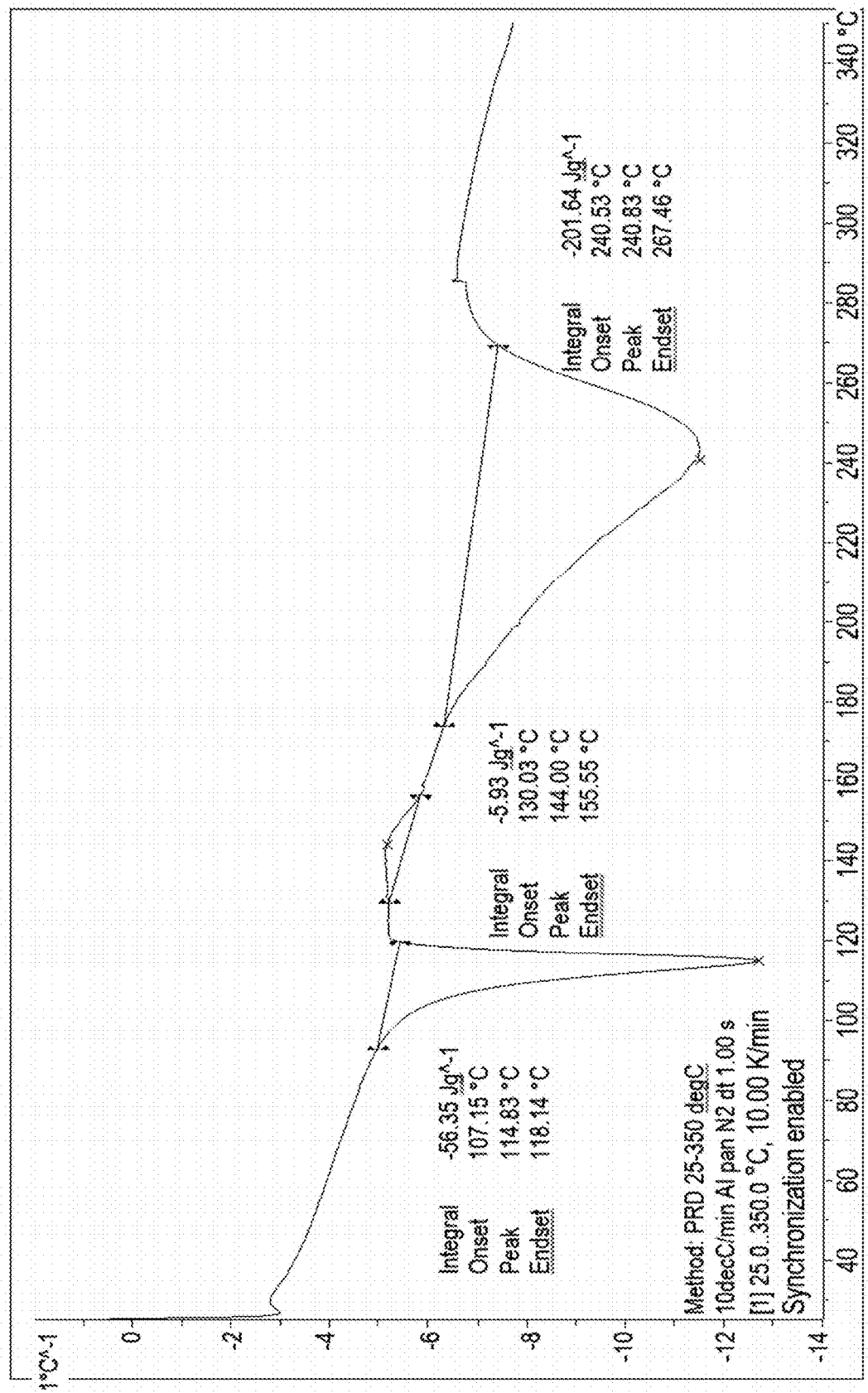

FIG. 144 shows a DSC profile of crystalline compound 1 monofumarate, analysis was acquired at a ramp rate of +10° C./minute.

Figure 145:
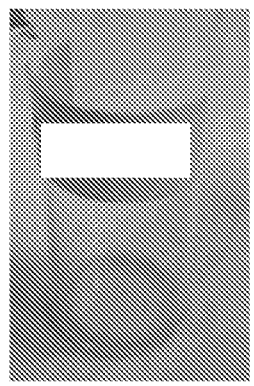

FIG. 145 shows an image of an experiment in which crystalline compound 1 monofumarate Form A was obtained by way of evaporation from acetone.

Figure 146:
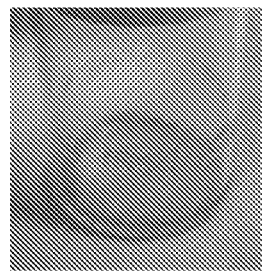

FIG. 146 shows an image of an experiment in which crystalline compound 1 monofumarate Form A was obtained by way of evaporation from MeCN.

Figure 147:

FIG. 147 shows an image of an experiment in which crystalline compound 1 monofumarate Form A was obtained by way of evaporation from IPA.

Figure 148:
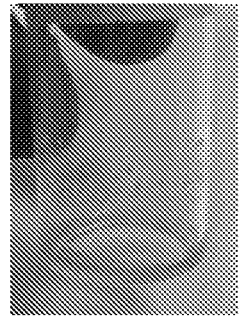

FIG. 148 shows an image of an experiment in which crystalline compound 1 monofumarate Form A was obtained by way of evaporation from MEK.

Figure 149:
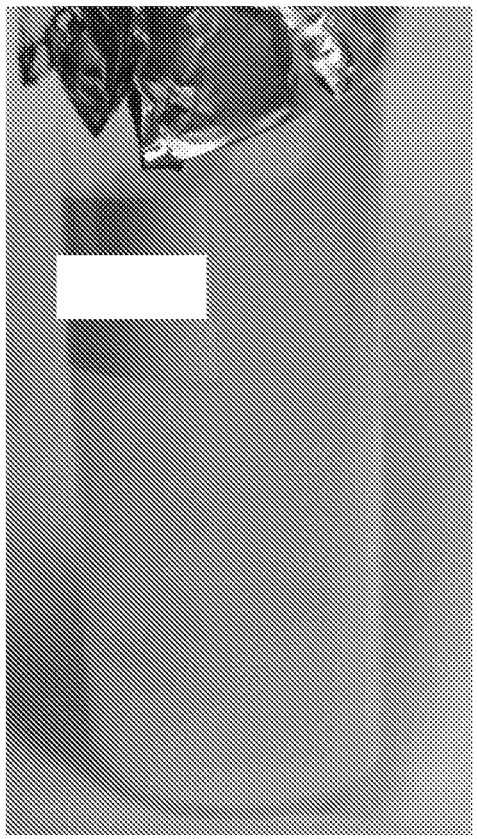

FIG. 149 shows an image of an experiment in which crystalline compound 1 monofumarate Form A was obtained by way of evaporation from 2-MeTHF.

Figure 150:
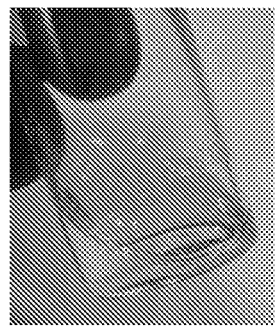

FIG. 150 shows an image of an experiment in which crystalline compound 1 monofumarate Form A was obtained by way of evaporation from BuOH.

Figure 151:
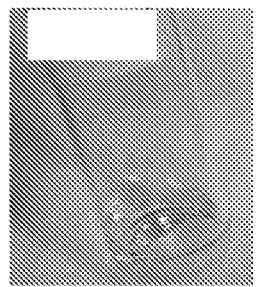

FIG. 151 shows an image of an experiment in which small solids were obtained by way of evaporation from dioxane.

Figure 152:
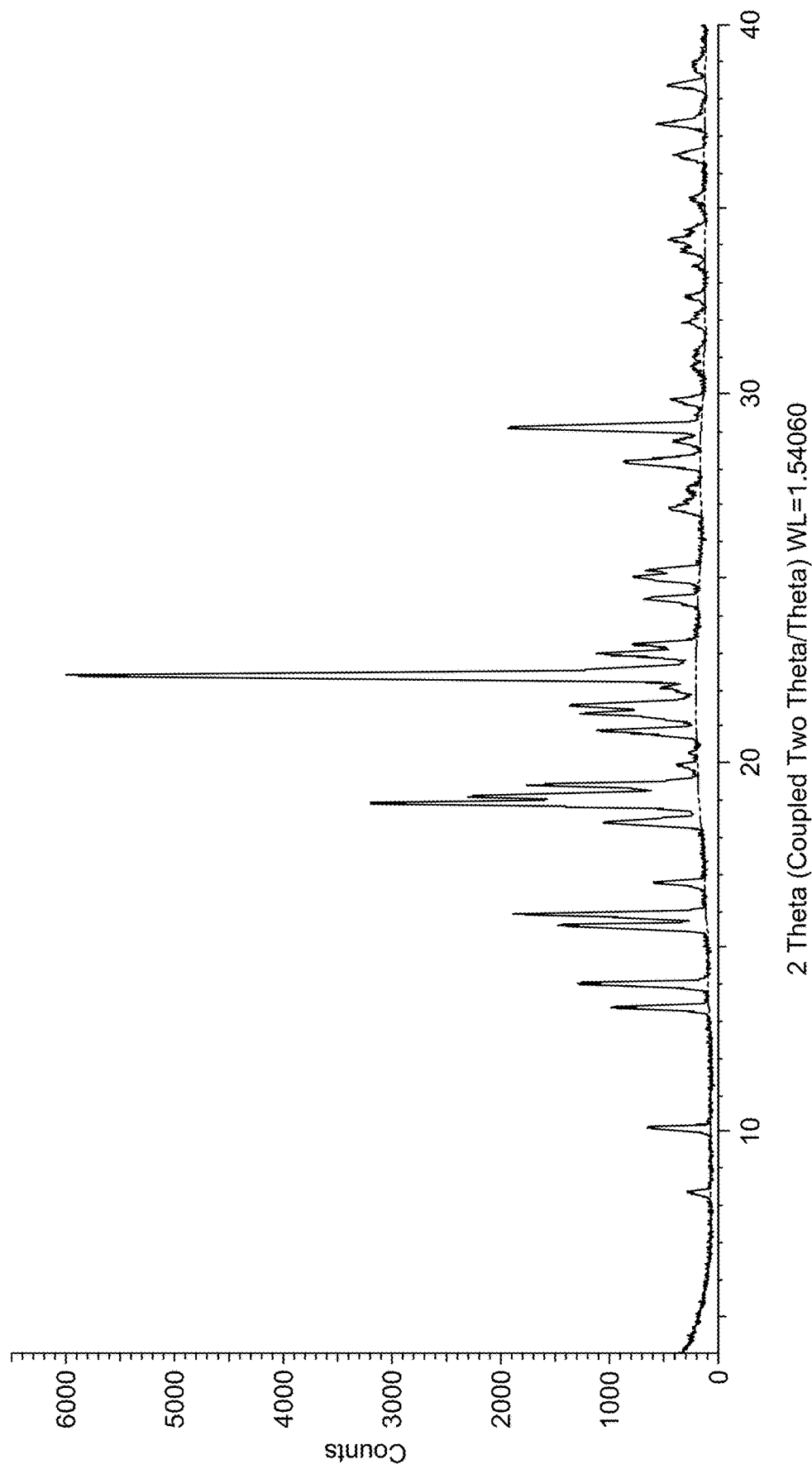

FIG. 152 shows a XRPD profile of crystalline compound 1 monofumarate Form A prior to treatment with water.

Figure 153:
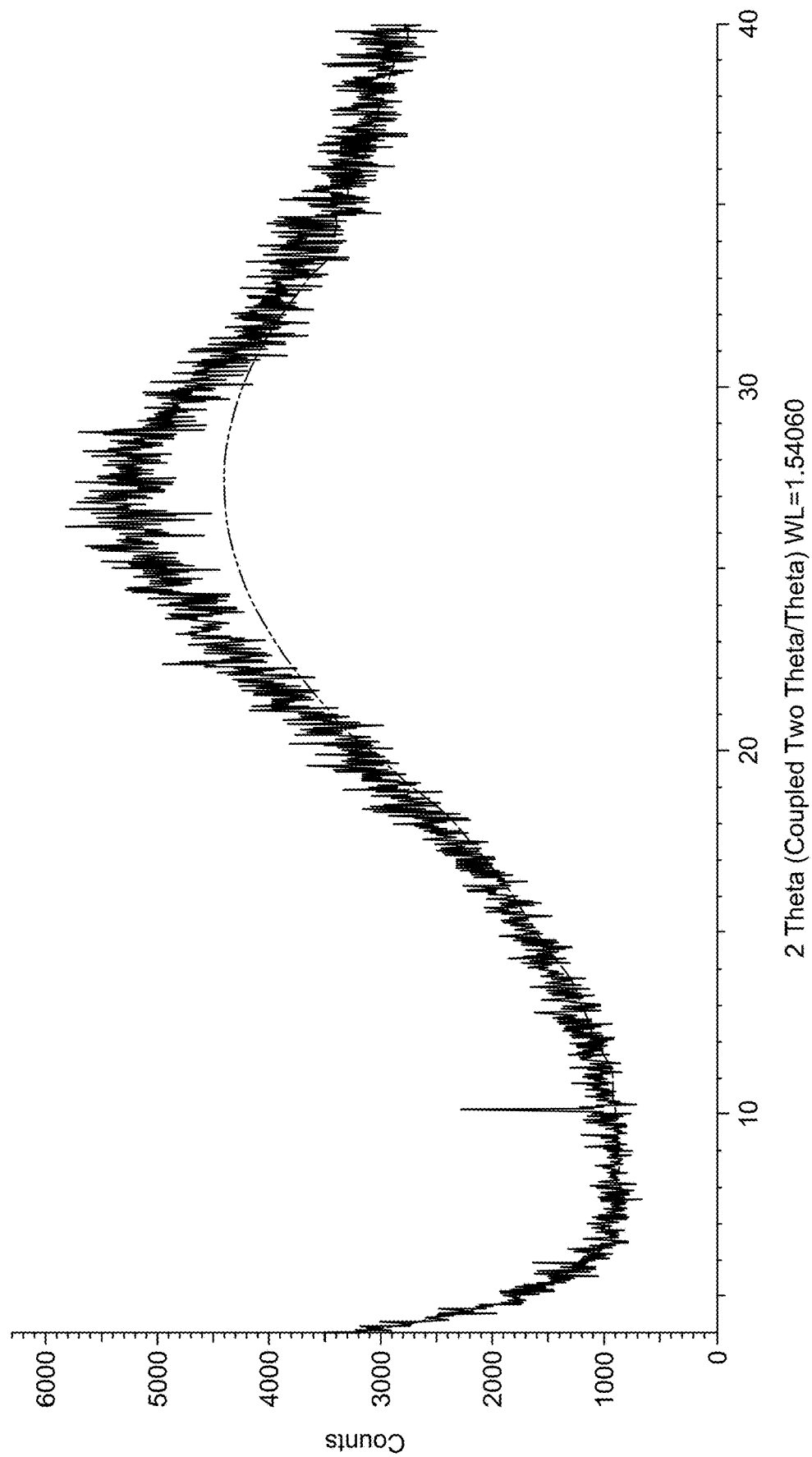

FIG. 153 shows a XRPD profile of material that resulted from the treatment of crystalline compound 1 monofumarate form A with water, 9 minutes after treating the Form A with water.

Figure 154:
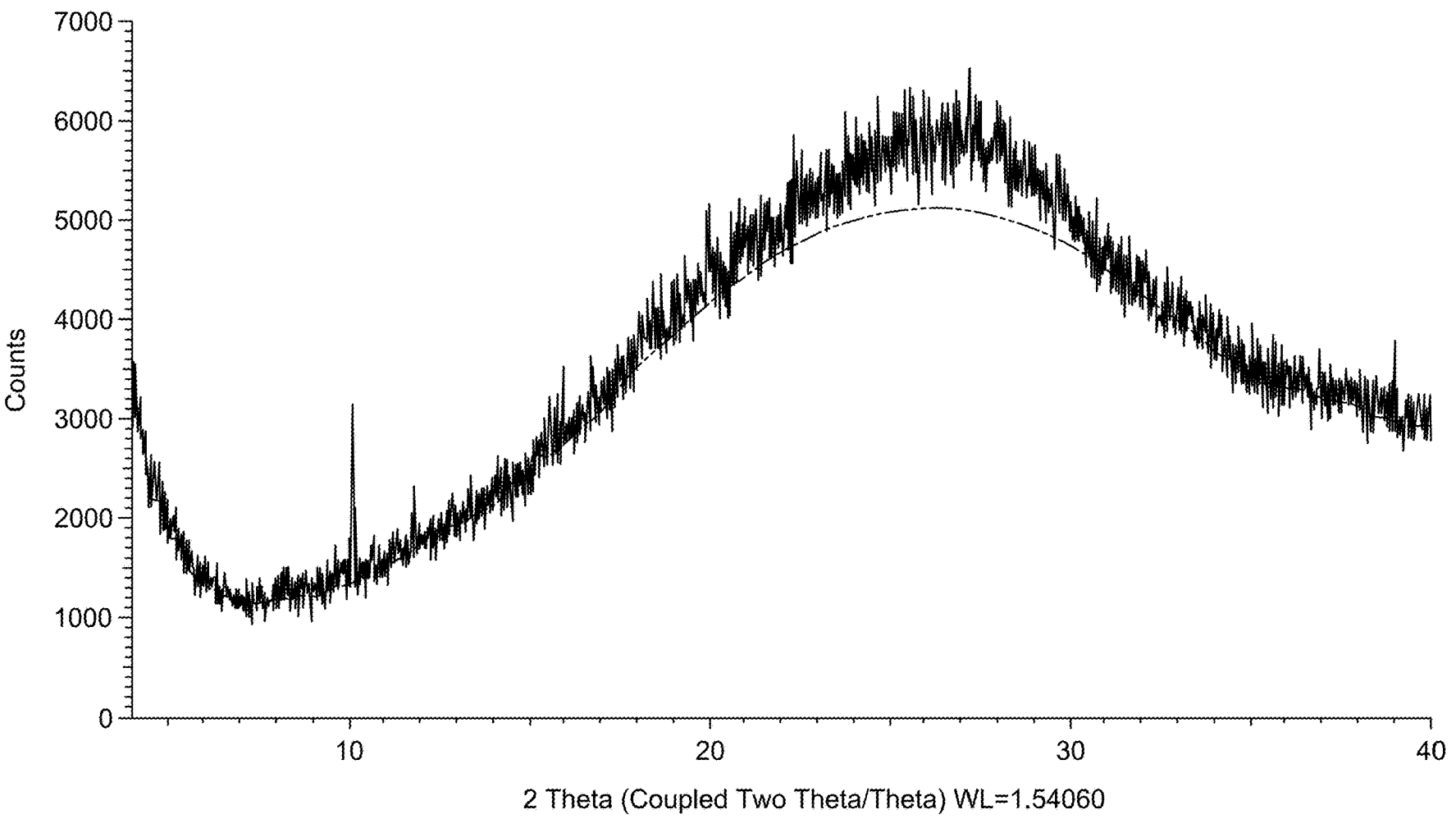

FIG. 154 shows a XRPD profile of material that resulted from the treatment of crystalline compound 1 monofumarate form A with water, 18 minutes after treating the Form A with water.

Figure 155:
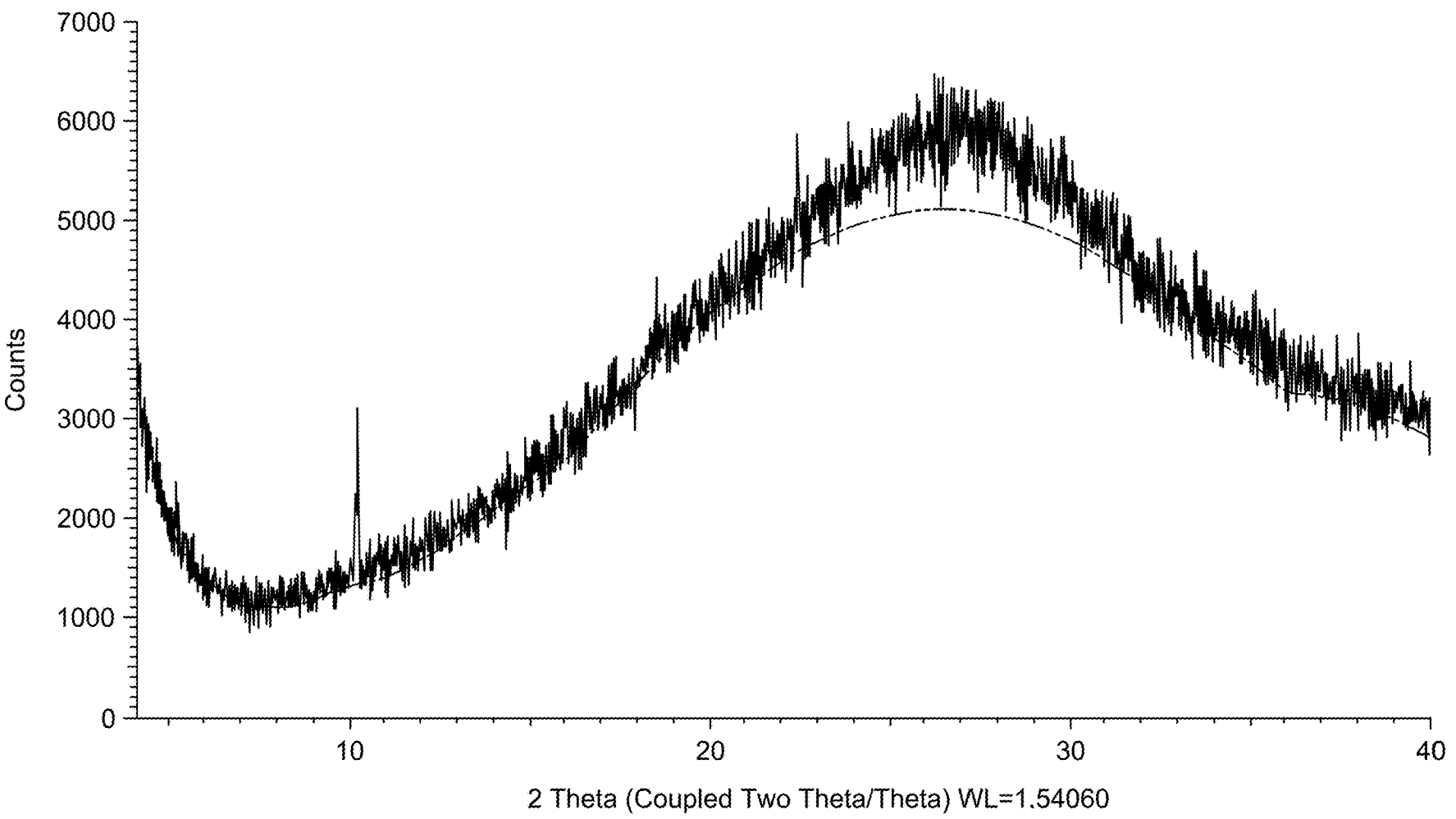

FIG. 155 shows a XRPD profile of material that resulted from the treatment of crystalline compound 1 monofumarate Form A with water, 27 minutes after treating the Form A with water.

Figure 156:
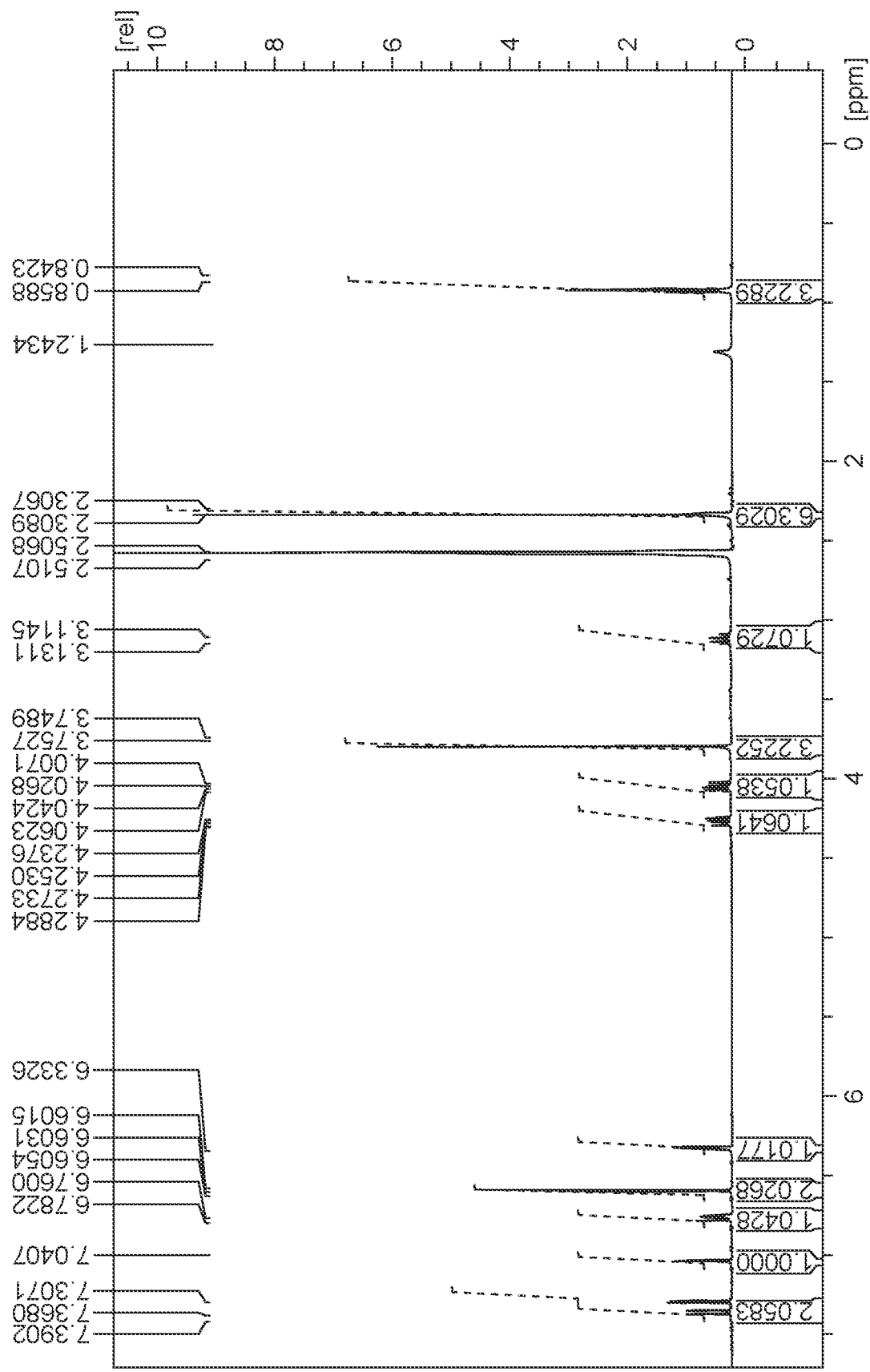

FIG. 156 shows a $^1$H NMR spectrum of crystalline compound 1 monofumarate Form A, spectrum was acquired in DMSO-d$_6$ and calibrated to the non-deuterated solvent residual at 2.50 ppm. MEK n.d.

Figure 157:
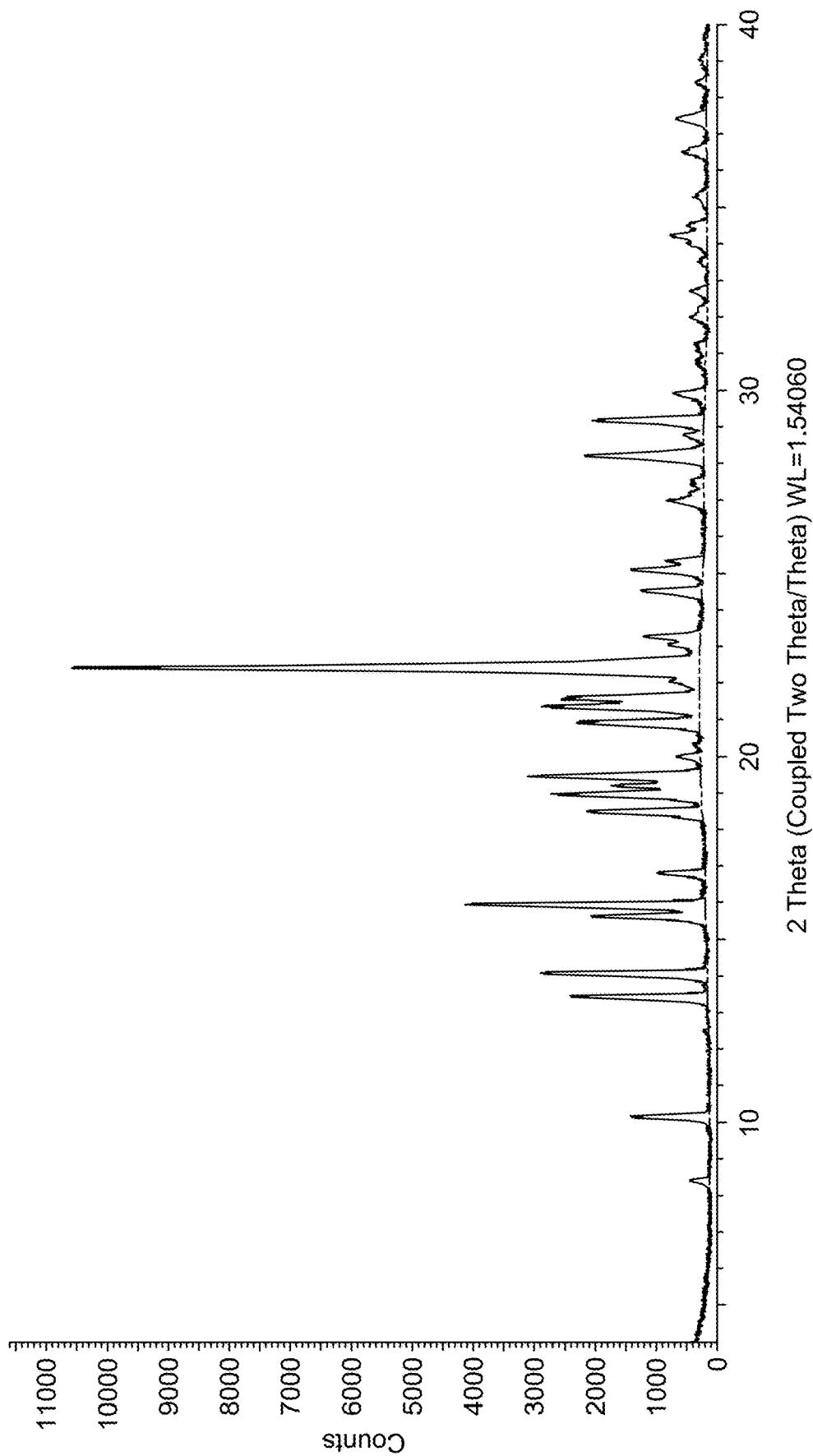

FIG. 157 shows a XRPD profile of crystalline compound 1 monofumarate Form A

Figure 158:
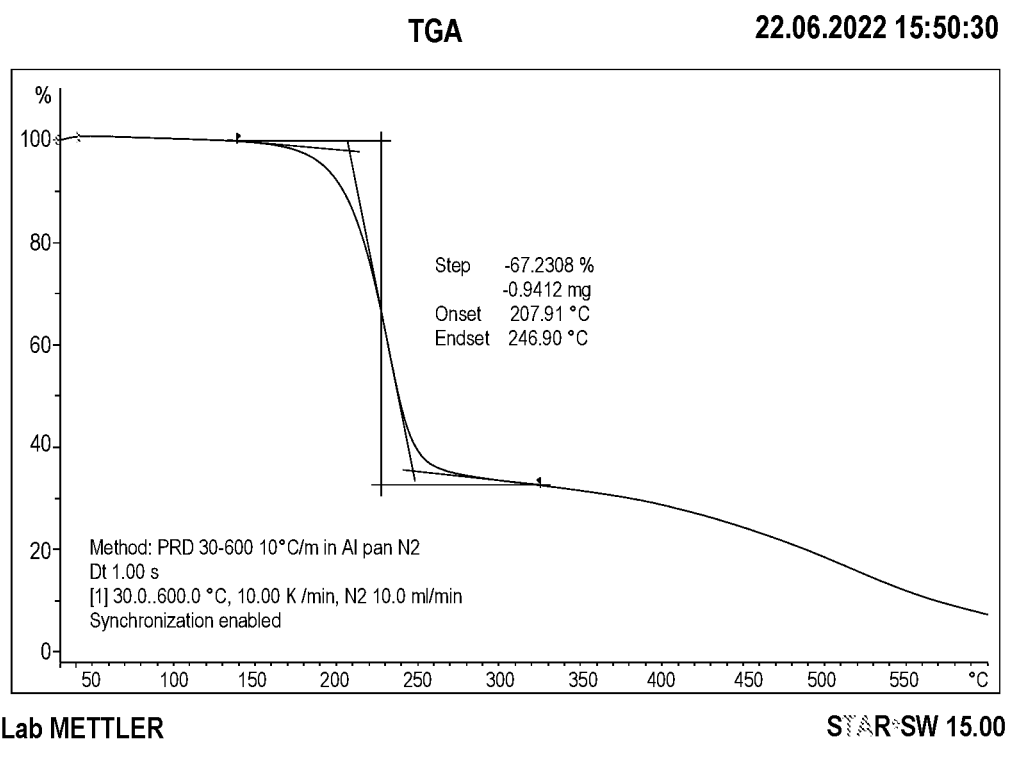

FIG. 158 shows a TGA thermogram of crystalline compound 1 monofumarate Form A, analysis was acquired at a ramp rate of +10° C./minute.

Figure 159:
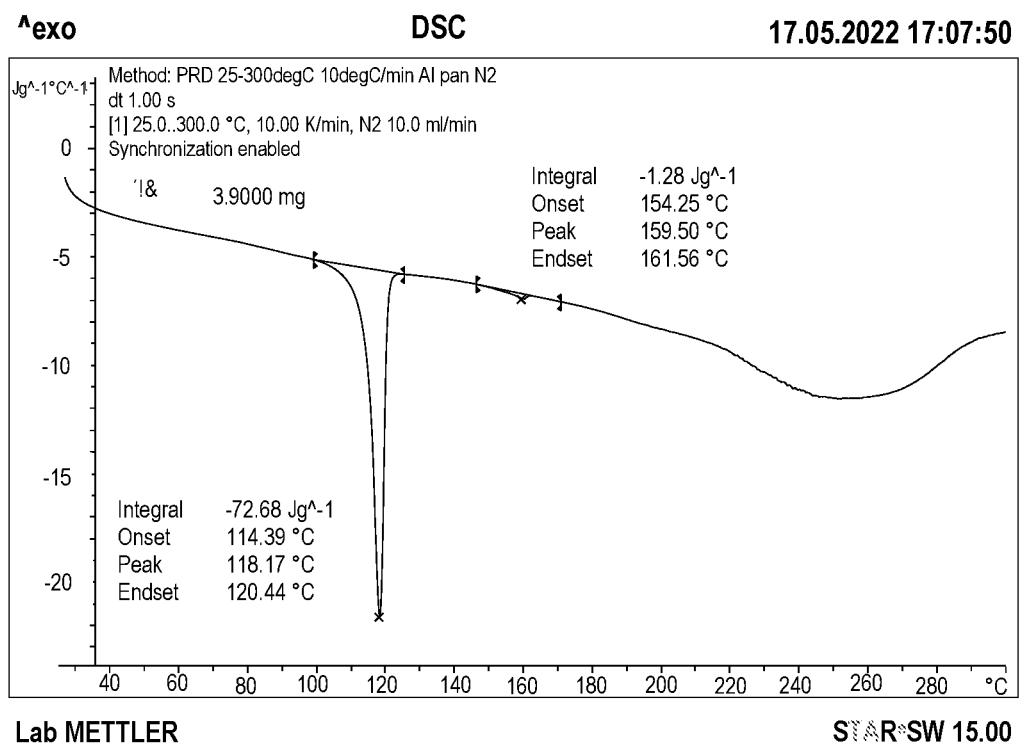

FIG. 159 shows a DSC profile of crystalline compound 1 monofumarate Form A, analysis was acquired at a ramp rate of +10° C./minute.

Figure 160:
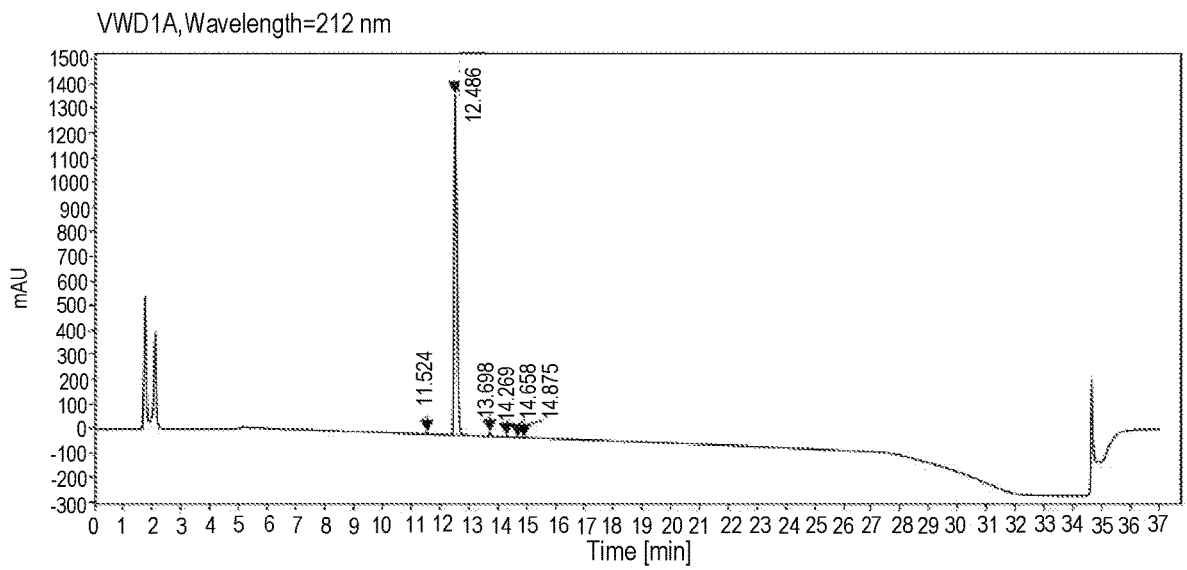

FIG. 160 shows a HPLC profile of crystalline compound 1 monofumarate Form A.

Figure 161:
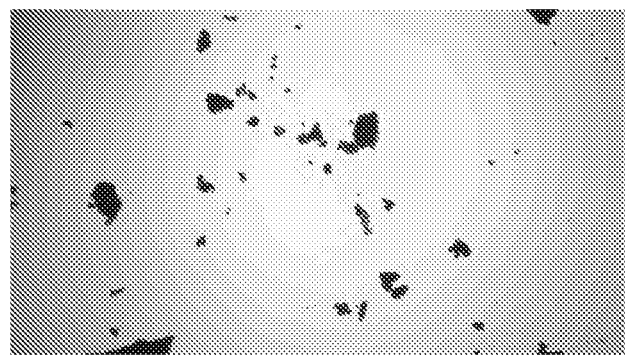

FIG. 161 shows an image of crystalline compound 1 monofumarate Form A, normal polarised (magnification×2).

Figure 162:
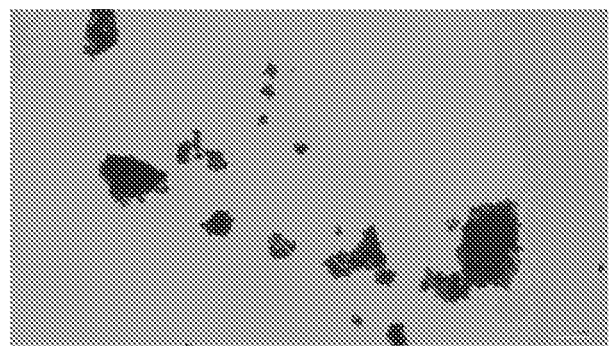

FIG. 162 shows an image of crystalline compound 1 monofumarate Form A, normal polarised (magnification×5).

Figure 163:
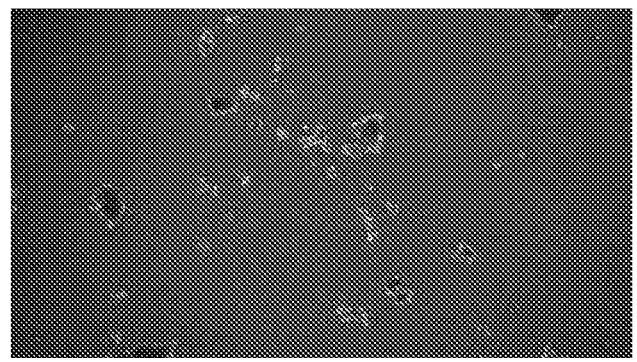

FIG. 163 shows an image of crystalline compound 1 monofumarate Form A, cross polarised (magnification×2).

Figure 164:
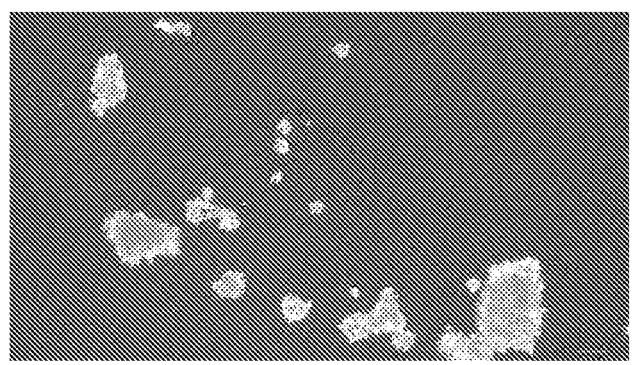

FIG. 164 shows an image of crystalline compound 1 monofumarate Form A, cross polarised (magnification×5).

Figure 165:
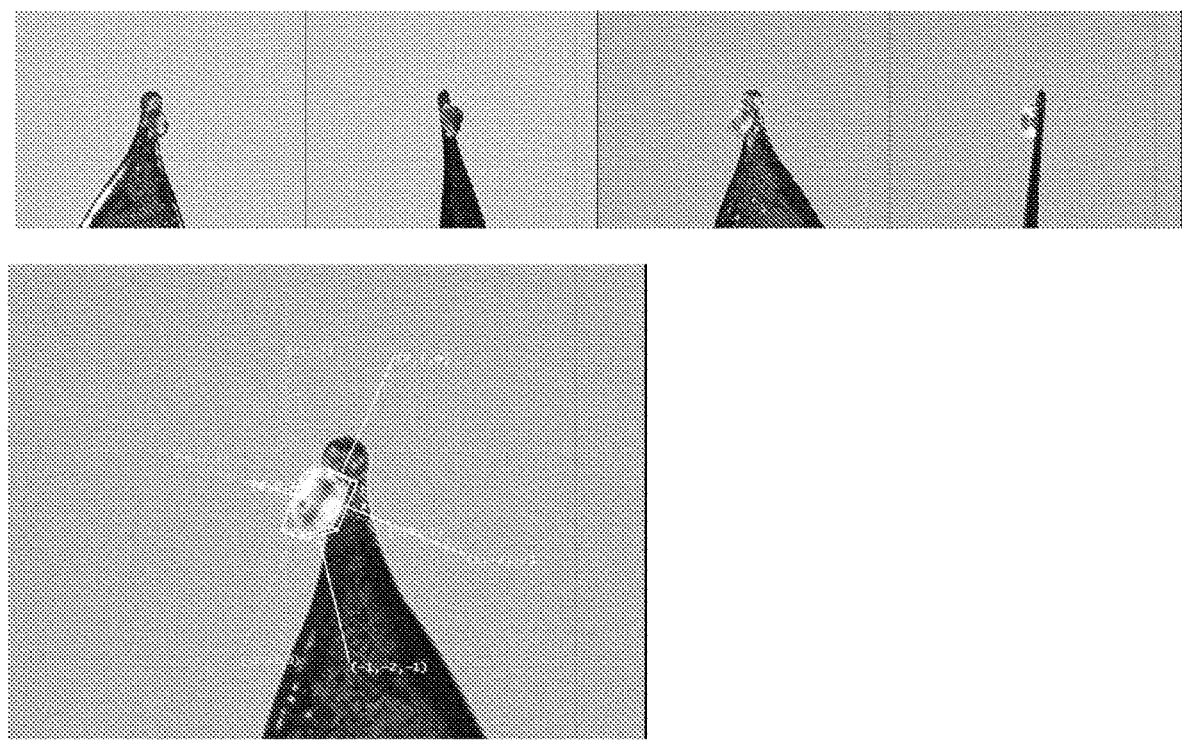
Figure 166:
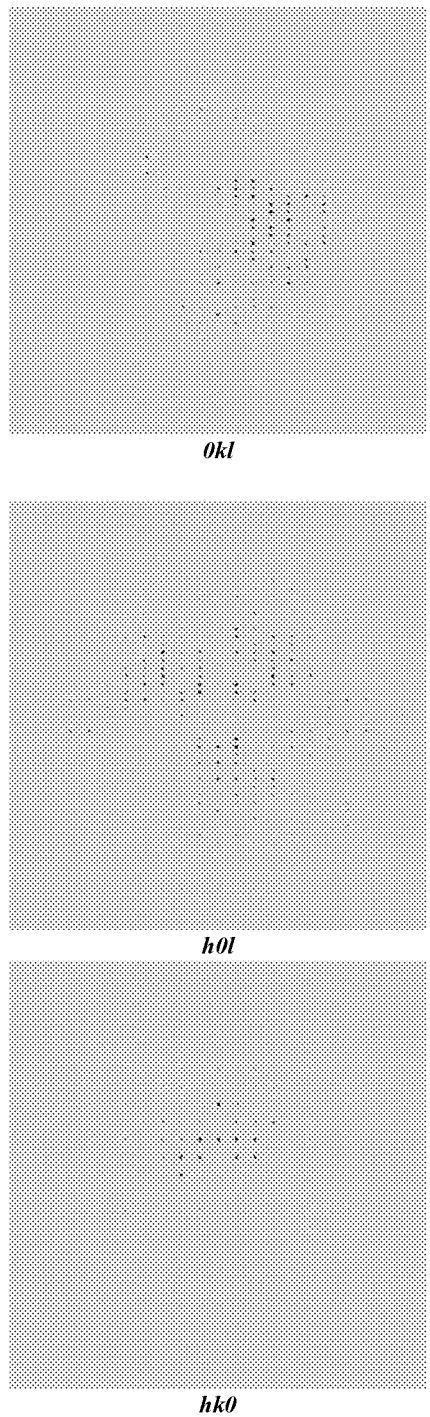
Figure 167:
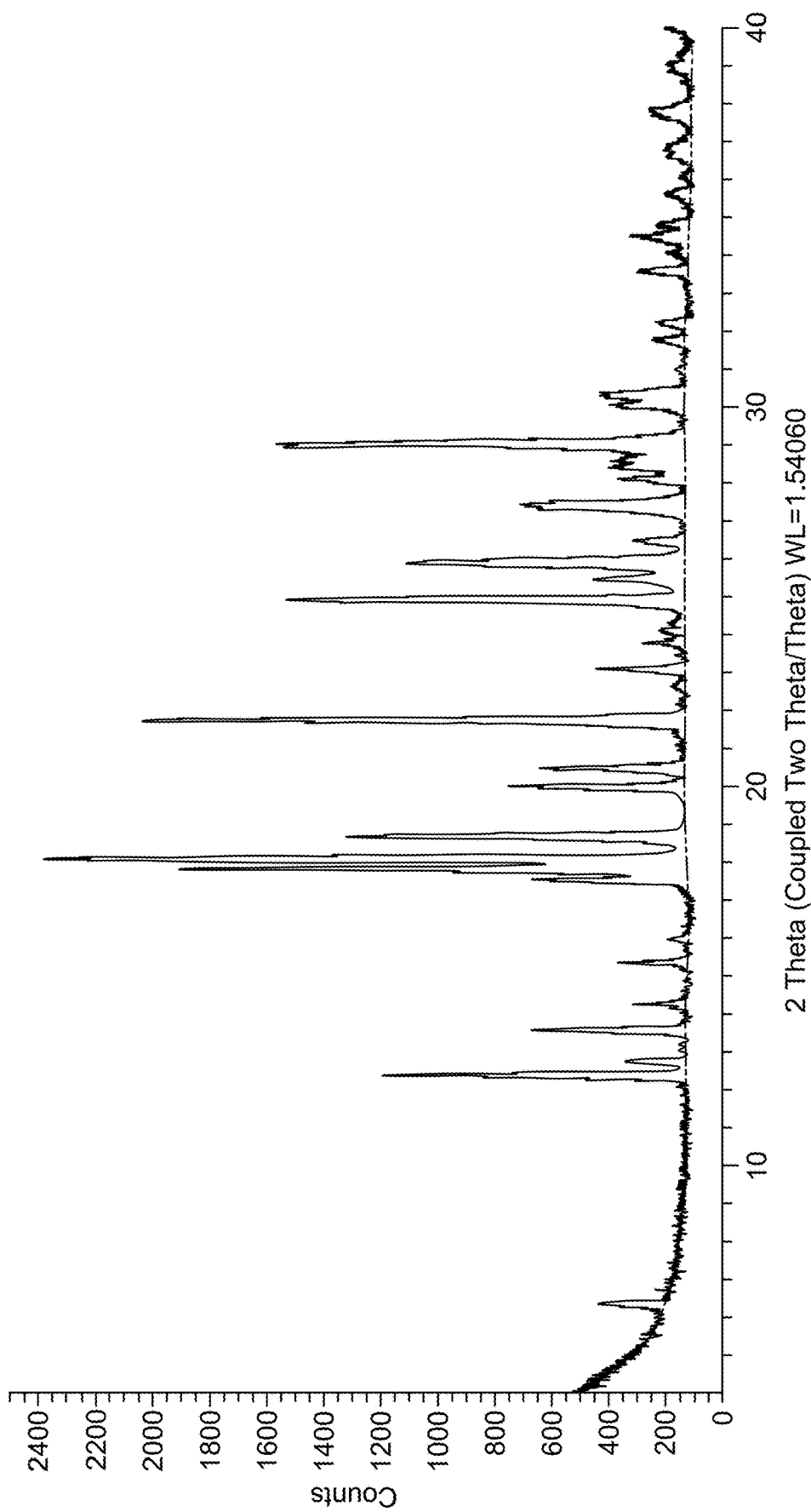

FIG. 165 is a series of images of a single crystal of crystalline compound 1 monofumarate salt Form A on a diffractometer FIG. 166 is a series of precession images generated from a single crystal of crystalline compound 1 monofumarate salt Form A FIG. 167 shows an XRPD diffractogram of compound 1·hydrochloride, Form A. XRPD signals shown in this diffractogram are characterized in Table 41.

Figure 168:
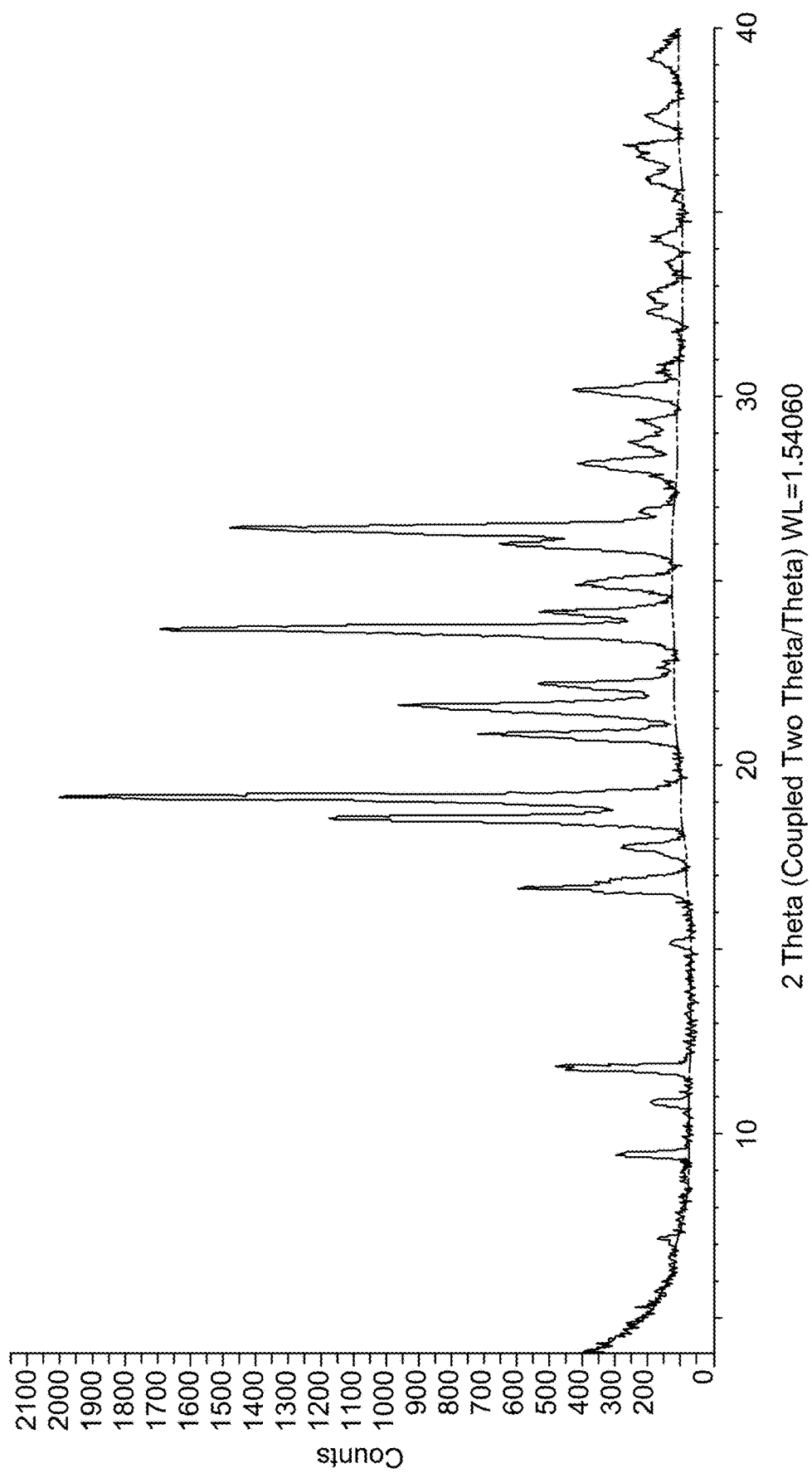

FIG. 168 shows an XRPD diffractogram of compound 1·maleate. XRPD signals shown in this diffractogram are characterized in Table 44.

Figure 169:
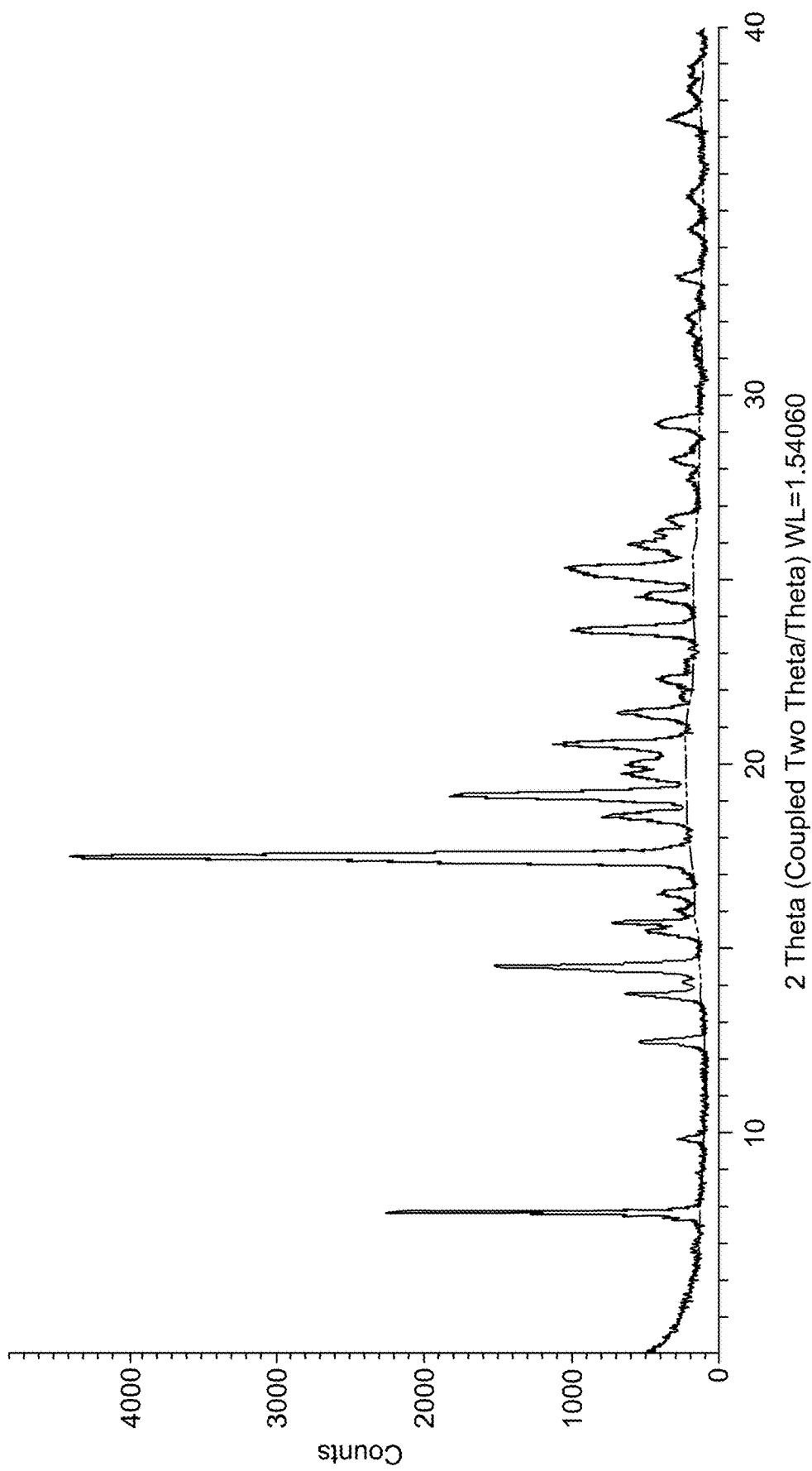

FIG. 169 shows XRPD diffractogram of compound 1·benzoate. XRPD signals shown in this diffractogram are characterized in Table 46.

Figure 170:
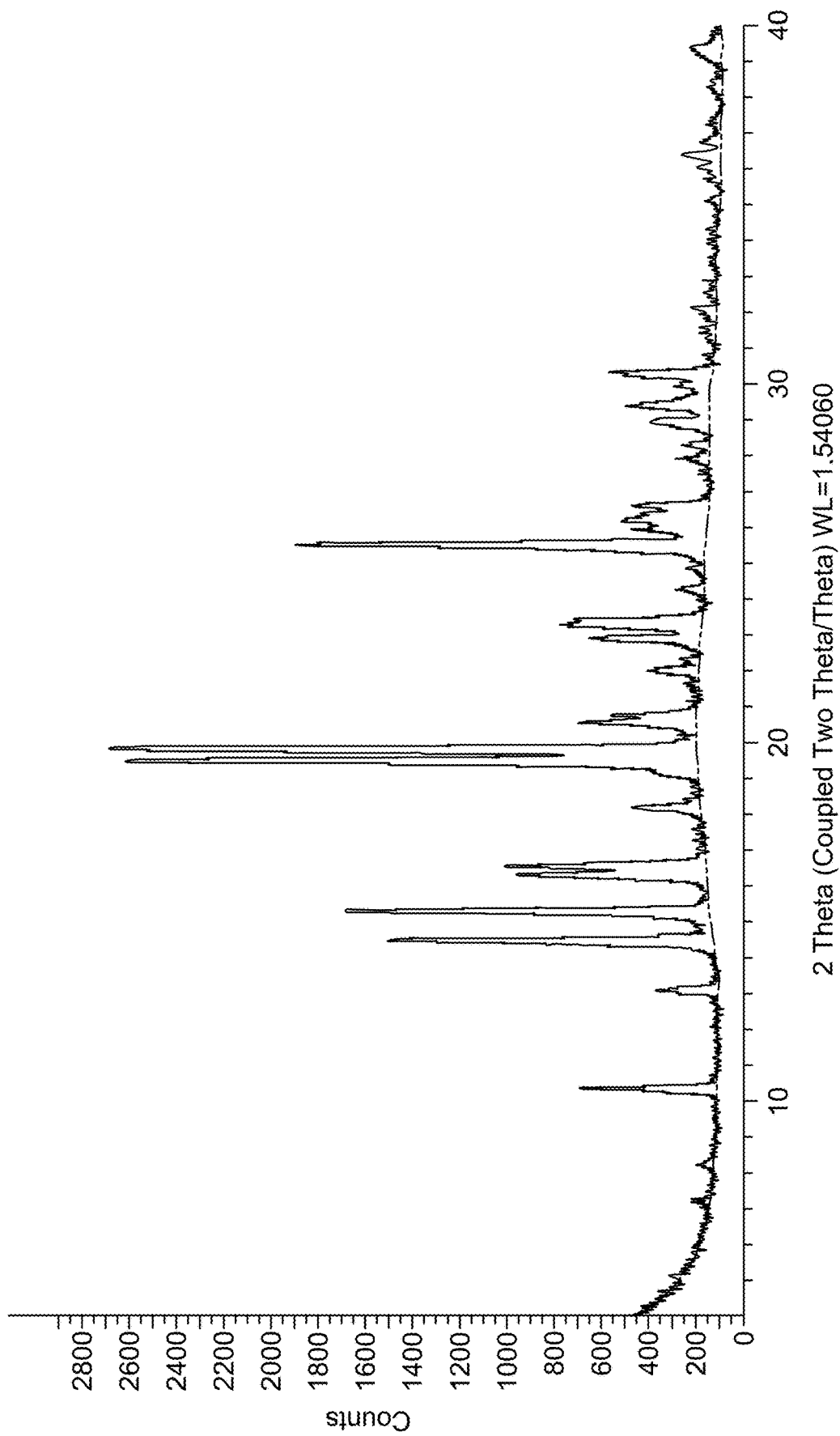

FIG. 170 shows XRPD diffractogram of compound 1·tosylate. XRPD signals shown in this diffractogram are characterized in Table 113.

Figure 171:
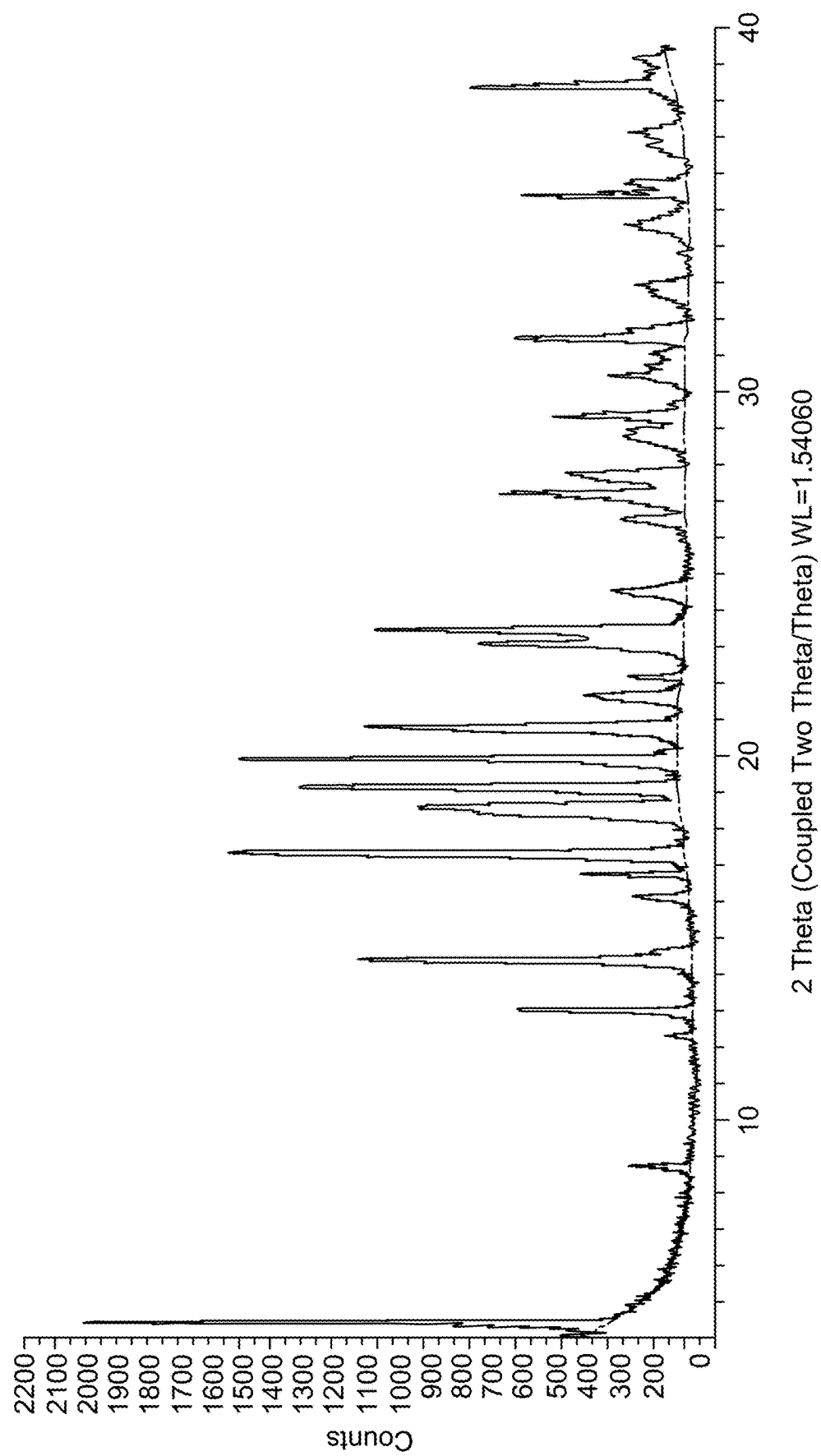

FIG. 171 shows XRPD diffractogram of compound 1 tartrate. XRPD signals shown in this diffractogram are characterized in Table 47.

Figure 172:
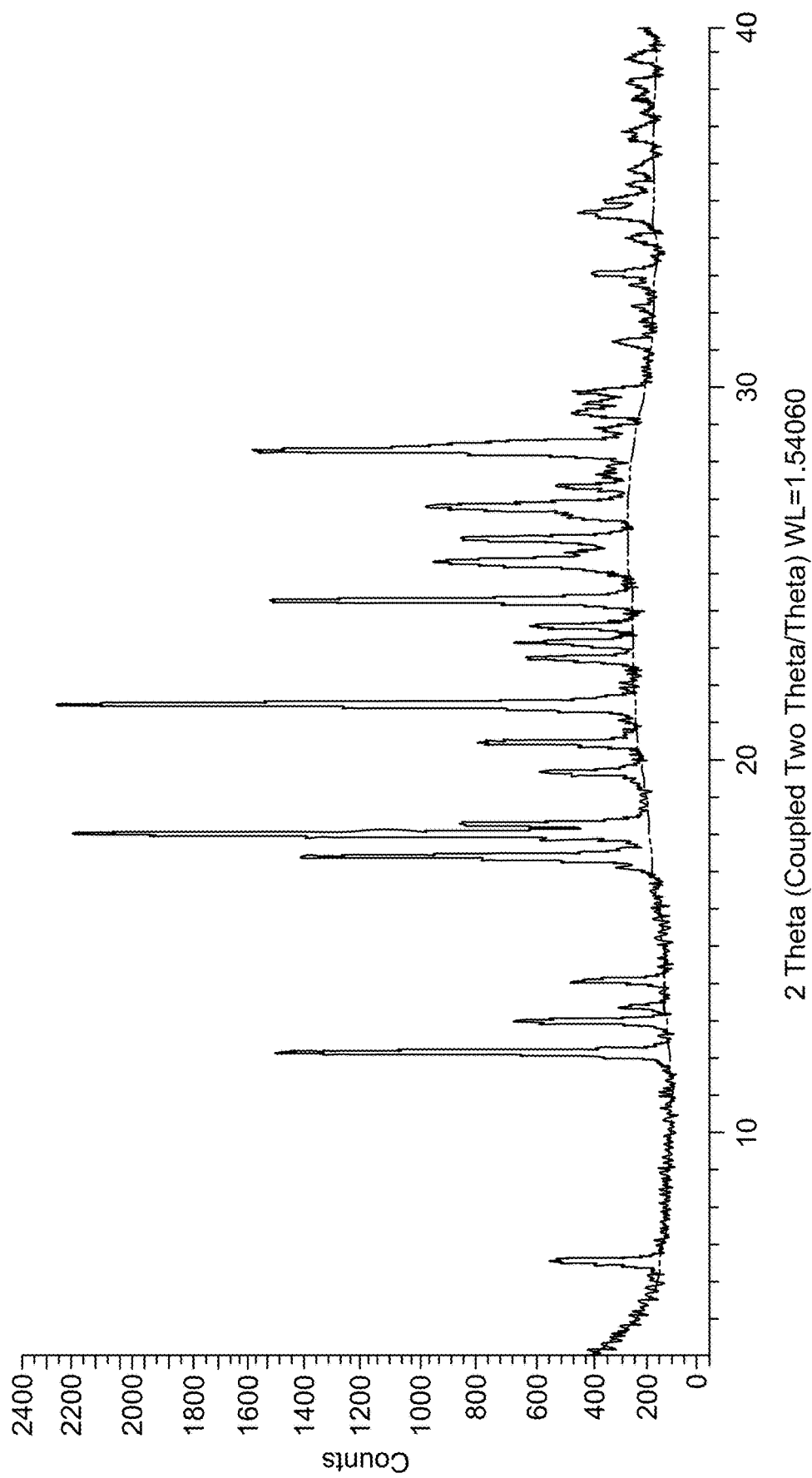

FIG. 172 shows XRPD diffractogram of compound 1·hydrobromide. XRPD signals shown in this diffractogram are characterized in Table 48.

Figure 173:
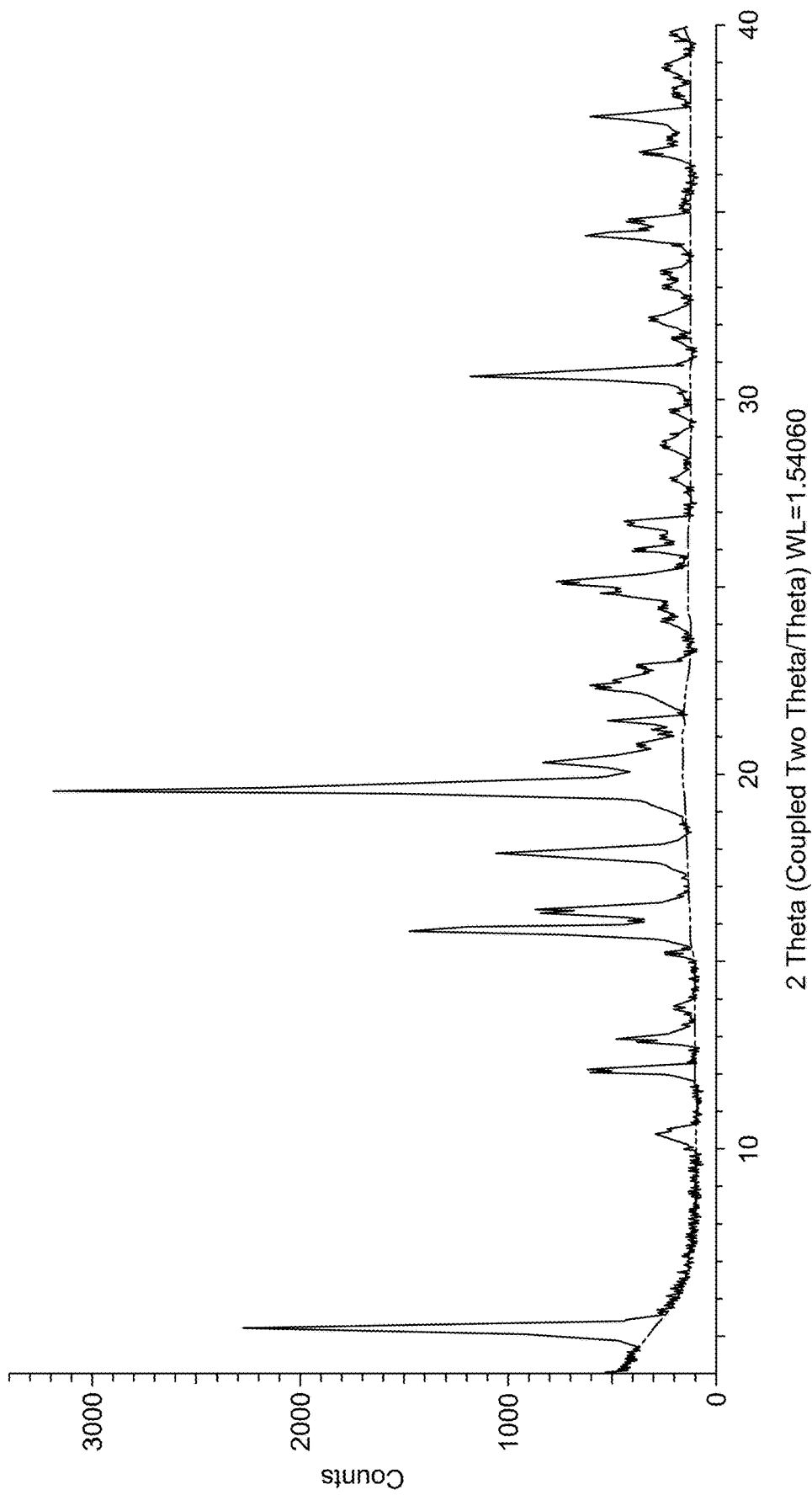

FIG. 173 shows XRPD diffractogram of compound 1·galactarate. XRPD signals shown in this diffractogram are characterized in Table 49.

Figure 174:
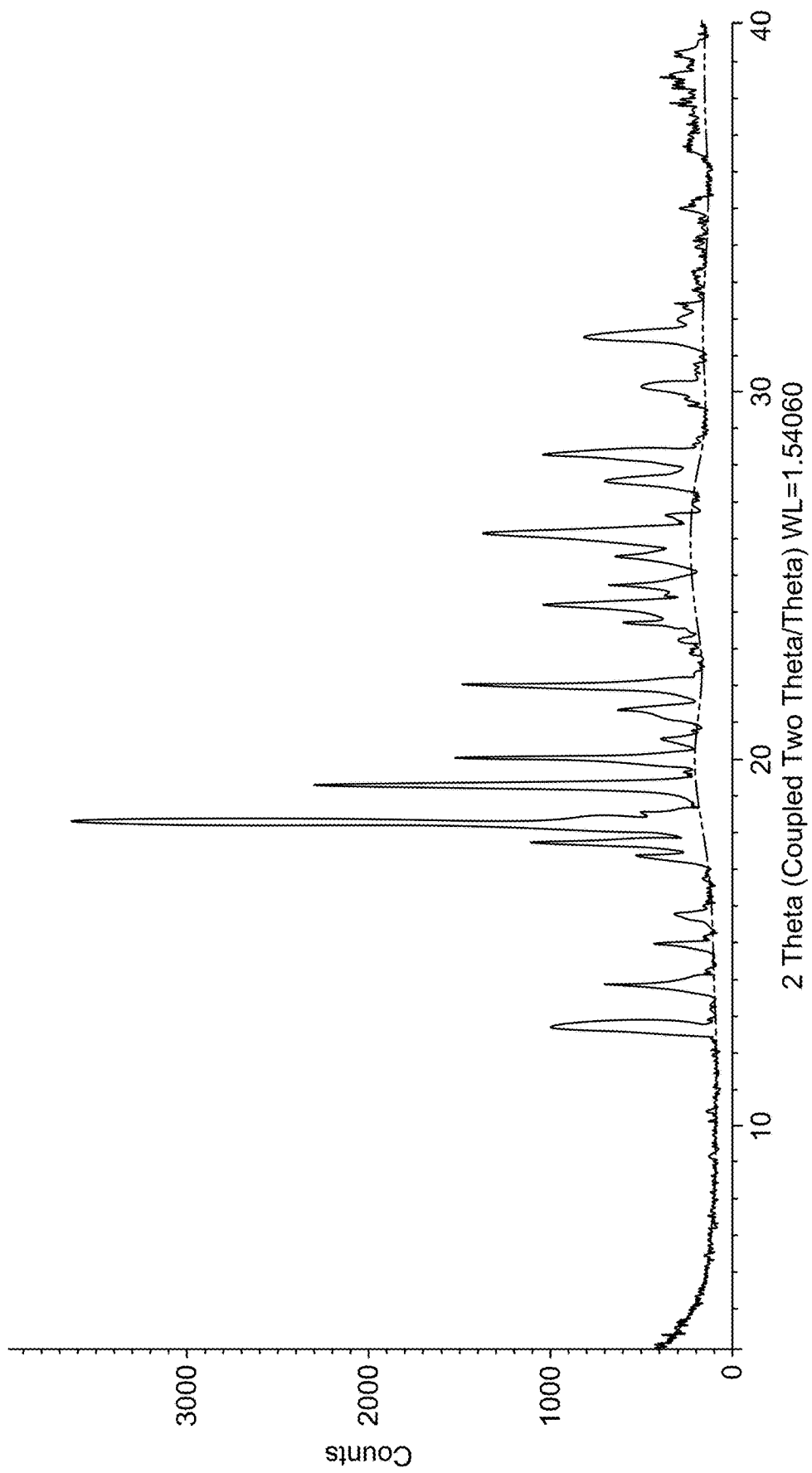

FIG. 174 shows XRPD diffractogram of compound 1·succinate. XRPD signals shown in this diffractogram are characterized in Table 50.

Figure 175:
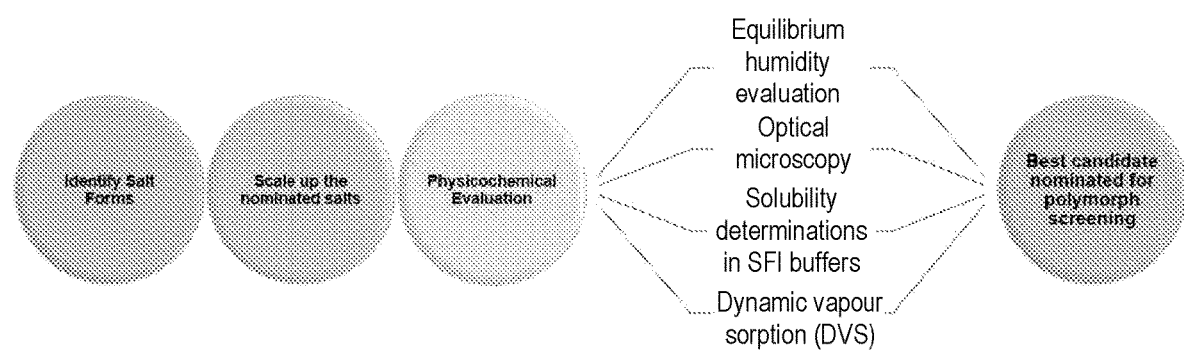

FIG. 175 shows a graphic describing the work performed during the salt screen.

Figure 176:
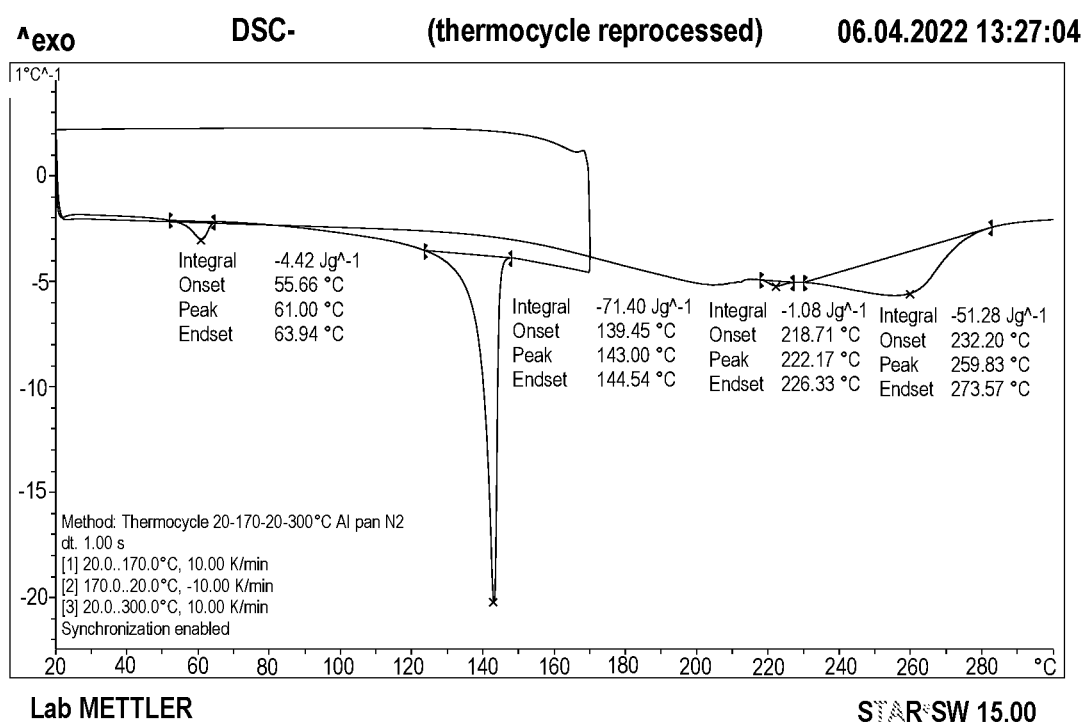
Figure 177:
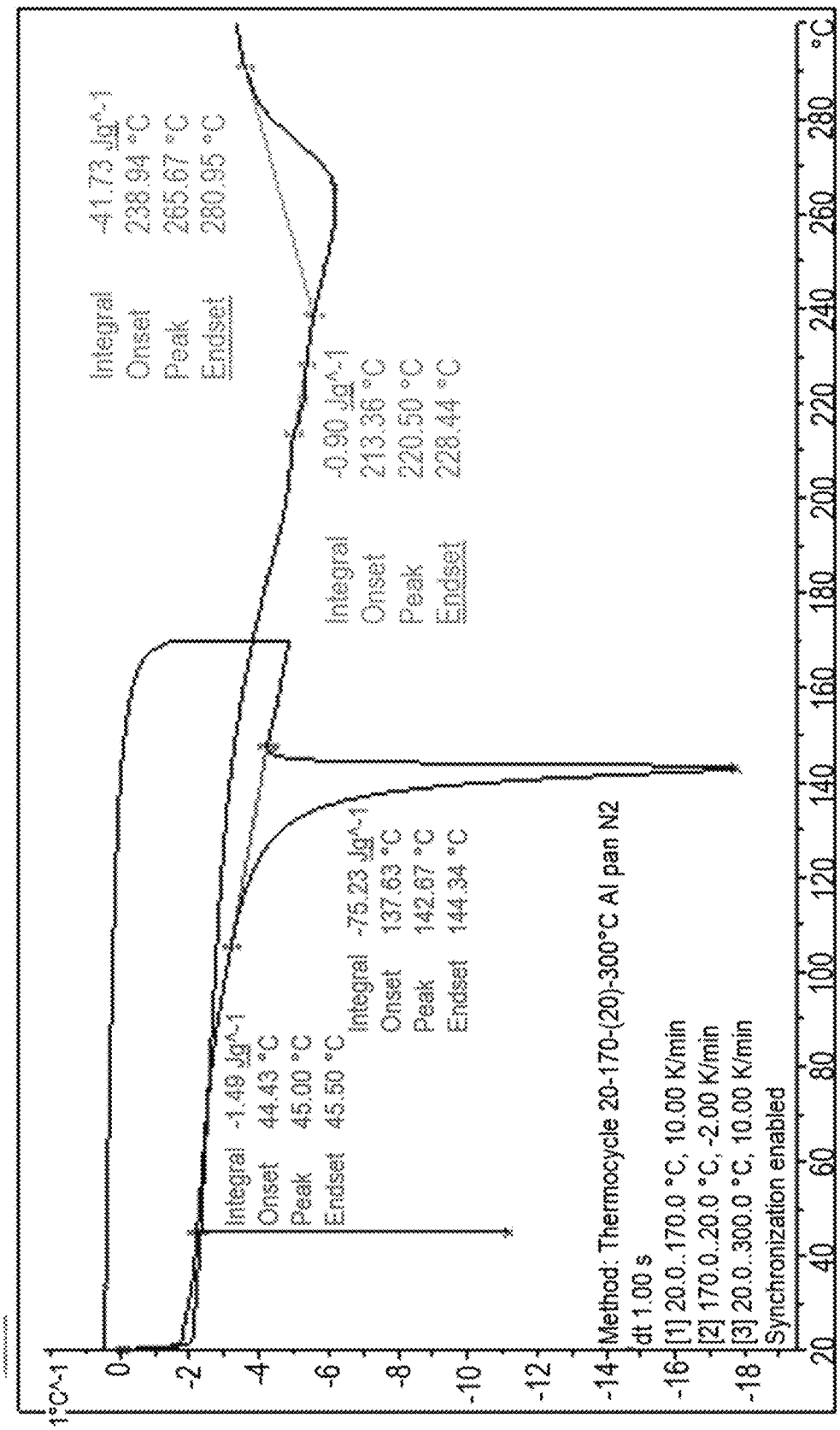
Figure 178:
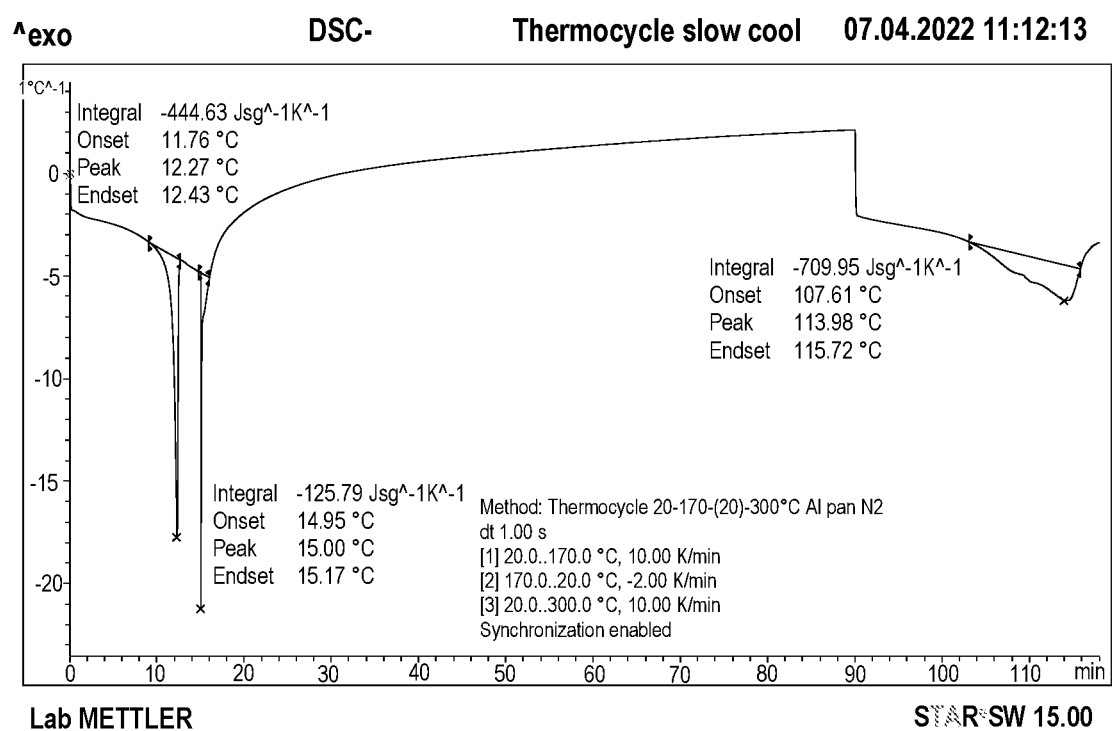
Figure 179:
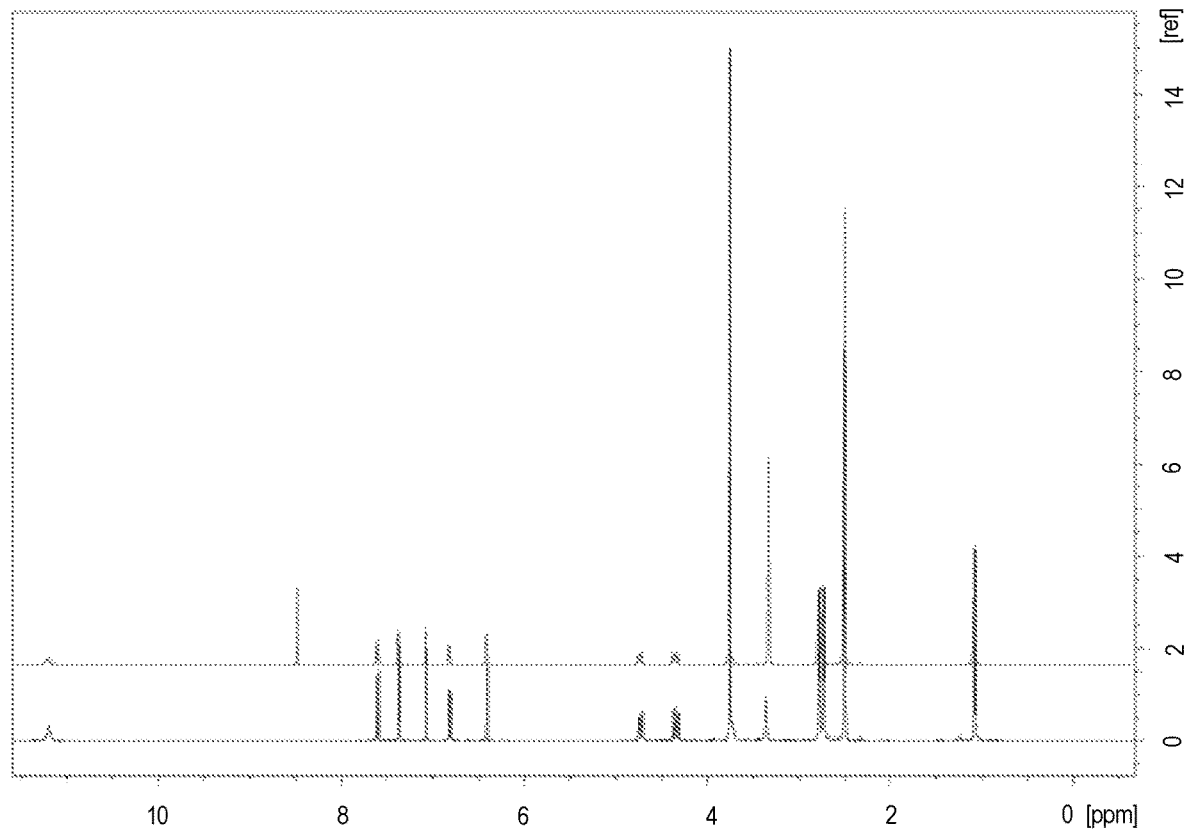

FIG. 176 shows the DSC profile of crystalline compound 1 maleate salt, thermocycle reprocessed FIG. 177 shows the DSC profile of crystalline compound 1 maleate, thermocycle slow cool FIG. 178 shows DSC profile of crystalline compound 1 maleate, thermocycle slow cool time FIG. 179 shows a $^1$H NMR spectrum overlay of two preparations of crystalline compound 1 HCl.

Figure 180:
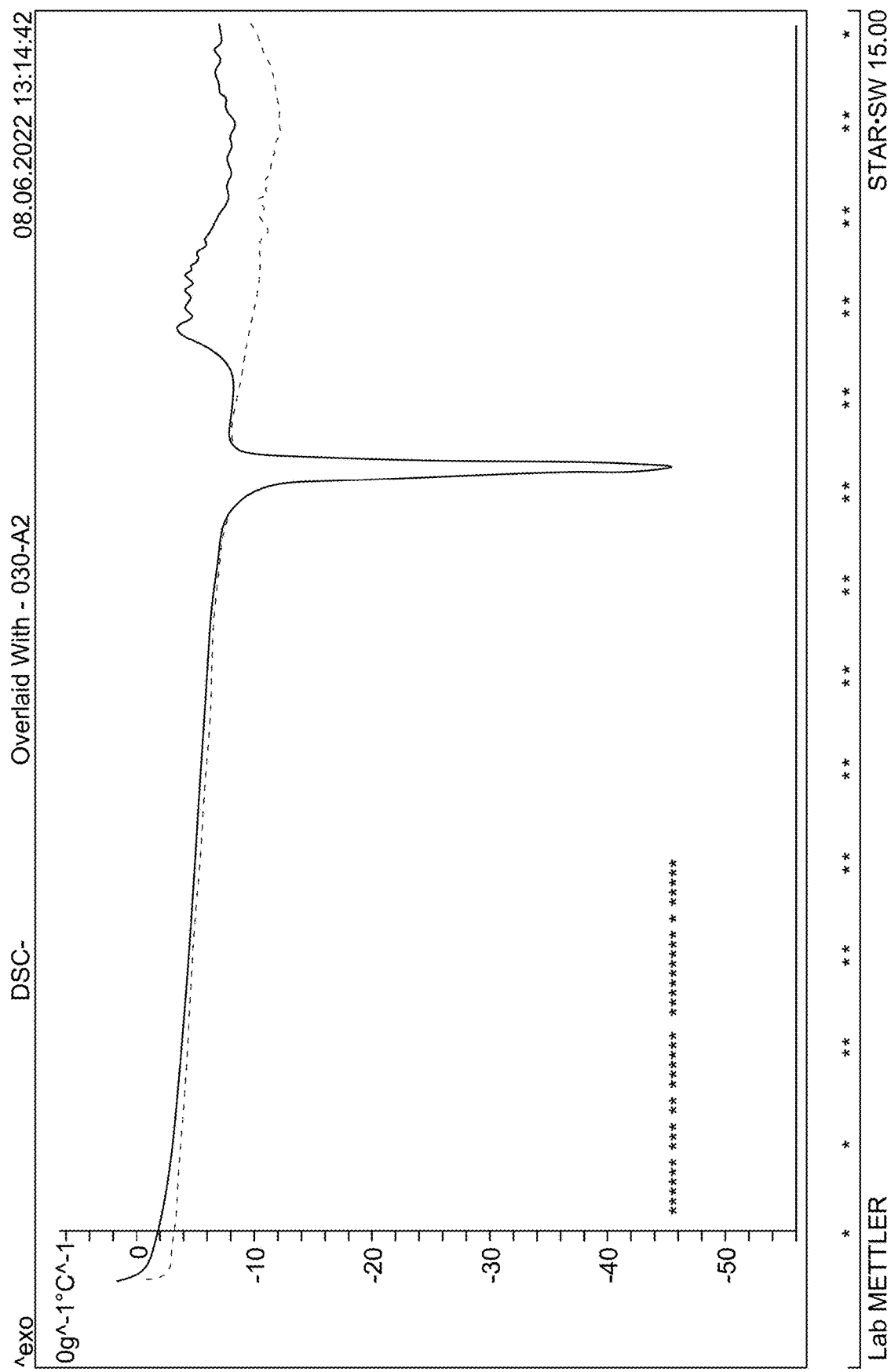

FIG. 180 shows a DSC thermogram overlay of two preparations of crystalline compound 1 HCl.

Figure 181:
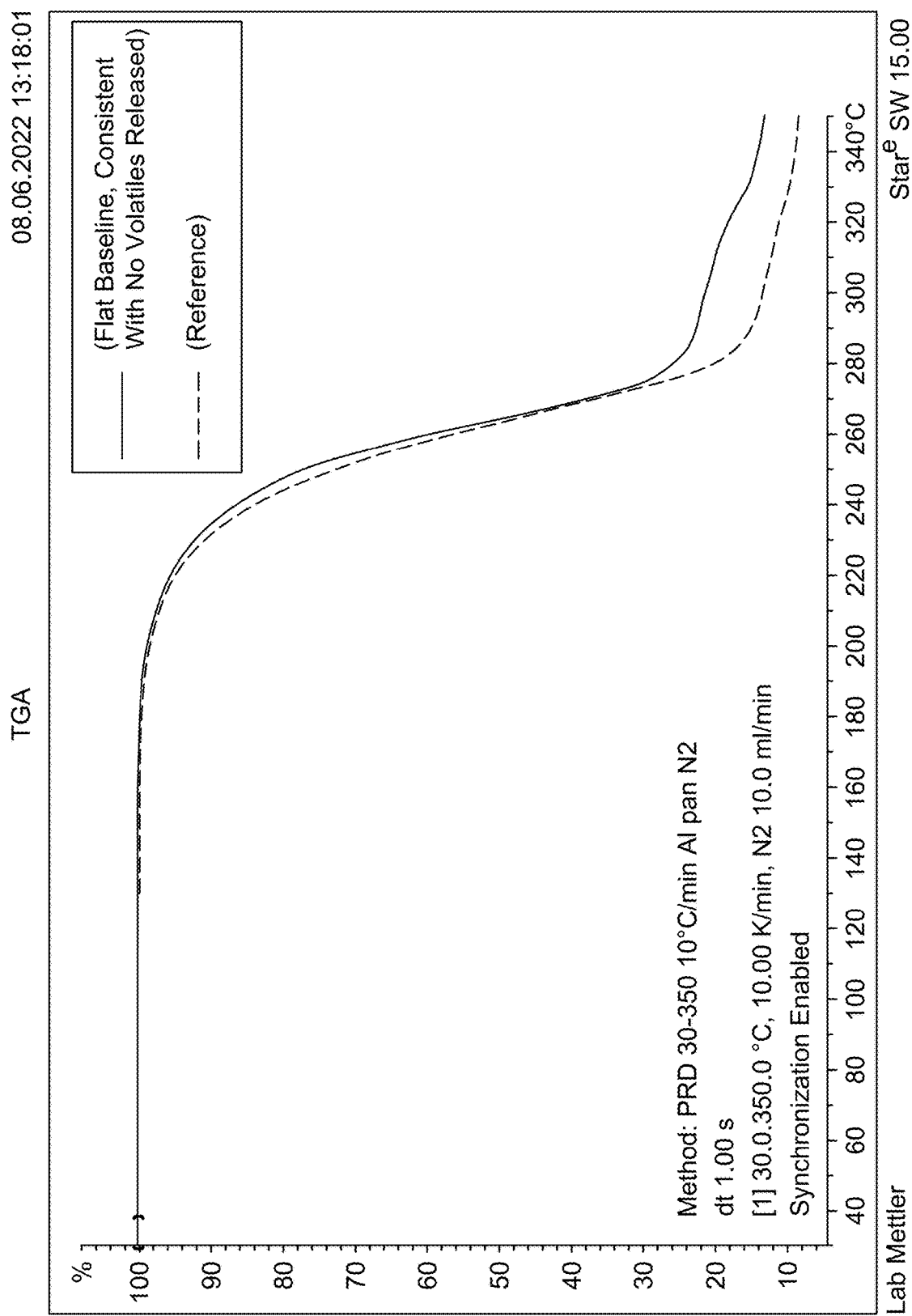

FIG. 181 shows TGA thermogram overlay of two preparations of crystalline compound 1 HCl.

Figure 182:
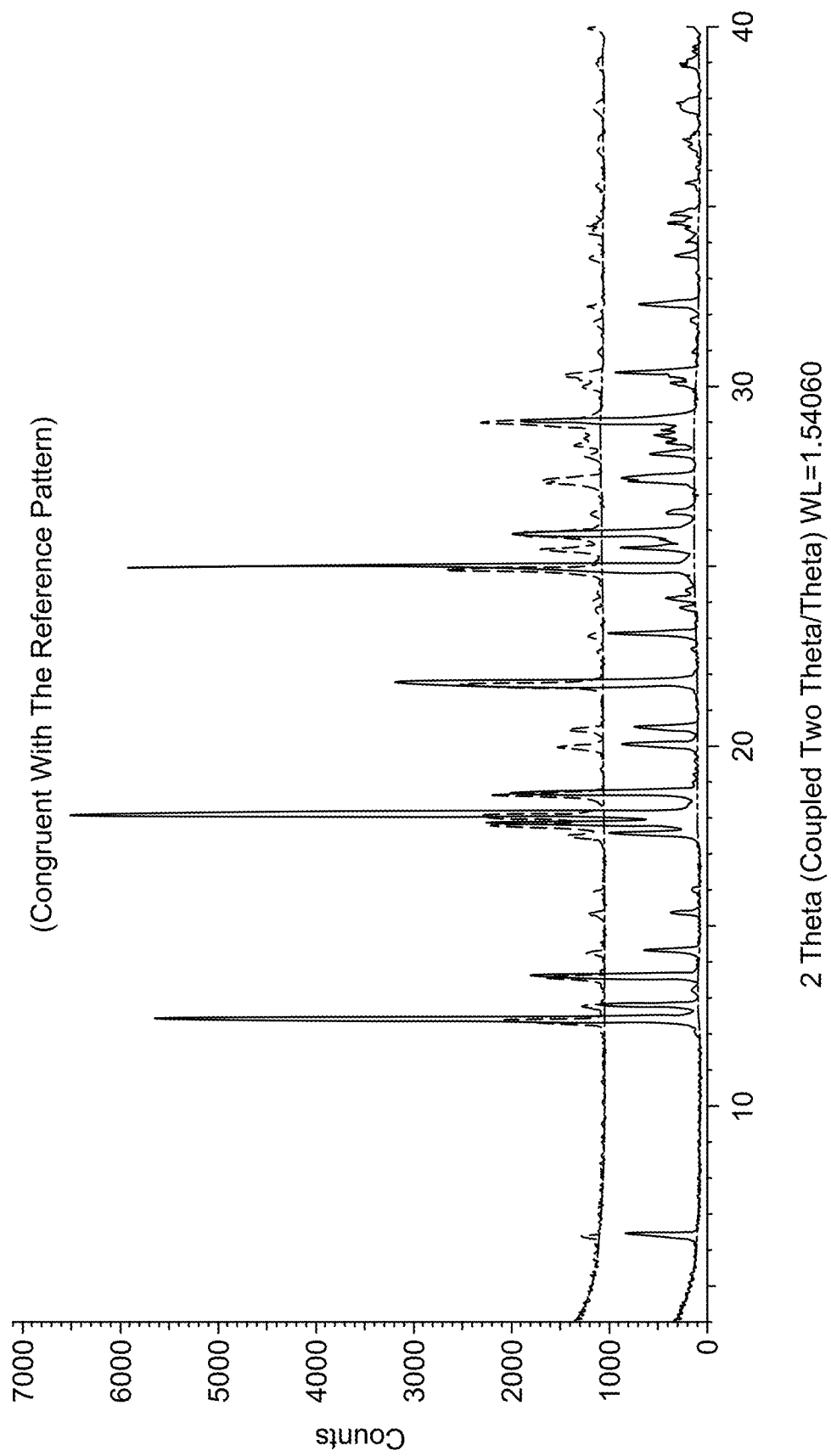

FIG. 182 shows a XRPD diffractogram overlay of two preparations of crystalline compound 1 HCl.

Figure 183:
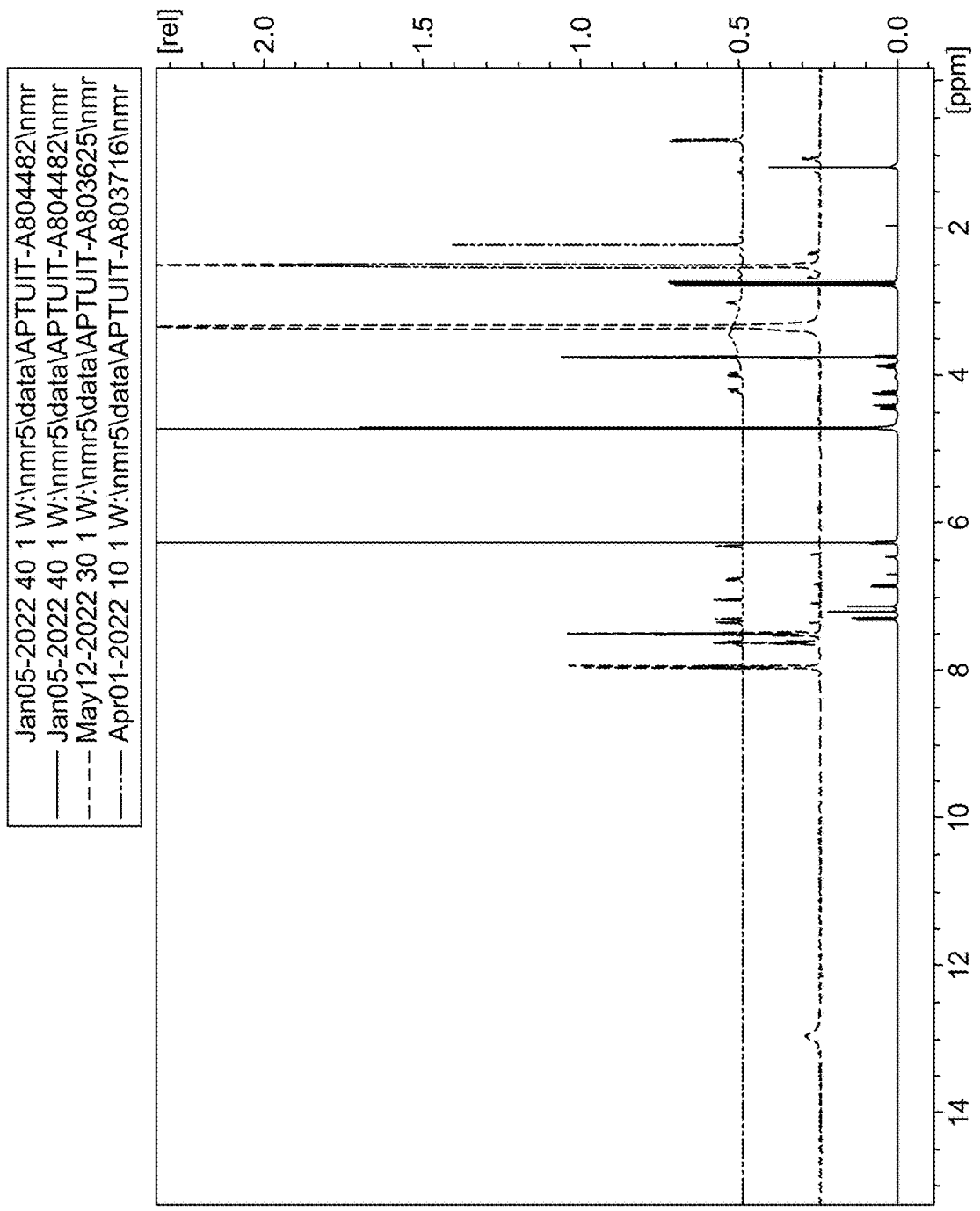

FIG. 183 shows a $^1$H NMR spectra overlay of crystalline compound 1 benzoate (top), dry pellet at T=24 h API/benzoic acid 1/16 (middle) and amorphous compound 1 (bottom).

Figure 184:
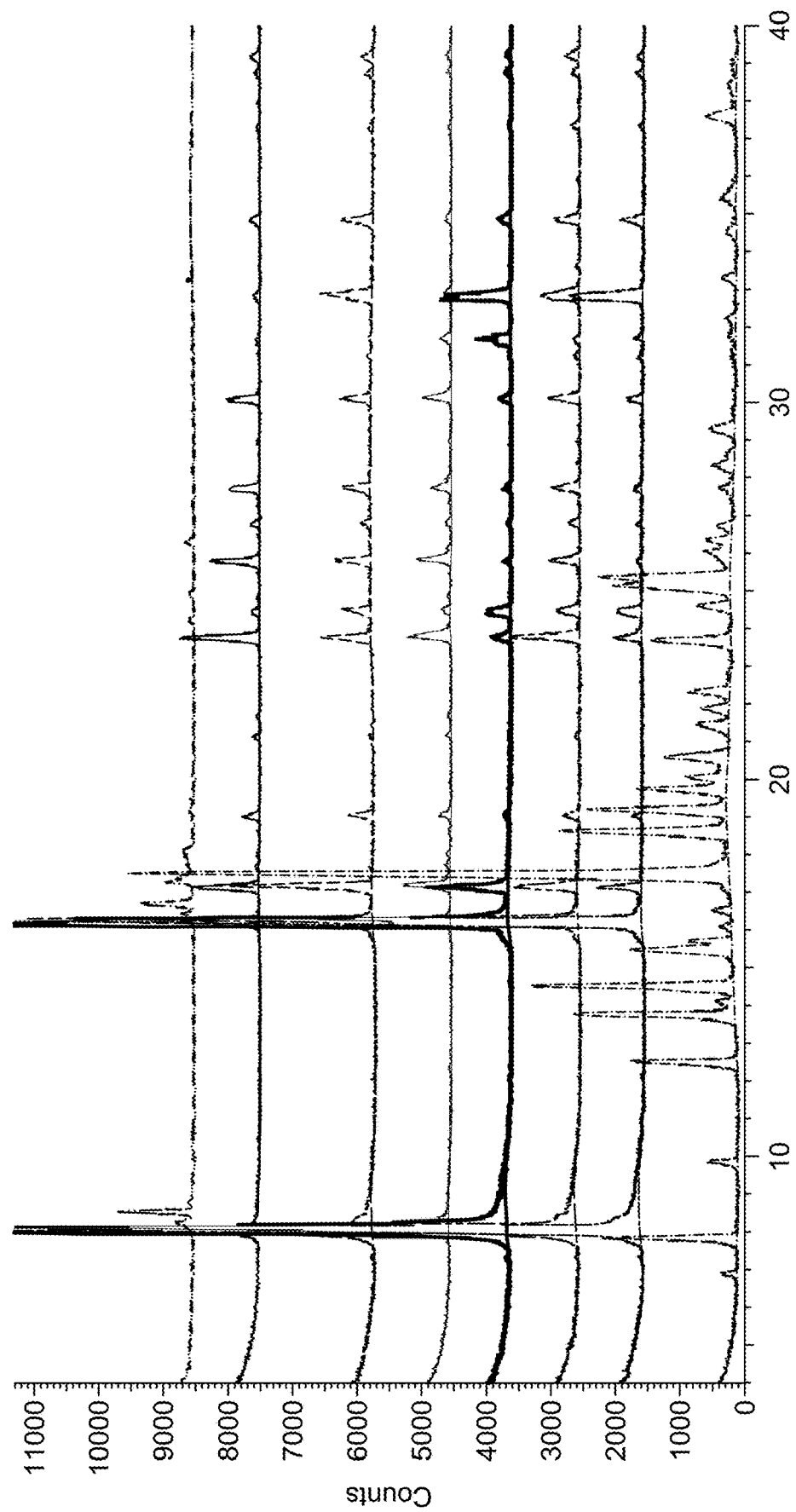

FIG. 184 shows overlaid XRPD profiles of crystalline compound 1 benzoate (bottom), a sample of crystalline compound 1 benzoate that was isolated from FaSSGF buffer (pH 1.6) at t=1 h and not dried, (second from bottom), a sample of crystalline compound 1 benzoate that was isolated from FaSSGF buffer (pH 1.6) at t=1 h and dried (third from bottom), a sample of crystalline compound 1 benzoate that was isolated from FaSSGF buffer (pH 1.6) at t=3 h and not dried (fourth from bottom), a sample of crystalline compound 1 benzoate that was isolated from a FaSSGF buffer (pH 1.6) at t=3 h and dried (fifth from bottom), a sample of crystalline compound 1 benzoate that was isolated from a FaSSGF buffer (pH 1.6) at t=24 h and not dried (third from top), a sample of crystalline compound 1 benzoate that was isolated from FaSSGF buffer (pH 1.6) at t=24 h and dried (second from top) and crystalline benzoic acid (top).

Figure 185:
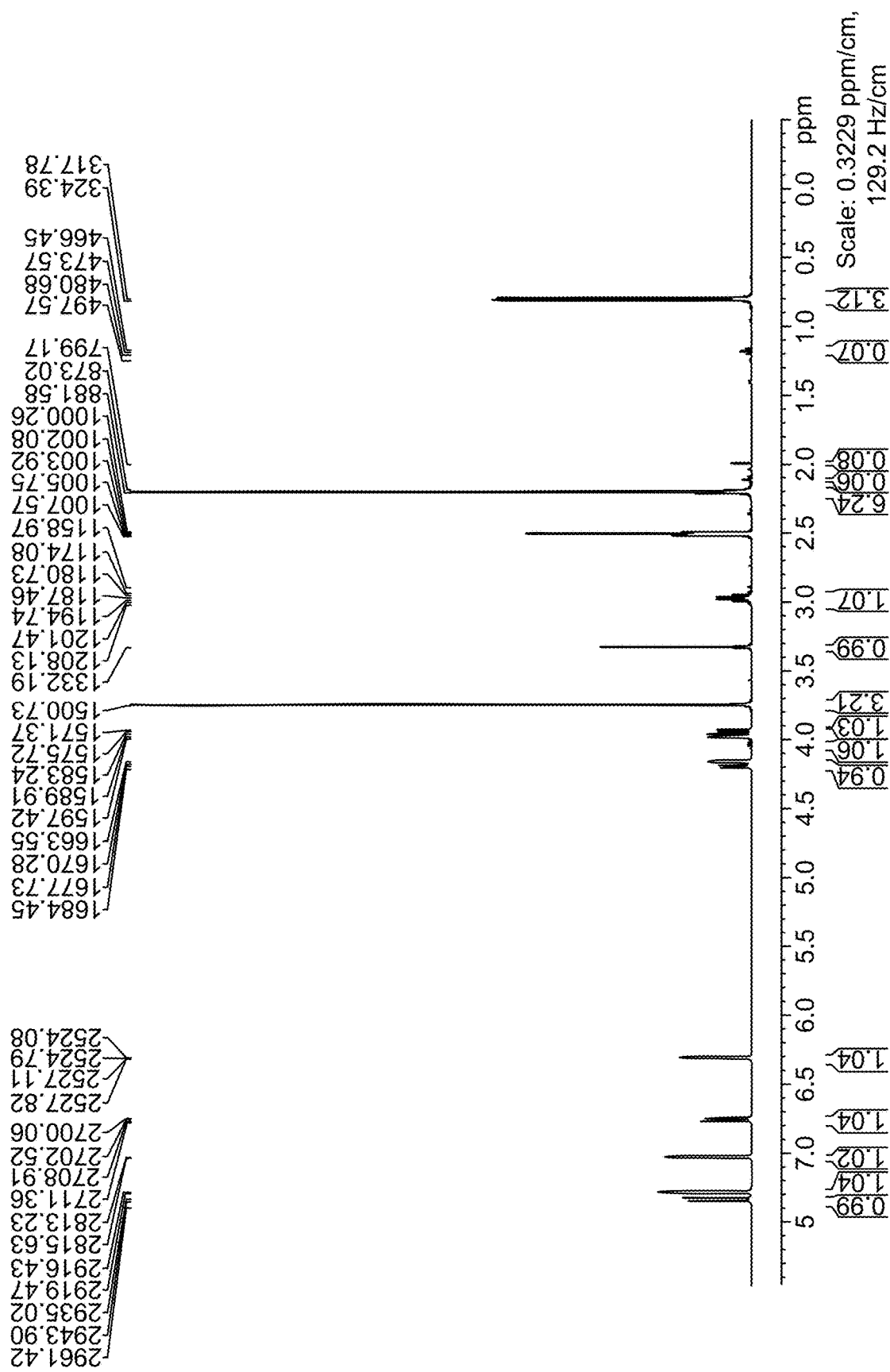

FIG. 185 shows $^1$H NMR spectrum of compound 1 free base.

Figure 186:
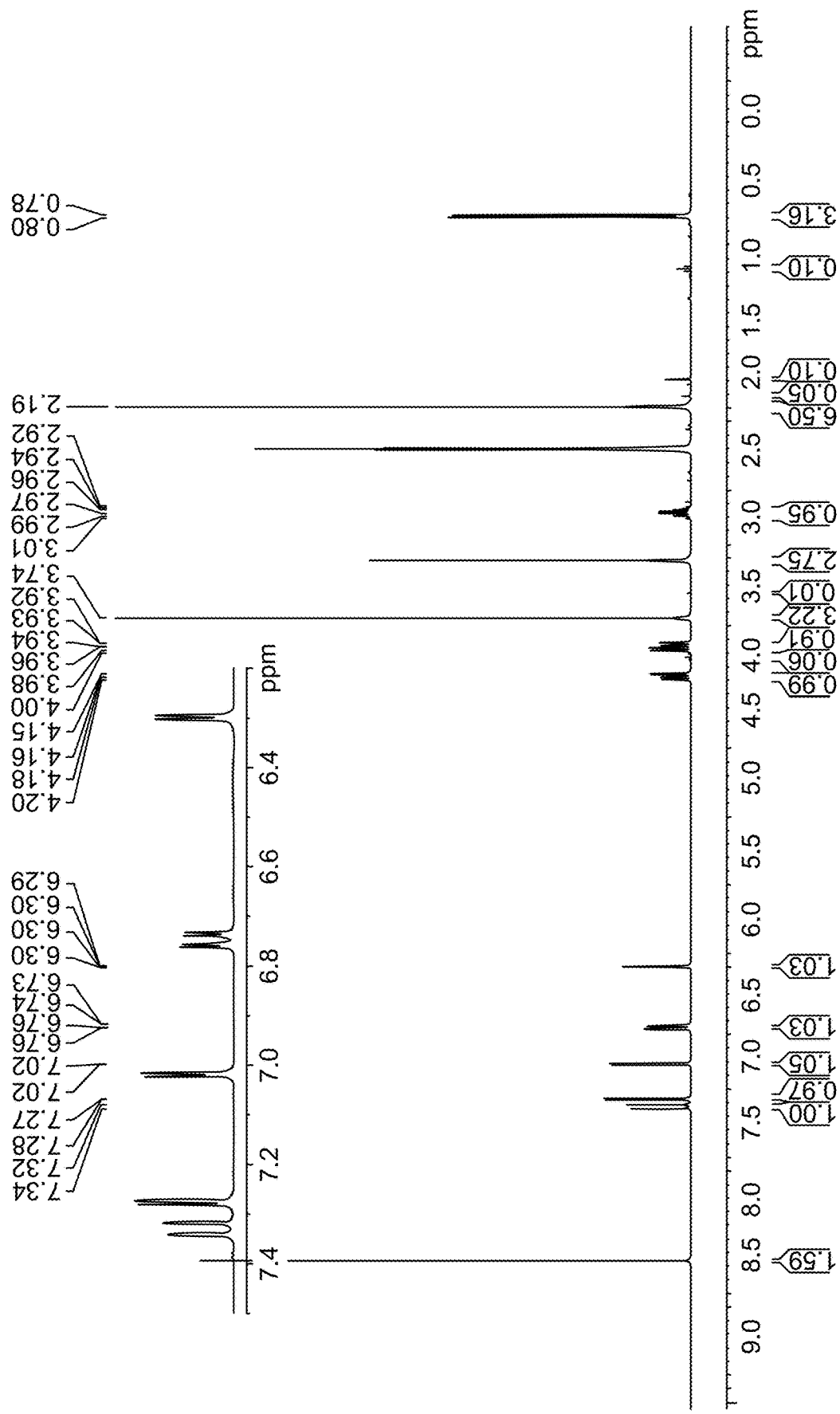

FIG. 186 shows a Q $^1$H NMR assay spectrum of compound 1 free base.

Figure 187:
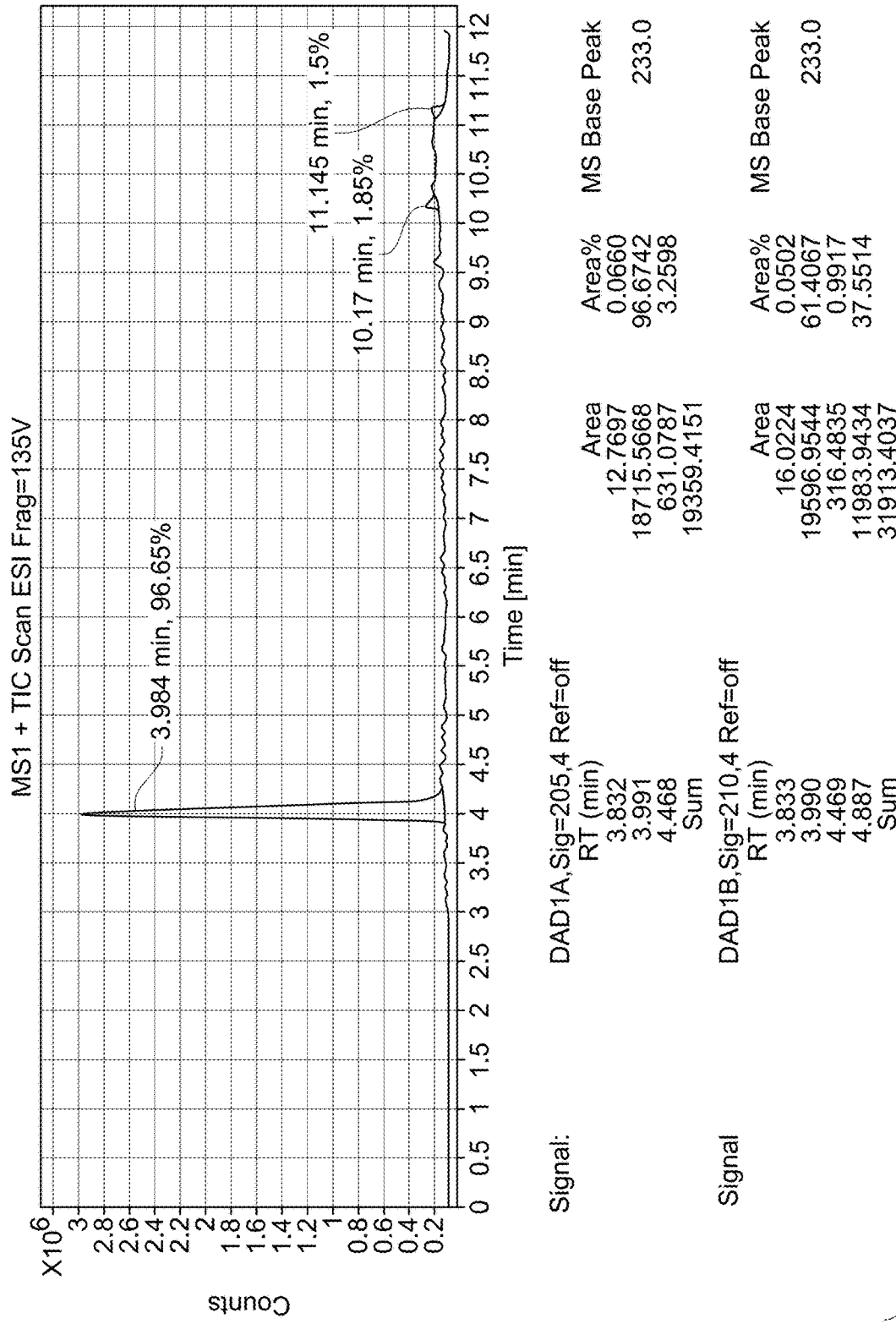

FIG. 187 shows LC-MS profile of compound 1 free base.

Figure 188:
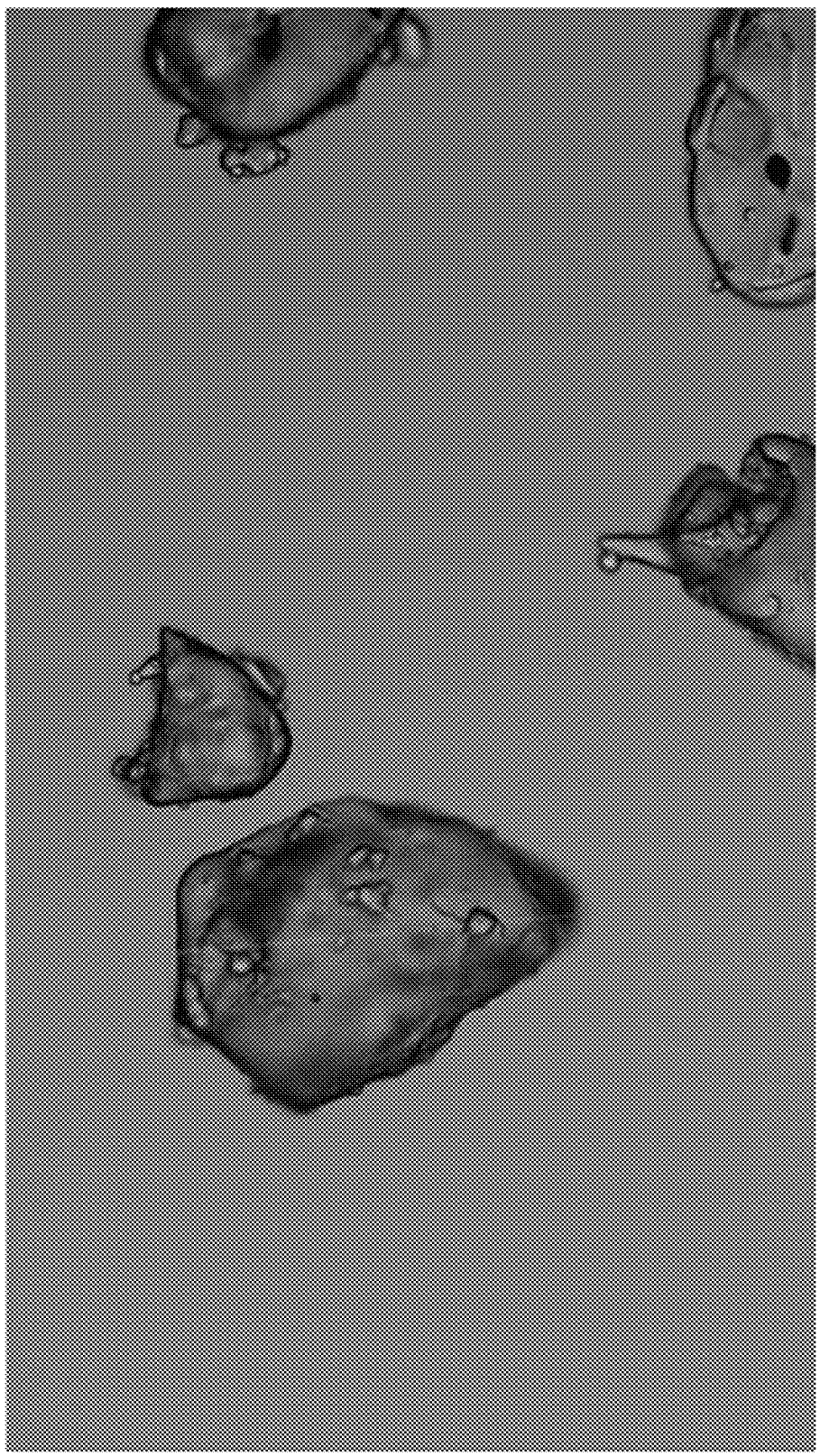

FIG. 188 shows PLM of compound 1 free base (5× magnification)

Figure 189:
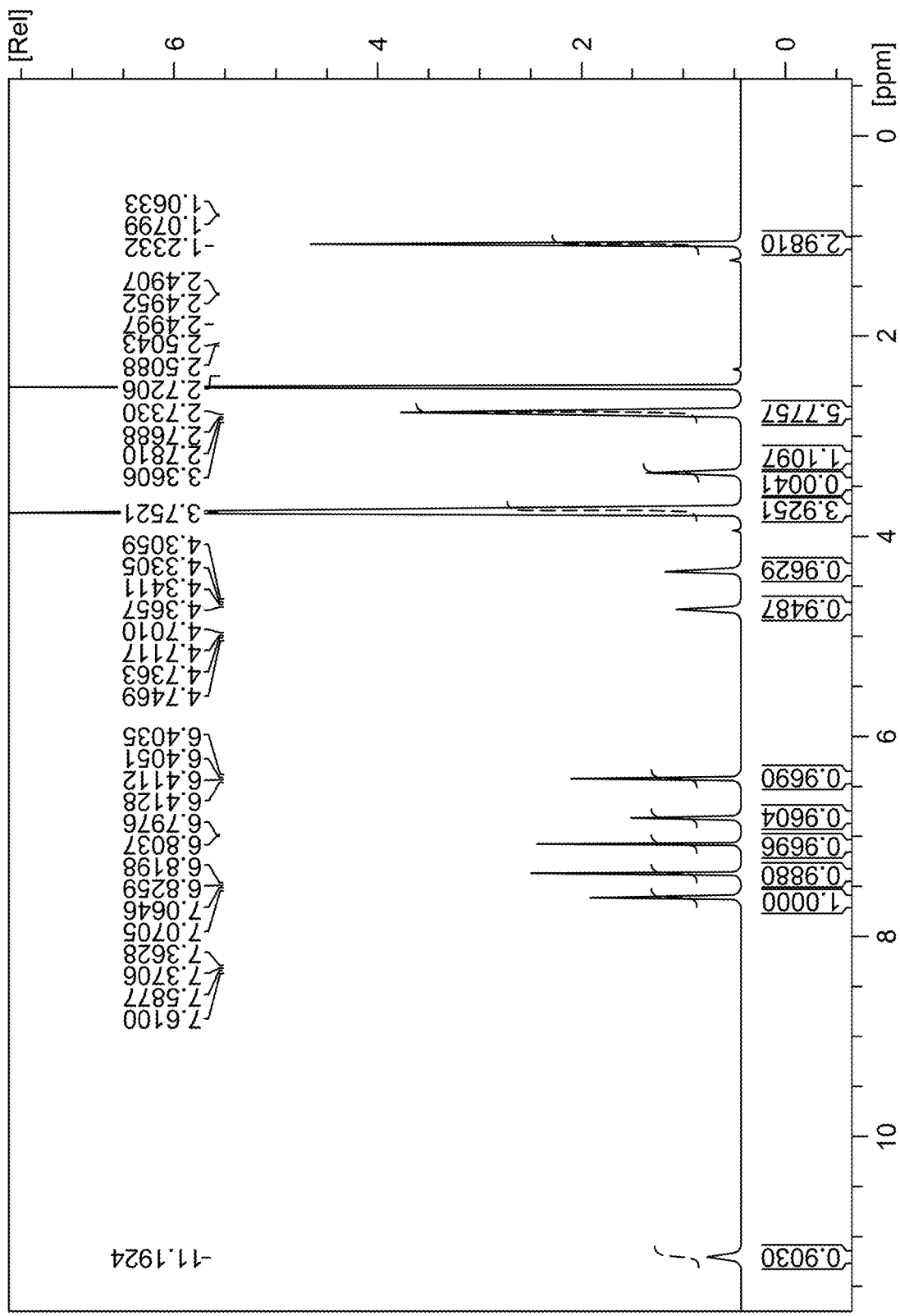

FIG. 189 shows $^1$H NMR spectrum of crystalline compound 1 HCl Form A in DMSO-d6 as deuterated solvent.

Figure 190:
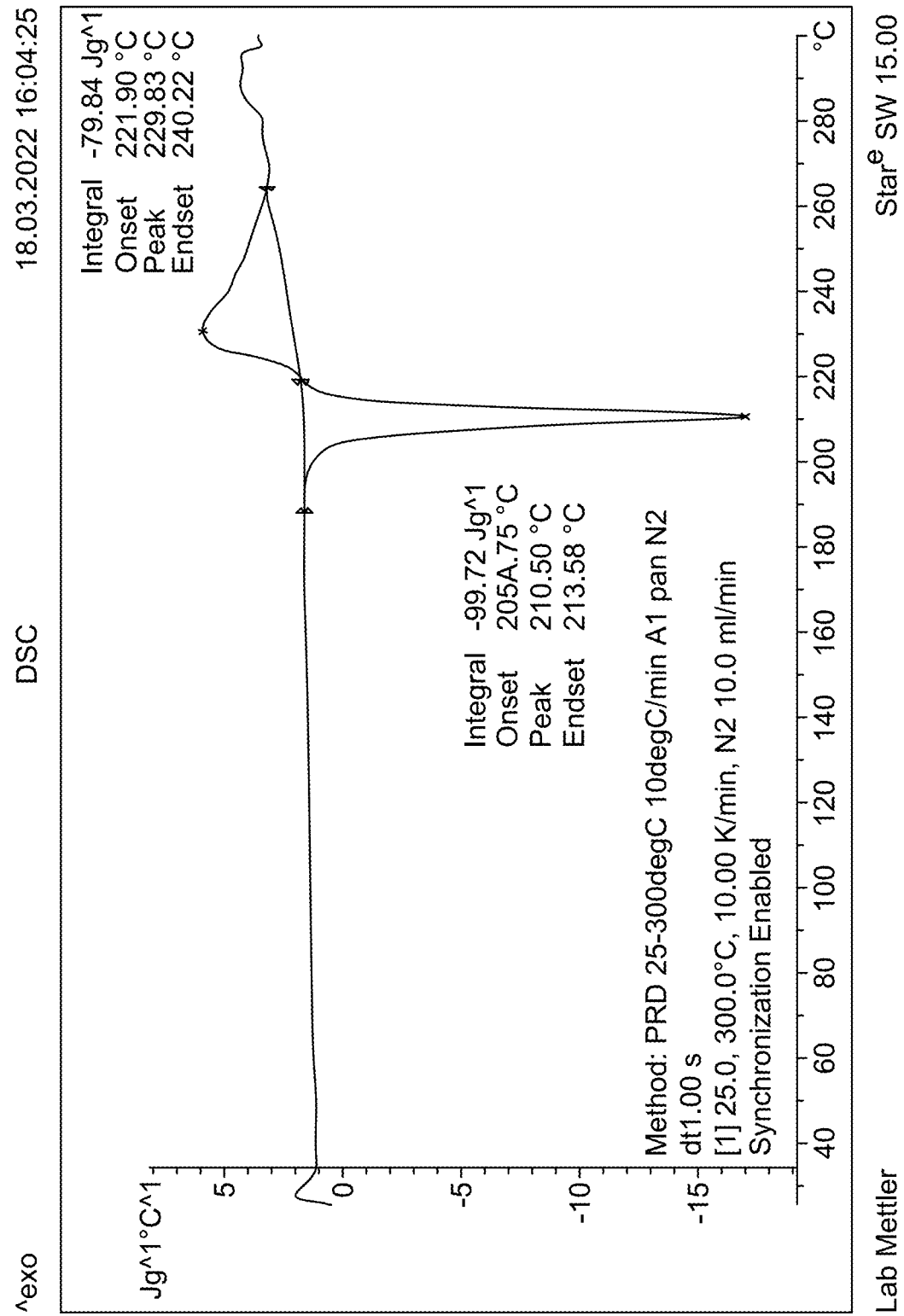

FIG. 190 shows a DSC profile of crystalline compound 1·HCl Form A.

Figure 191:
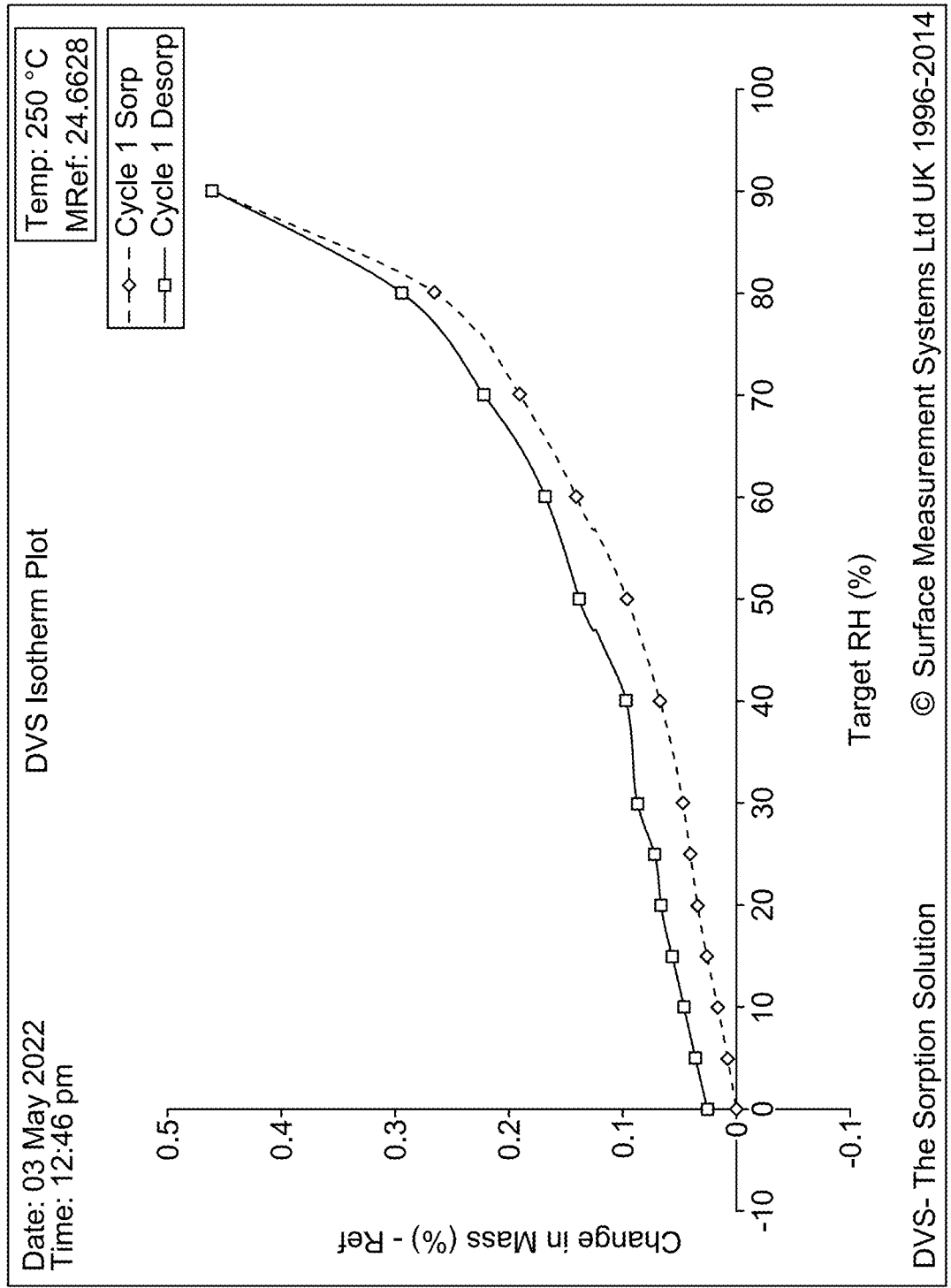

FIG. 191 shows a DVS isotherm plot of compound 1·HCl Form A.

Figure 192:
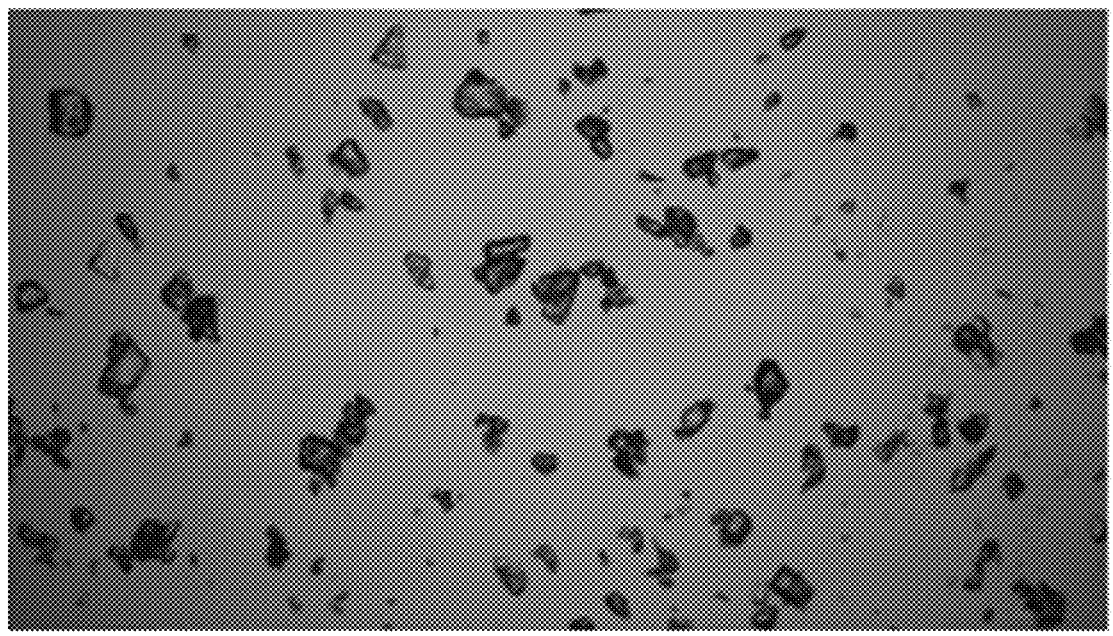

FIG. 192 shows a PLM of crystalline compound 1 HCl Form A salt×2 mag, no polarizers (NP).

Figure 193:
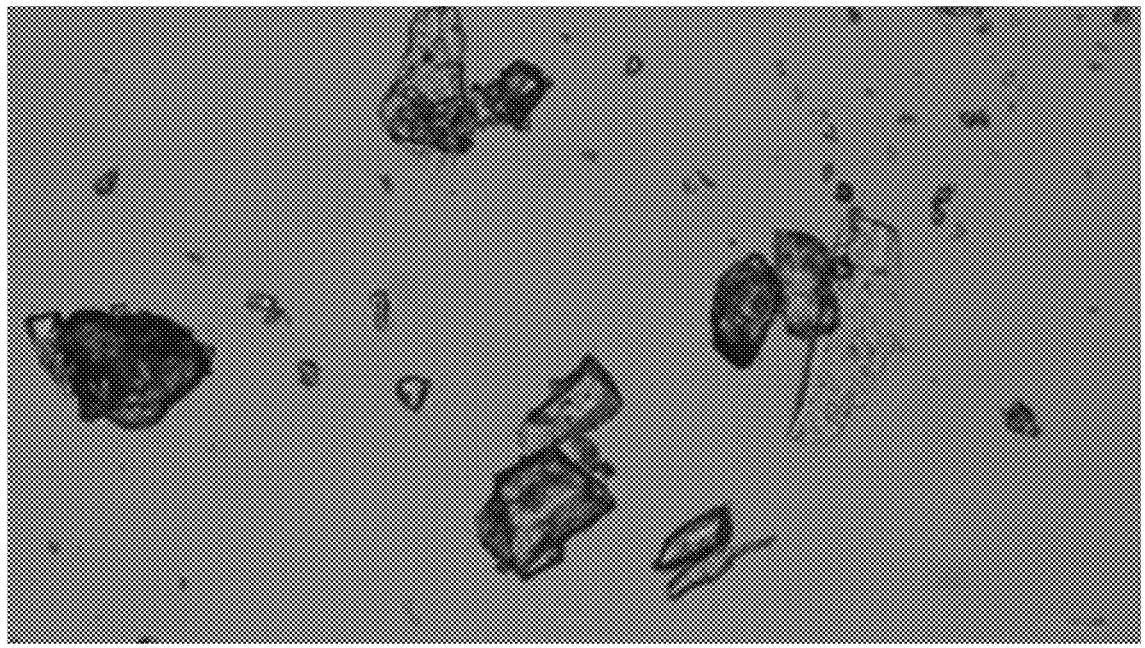

FIG. 193 shows a PLM of crystalline compound 1 HCl Form A×5 mag, NP.

Figure 194:
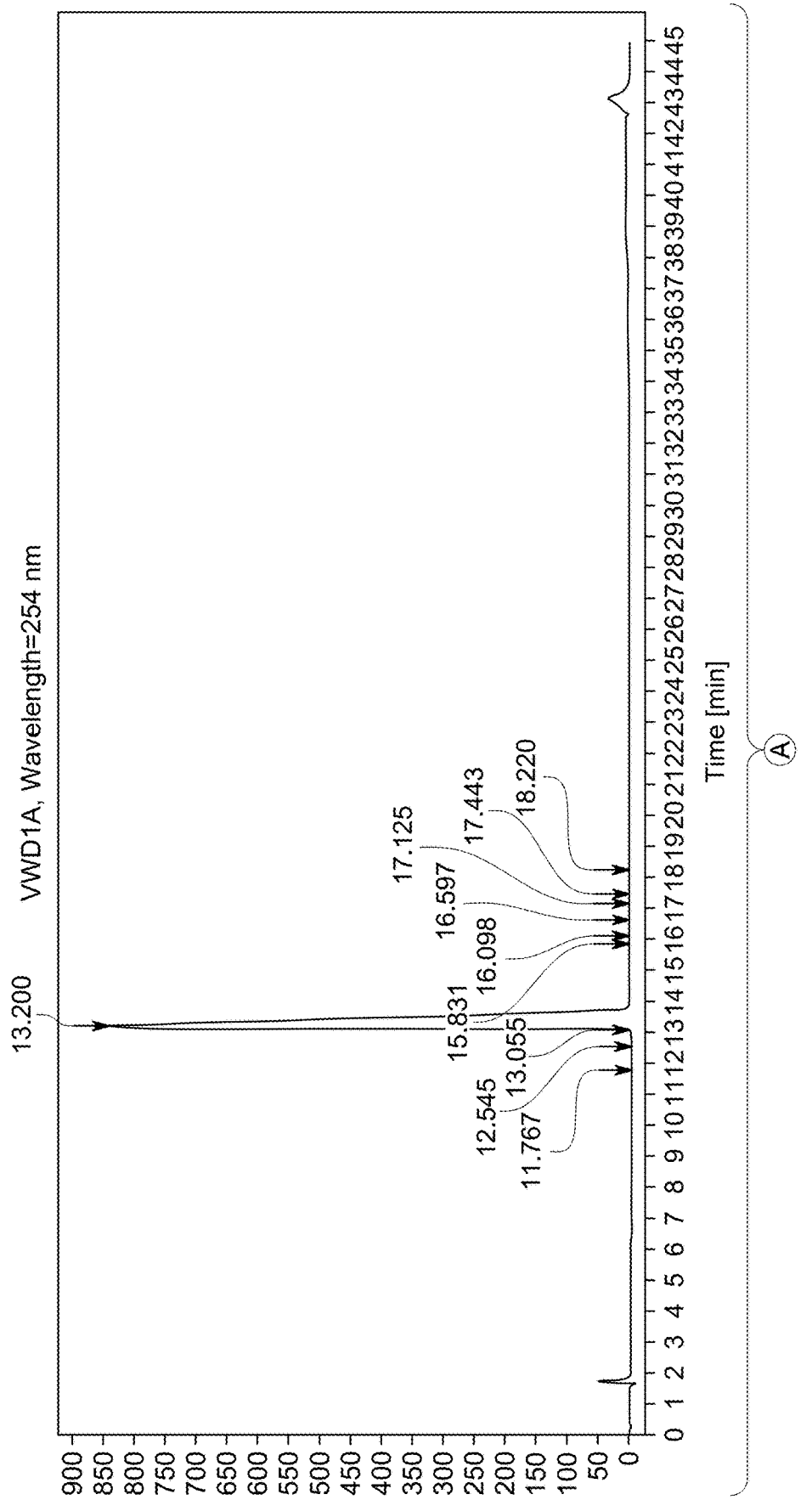

FIG. 194 shows a HPLC profile of crystalline compound 1·HCl Form A.

Figure 195:
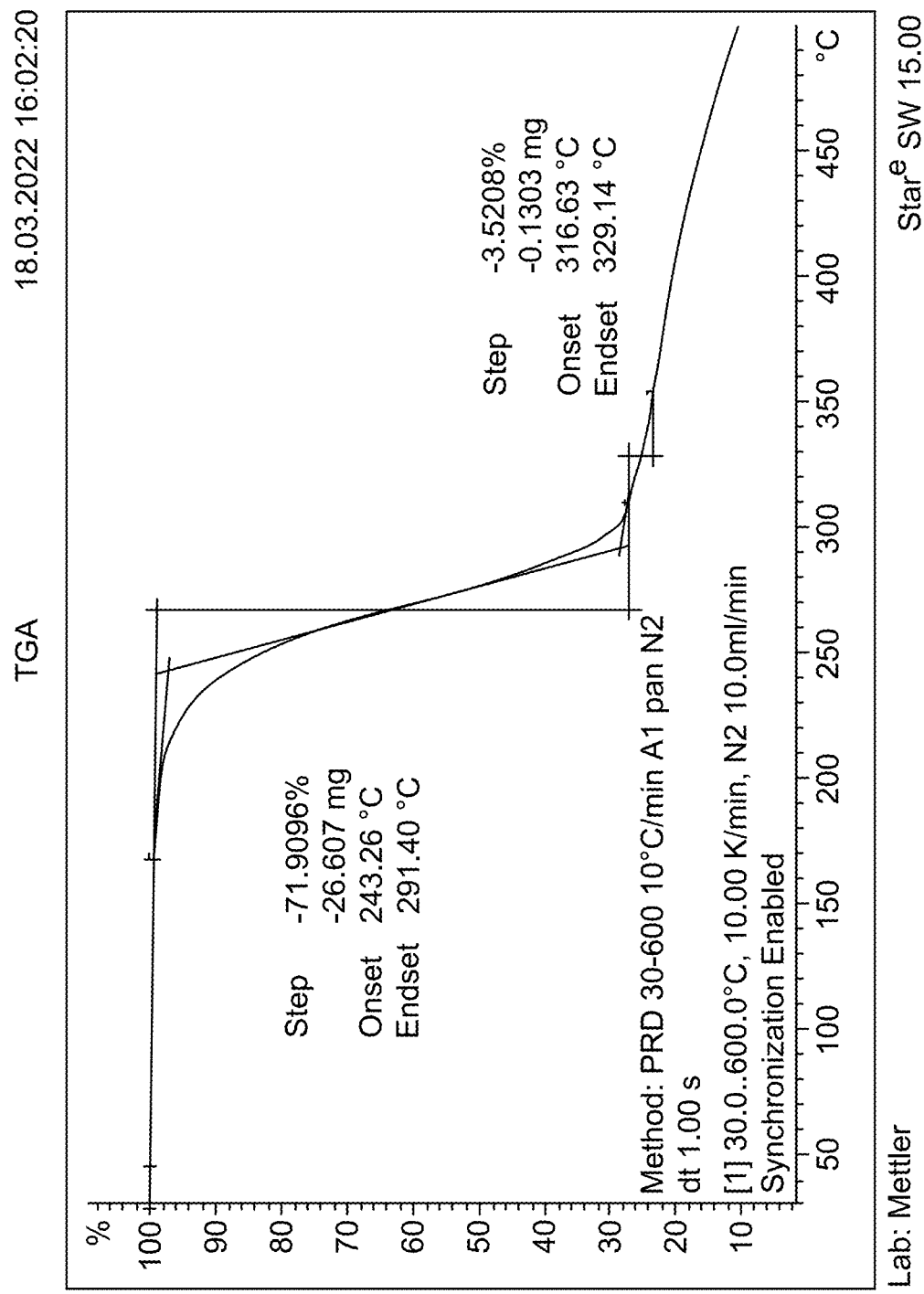

FIG. 195 shows a TGA profile of crystalline compound 1·HCl Form A.

Figure 196:
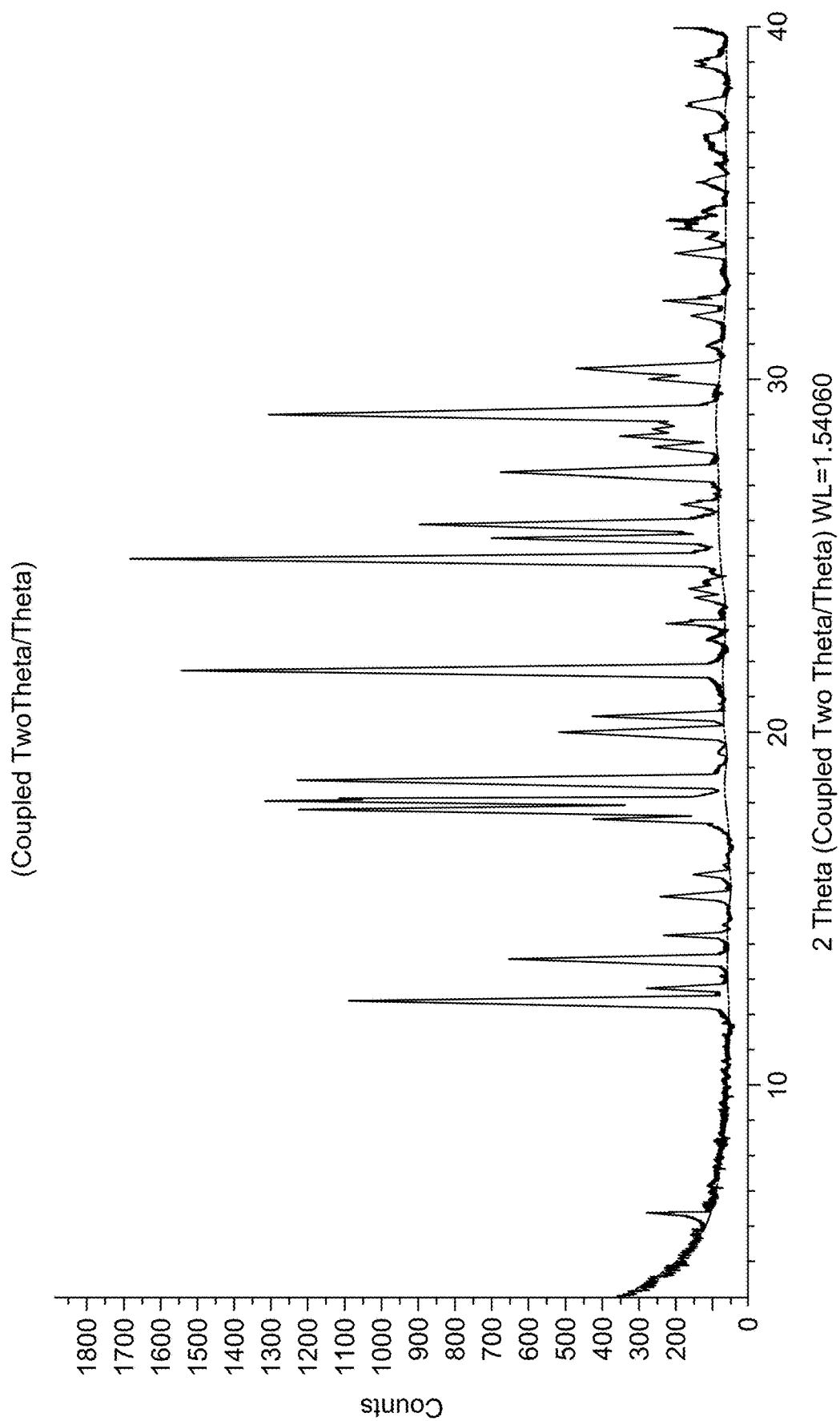

FIG. 196 shows a XRPD profile of crystalline compound 1 HCl Form A.

Figure 197:
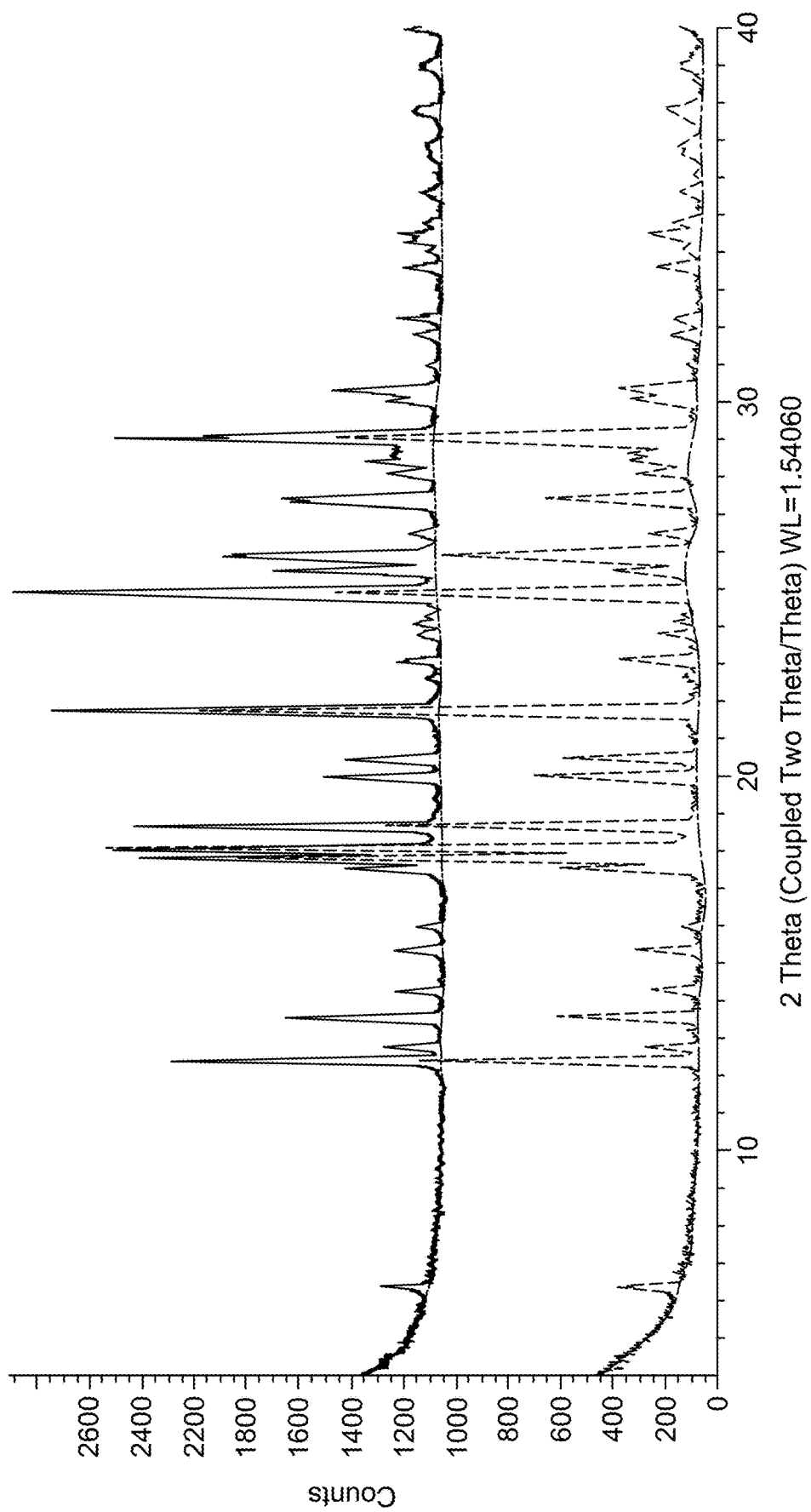

FIG. 197 shows overlaid of XRPD profiles of two preparations of crystalline compound 1 HCl.

Figure 198:
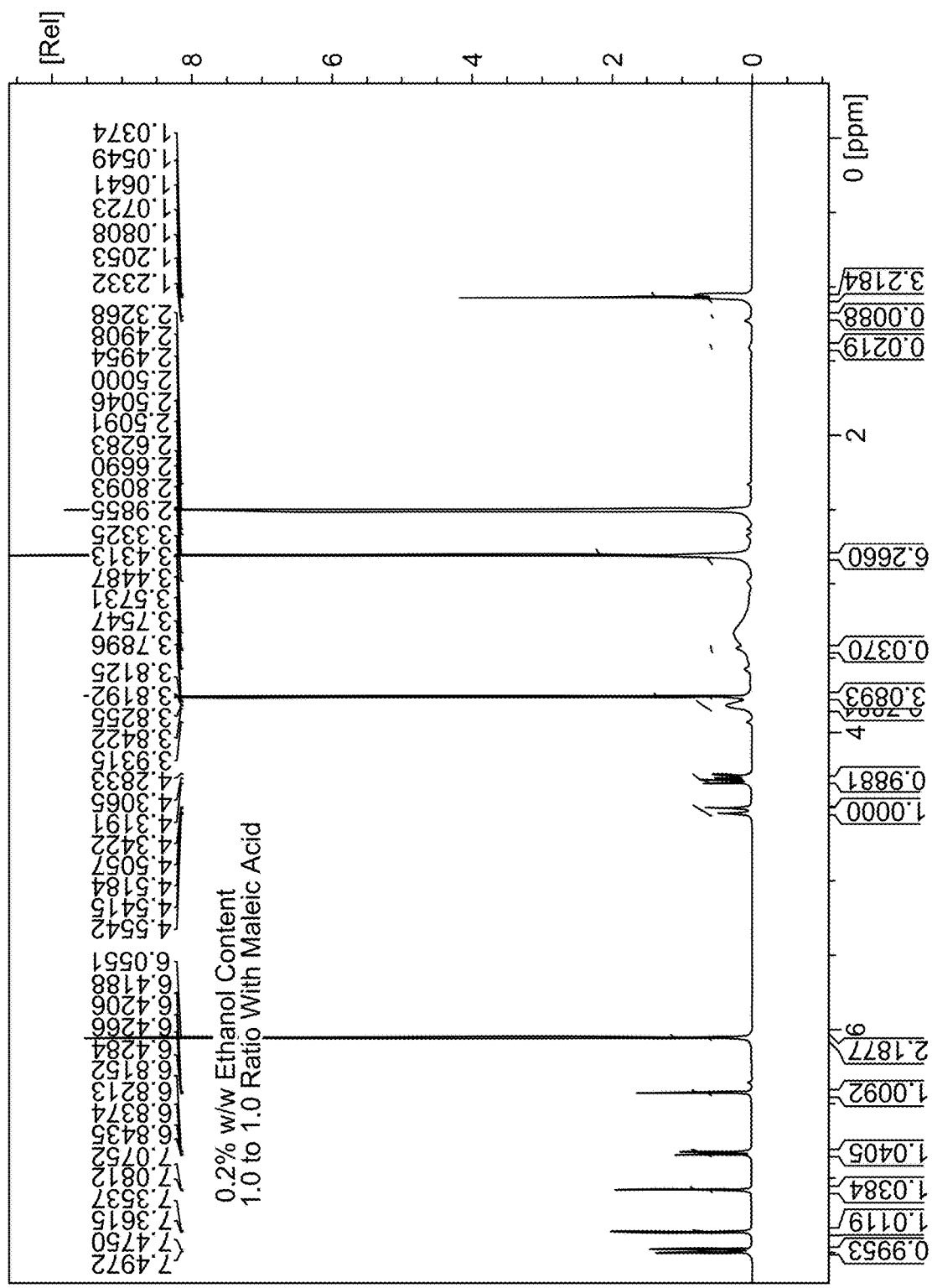

FIG. 198 shows $^1$H NMR spectrum of crystalline compound 1 maleate.

Figure 199:
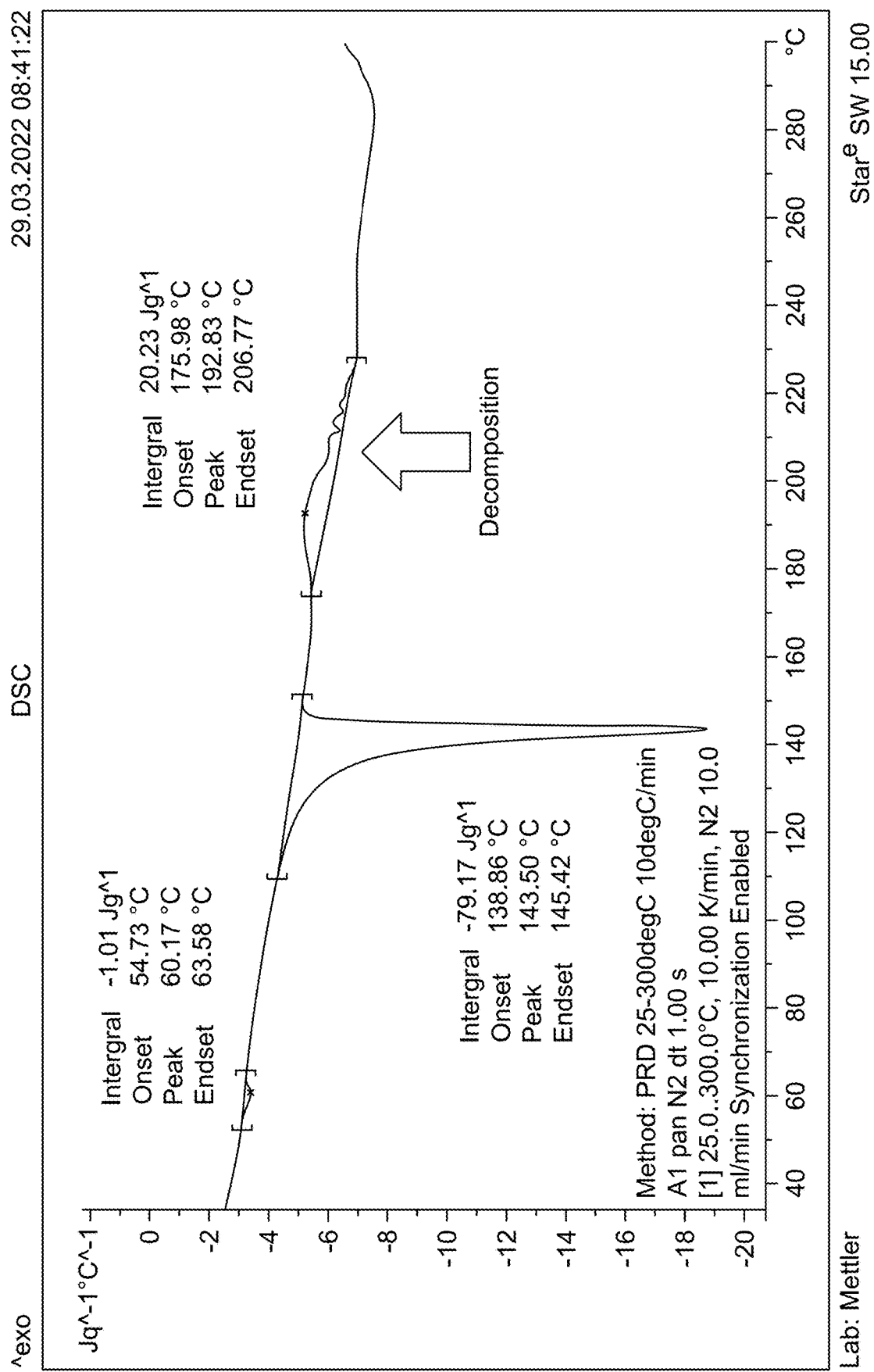

FIG. 199 shows DSC profile of crystalline compound 1 maleate.

Figure 200:
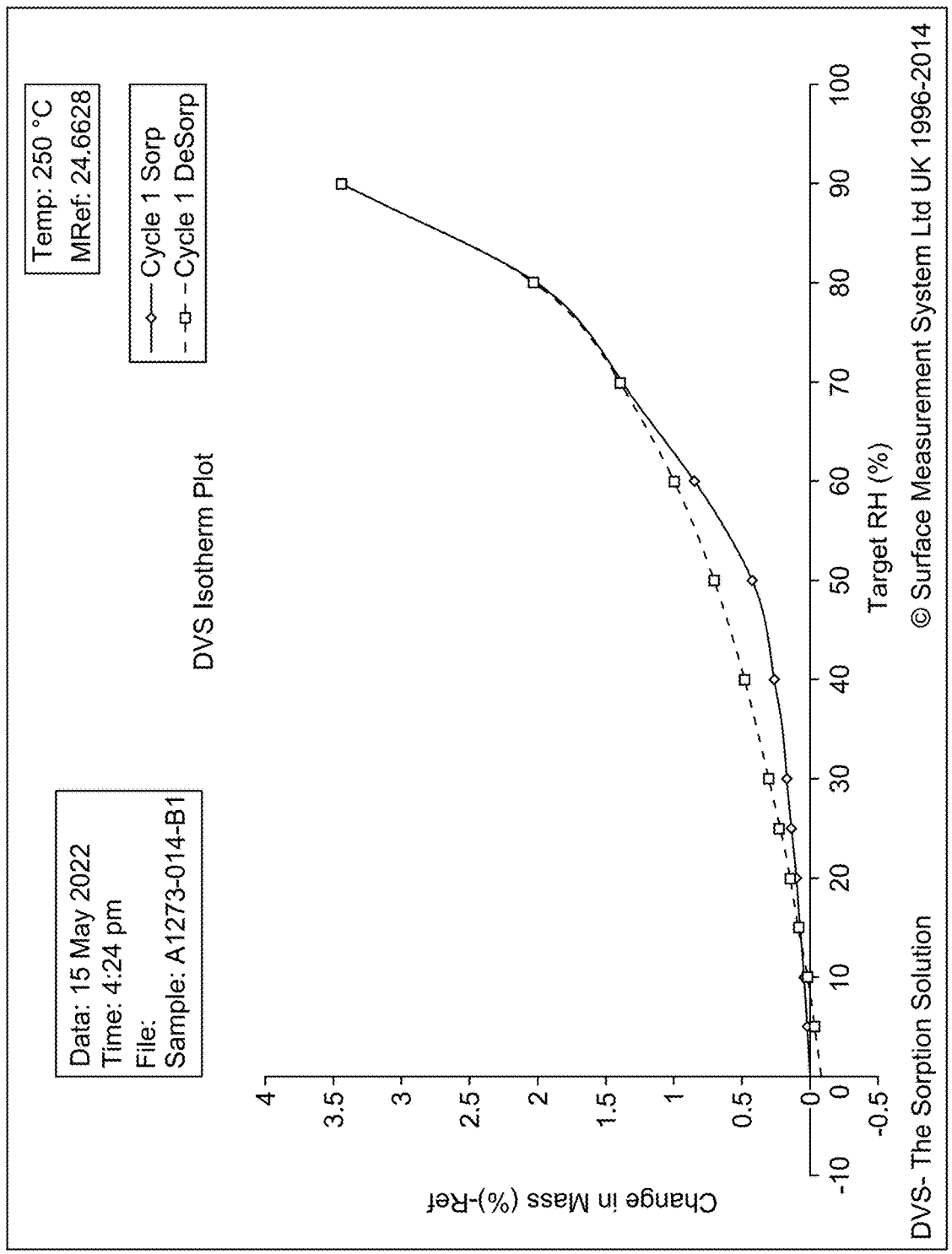

FIG. 200 shows DVS isotherm plot of crystalline compound 1 maleate.

Figure 201:
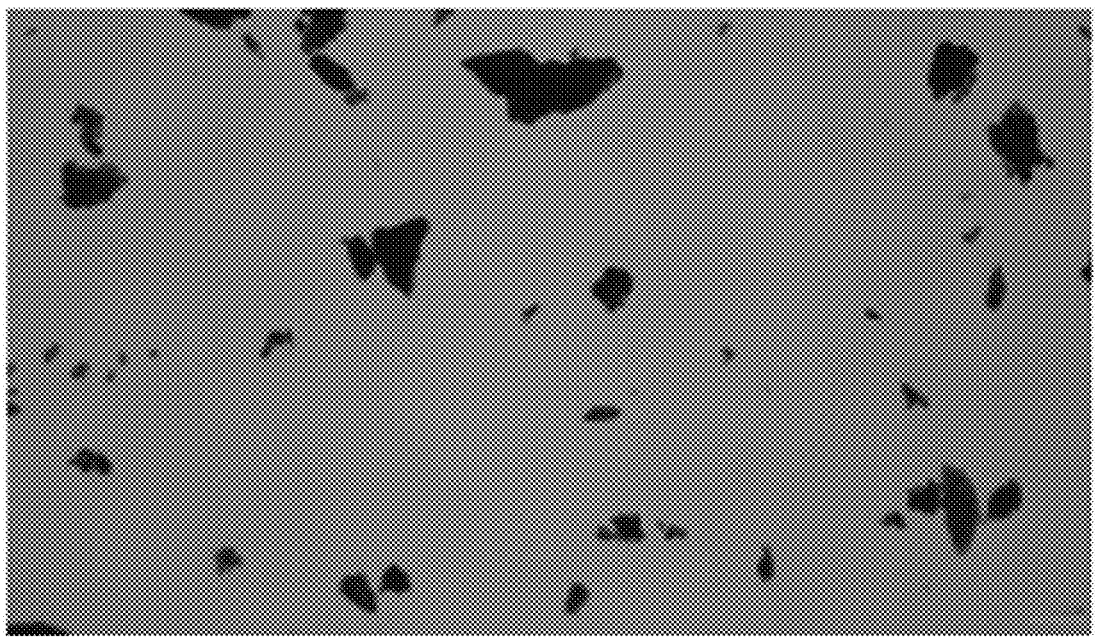

FIG. 201 shows PLM of crystalline compound 1 maleate×2 mag, NP.

Figure 202:
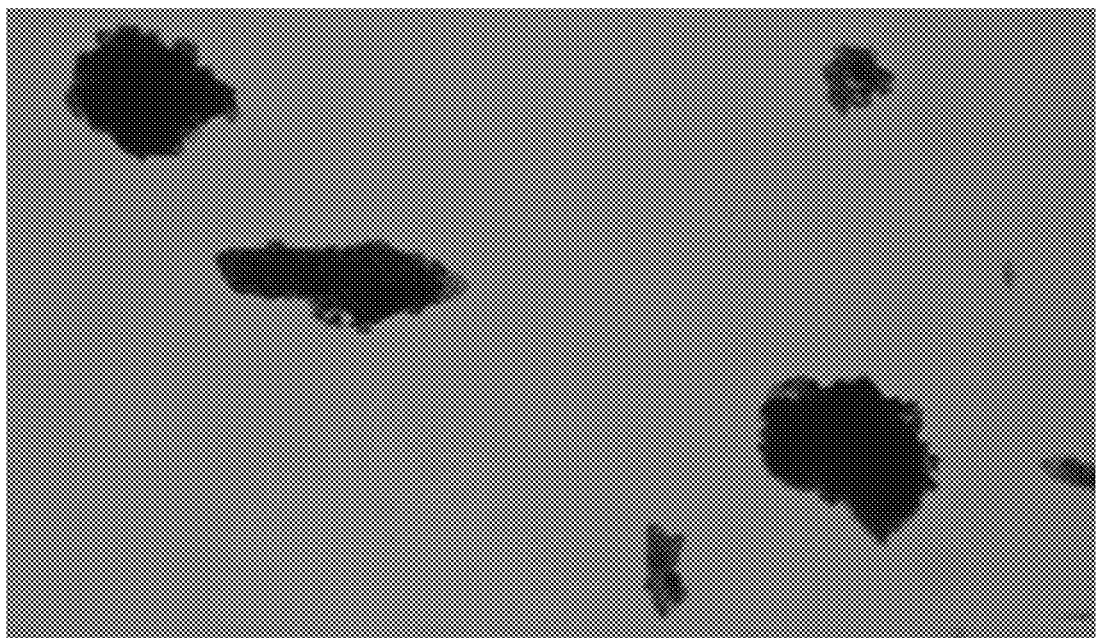

FIG. 202 shows PLM of crystalline compound 1 maleate×5 mag, NP.

Figure 203:
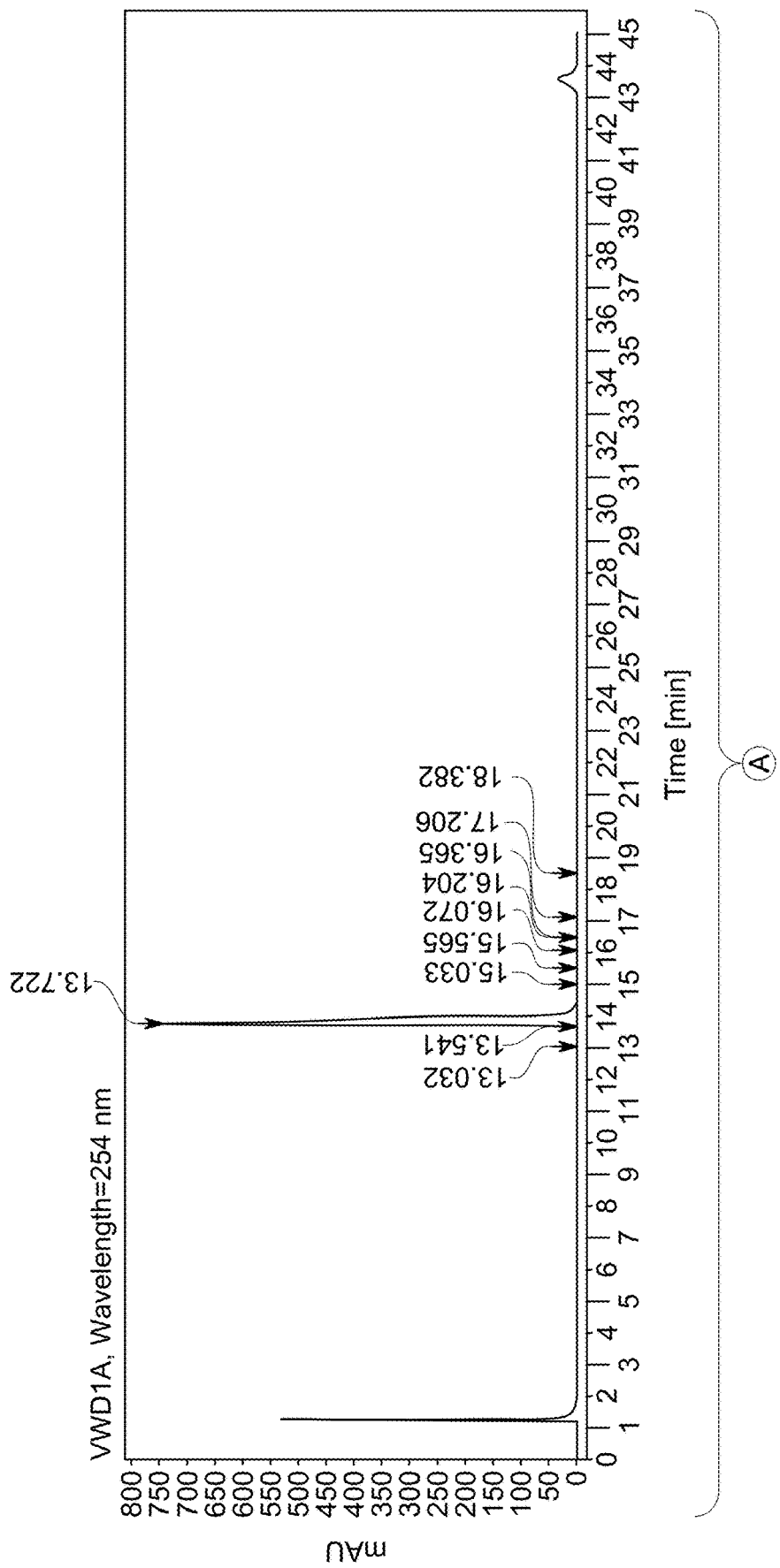

FIG. 203 shows HPLC profile of crystalline compound 1 maleate.

Figure 204:
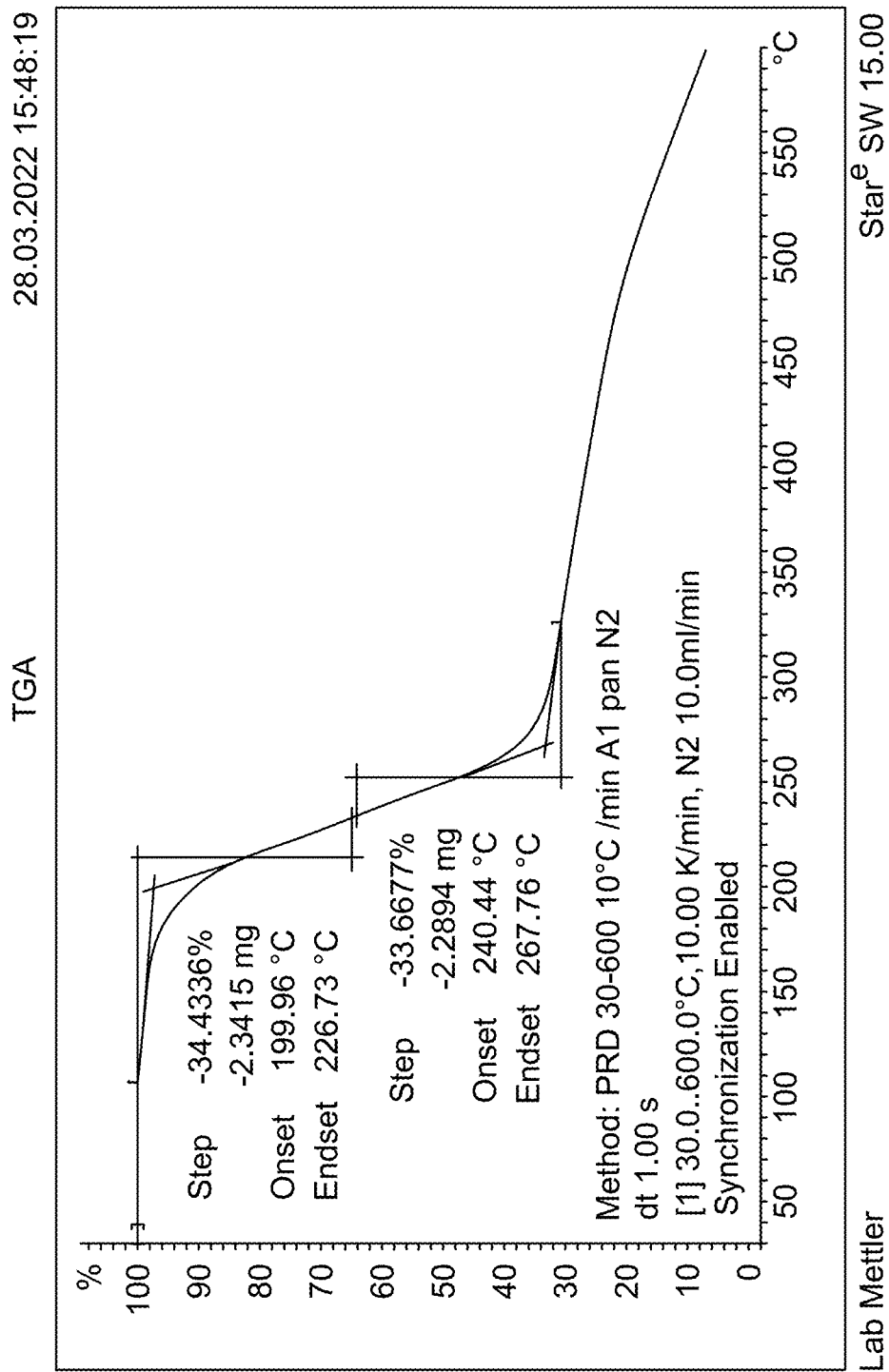

FIG. 204 shows TGA profile of crystalline compound 1 maleate

Figure 205:
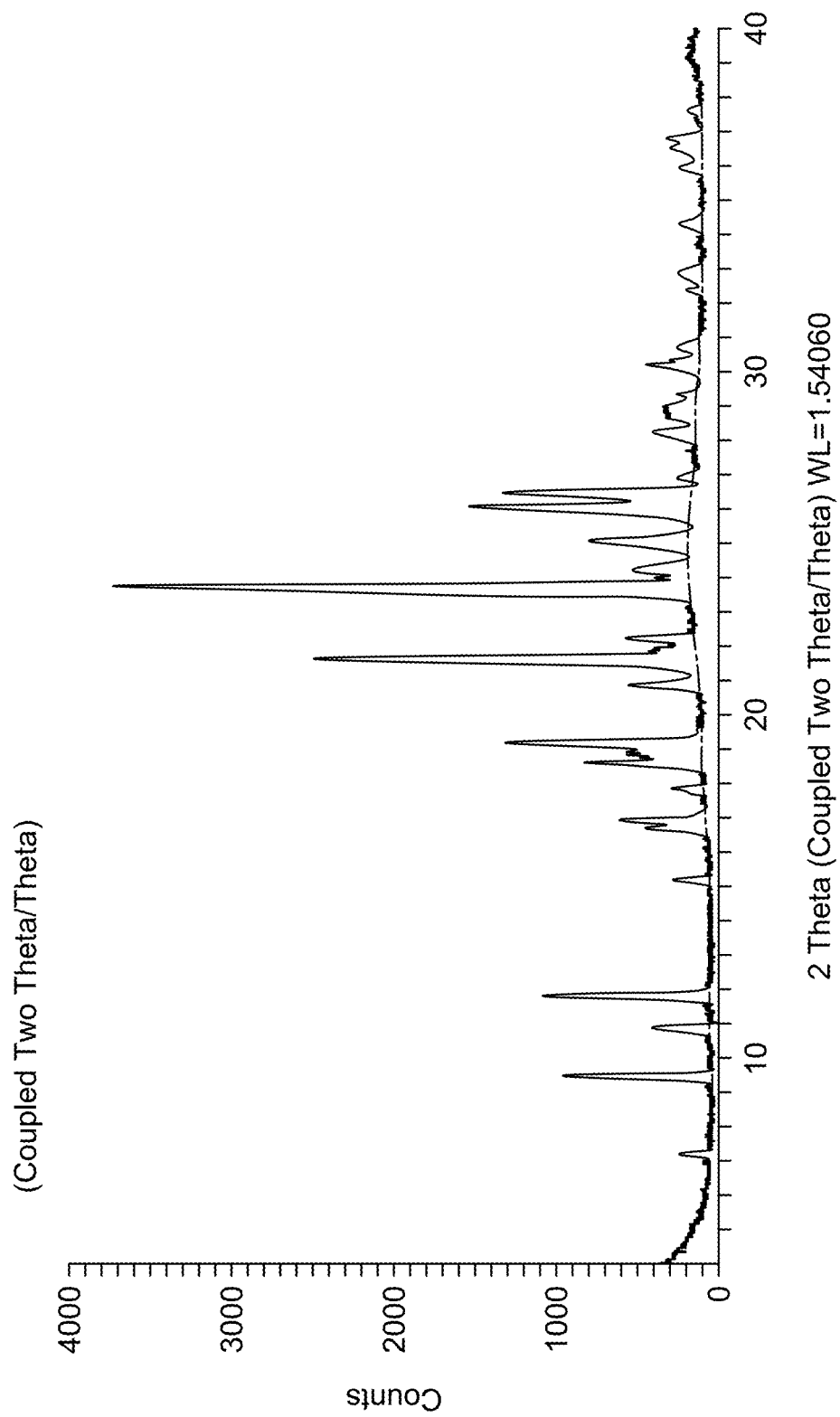

FIG. 205 shows XRPD profile of crystalline compound 1 maleate.

Figure 206:
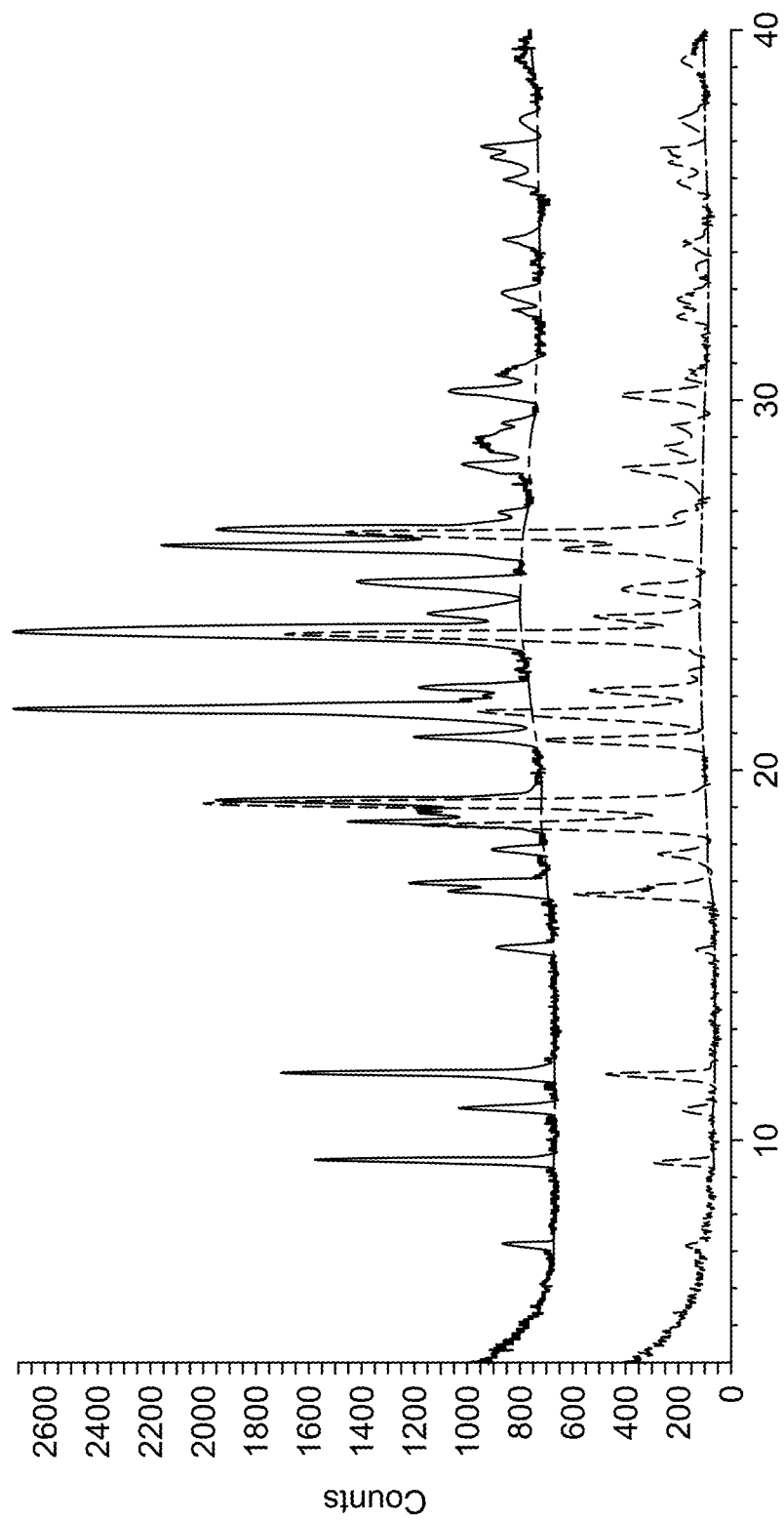

FIG. 206 shows overlaid XRPD profiles of two preparations of crystalline compound 1 maleate.

Figure 207:
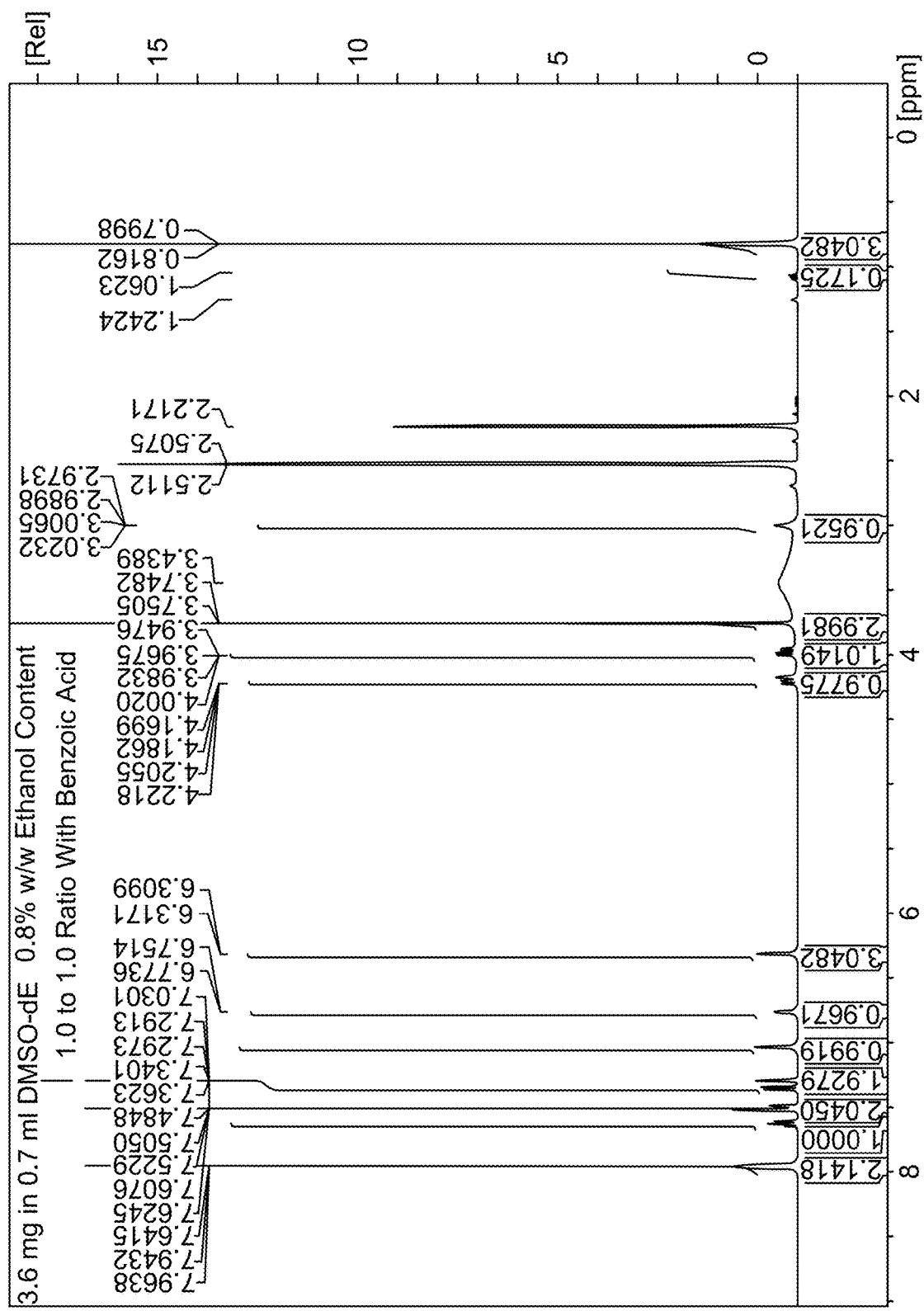

FIG. 207 shows $^1$H NMR spectrum of crystalline compound 1 benzoate.

Figure 208:
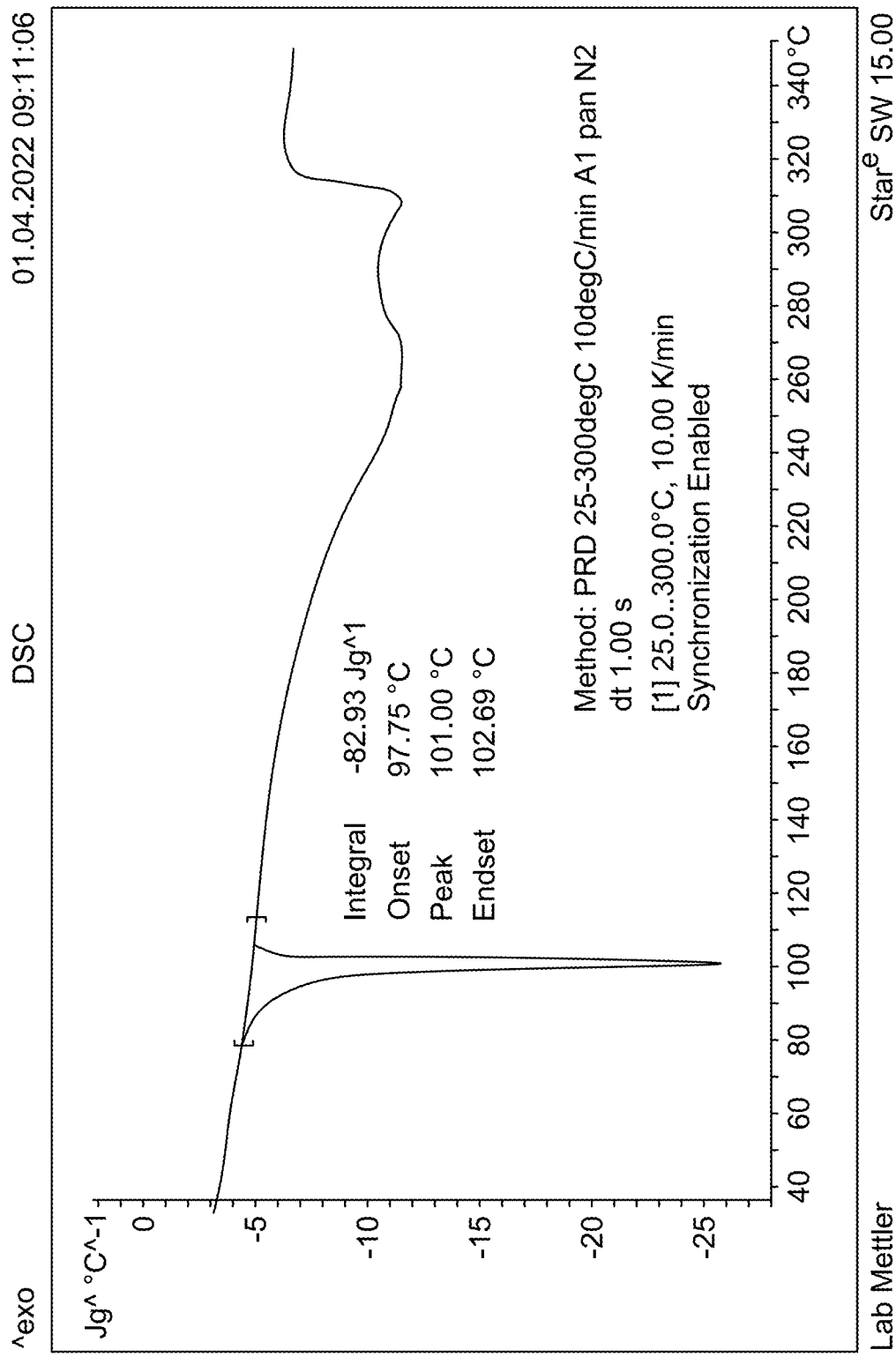

FIG. 208 shows DSC profile of crystalline compound 1 benzoate.

Figure 209:
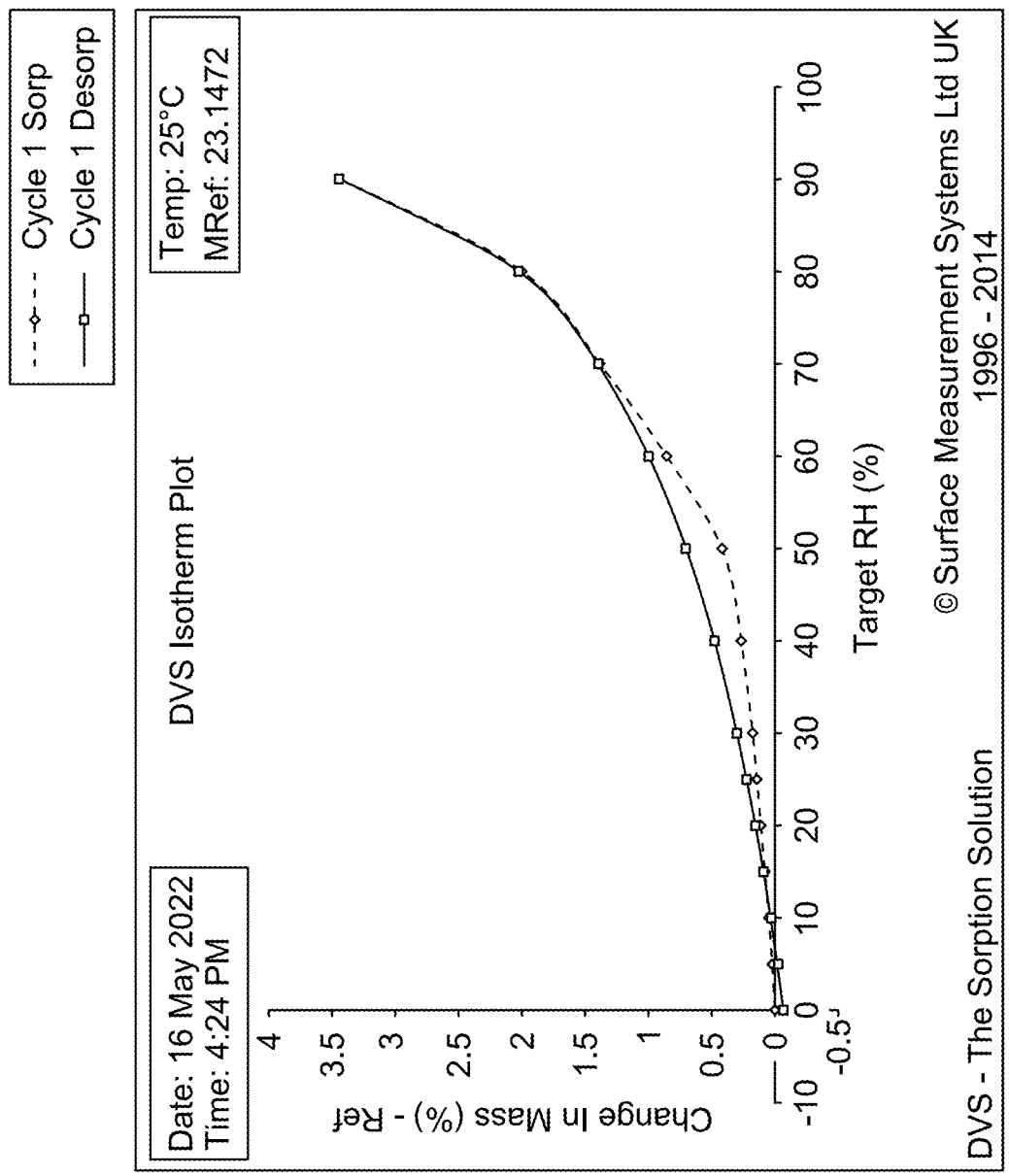

FIG. 209 shows DVS isotherm plot of crystalline compound 1 benzoate.

Figure 210:
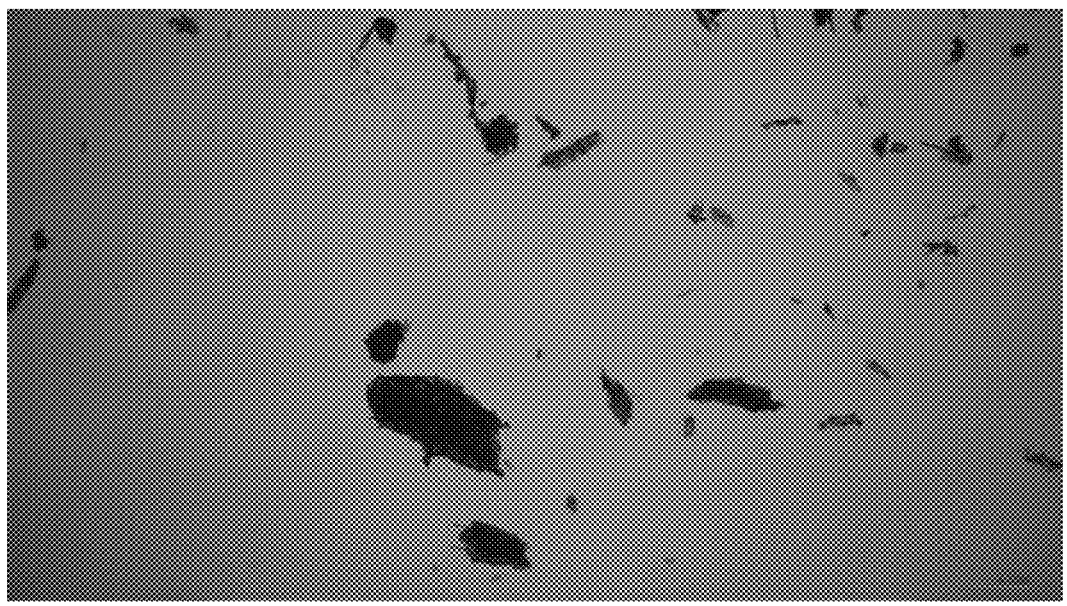

FIG. 210 shows PLM of crystalline compound 1 benzoate×2 mag, no polarizers (NP).

Figure 211:
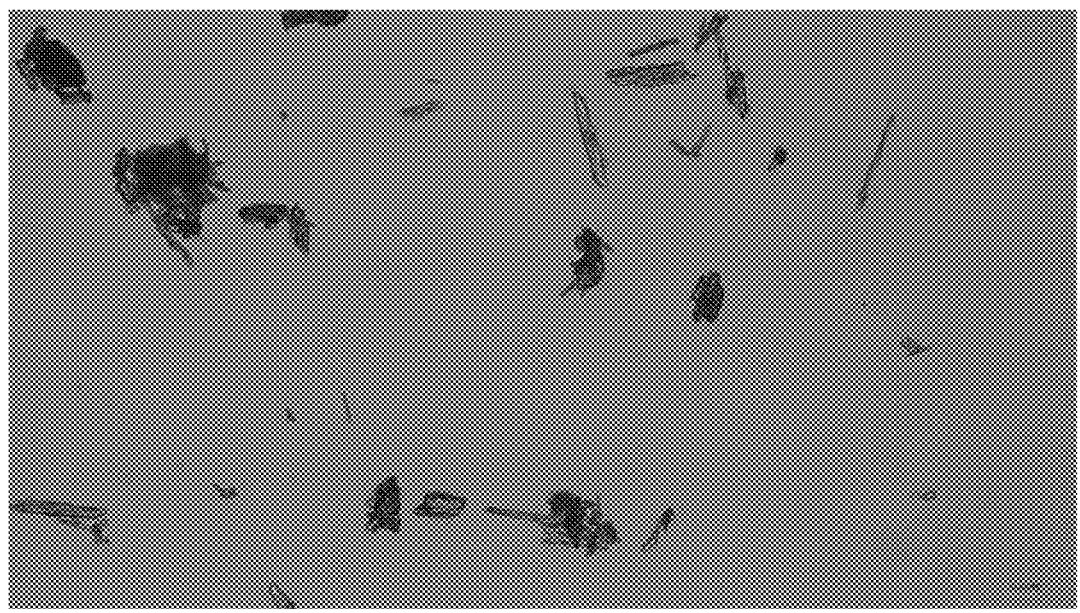

FIG. 211 shows PLM of crystalline compound 1 benzoate×5 mag, NP

Figure 212:
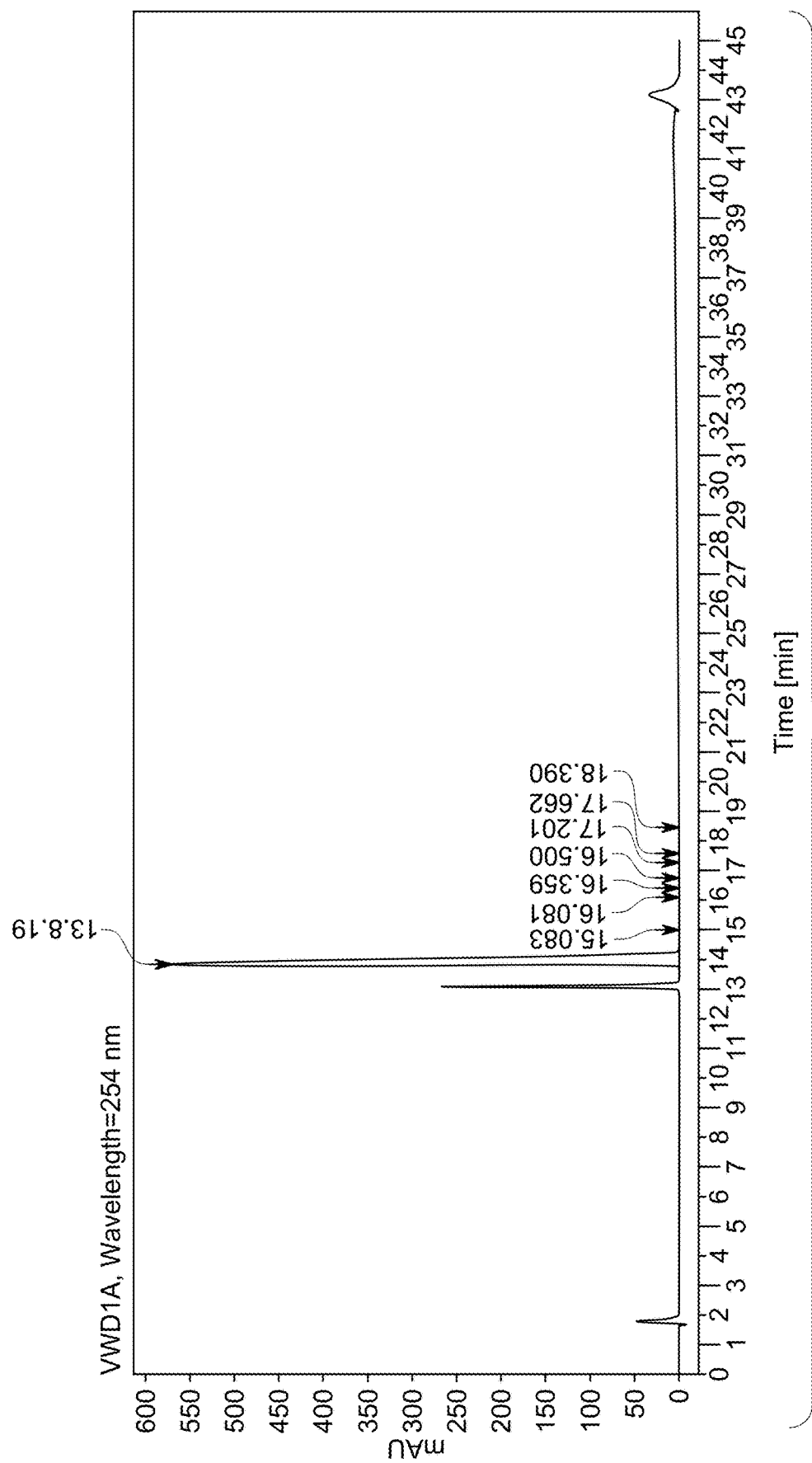

FIG. 212 shows HPLC profile of crystalline compound 1 benzoate

Figure 213:
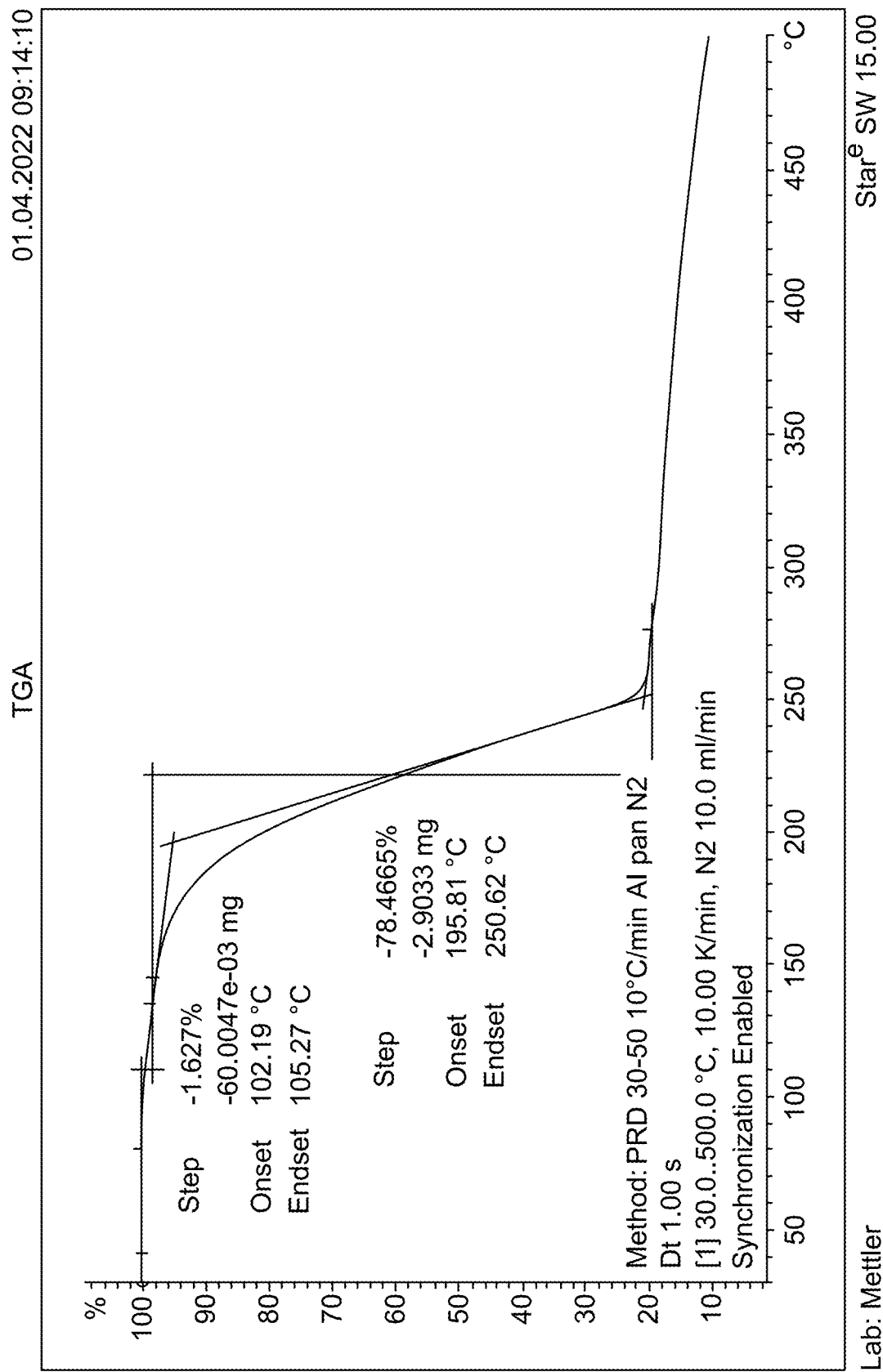

FIG. 213 shows TGA profile of crystalline compound 1 benzoate.

Figure 214:
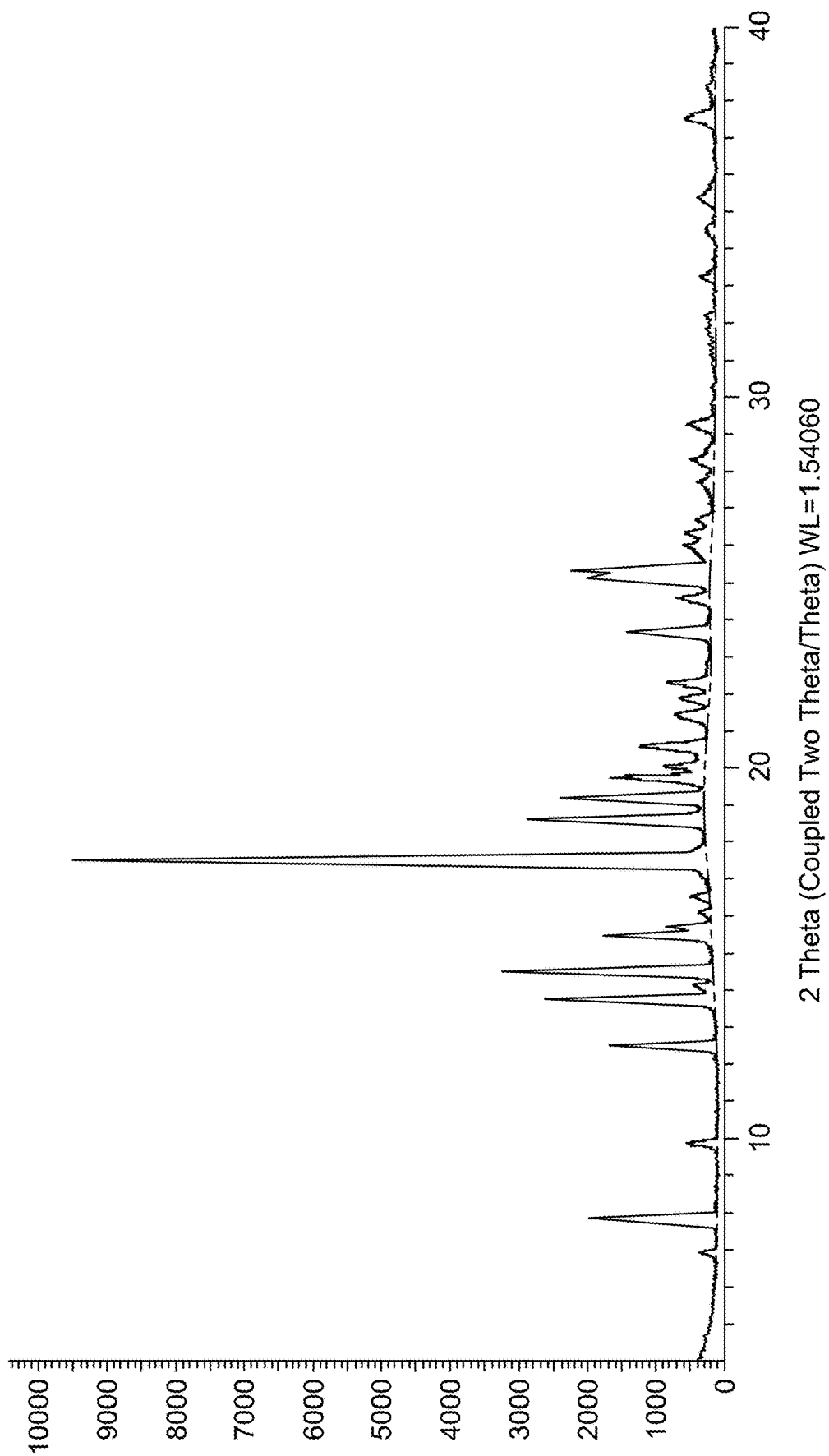

FIG. 214 shows XRPD profile of crystalline compound 1 benzoate.

Figure 215:
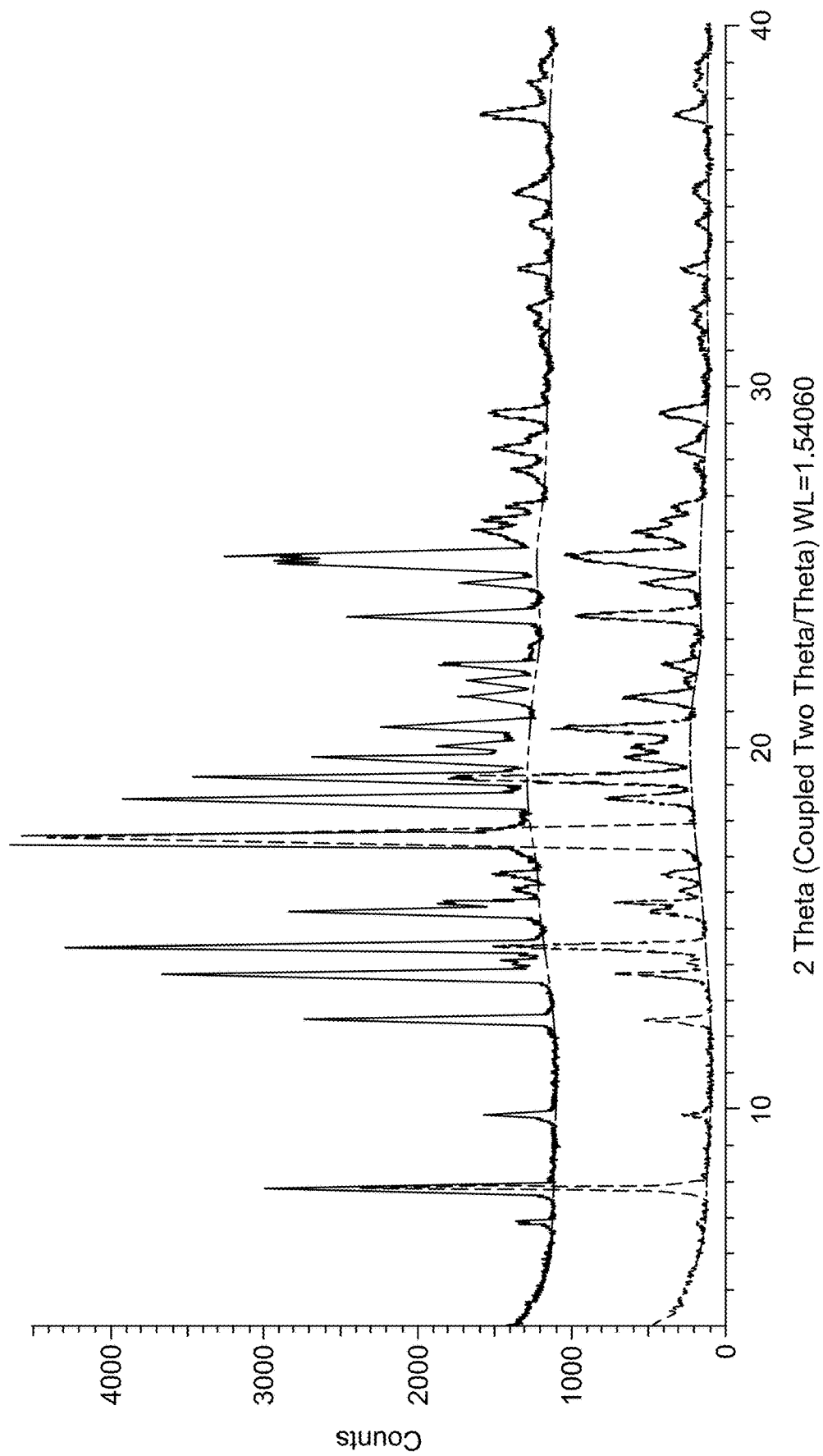

FIG. 215 shows overlaid of XRPD profiles of two preparations of crystalline compound 1 benzoate.

Figure 216:
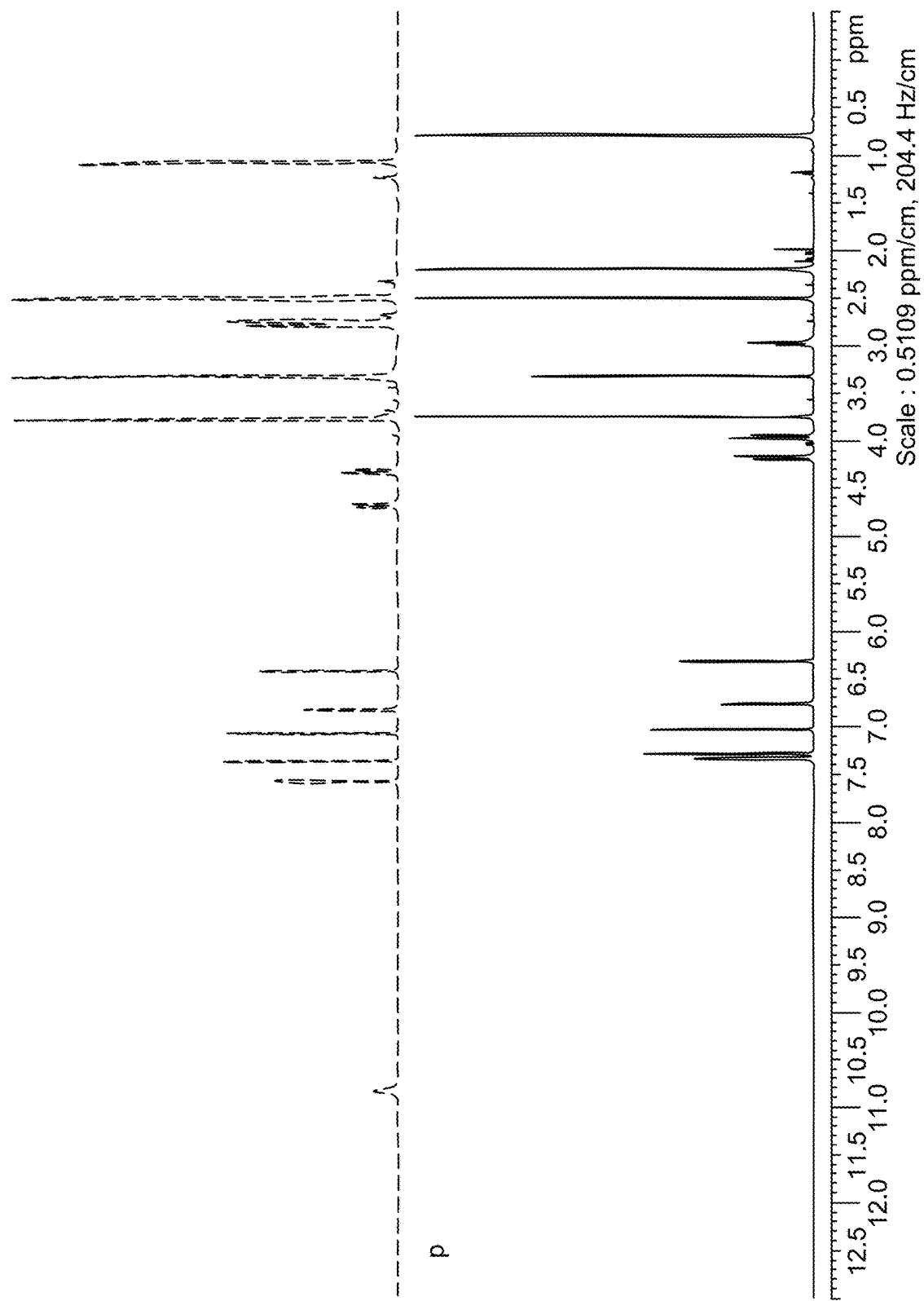

FIG. 216 shows Overlaid of $^1$H NMR spectra of crystalline compound 1 HCl (top, red) and amorphous compound 1 (bottom).

Figure 217:
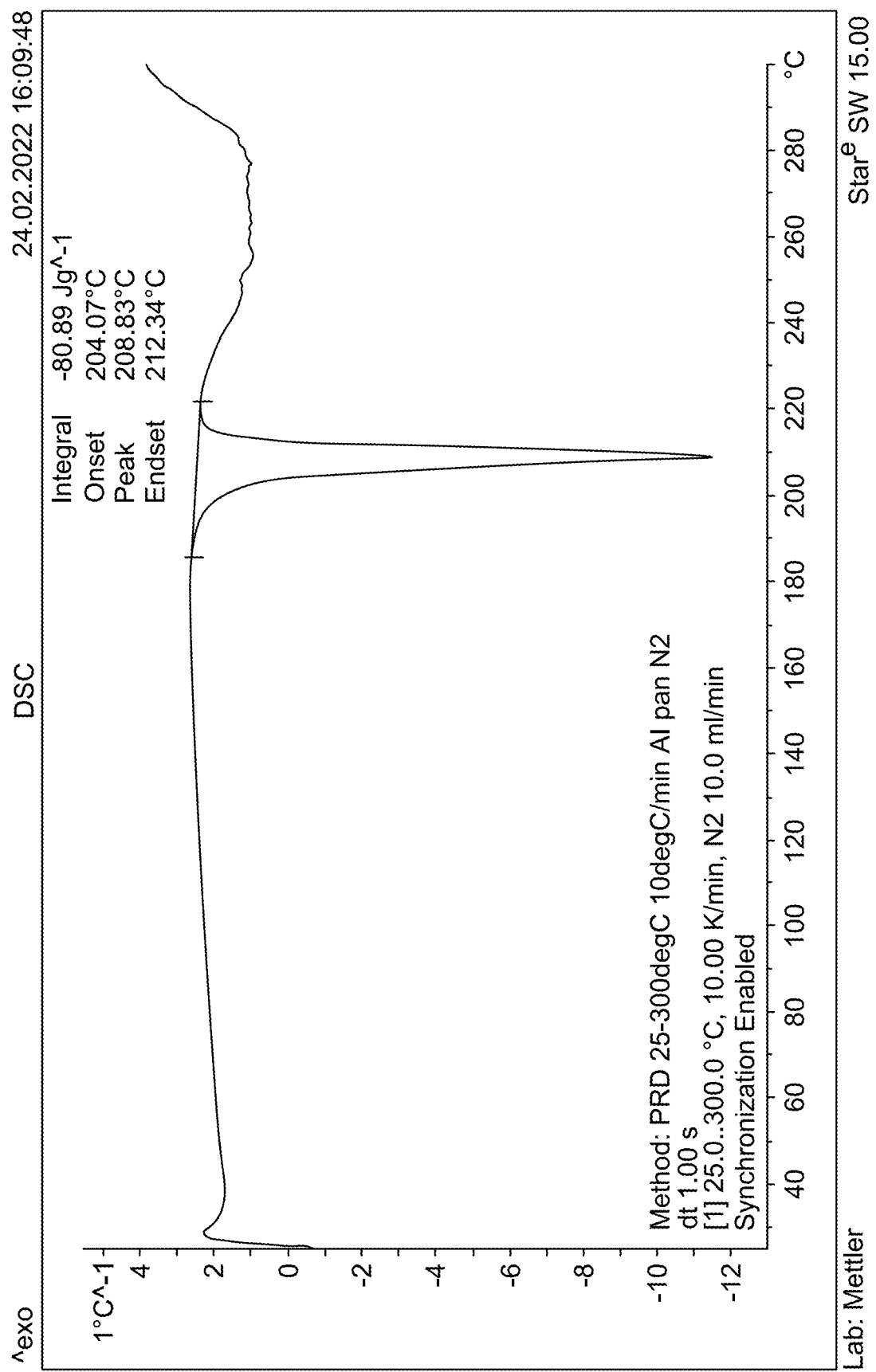

FIG. 217 shows a DSC profile of crystalline compound 1 HCl Form A.

Figure 218:
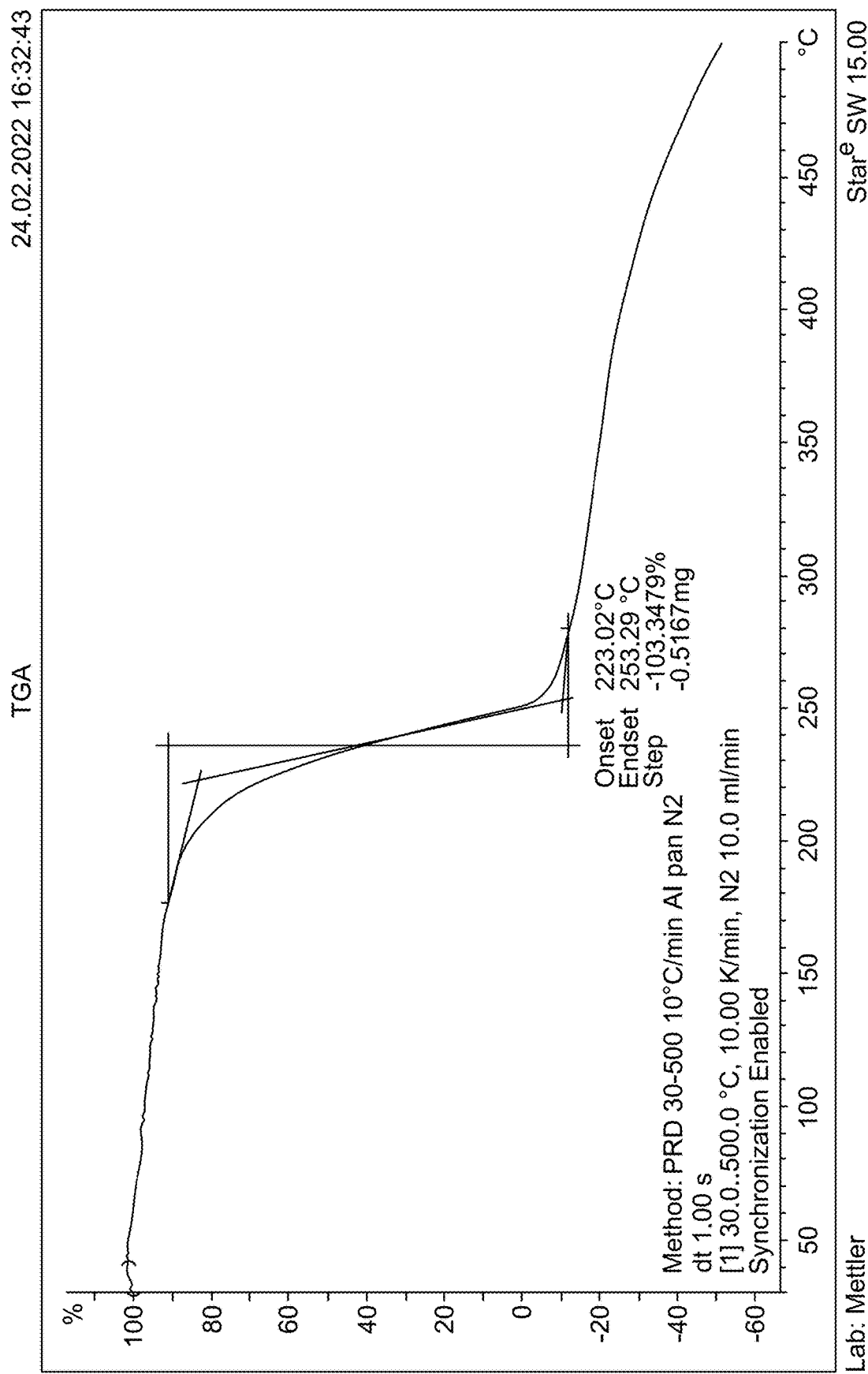

FIG. 218 shows a TGA profile of crystalline compound 1 HCl Form A.

Figure 219:
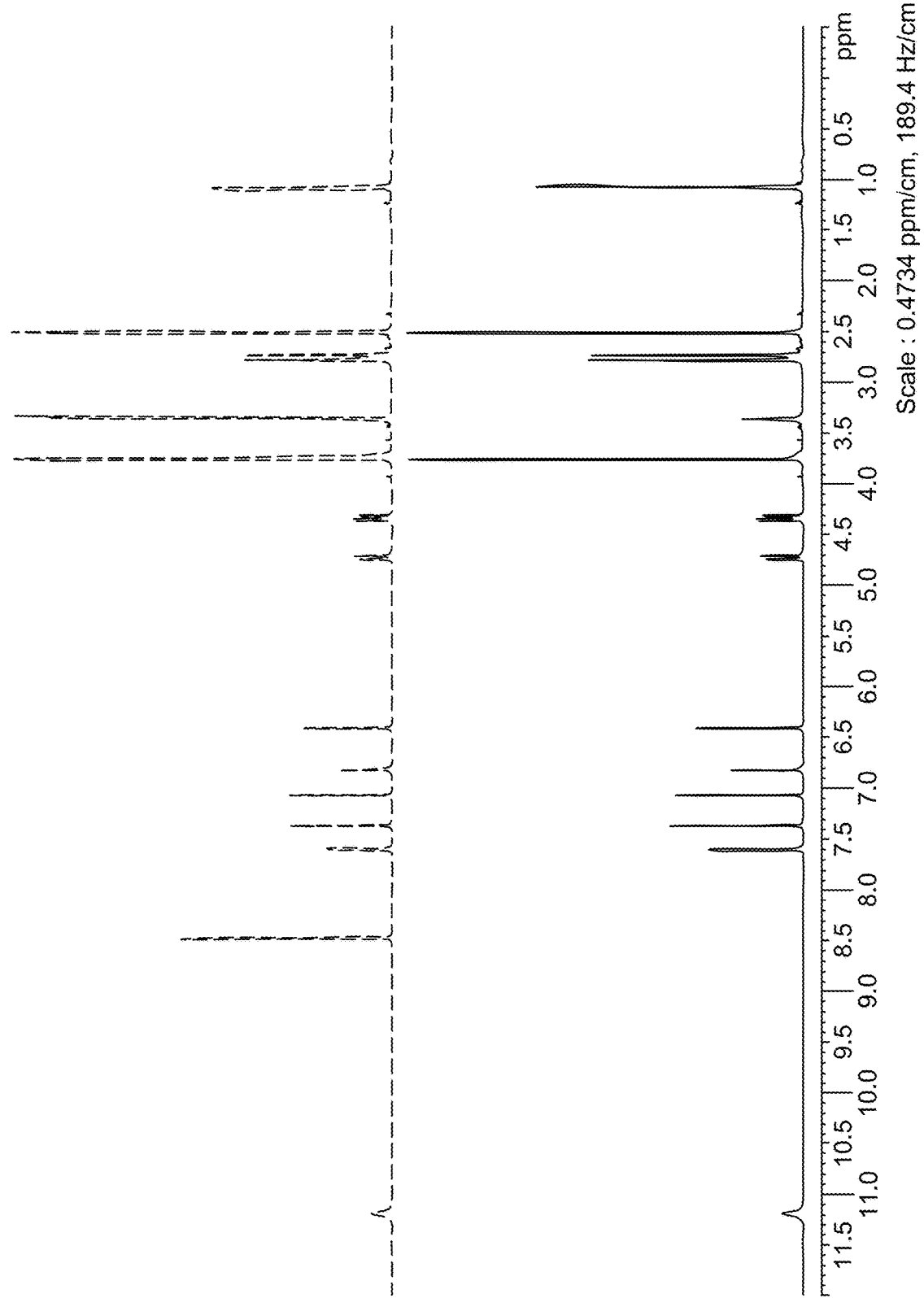

FIG. 219 shows overlaid $^1$H NMR spectra of two samples of crystalline compound 1 HCl Form A.

Figure 220:
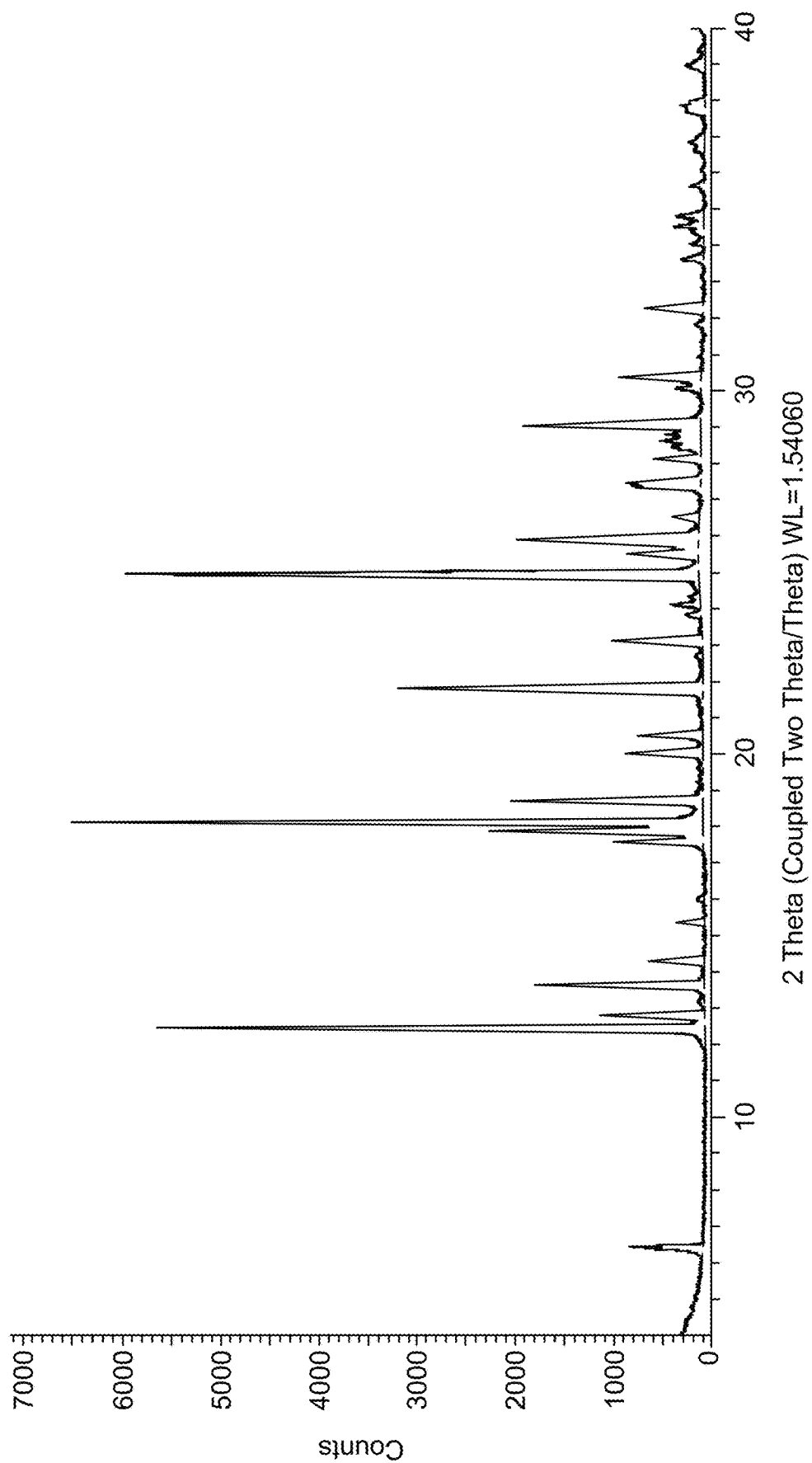

FIG. 220 shows XRPD profile of crystalline compound 1 HCl Form A.

Figure 221:
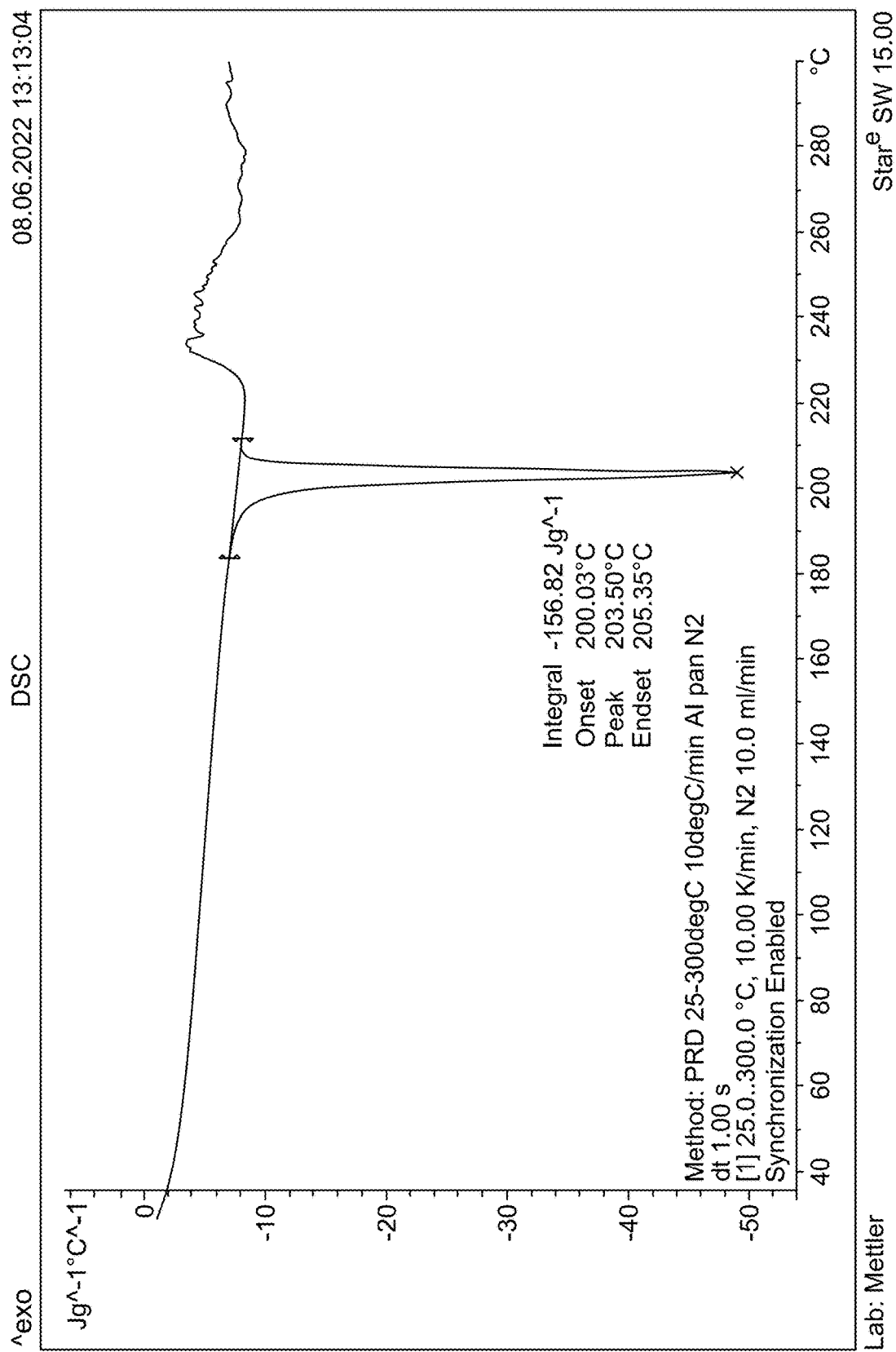

FIG. 221 shows DSC profile of crystalline compound 1 HCl Form A.

Figure 222:
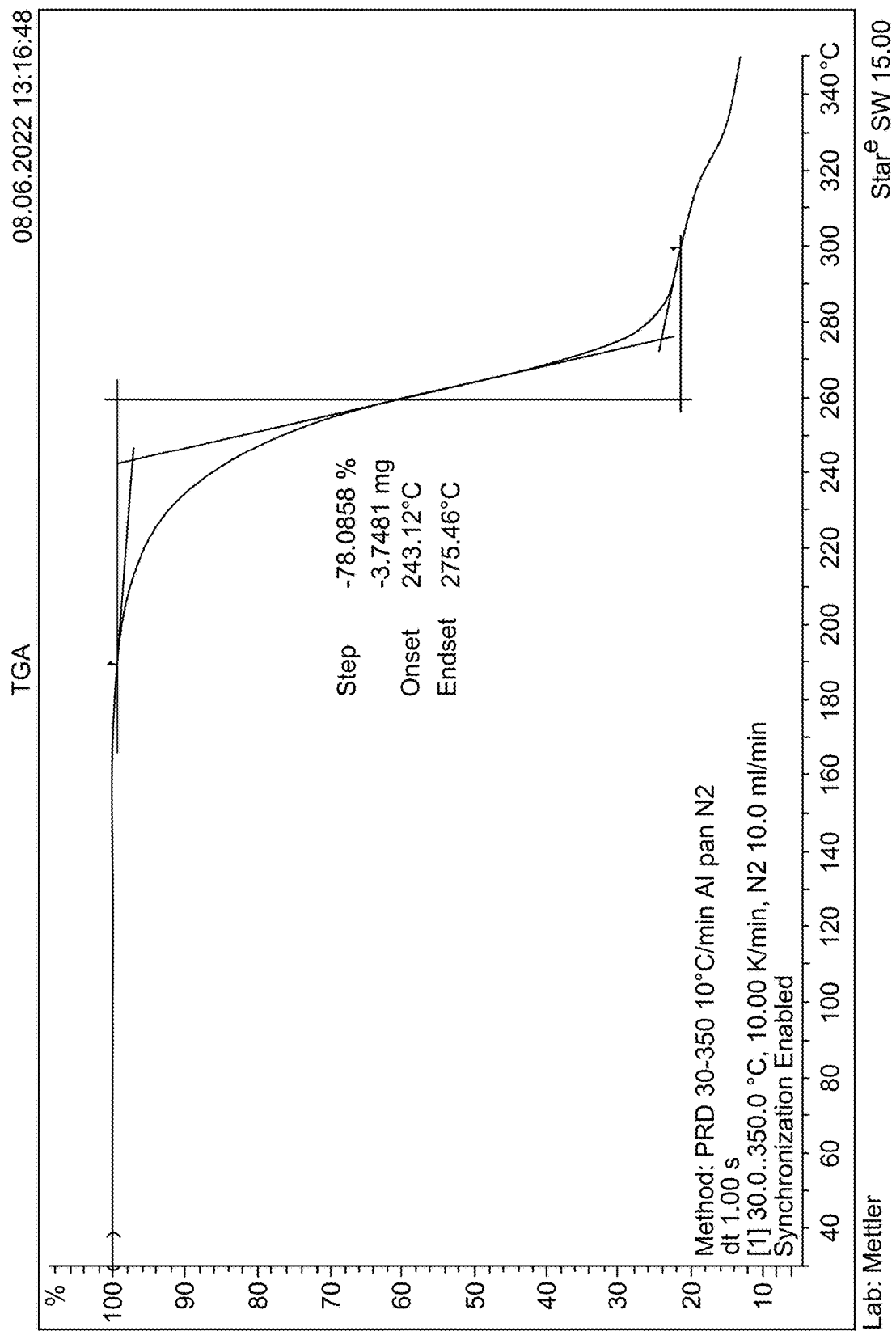

FIG. 222 shows TGA profile of crystalline compound 1 HCl Form A.

Figure 223:
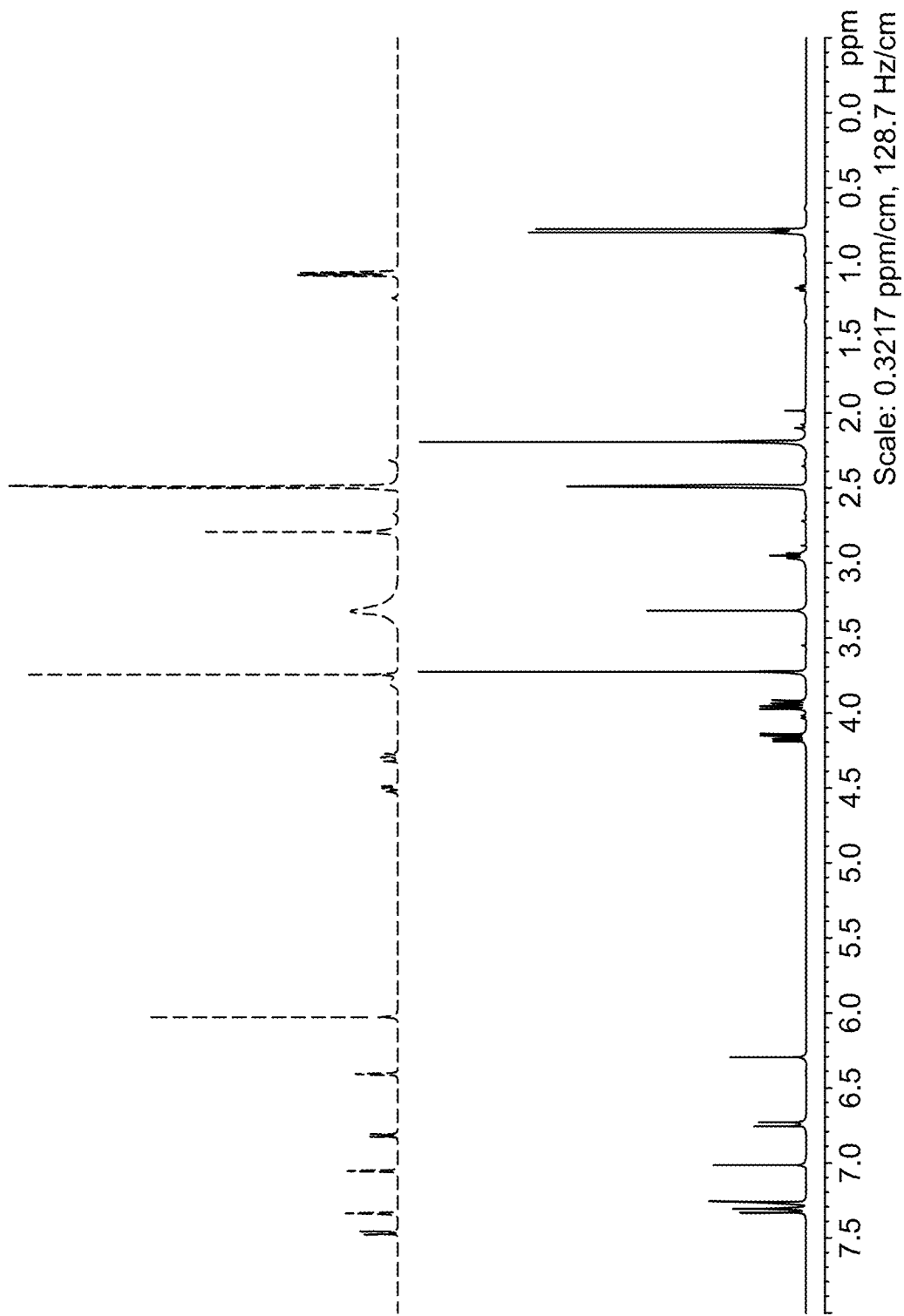

FIG. 223 shows Overlaid of $^1$H NMR spectra of crystalline compound 1 maleate (top) and amorphous compound 1 (bottom).

Figure 224:
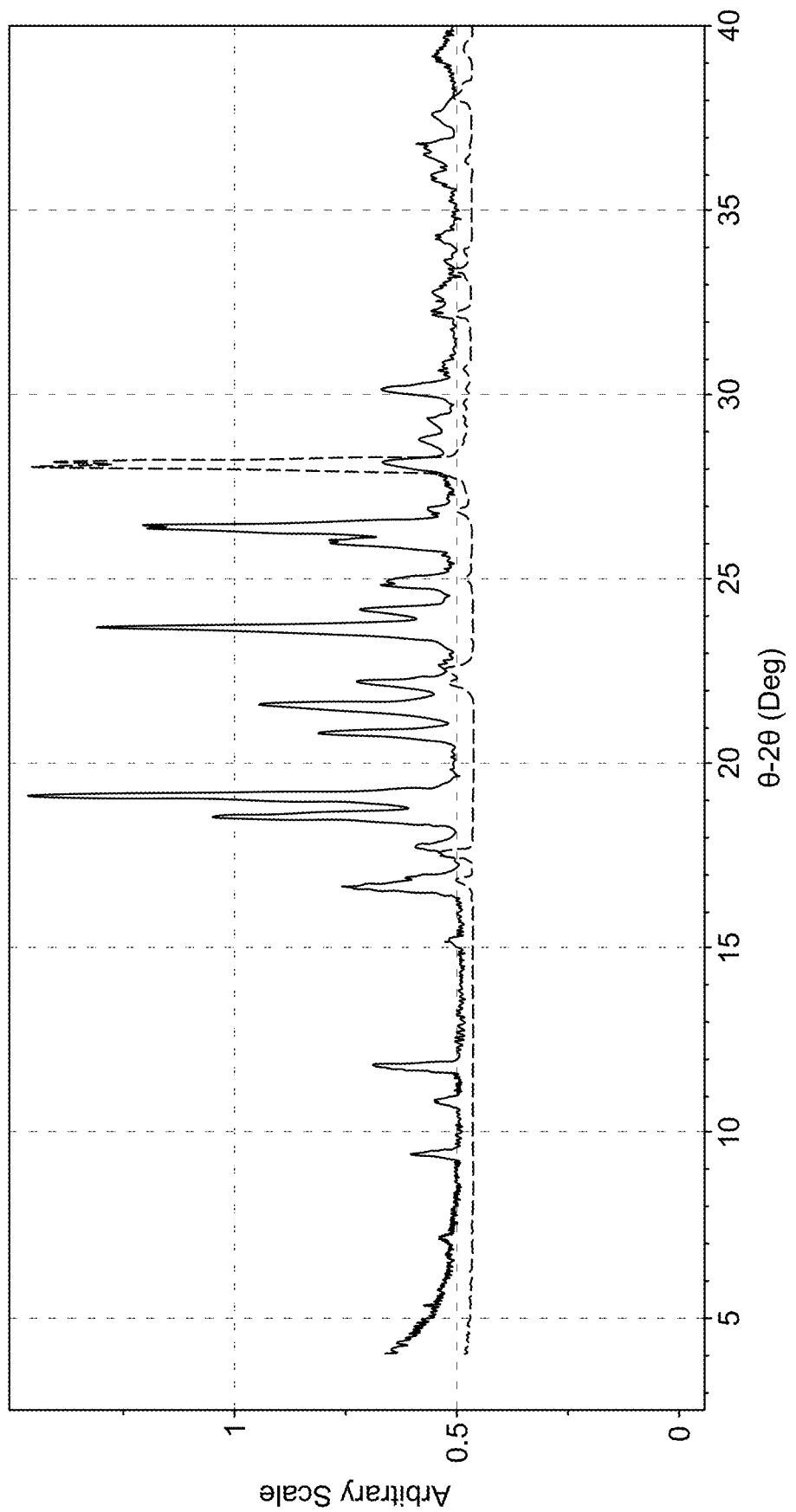

FIG. 224 shows Overlaid of XRPD profiles of crystalline compound 1 maleate (top) and maleic acid, non-ionise (bottom).

Figure 225:
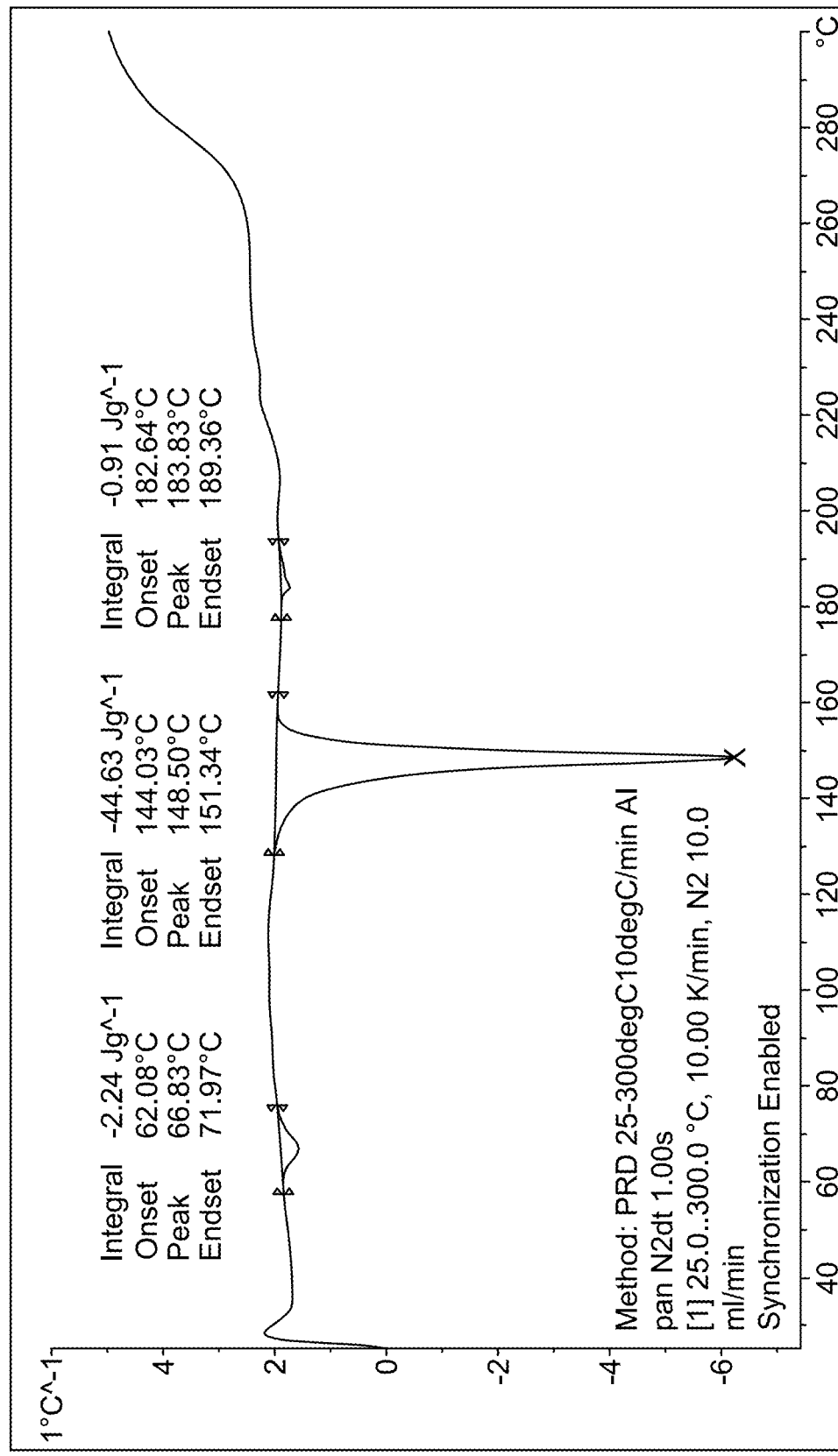

FIG. 225 shows DSC profile of crystalline compound 1 maleate.

Figure 226:
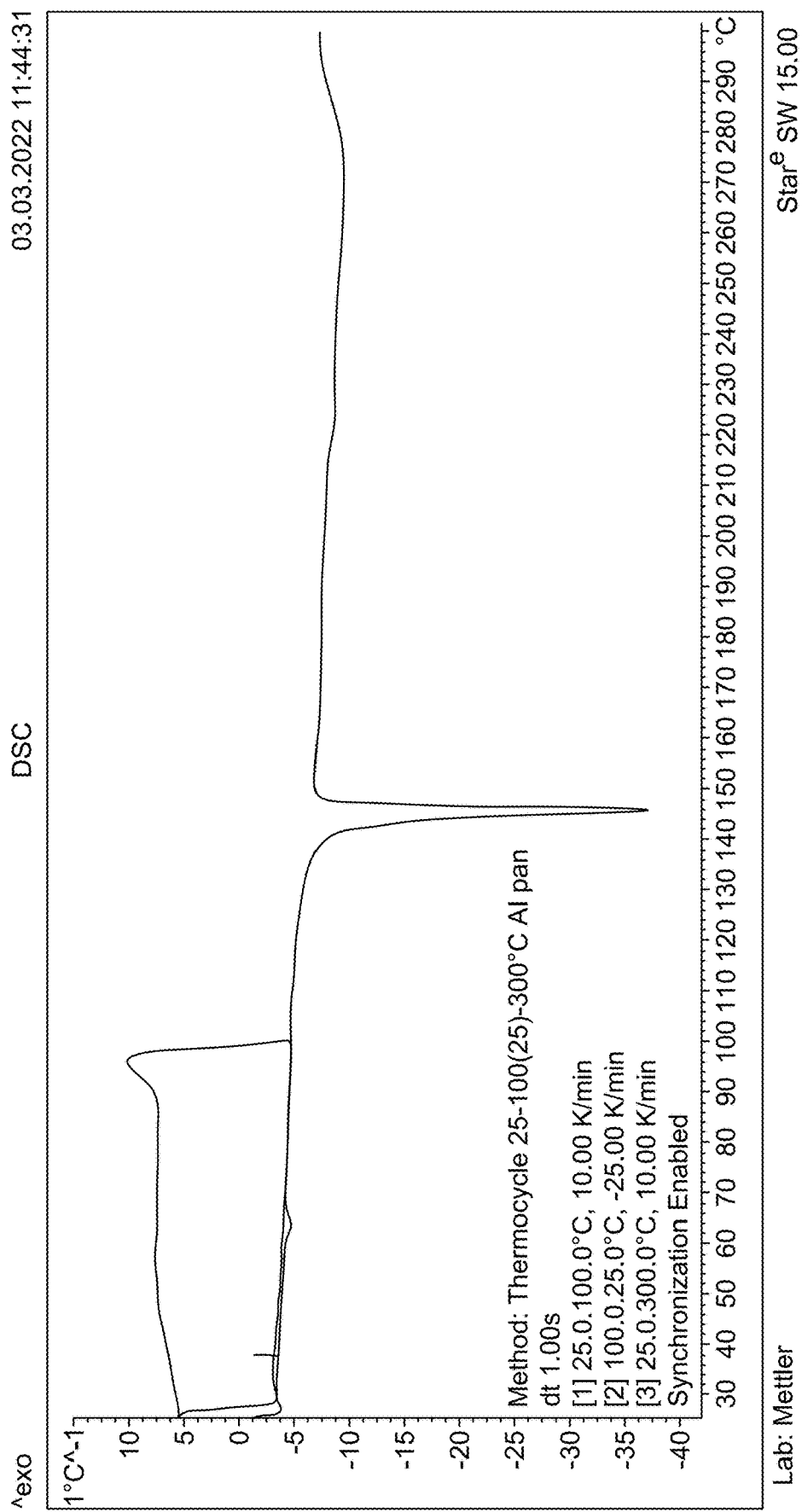

FIG. 226 shows DSC thermocycle profile of crystalline compound 1 maleate.

Figure 227:
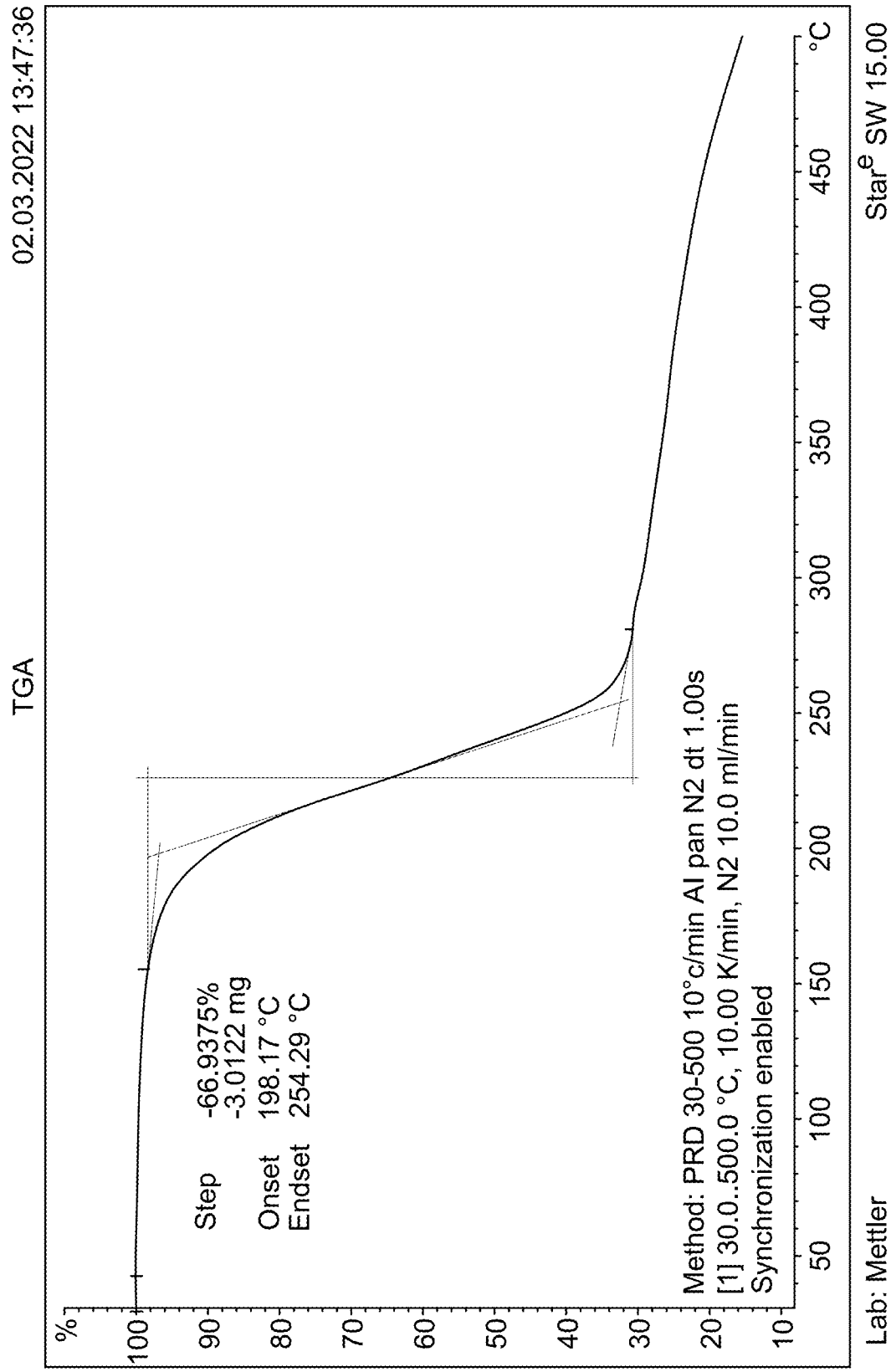

FIG. 227 shows TGA profile of crystalline compound 1 maleate.

Figure 228:
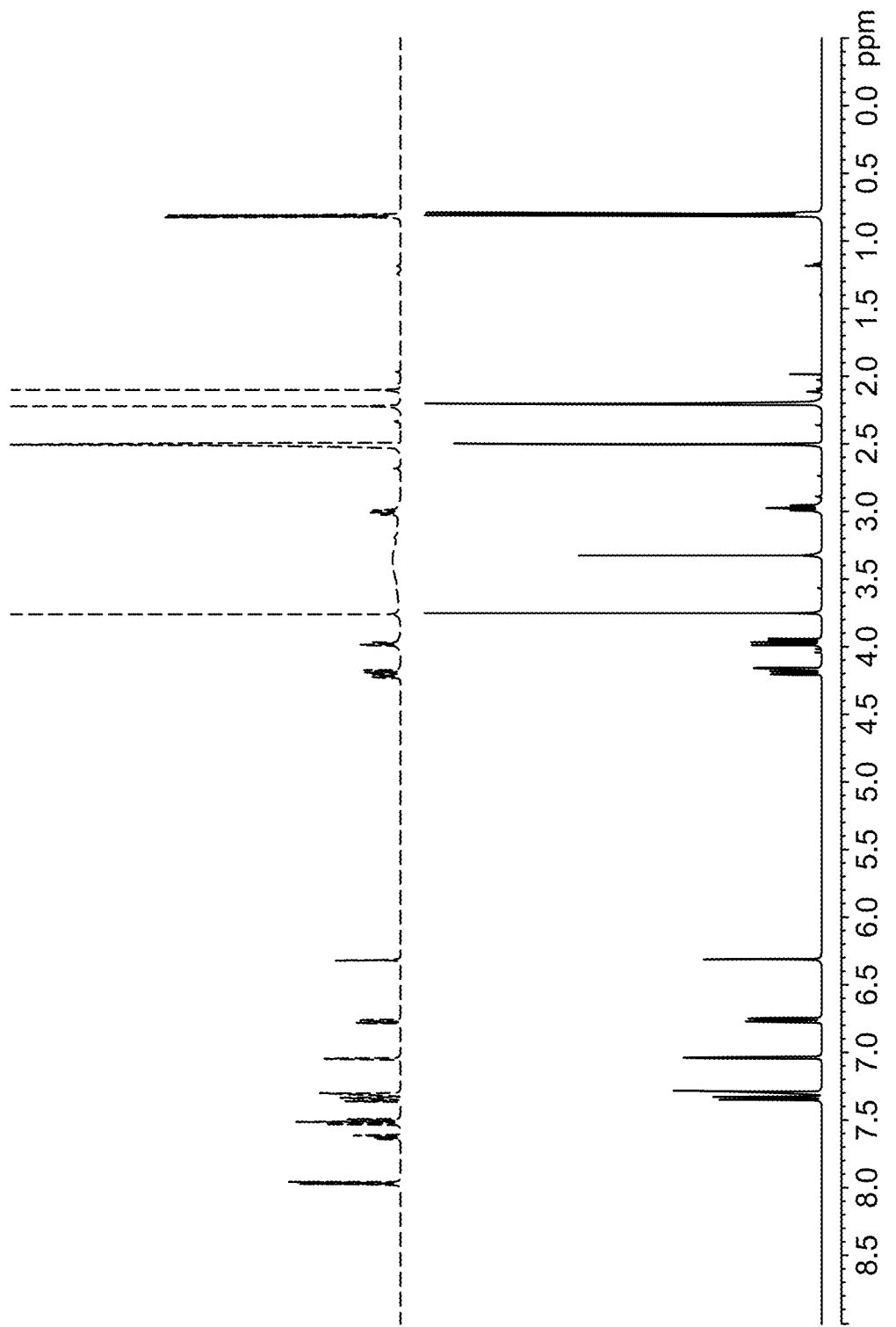

FIG. 228 shows Overlaid of $^1$H NMR spectra of crystalline compound 1 benzoate (top) and amorphous compound 1 (bottom).

Figure 229:
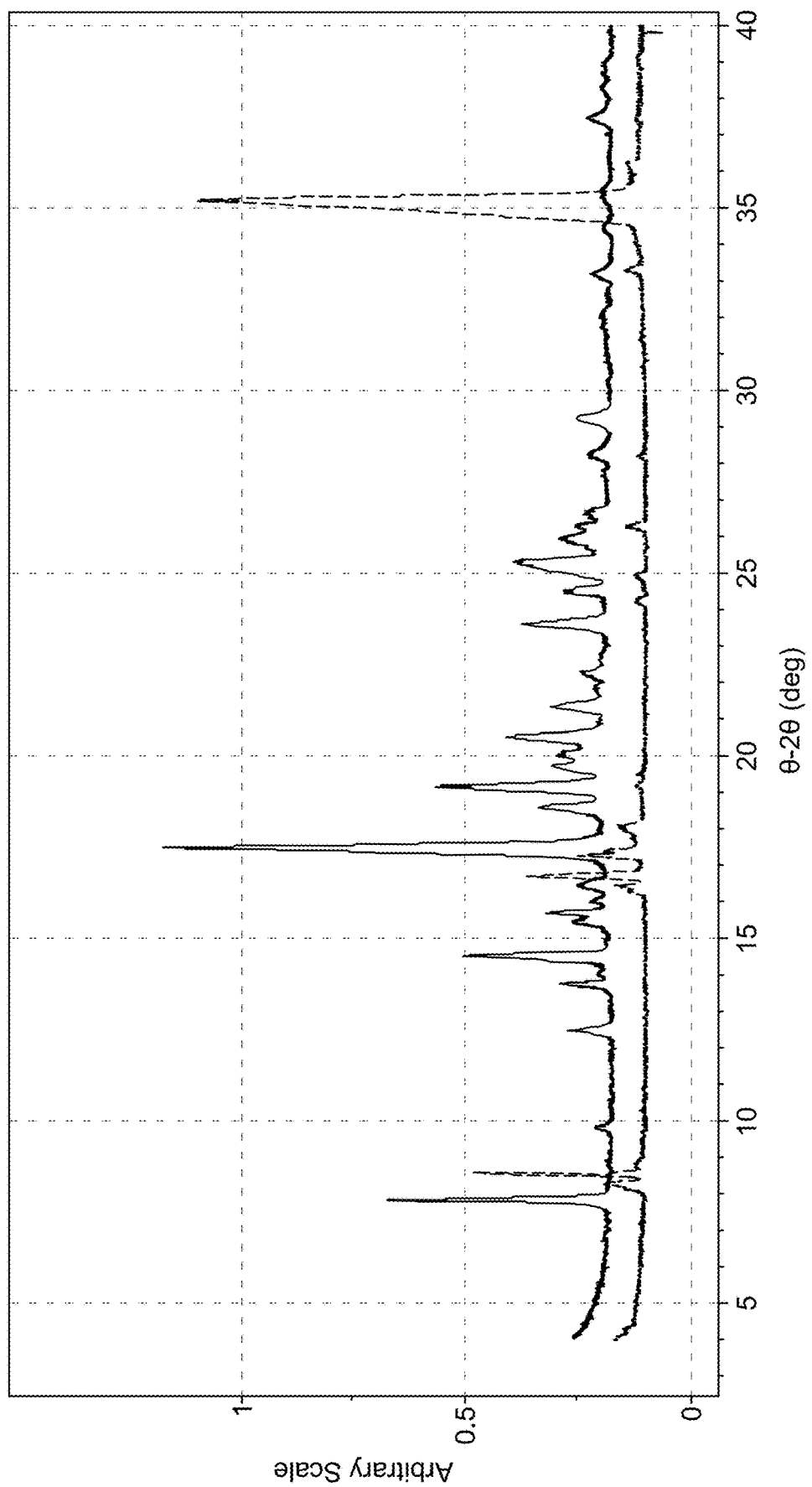

FIG. 229 shows overlaid XRPD profiles of crystalline compound 1 benzoate and benzoic acid, non-ionized (bottom).

Figure 230:
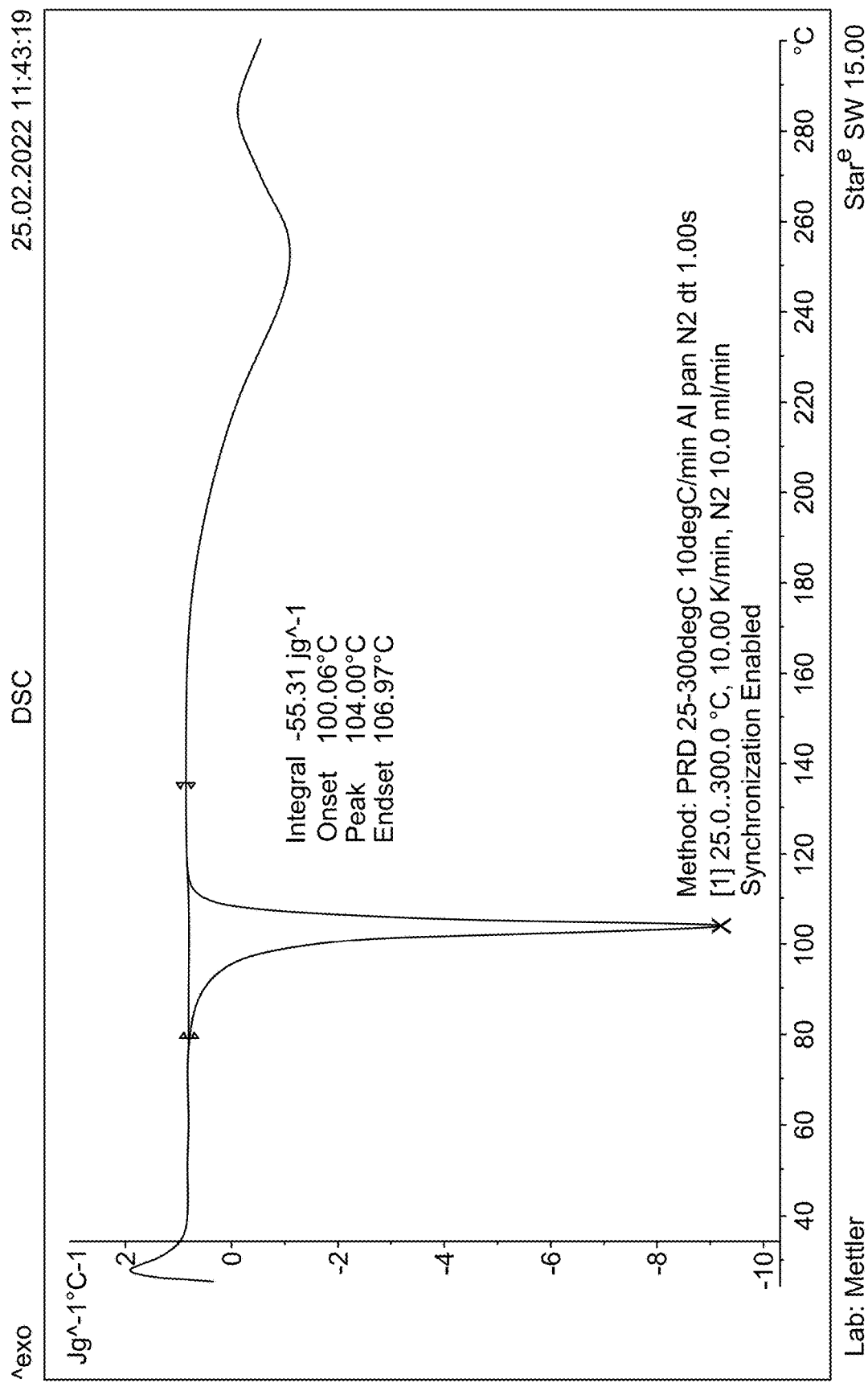

FIG. 230 shows a DSC profile of crystalline compound 1 benzoate.

Figure 231:
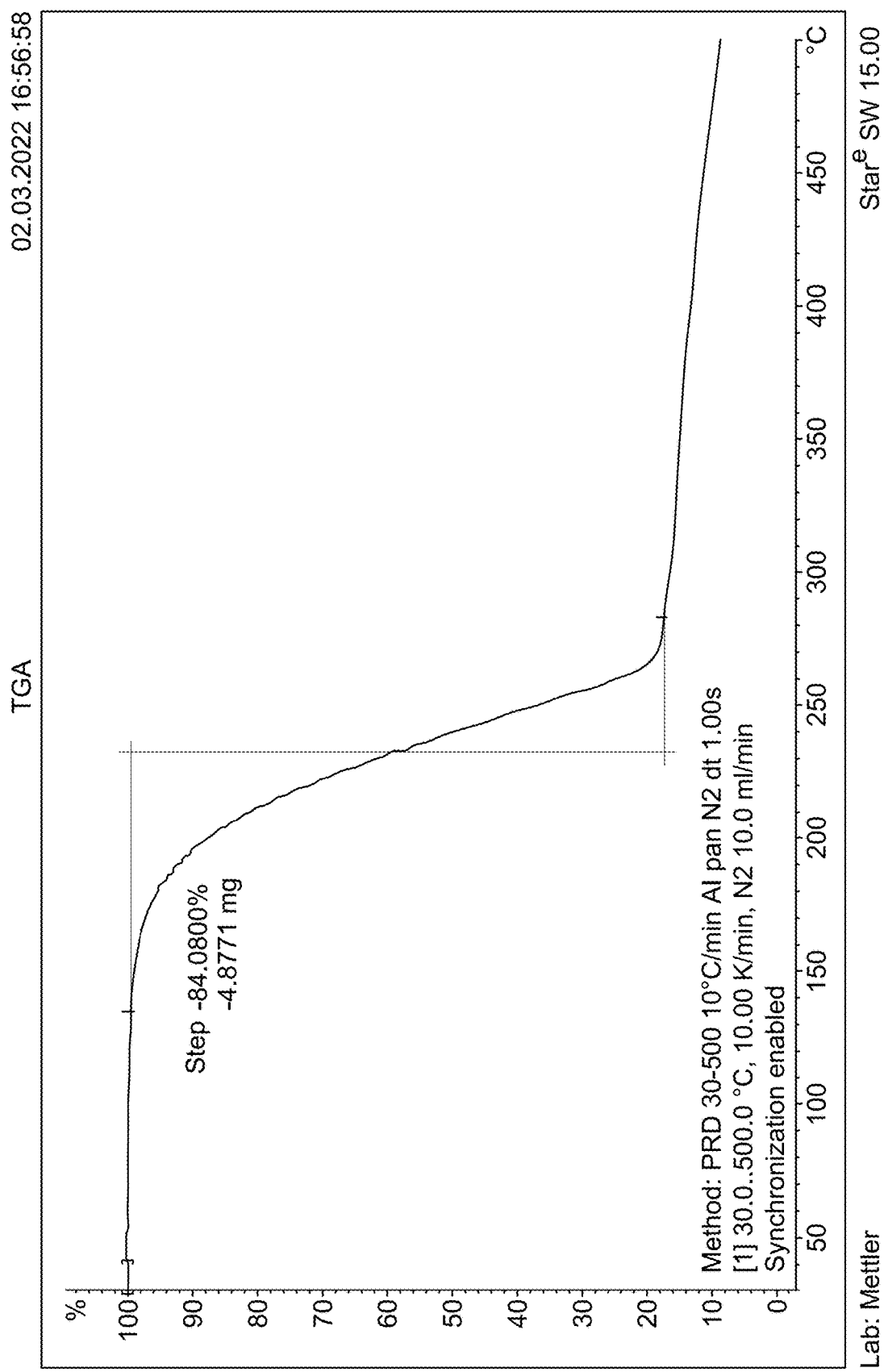

FIG. 231 shows a TGA profile of crystalline compound 1 benzoate

Figure 232:
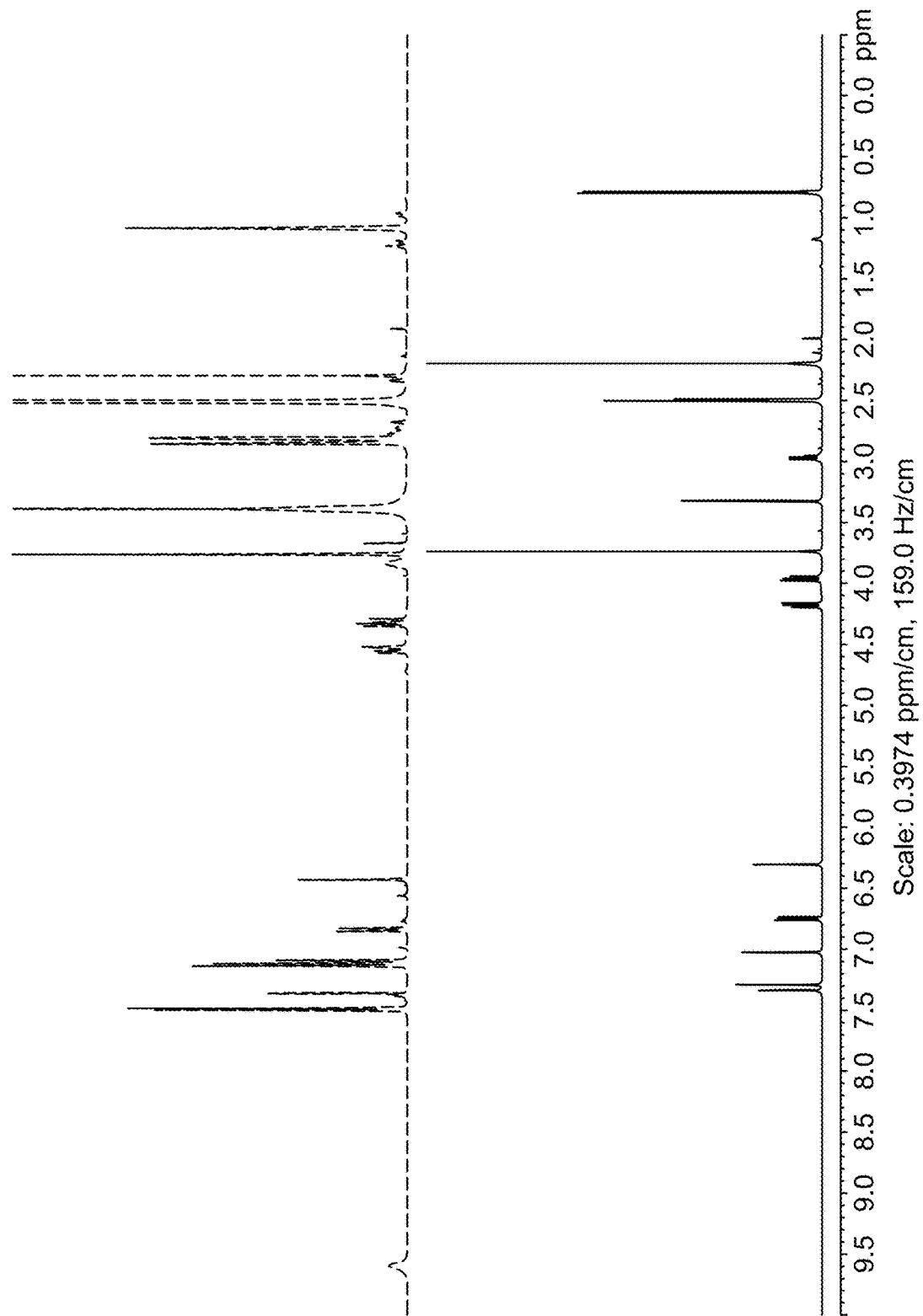

FIG. 232 shows overlaid of NMR spectra of crystalline compound 1 tosylate (top) and amorphous compound 1.

Figure 233:
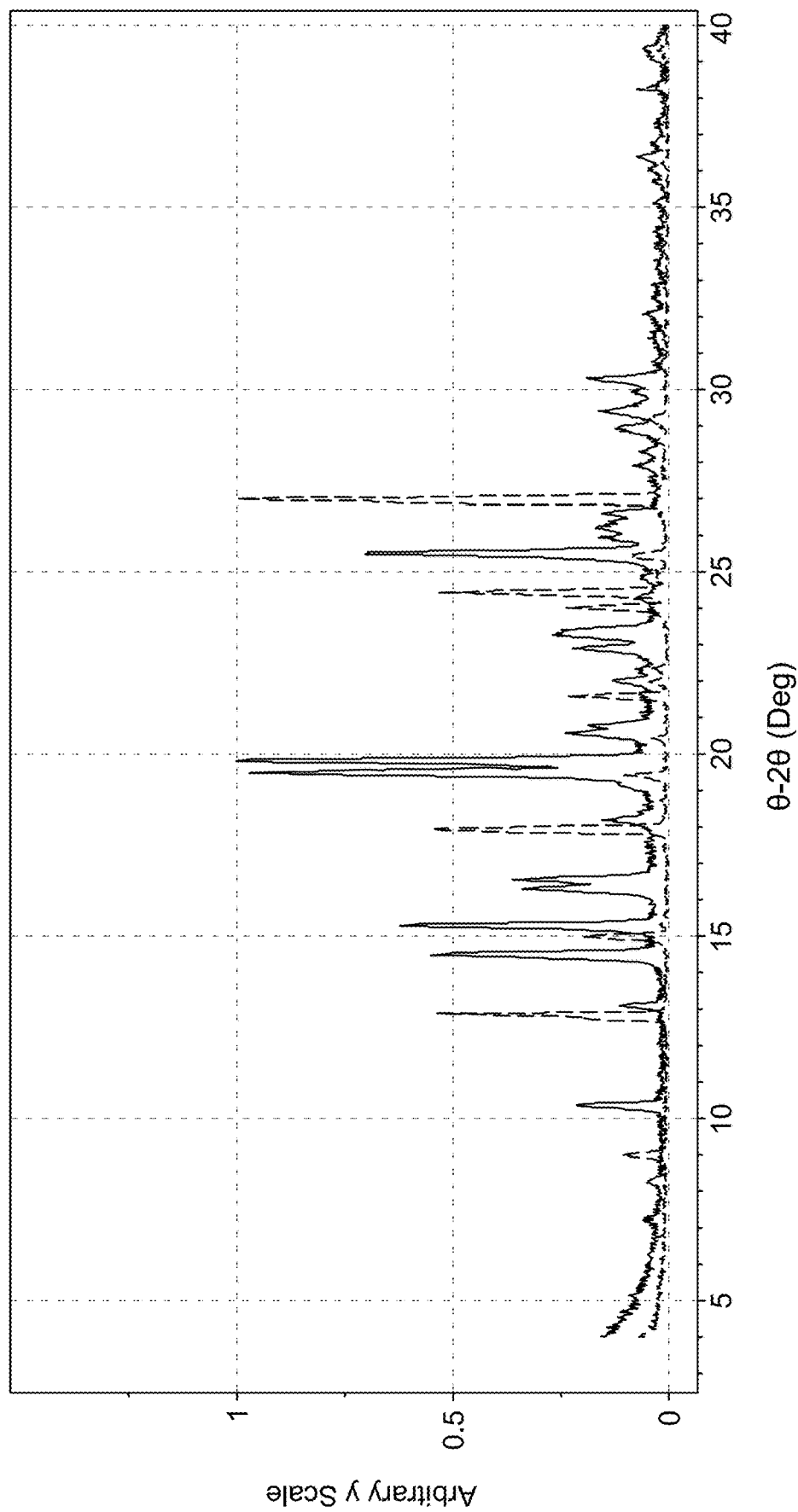

FIG. 233 shows overlaid XRPD profiles of crystalline compound 1 tosylate (top) and 4-toluene sulfonic acid, non-ionized.

Figure 234:
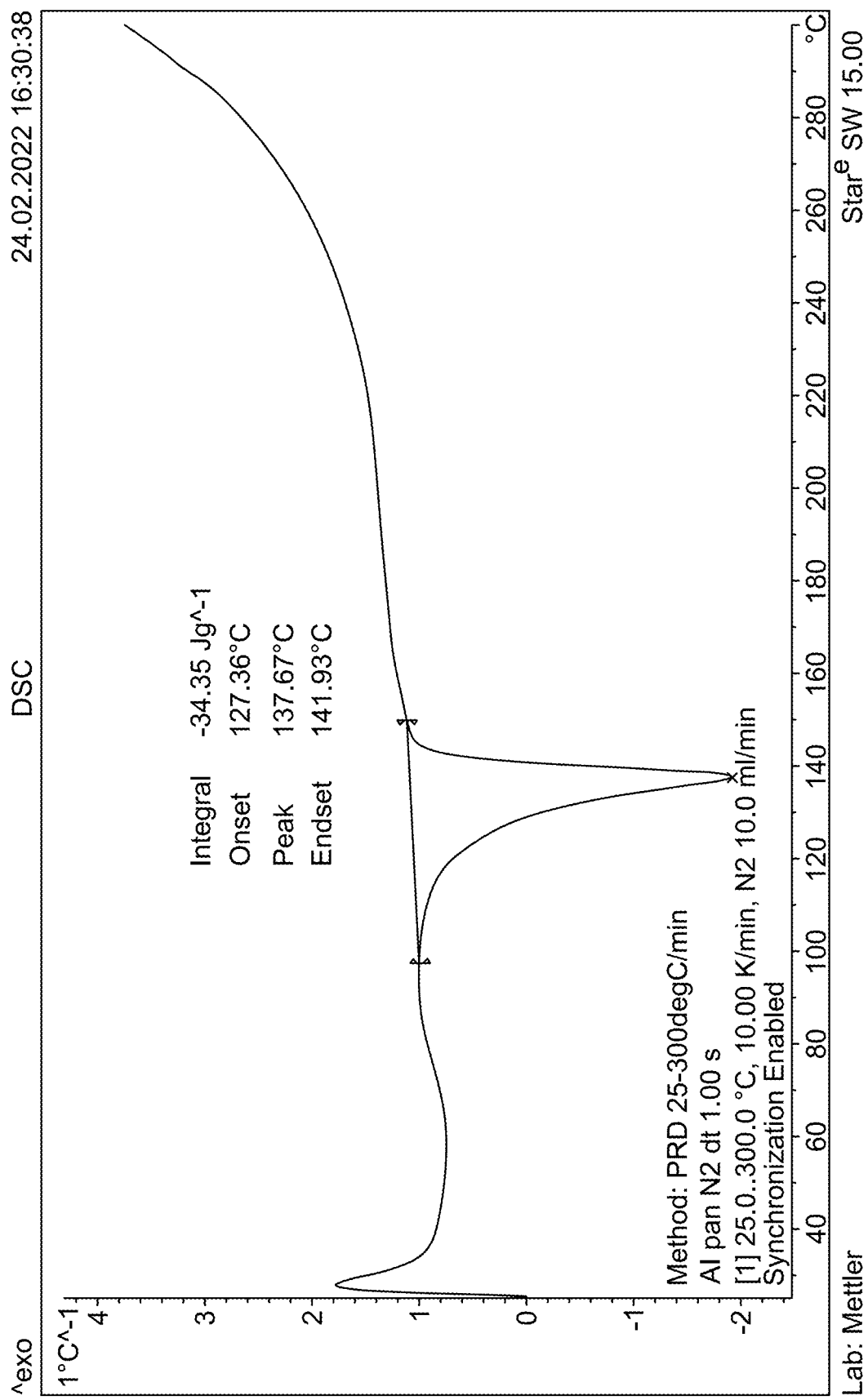

FIG. 234 shows a DSC profile of crystalline compound 1 tosylate.

Figure 235:
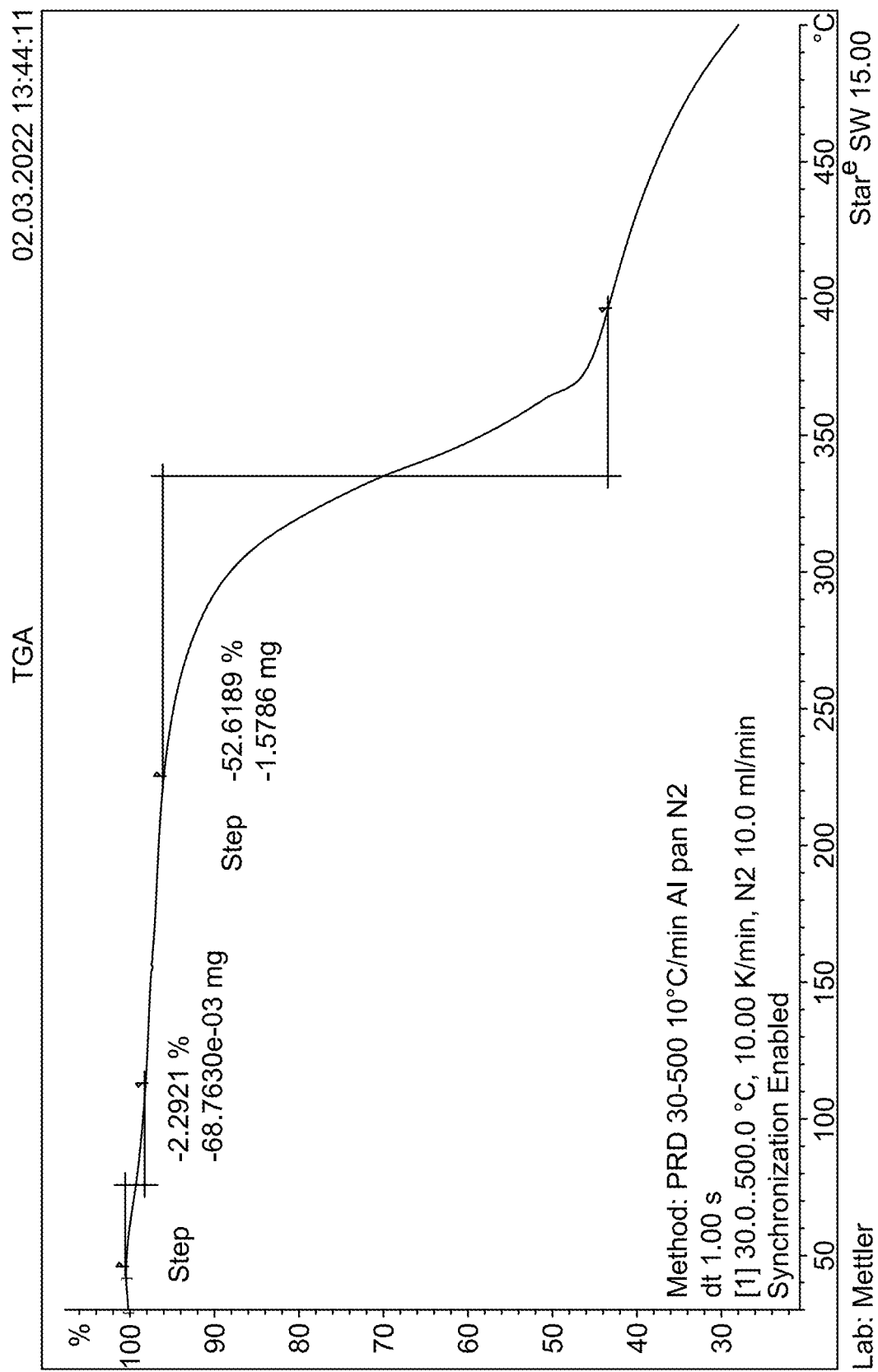

FIG. 235 shows a TGA profile of crystalline compound 1 tosylate.

Figure 236:
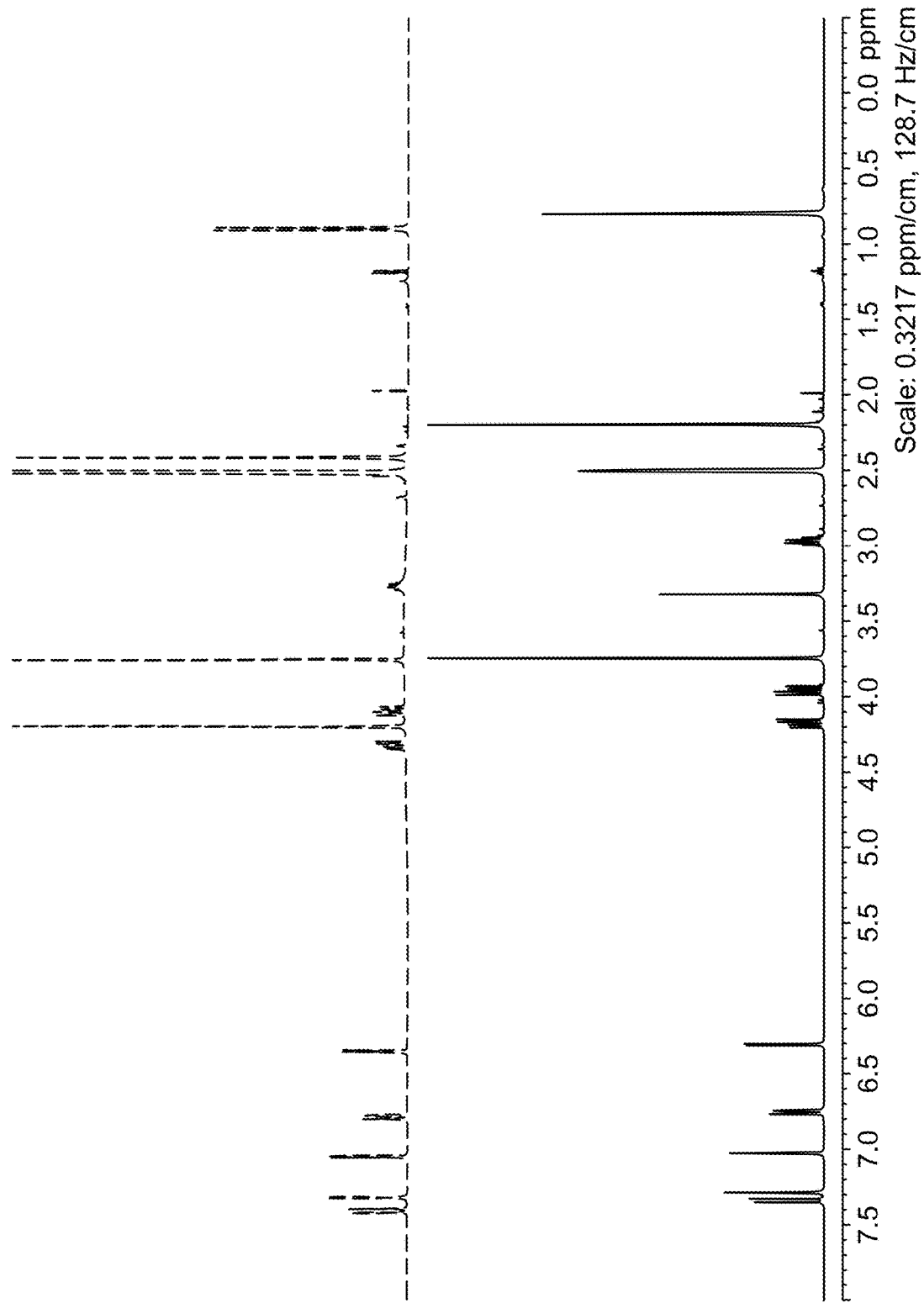

FIG. 236 shows Overlaid of $^1$H NMR spectra of crystalline compound 1 tartrate (top) and amorphous compound 1.

Figure 237:
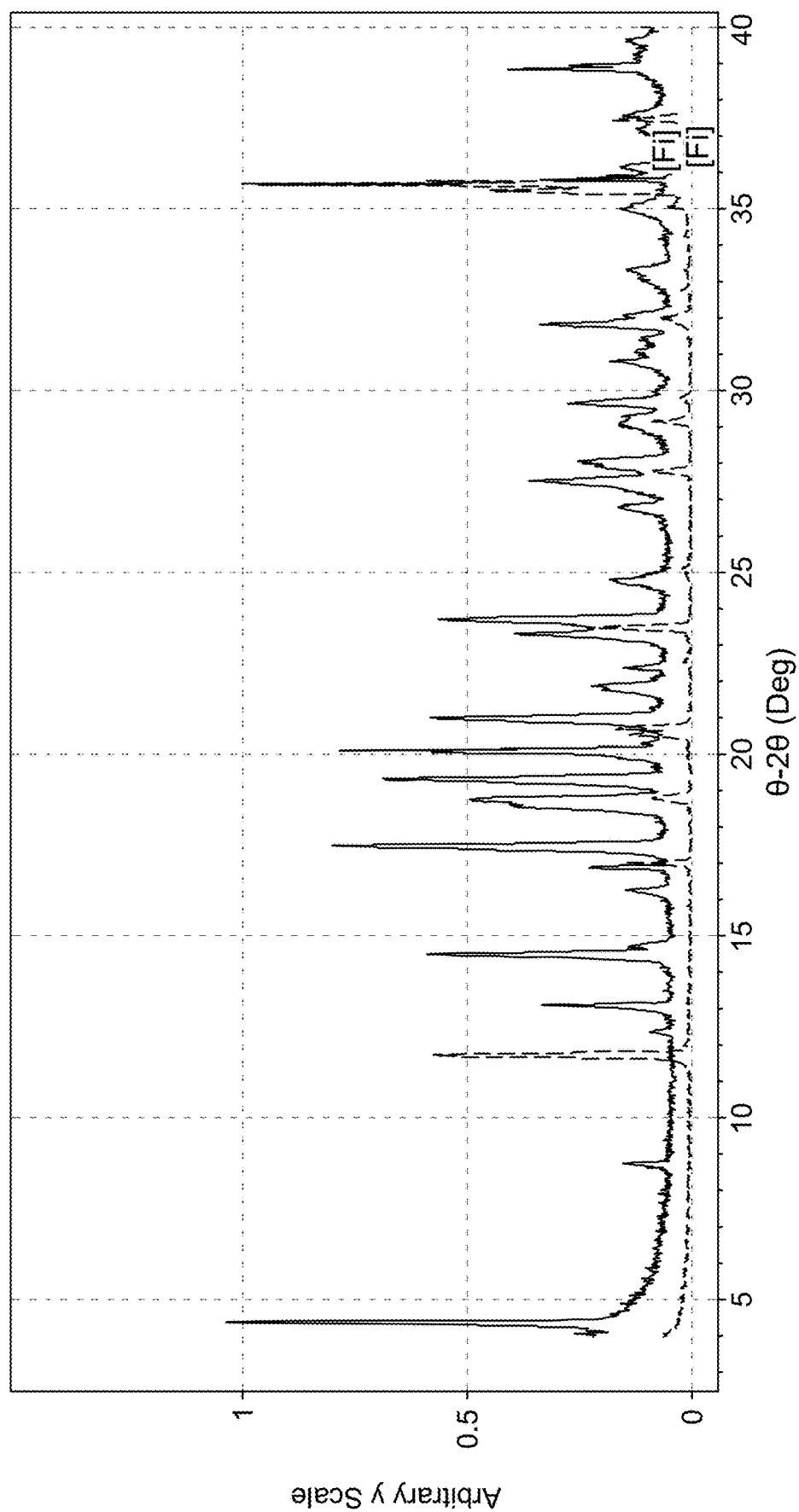

FIG. 237 shows Overlaid of XRPD profiles of crystalline compound 1 tartrate (top) and tartaric acid, non-ionized.

Figure 238:
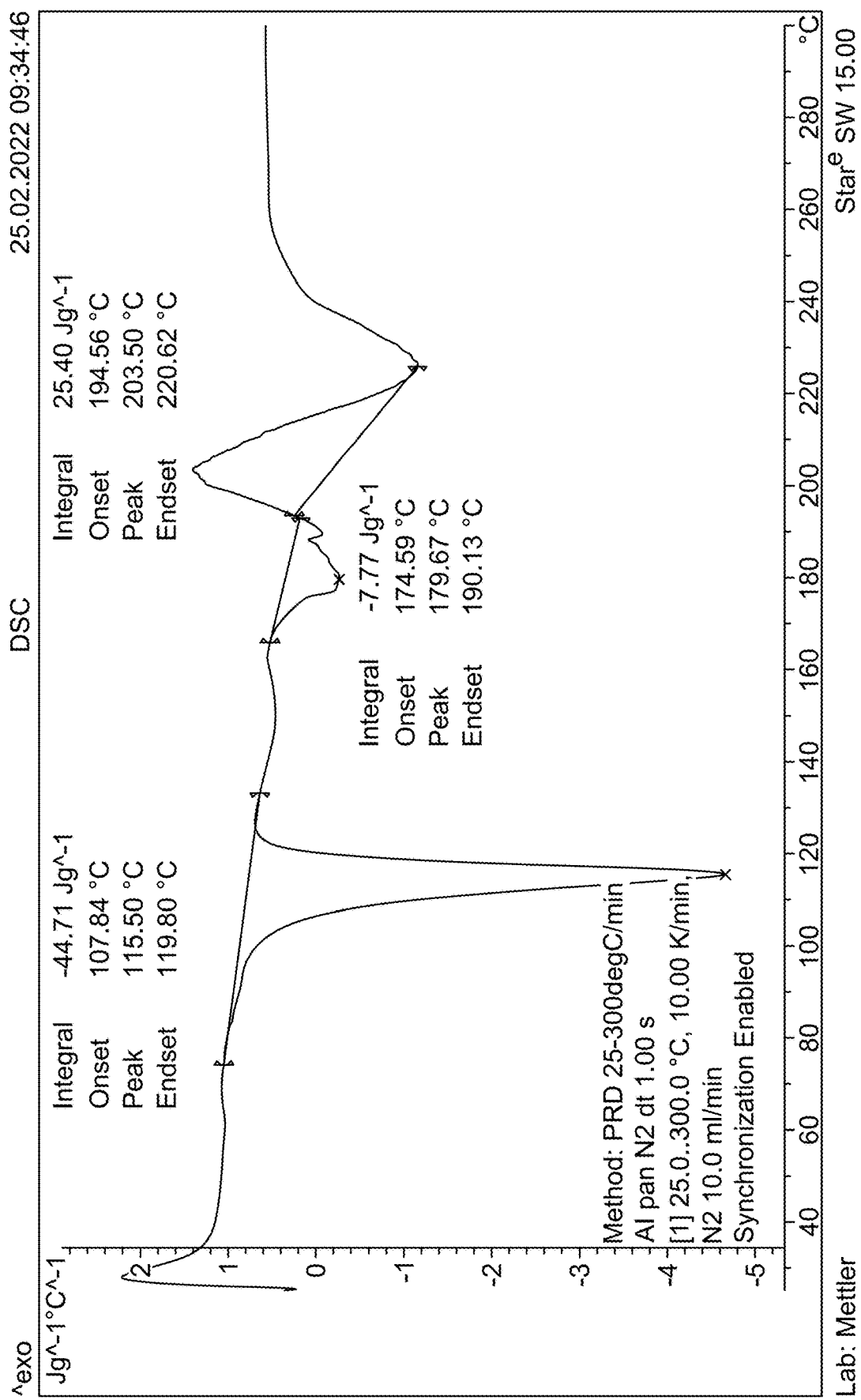

FIG. 238 shows a DSC profile of crystalline compound 1 tartrate.

Figure 239:
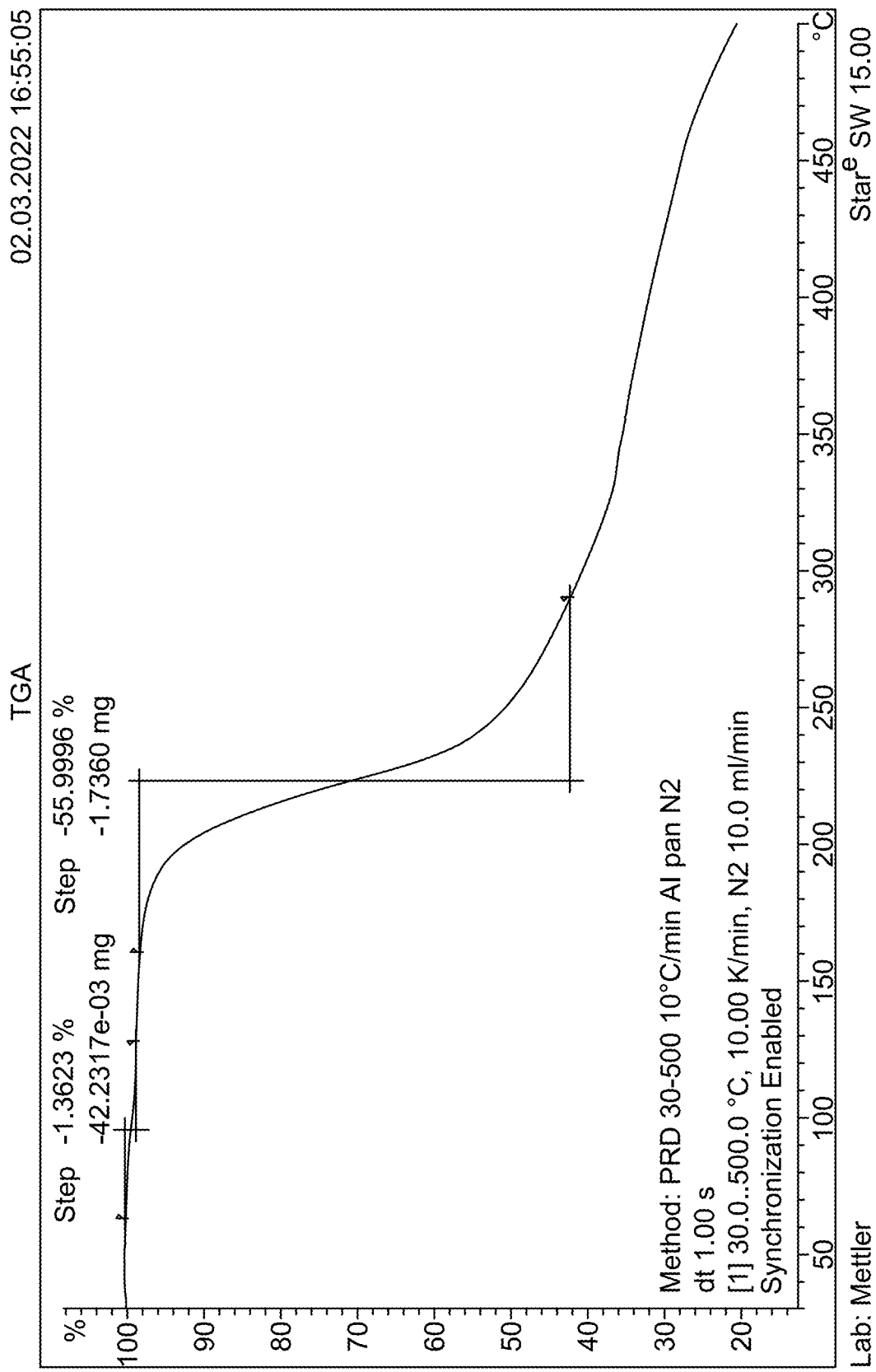

FIG. 239 shows a TGA profile of crystalline compound 1 tartrate.

Figure 240:
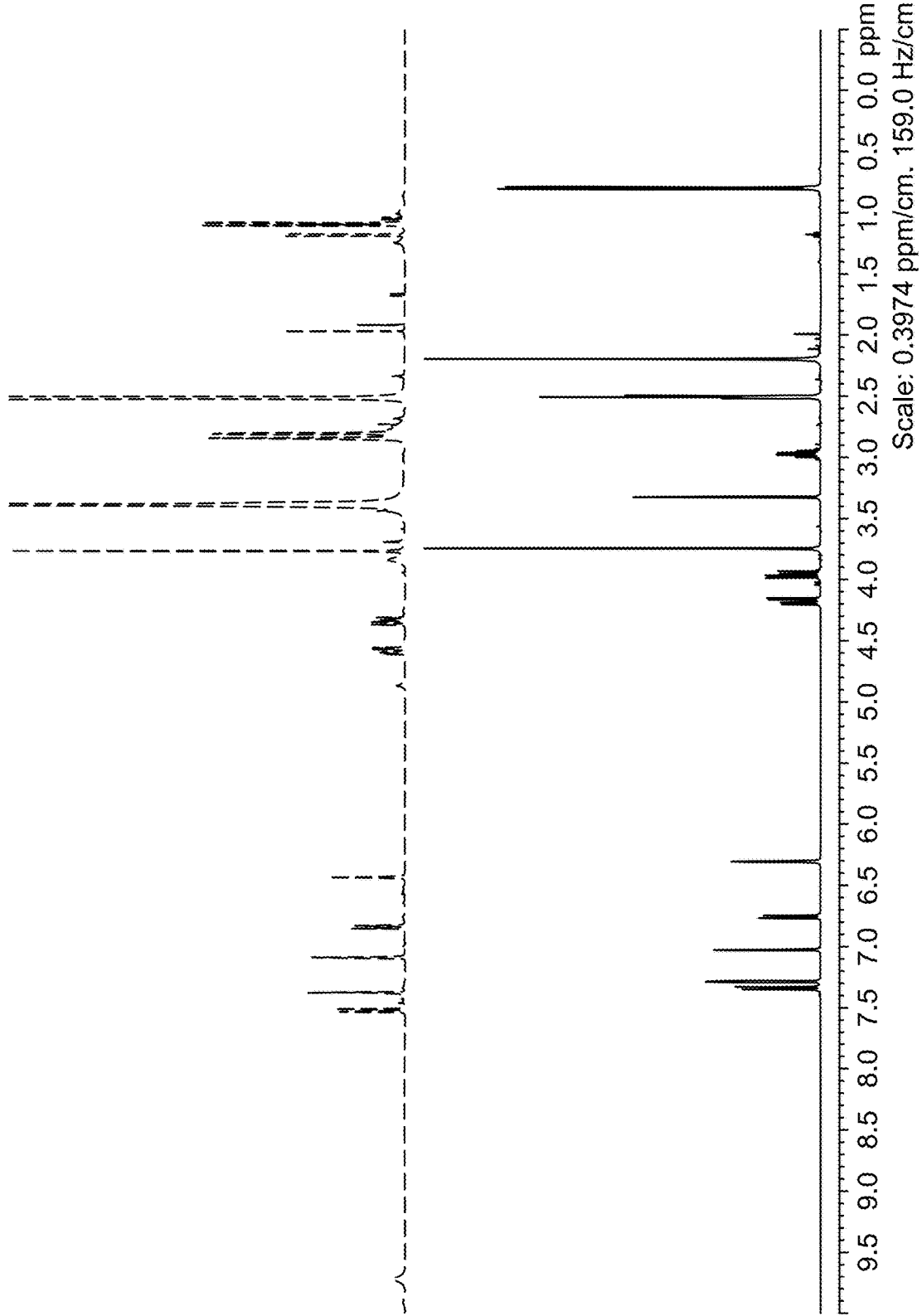

FIG. 240 shows overlaid of $^1$H NMR spectra of crystalline compound 1 HBr (top) and amorphous compound 1 (bottom).

Figure 241:
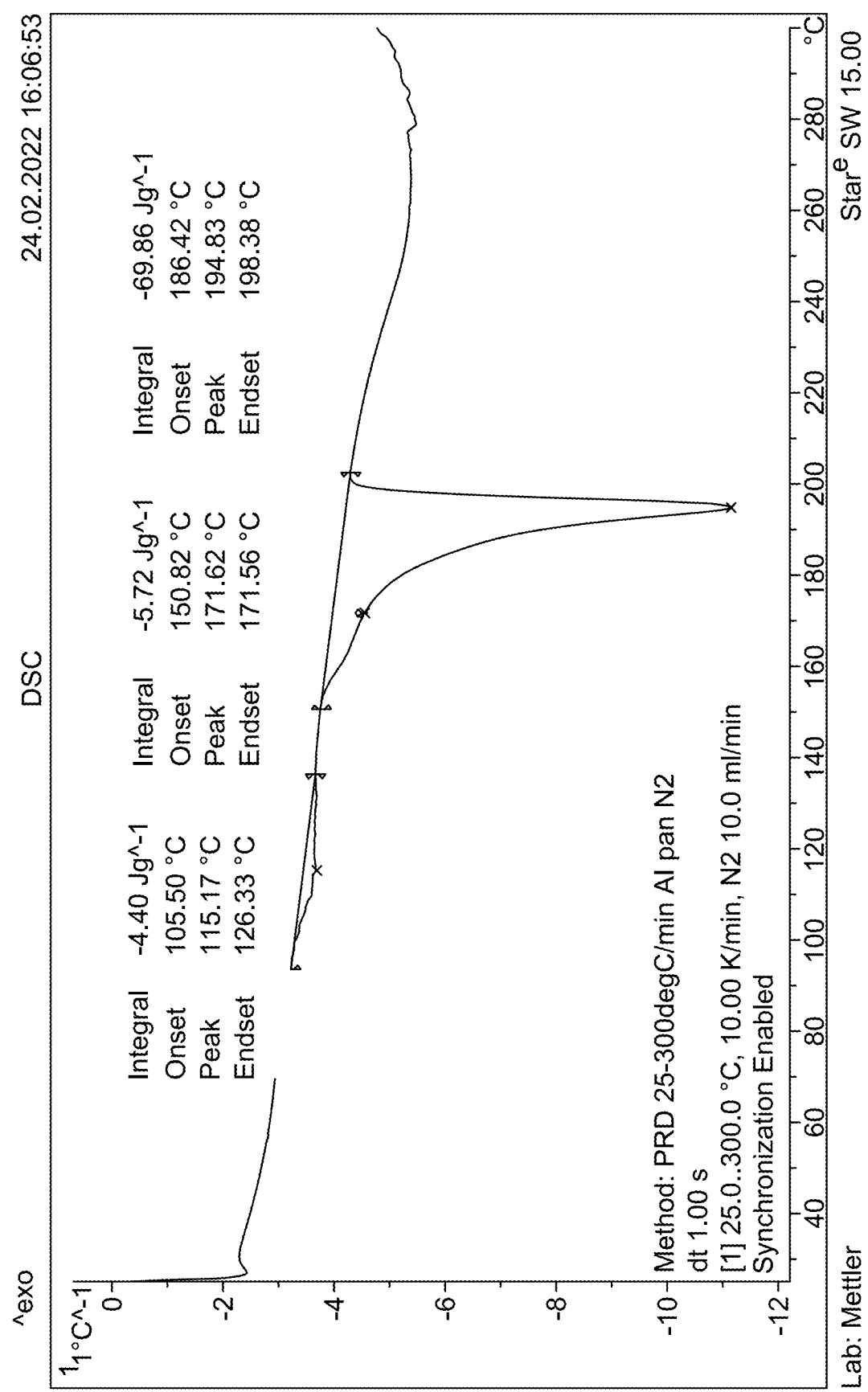

FIG. 241 shows a DSC profile of crystalline compound 1 HBr.

Figure 242:
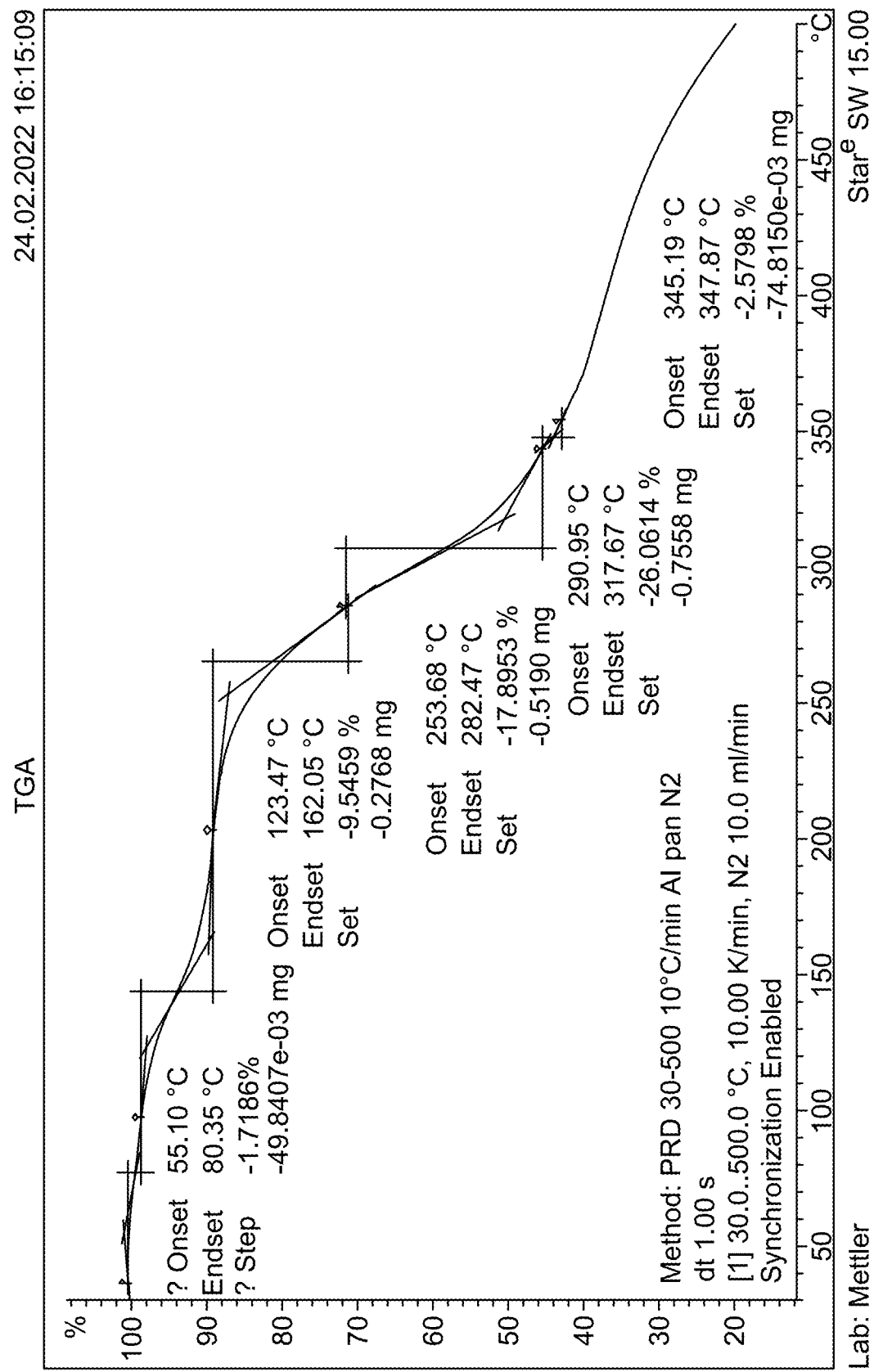

FIG. 242 shows a TGA profile of crystalline compound 1 HBr.

Figure 243:
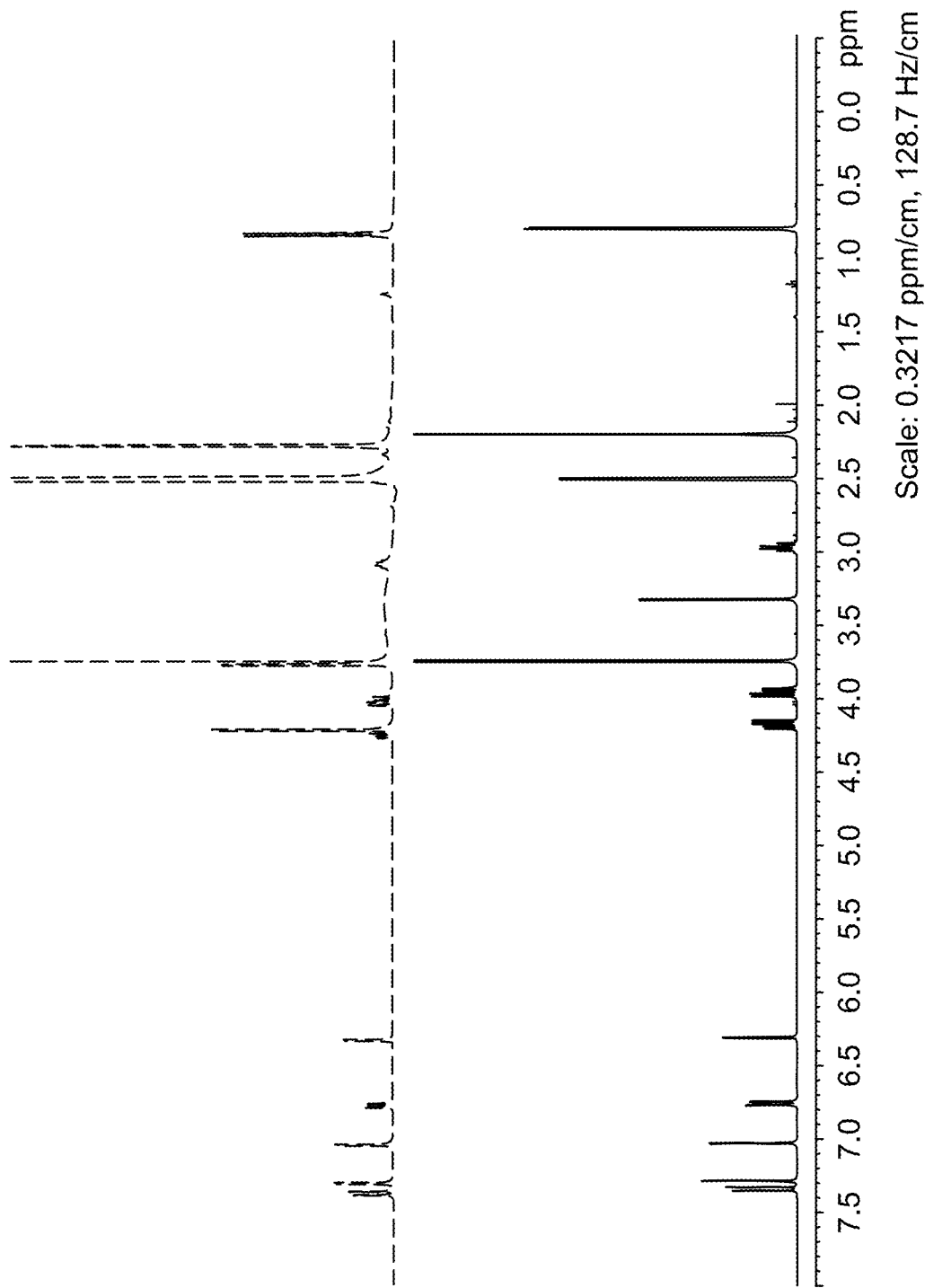

FIG. 243 shows overlaid $^1$H NMR spectra of crystalline compound 1 galactarate (top) and amorphous compound 1.

Figure 244:
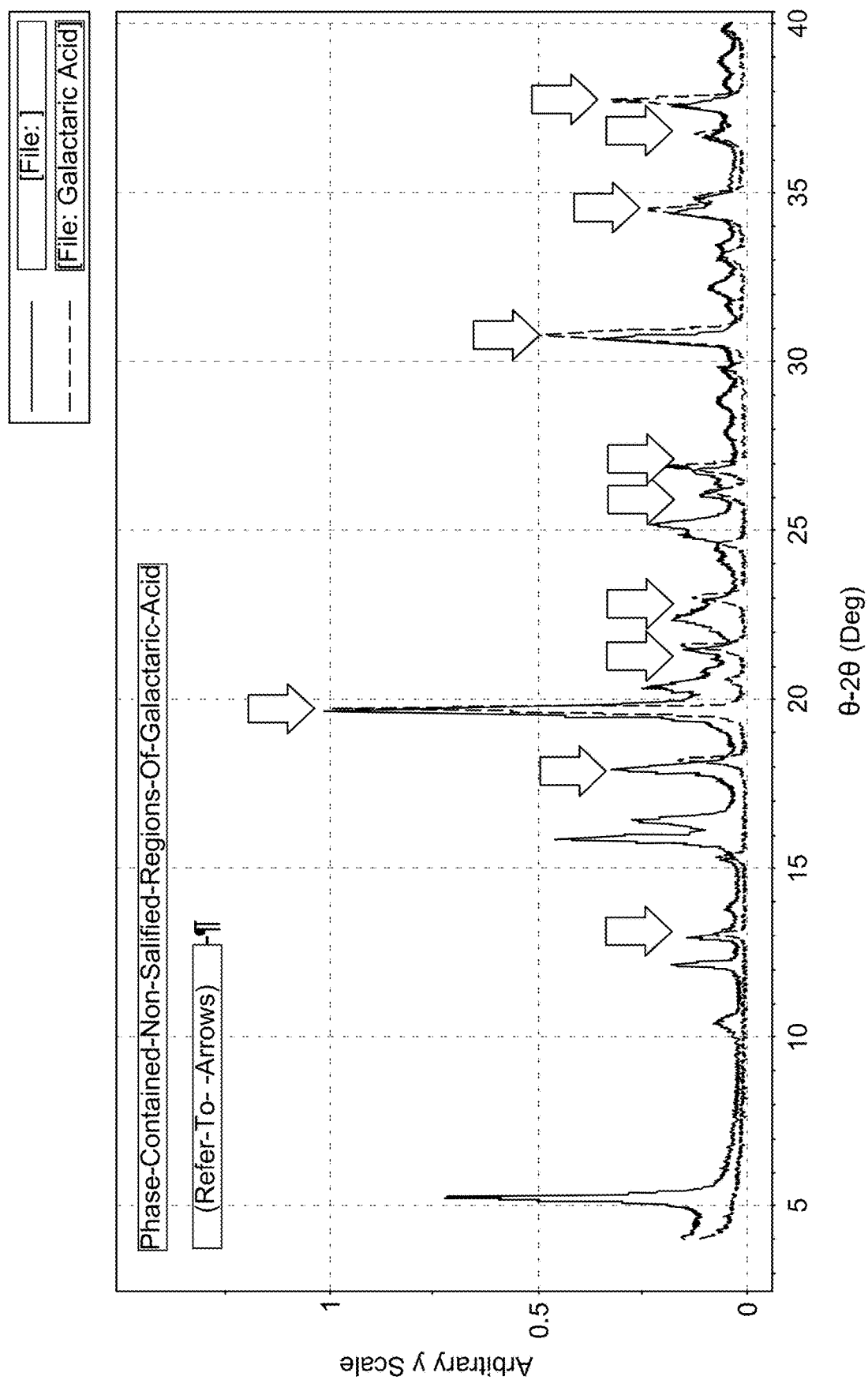

FIG. 244 shows overlaid of XRPD profiles of crystalline compound 1 galactarate top) and galactaric acid, non-ionized.

Figure 245:
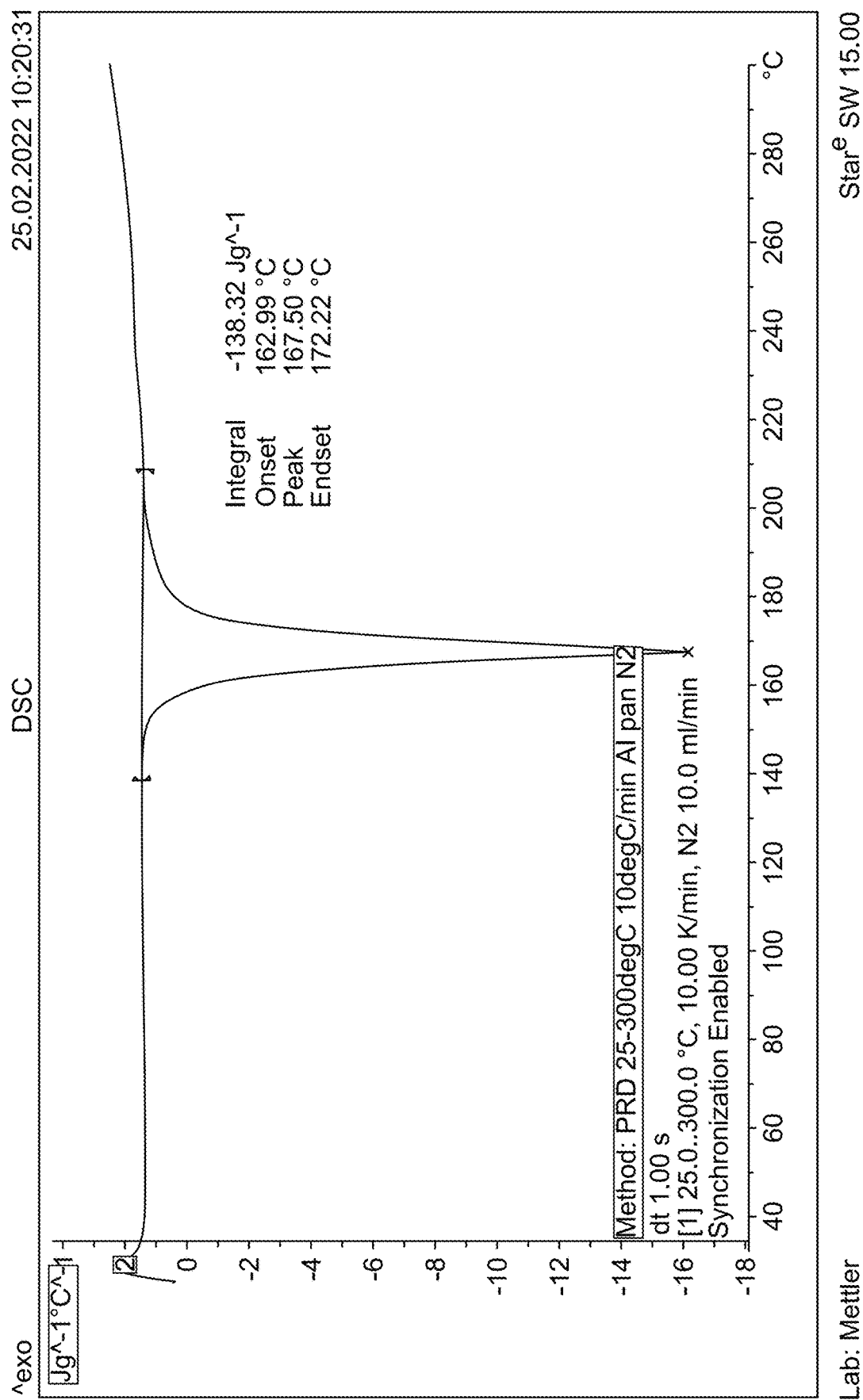

FIG. 245 shows a DSC profile of crystalline compound 1 Galactarate

Figure 246:
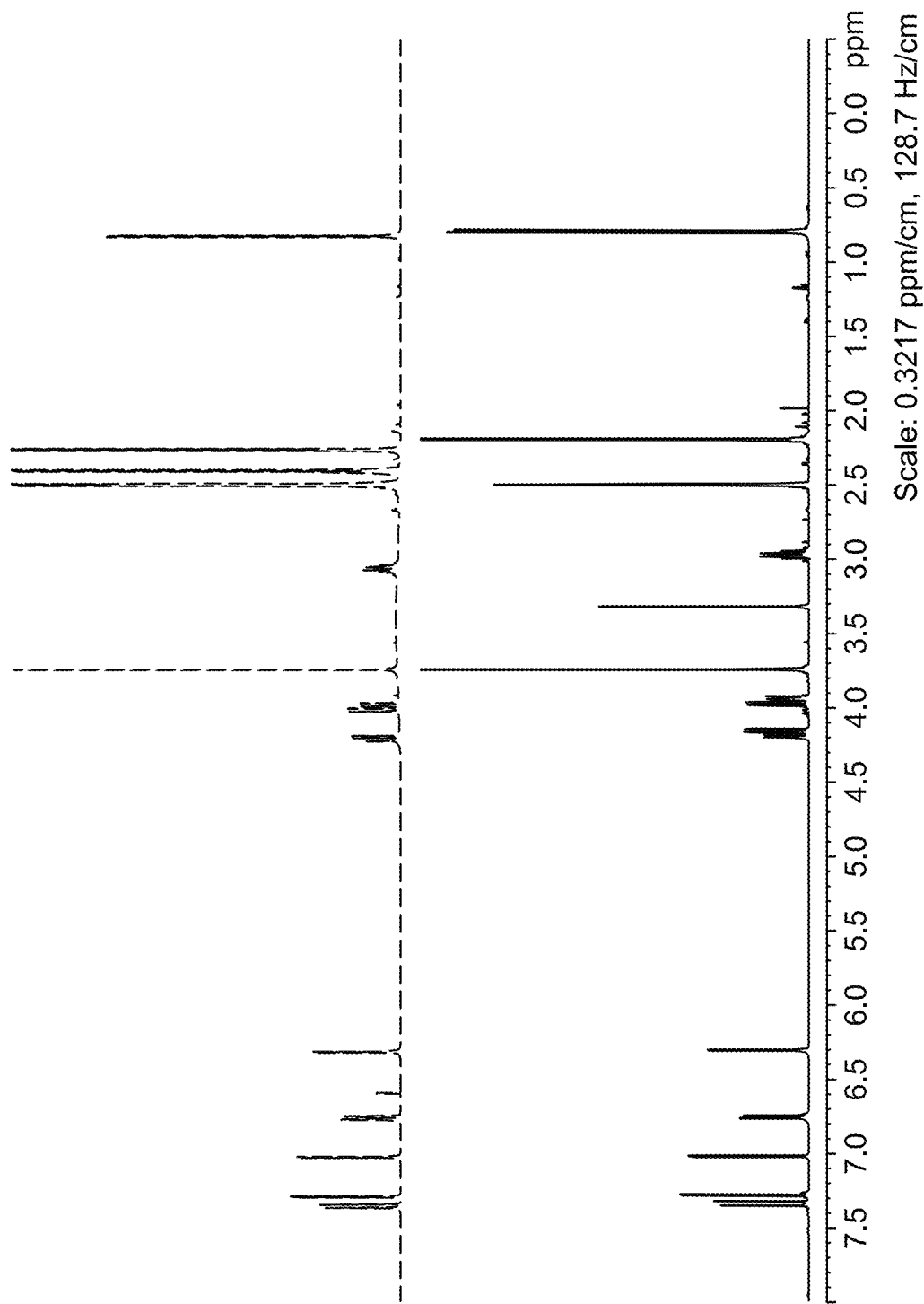

FIG. 246 shows overlaid of $^1$H NMR spectra of crystalline compound 1 Succinate and amorphous compound 1.

Figure 247:
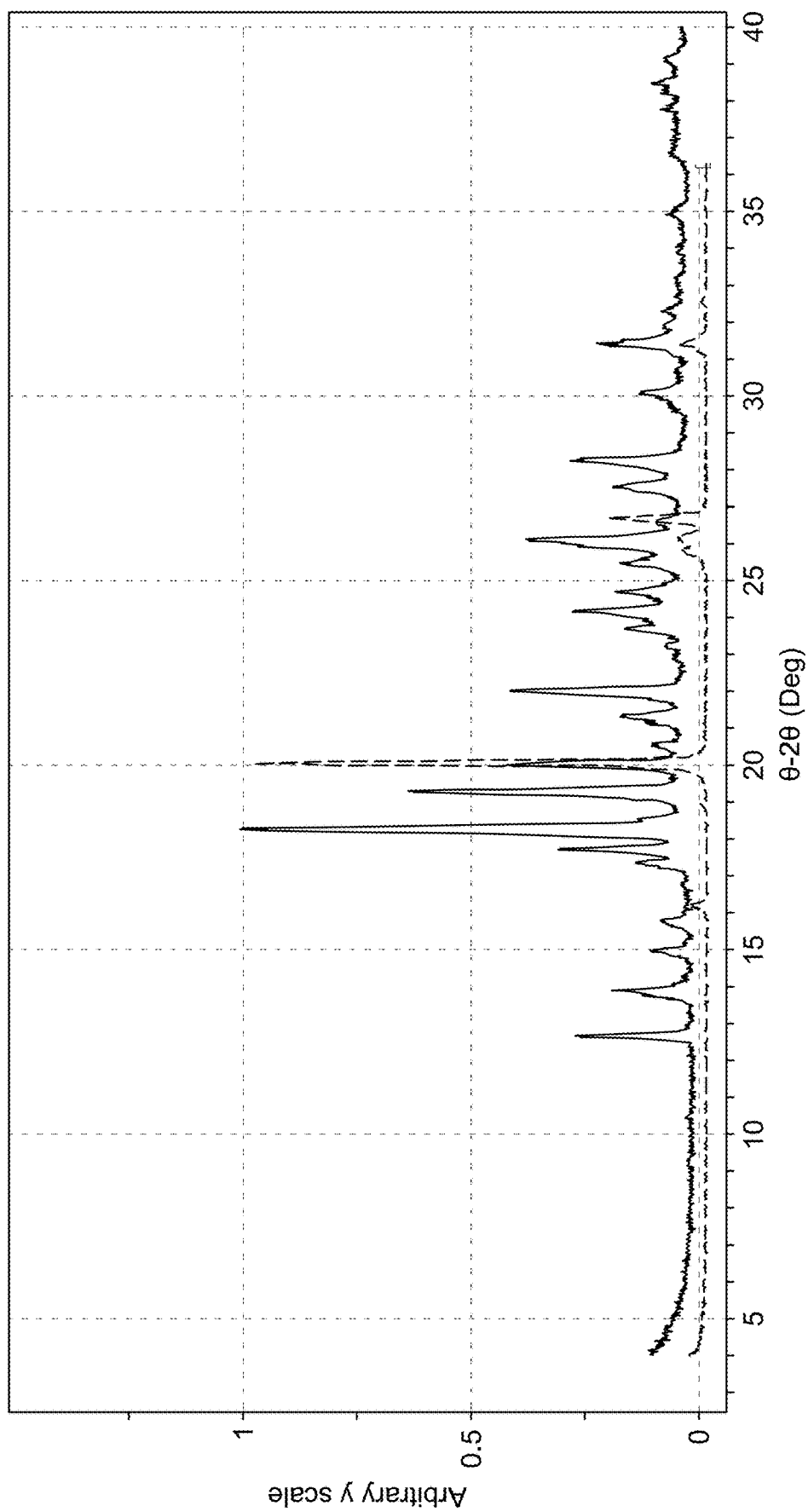

FIG. 247 shows overlaid XRPD profiles of crystalline compound 1 Succinate (top) and succinic acid, non-ionized (bottom).

Figure 248:
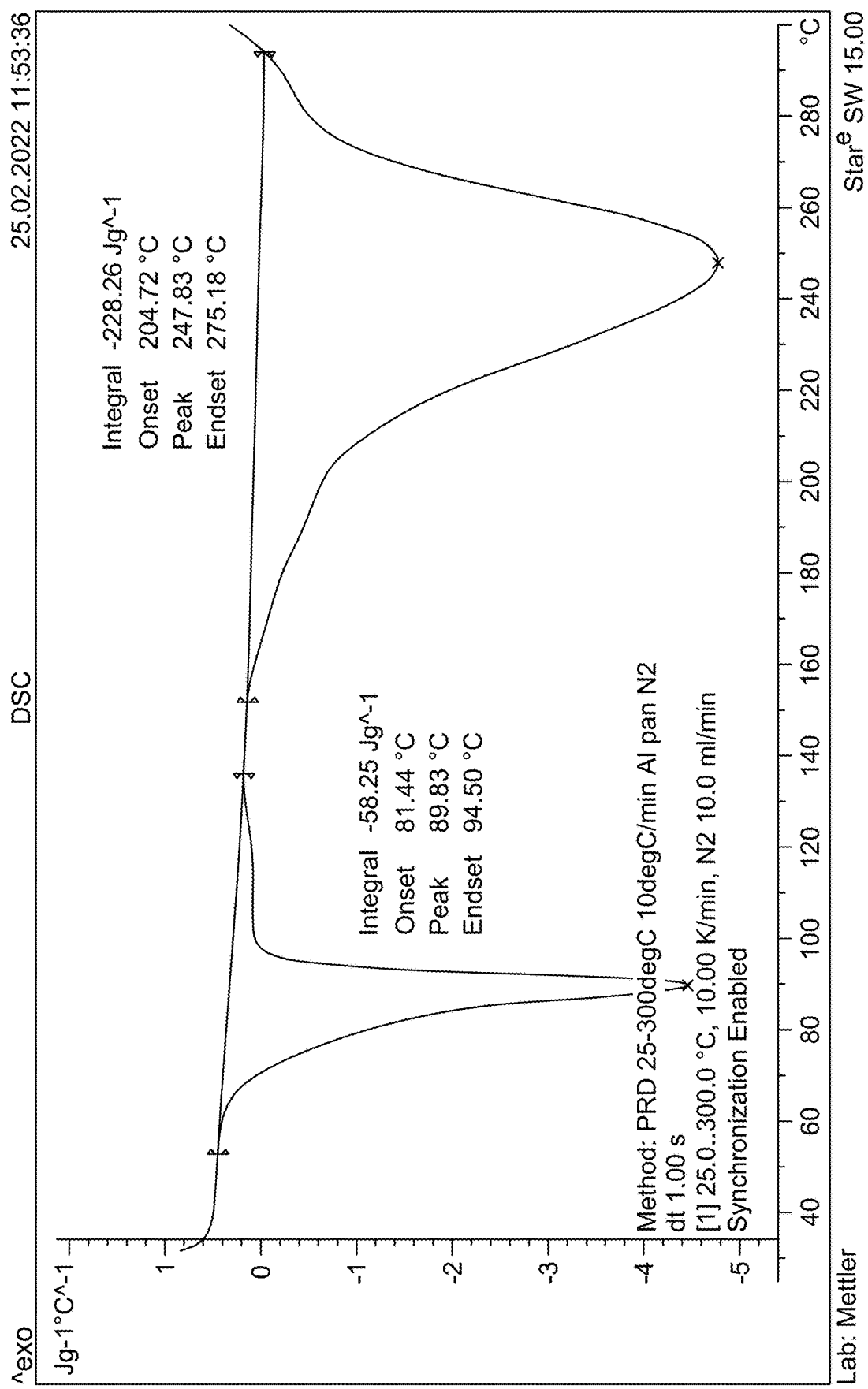

FIG. 248 shows a DSC profile of crystalline compound 1 Succinate.

Figure 249:
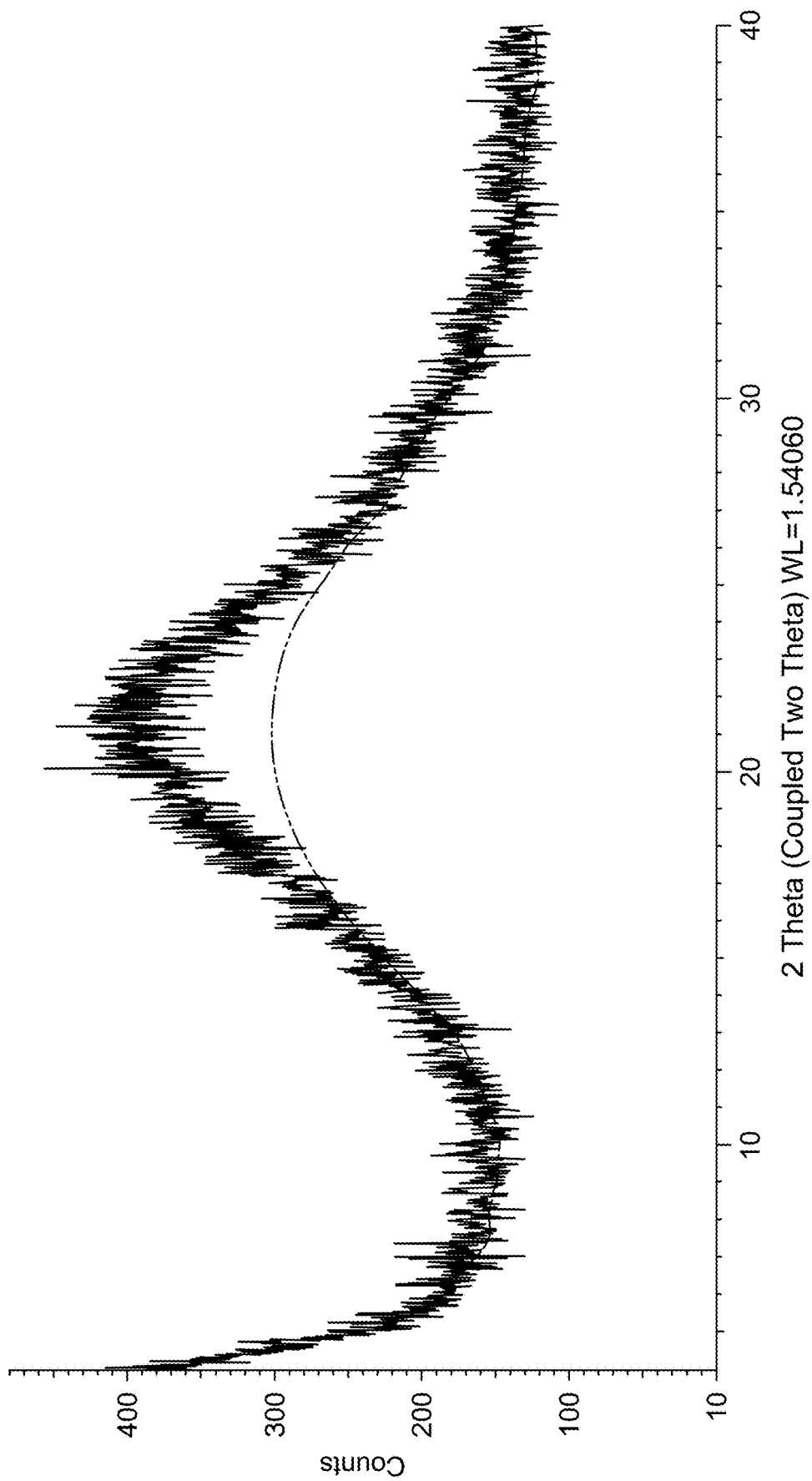

FIG. 249 shows an XRPD profile of crystalline compound 1 Sulfate.

Figure 250:
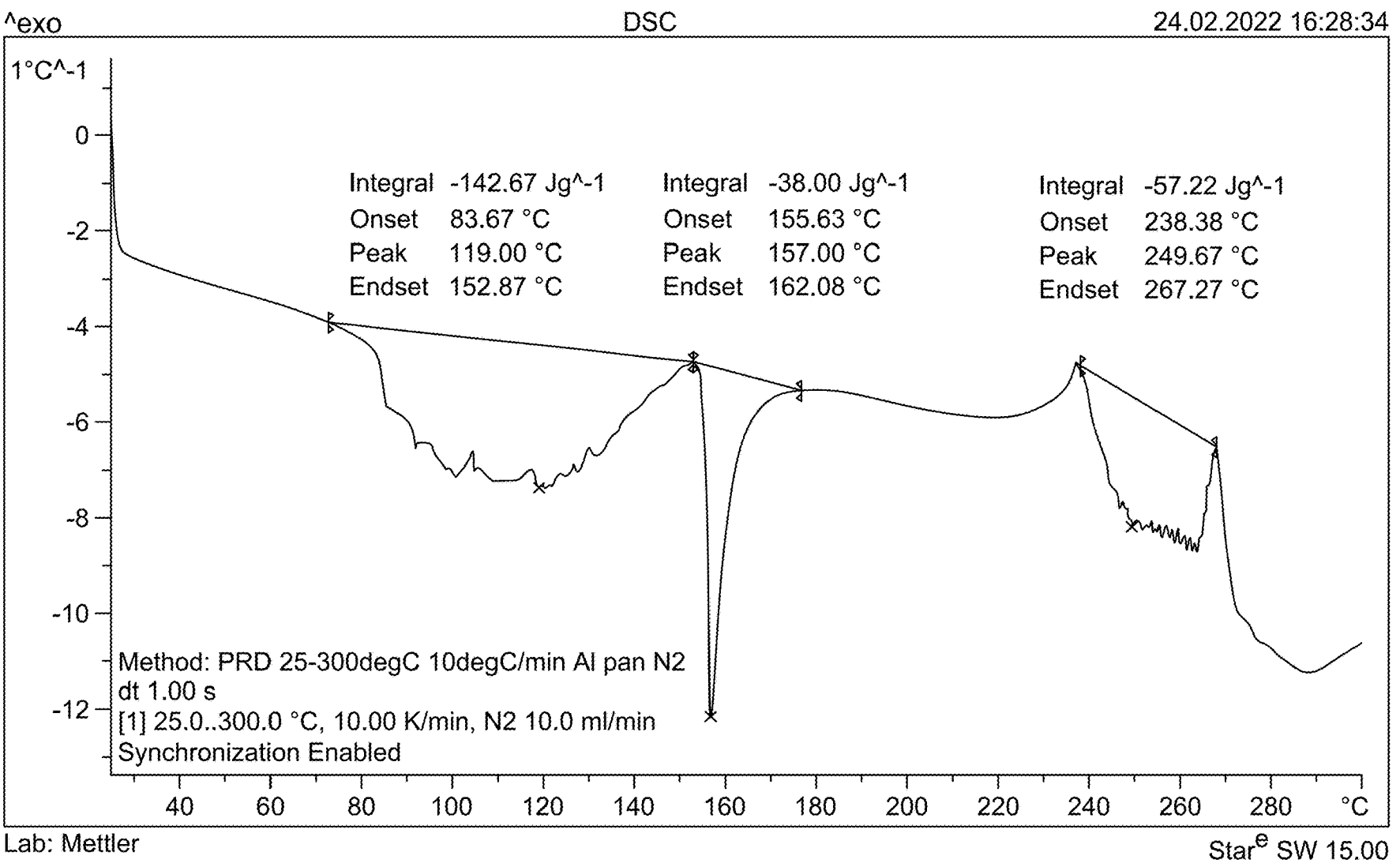

FIG. 250 shows a DSC profile of crystalline compound 1 Sulfate.

Figure 251:
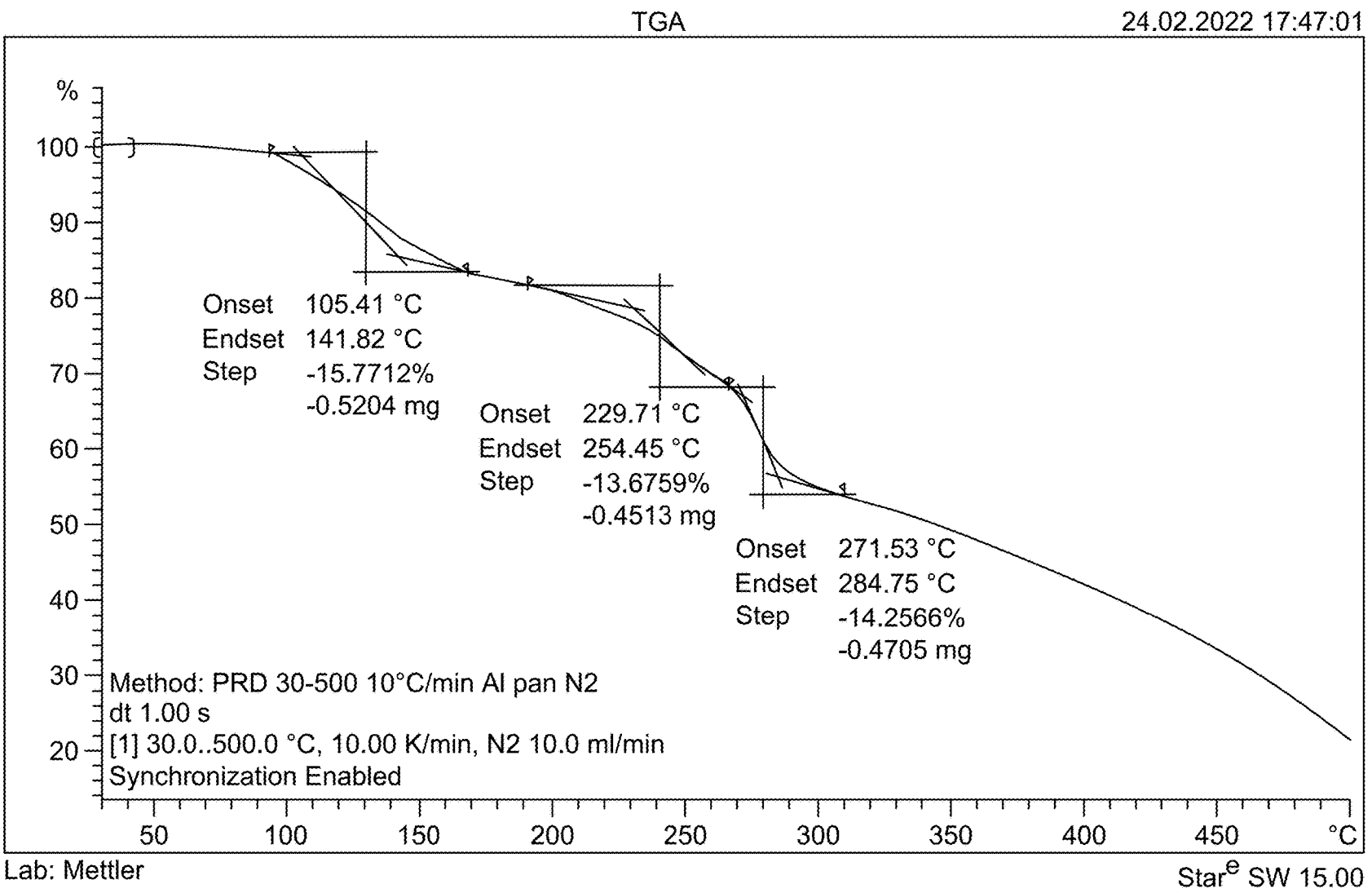

FIG. 251 shows a TGA profile of crystalline compound 1 Sulfate.

Figure 252:
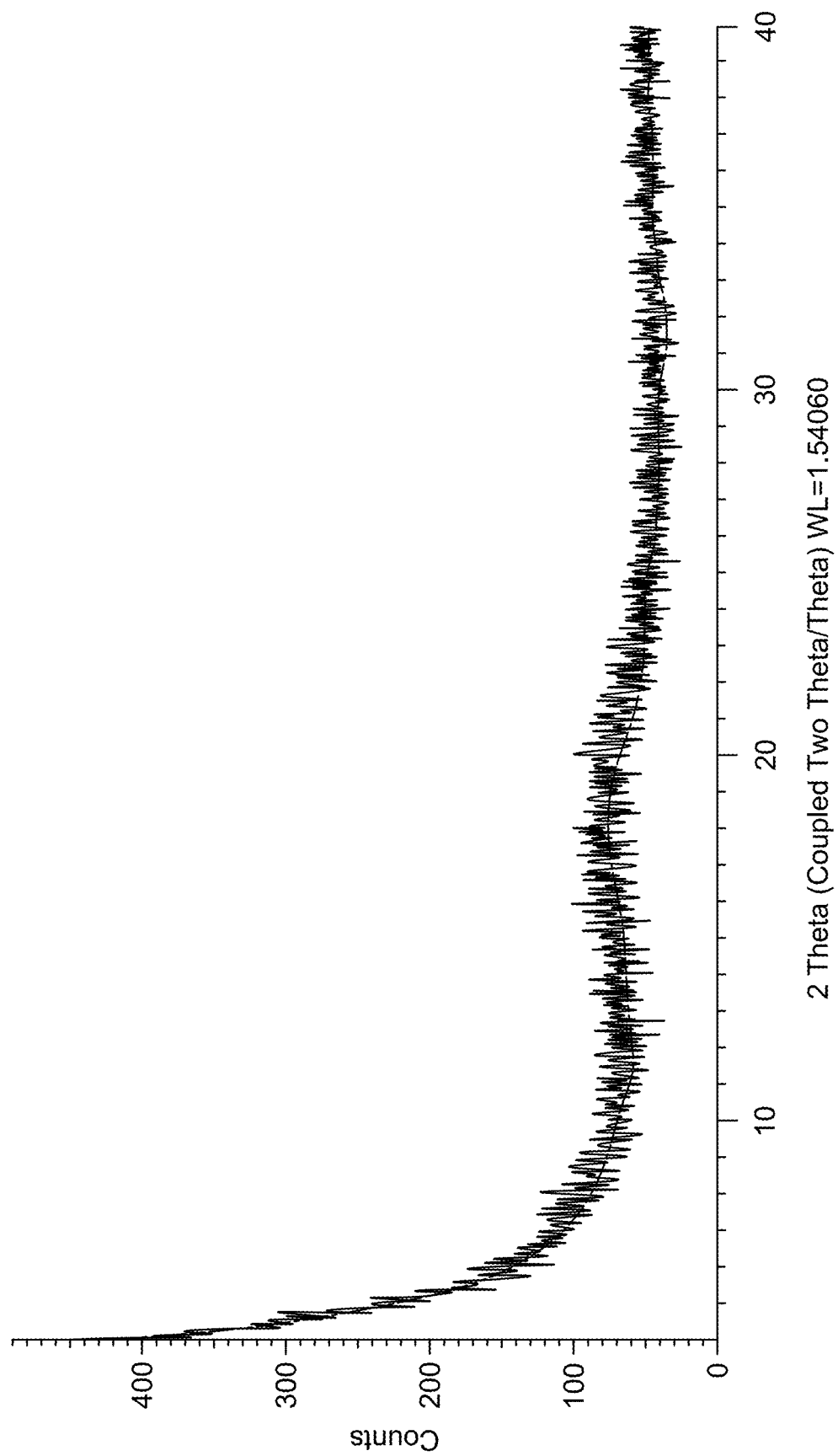
Figure 253:
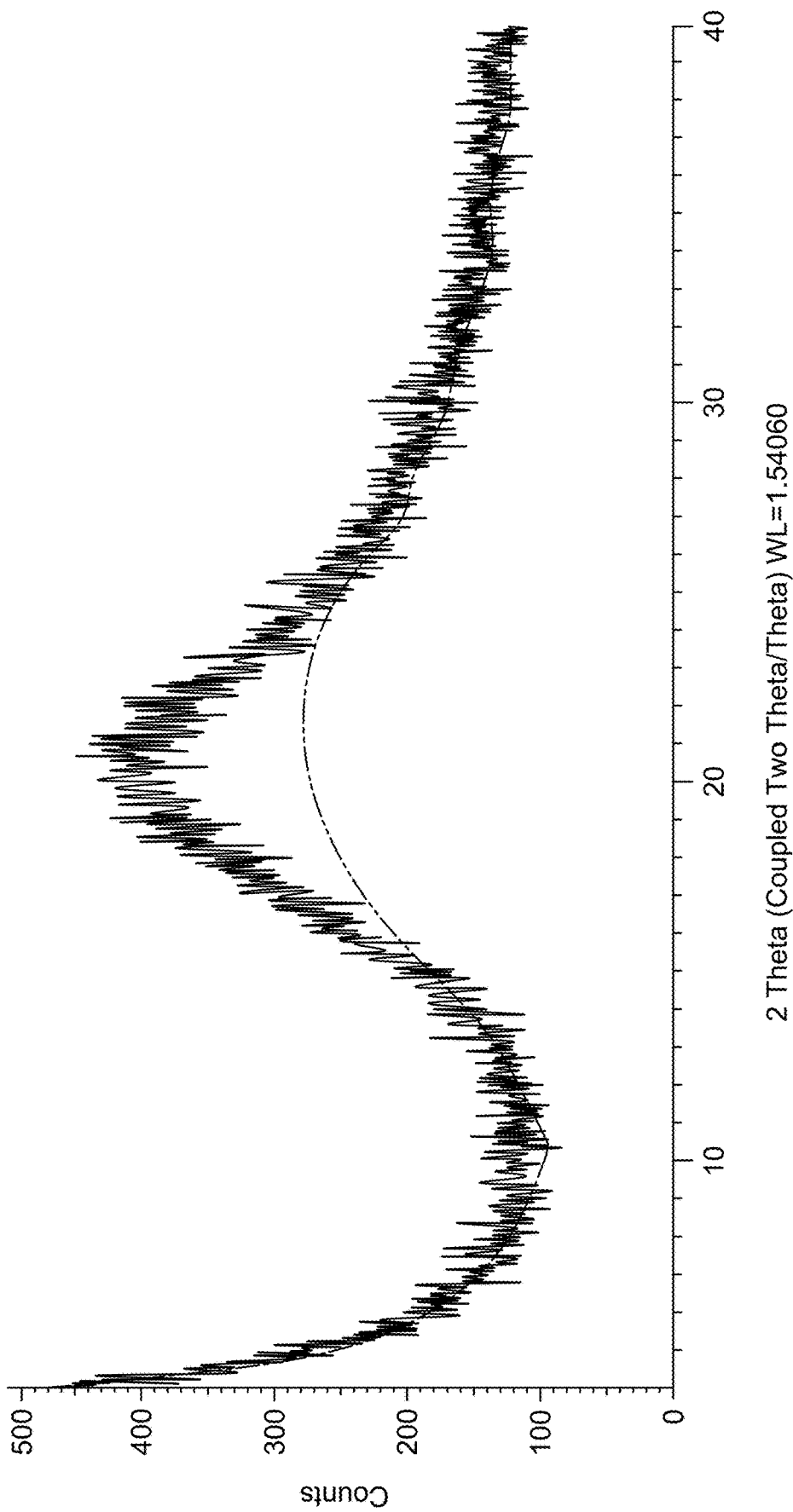

FIG. 252 shows an XRPD profile of compound 1 Esylate. Insufficient sample was gathered for further analyses FIG. 253 shows an XRPD profile of compound 1 Mesylate.

Figure 254:
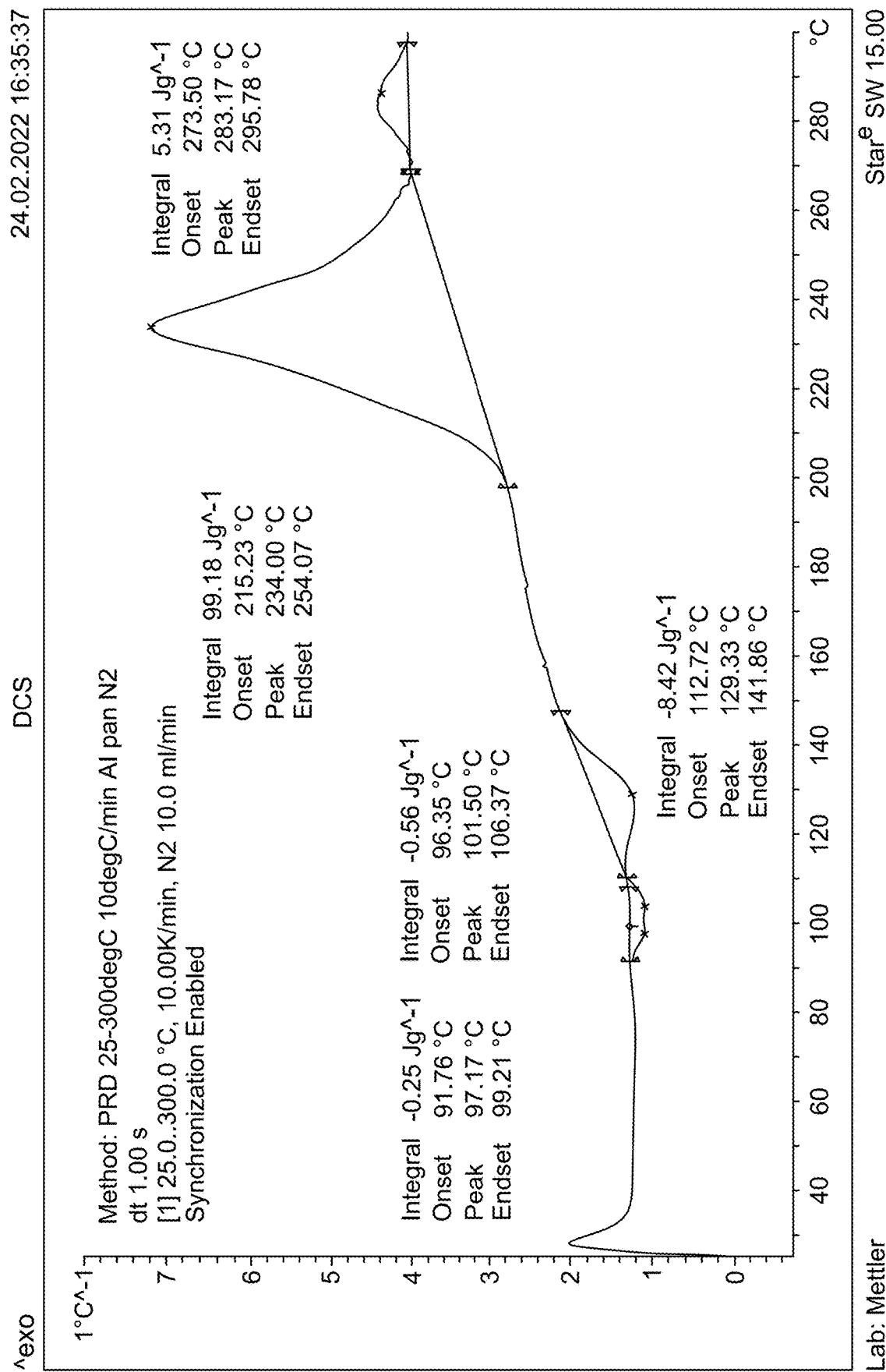

FIG. 254 shows a DSC profile of compound 1 Methanesulfonate.

Figure 255:
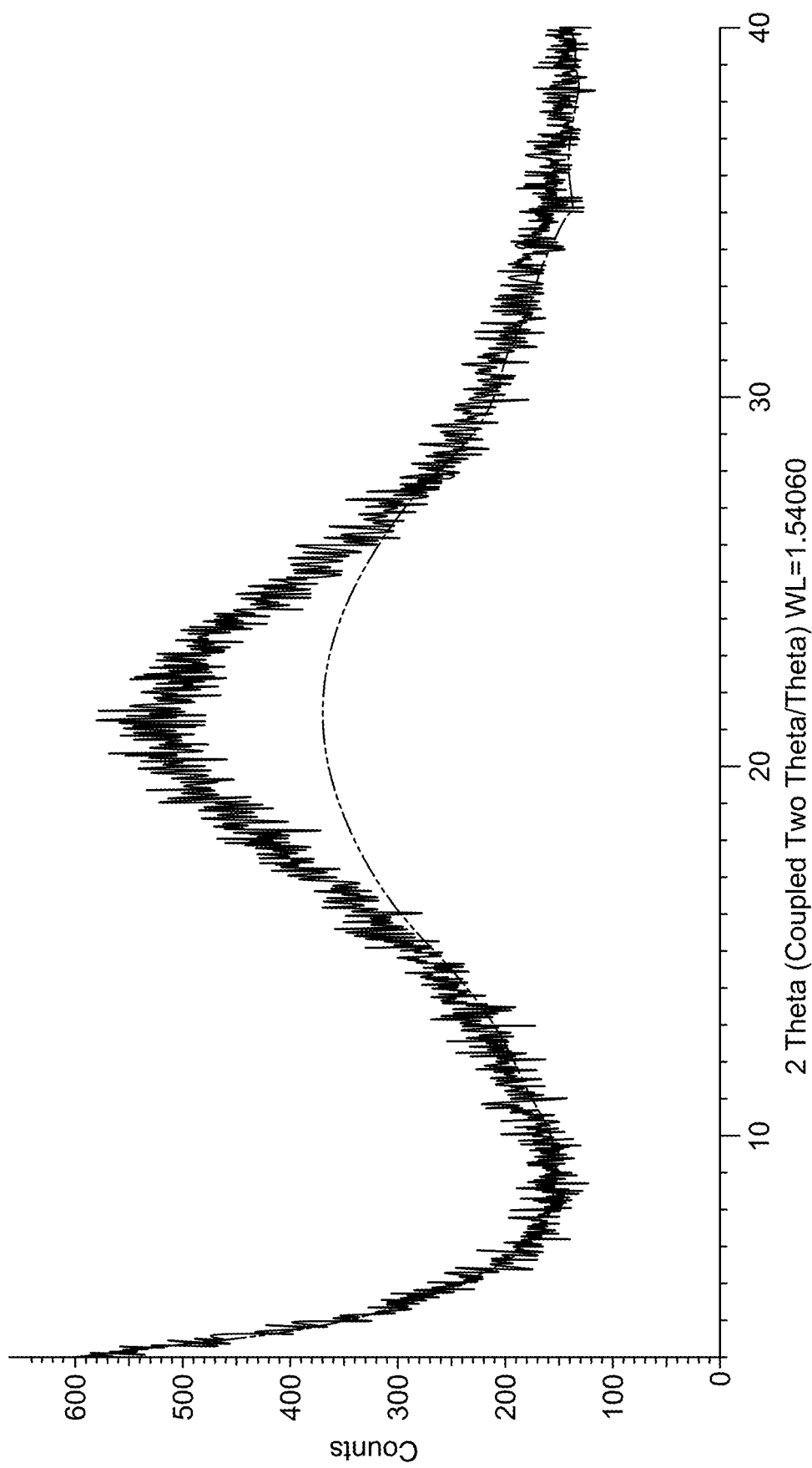

FIG. 255 shows a DSC profile of compound 1 Methanesulfonate.

Figure 256:
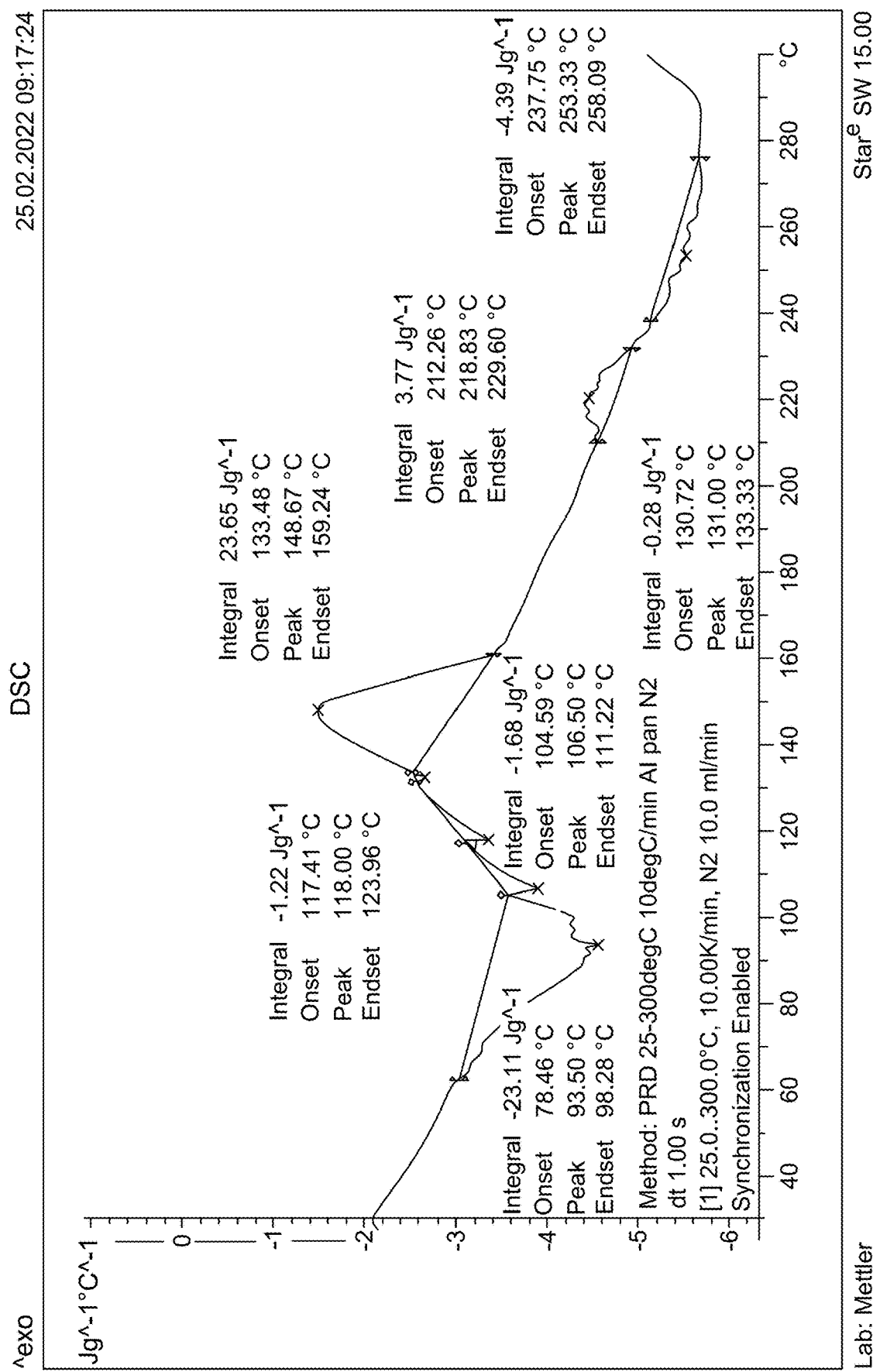

FIG. 256 shows an XRPD profile of compound 1·Phosphate.

Figure 257:
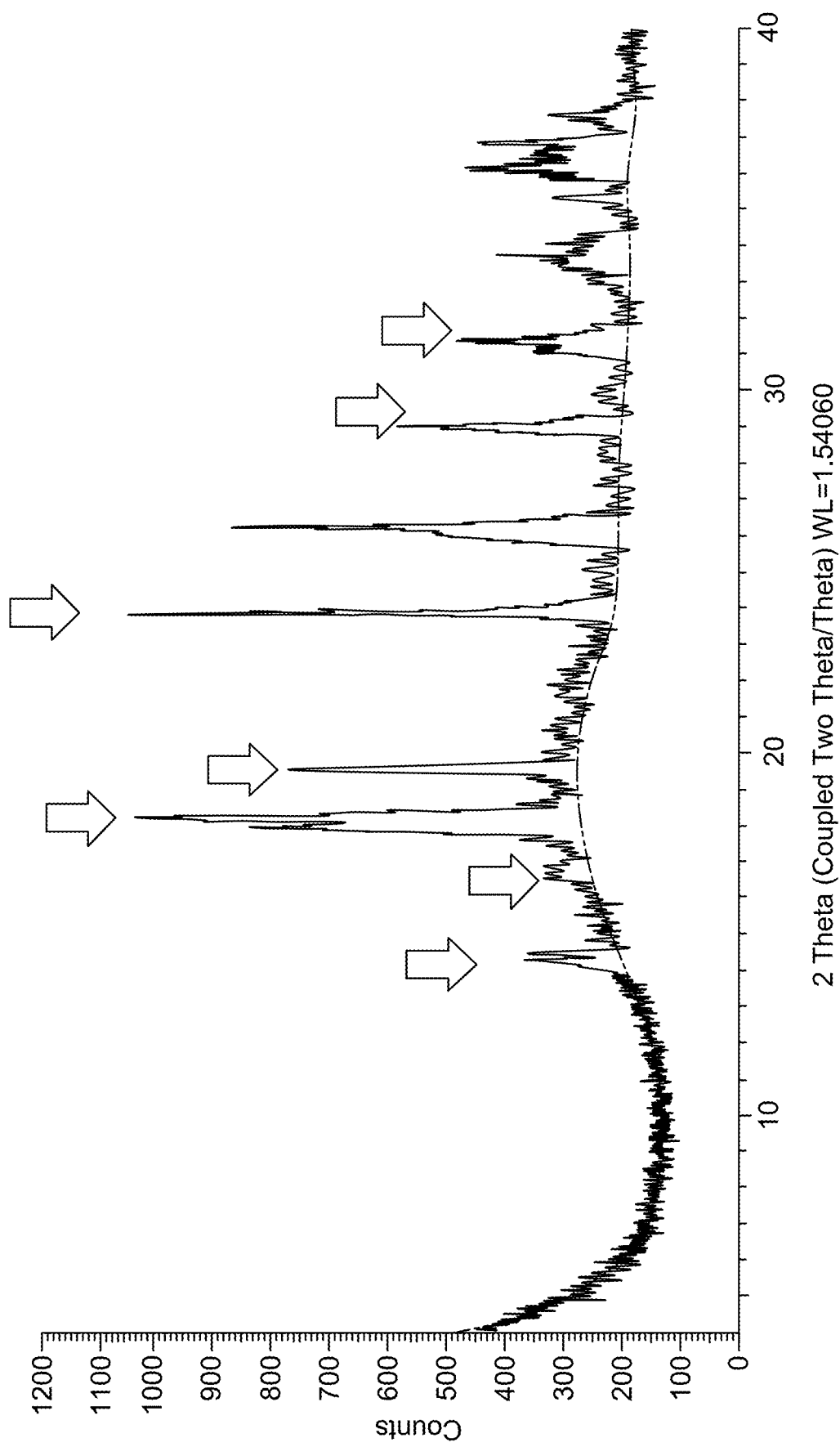
Figure 258:
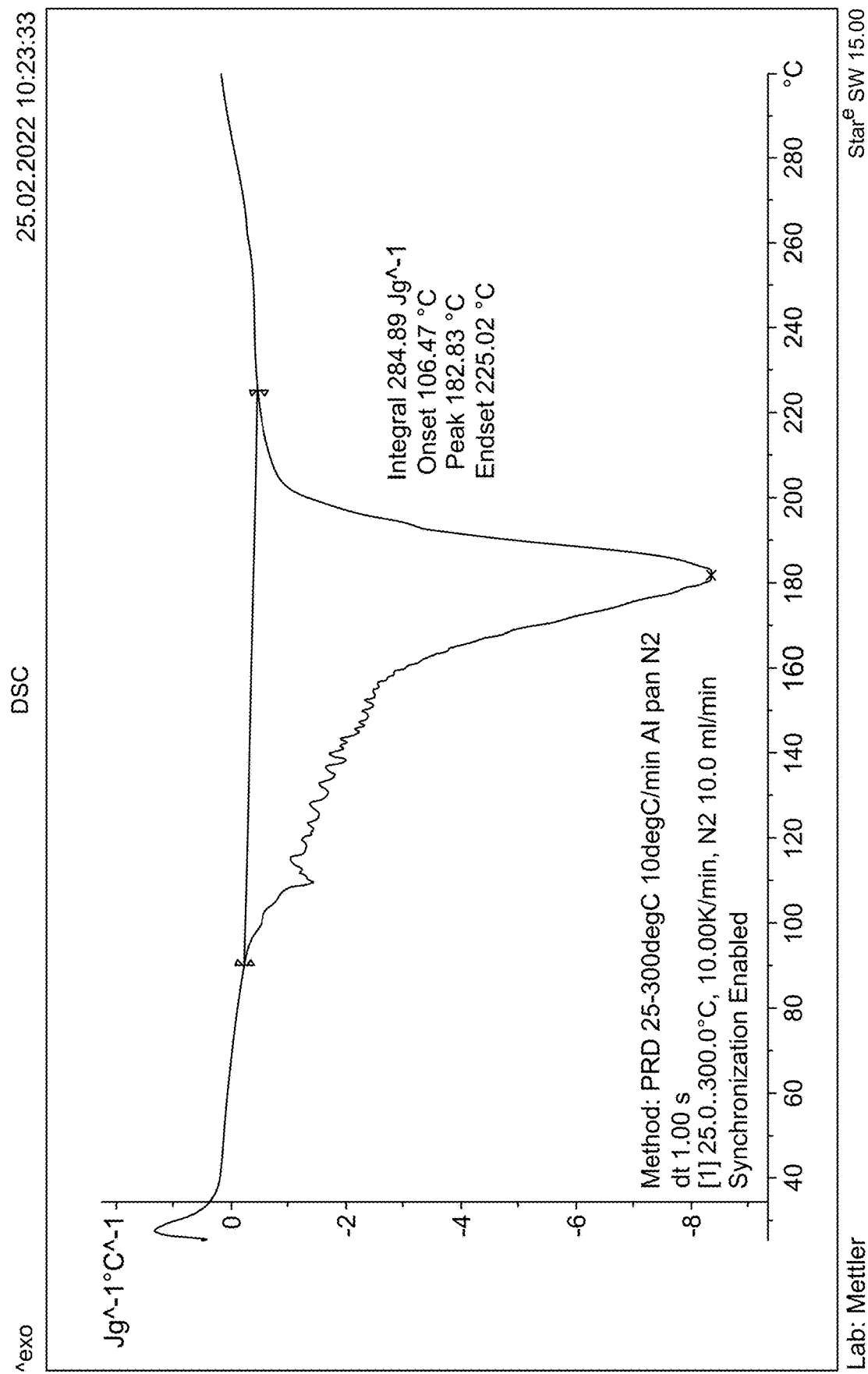

FIG. 257 shows an XRPD profile of crystalline compound 1 Citrate. Arrows designate presence of non-ionized citric acid FIG. 258 shows a DSC profile of compound 1 Citrate.

Figure 259:
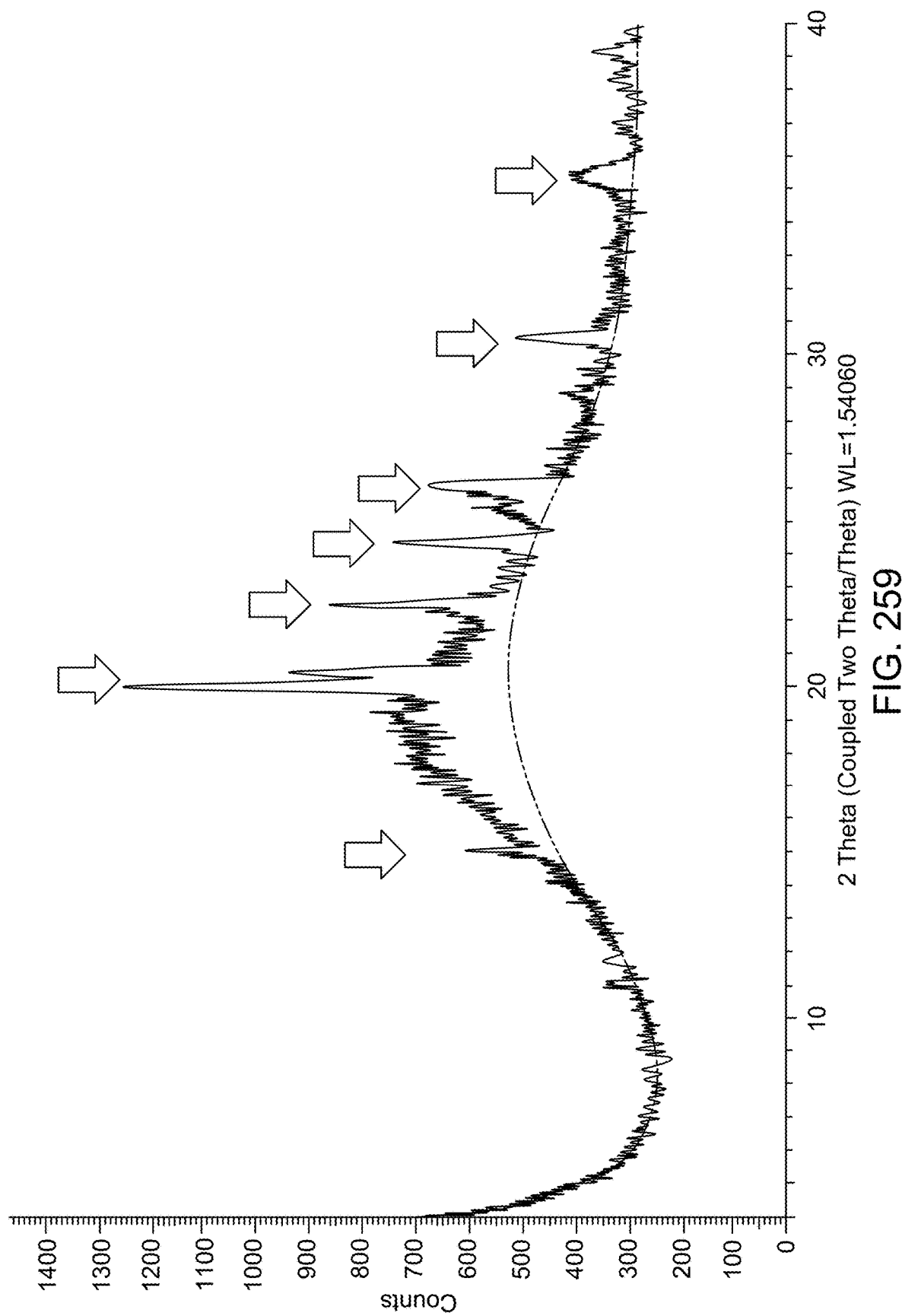

FIG. 259 shows a XRPD profile of crystalline compound 1 Glucuronate. Arrows designate presence of non-ionized glucuronic acid.

Figure 260:
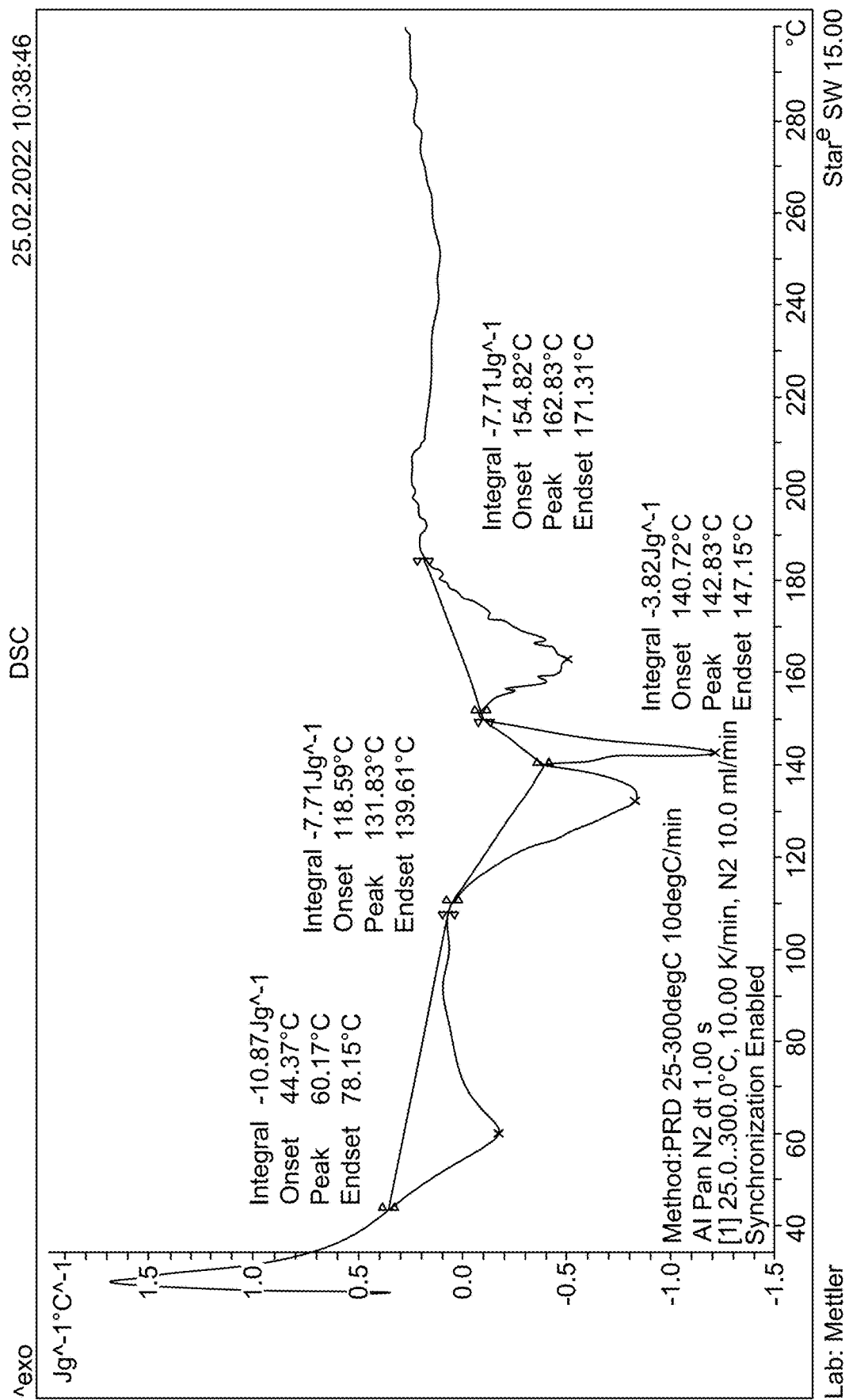

FIG. 260 shows a DSC profile of compound 1 Glucuronate.

Figure 261:
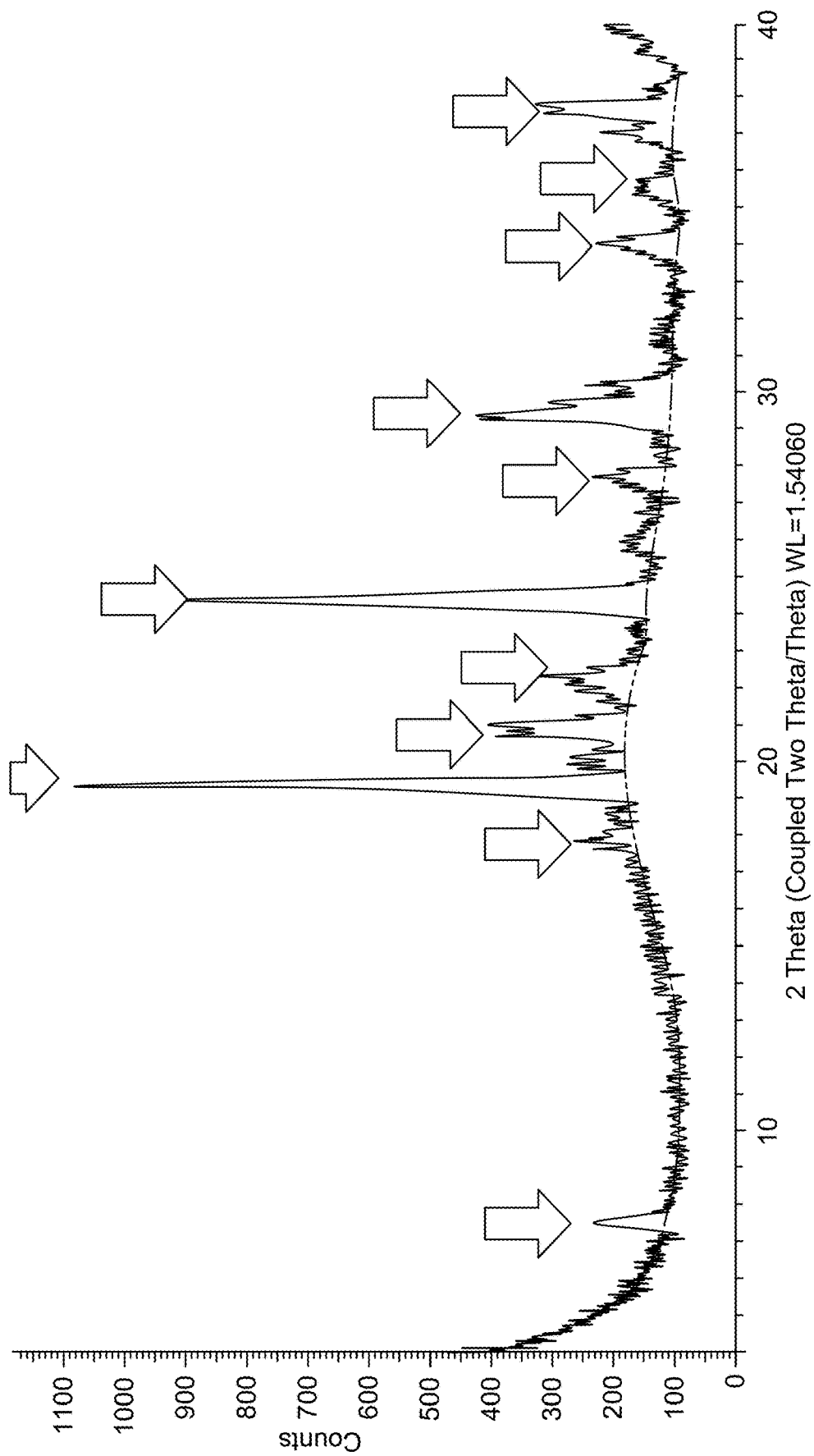

FIG. 261 shows an XRPD profile of crystalline compound 1 Malate. Arrows designate presence of non-ionized malic acid.

Figure 262:
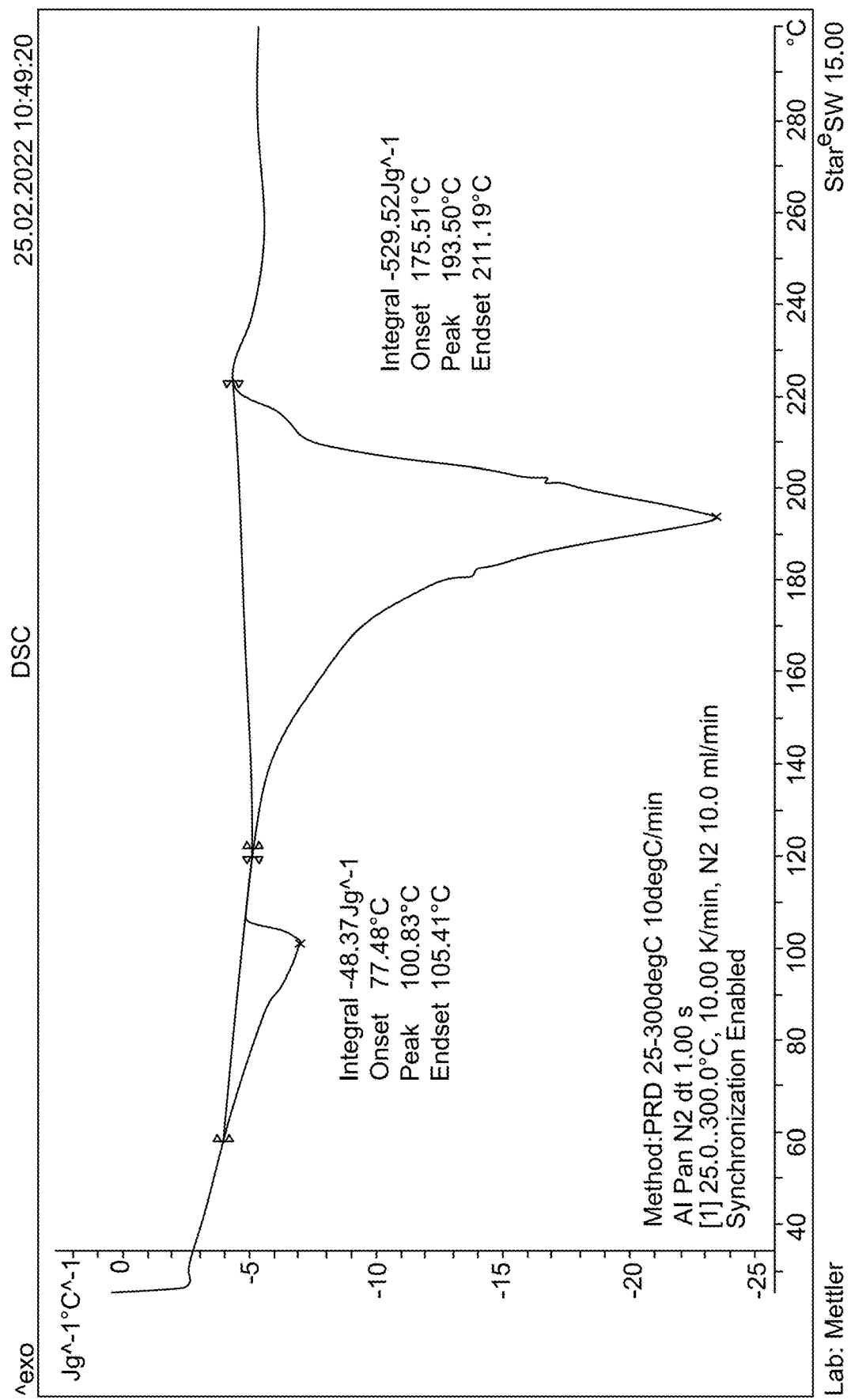

FIG. 262 shows a DSC profile of compound 1 Malate.

Figure 263:
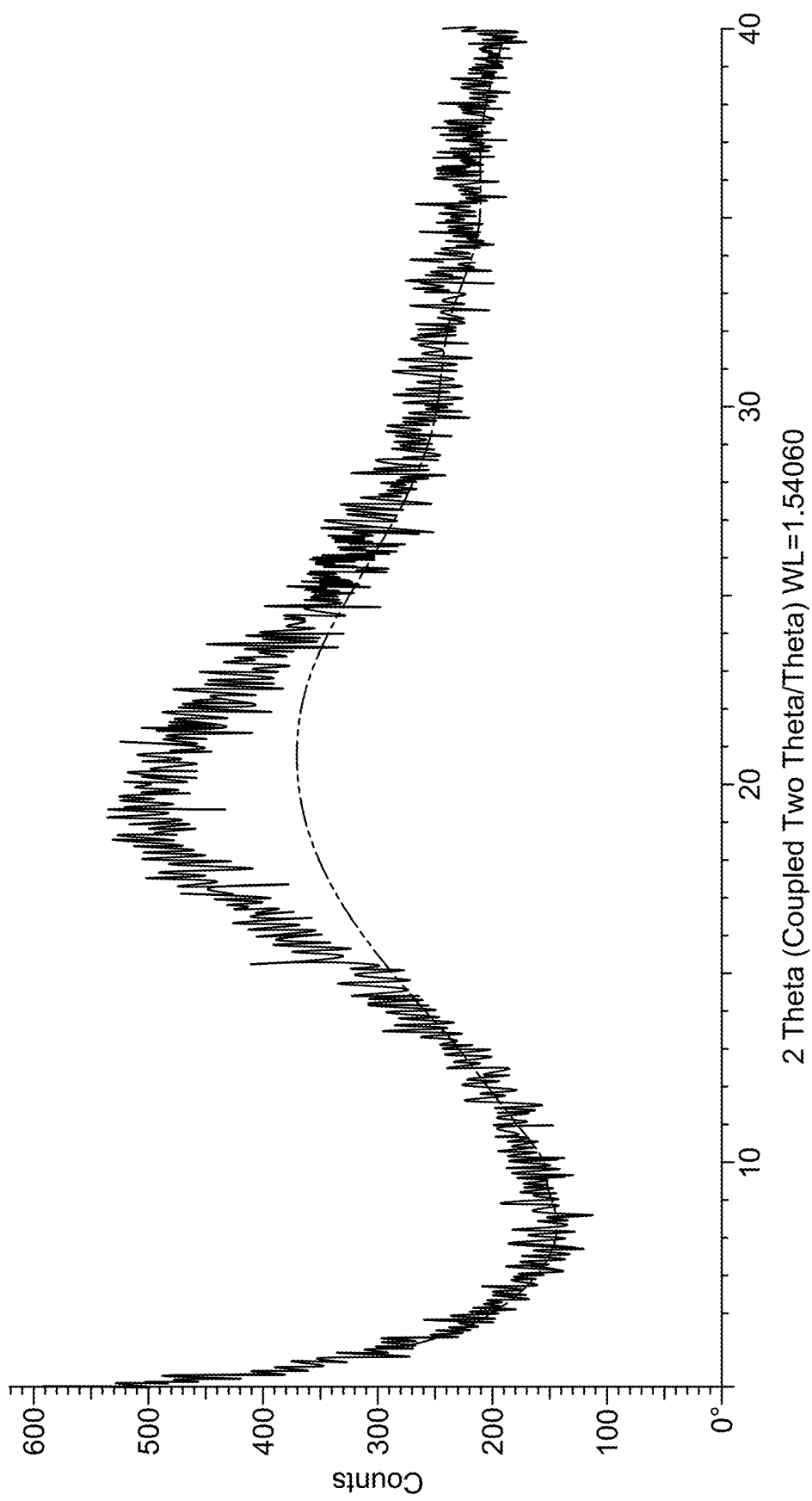

FIG. 263 shows an XRPD profile of compound 1 Gluconate.

Figure 264:
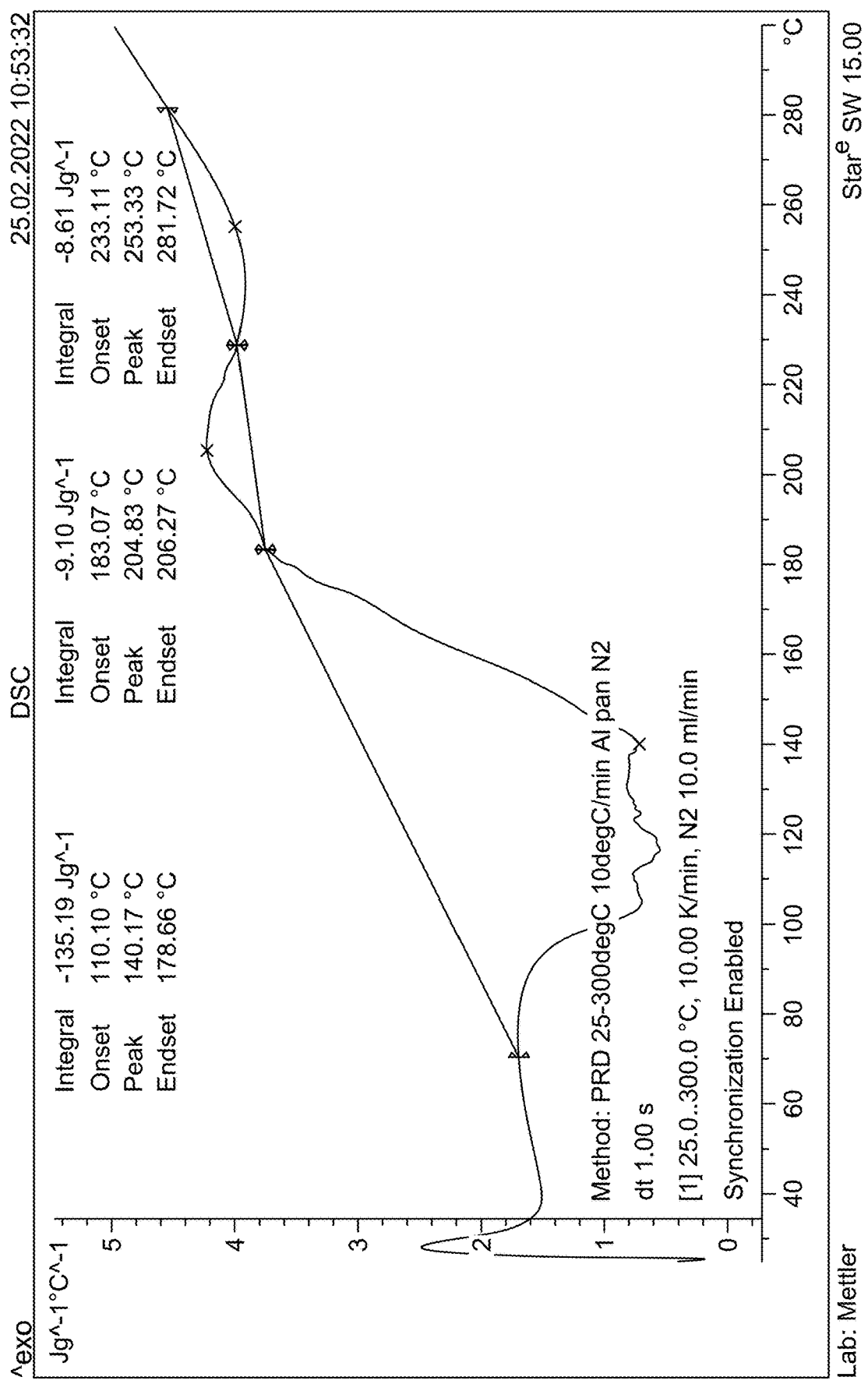

FIG. 264 shows a DSC profile of compound 1 Gluconate.

Figure 265:
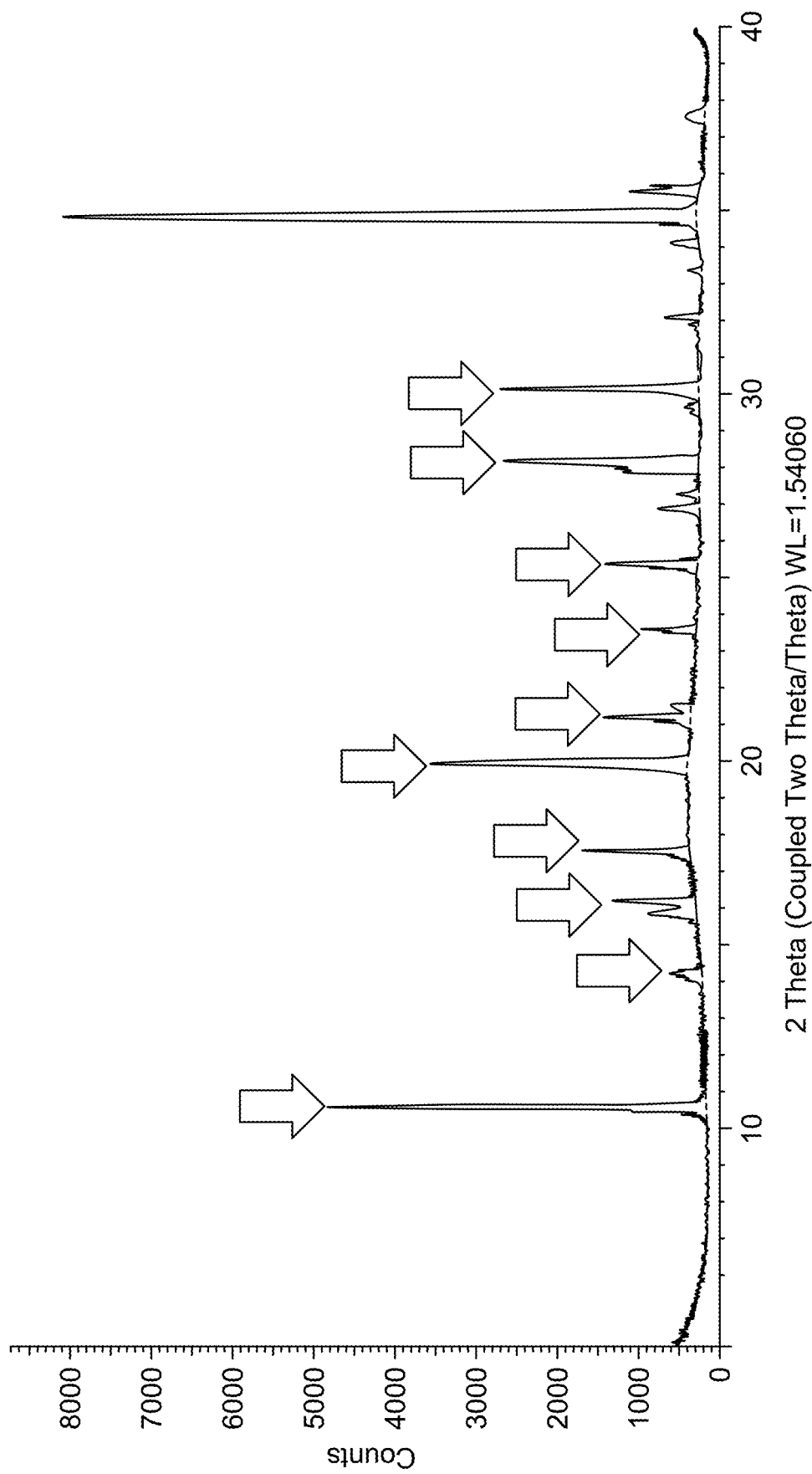

FIG. 265 shows an XRPD profile of crystalline compound 1 Ascorbate. Blue arrows aligned with presence of non-ionized ascorbic acid.

Figure 266:
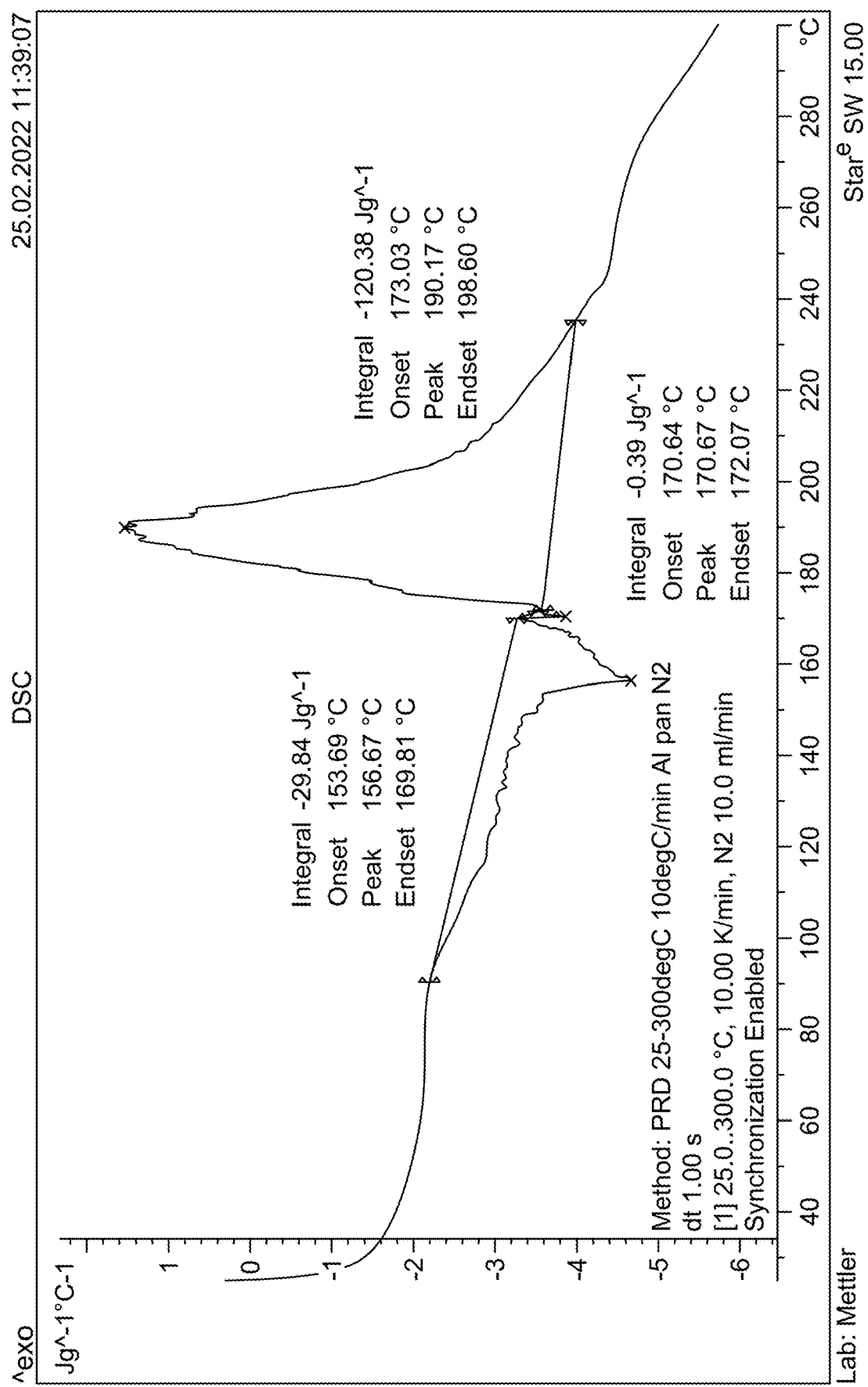

FIG. 266 shows a DSC profile of crystalline compound 1 Ascorbate.

Figure 267:
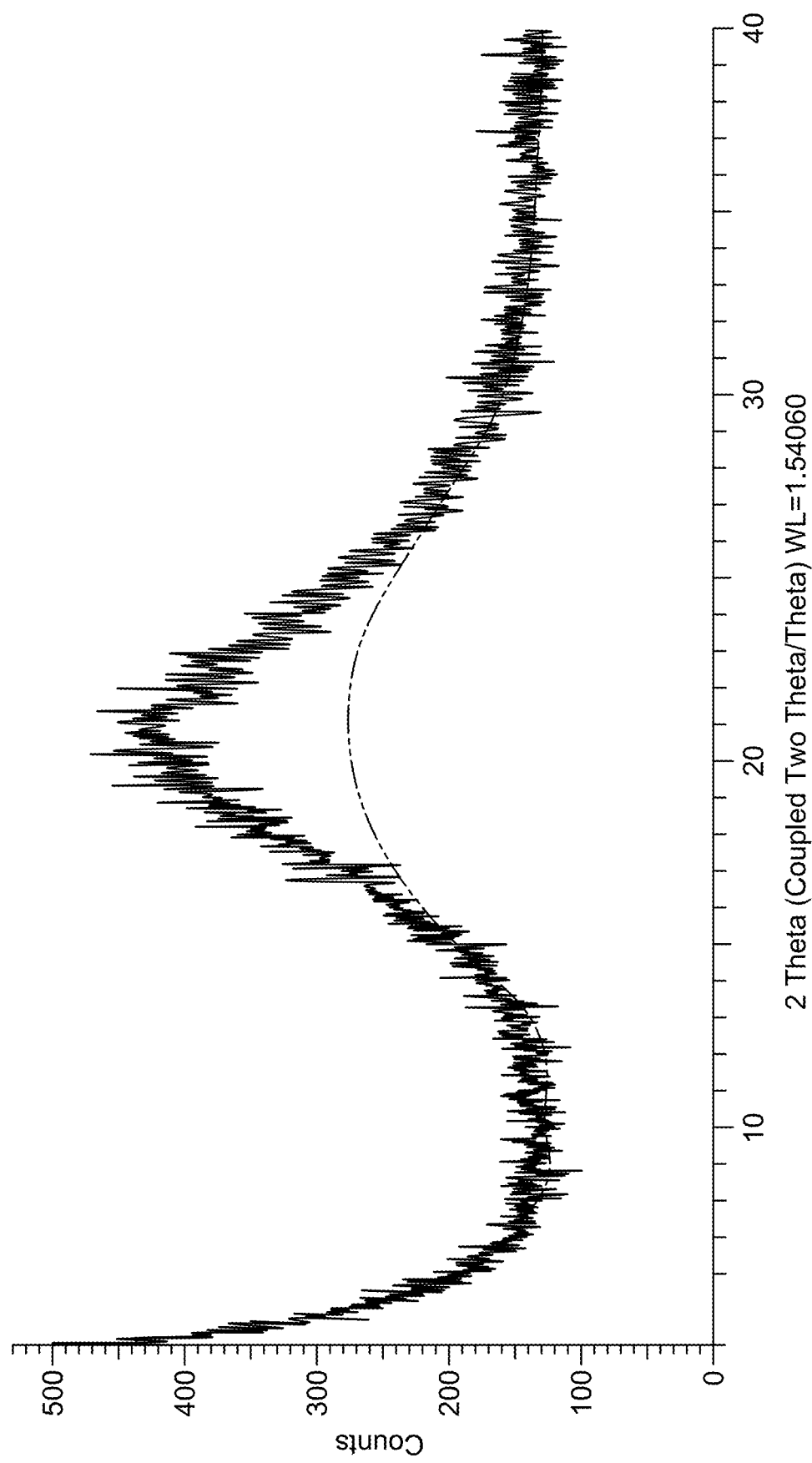

FIG. 267 shows an XRPD profile of compound 1 EDSA.

Figure 268:
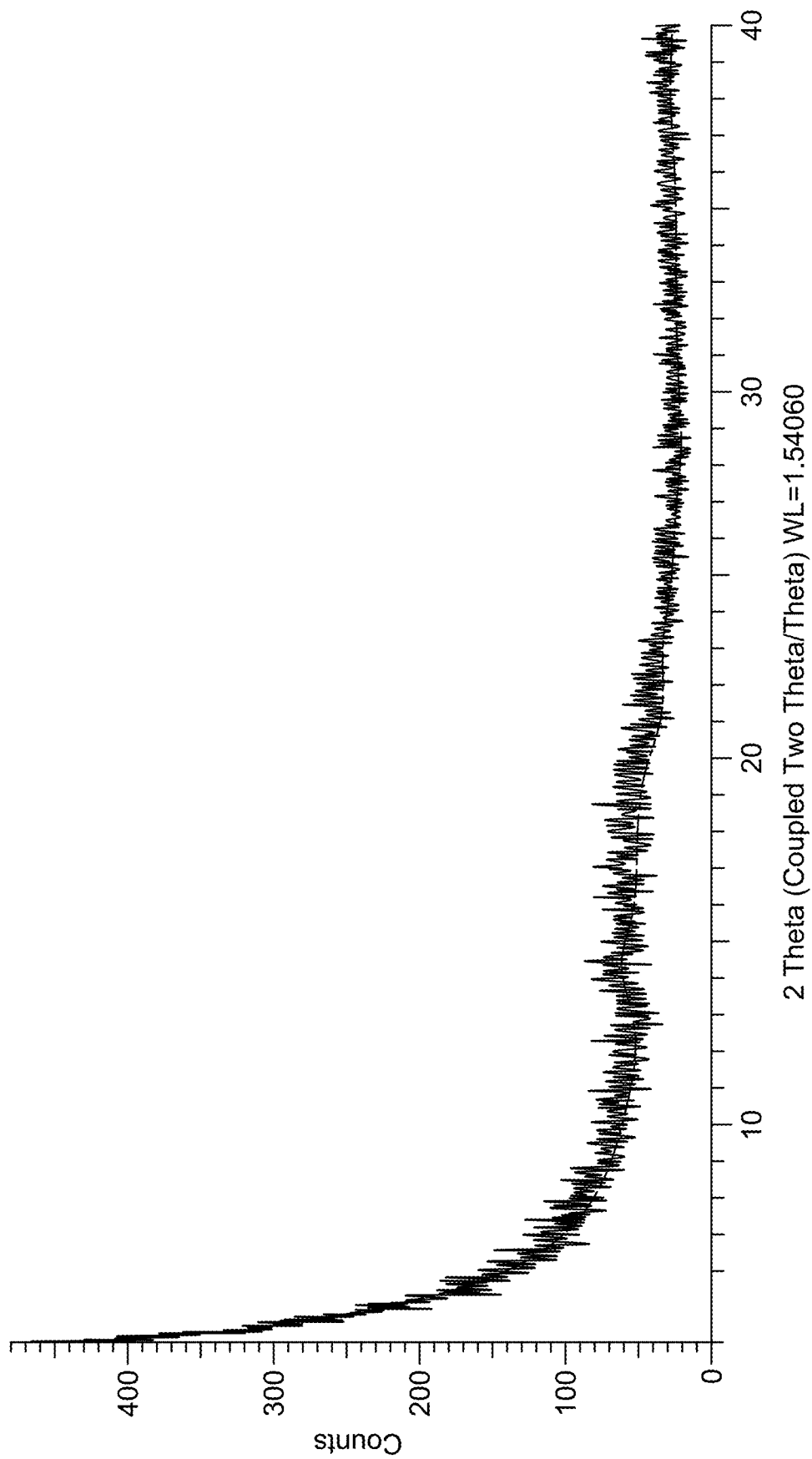

FIG. 268 shows an XRPD profile of compound 1 Adipate.

Figure 269:
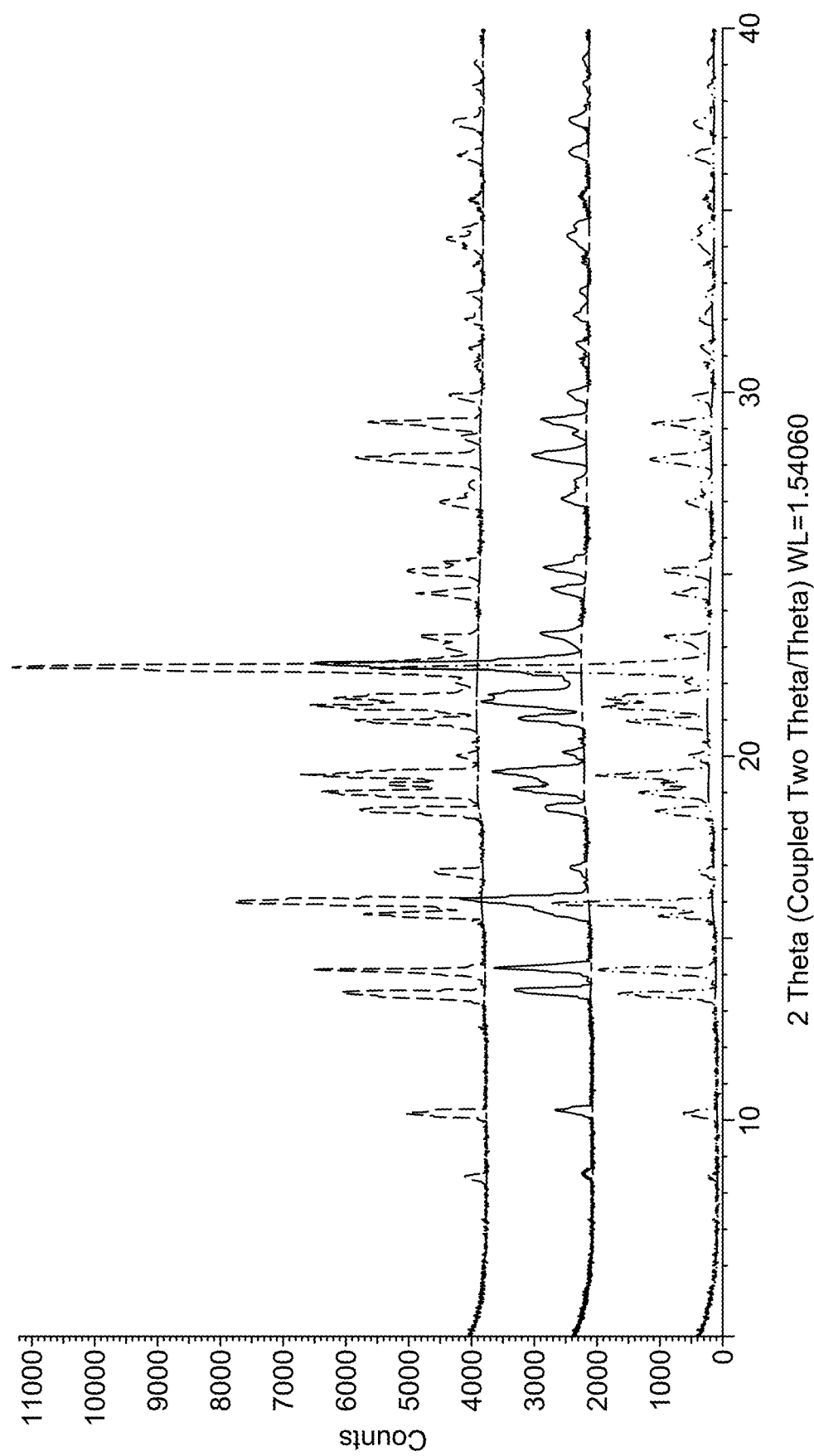

FIG. 269 shows an overlay of XRPD profiles of crystalline compound 1 monofumarate Form A after storage for 0 days (top), 10 days (middle) and 5 days (bottom) at 40° C./75% RH.

Figure 270:
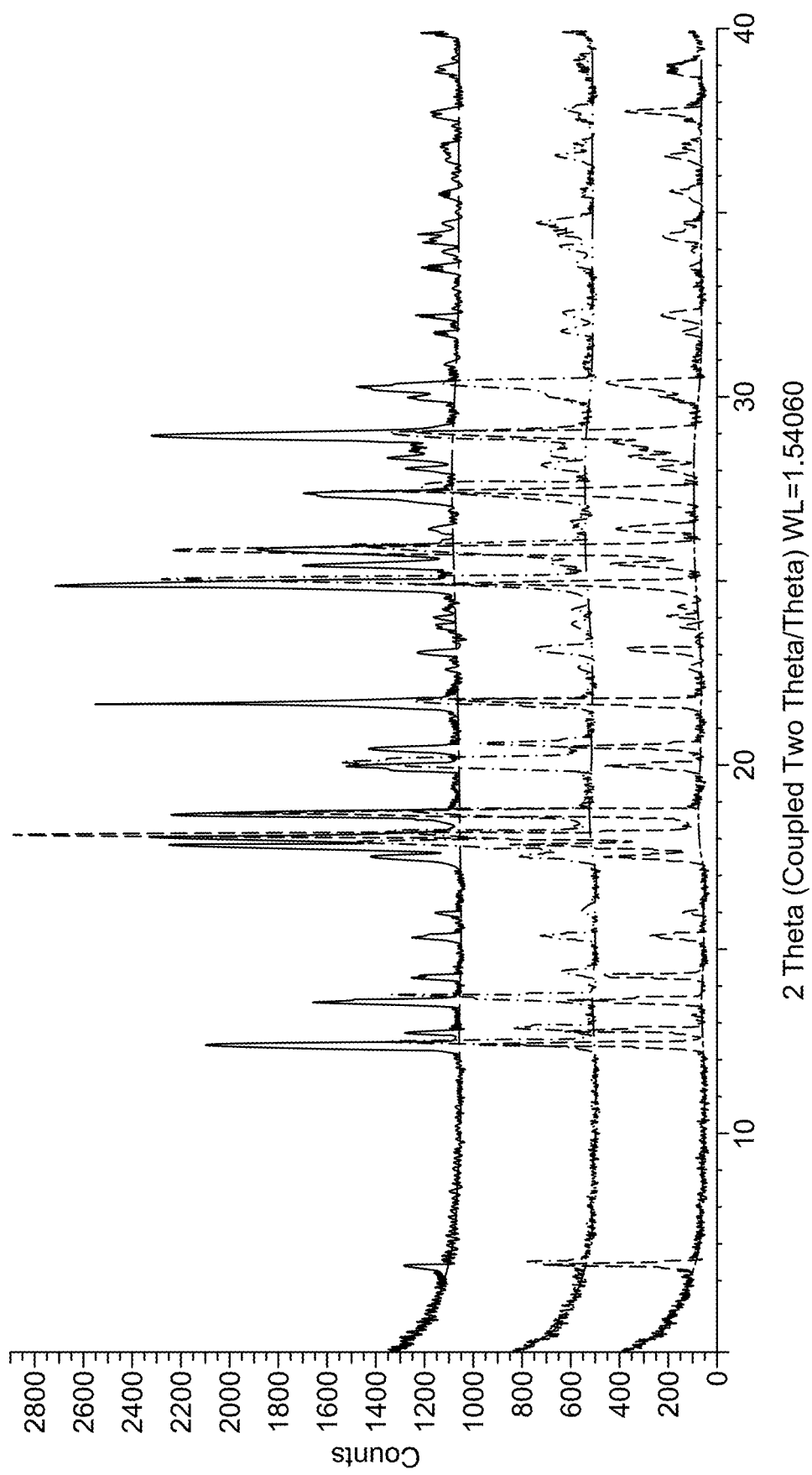

FIG. 270 shows an overlay of XRPD profiles of crystalline compound 1 HCl Form A after storage for 0 days (top), 10 days (middle) and 5 days (bottom) at 40° C./75% RH.

Figure 271:
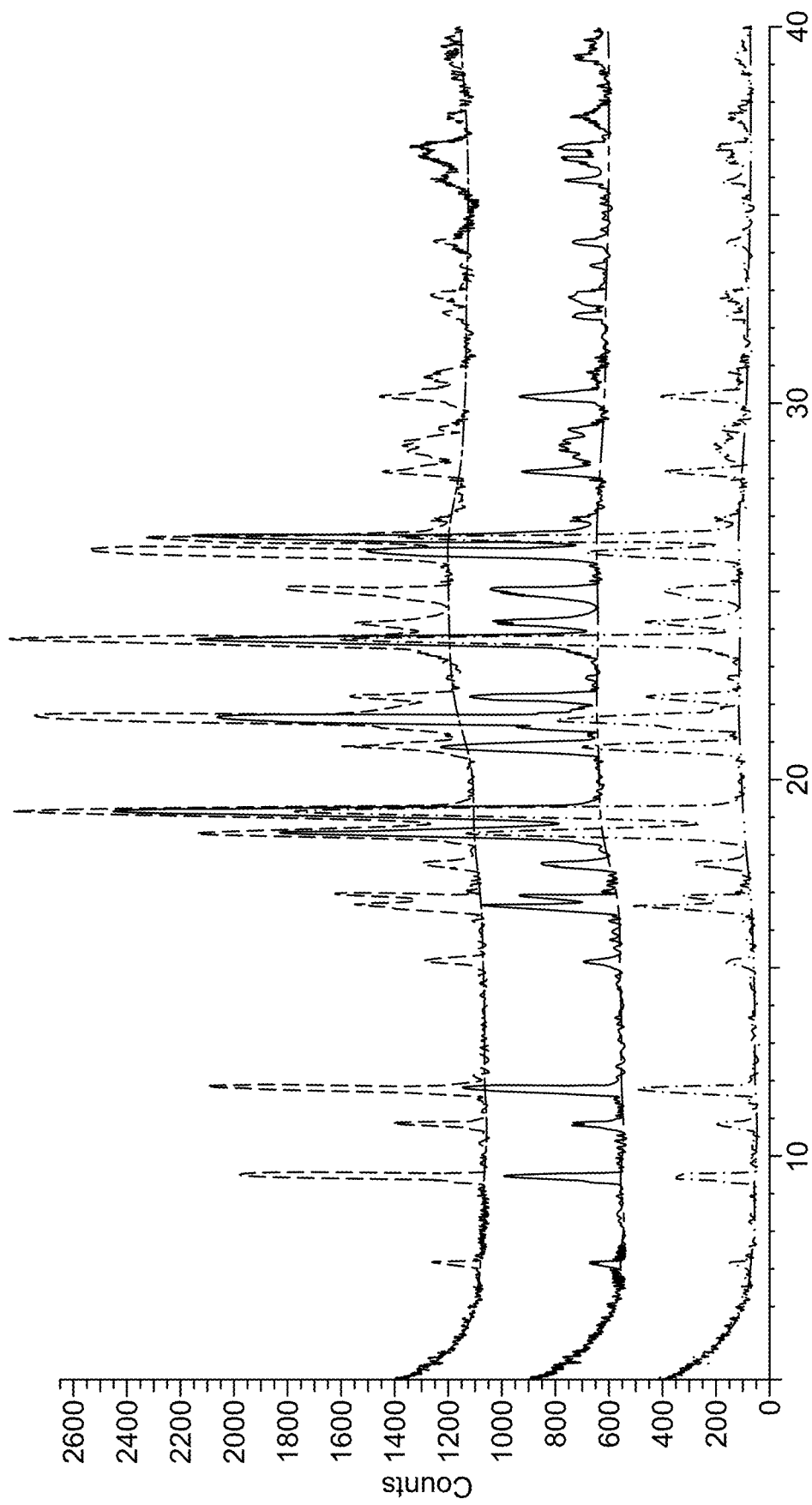

FIG. 271 shows an overlay of XRPD profiles of crystalline compound 1 Maleate after storage for T=0 days (top), T=10 days (middle) and T=5 days (bottom) at 40° C./75% RH.

Figure 272:
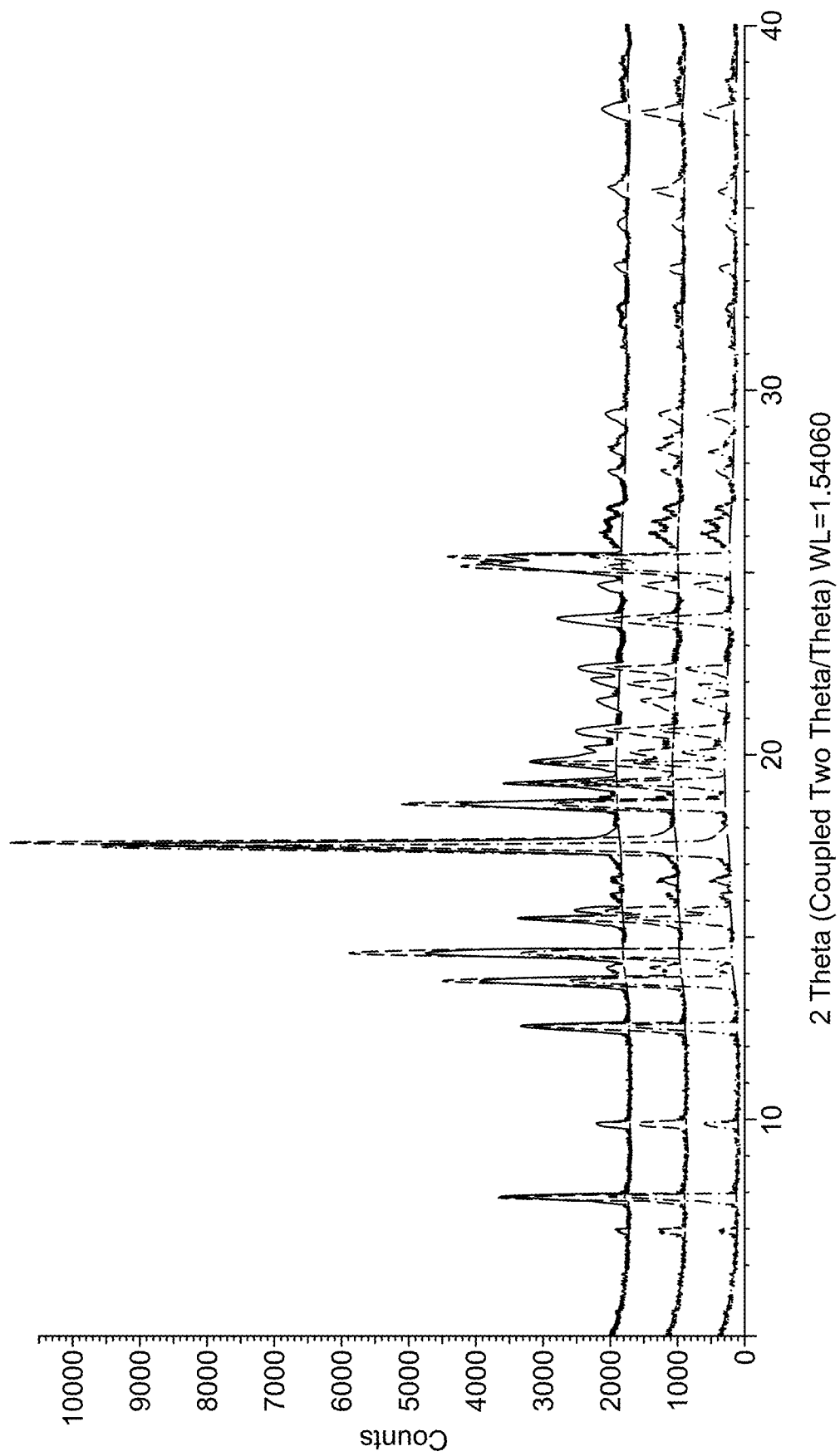

FIG. 272 shows an overlay of XRPD profiles of crystalline compound 1 Benzoate after storage for 0 days (bottom), 10 days (top) and 5 days (middle) at 40° C./75% RH.

Figure 273:
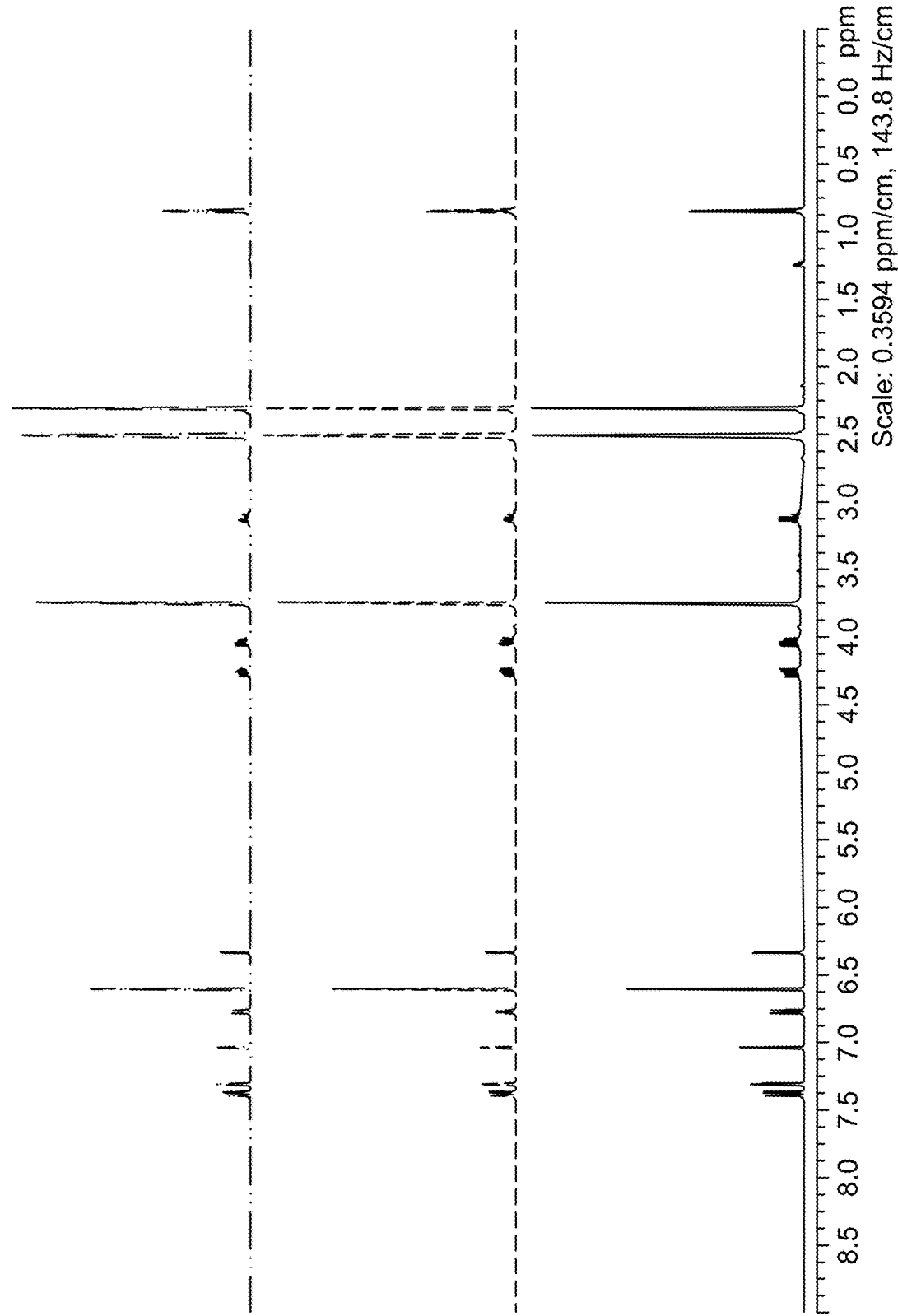

FIG. 273 shows an overlay of $^1$H NMR spectra of crystalline compound 1 monofumarate after storage for 0 days (bottom), 10 days (top) and 5 days (middle) at 40° C./75% RH. DMSO-d6 was used as deuterated solvent.

Figure 274:
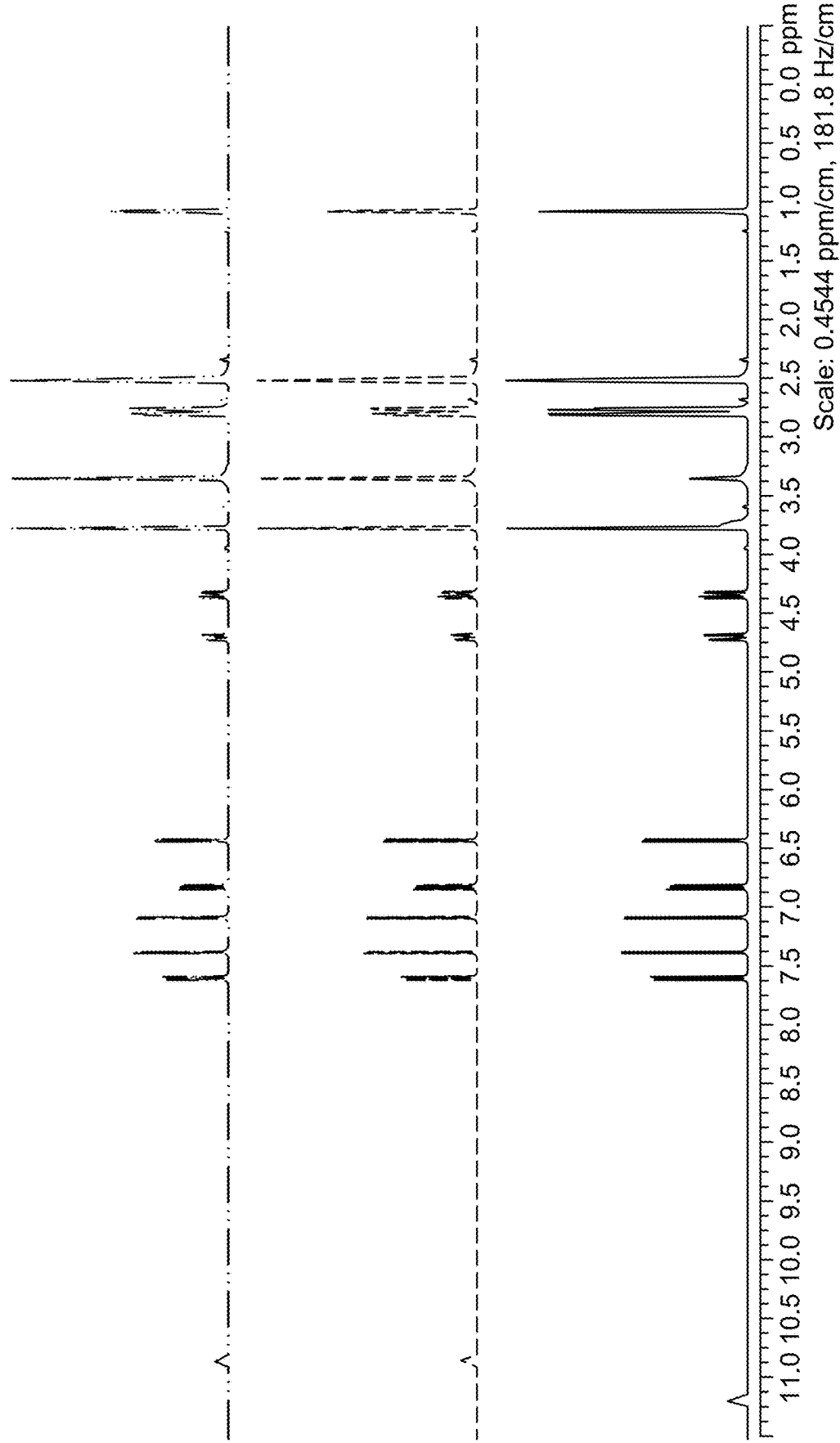

FIG. 274 shows an overlay of $^1$H NMR spectra of crystalline compound 1 HCl Form A after storage for 0 days (bottom, 0.02% w/w EtOH), 10 days (top) and 5 days (middle) at 40° C./75% RH. DMSO-d6 was used as deuterated solvent.

Figure 275:
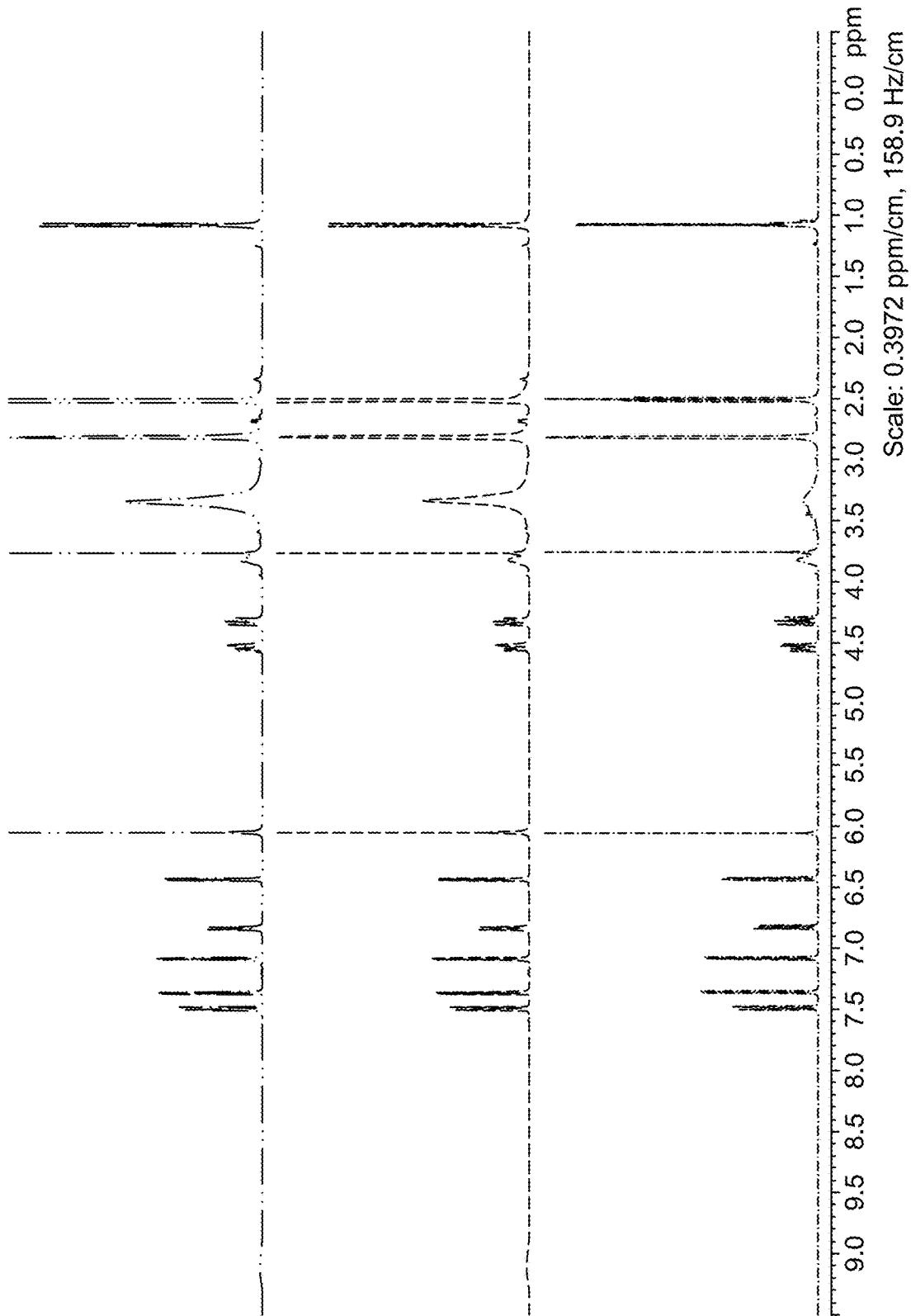
Figure 276:
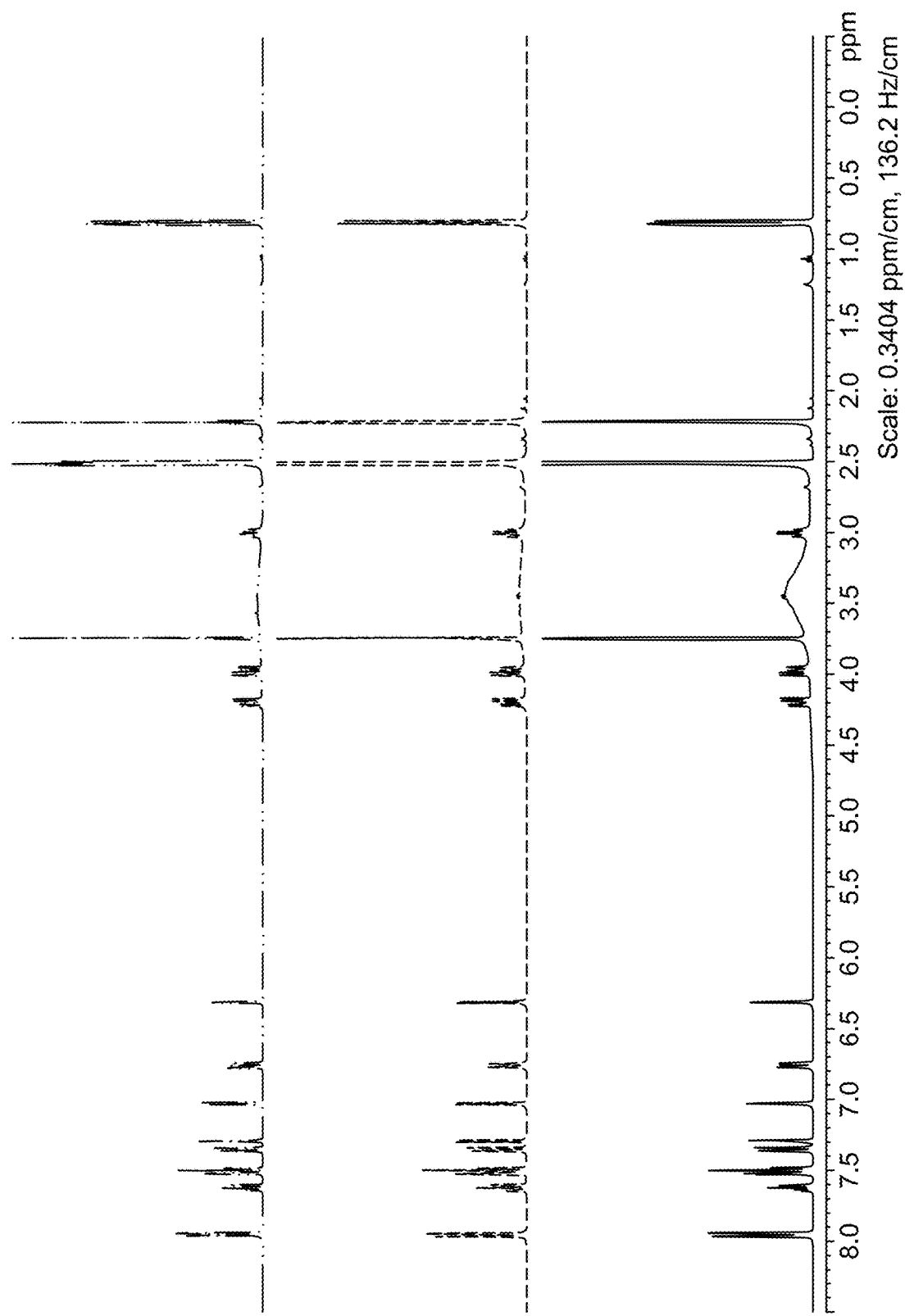

FIG. 275 shows an overlay of $^1$H NMR spectra of crystalline compound 1 Maleate after storage for 0 days (bottom), 10 days (top) and 5 days (middle) at 40° C./75% RH. DMSO-d6 was used as deuterated solvent FIG. 276 shows an overlay of $^1$H NMR spectra of crystalline compound 1 Benzoate after storage for 0 days (bottom), 10 days (top) and 5 days (middle) at 40° C./75% RH.

Figure 277:
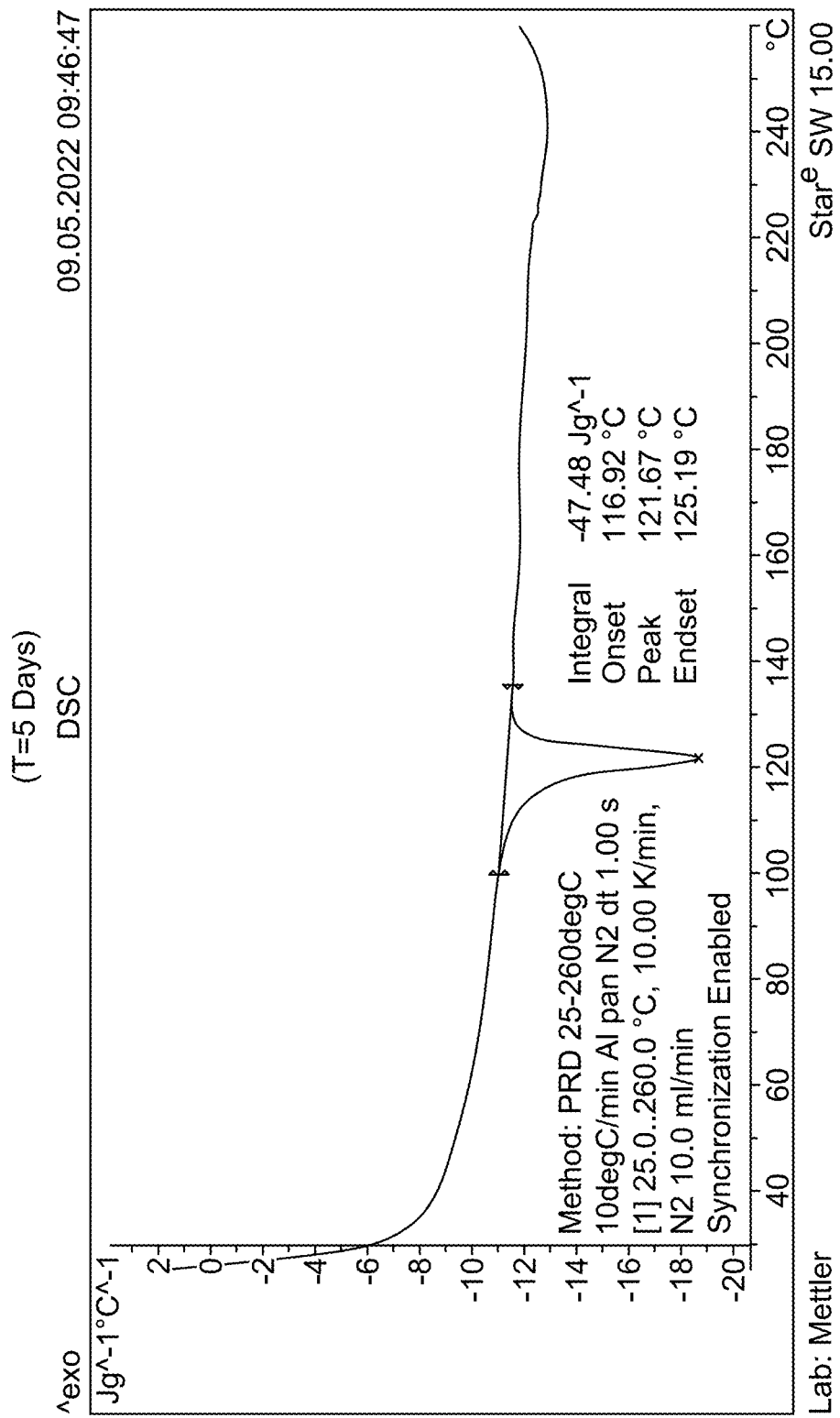
Figure 277:
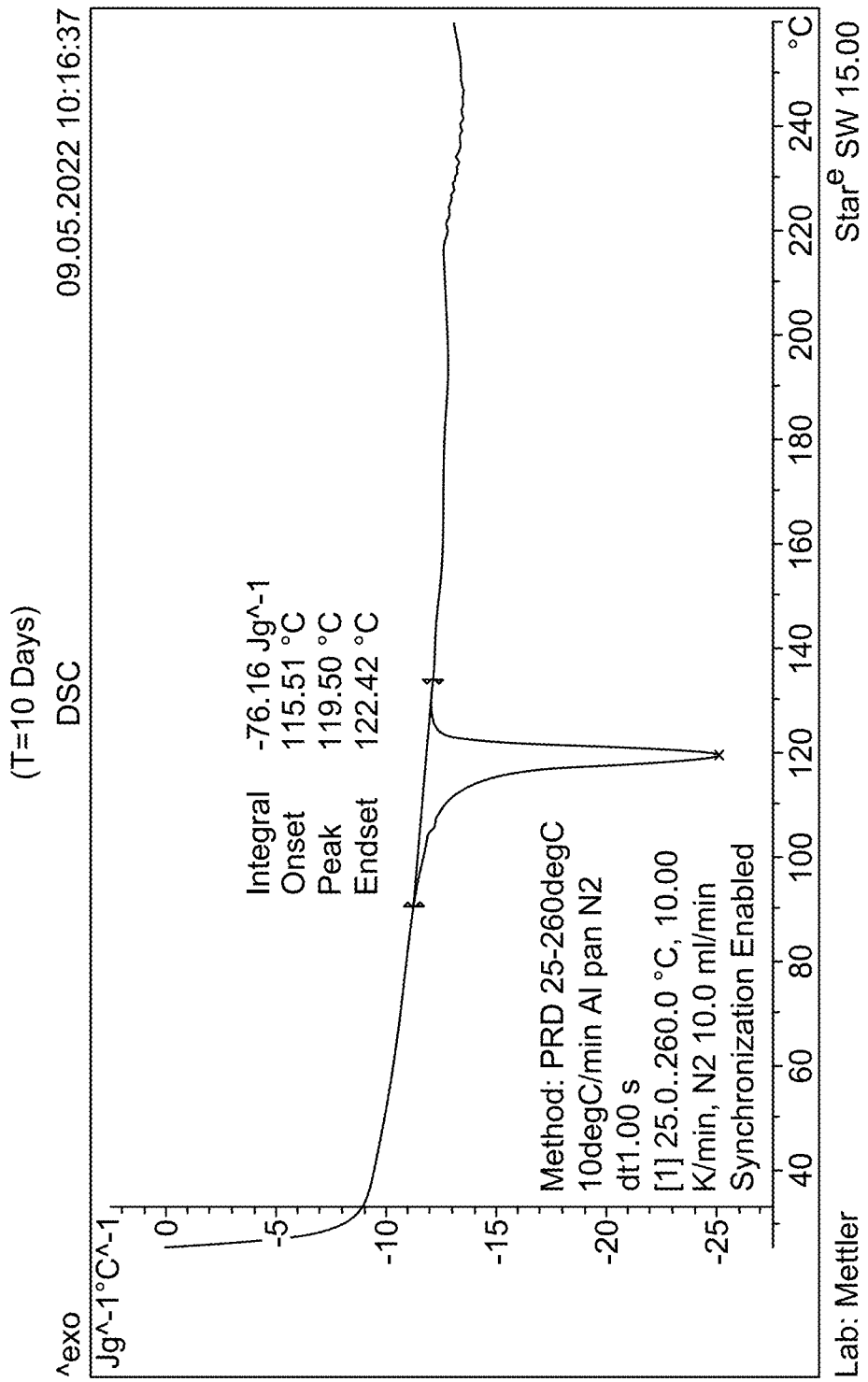

FIG. 277 shows DSC profiles of crystalline compound 1 monofumarate Form A at 5 (left) and 10 (right) days in storage at 40° C./75% RH.

Figure 278:
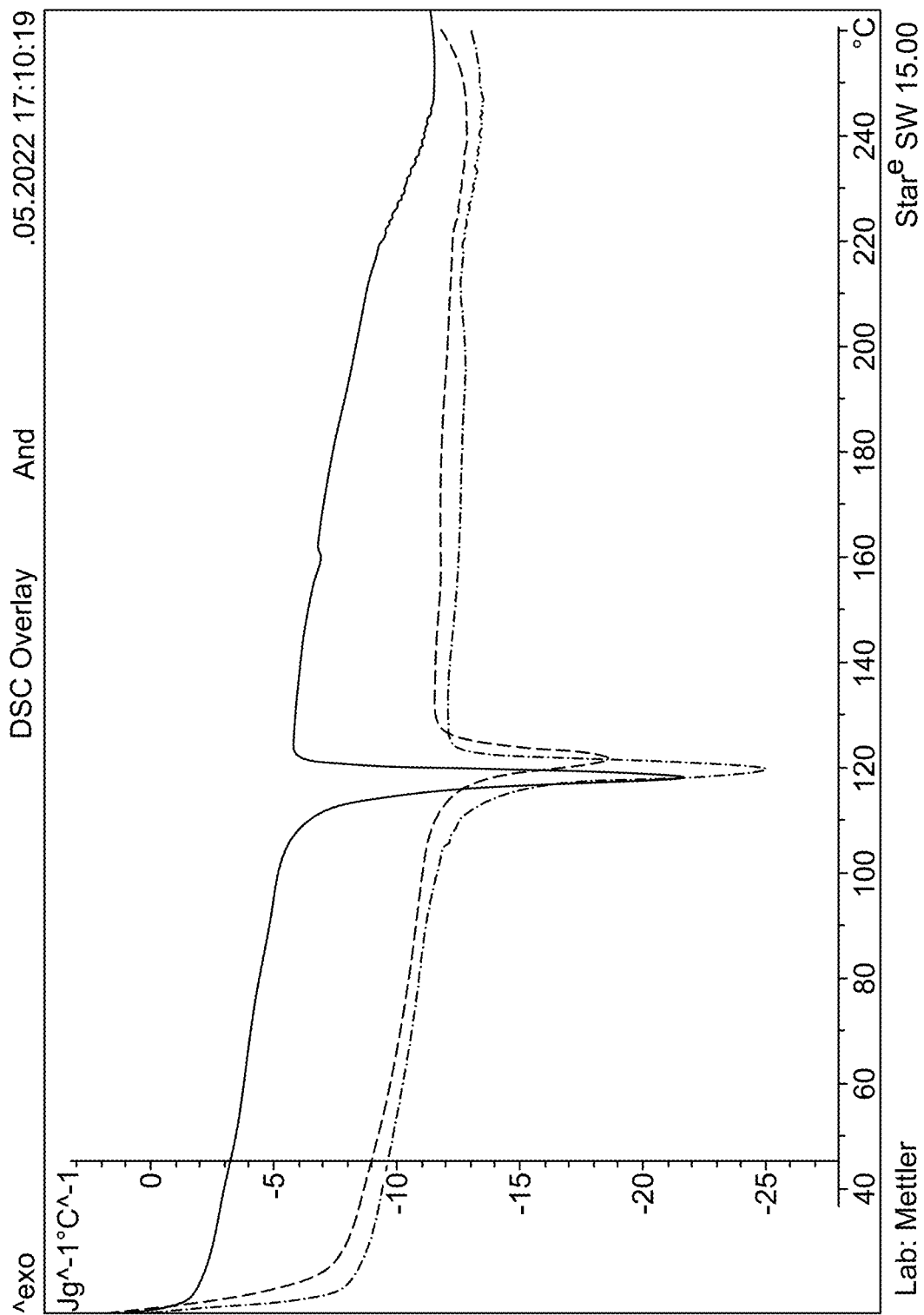

FIG. 278 shows an overlay of DSC profiles of a reference sample of crystalline compound 1 monofumarate Form A (top), a sample of crystalline compound 1 monofumarate after storage for 5 days at 40° C./75% RH (middle) and a sample of crystalline compound 1 monofumarate for 10 days at 40° C./75% RH (bottom).

Figure 279:
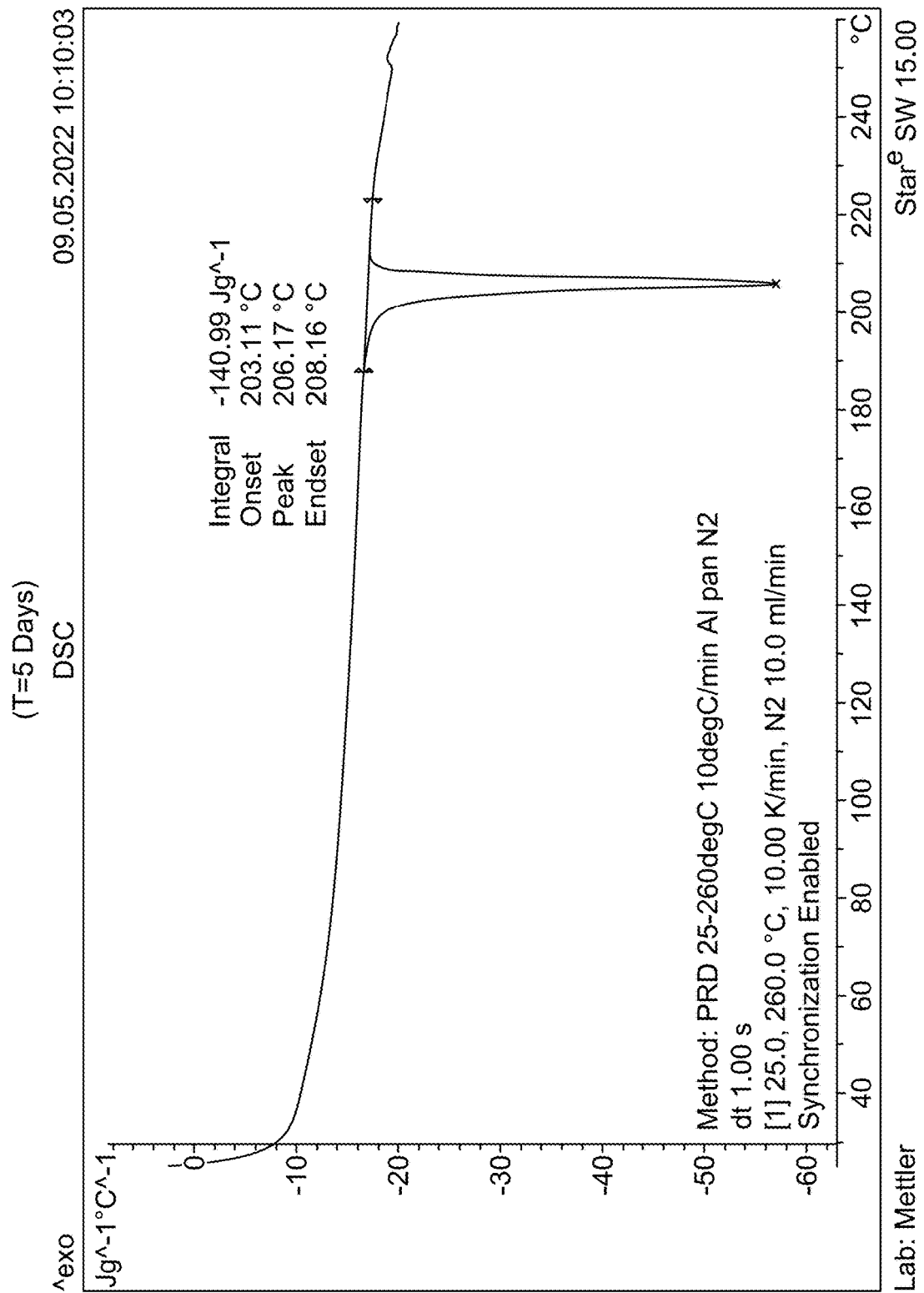
Figure 279:
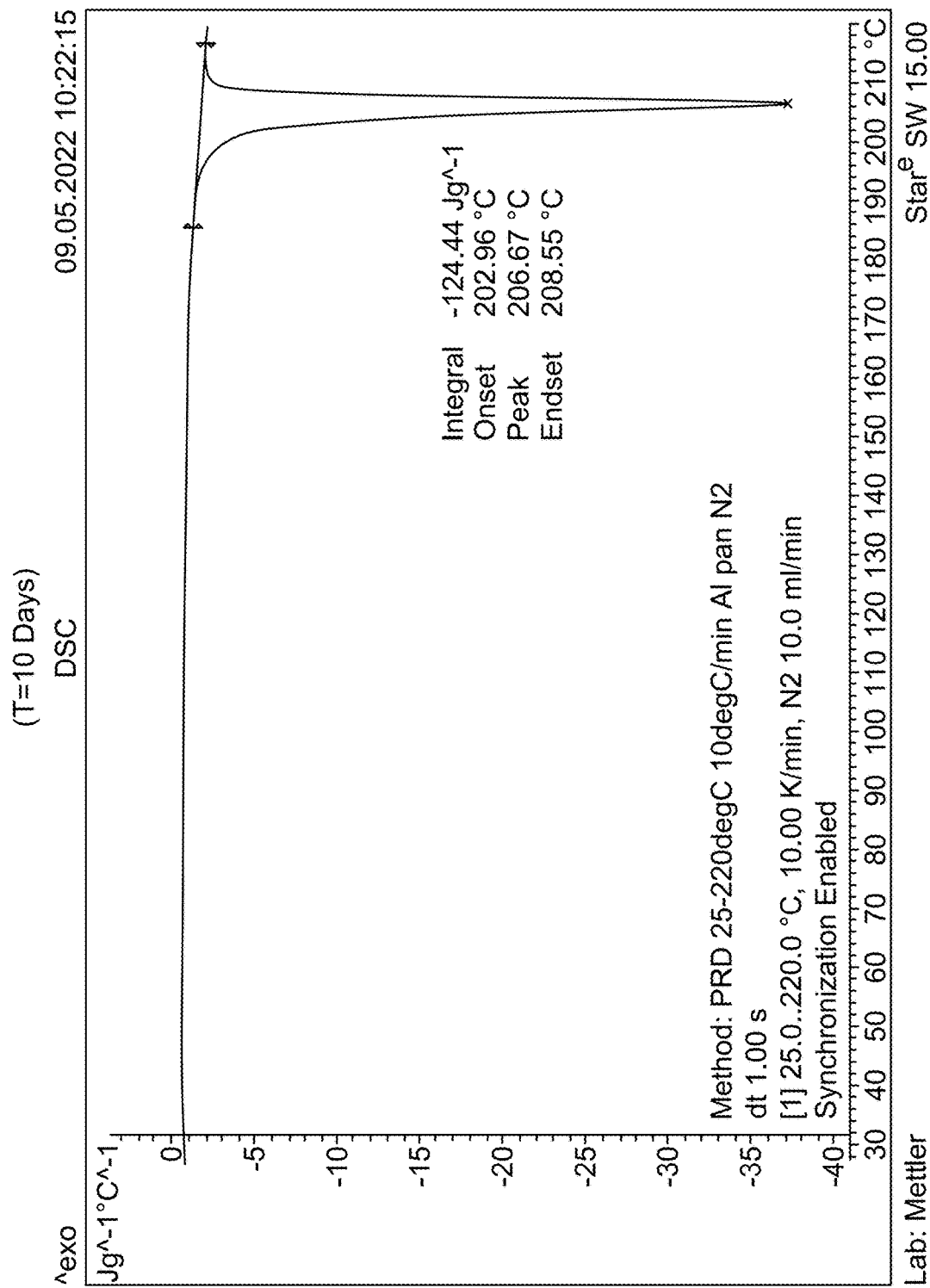

FIG. 279 shows DSC profiles of crystalline compound 1 HCl Form A at 5 (left) and 10 (right) days in storage at 40° C./75% RH.

Figure 280:
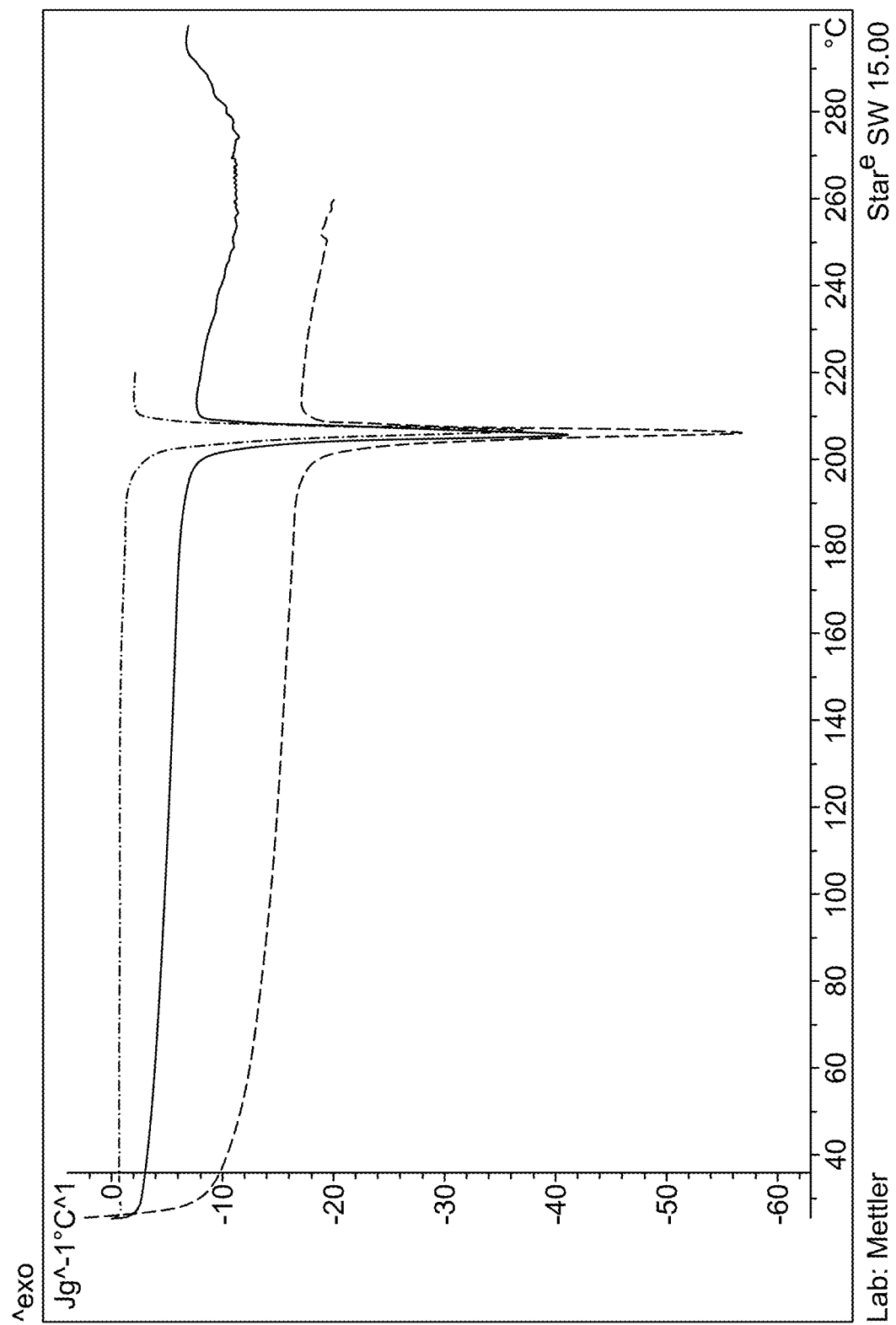

FIG. 280 shows overlaid DSC profiles of a reference sample of crystalline compound 1 HCl Form A (middle), a sample of crystalline compound 1 HCl Form A after storage for 5 days at 40° C./75% RH (bottom) and a sample of crystalline compound 1 HCl Form A for 10 days at 40° C./75% RH (top).

Figure 281:
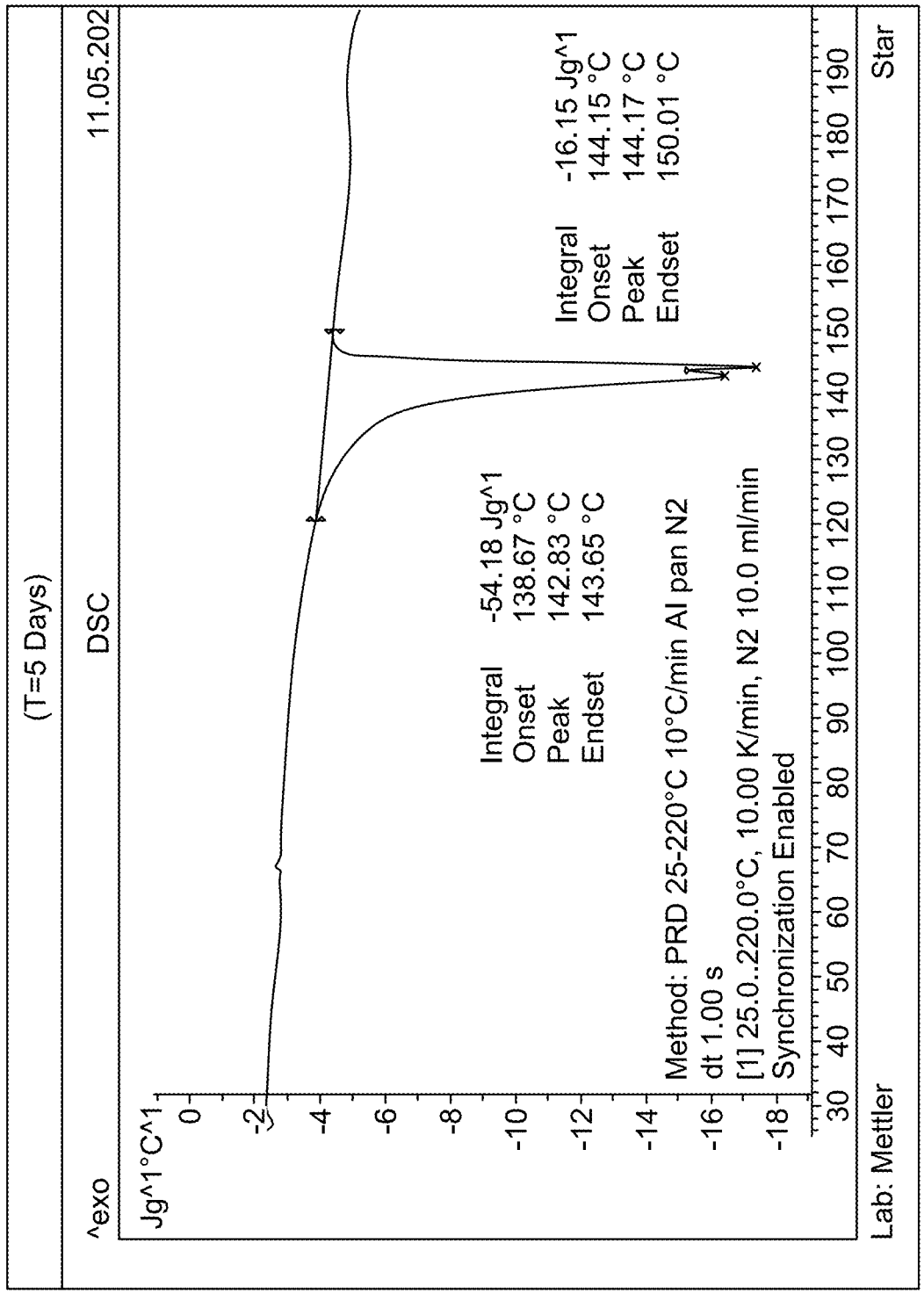
Figure 281:
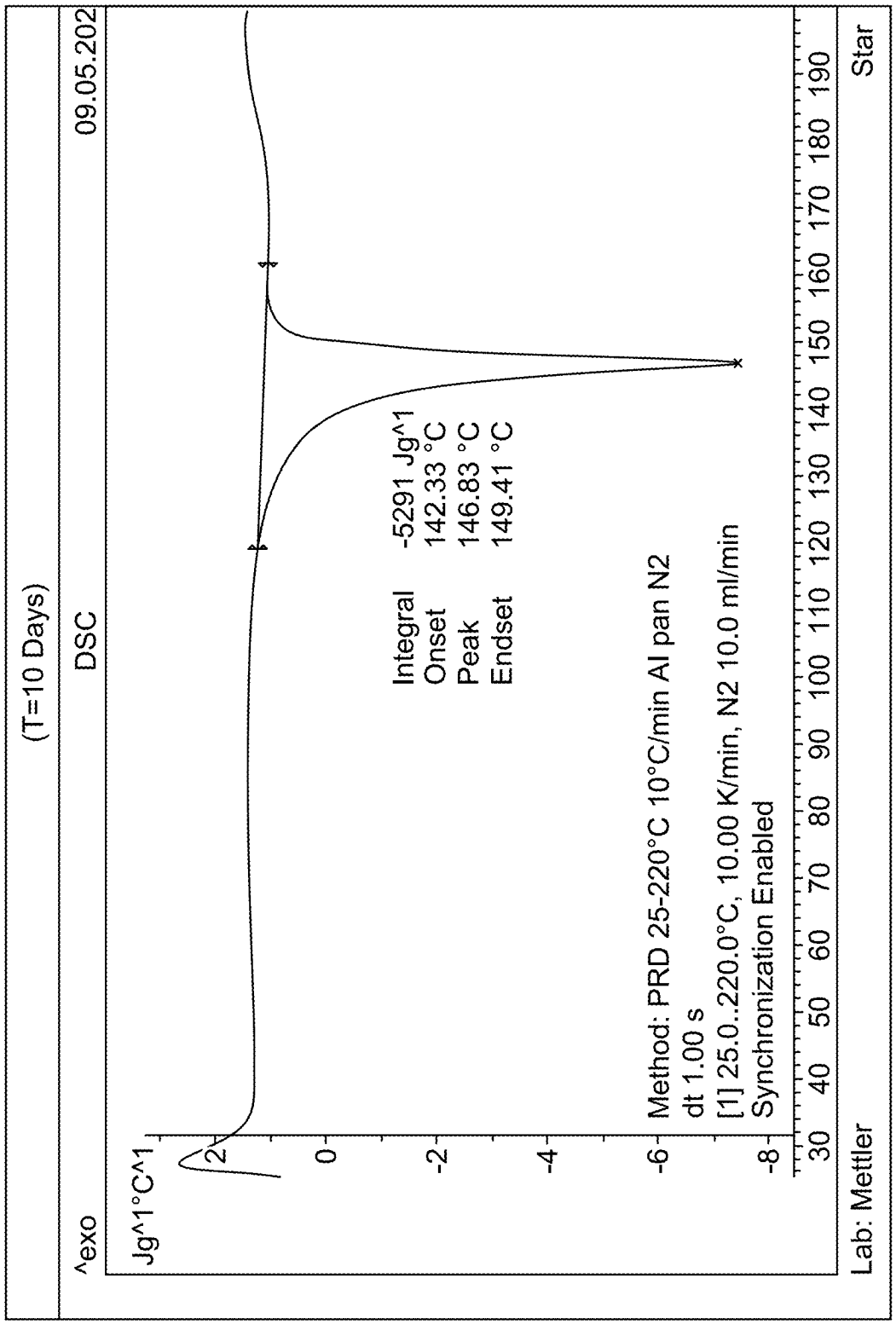

FIG. 281 shows DSC profiles of crystalline compound 1 maleate at 5 (left) and 10 (right) days in storage at 40° C./75% RH.

Figure 282:
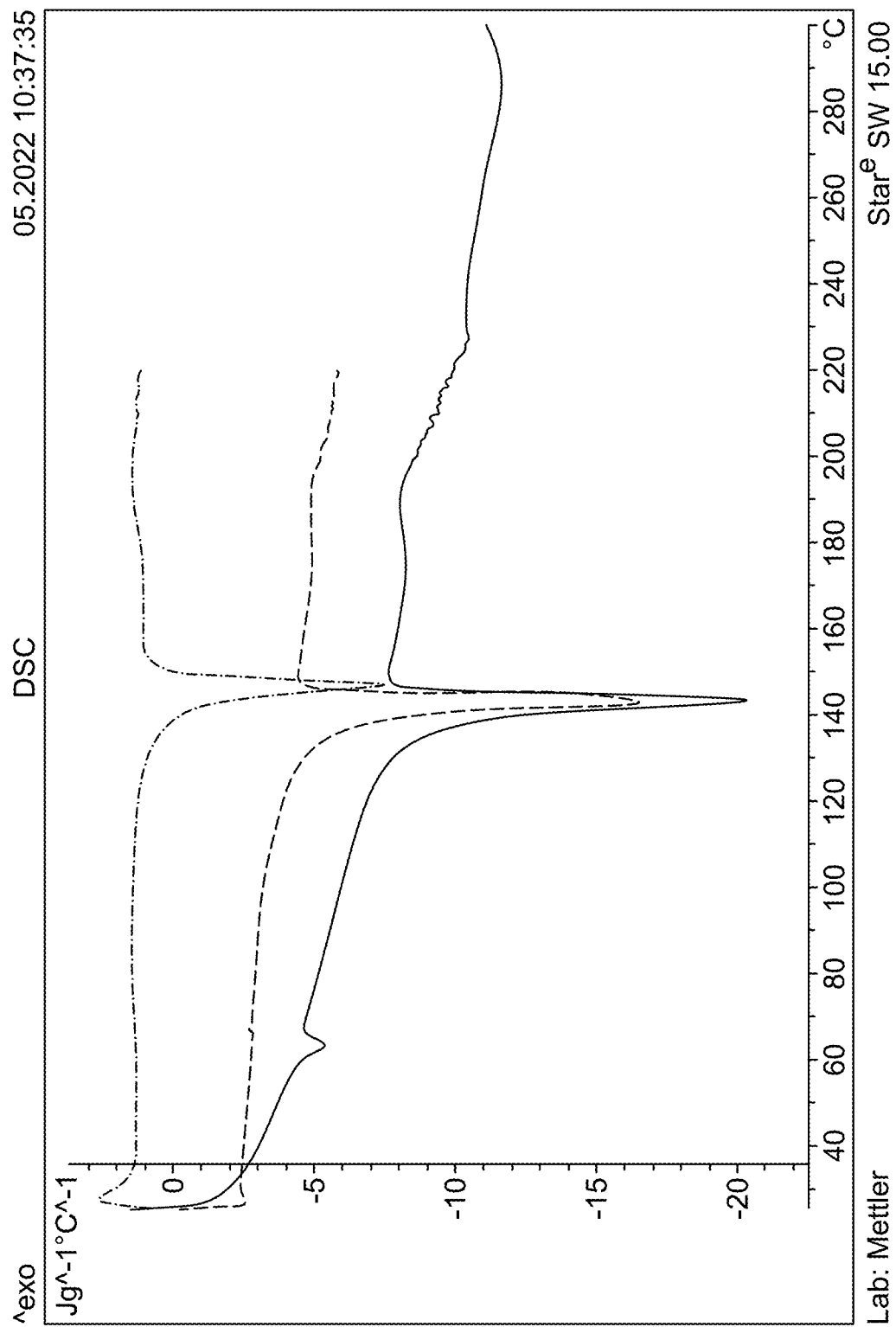

FIG. 282 shows an overlay of DSC profiles of a reference sample of crystalline compound 1 maleate (bottom), a sample of crystalline compound 1 maleate after storage for 5 days at 40° C./75% RH (middle) and a sample of crystalline compound 1 maleate for 10 days at 40° C./75% RH (top).

Figure 283:
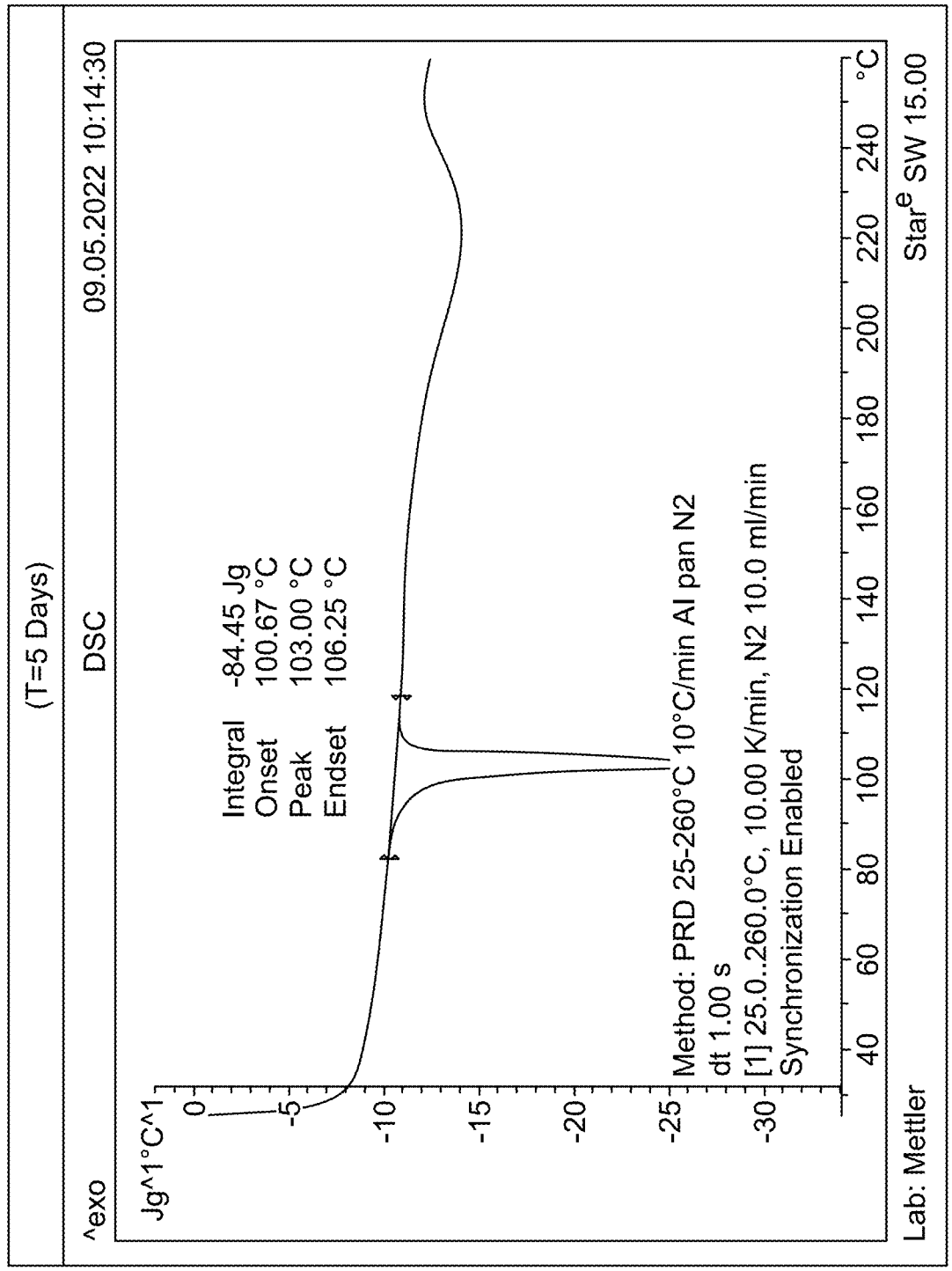
Figure 283:
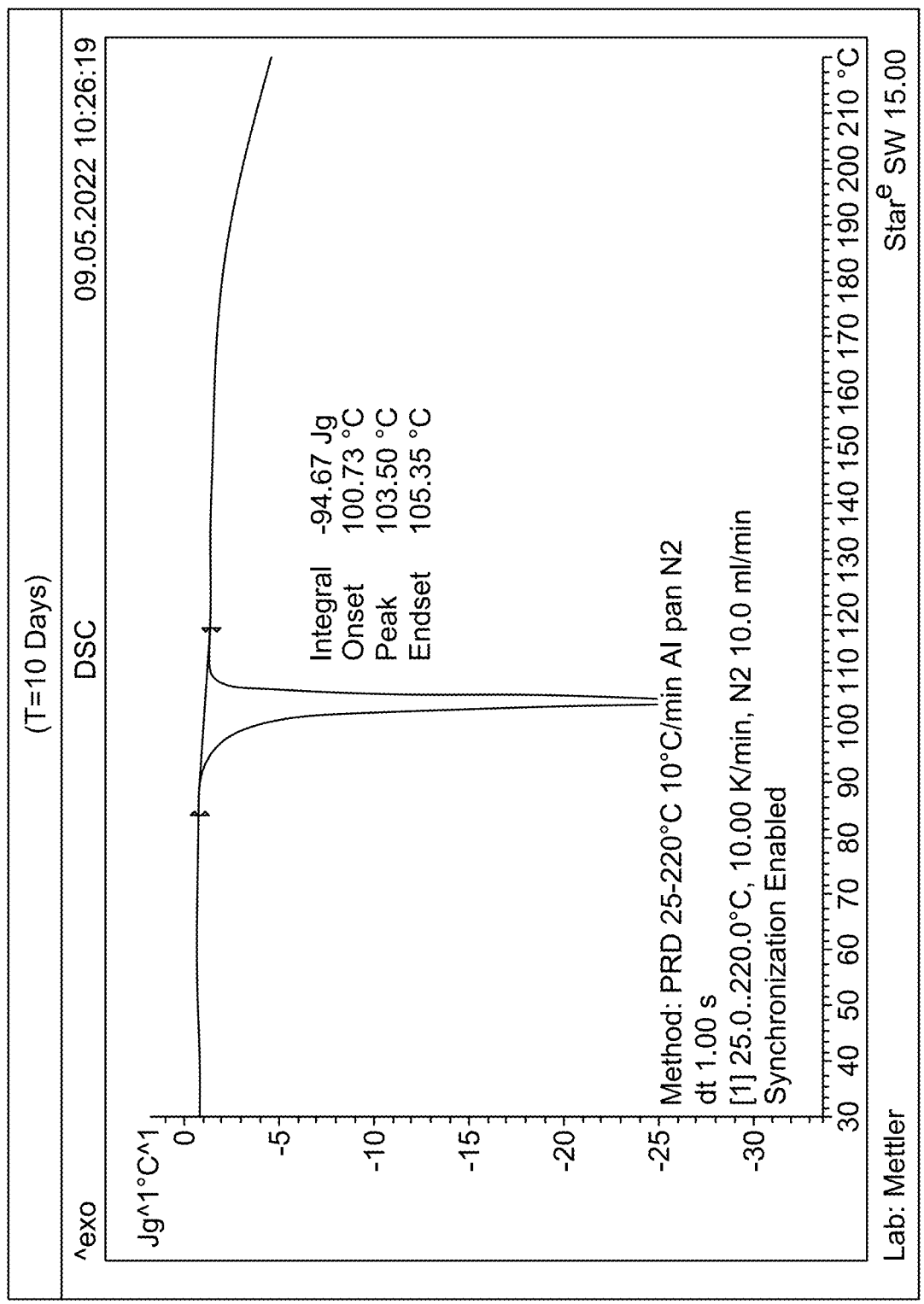

FIG. 283 shows DSC profiles of crystalline compound 1 benzoate at 5 (left) and 10 (right) days in storage at 40° C./75% RH.

Figure 284:
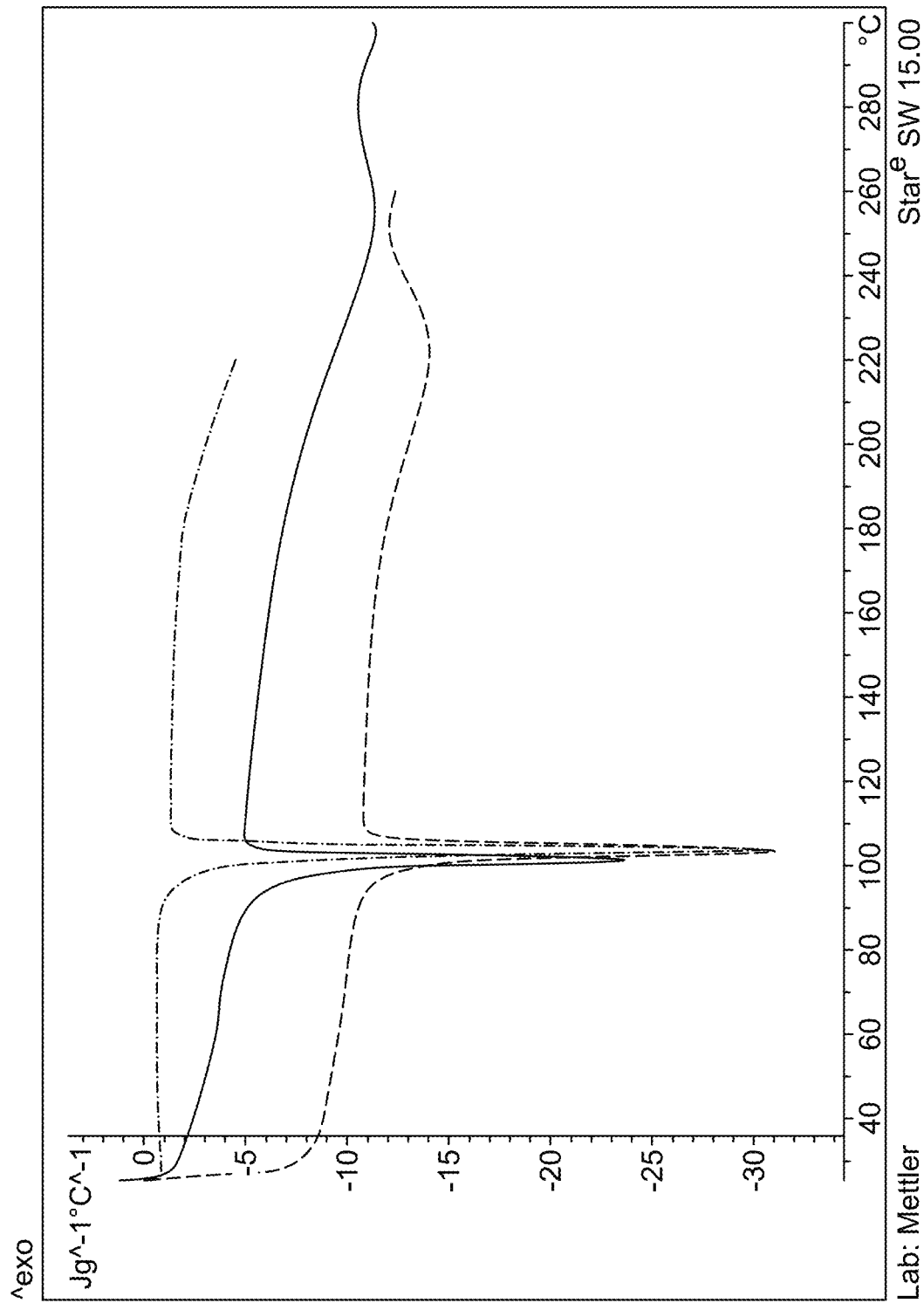

FIG. 284 shows an overlay of DSC profiles of a reference sample of crystalline compound 1 benzoate (middle), a sample of crystalline compound 1 benzoate after storage for 5 days at 40° C./75% RH (bottom) and a sample of crystalline compound 1 benzoate for 10 days at 40° C./75% RH (top).

Figure 285:
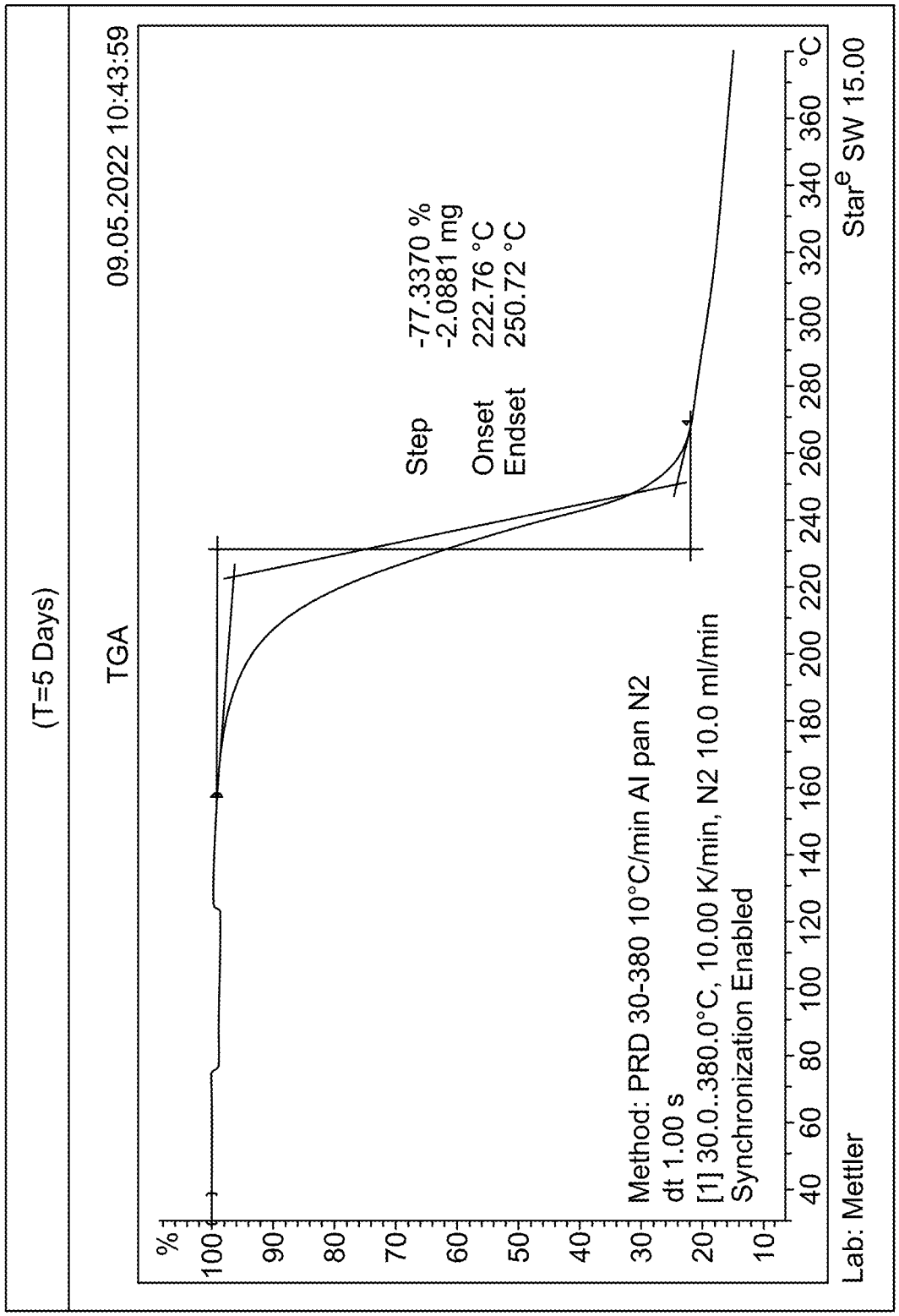
Figure 285:
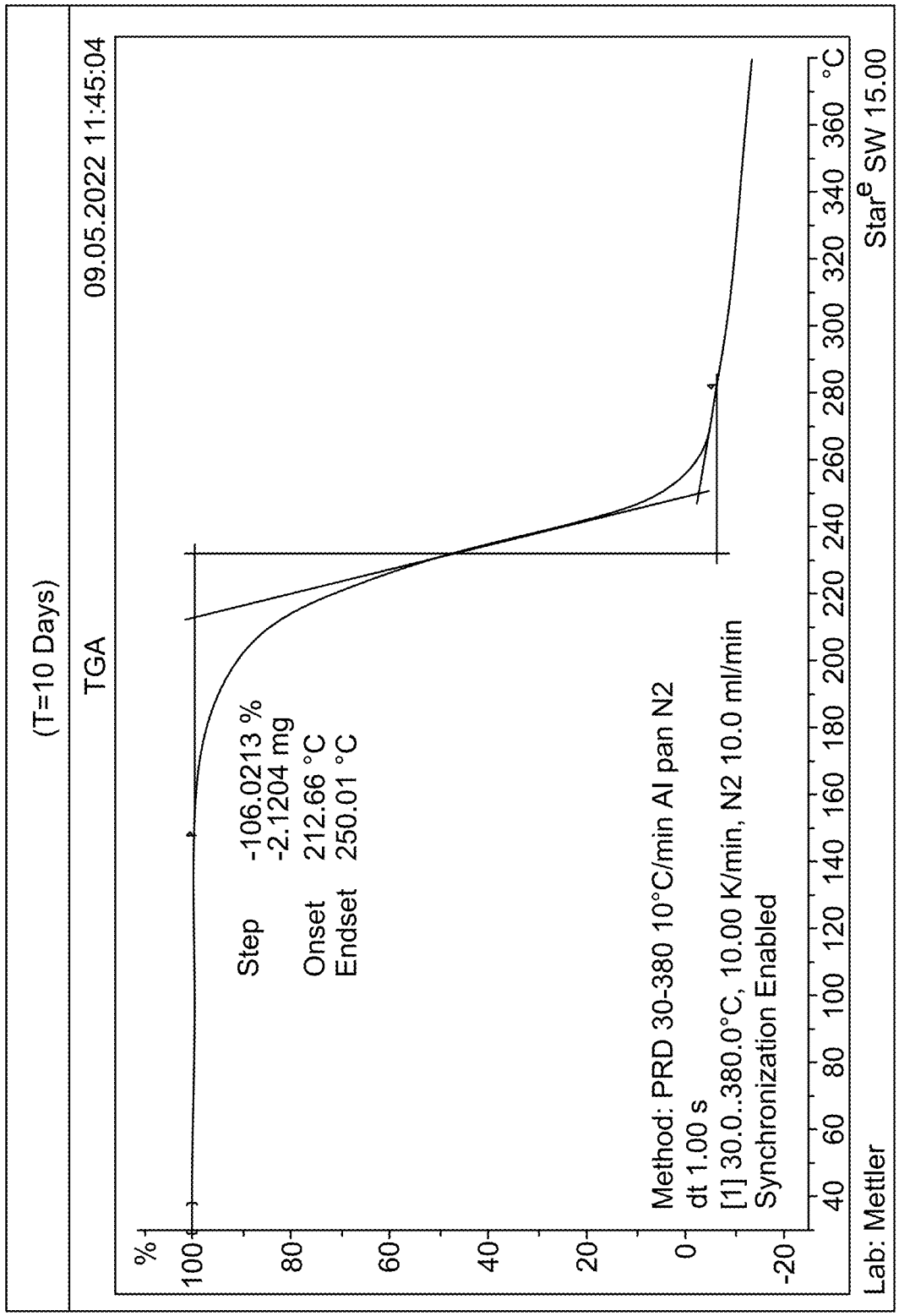

FIG. 285 shows TGA profiles of crystalline compound 1 monofumarate Form A at 5 (left) and 10 (right) days in storage at 40° C./75% RH.

Figure 286:
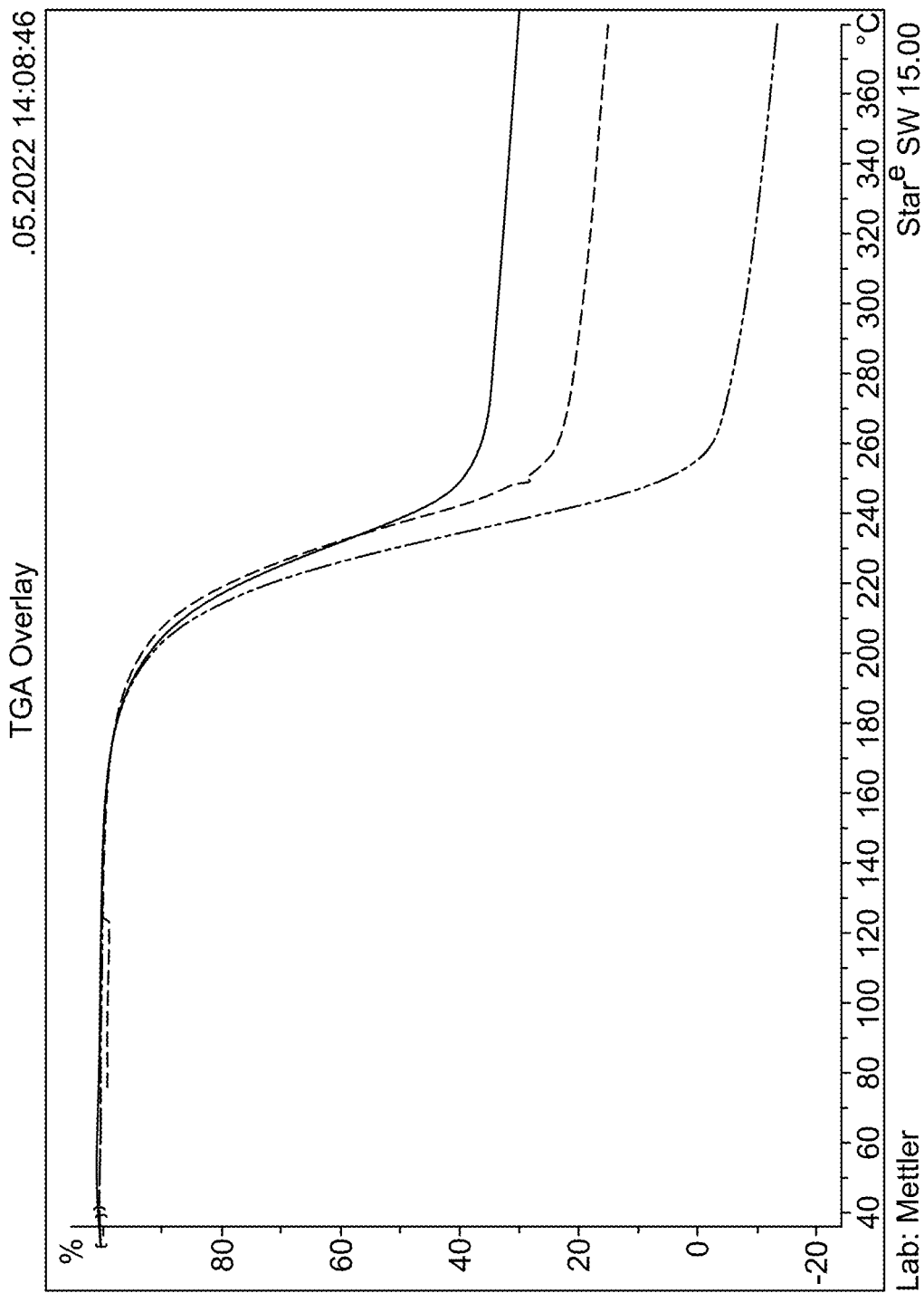

FIG. 286 shows an overlay of TGA profiles of a reference sample of crystalline compound 1 fumarate Form A (top), a sample of crystalline compound 1 monofumarate Form A after storage for 5 days at 40° C./75% RH (middle) and a sample of crystalline compound 1 monofumarate Form A for 10 days at 40° C./75% RH (bottom).

Figure 287:
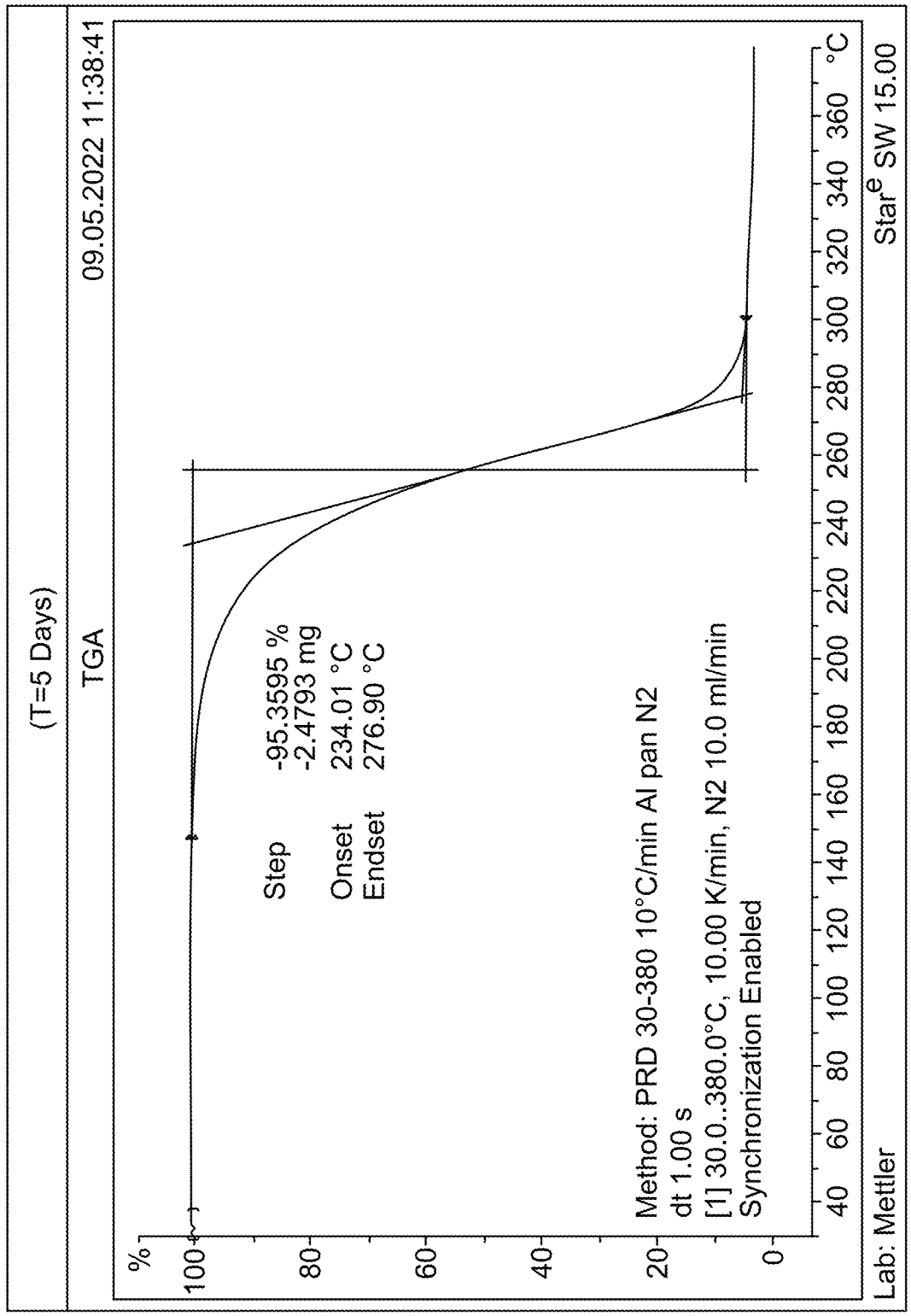
Figure 287:
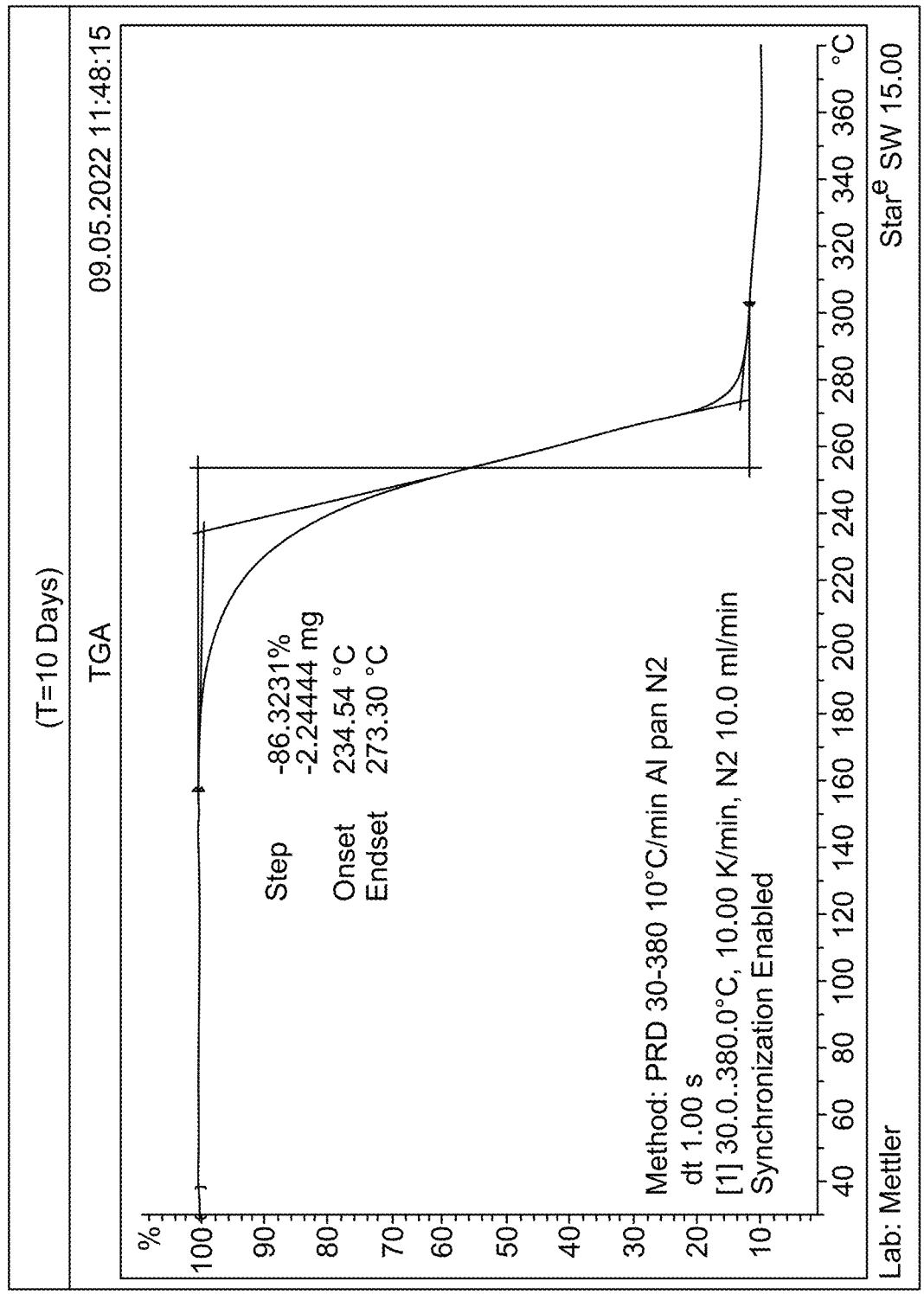

FIG. 287 shows TGA profiles of crystalline compound 1 HCl Form A at 5 (left) and 10 (right) days in storage at 40° C./75% RH.

Figure 288:
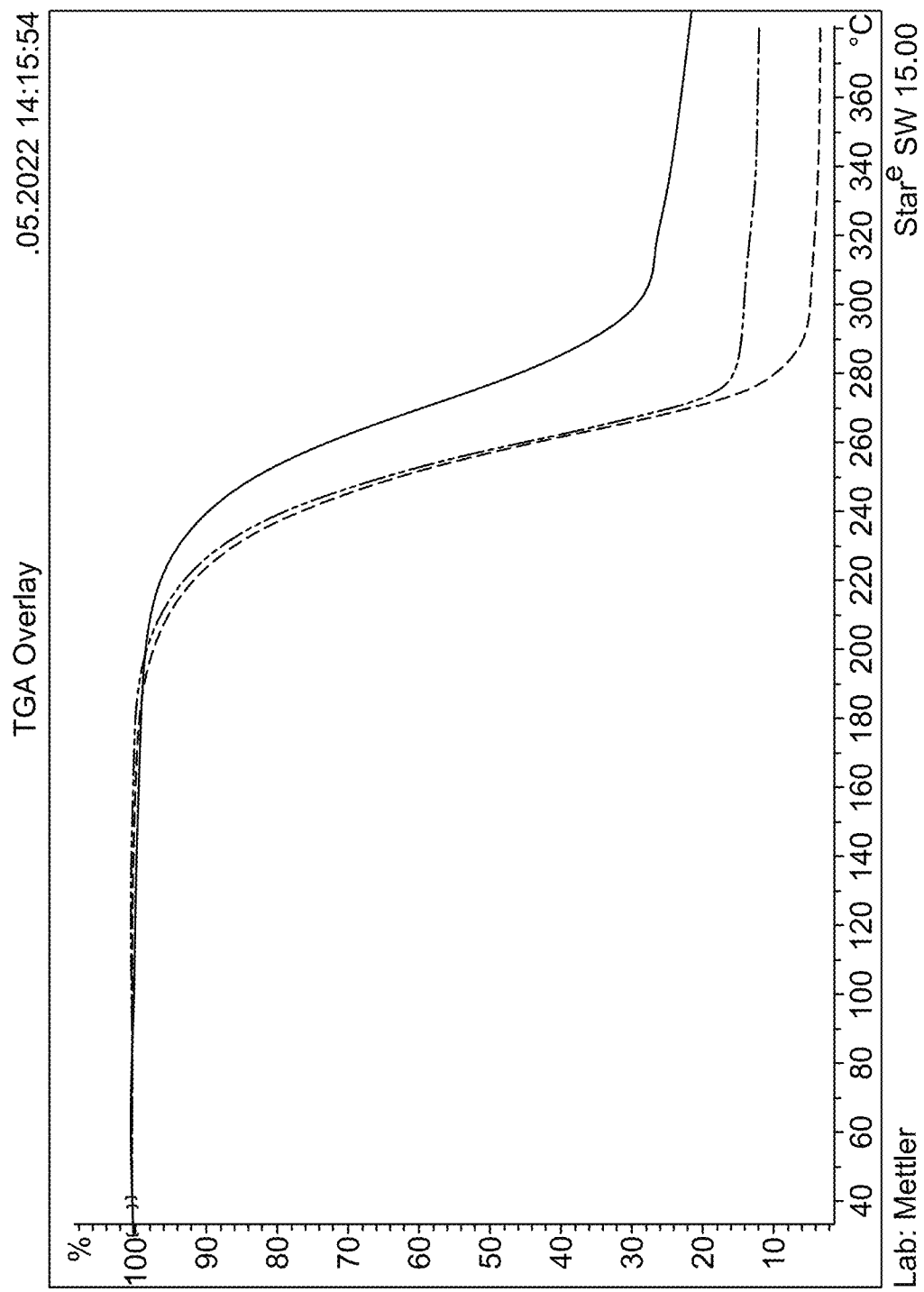

FIG. 288 shows an overlay of TGA profiles of a reference sample of crystalline compound 1 HCl Form A (top), a sample of crystalline compound 1 HCl Form A after storage for 5 days at 40° C./75% RH (middle) and a sample of crystalline compound 1 HCl Form A for 10 days at 40° C./75% RH (bottom).

Figure 289:
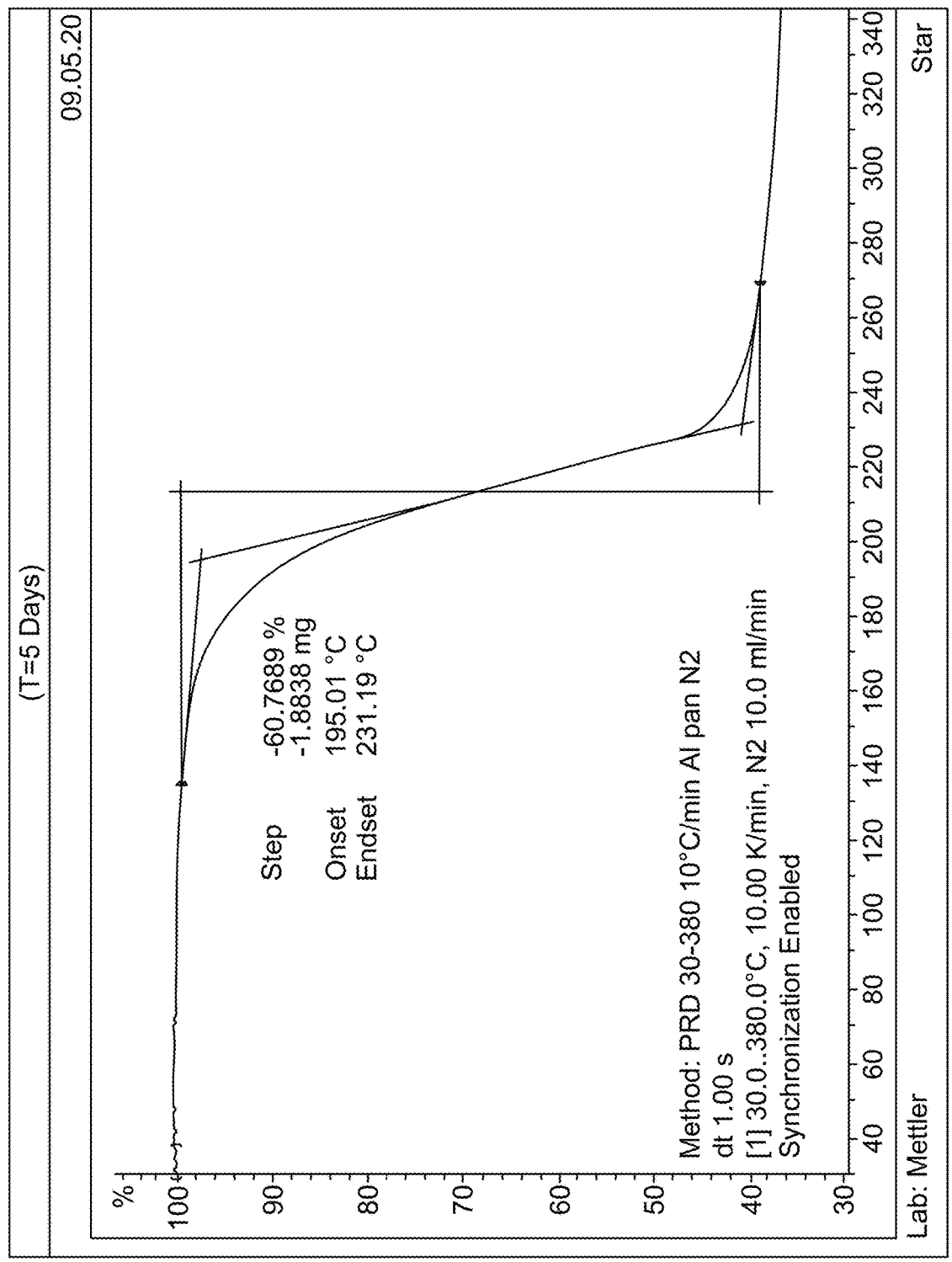
Figure 289:
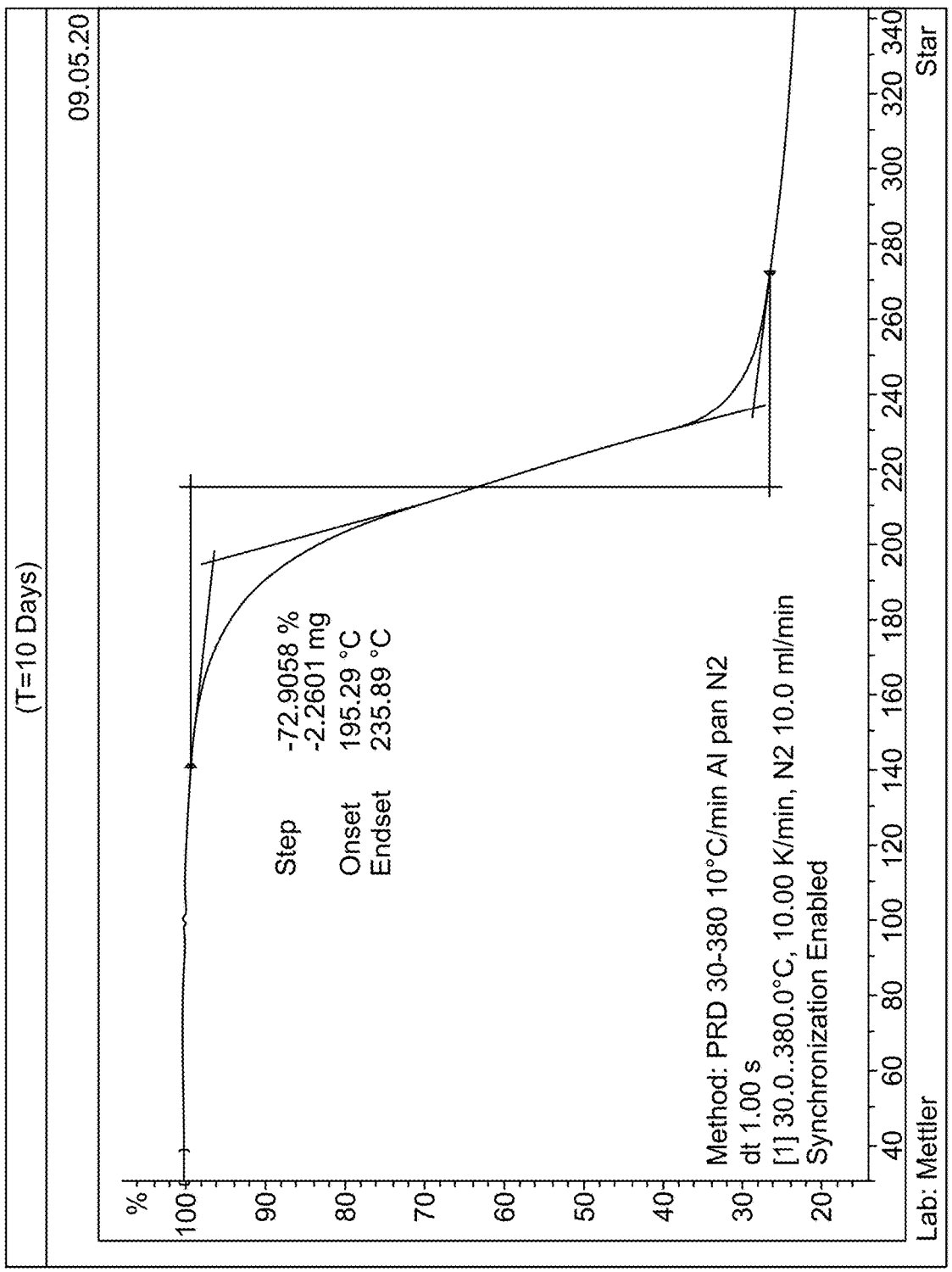

FIG. 289 shows TGA profiles of crystalline compound 1 maleate at 5 (left) and 10 (right) days in storage at 40° C./75% RH.

Figure 290:
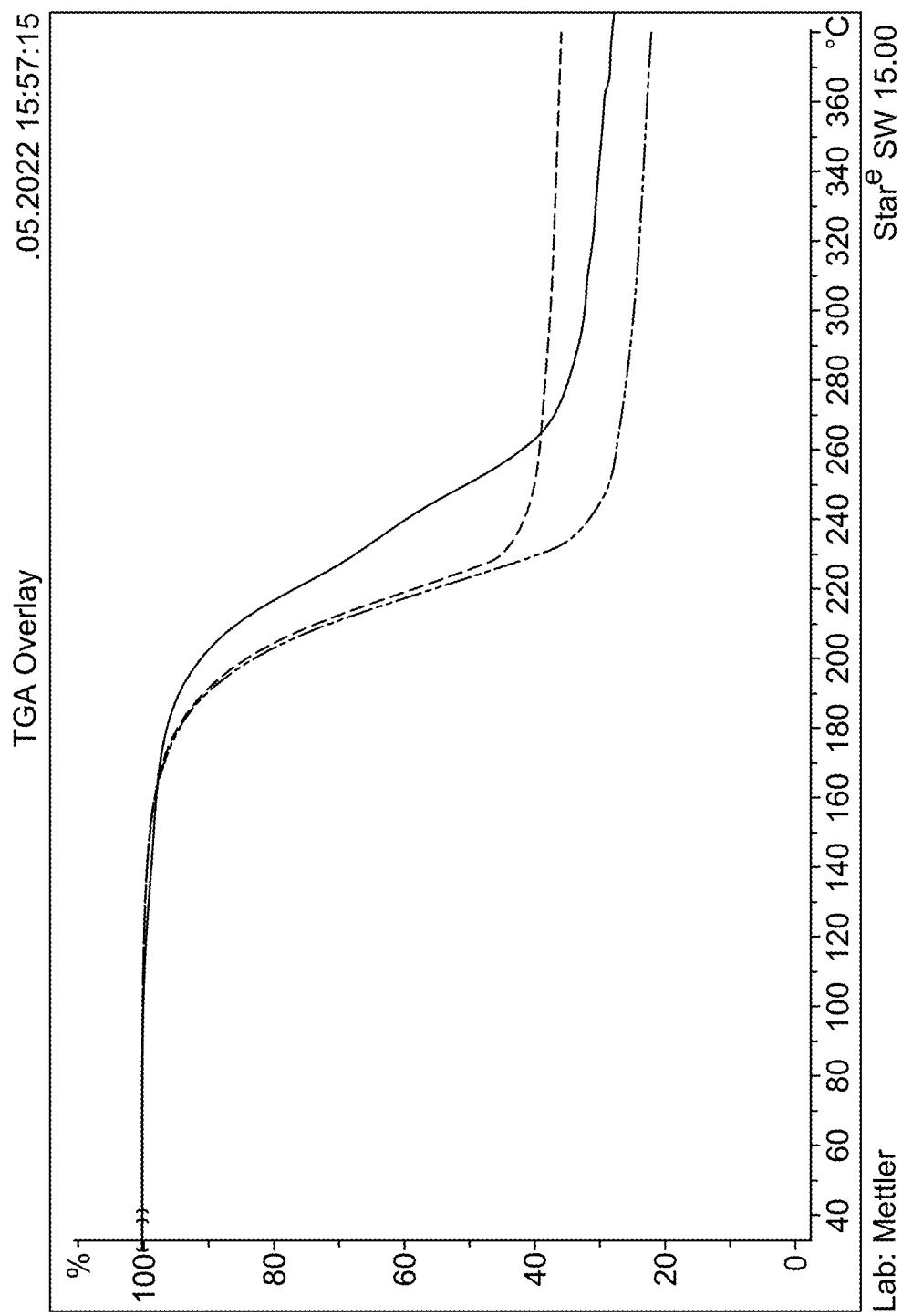

FIG. 290 shows an overlay of TGA profiles of a reference sample of crystalline compound 1 maleate (top), a sample of crystalline compound 1 maleate after storage for 5 days at 40° C./75% RH (middle) and a sample of crystalline compound 1 maleate for 10 days at 40° C./75% RH (bottom).

Figure 291:
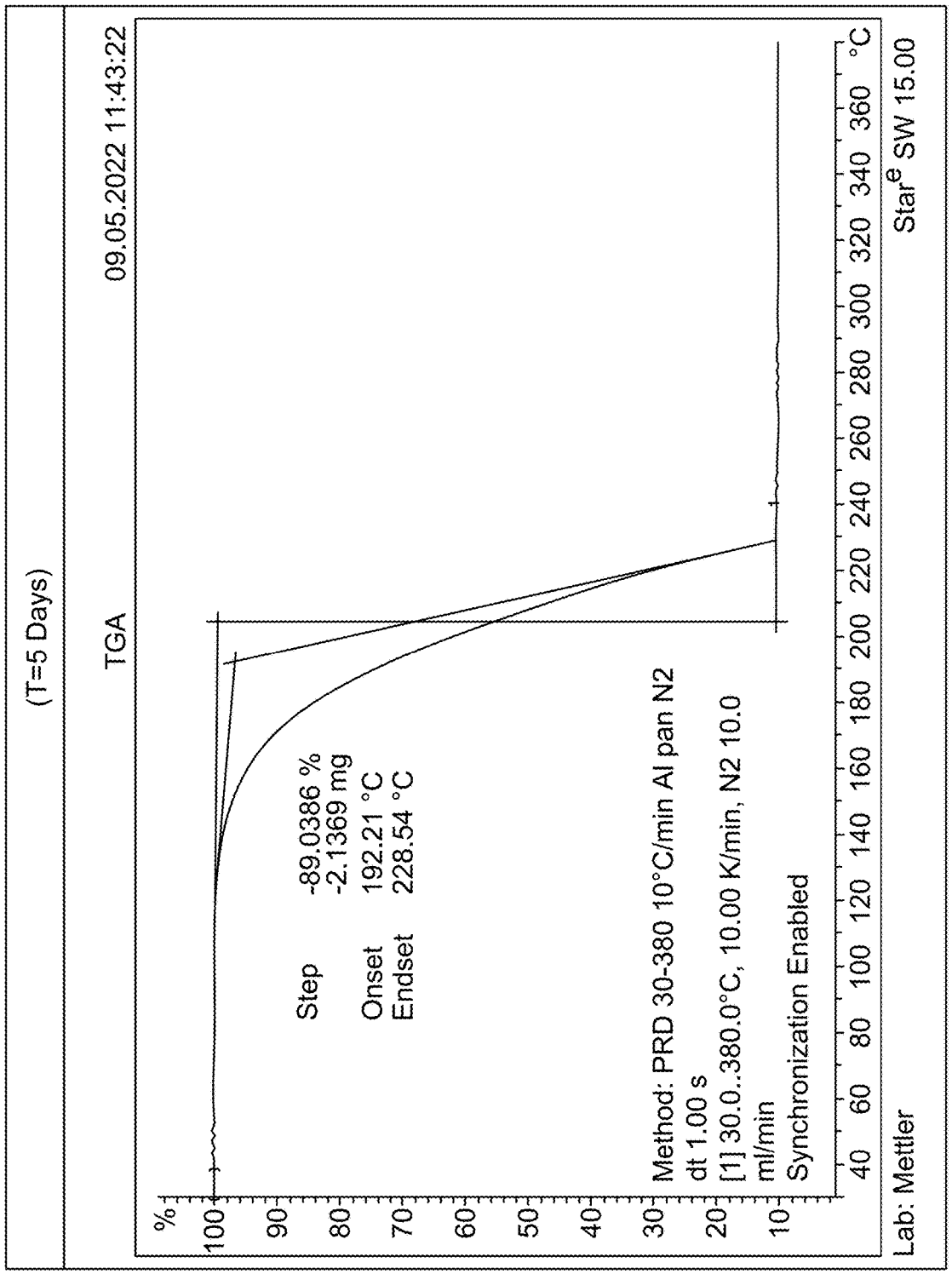
Figure 291:
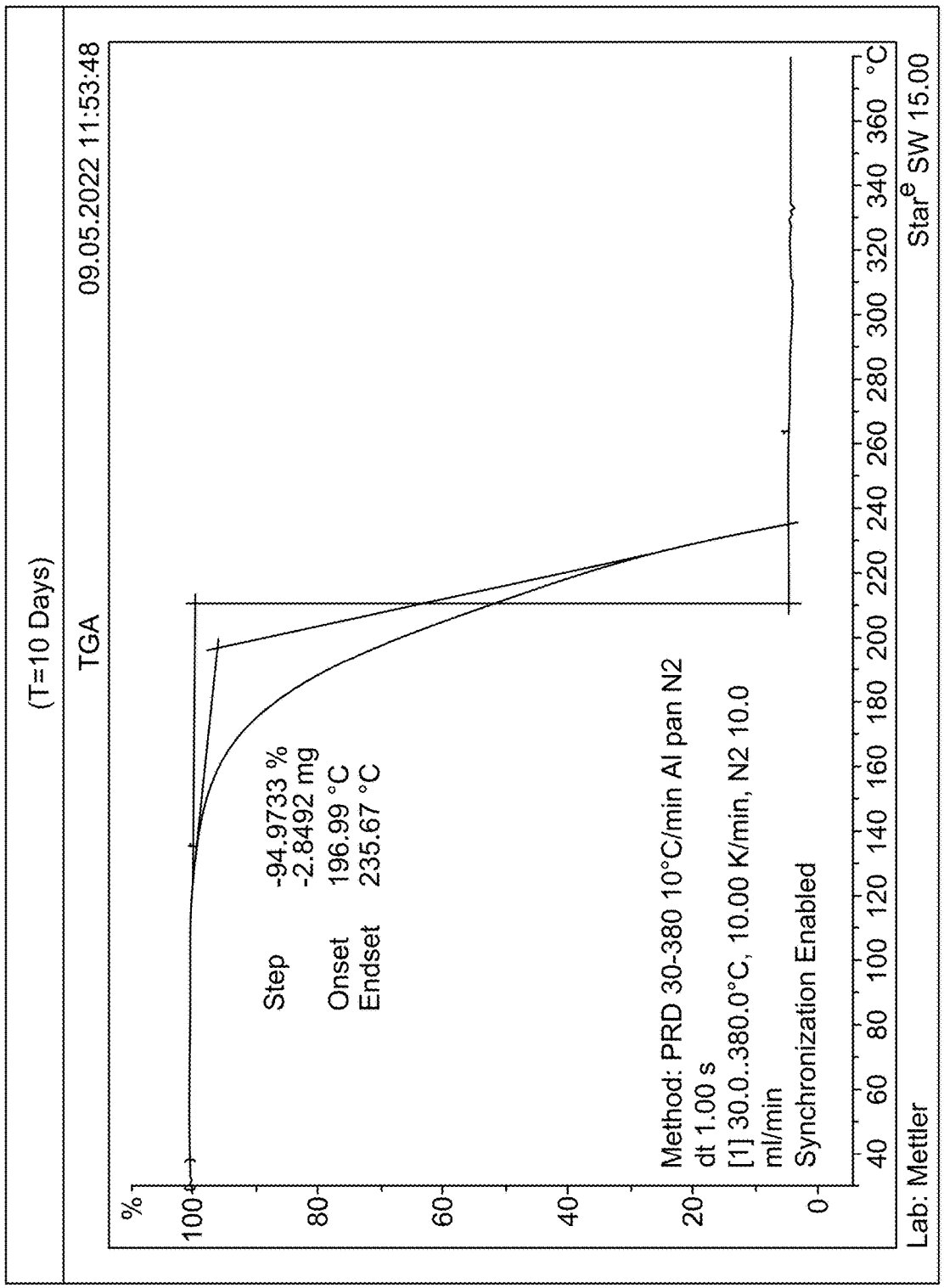

FIG. 291 shows an overlay of TGA profiles of crystalline compound 1 benzoate at 5 (left) and 10 (right) days in storage at 40° C./75% RH.

Figure 292:
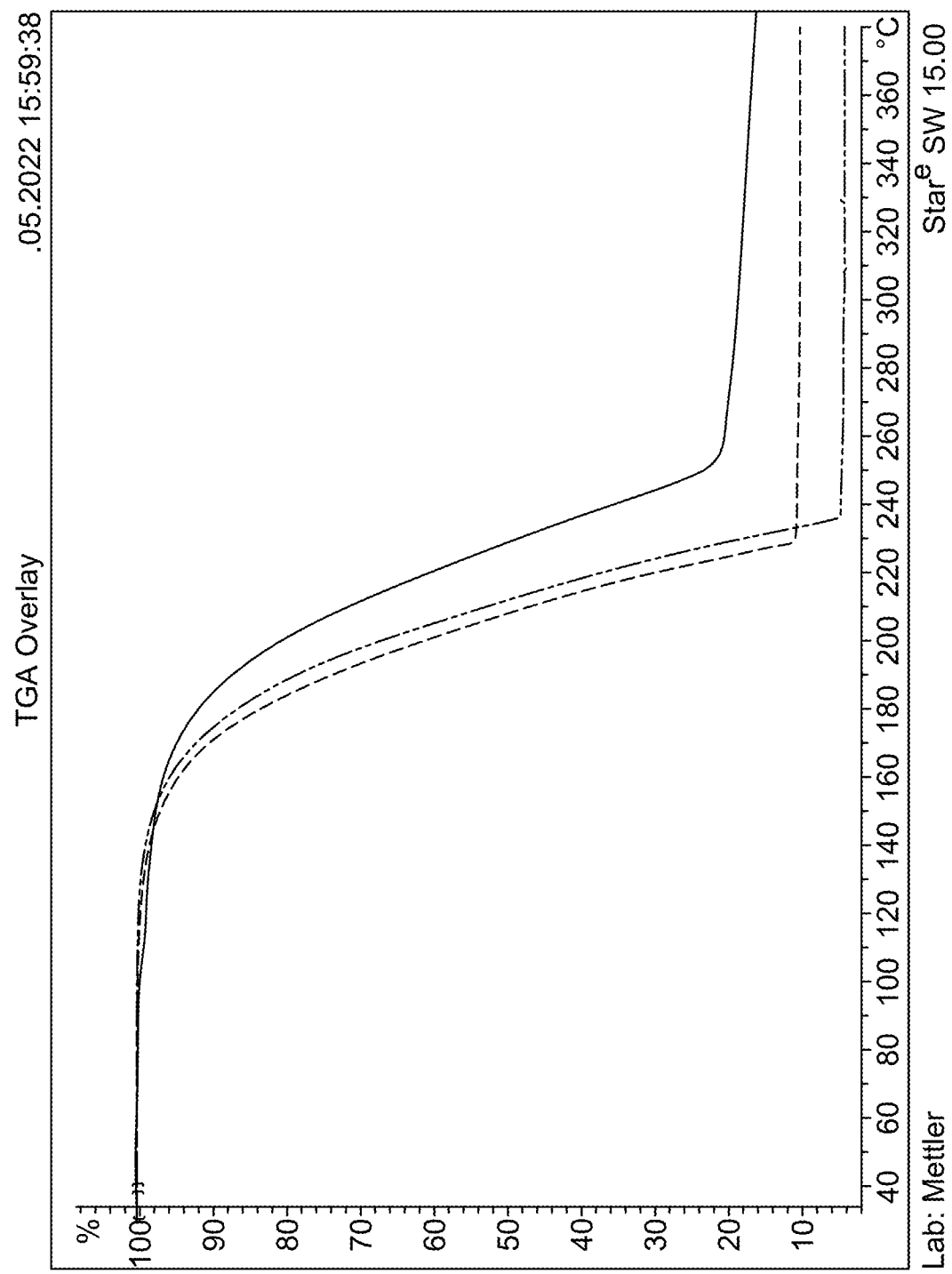

FIG. 292 shows an overlay of TGA profiles of a reference sample of crystalline compound 1 benzoate (top), a sample of crystalline compound 1 benzoate after storage for 5 days at 40° C./75% RH (middle) and a sample of crystalline compound 1 benzoate for 10 days at 40° C./75% RH (bottom).

Figure 293:
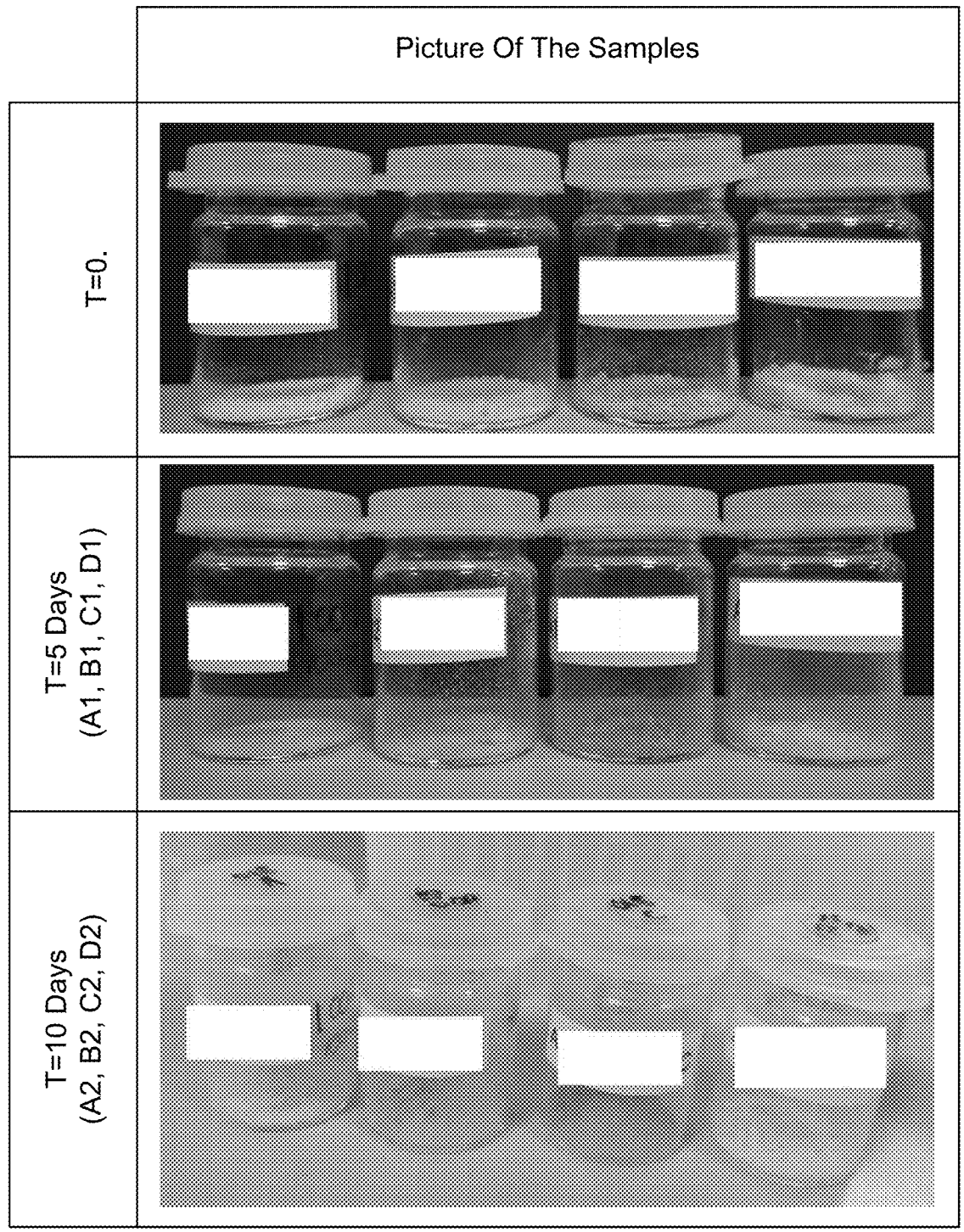

FIG. 293 shows images of various crystalline compound 1 salts at 0, 5 and 10 days at 40° C./75% RH. From left to right, the salts are the crystalline compound 1 monofumarate Form A salt, the crystalline HCl Form A salt, the crystalline maleate salt, and the crystalline benzoate salt.

Figure 294:
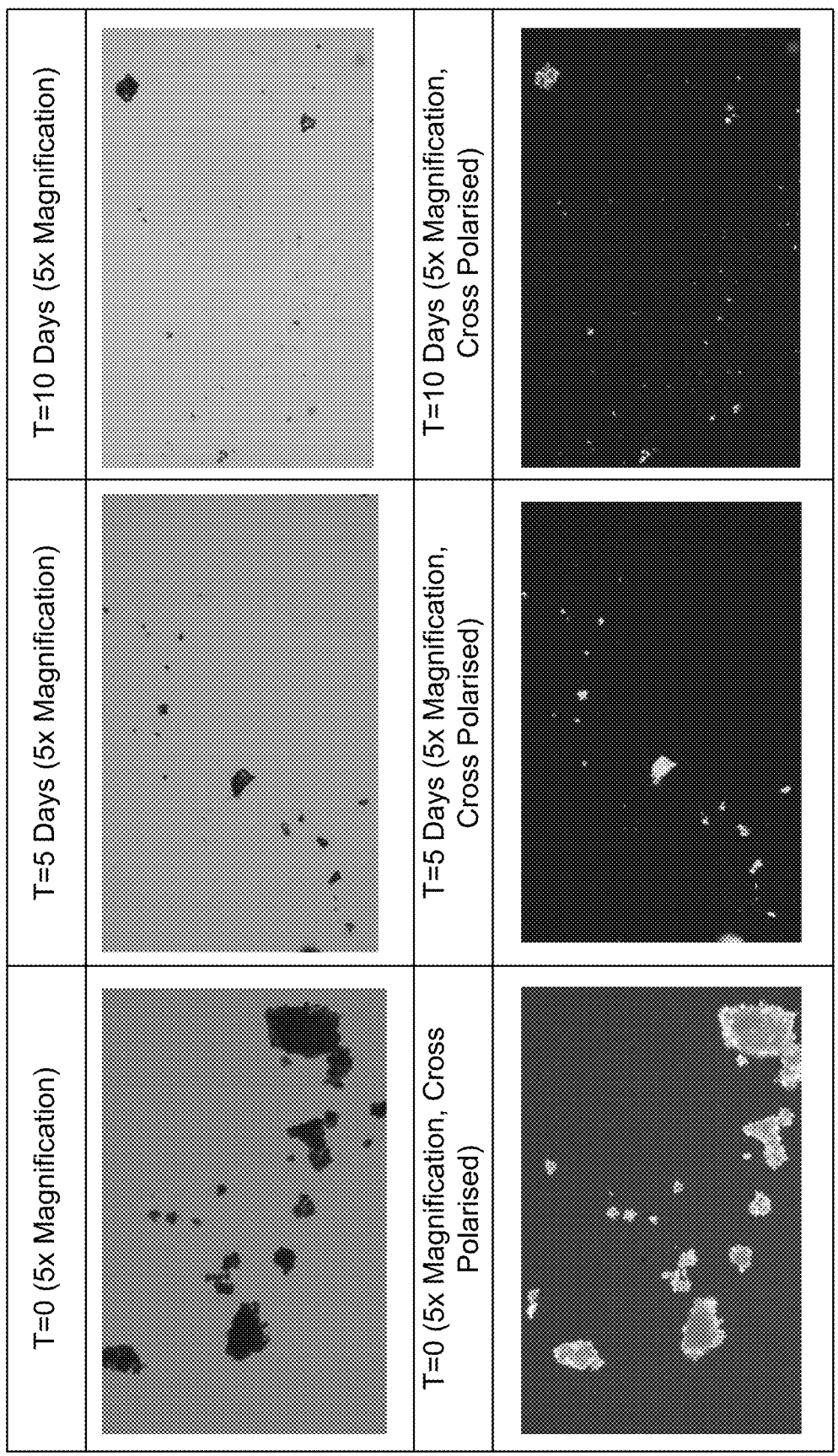

FIG. 294 shows optical microscopy images of a reference sample of crystalline compound 1 monofumarate Form A (left column), a sample of crystalline compound 1 monofumarate Form A after 5 days at 40° C./75% RH (center column), and a sample of crystalline compound 1 monofumarate Form A after 10 days at 40° C./75% RH.

Figure 295:
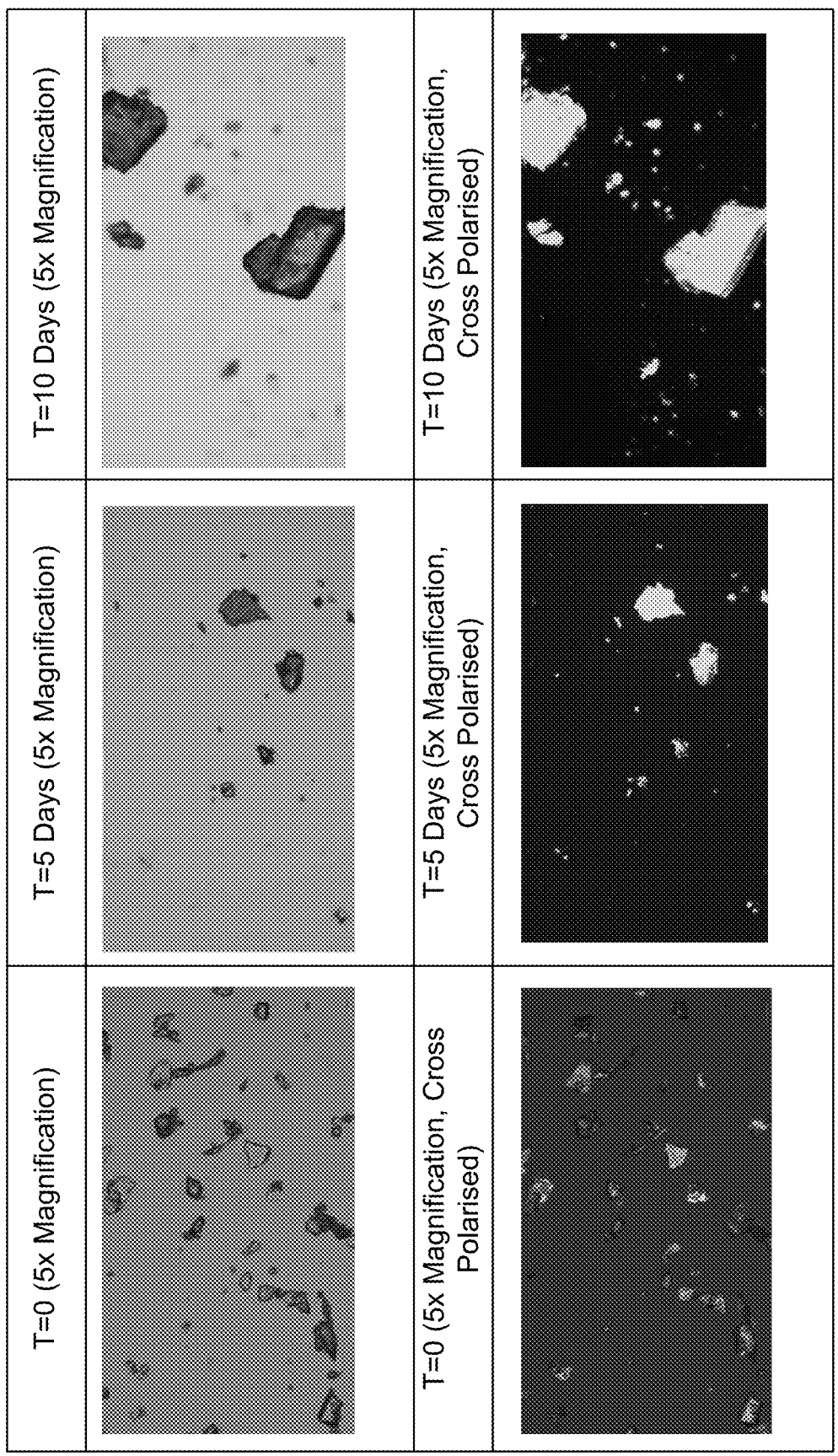

FIG. 295 shows optical microscopy images of a reference sample of crystalline compound 1 HCl (Form A left column), a sample of crystalline compound 1 HCl Form A after 5 days at 40° C./75% RH (center column), and a sample of crystalline compound 1 HCl Form A 10 days at 40° C./75% RH.

Figure 296:
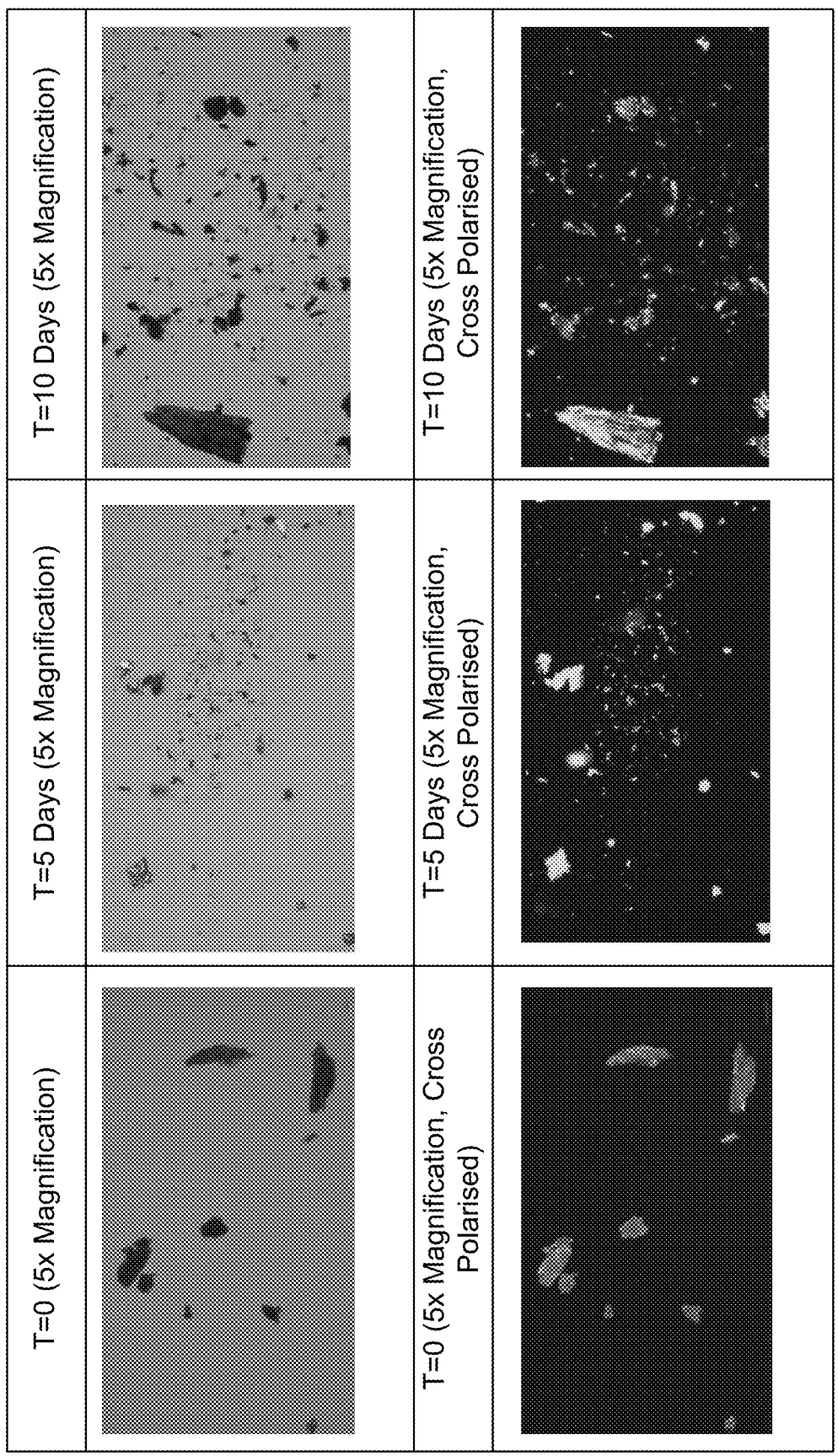

FIG. 296 shows optical microscopy images of a reference sample of crystalline compound 1 maleate (left column), a sample of crystalline compound 1 maleate after 5 days at 40° C./75% RH (center column), and a sample of crystalline compound 1 maleate 10 days at 40° C./75% RH.

Figure 297:

FIG. 297 shows optical microscopy images of a reference sample of crystalline compound 1 benzoate (left column), a sample of crystalline compound 1 benzoate after 5 days at 40° C./75% RH (center column), and a sample of crystalline compound 1 benzoate 10 days at 40° C./75% RH.

Figure 298:
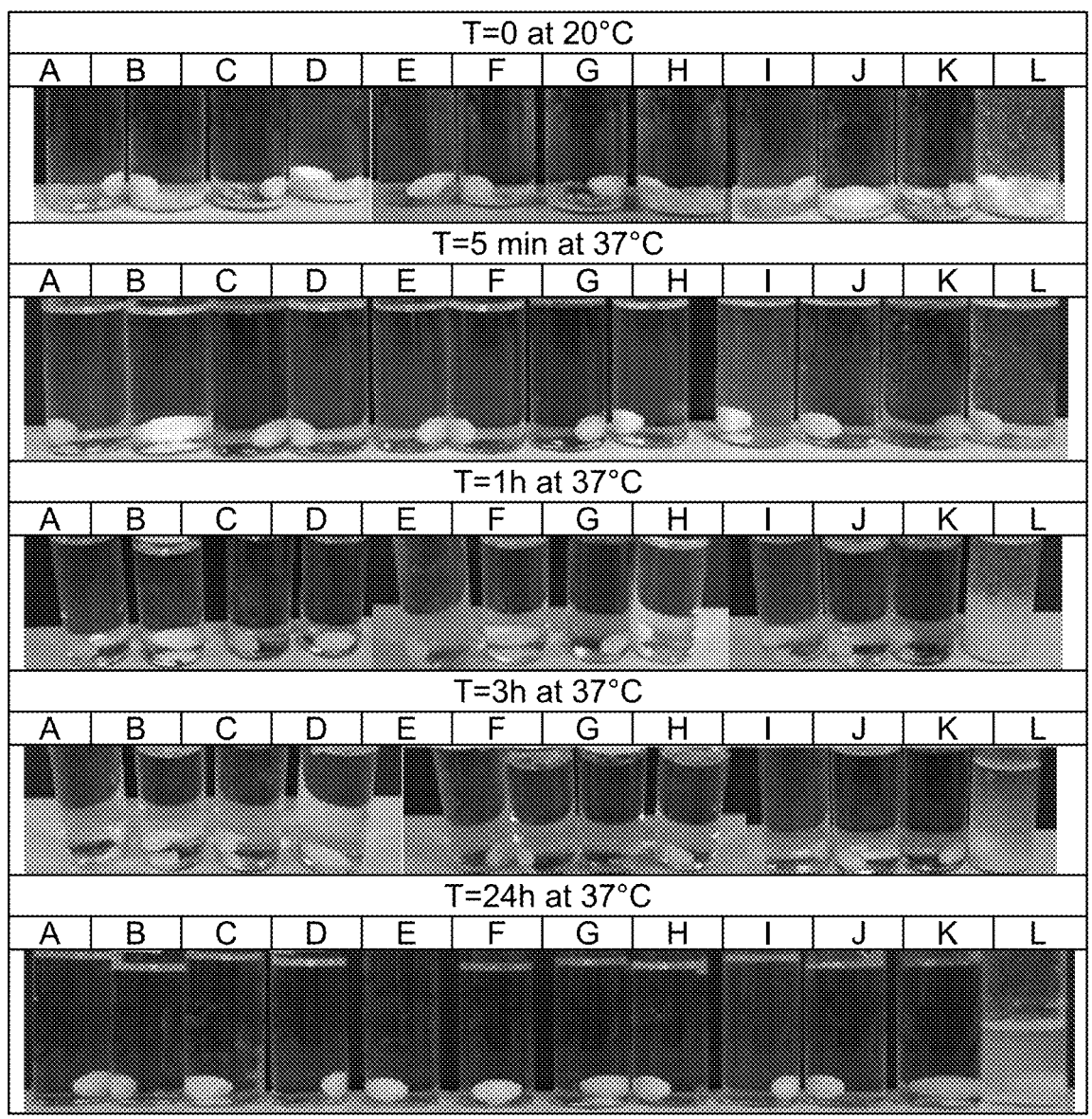

FIG. 298 shows images of various crystalline compound 1 salts dissolved in SFI buffers. Column A shows crystalline compound 1 monofumarate Form A in FaSSIF buffer (pH 6.5); column B shows crystalline compound 1 HCl Form A in FaSSIF buffer (pH 6.5), column C shows crystalline compound 1 maleate in FaSSIF buffer (pH 6.5), column D shows crystalline compound 1 benzoate in FaSSEF buffer (pH 5.0), column E shows crystalline compound 1 monofumarate Form A in FaSSEF buffer (pH 5.0), column F shows crystalline compound 1 HCl Form A FaSSEF buffer (pH 5.0), column G shows crystalline compound 1 maleate in FaSSEF buffer (pH 5.0), column H shows crystalline compound 1 benzoate Form A in FaSSEF buffer (pH 5.0), column I shows crystalline compound 1 monofumarate Form A in FaSSGF buffer (pH 1.6), column J shows crystalline compound 1 HCl Form A in FaSSGF buffer (pH 1.6), column K shows crystalline compound 1 maleate in FaSSGF buffer (pH 1.6), and column L shows crystalline compound 1 benzoate in FaSSGF buffer (pH 1.6).

Figure 299:
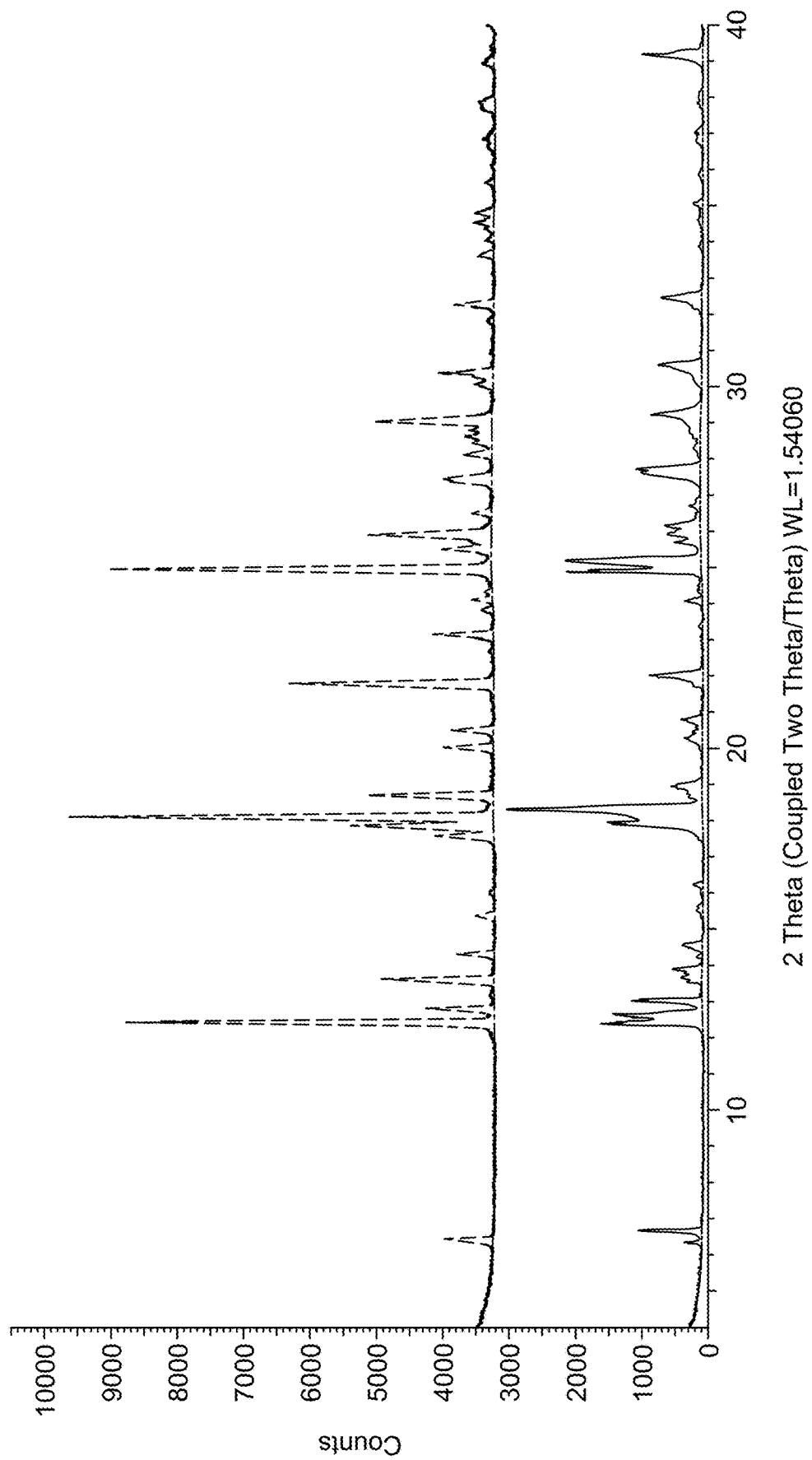

FIG. 299 shows XRPD profiles for crystalline compound 1 HCl Form B salt pattern 1 (bottom) and crystalline compound 1 HCL Form A (top).

Figure 300:
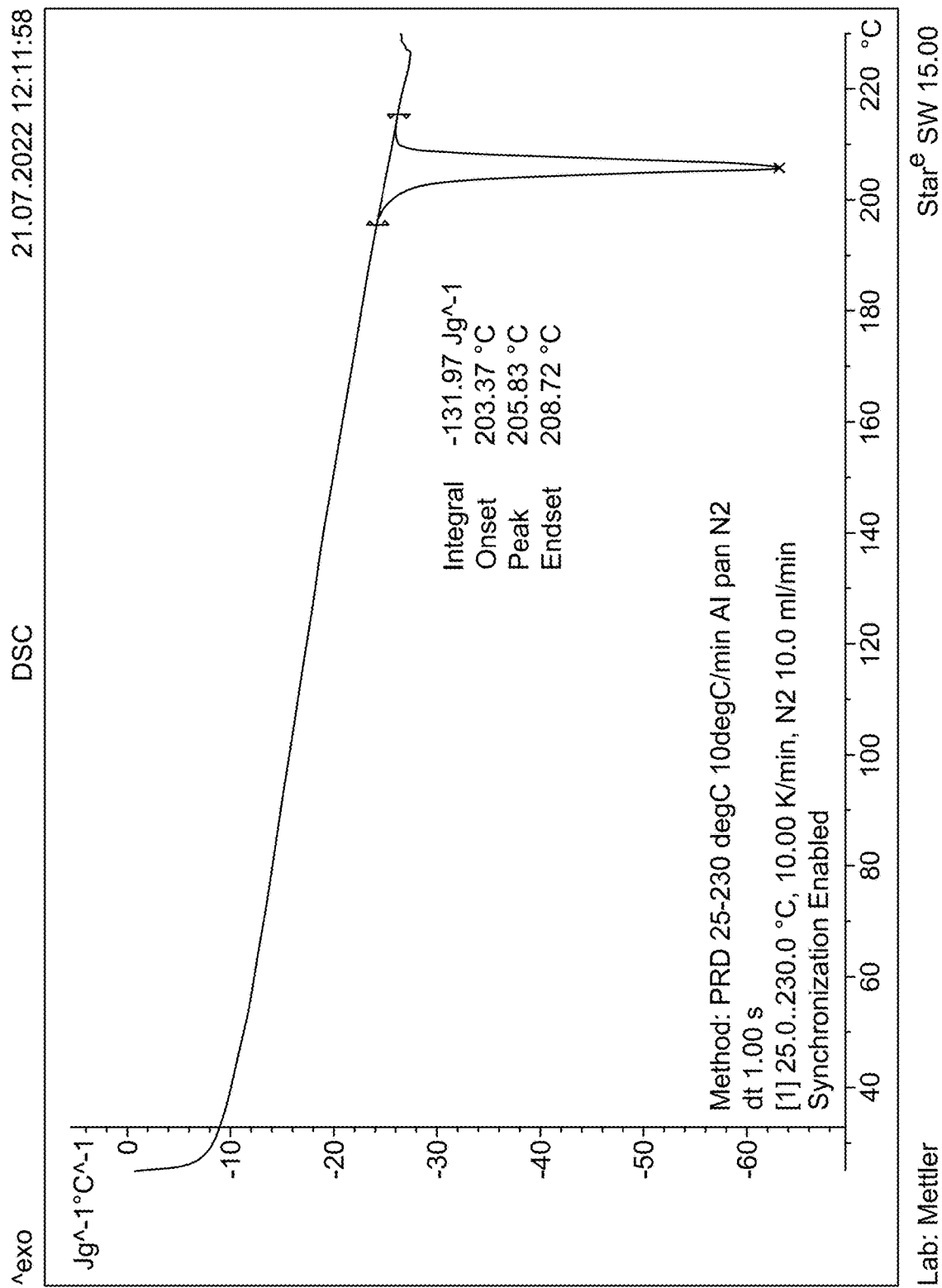

FIG. 300 shows a DSC profile of crystalline compound 1 HCl Form A obtained when attempting to re-prepare crystalline compound 1 HCl Form B.

Figure 301:
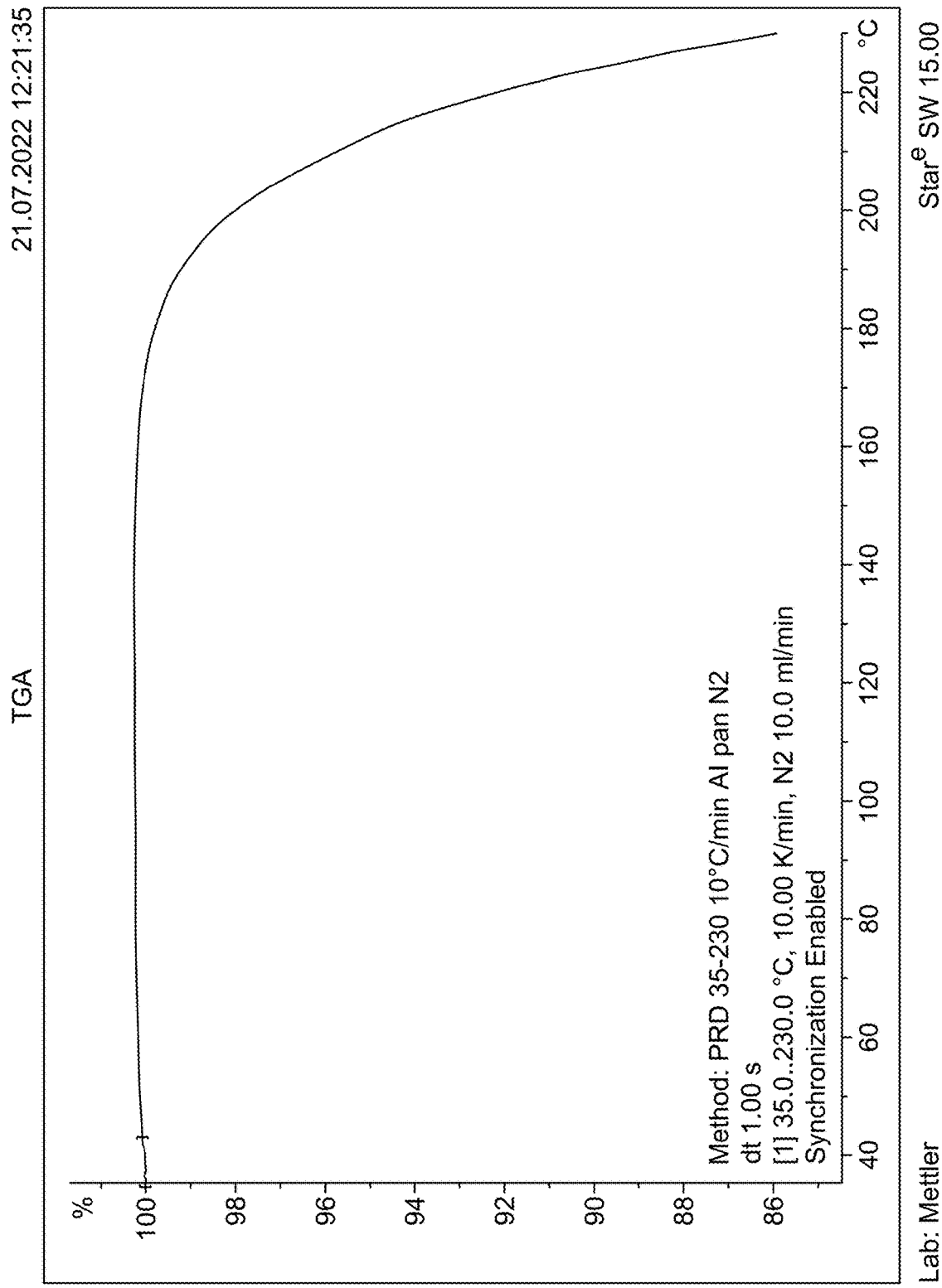

FIG. 301 shows a TGA profile of crystalline compound 1 HCl Form A obtained when attempting to re-prepare crystalline compound 1 HCl Form B.

Figure 302:
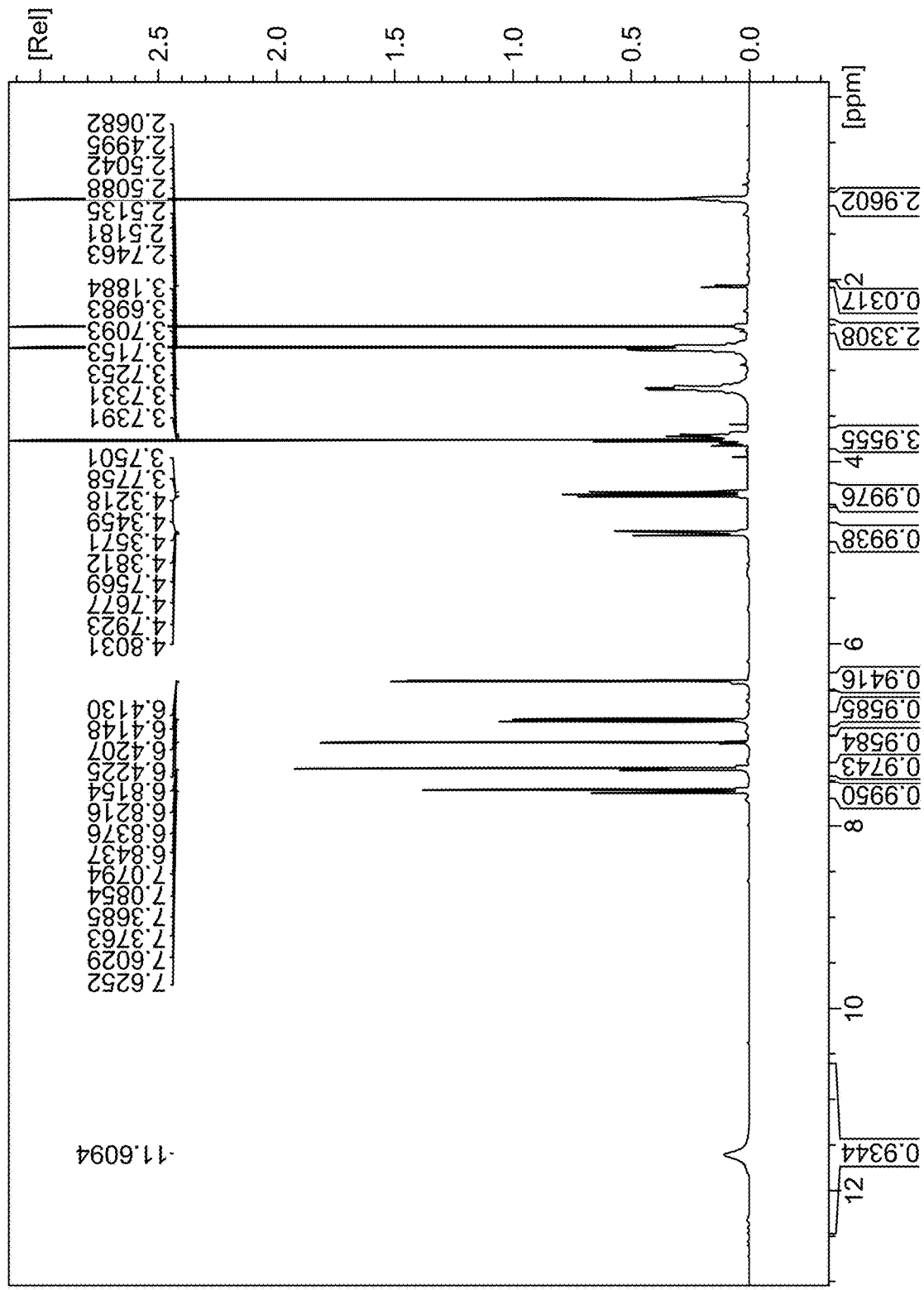

FIG. 302 shows a $^1$H NMR of crystalline compound 1 HCl Form A obtained when attempting to re-prepare crystalline compound 1 HCl Form B.

Figure 303:
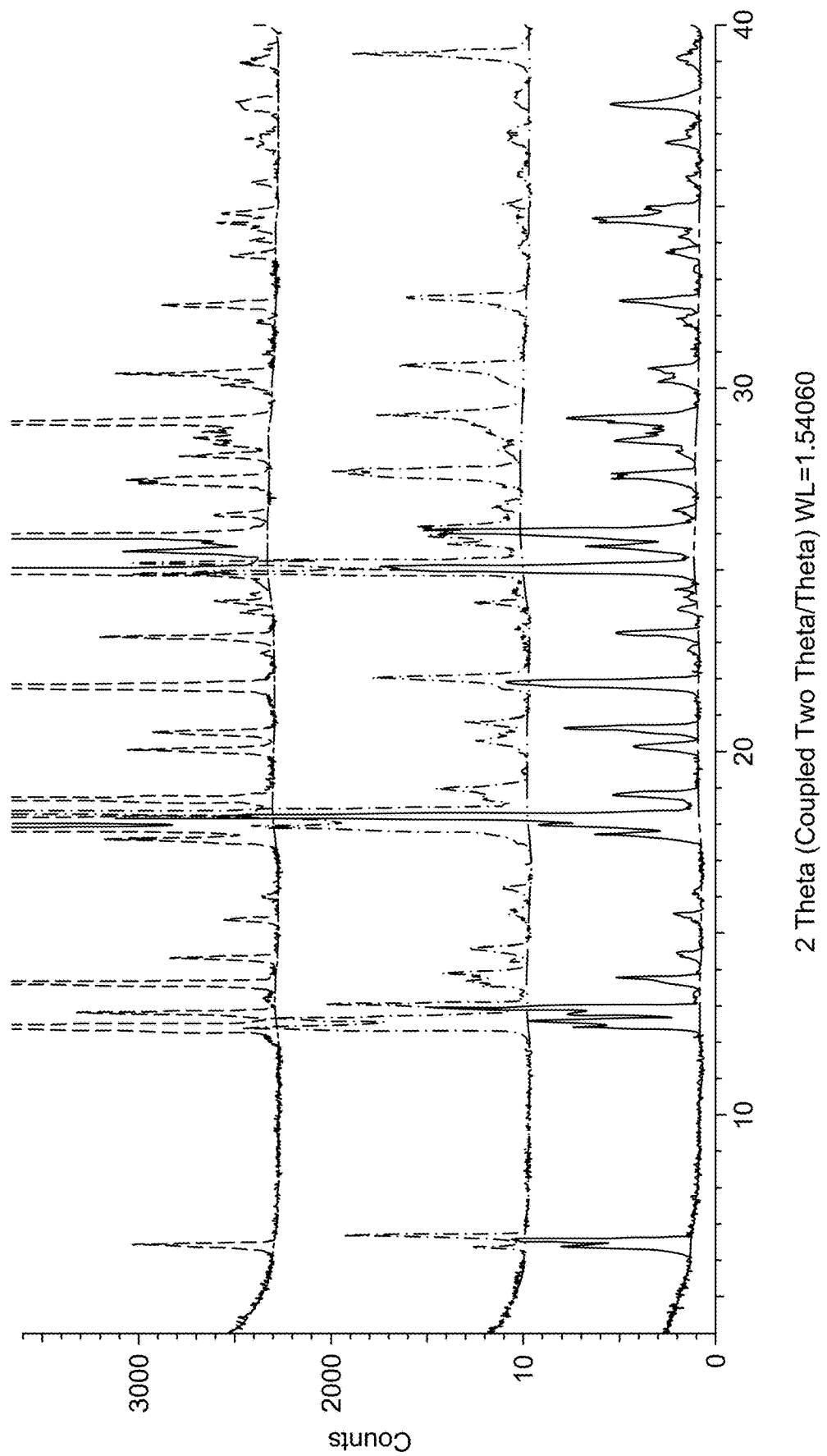

FIG. 303 shows an overlay of the XRPD profiles of a reference sample of crystalline compound 1 HCL Form A (top), a reference sample of crystalline compound 1 HCl Pattern 1 (middle) and Form B obtained by way of controlled heat-up/cool-down in acetonitrile/water (bottom).

Figure 304:
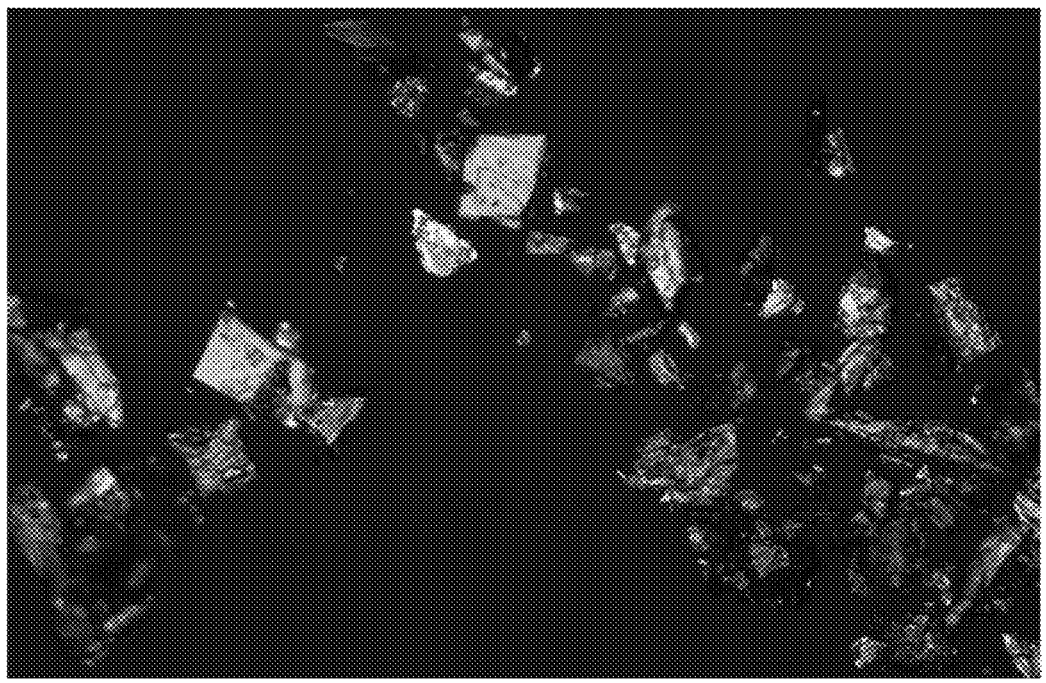

FIG. 304 shows a polarized light microscopy image of crystalline compound 1 HCl Form A obtained while attempting to re-prepare crystalline compound 1 HCl Form B.

Figure 305:
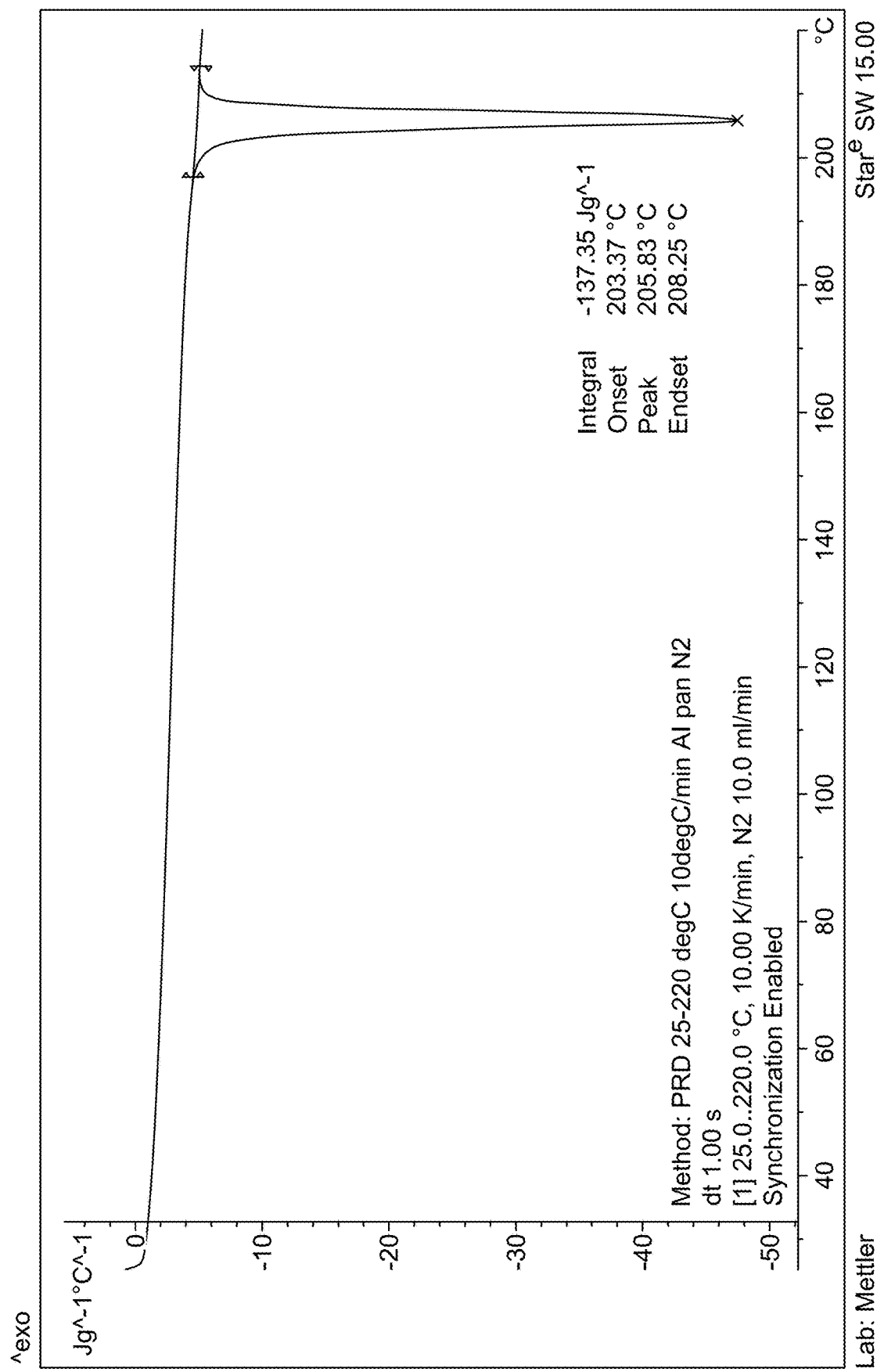

FIG. 305 shows a DCS profile of a sample of crystalline compound 1 HCl.

Figure 306:
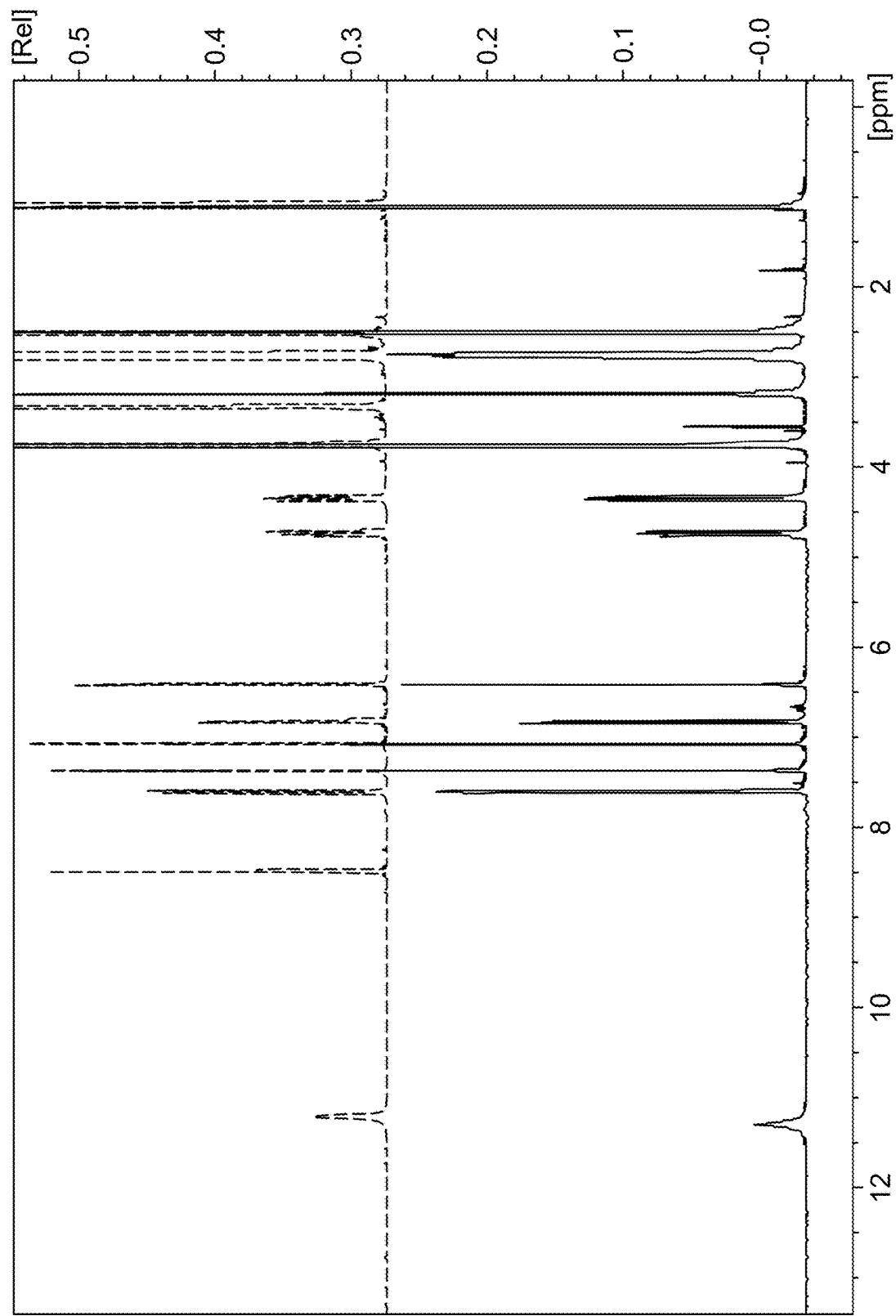

FIG. 306 is an overlay of a reference sample of crystalline compound 1 HCl Form A (top) and crystalline compound 1 HCl Form A obtained by way of binary solvent evaporation crystallization from acetone and water (bottom).

Figure 307:
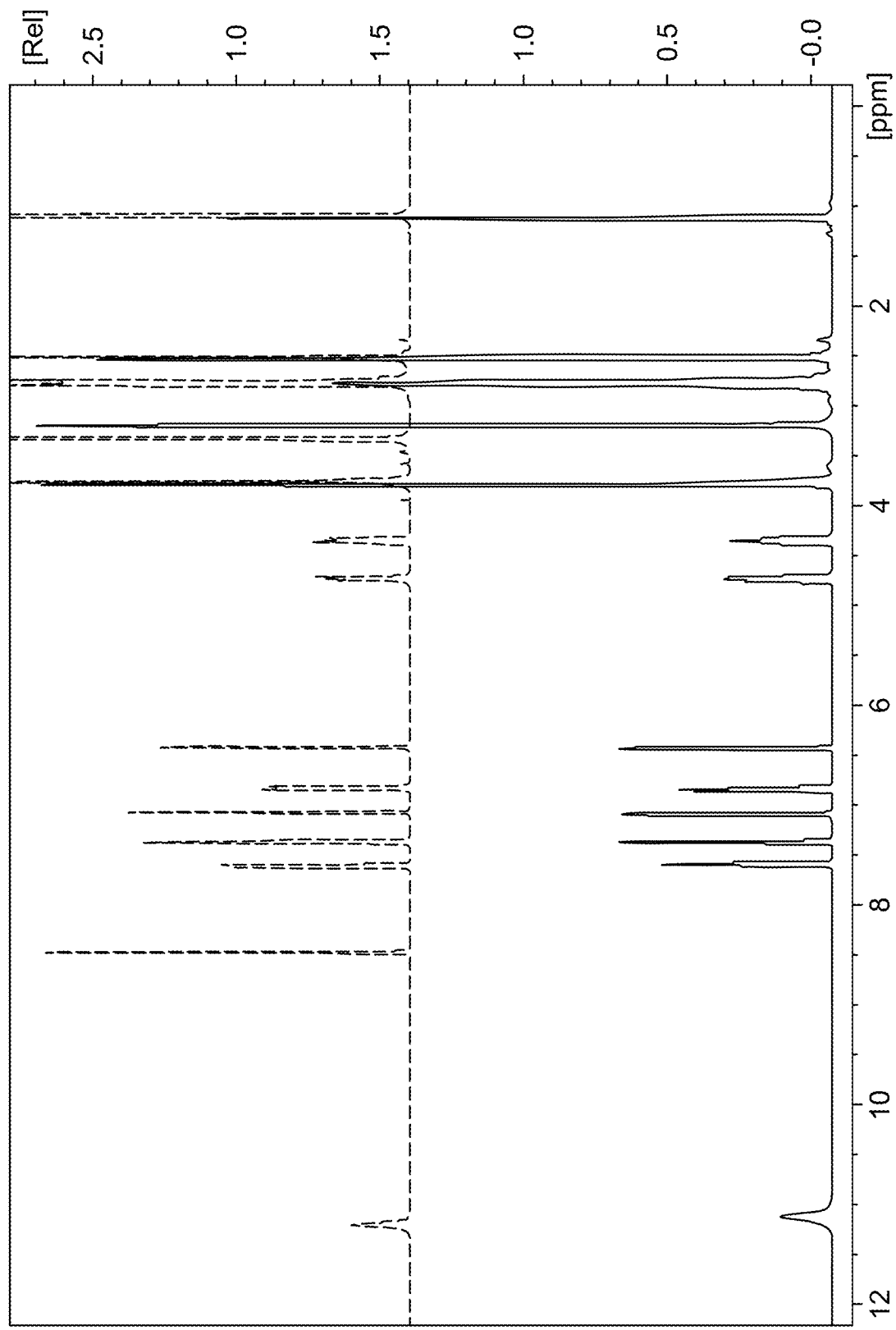

FIG. 307 is an overlay of a reference sample of crystalline compound 1 HCl Form A (top) and crystalline compound 1 HCl Form A obtained by way of binary solvent evaporation crystallization from acetonitrile and water (bottom).

Figure 308:
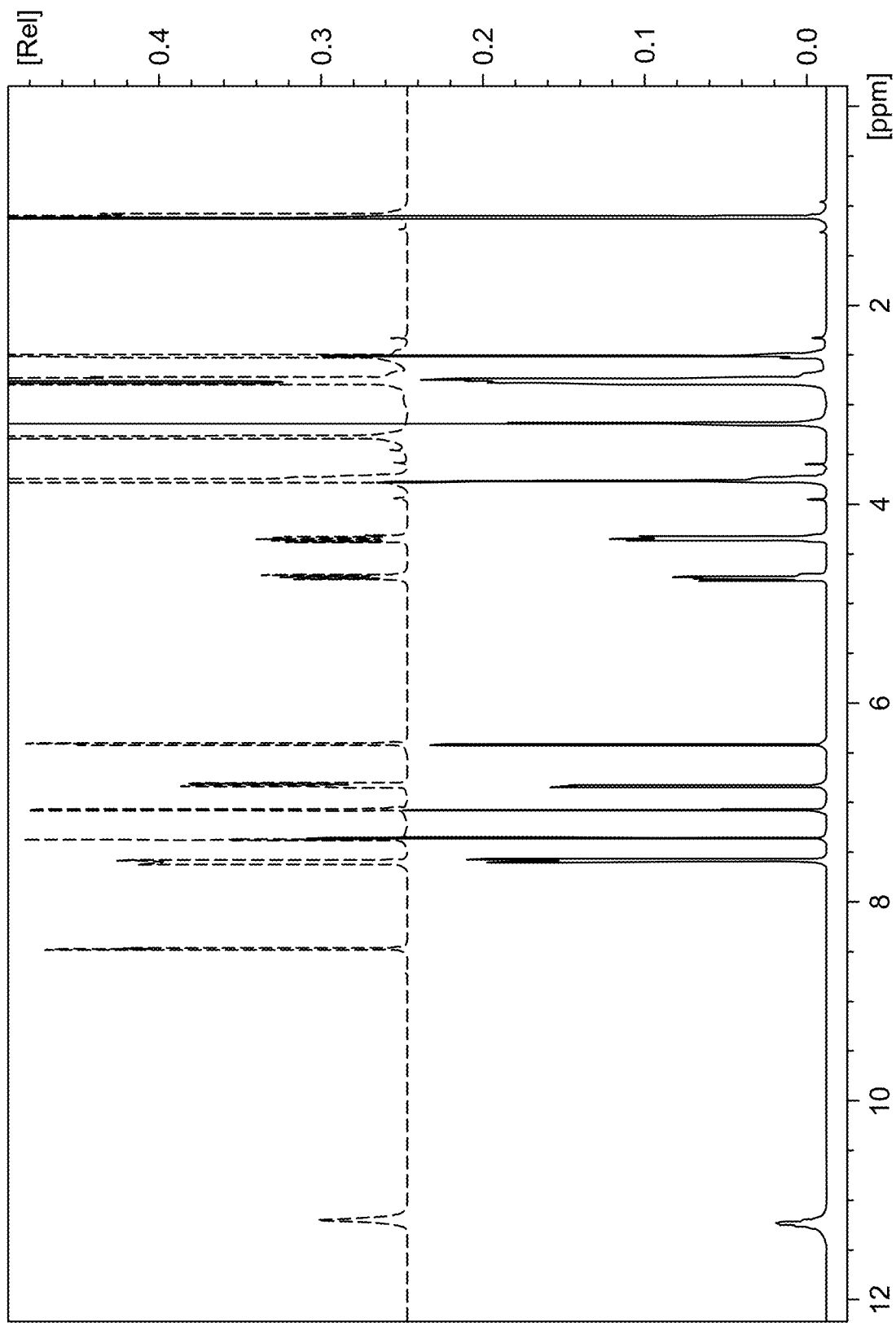

FIG. 308 is an overlay of a reference sample of crystalline compound 1 HCl Form A (top) and crystalline compound 1 HCl Form A obtained by way of binary solvent evaporation crystallization from THF and water (bottom).

Figure 309:
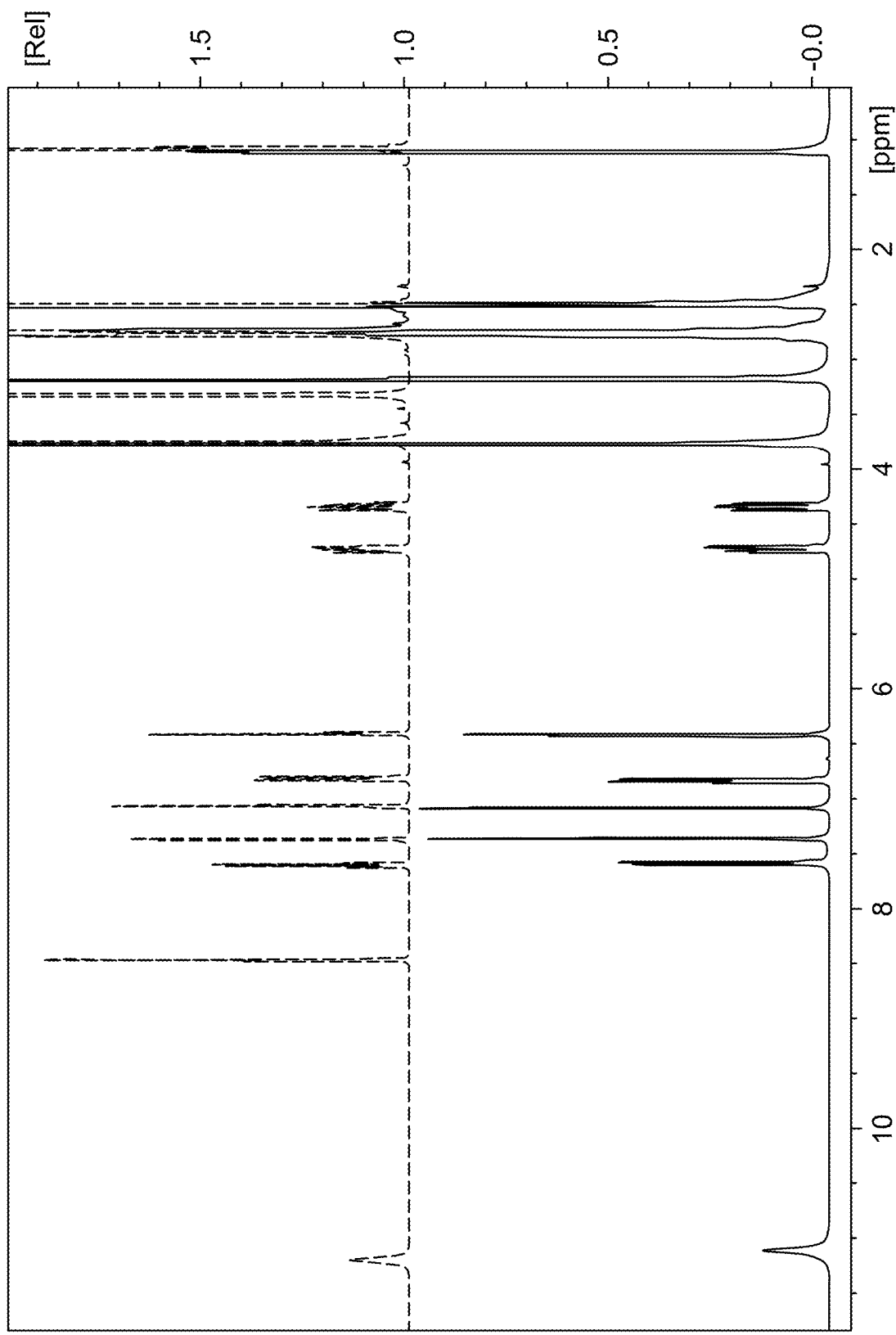

FIG. 309 is an overlay of a reference sample of crystalline compound 1 HCl Form A (top) and crystalline compound 1 HCl Form A obtained by way of binary solvent evaporation crystallization from methanol and water (bottom).

Figure 310:
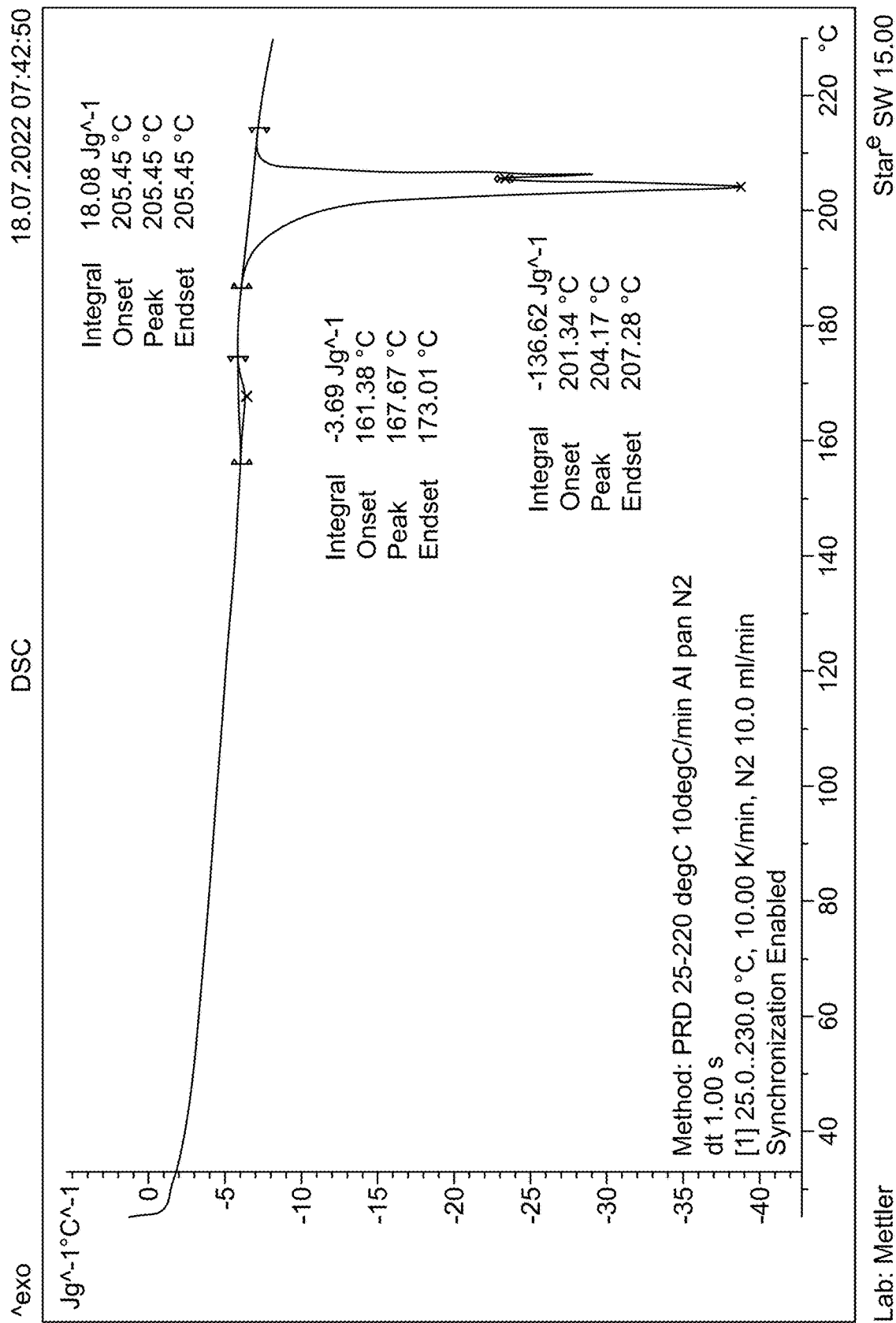

FIG. 310 shows a DSC profile for crystalline compound 1 HCl Form A obtained by way of binary solvent evaporation crystallization from acetone and water. The specimen may have contained a small quantity of amorphous material, in the 170° C. region, the split signal is most likely attributed to poor thermal contact within the DSC crucible. DSC analysis was repeated in FIG. 326 and the split signal was absent. Fusion temperatures aligned with Form A.

Figure 311:
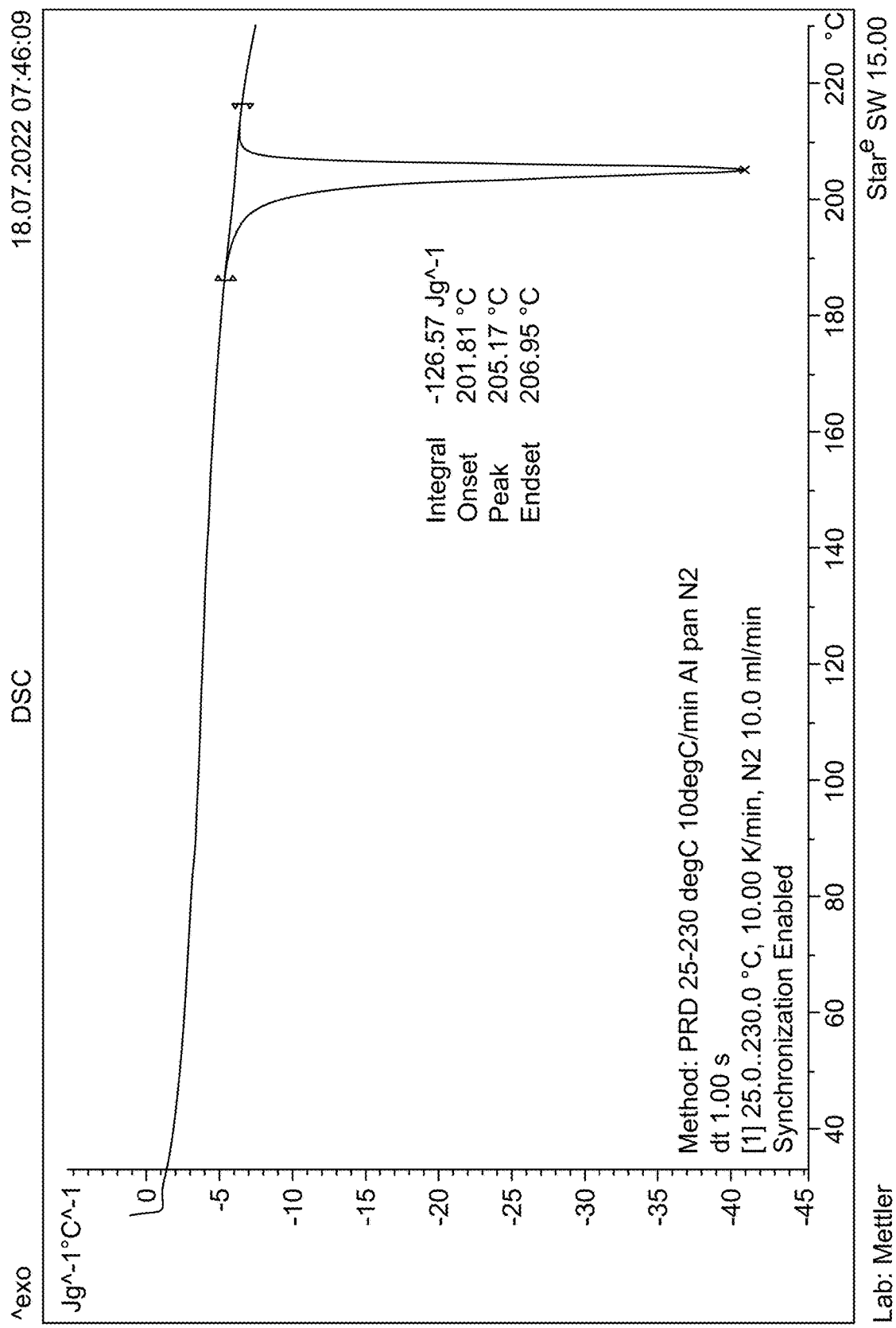

FIG. 311 shows a DSC profile for crystalline compound 1 HCl Form A obtained by way of binary solvent evaporation crystallization from acetonitrile and water. Fusion temperatures aligned with Form A.

Figure 312:
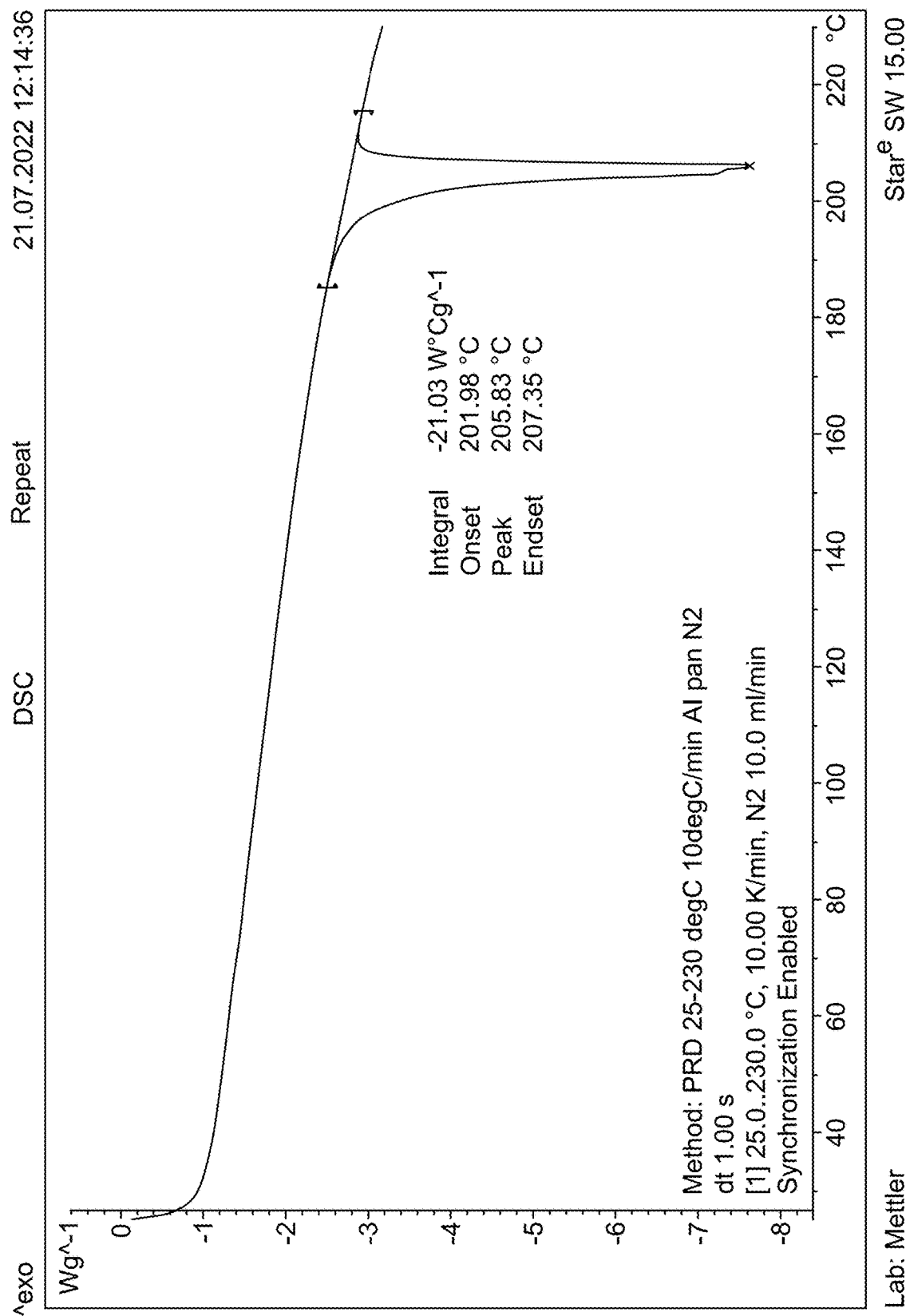

FIG. 312 shows a DSC profile for crystalline compound 1 HCl Form A obtained by way of binary solvent evaporation crystallization from acetone and water. Fusion temperatures aligned with Form A. Repeat of the experiment shown in FIG. 324, confirmed a single melting event.

Figure 313:
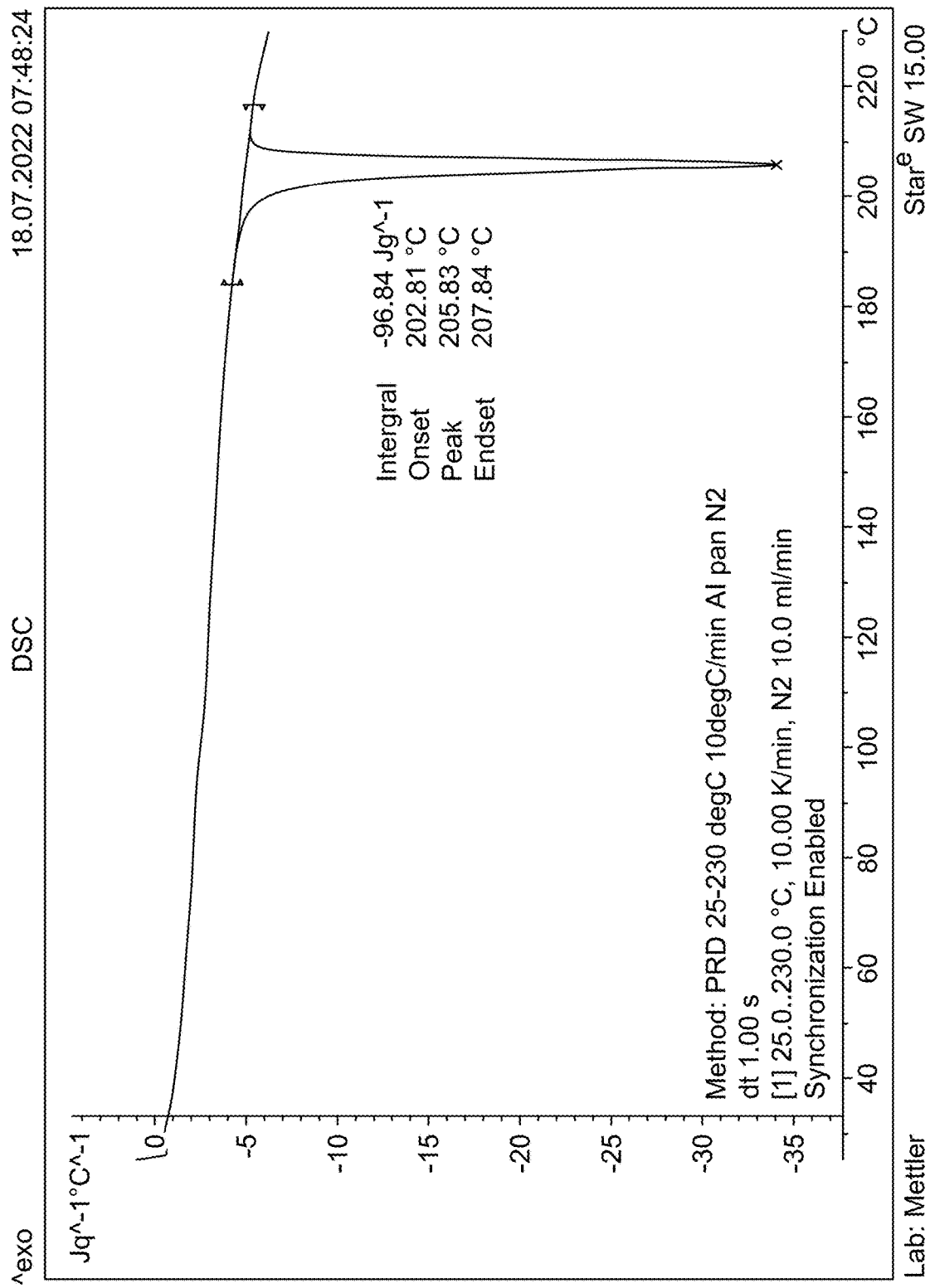

FIG. 313 shows a DSC profile for crystalline compound 1 HCl Form A obtained by way of binary solvent evaporation crystallization from THF and water. Fusion temperatures aligned with Form A.

Figure 314:
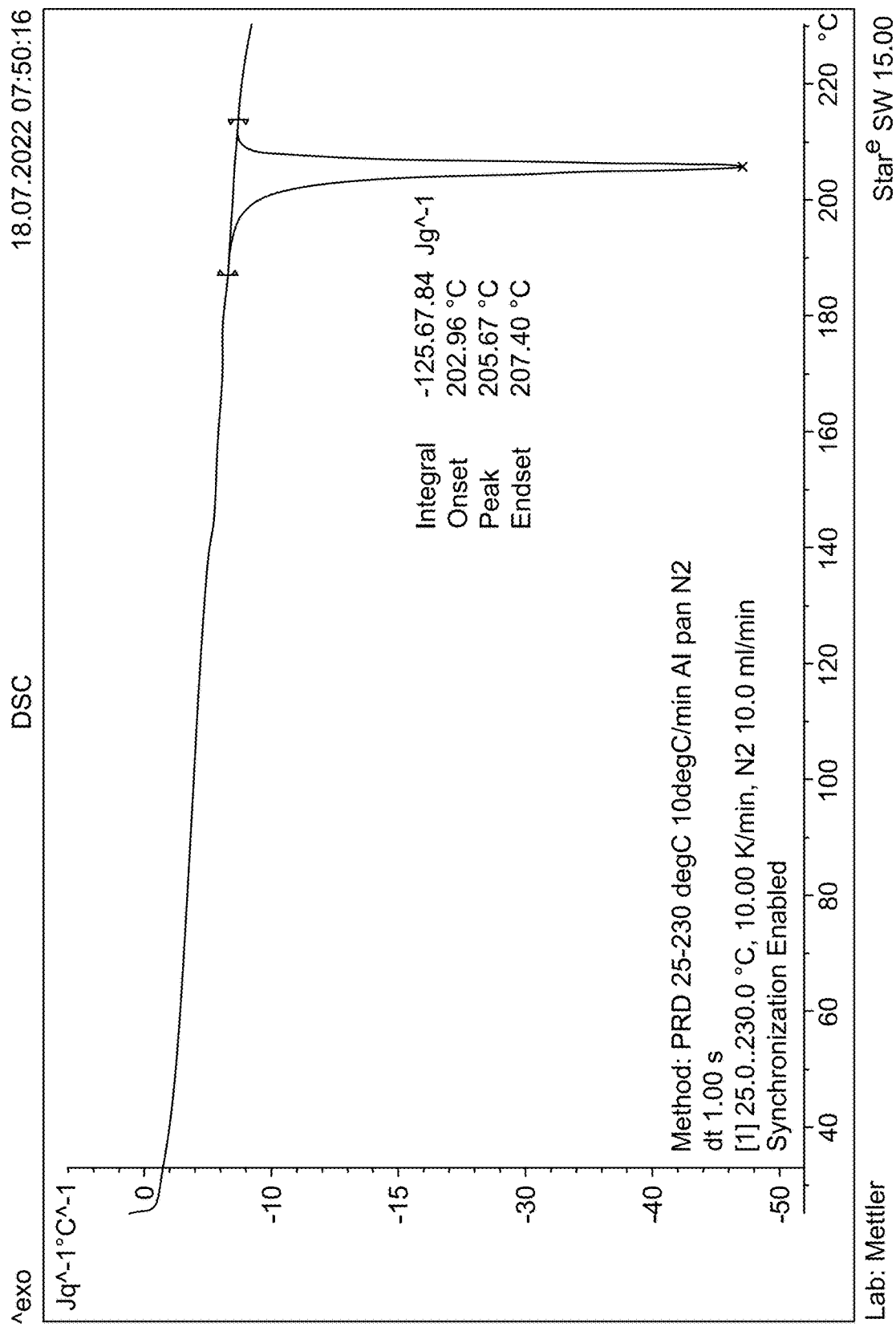

FIG. 314 shows a DSC profile for crystalline compound 1 HCl Form A obtained by way of binary solvent evaporation crystallization from methanol and water. Fusion temperatures aligned with Form A.

Figure 315:
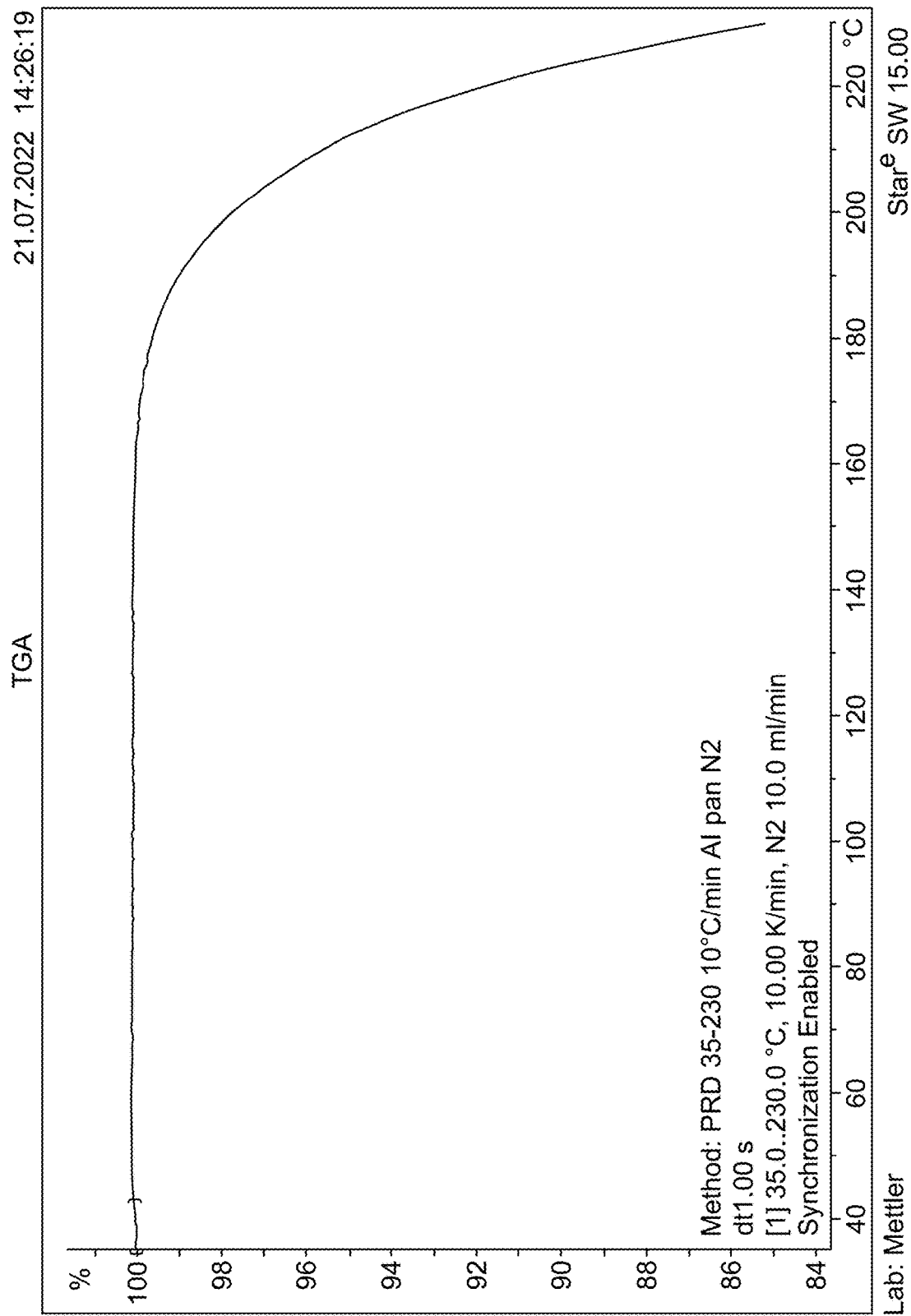

FIG. 315 shows a TGA profile for crystalline compound 1 HCl Form A obtained by way of binary solvent evaporation crystallization from acetone and water.

Figure 316:
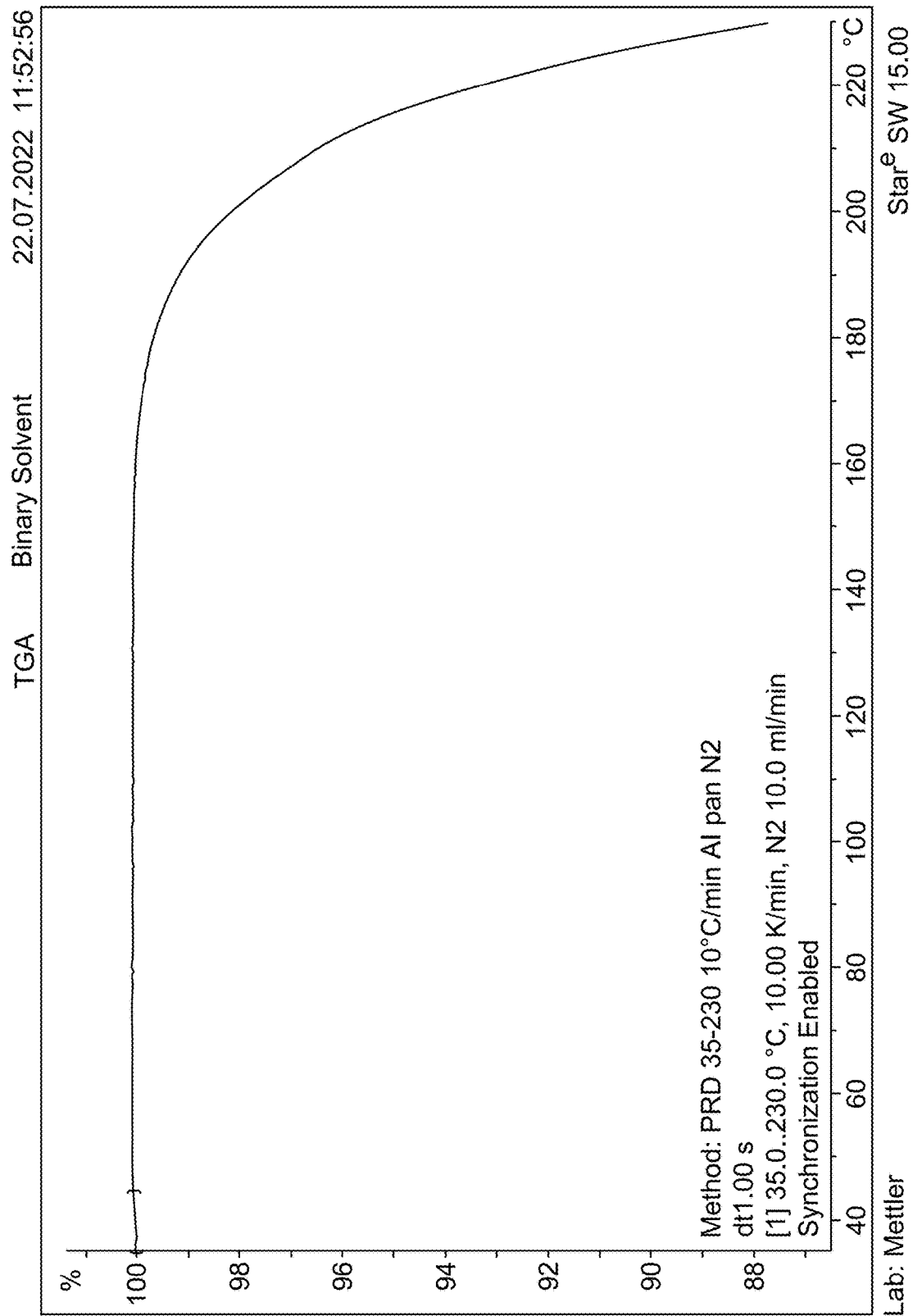

FIG. 316 shows a TGA profile for crystalline compound 1 HCl Form A obtained by way of binary solvent evaporation crystallization from acetone and water.

Figure 317:
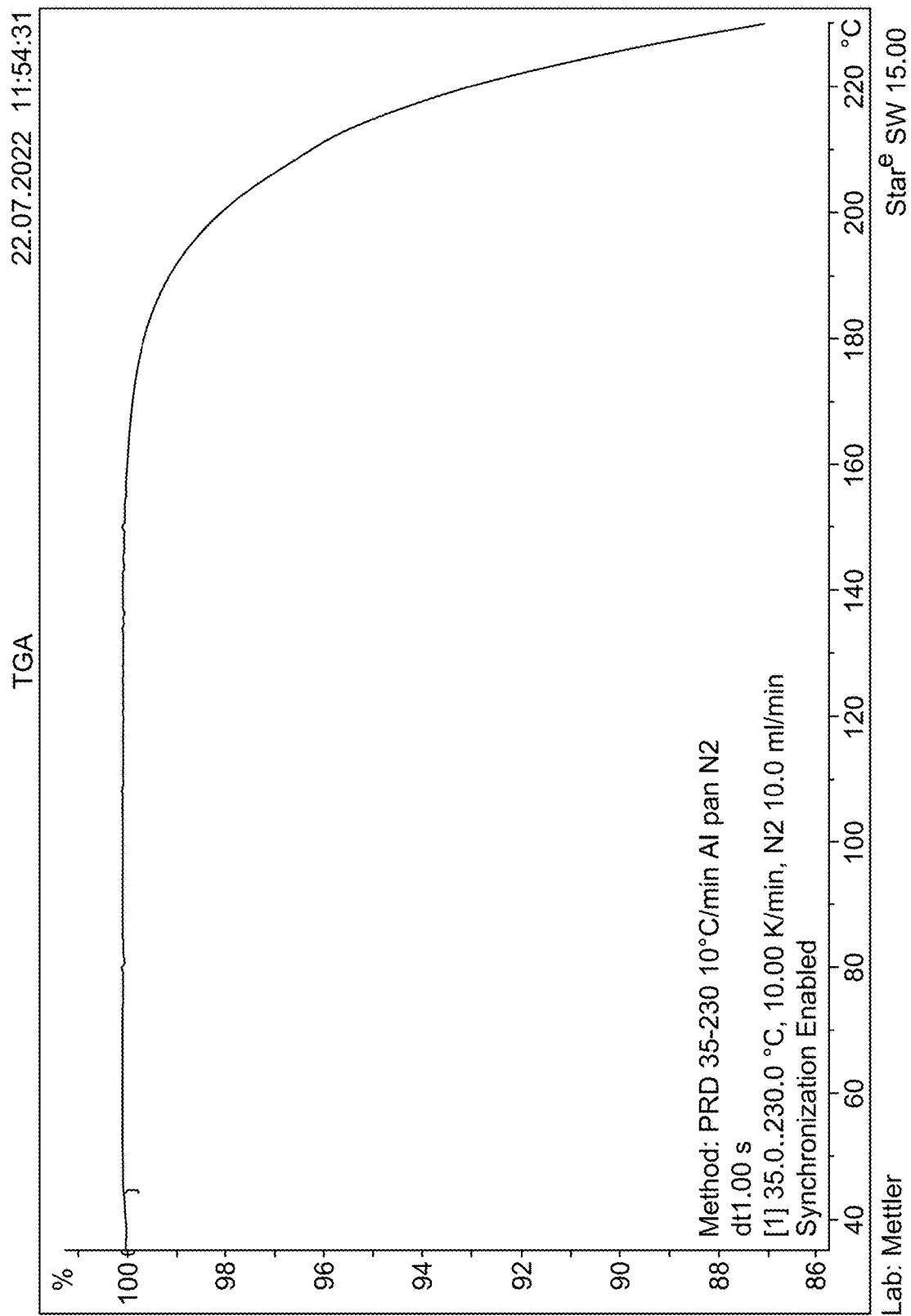

FIG. 317 shows a TGA profile for crystalline compound 1 HCl Form A obtained by way of binary solvent evaporation crystallization from THF and water.

Figure 318:
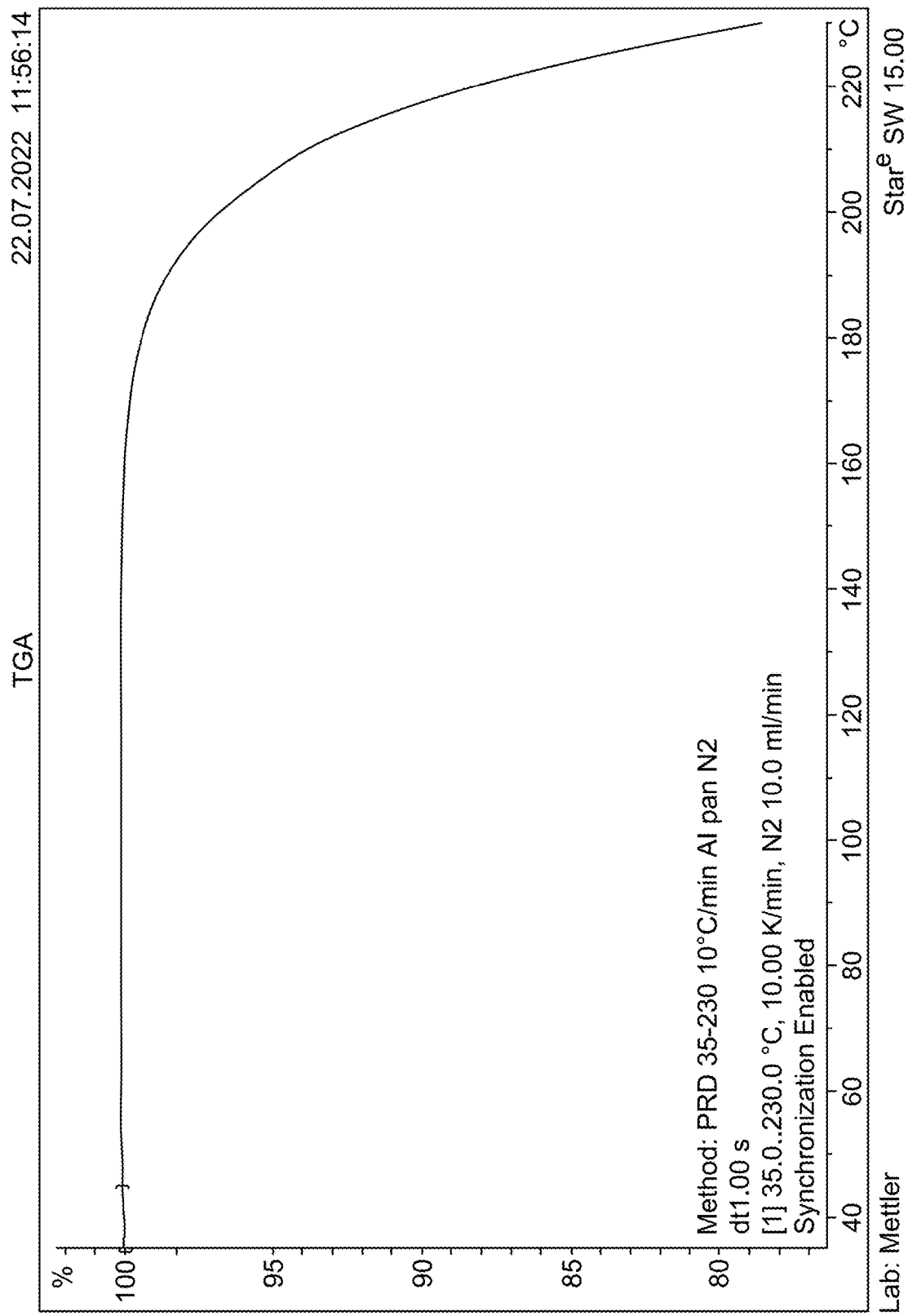

FIG. 318 shows a TGA profile for crystalline compound 1 HCl Form A obtained by way of binary solvent evaporation crystallization from methanol and water.

Figure 319:
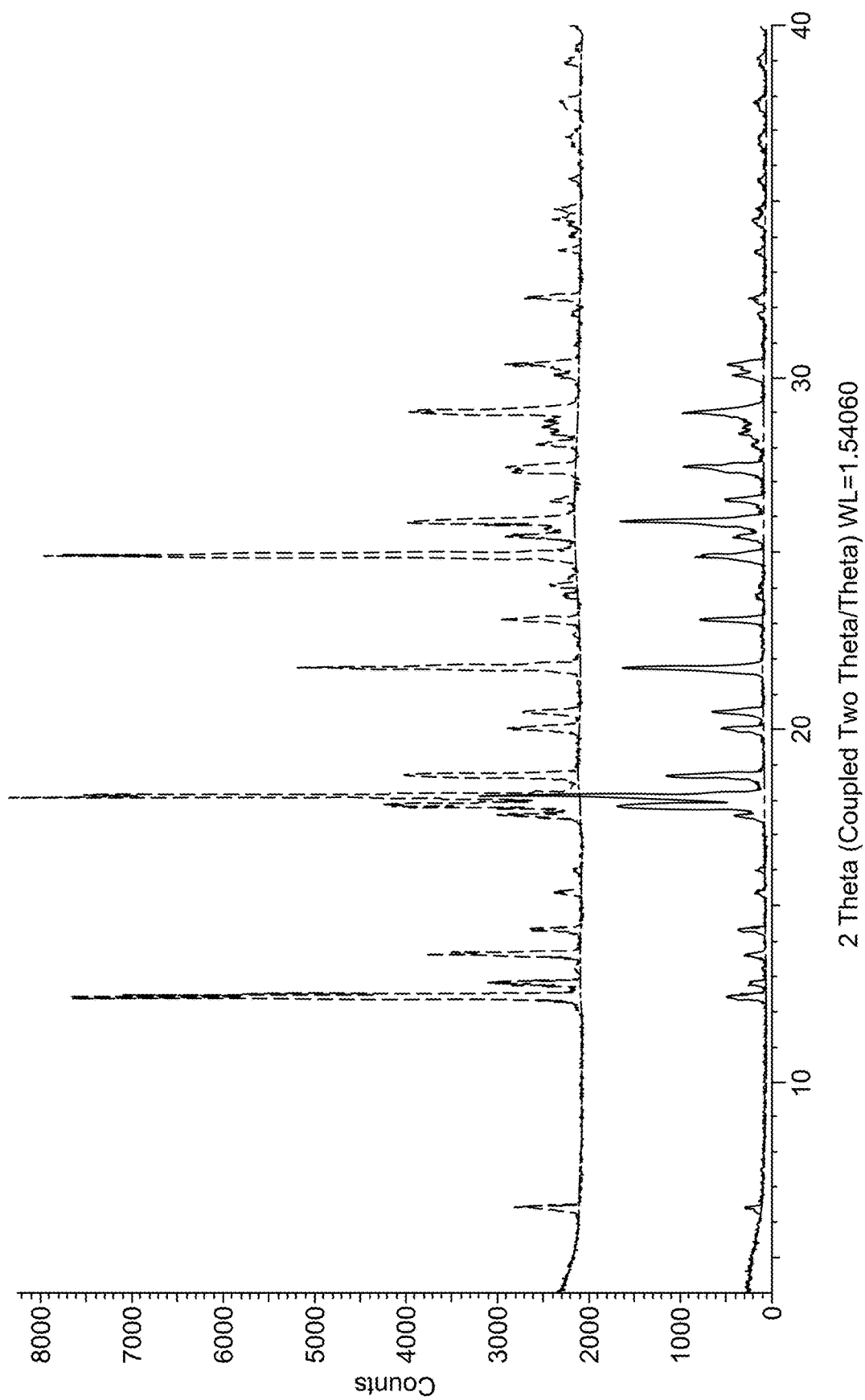

FIG. 319 shows an overlay of XRPD profiles for a reference sample of crystalline compound 1 HCl Form A (top) and crystalline compound 1 HCl Form A obtained by way of binary solvent evaporation crystallization from acetone and water.

Figure 320:
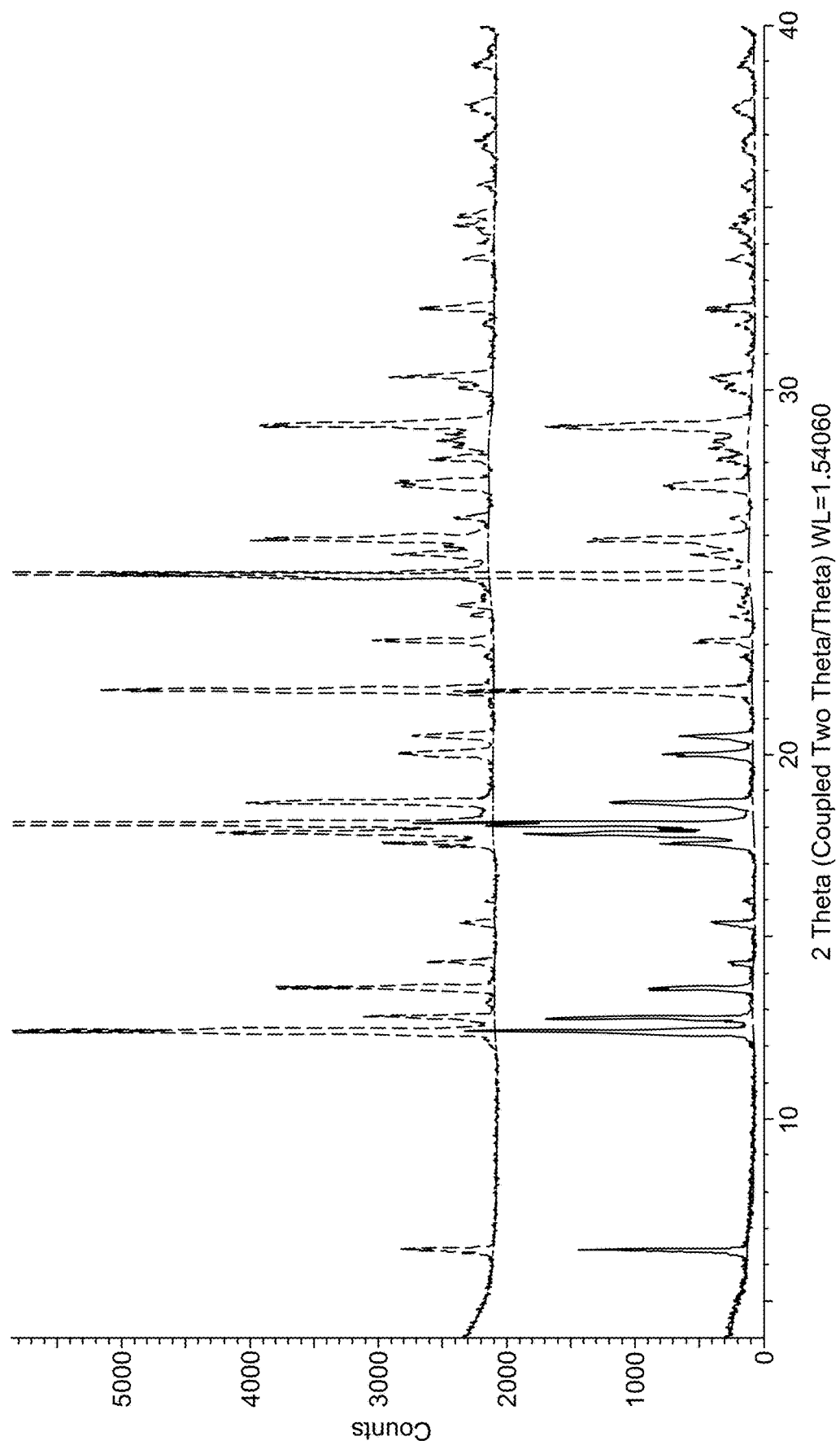

FIG. 320 shows an overlay of XRPD profiles for a reference sample of crystalline compound 1 HCl Form A (top) and crystalline compound 1 HCl Form A obtained by way of binary solvent evaporation crystallization from acetone and water.

Figure 321:
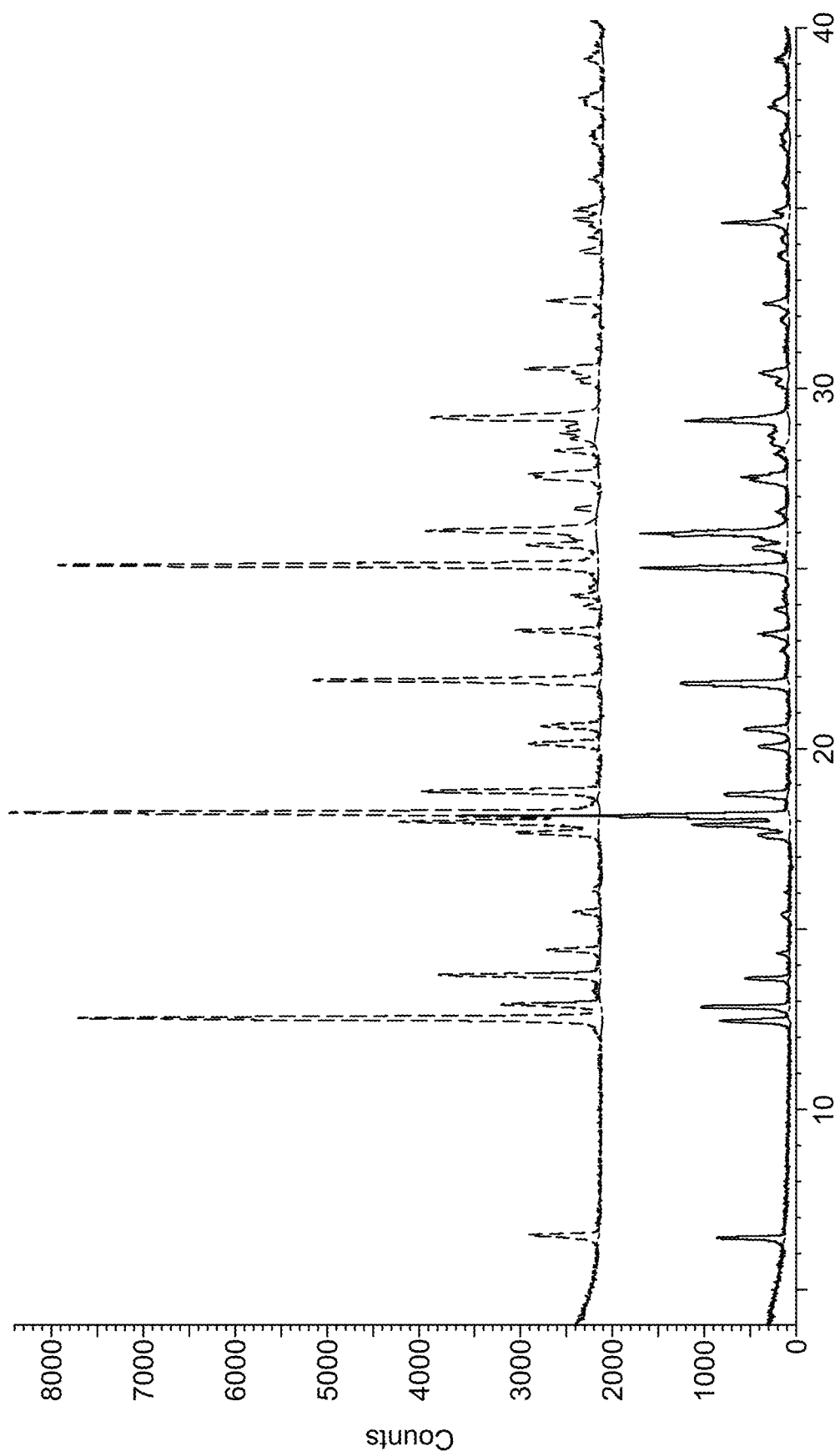

FIG. 321 shows an overlay of XRPD profiles for a reference sample of crystalline compound 1 HCl Form A (top) and crystalline compound 1 HCl Form A obtained by way of binary solvent evaporation crystallization from acetone and water.

Figure 322:
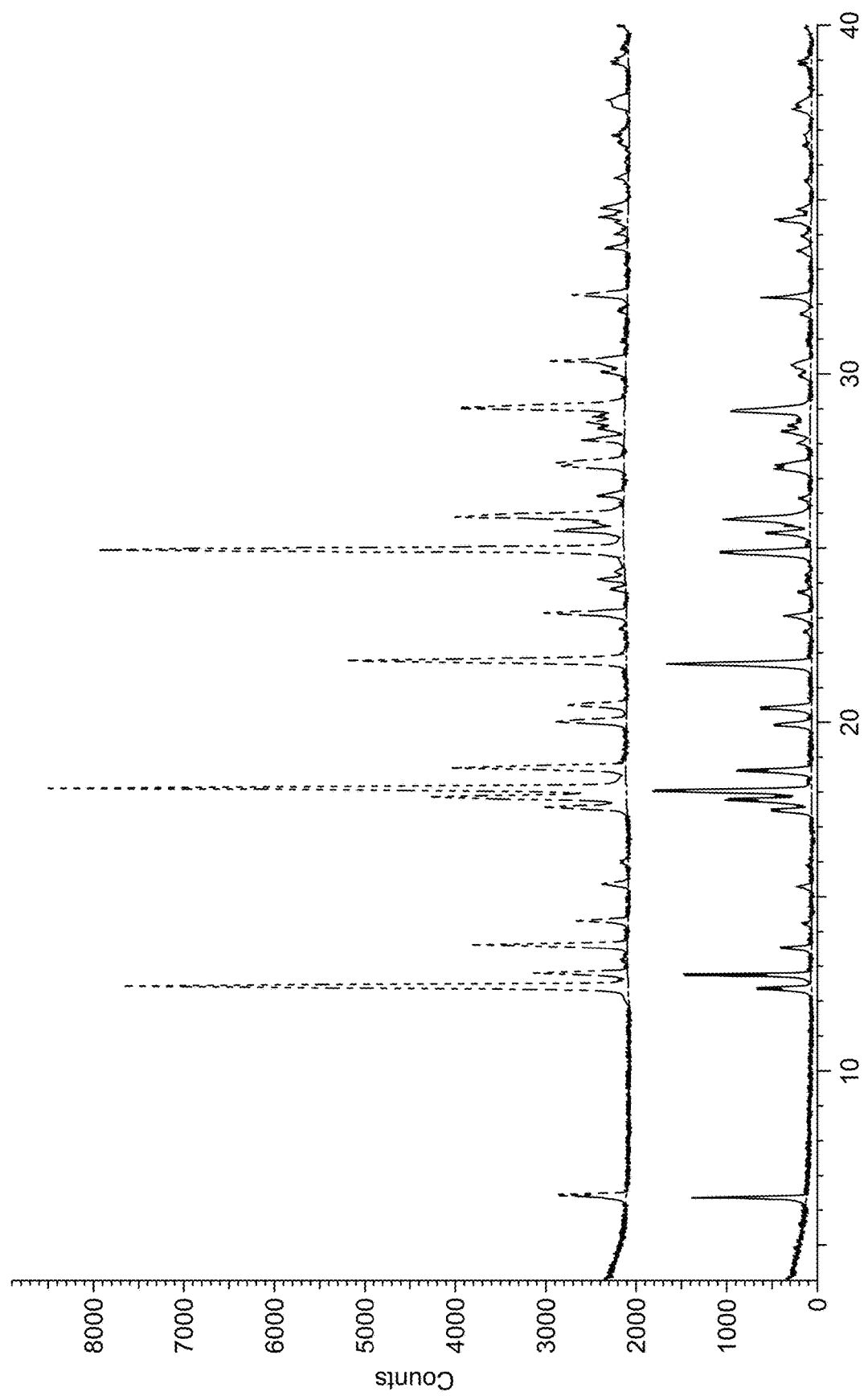

FIG. 322 shows an overlay of XRPD profiles for a reference sample of crystalline compound 1 HCl Form A (top) and crystalline compound 1 HCl Form A obtained by way of binary solvent evaporation crystallization from acetone and water.

Figure 323:
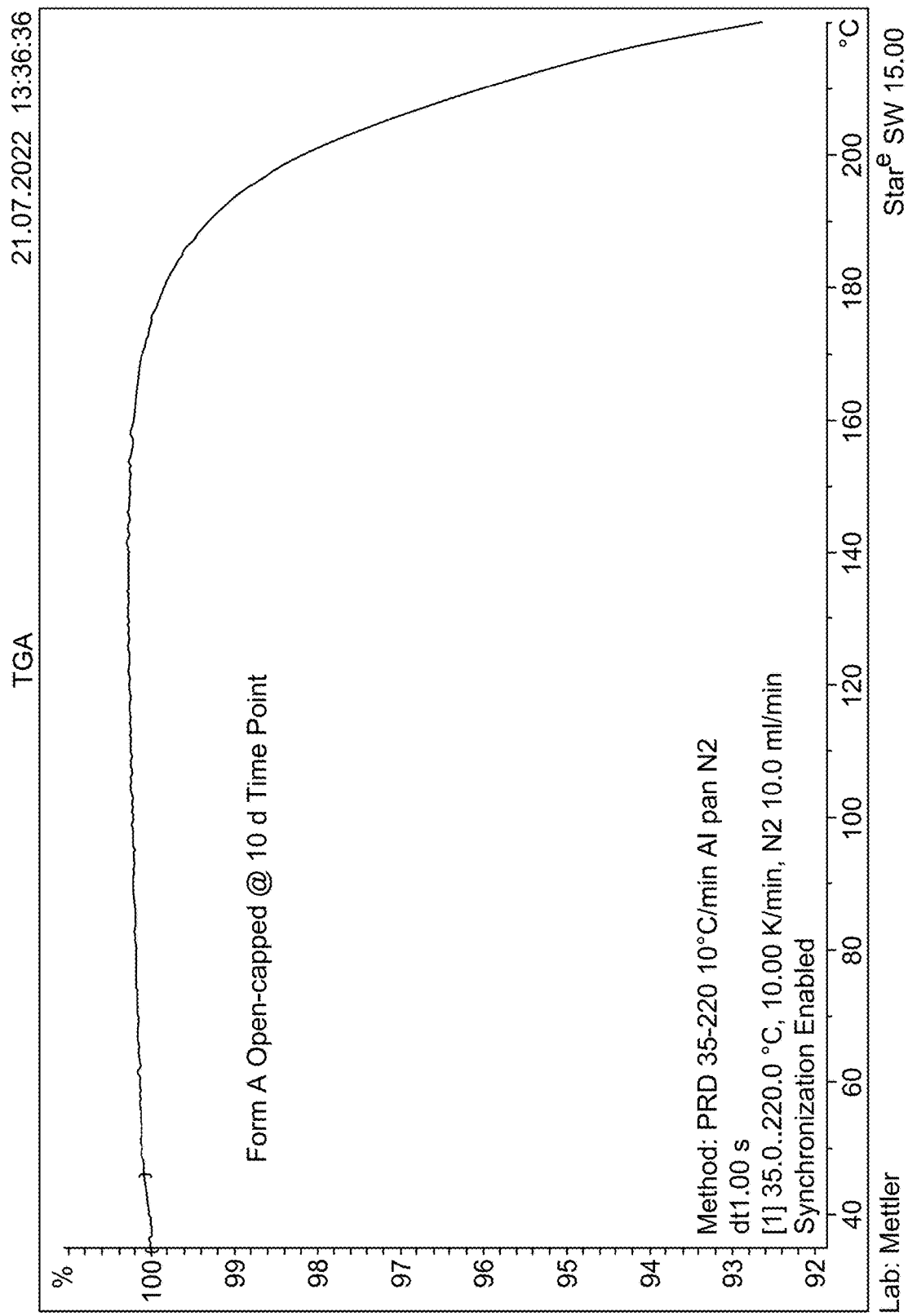

FIG. 323 shows a TGA profile of crystalline compound 1 HCl Form A after 10 days in an open-capped vial at 95% RH/20° C.

Figure 324:
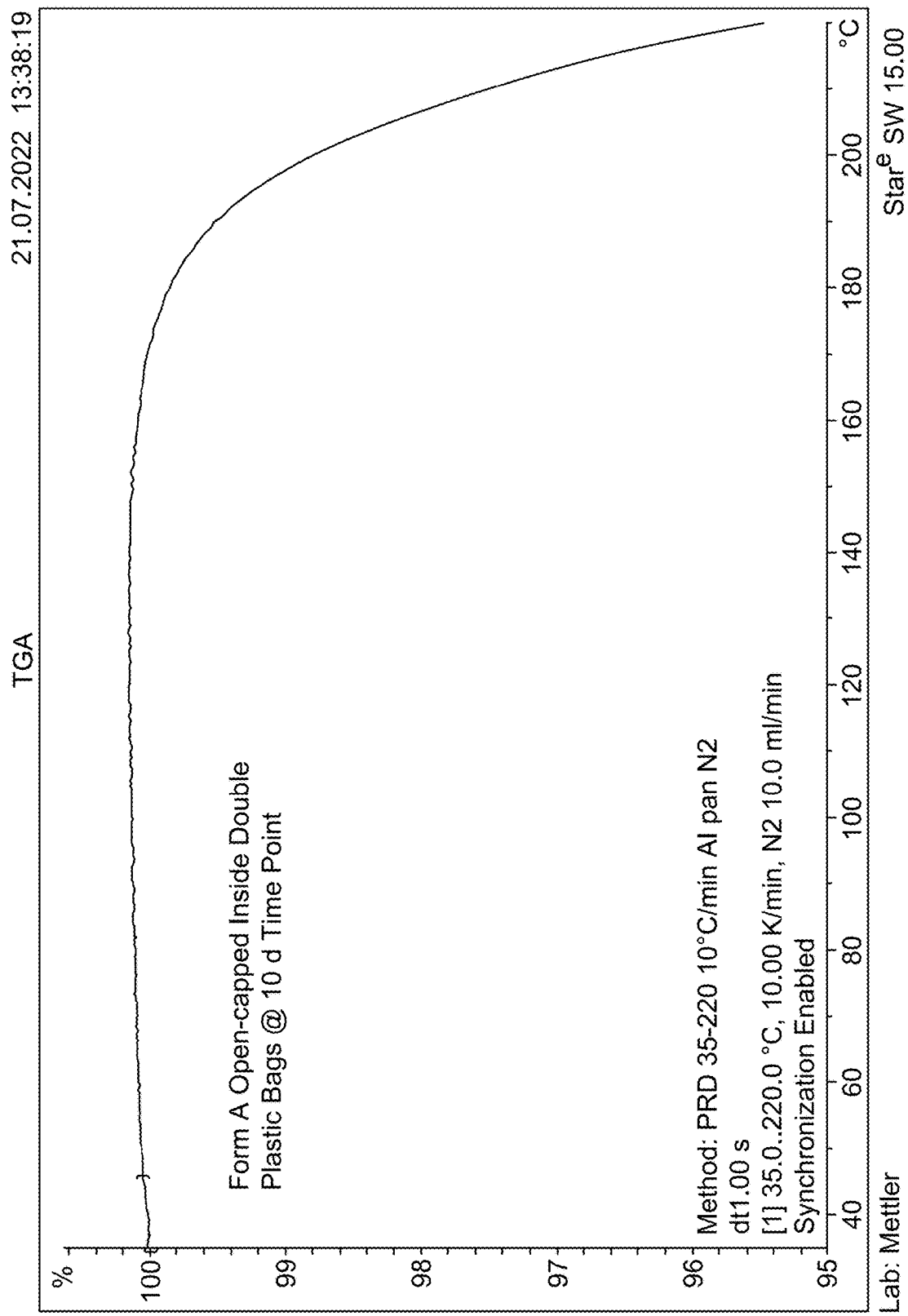

FIG. 324 shows a TGA profile of crystalline compound 1 HCl Form A after 10 days in an open-capped vial inside double plastic bags at 95% RH/20° C.

Figure 325:
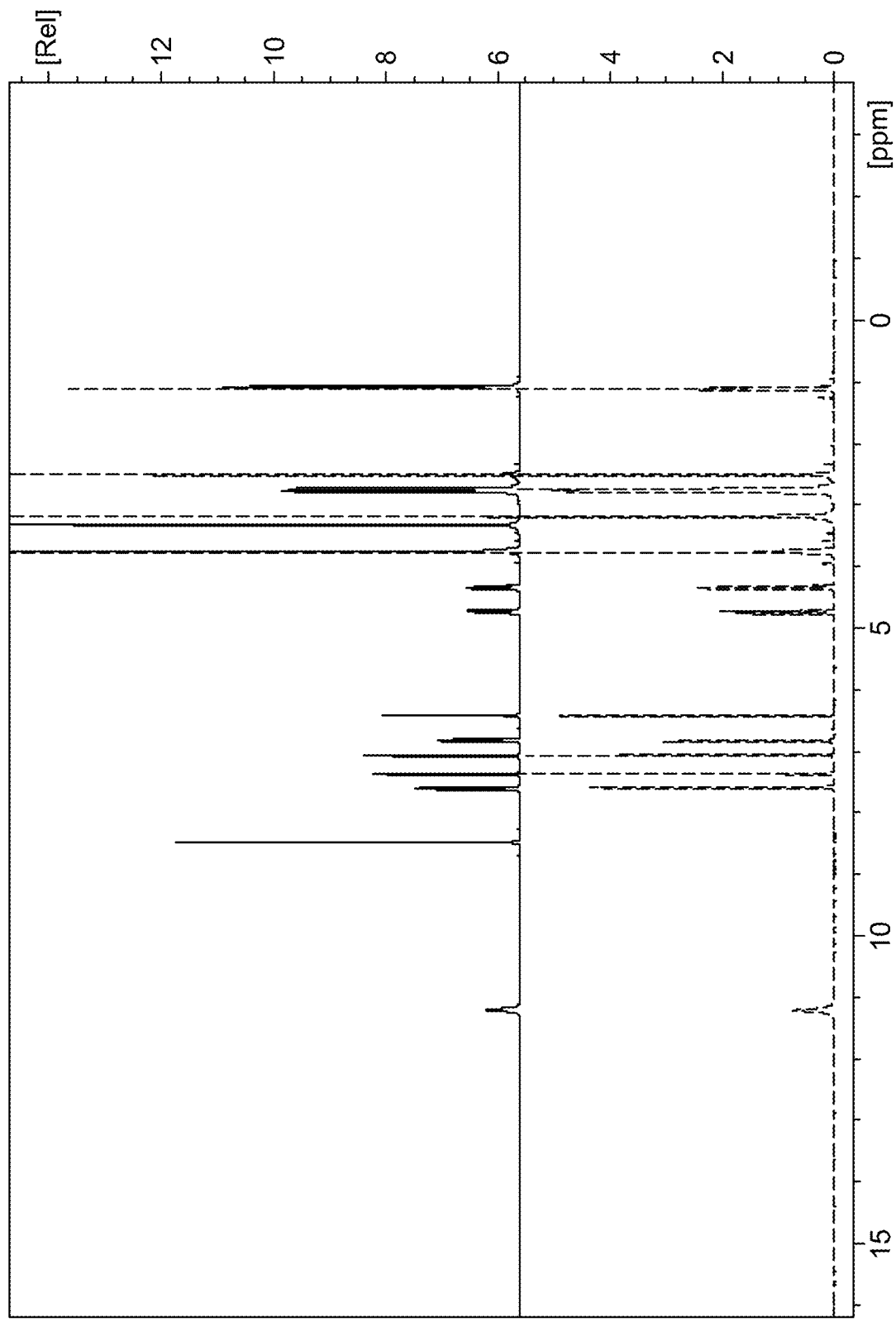

FIG. 325 shows an overlay of NMR spectra of a reference sample of crystalline compound 1 HCl Form A (top) and crystalline compound 1 HCl Form A after 10 days in an open-capped vial at 95% RH/20° C. (bottom).

Figure 326:
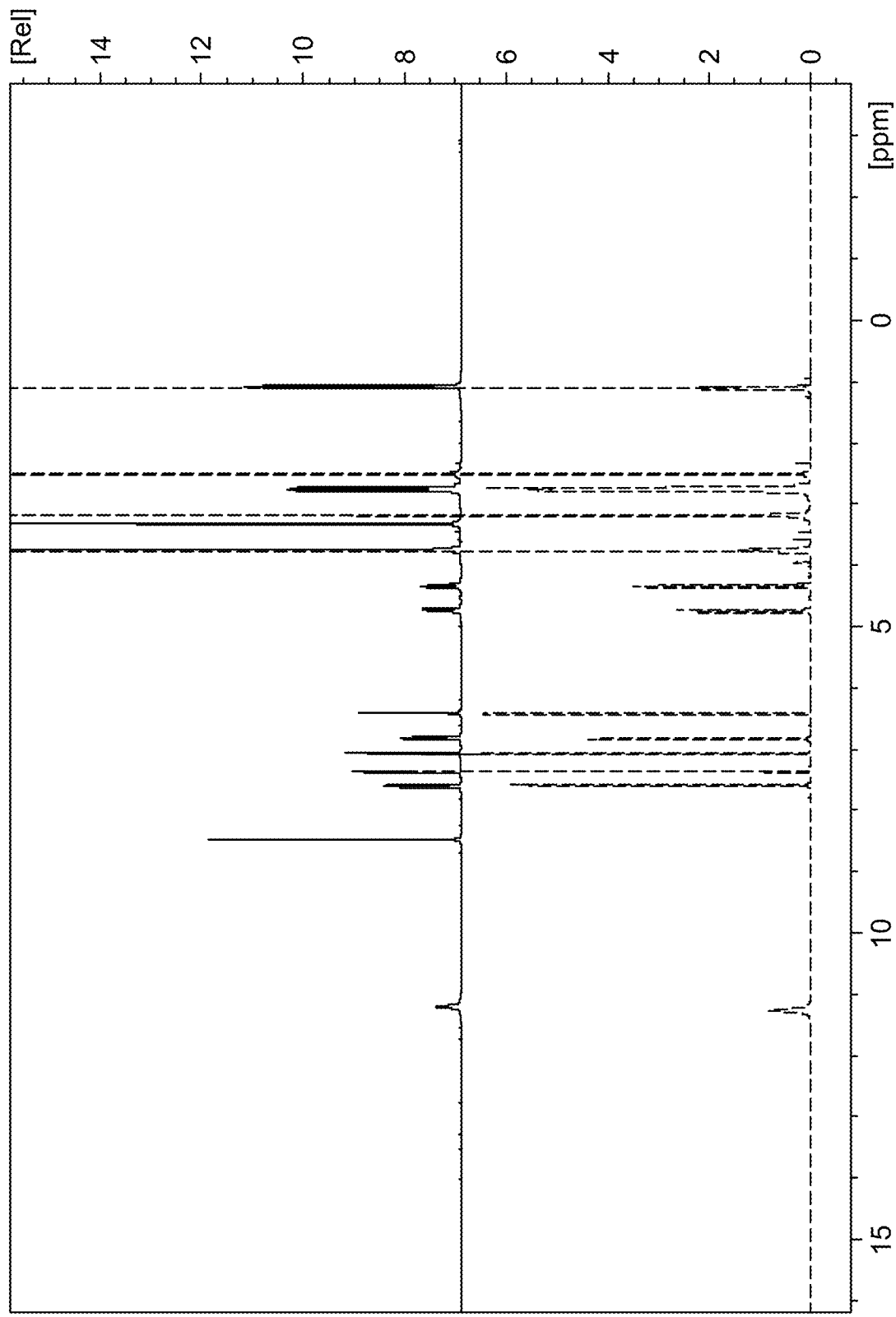

FIG. 326 shows an overlay of NMR spectra of a reference sample of crystalline compound 1 HCl Form A (top) and crystalline compound 1 HCl Form A after 10 days in an open-capped vial inside double plastic bags at 95% RH/20° C. (bottom).

Figure 327:
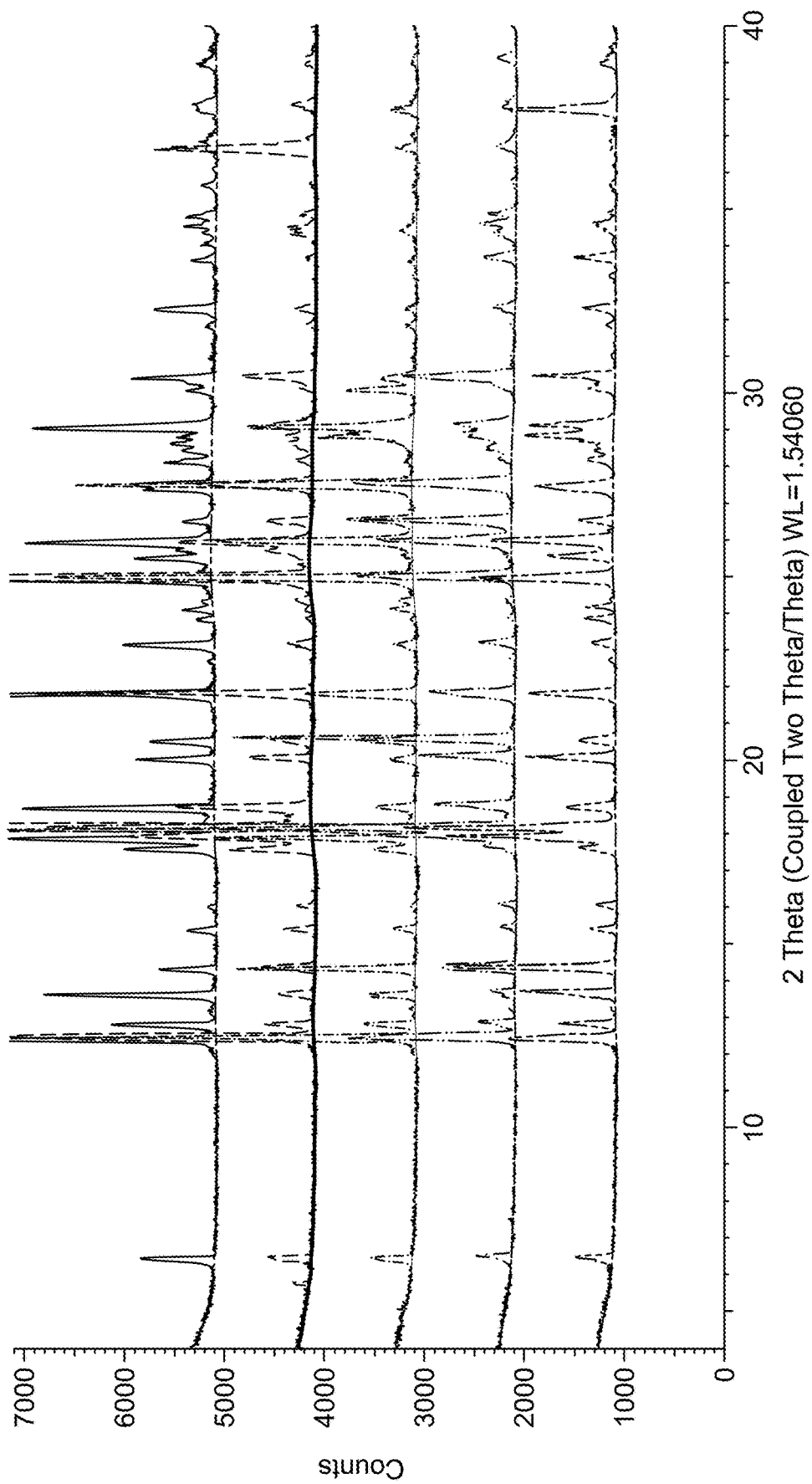

FIG. 327 shows an overlay of XRPD profiles of (i) a reference sample of crystalline compound 1 HCl Form A (top), (ii) crystalline compound 1 HCl Form A after 5 days in an open-capped vial at 95% RH/20° C. (second from top), (iii) crystalline compound 1 HCl Form A after 5 days in an open-capped vial inside double plastic bags at 95% RH/20° C. (third from top), (iv) crystalline compound 1 HCl Form A after 10 days in an open-capped vial at 95% RH/20° C., and (v) crystalline compound 1 HCl Form A after 10 days in an open-capped vial inside double plastic bags at 95% RH/20° C.

Figure 328:
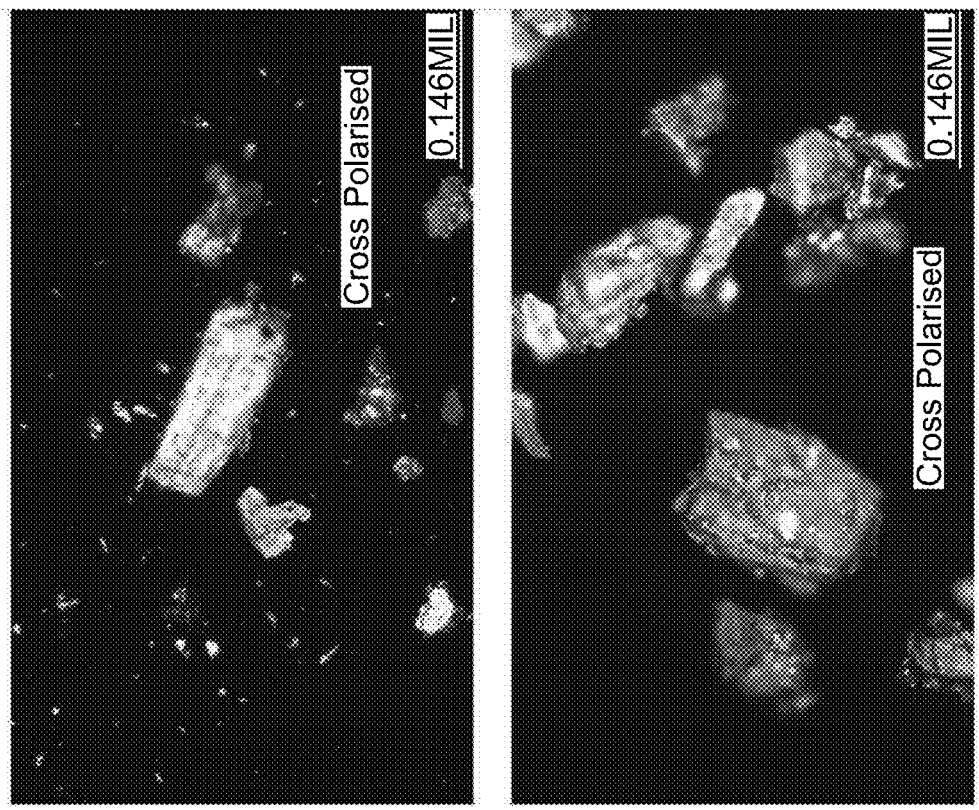
Figure 328:
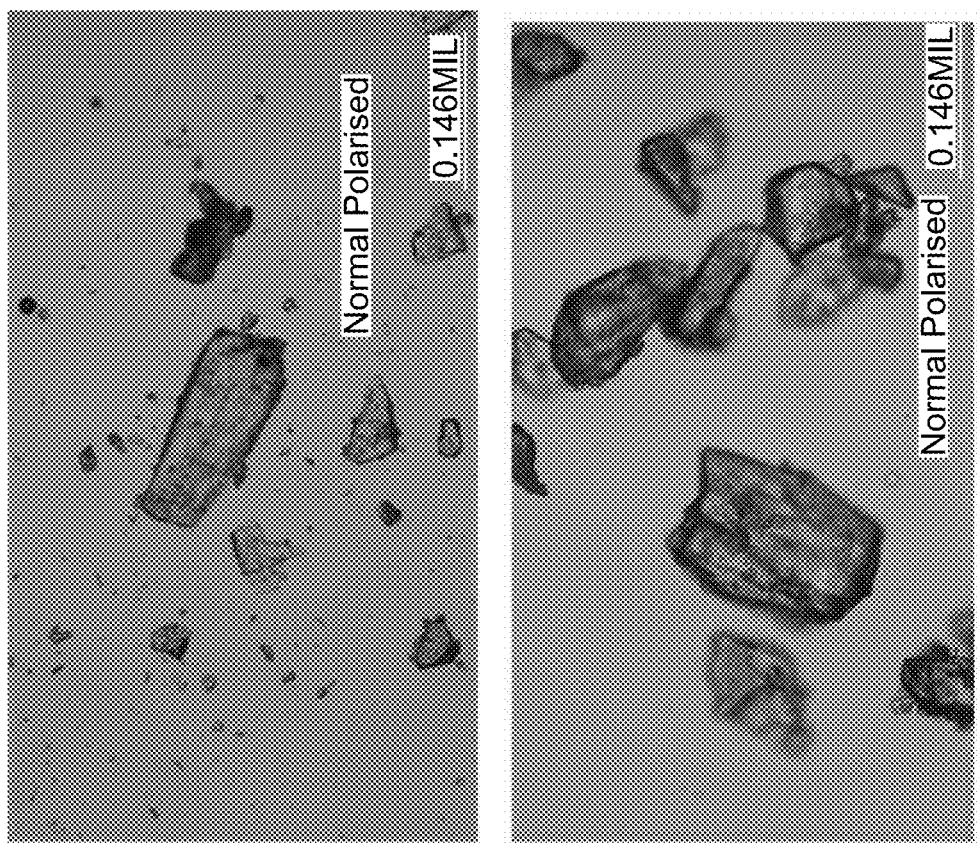

FIG. 328 shows normal and cross-polarized images of crystalline compound 1 HCl Form A after 10 days in an open-capped vial at 95% RH/20° C. (top row) and crystalline compound 1 HCl Form A after 10 days in an open-capped vial inside double bags at 95% RH/20° C. (bottom row)

Figure 329:
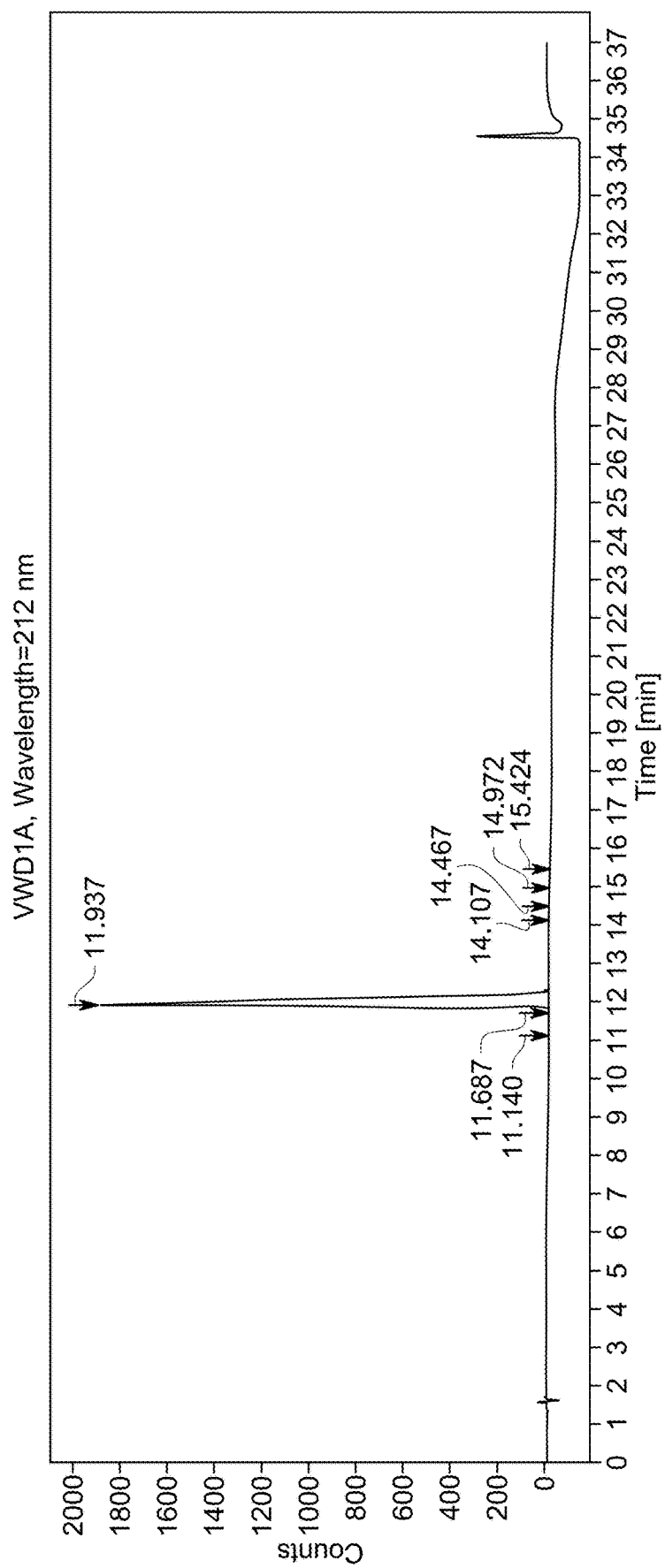

FIG. 329 shows an HPLC trace of crystalline compound 1 HCl Form A after 10 days in an open-capped vial at 95% RH/20° C.

Figure 330:
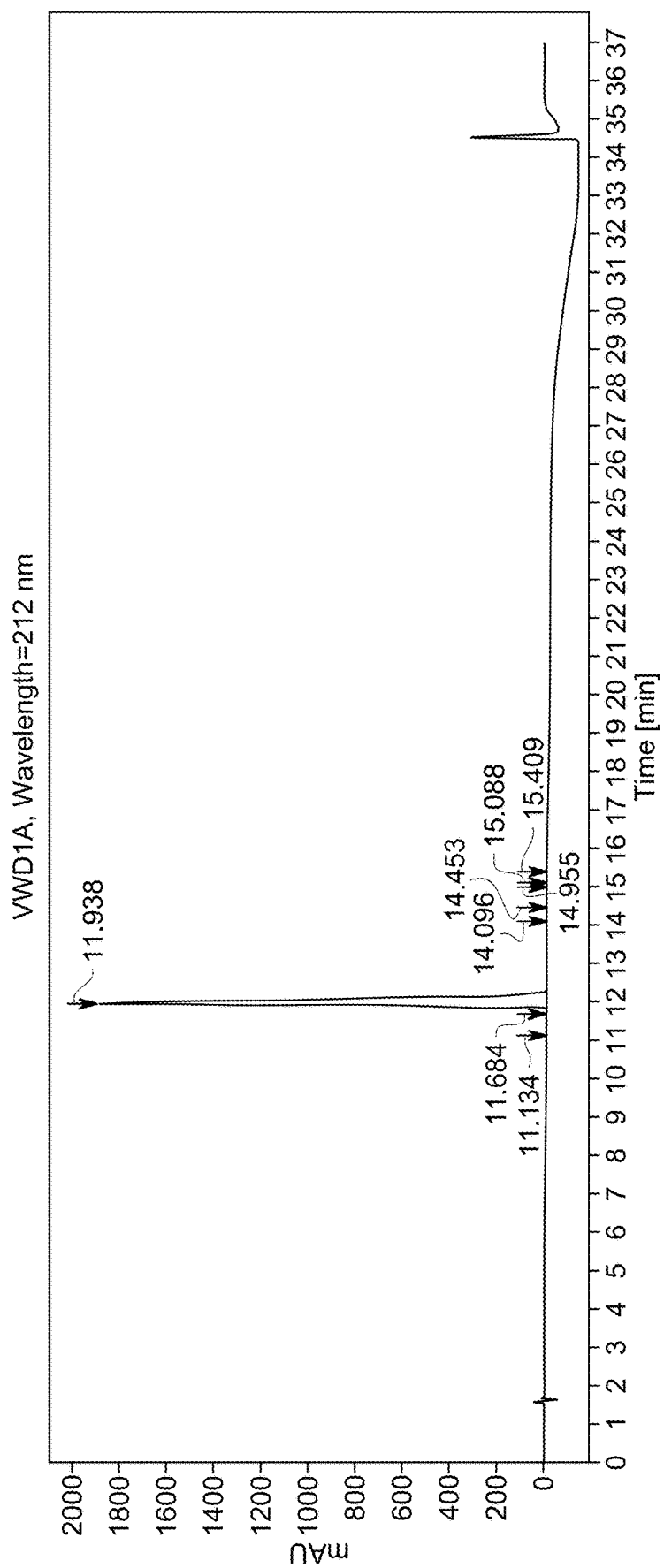

FIG. 330 shows an HPLC trace of crystalline compound 1 HCl Form A after 10 days in an open-capped vial inside double bags at 95% RH/20° C.

Figure 331:
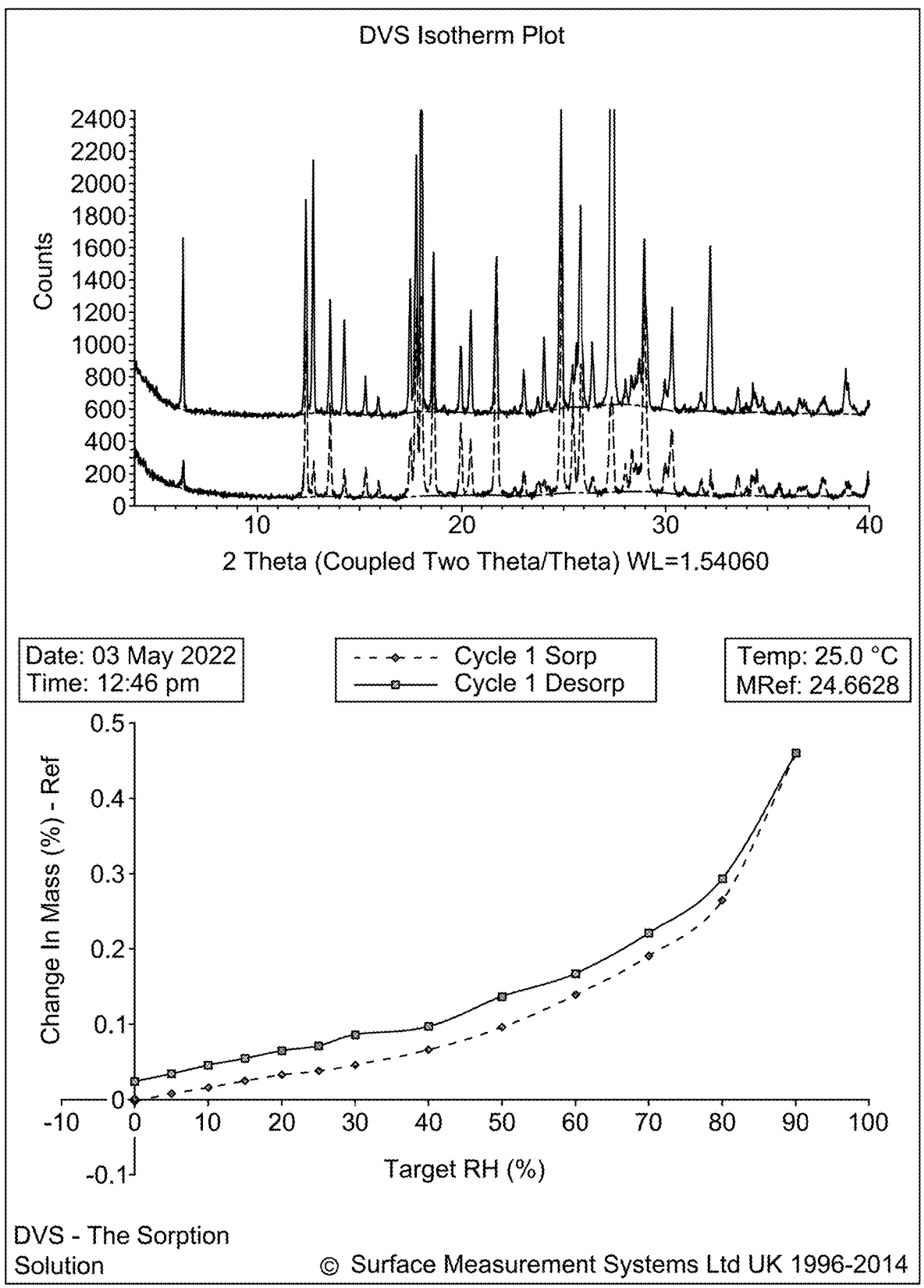

FIG. 331 shows a DVS isotherm for crystalline compound 1 HCL Form A.

Figure 332:
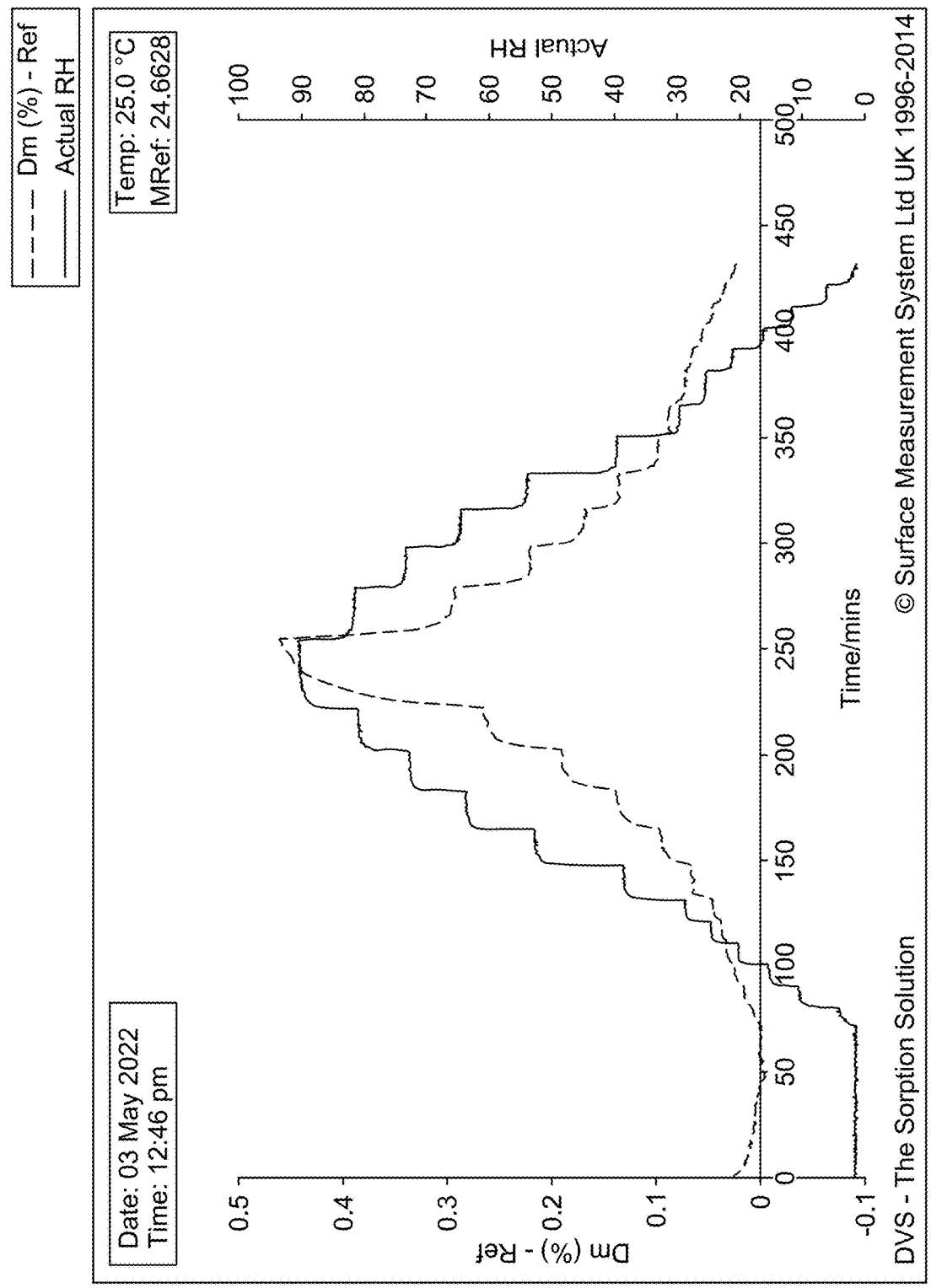

FIG. 332 shows DVS analysis for crystalline compound 1 HCL Form A.

Figure 333:
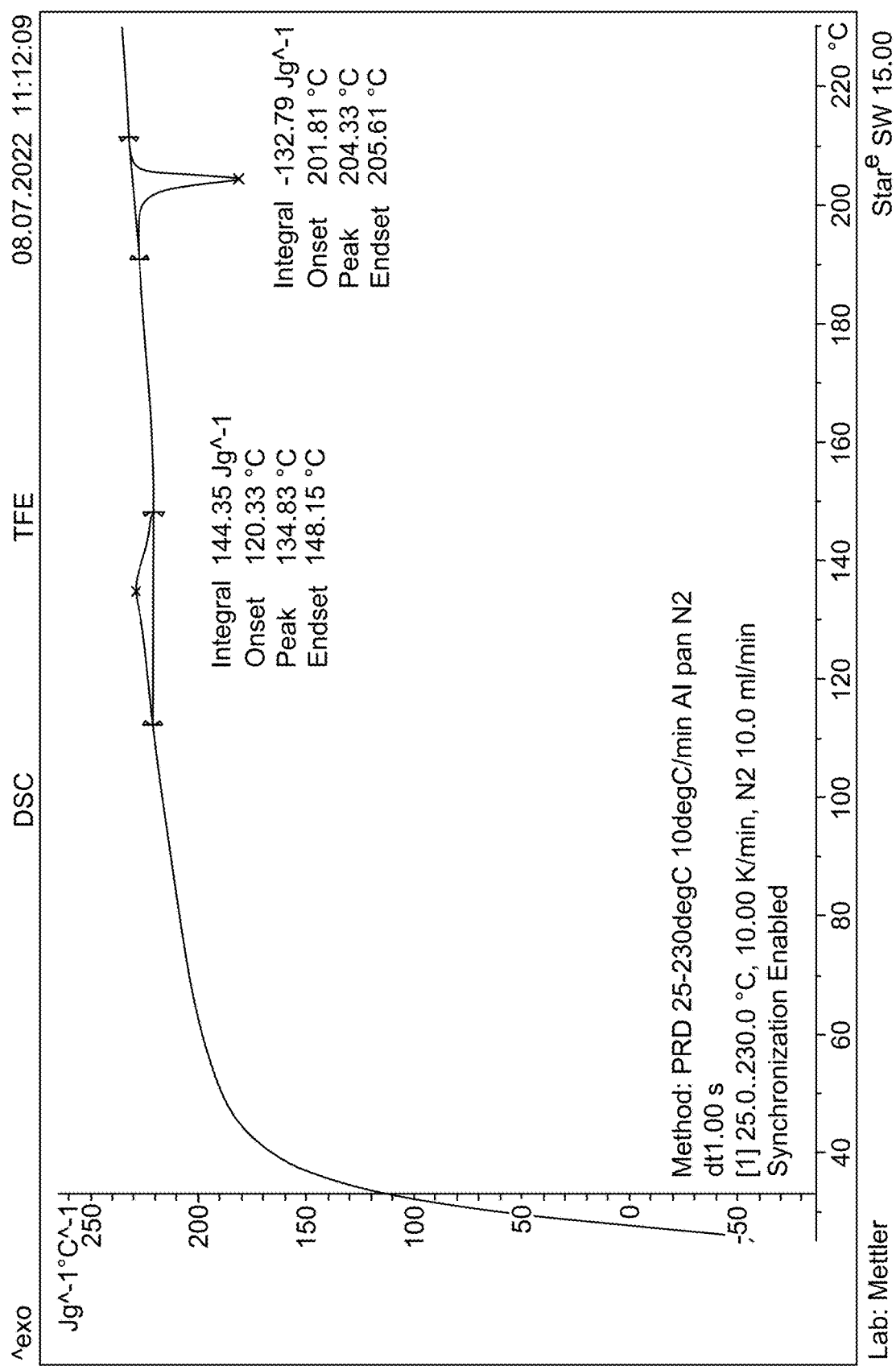

FIG. 333 shows a DSC profile of material obtained by way of liquid assisted grinding with trifluoroethanol as liquid assist.

Figure 334:
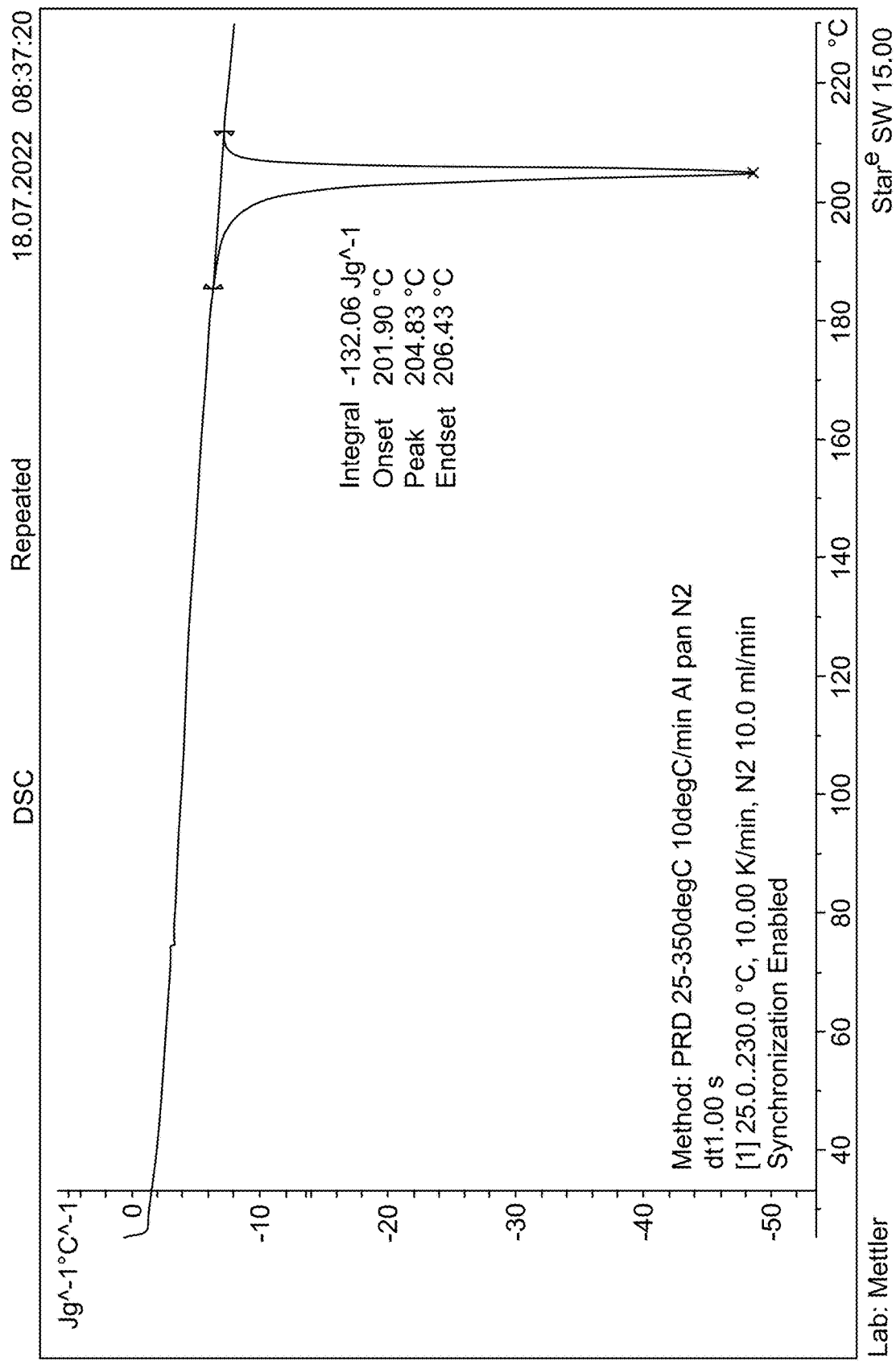

FIG. 334 shows a DSC profile of material obtained by way of liquid assisted grinding with trifluoroethanol as liquid assist. The fusion temperature remained consistent with crystalline compound 1 HCl Form A.

Figure 335:
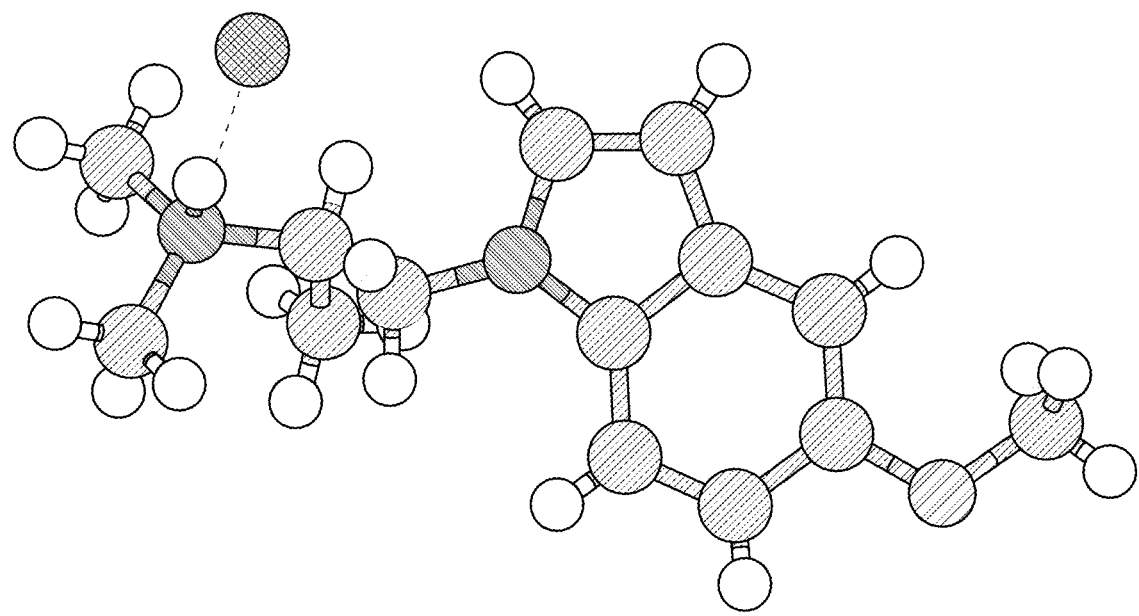

FIG. 335 shows the structure of crystalline compound 1 HCl Form A solved by single crystal structure determination.

Figure 336:
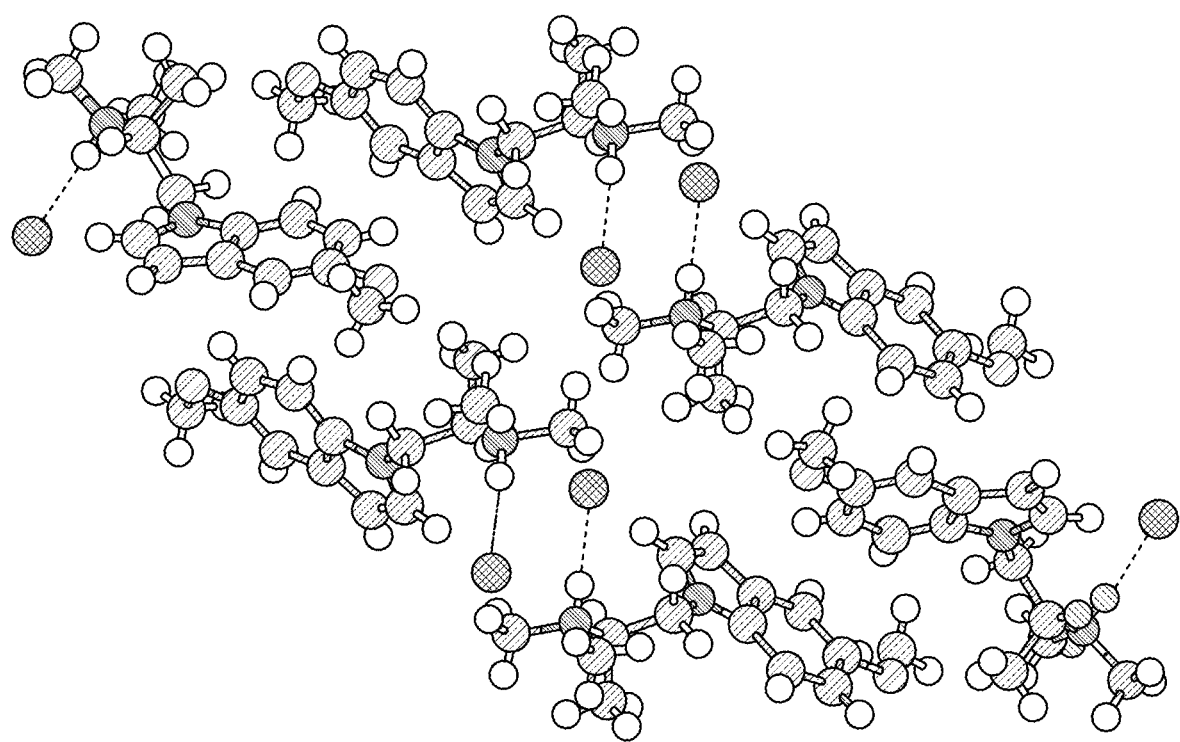

FIG. 336 shows the packed structure of crystalline compound 1 HCl Form A determined by single crystal structure determination.

Figure 337:
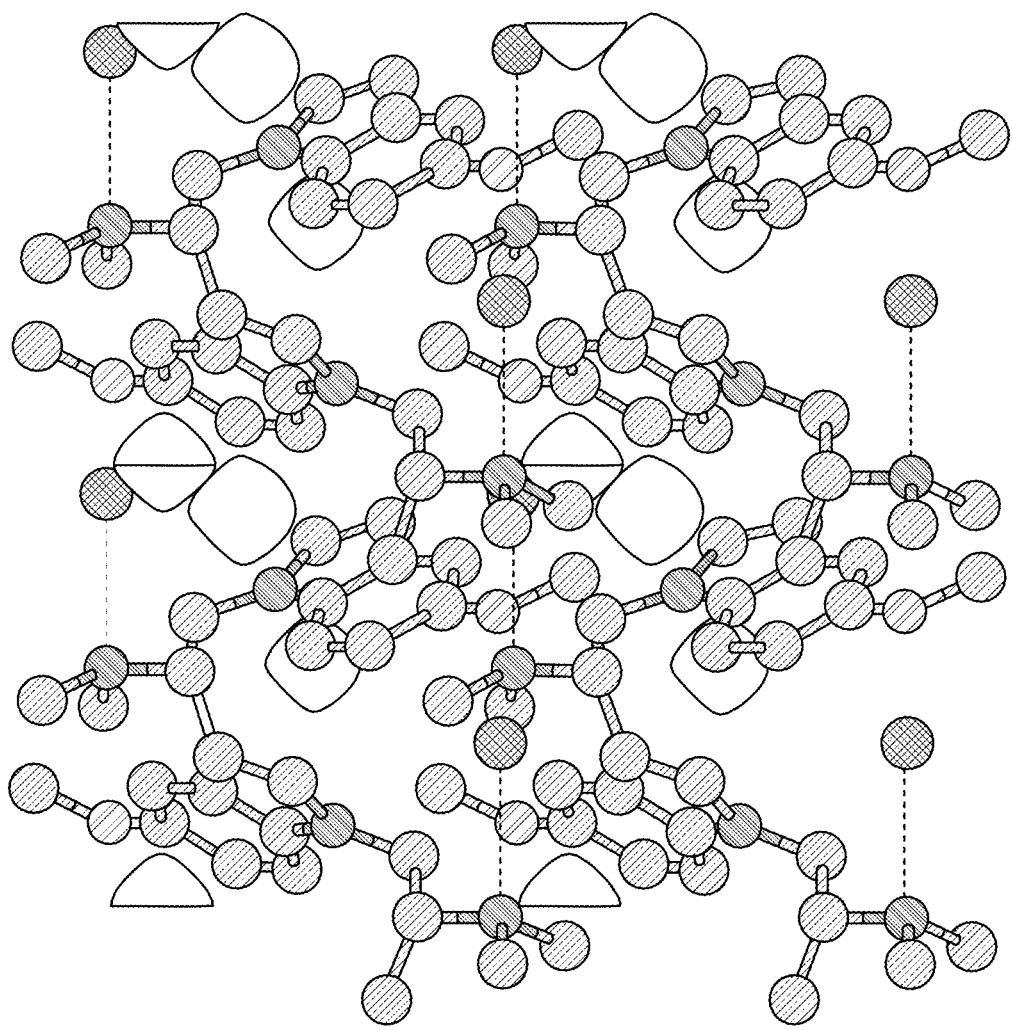

FIG. 337 shows void analysis of the structure of crystalline compound 1 HCl determined by single crystal structure determination.

Figure 338:
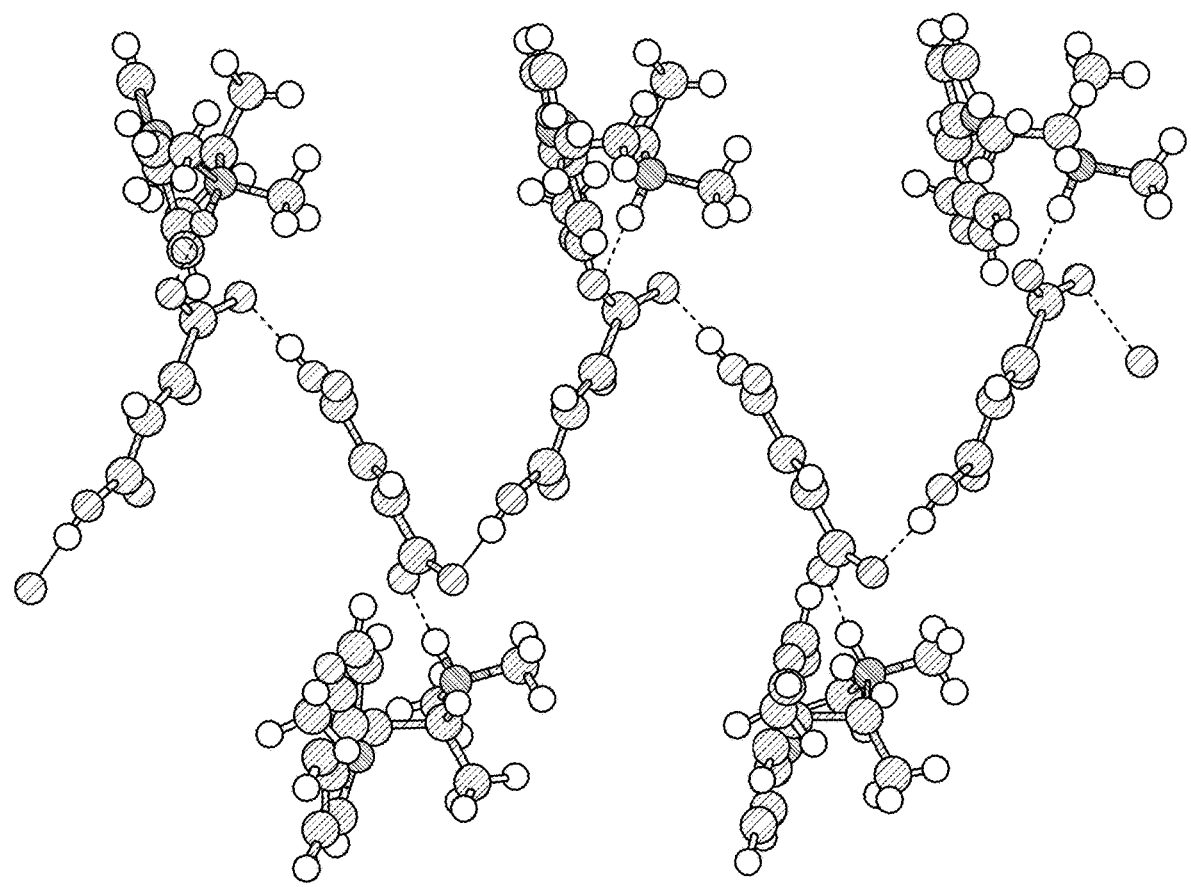

FIG. 338 shows the hydrogen bonding network of crystalline compound 1 fumarate Form A determined by single crystal structure determination.

Figure 339:
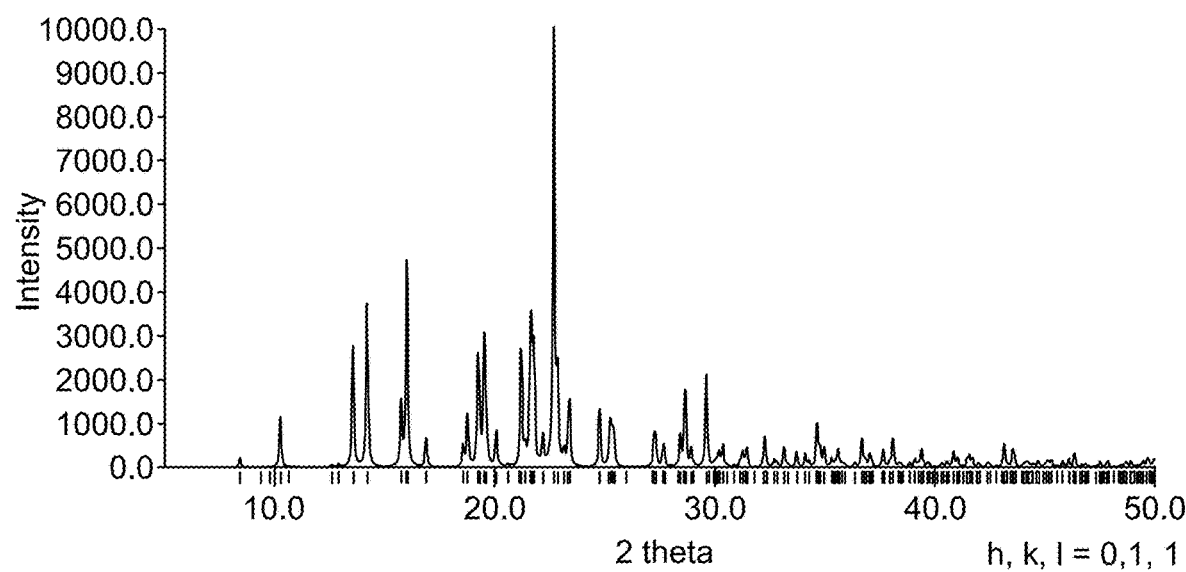
Figure 339:
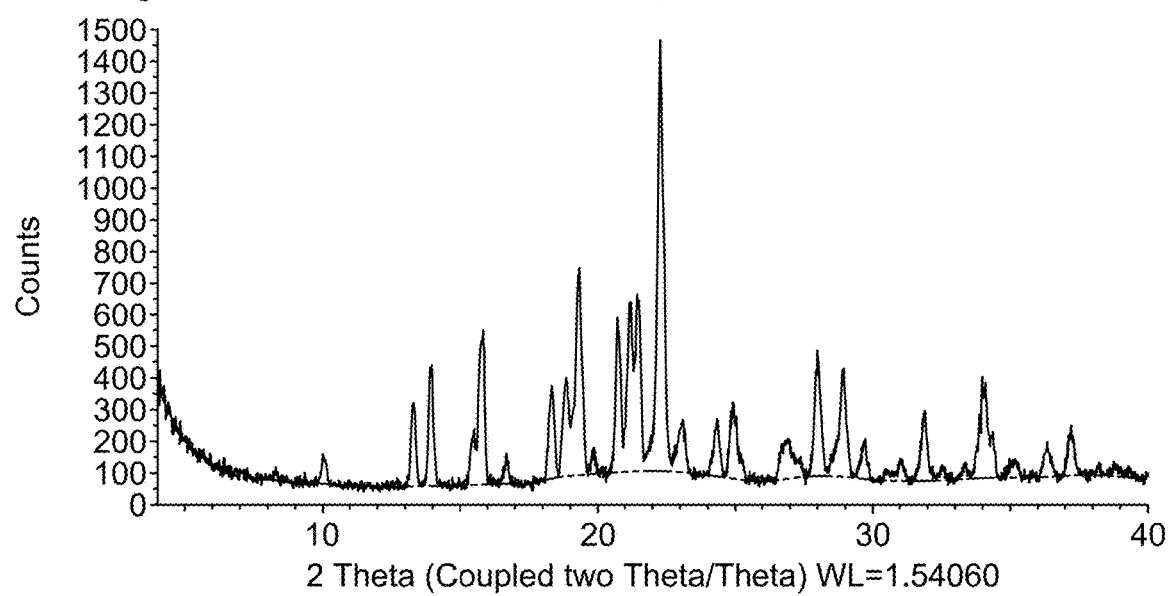

FIG. 339 shows overlaid XRPD profiles of a calculated pattern for crystalline compound 1 fumarate Form A (top) and a reference sample of crystalline compound 1 Form A (bottom).

Figure 340:
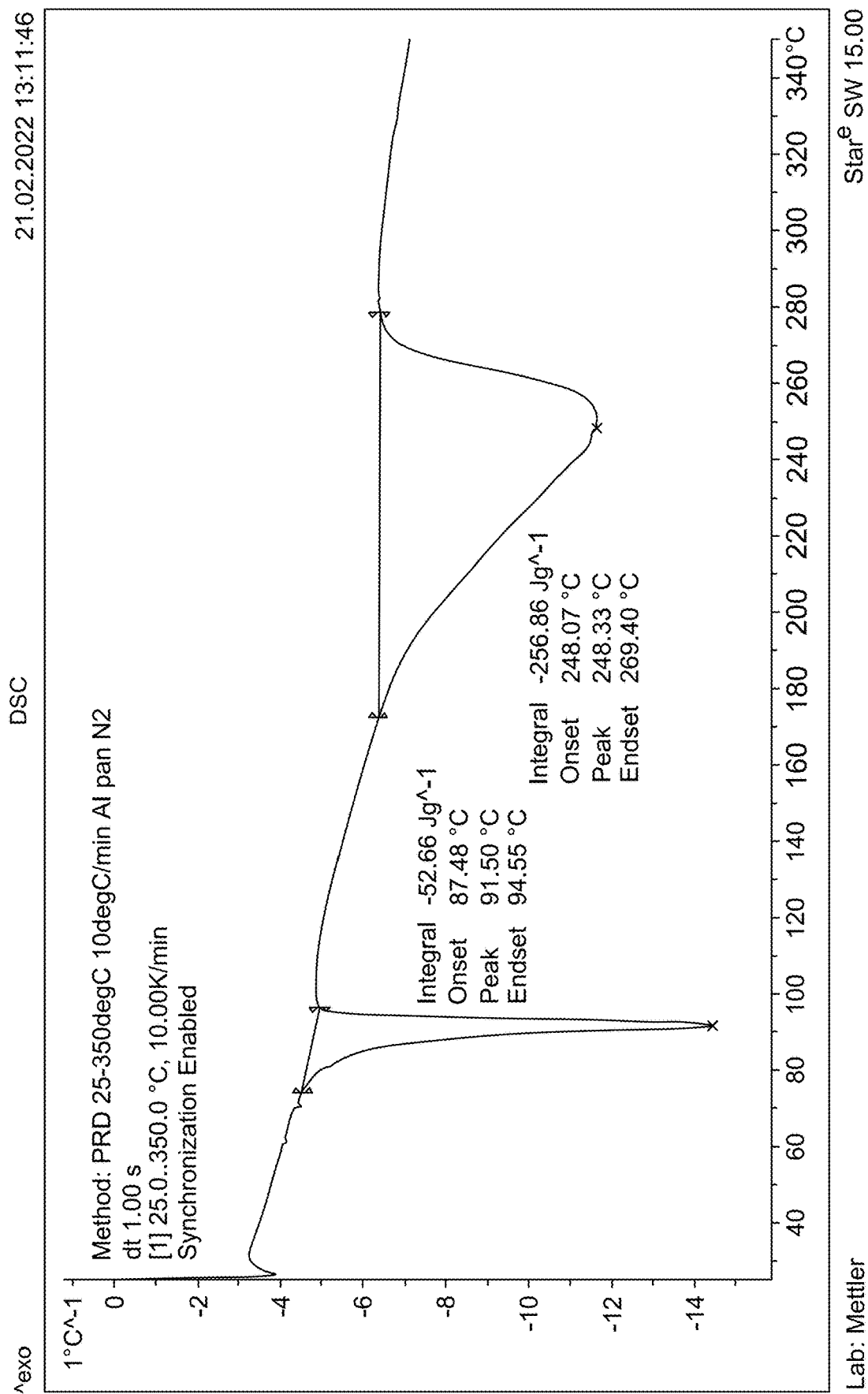

FIG. 340 shows a DSC profile of crystalline compound 1 fumarate Pattern #2.

Figure 341:
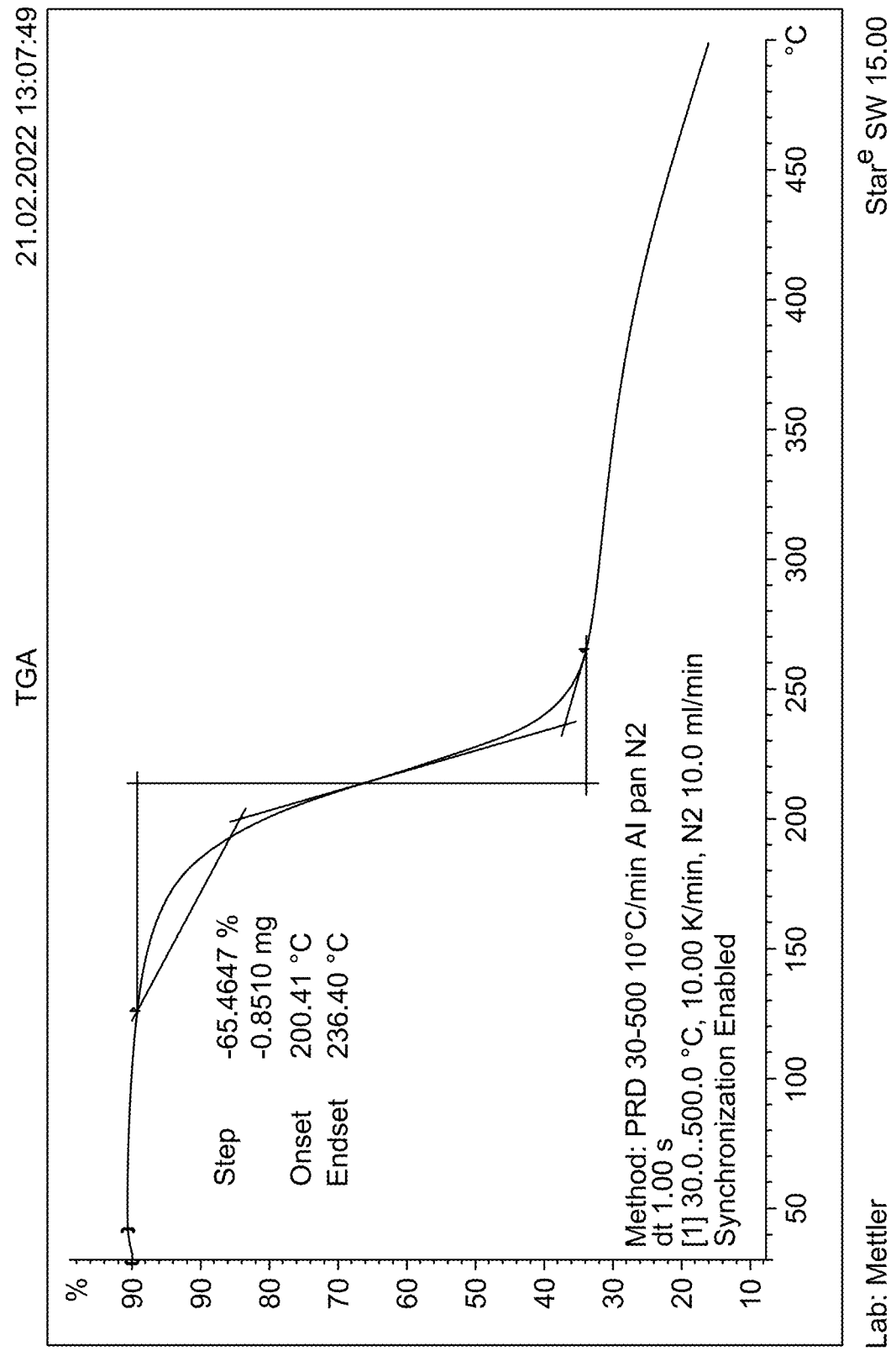

FIG. 341 shows a TGA profile of crystalline compound 1 fumarate Pattern #2.

Figure 342:
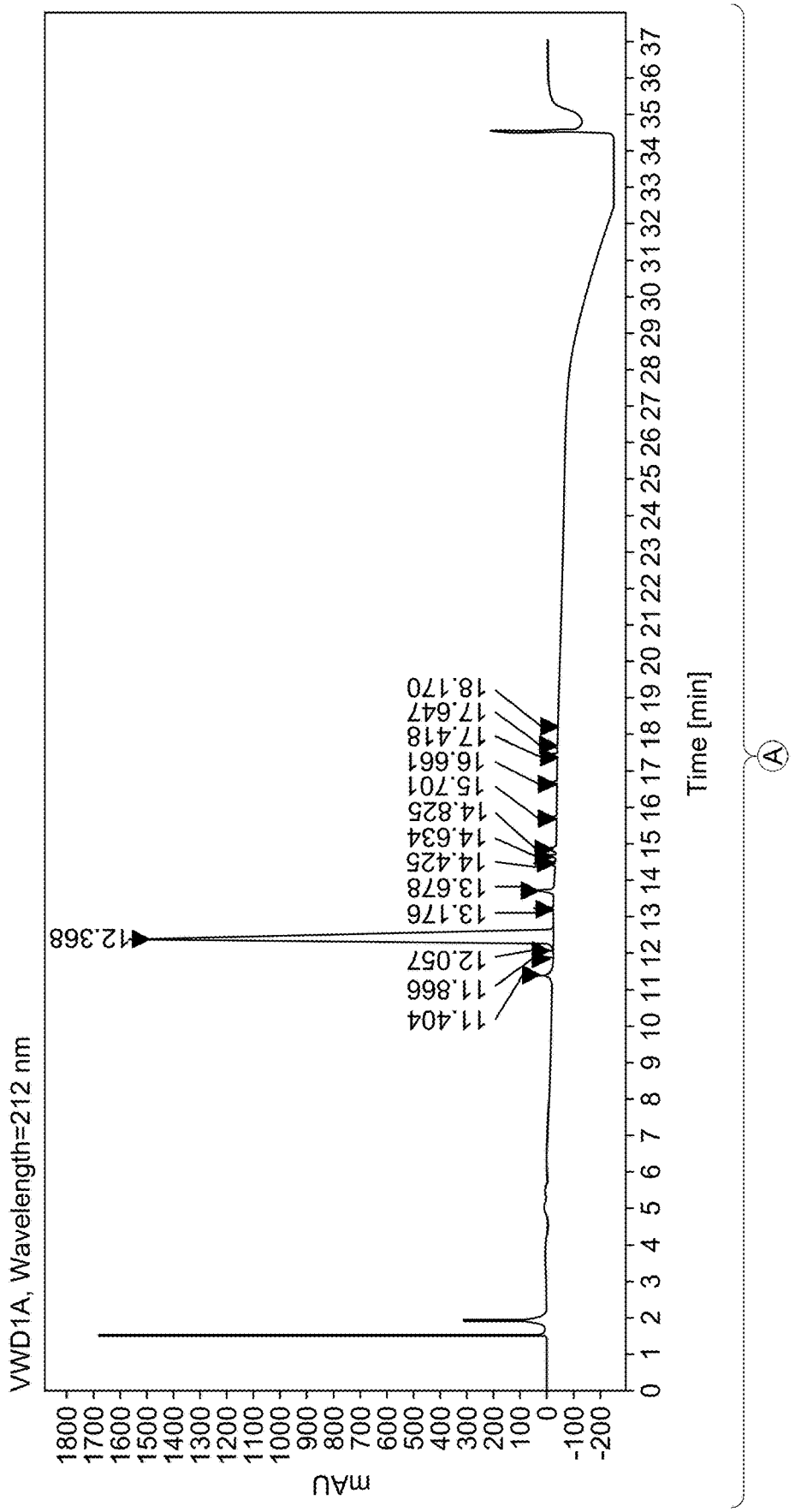

FIG. 342 shows a HPLC profile of amorphous compound 1 fumarate.

Figure 343:
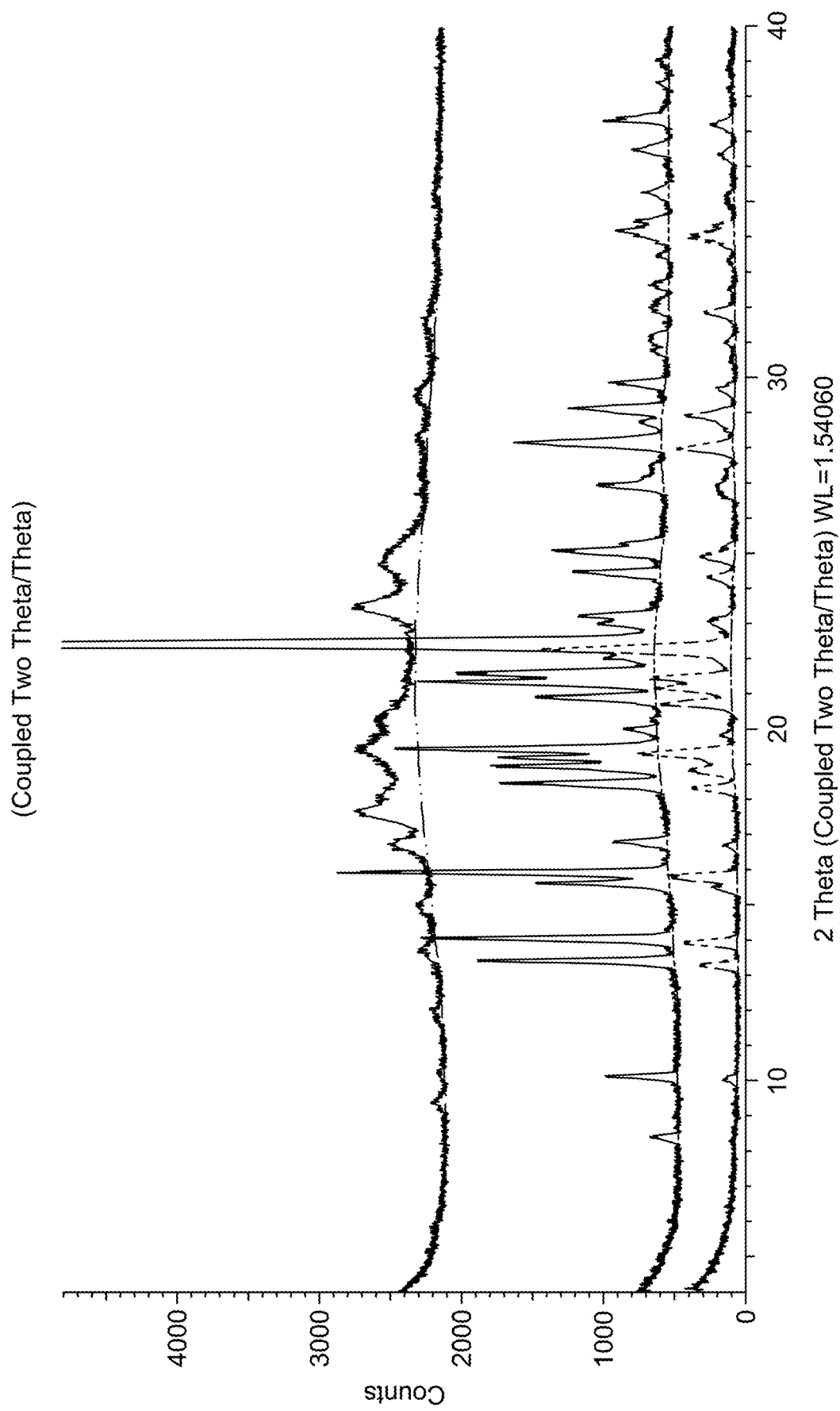

FIG. 343 shows an overlay of XRPD profiles of crystalline compound 1 monofumarate Form B (top), crystalline compound 1 Form A monofumarate generated by way of suspension in tBME (middle) and crystalline compound 1 Form A generated by way of suspension in iPAC.

Figure 344:
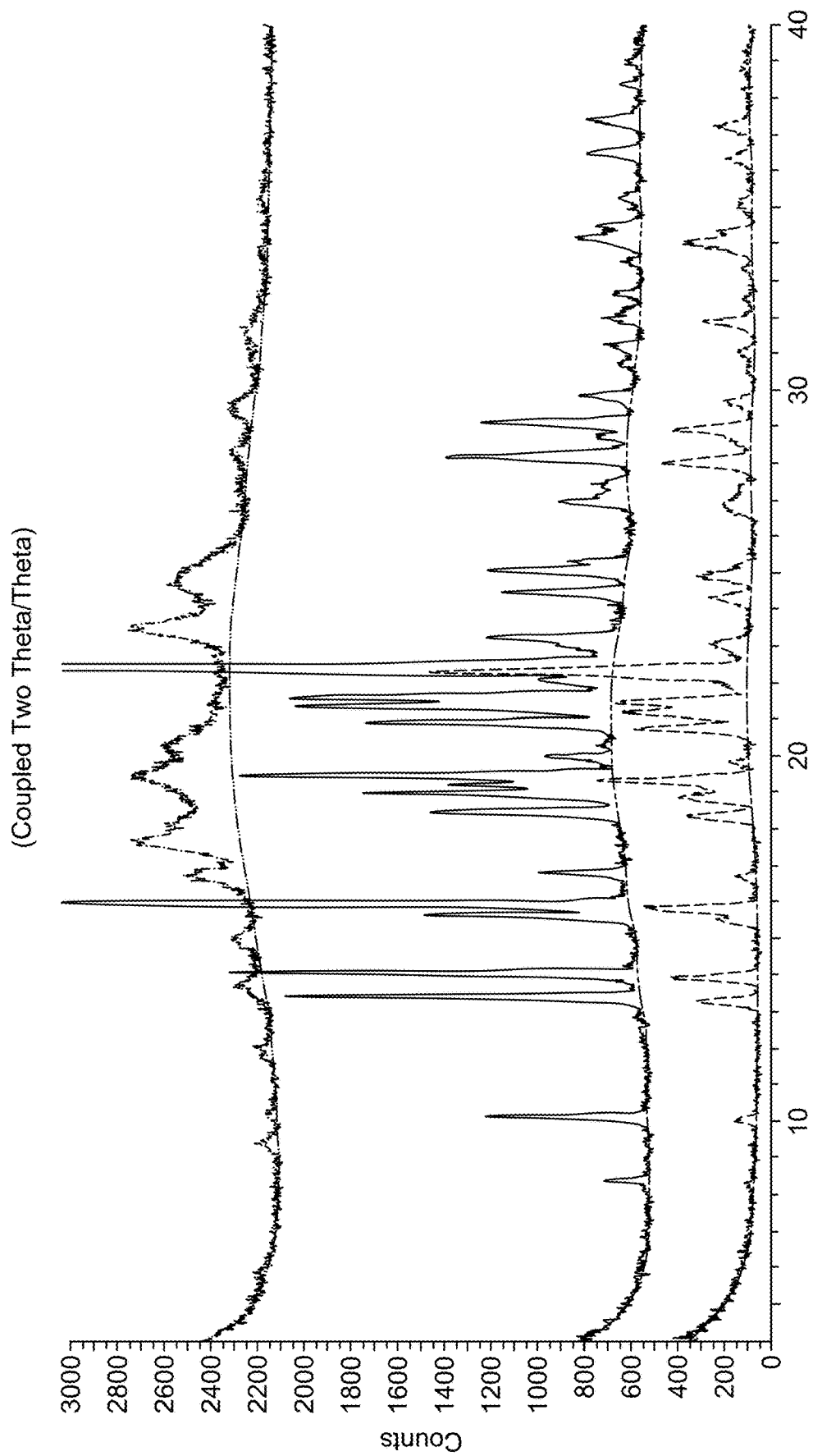

FIG. 344 shows an overlay of XRPD profiles of crystalline compound 1 monofumarate Form B (top), crystalline compound 1 Form A monofumarate generated by way of suspension in tBME (middle) and crystalline compound 1 Form A generated by way of suspension in iPAC.

Figure 345:
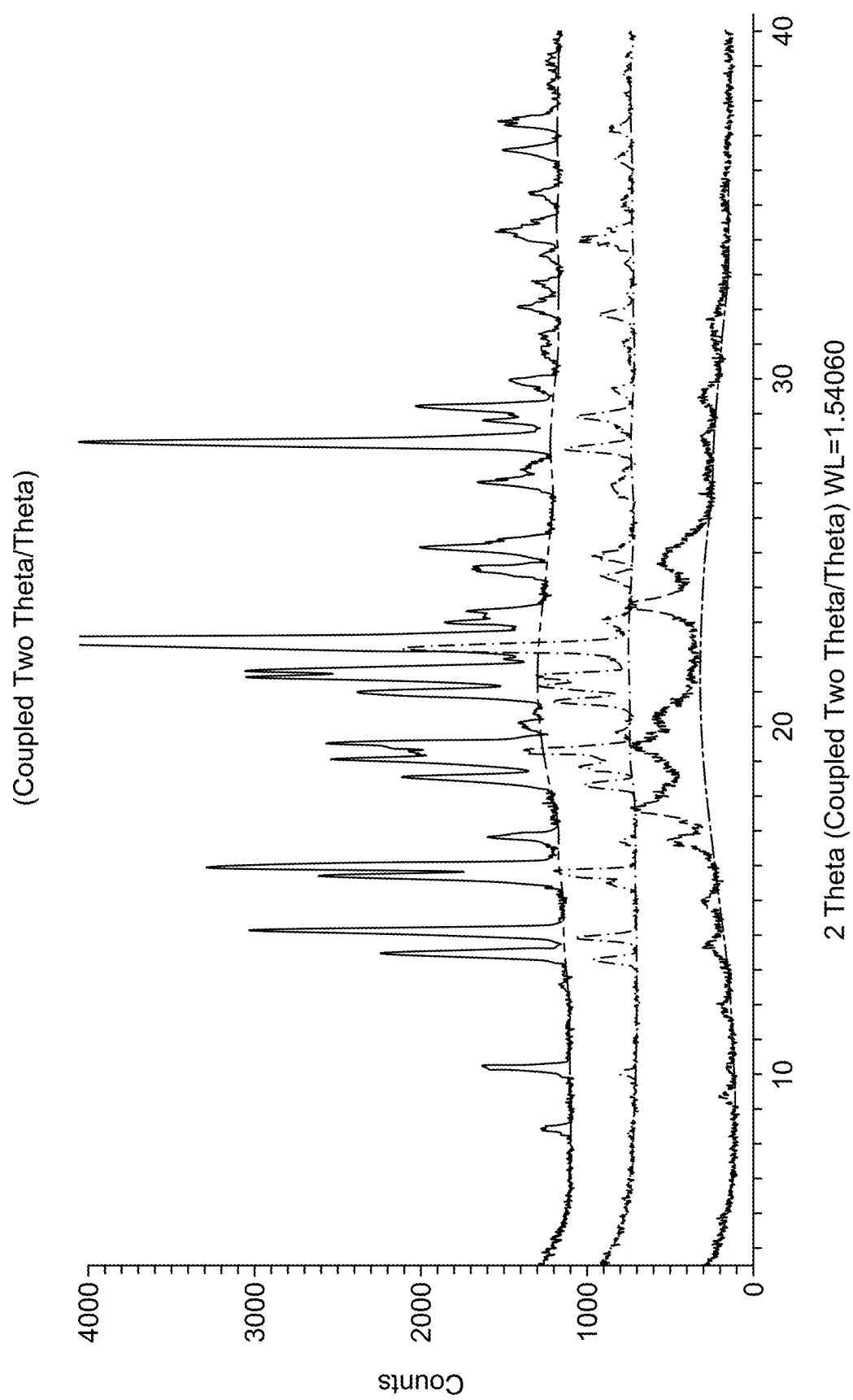

FIG. 345 shows an overlay of XRPD profiles of crystalline compound 1 monofumarate Form A generated by way of suspension in tBME (top); crystalline compound 1 monofumarate Form A generated by way of suspension in IPA (middle); and crystalline compound 1 monofumarate Form B.

Figure 346:
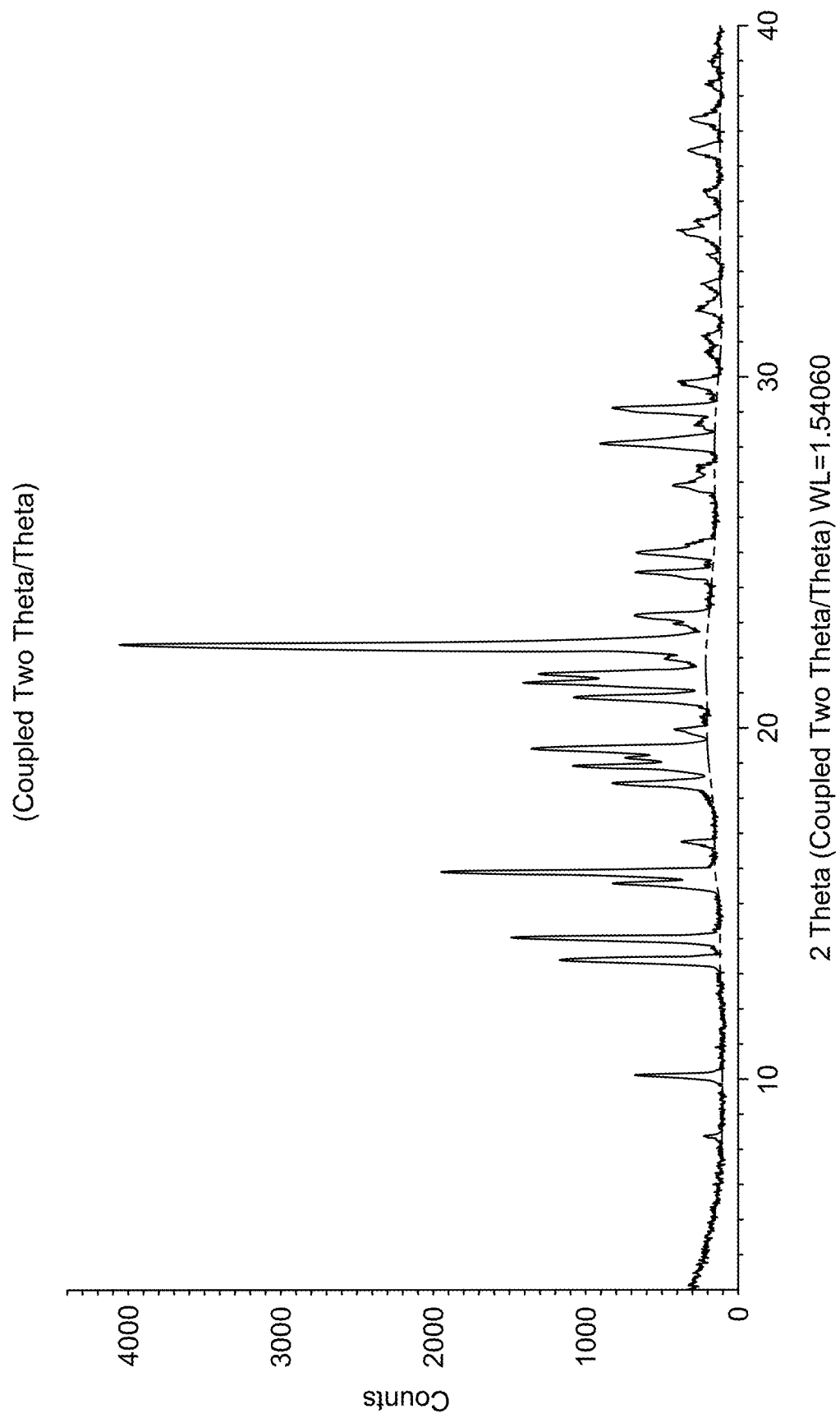

FIG. 346 shows a XRPD profile of crystalline compound 1 monofumarate Form A prepared by suspension in tBME at 20° C.

Figure 347:
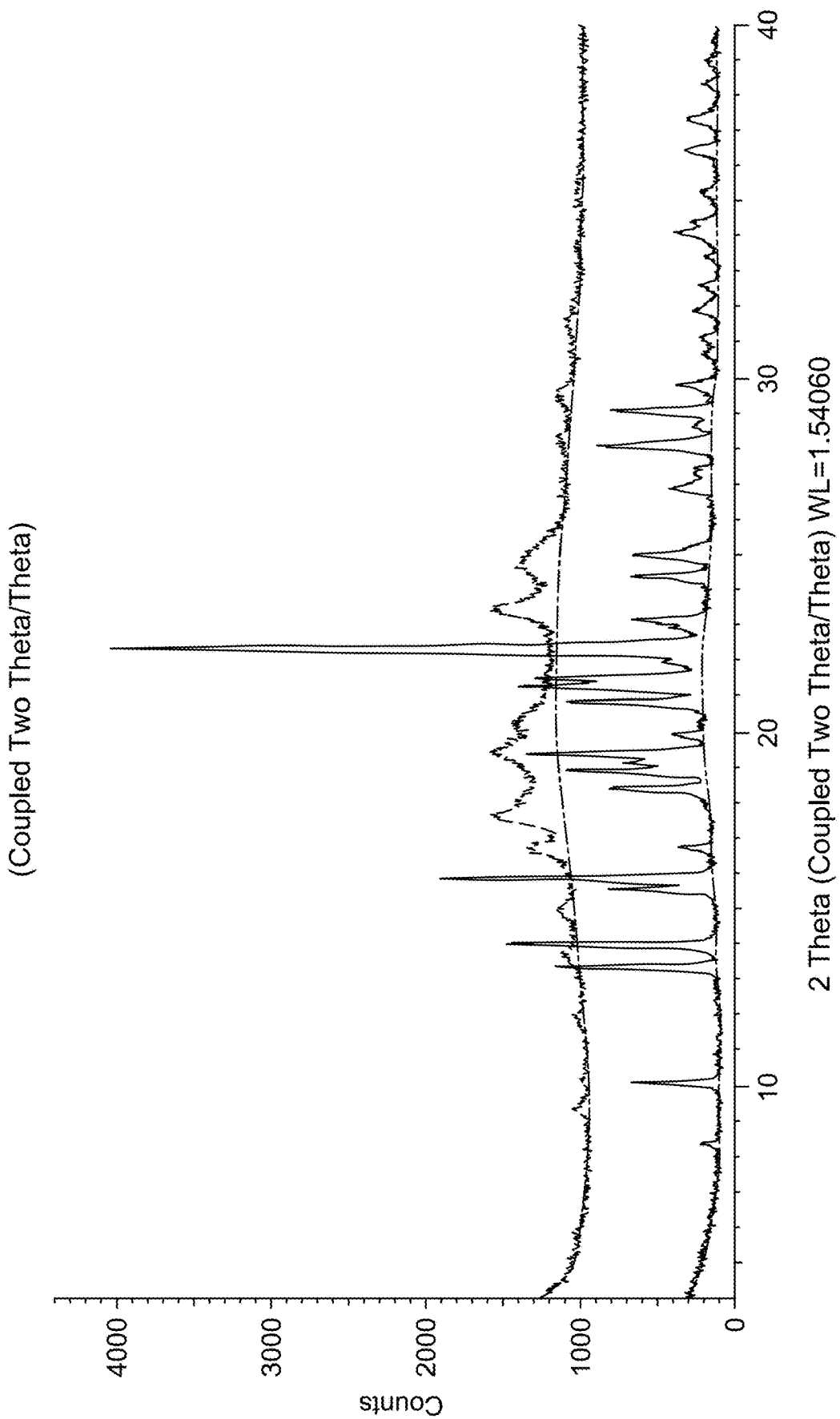

FIG. 347 shows an overlay of XRPD profiles of a reference sample of crystalline compound 1 monofumarate Form B (top) and a sample of crystalline compound 1 monofumarate Form A prepared by suspension in tBME at 20° C.

Figure 348:
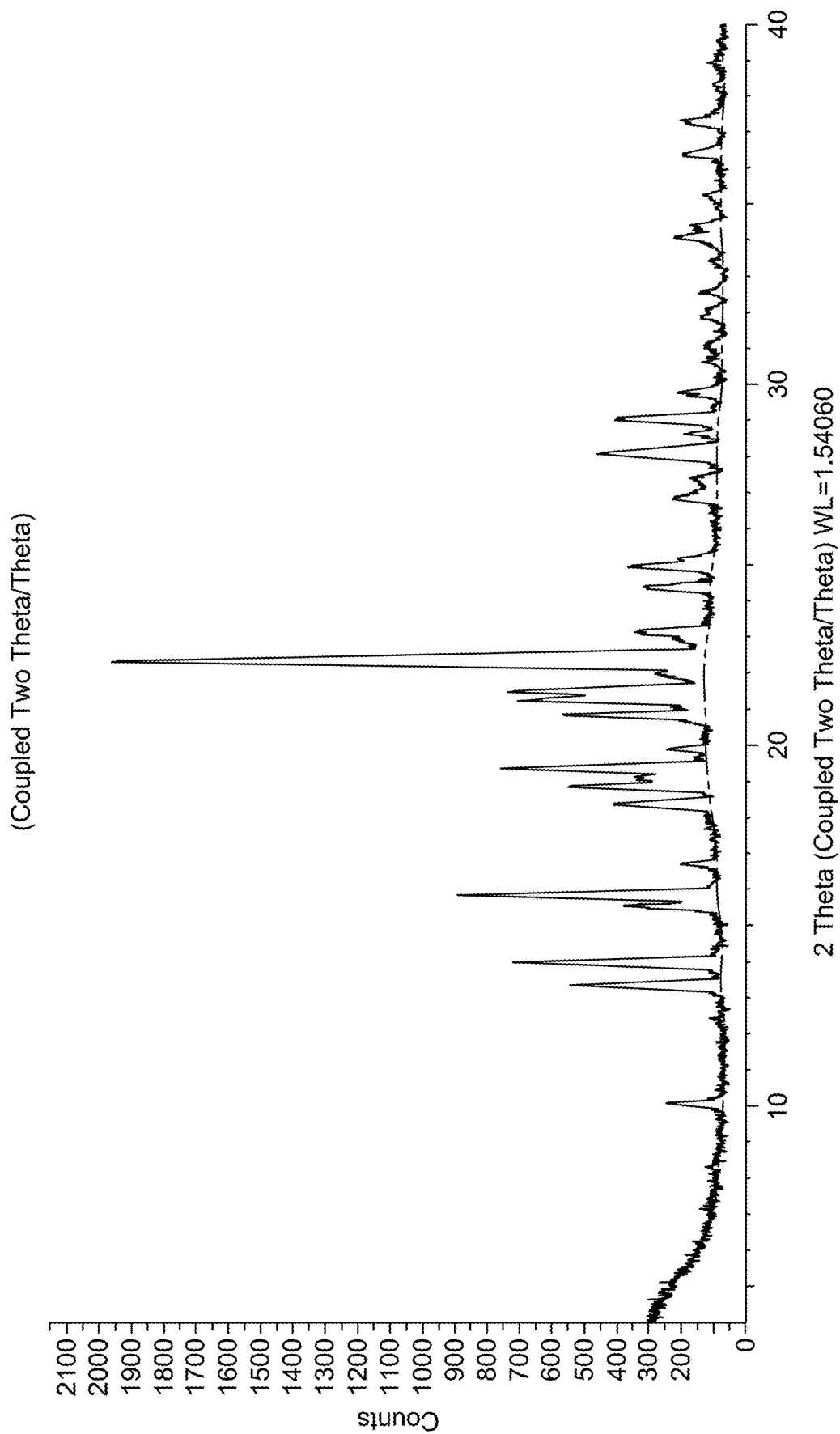

FIG. 348 shows a XRPD profile of crystalline compound 1 monofumarate Form A prepared by suspension in tBME at 20° C.

Figure 349:
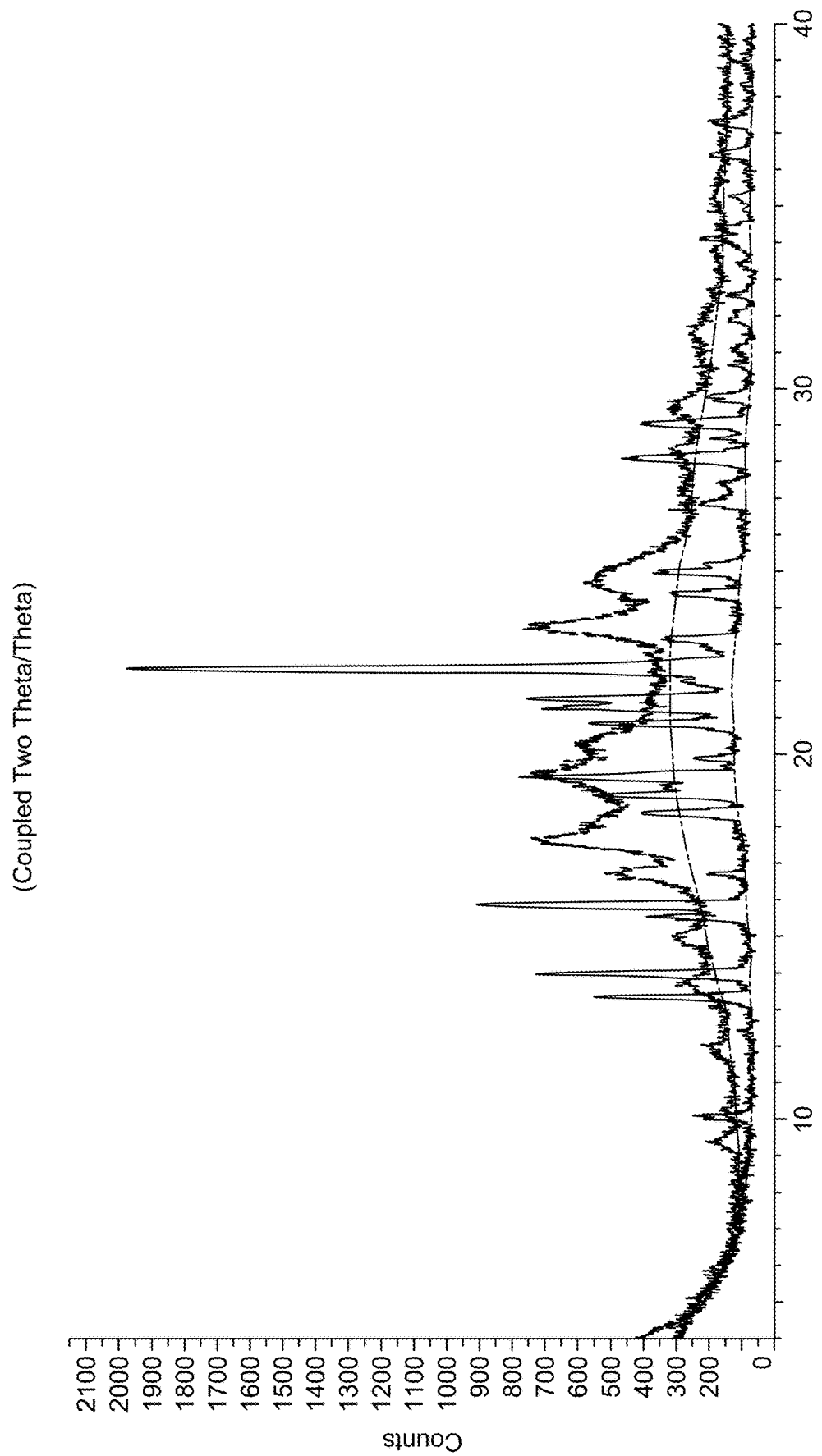

FIG. 349 shows an overlay of XRPD profiles of a reference sample of crystalline compound 1 monofumarate Form B (top) and a sample of crystalline compound 1 monofumarate Form A prepared by suspension in tBME at 20° C.

Figure 350:
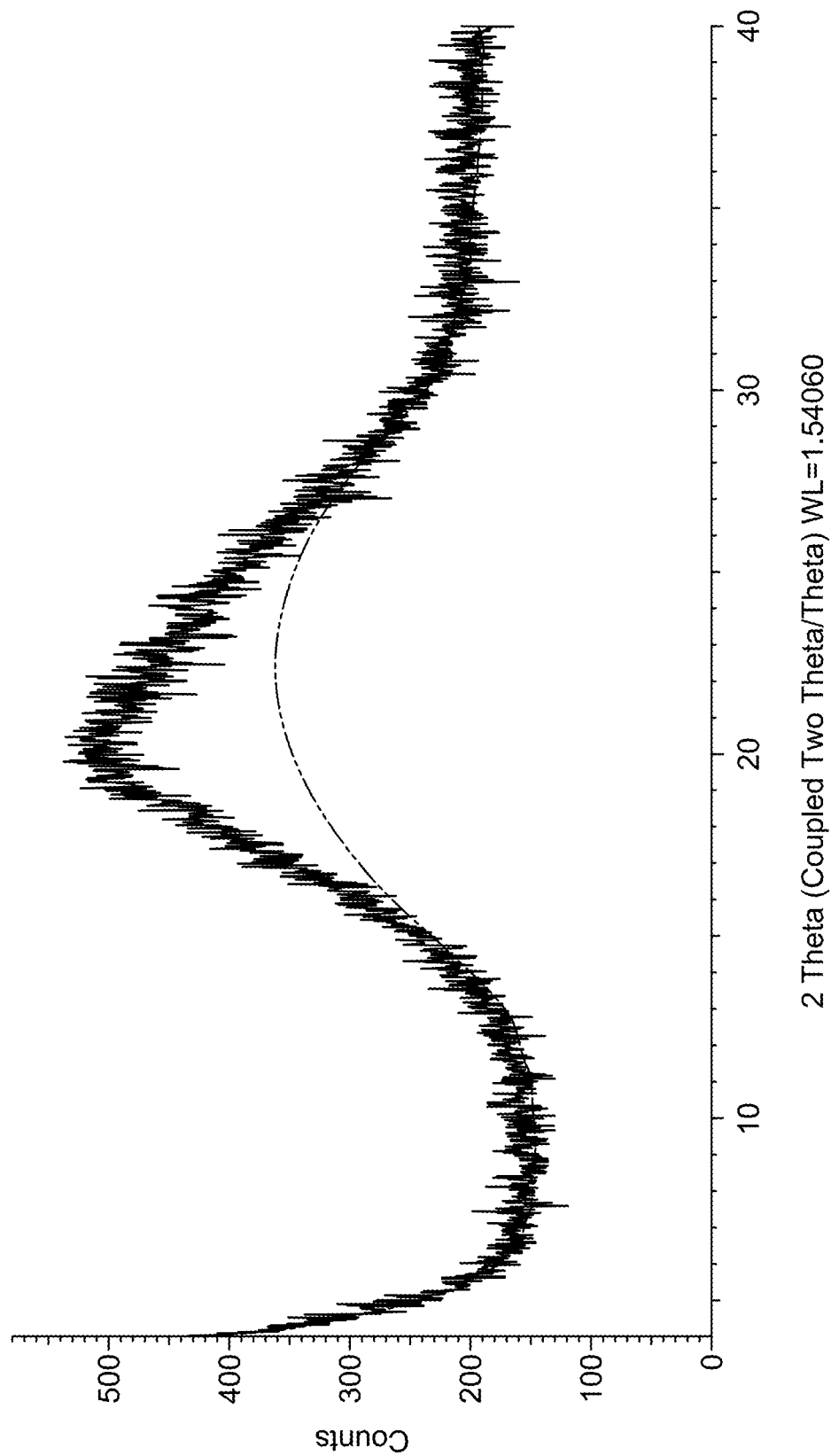

FIG. 350 shows an XRPD profile of amorphous compound 1 produced by a previously published method.

Figure 351:
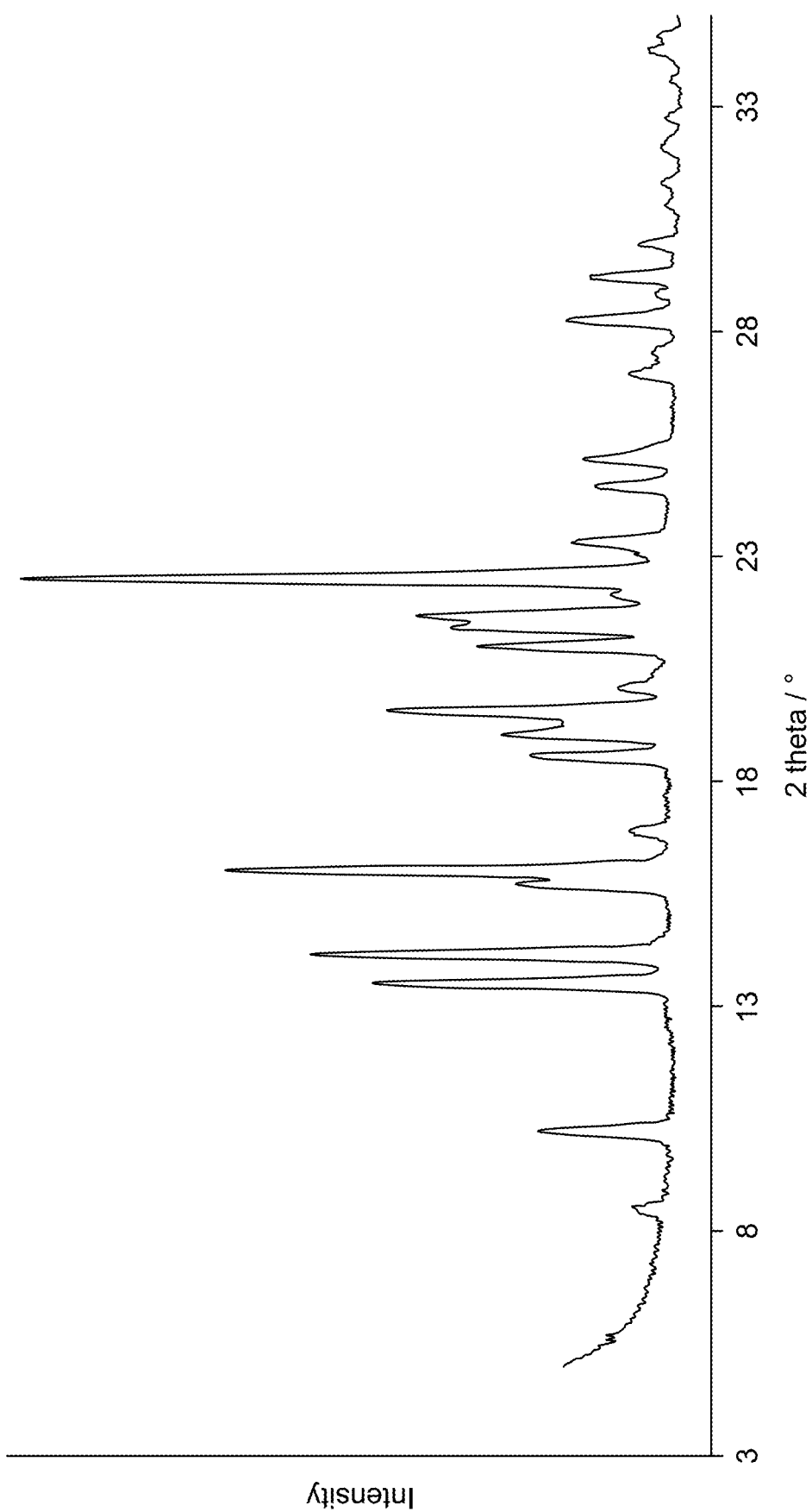

FIG. 351 shows a XRPD profile of crystalline compound 1 monofumarate Form A produced by a method disclosed herein.

Figure 352:
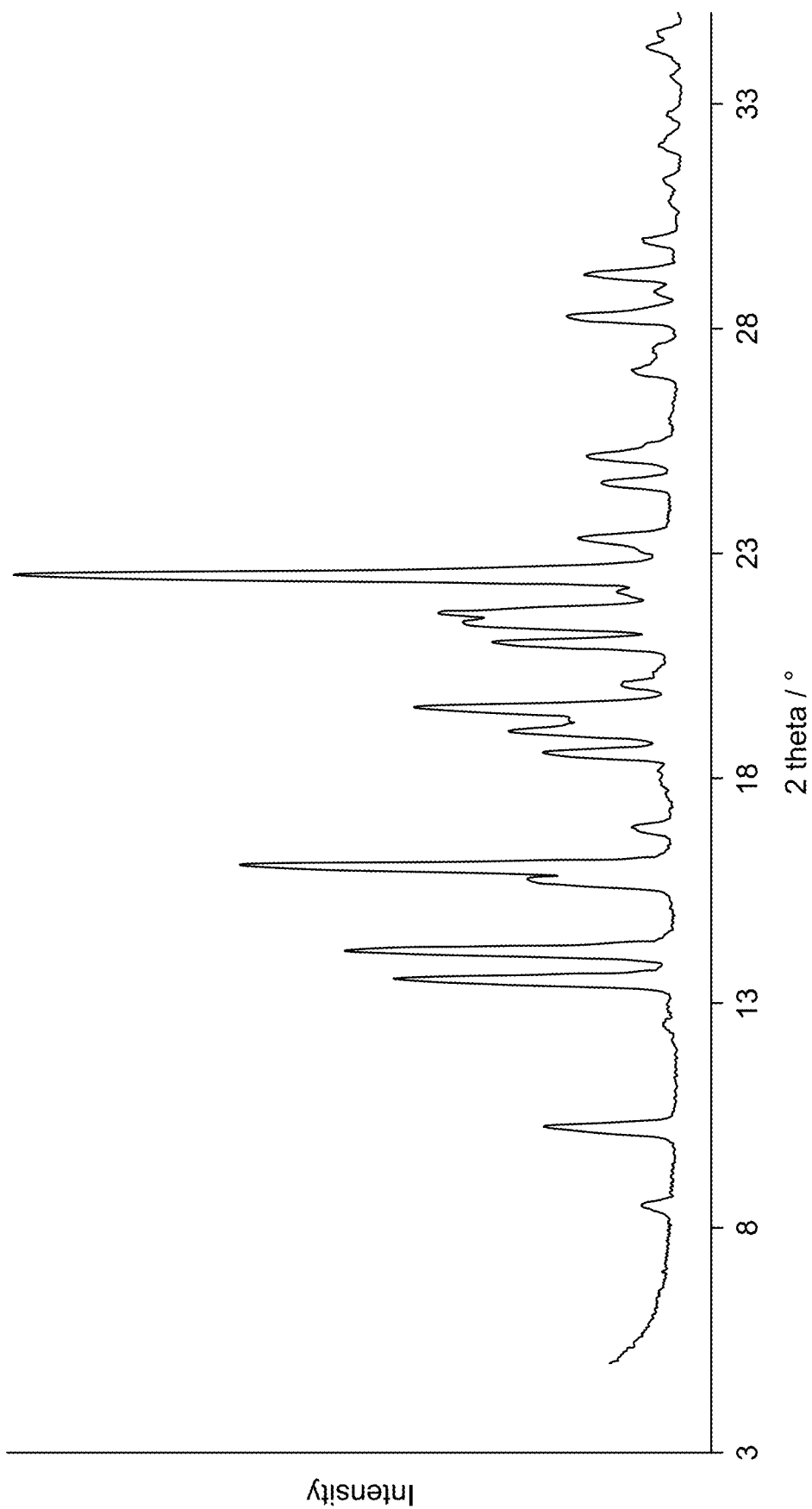

FIG. 352 shows a XRPD profile of crystalline compound 1 monofumarate Form A produced by a method disclosed herein.

Figure 353:
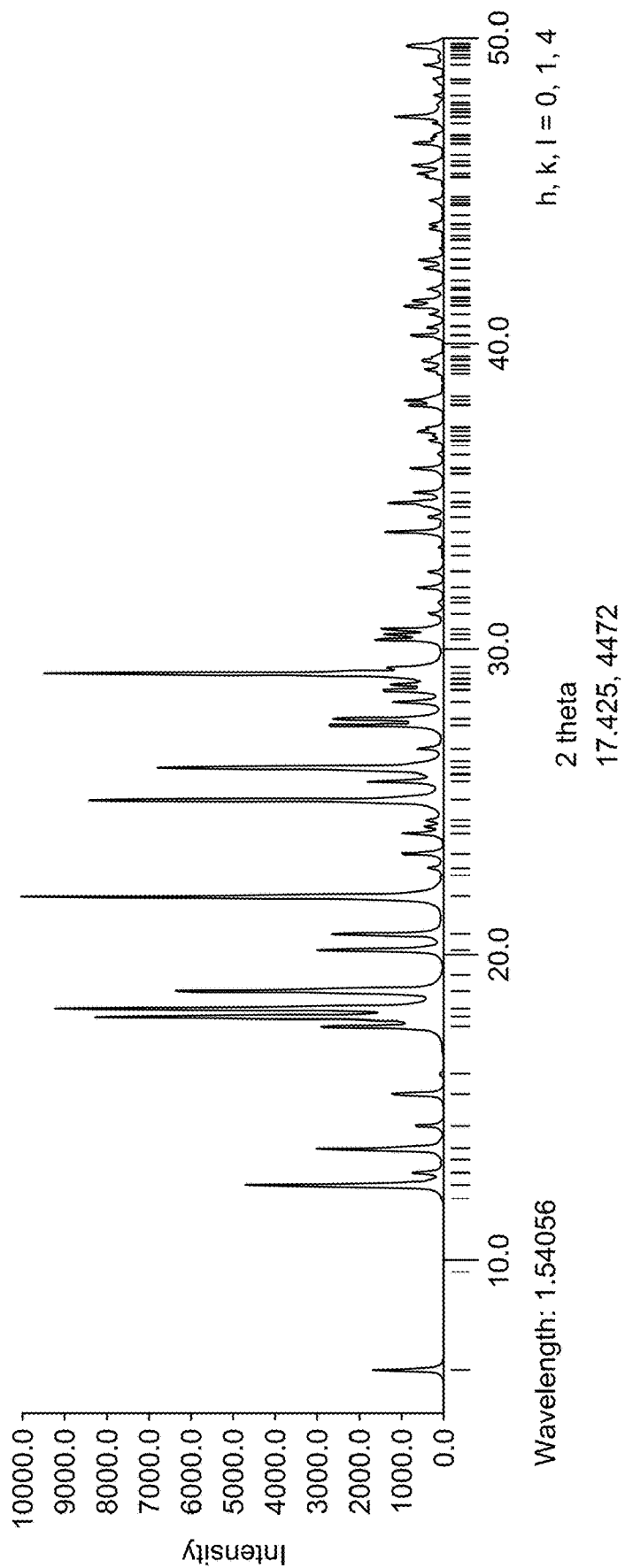

FIG. 353 shows a calculated XRPD profile of crystalline compound 1 HCl. XRPD signals observed in this profile are characterized in Table 114.

Figure 354:
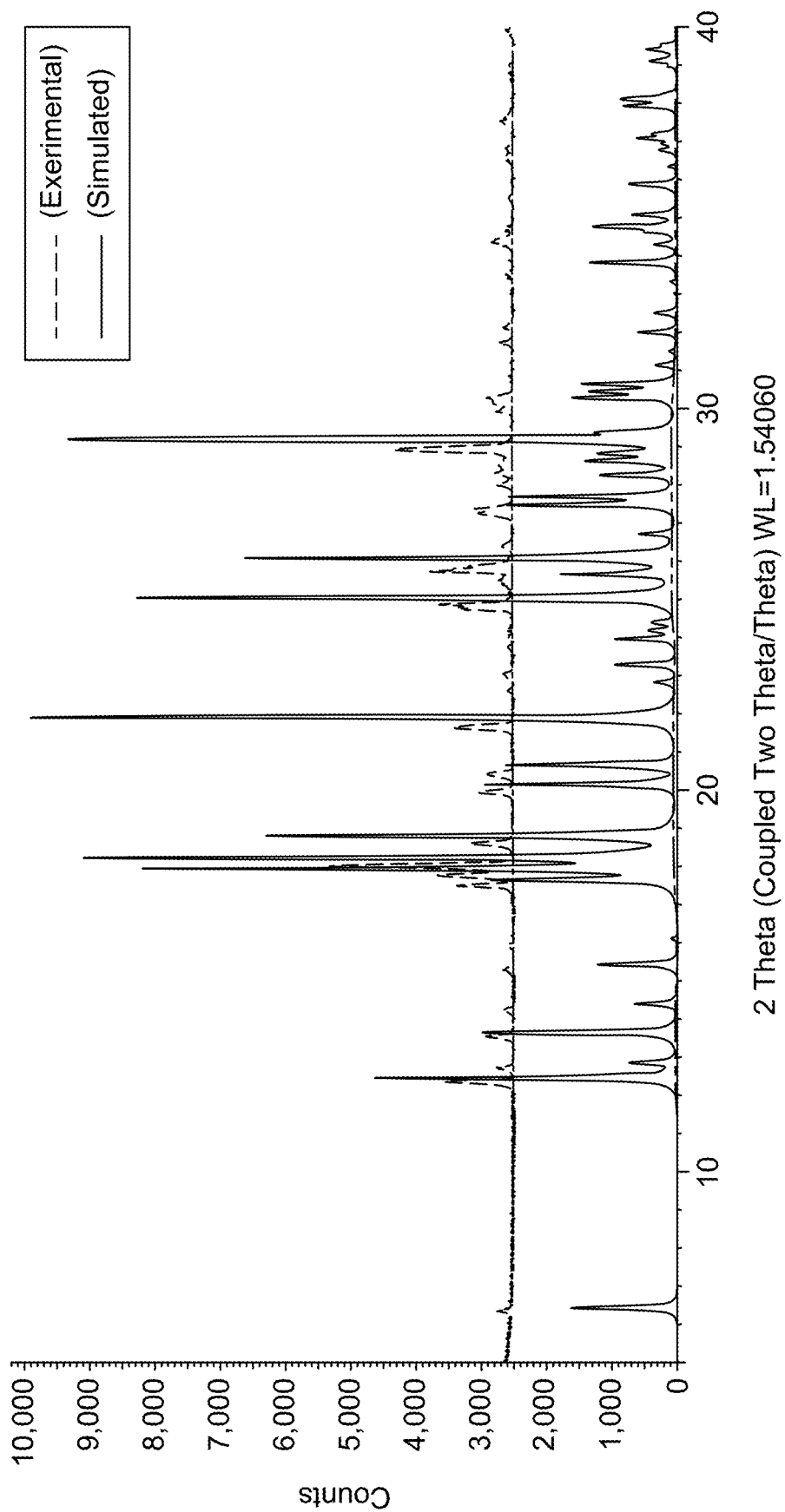

FIG. 354 shows an overlay of an experimentally observed XRPD profile of a sample of crystalline compound 1 HCl (top) and a calculated XRPD profile of crystalline compound 1 HCl.

Figure 355:
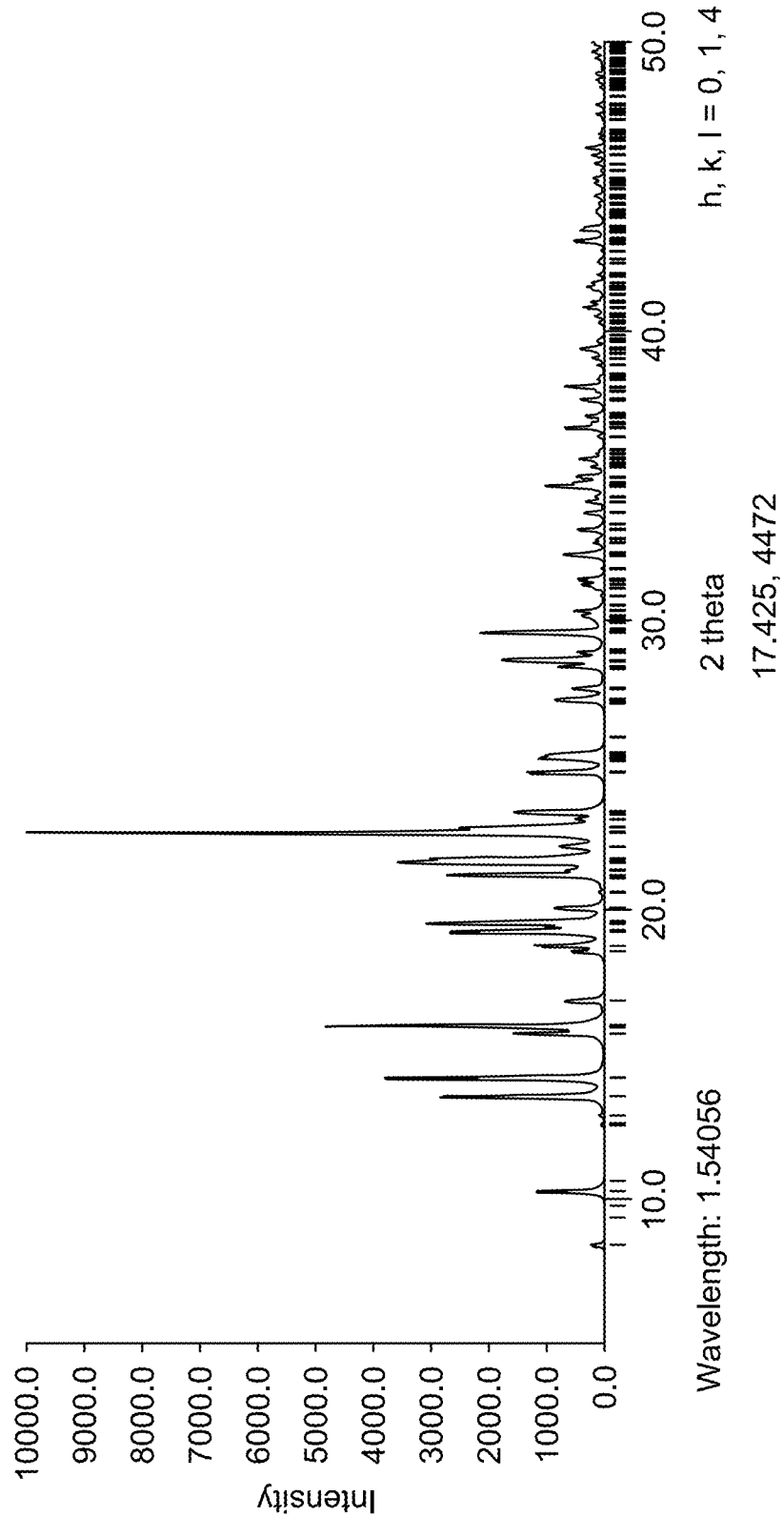

FIG. 355 shows a calculated XRPD profile of crystalline compound 1 monofumarate Form A. XRPD signals observed in this profile are characterized in Table 115.

Figure 356:
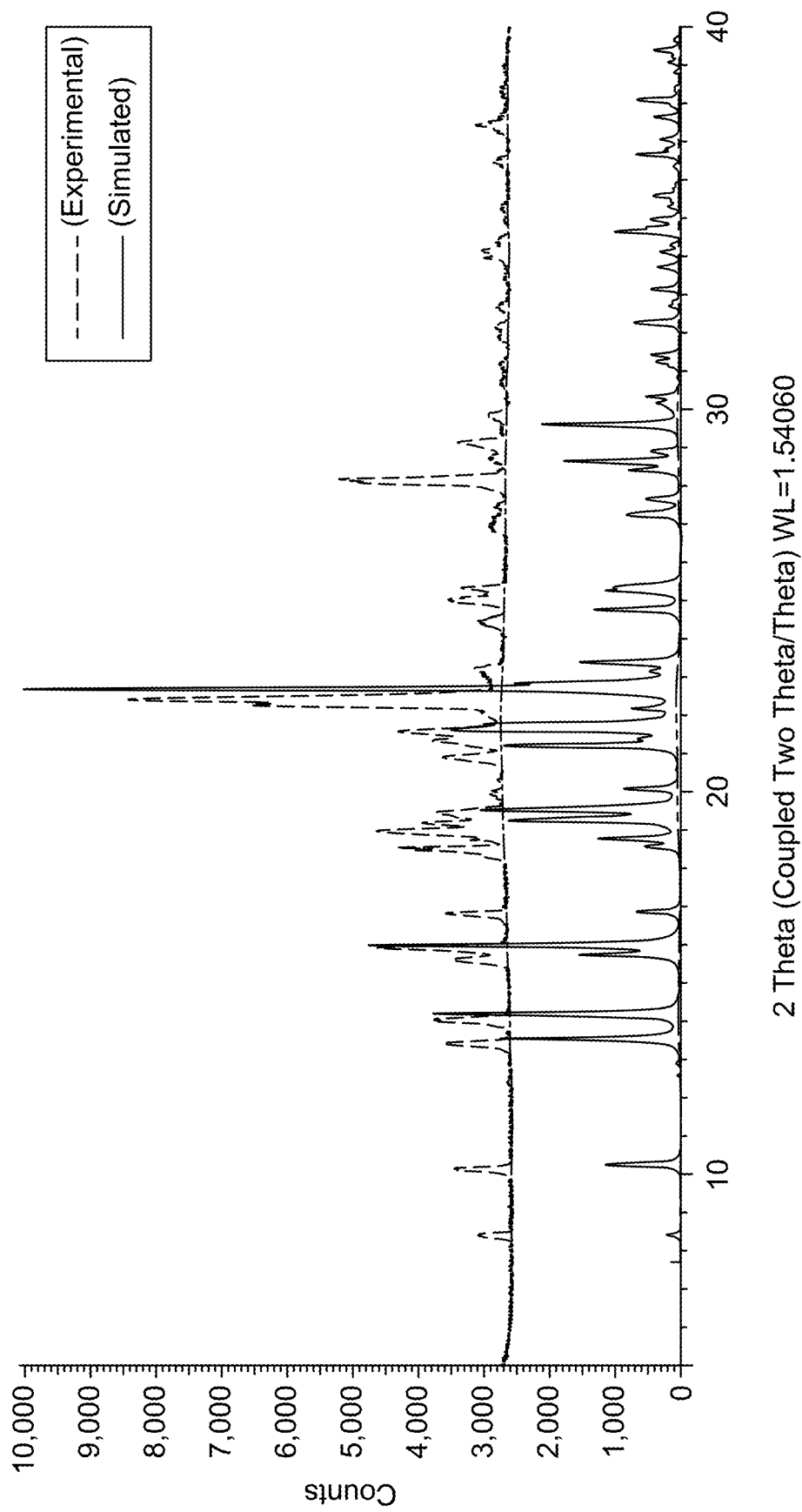

FIG. 356 shows an overlay of an experimentally observed XRPD profile of a sample of crystalline compound 1 monofumarate Form A (top) and a calculated XRPD profile of crystalline compound 1 monofumarate Form A (bottom).

Figure 357:
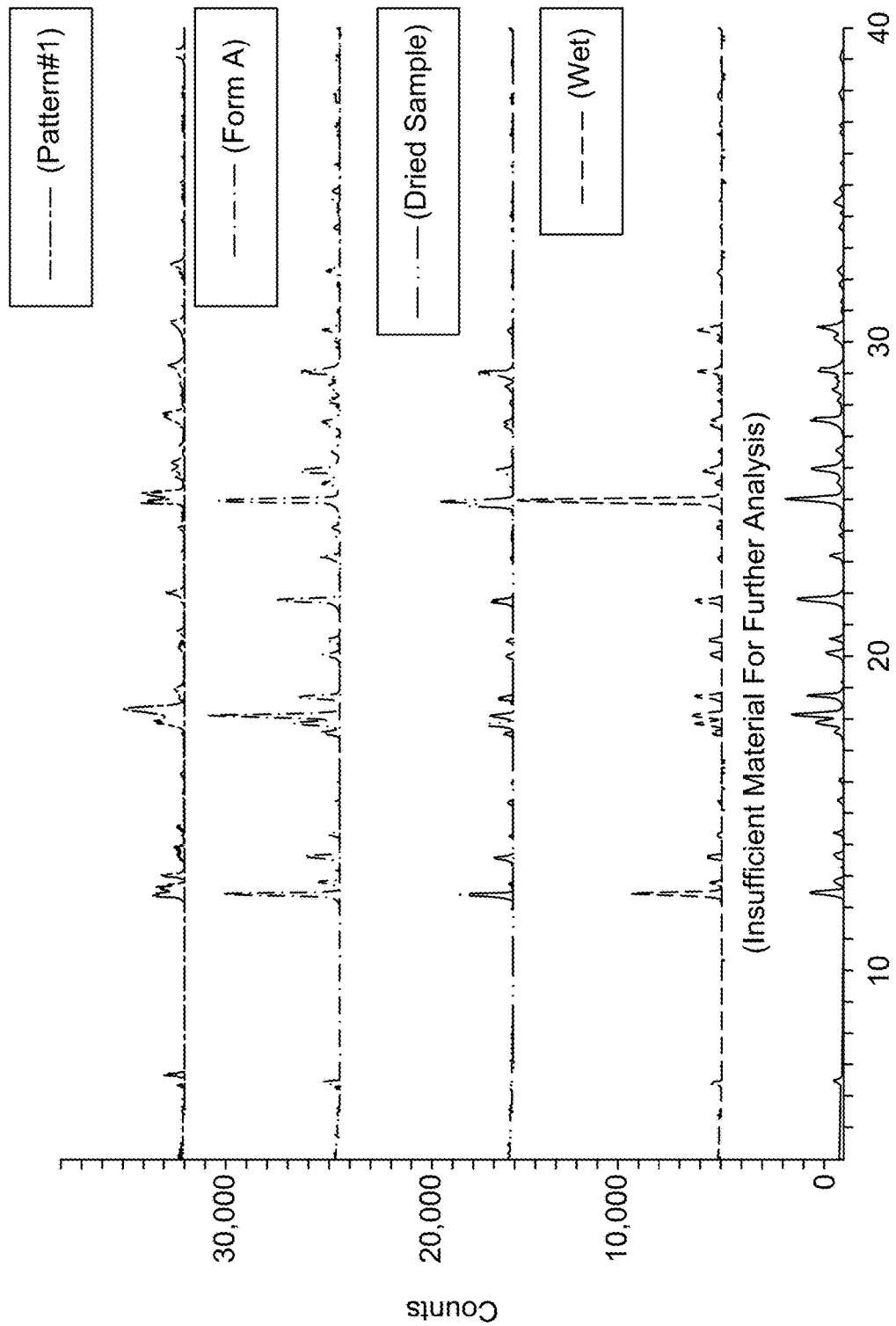

FIG. 357 shows overlay of XRPD profiles crystalline compound 1 HCl Pattern #1 Form B, (top), crystalline compound 1 HCl Form A (second from top), the experimentally obtained sample after drying (third from top), the experimentally obtained sample before drying (second from bottom), and a second experimentally obtained sample.

Figure 358:
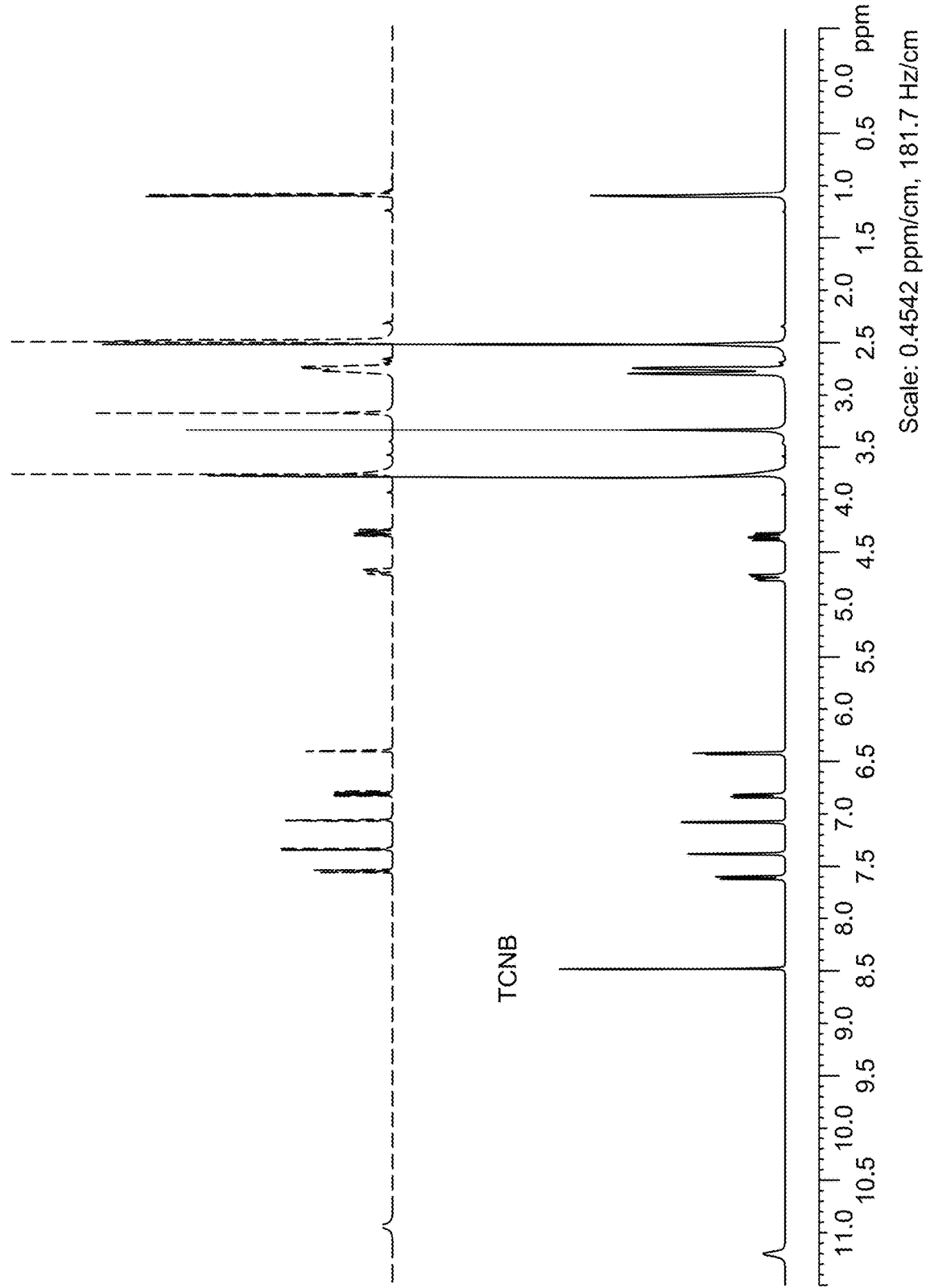

FIG. 358 shows overlaid $^1$H NMR spectra of a reference sample of crystalline compound 1 HCl Form A (bottom) and a sample of crystalline compound 1 Form A that has been pulverized in a liquid assisted grinding experiment.

Figure 359:
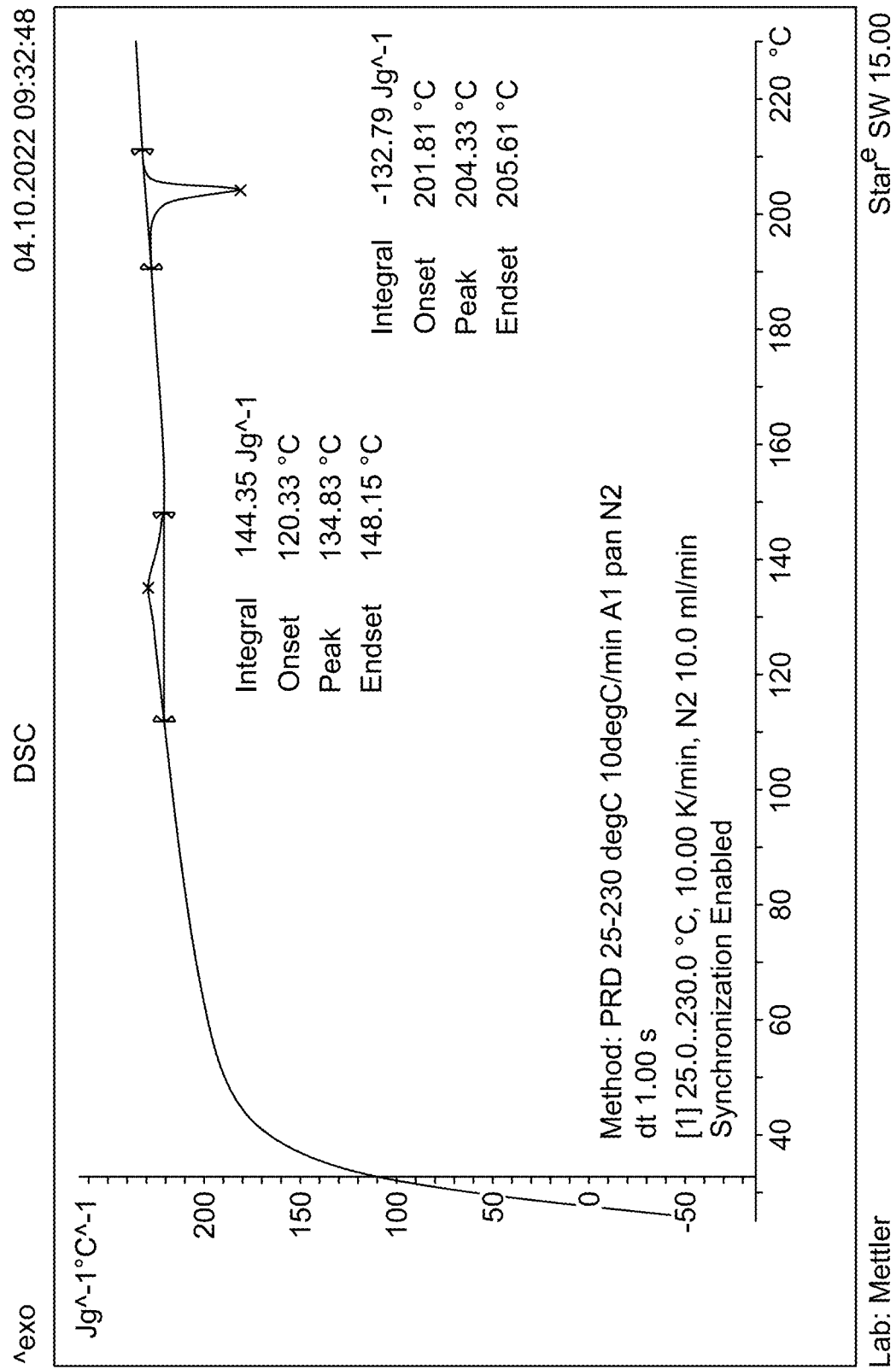

FIG. 359 shows the DSC profile of the sample of crystalline compound 1 HCl Form A that has been subjected to liquid assisted grinding with trifluoroethanol as the liquid assist and exhibited a probable crystallization event.

Figure 360:
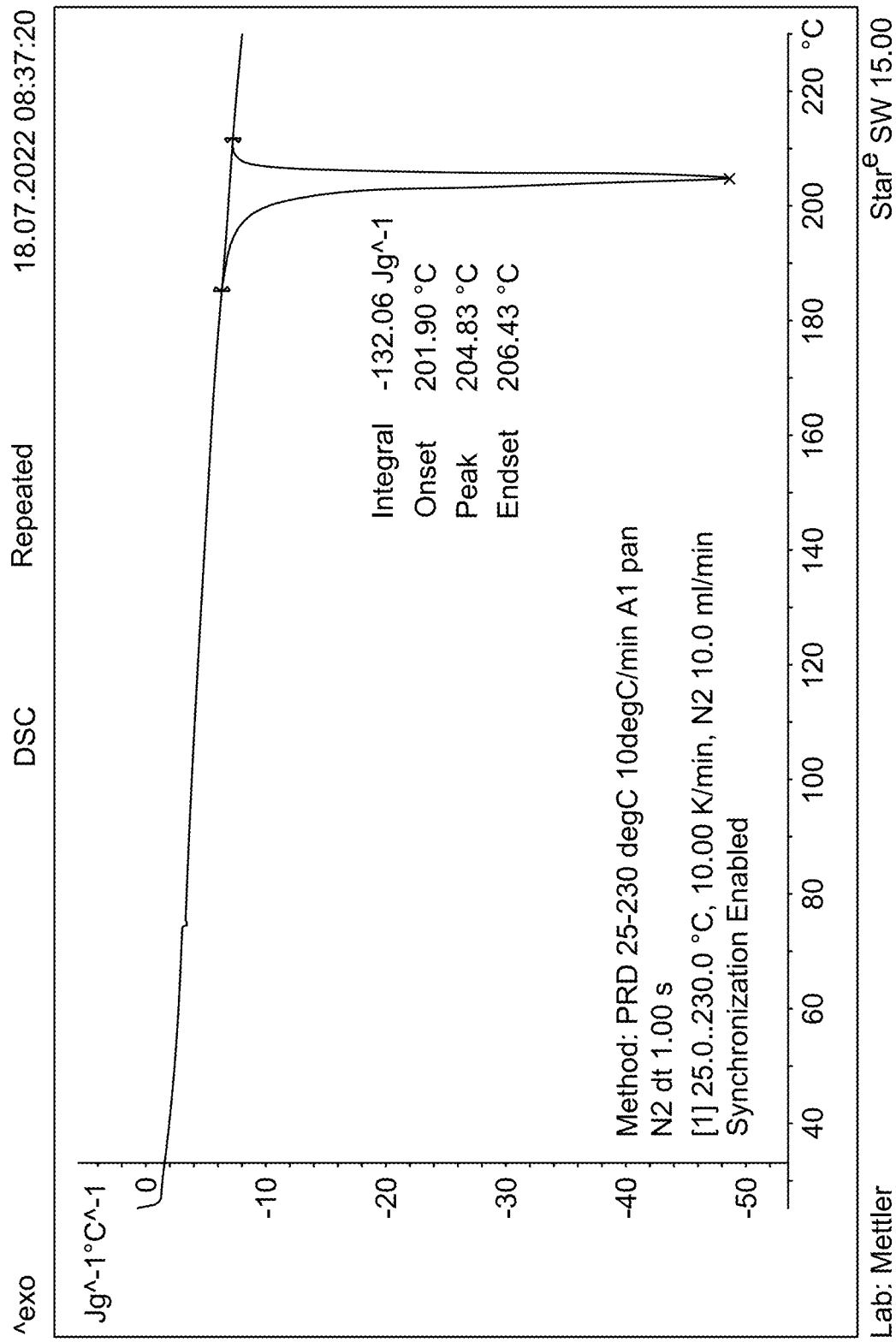

FIG. 360 shows a DSC profile of the sample of crystalline compound 1 HCl Form A that had been subjected to liquid assisted grinding with trifluoroethanol as the liquid assist and was measured at an earlier time point in FIG. 359. At the time point the measurement was taken that resulted in FIG. 374, the first endotherm was absent.

Figure 361:
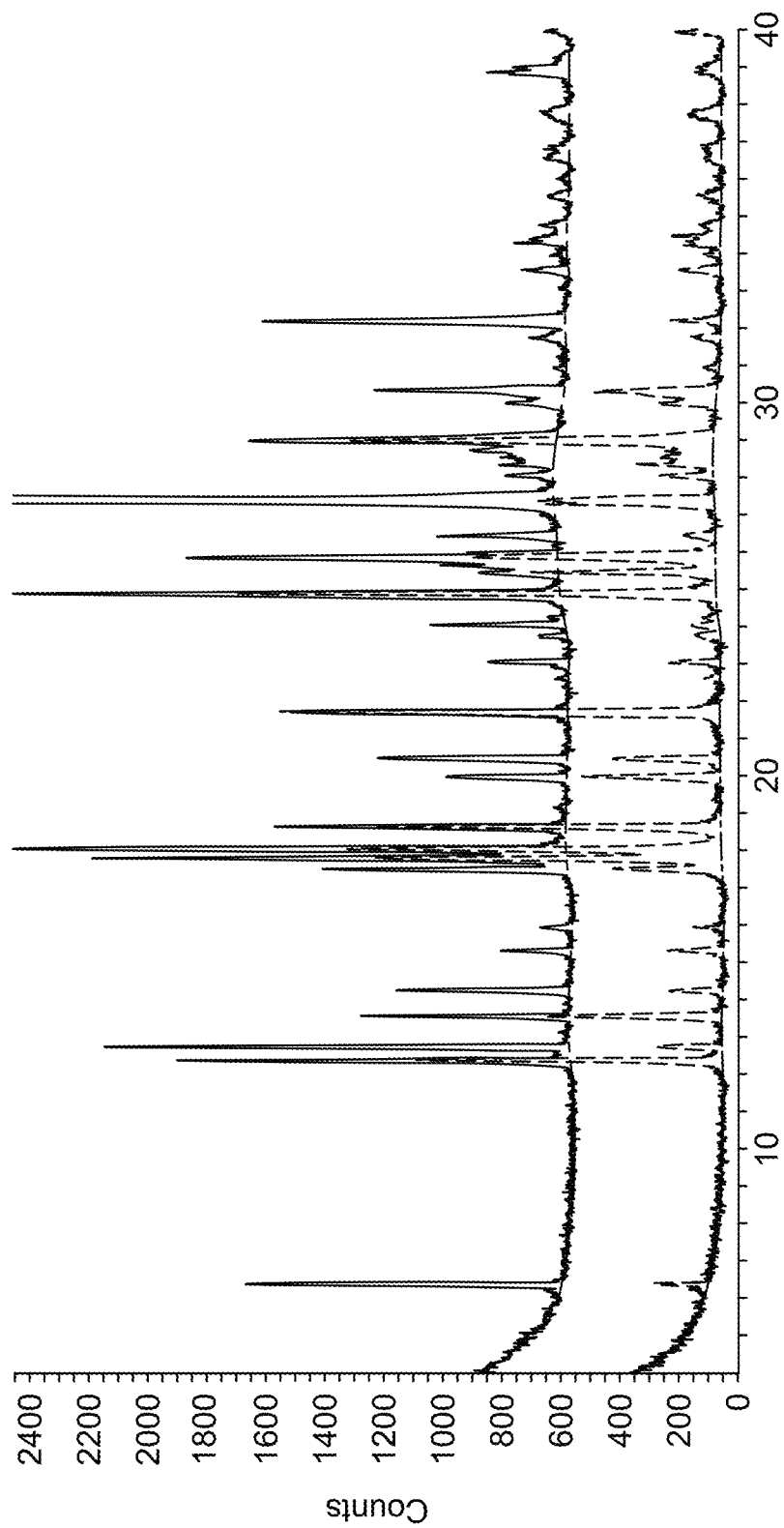

FIG. 361 shows overlaid crystalline compound 1 HCl Form A XRPD profiles pre (bottom) and post-DVS analysis (top).

Figure 362:
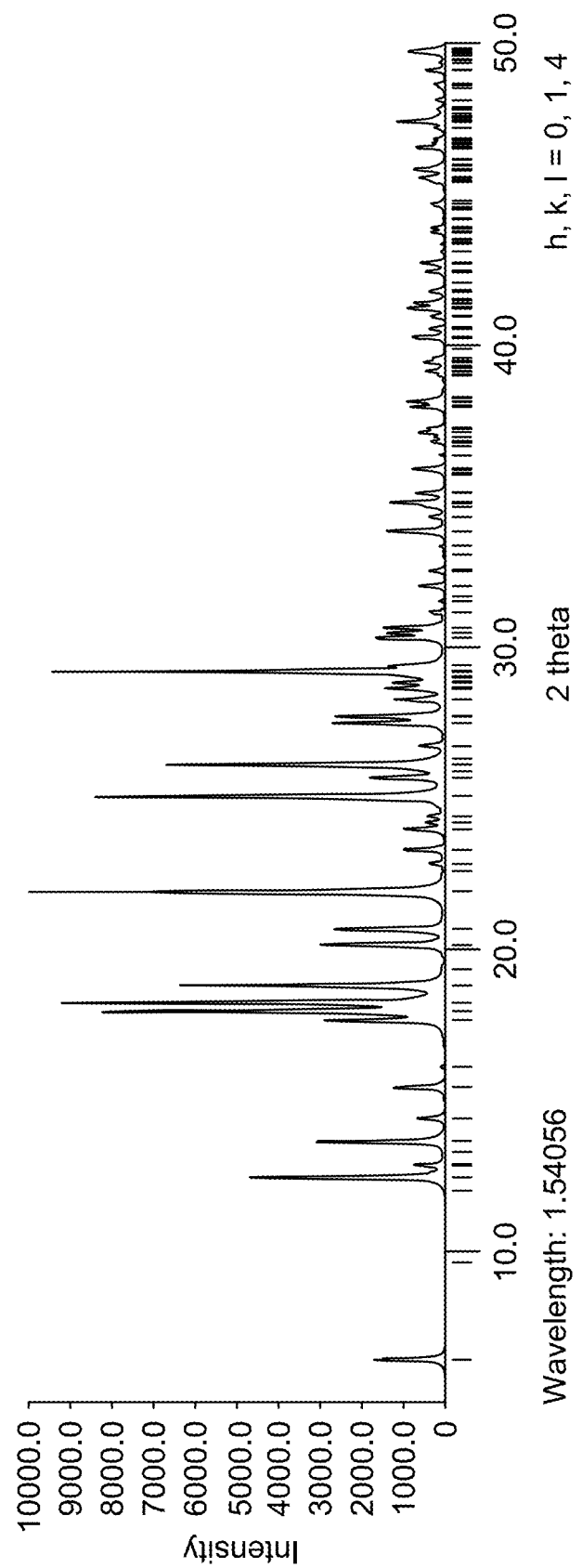

FIG. 362 shows a simulated XRPD pattern of crystalline compound 1 HCl Form A.

Figure 363:
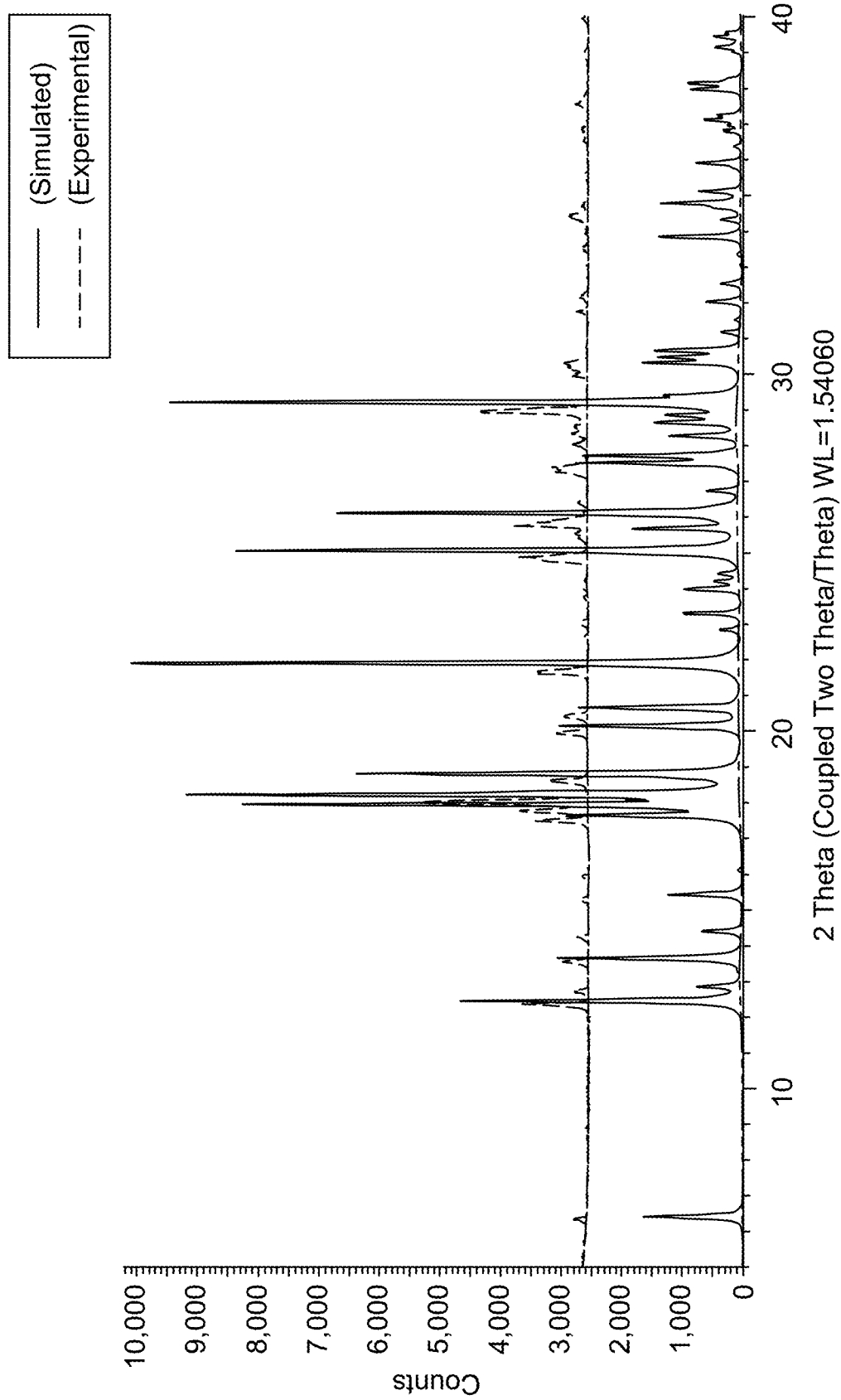

FIG. 363 shows overlaid simulated (bottom) and experimentally observed (top) XRPD profiles of crystalline compound 1 HCl Form A. a simulated XRPD pattern of crystalline compound 1 HCl Form A.

Figure 364:
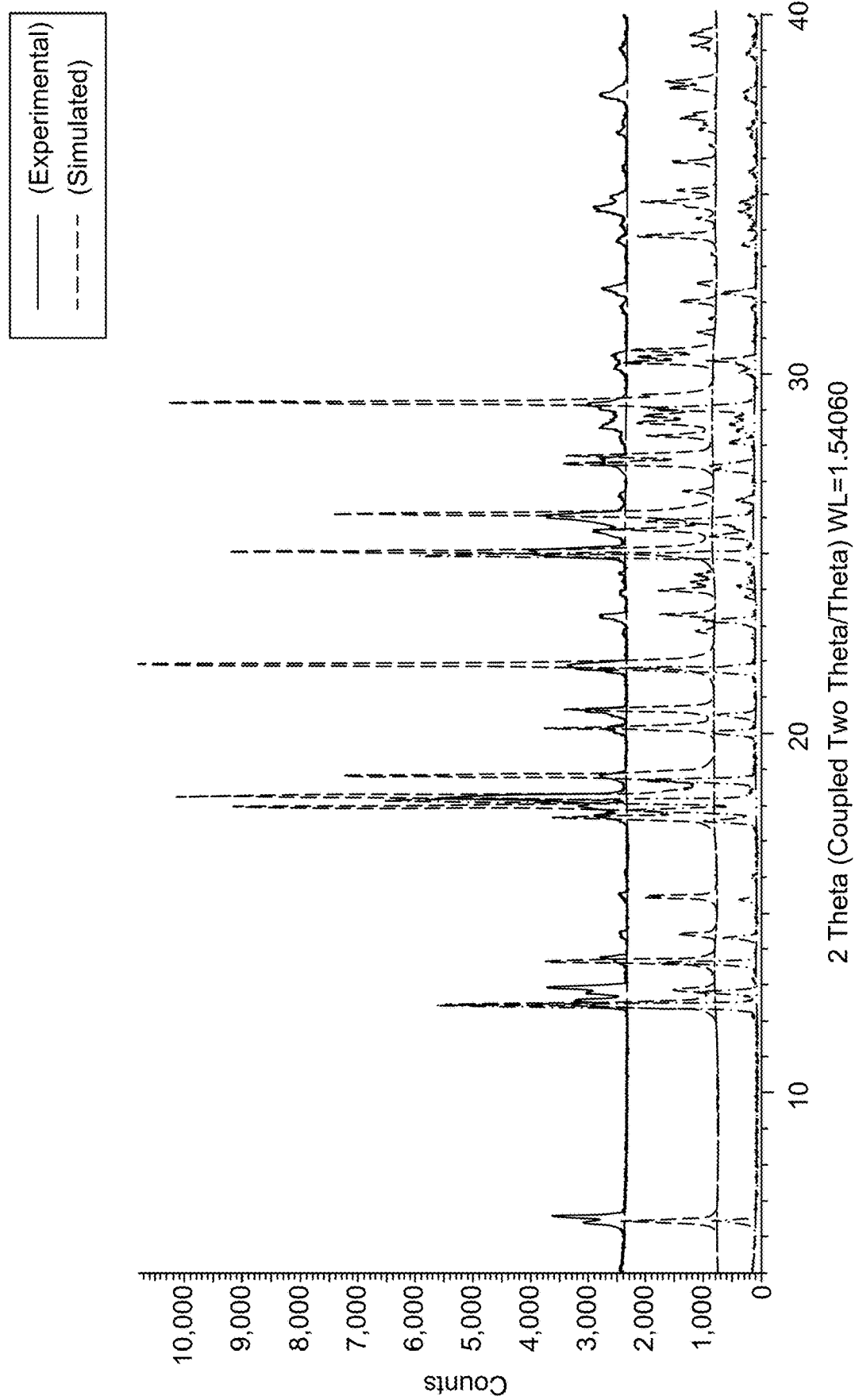

FIG. 364 shows overlaid XRPD profiles of simulated powder pattern of Form A, from SCXRD data at T=100(2) K (middle), experimental Form B powder pattern of bulk phase at T=298 K (Form B, Pattern #1 with minor component of Form A, top) and a reference sample of Form A (blue, bottom).

Figure 365:
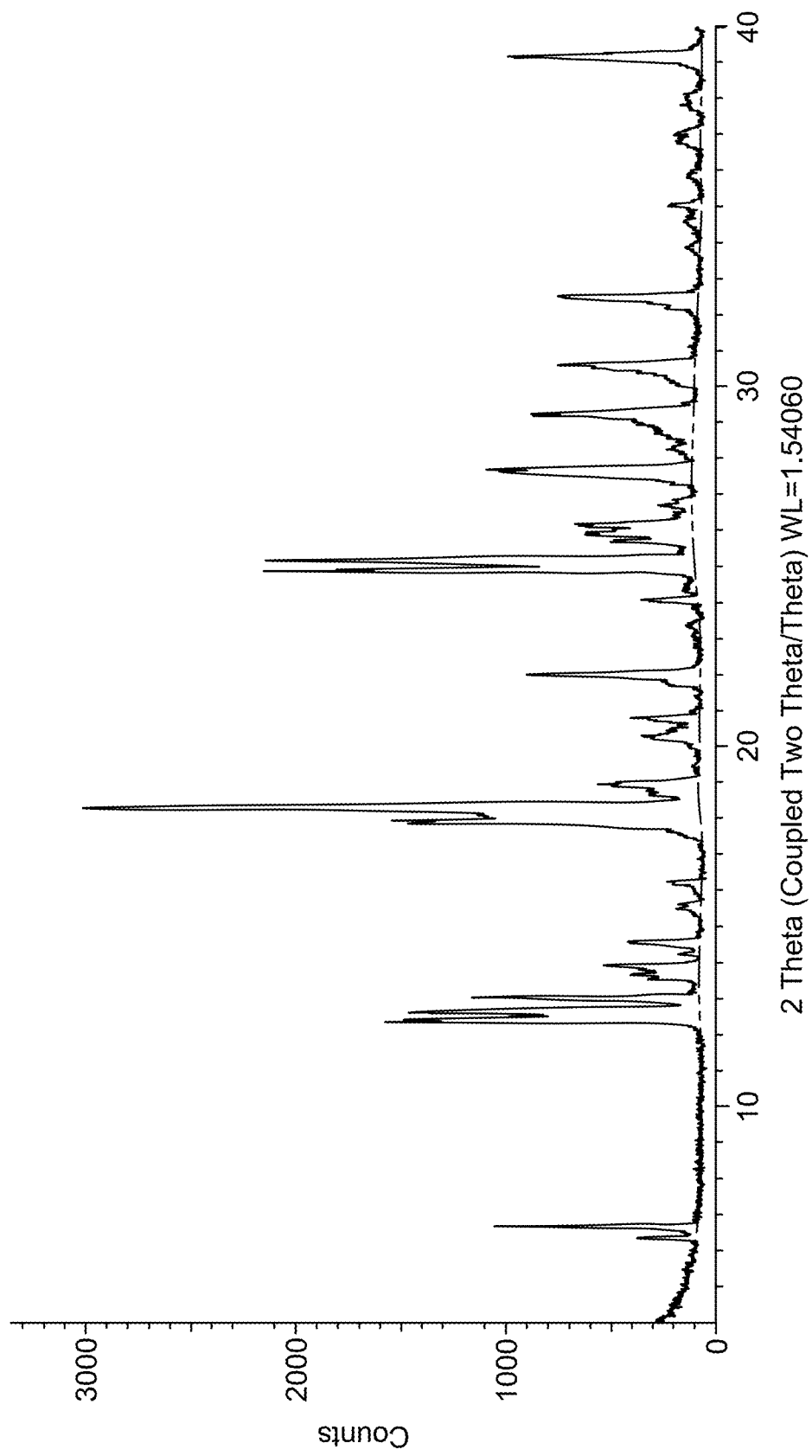

FIG. 365 shows an XRPD profile of crystalline compound 1 HCl Form B.

Figure 366:
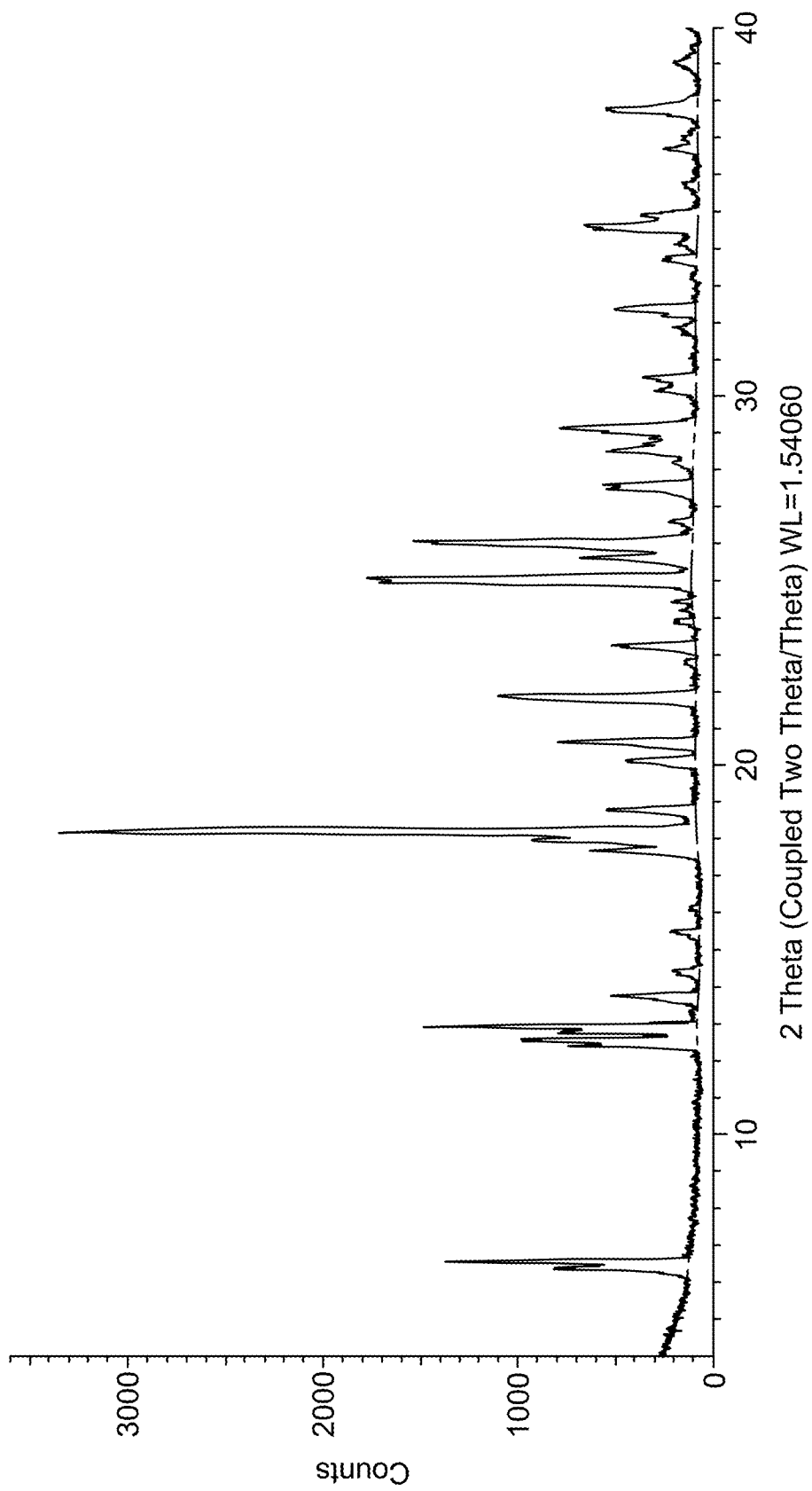

FIG. 366 shows an XRPD profile of crystalline compound 1 HCl Form B obtained by way of the application of controlled heat-up/cool-down.

Figure 367:
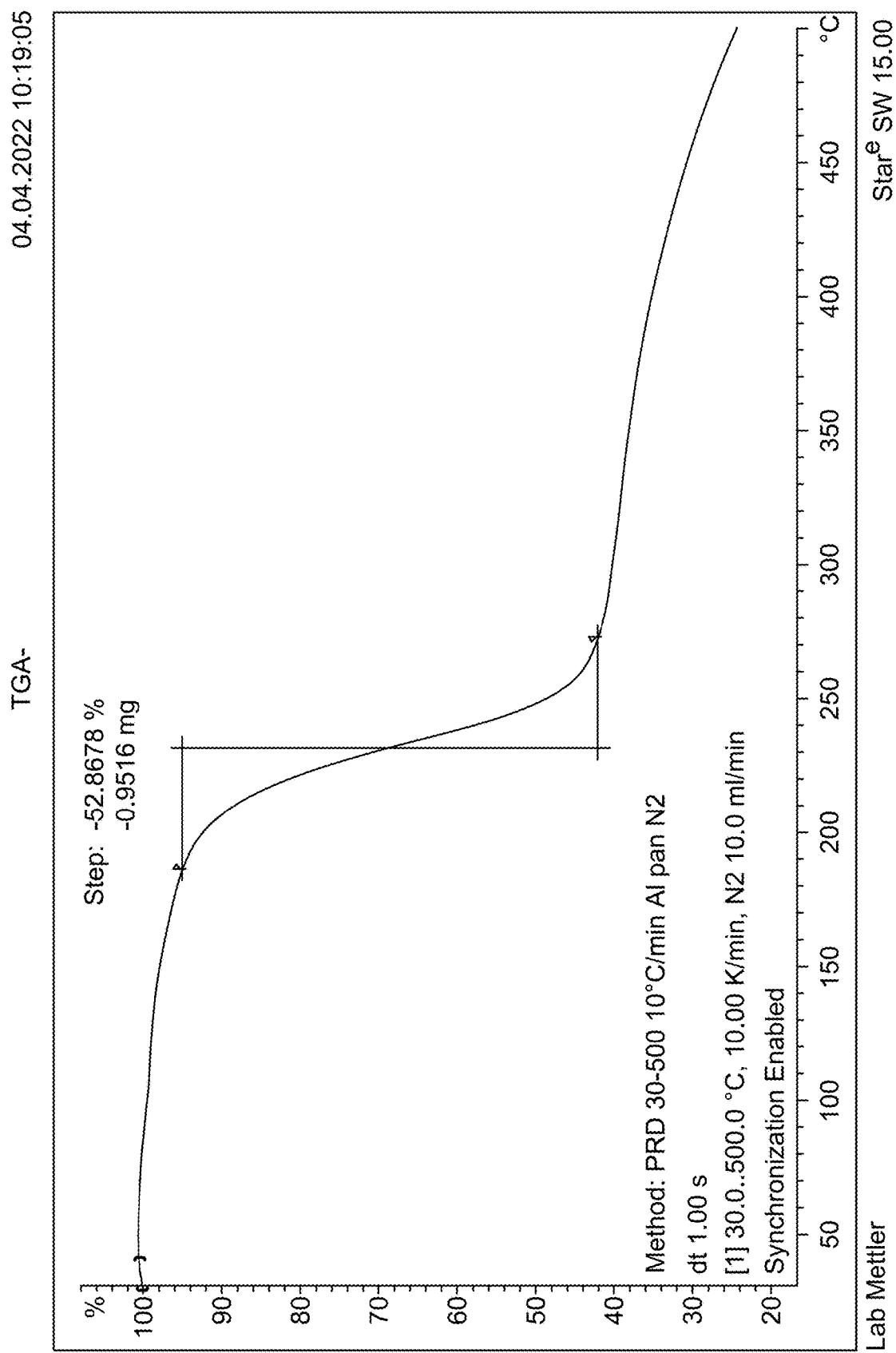

FIG. 367 shows a TGA thermogram of crystalline compound monofumarate Form A, analysis was acquired at a ramp rate of +10° C./minute.

Figure 368:
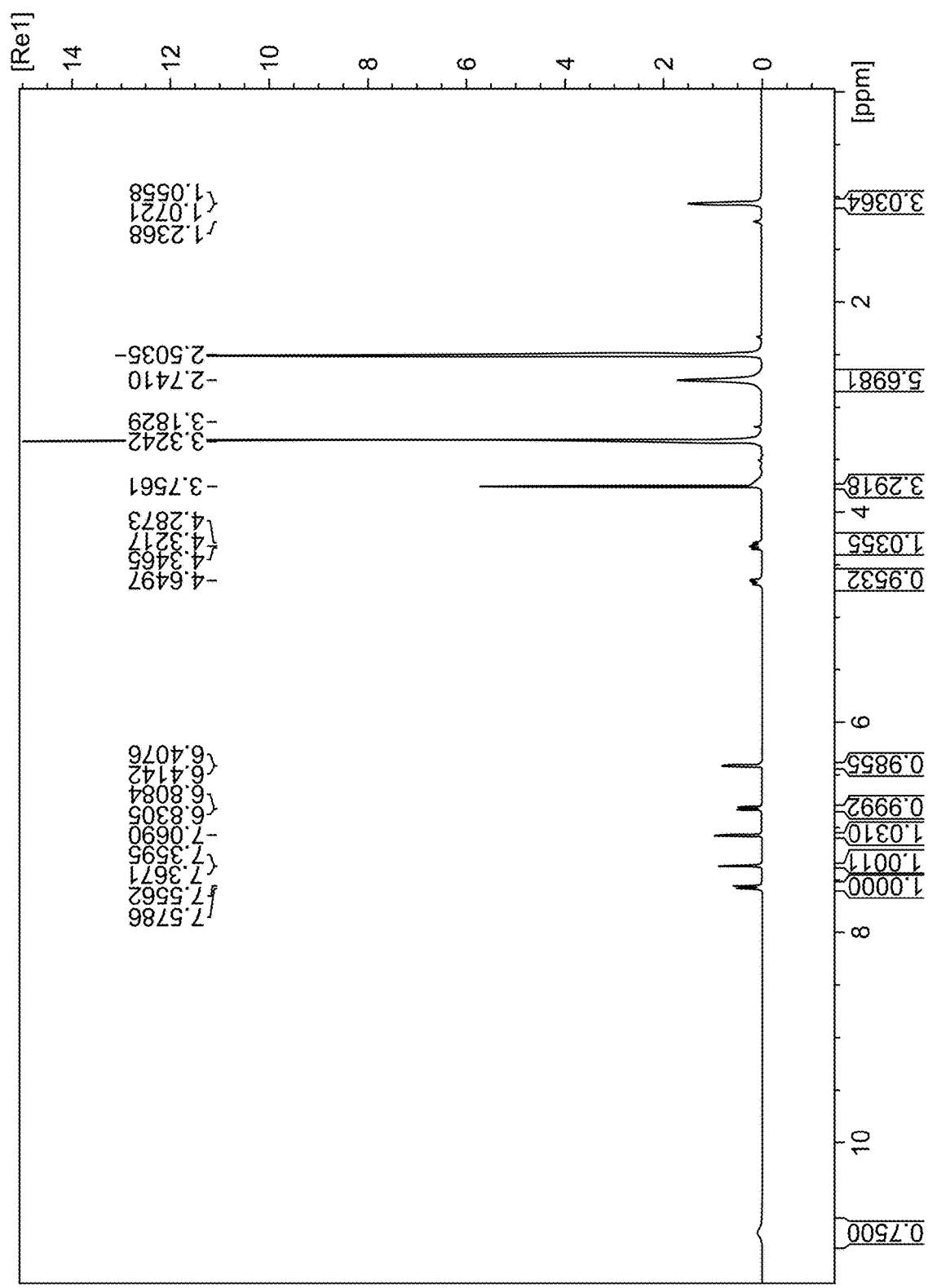

FIG. 368 shows a $^1$H NMR spectrum of amorphous compound 1 HCl.

Figure 369:
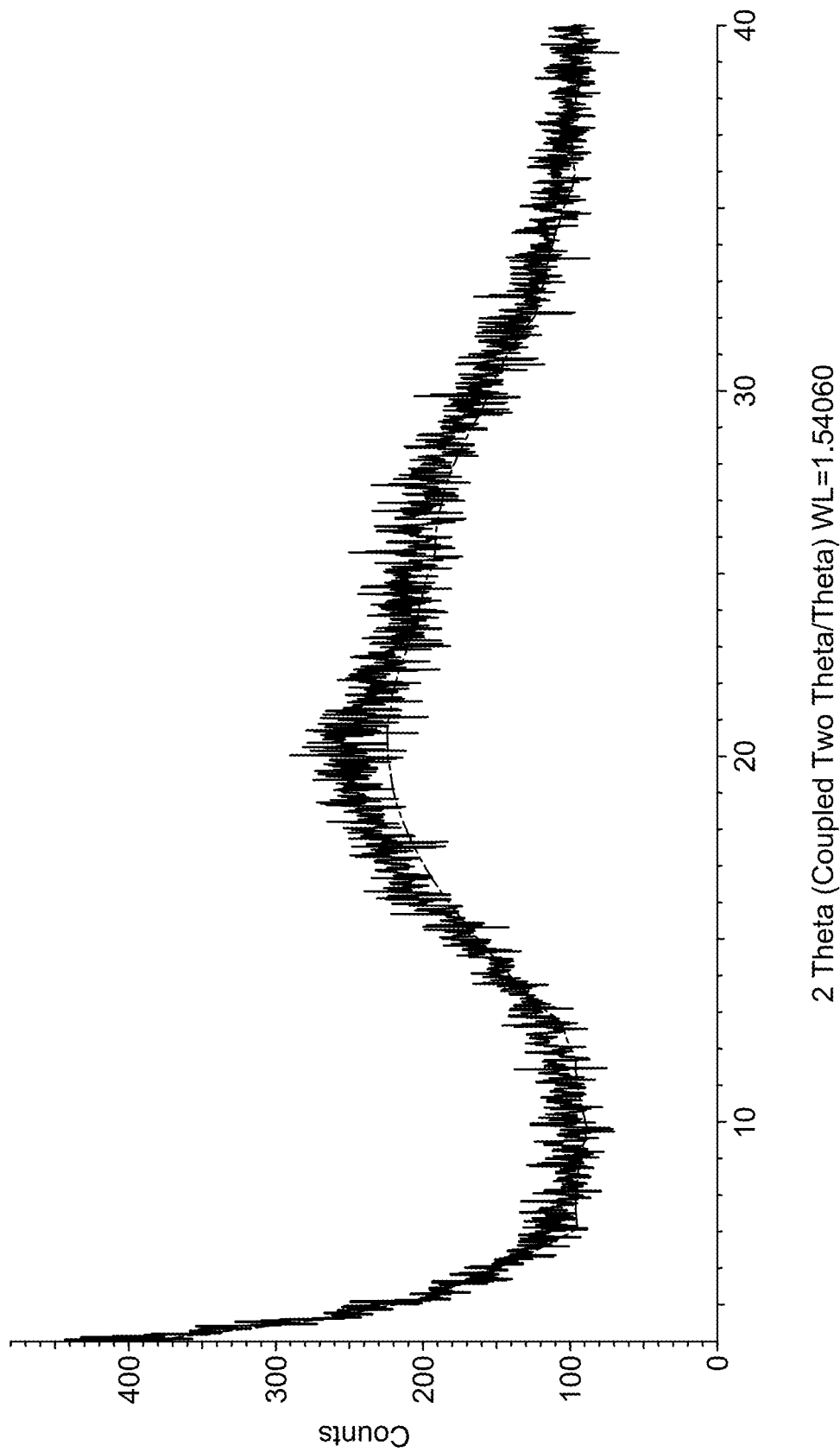

FIG. 369 shows an XRPD profile of amorphous compound 1 HCl.

Figure 370:
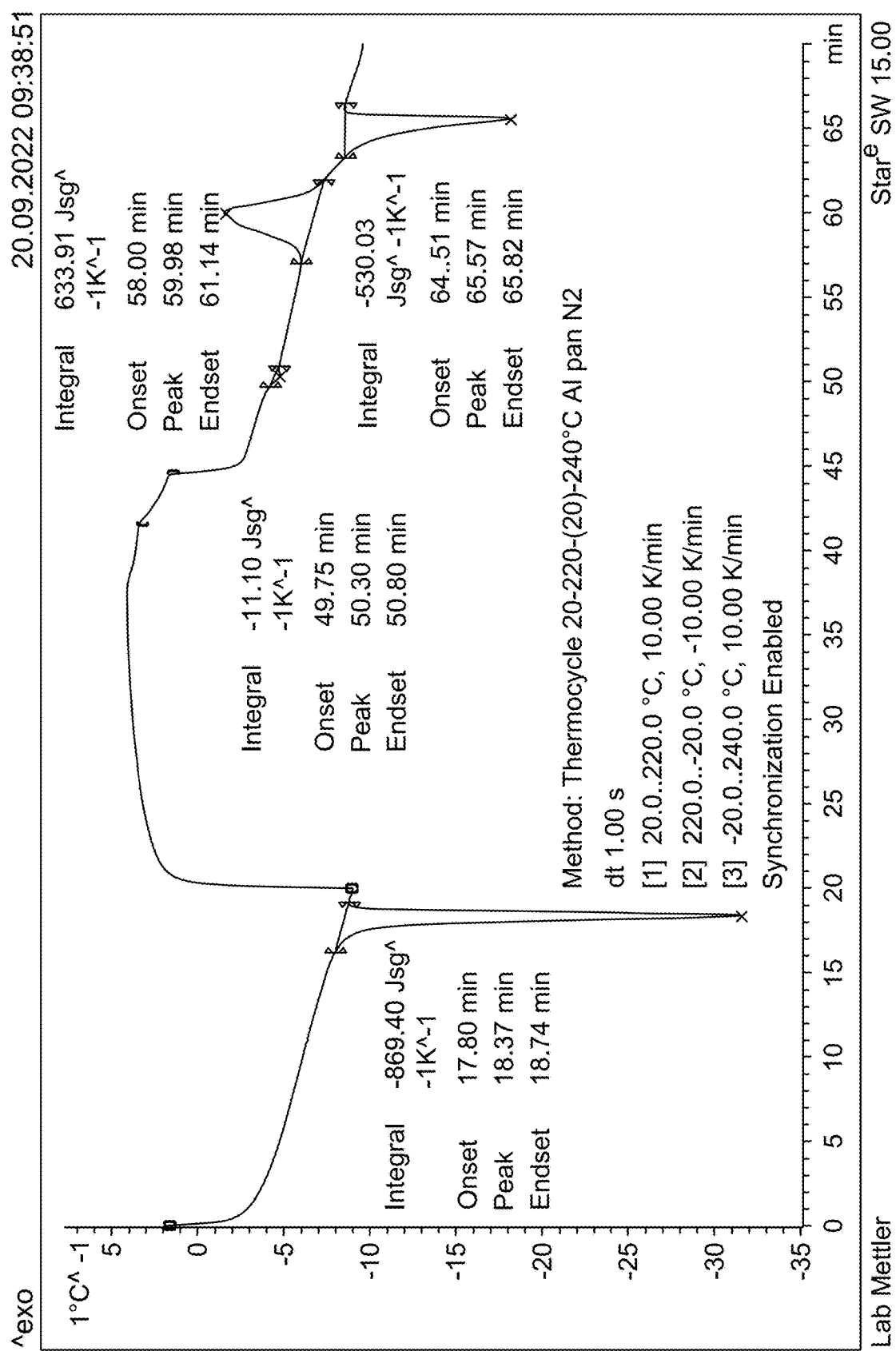

FIG. 370 shows a thermocycle DSC profile of amorphous compound 1 HCl (amorphous compound 1, heat flow vs. time).

Figure 371:
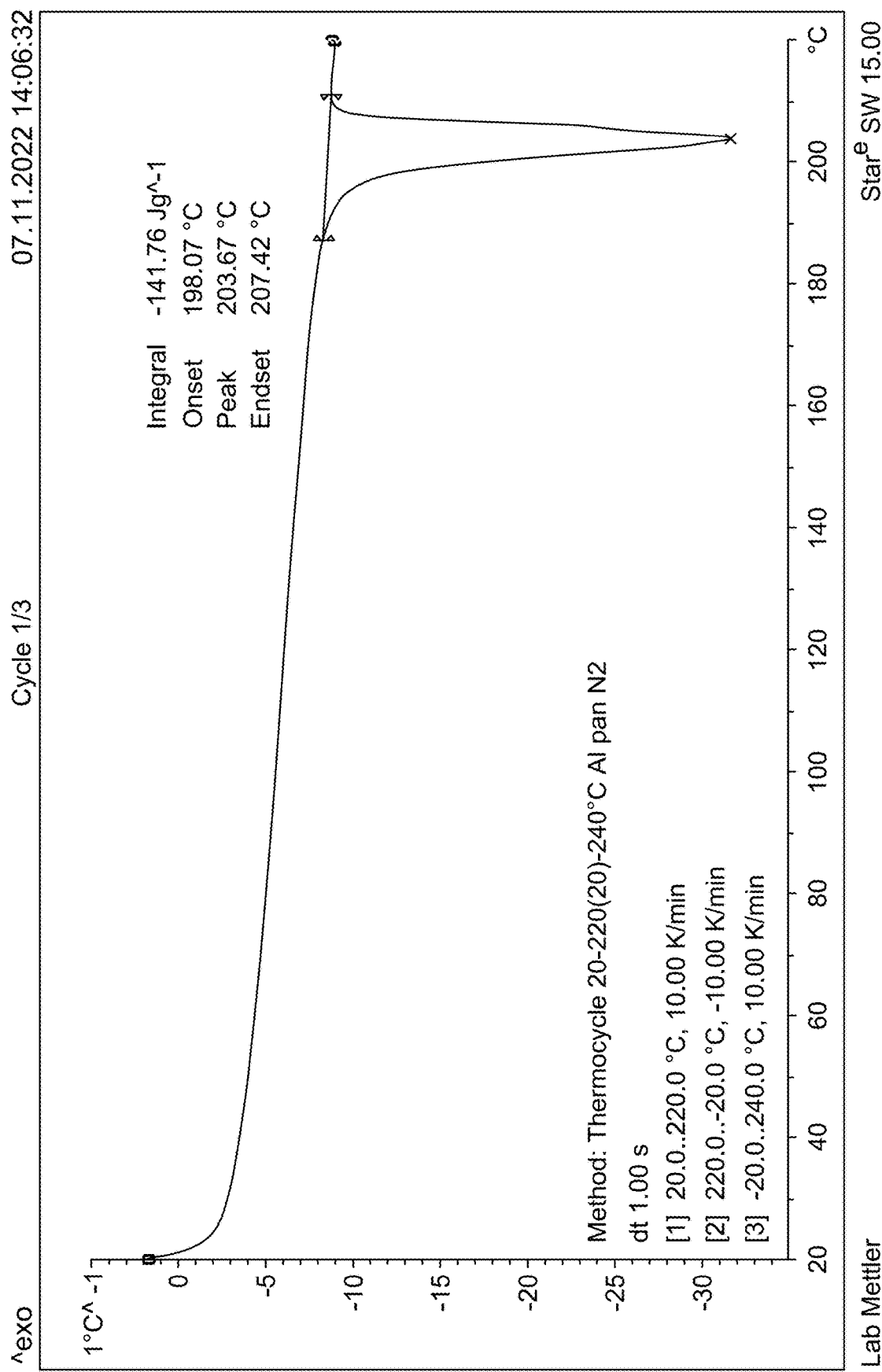

FIG. 371 shows a DSC profile of amorphous compound 1 HCl (amorphous compound 1 HCl, 20 to 220° C., heat flow vs. temperature, extracted from FIG. 370), cycle 1/3.

Figure 372:
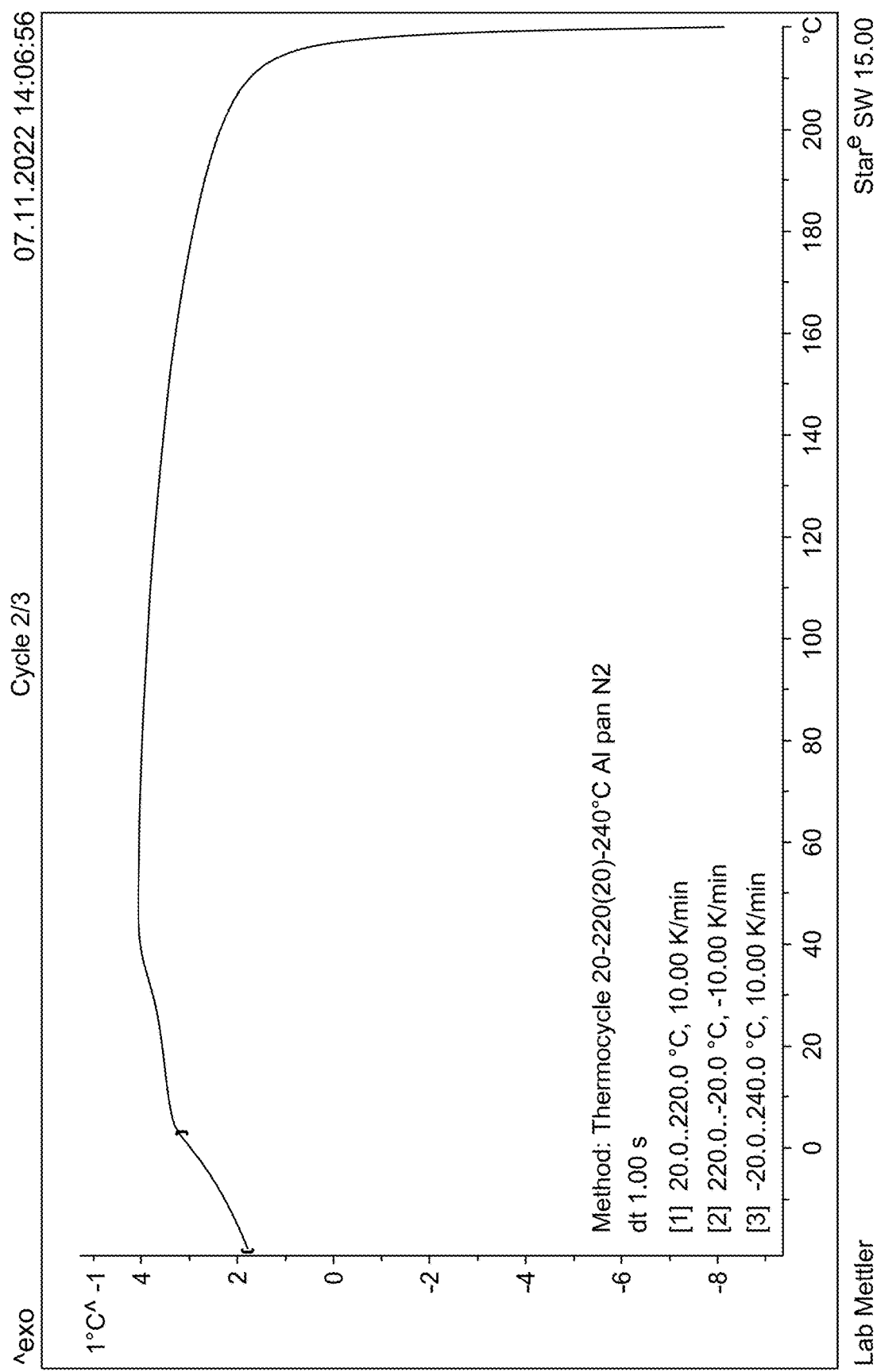

FIG. 372 shows a DSC profile of amorphous compound 1 HCl (amorphous compound 1 HCl, 220 to −20° C., heat flow vs. temperature, extracted from FIG. 370), cycle 2/3.

Figure 373:
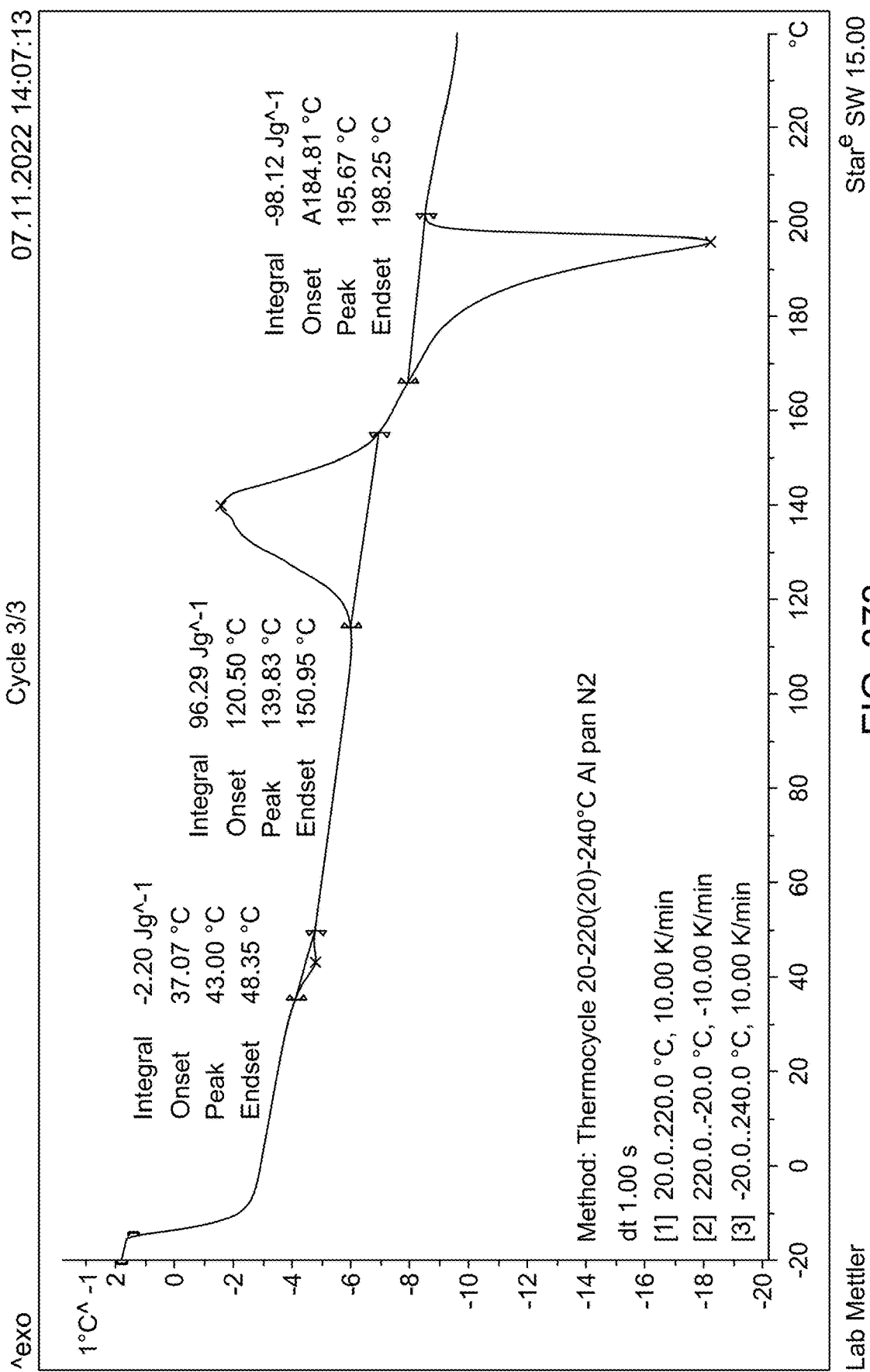

FIG. 373 shows a DSC profile of amorphous compound 1 HCl (amorphous compound 1 HCl −20 to 250° C., heat flow vs temperature, extracted from FIG. 370) Cycle 3/3.

Figure 374:
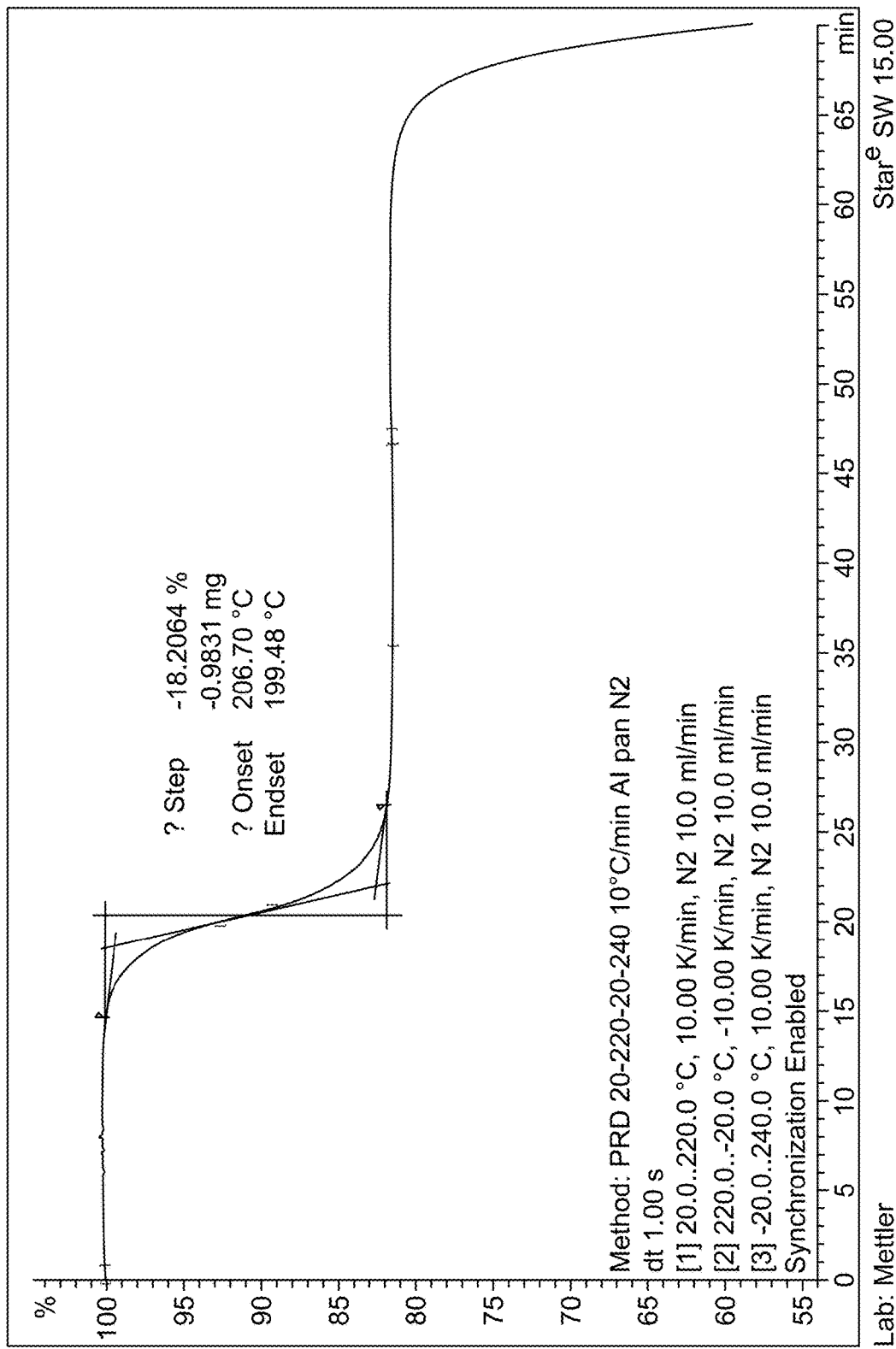

FIG. 374 shows a thermocycle TGA profile of amorphous compound 1 HCl (amorphous compound 1 HCl, mass loss vs time).

Figure 375:
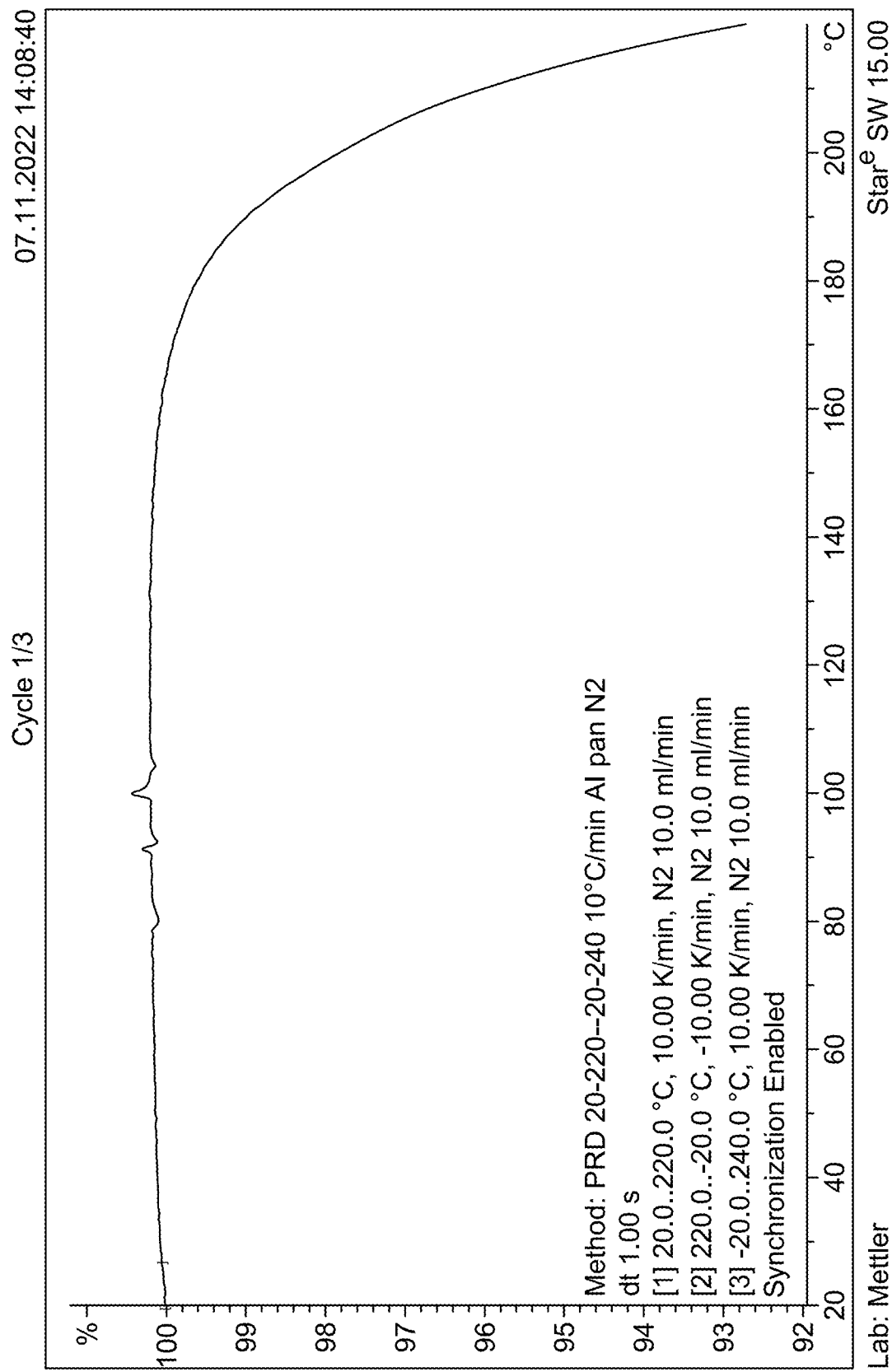

FIG. 375 shows a TGA profile of amorphous compound 1 HCl (amorphous compound 1 HCl, 20 to 220° C., heat flow vs temperature, extracted from FIG. 374) Cycle 1/3.

Figure 376:
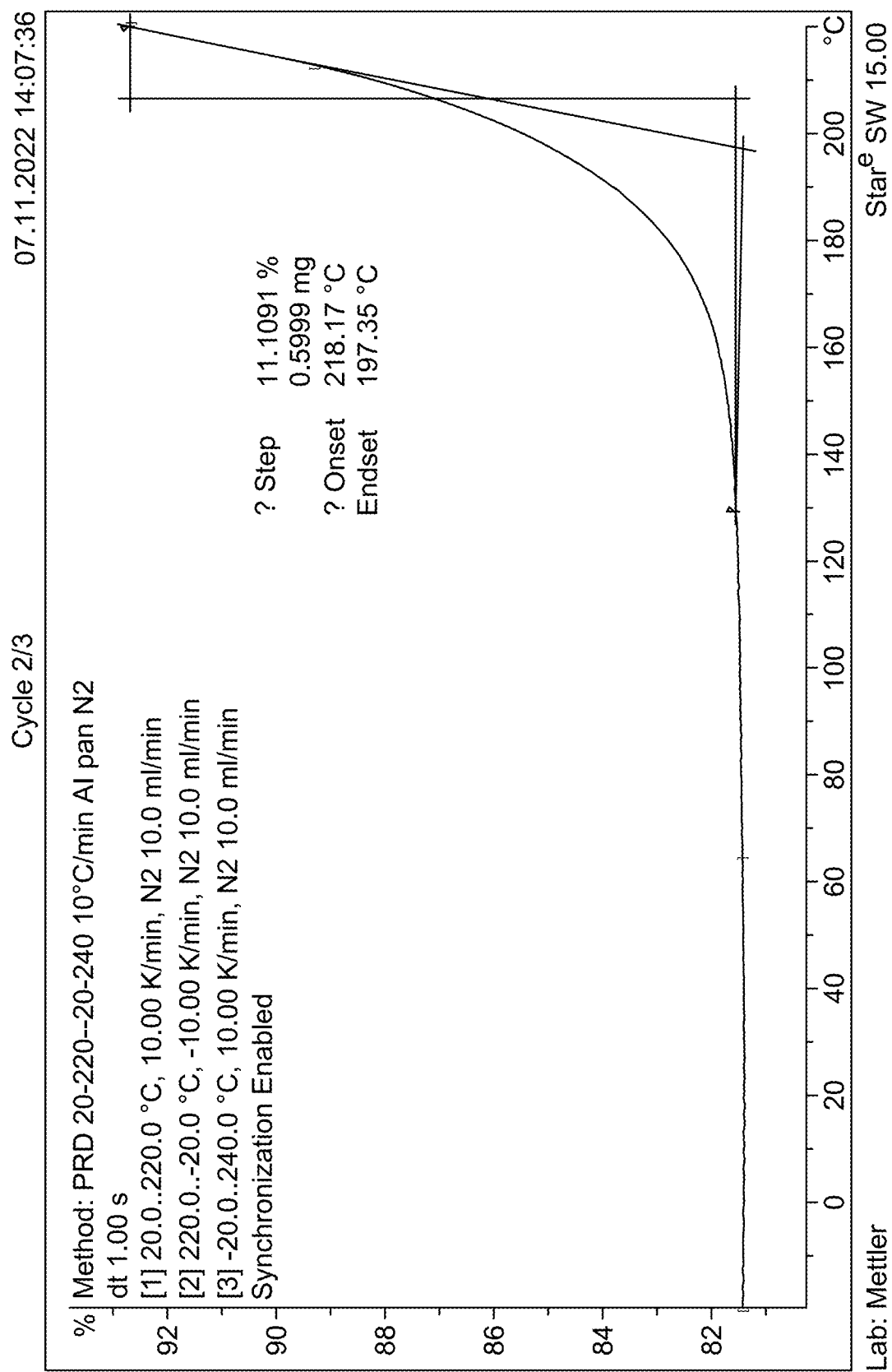

FIG. 376 shows an TGA profile of amorphous compound 1 HCl (amorphous compound 1 HCl, 220 to −20° C., heat flow vs temperature, extracted from FIG. 374) Cycle 2/3.

Figure 377:
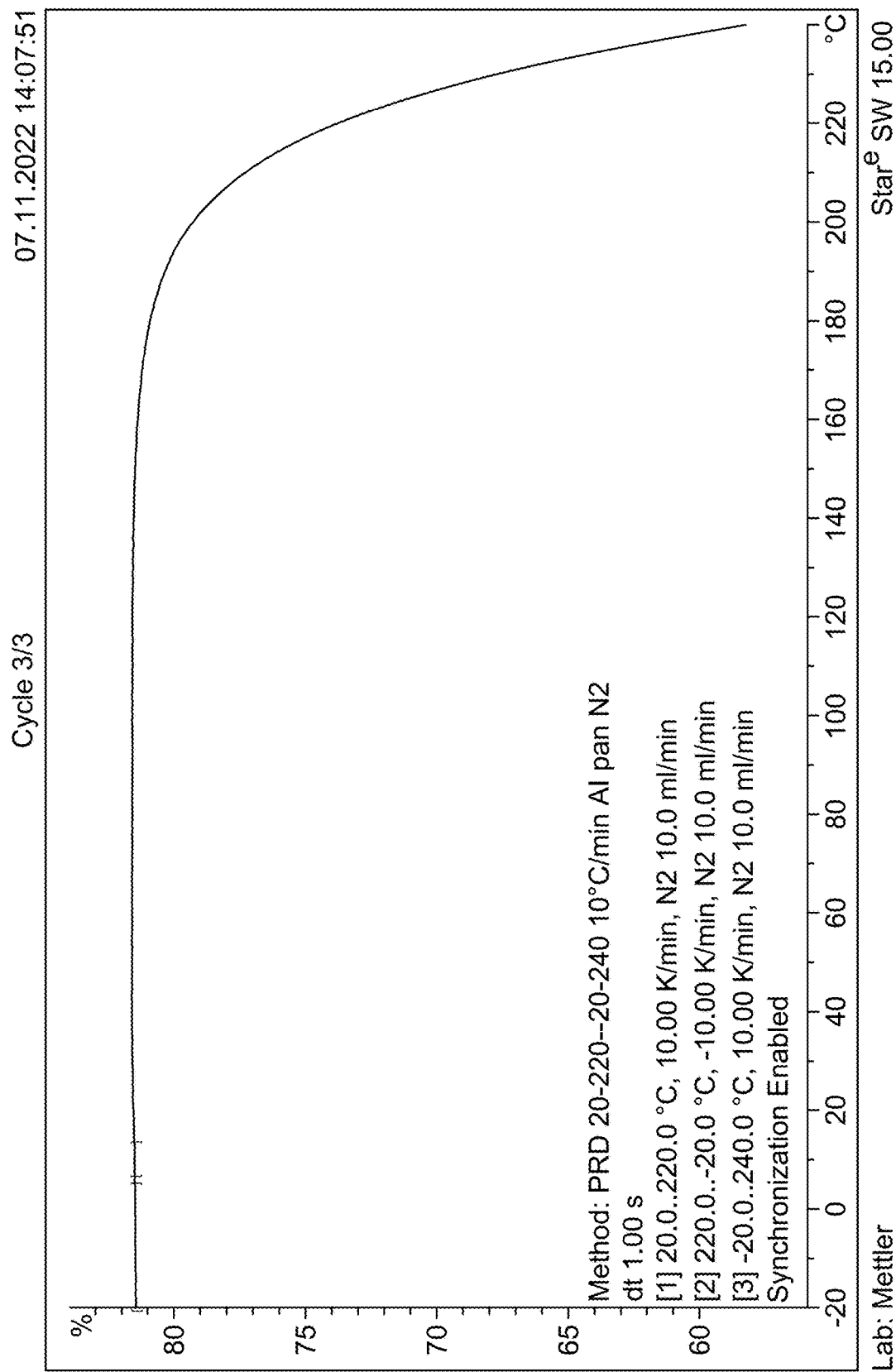

FIG. 377 shows an TGA profile of amorphous compound 1 HCl (amorphous compound 1 HCl, −20 to 250° C., heat flow vs temperature, extracted) Cycle 3/3.

Figure 378:
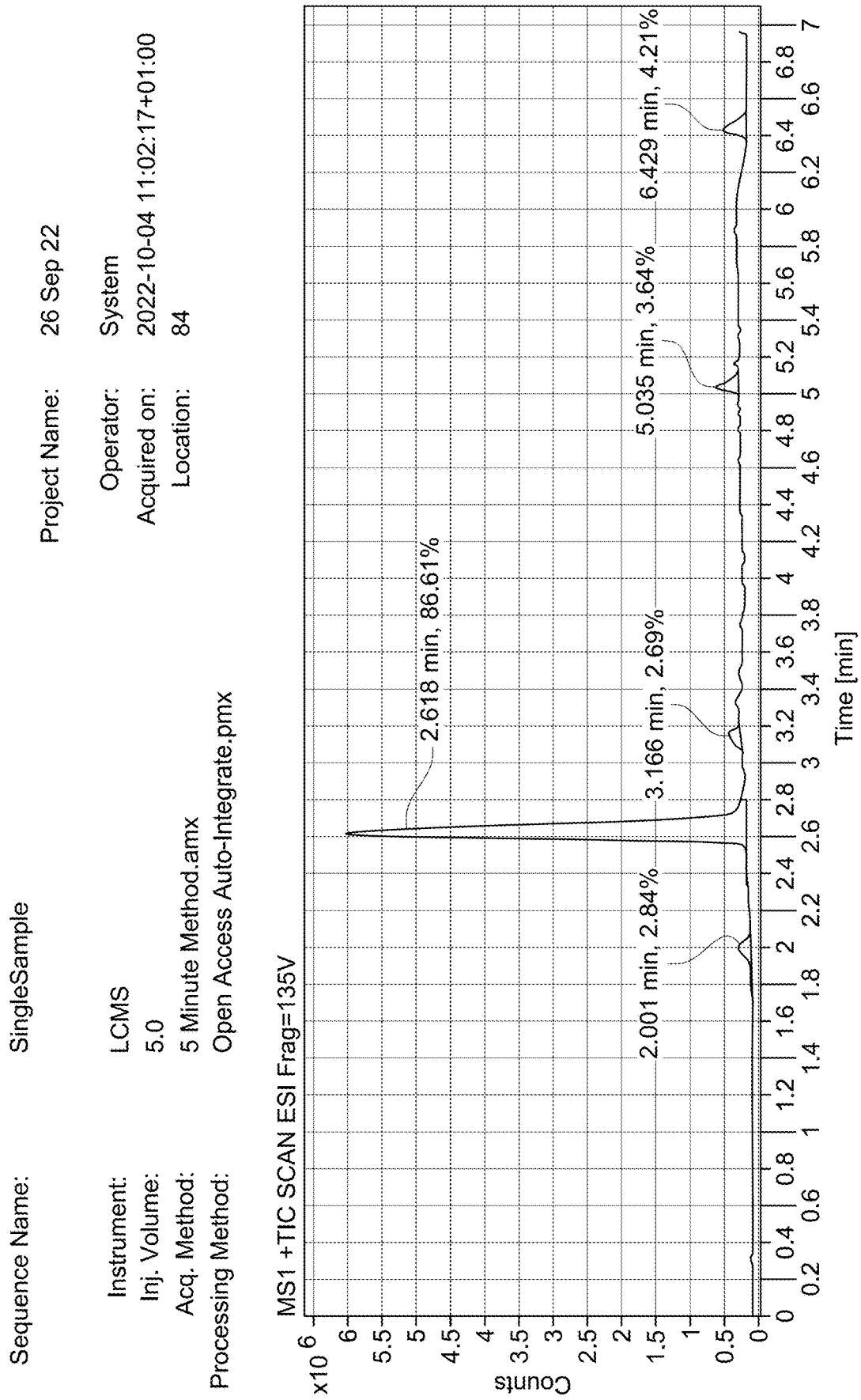

FIG. 378 shows a LC profile of amorphous compound 1 HCl.

Figure 379:
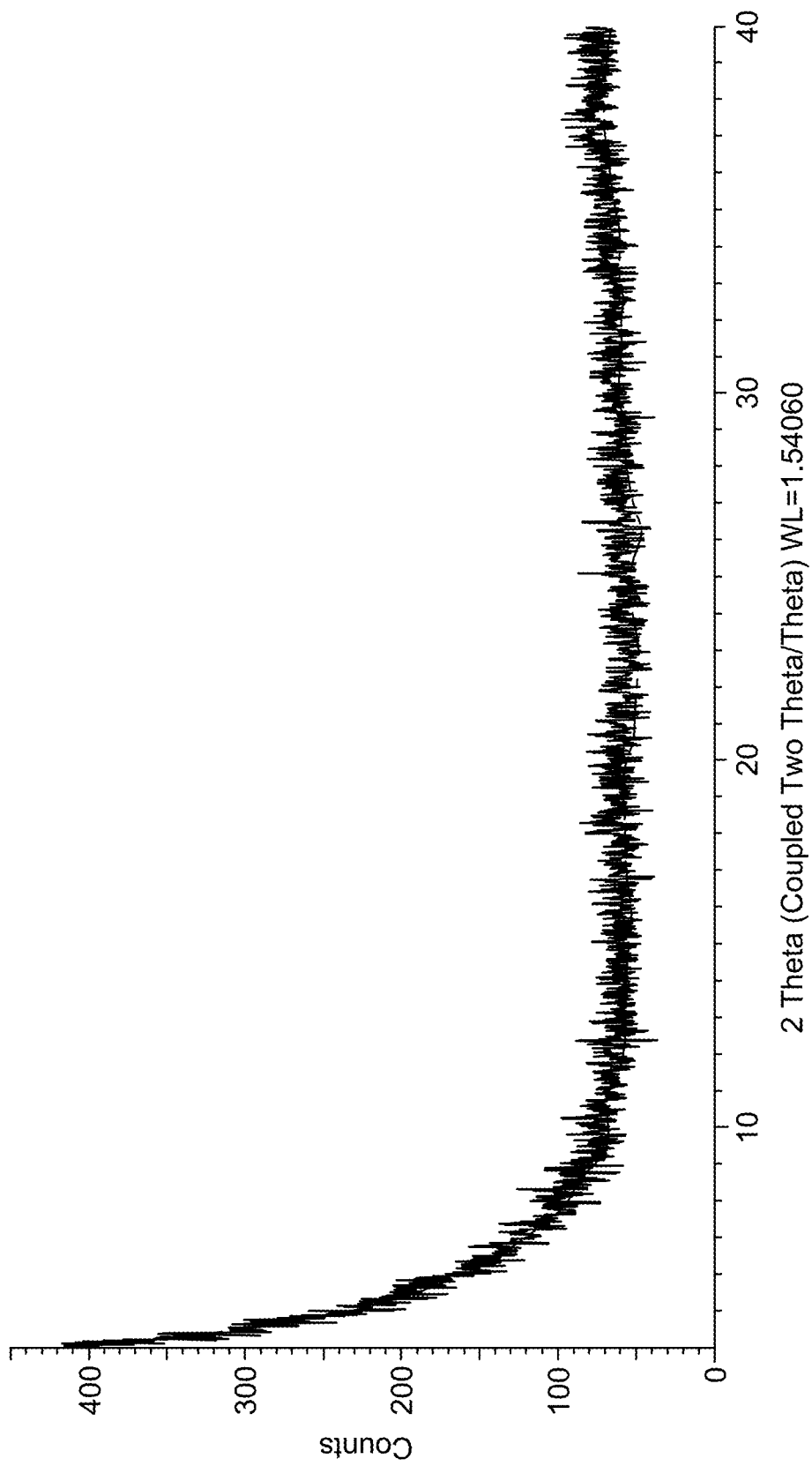

FIG. 379 shows a XRPD profile of amorphous compound 1 monofumarate.

Figure 380:
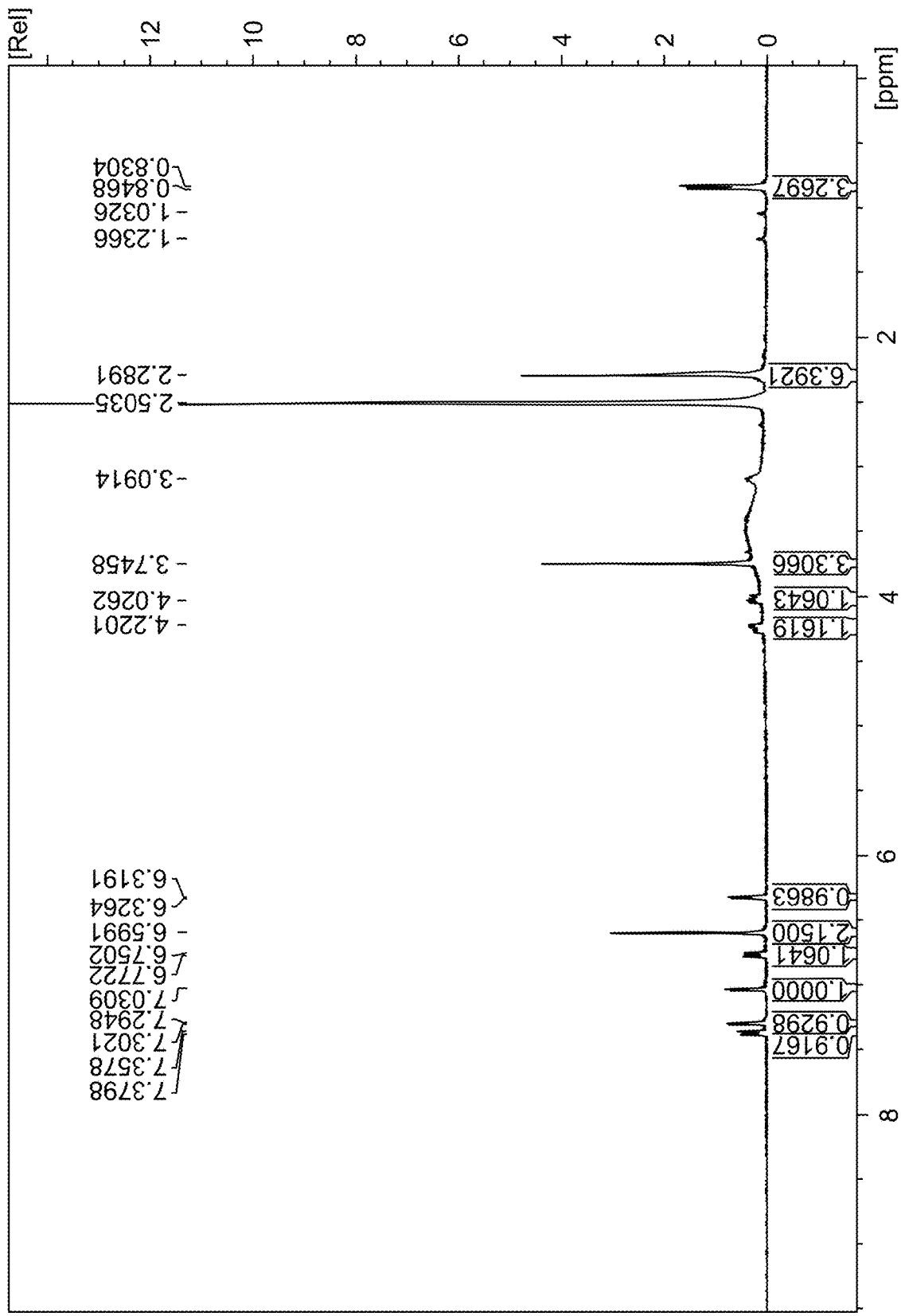

FIG. 380 shows a $^1$H NMR spectrum of amorphous compound 1 monofumarate.

Figure 381:
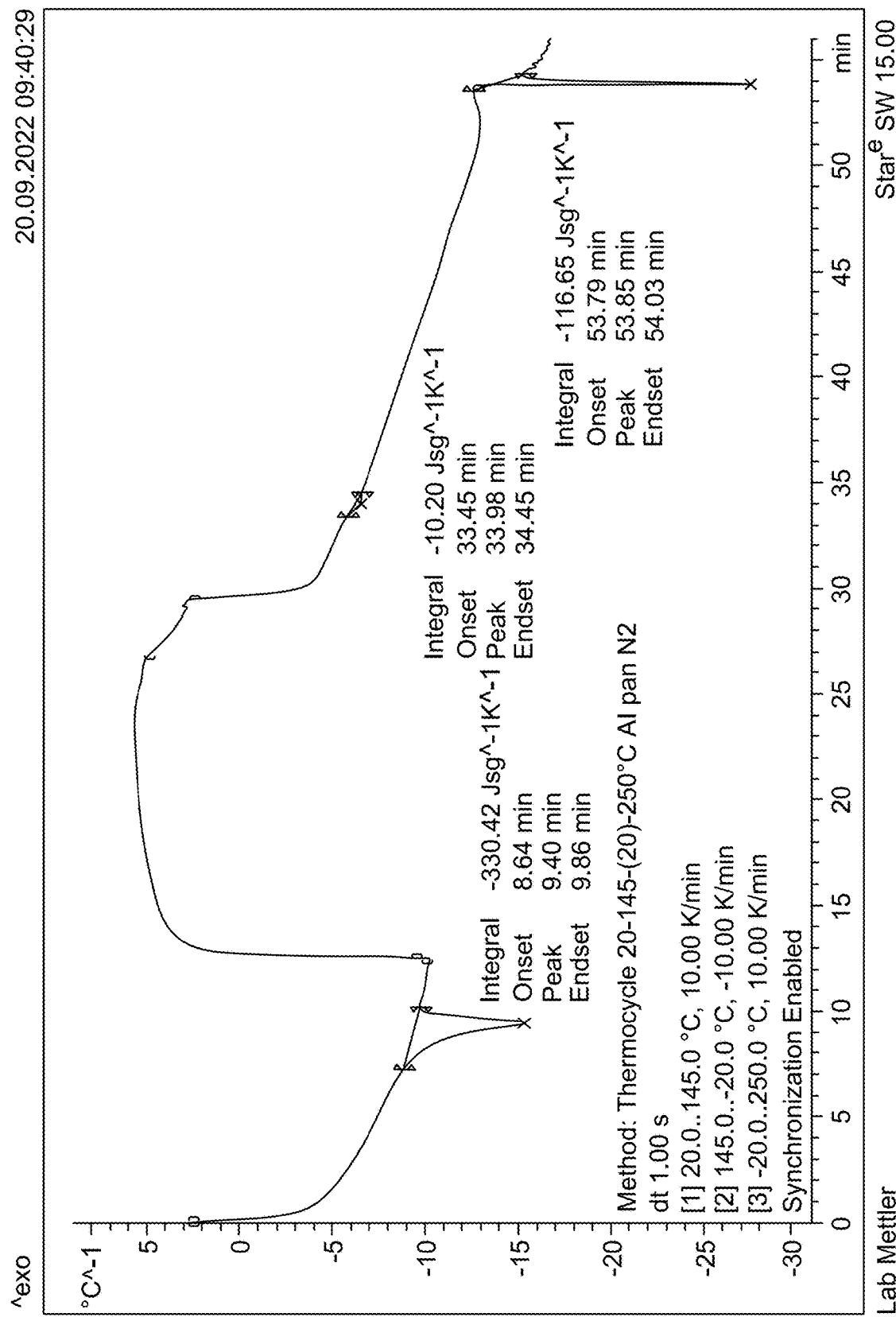

FIG. 381 shows a thermocycle DSC profile of amorphous compound 1 monofumarate (amorphous compound 1 monofumarate, heat flow vs time).

Figure 382:
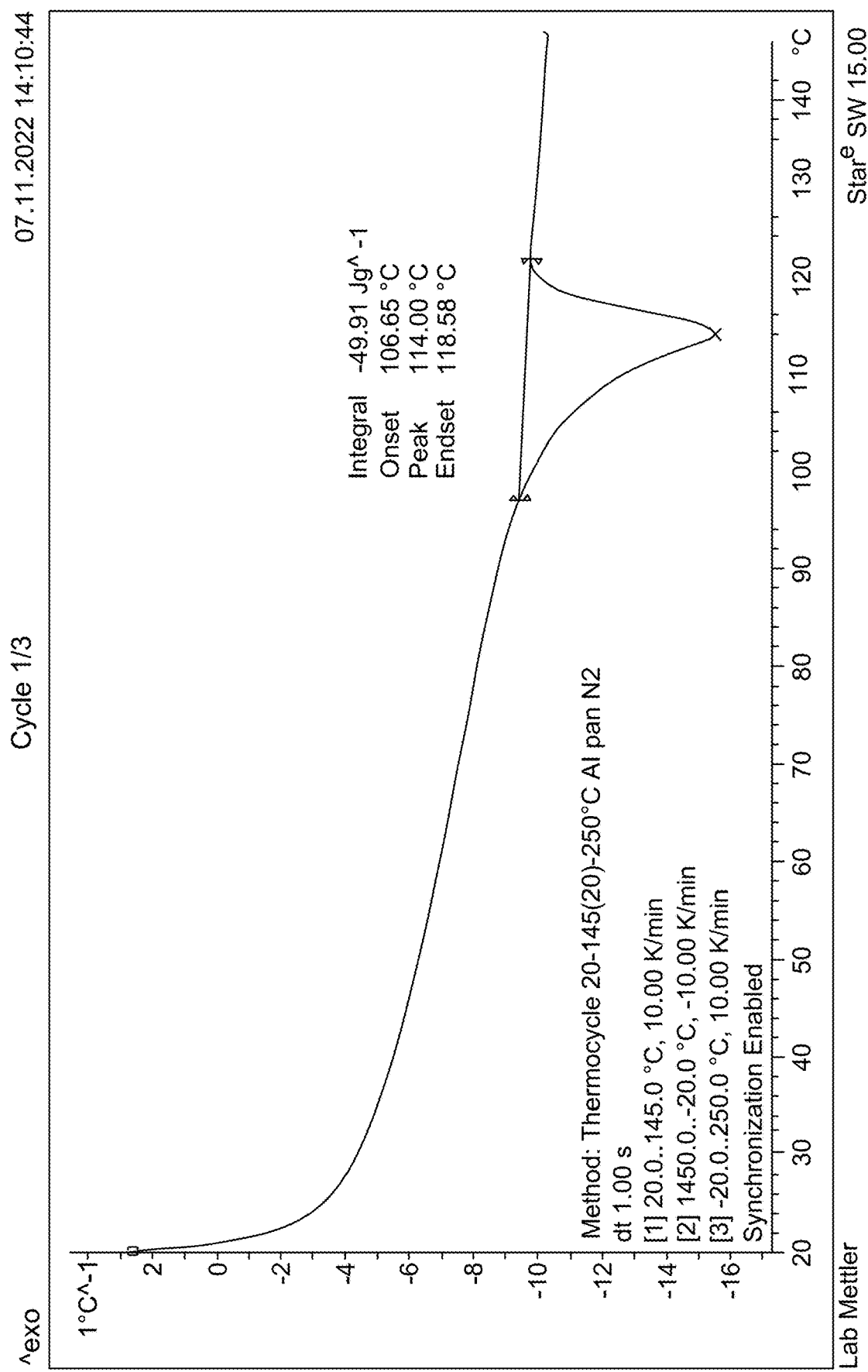

FIG. 382 shows a DSC profile of amorphous compound 1 monofumarate (amorphous compound 1 monofumarate, 20 to 145° C., heat flow vs temperature, extracted from FIG. 381) Cycle 1/3.

Figure 383:
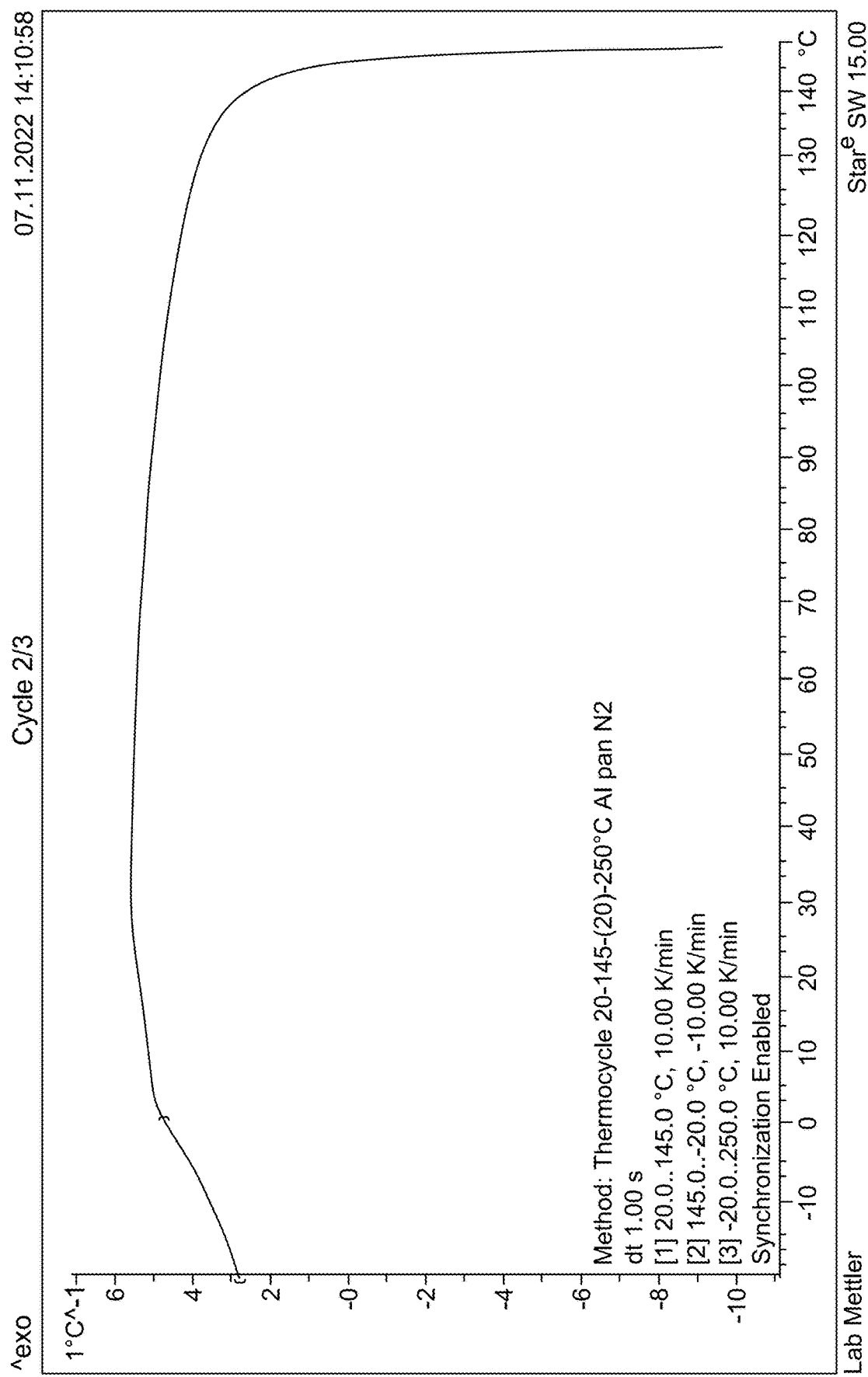

FIG. 383 shows a DSC profile of amorphous compound 1 monofumarate (amorphous compound 1 monofumarate, 145 to −20° C., heat flow vs temperature, extracted from FIG. 381) Cycle 2/3.

Figure 384:
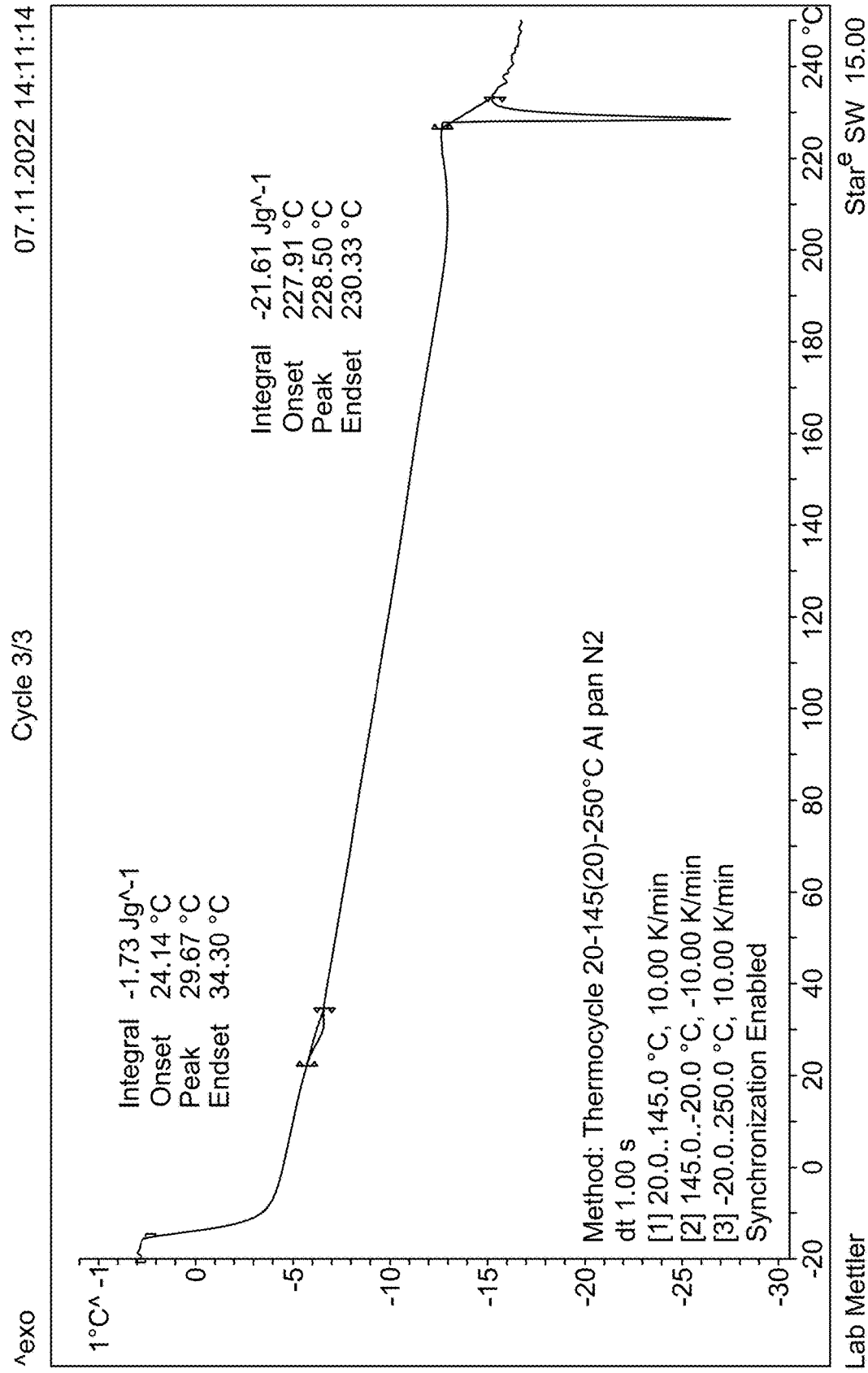

FIG. 384 shows a DSC profile of amorphous compound 1 monofumarate (amorphous compound 1 monofumarate, −20 to 230° C., heat flow vs temperature, extracted from FIG. 381) Cycle 3/3.

Figure 385:
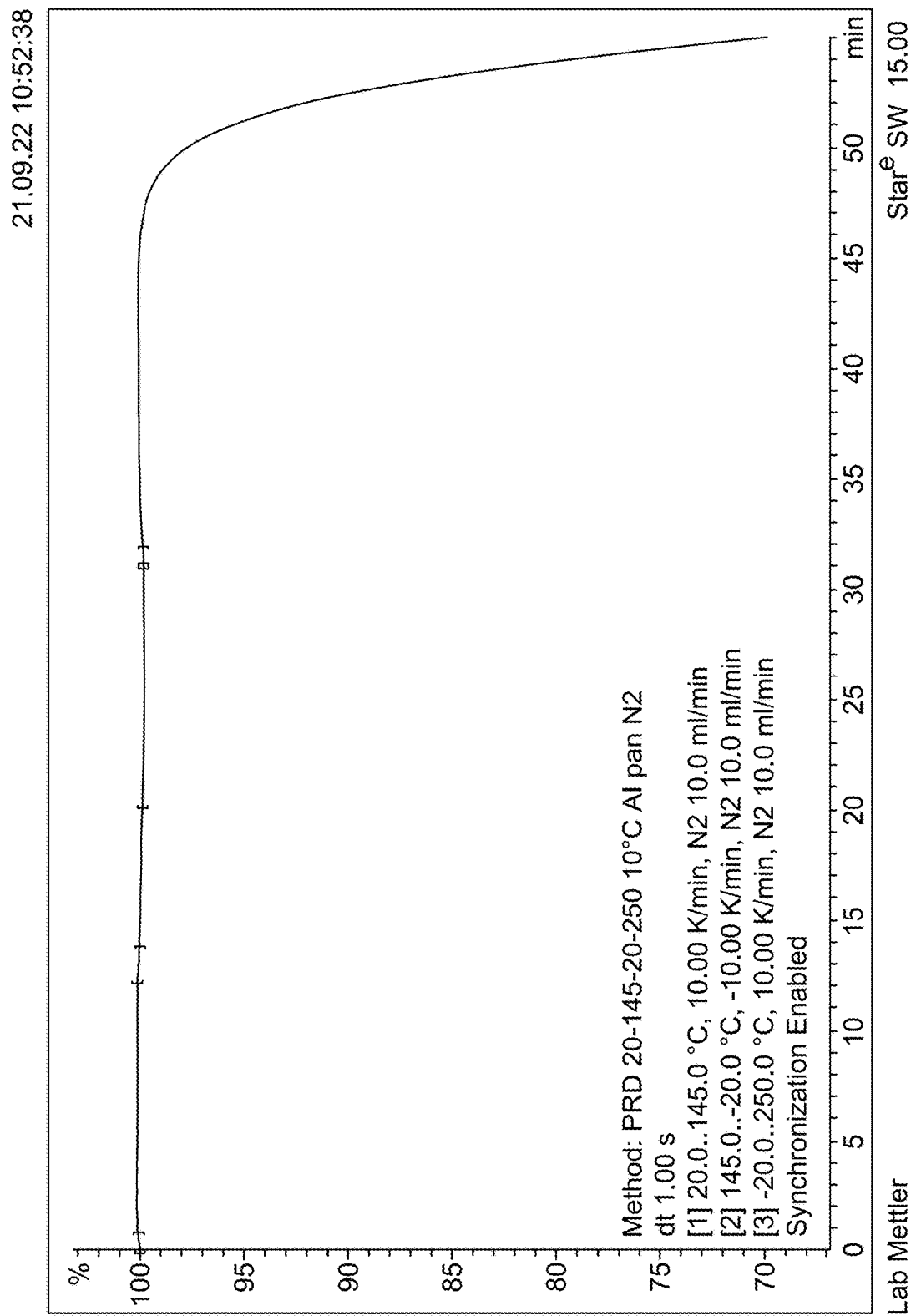

FIG. 385 shows a thermocycle TGA profile of amorphous compound 1 monofumarate (amorphous compound 1 monofumarate, mass loss vs time).

Figure 386:
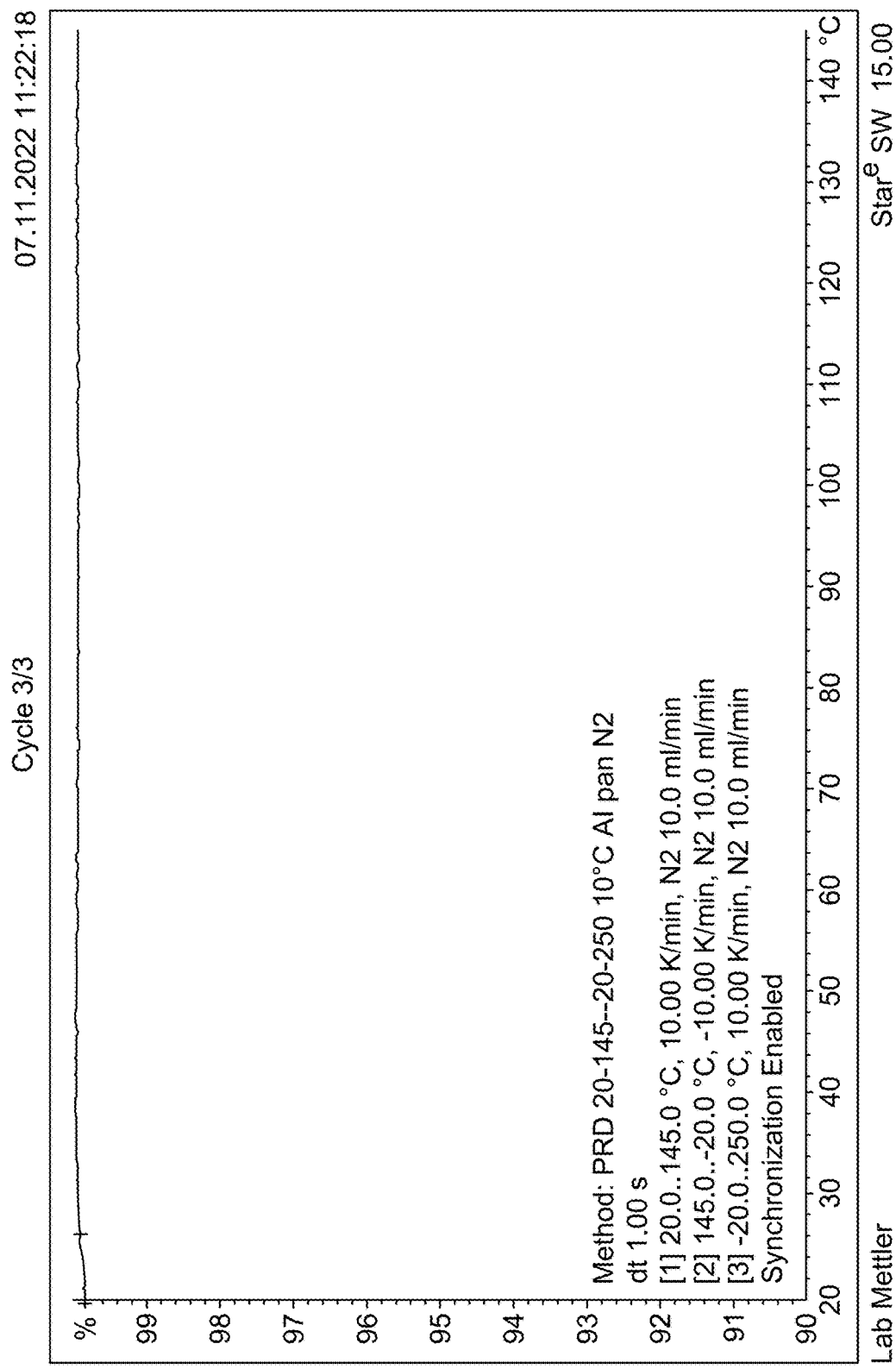

FIG. 386 shows a TGA profile of amorphous compound 1 monofumarate (amorphous compound 1 monofumarate, 20 to 145° C., heat flow vs temperature, extracted from FIG. 385) Cycle 1/3.

Figure 387:
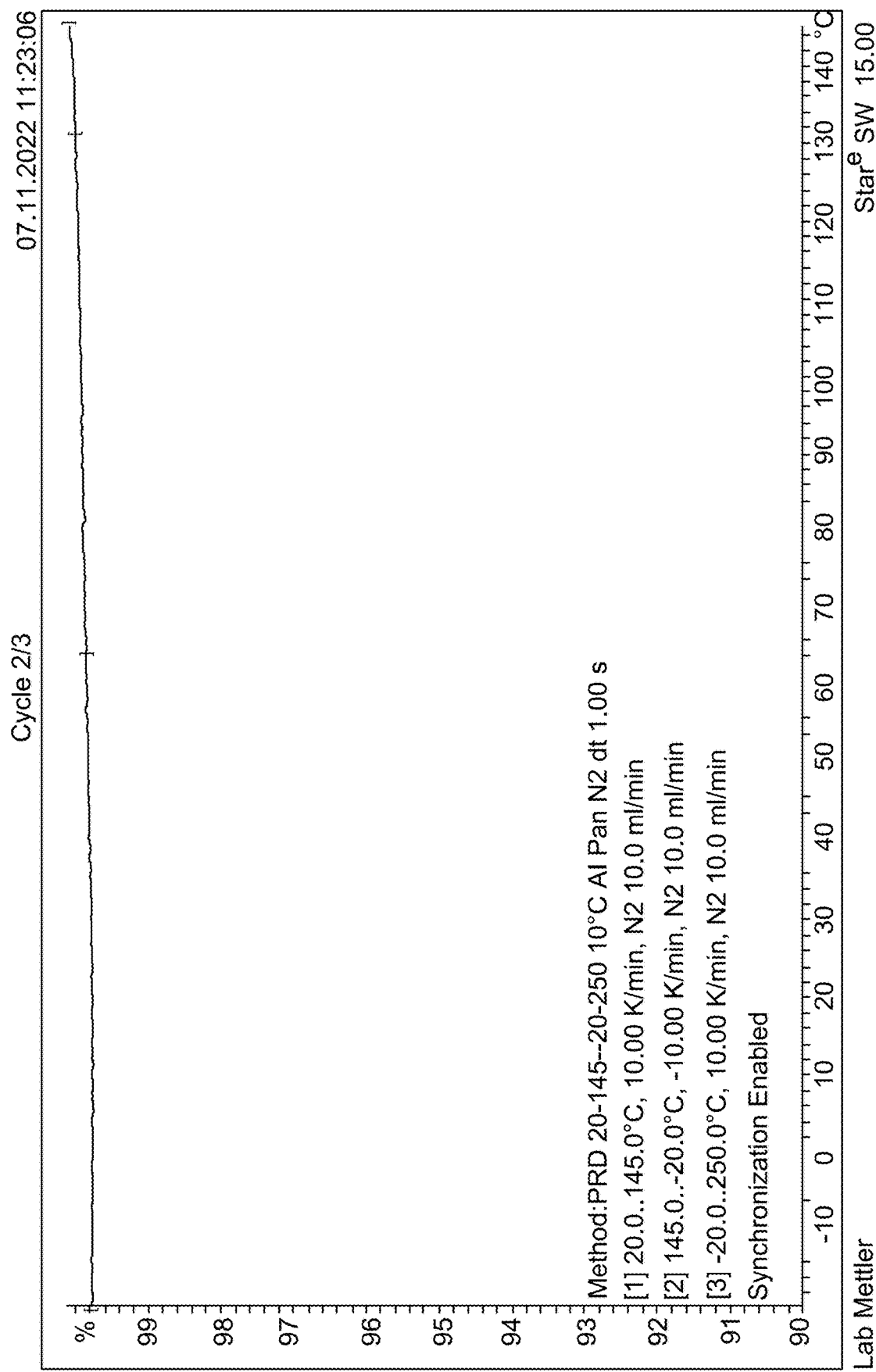

FIG. 387 shows a TGA profile of amorphous compound 1 monofumarate (amorphous compound 1 monofumarate, 145 to −20° C., heat flow vs temperature, extracted from FIG. 385) Cycle 2/3.

Figure 388:
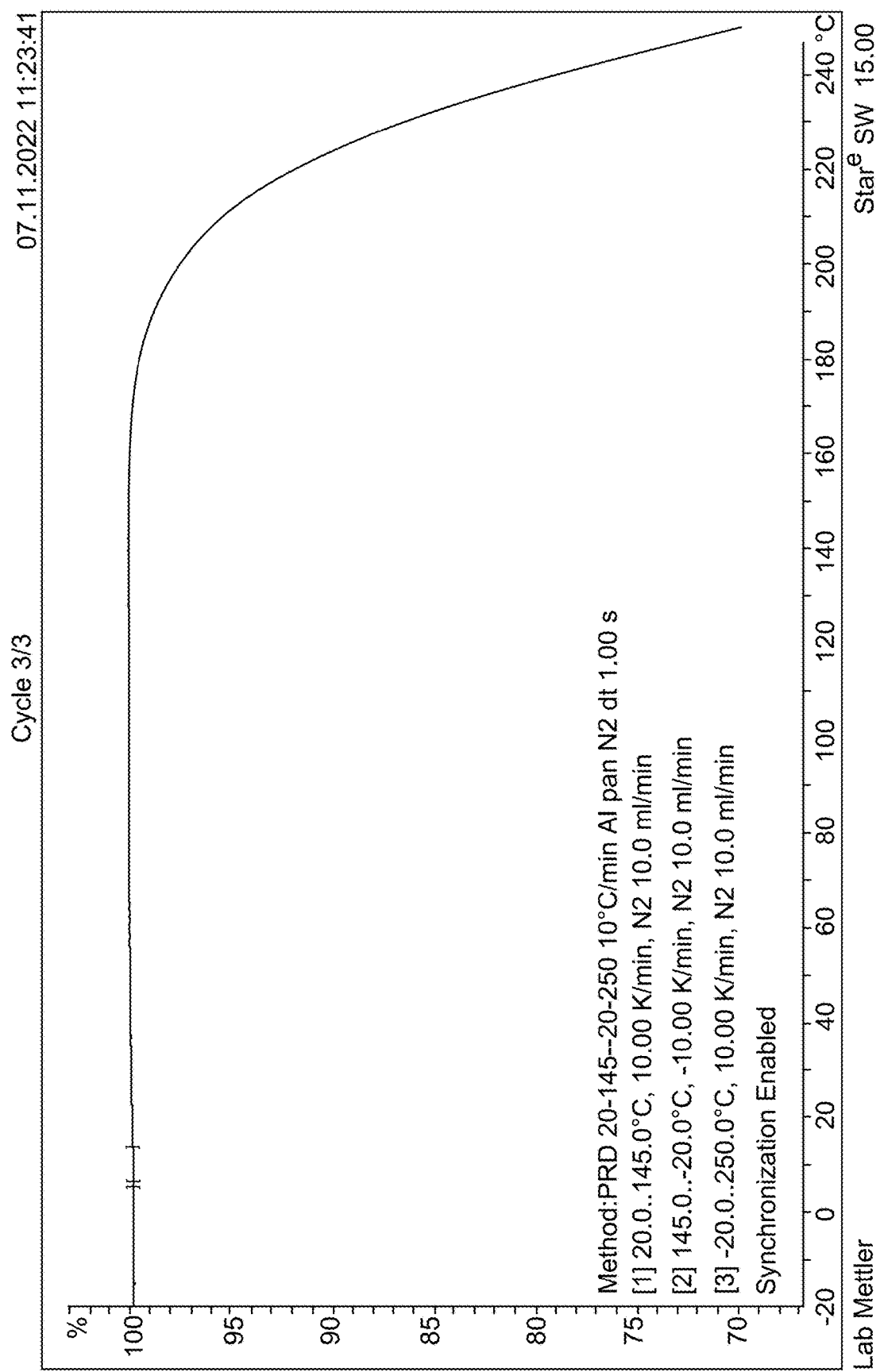

FIG. 388 shows a TGA profile of amorphous compound 1 monofumarate (amorphous compound 1 monofumarate, −20 to 230° C., heat flow vs temperature, extracted from FIG. 385) Cycle 3/3.

Figure 389:
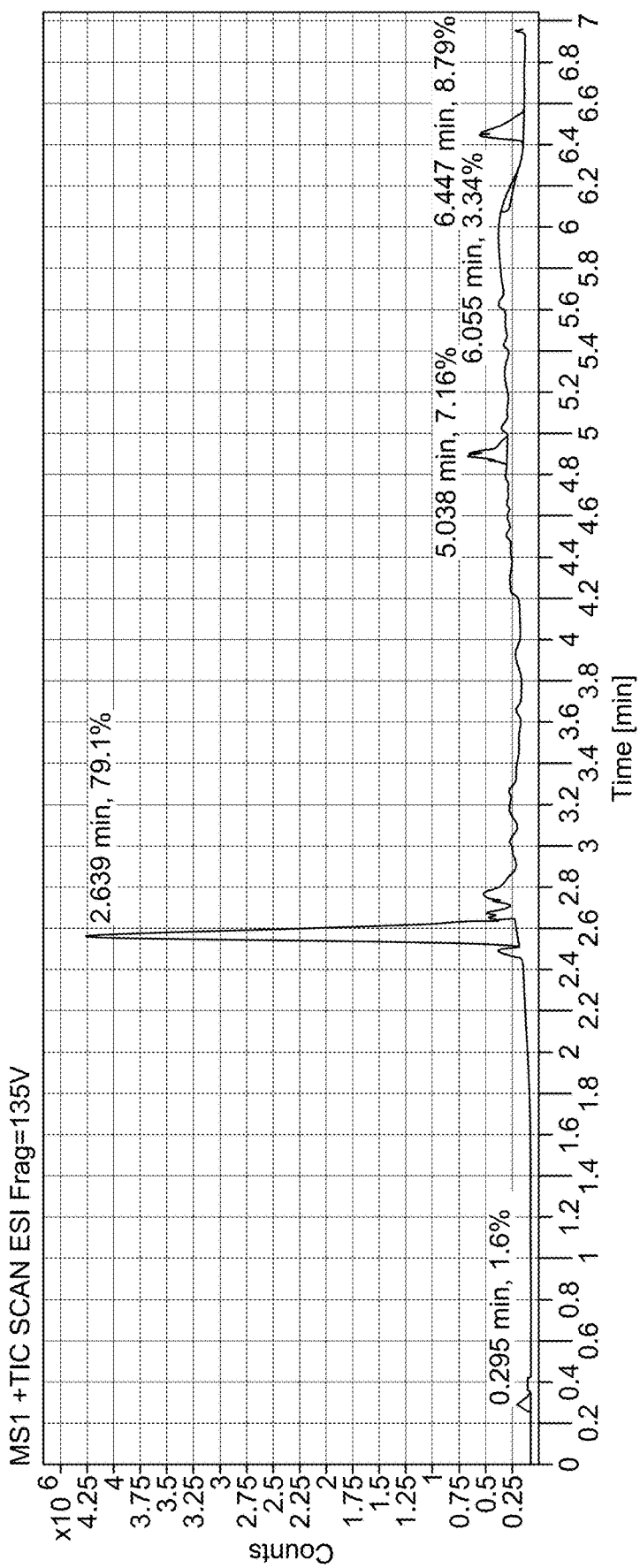

FIG. 389 shows a LC profile of amorphous compound 1 monofumarate.

FIG. 390 shows a XRPD profile of amorphous compound 1 monofumarate.

FIG. 391 shows a XRPD profile of crystalline compound 1 HCl Form A.

DETAILED DESCRIPTION

1. Definitions

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. All references, including patents and patent applications cited herein, are incorporated by reference in their entirety, unless otherwise specified.

The term "about" is used herein to mean approximately, in the region of, roughly or around. When the term "about" is used in conjunction with a numerical range, it modifies that range by extending the boundaries above and below the numerical values set forth. In general, the term "about" is used herein to modify a numerical value above and below the stated value by a variance of 20%, a variance of 10%, a variance of 5%, a variance of 3%, or a variance of 1%. When used in the context of XRPD signal values, the term "about" can indicate a signal value ±0.20, ±0.15, ±0.10, ±0.05, or ±0.01°2θ. In some embodiments, when used in the context of XRPD signal values "about" can indicate a signal value at substantially exactly the disclosed signal value.

Unless explained otherwise, all technical and scientific terms used herein have the same meaning as commonly understood by one of ordinary skill in the art to which this disclosure pertains. Although methods and materials similar or equivalent to those described herein can be used in the practice or testing of the present disclosure, suitable methods and materials are described below. The materials, methods, and examples are illustrative only and not intended to be limiting.

"Administering" refers to any suitable mode of administration, including, oral administration, administration as a suppository, topical contact, parenteral, intravenous, intraperitoneal, intramuscular, intralesional, intranasal or subcutaneous administration, intrathecal administration, or the implantation of a slow-release device e.g., a mini-osmotic pump, to the subject.

As used herein, the name "(R)-1-(5-methoxy-1H-indol-1-yl)-N,N-dimethylpropan-2-amine" refers to the compound

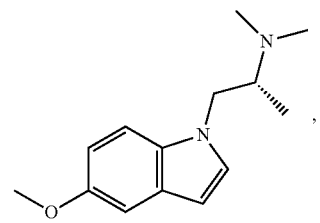

which also is referred to herein as "Compound 1."

As used herein, the name "(R)-1-(5-methoxy-1H-indol-1-yl)-N,N-dimethylpropan-2-amine fumarate" refers to the fumaric acid salt of (R)-1-(5-methoxy-1H-indol-1-yl)-N,N-dimethylpropan-2-amine

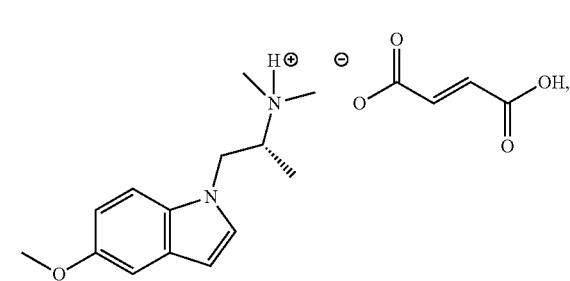

which also is referred to herein as "Compound 1 fumarate."

As used herein, the name "(R)-1-(5-methoxy-1H-indol-1-yl)-N,N-dimethylpropan-2-amine hemifumarate" refers to the hemifumaric acid salt of (R)-1-(5-methoxy-1H-indol-1-yl)-N,N-dimethylpropan-2-amine

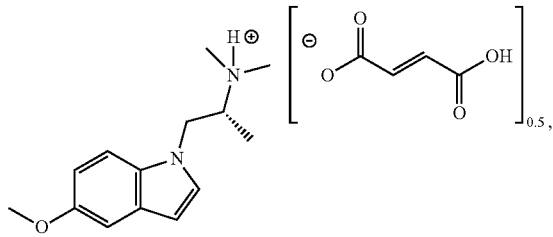

which also is referred to herein as "Compound 1·hemifumarate."

As used herein, other Compound 1 salts are referred to in similar manner as described above. A person of ordinary skill in the art would understand such nomenclature (e.g. Compound 1 HCl, etc.).

As used herein, the term "subject" refers to an animal, such as a mammal, including, but not limited to, primates (e.g., humans), cows, sheep, goats, horses, dogs, cats, rabbits, rats, mice and the like. In certain embodiments, the subject is a human subject.

As used herein, the term "therapeutically effective amount" or "therapeutically sufficient amount" or "effective or sufficient amount" refers to a dose that produces therapeutic effects for which it is administered. The exact dose will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins). In sensitized cells, the therapeutically effective dose can often be lower than the conventional therapeutically effective dose for non-sensitized cells.

As used herein, the term "neuronal plasticity" refers to the ability of the brain to change its structure and/or function continuously throughout a subject's life. Examples of the changes to the brain include, but are not limited to, the ability to adapt or respond to internal and/or external stimuli, such as due to an injury, and the ability to produce new neurites, dendritic spines, and synapses.

As used herein, the term "brain disorder" refers to a neurological disorder which affects the brain's structure and function. Brain disorders can include, but are not limited to, Alzheimer's, Parkinson's disease, psychological disorder, depression, treatment resistant depression, addiction, anxiety, post-traumatic stress disorder, suicidal ideation, major depressive disorder, bipolar disorder, schizophrenia, stroke, traumatic brain injury, and substance use disorder.

As used herein, the term "combination therapy" refers to a method of treating a disease or disorder, wherein two or more different pharmaceutical agents are administered in overlapping regimens so that the subject is simultaneously exposed to both agents. For example, the compounds of the invention can be used in combination with other pharmaceutically active compounds. The compounds of the invention can be administered simultaneously (as a single preparation or separate preparation) or sequentially to the other drug therapy. In general, a combination therapy envisions administration of two or more drugs during a single cycle or course of therapy.

As used herein, the term "neurotrophic factors" refers to a family of soluble peptides or proteins which support the survival, growth, and differentiation of developing and mature neurons.

As used herein, the term "modulate" or "modulating" or "modulation" refers to an increase or decrease in the amount, quality, or effect of a particular activity, function or molecule. By way of illustration and not limitation, agonists, partial agonists, antagonists, and allosteric modulators (e.g., a positive allosteric modulator) of a G protein-coupled receptor (e.g., $5HT_{2A}$) are modulators of the receptor.

As used herein, the terms "powder X-ray diffraction pattern", "PXRD pattern", "X-ray powder diffraction pattern", and "XRPD pattern" are used interchangeably and refer to the experimentally observed diffractogram or parameters derived therefrom. Powder X-ray diffraction patterns are typically characterized by signal position (abscissa) and signal intensities (ordinate). The term "signal intensities" refers to relative signal intensities within a given X-ray diffraction pattern. Factors which can affect the relative signal intensities are sample thickness and preferred orientation (i.e., the crystalline particles are not distributed randomly). The term "signal positions" as used herein refers to X-ray reflection positions as measured and observed in powder X-ray diffraction experiments. Signal positions are directly related to the dimensions of the unit cell. The signals, identified by their respective signal positions, are extracted from the diffraction patterns for the various polymorphic forms of salts of R-ketamine.

As used herein, the term "2 theta value", "2θ" or "2 θ" refers to the signal position in degrees based on the experimental setup of the X-ray diffraction experiment and is a common abscissa unit in diffraction patterns. In general, the experimental setup requires that if a reflection is diffracted when the incoming beam forms an angle theta (θ) with a certain lattice plane, the reflected beam is recorded at an angle 2 theta (2 θ). It should be understood that reference herein to specific 2θ values for a specific polymorphic form is intended to mean the 2θ values (in degrees) as measured using the X-ray diffraction experimental conditions as described herein.

As used herein, the term "preferred orientation effects" refer to variable signal intensities or relative intensity differences between different PXRD measurements of the same samples that can be due to the orientation of the particles. Without wishing to be bound by theory, in PXRD it can be desirable to have a sample in which particles are oriented randomly (e.g., a powder). However, it can be difficult or in some cases impossible to achieve truly random particle orientations in practice. As particle size increases, the randomness of particle orientation can decrease, leading to increased challenges with achieving a preferred orientation. Without wishing to be bound by theory, a smaller particle size can reduce technical challenges associated with preferred orientation and allow for more accurate representation of signals. However, one of skill in the art will understand how to reduce or mitigate preferred orientation effects and will recognize preferred orientation effects that can exist even between two different measurements of the same sample. For instance, in some embodiments, differences in resolution or relative signal intensities can be attributed to preferred orientation effects.

As used herein, the term "substantially pure" with reference to a particular salt (or to a mixture of two or more salts) of a compound indicates the salt (or a mixture) includes less than 10%, less than 5%, less than 3%, less than 1%, less than 0.5%, less than 0.2%, or less than 0.1% by weight of impurities, including other salt forms of the compound. Such purity may be determined, for example, by powder X-ray diffraction.

As used herein, the term "polymorph" or "salt form" refers to different crystalline forms of the same compound and other solid state molecular forms including pseudopolymorphs, such as hydrates (e.g., bound water present in the crystalline structure) and solvates (e.g., bound solvents other than water) of the same compound. Different crystalline polymorphs have different crystal structures due to a different packing of the molecules in the lattice. This results in a different crystal symmetry and/or unit cell parameters which directly influences its physical properties such as the X-ray diffraction characteristics of crystals or powders. A different polymorph, for example, will in general diffract at a different set of angles and will give different values for the intensities. Therefore, X-ray powder diffraction can be used to identify different polymorphs, or a solid form that comprises more than one polymorph, in a reproducible and reliable way (S. Byrn et al, Pharmaceutical Solids: A Strategic Approach to Regulatory Considerations, Pharmaceutical research, Vol. 12, No. 7, p. 945-954, 1995; J. K. Haleblian and W. McCrone, Pharmacetical Applications of Polymorphism, Journal of Pharmaceutical Sciences, Vol. 58, No. 8, p. 911-929, 1969).

Crystalline polymorphic forms are of interest to the pharmaceutical industry and especially to those involved in the development of suitable dosage forms. If the polymorphic form is not held constant during clinical or stability studies, the exact dosage form used or studied may not be comparable from one lot to another. It is also desirable to have processes for producing a compound with the selected polymorphic form in high purity when the compound is used in clinical studies or commercial products since impurities present may produce undesired toxicological effects. Certain polymorphic forms may exhibit enhanced thermodynamic stability or may be more readily manufactured in high purity in large quantities, and thus are more suitable for inclusion in pharmaceutical formulations. Certain polymorphs may display other advantageous physical properties such as lack of hygroscopic tendencies, improved solubility, and enhanced rates of dissolution due to different lattice energies.

The term "amorphous" refers to any solid substance which (i) lacks order in three dimensions, or (ii) exhibits order in less than three dimensions, order only over short distances (e.g., less than 10 A), or both. Thus, amorphous substances include partially crystalline materials and crystalline mesophases with, e.g., one- or two-dimensional translational order (liquid crystals), orientational disorder (orientationally disordered crystals), or conformational disorder (conformationally disordered crystals). Amorphous solids may be characterized by known techniques, including powder X-ray diffraction (PXRD) crystallography, solid state nuclear magnet resonance (ssNMR) spectroscopy, differential scanning calorimetry (DSC), or some combination of these techniques. Amorphous solids may give diffuse PXRD patterns, typically comprised of one or two broad signals (i.e., signals having base widths of about 5°2Θ or greater).

As used herein, the term "crystalline" refers to any solid substance exhibiting three-dimensional order, which in contrast to an amorphous solid substance, gives a distinctive PXRD pattern with sharply defined signals.

As used herein, the term "ambient temperature" refers to a temperature condition typically encountered in a laboratory setting. This includes the approximate temperature range of about 20 to about 30° C.

As used herein, the term "detectable amount" refers to an amount or amount per unit volume that can be detected using conventional techniques, such as X-ray powder diffraction, differential scanning calorimetry, HPLC, Fourier Transform Infrared Spectroscopy (FT-IR), Raman spectroscopy, and the like.

As used herein, the term "solvate" describes a molecular complex comprising the drug substance and a stoichiometric or non-stoichiometric amount of one or more solvent molecules (e.g., ethanol). When the solvent is tightly bound to the drug the resulting complex will have a well-defined stoichiometry that is independent of humidity. When, however, the solvent is weakly bound, as in channel solvates and hygroscopic compounds, the solvent content will be dependent on humidity and drying conditions. In such cases, the complex may be non-stoichiometric.

As used herein, the term "hydrate" describes a solvate comprising the drug substance and a stoichiometric or non-stoichiometric amount of water.

As used herein, the term "relative humidity" refers to the ratio of the amount of water vapor in air at a given temperature to the maximum amount of water vapor that can be held at that temperature and pressure, expressed as a percentage.

As used herein, the term "relative intensity" refers to an intensity value derived from a sample X-ray diffraction pattern. The complete ordinate range scale for a diffraction pattern is assigned a value of 100. A signal having intensity falling between about 50% to about 100% on this scale intensity is termed very strong (vs); a signal having intensity falling between about 50% to about 25% is termed strong (s). Additional weaker signals are present in typical diffraction patterns and are also characteristic of a given polymorph, wherein the additional signals are termed medium (m), weak (w) and very weak (vw).

As used herein, the term "slurry" refers to a solid substance suspended in a liquid medium, typically water or an organic solvent.

As used herein, the term "under vacuum" refers to typical pressures obtainable by a laboratory oil or oil-free diaphragm vacuum pump.

As used herein, the term "agonism" refers to the activation of a receptor or enzyme by a modulator, or agonist, to produce a biological response.

As used herein, the term "agonist" refers to a modulator that binds to a receptor or enzyme and activates the receptor to produce a biological response. By way of example only, "$5HT_{2A}$ agonist" can be used to refer to a compound that exhibits an ECo with respect to $5HT_{2A}$ activity of no more than about 100 mM. In some embodiments, the term "agonist" includes full agonists or partial agonists. "Full agonist" refers to a modulator that binds to and activates a receptor with the maximum response that an agonist can elicit at the receptor. "Partial agonist" refers to a modulator that binds to and activates a given receptor, but has partial efficacy, that is, less than the maximal response, at the receptor relative to a full agonist.

As used herein, the term "positive allosteric modulator" refers to a modulator that binds to a site distinct from the orthosteric binding site and enhances or amplifies the effect of an agonist.

As used herein, the term "antagonism" refers to the inactivation of a receptor or enzyme by a modulator, or antagonist. Antagonism of a receptor, for example, is when a molecule binds to the receptor and does not allow activity to occur.

As used herein, the term "antagonist" or "neutral antagonist" refers to a modulator that binds to a receptor or enzyme and blocks a biological response. An antagonist has no activity in the absence of an agonist or inverse agonist but can block the activity of either, causing no change in the biological response.

As used herein, the term "composition" refers to a product comprising the specified ingredients in the specified amounts, as well as any product, which results, directly or indirectly, from combination of the specified ingredients in the specified amounts. By "pharmaceutically acceptable" it is meant the carrier, diluent or excipient must be compatible with the other ingredients of the formulation.

As used herein, the term "pharmaceutically acceptable excipient" refers to a substance that aids the administration of an active agent to and absorption by a subject. Pharmaceutical excipients useful in the present invention include, but are not limited to, binders, fillers, disintegrants, lubricants, coatings, sweeteners, flavors and colors. One of skill in the art will recognize that other pharmaceutical excipients are useful in the present invention.

Compounds

In some embodiments, the present disclosure relates to new salts and solid forms of (R)-1-(5-methoxy-1H-indol-1-yl)-N,N-dimethylpropan-2-amine, which is referred to as "compound 1."

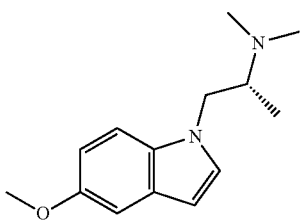

(R)-1-(5-methoxy-1H-indol-1-yl)-N,N-dimethylpropan-2-amine, "Compound 1"

The preparation of compound 1 fumarate salt according to literature methods yields the salt in a non-crystalline, gel form which affords various difficulties, especially in the manufacturability of Compound 1 into a suitable dosage form. Disclosed herein are salts and solid forms of (R)-1-(5-methoxy-1H-indol-1-yl)-N,N-dimethylpropan-2-amine that are useful to treat various disorders, such as brain disorders. Also disclosed are methods for making the salts and solid forms of (R)-1-(5-methoxy-1H-indol-1-yl)-N,N-dimethylpropan-2-amine and salts thereof, as well as a method of administering the salts, solid forms and salts thereof.

Solid Forms

A solid form of a salt may be a crystalline form or an amorphous form. Solid forms of compounds, such as crystalline forms of (R)-1-(5-methoxy-1H-indol-1-yl)-N,N-dimethylpropan-2-amine fumarate, may exist in more than one crystal form. Such different forms are referred to as polymorphs.

In some embodiments, the solid form of (R)-1-(5-methoxy-1H-indol-1-yl)-N,N-dimethylpropan-2-amine fumarate disclosed herein is selected to be a crystalline form, such as a particular polymorph of a crystalline form of (R)-1-(5-methoxy-1H-indol-1-yl)-N,N-dimethylpropan-2-amine fumarate, that provides one or more desired properties. In one embodiment, the crystalline form offers advantages over the amorphous form of the molecule. In another embodiment, the disclosed polymorph offers improved properties as compared to another polymorph of the molecule. The one or more desired properties may include, but are not limited to, physical properties, including but not limited to, melting point, glass transition temperature, flowability, and/or stability, such as thermal stability, mechanical stability, shelf life, stability against polymorphic transition, etc.; chemical properties, such as, but not limited to, hygroscopic properties, solubility in water and/or organic solvents, reactivity, compatibility with excipients and/or delivery vehicles; and/or pharmacokinetic properties, such as, but not limited to, bioavailability, absorption, distribution, metabolism, excretion, toxicity including cytotoxicity, dissolution rate, and/or half-life.

The desired polymorph may be produced by techniques as described herein and also are known to persons of ordinary skill in the art. Such techniques include, but are not limited to, crystallization in particular solvents and/or at particular temperatures, supersaturation, using a precipitation agent, such as a salt, glycol, alcohol, etc., co-crystallization, lyophilization, spray drying, freeze drying, and/or complexing with an inert agent.

Techniques to identify a particular solid form of a compound are described herein and include, but are not limited to, X-ray crystallography, X-ray diffraction, electron crystallography, powder diffraction, including X-ray, neutron, or electron diffraction, X-ray fiber diffraction, small-angle X-ray scattering, and/or melting point. When XRPD data are presented in table format, relative intensity values in peak tables are calculated using the net intensity values.

Salts

In some embodiments, (R)-1-(5-methoxy-1H-indol-1-yl)-N,N-dimethylpropan-2-amine is prepared in the form of a salt of (R)-1-(5-methoxy-1H-indol-1-yl)-N,N-dimethylpropan-2-amine. Suitable salts include pharmaceutically acceptable salts of (R)-1-(5-methoxy-1H-indol-1-yl)-N,N-dimethylpropan-2-amine. In some embodiments, the salt is provided as a solid form of a (R)-1-(5-methoxy-1H-indol-1-yl)-N,N-dimethylpropan-2-amine fumarate acid-addition salt. In some embodiments, the salt is provided as a solid form of (R)-1-(5-methoxy-1H-indol-1-yl)-N,N-dimethylpropan-2-amine that is not a (R)-1-(5-methoxy-1H-indol-1-yl)-N,N-dimethylpropan-2-amine fumarate.

In some embodiments, the salt of (R)-1-(5-methoxy-1H-indol-1-yl)-N,N-dimethylpropan-2-amine is formed from a suitable pharmaceutically acceptable acid, including, without limitation, inorganic acids such as hydrobromic acid, sulfuric acid, nitric acid, phosphoric acid, and the like, as well as organic acids such as formic acid, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, benzene sulfonic acid, isethionic acid, methanesulfonic acid, ethanesulfonic acid, p-toluenesulfonic acid, salicylic acid, xinafoic acid and the like.

In other embodiments, the salt of (R)-1-(5-methoxy-1H-indol-1-yl)-N,N-dimethylpropan-2-amine may be formed from a suitable pharmaceutically acceptable base, including, without limitation, inorganic bases such as sodium, potassium, lithium, ammonium, calcium, magnesium, iron, zinc, copper, manganese, aluminum salts and the like. Salts derived from pharmaceutically acceptable organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, tris(hydroxymethyl)aminomethane (Tris), ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Additional information concerning pharmaceutically acceptable salts can be found in, for example, S. M. Berge, et al., "Pharmaceutical Salts," J. Pharm. Sci., 1977; 66:1-19 which is incorporated herein by reference.

In some embodiments, the salt is formed using an acid from Table 1a.

TABLE 1a

| | |
|---|---|
| naphthalene-1,5-disulfonic acid | citric acid |
| sulfuric acid | d-glucuronic acid |
| ethane-1,2-disulfonic acid | lactobionic acid |
| p-toluenesulfonic acid | D-glucoheptonic acid |
| thiocyanic acid | (−)-L-pyroglutamic acid |
| methanesulfonic acid | L-malic acid |
| dodecylsulfuric acid | hippuric acid |
| naphthalene-2-sulfonic acid | D-gluconic acid |
| benzenesulfonic acid | D,L-lactic acid |
| oxalic acid | oleic acid |
| glycerophosphoric acid | succinic acid |
| ethanesulfonic acid, 2-hydroxy | glutaric acid |
| L-aspartic acid | cinnamic acid |
| maleic acid | adipic acid |
| phosphoric acid | sebacic acid |
| ethanesulfonic acid | (+)-camphoric acid |
| glutamic acid | acetic acid |
| pamoic (embonic) acid | nicotinic acid |
| glutaric acid, 2-oxo- | isobutyric acid |
| 2-naphthoic acid, 1-hydroxy | propionic acid |
| malonic acid | lauric acid |
| gentisic acid | stearic acid |
| L-tartaric acid | orotic acid |
| fumaric acid | carbonic acid |
| galactaric (mucic) acid | |

The acid salts of (R)-1-(5-methoxy-1H-indol-1-yl)-N,N-dimethylpropan-2-amine disclosed herein can have any suitable stoichiometric ratio of acid to (R)-1-(5-methoxy-1H-indol-1-yl)-N,N-dimethylpropan-2-amine. In one embodiment, the molar ratio of acid is from about 0.4 to about 2.2 acid to (R)-1-(5-methoxy-1H-indol-1-yl)-N,N-dimethylpropan-2-amine, such as forms wherein the salt has a stoichiometric ratio of from about 0.5 to about 2, such as about 0.5, about 1 or about 2 moles of the acid for each mole of amine.

Purity

In some embodiments, the solid forms of compound 1 disclosed herein, and compositions comprising the same, are at least 50%, e.g., at least 55%, at least 60%, at least 65%, at least 70%, at least 80%, at least 85%, at least 90%, at least 95%, at least 96%, at least 97%, at least 98%, or at least 99% pure. In some embodiments, the solid forms of compound 1 disclosed herein, and compositions comprising the same, comprise less than 50%, less than 45%, less than 40%, less than 35%, less than 30%, less than 25% less than 20%, less than 15%, less than 10%, less than 5%, less than 4%, less than 3%, less than 2%, or less than 1% impurity. In some embodiments, the solid forms of compound 1 disclosed herein, and compositions comprising the same, comprise less than 50%, less than 45%, less than 40%, less than 35%, less than 30%, less than 25% less than 20%, less than 15%, less than 10%, less than 5%, less than 4%, less than 3%, less than 2%, or less than 1% of an alternative solid form, e.g., an alternative polymorph of compound 1. In some embodiments, the solid forms of compound 1 disclosed herein, and compositions comprising the same, comprise less than 50%, less than 45%, less than 40%, less than 35%, less than 30%, less than 25% less than 20%, less than 15%, less than 10%, less than 5%, less than 4%, less than 3%, less than 2%, or less than 1% of a compound other than compound 1. The purity of a sample of a solid form of compound 1 may be determined by any suitable means, for example, by powder X-ray diffraction.

As set forth below, compound 1 can form salts with different acids. In some embodiments, the compound 1 salts described herein exist in various crystalline forms. All XRPD signals described herein are in (±0.2°2θ; ±0.1°2θ; or ±0.0°2θ; Cu Kα1 radiation).

In some embodiments, the compound 1 salt is a compound 1 fumarate salt. In some embodiments, the compound 1 fumarate salt is amorphous. In some embodiments, the compound 1 fumarate salt is crystalline. In some embodiments, the compound 1 fumarate salt is a 1:1 compound 1:fumarate salt. In some embodiments, the compound 1 fumarate salt is a 2:1 compound 1:fumarate salt.

Compound 1 Fumarate Salts

In some embodiments, the compound 1 salt is a compound 1 fumarate salt. In some embodiments, the compound 1 fumarate salt is amorphous. In some embodiments, the compound 1 fumarate salt is crystalline. In some embodiments, the compound 1 fumarate salt is a 1:1 compound 1:fumarate salt. In some embodiments, the compound 1 fumarate salt is a 2:1 compound 1:fumarate salt.

Amorphous Compound 1 Fumarate Salts

In some embodiments, the compound 1 fumarate salt is an amorphous compound 1 fumarate salt characterized by a glass temperature (Tg) of about 24° C. In some embodiments, the amorphous compound 1 fumarate salt is characterized by a XRPD pattern that is substantially similar to that shown in FIG. 379. In some embodiments, the amorphous compound 1 fumarate salt is characterized by an XRPD pattern that is substantially similar to that shown in FIG. 390. In some embodiments, the amorphous compound 1 fumarate salt is characterized by a DSC profile that is substantially similar to that shown in any one of FIG. 384. In some embodiments, the amorphous compound 1 fumarate salt is characterized by a TGA profile that is substantially similar to that shown in any one of FIG. 388. In some embodiments, the amorphous compound 1 fumarate salt is characterized by a $^1$H NMR spectrum that is substantially similar to that shown in FIG. 380. In some embodiments, the amorphous form is characterized by the LC profile shown in FIG. 389.

Compound 1 Monofumarate Salt: Form A

In some embodiments, the compound 1 fumarate salt is Form A crystalline monofumarate polymorph. In some embodiments, the crystalline compound 1 monofumarate salt Form A is characterized by the XRPD signals set for the below in any one of Tables 1 to 30. In some embodiments, the compound 1 monofumarate salt Form A XRPD pattern is substantially similar to that shown in FIG. 54, 61, 69, 6, 8, 72, 73, 74, 75, 77, 92, 93, 94, 95, 103, 104, 105, 109, 110, 126, 127, 128, 129, 130, 131, 132, or 133. In some embodiments, the compound 1 monofumarate salt Form A $^1$H-NMR spectrum is substantially similar to that shown in any one of FIG. 63, 64, 65, 66, 89, 90, 91, 92, 118, 119, 120, 121, 122, 123, 124, or 125. In some embodiments, the compound 1 monofumarate salt Form A DVS is substantially similar to that shown in FIG. 12. In some embodiments, the compound 1 monofumarate salt TGA spectrum is substantially similar to that shown in any one of FIGS. 79, 80, 81, 82, 96, 97, 98, 367, 111, 134, 135, 136, 137, 138, 139, and 140. In some embodiments, the crystalline compound 1 monofumarate Form A is DSC spectrum is substantially similar to that shown in any one of FIGS. 84, 85, 86, 87, 99, 100, 101, 102, and 12.

In some embodiments, the crystalline compound 1 monofumarate Form A Is a crystalline polymorphic form characterized by DSC having a melting signal at about 118.2° C. In some embodiments, the crystalline compound 1 monofumarate Form A Is a crystalline polymorphic form characterized by TGA having an onset at about 207.9° C.

In some embodiments, the crystalline compound 1 monofumarate Form A is a 1:1 compound 1:fumarate salt.

In some embodiments, the compound 1 monofumarate salt is crystalline polymorphic Form A characterized by an XRPD signal at 10.2°2θ (±0.2°2θ; ±0.1°2θ; or ±0.0°2θ; Cu Kα1 radiation).

In some embodiments, the compound 1 monofumarate salt is crystalline polymorphic Form A characterized by XRPD signals at 10.2°2θ, and 22.5°2θ, (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.2°2θ, 22.5°2θ, and 28.2°2θ, (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.2°2θ, 22.5°2θ, and 28.2°2θ (±0.2°2θ; ±0.1°2θ; or ±0.0° 2θ; Cu Kα1 radiation).

In some embodiments, the compound 1 monofumarate salt is crystalline polymorphic Form A characterized by two or more, or three or more XRPD signals selected from the group consisting of 10.2°2θ, 16.1°2θ, 22.5°2θ, and 28.2°2θ, (±0.2°2θ; ±0.1°2θ; or ±0.0°2θ; Cu Kα1 radiation).

In some embodiments, the compound 1 monofumarate salt is crystalline polymorphic Form A characterized by XRPD signals at 10.2°2θ, 16.1°2θ, 22.5°2θ, and 28.2°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.2°2θ, 16.1°2θ, 19.5°2θ, 22.5°2θ, and 28.2°2θ, (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.2°2θ, 16.1°2θ, 19.5°2θ, 22.5°2θ, and 28.2°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.2°2θ, 16.1°2θ, 19.5°2θ, 22.5°2θ, 25.2°2θ, and 28.2°2θ, (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.2°2θ, 16.1°2θ, 19.5°2θ, 22.5°2θ, 25.2°2θ, and 28.2°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.2°2θ, 16.1°2θ, 19.5°2θ, 21.0°2θ, 22.5°2θ, 25.2°2θ, and 28.2°2θ, (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.2°2θ, 16.1°2θ, 19.5°2θ, 21.0°2θ, 22.5°2θ, 25.2°2θ, and 28.2°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.2°2θ, 16.1°2θ, 19.4°2θ, 19.5°2θ, 21.0°2θ, 22.5°2θ, 25.2°2θ, and 28.2°2θ, (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.2°2θ, 16.1°2θ, 19.4°2θ, 19.5°2θ, 21.0°2θ, 22.5°2θ, 25.2°2θ, and 28.2°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.2°2θ, 16.1°2θ, 19.1°2θ, 19.4°2θ, 19.5°2θ, 21.0°2θ, 22.5°2θ, 25.2°2θ, and 28.2°2θ, (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.2°2θ, 16.1°2θ, 19.1°2θ, 19.4°2θ, 19.5°2θ, 21.0°2θ, 22.5°2θ, 25.2°2θ, and 28.2°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.2°2θ, 14.2°2θ, 16.1°2θ, 19.1°2θ, 19.4°2θ, 19.5°2θ, 21.0°2θ, 22.5°2θ, 25.2°2θ, and 28.2° 2θ, (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.2°2θ, 14.2°2θ, 16.1°2θ, 19.1°2θ, 19.4°2θ, 19.5°2θ, 21.0°2θ, 22.5°2θ, 25.2°2θ, and 28.2°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.2°2θ, 14.2°2θ, 16.1°2θ, 19.1°2θ, 19.4°2θ, 19.5°2θ, 21.0°2θ, 21.5°2θ, 22.5°2θ, 25.2°2θ, and 28.2°2θ, (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.2°2θ, 14.2°2θ, 16.1°2θ, 19.1°2θ, 19.4°2θ, 19.5°2θ, 21.0°2θ, 21.5°2θ, 22.5°2θ, 25.2°2θ, and 28.2°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.2°2θ, 14.2°2θ, 16.1°2θ, 19.1°2θ, 19.4°2θ, 19.5°2θ, 21.0°2θ, 21.5°2θ, 21.7°2θ, 22.5°2θ, 25.2°2θ, and 28.2°2θ, (±0.2°2θ; ±0.1°2θ; or ±0.0°2θ. Cu Kα1 radiation). In some embodiments, the compound 1 monofumarate salt is crystalline polymorphic Form A characterized by XRPD signals at 10.2°2θ, 14.2°2θ, 16.1°2θ, 19.1°2θ, 19.4°2θ, 19.5°2θ, 21.0°2θ, 21.5°2θ, 21.7°2θ, 22.5°2θ, 25.2°2θ, and 28.2°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.2°2θ, 13.5°2θ, 14.2°2θ, 16.1°2θ, 19.1°2θ, 19.4°2θ, 19.5°2θ, 21.0°2θ, 21.5°2θ, 21.7°2θ, 22.5°2θ, 25.2°2θ, and 28.2°2θ, (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.2°2θ, 13.5°2θ, 14.2°2θ, 16.1°2θ, 19.1°2θ, 19.4°2θ, 19.5°2θ, 21.0°2θ, 21.5°2θ, 21.7°2θ, 22.5°2θ, 25.2°2θ, and 28.2°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.2°2θ, 13.5°2θ, 14.2°2θ, 16.1°2θ, 19.1°2θ, 19.4°2θ, 19.5°2θ, 21.0°2θ, 21.5°2θ, 21.7°2θ, 22.5°2θ, 25.2°2θ, 25.3°2θ, 28.2°2θ, and 29.2°2θ, (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.2°2θ, 13.5°2θ, 14.2°2θ, 16.1°2θ, 19.1°2θ, 19.4°2θ, 19.5°2θ, 21.0°2θ, 21.5°2θ, 21.7°2θ, 22.5°2θ, 25.2°2θ, 25.3°2θ, 28.2°2θ, and 29.2°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.2°2θ, 13.5°2θ, 14.2°2θ, 15.8°2θ, 16.1°2θ, 19.1°2θ, 19.4°2θ, 19.5°2θ, 21.0°2θ, 21.5°2θ, 21.7°2θ, 22.5°2θ, 25.2°2θ, 25.3°2θ, 28.2°2θ, and 29.2°2θ, (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.2°2θ, 13.5°2θ, 14.2°2θ, 15.8°2θ, 16.1°2θ, 19.1°2θ, 19.4°2θ, 19.5°2θ, 21.0°2θ, 21.5°2θ, 21.7°2θ, 22.5°2θ, 25.2°2θ, 25.3°2θ, 28.2°2θ, and 29.2°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.2°2θ, 13.5°2θ, 14.2°2θ, 15.8°2θ, 16.1°2θ, 18.6°2θ, 19.1°2θ, 19.4°2θ, 19.5°2θ, 21.0°2θ, 21.5°2θ, 21.7°2θ, 22.5°2θ, 25.2°2θ, 25.3°2θ, 28.2°2θ, and 29.2°2θ, (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.2°2θ, 13.5°2θ, 14.2°2θ, 15.8°2θ, 16.1°2θ, 18.6°2θ, 19.1°2θ, 19.4°2θ, 19.5°2θ, 21.0°2θ, 21.5°2θ, 21.7°2θ, 22.5°2θ, 25.2°2θ, 25.3°2θ, 28.2°2θ, and 29.2°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.2°2θ, 13.5°2θ, 14.2°2θ, 15.8°2θ, 16.1°2θ, 18.6°2θ, 19.1°2θ, 19.4°2θ, 19.5°2θ, 21.0°2θ, 21.5°2θ, 21.7°2θ, 22.5°2θ, 25.2°2θ, 25.3°2θ, 28.2°2θ, 29.2°2θ, and 32.8°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.2°2θ, 13.5°2θ, 14.2°2θ, 15.8°2θ, 16.1°2θ, 18.6°2θ, 19.1°2θ, 19.4°2θ, 19.5°2θ, 21.0°2θ, 21.5°2θ, 21.7°2θ, 22.5°2θ, 25.2°2θ, 25.3°2θ, 28.2°2θ, 29.2°2θ, and 32.8°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.2°2θ, 13.5°2θ, 14.2°2θ, 15.8°2θ, 16.1°2θ, 16.9°2θ, 18.6°2θ, 19.1°2θ, 19.4°2θ, 19.5°2θ, 21.0°2θ, 21.5°2θ, 21.7°2θ, 22.5°2θ, 25.2°2θ, 25.3°2θ, 28.2°2θ, 29.2°2θ, and 32.8°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.2°2θ, 13.5°2θ, 14.2°2θ, 15.80°2θ, 16.10°2θ, 16.90°2θ, 18.6°2θ, 19.1°2θ, 19.4°2θ, 19.50°2θ, 21.00°2θ, 21.5°2θ, 21.7°2θ, 22.5°2θ, 25.2°2θ, 25.3°2θ, 28.2°2θ, 29.2°2θ, and 32.8°2θ (±0.2°2θ; ±0.1°2θ; or ±0.0°2θ; Cu Kα1 radiation).

In some embodiments, crystalline polymorphic monofumarate Form A is characterized by one, two, three, four, five, six, seven, eight, nine, ten, eleven, twelve, thirteen, fourteen, fifteen, sixteen, seventeen, eighteen, nineteen, or twenty XRPD signals selected from those set forth in Table 1.

TABLE 1

XRPD Signals for Compound 1 monofumarate salt Form A Post-DVS (±0.2 °2θ; ±0.1 °2θ; or ±0.0 °2θ; Cu Kα1 radiation)

| 2-θ (°) | d Value | Net Intensity (counts) | Gross Intensity (counts) | Rel. Intensity (%) |
| --- | --- | --- | --- | --- |
| 10.2 | 8.66 | 2783.7 | 2910.1 | 61.5 |
| 13.5 | 6.53 | 849.1 | 1002.0 | 18.8 |
| 14.2 | 6.24 | 1062.6 | 1225.8 | 23.5 |
| 15.8 | 5.62 | 678.8 | 870.8 | 15.0 |
| 15.8 | 5.62 | 682.6 | 874.9 | 15.1 |
| 16.1 | 5.52 | 1627.9 | 1827.2 | 36.0 |
| 16.9 | 5.25 | 603.7 | 816.4 | 13.3 |
| 18.6 | 4.77 | 672.8 | 934.9 | 14.9 |
| 19.1 | 4.64 | 1068.8 | 1351.8 | 23.6 |
| 19.4 | 4.56 | 1134.2 | 1427.1 | 25.1 |
| 19.5 | 4.55 | 1323.1 | 1618.1 | 29.2 |
| 21.0 | 4.22 | 1138.5 | 1461.4 | 25.2 |
| 21.5 | 4.13 | 1030.7 | 1355.4 | 22.8 |
| 21.7 | 4.10 | 1029.0 | 1353.6 | 22.7 |
| 22.5 | 3.95 | 4523.6 | 4841.6 | 100.0 |
| 25.2 | 3.53 | 1144.0 | 1408.0 | 25.3 |
| 25.3 | 3.52 | 697.0 | 958.4 | 15.4 |
| 28.2 | 3.16 | 2111.6 | 2357.7 | 46.7 |
| 29.2 | 3.05 | 701.3 | 937.3 | 15.5 |
| 32.8 | 2.73 | 665.1 | 855.1 | 14.7 |

In some embodiments, the compound 1 monofumarate salt is crystalline polymorphic Form A characterized by an XRPD signal at 22.3°2θ (±0.2°2θ; ±0.1°2θ; or ±0.0°2θ; Cu Kα1 radiation).

In some embodiments, the compound 1 monofumarate salt is crystalline polymorphic Form A characterized by XRPD signals at 15.9°2θ, and 22.3°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.0°2θ, 15.9°2θ, and 22.3°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.0°2θ, 15.9°2θ, and 22.3°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.0°2θ, 15.9°2θ, 19.4°2θ, and 22.3°2θ (±0.2°2θ; ±0.1°2θ; or ±0.0°2θ; Cu Kα1 radiation).

In some embodiments, the compound 1 monofumarate salt is crystalline polymorphic Form A characterized by XRPD signals at 14.0°2θ, 15.9°2θ, 19.4°2θ, and 22.3°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.0°2θ, 15.9°2θ, 19.4°2θ, 21.5°2θ, and 22.3°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.0°2θ, 15.9°2θ, 19.4°2θ, 21.5°2θ, and 22.3°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.0°2θ, 15.9°2θ, 19.4°2θ, 21.3°2θ, 21.5°2θ, and 22.3°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.0°2θ, 15.9°2θ, 19.4°2θ, 21.3°2θ, 21.5°2θ, and 22.3°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 19.4°2θ, 21.3°2θ, 21.5°2θ, and 22.3°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 19.4°2θ, 21.3°2θ, 21.5°2θ, and 22.3°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 19.4°2θ, 20.8°2θ, 21.3°2θ, 21.5°2θ, and 22.3°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 19.4°2θ, 20.8°2θ, 21.3°2θ, 21.5°2θ, and 22.3°2θ, (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 18.9°2θ, 19.4°2θ, 20.8°2θ, 21.3°2θ, 21.5°2θ, and 22.3°2θ, (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 18.9°2θ, 19.4°2θ, 20.8°2θ, 21.3°2θ, 21.5°2θ, and 22.3°2θ, (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 18.9°2θ, 19.4°2θ, 20.8°2θ, 21.3°2θ, 21.5°2θ, and 22.3°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 18.9°2θ, 19.4°2θ, 20.8°2θ, 21.3°2θ, 21.5°2θ, and 22.3°2θ, (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 18.9°2θ, 19.4°2θ, 20.8°2θ, 21.3°2θ, 21.5°2θ, 22.3°2θ, and 28.1° 2θ, (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 18.9°2θ, 19.4°2θ, 20.8°2θ, 21.3°2θ, 21.5°2θ, 22.3°2θ, and 28.1°2θ, (±0.2° 2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 18.4°2θ, 18.9°2θ, 19.4°2θ, 20.8°2θ, 21.3°2θ, 21.5°2θ, 22.3°2θ, and 28.1°2θ, (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 18.4°2θ, 18.9°2θ, 19.4°2θ, 20.8°2θ, 21.3°2θ, 21.5°2θ, 22.3°2θ, and 28.1°2θ, (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.4°2θ, 18.9°2θ, 19.4°2θ, 20.8°2θ, 21.3°2θ, 21.5°2θ, 22.3°2θ, and 28.1°2θ, (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.4°2θ, 18.9°2θ, 19.4°2θ, 20.8°2θ, 21.3°2θ, 21.5°2θ, 22.3°2θ, and 28.1°2θ, (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.4°2θ, 18.9°2θ, 19.4°2θ, 20.8°2θ, 21.3°2θ, 21.5°2θ, 22.3°2θ, 28.1°2θ, and 29.0°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.4°2θ, 18.9°2θ, 19.4°2θ, 20.8°2θ, 21.3°2θ, 21.5°2θ, 22.3°2θ, 28.1°2θ, and 29.0°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.4°2θ, 18.9°2θ, 19.4°2θ, 20.8°2θ, 21.3°2θ, 21.5°2θ, 22.3°2θ, 25.0°2θ, 28.1°2θ, and 29.0°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.4°2θ, 18.9°2θ, 19.4°2θ, 20.8°2θ, 21.3°2θ, 21.5°2θ, 22.3°2θ, 25.0°2θ, 28.1°2θ, and 29.0°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.4°2θ, 18.9°2θ, 19.2°2θ, 19.4°2θ, 20.8°2θ, 21.3°2θ, 21.5°2θ, 22.3°2θ, 25.0°2θ, 28.1°2θ, and 29.0°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.4°2θ, 18.9°2θ, 19.2°2θ, 19.4°2θ, 20.8°2θ, 21.3°2θ, 21.5°2θ, 22.3°2θ, 25.0°2θ, 28.1°2θ, and 29.0°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.4°2θ, 18.9°2θ, 19.2°2θ, 19.4°2θ, 20.8°2θ, 21.3°2θ, 21.5°2θ, 22.3°2θ, 23.2°2θ, 25.0°2θ, 28.1°2θ, and 29.0°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.4°2θ, 18.9°2θ, 19.2°2θ, 19.4°2θ, 20.8°2θ, 21.3°2θ, 21.5°2θ, 22.3°2θ, 23.2°2θ, 25.0°2θ, 28.1°2θ, and 29.0°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.4°2θ, 18.9°2θ, 19.2°2θ, 19.4°2θ, 20.8°2θ, 21.3°2θ, 21.5°2θ, 22.3°2θ, 23.2°2θ, 24.4°2θ, 25.0°2θ, 28.1°2θ, and 29.0°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.4°2θ, 18.9°2θ, 19.2°2θ, 19.4°2θ, 20.8°2θ, 21.3°2θ, 21.5°2θ, 22.3°2θ, 23.2°2θ, 24.4°2θ, 25.0°2θ, 28.1°2θ, and 29.0°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.1°2θ, 13.4°2θ, 14.0°2θ, 15.6°2θ, 15.9°2θ, 18.4°2θ, 18.9°2θ, 19.2°2θ, 19.4°2θ, 20.8°2θ, 21.3°2θ, 21.5°2θ, 22.3°2θ, 23.2°2θ, 24.4°2θ, 25.0°2θ, 28.1°2θ, and 29.0°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.1°2θ, 13.4°2θ, 14.0°2θ, 15.6°2θ, 15.9°2θ, 18.4°2θ, 18.9°2θ, 19.2°2θ, 19.4°2θ, 20.8°2θ, 21.3°2θ, 21.5°2θ, 22.3°2θ, 23.2°2θ, 24.4°2θ, 25.0°2θ, 28.1°2θ, and 29.0°2θ (±0.2°2θ; ±0.1°2θ; or ±0.0°2θ; Cu Kα1 radiation).

In some embodiments, crystalline polymorphic Form A is characterized by one, two, three, four, five, six, seven, eight, nine, ten, eleven, twelve, thirteen, fourteen, fifteen, sixteen, seventeen, or eighteen XRPD signals selected from those set forth in Table 2.

TABLE 2

Compound 1 monofumarate salt Form A (post-DVS)
(±0.2 °2θ; ±0.1 °2θ; or ±0.0 °2θ; Cu Kα1 radiation)

| Signal number | 2-θ (°) | d Value | Net Intensity (counts) | Gross Intensity (counts) | Rel. Intensity (%) |
|---|---|---|---|---|---|
| Signal #2 | 10.1 | 8.78 | 453.1 | 521.7 | 11.0 |
| Signal #5 | 13.4 | 6.63 | 1120.5 | 1198.0 | 27.1 |
| Signal #6 | 14.0 | 6.33 | 1355.3 | 1438.8 | 32.8 |
| Signal #7 | 15.6 | 5.69 | 683.6 | 775.7 | 16.5 |
| Signal #8 | 15.9 | 5.59 | 1850.5 | 1944.7 | 44.8 |
| Signal #10 | 18.4 | 4.82 | 713.8 | 834.9 | 17.3 |
| Signal #11 | 18.9 | 4.69 | 900.7 | 1030.6 | 21.8 |
| Signal #12 | 19.2 | 4.63 | 546.6 | 679.8 | 13.2 |
| Signal #13 | 19.4 | 4.58 | 1352.2 | 1487.4 | 32.7 |
| Signal #16 | 20.8 | 4.26 | 951.2 | 1097.0 | 23.0 |
| Signal #17 | 21.3 | 4.17 | 1252.1 | 1404.5 | 30.3 |
| Signal #18 | 21.5 | 4.13 | 1300.3 | 1454.9 | 31.5 |
| Signal #20 | 22.3 | 3.98 | 4134.4 | 4291.9 | 100.0 |
| Signal #21 | 23.2 | 3.84 | 523.4 | 674.7 | 12.7 |
| Signal #22 | 24.4 | 3.65 | 487.6 | 626.9 | 11.8 |
| Signal #23 | 25.0 | 3.56 | 579.6 | 710.2 | 14.0 |
| Signal #26 | 28.1 | 3.17 | 789.5 | 930.8 | 19.1 |
| Signal #28 | 29.0 | 3.07 | 652.5 | 789.7 | 15.8 |

In some embodiments, the compound 1 monofumarate salt is crystalline polymorphic Form A characterized by an XRPD signal at 22.3°2θ (±0.20°2θ; ±0.1°2θ, or ±0.00°2θ; Cu Kα1 radiation).

In some embodiments, the compound 1 monofumarate salt is crystalline polymorphic Form A characterized by XRPD signals at 15.9°2θ, and 22.3°2θ (±0.2°2θ, ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 15.9°2θ, 19.4°2θ, and 22.3°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 15.9°2θ, 19.4°2θ, and 22.3°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 15.9°2θ, 19.4°2θ, 20.9°2θ, and 22.3°2θ (±0.2°2θ; ±0.1°2θ, or ±0.0°2θ; Cu Kα1 radiation). In some embodiments, the compound 1 monofumarate salt is crystalline polymorphic Form A characterized by XRPD signals at 15.9°2θ, 19.4°2θ, 20.9°2θ, and 22.3°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 15.9°2θ, 19.4°2θ, 20.9°2θ, 21.3°2θ, and 22.3°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 15.9°2θ, 19.4°2θ, 20.9°2θ, 21.3°2θ, and 22.3°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.0°2θ, 15.9°2θ, 19.4°2θ, 20.9°2θ, 21.3°2θ, and 22.3°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.0°2θ, 15.9°2θ, 19.4°2θ, 20.9°2θ, 21.3°2θ, and 22.3°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 19.4°2θ, 20.9°2θ, 21.3°2θ, and 22.3°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 19.4°2θ, 20.9°2θ, 21.3°2θ, and 22.3°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 19.4°2θ, 20.9°2θ, 21.3°2θ, 21.5°2θ, and 22.3°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 19.4°2θ, 20.9°2θ, 21.3°2θ, 21.5°2θ, and 22.3°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 18.9°2θ, 19.4°2θ, 20.9°2θ, 21.3°2θ, 21.5°2θ, and 22.3°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 18.9°2θ, 19.4°2θ, 20.9°2θ, 21.3°2θ, 21.5°2θ, and 22.3°2θ (±0.2°2θ; ±0.1° 2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 18.9°2θ, 19.4°2θ, 20.9°2θ, 21.3°2θ, 21.5°2θ, 22.3°2θ, and 28.1° 2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 18.9°2θ, 19.4°2θ, 20.9°2θ, 21.3°2θ, 21.5°2θ, 22.3°2θ, and 28.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 18.4°2θ, 18.9°2θ, 19.4°2θ, 20.9°2θ, 21.3°2θ, 21.5°2θ, 22.3°2θ, and 28.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 18.4°2θ, 18.9°2θ, 19.4°2θ, 20.9°2θ, 21.3°2θ, 21.5°2θ, 22.3°2θ, and 28.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 18.4°2θ, 18.9°2θ, 19.4°2θ, 20.9°2θ, 21.3°2θ, 21.5°2θ, 22.3°2θ, 28.1°2θ, and 29.0°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 18.4°2θ, 18.9°2θ, 19.4°2θ, 20.9°2θ, 21.3°2θ, 21.5°2θ, 22.3°2θ, 28.1°2θ, and 29.0°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.4°2θ, 18.9°2θ, 19.4°2θ, 20.9°2θ, 21.3°2θ, 21.5°2θ, 22.3°2θ, 28.1°2θ, and 29.0°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.4°2θ, 18.9°2θ, 19.4°2θ, 20.9°2θ, 21.3°2θ, 21.5°2θ, 22.3°2θ, 28.1°2θ, and 29.0°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.4°2θ, 18.9°2θ, 19.4°2θ, 20.9°2θ, 21.3°2θ, 21.5°2θ, 22.3°2θ, 25.0°2θ, 28.1°2θ, and 29.0°2θ (±0.2°2θ; ±0.1°2θ; or 3±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.4°2θ, 18.9°2θ, 19.4°2θ, 20.9°2θ, 21.3°2θ, 21.5°2θ, 22.3°2θ, 25.0°2θ, 28.1°2θ, and 29.0°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.4°2θ, 18.9°2θ, 19.4°2θ, 20.9°2θ, 21.3°2θ, 21.5°2θ, 22.3°2θ, 23.1°2θ, 25.0°2θ, 28.1°2θ, and 29.0°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.4°2θ, 18.9°2θ, 19.4°2θ, 20.9°2θ, 21.3°2θ, 21.5°2θ, 22.3°2θ, 23.1°2θ, 25.0°2θ, 28.1°2θ, and 29.0°2θ (±0.2°2θ; ±0.1°2θ; or ±0.0°2θ; Cu Kα1 radiation).

In some embodiments, crystalline polymorphic Form A is characterized by one, two, three, four, five, six, seven, eight, nine, ten, eleven, twelve, thirteen, fourteen, or fifteen XRPD signals selected from those set forth in Table 3.

TABLE 3

Compound 1 monofumarate salt Form A
(±0.2 °2θ; ±0.1 °2θ; or ±0.0 °2θ; Cu Kα1 radiation)

| Signal number | 2-θ (0) | d Value | Net Intensity (counts) | Gross Intensity (counts) | Rel. Intensity (%) |
|---|---|---|---|---|---|
| Signal #1 | 13.4 | 6.62 | 1035.4 | 1153.0 | 22.4 |
| Signal #2 | 14.0 | 6.32 | 1105.3 | 1227.3 | 23.9 |
| Signal #3 | 15.6 | 5.69 | 716.8 | 856.4 | 15.5 |
| Signal #4 | 15.9 | 5.59 | 2137.7 | 2280.4 | 46.2 |
| Signal #5 | 18.4 | 4.82 | 810.5 | 975.6 | 17.5 |
| Signal #6 | 18.9 | 4.69 | 1013.7 | 1194.0 | 21.9 |
| Signal #7 | 19.4 | 4.58 | 1914.2 | 2105.2 | 41.4 |
| Signal #8 | 20.9 | 4.25 | 1156.2 | 1370.3 | 25.0 |
| Signal #9 | 21.3 | 4.16 | 1142.2 | 1364.4 | 24.7 |
| Signal #10 | 21.5 | 4.14 | 1033.9 | 1258.0 | 22.4 |
| Signal #11 | 22.3 | 3.98 | 4623.4 | 4853.4 | 100.0 |
| Signal #12 | 23.1 | 3.84 | 483.4 | 709.0 | 10.5 |
| Signal #13 | 25.0 | 3.56 | 543.9 | 725.0 | 11.8 |
| Signal #14 | 28.1 | 3.17 | 920.9 | 1104.2 | 19.9 |
| Signal #15 | 29.0 | 3.07 | 809.6 | 991.1 | 17.5 |

In some embodiments, the compound 1 monofumarate salt is crystalline polymorphic Form A characterized by two an XRPD signal at 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 19.4°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 15.9°2θ, 19.4°2θ, and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 15.9°2θ, 19.4°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.0°2θ, 15.9°2θ, 19.4°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by XRPD signals at 14.0°2θ, 15.9°2θ, 19.4°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.0°2θ, 15.9°2θ, 19.4°2θ, 21.3°2θ, and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.0°2θ, 15.9°2θ, 19.4°2θ, 21.3°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.0°2θ, 15.9°2θ, 19.4°2θ, 21.3°2θ, 21.5°2θ, and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.0°2θ, 15.9°2θ, 19.4°2θ, 21.3°2θ, 21.5°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 19.4°2θ, 21.3°2θ, 21.5°2θ, and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 19.4°2θ, 21.3°2θ, 21.5°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 19.4°2θ, 21.3°2θ, 21.5°2θ, 22.4°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 19.4°2θ, 21.3°2θ, 21.5°2θ, 22.4°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 19.4°2θ, 20.8°2θ, 21.3°2θ, 21.5°2θ, 22.4°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 19.4°2θ, 20.8°2θ, 21.3°2θ, 21.5°2θ, 22.4°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 19.4°2θ, 20.8°2θ, 21.3°2θ, 21.5°2θ, 22.4°2θ, 28.1°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 19.4°2θ, 20.8°2θ, 21.3°2θ, 21.5°2θ, 22.4°2θ, 28.1°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 18.9°2θ, 19.4°2θ, 20.8°2θ, 21.3°2θ, 21.5°2θ, 22.4°2θ, 28.1°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.9°2θ, 19.4°2θ, 20.8°2θ, 21.3°2θ, 21.5°2θ, 22.4°2θ, 28.1°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.9°2θ, 19.4°2θ, 20.8°2θ, 21.3°2θ, 21.5°2θ, 22.4°2θ, 25.0°2θ, 28.1°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.9°2θ, 19.4°2θ, 20.8°2θ, 21.3°2θ, 21.5°2θ, 22.4°2θ, 25.0°2θ, 28.1°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.4°2θ, 18.9°2θ, 19.4°2θ, 20.8°2θ, 21.3°2θ, 21.5°2θ, 22.4°2θ, 25.0°2θ, 28.1°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.4°2θ, 18.9°2θ, 19.4°2θ, 20.8°2θ, 21.3°2θ, 21.5°2θ, 22.4°2θ, 25.0°2θ, 28.1°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.4°2θ, 18.9°2θ, 19.4°2θ, 20.8°2θ, 21.3°2θ, 21.5°2θ, 22.4°2θ, 24.4°2θ, 25.0°2θ, 28.1°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.4°2θ, 18.9°2θ, 19.4°2θ, 20.8°2θ, 21.3°2θ, 21.5°2θ, 22.4°2θ, 24.4°2θ, 25.0°2θ, 28.1°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.4°2θ, 18.9°2θ, 19.4°2θ, 20.8°2θ, 21.3°2θ, 21.5°2θ, 22.4°2θ, 23.2°2θ, 24.4°2θ, 25.0°2θ, 28.1°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.4°2θ, 18.9°2θ, 19.4°2θ, 20.8°2θ, 21.3°2θ, 21.5°2θ, 22.4°2θ, 23.2°2θ, 24.4°2θ, 25.0°2θ, 28.1°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.1°2θ, 13.4°2θ, 14.0°2θ, 15.6°2θ, 15.9°2θ, 18.4°2θ, 18.9°2θ, 19.4°2θ, 20.8°2θ, 21.3°2θ, 21.5°2θ, 22.4°2θ, 23.2°2θ, 24.4°2θ, 25.0°2θ, 28.1°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.1°2θ, 13.4°2θ, 14.0°2θ, 15.6°2θ, 15.9°2θ, 18.4°2θ, 18.9°2θ, 19.4°2θ, 20.8°2θ, 21.3°2θ, 21.5°2θ, 22.4°2θ, 23.2°2θ, 24.4°2θ, 25.0°2θ, 28.1°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.1°2θ, 13.4°2θ, 14.0°2θ, 15.6°2θ, 15.9°2θ, 17.6°2θ, 18.4°2θ, 18.9°2θ, 19.4°2θ, 20.8°2θ, 21.3°2θ, 21.5°2θ, 22.4°2θ, 23.2°2θ, 24.4°2θ, 25.0°2θ, 28.1°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.1°2θ, 13.4°2θ, 14.0°2θ, 15.6°2θ, 15.9°2θ, 17.6°2θ, 18.4°2θ, 18.9°2θ, 19.4°2θ, 20.8°2θ, 21.3°2θ, 21.5°2θ, 22.4°2θ, 23.2°2θ, 24.4°2θ, 25.0°2θ, 28.1°2θ, and 29.1°2θ (±0.2°2θ; ±0.1°2θ; or ±0.0°2θ; Cu Kα1 radiation).

In some embodiments, crystalline polymorphic Form A is characterized by one, two, three, four, five, six, seven, eight, nine, ten, eleven, twelve, thirteen, fourteen, fifteen, sixteen, seventeen, eighteen, or nineteen XRPD signals selected from those set forth in Table 4.

TABLE 4

Compound 1 monofumarate salt Form A
(±0.2 °2θ; ±0.1 °2θ; or ±0.0 °2θ; Cu Kα1 radiation)

| Signal number | 2-θ (0) | d Value | Net Intensity (counts) | Gross Intensity (counts) | Rel. Intensity (%) |
|---|---|---|---|---|---|
| Signal #1 | 10.1 | 8.75 | 295.1 | 396.3 | 11.2 |
| Signal #2 | 13.4 | 6.61 | 590.2 | 708.3 | 22.4 |
| Signal #3 | 14.0 | 6.32 | 971.2 | 1099.6 | 36.8 |
| Signal #4 | 15.6 | 5.66 | 478.4 | 640.3 | 18.1 |
| Signal #5 | 15.9 | 5.57 | 1179.8 | 1347.3 | 44.8 |
| Signal #6 | 17.6 | 5.02 | 283.5 | 493.6 | 10.8 |
| Signal #7 | 18.4 | 4.82 | 450.4 | 690.1 | 17.1 |
| Signal #8 | 18.9 | 4.68 | 578.0 | 834.6 | 21.9 |
| Signal #9 | 19.4 | 4.57 | 1377.9 | 1646.8 | 52.3 |
| Signal #10 | 20.8 | 4.26 | 588.1 | 879.4 | 22.3 |
| Signal #11 | 21.3 | 4.17 | 807.9 | 1101.5 | 30.7 |
| Signal #12 | 21.5 | 4.13 | 632.4 | 926.3 | 24.0 |
| Signal #13 | 22.4 | 3.97 | 2635.8 | 2925.6 | 100.0 |
| Signal #14 | 23.2 | 3.83 | 366.2 | 644.3 | 13.9 |
| Signal #15 | 24.4 | 3.64 | 372.9 | 619.1 | 14.1 |
| Signal #16 | 25.0 | 3.56 | 473.5 | 698.5 | 18.0 |
| Signal #17 | 25.0 | 3.55 | 470.7 | 695.2 | 17.9 |
| Signal #18 | 28.1 | 3.17 | 584.1 | 770.6 | 22.2 |
| Signal #19 | 29.1 | 3.07 | 589.6 | 768.1 | 22.4 |

In some embodiments, the compound 1 monofumarate salt is crystalline polymorphic Form A characterized by an XRPD signal at 22.3°2θ (±0.2°2θ; ±0.1°2θ; or ±0.0°2θ; Cu Kα1 radiation).

In some embodiments, the compound 1 monofumarate salt is crystalline polymorphic Form A characterized by XRPD signals at 19.3°2θ and 22.3°2θ (±0.2°2θ; ±0.1°2θ; or ±0.0°2θ; Cu Kα1 radiation).

In some embodiments, the compound 1 monofumarate salt is crystalline polymorphic Form A characterized by two or more XRPD signals selected from the group consisting of 19.3°2θ, and 22.3°2θ (±0.2°2θ; ±0.1°2θ; or ±0.0°2θ. Cu Kα1 radiation). In some embodiments, the compound 1 monofumarate salt is crystalline polymorphic Form A characterized by XRPD signals at 19.3°2θ, and 22.3°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 19.3°2θ, 21.4°2θ, and 22.3°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 19.3°2θ, 21.4°2θ, and 22.3°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 19.3°2θ, 21.2°2θ, 21.4°2θ, and 22.3°2θ (±0.2°2θ; ±0.1°2θ; or ±0.0°2θ; Cu Kα1 radiation).

In some embodiments, the compound 1 monofumarate salt is crystalline polymorphic Form A characterized by XRPD signals at 19.3°2θ, 21.2°2θ, 21.4°2θ, and 22.3°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 15.8°2θ, 19.3°2θ, 21.2°2θ, 21.4°2θ, and 22.3°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 15.8°2θ, 19.3°2θ, 21.2°2θ, 21.4°2θ, and 22.3°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 15.8°2θ, 19.3°2θ, 20.7°2θ, 21.2°2θ, 21.4°2θ, and 22.3°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 15.8°2θ, 19.3°2θ, 20.7°2θ, 21.2°2θ, 21.4°2θ, and 22.3°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 15.8°2θ, 19.3°2θ, 20.7°2θ, 21.2°2θ, 21.4°2θ, 22.3°2θ, and 28.0°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 15.8°2θ, 19.3°2θ, 20.7°2θ, 21.2°2θ, 21.4°2θ, 22.3°2θ, and 28.0°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.9°2θ, 15.8°2θ, 19.3°2θ, 20.7°2θ, 21.2°2θ, 21.4°2θ, 22.3°2θ, and 28.0°2θ (±0.2°2θ; ±0.1° 2θ; or ±0.0°2θ; Cu Kα1 radiation). In some embodiments, the compound 1 monofumarate salt is crystalline polymorphic Form A characterized by XRPD signals at 13.9°2θ, 15.8°2θ, 19.3°2θ, 20.7°2θ, 21.2°2θ, 21.4°2θ, 22.3°2θ, and 28.0°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.9°2θ, 15.8°2θ, 19.3°2θ, 20.7°2θ, 21.2°2θ, 21.4°2θ, 22.3°2θ, 28.0°2θ, and 28.9°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.9°2θ, 15.8°2θ, 19.3°2θ, 20.7°2θ, 21.2°2θ, 21.4°2θ, 22.3°2θ, 28.0°2θ, and 28.9°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.9°2θ, 15.8°2θ, 18.8°2θ, 19.3°2θ, 20.7°2θ, 21.2°2θ, 21.4°2θ, 22.3°2θ, 28.0°2θ, and 28.9°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.9°2θ, 15.8°2θ, 18.8°2θ, 19.3°2θ, 20.7°2θ, 21.2°2θ, 21.4°2θ, 22.3°2θ, 28.0°2θ, and 28.9°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.9°2θ, 15.8°2θ, 18.3°2θ, 18.8°2θ, 19.3°2θ, 20.7°2θ, 21.2°2θ, 21.4°2θ, 22.3°2θ, 28.0°2θ, and 28.9°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.9°2θ, 15.8°2θ, 18.3°2θ, 18.8°2θ, 19.3°2θ, 20.7°2θ, 21.2°2θ, 21.4°2θ, 22.3°2θ, 28.0°2θ, and 28.9°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.9°2θ, 15.8°2θ, 18.3°2θ, 18.8°2θ, 19.3°2θ, 20.7°2θ, 21.2°2θ, 21.4°2θ, 22.3°2θ, 28.0°2θ, 28.9°2θ, and 34.0°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.9°2θ, 15.8°2θ, 18.3°2θ, 18.8°2θ, 19.3°2θ, 20.7°2θ, 21.2°2θ, 21.4°2θ, 22.3°2θ, 28.0°2θ, 28.9°2θ, and 34.0°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.3°2θ, 13.9°2θ, 15.8°2θ, 18.3°2θ, 18.8°2θ, 19.3°2θ, 20.7°2θ, 21.2°2θ, 21.4°2θ, 22.3°2θ, 28.0°2θ, 28.9°2θ, and 34.0°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.3°2θ, 13.9°2θ, 15.8°2θ, 18.3°2θ, 18.8°2θ, 19.3°2θ, 20.7°2θ, 21.2°2θ, 21.4°2θ, 22.3°2θ, 28.0°2θ, 28.9°2θ, and 34.0°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.3°2θ, 13.9°2θ, 15.8°2θ, 18.3°2θ, 18.8°2θ, 19.3°2θ, 20.7°2θ, 21.2°2θ, 21.4°2θ, 22.3°2θ, 24.9°2θ, 28.0°2θ, 28.9°2θ, and 34.0°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.3°2θ, 13.9°2θ, 15.8°2θ, 18.3°2θ, 18.8°2θ, 19.3°2θ, 20.7°2θ, 21.2°2θ, 21.4°2θ, 22.3°2θ, 24.9°2θ, 28.0°2θ, 28.9°2θ, and 34.0°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.3°2θ, 13.9°2θ, 15.8°2θ, 18.3°2θ, 18.8°2θ, 19.3°2θ, 20.7°2θ, 21.2°2θ, 21.4°2θ, 22.3°2θ, 24.9°2θ, 28.0°2θ, 28.9°2θ, 31.8°2θ, and 34.0°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.3°2θ, 13.9°2θ, 15.8°2θ, 18.3°2θ, 18.8°2θ, 19.3°2θ, 20.7°2θ, 21.2°2θ, 21.4°2θ, 22.3°2θ, 24.9°2θ, 28.0°2θ, 28.9°2θ, 31.8°2θ, and 34.0°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.3°2θ, 13.9°2θ, 15.8°2θ, 18.3°2θ, 18.8°2θ, 19.3°2θ, 20.7°2θ, 21.2°2θ, 21.4°2θ, 22.3°2θ, 24.3°2θ, 24.9°2θ, 28.0°2θ, 28.9°2θ, 31.8°2θ, and 34.0°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.3°2θ, 13.9°2θ, 15.8°2θ, 18.3°2θ, 18.8°2θ, 19.3°2θ, 20.7°2θ, 21.2°2θ, 21.4°2θ, 22.3°2θ, 24.3°2θ, 24.9°2θ, 28.0°2θ, 28.9°2θ, 31.8°2θ, and 34.0°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.3°2θ, 13.9°2θ, 15.5°2θ, 15.8°2θ, 18.3°2θ, 18.8°2θ, 19.3°2θ, 20.7°2θ, 21.2°2θ, 21.4°2θ, 22.3°2θ, 24.3°2θ, 24.9°2θ, 28.0°2θ, 28.9°2θ, 31.8°2θ, and 34.0°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.3°2θ, 13.9°2θ, 15.5°2θ, 15.8°2θ, 18.3°2θ, 18.8°2θ, 19.3°2θ, 20.7°2θ, 21.2°2θ, 21.4°2θ, 22.3°2θ, 24.3°2θ, 24.9°2θ, 28.0°2θ, 28.9°2θ, 31.8°2θ, and 34.0°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.3°2θ, 13.9°2θ, 15.5°2θ, 15.8°2θ, 18.3°2θ, 18.8°2θ, 19.3°2θ, 20.7°2θ, 21.2°2θ, 21.4°2θ, 22.3°2θ, 23.0°2θ, 24.3°2θ, 24.9°2θ, 28.0°2θ, 28.9°2θ, 31.8°2θ, and 34.0°2θ (±0.2°2θ; ±0.1° 2θ; or ±0.0°2θ; Cu Kα1 radiation). In some embodiments, the compound 1 monofumarate salt is crystalline polymorphic Form A characterized by XRPD signals at 13.3°2θ, 13.9°2θ, 15.5°2θ, 15.8°2θ, 18.3°2θ, 18.8°2θ, 19.3°2θ, 20.7°2θ, 21.2°2θ, 21.4°2θ, 22.3°2θ, 23.0°2θ, 24.3°2θ, 24.9°2θ, 28.0°2θ, 28.9°2θ, 31.8°2θ, and 34.0°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.3°2θ, 13.9°2θ, 15.5°2θ, 15.8°2θ, 18.3°2θ, 18.8°2θ, 19.3°2θ, 20.7°2θ, 21.2°2θ, 21.4°2θ, 22.3°2θ, 23.0°2θ, 24.3°2θ, 24.9°2θ, 28.0°2θ, 28.9°2θ, 31.8°2θ, 34.0°2θ, and 37.2°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.3°2θ, 13.9°2θ, 15.5°2θ, 15.8°2θ, 18.3°2θ, 18.8°2θ, 19.3°2θ, 20.7°2θ, 21.2°2θ, 21.4°2θ, 22.3°2θ, 23.0°2θ, 24.3°2θ, 24.9°2θ, 28.0°2θ, 28.9°2θ, 31.8°2θ, 34.0°2θ, and 37.2°2θ (±0.2°2θ; ±0.1°2θ; or ±0.0°2θ; Cu Kα1 radiation).

In some embodiments, crystalline polymorphic Form A is characterized by one, two, three, four, five, six, seven, eight, nine, ten, eleven, twelve, thirteen, fourteen, fifteen, sixteen, seventeen, eighteen, or nineteen XRPD signals selected from those set forth in Table 5.

TABLE 5

Compound 1 monofumarate salt Form A
(±0.2 °2θ; ±0.1 °2θ; or ±0.0 °2θ; Cu Kα1 radiation)

| Signal number | 2-θ (°) | d Value | Net Intensity (counts) | Gross Intensity (counts) | Rel. Intensity (%) |
|---|---|---|---|---|---|
| Signal #1 | 13.3 | 6.66 | 259.1 | 316.1 | 19.6 |
| Signal #2 | 13.9 | 6.36 | 348.6 | 406.8 | 26.3 |
| Signal #3 | 15.5 | 5.71 | 161.2 | 222.6 | 12.2 |
| Signal #4 | 15.8 | 5.61 | 451.0 | 514.1 | 34.1 |
| Signal #5 | 18.3 | 4.84 | 286.1 | 367.1 | 21.6 |
| Signal #6 | 18.8 | 4.71 | 309.7 | 397.7 | 23.4 |
| Signal #7 | 19.3 | 4.59 | 655.8 | 748.2 | 49.6 |
| Signal #8 | 20.7 | 4.28 | 448.6 | 549.2 | 33.9 |
| Signal #9 | 21.2 | 4.19 | 529.5 | 633.3 | 40.0 |
| Signal #10 | 21.4 | 4.14 | 531.4 | 636.2 | 40.2 |
| Signal #11 | 22.3 | 3.99 | 1323.1 | 1428.1 | 100.0 |
| Signal #12 | 23.0 | 3.86 | 149.6 | 249.9 | 11.3 |
| Signal #13 | 24.3 | 3.66 | 170.1 | 258.4 | 12.9 |
| Signal #14 | 24.9 | 3.57 | 236.3 | 318.5 | 17.9 |
| Signal #15 | 28.0 | 3.19 | 365.6 | 453.9 | 27.6 |
| Signal #16 | 28.9 | 3.09 | 312.5 | 399.2 | 23.6 |
| Signal #17 | 31.8 | 2.81 | 210.2 | 285.0 | 15.9 |
| Signal #18 | 34.0 | 2.63 | 270.9 | 355.3 | 20.5 |
| Signal #19 | 37.2 | 2.42 | 143.4 | 234.5 | 10.8 |

In some embodiments, the compound 1 monofumarate salt is crystalline polymorphic Form A characterized an XRPD at 22.3°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 15.9°2θ, and 22.3°2θ, (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.0°2θ, 15.9°2θ, and 22.3°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.0°2θ, 15.9°2θ, and 22.3°2θ, (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.0°2θ, 15.9°2θ, 19.4°2θ, and 22.3°2θ (±0.2°2θ; ±0.1°2θ; or ±0.0°2θ; Cu Kα1 radiation).

In some embodiments, the compound 1 monofumarate salt is crystalline polymorphic Form A characterized by XRPD signals at 14.0°2θ, 15.9°2θ, 19.4°2θ, and 22.3°2θ, (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.0°2θ, 15.9°2θ, 19.4°2θ, 21.3°2θ, and 22.3°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.0°2θ, 15.9°2θ, 19.4°2θ, 21.3°2θ, and 22.3°2θ, (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.0°2θ, 15.9°2θ, 19.4°2θ, 21.3°2θ, 21.5°2θ, and 22.3°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.0°2θ, 15.9°2θ, 19.4°2θ, 21.3°2θ, 21.5°2θ, and 22.3°2θ, (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 19.4°2θ, 21.3°2θ, 21.5°2θ, and 22.3°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 19.4°2θ, 21.3°2θ, 21.5°2θ, and 22.3°2θ, (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 18.9°2θ, 19.4°2θ, 21.3°2θ, 21.5°2θ, and 22.3°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 18.9°2θ, 19.4°2θ, 21.3°2θ, 21.5°2θ, and 22.3°2θ, (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 18.9°2θ, 19.4°2θ, 20.8°2θ, 21.3°2θ, 21.5°2θ, and 22.3°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 18.9°2θ, 19.4°2θ, 20.8°2θ, 21.3°2θ, 21.5°2θ, and 22.3°2θ, (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 18.9°2θ, 19.2°2θ, 19.4°2θ, 20.8°2θ, 21.3°2θ, 21.5°2θ, and 22.3°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 18.9°2θ, 19.2°2θ, 19.4°2θ, 20.8°2θ, 21.3°2θ, 21.5°2θ, and 22.3°2θ, (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.9°2θ, 19.2°2θ, 19.4°2θ, 20.8°2θ, 21.3°2θ, 21.5°2θ, and 22.3°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.9°2θ, 19.2°2θ, 19.4°2θ, 20.8°2θ, 21.3°2θ, 21.5°2θ, and 22.3°2θ, (±0.2°2θ, ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.9°2θ, 19.2°2θ, 19.4°2θ, 20.8°2θ, 21.3°2θ, 21.5°2θ, 22.3°2θ, and 28.1°2θ, (0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.9°2θ, 19.2°2θ, 19.4°2θ, 20.8°2θ, 21.3°2θ, 21.5°2θ, 22.3°2θ, and 28.1°2θ, (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.4°2θ, 18.9°2θ, 19.2°2θ, 19.4°2θ, 20.8°2θ, 21.3°2θ, 21.5°2θ, 22.3°2θ, and 28.1°2θ, (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.4°2θ, 18.9°2θ, 19.2°2θ, 19.4°2θ, 20.8°2θ, 21.3°2θ, 21.5°2θ, 22.3°2θ, and 28.1°2θ, (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.4°2θ, 18.9°2θ, 19.2°2θ, 19.4°2θ, 20.8°2θ, 21.3°2θ, 21.5°2θ, 22.3°2θ, 25.0°2θ, and 28.1°2θ, (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.4°2θ, 18.9°2θ, 19.2°2θ, 19.4°2θ, 20.8°2θ, 21.3°2θ, 21.5°2θ, 22.3°2θ, 25.0°2θ, and 28.1°2θ, (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.4°2θ, 18.9°2θ, 19.2°2θ, 19.4°2θ, 20.8°2θ, 21.3°2θ, 21.5°2θ, 22.3°2θ, 25.0°2θ, 28.1°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.4°2θ, 18.9°2θ, 19.2°2θ, 19.4°2θ, 20.8°2θ, 21.3°2θ, 21.5°2θ, 22.3°2θ, 25.0°2θ, 28.1°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.4°2θ, 18.9°2θ, 19.2°2θ, 19.4°2θ, 20.8°2θ, 21.3°2θ, 21.5°2θ, 22.3°2θ, 23.2°2θ, 25.0°2θ, 28.1°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.4°2θ, 18.9°2θ, 19.2°2θ, 19.4°2θ, 20.8°2θ, 21.3°2θ, 21.5°2θ, 22.3°2θ, 23.2°2θ, 25.0°2θ, 28.1°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.1°2θ, 13.4°2θ, 14.0°2θ, 15.6°2θ, 15.9°2θ, 18.4°2θ, 18.9°2θ, 19.2°2θ, 19.4°2θ, 20.8°2θ, 21.3°2θ, 21.5°2θ, 22.3°2θ, 23.2°2θ, 25.0°2θ, 28.1°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.1°2θ, 13.4°2θ, 14.0°2θ, 15.6°2θ, 15.9°2θ, 18.4°2θ, 18.9°2θ, 19.2°2θ, 19.4°2θ, 20.8°2θ, 21.3°2θ, 21.5°2θ, 22.3°2θ, 23.2°2θ, 25.0°2θ, 28.1°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.1°2θ, 13.4°2θ, 14.0°2θ, 15.6°2θ, 15.9°2θ, 18.4°2θ, 18.9°2θ, 19.2°2θ, 19.4°2θ, 20.8°2θ, 21.3°2θ, 21.5°2θ, 22.3°2θ, 23.2°2θ, 24.4°2θ, 25.0°2θ, 28.1°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.1°2θ, 13.4°2θ, 14.0°2θ, 15.6°2θ, 15.9°2θ, 18.4°2θ, 18.9°2θ, 19.2°2θ, 19.4°2θ, 20.8°2θ, 21.3°2θ, 21.5°2θ, 22.3°2θ, 23.2°2θ, 24.4°2θ, 25.0°2θ, 28.1°2θ, and 29.1°2θ (0.2°2θ; ±0.1°2θ; or 0.0°2θ; Cu Kα1 radiation).

In some embodiments, crystalline polymorphic Form A is characterized by one, two, three, four, five, six, seven, eight, nine, ten, eleven, twelve, thirteen, fourteen, fifteen, sixteen, seventeen, or eighteen XRPD signals selected from those set forth in Table 6.

TABLE 6

Compound 1 monofumarate salt Form A
(±0.2 °2θ; ±0.1 °2θ; or ±0.0 °2θ; Cu Kα1 radiation)Signal

| Signal number | 2-θ (°) | d Value | Net Intensity (counts) | Gross Intensity (counts) | Rel. Intensity (%) |
|---|---|---|---|---|---|
| Signal #1 | 10.1 | 8.78 | 554.9 | 650.3 | 12.3 |
| Signal #2 | 13.4 | 6.62 | 1186.0 | 1292.9 | 26.2 |
| Signal #3 | 14.0 | 6.32 | 1684.2 | 1793.9 | 37.2 |
| Signal #4 | 15.6 | 5.68 | 810.5 | 932.6 | 17.9 |
| Signal #5 | 15.9 | 5.58 | 2220.1 | 2346.2 | 49.1 |
| Signal #6 | 18.4 | 4.82 | 766.6 | 921.6 | 17.0 |
| Signal #7 | 18.9 | 4.69 | 1061.8 | 1230.2 | 23.5 |
| Signal #8 | 19.2 | 4.62 | 876.7 | 1051.4 | 19.4 |
| Signal #9 | 19.4 | 4.58 | 1606.4 | 1784.3 | 35.5 |
| Signal #10 | 20.8 | 4.26 | 962.8 | 1157.4 | 21.3 |
| Signal #11 | 21.3 | 4.16 | 1373.5 | 1572.2 | 30.4 |
| Signal #12 | 21.5 | 4.13 | 1288.6 | 1488.0 | 28.5 |
| Signal #13 | 22.3 | 3.98 | 4522.3 | 4718.8 | 100.0 |
| Signal #14 | 23.2 | 3.84 | 596.9 | 781.2 | 13.2 |
| Signal #15 | 24.4 | 3.64 | 515.6 | 688.9 | 11.4 |
| Signal #16 | 25.0 | 3.56 | 740.1 | 905.6 | 16.4 |
| Signal #17 | 28.1 | 3.17 | 804.6 | 970.8 | 17.8 |
| Signal #18 | 29.1 | 3.07 | 720.0 | 878.9 | 15.9 |

In some embodiments, the compound 1 monofumarate salt is crystalline polymorphic Form A characterized an XRPD signal at 22.6°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 19.6°2θ and 22.6°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 19.3°2θ, 19.6°2θ, and 22.6°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 19.3°2θ, 19.6°2θ, and 22.6°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 19.3°2θ, 19.6°2θ, 21.6°2θ and 22.6°2θ (±0.2°2θ; ±0.1°2θ; or ±0.0°2θ; Cu Kα1 radiation).

In some embodiments, the compound 1 fumarate salt is crystalline polymorphic Form A characterized by XRPD signals at 19.3°2θ, 19.6°2θ, 21.6°2θ, and 22.6°2θ (±0.2°2θ; ±0.1°2θ; or 0.0°2θ; Cu Kα1 radiation).

In some embodiments, the compound 1 monofumarate salt is crystalline polymorphic Form A characterized by two or more, or three or more XRPD signals selected from the group consisting of 18.5°2θ, 19.3°2θ, 19.6°2θ, 21.6°2θ, and 22.6°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 18.5°2θ, 19.3°2θ, 19.6°2θ, 21.6°2θ, and 22.6°2θ (±0.2°2θ; ±0.1°2θ; or 0.0°2θ; Cu Kα1 radiation).

In some embodiments, the compound 1 monofumarate salt is crystalline polymorphic Form A characterized by two or more, or three or more XRPD signals selected from the group consisting of 18.5°2θ, 19.3°2θ, 19.6°2θ, 21.6°2θ, 21.7°2θ, and 22.6°2θ (±0.2°2θ; ±0.1°2θ; or 0.0°2θ; Cu Kα1 radiation). In some embodiments, the compound 1 monofumarate salt is crystalline polymorphic Form A characterized by XRPD signals at 18.5°2θ, 19.3°2θ, 19.6°2θ, 21.6°2θ, 21.7°2θ, and 22.6°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 18.5°2θ, 19.3°2θ, 19.6°2θ, 21.6°2θ, 21.7°2θ, 22.6°2θ, and 25.2°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 18.5°2θ, 19.3°2θ, 19.6°2θ, 21.6°2θ, 21.7°2θ, 22.6°2θ, and 25.2°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 18.5°2θ, 19.3°2θ, 19.6°2θ, 21.6°2θ, 21.7°2θ, 22.6°2θ, 23.6°2θ, and 25.2°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 18.5°2θ, 19.3°2θ, 19.6°2θ, 21.6°2θ, 21.7°2θ, 22.6°2θ, 23.6°2θ, and 25.2°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 18.5°2θ, 19.3°2θ, 19.6°2θ, 21.6°2θ, 21.7°2θ, 22.6°2θ, 23.6°2θ, 23.9°2θ, and 25.2°2θ (±0.2°2θ; ±0.1°2θ, or ±0.0°2θ; Cu Kα1 radiation). In some embodiments, the compound 1 monofumarate salt is crystalline polymorphic Form A characterized by XRPD signals at 18.5°2θ, 19.3°2θ, 19.6°2θ, 21.6°2θ, 21.7°2θ, 22.6°2θ, 23.6°2θ, 23.9°2θ, and 25.2°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 17.8°2θ, 18.5°2θ, 19.3°2θ, 19.6°2θ, 21.6°2θ, 21.7°2θ, 22.6°2θ, 23.6°2θ, 23.9°2θ, and 25.2°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 17.8°2θ, 18.5°2θ, 19.3°2θ, 19.6°2θ, 21.6°2θ, 21.7°2θ, 22.6°2θ, 23.6°2θ, 23.9°2θ, and 25.2°2θ (±0.2°2θ; ±0.1°2θ; or ±0.0°2θ. Cu Kα1 radiation).

In some embodiments, the compound 1 monofumarate salt is crystalline polymorphic Form A characterized by two or more, or three or more XRPD signals selected from the group consisting of 14.2°2θ, 17.8°2θ, 18.5°2θ, 19.3°2θ, 19.6°2θ, 21.6°2θ, 21.7°2θ, 22.6°2θ, 23.6°2θ, 23.9°2θ, and 25.2°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.2°2θ, 17.8°2θ, 18.5°2θ, 19.3°2θ, 19.6°2θ, 21.6°2θ, 21.7°2θ, 22.6°2θ, 23.6°2θ, 23.9°2θ, and 25.2°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.2°2θ, 16.1°2θ, 17.8°2θ, 18.5°2θ, 19.3°2θ, 19.6°2θ, 21.6°2θ, 21.7°2θ, 22.6°2θ, 23.6°2θ, 23.9°2θ, and 25.2°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.2°2θ, 16.1°2θ, 17.8°2θ, 18.5°2θ, 19.3°2θ, 19.6°2θ, 21.6°2θ, 21.7°2θ, 22.6°2θ, 23.6°2θ, 23.9°2θ, and 25.2°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.2°2θ, 16.1°2θ, 17.8°2θ, 18.5°2θ, 19.3°2θ, 19.6°2θ, 21.1°2θ, 21.6°2θ, 21.7°2θ, 22.6°2θ, 23.6°2θ, 23.9°2θ, and 25.2°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.2°2θ, 16.1°2θ, 17.8°2θ, 18.5°2θ, 19.3°2θ, 19.6°2θ, 21.1°2θ, 21.6°2θ, 21.7°2θ, 22.6°2θ, 23.6°2θ, 23.9°2θ, and 25.2°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.2°2θ, 16.1°2θ, 16.2°2θ, 17.8°2θ, 18.5°2θ, 19.3°2θ, 19.6°2θ, 21.1°2θ, 21.6°2θ, 21.7°2θ, 22.6°2θ, 23.6°2θ, 23.9°2θ, and 25.2°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.2°2θ, 16.1°2θ, 16.2°2θ, 17.8°2θ, 18.5°2θ, 19.3°2θ, 19.6°2θ, 21.1°2θ, 21.6°2θ, 21.7°2θ, 22.6°2θ, 23.6°2θ, 23.9°2θ, and 25.2°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.2°2θ, 16.1°2θ, 16.2°2θ, 17.8°2θ, 18.5°2θ, 19.3°2θ, 19.6°2θ, 21.1°2θ, 21.6°2θ, 21.7°2θ, 22.6°2θ, 23.6°2θ, 23.9°2θ, 25.2°2θ, and 28.3°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.2°2θ, 16.1°2θ, 16.2°2θ, 17.8°2θ, 18.5°2θ, 19.3°2θ, 19.6°2θ, 21.1°2θ, 21.6°2θ, 21.7°2θ, 22.6°2θ, 23.6°2θ, 23.9°2θ, 25.2°2θ, and 28.3°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.6°2θ, 14.2°2θ, 16.1°2θ, 16.2°2θ, 17.8°2θ, 18.5°2θ, 19.3°2θ, 19.6°2θ, 21.1°2θ, 21.6°2θ, 21.7°2θ, 22.6°2θ, 23.6°2θ, 23.9°2θ, 25.2°2θ, and 28.3°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.6°2θ, 14.2°2θ, 16.1°2θ, 16.2°2θ, 17.8°2θ, 18.5°2θ, 19.3°2θ, 19.6°2θ, 21.1°2θ, 21.6°2θ, 21.7°2θ, 22.6°2θ, 23.6°2θ, 23.9°2θ, 25.2°2θ, and 28.3°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.3°2θ, 13.6°2θ, 14.2°2θ, 16.1°2θ, 16.2°2θ, 17.8°2θ, 18.5°2θ, 19.3°2θ, 19.6°2θ, 21.1°2θ, 21.6°2θ, 21.7°2θ, 22.6°2θ, 23.6°2θ, 23.9°2θ, 25.2°2θ, and 28.3°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.3°2θ, 13.6°2θ, 14.2°2θ, 16.1°2θ, 16.2°2θ, 17.8°2θ, 18.5°2θ, 19.3°2θ, 19.6°2θ, 21.1°2θ, 21.6°2θ, 21.7°2θ, 22.6°2θ, 23.6°2θ, 23.9°2θ, 25.2°2θ, and 28.3°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.3°2θ, 13.6°2θ, 14.2°2θ, 16.1°2θ, 16.2°2θ, 17.8°2θ, 18.5°2θ, 19.3°2θ, 19.6°2θ, 21.1°2θ, 21.6°2θ, 21.7°2θ, 22.6°2θ, 23.6°2θ, 23.9°2θ, 25.2°2θ, 28.3°2θ, and 29.9°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.3°2θ, 13.6°2θ, 14.2°2θ, 16.1°2θ, 16.2°2θ, 17.8°2θ, 18.5°2θ, 19.3°2θ, 19.6°2θ, 21.1°2θ, 21.6°2θ, 21.7°2θ, 22.6°2θ, 23.6°2θ, 23.9°2θ, 25.2°2θ, 28.3°2θ, and 29.9°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.3°2θ, 13.6°2θ, 14.2°2θ, 16.1°2θ, 16.2°2θ, 16.9°2θ, 17.8°2θ, 18.5°2θ, 19.3°2θ, 19.6°2θ, 21.1°2θ, 21.6°2θ, 21.7°2θ, 22.6°2θ, 23.6°2θ, 23.9°2θ, 25.2°2θ, 28.3°2θ, and 29.9°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.3°2θ, 13.6°2θ, 14.2°2θ, 16.1°2θ, 16.2°2θ, 16.9°2θ, 17.8°2θ, 18.5°2θ, 19.3°2θ, 19.6°2θ, 21.1°2θ, 21.6°2θ, 21.7°2θ, 22.6°2θ, 23.6°2θ, 23.9°2θ, 25.2°2θ, 28.3°2θ, and 29.9°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.3°2θ, 13.6°2θ, 14.2°2θ, 16.1°2θ, 16.2°2θ, 16.9°2θ, 17.8°2θ, 18.5°2θ, 19.3°2θ, 19.6°2θ, 21.1°2θ, 21.6°2θ, 21.7°2θ, 22.6°2θ, 23.6°2θ, 23.9°2θ, 25.2°2θ, 28.3°2θ, 29.8°2θ, and 29.9° 2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.3°2θ, 13.6°2θ, 14.2°2θ, 16.1°2θ, 16.2°2θ, 16.9°2θ, 17.8°2θ, 18.5°2θ, 19.3°2θ, 19.6°2θ, 21.1°2θ, 21.6°2θ, 21.7°2θ, 22.6°2θ, 23.6°2θ, 23.9°2θ, 25.2°2θ, 28.3°2θ, 29.8°2θ, and 29.9°2θ (±0.2°2θ; ±0.1°2θ, or ±0.0°2θ; Cu Kα1 radiation).

In some embodiments, the compound 1 monofumarate salt is crystalline polymorphic Form A characterized by two or more, or three or more XRPD signals selected from the group consisting of 10.3°2θ, 13.6°2θ, 14.2°2θ, 16.1°2θ, 16.2°2θ, 16.9°2θ, 17.8°2θ, 18.5°2θ, 19.3°2θ, 19.6°2θ, 21.1°2θ, 21.6°2θ, 21.7°2θ, 22.6°2θ, 23.6°2θ, 23.9°2θ, 25.2°2θ, 28.3°2θ, 29.8°2θ, and 29.9° 2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.3°2θ, 13.6°2θ, 14.2°2θ, 16.1°2θ, 16.2°2θ, 16.9°2θ, 17.8°2θ, 18.5°2θ, 19.3°2θ, 19.6°2θ, 21.1°2θ, 21.6°2θ, 21.7°2θ, 22.6°2θ, 23.6°2θ, 23.9°2θ, 25.2°2θ, 28.3°2θ, 29.8°2θ, and 29.9°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.3°2θ, 13.6°2θ, 14.2°2θ, 16.1°2θ, 16.2°2θ, 16.9°2θ, 17.8°2θ, 18.5°2θ, 19.3°2θ, 19.6°2θ, 21.1°2θ, 21.6°2θ, 21.7°2θ, 22.6°2θ, 23.6°2θ, 23.9°2θ, 25.2°2θ, 28.3°2θ, 29.3°2θ, 29.8°2θ, 29.9°2θ, and 36.7°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.3°2θ, 13.6°2θ, 14.2°2θ, 16.1°2θ, 16.2°2θ, 16.9°2θ, 17.8°2θ, 18.5°2θ, 19.3°2θ, 19.6°2θ, 21.1°2θ, 21.6°2θ, 21.7°2θ, 22.6°2θ, 23.6°2θ, 23.9°2θ, 25.2°2θ, 28.3°2θ, 29.3°2θ, 29.8°2θ, 29.9°2θ, and 36.7°2θ (±0.2°2θ; ±0.1°2θ; or ±0.0°2θ; Cu Kα1 radiation).

In some embodiments, crystalline polymorphic Form A is characterized by one, two, three, four, five, six, seven, eight, nine, ten, eleven, twelve, thirteen, fourteen, fifteen, sixteen, seventeen, eighteen, nineteen, twenty, twenty-one, twenty-two, or twenty-three XRPD signals selected from those set forth in Table 7.

TABLE 7

Compound 1 monofumarate salt Form A
(±0.2 °2θ; ±0.1 °2θ; or ±0.0 °2θ; Cu Kα1 radiation) Signal

| Signal number | 2-θ (°) | d Value | Net Intensity (counts) | Gross Intensity (counts) | Rel. Intensity (%) |
| --- | --- | --- | --- | --- | --- |
| Signal #1 | 10.3 | 8.58 | 169.1 | 350.6 | 18.1 |
| Signal #2 | 13.6 | 6.50 | 286.0 | 545.7 | 30.6 |
| Signal #3 | 14.2 | 6.24 | 339.2 | 620.7 | 36.3 |
| Signal #5 | 16.1 | 5.51 | 328.6 | 691.8 | 35.2 |
| Signal #4 | 16.2 | 5.47 | 310.8 | 677.7 | 33.3 |
| Signal #6 | 16.9 | 5.24 | 158.5 | 551.1 | 17.0 |
| Signal #7 | 17.8 | 4.98 | 351.8 | 771.4 | 37.7 |
| Signal #8 | 18.5 | 4.79 | 464.5 | 900.4 | 49.7 |
| Signal #9 | 19.3 | 4.60 | 542.6 | 991.7 | 58.1 |
| Signal #10 | 19.6 | 4.52 | 716.5 | 1170.2 | 76.7 |
| Signal #11 | 21.1 | 4.21 | 325.1 | 788.7 | 34.8 |
| Signal #12 | 21.6 | 4.11 | 533.8 | 996.9 | 57.2 |
| Signal #13 | 21.7 | 4.10 | 420.6 | 883.5 | 45.0 |
| Signal #14 | 22.6 | 3.94 | 933.9 | 1390.6 | 100.0 |
| Signal #16 | 23.6 | 3.77 | 398.5 | 840.6 | 42.7 |
| Signal #17 | 23.6 | 3.76 | 412.2 | 853.5 | 44.1 |
| Signal #15 | 23.9 | 3.72 | 377.4 | 813.5 | 40.4 |
| Signal #18 | 25.2 | 3.53 | 403.3 | 806.0 | 43.2 |
| Signal #19 | 28.3 | 3.15 | 286.5 | 627.2 | 30.7 |
| Signal #20 | 29.3 | 3.04 | 150.8 | 473.9 | 16.1 |
| Signal #22 | 29.8 | 2.99 | 156.9 | 467.8 | 16.8 |
| Signal #21 | 29.9 | 2.99 | 163.3 | 473.4 | 17.5 |
| Signal #23 | 36.7 | 2.45 | 95.9 | 313.9 | 10.3 |

In some embodiments, the compound 1 monofumarate salt is crystalline polymorphic Form A characterized by an XRPD signal at 22.3°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 15.8°2θ and 22.3°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 15.8°2θ, 21.3°2θ, and 22.3°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 15.8°2θ, 21.3°2θ, and 22.3°2θ (±0.2°2θ; ±0.1°2θ; or ±0.0° 2θ; Cu Kα1 radiation).

In some embodiments, the compound 1 monofumarate salt is crystalline polymorphic Form A characterized by two or more, or three or more XRPD signals selected from the group consisting of 14.0°2θ, 15.8°2θ, 21.3°2θ, and 22.3°2θ (±0.2°2θ; ±0.1°2θ; or ±0.0°2θ; Cu Kα1 radiation).

In some embodiments, the compound 1 monofumarate salt is crystalline polymorphic Form A characterized by XRPD signals at 14.0°2θ, 15.8°2θ, 21.3°2θ, and 22.3°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.0°2θ, 15.8°2θ, 19.3°2θ, 21.3°2θ, and 22.3°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.0°2θ, 15.8°2θ, 19.3°2θ, 21.3°2θ, and 22.3°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.0°2θ, 15.8°2θ, 19.3°2θ, 21.3°2θ, 21.4°2θ, and 22.3°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.0°2θ, 15.8°2θ, 19.3°2θ, 21.3°2θ, 21.4°2θ, and 22.3°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.3°2θ, 14.0°2θ, 15.8°2θ, 19.3°2θ, 21.3°2θ, 21.4°2θ, and 22.3°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.3°2θ, 14.0°2θ, 15.8°2θ, 19.3°2θ, 21.3°2θ, 21.4°2θ, and 22.3°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.3°2θ, 14.0°2θ, 15.8°2θ, 19.3°2θ, 20.8°2θ, 21.3°2θ, 21.4°2θ, and 22.3°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.3°2θ, 14.0°2θ, 15.8°2θ, 19.3°2θ, 20.8°2θ, 21.3°2θ, 21.4°2θ, and 22.3°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.3°2θ, 14.0°2θ, 15.8°2θ, 19.3°2θ, 20.8°2θ, 21.3°2θ, 21.4°2θ, 22.3°2θ, and 28.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.3°2θ, 14.0°2θ, 15.8°2θ, 19.3°2θ, 20.8°2θ, 21.3°2θ, 21.4°2θ, 22.3°2θ, and 28.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.3°2θ, 14.0°2θ, 15.8°2θ, 18.9°2θ, 19.3°2θ, 20.8°2θ, 21.3°2θ, 21.4°2θ, 22.3°2θ, and 28.1°2θ (±0.2°2θ; ±0.1°2θ; or ±0.0°2θ. Cu Kα1 radiation).

In some embodiments, the compound 1 monofumarate salt is crystalline polymorphic Form A characterized by two or more, or three or more XRPD signals selected from the group consisting of 13.3°2θ, 14.0°2θ, 15.8°2θ, 18.9°2θ, 19.3°2θ, 20.8°2θ, 21.3°2θ, 21.4°2θ, 22.3°2θ, 28.1°2θ, and 29.0°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.3°2θ, 14.0°2θ, 15.8°2θ, 18.9°2θ, 19.3°2θ, 20.8°2θ, 21.3°2θ, 21.4°2θ, 22.3°2θ, 28.1°2θ, and 29.0°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.3°2θ, 14.0°2θ, 15.5°2θ, 15.8°2θ, 18.9°2θ, 19.3°2θ, 20.8°2θ, 21.3°2θ, 21.4°2θ, 22.3°2θ, 28.1°2θ, and 29.0°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.3°2θ, 14.0°2θ, 15.5°2θ, 15.8°2θ, 18.9°2θ, 19.3°2θ, 20.8°2θ, 21.3°2θ, 21.4°2θ, 22.3°2θ, 28.1°2θ, and 29.0°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.3°2θ, 14.0°2θ, 15.5°2θ, 15.8°2θ, 18.4°2θ, 18.9°2θ, 19.3°2θ, 20.8°2θ, 21.3°2θ, 21.4°2θ, 22.3°2θ, 28.1°2θ, and 29.0°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.3°2θ, 14.0°2θ, 15.5°2θ, 15.8°2θ, 18.4°2θ, 18.9°2θ, 19.3°2θ, 20.8°2θ, 21.3°2θ, 21.4°2θ, 22.3°2θ, 28.1°2θ, and 29.0°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.3°2θ, 14.0°2θ, 15.5°2θ, 15.8°2θ, 18.4°2θ, 18.9°2θ, 19.3°2θ, 20.8°2θ, 21.3°2θ, 21.4°2θ, 22.3°2θ, 24.4°2θ, 28.1°2θ, and 29.0°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.3°2θ, 14.0°2θ, 15.5°2θ, 15.8°2θ, 18.4°2θ, 18.9°2θ, 19.3°2θ, 20.8°2θ, 21.3°2θ, 21.4°2θ, 22.3°2θ, 24.4°2θ, 28.1°2θ, and 29.0°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.3°2θ, 14.0°2θ, 15.5°2θ, 15.8°2θ, 18.4°2θ, 18.9°2θ, 19.3°2θ, 20.8°2θ, 21.3°2θ, 21.4°2θ, 22.3°2θ, 23.1°2θ, 24.4°2θ, 28.1°2θ, and 29.0°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.3°2θ, 14.0°2θ, 15.5°2θ, 15.8°2θ, 18.4°2θ, 18.9°2θ, 19.3°2θ, 20.8°2θ, 21.3°2θ, 21.4°2θ, 22.3°2θ, 23.1°2θ, 24.4°2θ, 28.1°2θ, and 29.0°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.3°2θ, 14.0°2θ, 15.5°2θ, 15.8°2θ, 18.4°2θ, 18.9°2θ, 19.3°2θ, 20.8°2θ, 21.3°2θ, 21.4°2θ, 22.3°2θ, 23.1°2θ, 24.4°2θ, 25.0°2θ, 28.1°2θ, and 29.0°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.3°2θ, 14.0°2θ, 15.5°2θ, 15.8°2θ, 18.4°2θ, 18.9°2θ, 19.3°2θ, 20.8°2θ, 21.3°2θ, 21.4°2θ, 22.3°2θ, 23.1°2θ, 24.4°2θ, 25.0°2θ, 28.1°2θ, and 29.0°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.0°2θ, 13.3°2θ, 14.0°2θ, 15.5°2θ, 15.8°2θ, 18.4°2θ, 18.9°2θ, 19.3°2θ, 20.8°2θ, 21.3°2θ, 21.4°2θ, 22.3°2θ, 23.1°2θ, 24.4°2θ, 25.0°2θ, 28.1°2θ, and 29.0°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.0°2θ, 13.3°2θ, 14.0°2θ, 15.5°2θ, 15.8°2θ, 18.4°2θ, 18.9°2θ, 19.3°2θ, 20.8°2θ, 21.3°2θ, 21.4°2θ, 22.3°2θ, 23.1°2θ, 24.4°2θ, 25.0°2θ, 28.1°2θ, and 29.0°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.0°2θ, 13.3°2θ, 14.0°2θ, 15.5°2θ, 15.8°2θ, 18.4°2θ, 18.9°2θ, 19.3°2θ, 20.8°2θ, 21.3°2θ, 21.4°2θ, 22.3°2θ, 23.1°2θ, 24.4°2θ, 25.0°2θ, 28.1°2θ, 29.0°2θ, and 34.0°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.0°2θ, 13.3°2θ, 14.0°2θ, 15.5°2θ, 15.8°2θ, 18.4°2θ, 18.9°2θ, 19.3°2θ, 20.8°2θ, 21.3°2θ, 21.4°2θ, 22.3°2θ, 23.1°2θ, 24.4°2θ, 25.0°2θ, 28.1°2θ, 29.0°2θ, and 34.0°2θ (±0.2°2θ; ±0.1°2θ; or ±0.0°2θ; Cu Kα1 radiation). In some embodiments, crystalline polymorphic Form A is characterized by one, two, three, four, five, six, seven, eight, nine, ten, eleven, twelve, thirteen, fourteen, fifteen, sixteen, seventeen, or eighteen XRPD signals selected from those set forth in Table 8.

TABLE 8

Compound 1 monofumarate salt Form A
(±0.2 °2θ; ±0.1 °2θ; or ±0.0 °2θ; Cu Kα1 radiation)Signal

| Signal number | 2-θ (°) | d Value | Net Intensity (counts) | Gross Intensity (counts) | Rel. Intensity (%) |
|---|---|---|---|---|---|
| Signal #1 | 10.0 | 8.80 | 327.3 | 398.8 | 10.4 |
| Signal #2 | 13.3 | 6.64 | 779.1 | 861.7 | 24.8 |
| Signal #3 | 14.0 | 6.34 | 969.1 | 1053.7 | 30.8 |
| Signal #4 | 15.5 | 5.70 | 492.9 | 588.2 | 15.7 |
| Signal #5 | 15.8 | 5.59 | 1218.2 | 1315.3 | 38.8 |
| Signal #6 | 18.4 | 4.83 | 475.9 | 597.0 | 15.1 |
| Signal #7 | 18.9 | 4.70 | 613.6 | 746.3 | 19.5 |
| Signal #8 | 19.3 | 4.58 | 930.0 | 1071.4 | 29.6 |
| Signal #9 | 20.8 | 4.27 | 721.0 | 878.3 | 22.9 |
| Signal #10 | 21.3 | 4.18 | 1004.6 | 1167.5 | 32.0 |
| Signal #11 | 21.4 | 4.14 | 893.7 | 1058.3 | 28.4 |
| Signal #12 | 22.3 | 3.98 | 3143.2 | 3310.3 | 100.0 |
| Signal #13 | 23.1 | 3.85 | 405.0 | 566.9 | 12.9 |
| Signal #14 | 24.4 | 3.65 | 412.2 | 561.1 | 13.1 |
| Signal #15 | 25.0 | 3.56 | 386.4 | 527.1 | 12.3 |
| Signal #16 | 28.1 | 3.18 | 696.5 | 841.4 | 22.2 |

TABLE 8-continued

Compound 1 monofumarate salt Form A
(±0.2 °2θ; ±0.1 °2θ; or ±0.0 °2θ; Cu Kα1 radiation)Signal

| Signal number | 2-θ (°) | d Value | Net Intensity (counts) | Gross Intensity (counts) | Rel. Intensity (%) |
|---|---|---|---|---|---|
| Signal #17 | 29.0 | 3.08 | 572.2 | 714.7 | 18.2 |
| Signal #18 | 34.0 | 2.63 | 323.7 | 447.5 | 10.3 |

In some embodiments, the compound 1 monofumarate salt is crystalline polymorphic Form A characterized an XRPD signal at 22.4°2θ (±0.2°2θ; ±0.1°2θ; or ±0.0°2θ; Cu Kα1 radiation).

In some embodiments, the compound 1 monofumarate salt is crystalline polymorphic Form A characterized by XRPD signals at 15.9°2θ, and 22.4°2θ (±0.2°2θ; 0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 15.9°2θ, 19.5°2θ, and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 15.9°2θ, 19.5°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 15.9°2θ, 19.5°2θ, 21.6°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by XRPD signals at 15.9°2θ, 19.5°2θ, 21.6°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.1°2θ, 15.9°2θ, 19.5°2θ, 21.6°2θ, and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.1°2θ, 15.9°2θ, 19.5°2θ, 21.6°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.1°2θ, 15.9°2θ, 16.8°2θ, 19.5°2θ, 21.6°2θ, and 22.4°2θ (±0.2°2θ; ±0.1°2θ; or ±0.0°2θ; Cu Kα1 radiation). In some embodiments, the compound 1 fumarate salt is crystalline polymorphic Form A characterized by XRPD signals at 14.1°2θ, 15.9°2θ, 16.8°2θ, 19.5°2θ, 21.6°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.1°2θ, 15.9°2θ, 16.8°2θ, 19.5°2θ, 21.4°2θ, 21.6°2θ, and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.1°2θ, 15.9°2θ, 16.8°2θ, 19.5°2θ, 21.4°2θ, 21.6°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.1°2θ, 15.7°2θ, 15.9°2θ, 16.8°2θ, 19.5°2θ, 21.4°2θ, 21.6°2θ, and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.1°2θ, 15.7°2θ, 15.9°2θ, 16.8°2θ, 19.5°2θ, 21.4°2θ, 21.6°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.1°2θ, 15.7°2θ, 15.9°2θ, 16.8°2θ, 19.3°2θ, 19.5°2θ, 21.4°2θ, 21.6°2θ, and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.1°2θ, 15.7°2θ, 15.9°2θ, 16.8°2θ, 19.3°2θ, 19.5°2θ, 21.4°2θ, 21.6°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.1°2θ, 15.7°2θ, 15.9°2θ, 16.8°2θ, 19.3°2θ, 19.5°2θ, 21.4°2θ, 21.6°2θ, and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.1°2θ, 15.7°2θ, 15.9°2θ, 16.8°2θ, 19.3°2θ, 19.5°2θ, 21.4°2θ, 21.6°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.1°2θ, 15.7°2θ, 15.9°2θ, 16.8°2θ, 19.3°2θ, 19.5°2θ, 21.4°2θ, 21.6°2θ, 22.4°2θ, and 25.3°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.1°2θ, 15.7°2θ, 15.9°2θ, 16.8°2θ, 19.3°2θ, 19.5°2θ, 21.4°2θ, 21.6°2θ, 22.4°2θ, and 25.3°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.1°2θ, 15.7°2θ, 15.9°2θ, 16.8°2θ, 19.3°2θ, 19.5°2θ, 20.9°2θ, 21.4°2θ, 21.6°2θ, 22.4°2θ, and 25.3°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.1°2θ, 15.7°2θ, 15.9°2θ, 16.8°2θ, 19.3°2θ, 19.5°2θ, 20.9°2θ, 21.4°2θ, 21.6°2θ, 22.4°2θ, and 25.3°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.1°2θ, 15.7°2θ, 15.9°2θ, 16.8°2θ, 19.3°2θ, 19.5°2θ, 20.9°2θ, 21.4°2θ, 21.6°2θ, 22.4°2θ, 25.1°2θ, and 25.3°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.1°2θ, 15.7°2θ, 15.9°2θ, 16.8°2θ, 19.0°2θ, 19.3°2θ, 19.5°2θ, 20.9°2θ, 21.4°2θ, 21.6°2θ, 22.4°2θ, 25.1°2θ, and 25.3°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.1°2θ, 15.7°2θ, 15.9°2θ, 16.8°2θ, 19.0°2θ, 19.3°2θ, 19.5°2θ, 20.9°2θ, 21.4°2θ, 21.6°2θ, 22.4°2θ, 25.1°2θ, and 25.3°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.1°2θ, 15.7°2θ, 15.9°2θ, 16.8°2θ, 19.0°2θ, 19.3°2θ, 19.5°2θ, 20.9°2θ, 21.4°2θ, 21.6°2θ, 22.4°2θ, 25.1°2θ, and 25.3°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.1°2θ, 15.7°2θ, 15.9°2θ, 16.8°2θ, 19.0°2θ, 19.3°2θ, 19.5°2θ, 20.9°2θ, 21.4°2θ, 21.6°2θ, 22.4°2θ, 25.1°2θ, 25.3°2θ, and 28.2°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.1°2θ, 15.7°2θ, 15.9°2θ, 16.8°2θ, 19.0°2θ, 19.3°2θ, 19.5°2θ, 20.9°2θ, 21.4°2θ, 21.6°2θ, 22.4°2θ, 25.1°2θ, 25.3°2θ, and 28.2°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.1°2θ, 15.7°2θ, 15.9°2θ, 16.8°2θ, 19.0°2θ, 19.3°2θ, 19.5°2θ, 20.9°2θ, 21.4°2θ, 21.6°2θ, 22.4°2θ, 23.2°2θ, 25.1°2θ, 25.3°2θ, and 28.2°2θ (±0.2°2θ; 0.1°2θ; or ±0.0°2θ; Cu Kα1 radiation). In some embodiments, the compound 1 monofumarate salt is crystalline polymorphic Form A characterized by XRPD signals at 13.4°2θ, 14.1°2θ, 15.7°2θ, 15.9°2θ, 16.8°2θ, 19.0°2θ, 19.3°2θ, 19.5°2θ, 20.9°2θ, 21.4°2θ, 21.6°2θ, 22.4°2θ, 23.2°2θ, 25.1°2θ, 25.3°2θ, and 28.2°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.1°2θ, 15.7°2θ, 15.9°2θ, 16.8°2θ, 18.5°2θ, 19.0°2θ, 19.3°2θ, 19.5°2θ, 20.9°2θ, 21.4°2θ, 21.6°2θ, 22.4°2θ, 23.2°2θ, 25.1°2θ, 25.3°2θ, and 28.2°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.1°2θ, 15.7°2θ, 15.9°2θ, 16.8°2θ, 18.5°2θ, 19.0°2θ, 19.3°2θ, 19.5°2θ, 20.9°2θ, 21.4°2θ, 21.6°2θ, 22.4°2θ, 23.2°2θ, 25.1°2θ, 25.3°2θ, and 28.2°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.1°2θ, 15.7°2θ, 15.9°2θ, 16.8°2θ, 18.5°2θ, 19.0°2θ, 19.3°2θ, 19.5°2θ, 20.9°2θ, 21.4°2θ, 21.6°2θ, 22.4°2θ, 23.2°2θ, 25.1°2θ, 25.3°2θ, 28.2°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.1°2θ, 15.7°2θ, 15.9°2θ, 16.8°2θ, 18.5°2θ, 19.0°2θ, 19.3°2θ, 19.5°2θ, 20.9°2θ, 21.4°2θ, 21.6°2θ, 22.4°2θ, 23.2°2θ, 25.1°2θ, 25.3°2θ, 28.2°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.1°2θ, 15.7°2θ, 15.9°2θ, 16.8°2θ, 18.5°2θ, 19.0°2θ, 19.3°2θ, 19.5°2θ, 20.9°2θ, 21.4°2θ, 21.6°2θ, 22.4°2θ, 23.2°2θ, 25.1°2θ, 25.3°2θ, 28.2°2θ, 29.1°2θ, and 34.0°2θ (±0.2° 2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.1°2θ, 15.7°2θ, 15.9°2θ, 16.8°2θ, 18.5°2θ, 19.0°2θ, 19.3°2θ, 19.5°2θ, 20.9°2θ, 21.4°2θ, 21.6°2θ, 22.4°2θ, 23.2°2θ, 25.1°2θ, 25.3°2θ, 28.2°2θ, 29.1°2θ, and 34.0 (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.1°2θ, 15.7°2θ, 15.9°2θ, 16.8°2θ, 18.5°2θ, 19.0°2θ, 19.3°2θ, 19.5°2θ, 20.9°2θ, 21.4°2θ, 21.6°2θ, 22.4°2θ, 23.2°2θ, 24.5°2θ, 25.1°2θ, 25.3°2θ, 28.2°2θ, 29.1°2θ, and 34.0°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.1°2θ, 15.7°2θ, 15.9°2θ, 16.8°2θ, 18.5°2θ, 19.0°2θ, 19.3°2θ, 19.5°2θ, 20.9°2θ, 21.4°2θ, 21.6°2θ, 22.4°2θ, 23.2°2θ, 24.5°2θ, 25.1°2θ, 25.3°2θ, 28.2°2θ, 29.1°2θ, and 34.0 (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 8.4°2θ, 13.4°2θ, 14.1°2θ, 15.7°2θ, 15.9°2θ, 16.8°2θ, 18.5°2θ, 19.0°2θ, 19.3°2θ, 19.5°2θ, 20.9°2θ, 21.4°2θ, 21.6°2θ, 22.4°2θ, 23.2°2θ, 24.5°2θ, 25.1°2θ, 25.3°2θ, 28.2°2θ, 29.1°2θ, and 34.0°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 8.4°2θ, 13.4°2θ, 14.1°2θ, 15.7°2θ, 15.9°2θ, 16.8°2θ, 18.5°2θ, 19.0°2θ, 19.3°2θ, 19.5°2θ, 20.9°2θ, 21.4°2θ, 21.6°2θ, 22.4°2θ, 23.2°2θ, 24.5°2θ, 25.1°2θ, 25.3°2θ, 28.2°2θ, 29.1°2θ, and 34.0 (±0.2°2θ; ±0.1°2θ; or ±0.0°2θ; Cu Kα1 radiation).

In some embodiments, crystalline polymorphic Form A is characterized by one, two, three, four, five, six, seven, eight, nine, ten, eleven, twelve, thirteen, fourteen, fifteen, sixteen, seventeen, eighteen, nineteen, twenty, or twenty-one XRPD signals selected from those set forth in Table 9.

TABLE 9

Compound 1 monofumarate salt Form A(±0.2 °2θ; ±0.1 °2θ; or ±0.0 °2θ; Cu Kα1 radiation)Signal

| Signal number | 2-θ (°) | d Value | Net Intensity (counts) | Gross Intensity (counts) | Rel. Intensity (%) | Signal number |
|---|---|---|---|---|---|---|
| Signal #1 | 8.4 | 10.48 | 436.6 | 566.4 | 0.1 | 10.7 |
| Signal #2 | 13.4 | 6.59 | 877.2 | 1027.5 | 0.2 | 21.5 |
| Signal #3 | 14.1 | 6.29 | 1164.6 | 1322.0 | 0.3 | 28.5 |
| Signal #4 | 15.7 | 5.66 | 1107.0 | 1305.8 | 0.3 | 27.1 |
| Signal #5 | 15.9 | 5.56 | 3118.1 | 3328.0 | 0.8 | 76.3 |
| Signal #6 | 16.8 | 5.26 | 1123.8 | 1361.3 | 0.3 | 27.5 |
| Signal #7 | 18.5 | 4.80 | 594.0 | 879.0 | 0.1 | 14.5 |
| Signal #8 | 19.0 | 4.67 | 718.4 | 1015.6 | 0.2 | 17.6 |
| Signal #9 | 19.3 | 4.61 | 980.6 | 1282.0 | 0.2 | 24.0 |
| Signal #10 | 19.5 | 4.56 | 2391.0 | 2695.4 | 0.6 | 58.5 |
| Signal #11 | 20.9 | 4.24 | 775.7 | 1086.9 | 0.2 | 19.0 |
| Signal #12 | 21.4 | 4.15 | 1110.8 | 1421.3 | 0.3 | 27.2 |
| Signal #13 | 21.6 | 4.12 | 1642.3 | 1951.7 | 0.4 | 40.2 |
| Signal #14 | 22.4 | 3.96 | 4086.6 | 4385.1 | 1.0 | 100.0 |
| Signal #15 | 23.2 | 3.83 | 618.3 | 897.3 | 0.2 | 15.1 |
| Signal #16 | 24.5 | 3.63 | 480.9 | 732.4 | 0.1 | 11.8 |
| Signal #17 | 25.1 | 3.54 | 764.1 | 1011.1 | 0.2 | 18.7 |
| Signal #18 | 25.3 | 3.52 | 867.9 | 1112.1 | 0.2 | 21.2 |
| Signal #19 | 28.2 | 3.17 | 714.4 | 940.2 | 0.2 | 17.5 |
| Signal #20 | 29.1 | 3.06 | 544.6 | 761.8 | 0.1 | 13.3 |
| Signal #21 | 34.0 | 2.63 | 488.8 | 672.7 | 0.1 | 12.0 |

In some embodiments, the compound 1 monofumarate salt is crystalline polymorphic Form A characterized an XRPD signal at 22.3°2θ (±0.2°2θ, ±0.1°2θ; or ±0.0°2θ; Cu Kα1 radiation).

In some embodiments, the compound 1 monofumarate salt is crystalline polymorphic Form A characterized by XRPD signals at 15.9°2θ, and 22.3°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 15.9°2θ, 19.4°2θ, and 22.3°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 15.9°2θ, 19.4°2θ, and 22.3°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 15.9°2θ, 19.4°2θ, 21.5°2θ, and 22.3°2θ (±0.2°2θ; ±0.1°2θ; or ±0.0°2θ; Cu Kα1 radiation).

In some embodiments, the compound 1 monofumarate salt is crystalline polymorphic Form A characterized by XRPD signals at 15.9°2θ, 19.4°2θ, 21.5°2θ, and 22.3°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 15.9°2θ, 19.4°2θ, 21.4°2θ, 21.5°2θ, and 22.3°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 15.9°2θ, 19.4°2θ, 21.4°2θ, 21.5°2θ, and 22.3°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.0°2θ, 15.9°2θ, 19.4°2θ, 21.4°2θ, 21.5°2θ, and 22.3°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.0°2θ, 15.9°2θ, 19.4°2θ, 21.4°2θ, 21.5°2θ, and 22.3°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.0°2θ, 15.9°2θ, 19.4°2θ, 21.4°2θ, 21.5°2θ, 22.3°2θ, and 28.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.0°2θ, 15.9°2θ, 19.4°2θ, 21.4°2θ, 21.5°2θ, 22.3°2θ, and 28.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.0°2θ, 15.9°2θ, 19.4°2θ, 20.9°2θ, 21.4°2θ, 21.5°2θ, 22.3°2θ, and 28.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.0°2θ, 15.9°2θ, 19.4°2θ, 20.9°2θ, 21.4°2θ, 21.5°2θ, 22.3°2θ, and 28.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 19.4°2θ, 20.9°2θ, 21.4°2θ, 21.5°2θ, 22.3°2θ, and 28.1°2θ (±0.2°2θ; ±0.1°2θ, or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 19.4°2θ, 20.9°2θ, 21.4°2θ, 21.5°2θ, 22.3°2θ, and 28.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 19.0°2θ, 19.4°2θ, 20.9°2θ, 21.4°2θ, 21.5°2θ, 22.3°2θ, and 28.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 19.0°2θ, 19.4°2θ, 20.9°2θ, 21.4°2θ, 21.5°2θ, 22.3°2θ, and 28.1°2θ (±0.2°2θ; ±0.1°2θ; or ±0.0°2θ. Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 19.0°2θ, 19.4°2θ, 20.9°2θ, 21.4°2θ, 21.5°2θ, 22.3°2θ, and 28.1°2θ (±0.2°2θ; 0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 19.0°2θ, 19.4°2θ, 20.9°2θ, 21.4°2θ, 21.5°2θ, 22.3°2θ, and 28.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 19.0°2θ, 19.4°2θ, 20.9°2θ, 21.4°2θ, 21.5°2θ, 22.3°2θ, 25.0°2θ, and 28.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 19.0°2θ, 19.4°2θ, 20.9°2θ, 21.4°2θ, 21.5°2θ, 22.3°2θ, 25.0°2θ, and 28.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 19.0°2θ, 19.4°2θ, 20.9°2θ, 21.4°2θ, 22.3°2θ, 25.0°2θ, 28.1°2θ, and 29.1°2θ (±0.2°2θ; ±0.1°2θ, or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 19.0°2θ, 19.4°2θ, 20.9°2θ, 21.4°2θ, 21.5°2θ, 22.3°2θ, 25.0°2θ, 28.1°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.4°2θ, 19.0°2θ, 19.4°2θ, 20.9°2θ, 21.4°2θ, 21.5°2θ, 22.3°2θ, 25.0°2θ, 28.1°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.4°2θ, 19.0°2θ, 19.4°2θ, 20.9°2θ, 21.4°2θ, 21.5°2θ, 22.3°2θ, 25.0°2θ, 28.1°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.4°2θ, 19.0°2θ, 19.4°2θ, 20.9°2θ, 21.4°2θ, 21.5°2θ, 22.3°2θ, 23.1°2θ, 25.0°2θ, 28.1°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.4°2θ, 19.0°2θ, 19.4°2θ, 20.9°2θ, 21.4°2θ, 21.5°2θ, 22.3°2θ, 23.1°2θ, 25.0°2θ, 28.1°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.4°2θ, 19.0°2θ, 19.4°2θ, 20.9°2θ, 21.4°2θ, 21.5°2θ, 22.3°2θ, 23.1°2θ, 25.0°2θ, 25.1°2θ, 28.1°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.4°2θ, 19.0°2θ, 19.4°2θ, 20.9°2θ, 21.4°2θ, 21.5°2θ, 22.3°2θ, 23.1°2θ, 25.0°2θ, 25.1°2θ, 28.1°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 16.7°2θ, 18.4°2θ, 19.0°2θ, 19.4°2θ, 20.9°2θ, 21.4°2θ, 21.5°2θ, 22.3°2θ, 23.1°2θ, 25.0°2θ, 25.1°2θ, 28.1°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 16.7°2θ, 18.4°2θ, 19.0°2θ, 19.4°2θ, 20.9°2θ, 21.4°2θ, 21.5°2θ, 22.3°2θ, 23.1°2θ, 25.0°2θ, 25.1°2θ, 28.1°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 16.7°2θ, 18.4°2θ, 19.0°2θ, 19.4°2θ, 20.9°2θ, 21.4°2θ, 21.5°2θ, 22.3°2θ, 23.1°2θ, 24.4°2θ, 25.0°2θ, 25.1°2θ, 28.1°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 16.7°2θ, 18.4°2θ, 19.0°2θ, 19.4°2θ, 20.9°2θ, 21.4°2θ, 21.5°2θ, 22.3°2θ, 23.1, °2θ, 24.4°2θ, 25.0°2θ, 25.1°2θ, 28.1°2θ, and 29.1°2θ (±0.2°2θ; ±0.1°2θ; or ±0.0°2θ; Cu Kα1 radiation).

In some embodiments, crystalline polymorphic Form A is characterized by one, two, three, four, five, six, seven, eight, nine, ten, eleven, twelve, thirteen, fourteen, fifteen, sixteen, seventeen, or eighteen XRPD signals selected from those set forth in Table 10.

TABLE 10

Compound 1 monofumarate salt Form A(±0.2 °2θ; ±0.1 °2θ; or ±0.0 °2θ; Cu Kα1 radiation)Signal

| Signal number | 2-θ (°) | d Value | Net Intensity (counts) | Gross Intensity (counts) | Rel. Intensity (%) | Signal number |
|---|---|---|---|---|---|---|
| Signal #3 | 13.4 | 6.61 | 407.6 | 504.5 | 0.2 | 20.6 |
| Signal #4 | 14.0 | 6.31 | 505.5 | 604.4 | 0.3 | 25.5 |
| Signal #5 | 15.6 | 5.68 | 361.8 | 469.7 | 0.2 | 18.3 |
| Signal #6 | 15.9 | 5.58 | 991.7 | 1102.1 | 0.5 | 50.1 |
| Signal #7 | 16.7 | 5.30 | 247.2 | 366.0 | 0.1 | 12.5 |
| Signal #9 | 18.4 | 4.82 | 293.7 | 439.1 | 0.1 | 14.8 |
| Signal #10 | 19.0 | 4.68 | 367.8 | 520.4 | 0.2 | 18.6 |
| Signal #11 | 19.4 | 4.58 | 815.1 | 971.1 | 0.4 | 41.2 |
| Signal #13 | 20.9 | 4.25 | 429.2 | 593.0 | 0.2 | 21.7 |
| Signal #14 | 21.4 | 4.16 | 590.7 | 759.0 | 0.3 | 29.8 |
| Signal #15 | 21.5 | 4.14 | 618.4 | 787.4 | 0.3 | 31.2 |
| Signal #16 | 22.3 | 3.97 | 1979.5 | 2150.0 | 1.0 | 100.0 |
| Signal #17 | 23.1 | 3.84 | 284.4 | 450.0 | 0.1 | 14.4 |
| Signal #18 | 24.4 | 3.65 | 245.5 | 397.7 | 0.1 | 12.4 |
| Signal #19 | 25.0 | 3.56 | 358.3 | 503.2 | 0.2 | 18.1 |
| Signal #20 | 25.1 | 3.54 | 250.4 | 393.7 | 0.1 | 12.6 |
| Signal #23 | 28.1 | 3.17 | 462.2 | 605.5 | 0.2 | 23.3 |
| Signal #25 | 29.1 | 3.07 | 313.7 | 452.9 | 0.2 | 15.8 |

In some embodiments, the compound 1 monofumarate salt is crystalline polymorphic Form A characterized by an XRPD signal at 22.3°2θ (±0.2°2θ; ±0.1°2θ; or ±0.0°2θ; Cu Kα1 radiation).

In some embodiments, the compound 1 monofumarate salt is crystalline polymorphic Form A characterized by XRPD signals at 15.9°2θ, and 22.3°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 15.9°2θ, 21.5°2θ, and 22.3°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 15.9°2θ, 21.5°2θ, and 22.3°2θ (±0.2°2θ; ±0.1°2θ; or ±0.0° 2θ; Cu Kα1 radiation).

In some embodiments, the compound 1 monofumarate salt is crystalline polymorphic Form A characterized by two or more, or three or more XRPD signals selected from the group consisting of 15.9°2θ, 19.4°2θ, 21.5°2θ, and 22.3°2θ (±0.2°2θ; ±0.1°2θ; or ±0.0°2θ; Cu Kα1 radiation).

In some embodiments, the compound 1 monofumarate salt is crystalline polymorphic Form A characterized by XRPD signals at 15.9°2θ, 19.4°2θ, 21.5°2θ, and 22.3°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 15.9°2θ, 19.4°2θ, 21.3°2θ, 21.5°2θ, and 22.3°2θ (±0.2°2θ; ±0.1°2θ; or ±0.0°2θ; Cu Kα1 radiation).

In some embodiments, the compound 1 fumarate salt is crystalline polymorphic Form A characterized by XRPD signals at 15.9°2θ, 19.4°2θ, 21.3°2θ, 21.5°2θ, and 22.3°2θ (±0.2°2θ; ±0.1°2θ; or ±0.0°2θ; Cu Kα1 radiation).

In some embodiments, the compound 1 fumarate salt is crystalline polymorphic Form A characterized by two or more, or three or more XRPD signals selected from the group consisting of 14.0°2θ, 15.9°2θ, 19.4°2θ, 21.3°2θ, 21.5°2θ, and 22.3°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.0°2θ, 15.9°2θ, 19.4°2θ, 21.3°2θ, 21.5°2θ, and 22.3°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 19.4°2θ, 21.3°2θ, 21.5°2θ, and 22.3°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 19.4°2θ, 21.3°2θ, 21.5°2θ, and 22.3°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 19.4°2θ, 20.8°2θ, 21.3°2θ, 21.5°2θ, and 22.3°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 19.4°2θ, 20.8°2θ, 21.3°2θ, 21.5°2θ, and 22.3°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 18.9°2θ, 19.4°2θ, 20.8°2θ, 21.3°2θ, 21.5°2θ, and 22.3°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 18.9°2θ, 19.4°2θ, 20.8°2θ, 21.3°2θ, 21.5°2θ, and 22.3°2θ (±0.2°2θ; ±0.1° 2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 18.9°2θ, 19.4°2θ, 20.8°2θ, 21.3°2θ, 21.5°2θ, 22.3°2θ, and 28.1° 2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 18.9°2θ, 19.4°2θ, 20.8°2θ, 21.3°2θ, 21.5°2θ, 22.3°2θ, and 28.1°2θ (±0.2°2θ; ±0.1°2θ; or ±0.0°2θ. Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 18.4°2θ, 18.9°2θ, 19.4°2θ, 20.8°2θ, 21.3°2θ, 21.5°2θ, 22.3°2θ, and 28.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 18.4°2θ, 18.9°2θ, 19.4°2θ, 20.8°2θ, 21.3°2θ, 21.5°2θ, 22.3°2θ, and 28.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.4°2θ, 18.9°2θ, 19.4°2θ, 20.8°2θ, 21.3°2θ, 21.5°2θ, 22.3°2θ, and 28.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.4°2θ, 18.9°2θ, 19.4°2θ, 20.8°2θ, 21.3°2θ, 21.5°2θ, 22.3°2θ, and 28.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.4°2θ, 18.9°2θ, 19.4°2θ, 20.8°2θ, 21.3°2θ, 21.5°2θ, 22.3°2θ, 28.1°2θ, and 29.0°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.4°2θ, 18.9°2θ, 19.4°2θ, 20.8°2θ, 21.3°2θ, 21.5°2θ, 22.3°2θ, 28.1°2θ, and 29.0°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.4°2θ, 18.9°2θ, 19.4°2θ, 20.8°2θ, 21.3°2θ, 21.5°2θ, 22.3°2θ, 23.2°2θ, 28.1°2θ, and 29.0°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.4°2θ, 18.9°2θ, 19.4°2θ, 20.8°2θ, 21.3°2θ, 21.5°2θ, 22.3°2θ, 23.2°2θ, 28.1°2θ, and 29.0°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.4°2θ, 18.9°2θ, 19.4°2θ, 20.8°2θ, 21.3°2θ, 21.5°2θ, 22.3°2θ, 23.2°2θ, 25.0°2θ, 28.1°2θ, and 29.0°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.4°2θ, 18.9°2θ, 19.4°2θ, 20.8°2θ, 21.3°2θ, 21.5°2θ, 22.3°2θ, 23.2°2θ, 25.0°2θ, 28.1°2θ, and 29.0°2θ (±0.2°2θ; ±0.1°2θ; or 35 0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.4°2θ, 18.9°2θ, 19.4°2θ, 20.8°2θ, 21.3°2θ, 21.5°2θ, 22.3°2θ, 23.2°2θ, 24.4°2θ, 25.0°2θ, 28.1°2θ, and 29.0°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.4°2θ, 18.9°2θ, 19.4°2θ, 20.8°2θ, 21.3°2θ, 21.5°2θ, 22.3°2θ, 23.2°2θ, 24.4°2θ, 25.0°2θ, 28.1°2θ, and 29.0°2θ (±0.2°2θ; ±0.1°2θ; or ±0.0°2θ; Cu Kα1 radiation).

In some embodiments, crystalline polymorphic Form A is characterized by one, two, three, four, five, six, seven, eight, nine, ten, eleven, twelve, thirteen, fourteen, fifteen, or sixteen XRPD signals selected from those set forth in Table 11.

TABLE 11

Compound 1 monofumarate salt Form A
(±0.2 °2θ; ±0.1 °2θ; or ±0.0 °2θ; Cu Kα1 radiation)Signal

| Signal number | 2-θ (°) | d Value | Net Intensity (counts) | Gross Intensity (counts) | Rel. Intensity (%) |
|---|---|---|---|---|---|
| Signal #1 | 13.4 | 6.62 | 569.1 | 662.3 | 25.8 |
| Signal #2 | 14.0 | 6.32 | 694.4 | 791.0 | 31.5 |
| Signal #3 | 15.6 | 5.69 | 411.6 | 522.8 | 18.7 |
| Signal #4 | 15.9 | 5.58 | 980.0 | 1095.7 | 44.5 |
| Signal #5 | 18.4 | 4.82 | 432.7 | 587.2 | 19.6 |
| Signal #6 | 18.9 | 4.69 | 518.5 | 680.2 | 23.5 |
| Signal #7 | 19.4 | 4.57 | 824.8 | 991.1 | 37.4 |
| Signal #8 | 20.8 | 4.26 | 543.2 | 719.5 | 24.7 |
| Signal #9 | 21.3 | 4.17 | 754.5 | 932.7 | 34.3 |
| Signal #10 | 21.5 | 4.13 | 837.3 | 1015.7 | 38.0 |
| Signal #11 | 22.3 | 3.98 | 2202.8 | 2377.8 | 100.0 |
| Signal #12 | 23.2 | 3.84 | 323.0 | 487.9 | 14.7 |
| Signal #13 | 24.4 | 3.65 | 293.9 | 445.4 | 13.3 |
| Signal #14 | 25.0 | 3.56 | 306.4 | 449.4 | 13.9 |
| Signal #15 | 28.1 | 3.18 | 467.1 | 609.7 | 21.2 |
| Signal #16 | 29.0 | 3.07 | 371.6 | 504.6 | 16.9 |

In some embodiments, the compound 1 monofumarate salt is crystalline polymorphic Form A characterized an XRPD signal at 22.4°2θ (±0.2°2θ, ±0.1°2θ; or ±0.0°2θ; Cu Kα1 radiation).

In some embodiments, the compound 1 monofumarate salt is crystalline polymorphic Form A characterized by XRPD signals at 15.9°2θ, and 24.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 15.9°2θ, 19.4°2θ, and 22.4°2θ (±0.2°2θ; ±0.1°2θ, or ±0.0°2θ; Cu Kα1 radiation). In some embodiments, the compound 1 monofumarate salt is crystalline polymorphic Form A characterized by XRPD signals at 15.9°2θ, 19.4°2θ, and 24.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 15.9°2θ, 19.4°2θ, 21.5°2θ, and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 15.9°2θ, 19.4°2θ, 21.5°2θ, and 24.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 15.9°2θ, 19.4°2θ, 21.4°2θ, 21.5°2θ, and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 15.9°2θ, 19.4°2θ, 21.4°2θ, 21.5°2θ, and 24.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.0°2θ, 15.9°2θ, 19.4°2θ, 21.4°2θ, 21.5°2θ, and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.0°2θ, 15.9°2θ, 19.4°2θ, 21.4°2θ, 21.5°2θ, and 24.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 19.4°2θ, 21.4°2θ, 21.5°2θ, and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 19.4°2θ, 21.4°2θ, 21.5°2θ, and 24.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 19.4°2θ, 20.9°2θ, 21.4°2θ, 21.5°2θ, and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 19.4°2θ, 20.9°2θ, 21.4°2θ, 21.5°2θ, and 24.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 19.4°2θ, 20.9°2θ, 21.4°2θ, 21.5°2θ, 22.4°2θ, and 28.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 19.4°2θ, 20.9°2θ, 21.4°2θ, 21.5°2θ, 24.4°2θ, and 28.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 18.9°2θ, 19.4°2θ, 20.9°2θ, 21.4°2θ, 21.5°2θ, 22.4°2θ, and 28.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 18.9°2θ, 19.4°2θ, 20.9°2θ, 21.4°2θ, 21.5°2θ, 24.4°2θ, and 28.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 18.4°2θ, 18.9°2θ, 19.4°2θ, 20.9°2θ, 21.4°2θ, 21.5°2θ, 22.4°2θ, and 28.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 18.4°2θ, 18.9°2θ, 19.4°2θ, 20.9°2θ, 21.4°2θ, 21.5°2θ, 22.4°2θ, and 28.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 18.4°2θ, 18.9°2θ, 19.4°2θ, 20.9°2θ, 21.4°2θ, 21.5°2θ, 22.4°2θ, 23.1°2θ, and 28.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 18.4°2θ, 18.9°2θ, 19.4°2θ, 20.9°2θ, 21.4°2θ, 21.5°2θ, 23.1°2θ, 24.4°2θ, and 28.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 18.4°2θ, 18.9°2θ, 19.4°2θ, 20.9°2θ, 21.4°2θ, 21.5°2θ, 22.4°2θ, 23.1°2θ, 28.1°2θ, and 29.0°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 18.4°2θ, 18.9°2θ, 19.4°2θ, 20.9°2θ, 21.4°2θ, 21.5°2θ, 23.1°2θ, 24.4°2θ, 28.1°2θ, and 29.0°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 18.4°2θ, 18.9°2θ, 19.4°2θ, 20.9°2θ, 21.4°2θ, 21.5°2θ, 22.4°2θ, 23.1°2θ, 25.0°2θ, 28.1°2θ, and 29.0°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 18.4°2θ, 18.9°2θ, 19.4°2θ, 20.9°2θ, 21.4°2θ, 21.5°2θ, 23.1°2θ, 24.4°2θ, 25.0°2θ, 28.1°2θ, and 29.0°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.4°2θ, 18.9°2θ, 19.4°2θ, 20.9°2θ, 21.4°2θ, 21.5°2θ, 22.4°2θ, 23.1°2θ, 25.0°2θ, 28.1°2θ, and 29.0°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.4°2θ, 18.9°2θ, 19.4°2θ, 20.9°2θ, 21.4°2θ, 21.5°2θ, 23.1°2θ, 24.4°2θ, 25.0°2θ, 28.1°2θ, and 29.0°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.4°2θ, 18.9°2θ, 19.4°2θ, 20.9°2θ, 21.4°2θ, 21.5°2θ, 22.4°2θ, 23.1°2θ, 24.4°2θ, 25.0°2θ, 28.1°2θ, and 29.0°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.4°2θ, 18.9°2θ, 19.4°2θ, 20.9°2θ, 21.4°2θ, 21.5°2θ, 22.4°2θ, 23.1°2θ, 24.4°2θ, 25.0°2θ, 28.1°2θ, and 29.0°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.1°2θ, 13.4°2θ, 14.0°2θ, 15.6°2θ, 15.9°2θ, 18.4°2θ, 18.9°2θ, 19.4°2θ, 20.9°2θ, 21.4°2θ, 21.5°2θ, 22.4°2θ, 23.1°2θ, 24.4°2θ, 25.0°2θ, 28.1°2θ, and 29.0°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.1°2θ, 13.4°2θ, 14.0°2θ, 15.6°2θ, 15.9°2θ, 18.4°2θ, 18.9°2θ, 19.4°2θ, 20.9°2θ, 21.4°2θ, 21.5°2θ, 22.4°2θ, 23.1°2θ, 24.4°2θ, 25.0°2θ, 28.1°2θ, and 29.0°2θ (±0.2°2θ; ±0.1°2θ; or ±0.0°2θ; Cu Kα1 radiation).

In some embodiments, crystalline polymorphic Form A is characterized by one, two, three, four, five, six, seven, eight, nine, ten, eleven, twelve, thirteen, fourteen, fifteen, sixteen, or seventeen XRPD signals selected from those set forth in Table 12.

TABLE 12

Compound 1 monofumarate salt Form A
(±0.2 °2θ; ±0.1 °2θ; or ±0.0 °2θ; Cu Kα1 radiation)Signal

| Signal number | 2-θ (°) | d Value | Net Intensity (counts) | Gross Intensity (counts) | Rel. Intensity (%) |
|---|---|---|---|---|---|
| Signal #1 | 10.1 | 8.77 | 194.5 | 298.0 | 10.1 |
| Signal #2 | 13.4 | 6.62 | 573.6 | 683.1 | 29.8 |
| Signal #3 | 14.0 | 6.32 | 636.9 | 751.1 | 33.1 |
| Signal #4 | 15.6 | 5.66 | 310.4 | 439.0 | 16.1 |
| Signal #5 | 15.9 | 5.58 | 965.4 | 1096.1 | 50.2 |
| Signal #6 | 18.4 | 4.82 | 382.9 | 551.9 | 19.9 |
| Signal #7 | 18.9 | 4.69 | 447.1 | 622.0 | 23.2 |
| Signal #8 | 19.4 | 4.57 | 726.7 | 904.9 | 37.8 |
| Signal #9 | 20.9 | 4.26 | 472.2 | 653.1 | 24.5 |
| Signal #10 | 21.4 | 4.15 | 688.8 | 871.1 | 35.8 |
| Signal #11 | 21.5 | 4.13 | 701.5 | 883.7 | 36.5 |
| Signal #12 | 22.4 | 3.97 | 1923.9 | 2102.0 | 100.0 |
| Signal #13 | 23.1 | 3.84 | 338.5 | 506.6 | 17.6 |
| Signal #14 | 24.4 | 3.64 | 227.0 | 380.2 | 11.8 |
| Signal #15 | 25.0 | 3.56 | 311.8 | 460.2 | 16.2 |
| Signal #16 | 28.1 | 3.17 | 447.9 | 581.8 | 23.3 |
| Signal #17 | 29.0 | 3.07 | 328.0 | 453.4 | 17.0 |

In some embodiments, the compound 1 monofumarate salt is crystalline polymorphic Form A characterized by an XRPD signal at 22.5°2θ (±0.2°2θ; ±0.1°2θ; or ±0.0°2θ; Cu Kα1 radiation).

In some embodiments, the compound 1 monofumarate salt is crystalline polymorphic Form A characterized by XRPD signals at 21.0°2θ, and 22.5°2θ (±0.2°2θ; ±0.1°2θ, or ±0.0°2θ; Cu Kα1 radiation).

In some embodiments, the compound 1 monofumarate salt is crystalline polymorphic Form A characterized by two or more, or three or more XRPD signals selected from the group consisting of 16.0°2θ, 21.0°2θ, and 22.5°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 16.0°2θ, 21.0°2θ, and 22.5°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 16.0°2θ, 21.0°2θ, 22.5°2θ, and 29.1°2θ (±0.2°2θ; ±0.1°2θ; or 35 0.0°2θ; Cu Kα1 radiation).

In some embodiments, the compound 1 monofumarate salt is crystalline polymorphic Form A characterized by XRPD signals at 16.0°2θ, 21.0°2θ, 22.5°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 16.0°2θ, 21.0°2θ, 21.4°2θ, 22.5°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 16.0°2θ, 21.0°2θ, 21.4°2θ, 22.5°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.1°2θ, 16.0°2θ, 21.0°2θ, 21.4°2θ, 22.5°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.1°2θ, 16.0°2θ, 21.0°2θ, 21.4°2θ, 22.5°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.1°2θ, 16.0°2θ, 21.0°2θ, 21.4°2θ, 22.5°2θ, 25.1°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.1°2θ, 16.0°2θ, 21.0°2θ, 21.4°2θ, 22.5°2θ, 25.1°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.1°2θ, 16.0°2θ, 21.0°2θ, 21.4°2θ, 21.6°2θ, 22.5°2θ, 25.1°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.1°2θ, 16.0°2θ, 21.0°2θ, 21.4°2θ, 21.6°2θ, 22.5°2θ, 25.1°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.1°2θ, 16.0°2θ, 19.5°2θ, 21.0°2θ, 21.4°2θ, 21.6°2θ, 22.5°2θ, 25.1°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.1°2θ, 16.0°2θ, 19.5°2θ, 21.0°2θ, 21.4°2θ, 21.6°2θ, 22.5°2θ, 25.1°2θ, and 29.1°2θ (±0.2°2θ; ±0.1° 2θ; or ±0.0°2θ; Cu Kα1 radiation).

In some embodiments, the compound 1 monofumarate salt is crystalline polymorphic Form A characterized by XRPD signals at 13.5°2θ, 14.1°2θ, 16.0°2θ, 19.5°2θ, 21.0°2θ, 21.4°2θ, 21.6°2θ, 22.5°2θ, 25.1°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.5°2θ, 14.1°2θ, 16.0°2θ, 19.0°2θ, 19.5°2θ, 21.0°2θ, 21.4°2θ, 21.6°2θ, 22.5°2θ, 25.1°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.5°2θ, 14.1°2θ, 16.0°2θ, 19.0°2θ, 19.5°2θ, 21.0°2θ, 21.4°2θ, 21.6°2θ, 22.5°2θ, 25.1°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.5°2θ, 14.1°2θ, 16.0°2θ, 19.0°2θ, 19.5°2θ, 21.0°2θ, 21.4°2θ, 21.6°2θ, 22.5°2θ, 25.1°2θ, 28.2°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.5°2θ, 14.1°2θ, 16.0°2θ, 19.0°2θ, 19.5°2θ, 21.0°2θ, 21.4°2θ, 21.6°2θ, 22.5°2θ, 25.1°2θ, 28.2°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.5°2θ, 14.1°2θ, 15.7°2θ, 16.0°2θ, 19.0°2θ, 19.5°2θ, 21.0°2θ, 21.4°2θ, 21.6°2θ, 22.5°2θ, 25.1°2θ, 28.2°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.5°2θ, 14.1°2θ, 15.7°2θ, 16.0°2θ, 19.0°2θ, 19.5°2θ, 21.0°2θ, 21.4°2θ, 21.6°2θ, 22.5°2θ, 25.1°2θ, 28.2°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.5°2θ, 14.1°2θ, 15.7°2θ, 16.0°2θ, 16.8°2θ, 19.0°2θ, 19.5°2θ, 21.0°2θ, 21.4°2θ, 21.6°2θ, 22.5°2θ, 25.1°2θ, 28.2°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.5°2θ, 14.1°2θ, 15.7°2θ, 16.0°2θ, 16.8°2θ, 19.0°2θ, 19.5°2θ, 21.0°2θ, 21.4°2θ, 21.6°2θ, 22.5°2θ, 25.1°2θ, 28.2°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.5°2θ, 14.1°2θ, 15.7°2θ, 16.0°2θ, 16.8°2θ, 19.0°2θ, 19.5°2θ, 21.0°2θ, 21.4°2θ, 21.6°2θ, 22.5°2θ, 23.2°2θ, 25.1°2θ, 28.2°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.5°2θ, 14.1°2θ, 15.7°2θ, 16.0°2θ, 16.8°2θ, 19.0°2θ, 19.5°2θ, 21.0°2θ, 21.4°2θ, 21.6°2θ, 22.5°2θ, 23.2°2θ, 25.1°2θ, 28.2°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.5°2θ, 14.1°2θ, 15.7°2θ, 16.0°2θ, 16.8°2θ, 18.5°2θ, 19.0°2θ, 19.5°2θ, 21.0°2θ, 21.4°2θ, 21.6°2θ, 22.5°2θ, 23.2°2θ, 25.1°2θ, 28.2°2θ, and 29.1°2θ (±0.2°2θ; 0.1°2θ; or ±0.0°2θ; Cu Kα1 radiation). In some embodiments, the compound 1 monofumarate salt is crystalline polymorphic Form A characterized by XRPD signals at 13.5°2θ, 14.1°2θ, 15.7°2θ, 16.0°2θ, 16.8°2θ, 18.5°2θ, 19.0°2θ, 19.5°2θ, 21.0°2θ, 21.4°2θ, 21.6°2θ, 22.5°2θ, 23.2°2θ, 25.1°2θ, 28.2°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.2°2θ, 13.5°2θ, 14.1°2θ, 15.7°2θ, 16.0°2θ, 16.8°2θ, 18.5°2θ, 19.0°2θ, 19.5°2θ, 21.0°2θ, 21.4°2θ, 21.6°2θ, 22.5°2θ, 23.2°2θ, 25.1°2θ, 28.2°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.2°2θ, 13.5°2θ, 14.1°2θ, 15.7°2θ, 16.0°2θ, 16.8°2θ, 18.5°2θ, 19.0°2θ, 19.5°2θ, 21.0°2θ, 21.4°2θ, 21.6°2θ, 22.5°2θ, 23.2°2θ, 25.1°2θ, 28.2°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.2°2θ, 13.5°2θ, 14.1°2θ, 15.7°2θ, 16.0°2θ, 16.8°2θ, 18.5°2θ, 19.0°2θ, 19.5°2θ, 21.0°2θ, 21.4°2θ, 21.6°2θ, 22.5°2θ, 23.2°2θ, 25.1°2θ, 25.3°2θ, 28.2°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.2°2θ, 13.5°2θ, 14.1°2θ, 15.7°2θ, 16.0°2θ, 16.8°2θ, 18.5°2θ, 19.0°2θ, 19.5°2θ, 21.0°2θ, 21.4°2θ, 21.6°2θ, 22.5°2θ, 23.2°2θ, 25.1°2θ, 25.3°2θ, 28.2°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.2°2θ, 13.5°2θ, 14.1°2θ, 15.7°2θ, 16.0°2θ, 16.8°2θ, 18.5°2θ, 19.0°2θ, 19.5°2θ, 20.0°2θ, 21.0°2θ, 21.4°2θ, 21.6°2θ, 22.5°2θ, 23.2°2θ, 25.1°2θ, 25.3°2θ, 28.2°2θ, and 29.1°2θ (±0.2° 2θ; ±0.1°2θ; or ±0.0°2θ; Cu Kα1 radiation). In some embodiments, the compound 1 monofumarate salt is crystalline polymorphic Form A characterized by XRPD signals at 10.2°2θ, 13.5°2θ, 14.1°2θ, 15.7°2θ, 16.0°2θ, 16.8°2θ, 18.5°2θ, 19.0°2θ, 19.5°2θ, 20.0°2θ, 21.0°2θ, 21.4°2θ, 21.6°2θ, 22.5°2θ, 23.2°2θ, 25.1°2θ, 25.3°2θ, 28.2°2θ, and 29.1°2θ (±0.2°2θ; ±0.1°2θ; or 0.0°2θ; Cu Kα1 radiation).

In some embodiments, the compound 1 monofumarate salt is crystalline polymorphic Form A characterized by two or more, or three or more XRPD signals selected from the group consisting of 10.2°2θ, 13.5°2θ, 14.1°2θ, 15.7°2θ, 16.0°2θ, 16.8°2θ, 18.5°2θ, 19.0°2θ, 19.5°2θ, 20.0°2θ, 21.0°2θ, 21.4°2θ, 21.6°2θ, 22.5°2θ, 23.2°2θ, 23.3°2θ, 25.1°2θ, 25.3°2θ, 28.2°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.2°2θ, 13.5°2θ, 14.1°2θ, 15.7°2θ, 16.0°2θ, 16.8°2θ, 18.5°2θ, 19.0°2θ, 19.5°2θ, 20.0°2θ, 21.0°2θ, 21.4°2θ, 21.6°2θ, 22.5°2θ, 23.2°2θ, 23.3°2θ, 25.1°2θ, 25.3°2θ, 28.2°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.2°2θ, 13.5°2θ, 14.1°2θ, 15.7°2θ, 16.0°2θ, 16.8°2θ, 18.5°2θ, 19.0°2θ, 19.5°2θ, 20.0°2θ, 21.0°2θ, 21.4°2θ, 21.6°2θ, 22.5°2θ, 23.2°2θ, 23.3°2θ, 24.5°2θ, 25.1°2θ, 25.3°2θ, 28.2°2θ, and 29.1°2θ (±0.2°2θ; ±0.1°2θ; or ±0.0°2θ; Cu Kα1 radiation). In some embodiments, the compound 1 fumarate salt is crystalline polymorphic Form A characterized by XRPD signals at 10.2°2θ, 13.5°2θ, 14.1°2θ, 15.7°2θ, 16.0°2θ, 16.8°2θ, 18.5°2θ, 19.0°2θ, 19.5°2θ, 20.0°2θ, 21.0°2θ, 21.4°2θ, 21.6°2θ, 22.5°2θ, 23.2°2θ, 23.3°2θ, 24.5°2θ, 25.1°2θ, 25.3°2θ, 28.2°2θ, and 29.1°2θ (±0.2°2θ; ±0.1°2θ; or ±0.0°2θ; Cu Kα1 radiation).

In some embodiments, crystalline polymorphic Form A is characterized by one, two, three, four, five, six, seven, eight, nine, ten, eleven, twelve, thirteen, fourteen, fifteen, sixteen, seventeen, eighteen, nineteen, twenty, twenty-one, or twenty-two XRPD signals selected from those set forth in Table 13.

TABLE 13

Compound 1 monofumarate salt Form A
(±0.2 °2θ; ±0.1 °2θ; or ±0.0 °2θ; Cu Kα1 radiation)Signal

| Signal number | 2-θ (°) | d Value | Net Intensity (counts) | Gross Intensity (counts) | Rel. Intensity (%) |
|---|---|---|---|---|---|
| Signal #1 | 10.2 | 8.70 | 584.4 | 675.3 | 13.3 |
| Signal #2 | 13.5 | 6.57 | 1164.2 | 1289.7 | 26.6 |
| Signal #3 | 14.1 | 6.28 | 1657.0 | 1789.0 | 37.8 |
| Signal #4 | 15.7 | 5.64 | 978.5 | 1129.7 | 22.3 |
| Signal #5 | 16.0 | 5.55 | 2085.3 | 2240.7 | 47.6 |
| Signal #6 | 16.8 | 5.26 | 708.5 | 870.2 | 16.2 |
| Signal #7 | 18.5 | 4.79 | 603.7 | 803.8 | 13.8 |
| Signal #8 | 19.0 | 4.66 | 1002.4 | 1218.2 | 22.9 |
| Signal #10 | 19.5 | 4.55 | 1564.7 | 1791.1 | 35.7 |
| Signal #9 | 19.5 | 4.54 | 1397.8 | 1625.2 | 31.9 |
| Signal #11 | 20.0 | 4.44 | 538.7 | 773.6 | 12.3 |
| Signal #12 | 21.0 | 4.23 | 2225.4 | 2471.7 | 50.8 |
| Signal #13 | 21.4 | 4.15 | 1663.7 | 1913.6 | 38.0 |
| Signal #14 | 21.6 | 4.10 | 1419.5 | 1670.0 | 32.4 |
| Signal #15 | 22.5 | 3.96 | 4382.9 | 4629.8 | 100.0 |
| Signal #17 | 23.2 | 3.82 | 656.3 | 890.9 | 15.0 |
| Signal #16 | 23.3 | 3.81 | 511.7 | 744.2 | 11.7 |
| Signal #18 | 24.5 | 3.63 | 453.5 | 669.3 | 10.3 |
| Signal #19 | 25.1 | 3.54 | 1554.4 | 1762.4 | 35.5 |
| Signal #20 | 25.3 | 3.52 | 559.7 | 764.4 | 12.8 |
| Signal #21 | 28.2 | 3.16 | 1001.2 | 1195.7 | 22.8 |
| Signal #22 | 29.1 | 3.07 | 1713.2 | 1907.7 | 39.1 |

In some embodiments, the compound 1 monofumarate salt is crystalline polymorphic Form A characterized by an XRPD signal at 22.4°2θ (±0.2°2θ; ±0.1°2θ; or ±0.0°2θ; Cu Kα1 radiation).

In some embodiments, the compound 1 monofumarate salt is crystalline polymorphic Form A characterized by XRPD signals at 15.9°2θ, and 22.4°2θ (±0.2°2θ; ±0.1°2θ, or ±0.0°2θ, Cu Kα1 radiation).

In some embodiments, the compound 1 monofumarate salt is crystalline polymorphic Form A characterized by two or more, or three or more XRPD signals selected from the group consisting of 14.0°2θ, 15.9°2θ, and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.0°2θ, 15.9°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.0°2θ, 15.9°2θ, 21.4°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by XRPD signals at 14.0°2θ, 15.9°2θ, 21.4°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.0°2θ, 15.9°2θ, 19.4°2θ, 21.4°2θ, and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.0°2θ, 15.9°2θ, 19.4°2θ, 21.4°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.0°2θ, 15.9°2θ, 19.4°2θ, 21.4°2θ, 21.5°2θ, and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.0°2θ, 15.9°2θ, 19.4°2θ, 21.4°2θ, 21.5°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 19.4°2θ, 21.4°2θ, 21.5°2θ, and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 19.4°2θ, 21.4°2θ, 21.5°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 18.9°2θ, 19.4°2θ, 21.4°2θ, 21.5°2θ, and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 18.9°2θ, 19.4°2θ, 21.4°2θ, 21.5°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 18.9°2θ, 19.4°2θ, 20.9°2θ, 21.4°2θ, 21.5°2θ, and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 18.9°2θ, 19.4°2θ, 20.9°2θ, 21.4°2θ, 21.5°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 18.9°2θ, 19.4°2θ, 20.9°2θ, 21.4°2θ, 21.5°2θ, 22.4°2θ, and 28.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 18.9°2θ, 19.4°2θ, 20.9°2θ, 21.4°2θ, 21.5°2θ, 22.4°2θ, and 28.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 18.4°2θ, 18.9°2θ, 19.4°2θ, 20.9°2θ, 21.4°2θ, 21.5°2θ, 22.4°2θ, and 28.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 18.4°2θ, 18.9°2θ, 19.4°2θ, 20.9°2θ, 21.4°2θ, 21.5°2θ, 22.4°2θ, and 28.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 18.4°2θ, 18.9°2θ, 19.4°2θ, 20.9°2θ, 21.4°2θ, 21.5°2θ, 22.4°2θ, 28.1°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 18.4°2θ, 18.9°2θ, 19.4°2θ, 20.9°2θ, 21.4°2θ, 21.5°2θ, 22.4°2θ, 28.1°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.4°2θ, 18.9°2θ, 19.4°2θ, 20.9°2θ, 21.4°2θ, 21.5°2θ, 22.4°2θ, 28.1°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.4°2θ, 18.9°2θ, 19.4°2θ, 20.9°2θ, 21.4°2θ, 21.5°2θ, 22.4°2θ, 28.1°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.4°2θ, 18.9°2θ, 19.4°2θ, 20.9°2θ, 21.4°2θ, 21.5°2θ, 22.4°2θ, 25.0°2θ, 28.1°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.4°2θ, 18.9°2θ, 19.4°2θ, 20.9°2θ, 21.4°2θ, 21.5°2θ, 22.4°2θ, 25.0°2θ, 28.1°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.4°2θ, 18.9°2θ, 19.4°2θ, 20.9°2θ, 21.4°2θ, 21.5°2θ, 22.4°2θ, 23.2°2θ, 25.0°2θ, 28.1°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.4°2θ, 18.9°2θ, 19.4°2θ, 20.9°2θ, 21.4°2θ, 21.5°2θ, 22.4°2θ, 23.2°2θ, 25.0°2θ, 28.1°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.1°2θ, 13.4°2θ, 14.0°2θ, 15.6°2θ, 15.9°2θ, 18.4°2θ, 18.9°2θ, 19.4°2θ, 20.9°2θ, 21.4°2θ, 21.5°2θ, 22.4°2θ, 23.2°2θ, 25.0°2θ, 28.1°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.1°2θ, 13.4°2θ, 14.0°2θ, 15.6°2θ, 15.9°2θ, 18.4°2θ, 18.9°2θ, 19.4°2θ, 20.9°2θ, 21.4°2θ, 21.5°2θ, 22.4°2θ, 23.2°2θ, 25.0°2θ, 28.1°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.1°2θ, 13.4°2θ, 14.0°2θ, 15.6°2θ, 15.9°2θ, 18.4°2θ, 18.9°2θ, 19.2°2θ, 19.4°2θ, 20.9°2θ, 21.4°2θ, 21.5°2θ, 22.4°2θ, 23.2°2θ, 25.0°2θ, 28.1°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.1°2θ, 13.4°2θ, 14.0°2θ, 15.6°2θ, 15.9°2θ, 18.4°2θ, 18.9°2θ, 19.2°2θ, 19.4°2θ, 20.9°2θ, 21.4°2θ, 21.5°2θ, 22.4°2θ, 23.2°2θ, 24.4°2θ, 25.0°2θ, 28.1°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.1°2θ, 13.4°2θ, 14.0°2θ, 15.6°2θ, 15.9°2θ, 18.4°2θ, 18.9°2θ, 19.2°2θ, 19.4°2θ, 20.9°2θ, 21.4°2θ, 21.5°2θ, 22.4°2θ, 23.2°2θ, 24.4°2θ, 25.0°2θ, 28.1°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.1°2θ, 13.4°2θ, 14.0°2θ, 15.6°2θ, 15.9°2θ, 18.4°2θ, 18.9°2θ, 19.2°2θ, 19.4°2θ, 20.9°2θ, 21.4°2θ, 21.5°2θ, 22.4°2θ, 23.2°2θ, 24.4°2θ, 25.0°2θ, 28.1°2θ, and 29.1°2θ (±0.2°2θ; ±0.1°2θ; or ±0.0°2θ; Cu Kα1 radiation).

In some embodiments, crystalline polymorphic Form A is characterized by one, two, three, four, five, six, seven, eight, nine, ten, eleven, twelve, thirteen, fourteen, fifteen, sixteen, seventeen, or eighteen XRPD signals selected from those set forth in Table 14.

TABLE 14

Compound 1 monofumarate salt Form A
(±0.2 °2θ; ±0.1 °2θ; or ±0.0 °2θ; Cu Kα1 radiation)

| Signal number | 2-θ (°) | d Value | Net Intensity (counts) | Gross Intensity (counts) | Rel. Intensity (%) |
|---|---|---|---|---|---|
| Signal #1 | 10.1 | 8.74 | 390.6 | 456.0 | 12.0 |
| Signal #2 | 13.4 | 6.61 | 888.1 | 970.6 | 27.2 |
| Signal #3 | 14.0 | 6.31 | 1124.2 | 1211.0 | 34.5 |
| Signal #4 | 15.6 | 5.66 | 517.1 | 616.4 | 15.8 |
| Signal #5 | 15.9 | 5.57 | 1498.7 | 1602.6 | 45.9 |
| Signal #6 | 18.4 | 4.81 | 578.0 | 724.0 | 17.7 |
| Signal #7 | 18.9 | 4.68 | 820.7 | 978.3 | 25.2 |
| Signal #8 | 19.2 | 4.61 | 389.6 | 552.7 | 11.9 |
| Signal #9 | 19.4 | 4.57 | 1069.6 | 1235.5 | 32.8 |
| Signal #10 | 20.9 | 4.25 | 751.3 | 935.0 | 23.0 |
| Signal #11 | 21.4 | 4.16 | 1081.1 | 1268.3 | 33.1 |
| Signal #12 | 21.5 | 4.12 | 978.3 | 1166.1 | 30.0 |
| Signal #13 | 22.4 | 3.97 | 3262.5 | 3448.2 | 100.0 |
| Signal #14 | 23.2 | 3.83 | 418.2 | 593.7 | 12.8 |
| Signal #15 | 24.4 | 3.64 | 358.7 | 518.8 | 11.0 |
| Signal #16 | 25.0 | 3.55 | 446.9 | 599.2 | 13.7 |
| Signal #17 | 28.1 | 3.17 | 615.9 | 771.0 | 18.9 |
| Signal #18 | 29.1 | 3.07 | 544.1 | 691.4 | 16.7 |

In some embodiments, the compound 1 monofumarate salt is crystalline polymorphic Form A characterized by two an XRPD signal at and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by XRPD signals at 15.9°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 15.9°2θ, 19.4°2θ and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 15.9°2θ, 19.4°2θ and 22.4°2θ (±0.2°θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 15.9°2θ, 19.4°2θ, 21.4°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by XRPD signals at 15.9°2θ, 19.4°2θ, 21.4°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.0°2θ, 15.9°2θ, 19.4°2θ, 21.4°2θ, and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.0°2θ, 15.9°2θ, 19.4°2θ, 21.4°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.0°2θ, 15.9°2θ, 19.4°2θ, 21.4°2θ, 21.6°2θ, and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.0°2θ, 15.9°2θ, 19.4°2θ, 21.4°2θ, 21.6°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 19.4°2θ, 21.4°2θ, 21.6°2θ, and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 19.4°2θ, 21.4°2θ, 21.6°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 19.4°2θ, 21.4°2θ, 21.6°2θ, 22.4°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 19.4°2θ, 21.4°2θ, 21.6°2θ, 22.4°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 19.0°2θ, 19.4°2θ, 21.4°2θ, 21.6°2θ, 22.4°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 19.0°2θ, 19.4°2θ, 21.4°2θ, 21.6°2θ, 22.4°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 19.0°2θ, 19.4°2θ, 20.9°2θ, 21.4°2θ, 21.6°2θ, 22.4°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 19.0°2θ, 19.4°2θ, 20.9°2θ, 21.4°2θ, 21.6°2θ, 22.4°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 19.0°2θ, 19.4°2θ, 20.9°2θ, 21.4°2θ, 21.6°2θ, 22.4°2θ, 29.1°2θ (±0.2°2θ; ±0.1°2θ; or ±0.0°2θ; Cu Kα1 radiation).

In some embodiments, the compound 1 monofumarate salt is crystalline polymorphic Form A characterized by XRPD signals at 13.4°2θ, 14.0°2θ, 15.6°2θ, 15.9°2θ, 19.0°2θ, 19.4°2θ, 20.9°2θ, 21.4°2θ, 21.6°2θ, 22.4°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 19.0°2θ, 19.4°2θ, 20.9°2θ, 21.4°2θ, 21.6°2θ, 22.4°2θ, 28.2°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 19.0°2θ, 19.4°2θ, 20.9°2θ, 21.4°2θ, 21.6°2θ, 22.4°2θ, 28.2°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.5°2θ, 19.0°2θ, 19.4°2θ, 20.9°2θ, 21.4°2θ, 21.6°2θ, 22.4°2θ, 28.2°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.5°2θ, 19.0°2θ, 19.4°2θ, 20.9°2θ, 21.4°2θ, 21.6°2θ, 22.4°2θ, 28.2°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.5°2θ, 19.0°2θ, 19.4°2θ, 20.9°2θ, 21.4°2θ, 21.6°2θ, 22.4°2θ, 25.1°2θ, 28.2°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.5°2θ, 19.0°2θ, 19.4°2θ, 20.9°2θ, 21.4°2θ, 21.6°2θ, 22.4°2θ, 25.1°2θ, 28.2°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 16.8°2θ, 18.5°2θ, 19.0°2θ, 19.4°2θ, 20.9°2θ, 21.4°2θ, 21.6°2θ, 22.4°2θ, 25.1°2θ, 28.2°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 16.8°2θ, 18.5°2θ, 19.0°2θ, 19.4°2θ, 20.9°2θ, 21.4°2θ, 21.6°2θ, 22.4°2θ, 25.1°2θ, 28.2°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.1°2θ, 13.4°2θ, 14.0°2θ, 15.6°2θ, 15.9°2θ, 16.8°2θ, 18.5°2θ, 19.0°2θ, 19.4°2θ, 20.9°2θ, 21.4°2θ, 21.6°2θ, 22.4°2θ, 25.1°2θ, 28.2°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.1°2θ, 13.4°2θ, 14.0°2θ, 15.6°2θ, 15.9°2θ, 16.8°2θ, 18.5°2θ, 19.0°2θ, 19.4°2θ, 20.9°2θ, 21.4°2θ, 21.6°2θ, 22.4°2θ, 25.1°2θ, 28.2°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.1°2θ, 13.4°2θ, 14.0°2θ, 15.6°2θ, 15.9°2θ, 16.8°2θ, 18.5°2θ, 19.0°2θ, 19.4°2θ, 20.9°2θ, 21.4°2θ, 21.6°2θ, 22.4°2θ, 24.5°2θ, 25.1°2θ, 28.2°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.1°2θ, 13.4°2θ, 14.0°2θ, 15.6°2θ, 15.9°2θ, 16.8°2θ, 18.5°2θ, 19.0°2θ, 19.4°2θ, 20.9°2θ, 21.4°2θ, 21.6°2θ, 22.4°2θ, 24.5°2θ, 25.1°2θ, 28.2°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.1°2θ, 13.4°2θ, 14.0°2θ, 15.6°2θ, 15.9°2θ, 16.8°2θ, 18.5°2θ, 19.0°2θ, 19.4°2θ, 20.9°2θ, 21.4°2θ, 21.6°2θ, 22.4°2θ, 23.2°2θ, 24.5°2θ, 25.1°2θ, 28.2°2θ, and 29.1°2θ (±0.2°2θ; ±0.1° 2θ; or ±0.0°2θ; Cu Kα1 radiation). In some embodiments, the compound 1 monofumarate salt is crystalline polymorphic Form A characterized by XRPD signals at 10.1°2θ, 13.4°2θ, 14.0°2θ, 15.6°2θ, 15.9°2θ, 16.8°2θ, 18.5°2θ, 19.0°2θ, 19.4°2θ, 20.9°2θ, 21.4°2θ, 21.6°2θ, 22.4°2θ, 23.2°2θ, 24.5°2θ, 25.1°2θ, 28.2°2θ, and 29.1°2θ (±0.2°2θ; ±0.1°2θ; or ±0.0°2θ; Cu Kα1 radiation).

In some embodiments, crystalline polymorphic Form A is characterized by one, two, three, four, five, six, seven, eight, nine, ten, eleven, twelve, thirteen, fourteen, fifteen, sixteen, seventeen, or eighteen XRPD signals selected from those set forth in Table 15.

TABLE 15

Compound 1 monofumarate salt Form A(±0.2 °2θ; ± 0.1 °2θ; or ±0.0 °2θ; Cu Kα1 radiation)

| Signal number | 2-θ (°) | d Value | Net Intensity (counts) | Gross Intensity (counts) | Rel. Intensity (%) |
|---|---|---|---|---|---|
| Signal #1 | 10.1 | 8.74 | 587.6 | 674.4 | 12.7 |
| Signal #2 | 13.4 | 6.60 | 1464.0 | 1577.0 | 31.8 |
| Signal #3 | 14.0 | 6.30 | 1620.4 | 1738.7 | 35.2 |
| Signal #4 | 15.6 | 5.68 | 947.7 | 1085.3 | 20.6 |
| Signal #5 | 15.9 | 5.57 | 3837.6 | 3982.9 | 83.3 |
| Signal #6 | 16.8 | 5.27 | 587.6 | 747.5 | 12.7 |
| Signal #7 | 18.5 | 4.80 | 769.8 | 950.4 | 16.7 |
| Signal #8 | 19.0 | 4.67 | 1135.3 | 1329.5 | 24.6 |
| Signal #9 | 19.4 | 4.57 | 2103.0 | 2305.6 | 45.6 |
| Signal #10 | 20.9 | 4.24 | 1041.9 | 1261.2 | 22.6 |
| Signal #11 | 21.4 | 4.16 | 1630.8 | 1855.4 | 35.4 |
| Signal #12 | 21.6 | 4.12 | 1509.5 | 1735.8 | 32.8 |
| Signal #13 | 22.4 | 3.97 | 4609.0 | 4835.8 | 100.0 |
| Signal #14 | 23.2 | 3.84 | 565.4 | 784.0 | 12.3 |
| Signal #15 | 24.5 | 3.64 | 573.9 | 777.1 | 12.5 |
| Signal #16 | 25.1 | 3.55 | 599.1 | 792.5 | 13.0 |
| Signal #17 | 28.2 | 3.17 | 923.2 | 1105.3 | 20.0 |
| Signal #18 | 29.1 | 3.06 | 1197.4 | 1378.0 | 26.0 |

In some embodiments, the compound 1 monofumarate salt is crystalline polymorphic Form A characterized by an XRPD signal at 22.4°2θ (±0.2°2θ; ±0.1°2θ, or ±0.0°2θ; Cu Kα1 radiation).

In some embodiments, the compound 1 monofumarate salt is crystalline polymorphic Form A characterized by XRPD signals at 15.9°2θ and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 15.9°2θ, 19.4°2θ, and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 15.9°2θ, 19.4°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 15.9°2θ, 19.4°2θ, 21.3°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by XRPD signals at 15.9°2θ, 19.4°2θ, 21.3°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.0°2θ, 15.9°2θ, 19.4°2θ, 21.3°2θ, and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.0°2θ, 15.9°2θ, 19.4°2θ, 21.3°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.0°2θ, 15.9°2θ, 19.4°2θ, 21.3°2θ, 21.5°2θ, and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.0°2θ, 15.9°2θ, 19.4°2θ, 21.3°2θ, 21.5°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 19.4°2θ, 21.3°2θ, 21.5°2θ, and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 19.4°2θ, 21.3°2θ, 21.5°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 19.4°2θ, 20.9°2θ, 21.3°2θ, 21.5°2θ, and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 19.4°2θ, 20.9°2θ, 21.3°2θ, 21.5°2θ, and 22.4°2θ (±0.2°2θ; ±0.1°2θ, or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 18.9°2θ, 19.4°2θ, 20.9°2θ, 21.3°2θ, 21.5°2θ, and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 18.9°2θ, 19.4°2θ, 20.9°2θ, 21.3°2θ, 21.5°2θ, and 22.4°2θ (±0.2°2θ; ±0.1° 2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 18.9°2θ, 19.4°2θ, 20.9°2θ, 21.3°2θ, 21.5°2θ, 22.4°2θ, and 28.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 18.9°2θ, 19.4°2θ, 20.9°2θ, 21.3°2θ, 21.5°2θ, 22.4°2θ, and 28.1°2θ (±0.2° 2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 18.4°2θ, 18.9°2θ, 19.4°2θ, 20.9°2θ, 21.3°2θ, 21.5°2θ, 22.4°2θ, and 28.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 18.4°2θ, 18.9°2θ, 19.4°2θ, 20.9°2θ, 21.3°2θ, 21.5°2θ, 22.4°2θ, and 28.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.4°2θ, 18.9°2θ, 19.4°2θ, 20.9°2θ, 21.3°2θ, 21.5°2θ, 22.4°2θ, and 28.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.4°2θ, 18.9°2θ, 19.4°2θ, 20.9°2θ, 21.3°2θ, 21.5°2θ, 22.4°2θ, and 28.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.4°2θ, 18.9°2θ, 19.4°2θ, 20.9°2θ, 21.3°2θ, 21.5°2θ, 22.4°2θ, 25.0°2θ, and 28.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.4°2θ, 18.9°2θ, 19.4°2θ, 20.9°2θ, 21.3°2θ, 21.5°2θ, 22.4°2θ, 25.0°2θ, and 28.1°2θ (±0.2°2θ; 0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.4°2θ, 18.9°2θ, 19.4°2θ, 20.9°2θ, 21.3°2θ, 21.5°2θ, 22.4°2θ, 25.0°2θ, 28.1°2θ, and 29.0°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.4°2θ, 18.9°2θ, 19.4°2θ, 20.9°2θ, 21.3°2θ, 21.5°2θ, 22.4°2θ, 25.0°2θ, 28.1°2θ, and 29.0°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.4°2θ, 18.9°2θ, 19.4°2θ, 20.9°2θ, 21.3°2θ, 21.5°2θ, 22.4°2θ, 24.4°2θ, 25.0°2θ, 28.1°2θ, and 29.0°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.4°2θ, 18.9°2θ, 19.4°2θ, 20.9°2θ, 21.3°2θ, 21.5°2θ, 22.4°2θ, 24.4°2θ, 25.0°2θ, 28.1°2θ, and 29.0°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.4°2θ, 18.9°2θ, 19.4°2θ, 20.9°2θ, 21.3°2θ, 21.5°2θ, 22.4°2θ, 23.2°2θ, 24.4°2θ, 25.0°2θ, 28.1°2θ, and 29.0°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.4°2θ, 18.9°2θ, 19.4°2θ, 20.9°2θ, 21.3°2θ, 21.5°2θ, 22.4°2θ, 23.2°2θ, 24.4°2θ, 25.0°2θ, 28.1°2θ, and 29.0°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.4°2θ, 18.9°2θ, 19.4°2θ, 20.9°2θ, 21.3°2θ, 21.5°2θ, 22.4°2θ, 23.2°2θ, 24.4°2θ, 25.0°2θ, 28.1°2θ, 28.8°2θ, and 29.0°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.4°2θ, 18.9°2θ, 19.4°2θ, 20.9°2θ, 21.3°2θ, 21.5°2θ, 22.4°2θ, 23.2°2θ, 24.4°2θ, 25.0°2θ, 28.1°2θ, 28.8°2θ, and 29.0°2θ (±0.2°2θ; ±0.1°2θ; or ±0.0°2θ; Cu Kα1 radiation).

In some embodiments, crystalline polymorphic Form A is characterized by one, two, three, four, five, six, seven, eight, nine, ten, eleven, twelve, thirteen, fourteen, fifteen, sixteen, or seventeen XRPD signals selected from those set forth in Table 16.

TABLE 16

Compound 1 monofumarate salt Form A(±0.2 °2θ; ±0.1 °2θ; or ±0.0 °2θ; Cu Kα1 radiation)

| Signal number | 2-θ (°) | d Value | Net Intensity (counts) | Gross Intensity (counts) | Rel. Intensity (%) |
|---|---|---|---|---|---|
| Signal #3 | 13.4 | 6.61 | 606.0 | 707.0 | 25.4 |
| Signal #4 | 14.0 | 6.31 | 771.3 | 877.6 | 32.4 |
| Signal #5 | 15.6 | 5.67 | 395.2 | 537.1 | 16.6 |
| Signal #6 | 15.9 | 5.57 | 1178.8 | 1327.2 | 49.5 |
| Signal #8 | 18.4 | 4.82 | 404.2 | 604.9 | 17.0 |
| Signal #9 | 18.9 | 4.69 | 518.3 | 734.1 | 21.7 |
| Signal #10 | 19.4 | 4.57 | 812.4 | 1040.2 | 34.1 |
| Signal #12 | 20.9 | 4.26 | 564.5 | 813.3 | 23.7 |
| Signal #13 | 21.3 | 4.16 | 804.2 | 1055.1 | 33.7 |
| Signal #14 | 21.5 | 4.13 | 716.9 | 968.0 | 30.1 |
| Signal #15 | 22.4 | 3.97 | 2383.2 | 2630.9 | 100.0 |
| Signal #16 | 23.2 | 3.84 | 313.7 | 551.0 | 13.2 |
| Signal #17 | 24.4 | 3.65 | 345.1 | 564.0 | 14.5 |
| Signal #18 | 25.0 | 3.56 | 382.6 | 590.3 | 16.1 |
| Signal #21 | 28.1 | 3.17 | 468.2 | 655.0 | 19.6 |
| Signal #22 | 28.8 | 3.10 | 264.7 | 443.2 | 11.1 |
| Signal #23 | 29.0 | 3.07 | 374.4 | 549.1 | 15.7 |

In some embodiments, the compound 1 monofumarate salt is crystalline polymorphic Form A characterized by an XRPD signals at 22.4°2θ (±0.2°2θ; ±0.1°2θ; or ±0.0°2θ; Cu Kα1 radiation).

In some embodiments, the compound 1 monofumarate salt is crystalline polymorphic Form A characterized by XRPD signals at 15.9°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 15.9°2θ, 19.5°2θ, and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 15.9°2θ, 19.5°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.1°2θ, 15.9°2θ, 19.5°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by XRPD signals at 14.1°2θ, 15.9°2θ, 19.5°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.1°2θ, 15.9°2θ, 19.0°2θ, 19.5°2θ, and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.1°2θ, 15.9°2θ, 19.0°2θ, 19.5°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.1°2θ, 15.9°2θ, 19.0°2θ, 19.5°2θ, 21.4°2θ, and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.1°2θ, 15.9°2θ, 19.0°2θ, 19.5°2θ, 21.4°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.1°2θ, 15.9°2θ, 19.0°2θ, 19.5°2θ, 21.4°2θ, 21.6°2θ, and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.1°2θ, 15.9°2θ, 19.0°2θ, 19.5°2θ, 21.4°2θ, 21.6°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.1°2θ, 15.9°2θ, 19.0°2θ, 19.5°2θ, 21.4°2θ, 21.6°2θ, and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.1°2θ, 15.9°2θ, 19.0°2θ, 19.5°2θ, 21.4°2θ, 21.6°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.1°2θ, 15.9°2θ, 19.0°2θ, 19.5°2θ, 21.4°2θ, 21.6°2θ, 22.4°2θ, and 28.2°2θ (±0.2° 2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.1°2θ, 15.9°2θ, 19.0°2θ, 19.5°2θ, 21.4°2θ, 21.6°2θ, 22.4°2θ, and 28.2°2θ, (±0.2°2θ; ±0.1° 2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.1°2θ, 15.9°2θ, 19.0°2θ, 19.5°2θ, 20.9°2θ, 21.4°2θ, 21.6°2θ, 22.4°2θ, and 28.2°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.1°2θ, 15.9°2θ, 19.0°2θ, 19.5°2θ, 20.9°2θ, 21.4°2θ, 21.6°2θ, 22.4°2θ, and 28.2°2θ, (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.1°2θ, 15.9°2θ, 18.5°2θ, 19.0°2θ, 19.5°2θ, 20.9°2θ, 21.4°2θ, 21.6°2θ, 22.4°2θ, and 28.2°2θ (±0.2°2θ; ±0.1°2θ; or ±0.0°2θ, Cu Kα1 radiation). In some embodiments, the compound 1 monofumarate salt is crystalline polymorphic Form A characterized by XRPD signals at 13.4°2θ, 14.1°2θ, 15.9°2θ, 18.5°2θ, 19.0°2θ, 19.5°2θ, 20.9°2θ, 21.4°2θ, 21.6°2θ, 22.4°2θ, and 28.2°2θ, (±0.2°2θ, ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.1°2θ, 15.6°2θ, 15.9°2θ, 18.5°2θ, 19.0°2θ, 19.5°2θ, 20.9°2θ, 21.4°2θ, 21.6°2θ, 22.4°2θ, and 28.2°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.1°2θ, 15.6°2θ, 15.9°2θ, 18.5°2θ, 19.0°2θ, 19.5°2θ, 20.9°2θ, 21.4°2θ, 21.6°2θ, 22.4°2θ, and 28.2°2θ, (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.1°2θ, 15.6°2θ, 15.9°2θ, 18.5°2θ, 19.0°2θ, 19.5°2θ, 20.9°2θ, 21.4°2θ, 21.6°2θ, 22.4°2θ, 28.2°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.1°2θ, 15.6°2θ, 15.9°2θ, 18.5°2θ, 19.0°2θ, 19.5°2θ, 20.9°2θ, 21.4°2θ, 21.6°2θ, 22.4°2θ, 28.2°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.1°2θ, 15.6°2θ, 15.9°2θ, 18.5°2θ, 19.0°2θ, 19.2°2θ, 19.5°2θ, 20.9°2θ, 21.4°2θ, 21.6°2θ, 22.4°2θ, 28.2°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.1°2θ, 15.6°2θ, 15.9°2θ, 18.5°2θ, 19.0°2θ, 19.2°2θ, 19.5°2θ, 20.9°2θ, 21.4°2θ, 21.6°2θ, 22.4°2θ, 28.2°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.1°2θ, 13.4°2θ, 14.1°2θ, 15.6°2θ, 15.9°2θ, 18.5°2θ, 19.0°2θ, 19.2°2θ, 19.5°2θ, 20.9°2θ, 21.4°2θ, 21.6°2θ, 22.4°2θ, 28.2°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.1°2θ, 13.4°2θ, 14.1°2θ, 15.6°2θ, 15.9°2θ, 18.5°2θ, 19.0°2θ, 19.2°2θ, 19.5°2θ, 20.9°2θ, 21.4°2θ, 21.6°2θ, 22.4°2θ, 28.2°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.1°2θ, 13.4°2θ, 14.1°2θ, 15.6°2θ, 15.9°2θ, 18.5°2θ, 19.0°2θ, 19.2°2θ, 19.5°2θ, 20.9°2θ, 21.420, 21.6°2θ, 22.4°2θ, 25.1°2θ, 28.2°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.1°2θ, 13.4°2θ, 14.1°2θ, 15.6°2θ, 15.9°2θ, 18.5°2θ, 19.0°2θ, 19.2°2θ, 19.5°2θ, 20.9°2θ, 21.4°2θ, 21.6°2θ, 22.4°2θ, 25.1°2θ, 28.2°2θ, and 29.1°2θ (±0.2°2θ; ±0.1°2θ; or ±0.0°2θ; Cu Kα1 radiation).

In some embodiments, crystalline polymorphic Form A is characterized by one, two, three, four, five, six, seven, eight, nine, ten, eleven, twelve, thirteen, fourteen, fifteen, or sixteen XRPD signals selected from those set forth in Table 17.

TABLE 17

Compound 1 monofumarate salt Form A(±0.2 °2θ; ±0.1 °2θ; or ±0.0 °2θ; Cu Kα1 radiation)

| Signal number | 2-θ (0) | d Value | Net Intensity (counts) | Gross Intensity (counts) | Rel. Intensity (%) |
| --- | --- | --- | --- | --- | --- |
| Signal #1 | 10.1 | 8.71 | 1241.3 | 1366.7 | 12.2 |
| Signal #2 | 13.4 | 6.58 | 2022.8 | 2186.1 | 20.0 |
| Signal #3 | 14.1 | 6.28 | 2609.3 | 2775.8 | 25.7 |
| Signal #4 | 15.6 | 5.66 | 1772.9 | 1965.9 | 17.5 |
| Signal #5 | 15.9 | 5.56 | 3719.6 | 3919.4 | 36.7 |
| Signal #6 | 18.5 | 4.79 | 1791.7 | 2042.1 | 17.7 |
| Signal #7 | 19.0 | 4.67 | 2443.2 | 2709.9 | 24.1 |
| Signal #8 | 19.2 | 4.61 | 1426.7 | 1699.6 | 14.1 |
| Signal #9 | 19.5 | 4.56 | 2668.2 | 2946.1 | 26.3 |
| Signal #10 | 20.9 | 4.24 | 1856.7 | 2150.6 | 18.3 |
| Signal #11 | 21.4 | 4.15 | 2295.4 | 2595.2 | 22.7 |
| Signal #12 | 21.6 | 4.12 | 2171.5 | 2472.4 | 21.4 |
| Signal #13 | 22.4 | 3.96 | 10134.2 | 10431.2 | 100.0 |
| Signal #14 | 25.1 | 3.55 | 1151.0 | 1390.8 | 11.4 |
| Signal #15 | 28.2 | 3.16 | 1918.1 | 2148.9 | 18.9 |
| Signal #16 | 29.1 | 3.06 | 1701.6 | 1923.7 | 16.8 |

In some embodiments, the compound 1 monofumarate salt is crystalline polymorphic Form A characterized by an XRPD signal at of 22.4°2θ (±0.2°2θ; ±0.1°2θ; or ±0.0°2θ; Cu Kα1 radiation).

In some embodiments, the compound 1 monofumarate salt is crystalline polymorphic Form A characterized by XRPD signals at 15.9°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 15.9°2θ, 19.4°2θ, and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 15.9°2θ, 19.4°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.0°2θ, 15.9°2θ, 19.4°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by XRPD signals at 14.0°2θ, 15.9°2θ, 19.4°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.0°2θ, 15.9°2θ, 19.4°2θ, 21.5°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by XRPD signals at 14.0°2θ, 15.9°2θ, 19.4°2θ, 21.5°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 19.4°2θ, 21.5°2θ, and 22.4°2θ (±0.2°2θ; ±0.1°2θ, or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 19.4°2θ, 21.5°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 19.4°2θ, 21.4°2θ, 21.5°2θ, and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 19.4°2θ, 21.4°2θ, 21.5°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 19.0°2θ, 19.4°2θ, 21.4°2θ, 21.5°2θ, and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 19.0°2θ, 19.4°2θ, 21.4°2θ, 21.5°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 19.0°2θ, 19.4°2θ, 20.9°2θ, 21.4°2θ, 21.5°2θ, and 22.4°2θ (±0.2°2θ; ±0.1°2θ, or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 19.0°2θ, 19.4°2θ, 20.9°2θ, 21.4°2θ, 21.5°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 19.0°2θ, 19.4°2θ, 20.9°2θ, 21.4°2θ, 21.5°2θ, and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 19.0°2θ, 19.4°2θ, 20.9°2θ, 21.4°2θ, 21.5°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 19.0°2θ, 19.4°2θ, 20.9°2θ, 21.4°2θ, 21.5°2θ, 22.4°2θ, and 28.1°2θ, (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 19.0°2θ, 19.4°2θ, 20.9°2θ, 21.4°2θ, 21.5°2θ, 22.4°2θ, and 28.1°2θ, (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 19.0°2θ, 19.4°2θ, 20.9°2θ, 21.4°2θ, 21.5°2θ, 22.4°2θ, 25.0°2θ, and 28.1°2θ, (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 19.0°2θ, 19.4°2θ, 20.9°2θ, 21.4°2θ, 21.5°2θ, 22.4°2θ, 25.0°2θ, and 28.1°2θ, (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.4°2θ, 19.0°2θ, 19.4°2θ, 20.9°2θ, 21.4°2θ, 21.5°2θ, 22.4°2θ, 25.0°2θ, and 28.1°2θ, (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.4°2θ, 19.0°2θ, 19.4°2θ, 20.9°2θ, 21.4°2θ, 21.5°2θ, 22.4°2θ, 25.0°2θ, and 28.1°2θ, (±0.2°2θ; ±0.1°2θ; or ±0.0° 2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.4°2θ, 19.0°2θ, 19.4°2θ, 20.9°2θ, 21.4°2θ, 21.5°2θ, 22.4°2θ, 25.0°2θ, 28.1°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.4°2θ, 19.0°2θ, 19.4°2θ, 20.9°2θ, 21.4°2θ, 21.5°2θ, 22.4°2θ, 25.0°2θ, 28.1°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.4°2θ, 19.0°2θ, 19.2°2θ, 19.4°2θ, 20.9°2θ, 21.4°2θ, 21.5°2θ, 22.4°2θ, 25.0°2θ, 28.1°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.4°2θ, 19.0°2θ, 19.2°2θ, 19.4°2θ, 20.9°2θ, 21.4°2θ, 21.5°2θ, 22.4°2θ, 25.0°2θ, 28.1°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.1°2θ, 13.4°2θ, 14.0°2θ, 15.6°2θ, 15.9°2θ, 18.4°2θ, 19.0°2θ, 19.2°2θ, 19.4°2θ, 20.9°2θ, 21.4°2θ, 21.5°2θ, 22.4°2θ, 25.0°2θ, 28.1°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.1°2θ, 13.4°2θ, 14.0°2θ, 15.6°2θ, 15.9°2θ, 18.4°2θ, 19.0°2θ, 19.2°2θ, 19.4°2θ, 20.9°2θ, 21.4°2θ, 21.5°2θ, 22.4°2θ, 25.0°2θ, 28.1°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.1°2θ, 13.4°2θ, 14.0°2θ, 15.6°2θ, 15.9°2θ, 18.4°2θ, 19.0°2θ, 19.2°2θ, 19.4°2θ, 20.9°2θ, 21.4°2θ, 21.5°2θ, 22.4°2θ, 23.2°2θ, 25.0°2θ, 28.1°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.1°2θ, 13.4°2θ, 14.0°2θ, 15.6°2θ, 15.9°2θ, 18.4°2θ, 19.0°2θ, 19.2°2θ, 19.4°2θ, 20.9°2θ, 21.4°2θ, 21.5°2θ, 22.4°2θ, 23.2°2θ, 25.0°2θ, 28.1°2θ and 29.1°2θ (0.2°2θ, 0.1°2θ; or 30.0°2θ; Cu Kα1 radiation).

In some embodiments, crystalline polymorphic Form A is characterized by one, two, three, four, five, six, seven, eight, nine, ten, eleven, twelve, thirteen, fourteen, fifteen, sixteen, or seventeen XRPD signals selected from those set forth in Table 18.

TABLE 18

Compound 1 monofumarate salt Form A (±0.2 °2θ; ±0.1 °2θ; or ±0.0 °2θ; Cu Kα1 radiation)

| Signal number | 2-θ (0) | d Value | Net Intensity (counts) | Gross Intensity (counts) | Rel. Intensity (%) |
|---|---|---|---|---|---|
| Signal #1 | 10.1 | 8.74 | 612.0 | 721.1 | 11.1 |
| Signal #2 | 13.4 | 6.60 | 1367.1 | 1491.1 | 24.7 |
| Signal #3 | 14.0 | 6.31 | 1721.6 | 1849.3 | 31.2 |
| Signal #4 | 15.6 | 5.67 | 1053.0 | 1192.0 | 19.1 |
| Signal #5 | 15.9 | 5.57 | 2505.2 | 2648.3 | 45.3 |
| Signal #6 | 18.4 | 4.81 | 753.0 | 928.6 | 13.6 |
| Signal #7 | 19.0 | 4.68 | 1208.8 | 1400.0 | 21.9 |
| Signal #8 | 19.2 | 4.62 | 739.1 | 936.6 | 13.4 |
| Signal #9 | 19.4 | 4.57 | 1838.3 | 2040.4 | 33.3 |
| Signal #10 | 20.9 | 4.25 | 1068.5 | 1288.1 | 19.3 |
| Signal #11 | 21.4 | 4.15 | 1265.1 | 1488.6 | 22.9 |
| Signal #12 | 21.5 | 4.12 | 1503.7 | 1727.7 | 27.2 |
| Signal #13 | 22.4 | 3.97 | 5524.7 | 5745.0 | 100.0 |
| Signal #14 | 23.2 | 3.83 | 581.3 | 788.0 | 10.5 |
| Signal #15 | 25.0 | 3.55 | 764.5 | 941.7 | 13.8 |
| Signal #16 | 28.1 | 3.17 | 845.5 | 1019.4 | 15.3 |
| Signal #17 | 29.1 | 3.07 | 744.7 | 908.1 | 13.5 |

In some embodiments, the compound 1 monofumarate salt is crystalline polymorphic Form A characterized an XRPD signal at 22.5°2θ (±0.2°2θ; ±0.1°2θ; or ±0.0°2θ; Cu Kα1 radiation).

In some embodiments, the compound 1 monofumarate salt is crystalline polymorphic Form A characterized by XRPD signals at 16.0°2θ, and 22.5°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.1°2θ, 16.0°2θ, and 22.5°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.1°2θ, 16.0°2θ, and 22.5°2θ (±0.2°2θ; ±0.1°2θ; or ±0.0° 2θ; Cu Kα1 radiation).

In some embodiments, the compound 1 monofumarate salt is crystalline polymorphic Form A characterized by two or more, or three or more XRPD signals selected from the group consisting of 14.1°2θ, 16.0°2θ, 19.5°2θ, and 22.5°2θ (±0.2°2θ; ±0.1°2θ; or 0.0°2θ; Cu Kα1 radiation).

In some embodiments, the compound 1 monofumarate salt is crystalline polymorphic Form A characterized by XRPD signals at 14.1°2θ, 16.0°2θ, 19.5°2θ, and 22.5°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.1°2θ, 16.0°2θ, 19.5°2θ, 21.5°2θ, and 22.5°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.1°2θ, 16.0°2θ, 19.5°2θ, 21.5°2θ, and 22.5°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.1°2θ, 15.7°2θ, 16.0°2θ, 19.5°2θ, 21.5°2θ, and 22.5°2θ (±0.2°2θ; ±0.1°2θ, or ±0.0°2θ; Cu Kα1 radiation). In some embodiments, the compound 1 monofumarate salt is crystalline polymorphic Form A characterized by XRPD signals at 14.1°2θ, 15.7°2θ, 16.0°2θ, 19.5°2θ, 21.5°2θ, and 22.5°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.1°2θ, 15.7°2θ, 16.0°2θ, 19.2°2θ, 19.5°2θ, 21.5°2θ, and 22.5°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.1°2θ, 15.7°2θ, 16.0°2θ, 19.2°2θ, 19.5°2θ, 21.5°2θ, and 22.5°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.1°2θ, 15.7°2θ, 16.0°2θ, 19.2°2θ, 19.5°2θ, 21.5°2θ, 21.6°2θ, and 22.5°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.1°2θ, 15.7°2θ, 16.0°2θ, 19.2°2θ, 19.5°2θ, 21.5°2θ, 21.6°2θ, and 22.5°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.1°2θ, 15.7°2θ, 16.0°2θ, 19.1°2θ, 19.2°2θ, 19.5°2θ, 21.5°2θ, 21.6°2θ, and 22.5°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.1°2θ, 15.7°2θ, 16.0°2θ, 19.1°2θ, 19.2°2θ, 19.5°2θ, 21.0°2θ, 21.5°2θ, 21.6°2θ, and 22.5°2θ (±0.2°2θ; ±0.1°2θ, or ±0.0°2θ; Cu Kα1 radiation).

In some embodiments, the compound 1 monofumarate salt is crystalline polymorphic Form A characterized by two or more, or three or more XRPD signals selected from the group consisting of 14.1°2θ, 15.7°2θ, 16.0°2θ, 19.1°2θ, 19.2°2θ, 19.5°2θ, 21.0°2θ, 21.5°2θ, 21.6°2θ, 22.5°2θ, and 28.2°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.1°2θ, 15.7°2θ, 16.0°2θ, 19.1°2θ, 19.2°2θ, 19.5°2θ, 21.0°2θ, 21.5°2θ, 21.6°2θ, 22.5°2θ, and 28.2°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.1°2θ, 15.7°2θ, 16.0°2θ, 18.5°2θ, 19.1°2θ, 19.2°2θ, 19.5°2θ, 21.0°2θ, 21.5°2θ, 21.6°2θ, 22.5°2θ, and 28.2°2θ (±0.2 2θ; 0.1°2θ; or ±0.0°2θ; Cu Kα1 radiation). In some embodiments, the compound 1 monofumarate salt is crystalline polymorphic Form A characterized by XRPD signals at 14.1°2θ, 15.7°2θ, 16.0°2θ, 18.5°2θ, 19.1°2θ, 19.2°2θ, 19.5°2θ, 21.0°2θ, 21.5°2θ, 21.6°2θ, 22.5°2θ, and 28.2°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.1°2θ, 15.7°2θ, 16.0°2θ, 18.5°2θ, 19.1°2θ, 19.2°2θ, 19.5°2θ, 21.0°2θ, 21.5°2θ, 21.6°2θ, 22.5°2θ, 25.1°2θ, and 28.2°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.1°2θ, 15.7°2θ, 16.0°2θ, 18.5°2θ, 19.1°2θ, 19.2°2θ, 19.5°2θ, 21.0°2θ, 21.5°2θ, 21.6°2θ, 22.5°2θ, 25.1°2θ, and 28.2°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.5°2θ, 14.1°2θ, 15.7°2θ, 16.0°2θ, 18.5°2θ, 19.1°2θ, 19.2°2θ, 19.5°2θ, 21.0°2θ, 21.5°2θ, 21.6°2θ, 22.5°2θ, 25.1°2θ, and 28.2°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.5°2θ, 14.1°2θ, 15.7°2θ, 16.0°2θ, 18.5°2θ, 19.1°2θ, 19.2°2θ, 19.5°2θ, 21.0°2θ, 21.5°2θ, 21.6°2θ, 22.5°2θ, 25.1°2θ, and 28.2°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.2°2θ, 13.5°2θ, 14.1°2θ, 15.7°2θ, 16.0°2θ, 18.5°2θ, 19.1°2θ, 19.2°2θ, 19.5°2θ, 21.0°2θ, 21.5°2θ, 21.6°2θ, 22.5°2θ, 25.1°2θ, and 28.2°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.2°2θ, 13.5°2θ, 14.1°2θ, 15.7°2θ, 16.0°2θ, 18.5°2θ, 19.1°2θ, 19.2°2θ, 19.5°2θ, 21.0°2θ, 21.5°2θ, 21.6°2θ, 22.5°2θ, 25.1°2θ, and 28.2°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.2°2θ, 13.5°2θ, 14.1°2θ, 15.7°2θ, 16.0°2θ, 18.5°2θ, 19.1°2θ, 19.2°2θ, 19.5°2θ, 21.0°2θ, 21.5°2θ, 21.6°2θ, 22.5°2θ, 25.1°2θ, 28.2°2θ, and 29.2°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.2°2θ, 13.5°2θ, 14.1°2θ, 15.7°2θ, 16.0°2θ, 18.5°2θ, 19.1°2θ, 19.2°2θ, 19.5°2θ, 21.0°2θ, 21.5°2θ, 21.6°2θ, 22.5°2θ, 25.1°2θ, 28.2°2θ, and 29.2°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.2°2θ, 13.5°2θ, 14.1°2θ, 15.7°2θ, 16.0°2θ, 18.5°2θ, 19.1°2θ, 19.2°2θ, 19.5°2θ, 21.0°2θ, 21.5°2θ, 21.6°2θ, 22.5°2θ, 23.1°2θ, 25.1°2θ, 28.2°2θ, and 29.2°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.2°2θ, 13.5°2θ, 14.1°2θ, 15.7°2θ, 16.0°2θ, 18.5°2θ, 19.1°2θ, 19.2°2θ, 19.5°2θ, 21.0°2θ, 21.5°2θ, 21.6°2θ, 22.5°2θ, 23.1°2θ, 25.1°2θ, 28.2°2θ, and 29.2°2θ (±0.2°2θ; ±0.1°2θ; or ±0.0°2θ; Cu Kα1 radiation).

In some embodiments, crystalline polymorphic Form A is characterized by one, two, three, four, five, six, seven, eight, nine, ten, eleven, twelve, thirteen, fourteen, fifteen, sixteen, or seventeen XRPD signals selected from those set forth in Table 19.

TABLE 19

Compound 1 monofumarate salt Form A(±0.2 °2θ; ±0.1 °2θ; or ±0.0 °2θ; Cu Kα1 radiation)

| Signal number | 2-θ (°) | d Value | Net Intensity (counts) | Gross Intensity (counts) | Rel. Intensity (%) |
| --- | --- | --- | --- | --- | --- |
| Signal #1 | 10.2 | 8.67 | 793.3 | 924.2 | 13.2 |
| Signal #2 | 13.5 | 6.56 | 856.6 | 1014.7 | 14.3 |
| Signal #3 | 14.1 | 6.26 | 1820.6 | 1986.6 | 30.3 |
| Signal #4 | 15.7 | 5.64 | 1413.2 | 1606.9 | 23.5 |
| Signal #5 | 16.0 | 5.54 | 2051.0 | 2251.0 | 34.2 |
| Signal #6 | 18.5 | 4.78 | 922.8 | 1178.2 | 15.4 |
| Signal #7 | 19.1 | 4.65 | 1096.9 | 1373.4 | 18.3 |
| Signal #8 | 19.2 | 4.61 | 1291.3 | 1572.6 | 21.5 |
| Signal #9 | 19.5 | 4.55 | 1732.1 | 2021.0 | 28.9 |
| Signal #10 | 21.0 | 4.23 | 1067.6 | 1379.5 | 17.8 |
| Signal #11 | 21.5 | 4.13 | 1539.9 | 1851.6 | 25.7 |
| Signal #12 | 21.6 | 4.11 | 1254.6 | 1565.6 | 20.9 |
| Signal #13 | 22.5 | 3.95 | 6003.1 | 6302.2 | 100.0 |
| Signal #14 | 23.1 | 3.84 | 619.4 | 902.2 | 10.3 |
| Signal #15 | 25.1 | 3.54 | 882.6 | 1126.2 | 14.7 |
| Signal #16 | 28.2 | 3.16 | 1027.2 | 1247.6 | 17.1 |
| Signal #17 | 29.2 | 3.06 | 666.9 | 879.4 | 11.1 |

In some embodiments, the compound 1 monofumarate salt is crystalline polymorphic Form A characterized by an XRPD signal at 22.4°2θ (±0.2°2θ; ±0.1°2θ; or ±0.0°2θ; Cu Kα1 radiation).

In some embodiments, the compound 1 monofumarate salt is crystalline polymorphic Form A characterized by XRPD signals at 16.0°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.1°2θ, 16.0°2θ, and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.1°2θ, 16.0°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.1°2θ, 16.0°2θ, 18.5°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by XRPD signals at 10.1°2θ, 16.0°2θ, 18.5°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.1°2θ, 13.4°2θ, 16.0°2θ, 18.5°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by XRPD signals at 10.1°2θ, 13.4°2θ, 16.0°2θ, 18.5°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.1°2θ, 13.4°2θ, 16.0°2θ, 18.5°2θ, 19.5°2θ, and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.1°2θ, 13.4°2θ, 16.0°2θ, 18.5°2θ, 19.5°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.1°2θ, 13.4°2θ, 14.1°2θ, 16.0°2θ, 18.5°2θ, 19.5°2θ, and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.1°2θ, 13.4°2θ, 14.1°2θ, 16.0°2θ, 18.5°2θ, 19.5°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.1°2θ, 13.4°2θ, 14.1°2θ, 16.0°2θ, 18.5°2θ, 19.0°2θ, 19.5°2θ, and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.1°2θ, 13.4°2θ, 14.1°2θ, 16.0°2θ, 18.5°2θ, 19.0°2θ, 19.5°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.1°2θ, 13.4°2θ, 14.1°2θ, 16.0°2θ, 18.5°2θ, 19.0°2θ, 19.5°2θ, 21.4°2θ, and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.1°2θ, 13.4°2θ, 14.1°2θ, 16.0°2θ, 18.5°2θ, 19.0°2θ, 19.5°2θ, 21.4°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.1°2θ, 13.4°2θ, 14.1°2θ, 16.0°2θ, 18.5°2θ, 19.0°2θ, 19.5°2θ, 21.4°2θ, 21.6°2θ, and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.1°2θ, 13.4°2θ, 14.1°2θ, 16.0°2θ, 18.5°2θ, 19.0°2θ, 19.5°2θ, 21.4°2θ, 21.6°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.1°2θ, 13.4°2θ, 14.1°2θ, 16.0°2θ, 18.5°2θ, 19.0°2θ, 19.5°2θ, 21.4°2θ, 21.6°2θ, 22.4°2θ, and 28.2°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.1°2θ, 13.4°2θ, 14.1°2θ, 16.0°2θ, 18.5°2θ, 19.0°2θ, 19.5°2θ, 21.4°2θ, 21.6°2θ, 22.4°2θ, and 28.2°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.1°2θ, 13.4°2θ, 14.1°2θ, 16.0°2θ, 18.5°2θ, 19.0°2θ, 19.5°2θ, 20.9°2θ, 21.4°2θ, 21.6°2θ, 22.4°2θ, and 28.2°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.1°2θ, 13.4°2θ, 14.1°2θ, 16.0°2θ, 18.5°2θ, 19.0°2θ, 19.5°2θ, 20.9°2θ, 21.4°2θ, 21.6°2θ, 22.4°2θ, and 28.2°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.1°2θ, 13.4°2θ, 14.1°2θ, 15.6°2θ, 16.0°2θ, 18.5°2θ, 19.0°2θ, 19.5°2θ, 20.9°2θ, 21.4°2θ, 21.6°2θ, 22.4°2θ, and 28.2°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.1°2θ, 13.4°2θ, 14.1°2θ, 15.6°2θ, 16.0°2θ, 18.5°2θ, 19.0°2θ, 19.5°2θ, 20.9°2θ, 21.4°2θ, 21.6°2θ, 22.4°2θ, and 28.2°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.1°2θ, 13.4°2θ, 14.1°2θ, 15.6°2θ, 16.0°2θ, 18.5°2θ, 19.0°2θ, 19.5°2θ, 20.9°2θ, 21.4°2θ, 21.6°2θ, 22.4°2θ, 28.2°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.1°2θ, 13.4°2θ, 14.1°2θ, 15.6°2θ, 16.0°2θ, 18.5°2θ, 19.0°2θ, 19.5°2θ, 20.9°2θ, 21.4°2θ, 21.6°2θ, 22.4°2θ, 28.2°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.1°2θ, 13.4°2θ, 14.1°2θ, 15.6°2θ, 16.0°2θ, 18.5°2θ, 19.0°2θ, 19.2°2θ, 19.5°2θ, 20.9°2θ, 21.4°2θ, 21.6°2θ, 22.4°2θ, 28.2°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.1°2θ, 13.4°2θ, 14.1°2θ, 15.6°2θ, 16.0°2θ, 18.5°2θ, 19.0°2θ, 19.2°2θ, 19.5°2θ, 20.9°2θ, 21.4°2θ, 21.6°2θ, 22.4°2θ, 28.2°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.1°2θ, 13.4°2θ, 14.1°2θ, 15.6°2θ, 16.0°2θ, 18.5°2θ, 19.0°2θ, 19.2°2θ, 19.5°2θ, 20.9°2θ, 21.4°2θ, 21.6°2θ, 22.4°2θ, 25.1°2θ, 28.2°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.1°2θ, 13.4°2θ, 14.1°2θ, 15.6°2θ, 16.0°2θ, 18.5°2θ, 19.0°2θ, 19.2°2θ, 19.5°2θ, 20.9°2θ, 21.4°2θ, 21.6°2θ, 22.4°2θ, 25.1°2θ, 28.2°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.1°2θ, 13.4°2θ, 14.1°2θ, 15.6°2θ, 16.0°2θ, 18.5°2θ, 19.0°2θ, 19.2°2θ, 19.5°2θ, 20.9°2θ, 21.4°2θ, 21.6°2θ, 22.4°2θ, 25.1°2θ, 28.2°2θ, 29.1°2θ, and 37.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.1°2θ, 13.4°2θ, 14.1°2θ, 15.6°2θ, 16.0°2θ, 18.5°2θ, 19.0°2θ, 19.2°2θ, 19.5°2θ, 20.9°2θ, 21.4°2θ, 21.6°2θ, 22.4°2θ, 25.1°2θ, 28.2°2θ, 29.1°2θ, and 37.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.1°2θ, 13.4°2θ, 14.1°2θ, 15.6°2θ, 16.0°2θ, 18.5°2θ, 19.0°2θ, 19.2°2θ, 19.5°2θ, 20.9°2θ, 21.4°2θ, 21.6°2θ, 22.4°2θ, 24.5°2θ, 25.1°2θ, 28.2°2θ, 29.1°2θ, and 37.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.1°2θ, 13.4°2θ, 14.1°2θ, 15.6°2θ, 16.0°2θ, 18.5°2θ, 19.0°2θ, 19.2°2θ, 19.5°2θ, 20.9°2θ, 21.4°2θ, 21.6°2θ, 22.4°2θ, 24.5°2θ, 25.1°2θ, 28.2°2θ, 29.1°2θ, and 37.4°2θ (±0.2°2θ; ±0.1°2θ; or ±0.0°2θ; Cu Kα1 radiation).

In some embodiments, crystalline polymorphic Form A is characterized by one, two, three, four, five, six, seven, eight, nine, ten, eleven, twelve, thirteen, fourteen, fifteen, sixteen, seventeen, or eighteen XRPD signals selected from those set forth in Table 20.

TABLE 20

Compound 1 monofumarate salt Form A (±0.2 °2θ; ±0.1 °2θ; or ±0.0 °2θ; Cu Kα1 radiation)

| Signal number | 2-θ (°) | d Value | Net Intensity (counts) | Gross Intensity (counts) | Rel. Intensity (%) |
|---|---|---|---|---|---|
| Signal #1 | 10.1 | 8.72 | 2634.4 | 2789.7 | 40.6 |
| Signal #2 | 13.4 | 6.58 | 2205.9 | 2401.6 | 34.0 |
| Signal #3 | 14.1 | 6.28 | 1902.4 | 2105.8 | 29.3 |
| Signal #4 | 15.6 | 5.66 | 1239.3 | 1480.2 | 19.1 |
| Signal #5 | 16.0 | 5.55 | 2878.5 | 3127.2 | 44.4 |
| Signal #6 | 18.5 | 4.80 | 2281.8 | 2593.0 | 35.2 |
| Signal #7 | 19.0 | 4.67 | 1641.7 | 1970.6 | 25.3 |
| Signal #8 | 19.2 | 4.61 | 934.0 | 1269.5 | 14.4 |
| Signal #10 | 19.5 | 4.56 | 1981.8 | 2323.4 | 30.5 |
| Signal #11 | 20.9 | 4.24 | 1261.1 | 1625.6 | 19.4 |
| Signal #12 | 21.4 | 4.14 | 1457.3 | 1828.0 | 22.5 |
| Signal #13 | 21.6 | 4.12 | 1409.8 | 1781.7 | 21.7 |
| Signal #14 | 22.4 | 3.96 | 6490.3 | 6861.4 | 100.0 |
| Signal #15 | 24.5 | 3.63 | 713.5 | 1045.2 | 11.0 |
| Signal #16 | 25.1 | 3.55 | 840.4 | 1155.0 | 12.9 |
| Signal #17 | 28.2 | 3.16 | 1318.9 | 1588.1 | 20.3 |
| Signal #18 | 29.1 | 3.06 | 1088.5 | 1343.6 | 16.8 |
| Signal #19 | 37.4 | 2.40 | 817.7 | 1014.0 | 12.6 |

In some embodiments, the compound 1 monofumarate salt is crystalline polymorphic Form A characterized by an XRPD signal at 22.6°2θ (±0.2°2θ; ±0.1°2θ; or 0.0°2θ; Cu Kα1 radiation).

In some embodiments, the compound 1 monofumarate salt is crystalline polymorphic Form A characterized by XRPD signals at 16.1°2θ and 22.6°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 16.1°2θ, 21.6°2θ, and 22.6°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 16.1°2θ, 21.6°2θ, and 22.6°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 16.1°2θ, 19.2°2θ, 21.6°2θ, and 22.6°2θ (±0.2°2θ; ±0.1°2θ; or ±0.0°2θ; Cu Kα1 radiation).

In some embodiments, the compound 1 monofumarate salt is crystalline polymorphic Form A characterized by XRPD signals at 16.1°2θ, 19.2°2θ, 21.6°2θ, and 22.6°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 15.9°2θ, 16.1°2θ, 19.2°2θ, 21.6°2θ, and 22.6°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 15.9°2θ, 16.1°2θ, 19.2°2θ, 21.6°2θ, and 22.6°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 15.9°2θ, 16.1°2θ, 19.2°2θ, 19.5°2θ, 21.6°2θ, and 22.6°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 15.9°2θ, 16.1°2θ, 19.2°2θ, 19.5°2θ, 21.6°2θ, and 22.6°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 15.9°2θ, 16.1°2θ, 19.2°2θ, 19.5°2θ, 21.6°2θ, 22.6°2θ, and 29.2°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 15.9°2θ, 16.1°2θ, 19.2°2θ, 19.5°2θ, 21.6°2θ, 22.6°2θ, and 29.2°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 15.9°2θ, 16.1°2θ, 19.2°2θ, 19.5°2θ, 21.6°2θ, 22.6°2θ, 28.3°2θ, and 29.2°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 15.9°2θ, 16.1°2θ, 19.2°2θ, 19.5°2θ, 21.3°2θ, 21.6°2θ, 22.6°2θ, 28.3°2θ, and 29.2°2θ (±0.2°2θ; ±0.1° 2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.2°2θ, 15.9°2θ, 16.1°2θ, 19.2°2θ, 19.5°2θ, 21.3°2θ, 21.6°2θ, 22.6°2θ, 28.3°2θ, and 29.2°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.2°2θ, 15.9°2θ, 16.1°2θ, 19.2°2θ, 19.5°2θ, 21.3°2θ, 21.6°2θ, 22.6°2θ, 28.3°2θ, and 29.2°2θ (±0.2° 2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.2°2θ, 15.9°2θ, 16.1°2θ, 19.2°2θ, 19.5°2θ, 21.2°2θ, 21.3°2θ, 21.6°2θ, 22.6°2θ, 28.3°2θ, and 29.2°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.2°2θ, 15.9°2θ, 16.1°2θ, 19.2°2θ, 19.5°2θ, 21.2°2θ, 21.3°2θ, 21.6°2θ, 22.6°2θ, 28.3°2θ, and 29.2°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.2°2θ, 15.9°2θ, 16.1°2θ, 19.2°2θ, 19.5°2θ, 21.2°2θ, 21.3°2θ, 21.6°2θ, 22.6°2θ, 25.2°2θ, 28.3°2θ, and 29.2°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.2°2θ, 15.9°2θ, 16.1°2θ, 19.2°2θ, 19.5°2θ, 21.2°2θ, 21.3°2θ, 21.6°2θ, 22.6°2θ, 25.2°2θ, 28.3°2θ, and 29.2°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.2°2θ, 15.9°2θ, 16.1°2θ, 17.0°2θ, 19.2°2θ, 19.5°2θ, 21.2°2θ, 21.3°2θ, 21.6°2θ, 22.6°2θ, 25.2°2θ, 28.3°2θ, and 29.2°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.2°2θ, 15.9°2θ, 16.1°2θ, 17.0°2θ, 19.2°2θ, 19.5°2θ, 21.2°2θ, 21.3°2θ, 21.6°2θ, 22.6°2θ, 25.2°2θ, 28.3°2θ, and 29.2°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.2°2θ, 15.9°2θ, 16.1°2θ, 17.0°2θ, 19.2°2θ, 19.5°2θ, 21.2°2θ, 21.3°2θ, 21.6°2θ, 22.6°2θ, 25.2°2θ, 25.5°2θ, 28.3°2θ, and 29.2°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.2°2θ, 15.9°2θ, 16.1°2θ, 17.0°2θ, 19.2°2θ, 19.5°2θ, 21.2°2θ, 21.3°2θ, 21.6°2θ, 22.6°2θ, 25.2°2θ, 25.5°2θ, 28.3°2θ, and 29.2°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.2°2θ, 15.9°2θ, 16.1°2θ, 17.0°2θ, 18.7°2θ, 19.2°2θ, 19.5°2θ, 21.2°2θ, 21.3°2θ, 21.6°2θ, 22.6°2θ, 25.2°2θ, 25.5°2θ, 28.3°2θ, and 29.2°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.2°2θ, 15.9°2θ, 16.1°2θ, 17.0°2θ, 18.7°2θ, 19.2°2θ, 19.5°2θ, 21.2°2θ, 21.3°2θ, 21.6°2θ, 22.6°2θ, 25.2°2θ, 25.5°2θ, 28.3°2θ, and 29.2°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.6°2θ, 14.2°2θ, 15.9°2θ, 16.1°2θ, 17.0°2θ, 18.7°2θ, 19.2°2θ, 19.5°2θ, 21.2°2θ, 21.3°2θ, 21.6°2θ, 22.6°2θ, 25.2°2θ, 25.5°2θ, 28.3°2θ, and 29.2°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.6°2θ, 14.2°2θ, 15.9°2θ, 16.1°2θ, 17.0°2θ, 18.7°2θ, 19.2°2θ, 19.5°2θ, 21.2°2θ, 21.3°2θ, 21.6°2θ, 22.6°2θ, 25.2°2θ, 25.5°2θ, 28.3°2θ, and 29.2°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.3°2θ, 13.6°2θ, 14.2°2θ, 15.9°2θ, 16.1°2θ, 17.0°2θ, 18.7°2θ, 19.2°2θ, 19.5°2θ, 21.2°2θ, 21.3°2θ, 21.6°2θ, 22.6°2θ, 25.2°2θ, 25.5°2θ, 28.3°2θ, and 29.2°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.3°2θ, 13.6°2θ, 14.2°2θ, 15.9°2θ, 16.1°2θ, 17.0°2θ, 18.7°2θ, 19.2°2θ, 19.5°2θ, 21.2°2θ, 21.3°2θ, 21.6°2θ, 22.6°2θ, 25.2°2θ, 25.5°2θ, 28.3°2θ, and 29.2°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.3°2θ, 13.6°2θ, 14.2°2θ, 15.9°2θ, 16.1°2θ, 17.0°2θ, 18.7°2θ, 19.2°2θ, 19.5°2θ, 21.2°2θ, 21.3°2θ, 21.6°2θ, 22.6°2θ, 25.2°2θ, 25.5°2θ, 28.3°2θ, 29.2°2θ, and 34.3°2θ (±0.2°2θ; ±0.1 15°2θ; or ±0.0°2θ; Cu Kα1 radiation). In some embodiments, the compound 1 monofumarate salt is crystalline polymorphic Form A characterized by XRPD signals at 10.3°2θ, 13.6°2θ, 14.2°2θ, 15.9°2θ, 16.1°2θ, 17.0°2θ, 18.7°2θ, 19.2°2θ, 19.5°2θ, 21.2°2θ, 21.3°2θ, 21.6°2θ, 22.6°2θ, 25.2°2θ, 25.5°2θ, 28.3°2θ, 29.2°2θ, and 34.3°2θ (±0.2°2θ; ±0.1°2θ; or ±0.0°2θ; Cu Kα1 radiation).

In some embodiments, crystalline polymorphic Form A is characterized by one, two, three, four, five, six, seven, eight, nine, ten, eleven, twelve, thirteen, fourteen, fifteen, sixteen, seventeen, or eighteen XRPD signals selected from those set forth in Table 21.

TABLE 21

Compound 1 monofumarate salt Form A(±0.2 °2θ; ±0.1 °2θ; or ±0.0 °2θ; Cu Kα1 radiation)

| Signal number | 2-θ (°) | d Value | Net Intensity (counts) | Gross Intensity (counts) | Rel. Intensity (%) |
| --- | --- | --- | --- | --- | --- |
| Signal #1 | 10.3 | 8.59 | 447.0 | 567.1 | 10.7 |
| Signal #2 | 13.6 | 6.50 | 472.0 | 623.8 | 11.3 |
| Signal #3 | 14.2 | 6.24 | 712.7 | 870.2 | 17.1 |
| Signal #4 | 15.9 | 5.58 | 1094.4 | 1286.5 | 26.3 |
| Signal #5 | 16.1 | 5.51 | 1803.9 | 2000.9 | 43.3 |
| Signal #6 | 17.0 | 5.21 | 524.9 | 738.8 | 12.6 |
| Signal #7 | 18.7 | 4.75 | 498.7 | 763.4 | 12.0 |
| Signal #8 | 19.2 | 4.61 | 1141.3 | 1424.3 | 27.4 |
| Signal #9 | 19.5 | 4.55 | 1054.1 | 1343.4 | 25.3 |
| Signal #10 | 21.2 | 4.18 | 635.5 | 947.9 | 15.3 |
| Signal #12 | 21.3 | 4.17 | 715.0 | 1027.4 | 17.2 |
| Signal #11 | 21.6 | 4.12 | 1330.4 | 1642.4 | 31.9 |
| Signal #13 | 22.6 | 3.94 | 4165.8 | 4467.5 | 100.0 |
| Signal #14 | 25.2 | 3.53 | 609.3 | 857.8 | 14.6 |
| Signal #15 | 25.5 | 3.49 | 499.2 | 742.4 | 12.0 |
| Signal #16 | 28.3 | 3.15 | 800.0 | 1030.3 | 19.2 |
| Signal #17 | 29.2 | 3.06 | 972.6 | 1197.2 | 23.3 |
| Signal #18 | 34.3 | 2.61 | 431.9 | 624.2 | 10.4 |

In some embodiments, the compound 1 monofumarate salt is crystalline polymorphic Form A characterized an XRPD signal at 22.4°2θ (±0.2°2θ; ±0.1°2θ; or ±0.0°2θ; Cu Kα1 radiation).

In some embodiments, the compound 1 monofumarate salt is crystalline polymorphic Form A characterized by XRPD signals at 19.4°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 15.9°2θ, 19.4°2θ, and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 15.9°2θ, 19.4°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.1°2θ, 15.9°2θ, 19.4°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by XRPD signals at 14.1°2θ, 15.9°2θ, 19.4°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.1°2θ, 15.9°2θ, 16.8°2θ, 19.4°2θ, and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.1°2θ, 15.9°2θ, 16.8°2θ, 19.4°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.1°2θ, 15.9°2θ, 16.8°2θ, 19.4°2θ, 22.4°2θ, and 25.3°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.1°2θ, 15.9°2θ, 16.8°2θ, 19.4°2θ, 22.4°2θ, and 25.3°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.1°2θ, 15.9°2θ, 16.8°2θ, 19.4°2θ, 21.6°2θ, 22.4°2θ, and 25.3°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.1°2θ, 15.9°2θ, 16.8°2θ, 19.4°2θ, 21.6°2θ, 22.4°2θ, and 25.3°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.1°2θ, 15.9°2θ, 16.8°2θ, 19.4°2θ, 21.4°2θ, 21.6°2θ, 22.4°2θ, and 25.3°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.1°2θ, 15.9°2θ, 16.8°2θ, 19.4°2θ, 21.4°2θ, 21.6°2θ, 22.4°2θ, and 25.3°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.1°2θ, 15.9°2θ, 16.8°2θ, 19.4°2θ, 21.4°2θ, 21.6°2θ, 22.4°2θ, and 25.3°2θ (±0.2° 2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.1°2θ, 15.9°2θ, 16.8°2θ, 19.4°2θ, 21.4°2θ, 21.6°2θ, 22.4°2θ, and 25.3°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.1°2θ, 15.9°2θ, 16.8°2θ, 19.4°2θ, 21.4°2θ, 21.6°2θ, 22.4°2θ, 25.3°2θ, and 34.0°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.1°2θ, 15.9°2θ, 16.8°2θ, 19.4°2θ, 21.4°2θ, 21.6°2θ, 22.4°2θ, 25.3°2θ, and 34.0°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.1°2θ, 15.9°2θ, 16.8°2θ, 19.0°2θ, 19.4°2θ, 21.4°2θ, 21.6°2θ, 22.4°2θ, 25.3°2θ, and 34.0°2θ (±0.2°2θ; ±0.1°2θ; or ±0.0°2θ. Cu Kα1 radiation). In some embodiments, the compound 1 monofumarate salt is crystalline polymorphic Form A characterized by XRPD signals at 13.4°2θ, 14.1°2θ, 15.9°2θ, 16.8°2θ, 19.0°2θ, 19.4°2θ, 21.4°2θ, 21.6°2θ, 22.4°2θ, 25.3°2θ, and 34.0°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.1°2θ, 15.7°2θ, 15.9°2θ, 16.8°2θ, 19.0°2θ, 19.4°2θ, 21.4°2θ, 21.6°2θ, 22.4°2θ, 25.3°2θ, and 34.0°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.1°2θ, 15.7°2θ, 15.9°2θ, 16.8°2θ, 19.0°2θ, 19.4°2θ, 20.9°2θ, 21.4°2θ, 21.6°2θ, 22.4°2θ, 25.3°2θ, and 34.0°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.1°2θ, 15.7°2θ, 15.9°2θ, 16.8°2θ, 18.5°2θ, 19.0°2θ, 19.4°2θ, 20.9°2θ, 21.4°2θ, 21.6°2θ, 22.4°2θ, 25.3°2θ, and 34.0°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.1°2θ, 15.7°2θ, 15.9°2θ, 16.8°2θ, 18.5°2θ, 19.0°2θ, 19.4°2θ, 20.9°2θ, 21.4°2θ, 21.6°2θ, 22.4°2θ, 25.3°2θ, and 34.0°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.1°2θ, 15.7°2θ, 15.9°2θ, 16.8°2θ, 18.5°2θ, 19.0°2θ, 19.4°2θ, 20.9°2θ, 21.4°2θ, 21.6°2θ, 22.4°2θ, 25.3°2θ, 28.2°2θ, and 34.0°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.1°2θ, 15.7°2θ, 15.9°2θ, 16.8°2θ, 18.5°2θ, 19.0°2θ, 19.4°2θ, 20.9°2θ, 21.4°2θ, 21.6°2θ, 22.4°2θ, 25.3°2θ, 28.2°2θ, and 34.0°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.1°2θ, 15.7°2θ, 15.9°2θ, 16.8°2θ, 18.5°2θ, 19.0°2θ, 19.4°2θ, 20.9°2θ, 21.4°2θ, 21.6°2θ, 22.4°2θ, 23.2°2θ, 25.3°2θ, 28.2°2θ, and 34.0°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.1°2θ, 15.7°2θ, 15.9°2θ, 16.8°2θ, 18.5°2θ, 19.0°2θ, 19.4°2θ, 20.9°2θ, 21.4°2θ, 21.6°2θ, 22.4°2θ, 23.2°2θ, 25.3°2θ, 28.2°2θ, and 34.0°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.1°2θ, 15.7°2θ, 15.9°2θ, 16.8°2θ, 18.5°2θ, 19.0°2θ, 19.4°2θ, 20.9°2θ, 21.4°2θ, 21.6°2θ, 22.4°2θ, 23.2°2θ, 25.0°2θ, 25.3°2θ, 28.2°2θ, and 34.0°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.1°2θ, 15.7°2θ, 15.9°2θ, 16.8°2θ, 18.5°2θ, 19.0°2θ, 19.4°2θ, 20.9°2θ, 21.4°2θ, 21.6°2θ, 22.4°2θ, 23.2°2θ, 25.0°2θ, 25.3°2θ, 28.2°2θ, and 34.0°2θ (±0.2°2θ; ±0.1°2θ; or ±0.0°2θ; Cu Kα1 radiation).

In some embodiments, crystalline polymorphic Form A is characterized by one, two, three, four, five, six, seven, eight, nine, ten, eleven, twelve, thirteen, fourteen, fifteen, sixteen, or seventeen XRPD signals selected from those set forth in Table 22.

TABLE 22

Compound 1 monofumarate salt Form A(±0.2 °2θ; ±0.1 °2θ; or ±0.0 °2θ; Cu Kα1 radiation)

| Signal number | 2-θ (°) | d Value | Net Intensity (counts) | Gross Intensity (counts) | Rel. Intensity (%) |
|---|---|---|---|---|---|
| Signal #1 | 13.4 | 6.59 | 975.2 | 1094.5 | 15.3 |
| Signal #2 | 14.1 | 6.29 | 1496.5 | 1617.5 | 23.5 |
| Signal #3 | 15.7 | 5.65 | 891.2 | 1037.8 | 14.0 |
| Signal #4 | 15.9 | 5.57 | 2189.1 | 2341.4 | 34.3 |
| Signal #5 | 16.8 | 5.28 | 1470.6 | 1636.4 | 23.1 |
| Signal #6 | 18.5 | 4.80 | 823.4 | 1023.6 | 12.9 |
| Signal #7 | 19.0 | 4.66 | 923.4 | 1140.2 | 14.5 |
| Signal #8 | 19.4 | 4.57 | 2755.9 | 2981.2 | 43.2 |
| Signal #9 | 20.9 | 4.24 | 873.9 | 1118.7 | 13.7 |
| Signal #10 | 21.4 | 4.15 | 1076.3 | 1328.0 | 16.9 |
| Signal #12 | 21.6 | 4.12 | 1283.0 | 1536.0 | 20.1 |
| Signal #11 | 22.4 | 3.97 | 6373.2 | 6626.6 | 100.0 |
| Signal #13 | 23.2 | 3.83 | 699.3 | 941.4 | 11.0 |
| Signal #14 | 25.0 | 3.56 | 643.1 | 859.0 | 10.1 |
| Signal #15 | 25.3 | 3.52 | 1342.9 | 1554.8 | 21.1 |
| Signal #16 | 28.2 | 3.17 | 723.1 | 914.8 | 11.3 |
| Signal #17 | 34.0 | 2.64 | 923.9 | 1077.2 | 14.5 |

In some embodiments, the compound 1 monofumarate salt is crystalline polymorphic Form A characterized by an XRPD signal at 22.3°2θ (±0.2°2θ; ±0.1°2θ; or ±0.0°2θ; Cu Kα1 radiation).

In some embodiments, the compound 1 monofumarate salt is crystalline polymorphic Form A characterized by XRPD signals at 15.9°2θ and 22.3°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 15.9°2θ, 21.3°2θ, and 22.3°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 15.9°2θ, 21.3°2θ, and 22.3°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 15.9°2θ, 19.4°2θ, 21.3°2θ, and 22.3°2θ (±0.2°2θ; ±0.1°2θ; or ±0.0°2θ; Cu Kα1 radiation).

In some embodiments, the compound 1 monofumarate salt is crystalline polymorphic Form A characterized by XRPD signals at 15.9°2θ, 19.4°2θ, 21.3°2θ, and 22.3°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.0°2θ, 15.9°2θ, 19.4°2θ, 21.3°2θ, and 22.3°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.0°2θ, 15.9°2θ, 19.4°2θ, 21.3°2θ, and 22.3°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.0°2θ, 15.9°2θ, 19.4°2θ, 21.3°2θ, 21.5°2θ, and 22.3°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.0°2θ, 15.9°2θ, 19.4°2θ, 21.3°2θ, 21.5°2θ, and 22.3°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 19.4°2θ, 21.3°2θ, 21.5°2θ, and 22.3°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 19.4°2θ, 21.3°2θ, 21.5°2θ, and 22.3°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 18.9°2θ, 19.4°2θ, 21.3°2θ, 21.5°2θ, and 22.3°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 18.9°2θ, 19.4°2θ, 21.3°2θ, 21.5°2θ, and 22.3°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 18.9°2θ, 19.4°2θ, 20.9°2θ, 21.3°2θ, 21.5°2θ, and 22.3°2θ (±0.2° 2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 18.9°2θ, 19.4°2θ, 20.9°2θ, 21.3°2θ, 21.5°2θ, and 22.3°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.9°2θ, 19.4°2θ, 20.9°2θ, 21.3°2θ, 21.5°2θ, and 22.3°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.9°2θ, 19.4°2θ, 20.9°2θ, 21.3°2θ, 21.5°2θ, and 22.3°2θ (±0.2° 2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.9°2θ, 19.4°2θ, 20.9°2θ, 21.3°2θ, 21.5°2θ, 22.3°2θ, and 28.1°2θ (±0.2°2θ; ±0.1°2θ; or ±0.0°2θ. Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.9°2θ, 19.4°2θ, 20.9°2θ, 21.3°2θ, 21.5°2θ, 22.3°2θ, and 28.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.9°2θ, 19.4°2θ, 20.9°2θ, 21.3°2θ, 21.5°2θ, 22.3°2θ, 25.0°2θ, and 28.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.9°2θ, 19.4°2θ, 20.9°2θ, 21.3°2θ, 21.5°2θ, 22.3°2θ, 25.0°2θ, and 28.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.9°2θ, 19.4°2θ, 20.9°2θ, 21.3°2θ, 21.5°2θ, 22.3°2θ, 23.2°2θ, 25.0°2θ, and 28.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.9°2θ, 19.4°2θ, 20.9°2θ, 21.3°2θ, 21.5°2θ, 22.3°2θ, 23.2°2θ, 25.0°2θ, and 28.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.9°2θ, 19.4°2θ, 20.9°2θ, 21.3°2θ, 21.5°2θ, 22.3°2θ, 23.2°2θ, 25.0°2θ, 28.1°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.9°2θ, 19.4°2θ, 20.9°2θ, 21.3°2θ, 21.5°2θ, 22.3°2θ, 23.2°2θ, 25.0°2θ, 28.1°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.9°2θ, 19.4°2θ, 20.9°2θ, 21.3°2θ, 21.5°2θ, 22.1°2θ, 22.3°2θ, 23.2°2θ, 25.0°2θ, 28.1°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.9°2θ, 19.4°2θ, 20.9°2θ, 21.3°2θ, 21.5°2θ, 22.1°2θ, 22.3°2θ, 23.2°2θ, 25.0°2θ, 28.1°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.4°2θ, 18.9°2θ, 19.4°2θ, 20.9°2θ, 21.3°2θ, 21.5°2θ, 22.1°2θ, 22.3°2θ, 23.2°2θ, 25.0°2θ, 28.1°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.4°2θ, 18.9°2θ, 19.4°2θ, 20.9°2θ, 21.3°2θ, 21.5°2θ, 22.1°2θ, 22.3°2θ, 23.2°2θ, 25.0°2θ, 28.1°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.4°2θ, 18.9°2θ, 19.4°2θ, 20.9°2θ, 21.3°2θ, 21.5°2θ, 22.1°2θ, 22.3°2θ, 23.2°2θ, 24.4°2θ, 25.0°2θ, 28.1°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.4°2θ, 18.9°2θ, 19.4°2θ, 20.9°2θ, 21.3°2θ, 21.5°2θ, 22.1°2θ, 22.3°2θ, 23.2°2θ, 24.4°2θ, 25.0°2θ, 28.1°2θ, and 29.1°2θ (±0.2°2θ; ±0.1°2θ; or ±0.0°2θ; Cu Kα1 radiation).

In some embodiments, crystalline polymorphic Form A is characterized by one, two, three, four, five, six, seven, eight, nine, ten, eleven, twelve, thirteen, fourteen, fifteen, sixteen, or seventeen XRPD signals selected from those set forth in Table 23.

TABLE 23

Compound 1 monofumarate salt Form A(±0.2 °2θ; ±0.1 °2θ; or ±0.0 °2θ; Cu Kα1 radiation)

| Signal number | 2-θ (°) | d Value | Net Intensity (counts) | Gross Intensity (counts) | Rel. Intensity (%) |
|---|---|---|---|---|---|
| Signal #1 | 13.4 | 6.62 | 878.7 | 981.0 | 21.9 |
| Signal #2 | 14.0 | 6.32 | 974.4 | 1083.3 | 24.3 |
| Signal #3 | 15.6 | 5.68 | 612.1 | 735.5 | 15.3 |
| Signal #4 | 15.9 | 5.58 | 1461.0 | 1588.6 | 36.4 |
| Signal #5 | 18.4 | 4.82 | 464.7 | 638.8 | 11.6 |
| Signal #6 | 18.9 | 4.69 | 748.4 | 933.1 | 18.7 |
| Signal #7 | 19.4 | 4.57 | 993.5 | 1184.9 | 24.8 |
| Signal #8 | 20.9 | 4.26 | 717.0 | 921.7 | 17.9 |
| Signal #9 | 21.3 | 4.17 | 1316.0 | 1528.6 | 32.8 |
| Signal #10 | 21.5 | 4.13 | 939.4 | 1154.6 | 23.4 |
| Signal #12 | 22.1 | 4.01 | 491.3 | 711.8 | 12.2 |
| Signal #11 | 22.3 | 3.98 | 4011.6 | 4232.6 | 100.0 |
| Signal #13 | 23.2 | 3.84 | 563.9 | 781.1 | 14.1 |
| Signal #14 | 24.4 | 3.65 | 432.1 | 633.7 | 10.8 |
| Signal #15 | 25.0 | 3.56 | 574.5 | 767.9 | 14.3 |
| Signal #16 | 28.1 | 3.17 | 594.0 | 764.7 | 14.8 |
| Signal #17 | 29.1 | 3.07 | 562.4 | 725.7 | 14.0 |

In some embodiments, the compound 1 monofumarate salt is crystalline polymorphic Form A characterized by an XRPD signal at 22.4°2θ (±0.2°2θ; ±0.1°2θ; or ±0.0°2θ; Cu Kα1 radiation).

In some embodiments, the compound 1 monofumarate salt is crystalline polymorphic Form A characterized by XRPD signals at 15.9°2θ, and 22.4°2θ (±0.2°2θ; 0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.0°2θ, 15.9°2θ, and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.0°2θ, 15.9°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.0°2θ, 15.9°2θ, 19.4°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by XRPD signals at 14.0°2θ, 15.9°2θ, 19.4°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.0°2θ, 15.9°2θ, 19.4°2θ, 21.6°2θ, and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.0°2θ, 15.9°2θ, 19.4°2θ, 21.6°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.0°2θ, 15.9°2θ, 19.4°2θ, 21.4°2θ, 21.6°2θ, and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.0°2θ, 15.9°2θ, 19.4°2θ, 21.4°2θ, 21.6°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 19.4°2θ, 21.4°2θ, 21.6°2θ, and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 19.4°2θ, 21.4°2θ, 21.6°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 19.4°2θ, 20.9°2θ, 21.4°2θ, 21.6°2θ, and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 19.4°2θ, 20.9°2θ, 21.4°2θ, 21.6°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 19.4°2θ, 20.9°2θ, 21.4°2θ, 21.6°2θ, 22.4°2θ, and 28.2°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 19.4°2θ, 20.9°2θ, 21.4°2θ, 21.6°2θ, 22.4°2θ, and 28.2°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 19.0°2θ, 19.4°2θ, 20.9°2θ, 21.4°2θ, 21.6°2θ, 22.4°2θ, and 28.2°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 19.0°2θ, 19.4°2θ, 20.9°2θ, 21.4°2θ, 21.6°2θ, 22.4°2θ, and 28.2°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 19.0°2θ, 19.4°2θ, 20.9°2θ, 21.4°2θ, 21.6°2θ, 22.4°2θ, and 28.2°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 19.0°2θ, 19.4°2θ, 20.9°2θ, 21.4°2θ, 21.6°2θ, 22.4°2θ, and 28.2°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 19.0°2θ, 19.4°2θ, 20.9°2θ, 21.4°2θ, 21.6°2θ, 22.4°2θ, 28.2°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 19.0°2θ, 19.4°2θ, 20.9°2θ, 21.4°2θ, 21.6°2θ, 22.4°2θ, 28.2°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 19.0°2θ, 19.4°2θ, 20.9°2θ, 21.4°2θ, 21.6°2θ, 22.4°2θ, 25.1°2θ, 28.2°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 19.0°2θ, 19.4°2θ, 20.9°2θ, 21.4°2θ, 21.6°2θ, 22.4°2θ, 25.1°2θ, 28.2°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.4°2θ, 19.0°2θ, 19.4°2θ, 20.9°2θ, 21.4°2θ, 21.6°2θ, 22.4°2θ, 25.1°2θ, 28.2°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.4°2θ, 19.0°2θ, 19.4°2θ, 20.9°2θ, 21.4°2θ, 21.6°2θ, 22.4°2θ, 25.1°2θ, 28.2°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.4°2θ, 19.0°2θ, 19.4°2θ, 20.9°2θ, 21.4°2θ, 21.6°2θ, 22.4°2θ, 23.2°2θ, 25.1°2θ, 28.2°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.4°2θ, 19.0°2θ, 19.4°2θ, 20.9°2θ, 21.4°2θ, 21.6°2θ, 22.4°2θ, 23.2°2θ, 25.1°2θ, 28.2°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.1°2θ, 13.4°2θ, 14.0°2θ, 15.6°2θ, 15.9°2θ, 18.4°2θ, 19.0°2θ, 19.4°2θ, 20.9°2θ, 21.4°2θ, 21.6°2θ, 22.4°2θ, 23.2°2θ, 24.5°2θ, 25.1°2θ, 28.2°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.1°2θ, 13.4°2θ, 14.0°2θ, 15.6°2θ, 15.9°2θ, 18.4°2θ, 19.0°2θ, 19.4°2θ, 20.9°2θ, 21.4°2θ, 21.6°2θ, 22.4°2θ, 23.2°2θ, 24.5°2θ, 25.1°2θ, 28.2°2θ, and 29.1°2θ (±0.2°2θ; ±0.1°2θ; or ±0.0°2θ; Cu Kα1 radiation).

In some embodiments, crystalline polymorphic Form A is characterized by one, two, three, four, five, six, seven, eight, nine, ten, eleven, twelve, thirteen, fourteen, fifteen, sixteen, or seventeen XRPD signals selected from those set forth in Table 24.

TABLE 24

Compound 1 monofumarate salt Form A(±0.2 °2θ; ±0.1 °2θ; or ±0.0 °2θ; Cu Kα1 radiation)

| Signal number | 2-θ (°) | d Value | Net Intensity (counts) | Gross Intensity (counts) | Rel. Intensity (%) |
|---|---|---|---|---|---|
| Signal #1 | 10.1 | 8.73 | 395.4 | 483.4 | 11.4 |
| Signal #2 | 13.4 | 6.60 | 941.6 | 1057.2 | 27.2 |
| Signal #3 | 14.0 | 6.30 | 1217.5 | 1345.7 | 35.1 |
| Signal #4 | 15.6 | 5.67 | 603.6 | 758.3 | 17.4 |
| Signal #5 | 15.9 | 5.56 | 1492.2 | 1652.8 | 43.0 |
| Signal #6 | 18.4 | 4.81 | 459.1 | 667.9 | 13.2 |
| Signal #7 | 19.0 | 4.68 | 726.9 | 950.7 | 21.0 |
| Signal #8 | 19.4 | 4.56 | 1194.5 | 1429.5 | 34.5 |
| Signal #9 | 20.9 | 4.25 | 771.4 | 1023.4 | 22.3 |
| Signal #10 | 21.4 | 4.15 | 1023.5 | 1275.3 | 29.5 |
| Signal #12 | 21.6 | 4.12 | 1190.5 | 1441.6 | 34.3 |
| Signal #11 | 22.4 | 3.97 | 3466.6 | 3708.9 | 100.0 |
| Signal #13 | 23.2 | 3.83 | 454.8 | 680.3 | 13.1 |
| Signal #14 | 24.5 | 3.64 | 386.2 | 586.7 | 11.1 |
| Signal #15 | 25.1 | 3.55 | 482.0 | 668.8 | 13.9 |
| Signal #16 | 28.2 | 3.17 | 745.2 | 916.8 | 21.5 |
| Signal #17 | 29.1 | 3.07 | 595.8 | 761.5 | 17.2 |

In some embodiments, the compound 1 monofumarate salt is crystalline polymorphic Form A characterized by two or more, or three or more XRPD signal at 25.2°2θ (±0.2°2θ; ±0.1°2θ; or ±0.0°2θ; Cu Kα1 radiation).

In some embodiments, the compound 1 monofumarate salt is crystalline polymorphic Form A characterized by XRPD signals at 16.8°2θ, and 25.2°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 16.8°2θ, 19.4°2θ, and 25.2°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 16.8°2θ, 19.4°2θ, and 25.2°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 15.9°2θ, 16.8°2θ, 19.4°2θ, and 25.2°2θ (±0.2°2θ; ±0.1°2θ; or ±0.0°2θ; Cu Kα1 radiation).

In some embodiments, the compound 1 monofumarate salt is crystalline polymorphic Form A characterized by XRPD signals at 15.9°2θ, 16.8°2θ, 19.4°2θ, and 25.2°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 15.9°2θ, 16.8°2θ, 19.4°2θ, 22.3°2θ, and 25.2°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 15.9°2θ, 16.8°2θ, 19.4°2θ, 22.3°2θ, and 25.2°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.0°2θ, 15.9°2θ, 16.8°2θ, 19.4°2θ, 22.3°2θ, and 25.2°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.0°2θ, 15.9°2θ, 16.8°2θ, 19.4°2θ, 22.3°2θ, and 25.2°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.0°2θ, 15.9°2θ, 16.8°2θ, 19.4°2θ, 22.3°2θ, 25.2°2θ, and 33.9°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.0°2θ, 15.9°2θ, 16.8°2θ, 19.4°2θ, 22.3°2θ, 25.2°2θ, and 33.9°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 8.4°2θ, 14.0°2θ, 15.9°2θ, 16.8°2θ, 19.4°2θ, 22.3°2θ, 25.2°2θ, and 33.9°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 8.4°2θ, 14.0°2θ, 15.9°2θ, 16.8°2θ, 19.4°2θ, 22.3°2θ, 25.2°2θ, and 33.9°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 8.4°2θ, 14.0°2θ, 15.9°2θ, 16.8°2θ, 19.4°2θ, 21.4°2θ, 22.3°2θ, 25.2°2θ, and 33.9°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 8.4°2θ, 14.0°2θ, 15.9°2θ, 16.8°2θ, 19.4°2θ, 21.4°2θ, 22.3°2θ, 25.2°2θ, and 33.9°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 8.4°2θ, 14.0°2θ, 15.9°2θ, 16.8°2θ, 19.4°2θ, 21.4°2θ, 21.5°2θ, 22.3°2θ, 25.2°2θ, and 33.9°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 8.4°2θ, 14.0°2θ, 15.9°2θ, 16.8°2θ, 19.4°2θ, 21.4°2θ, 21.5°2θ, 22.3°2θ, 25.2°2θ, and 33.9°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 8.4°2θ, 14.0°2θ, 15.6°2θ, 15.9°2θ, 16.8°2θ, 19.4°2θ, 21.4°2θ, 21.5°2θ, 22.3°2θ, 25.2°2θ, and 33.9°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 8.4°2θ, 14.0°2θ, 15.6°2θ, 15.9°2θ, 16.8°2θ, 19.4°2θ, 21.4°2θ, 21.5°2θ, 22.3°2θ, and 33.9°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 8.4°2θ, 14.0°2θ, 15.6°2θ, 15.9°2θ, 16.8°2θ, 19.4°2θ, 20.8°2θ, 21.4°2θ, 21.5°2θ, 22.3°2θ, 25.2°2θ, and 33.9°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 8.4°2θ, 14.0°2θ, 15.6°2θ, 15.9°2θ, 16.8°2θ, 19.4°2θ, 20.8°2θ, 21.4°2θ, 21.5°2θ, 22.3°2θ, 25.2°2θ, and 33.9°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 8.4°2θ, 14.0°2θ, 15.6°2θ, 15.9°2θ, 16.8°2θ, 18.9°2θ, 19.4°2θ, 20.8°2θ, 21.4°2θ, 21.5°2θ, 22.3°2θ, 25.2°2θ, and 33.9°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 8.4°2θ, 14.0°2θ, 15.6°2θ, 15.9°2θ, 16.8°2θ, 18.9°2θ, 19.4°2θ, 20.8°2θ, 21.4°2θ, 21.5°2θ, 22.3°2θ, 25.2°2θ, and 33.9°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 8.4°2θ, 14.0°2θ, 15.6°2θ, 15.9°2θ, 16.8°2θ, 18.4°2θ, 18.9°2θ, 19.4°2θ, 20.8°2θ, 21.4°2θ, 21.5°2θ, 22.3°2θ, 25.2°2θ, and 33.9°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 8.4°2θ, 14.0°2θ, 15.6°2θ, 15.9°2θ, 16.8°2θ, 18.4°2θ, 18.9°2θ, 19.4°2θ, 20.8°2θ, 21.4°2θ, 21.5°2θ, 22.3°2θ, 25.2°2θ, and 33.9°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 8.4°2θ, 14.0°2θ, 15.6°2θ, 15.9°2θ, 16.8°2θ, 18.4°2θ, 18.9°2θ, 19.4°2θ, 20.8°2θ, 21.4°2θ, 21.5°2θ, 22.3°2θ, 25.0°2θ, 25.2°2θ, and 33.9°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 8.4°2θ, 14.0°2θ, 15.6°2θ, 15.9°2θ, 16.8°2θ, 18.4°2θ, 18.9°2θ, 19.4°2θ, 20.8°2θ, 21.4°2θ, 21.5°2θ, 22.3°2θ, 25.0°2θ, 25.2°2θ, and 33.9°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 8.4°2θ, 14.0°2θ, 15.6°2θ, 15.9°2θ, 16.8°2θ, 18.4°2θ, 18.9°2θ, 19.4°2θ, 20.8°2θ, 21.4°2θ, 21.5°2θ, 22.3°2θ, 25.0°2θ, 25.2°2θ, 28.1°2θ, and 33.9°2θ (±0.2°2θ; 0.1°2θ; or ±0.0°2θ; Cu Kα1 radiation). In some embodiments, the compound 1 monofumarate salt is crystalline polymorphic Form A characterized by XRPD signals at 8.4°2θ, 14.0°2θ, 15.6°2θ, 15.9°2θ, 16.8°2θ, 18.4°2θ, 18.9°2θ, 19.4°2θ, 20.8°2θ, 21.4°2θ, 21.5°2θ, 22.3°2θ, 25.0°2θ, 25.2°2θ, 28.1°2θ, and 33.9°2θ (±0.2°2θ; ±0.1°2θ; or ±0.0°2θ; Cu Kα1 radiation).

In some embodiments, crystalline polymorphic Form A is characterized by one, two, three, four, five, six, seven, eight, nine, ten, eleven, twelve, thirteen, fourteen, fifteen, or sixteen XRPD signals selected from those set forth in Table 25.

TABLE 25

Compound 1 monofumarate salt Form A(±0.2 °2θ; ±0.1 °2θ; or ±0.0 °2θ; Cu Kα1 radiation)

| Signal number | 2-θ (°) | d Value | Net Intensity (counts) | Gross Intensity (counts) | Rel. Intensity (%) |
|---|---|---|---|---|---|
| Signal #1 | 8.4 | 10.57 | 1460.1 | 1522.2 | 27.4 |
| Signal #2 | 14.0 | 6.33 | 1608.8 | 1685.0 | 30.2 |
| Signal #3 | 15.6 | 5.69 | 912.4 | 1008.0 | 17.1 |
| Signal #4 | 15.9 | 5.58 | 1920.6 | 2022.6 | 36.0 |
| Signal #5 | 16.8 | 5.29 | 5017.4 | 5129.2 | 94.1 |
| Signal #6 | 18.4 | 4.82 | 567.0 | 692.0 | 10.6 |
| Signal #7 | 18.9 | 4.69 | 611.8 | 746.2 | 11.5 |

TABLE 25-continued

Compound 1 monofumarate salt Form A(±0.2 °2θ; ±0.1 °2θ; or ±0.0 °2θ; Cu Kα1 radiation)

| Signal number | 2-θ (°) | d Value | Net Intensity (counts) | Gross Intensity (counts) | Rel. Intensity (%) |
|---|---|---|---|---|---|
| Signal #8 | 19.4 | 4.58 | 2522.6 | 2662.6 | 47.3 |
| Signal #9 | 20.8 | 4.26 | 613.4 | 757.1 | 11.5 |
| Signal #10 | 21.4 | 4.16 | 1394.0 | 1542.5 | 26.1 |
| Signal #12 | 21.5 | 4.14 | 1279.1 | 1428.1 | 24.0 |
| Signal #11 | 22.3 | 3.98 | 1796.9 | 1943.3 | 33.7 |
| Signal #13 | 25.0 | 3.55 | 558.1 | 692.4 | 10.5 |
| Signal #14 | 25.2 | 3.52 | 5332.2 | 5466.0 | 100.0 |
| Signal #15 | 28.1 | 3.17 | 547.3 | 677.0 | 10.3 |
| Signal #16 | 33.9 | 2.64 | 1489.4 | 1602.8 | 27.9 |

In some embodiments, the compound 1 monofumarate salt is crystalline polymorphic Form A characterized by an XRPD signal at 22.4°2θ (±0.2°2θ; ±0.1°2θ; or 0.0°2θ; Cu Kα1 radiation).

In some embodiments, the compound 1 monofumarate salt is crystalline polymorphic Form A characterized by XRPD signals at 19.4°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 15.7°2θ, 19.4°2θ, and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 15.7°2θ, 19.4°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 15.7°2θ, 16.0°2θ, 19.4°2θ, and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 15.7°2θ, 16.0°2θ, 19.4°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 15.7°2θ, 16.0°2θ, 19.4°2θ, 21.6°2θ, and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 15.7°2θ, 16.0°2θ, 19.4°2θ, 21.6°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 15.7°2θ, 16.0°2θ, 19.4°2θ, 21.4°2θ, 21.6°2θ, and 22.4°2θ (±0.2°2θ; ±0.1°2θ, or ±0.0°2θ; Cu Kα1 radiation). In some embodiments, the compound 1 monofumarate salt is crystalline polymorphic Form A characterized by XRPD signals at 15.7°2θ, 16.0°2θ, 19.4°2θ, 21.4°2θ, 21.6°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.1°2θ, 15.7°2θ, 16.0°2θ, 19.4°2θ, 21.4°2θ, 21.6°2θ, and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.1°2θ, 15.7°2θ, 16.0°2θ, 19.4°2θ, 21.4°2θ, 21.6°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.1°2θ, 15.7°2θ, 16.0°2θ, 19.4°2θ, 21.0°2θ, 21.4°2θ, 21.6°2θ, and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.1°2θ, 15.7°2θ, 16.0°2θ, 19.4°2θ, 21.0°2θ, 21.4°2θ, 21.6°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.5°2θ, 14.1°2θ, 15.7°2θ, 16.0°2θ, 19.4°2θ, 21.0°2θ, 21.4°2θ, 21.6°2θ, and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.5°2θ, 14.1°2θ, 15.7°2θ, 16.0°2θ, 19.4°2θ, 21.0°2θ, 21.4°2θ, 21.6°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.5°2θ, 14.1°2θ, 15.7°2θ, 16.0°2θ, 19.0°2θ, 19.4°2θ, 21.0°2θ, 21.4°2θ, 21.6°2θ, and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.5°2θ, 14.1°2θ, 15.7°2θ, 16.0°2θ, 19.0°2θ, 19.4°2θ, 21.0°2θ, 21.4°2θ, 21.6°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.5°2θ, 14.1°2θ, 15.7°2θ, 16.0°2θ, 19.0°2θ, 19.4°2θ, 21.0°2θ, 21.4°2θ, 21.6°2θ, 22.4°2θ, and 28.2°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.5°2θ, 14.1°2θ, 15.7°2θ, 16.0°2θ, 19.0°2θ, 19.4°2θ, 21.0°2θ, 21.4°2θ, 21.6°2θ, 22.4°2θ, and 28.2°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.5°2θ, 14.1°2θ, 15.7°2θ, 16.0°2θ, 19.0°2θ, 19.4°2θ, 21.0°2θ, 21.4°2θ, 21.6°2θ, 22.4°2θ, 25.1°2θ, and 28.2°2θ (±0.2 20; 0.1°2θ; or ±0.0°2θ; Cu Kα1 radiation). In some embodiments, the compound 1 monofumarate salt is crystalline polymorphic Form A characterized by XRPD signals at 13.5°2θ, 14.1°2θ, 15.7°2θ, 16.0°2θ, 19.0°2θ, 19.4°2θ, 21.0°2θ, 21.4°2θ, 21.6°2θ, 22.4°2θ, 25.1°2θ, and 28.2°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.5°2θ, 14.1°2θ, 15.7°2θ, 16.0°2θ, 18.5°2θ, 19.0°2θ, 19.4°2θ, 21.0°2θ, 21.4°2θ, 21.6°2θ, 22.4°2θ, 25.1°2θ, and 28.2°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.5°2θ, 14.1°2θ, 15.7°2θ, 16.0°2θ, 18.5°2θ, 19.0°2θ, 19.4°2θ, 21.0°2θ, 21.4°2θ, 21.6°2θ, 22.4°2θ, 25.1°2θ, and 28.2°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.5°2θ, 14.1°2θ, 15.7°2θ, 16.0°2θ, 18.5°2θ, 19.0°2θ, 19.4°2θ, 21.0°2θ, 21.4°2θ, 21.6°2θ, 22.4°2θ, 25.1°2θ, 25.2°2θ, and 28.2°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.5°2θ, 14.1°2θ, 15.7°2θ, 16.0°2θ, 18.5°2θ, 19.0°2θ, 19.4°2θ, 21.0°2θ, 21.4°2θ, 21.6°2θ, 22.4°2θ, 25.1°2θ, 25.2°2θ, and 28.2°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.5°2θ, 14.1°2θ, 15.7°2θ, 16.0°2θ, 18.5°2θ, 19.0°2θ, 19.4°2θ, 21.0°2θ, 21.4°2θ, 21.6°2θ, 22.4°2θ, 23.2°2θ, 25.1°2θ, 25.2°2θ, and 28.2°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.5°2θ, 14.1°2θ, 15.7°2θ, 16.0°2θ, 18.5°2θ, 19.0°2θ, 19.4°2θ, 21.0°2θ, 21.4°2θ, 21.6°2θ, 22.4°2θ, 23.2°2θ, 25.1°2θ, 25.2°2θ, and 28.2°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.5°2θ, 14.1°2θ, 15.7°2θ, 16.0°2θ, 18.5°2θ, 19.0°2θ, 19.4°2θ, 21.0°2θ, 21.4°2θ, 21.6°2θ, 22.4°2θ, 23.2°2θ, 25.1°2θ, 25.2°2θ, 28.2°2θ, and 29.2°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.5°2θ, 14.1°2θ, 15.7°2θ, 16.0°2θ, 18.5°2θ, 19.0°2θ, 19.4°2θ, 21.0°2θ, 21.4°2θ, 21.6°2θ, 22.4°2θ, 23.2°2θ, 25.1°2θ, 25.2°2θ, 28.2°2θ, and 29.2°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.2°2θ, 13.5°2θ, 14.1°2θ, 15.7°2θ, 16.0°2θ, 18.5°2θ, 19.0°2θ, 19.4°2θ, 21.0°2θ, 21.4°2θ, 21.6°2θ, 22.4°2θ, 23.2°2θ, 25.1°2θ, 25.2°2θ, 28.2°2θ, and 29.2°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.2°2θ, 13.5°2θ, 14.1°2θ, 15.7°2θ, 16.0°2θ, 18.5°2θ, 19.0°2θ, 19.4°2θ, 21.0°2θ, 21.4°2θ, 21.6°2θ, 22.4°2θ, 23.2°2θ, 25.1°2θ, 25.2°2θ, 28.2°2θ, and 29.2°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.2°2θ, 13.5°2θ, 14.1°2θ, 15.7°2θ, 16.0°2θ, 18.5°2θ, 19.0°2θ, 19.4°2θ, 21.0°2θ, 21.4°2θ, 21.6°2θ, 22.4°2θ, 23.2°2θ, 24.5°2θ, 25.1°2θ, 25.2°2θ, 28.2°2θ, and 29.2°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.2°2θ, 13.5°2θ, 14.1°2θ, 15.7°2θ, 16.0°2θ, 18.5°2θ, 19.0°2θ, 19.4°2θ, 21.0°2θ, 21.4°2θ, 21.6°2θ, 22.4°2θ, 23.2°2θ, 24.5°2θ, 25.1°2θ, 25.2°2θ, 28.2°2θ, and 29.2°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.2°2θ, 13.5°2θ, 14.1°2θ, 15.7°2θ, 16.0°2θ, 18.5°2θ, 19.0°2θ, 19.4°2θ, 21.0°2θ, 21.4°2θ, 21.6°2θ, 22.4°2θ, 23.2°2θ, 24.5°2θ, 25.1°2θ, 25.2°2θ, 28.2°2θ, 29.2°2θ, and 34.3°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.2°2θ, 13.5°2θ, 14.1°2θ, 15.7°2θ, 16.0°2θ, 18.5°2θ, 19.0°2θ, 19.4°2θ, 21.0°2θ, 21.4°2θ, 21.6°2θ, 22.4°2θ, 23.2°2θ, 24.5°2θ, 25.1°2θ, 25.2°2θ, 28.2°2θ, 29.2°2θ, and 34.3°2θ (±0.2°2θ; ±0.1°2θ; or ±0.0°2θ; Cu Kα1 radiation).

In some embodiments, crystalline polymorphic Form A is characterized by one, two, three, four, five, six, seven, eight, nine, ten, eleven, twelve, thirteen, fourteen, fifteen, sixteen, seventeen, eighteen, or nineteen XRPD signals selected from those set forth in Table 26.

TABLE 26

Compound 1 monofumarate salt Form A(±0.2 °2θ; ±0.1 °2θ; or ±0.0 °2θ; Cu Kα1 radiation)

| Signal number | 2-θ (°) | d Value | Net Intensity (counts) | Gross Intensity (counts) | Rel. Intensity (%) |
|---|---|---|---|---|---|
| Signal #1 | 10.2 | 8.71 | 450.0 | 545.2 | 11.0 |
| Signal #2 | 13.5 | 6.57 | 969.9 | 1105.1 | 23.7 |
| Signal #3 | 14.1 | 6.28 | 1248.5 | 1390.8 | 30.5 |
| Signal #4 | 15.7 | 5.65 | 2079.2 | 2250.6 | 50.8 |
| Signal #5 | 16.0 | 5.55 | 2025.4 | 2204.5 | 49.5 |
| Signal #6 | 18.5 | 4.79 | 571.9 | 808.1 | 14.0 |
| Signal #7 | 19.0 | 4.67 | 892.9 | 1144.8 | 21.8 |
| Signal #8 | 19.4 | 4.56 | 2194.6 | 2457.6 | 53.6 |
| Signal #9 | 21.0 | 4.23 | 1051.0 | 1335.2 | 25.7 |
| Signal #10 | 21.4 | 4.15 | 1280.5 | 1568.9 | 31.3 |
| Signal #12 | 21.6 | 4.12 | 1486.4 | 1775.6 | 36.3 |
| Signal #11 | 22.4 | 3.96 | 4095.3 | 4382.0 | 100.0 |
| Signal #13 | 23.2 | 3.82 | 470.1 | 744.5 | 11.5 |
| Signal #14 | 24.5 | 3.63 | 448.6 | 701.5 | 11.0 |
| Signal #15 | 25.1 | 3.54 | 648.2 | 889.9 | 15.8 |
| Signal #16 | 25.2 | 3.53 | 481.3 | 721.5 | 11.8 |
| Signal #17 | 28.2 | 3.16 | 841.2 | 1055.2 | 20.5 |
| Signal #18 | 29.2 | 3.06 | 453.3 | 658.7 | 11.1 |
| Signal #19 | 34.3 | 2.62 | 421.1 | 580.4 | 10.3 |

In some embodiments, the compound 1 monofumarate salt is crystalline polymorphic Form A characterized by an XRPD signal at 22.3°2θ (±0.2°2θ; ±0.1°2θ; or ±0.0°2θ; Cu Kα1 radiation).

In some embodiments, the compound 1 monofumarate salt is crystalline polymorphic Form A characterized by XRPD signals at 15.9°2θ, and 22.3°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 15.9°2θ, 19.4°2θ, and 22.3°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 15.9°2θ, 19.4°2θ, and 22.3°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 15.9°2θ, 19.4°2θ, 22.3°2θ, and 28.1°2θ (±0.2°2θ; ±0.1°2θ; or ±0.0°2θ; Cu Kα1 radiation).

In some embodiments, the compound 1 monofumarate salt is crystalline polymorphic Form A characterized by XRPD signals at 15.9°2θ, 19.4°2θ, 22.3°2θ, and 28.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.0°2θ, 15.9°2θ, 19.4°2θ, 22.3°2θ, and 28.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.0°2θ, 15.9°2θ, 19.4°2θ, 22.3°2θ, and 28.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.0°2θ, 15.9°2θ, 19.4°2θ, 21.5°2θ, 22.3°2θ, and 28.1°2θ (±0.2°2θ; ±0.1°2θ, or ±0.0°2θ; Cu Kα1 radiation). In some embodiments, the compound 1 monofumarate salt is crystalline polymorphic Form A characterized by XRPD signals at 14.0°2θ, 15.9°2θ, 19.4°2θ, 21.5°2θ, 22.3°2θ, and 28.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.0°2θ, 15.9°2θ, 18.9°2θ, 19.4°2θ, 21.5°2θ, 22.3°2θ, and 28.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.0°2θ, 15.9°2θ, 18.9°2θ, 19.4°2θ, 21.5°2θ, 22.3°2θ, and 28.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.0°2θ, 15.6°2θ, 15.9°2θ, 18.9°2θ, 19.4°2θ, 21.5°2θ, 22.3°2θ, and 28.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.0°2θ, 15.6°2θ, 15.9°2θ, 18.9°2θ, 19.4°2θ, 21.5°2θ, 22.3°2θ, and 28.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.0°2θ, 15.6°2θ, 15.9°2θ, 18.9°2θ, 19.4°2θ, 21.5°2θ, 22.3°2θ, 28.1°2θ, and 29.0°2θ (±0.2° 2θ; ±0.1°2θ; or ±0.0°2θ; Cu Kα1 radiation). In some embodiments, the compound 1 monofumarate salt is crystalline polymorphic Form A characterized by XRPD signals at 14.0°2θ, 15.6°2θ, 15.9°2θ, 18.9°2θ, 19.4°2θ, 21.5°2θ, 22.3°2θ, 28.1°2θ, and 29.0°2θ, (±0.2°2θ; ±0.1° 2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.0°2θ, 15.6°2θ, 15.9°2θ, 18.9°2θ, 19.4°2θ, 20.8°2θ, 21.5°2θ, 22.3°2θ, 28.1°2θ, and 29.0°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.0°2θ, 15.6°2θ, 15.9°2θ, 18.9°2θ, 19.4°2θ, 20.8°2θ, 21.5°2θ, 22.3°2θ, 28.1°2θ, and 29.0°2θ, (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.0°2θ, 15.6°2θ, 15.9°2θ, 18.4°2θ, 18.9°2θ, 19.4°2θ, 20.8°2θ, 21.5°2θ, 22.3°2θ, 28.1°2θ, and 29.0°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.0°2θ, 15.6°2θ, 15.9°2θ, 18.4°2θ, 18.9°2θ, 19.4°2θ, 20.8°2θ, 21.5°2θ, 22.3°2θ, 28.1°2θ, and 29.0°2θ, (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.4°2θ, 18.9°2θ, 19.4°2θ, 20.8°2θ, 21.5°2θ, 22.3°2θ, 28.1°2θ, and 29.0°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.4°2θ, 18.9°2θ, 19.4°2θ, 20.8°2θ, 21.5°2θ, 22.3°2θ, 28.1°2θ, and 29.0°2θ, (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.4°2θ, 18.9°2θ, 19.4°2θ, 20.8°2θ, 21.3°2θ, 21.5°2θ, 22.3°2θ, 28.1°2θ, and 29.0°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.4°2θ, 18.9°2θ, 19.4°2θ, 20.8°2θ, 21.3°2θ, 21.5°2θ, 22.3°2θ, 28.1°2θ, and 29.0°2θ, (±0.2°2θ; ±0.1°2θ; or ±0.0° 2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.4°2θ, 18.9°2θ, 19.4°2θ, 20.8°2θ, 21.3°2θ, 21.5°2θ, 22.3°2θ, 26.9°2θ, 28.1°2θ, and 29.0°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.4°2θ, 18.9°2θ, 19.4°2θ, 20.8°2θ, 21.3°2θ, 21.5°2θ, 22.3°2θ, 26.9°2θ, 28.1°2θ, and 29.0°2θ, (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.4°2θ, 18.9°2θ, 19.2°2θ, 19.4°2θ, 20.8°2θ, 21.3°2θ, 21.5°2θ, 22.3°2θ, 26.9°2θ, 28.1°2θ, and 29.0°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.4°2θ, 18.9°2θ, 19.2°2θ, 19.4°2θ, 20.8°2θ, 21.3°2θ, 21.5°2θ, 22.3°2θ, 26.9°2θ, 28.1°2θ, and 29.0°2θ, (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.4°2θ, 18.9°2θ, 19.2°2θ, 19.4°2θ, 20.8°2θ, 21.3°2θ, 21.5°2θ, 22.3°2θ, 24.4°2θ, 26.9°2θ, 28.1°2θ, and 29.0°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.4°2θ, 18.9°2θ, 19.2°2θ, 19.4°2θ, 20.8°2θ, 21.3°2θ, 21.5°2θ, 22.3°2θ, 24.4°2θ, 26.9°2θ, 28.1°2θ, and 29.0°2θ, (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.4°2θ, 18.9°2θ, 19.2°2θ, 19.4°2θ, 20.8°2θ, 21.3°2θ, 21.5°2θ, 22.3°2θ, 24.4°2θ, 25.0°2θ, 26.9°2θ, 28.1°2θ, and 29.0°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.4°2θ, 18.9°2θ, 19.2°2θ, 19.4°2θ, 20.8°2θ, 21.3°2θ, 21.5°2θ, 22.3°2θ, 24.4°2θ, 25.0°2θ, 26.9°2θ, 28.1°2θ, and 29.0°2θ, (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.1°2θ, 13.4°2θ, 14.0°2θ, 15.6°2θ, 15.9°2θ, 18.4°2θ, 18.9°2θ, 19.2°2θ, 19.4°2θ, 20.8°2θ, 21.3°2θ, 21.5°2θ, 22.3°2θ, 24.4°2θ, 25.0°2θ, 26.9°2θ, 28.1°2θ, and 29.0°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.1°2θ, 13.4°2θ, 14.0°2θ, 15.6°2θ, 15.9°2θ, 18.4°2θ, 18.9°2θ, 19.2°2θ, 19.4°2θ, 20.8°2θ, 21.3°2θ, 21.5°2θ, 22.3°2θ, 24.4°2θ, 25.0°2θ, 26.9°2θ, 28.1°2θ, and 29.0°2θ, (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.1°2θ, 13.4°2θ, 14.0°2θ, 15.6°2θ, 15.9°2θ, 18.4°2θ, 18.9°2θ, 19.2°2θ, 19.4°2θ, 20.8°2θ, 21.3°2θ, 21.5°2θ, 22.3°2θ, 24.4°2θ, 25.0°2θ, 26.9°2θ, 28.1°2θ, 29.0°2θ, and 36.4°2θ, (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.1°2θ, 13.4°2θ, 14.0°2θ, 15.6°2θ, 15.9°2θ, 18.4°2θ, 18.9°2θ, 19.2°2θ, 19.4°2θ, 20.8°2θ, 21.3°2θ, 21.5°2θ, 22.3°2θ, 24.4°2θ, 25.0°2θ, 26.9°2θ, 28.1°2θ, 29.0°2θ, and 36.4°2θ, (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.1°2θ, 13.4°2θ, 14.0°2θ, 15.6°2θ, 15.9°2θ, 18.4°2θ, 18.9°2θ, 19.2°2θ, 19.4°2θ, 20.8°2θ, 21.3°2θ, 21.5°2θ, 22.3°2θ, 23.2°2θ, 24.4°2θ, 25.0°2θ, 26.9°2θ, 28.1°2θ, 29.0°2θ, and 36.4°2θ, (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.1°2θ, 13.4°2θ, 14.0°2θ, 15.6°2θ, 15.9°2θ, 18.4°2θ, 18.9°2θ, 19.2°2θ, 19.4°2θ, 20.8°2θ, 21.3°2θ, 21.5°2θ, 22.3°2θ, 23.2°2θ, 24.4°2θ, 25.0°2θ, 26.9°2θ, 28.1°2θ, 29.0°2θ, and 36.4°2θ, (±0.2°2θ; ±0.1°2θ; or ±0.0°2θ; Cu Kα1 radiation).

In some embodiments, crystalline polymorphic Form A is characterized by one, two, three, four, five, six, seven, eight, nine, ten, eleven, twelve, thirteen, fourteen, fifteen, sixteen, seventeen, eighteen, nineteen, or twenty XRPD signals selected from those set forth in Table 27.

TABLE 27

Compound 1 monofumarate salt Form A(±0.2 °2θ; ±0.1 °2θ; or ±0.0 °2θ; Cu Kα1 radiation)

| Signal number | 2-θ (°) | d Value | Net Intensity (counts) | Gross Intensity (counts) | Rel. Intensity (%) |
|---|---|---|---|---|---|
| Signal #1 | 10.1 | 8.78 | 398.9 | 462.8 | 12.3 |
| Signal #2 | 13.4 | 6.62 | 699.1 | 778.7 | 21.5 |
| Signal #3 | 14.0 | 6.32 | 920.9 | 1005.3 | 28.4 |
| Signal #4 | 15.6 | 5.69 | 872.3 | 972.4 | 26.9 |
| Signal #5 | 15.9 | 5.58 | 1387.2 | 1492.2 | 42.7 |
| Signal #6 | 18.4 | 4.82 | 700.2 | 837.4 | 21.6 |
| Signal #7 | 18.9 | 4.70 | 900.4 | 1050.3 | 27.7 |
| Signal #8 | 19.2 | 4.63 | 454.3 | 610.2 | 14.0 |
| Signal #9 | 19.4 | 4.57 | 1213.6 | 1374.1 | 37.4 |
| Signal #10 | 20.8 | 4.26 | 746.6 | 923.0 | 23.0 |
| Signal #12 | 21.3 | 4.16 | 676.0 | 855.8 | 20.8 |
| Signal #11 | 21.5 | 4.13 | 916.0 | 1096.4 | 28.2 |
| Signal #13 | 22.3 | 3.98 | 3247.0 | 3425.1 | 100.0 |
| Signal #14 | 23.2 | 3.84 | 355.8 | 523.4 | 11.0 |
| Signal #15 | 24.4 | 3.65 | 425.8 | 578.9 | 13.1 |
| Signal #16 | 25.0 | 3.56 | 404.8 | 551.8 | 12.5 |
| Signal #17 | 26.9 | 3.32 | 661.5 | 804.7 | 20.4 |
| Signal #18 | 28.1 | 3.17 | 1097.0 | 1239.8 | 33.8 |
| Signal #19 | 29.0 | 3.07 | 782.5 | 916.0 | 24.1 |
| Signal #20 | 36.4 | 2.46 | 367.7 | 478.5 | 11.3 |

In some embodiments, the compound 1 monofumarate salt is crystalline polymorphic Form A characterized an XRPD signal at 22.3°2θ (±0.2°2θ; ±0.1°2θ; or ±0.0°2θ; Cu Kα1 radiation).

In some embodiments, the compound 1 monofumarate salt is crystalline polymorphic Form A characterized by XRPD signals at 15.9°2θ and 22.3°2θ (±0.2°2θ; ±0.1°2θ, or ±0.0°2θ; Cu Kα1 radiation).

In some embodiments, the compound 1 monofumarate salt is crystalline polymorphic Form A characterized by two or more, or three or more XRPD signals selected from the group consisting of 15.9°2θ, 19.4°2θ, and 22.3°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 15.9°2θ, 19.4°2θ, and 22.3°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.0°2θ, 15.9°2θ, 19.4°2θ, and 22.3°2θ (±0.2°2θ; ±0.1°2θ; or ±0.0°2θ; Cu Kα1 radiation).

In some embodiments, the compound 1 monofumarate salt is crystalline polymorphic Form A characterized by XRPD signals at 14.0°2θ, 15.9°2θ, 19.4°2θ, and 22.3°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.0°2θ, 15.9°2θ, 19.4°2θ, 21.3°2θ, and 22.3°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.0°2θ, 15.9°2θ, 19.4°2θ, 21.3°2θ, and 22.3°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.0°2θ, 15.9°2θ, 19.4°2θ, 21.3°2θ, 21.5°2θ, and 22.3°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.0°2θ, 15.9°2θ, 19.4°2θ, 21.3°2θ, 21.5°2θ, and 22.3°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 19.4°2θ, 21.3°2θ, 21.5°2θ, and 22.3°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 19.4°2θ, 21.3°2θ, 21.5°2θ, and 22.3°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 19.4°2θ, 20.9°2θ, 21.3°2θ, 21.5°2θ, and 22.3°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 19.4°2θ, 20.9°2θ, 21.3°2θ, 21.5°2θ, and 22.3°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 18.9°2θ, 19.4°2θ, 20.9°2θ, 21.3°2θ, 21.5°2θ, and 22.3°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 18.9°2θ, 19.4°2θ, 20.9°2θ, 21.3°2θ, 21.5°2θ, and 22.3°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.9°2θ, 18.9°2θ, 19.4°2θ, 20.9°2θ, 21.3°2θ, 21.5°2θ, 22.3°2θ, and 28.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.9°2θ, 18.9°2θ, 19.4°2θ, 20.9°2θ, 21.3°2θ, 21.5°2θ, 22.3°2θ, and 28.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.9°2θ, 19.4°2θ, 20.9°2θ, 21.3°2θ, 21.5°2θ, 22.3°2θ, and 28.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.9°2θ, 19.4°2θ, 20.9°2θ, 21.3°2θ, 21.5°2θ, 22.3°2θ, and 28.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.9°2θ, 19.4°2θ, 20.9°2θ, 21.3°2θ, 21.5°2θ, 22.3°2θ, 28.1°2θ, and 29.0°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.9°2θ, 19.4°2θ, 20.9°2θ, 21.3°2θ, 21.5°2θ, 22.3°2θ, 28.1°2θ, and 29.0°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.4°2θ, 18.9°2θ, 19.4°2θ, 20.9°2θ, 21.3°2θ, 21.5°2θ, 22.3°2θ, 28.1°2θ, and 29.0°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.4°2θ, 18.9°2θ, 19.4°2θ, 20.9°2θ, 21.3°2θ, 21.5°2θ, 22.3°2θ, 28.1°2θ, and 29.0°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.4°2θ, 18.9°2θ, 19.2°2θ, 19.4°2θ, 20.9°2θ, 21.3°2θ, 21.5°2θ, 22.3°2θ, 28.1°2θ, and 29.0°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.4°2θ, 18.9°2θ, 19.2°2θ, 19.4°2θ, 20.9°2θ, 21.3°2θ, 21.5°2θ, 22.3°2θ, 28.1°2θ, and 29.0°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.4°2θ, 18.9°2θ, 19.2°2θ, 19.4°2θ, 20.9°2θ, 21.3°2θ, 21.5°2θ, 22.3°2θ, 25.0°2θ, 28.1°2θ, and 29.0°2θ (±0.2°2θ; ±0.1°2θ, or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.4°2θ, 18.9°2θ, 19.2°2θ, 19.4°2θ, 20.9°2θ, 21.3°2θ, 21.5°2θ, 22.3°2θ, 25.0°2θ, 28.1°2θ, and 29.0°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.4°2θ, 18.9°2θ, 19.2°2θ, 19.4°2θ, 20.9°2θ, 21.3°2θ, 21.5°2θ, 22.3°2θ, 23.2°2θ, 25.0°2θ, 28.1°2θ, and 29.0°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.4°2θ, 18.9°2θ, 19.2°2θ, 19.4°2θ, 20.9°2θ, 21.3°2θ, 21.5°2θ, 22.3°2θ, 23.2°2θ, 25.0°2θ, 28.1°2θ, and 29.0°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.4°2θ, 18.9°2θ, 19.2°2θ, 19.4°2θ, 20.9°2θ, 21.3°2θ, 21.5°2θ, 22.3°2θ, 23.2°2θ, 24.4°2θ, 25.0°2θ, 28.1°2θ, and 29.0°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.4°2θ, 18.9°2θ, 19.2°2θ, 19.4°2θ, 20.9°2θ, 21.3°2θ, 21.5°2θ, 22.3°2θ, 23.2°2θ, 24.4°2θ, 25.0°2θ, 28.1°2θ, and 29.0°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.1°2θ, 13.4°2θ, 14.0°2θ, 15.6°2θ, 15.9°2θ, 18.4°2θ, 18.9°2θ, 19.2°2θ, 19.4°2θ, 20.9°2θ, 21.3°2θ, 21.5°2θ, 22.3°2θ, 23.2°2θ, 24.4°2θ, 25.0°2θ, 28.1°2θ, and 29.0°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.1°2θ, 13.4°2θ, 14.0°2θ, 15.6°2θ, 15.9°2θ, 18.4°2θ, 18.9°2θ, 19.2°2θ, 19.4°2θ, 20.9°2θ, 21.3°2θ, 21.5°2θ, 22.3°2θ, 23.2°2θ, 24.4°2θ, 25.0°2θ, 28.1°2θ, and 29.0°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.1°2θ, 13.4°2θ, 14.0°2θ, 15.6°2θ, 15.9°2θ, 16.8°2θ, 18.4°2θ, 18.9°2θ, 19.2°2θ, 19.4°2θ, 20.9°2θ, 21.3°2θ, 21.5°2θ, 22.3°2θ, 23.2°2θ, 24.4°2θ, 25.0°2θ, 28.1°2θ, and 29.0°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.1°2θ, 13.4°2θ, 14.0°2θ, 15.6°2θ, 15.9°2θ, 16.8°2θ, 18.4°2θ, 18.9°2θ, 19.2°2θ, 19.4°2θ, 20.9°2θ, 21.3°2θ, 21.5°2θ, 22.3°2θ, 23.2°2θ, 24.4°2θ, 25.0°2θ, 28.1°2θ, and 29.0°2θ (±0.2°2θ; ±0.1°2θ; or ±0.0°2θ; Cu Kα1 radiation).

In some embodiments, crystalline polymorphic Form A is characterized by one, two, three, four, five, six, seven, eight, nine, ten, eleven, twelve, thirteen, fourteen, fifteen, sixteen, seventeen, eighteen, or nineteen XRPD signals selected from those set forth in Table 28.

TABLE 28

Compound 1 monofumarate salt Form A(±0.2 °2θ; ±0.1 °2θ; or ±0.0 °2θ; Cu Kα1 radiation)

| Signal number | 2-θ (°) | d Value | Net Intensity (counts) | Gross Intensity (counts) | Rel. Intensity (%) |
|---|---|---|---|---|---|
| Signal #1 | 10.1 | 8.76 | 526.5 | 604.7 | 11.5 |
| Signal #2 | 13.4 | 6.61 | 1161.5 | 1264.6 | 25.3 |
| Signal #3 | 14.0 | 6.31 | 1440.6 | 1549.3 | 31.3 |
| Signal #4 | 15.6 | 5.68 | 794.9 | 923.3 | 17.3 |
| Signal #5 | 15.9 | 5.57 | 2194.3 | 2328.4 | 47.7 |
| Signal #6 | 16.8 | 5.28 | 460.0 | 602.8 | 10.0 |
| Signal #7 | 18.4 | 4.82 | 665.3 | 834.4 | 14.5 |
| Signal #8 | 18.9 | 4.69 | 900.1 | 1084.5 | 19.6 |
| Signal #9 | 19.2 | 4.63 | 600.9 | 791.7 | 13.1 |
| Signal #10 | 19.4 | 4.57 | 1721.6 | 1918.1 | 37.4 |
| Signal #12 | 20.9 | 4.25 | 1037.9 | 1253.0 | 22.6 |
| Signal #11 | 21.3 | 4.17 | 1321.5 | 1540.5 | 28.7 |
| Signal #13 | 21.5 | 4.12 | 1318.8 | 1538.7 | 28.7 |
| Signal #14 | 22.3 | 3.97 | 4597.3 | 4814.5 | 100.0 |
| Signal #15 | 23.2 | 3.83 | 547.9 | 752.8 | 11.9 |
| Signal #16 | 24.4 | 3.64 | 535.6 | 725.6 | 11.7 |
| Signal #17 | 25.0 | 3.55 | 556.3 | 736.0 | 12.1 |
| Signal #18 | 28.1 | 3.17 | 874.5 | 1045.8 | 19.0 |
| Signal #19 | 29.0 | 3.07 | 714.6 | 878.3 | 15.5 |

In some embodiments, the compound 1 monofumarate salt is crystalline polymorphic Form A characterized by an XRPD at 22.4°2θ (±0.2°2θ; ±0.1°2θ; or ±0.0°2θ; Cu Kα1 radiation).

In some embodiments, the compound 1 monofumarate salt is crystalline polymorphic Form A characterized by XRPD signals at 16.0°2θ and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 16.0°2θ, 19.5°2θ, and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 16.0°2θ, 19.5°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.1°2θ, 16.0°2θ, 19.5°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by XRPD signals at 14.1°2θ, 16.0°2θ, 19.5°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.1°2θ, 16.0°2θ, 19.5°2θ, 21.4°2θ, and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.1°2θ, 16.0°2θ, 19.5°2θ, 21.4°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.1°2θ, 16.0°2θ, 19.5°2θ, 20.9°2θ, 21.4°2θ, and 22.4°2θ (±0.2°2θ; ±0.1°2θ, or ±0.0°2θ; Cu Kα1 radiation). In some embodiments, the compound 1 monofumarate salt is crystalline polymorphic Form A characterized by XRPD signals at 14.1°2θ, 16.0°2θ, 19.5°2θ, 20.9°2θ, 21.4°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.1°2θ, 16.0°2θ, 19.5°2θ, 20.9°2θ, 21.4°2θ, and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.1°2θ, 16.0°2θ, 19.5°2θ, 20.9°2θ, 21.4°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.1°2θ, 16.0°2θ, 19.5°2θ, 20.9°2θ, 21.4°2θ, 21.6°2θ, and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.1°2θ, 16.0°2θ, 19.5°2θ, 20.9°2θ, 21.4°2θ, 21.6°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.1°2θ, 16.0°2θ, 19.5°2θ, 20.9°2θ, 21.4°2θ, 21.6°2θ, 22.4°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.1°2θ, 16.0°2θ, 19.0°2θ, 19.5°2θ, 20.9°2θ, 21.4°2θ, 21.6°2θ, 22.4°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.1°2θ, 16.0°2θ, 19.0°2θ, 19.5°2θ, 20.9°2θ, 21.4°2θ, 21.6°2θ, 22.4°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.1°2θ, 15.6°2θ, 16.0°2θ, 19.0°2θ, 19.5°2θ, 20.9°2θ, 21.4°2θ, 21.6°2θ, 22.4°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.1°2θ, 15.6°2θ, 16.0°2θ, 19.0°2θ, 19.5°2θ, 20.9°2θ, 21.4°2θ, 21.6°2θ, 22.4°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.1°2θ, 15.6°2θ, 16.0°2θ, 19.0°2θ, 19.5°2θ, 20.9°2θ, 21.4°2θ, 21.6°2θ, 22.4°2θ, 28.2°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.1°2θ, 15.6°2θ, 16.0°2θ, 19.0°2θ, 19.5°2θ, 20.9°2θ, 21.4°2θ, 21.6°2θ, 22.4°2θ, 28.2°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.1°2θ, 15.6°2θ, 16.0°2θ, 18.5°2θ, 19.0°2θ, 19.5°2θ, 20.9°2θ, 21.4°2θ, 21.6°2θ, 22.4°2θ, 28.2°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.1°2θ, 15.6°2θ, 16.0°2θ, 18.5°2θ, 19.0°2θ, 19.5°2θ, 20.9°2θ, 21.4°2θ, 21.6°2θ, 22.4°2θ, 28.2°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.1°2θ, 15.6°2θ, 16.0°2θ, 18.5°2θ, 19.0°2θ, 19.2°2θ, 19.5°2θ, 20.9°2θ, 21.4°2θ, 21.6°2θ, 22.4°2θ, 28.2°2θ, and 29.1°2θ (±0.2°2θ; ±0.1°2θ; or 0.0°2θ; Cu Kα1 radiation). In some embodiments, the compound 1 monofumarate salt is crystalline polymorphic Form A characterized by XRPD signals at 13.4°2θ, 14.1°2θ, 15.6°2θ, 16.0°2θ, 18.5°2θ, 19.0°2θ, 19.2°2θ, 19.5°2θ, 20.9°2θ, 21.4°2θ, 21.6°2θ, 22.4°2θ, 28.2°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.2°2θ, 13.4°2θ, 14.1°2θ, 15.6°2θ, 16.0°2θ, 18.5°2θ, 19.0°2θ, 19.2°2θ, 19.5°2θ, 20.9°2θ, 21.4°2θ, 21.6°2θ, 22.4°2θ, 28.2°2θ, and 29.1°2θ (±0.2°2θ;

±0.1°2θ; or ±0.0°2θ; Cu Kα1 radiation). In some embodiments, the compound 1 monofumarate salt is crystalline polymorphic Form A characterized by XRPD signals at 10.2°2θ, 13.4°2θ, 14.1°2θ, 15.6°2θ, 16.0°2θ, 18.5°2θ, 19.0°2θ, 19.2°2θ, 19.5°2θ, 20.9°2θ, 21.4°2θ, 21.6°2θ, 22.4°2θ, 28.2°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.2°2θ, 13.4°2θ, 14.1°2θ, 15.6°2θ, 16.0°2θ, 18.5°2θ, 19.0°2θ, 19.2°2θ, 19.5°2θ, 20.9°2θ, 21.4°2θ, 21.6°2θ, 22.4°2θ, 25.1°2θ, 28.2°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.2°2θ, 13.4°2θ, 14.1°2θ, 15.6°2θ, 16.0°2θ, 18.5°2θ, 19.0°2θ, 19.2°2θ, 19.5°2θ, 20.9°2θ, 21.4°2θ, 21.6°2θ, 22.4°2θ, 25.1°2θ, 28.2°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.2°2θ, 13.4°2θ, 14.1°2θ, 15.6°2θ, 16.0°2θ, 18.5°2θ, 19.0°2θ, 19.2°2θ, 19.5°2θ, 20.9°2θ, 21.4°2θ, 21.6°2θ, 22.4°2θ, 23.2°2θ, 25.1°2θ, 28.2°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 10.2°2θ, 13.4°2θ, 14.1°2θ, 15.6°2θ, 16.0°2θ, 18.5°2θ, 19.0°2θ, 19.2°2θ, 19.5°2θ, 20.9°2θ, 21.4°2θ, 21.6°2θ, 22.4°2θ, 23.2°2θ, 25.1°2θ, 28.2°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 10.2°2θ, 13.4°2θ, 14.1°2θ, 15.6°2θ, 16.0°2θ, 18.5°2θ, 19.0°2θ, 19.2°2θ, 19.5°2θ, 20.9°2θ, 21.4°2θ, 21.6°2θ, 22.4°2θ, 23.2°2θ, 24.5°2θ, 25.1°2θ, 28.2°2θ, and 29.1°2θ (±0.2°2θ; ±0.1° 2θ; or ±0.0°2θ; Cu Kα1 radiation). In some embodiments, the compound 1 monofumarate salt is crystalline polymorphic Form A characterized by XRPD signals at 10.2°2θ, 13.4°2θ, 14.1°2θ, 15.6°2θ, 16.0°2θ, 18.5°2θ, 19.0°2θ, 19.2°2θ, 19.5°2θ, 20.9°2θ, 21.4°2θ, 21.6°2θ, 22.4°2θ, 23.2°2θ, 24.5°2θ, 25.1°2θ, 28.2°2θ, and 29.1°2θ (±0.2°2θ; ±0.1°2θ; or ±0.0°2θ; Cu Kα1 radiation).

In some embodiments, crystalline polymorphic Form A is characterized by one, two, three, four, five, six, seven, eight, nine, ten, eleven, twelve, thirteen, fourteen, fifteen, sixteen, seventeen, or eighteen XRPD signals selected from those set forth in Table 29.

TABLE 29

Compound 1 monofumarate salt Form A(±0.2 °2θ; ±0.1 °2θ; or ±0.0 °2θ; Cu Kα1 radiation)

| Signal number | 2-θ (°) | d Value | Net Intensity (counts) | Gross Intensity (counts) | Rel. Intensity (%) | Signal number |
|---|---|---|---|---|---|---|
| Signal #1 | 10.2 | 8.71 | 871.0 | 969.6 | 0.2 | 16.2 |
| Signal #2 | 13.4 | 6.58 | 1705.1 | 1833.2 | 0.3 | 31.7 |
| Signal #3 | 14.1 | 6.28 | 2032.9 | 2168.8 | 0.4 | 37.8 |
| Signal #4 | 15.6 | 5.66 | 1230.5 | 1385.6 | 0.2 | 22.9 |
| Signal #5 | 16.0 | 5.55 | 3225.3 | 3388.1 | 0.6 | 60.0 |
| Signal #6 | 18.5 | 4.80 | 959.6 | 1166.1 | 0.2 | 17.9 |
| Signal #7 | 19.0 | 4.67 | 1321.2 | 1544.0 | 0.2 | 24.6 |
| Signal #8 | 19.2 | 4.61 | 899.4 | 1129.3 | 0.2 | 16.7 |
| Signal #9 | 19.5 | 4.56 | 2150.2 | 2385.6 | 0.4 | 40.0 |
| Signal #10 | 20.9 | 4.24 | 1754.2 | 2009.8 | 0.3 | 32.6 |
| Signal #11 | 21.4 | 4.15 | 1857.8 | 2116.8 | 0.3 | 34.6 |
| Signal #12 | 21.6 | 4.11 | 1644.1 | 1903.6 | 0.3 | 30.6 |
| Signal #13 | 22.4 | 3.96 | 5375.6 | 5630.5 | 1.0 | 100.0 |
| Signal #14 | 23.2 | 3.83 | 678.4 | 918.8 | 0.1 | 12.6 |
| Signal #15 | 24.5 | 3.63 | 589.2 | 805.1 | 0.1 | 11.0 |
| Signal #16 | 25.1 | 3.55 | 866.1 | 1072.7 | 0.2 | 16.1 |
| Signal #17 | 28.2 | 3.17 | 973.5 | 1172.6 | 0.2 | 18.1 |
| Signal #18 | 29.1 | 3.06 | 1518.6 | 1710.8 | 0.3 | 28.2 |

In some embodiments, the compound 1 monofumarate salt is crystalline polymorphic Form A characterized by an XRPD signal at 22.4°2θ (35 0.2°2θ; ±0.1°2θ, or ±0.0°2θ; Cu Kα1 radiation).

In some embodiments, the compound 1 monofumarate salt is crystalline polymorphic Form A characterized by XRPD signals at 18.9°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 18.9°2θ, 19.1°2θ, and 22.4°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 18.9°2θ, 19.1°2θ, and 22.4°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 18.9°2θ, 19.1°2θ, 22.4°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by XRPD signals at 18.9°2θ, 19.1°2θ, 22.4°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 15.9°2θ, 18.9°2θ, 19.1°2θ, 22.4°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 15.9°2θ, 18.9°2θ, 19.1°2θ, 22.4°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 15.9°2θ, 18.9°2θ, 19.1°2θ, 19.4°2θ, 22.4°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 15.9°2θ, 18.9°2θ, 19.1°2θ, 19.4°2θ, 22.4°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 15.6°2θ, 15.9°2θ, 18.9°2θ, 19.1°2θ, 19.4°2θ, 22.4°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 15.6°2θ, 15.9°2θ, 18.9°2θ, 19.1°2θ, 19.4°2θ, 22.4°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.0°2θ, 15.6°2θ, 15.9°2θ, 18.9°2θ, 19.1°2θ, 19.4°2θ, 22.4°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.0°2θ, 15.6°2θ, 15.9°2θ, 18.9°2θ, 19.1°2θ, 19.4°2θ, 22.4°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.0°2θ, 15.6°2θ, 15.9°2θ, 18.9°2θ, 19.1°2θ, 19.4°2θ, 21.5°2θ, 22.4°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.0°2θ, 15.6°2θ, 15.9°2θ, 18.9°2θ, 19.1°2θ, 19.4°2θ, 21.5°2θ, 22.4°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 14.0°2θ, 15.6°2θ, 15.9°2θ, 18.9°2θ, 19.1°2θ, 19.4°2θ, 21.3°2θ, 21.5°2θ, 22.4°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.0°2θ, 15.6°2θ, 15.9°2θ, 18.9°2θ, 19.1°2θ, 19.4°2θ, 21.3°2θ, 21.5°2θ, 22.4°2θ, and 29.1°2θ (±0.2°2θ; ±0.1°2θ; or ±0.0°2θ. Cu Kα1 radiation).

In some embodiments, the compound 1 monofumarate salt is crystalline polymorphic Form A characterized by two or more, or three or more XRPD signals selected from the group consisting of 14.0°2θ, 15.6°2θ, 15.9°2θ, 18.9°2θ, 19.1°2θ, 19.4°2θ, 21.3°2θ, 21.5°2θ, 22.4°2θ, 22.9°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 14.0°2θ, 15.6°2θ, 15.9°2θ, 18.9°2θ, 19.1°2θ, 19.4°2θ, 21.3°2θ, 21.5°2θ, 22.4°2θ, 22.9°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.9°2θ, 19.1°2θ, 19.4°2θ, 21.3°2θ, 21.5°2θ, 22.4°2θ, 22.9°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.9°2θ, 19.1°2θ, 19.4°2θ, 21.3°2θ, 21.5°2θ, 22.4°2θ, 22.9°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.4°2θ, 18.9°2θ, 19.1°2θ, 19.4°2θ, 21.3°2θ, 21.5°2θ, 22.4°2θ, 22.9°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.4°2θ, 18.9°2θ, 19.1°2θ, 19.4°2θ, 21.3°2θ, 21.5°2θ, 22.4°2θ, 22.9°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.4°2θ, 18.9°2θ, 19.1°2θ, 19.4°2θ, 20.9°2θ, 21.3°2θ, 21.5°2θ, 22.4°2θ, 22.9°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.4°2θ, 18.9°2θ, 19.1°2θ, 19.4°2θ, 20.9°2θ, 21.3°2θ, 21.5°2θ, 22.4°2θ, 22.9°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.4°2θ, 18.9°2θ, 19.1°2θ, 19.4°2θ, 20.9°2θ, 21.3°2θ, 21.5°2θ, 22.4°2θ, 22.9°2θ, 28.1°2θ, and 29.1°2θ (±0.2°2θ; ±0.1°2θ; or ±0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.4°2θ, 18.9°2θ, 19.1°2θ, 19.4°2θ, 20.9°2θ, 21.3°2θ, 21.5°2θ, 22.4°2θ, 22.9°2θ, 28.1°2θ, and 29.1°2θ (±0.2°2θ; ±0.1°2θ; or ±0.0°2θ; Cu Kα1 radiation).

In some embodiments, the compound 1 monofumarate salt is crystalline polymorphic Form A characterized by two or more, or three or more XRPD signals selected from the group consisting of 13.4°2θ, 14.0°2θ, 15.6°2θ, 15.9°2θ, 18.4°2θ, 18.9°2θ, 19.1°2θ, 19.4°2θ, 20.9°2θ, 21.3°2θ, 21.5°2θ, 22.4°2θ, 22.9°2θ, 25.0°2θ, 28.1°2θ, and 29.1°2θ (±0.2°2θ; ±0.1°2θ; or 0.0°2θ; Cu Kα1 radiation). In some embodiments, the compound 1 monofumarate salt is crystalline polymorphic Form A characterized by XRPD signals at 13.4°2θ, 14.0°2θ, 15.6°2θ, 15.9°2θ, 18.4°2θ, 18.9°2θ, 19.1°2θ, 19.4°2θ, 20.9°2θ, 21.3°2θ, 21.5°2θ, 22.4°2θ, 22.9°2θ, 25.0°2θ, 28.1°2θ, and 29.1°2θ (±0.2°2θ; ±0.1°2θ; or ±0.0°2θ; Cu Kα1 radiation).

In some embodiments, crystalline polymorphic Form A is characterized by one, two, three, four, five, six, seven, eight, nine, ten, eleven, twelve, thirteen, fourteen, fifteen, or sixteen XRPD signals selected from those set forth in Table 30.

TABLE 30

Compound 1 monofumarate salt Form A(±0.2 °2θ; ±0.1 °2θ; or ±0.0 °2θ; Cu Kα1 radiation)

| Signal number | 2-θ (°) | d Value | Net Intensity (counts) | Gross Intensity (counts) | Rel. Intensity (%) |
|---|---|---|---|---|---|
| Signal #1 | 13.4 | 6.61 | 833.0 | 926.2 | 14.5 |
| Signal #2 | 14.0 | 6.31 | 1165.8 | 1261.8 | 20.3 |
| Signal #3 | 15.6 | 5.69 | 1271.3 | 1382.6 | 22.1 |
| Signal #4 | 15.9 | 5.58 | 1547.7 | 1665.7 | 27.0 |
| Signal #5 | 18.4 | 4.82 | 824.3 | 993.7 | 14.4 |
| Signal #6 | 18.9 | 4.68 | 2414.0 | 2598.1 | 42.0 |
| Signal #7 | 19.1 | 4.65 | 2102.6 | 2289.6 | 36.6 |
| Signal #8 | 19.4 | 4.57 | 1374.1 | 1566.8 | 23.9 |
| Signal #9 | 20.9 | 4.25 | 823.6 | 1031.8 | 14.3 |
| Signal #10 | 21.3 | 4.16 | 856.1 | 1070.4 | 14.9 |
| Signal #11 | 21.5 | 4.13 | 1119.8 | 1335.4 | 19.5 |
| Signal #12 | 22.4 | 3.97 | 5742.6 | 5958.4 | 100.0 |
| Signal #13 | 22.9 | 3.87 | 848.2 | 1057.7 | 14.8 |
| Signal #14 | 25.0 | 3.55 | 586.0 | 769.3 | 10.2 |
| Signal #15 | 28.1 | 3.17 | 674.3 | 847.8 | 11.7 |
| Signal #16 | 29.1 | 3.07 | 1761.5 | 1926.7 | 30.7 |

Calculated XRPD Profile of Crystalline Compound 1 Monofumarate Form a

In some embodiments, the crystalline compound 1 monofumarate Form A polymorph is characterized by a set of XRPD signals that are calculated. In some embodiments, the calculated set of XRPD signals is described in Table 115. A calculated XRPD profile for crystalline compound 1 monofumarate Form A is provided (FIG. 355) and is overlaid with an experimentally observed XRPD profile for crystalline compound 1 monofumarate Form A (FIG. 356).

TABLE 115

Calculated Crystalline Compound 1 Monofumarate XRPD signals (±0.2 °2θ; ±0.1 °2θ; or ±0.0 °2θ; Cu Kα1 radiation)

| Signal number | 2-θ (°) | d Value | Net Intensity (counts) | Gross Intensity (counts) | Rel. Intensity (%) |
|---|---|---|---|---|---|
| Signal #1 | 10.3 | 8.61 | 1126.6 | 1139.1 | 11.5 |
| Signal #2 | 13.6 | 6.53 | 2683.7 | 2720.5 | 27.4 |
| Signal #3 | 14.2 | 6.23 | 3675.4 | 3715.5 | 37.5 |
| Signal #4 | 15.7 | 5.62 | 1512.1 | 1550.0 | 15.4 |
| Signal #5 | 16.0 | 5.53 | 4660.4 | 4697.7 | 47.5 |
| Signal #6 | 18.8 | 4.72 | 1197.4 | 1238.8 | 12.2 |
| Signal #7 | 19.3 | 4.60 | 2498.7 | 2550.3 | 25.5 |
| Signal #8 | 19.5 | 4.54 | 2989.3 | 3044.4 | 30.5 |
| Signal #9 | 21.2 | 4.18 | 2615.2 | 2686.7 | 26.7 |
| Signal #10 | 21.7 | 4.09 | 3301.8 | 3377.4 | 33.7 |
| Signal #11 | 22.7 | 3.91 | 9809.5 | 9879.0 | 100.0 |
| Signal #12 | 23.4 | 3.80 | 1482.8 | 1536.3 | 15.1 |
| Signal #13 | 24.8 | 3.59 | 1286.3 | 1315.4 | 13.1 |
| Signal #14 | 25.3 | 3.52 | 983.5 | 1011.2 | 10.0 |
| Signal #15 | 28.7 | 3.11 | 1676.0 | 1727.6 | 17.1 |
| Signal #16 | 29.6 | 3.01 | 2058.9 | 2112.0 | 21.0 |

Compound 1 Form B Monofumarate Salt

Figure 67:
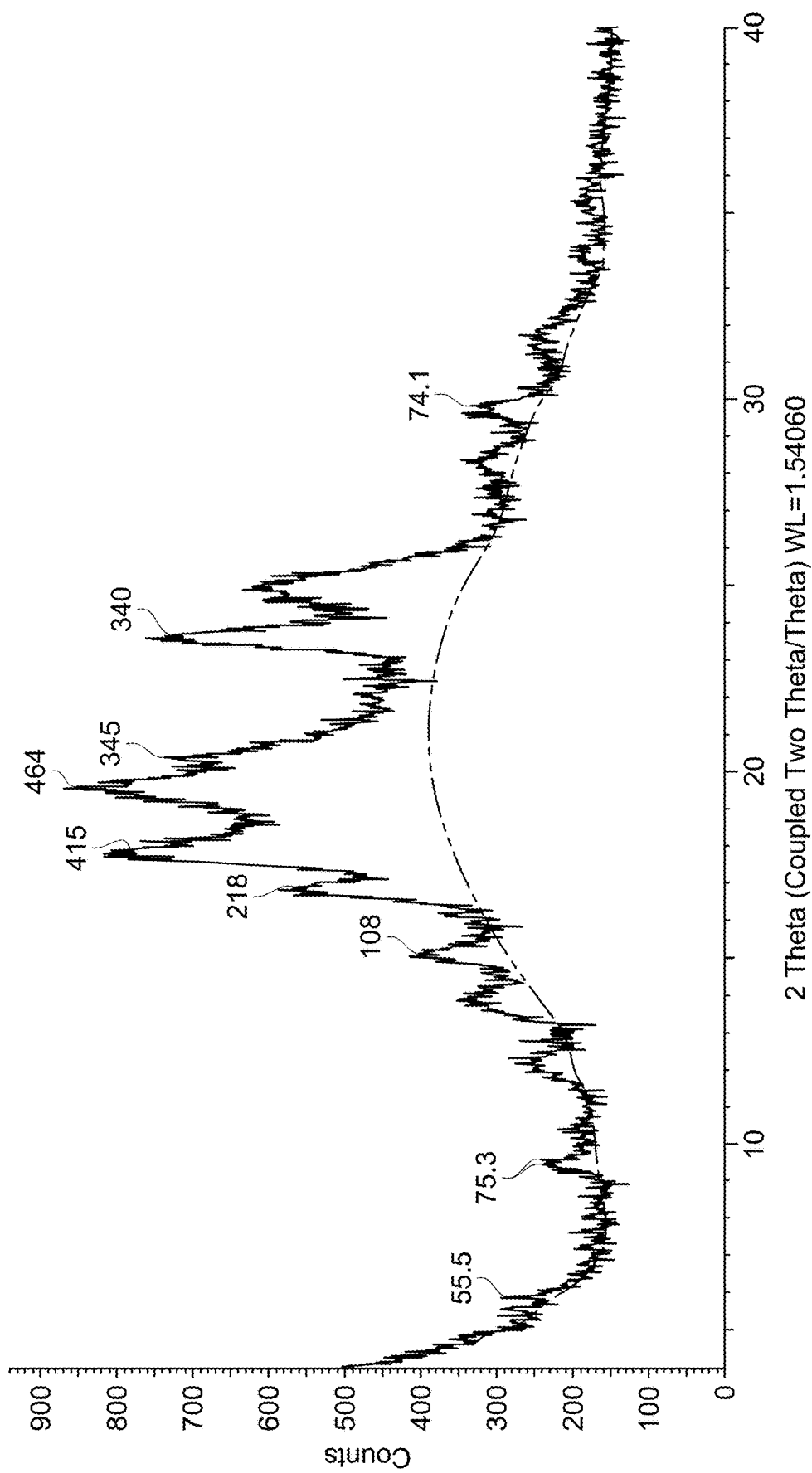
FIG. 67 shows a XRPD profile of crystalline compound 1 monofumarate Form B (wet pellet, Pattern #3b).

In some embodiments, the compound 1 fumarate salt is Form B crystalline monofumarate polymorph. In some embodiments, the compound 1 monofumarate salt Form B is characterized by the XRPD signals set forth below in Table 31 or 32. In some embodiments, the compound 1 monofumarate salt Form B is characterized by the XRPD signals in FIG. 67. In some embodiments, the compound 1 monofumarate salt Form B is characterized by the XRPD signals in FIG. 5. In some embodiments, the compound 1 fumarate salt TGA spectrum is substantially similar to that shown in FIG. 78.

In some embodiments, the crystalline compound 1 monofumarate Form B Is a crystalline polymorphic form characterized by DSC having a melting signal at about 66.2° C. In some embodiments, the crystalline compound 1 monofumarate Form B Is a crystalline polymorphic form characterized by TGA having an onset at about 208.4° C.

In some embodiments, the crystalline compound 1 monofumarate Form B is a 1:1 compound:fumarate salt In some embodiments, the compound 1 monofumarate salt is crystalline polymorphic Form B characterized by an XRPD signal at of 19.5°2θ (±0.2°2θ; ±0.1°2θ; or ±0.0°2θ; Cu Kα1 radiation).

In some embodiments, the compound 1 monofumarate salt is crystalline polymorphic Form B characterized by XRPD signals at 17.8°2θ, and 19.5°2θ (±0.2°2θ; ±0.1°2θ; or ±0.0°2θ; Cu Kα1 radiation).

In some embodiments, the compound 1 monofumarate salt is crystalline polymorphic Form B characterized by two or more, or three or more XRPD signals selected from the group consisting of 17.8°2θ, 19.5°2θ, and 20.3°2θ (±0.2°2θ; ±0.1°2θ; or ±0.0°2θ; Cu Kα1 radiation). In some embodiments, the compound 1 monofumarate salt is crystalline polymorphic Form B characterized by XRPD signals at 17.8°2θ, 19.5°2θ, and 20.3°2θ (±0.2°2θ; ±0.1°2θ; or ±0.0°2θ; Cu Kα1 radiation).

In some embodiments, the compound 1 monofumarate salt is crystalline polymorphic Form B characterized by two or more, or three or more XRPD signals selected from the group consisting of 17.8°2θ, 19.5°2θ, 20.3°2θ, and 23.6°2θ (±0.2°2θ; ±0.1°2θ; or ±0.0°2θ; Cu Kα1 radiation). In some embodiments, the compound 1 monofumarate salt is crystalline polymorphic Form B characterized by XRPD signals at 17.8°2θ, 19.5°2θ, 20.3°2θ, and 23.6°2θ (±0.2°2θ; ±0.1°2θ; or ±0.0°2θ; Cu Kα1 radiation).

In some embodiments, the compound 1 monofumarate salt is crystalline polymorphic Form B characterized by two or more, or three or more XRPD signals selected from the group consisting of 16.8°2θ, 17.8°2θ, 19.5°2θ, 20.3°2θ, and 23.6°2 0 (±0.2°2θ; ±0.1°2θ; or ±0.0°2θ; Cu Kα1 radiation). In some embodiments, the compound 1 monofumarate salt is crystalline polymorphic Form B characterized by XRPD signals at 16.8°2θ, 17.8°2θ, 19.5°2θ, 20.3°2θ, and 23.6°2θ (±0.2°2θ; ±0.1°2θ; or ±0.0°2θ; Cu Kα1 radiation).

In some embodiments, the compound 1 monofumarate salt is crystalline polymorphic Form B characterized by two or more, or three or more XRPD signals selected from the group consisting of 15.1°2θ, 16.8°2θ, 17.8°2θ, 19.5°2θ, 20.3°2θ, and 23.6°2θ (±0.2°2θ; ±0.1°2θ; or ±0.0°2θ; Cu Kα1 radiation). In some embodiments, the compound 1 monofumarate salt is crystalline polymorphic Form B characterized by XRPD signals at 15.1°2θ, 16.8°2θ, 17.8°2θ, 19.5°2θ, 20.3°2θ, and 23.6°2θ (±0.2°2θ; ±0.1°2θ; or ±0.0°2θ; Cu Kα1 radiation).

In some embodiments, the compound 1 monofumarate salt is crystalline polymorphic Form B characterized by two or more, or three or more XRPD signals selected from the group consisting of 9.5°2θ, 15.1°2θ, 16.8°2θ, 17.8°2θ, 19.5°2θ, 20.3°2θ, and 23.6°2 0 (±0.2°2θ; ±0.1°2θ; or ±0.0°2θ; Cu Kα1 radiation). In some embodiments, the compound 1 monofumarate salt is crystalline polymorphic Form B characterized by XRPD signals at 9.5°2θ, 15.1°2θ, 16.8°2θ, 17.8°2θ, 19.5°2θ, 20.3°2θ, and 23.6°2θ (±0.2°2θ; ±0.1°2θ; or ±0.0°2θ; Cu Kα1 radiation).

In some embodiments, the compound 1 monofumarate salt is crystalline polymorphic Form B characterized by two or more, or three or more XRPD signals selected from the group consisting of 9.5°2θ, 15.1°2θ, 16.8°2θ, 17.8°2θ, 19.5°2θ, 20.3°2θ, 23.6°2θ, and 29.8°2θ (±0.2°2θ; ±0.1°2θ; or ±0.0°2θ; Cu Kα1 radiation). In some embodiments, the compound 1 monofumarate salt is crystalline polymorphic Form B characterized by XRPD signals at 9.5°2θ, 15.1°2θ, 16.8°2θ, 17.8°2θ, 19.5°2θ, 20.3°2θ, 23.6°2θ, and 29.8°2θ (±0.2°2θ; ±0.1°2θ; or ±0.0°2θ; Cu Kα1 radiation).

In some embodiments, the compound 1 monofumarate salt is crystalline polymorphic Form B characterized by two or more, or three or more XRPD signals selected from the group consisting of 5.9°2θ, 9.5°2θ, 15.1°2θ, 16.8°2θ, 17.8°2θ, 19.5°2θ, 20.3°2θ, 23.6°2θ, and 29.8°2θ (±0.2°2θ; ±0.1°2θ, or ±0.0°2θ; Cu Kα1 radiation). In some embodiments, the compound 1 monofumarate salt is crystalline polymorphic Form B characterized by XRPD signals at 5.9°2θ, 9.5°2θ, 15.1°2θ, 16.8°2θ, 17.8°2θ, 19.5°2θ, 20.3°2θ, 23.6°2θ, and 29.8°2θ (70.2°2θ; ±0.1°2θ; or ±0.0°2θ; Cu Kα1 radiation).

In some embodiments, crystalline polymorphic Form B is characterized by one, two, three, four, five, six, seven, eight, or nine XRPD signals selected from those set forth in Table 31.

TABLE 31

Signal angle data of Form B (±0.2 °2θ; ±0.1 °2θ; or ±0.0 °2θ; Cu Kα1 radiation)

| Signal number | 2-θ (°) | d Value | Net Intensity (counts) | Gross Intensity (counts) | Rel. Intensity (%) |
|---|---|---|---|---|---|
| Signal #1 | 5.9 | 15.08 | 55.5 | 278.2 | 11.9 |
| Signal #2 | 9.5 | 9.34 | 75.3 | 242.5 | 16.2 |
| Signal #3 | 15.1 | 5.87 | 107.8 | 393.0 | 23.2 |
| Signal #4 | 16.8 | 5.26 | 218.1 | 551.5 | 47.0 |
| Signal #5 | 17.8 | 4.98 | 414.7 | 769.8 | 89.3 |
| Signal #6 | 19.5 | 4.54 | 464.1 | 843.6 | 100.0 |
| Signal #7 | 20.3 | 4.36 | 345.3 | 730.3 | 74.4 |
| Signal #8 | 23.6 | 3.77 | 340.2 | 708.2 | 73.3 |
| Signal #9 | 29.8 | 3.00 | 74.1 | 318.7 | 16.0 |

In some embodiments, the compound 1 monofumarate salt is crystalline polymorphic Form B characterized by an XRPD signal at 17.6°2θ (±0.2°2θ; ±0.1°2θ; or ±0.0°2θ; Cu Kα1 radiation). In some embodiments, the compound 1 monofumarate salt is crystalline polymorphic Form B characterized by XRPD signals at 17.6°2θ and 19.4°2θ (±0.2°2θ; ±0.1°2θ; or ±0.0°2θ; Cu Kα1 radiation).

In some embodiments, the compound 1 monofumarate salt is crystalline polymorphic Form B characterized by two or more, or three or more XRPD signals selected from the group consisting of 17.6°2θ, 19.4°2θ, and 23.5°2θ (±0.2°2θ; ±0.1°2θ; or ±0.0°2θ; Cu Kα1 radiation). In some embodiments, the compound 1 monofumarate salt is crystalline polymorphic Form B characterized by XRPD signals at 17.6°2θ, 19.4°2θ, and 23.5°2θ (±0.2°2θ; ±0.1°2θ; or ±0.0°2θ; Cu Kα1 radiation).

In some embodiments, the compound 1 monofumarate salt is crystalline polymorphic Form B characterized by two or more, or three or more XRPD signals selected from the group consisting of 17.6°2θ, 19.4°2θ, 23.5°2θ, and 24.7°2θ (±0.2°2θ; ±0.1°2θ; or ±0.0°2θ; Cu Kα1 radiation).

In some embodiments, the compound 1 monofumarate salt is crystalline polymorphic Form B characterized by XRPD signals at 17.6°2θ, 19.4°2θ, 23.5°2θ, and 24.7°2θ (±0.2°2θ; ±0.1°2θ; or 0.0°2θ; Cu Kα1 radiation).

In some embodiments, the compound 1 monofumarate salt is crystalline polymorphic Form B characterized by two or more, or three or more XRPD signals selected from the group consisting of 16.7°2θ, 17.6°2θ, 19.4°2θ, 23.5°2θ, and 24.7°2θ (±0.2°2θ; ±0.1°2θ; or ±0.0°2θ; Cu Kα1 radiation). In some embodiments, the compound 1 monofumarate salt is crystalline polymorphic Form B characterized by XRPD signals at 16.7°2θ, 17.6°2θ, 19.4°2θ, 23.5°2θ, and 24.7°2θ (±0.2°2θ; ±0.1°2θ; or ±0.0°2θ; Cu Kα1 radiation).

In some embodiments, the compound 1 monofumarate salt is crystalline polymorphic Form B characterized by two or more, or three or more XRPD signals selected from the group consisting of 16.7°2θ, 17.6°2θ, 19.4°2θ, 23.5°2θ, 24.7°2θ, and 24.9°2θ (±0.2°2θ; ±0.1°2θ; or ±0.0°2θ; Cu Kα1 radiation). In some embodiments, the compound 1 monofumarate salt is crystalline polymorphic Form B characterized by XRPD signals at 16.7°2θ, 17.6°2θ, 19.4°2θ, 23.5°2θ, 24.7°2θ, and 24.9°2θ (±0.2°2θ; ±0.1°2θ; or ±0.0°2θ; Cu Kα1 radiation).

In some embodiments, the compound 1 monofumarate salt is crystalline polymorphic Form B characterized by two or more, or three or more XRPD signals selected from the group consisting of 16.7°2θ, 17.6°2θ, 19.4°2θ, 23.5°2θ, 24.7°2θ, 24.9°2θ, and 29.5°2θ (±0.2°2θ; ±0.1°2θ; or ±0.0°2θ; Cu Kα1 radiation). In some embodiments, the compound 1 monofumarate salt is crystalline polymorphic Form B characterized by XRPD signals at 16.7°2θ, 17.6°2θ, 19.4°2θ, 23.5°2θ, 24.7°2θ, 24.9°2θ, and 29.5°2θ (±0.2°2θ; ±0.1°2θ; or ±0.0°2θ; Cu Kα1 radiation).

In some embodiments, the compound 1 monofumarate salt is crystalline polymorphic Form B characterized by two or more, or three or more XRPD signals selected from the group consisting of 13.7°2θ, 16.7°2θ, 17.6°2θ, 19.4°2θ, 23.5°2θ, 24.7°2θ, 24.9°2θ, and 29.5°2θ (±0.2°2θ; ±0.1°2θ; or ±0.0°2θ; Cu Kα1 radiation). In some embodiments, the compound 1 monofumarate salt is crystalline polymorphic Form B characterized by XRPD signals at 13.7°2θ, 16.7°2θ, 17.6°2θ, 19.4°2θ, 23.5°2θ, 24.7°2θ, 24.9°2θ, and 29.5°2θ (±0.2°2θ; ±0.1°2θ; or ±0.0°2θ; Cu Kα1 radiation).

In some embodiments, the compound 1 monofumarate salt is crystalline polymorphic Form B characterized by two or more, or three or more XRPD signals selected from the group consisting of 9.4°2θ, 13.7°2θ, 16.7°2θ, 17.6°2θ, 19.4°2θ, 23.5°2θ, 24.7°2θ, 24.9°2θ, and 29.5°2θ (±0.2°2θ; ±0.1°2θ; or ±0.0°2θ; Cu Kα1 radiation). In some embodiments, the compound 1 monofumarate salt is crystalline polymorphic Form B characterized by XRPD signals at 9.4°2θ, 13.7°2θ, 16.7°2θ, 17.6°2θ, 19.4°2θ, 23.5°2θ, 24.7°2θ, 24.9°2θ, and 29.5°2θ (±0.2°2θ; ±0.1°2θ; or ±0.0°2θ; Cu Kα1 radiation).

In some embodiments, the compound 1 monofumarate salt is crystalline polymorphic Form B characterized by two or more, or three or more XRPD signals selected from the group consisting of 9.4°2θ, 13.7°2θ, 14.9°2θ, 16.7°2θ, 17.6°2θ, 19.4°2θ, 23.5°2θ, 24.7°2θ, 24.9°2θ, and 29.5°2θ (±0.2°2θ; ±0.1°2θ; or ±0.0°2θ; Cu Kα1 radiation). In some embodiments, the compound 1 monofumarate salt is crystalline polymorphic Form B characterized by XRPD signals at 9.4°2θ, 13.7°2θ, 14.9°2θ, 16.7°2θ, 17.6°2θ, 19.4°2θ, 23.5°2θ, 24.7°2θ, 24.9°2θ, and 29.5°2θ (±0.2°2θ; ±0.1°2θ; or ±0.0°2θ. Cu Kα1 radiation).

In some embodiments, the compound 1 monofumarate salt is crystalline polymorphic Form B characterized by two or more, or three or more XRPD signals selected from the group consisting of 9.4°2θ, 13.6°2θ, 13.7°2θ, 14.9°2θ, 16.7°2θ, 17.6°2θ, 19.4°2θ, 23.5°2θ, 24.7°2θ, 24.9°2θ, 28.3°2θ, and 29.5°2θ (±0.2°2θ; ±0.1°2θ; or ±0.0°2θ; Cu Kα1 radiation). In some embodiments, the compound 1 monofumarate salt is crystalline polymorphic Form B characterized by XRPD signals at 9.4°2θ, 13.6°2θ, 13.7°2θ, 14.9°2θ, 16.7°2θ, 17.6°2θ, 19.4°2θ, 23.5°2θ, 24.7°2θ, 24.9°2θ, 28.3°2θ, and 29.5°2θ (±0.2°2θ; ±0.1°2θ; or ±0.0°2θ; Cu Kα1 radiation).

In some embodiments, the compound 1 monofumarate salt is crystalline polymorphic Form B characterized by two or more, or three or more XRPD signals selected from the group consisting of 9.4°2θ, 13.6°2θ, 13.7°2θ, 14.9°2θ, 15.0°2θ, 16.7°2θ, 17.6°2θ, 19.4°2θ, 23.5°2θ, 24.7°2θ, 24.9°2θ, 28.3°2θ, and 29.5°2θ (±0.2°2θ; ±0.1°2θ; or ±0.0°2θ; Cu Kα1 radiation). In some embodiments, the compound 1 monofumarate salt is crystalline polymorphic Form B characterized by XRPD signals at 9.4°2θ, 13.6°2θ, 13.7°2θ, 14.9°2θ, 15.0°2θ, 16.7°2θ, 17.6°2θ, 19.4°2θ, 23.5°2θ, 24.7°2θ, 24.9°2θ, 28.3°2θ, and 29.5°2θ (±0.2°2θ; ±0.1°2θ; or ±0.0°2θ; Cu Kα1 radiation).

In some embodiments, the compound 1 monofumarate salt is crystalline polymorphic Form B characterized by two or more, or three or more XRPD signals selected from the group consisting of 9.4°2θ, 11.8°2θ, 13.6°2θ, 13.7°2θ, 14.9°2θ, 15.0°2θ, 16.7°2θ, 17.6°2θ, 19.4°2θ, 23.5°2θ, 24.7°2θ, 24.9°2θ, 28.3°2θ, and 29.5°2θ (±0.2°2θ; ±0.1°2θ; or ±0.0°2θ; Cu Kα1 radiation). In some embodiments, the compound 1 monofumarate salt is crystalline polymorphic Form B characterized by XRPD signals at 9.4°2θ, 11.8°2θ, 13.6°2θ, 13.7°2θ, 14.9°2θ, 15.0°2θ, 16.7°2θ, 17.6°2θ, 19.4°2θ, 23.5°2θ, 24.7°2θ, 24.9°2θ, 28.3°2θ, and 29.5°2θ (±0.2°2θ; ±0.1°2θ; or ±0.0°2θ; Cu Kα1 radiation).

In some embodiments, crystalline polymorphic Form B is characterized by one, two, three, four, five, six, seven, eight, nine, ten, eleven, twelve, thirteen, or fourteen XRPD signals selected from those set forth in Table 32.

TABLE 32

Signal angle data of Form B (±0.2 °2θ; ±0.1 °2θ; or ±0.0 °2θ; Cu Kα1 radiation)

| Signal number | 2-θ (°) | d Value | Net Intensity (counts) | Gross Intensity (counts) | Rel. Intensity (%) |
|---|---|---|---|---|---|
| Signal #1 | 9.4 | 9.42 | 98.8 | 209.9 | 22.9 |
| Signal #2 | 11.8 | 7.51 | 43.5 | 177.3 | 10.1 |
| Signal #3 | 13.6 | 6.53 | 72.9 | 241.4 | 16.9 |
| Signal #4 | 13.7 | 6.44 | 109.5 | 283.5 | 25.4 |
| Signal #5 | 14.9 | 5.93 | 96.6 | 302.1 | 22.4 |
| Signal #6 | 15.0 | 5.91 | 67.0 | 273.7 | 15.5 |
| Signal #7 | 16.7 | 5.30 | 264.5 | 515.9 | 61.3 |
| Signal #8 | 17.6 | 5.02 | 431.5 | 705.7 | 100.0 |

TABLE 32-continued

Signal angle data of Form B (±0.2 °2θ; ±0.1 °2θ; or ±0.0 °2θ; Cu Kα1 radiation)

| Signal number | 2-θ (°) | d Value | Net Intensity (counts) | Gross Intensity (counts) | Rel. Intensity (%) |
|---|---|---|---|---|---|
| Signal #9 | 19.4 | 4.56 | 420.1 | 725.7 | 97.4 |
| Signal #10 | 23.5 | 3.79 | 375.0 | 685.9 | 86.9 |
| Signal #11 | 24.7 | 3.60 | 282.0 | 576.6 | 65.3 |
| Signal #12 | 24.9 | 3.58 | 248.8 | 540.7 | 57.7 |
| Signal #13 | 28.3 | 3.15 | 71.0 | 308.9 | 16.5 |
| Signal #14 | 29.5 | 3.03 | 111.1 | 329.4 | 25.8 |

Compound 1 Form I Hemi-Fumarate Salt

In some embodiments, the compound 1 salt is a crystalline hemi-fumarate Form I polymorph. In some embodiments, the compound 1 hemi-fumarate salt Form I is characterized by the XRPD signals set for the below in Table 33.

In some embodiments, the crystalline compound 1 hemi-fumarate Form I is a crystalline polymorphic form characterized by DSC having a melting signal at about 91.5° C. In some embodiments, the crystalline compound 1 hemi-fumarate Form I is a crystalline polymorphic form characterized by TGA having an onset at about 264.4° C.

In some embodiments, the compound 1 hemi-fumarate Form I salt is a 1:1 compound 1 fumarate salt.

In some embodiments, the compound 1 hemi-fumarate salt is crystalline polymorphic Form I characterized by an XRPD signal at 15.9°2θ (±0.2°2θ; ±0.1°2θ; or ±0.0°2θ; Cu Kα1 radiation).

In some embodiments, the compound 1 hemi-fumarate salt is crystalline polymorphic Form I characterized by XRPD signals at 15.9°2θ, and 21.0°2θ (±0.2°2θ; ±0.1°2θ; or ±0.0°2θ; Cu Kα1 radiation).

In some embodiments, the compound 1 hemi-fumarate salt is crystalline polymorphic Form I characterized by two or more, or three or more XRPD signals selected from the group consisting of 15.9°2θ, 19.4 20, and 21.0°2θ (±0.2°2θ; ±0.1°2θ; or ±0.0°2θ; Cu Kα1 radiation). In some embodiments, the compound 1 hemi-fumarate salt is crystalline polymorphic Form I characterized by XRPD signals at 15.9°2θ, 19.4°2θ, and 21.0°2θ (±0.2°2θ; ±0.1°2θ; or ±0.0°2θ; Cu Kα1 radiation).

In some embodiments, the compound 1 hemi-fumarate salt is crystalline polymorphic Form I characterized by two or more, or three or more XRPD signals selected from the group consisting of 15.9°2θ, 19.4°2θ, 21.0°2θ, and 27.1°2θ (±0.2°2θ; ±0.1°2θ; or 0.0°2θ; Cu Kα1 radiation). In some embodiments, the compound 1 hemi-fumarate salt is crystalline polymorphic Form I characterized by XRPD signals at 15.9°2θ, 19.4°2θ, 21.0°2θ, and 27.1°2θ (±0.2°2θ; ±0.1°2θ; or ±0.0°2θ; Cu Kα1 radiation).

In some embodiments, the compound 1 hemi-fumarate salt is crystalline polymorphic Form I characterized by two or more, or three or more XRPD signals selected from the group consisting of 15.2°2θ, 15.9°2θ, 19.4°2θ, 21.0°2θ, and 27.1°2θ (±0.2°2θ; ±0.1°2θ; or ±0.0°2θ; Cu Kα1 radiation). In some embodiments, the compound 1 hemi-fumarate salt is crystalline polymorphic Form I characterized by XRPD signals at 15.2°2θ, 15.9°2θ, 19.4°2θ, 21.0°2θ, and 27.1°2θ (±0.2°2θ; ±0.1°2θ; or ±0.0°2θ; Cu Kα1 radiation).

In some embodiments, the compound 1 hemi-fumarate salt is crystalline polymorphic Form I characterized by two or more, or three or more XRPD signals selected from the group consisting of 15.2°2θ, 15.9°2θ, 19.4°2θ, 21.0°2θ, 22.5°2θ, and 27.1°2θ (±0.2°2θ; ±0.1°2θ; or ±0.0°2θ; Cu Kα1 radiation). In some embodiments, the compound 1 hemi-fumarate salt is crystalline polymorphic Form I characterized by XRPD signals at 15.2°2θ, 15.9°2θ, 19.4°2θ, 21.0°2θ, 22.5°2θ, and 27.1°2θ (±0.2°2θ; ±0.1°2θ; or ±0.0°2θ; Cu Kα1 radiation).

In some embodiments, the compound 1 hemi-fumarate salt is crystalline polymorphic Form I characterized by two or more, or three or more XRPD signals selected from the group consisting of 15.2°2θ, 15.9°2θ, 18.9°2θ, 19.4°2θ, 21.0°2θ, 22.5°2θ, and 27.1°2θ (±0.2°2θ; ±0.1°2θ; or ±0.0°2θ; Cu Kα1 radiation). In some embodiments, the compound 1 hemi-fumarate salt is crystalline polymorphic Form I characterized by XRPD signals at 15.2°2θ, 15.9°2θ, 18.9°2θ, 19.4°2θ, 21.0°2θ, 22.5°2θ, and 27.1°2θ (±0.2°2θ; ±0.1°2θ; or ±0.0°2θ; Cu Kα1 radiation).

In some embodiments, the compound 1 hemi-fumarate salt is crystalline polymorphic Form I characterized by two or more, or three or more XRPD signals selected from the group consisting of 13.4°2θ, 15.2°2θ, 15.9°2θ, 18.9°2θ, 19.4°2θ, 21.0°2θ, 22.5°2θ, and 27.1°2θ (±0.2°2θ; ±0.1°2θ; or ±0.0°2θ; Cu Kα1 radiation). In some embodiments, the compound 1 hemi-fumarate salt is crystalline polymorphic Form I characterized by XRPD signals at 13.4°2θ, 15.2°2θ, 15.9°2θ, 18.9°2θ, 19.4°2θ, 21.0°2θ, 22.5°2θ, and 27.1°2θ (±0.2°2θ; ±0.1°2θ; or ±0.0°2θ; Cu Kα1 radiation).

In some embodiments, the compound 1 hemi-fumarate salt is crystalline polymorphic Form I characterized by two or more, or three or more XRPD signals selected from the group consisting of 13.4°2θ, 13.7°2θ, 15.2°2θ, 15.9°2θ, 18.9°2θ, 19.4°2θ, 21.0°2θ, 22.5°2θ, and 27.1°2θ (±0.2°2θ; ±0.1°2θ; or ±0.0°2θ; Cu Kα1 radiation). In some embodiments, the compound 1 hemi-fumarate salt is crystalline polymorphic Form I characterized by XRPD signals at 13.4°2θ, 13.7°2θ, 15.2°2θ, 15.9°2θ, 18.9°2θ, 19.4°2θ, 21.0°2θ, 22.5°2θ, and 27.1°2θ (±0.2°2θ; ±0.1°2θ; or ±0.0°2θ; Cu Kα1 radiation).

In some embodiments, the compound 1 hemi-fumarate salt is crystalline polymorphic Form I characterized by two or more, or three or more XRPD signals selected from the group consisting of 11.7°2θ, 13.4°2θ, 13.7°2θ, 15.2°2θ, 15.9°2θ, 18.9°2θ, 19.4°2θ, 21.0°2θ, 22.5°2θ, and 27.1°2θ (±0.2°2θ; ±0.1°2θ; or ±0.0°2θ; Cu Kα1 radiation). In some embodiments, the compound 1 hemi-fumarate salt is crystalline polymorphic Form I characterized by XRPD signals at 11.7°2θ, 13.4°2θ, 13.7°2θ, 15.2°2θ, 15.9°2θ, 18.9°2θ, 19.4°2θ, 21.0°2θ, 22.5°2θ, and 27.1°2θ (±0.2°2θ; ±0.1°2θ; or ±0.0°2θ; Cu Kα1 radiation).

In some embodiments, the compound 1 hemi-fumarate salt is crystalline polymorphic Form I characterized by two or more, or three or more XRPD signals selected from the group consisting of 11.7°2θ, 13.4°2θ, 13.7°2θ, 15.2°2θ, 15.9°2θ, 18.9°2θ, 19.4°2θ, 21.0°2θ, 21.6°2θ, 22.5°2θ, and 27.1°2θ (±0.2°2θ; ±0.1°2θ; or ±0.0°2θ; Cu Kα1 radiation). In some embodiments, the compound 1 hemi-fumarate salt is crystalline polymorphic Form I characterized by XRPD signals at 11.7°2θ, 13.4°2θ, 13.7°2θ, 15.2°2θ, 15.9°2θ, 18.9°2θ, 19.4°2θ, 21.0°2θ, 21.6°2θ, 22.5°2θ, and 27.1°2θ (±0.2°2θ; ±0.1°2θ; or ±0.0°2θ; Cu Kα1 radiation).

In some embodiments, the compound 1 hemi-fumarate salt is crystalline polymorphic Form I characterized by two or more, or three or more XRPD signals selected from the group consisting of 11.7°2θ, 13.4°2θ, 13.7°2θ, 15.2°2θ, 15.9°2θ, 18.9°2θ, 19.4°2θ, 21.0°2θ, 21.6°2θ, 22.5°2θ, 23.2°2θ, and 27.1°2θ (±0.2°2θ; ±0.1°2θ; or 0.0°2θ; Cu Kα1 radiation). In some embodiments, the compound 1 hemi-fumarate salt is crystalline polymorphic Form I characterized by XRPD signals at 11.7°2θ, 13.4°2θ, 13.7°2θ, 15.2°2θ, 15.9°2θ, 18.9°2θ, 19.4°2θ, 21.0°2θ, 21.6°2θ, 22.5°2θ, 23.2°2θ, and 27.1°2θ (±0.2°2θ; ±0.1°2θ; or ±0.0°2θ; Cu Kα1 radiation).

In some embodiments, crystalline polymorphic hemi-fumarate Form I is characterized by one, two, three, four, five, six, seven, eight, nine, ten, eleven, or twelve XRPD signals selected from those set forth in Table 33.

TABLE 33

Signal angle data of Form I (±0.2 °2θ; ±0.1 °2θ; or ±0.0 °2θ; Cu Kα1 radiation)

| Signal number | 2-θ (°) | d Value | Net Intensity (counts) | Gross Intensity (counts) | Rel. Intensity (%) |
|---|---|---|---|---|---|
| Signal #1 | 11.7 | 7.58 | 396.3 | 550.9 | 11.2 |
| Signal #2 | 13.4 | 6.59 | 537.7 | 711.0 | 15.2 |
| Signal #3 | 13.7 | 6.47 | 523.8 | 702.8 | 14.8 |
| Signal #4 | 15.2 | 5.82 | 1058.1 | 1311.0 | 29.9 |
| Signal #5 | 15.9 | 5.57 | 3537.4 | 3823.3 | 100.0 |
| Signal #6 | 18.9 | 4.69 | 600.6 | 984.8 | 17.0 |
| Signal #7 | 19.4 | 4.58 | 1172.9 | 1566.2 | 33.2 |
| Signal #8 | 21.0 | 4.22 | 1658.6 | 2060.6 | 46.9 |
| Signal #9 | 21.6 | 4.12 | 380.3 | 778.0 | 10.7 |
| Signal #10 | 22.5 | 3.95 | 613.9 | 995.6 | 17.4 |
| Signal #11 | 23.2 | 3.83 | 359.4 | 725.5 | 10.2 |
| Signal #12 | 27.1 | 3.29 | 1088.3 | 1356.6 | 30.8 |

In some embodiments, the compound 1 fumarate salt is crystalline polymorphic Form I characterized by an XRPD signal at 16.0°2θ (±0.2°2θ; ±0.1°2θ; or ±0.0°2θ; Cu Kα1 radiation).

In some embodiments, the compound 1 hemi-fumarate salt is crystalline polymorphic Form I characterized by XRPD signals at 16.0°2θ, and 21.2°2θ (±0.2°2θ; ±0.1°2θ; or ±0.0°2θ; Cu Kα1 radiation).

In some embodiments, the compound 1 hemi-fumarate salt is crystalline polymorphic Form I characterized by two or more, or three or more XRPD signals selected from the group consisting of 16.0°2θ, 21.2°2θ, and 27.2°2θ (±0.2°2θ; ±0.1°2θ; or ±0.0°2θ; Cu Kα1 radiation). In some embodiments, the compound 1 hemi-fumarate salt is crystalline polymorphic Form I characterized by XRPD signals at 16.0°2θ, 21.2°2θ, and 27.2°2θ (±0.2°2θ; ±0.1°2θ; or ±0.0°2θ; Cu Kα1 radiation).

In some embodiments, the compound 1 hemi-fumarate salt is crystalline polymorphic Form I characterized by two or more, or three or more XRPD signals selected from the group consisting of 16.0°2θ, 19.5°2θ, 21.2°2θ, and 27.2°2θ (±0.2°2θ; ±0.1°2θ; or ±0.0°2θ; Cu Kα1 radiation). In some embodiments, the compound 1 hemi-fumarate salt is crystalline polymorphic Form I characterized by XRPD signals at 16.0°2θ, 19.5°2θ, 21.2°2θ, and 27.2°2θ (±0.2°2θ; ±0.1°2θ; or ±0.0°2θ; Cu Kα1 radiation).

In some embodiments, the compound 1 hemi-fumarate salt is crystalline polymorphic Form I characterized by two or more, or three or more XRPD signals selected from the group consisting of 15.4°2θ, 16.0°2θ, 19.5°2θ, 21.2°2θ, and 27.2°2θ (±0.2°2θ; ±0.1°2θ; or ±0.0°2θ; Cu Kα1 radiation). In some embodiments, the compound 1 hemi-fumarate salt is crystalline polymorphic Form I characterized by XRPD signals at 15.4°2θ, 16.0°2θ, 19.5°2θ, 21.2°2θ, and 27.2°2θ (±0.2°2θ; ±0.1°2θ; or ±0.0°2θ; Cu Kα1 radiation).

In some embodiments, the compound 1 hemi-fumarate salt is crystalline polymorphic Form I characterized by two or more, or three or more XRPD signals selected from the group consisting of 15.4°2θ, 16.0°2θ, 19.5°2θ, 21.2°2θ, 22.6°2θ, and 27.2°2θ (±0.2°2θ; ±0.1°2θ; or ±0.0°2θ; Cu Kα1 radiation). In some embodiments, the compound 1 hemi-fumarate salt is crystalline polymorphic Form I characterized by XRPD signals at 15.4°2θ, 16.0°2θ, 19.5°2θ, 21.2°2θ, 22.6°2θ, and 27.2°2θ (±0.2°2θ; ±0.1°2θ; or ±0.0°2θ; Cu Kα1 radiation).

In some embodiments, the compound 1 hemi-fumarate salt is crystalline polymorphic Form I characterized by two or more, or three or more XRPD signals selected from the group consisting of 15.4°2θ, 16.0°2θ, 19.2°2θ, 19.5°2θ, 21.2°2θ, 22.6°2θ, and 27.2°2θ (±0.2°2θ; ±0.1°2θ; or ±0.0°2θ; Cu Kα1 radiation). In some embodiments, the compound 1 hemi-fumarate salt is crystalline polymorphic Form I characterized by XRPD signals at 15.4°2θ, 16.0°2θ, 19.2°2θ, 19.5°2θ, 21.2°2θ, 22.6°2θ, and 27.2°2θ (±0.2°2θ; ±0.1°2θ; or ±0.0°2θ; Cu Kα1 radiation).

In some embodiments, the compound 1 hemi-fumarate salt is crystalline polymorphic Form I characterized by two or more, or three or more XRPD signals selected from the group consisting of 13.7°2θ, 15.4°2θ, 16.0°2θ, 19.2°2θ, 19.5°2θ, 21.2°2θ, 22.6°2θ, and 27.2°2θ (±0.2°2θ; ±0.1°2θ; or ±0.0°2θ; Cu Kα1 radiation). In some embodiments, the compound 1 hemi-fumarate salt is crystalline polymorphic Form I characterized by XRPD signals at 13.7°2θ, 15.4°2θ, 16.0°2θ, 19.2°2θ, 19.5°2θ, 21.2°2θ, 22.6°2θ, and 27.2°2θ (±0.2°2θ; ±0.1°2θ; or ±0.0°2θ; Cu Kα1 radiation).

In some embodiments, the compound 1 hemi-fumarate salt is crystalline polymorphic Form I characterized by two or more, or three or more XRPD signals selected from the group consisting of 13.7°2θ, 15.4°2θ, 16.0°2θ, 19.2°2θ, 19.5°2θ, 21.2°2θ, 22.6°2θ, 27.2°2θ, and 30.4°2θ (±0.2°2θ; ±0.1°2θ; or ±0.0°2θ; Cu Kα1 radiation). In some embodiments, the compound 1 hemi-fumarate salt is crystalline polymorphic Form I characterized by XRPD signals at 13.7°2θ, 15.4°2θ, 16.0°2θ, 19.2°2θ, 19.5°2θ, 21.2°2θ, 22.6°2θ, 27.2°2θ, and 30.4°2θ (±0.2°2θ; ±0.1°2θ; or ±0.0°2θ; Cu Kα1 radiation).

In some embodiments, the compound 1 hemi-fumarate salt is crystalline polymorphic Form I characterized by two or more, or three or more XRPD signals selected from the group consisting of 13.7°2θ, 15.4°2θ, 16.0°2θ, 19.2°2θ, 19.5°2θ, 21.2°2θ, 22.6°2θ, 23.4°2θ, 27.2°2θ, and 30.4°2θ (±0.2°2θ; ±0.1°2θ; or ±0.0°2θ; Cu Kα1 radiation). In some embodiments, the compound 1 hemi-fumarate salt is crystalline polymorphic Form I characterized by XRPD signals at 13.7°2θ, 15.4°2θ, 16.0°2θ, 19.2°2θ, 19.5°2θ, 21.2°2θ, 22.6°2θ, 23.4°2θ, 27.2°2θ, and 30.4°2θ (±0.2°2θ; ±0.1°2θ; or ±0.0°2θ; Cu Kα1 radiation).

In some embodiments, the compound 1 hemi-fumarate salt is crystalline polymorphic Form I characterized by two or more, or three or more XRPD signals selected from the group consisting of 13.7°2θ, 15.4°2θ, 16.0°2θ, 19.2°2θ, 19.5°2θ, 21.2°2θ, 22.6°2θ, 23.4°2θ, 25.0°2θ, 27.2°2θ, and 30.4°2θ (±0.2°2θ; ±0.1°2θ; or 0.0°2θ; Cu Kα1 radiation). In some embodiments, the compound 1 hemi-fumarate salt is crystalline polymorphic Form I characterized by XRPD signals at 13.7°2θ, 15.4°2θ, 16.0°2θ, 19.2°2θ, 19.5°2θ, 21.2°2θ, 21.7°2θ, 22.6°2θ, 23.4°2θ, 25.0°2θ, 27.2°2θ, and 30.4°2θ (±0.2°2θ; ±0.1°2θ; or ±0.0°2θ; Cu Kα1 radiation).

In some embodiments, the compound 1 hemi-fumarate salt is crystalline polymorphic Form I characterized by two or more, or three or more XRPD signals selected from the group consisting of 13.7°2θ, 15.4°2θ, 16.0°2θ, 19.2°2θ, 19.5°2θ, 21.2°2θ, 21.7°2θ, 22.6°2θ, 23.4°2θ, 24.3°2θ, 25.0°2θ, 27.2°2θ, and 30.4°2θ (±0.2°2θ; ±0.1°2θ; or ±0.0°2θ; Cu Kα1 radiation). In some embodiments, the compound 1 hemi-fumarate salt is crystalline polymorphic Form I characterized by XRPD signals at 13.7°2θ, 15.4°2θ, 16.0°2θ, 19.2°2θ, 19.5°2θ, 21.2°2θ, 21.7°2θ, 22.6°2θ, 23.4°2θ, 24.3°2θ, 25.0°2θ, 27.2°2θ, and 30.4°2θ (±0.2°2θ; ±0.1°2θ; or ±0.0°2θ; Cu Kα1 radiation).

In some embodiments, the compound 1 hemi-fumarate salt is crystalline polymorphic Form I characterized by two or more, or three or more XRPD signals selected from the group consisting of 13.7°2θ, 15.4°2θ, 16.0°2θ, 19.2°2θ, 19.5°2θ, 21.2°2θ, 21.7°2θ, 22.6°2θ, 23.4°2θ, 24.3°2θ, 25.0°2θ, 27.2°2θ, 28.5°2θ, and 30.4°2θ (±0.2°2θ; ±0.1°2θ; or ±0.0°2θ; Cu Kα1 radiation). In some embodiments, the compound 1 hemi-fumarate salt is crystalline polymorphic Form I characterized by XRPD signals at 13.7°2θ, 15.4°2θ, 16.0°2θ, 19.2°2θ, 19.5°2θ, 21.2°2θ, 21.7°2θ, 22.6°2θ, 23.4°2θ, 24.3°2θ, 25.0°2θ, 27.2°2θ, 28.5°2θ, and 30.4°2θ (±0.2°2θ; ±0.1°2θ; or ±0.0°2θ; Cu Kα1 radiation).

In some embodiments, the compound 1 hemi-fumarate salt is crystalline polymorphic Form I characterized by two or more, or three or more XRPD signals selected from the group consisting of 11.8°2θ, 13.7°2θ, 15.4°2θ, 16.0°2θ, 19.2°2θ, 19.5°2θ, 21.2°2θ, 21.7°2θ, 22.6°2θ, 23.4°2θ, 24.3°2θ, 25.0°2θ, 27.2°2θ, 28.5°2θ, and 30.4°2θ (±0.2°2θ; ±0.1°2θ; or ±0.0°2θ; Cu Kα1 radiation). In some embodiments, the compound 1 hemi-fumarate salt is crystalline polymorphic Form I characterized by XRPD signals at 11.8°2θ, 13.7°2θ, 15.4°2θ, 16.0°2θ, 19.2°2θ, 19.5°2θ, 21.2°2θ, 21.7°2θ, 22.6°2θ, 23.4°2θ, 24.3°2θ, 25.0°2θ, 27.2°2θ, 28.5°2θ, and 30.4°2θ (±0.2°2θ; ±0.1°2θ; or ±0.0°2θ; Cu Kα1 radiation).

In some embodiments, crystalline polymorphic hemi-fumarate Form I is characterized by one, two, three, four, five, six, seven, eight, nine, ten, eleven, twelve, thirteen, fourteen, fifteen, or sixteen XRPD signals selected from those set forth in Table 34.

TABLE 34

Signal angle data of Form I (±0.2 °2θ; ±0.1 °2θ; or ±0.0 °2θ; Cu Kα1 radiation)

| Signal number | 2-θ (°) | d Value | Net Intensity (counts) | Gross Intensity (counts) | Rel. Intensity (%) |
|---|---|---|---|---|---|
| Signal #1 | 11.8 | 7.47 | 362.2 | 495.0 | 11.6 |
| Signal #2 | 13.7 | 6.48 | 633.6 | 792.3 | 20.4 |
| Signal #3 | 13.7 | 6.47 | 642.5 | 801.5 | 20.6 |
| Signal #4 | 15.4 | 5.76 | 950.4 | 1142.3 | 30.5 |
| Signal #5 | 16.0 | 5.53 | 3112.9 | 3322.2 | 100.0 |
| Signal #6 | 19.2 | 4.62 | 765.7 | 1033.7 | 24.6 |
| Signal #7 | 19.5 | 4.54 | 1450.4 | 1723.7 | 46.6 |

TABLE 34-continued

Signal angle data of Form I (±0.2 °2θ; ±0.1 °2θ; or ±0.0 °2θ; Cu Kα1 radiation)

| Signal number | 2-θ (°) | d Value | Net Intensity (counts) | Gross Intensity (counts) | Rel. Intensity (%) |
|---|---|---|---|---|---|
| Signal #8 | 21.2 | 4.19 | 1975.0 | 2267.5 | 63.4 |
| Signal #9 | 21.7 | 4.10 | 423.5 | 719.8 | 13.6 |
| Signal #10 | 22.6 | 3.93 | 770.3 | 1066.4 | 24.7 |
| Signal #11 | 23.4 | 3.79 | 481.9 | 769.3 | 15.5 |
| Signal #12 | 24.3 | 3.66 | 413.8 | 684.4 | 13.3 |
| Signal #13 | 25.0 | 3.56 | 440.0 | 690.2 | 14.1 |
| Signal #14 | 27.2 | 3.27 | 1495.2 | 1749.4 | 48.0 |
| Signal #15 | 28.5 | 3.13 | 376.5 | 627.2 | 12.1 |
| Signal #16 | 30.4 | 2.94 | 497.6 | 707.9 | 16.0 |

Compound 1 Form II Fumarate Salt

In some embodiments, the compound 1 salt is a crystalline hemi-fumarate Form II polymorph. In some embodiments, the compound 1 hemi-fumarate salt Form II is characterized by the XRPD signals set for the below in Table 35. In some embodiments, the compound 1 hemi-fumarate salt Form II XRPD pattern is substantially similar to that shown in FIG. 7. In some embodiments, the compound 1 hemi-fumarate salt Form $^1$H-NMR spectrum is substantially similar to that shown in FIG. 56 or 57. In some embodiments, the compound 1 hemi-fumarate Form II salt TGA spectrum is substantially similar to that shown in FIG. 59.

In some embodiments, the crystalline compound 1 hemi-fumarate Form II is a crystalline polymorphic form characterized by DSC having a melting signal at 97.2° C. In some embodiments, the crystalline compound 1 hemi-fumarate Form II Is a crystalline polymorphic form characterized by DSC having an associated enthalpy of 246.4° C.

In some embodiments, the compound 1 hemi-fumarate salt is crystalline polymorphic Form II characterized by an XRPD signal at 15.8° (±0.2°2θ, ±0.1°2θ; or ±0.0°2θ; Cu Kα1 radiation).

In some embodiments, the compound 1 hemi-fumarate salt is crystalline polymorphic Form II characterized by XRPD signals at 15.8°2θ and 20.9°2θ (±0.2°2θ; ±0.1°2θ; or ±0.0°2θ. Cu Kα1 radiation).

In some embodiments, the compound 1 hemi-fumarate salt is crystalline polymorphic Form II characterized by two or more, or three or more XRPD signals selected from the group consisting of 15.8°2θ, 20.9°2θ, and 26.9°2θ (±0.2°2θ; ±0.1°2θ; or 0.0°2θ; Cu Kα1 radiation). In some embodiments, the compound 1 hemi-fumarate salt is crystalline polymorphic Form II characterized by XRPD signals at 15.8°2θ, 20.9°2θ, and 26.9°2θ (±0.2°2θ; ±0.1°2θ; or ±0.0°2θ; Cu Kα1 radiation).

In some embodiments, the compound 1 hemi-fumarate salt is crystalline polymorphic Form II characterized by two or more, or three or more XRPD signals selected from the group consisting of 15.8°2θ, 19.2°2θ, 20.9°2θ and 26.9°2θ (±0.2°2θ; ±0.1°2θ; or ±0.0°2θ; Cu Kα1 radiation). In some embodiments, the compound 1 hemi-fumarate salt is crystalline polymorphic Form II characterized by XRPD signals at 15.8°2θ, 19.2°2θ, 20.9°2θ, and 26.9°2θ (±0.2°2θ; ±0.1°2θ; or ±0.0°2θ; Cu Kα1 radiation).

In some embodiments, the compound 1 hemi-fumarate salt is crystalline polymorphic Form II characterized by two or more, or three or more XRPD signals selected from the group consisting of 15.1°2θ, 15.8°2θ, 19.2°2θ, 20.9°2θ, and 26.9°2θ (±0.2°2θ; ±0.1°2θ; or ±0.0°2θ; Cu Kα1 radiation). In some embodiments, the compound 1 hemi-fumarate salt is crystalline polymorphic Form II characterized by XRPD signals at 15.1°2θ, 15.8°2θ, 19.2°2θ, 20.9°2θ, and 26.9°2θ (±0.2°2θ; ±0.1°2θ; or ±0.0°2θ; Cu Kα1 radiation).

In some embodiments, the compound 1 hemi-fumarate salt is crystalline polymorphic Form II characterized by two or more, or three or more XRPD signals selected from the group consisting of 15.1°2θ, 15.8°2θ, 19.2°2θ, 20.9°2θ, 22.4°2θ, and 26.9°2θ (±0.2°2θ; ±0.1°2θ; or ±0.0°2θ; Cu Kα1 radiation). In some embodiments, the compound 1 hemi-fumarate salt is crystalline polymorphic Form II characterized by XRPD signals at 15.1°2θ, 15.8°2θ, 19.2°2θ, 20.9°2θ, 22.4°2θ, and 26.9°2θ (±0.2°2θ; ±0.1°2θ; or ±0.0°2θ; Cu Kα1 radiation).

In some embodiments, the compound 1 hemi-fumarate salt is crystalline polymorphic Form II characterized by two or more, or three or more XRPD signals selected from the group consisting of 15.1°2θ, 15.8°2θ, 18.8°2θ, 19.2°2θ, 20.9°2θ, 22.4°2θ, and 26.9°2θ (±0.2°2θ; ±0.1°2θ; or ±0.0°2θ; Cu Kα1 radiation). In some embodiments, the compound 1 hemi-fumarate salt is crystalline polymorphic Form II characterized by XRPD signals at 15.1°2θ, 15.8°2θ, 18.8°2θ, 19.2°2θ, 20.9°2θ, 22.4°2θ, and 26.9°2θ (±0.2°2θ; ±0.1°2θ; or ±0.0°2θ; Cu Kα1 radiation).

In some embodiments, the compound 1 hemi-fumarate salt is crystalline polymorphic Form II characterized by two or more, or three or more XRPD signals selected from the group consisting of 15.1°2θ, 15.8°2θ, 18.8°2θ, 19.2°2θ, 20.9°2θ, 22.4°2θ, 26.9°2θ, and 30.2°2θ (±0.2°2θ; ±0.1°2θ; or ±0.0°2θ; Cu Kα1 radiation). In some embodiments, the compound 1 hemi-fumarate salt is crystalline polymorphic Form H characterized by XRPD signals at 15.1°2θ, 15.8°2θ, 18.8°2θ, 19.2°2θ, 20.9°2θ, 22.4°2θ, 26.9°2θ, and 30.2°2θ (±0.2°2θ; ±0.1°2θ; or ±0.0°2θ; Cu Kα1 radiation).

In some embodiments, the compound 1 hemi-fumarate salt is crystalline polymorphic Form II characterized by two or more, or three or more XRPD signals selected from the group consisting of 13.3°2θ, 15.1°2θ, 15.8°2θ, 18.8°2θ, 19.2°2θ, 20.9°2θ, 22.4°2θ, 26.9°2θ, and 30.2°2θ (±0.2°2θ; ±0.1°2θ; or ±0.0°2θ; Cu Kα1 radiation). In some embodiments, the compound 1 hemi-fumarate salt is crystalline polymorphic Form II characterized by XRPD signals at 13.3°2θ, 15.1°2θ, 15.8°2θ, 18.8°2θ, 19.2°2θ, 20.9°2θ, 22.4°2θ, 26.9°2θ, and 30.2°2θ (±0.2°2θ; ±0.1°2θ; or ±0.0°2θ; Cu Kα1 radiation).

In some embodiments, the compound 1 hemi-fumarate salt is crystalline polymorphic Form II characterized by two or more, or three or more XRPD signals selected from the group consisting of 13.3°2θ, 15.1°2θ, 15.8°2θ, 18.8°2θ, 19.2°2θ, 20.9°2θ, 22.4°2θ, 24.7°2θ, 26.9°2θ, and 30.2°2θ (±0.2°2θ; ±0.1°2θ; or ±0.0°2θ; Cu Kα1 radiation). In some embodiments, the compound 1 hemi-fumarate salt is crystalline polymorphic Form I characterized by XRPD signals at 13.3°2θ, 15.1°2θ, 15.8°2θ, 18.8°2θ, 19.2°2θ, 20.9°2θ, 22.4°2θ, 24.7°2θ, 26.9°2θ, and 30.2°2θ (±0.2°2θ; ±0.1°2θ; or ±0.0°2θ; Cu Kα1 radiation).

In some embodiments, the compound 1 hemi-fumarate salt is crystalline polymorphic Form II characterized by two or more, or three or more XRPD signals selected from the group consisting of 13.3°2θ, 15.1°2θ, 15.8°2θ, 18.8°2θ, 19.2°2θ, 20.9°2θ, 21.4°2θ, 22.4°2θ, 24.7°2θ, 26.9°2θ, and 30.2°2θ (±0.2°2θ; ±0.1°2θ; or ±0.0°2θ; Cu Kα1 radiation). In some embodiments, the compound 1 hemi-fumarate salt is crystalline polymorphic Form II characterized by XRPD signals at 13.3°2θ, 15.1°2θ, 15.8°2θ, 18.8°2θ, 19.2°2θ, 20.9°2θ, 21.4°2θ, 22.4°2θ, 24.7°2θ, 26.9°2θ, and 30.2°2θ (±0.2°2θ, ±0.1°2θ; or ±0.0°2θ; Cu Kα1 radiation).

In some embodiments, the compound 1 hemi-fumarate salt is crystalline polymorphic Form II characterized by two or more, or three or more XRPD signals selected from the group consisting of 13.3°2θ, 15.1°2θ, 15.8°2θ, 18.8°2θ, 19.2°2θ, 20.9°2θ, 21.4°2θ, 22.4°2θ, 24.7°2θ, 26.9°2θ, 28.2°2θ, and 30.2°2θ (±0.2°2θ; ±0.1°2θ; or 0.0°2θ; Cu Kα1 radiation). In some embodiments, the compound 1 hemi-fumarate salt is crystalline polymorphic Form II characterized by XRPD signals at 13.3°2θ, 15.1°2θ, 15.8°2θ, 18.8°2θ, 19.2°2θ, 20.9°2θ, 21.4°2θ, 22.4°2θ, 24.7°2θ, 26.9°2θ, 28.2°2θ, and 30.2°2θ (±0.2°2θ; ±0.1°2θ; or ±0.0°2θ; Cu Kα1 radiation).

In some embodiments, the compound 1 hemi-fumarate salt is crystalline polymorphic Form II characterized by two or more, or three or more XRPD signals selected from the group consisting of 13.3°2θ, 13.5°2θ, 15.1°2θ, 15.8°2θ, 18.8°2θ, 19.2°2θ, 20.9°2θ, 21.4°2θ, 22.4°2θ, 24.7°2θ, 26.9°2θ, 28.2°2θ, and 30.2°2θ (±0.2°2θ; ±0.1°2θ; or ±0.0°2θ; Cu Kα1 radiation). In some embodiments, the compound 1 hemi-fumarate salt is crystalline polymorphic Form II characterized by XRPD signals at 13.3°2θ, 13.5°2θ, 15.1°2θ, 15.8°2θ, 18.8°2θ, 19.2°2θ, 20.9°2θ, 21.4°2θ, 22.4°2θ, 24.7°2θ, 26.9°2θ, 28.2°2θ, and 30.2°2θ (±0.2°2θ; ±0.1°2θ; or ±0.0°2θ; Cu Kα1 radiation).

In some embodiments, the compound 1 hemi-fumarate salt is crystalline polymorphic Form II characterized by two or more, or three or more XRPD signals selected from the group consisting of 13.3°2θ, 13.5°2θ, 15.1°2θ, 15.8°2θ, 18.8°2θ, 19.2°2θ, 20.9°2θ, 21.4°2θ, 22.4°2θ, 23.1°2θ, 24.7°2θ, 26.9°2θ, 28.2°2θ, and 30.2°2θ (±0.2°2θ; ±0.1°2θ; or ±0.0°2θ; Cu Kα1 radiation). In some embodiments, the compound 1 hemi-fumarate salt is crystalline polymorphic Form II characterized by XRPD signals at 13.3°2θ, 13.5°2θ, 15.1°2θ, 15.8°2θ, 18.8°2θ, 19.2°2θ, 20.9°2θ, 21.4°2θ, 22.4°2θ, 23.1°2θ, 24.7°2θ, 26.9°2θ, 28.2°2θ, and 30.2°2θ (±0.2°2θ; ±0.1°2θ; or ±0.0°2θ; Cu Kα1 radiation).

In some embodiments, the compound 1 hemi-fumarate salt is crystalline polymorphic Form II characterized by two or more, or three or more XRPD signals selected from the group consisting of 11.5°2θ, 13.3°2θ, 13.5°2θ, 15.1°2θ, 15.8°2θ, 18.8°2θ, 19.2°2θ, 20.9°2θ, 21.4°2θ, 22.4°2θ, 23.1°2θ, 24.7°2θ, 26.9°2θ, 28.2°2θ, and 30.2°2θ (±0.2°2θ; ±0.1°2θ; or ±0.0°2θ; Cu Kα1 radiation). In some embodiments, the compound 1 hemi-fumarate salt is crystalline polymorphic Form II characterized by XRPD signals at 11.5°2θ, 13.3°2θ, 13.5°2θ, 15.1°2θ, 15.8°2θ, 18.8°2θ, 19.2°2θ, 20.9°2θ, 21.4°2θ, 22.4°2θ, 23.1°2θ, 24.7°2θ, 26.9°2θ, 28.2°2θ, and 30.2°2θ (±0.2°2θ; ±0.1°2θ; or ±0.0°2θ; Cu Kα1 radiation).

In some embodiments, the compound 1 hemi-fumarate salt is crystalline polymorphic Form II characterized by two or more, or three or more XRPD signals selected from the group consisting of 11.5°2θ, 13.3°2θ, 13.5°2θ, 15.1°2θ, 15.8°2θ, 18.8°2θ, 19.2°2θ, 20.9°2θ, 21.4°2θ, 22.4°2θ, 23.1°2θ, 24.0°2θ, 24.7°2θ, 26.9°2θ, 28.2°2θ, and 30.2°2θ (±0.2°2θ; ±0.1°2θ; or ±0.0°2θ; Cu Kα1 radiation). In some embodiments, the compound 1 hemi-fumarate salt is crystalline polymorphic Form II characterized by XRPD signals at 11.5°2θ, 13.3°2θ, 13.5°2θ, 15.1°2θ, 15.8°2θ, 18.8°2θ, 19.2°2θ, 20.9°2θ, 21.4°2θ, 22.4°2θ, 23.1°2θ, 24.0°2θ, 24.7°2θ, 26.9°2θ, 28.2°2θ, and 30.2°2θ (±0.2°2θ; 0.1°2θ; or ±0.0°2θ; Cu Kα1 radiation).

In some embodiments, crystalline polymorphic hemi-fumarate Form II is characterized by one, two, three, four, five, six, seven, eight, or nine XRPD signals selected from those set forth in Table 35.

TABLE 35

Signal angle data of Form II (±0.2 °2θ; ±0.1 °2θ; or ±0.0 °2θ; Cu Kα1 radiation)

| Signal number | 2-θ (°) | d Value | Net Intensity (counts) | Gross Intensity (counts) | Rel. Intensity (%) |
|---|---|---|---|---|---|
| Signal #1 | 11.5 | 7.66 | 194.5 | 253.7 | 11.8 |
| Signal #2 | 13.3 | 6.66 | 224.6 | 283.6 | 13.6 |
| Signal #3 | 13.5 | 6.54 | 208.8 | 268.5 | 12.6 |
| Signal #4 | 15.1 | 5.87 | 501.5 | 579.0 | 30.3 |
| Signal #5 | 15.8 | 5.62 | 1653.8 | 1737.1 | 100.0 |
| Signal #6 | 18.8 | 4.72 | 318.4 | 414.1 | 19.3 |
| Signal #7 | 19.2 | 4.61 | 717.1 | 814.7 | 43.4 |
| Signal #8 | 20.9 | 4.25 | 1133.9 | 1234.5 | 68.6 |
| Signal #9 | 21.4 | 4.14 | 215.3 | 317.8 | 13.0 |
| Signal #10 | 22.4 | 3.97 | 458.2 | 563.5 | 27.7 |
| Signal #11 | 23.1 | 3.85 | 208.3 | 312.7 | 12.6 |
| Signal #12 | 24.0 | 3.71 | 176.4 | 273.7 | 10.7 |
| Signal #13 | 24.7 | 3.60 | 219.7 | 305.7 | 13.3 |
| Signal #14 | 26.9 | 3.31 | 726.9 | 822.0 | 44.0 |
| Signal #15 | 28.2 | 3.16 | 215.2 | 312.5 | 13.0 |
| Signal #16 | 30.2 | 2.96 | 249.3 | 330.5 | 15.1 |

Compound 1 Fumarate Salt: Pattern 3a

Figure 70:
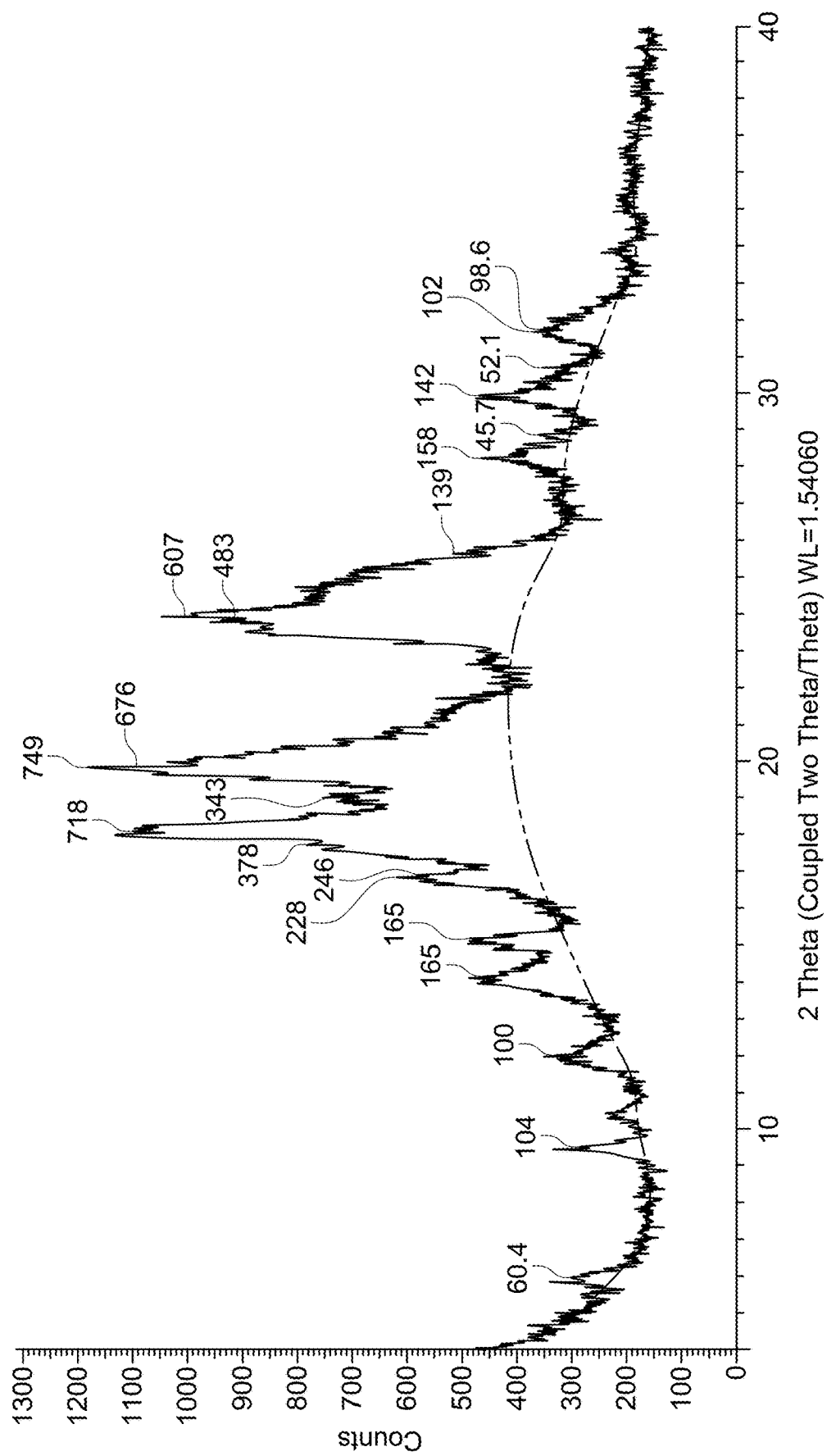
FIG. 70 shows a XRPD profile of crystalline compound 1 (wet pellet, Pattern #3a)

In some embodiments, the compound 1 fumarate salt is Pattern 3a crystalline polymorph. In some embodiments, the Pattern 3a crystalline polymorph is characterized by the XRPD signals set for the below in Table 36 or 37. In some embodiments, the Pattern 3a crystalline polymorph XRPD pattern is substantially similar to that shown in FIG. 68 or 70.

In some embodiments, the compound 1 fumarate salt is crystalline polymorphic Pattern 3a characterized by an XRPD signal at 23.9°2θ (±0.2°2θ; ±0.1°2θ; or ±0.0°2θ; Cu Kα1 radiation).

In some embodiments, the compound 1 fumarate salt is crystalline polymorphic Pattern 3a characterized by XRPD signals at 17.9°2θ and 23.9°2θ (±0.2°2θ; ±0.1°2θ; or ±0.0°2θ; Cu Kα1 radiation).

In some embodiments, the compound 1 fumarate salt is crystalline polymorphic Pattern 3a characterized by two or more, or three or more XRPD signals selected from the group consisting 10 of 17.9°2θ, 19.7°2θ, and 23.9°2θ (±0.2°2θ; ±0.1°2θ; or ±0.0°2θ; Cu Kα1 radiation). In some embodiments, the compound 1 fumarate salt is crystalline polymorphic Pattern 3a characterized by XRPD signals at 17.9°2θ, 19.7°2θ, and 23.9°2θ (±0.2°2θ; ±0.1°2θ; or ±0.0°2θ; Cu Kα1 radiation).

In some embodiments, the compound 1 fumarate salt is crystalline polymorphic Pattern 3a characterized by two or more, or three or more XRPD signals selected from the group consisting of 17.9°2θ, 19.7°2θ, 20.5°2θ, and 23.9°2θ (±0.2°2θ; ±0.1°2θ; or 0.0°2θ; Cu Kα1 radiation).

In some embodiments, the compound 1 fumarate salt is crystalline polymorphic Pattern 3a characterized by XRPD signals at 17.9°2θ, 19.7°2θ, 20.5°2θ, and 23.9°2θ (±0.2°2θ; ±0.1°2θ; or ±0.0°2θ; Cu Kα1 radiation).

In some embodiments, the compound 1 fumarate salt is crystalline polymorphic Pattern 3a characterized by two or more, or three or more XRPD signals selected from the group consisting of 17.9°2θ, 19.7°2θ, 20.5°2θ, 23.9°2θ, and 24.9°2θ (±0.2°2θ; ±0.1°2θ; or ±0.0°2θ; Cu Kα1 radiation). In some embodiments, the compound 1 fumarate salt is crystalline polymorphic Pattern 3a characterized by XRPD signals at 17.9°2θ, 19.7°2θ, 20.5°2θ, 23.9°2θ, and 24.9°2θ (±0.2°2θ; ±0.1°2θ, or 0.0°2θ; Cu Kα1 radiation).

In some embodiments, the compound 1 fumarate salt is crystalline polymorphic Pattern 3a characterized by two or more, or three or more XRPD signals selected from the group consisting of 17.9°2θ, 19.7°2θ, 20.5°2θ, 23.9°2θ, 24.9°2θ, and 25.2°2θ (±0.2°2θ; ±0.1°2θ; or ±0.0°2θ; Cu Kα1 radiation). In some embodiments, the compound 1 fumarate salt is crystalline 30 polymorphic Pattern 3a characterized by XRPD signals at 17.9°2θ, 19.7°2θ, 20.5°2θ, 23.9°2θ, 24.9°2θ, and 25.2°2θ (±0.2°2θ; ±0.1°2θ; or ±0.0°2θ; Cu Kα1 radiation).

In some embodiments, the compound 1 fumarate salt is crystalline polymorphic Pattern 3a characterized by two or more, or three or more XRPD signals selected from the group consisting of 16.9°2θ, 17.9°2θ, 19.7°2θ, 20.5°2θ, 23.9°2θ, 24.9°2θ, and 25.2°2θ (±0.2°2θ; ±0.1°2θ; or ±0.0°2θ; Cu Kα1 radiation). In some embodiments, the compound 1 fumarate salt is crystalline polymorphic Pattern 3a characterized by XRPD signals at 16.9°2θ, 17.9°2θ, 19.7°2θ, 20.5°2θ, 23.9°2θ, 24.9°2θ, and 25.2°2θ (±0.2°2θ; ±0.1°2θ; or ±0.0°2θ; Cu Kα1 radiation).

In some embodiments, the compound 1 fumarate salt is crystalline polymorphic Pattern 3a characterized by two or more, or three or more XRPD signals selected from the group consisting of 13.9°2θ, 16.9°2θ, 17.9°2θ, 19.7°2θ, 20.5°2θ, 23.9°2θ, 24.9°2θ, and 25.2°2θ (±0.2°2θ; ±0.1°2θ; or ±0.0°2θ; Cu Kα1 radiation). In some embodiments, the compound 1 fumarate salt is crystalline polymorphic Pattern 3a characterized by XRPD signals at 13.9°2θ, 16.9°2θ, 17.9°2θ, 19.7°2θ, 20.5°2θ, 23.9°2θ, 24.9°2θ, and 25.2°2θ (±0.2°2θ; ±0.1°2θ; or ±0.0°2θ; Cu Kα1 radiation).

In some embodiments, the compound 1 fumarate salt is crystalline polymorphic Pattern 3a characterized by two or more, or three or more XRPD signals selected from the group consisting of 13.9°2θ, 16.9°2θ, 17.9°2θ, 19.7°2θ, 20.5°2θ, 23.9°2θ, 24.9°2θ, 25.2°2θ, and 29.8°2θ (±0.2°2θ; ±0.1°2θ; or ±0.0°2θ; Cu Kα1 radiation). In some embodiments, the compound 1 fumarate salt is crystalline polymorphic Pattern 3a characterized by XRPD signals at 13.9°2θ, 16.9°2θ, 17.9°2θ, 19.7°2θ, 20.5°2θ, 23.9°2θ, 24.9°2θ, 25.2°2θ, and 29.8°2θ (±0.2°2θ; ±0.1°2θ; or ±0.0°2θ; Cu Kα1 radiation).

In some embodiments, the compound 1 fumarate salt is crystalline polymorphic Pattern 3a characterized by two or more, or three or more XRPD signals selected from the group consisting of 13.9°2θ, 15.2°2θ, 16.9°2θ, 17.9°2θ, 19.7°2θ, 20.5°2θ, 23.9°2θ, 24.9°2θ, 25.2°2θ, and 29.8°2θ (±0.2°2θ; ±0.1°2θ; or ±0.0°2θ; Cu Kα1 radiation).

In some embodiments, the compound 1 fumarate salt is crystalline polymorphic Pattern 3a characterized by two or more, or three or more XRPD signals selected from the group consisting 30 of 13.9°2θ, 15.2°2θ, 16.9°2θ, 17.9°2θ, 19.7°2θ, 20.5°2θ, 23.9°2θ, 24.9°2θ, 25.2°2θ, 28.5°2θ, and 29.8°2θ (±0.2°2θ; ±0.1°2θ; or ±0.0°2θ; Cu Kα1 radiation). In some embodiments, the compound 1 fumarate salt is crystalline polymorphic Pattern 3a characterized by XRPD signals at 13.9°2θ, 15.2°2θ, 16.9°2θ, 17.9°2θ, 19.7°2θ, 20.5°2θ, 23.9°2θ, 24.9°2θ, 25.2°2θ, 28.5°2θ, and 29.8°2θ (±0.2°2θ; ±0.1°2θ; or ±0.0°2θ; Cu Kα1 radiation).

In some embodiments, the compound 1 fumarate salt is crystalline polymorphic Pattern 3a characterized by two or more, or three or more XRPD signals selected from the group consisting of 9.6°2θ, 13.9°2θ, 15.2°2θ, 16.9°2θ, 17.9°2θ, 19.7°2θ, 20.5°2θ, 23.9°2θ, 24.9°2θ, 25.2°2θ, 28.5°2θ, and 29.8°2θ (±0.2°2θ; ±0.1°2θ; or ±0.0°2θ; Cu Kα1 radiation). In some embodiments, the compound 1 fumarate salt is crystalline polymorphic Pattern 3a characterized by XRPD signals at 9.6°2θ, 13.9°2θ, 15.2°2θ, 16.9°2θ, 17.9°2θ, 19.7°2θ, 20.5°2θ, 23.9°2θ, 24.9°2θ, 25.2°2θ, 28.5°2θ, and 29.8°2θ (±0.2°2θ; ±0.1°2θ; or ±0.0°2θ; Cu Kα1 radiation).

In some embodiments, crystalline polymorphic Pattern 3a is characterized by one, two, three, four, five, six, seven, eight, nine, ten, eleven, or twelve XRPD signals selected from those set forth in Table 36.

TABLE 36

Signal angle data of Pattern #3a (±0.2 °2θ; ±0.1 °2θ; or ±0.0 °2θ; Cu Kα1 radiation)

| Signal number | 2-θ (°) | d Value | Net Intensity (counts) | Gross Intensity (counts) | Rel. Intensity (%) |
| --- | --- | --- | --- | --- | --- |
| Signal #2 | 9.6 | 9.22 | 120.7 | 278.0 | 13.3 |
| Signal #6 | 13.9 | 6.35 | 281.2 | $ 32.2 | 31.1 |
| Signal #7 | 15.2 | 5.83 | 179.0 | 451.4 | 19.8 |
| Signal #8 | 16.9 | 5.24 | 302.2 | 623.0 | 33.4 |
| Signal #9 | 17.9 | 4.95 | 836.9 | 1191.4 | 92.4 |
| Signal #10 | 19.7 | 4.51 | 689.3 | 1085.0 | 76.1 |
| Signal #11 | 20.5 | 4.33 | 531.8 | 939.2 | 58.7 |
| Signal #12 | 23.9 | 3.73 | 905.6 | 1309.3 | 100.0 |
| Signal #13 | 24.9 | 3.57 | 452.6 | 838.1 | 50.0 |
| Signal #14 | 25.2 | 3.53 | 400.2 | 778.8 | 44.2 |
| Signal #15 | 28.5 | 3.13 | 130.4 | 469.6 | 14.4 |
| Signal #16 | 29.8 | 2.99 | 272.1 | 594.7 | 30.0 |

In some embodiments, the compound 1 fumarate salt is crystalline polymorphic Pattern 3a characterized by an XRPD signal at 19.8°2θ (±0.2°2θ; ±0.1°2θ; or ±0.0°2θ; Cu Kα1 radiation).

In some embodiments, the compound 1 fumarate salt is crystalline polymorphic Pattern 3a characterized by XRPD signals at 18.1°2θ, and 19.8°2θ (±0.2°2θ; ±0.1°2θ; or ±0.0°2θ; Cu Kα1 radiation).

In some embodiments, the compound 1 fumarate salt is crystalline polymorphic Pattern 3a characterized by two or more, or three or more XRPD signals selected from the group consisting of 18.1°2θ, 19.8°2θ, and 19.9°2θ (±0.2°2θ; ±0.1°2θ; or ±0.0°2θ; Cu Kα1 radiation). In some embodiments, the compound 1 fumarate salt is crystalline polymorphic Pattern 3a characterized by XRPD signals at 18.1°2θ, 19.8°2θ, and 19.9°2θ (±0.2°2θ; ±0.1°2θ; or ±0.0°2θ; Cu Kα1 radiation).

In some embodiments, the compound 1 fumarate salt is crystalline polymorphic Pattern 3a characterized by two or more, or three or more XRPD signals selected from the group consisting of 18.1°2θ, 19.8°2θ, 19.9°2θ, and 24.0°2θ (±0.2°2θ; ±0.1°2θ; or ±0.0°2θ; Cu Kα1 radiation).

In some embodiments, the compound 1 fumarate salt is crystalline polymorphic Pattern 3a characterized by XRPD signals at 18.1°2θ, 19.8°2θ, 19.9°2θ, and 24.0°2θ (±0.2°2θ; ±0.1°2θ; or ±0.0°2θ; Cu Kα1 radiation).

In some embodiments, the compound 1 fumarate salt is crystalline polymorphic Pattern 3a characterized by two or more, or three or more XRPD signals selected from the group consisting of 18.1°2θ, 19.8°2θ, 19.9°2θ, 23.6°2θ, and 24.0°2θ (±0.2°2θ; ±0.1°2θ; or ±0.0°2θ; Cu Kα1 radiation).

In some embodiments, the compound 1 fumarate salt is crystalline polymorphic Pattern 3a characterized by XRPD signals at 18.1°2θ, 19.8°2θ, 19.9°2θ, 23.6°2θ, and 24.0°2θ (±0.2°2θ; ±0.1°2θ; or ±0.0°2θ; Cu Kα1 radiation).

In some embodiments, the compound 1 fumarate salt is crystalline polymorphic Pattern 3a characterized by two or more, or three or more XRPD signals selected from the group consisting of 17.6°2θ, 18.1°2θ, 19.8°2θ, 19.9°2θ, 23.6°2θ, and 24.0°2θ (±0.2°2θ; ±0.1°2θ; or ±0.0°2θ; Cu Kα1 radiation). In some embodiments, the compound 1 fumarate salt is crystalline polymorphic Pattern 3a characterized by XRPD signals at 17.6°2θ, 18.1°2θ, 19.8°2θ, 19.9°2θ, 23.6°2θ, and 24.0°2θ (±0.2°2θ; ±0.1°2θ; or ±0.0°2θ; Cu Kα1 radiation).

In some embodiments, the compound 1 fumarate salt is crystalline polymorphic Pattern 3a characterized by two or more, or three or more XRPD signals selected from the group consisting of 17.6°2θ, 18.1°2θ, 19.0°2θ, 19.8°2θ, 19.9°2θ, 23.6°2θ, and 24.0°2θ (±0.2°2θ; ±0.1°2θ; or ±0.0°2θ; Cu Kα1 radiation). In some embodiments, the compound 1 fumarate salt is crystalline polymorphic Pattern 3a characterized by XRPD signals at 17.6°2θ, 18.1°2θ, 19.0°2θ, 19.8°2θ, 19.9°2θ, 23.6°2θ, and 24.0°2θ (±0.2°2θ; ±0.1°2θ; or ±0.0°2θ; Cu Kα1 radiation).

In some embodiments, the compound 1 fumarate salt is crystalline polymorphic Pattern 3a characterized by two or more, or three or more XRPD signals selected from the group consisting of 16.8°2θ, 17.6°2θ, 18.1°2θ, 19.0°2θ, 19.8°2θ, 19.9°2θ, 23.6°2θ, and 24.0°2θ (±0.2°2θ; ±0.1°2θ; or ±0.0°2θ; Cu Kα1 radiation). In some embodiments, the compound 1 fumarate salt is crystalline polymorphic Pattern 3a characterized by XRPD signals at 16.8°2θ, 17.6°2θ, 18.1°2θ, 19.0°2θ, 19.8°2θ, 19.9°2θ, 23.6°2θ, and 24.0°2θ (±0.2°2θ; ±0.1°2θ; or ±0.0°2θ; Cu Kα1 radiation).

In some embodiments, the compound 1 fumarate salt is crystalline polymorphic Pattern 3a characterized by two or more, or three or more XRPD signals selected from the group consisting of 14.1°2θ, 16.8°2θ, 17.6°2θ, 18.1°2θ, 19.0°2θ, 19.8°2θ, 19.9°2θ, and 24.0°2θ (±0.2 15°2θ; ±0.1°2θ; or ±0.0°2θ; Cu Kα1 radiation). In some embodiments, the compound 1 fumarate salt is crystalline polymorphic Pattern 3a characterized by XRPD signals at 14.1°2θ, 16.8°2θ, 17.6°2θ, 18.1°2θ, 19.0°2θ, 19.8°2θ, 19.9°2θ, 23.6°2θ, and 24.0°2θ (±0.2°2θ; ±0.1°2θ; or ±0.0°2θ; Cu Kα1 radiation).

In some embodiments, the compound 1 fumarate salt is crystalline polymorphic Pattern 3a characterized by two or more, or three or more XRPD signals selected from the group consisting of 14.1°2θ, 15.1°2θ, 16.8°2θ, 17.6°2θ, 18.1°2θ, 19.0°2θ, 19.8°2θ, 19.9°2θ, 23.6°2θ, and 24.0°2θ (±0.2°2θ; ±0.1°2θ; or ±0.0°2θ; Cu Kα1 radiation). In some embodiments, the compound 1 fumarate salt is crystalline polymorphic Pattern 3a characterized by XRPD signals at 14.1°2θ, 15.1°2θ, 16.8°2θ, 17.6°2θ, 18.1°2θ, 19.0°2θ, 19.8°2θ, 19.9°2θ, 23.6°2θ, and 24.0°2θ (±0.2 25°2θ; ±0.1°2θ; or ±0.0°2θ; Cu Kα1 radiation).

In some embodiments, the compound 1 fumarate salt is crystalline polymorphic Pattern 3a characterized by two or more, or three or more XRPD signals selected from the group consisting of 14.1°2θ, 15.1°2θ, 16.8°2θ, 17.6°2θ, 18.1°2θ, 19.0°2θ, 19.8°2θ, 19.9°2θ, 23.6°2θ, 24.0°2θ, and 28.3°2θ (±0.2°2θ; ±0.1°2θ; or ±0.0°2θ; Cu Kα1 radiation). In some embodiments, the compound 1 fumarate salt is crystalline polymorphic Pattern 3a characterized by XRPD signals at 14.1°2θ, 15.1°2θ, 16.8°2θ, 17.6°2θ, 18.1°2θ, 19.0°2θ, 19.8°2θ, 19.9°2θ, 23.6°2θ, 24.0°2θ, and 28.3°2θ (±0.2°2θ; ±0.1°2θ; or ±0.0°2θ; Cu Kα1 radiation).

In some embodiments, the compound 1 fumarate salt is crystalline polymorphic Pattern 3a characterized by two or more, or three or more XRPD signals selected from the group consisting of 14.1°2θ, 15.1°2θ, 16.8°2θ, 17.6°2θ, 18.1°2θ, 19.0°2θ, 19.8°2θ, 19.9°2θ, 23.6°2θ, 24.0°2θ, 28.3°2θ, and 30.0°2θ (±0.2°2θ; ±0.1°2θ; or ±0.0°2θ; Cu Kα1 radiation). In some embodiments, the compound 1 fumarate salt is crystalline polymorphic Pattern 3a characterized by XRPD signals at 14.1°2θ, 15.1°2θ, 16.8°2θ, 17.6°2θ, 18.1°2θ, 19.0°2θ, 19.8°2θ, 19.9°2θ, 23.6°2θ, 24.0°2θ, 28.3°2θ, and 30.0°2θ (±0.2°2θ; ±0.1°2θ; or ±0.0°2θ; Cu Kα1 radiation).

In some embodiments, the compound 1 fumarate salt is crystalline polymorphic Pattern 3a characterized by two or more, or three or more XRPD signals selected from the group consisting of 14.1°2θ, 15.1°2θ, 16.8°2θ, 17.6°2θ, 18.1°2θ, 19.0°2θ, 19.8°2θ, 19.9°2θ, 23.6°2θ, 24.0°2θ, 25.7°2θ, 28.3°2θ, and 30.0°2θ (±0.2°2θ; ±0.1°2θ; or ±0.0°2θ; Cu Kα1 radiation). In some embodiments, the compound 1 fumarate salt is crystalline polymorphic Pattern 3a characterized by XRPD signals at 14.1°2θ, 15.1°2θ, 16.8°2θ, 17.6°2θ, 18.1°2θ, 19.0°2θ, 19.8°2θ, 19.9°2θ, 23.6°2θ, 24.0°2θ, 25.7°2θ, 28.3°2θ, and 30.0°2θ (±0.2°2θ; ±0.1°2θ; or ±0.0°2θ; Cu Kα1 radiation).

In some embodiments, the compound 1 fumarate salt is crystalline polymorphic Pattern 3a characterized by two or more, or three or more XRPD signals selected from the group consisting of 9.5°2θ, 14.1°2θ, 15.1°2θ, 16.8°2θ, 17.6°2θ, 18.1°2θ, 19.0°2θ, 19.8°2θ, 19.9°2θ, 23.6°2θ, 24.0°2θ, 25.7°2θ, 28.3°2θ, and 30.0°2θ (±0.2°2θ; ±0.1°2θ; or ±0.0°2θ; Cu Kα1 radiation). In some embodiments, the compound 1 fumarate salt is crystalline polymorphic Pattern 3a characterized by XRPD signals at 9.5°2θ, 14.1°2θ, 15.1°2θ, 16.8°2θ, 17.6°2θ, 18.1°2θ, 19.0°2θ, 19.8°2θ, 19.9°2θ, 23.6°2θ, 24.0°2θ, 25.7°2θ, 28.3°2θ, and 30.0°2θ (±0.2°2θ; ±0.1°2θ; or ±0.0°2θ; Cu Kα1 radiation).

In some embodiments, the compound 1 fumarate salt is crystalline polymorphic Pattern 3a characterized by two or more, or three or more XRPD signals selected from the group consisting of 9.5°2θ, 11.9°2θ, 14.1°2θ, 15.1°2θ, 16.8°2θ, 17.6°2θ, 18.1°2θ, 19.0°2θ, 19.8°2θ, 19.9°2θ, 23.6°2θ, 24.0°2θ, 25.7°2θ, 28.3°2θ, and 30.0°2θ (±0.2°2θ; ±0.1°2θ; or ±0.0°2θ; Cu Kα1 radiation). In some embodiments, the compound 1 fumarate salt is crystalline polymorphic Pattern 3a characterized by XRPD signals at 9.5°2θ, 11.9°2θ, 14.1°2θ, 15.1°2θ, 16.8°2θ, 17.6°2θ, 18.1°2θ, 19.0°2θ, 19.8°2θ, 19.9°2θ, 23.6°2θ, 24.0°2θ, 25.7°2θ, 28.3°2θ and 30.0°2θ (±0.2°2θ; ±0.1°2θ or ±0.0°2θ; Cu Kα1 radiation).

In some embodiments, the compound 1 fumarate salt is crystalline polymorphic Pattern 3a characterized by two or more, or three or more XRPD signals selected from the group consisting of 9.5°2θ, 11.9°2θ, 14.1°2θ, 15.1°2θ, 16.82°2θ, 17.6°2θ, 18.1°2θ, 19.0°2θ, 19.82°2θ, 19.9°2θ, 23.6°2θ, 24.0°2θ, 25.7°2θ, 28.3°2θ, 30.0°2θ, and 31.7°2θ (±0.2°2θ; ±0.1°2θ; or ±0.0°2θ; Cu Kα1 radiation). In some embodiments, the compound 1 fumarate salt is crystalline polymorphic Pattern 3a characterized by XRPD signals at 9.5°2θ. 11.9°2θ, 14.1°2θ, 15.1°2θ, 16.8°2θ 17.6°2θ, 18.1°2θ, 19.0°2θ, 19.8°2θ, 19.9°2θ, 23.6°2θ, 24.0°2θ, 25.7°2θ, 28.3°2θ, 30.0°2θ, and 31.7°2θ (±0.2°2θ; ±0.1°2θ; or ±0.0°2θ; Cu Kα1 radiation).

In some embodiments, crystalline polymorphic Pattern 3a is characterized by one, two, three, four, five, six, seven, eight, nine, ten, eleven, twelve, thirteen, fourteen, fifteen, sixteen, or seventeen XRPD signals selected from those set forth in Table 37.

TABLE 37

Signal angle data of 3a (±0.2 °2θ; ±0.1 °2θ; or ±0.0 °2θ; Cu Kα1 radiation)

| Signal number | 2-θ (°) | d Value | Net Intensity (counts) | Gross Intensity (counts) | Rel. Intensity (%) |
|---|---|---|---|---|---|
| Signal #1 | 9.5 | 9.32 | 103.8 | 675.8 | 13.9 |
| Signal #2 | 11.9 | 7.42 | 100.1 | 711.3 | 13.4 |
| Signal #3 | 14.1 | 6.28 | 164.5 | 845.0 | 22.0 |
| Signal #4 | 15.1 | 5.85 | 164.5 | 874.9 | 22.0 |
| Signal #5 | 16.8 | 5.26 | 246.2 | 1007.3 | 32.9 |
| Signal #6 | 17.6 | 5.02 | 378.0 | 1158.8 | 50.5 |
| Signal #7 | 18.1 | 4.89 | 717.6 | 1508.4 | 95.8 |
| Signal #8 | 19.0 | 4.66 | 342.8 | 1147.4 | 45.8 |
| Signal #9 | 19.8 | 4.47 | 749.1 | 1561.2 | 100.0 |
| Signal #10 | 19.9 | 4.45 | 676.1 | 1488.8 | 90.2 |
| Signal #11 | 23.6 | 3.76 | 482.6 | 1276.6 | 64.4 |
| Signal #12 | 24.0 | 3.71 | 606.7 | 1395.2 | 81.0 |
| Signal #13 | 25.7 | 3.46 | 139.3 | 888.4 | 18.6 |
| Signal #14 | 28.3 | 3.16 | 158.3 | 868.8 | 21.1 |
| Signal #15 | 30.0 | 2.98 | 141.5 | 826.4 | 18.9 |
| Signal #16 | 31.7 | 2.82 | 102.1 | 747.4 | 13.6 |
| Signal #17 | 31.7 | 2.82 | 98.6 | 741.8 | 13.2 |

Compound 1 Fumarate Salt: Pattern 5

In some embodiments, the compound 1 fumarate salt is Pattern 5 crystalline polymorph. In some embodiments, the Pattern 5 crystalline polymorph is characterized by the XRPD signals set for the below in Table 38. In some embodiments, the Pattern 5 crystalline polymorph XRPD pattern is substantially similar to that shown in FIG. 1. In some embodiments, the Pattern 5 crystalline polymorph $^1$H-NMR spectrum is substantially similar to that shown in FIG. 39. In some embodiments, the Pattern 5 crystalline polymorph TGA spectrum is substantially similar to that shown in FIG. 40.

In some embodiments, the compound 1 fumarate salt is crystalline polymorphic Pattern 5 characterized by an XRPD signal at 7.9°2θ (±0.2°2θ; ±0.1°2θ; or ±0.0°2θ; Cu Kα1 radiation).

In some embodiments, the compound 1 fumarate salt is crystalline polymorphic Pattern 5 characterized by XRPD signals at 7.9°2θ and 21.6°2θ (±0.2°2θ; ±0.1°2θ; or ±0.0°2θ; Cu Kα1 radiation).

In some embodiments, the compound 1 fumarate salt is crystalline polymorphic Pattern 5 characterized by two or more, or three or more XRPD signals selected from the group consisting of 7.9°2θ, 20.2°2θ, and 21.6°2θ (±0.2°2θ; ±0.1°2θ; or ±0.0°2θ; Cu Kα1 radiation). In some embodiments, the compound 1 fumarate salt is crystalline polymorphic Pattern 5 characterized by XRPD signals at 7.9°2θ, 20.2°2θ, and 21.6°2θ (±0.2°2θ; ±0.1°2θ; or ±0.0°2θ; Cu Kα1 radiation).

In some embodiments, the compound 1 fumarate salt is crystalline polymorphic Pattern 5 characterized by two or more, or three or more XRPD signals selected from the group consisting of 7.9°2θ, 20.2°2θ, 21.6°2θ, and 23.7°2θ (±0.2°2θ; ±0.1°2θ; or ±0.0°2θ; Cu Kα1 radiation).

In some embodiments, the compound 1 fumarate salt is crystalline polymorphic Pattern 5 characterized by XRPD signals at 7.9°2θ, 20.2°2θ, 21.6°2θ, and 23.7°2θ (±0.2°2θ; ±0.1°2θ; or ±0.0°2θ; Cu Kα1 radiation).

In some embodiments, the compound 1 fumarate salt is crystalline polymorphic Pattern 5 characterized by two or more, or three or more XRPD signals selected from the group consisting of 7.9°2θ, 15.7°2θ, 20.2°2θ, 21.6°2θ, and 23.7°2θ (±0.2°2θ; ±0.1°2θ; or ±0.0°2θ; Cu Kα1 radiation). In some embodiments, the compound 1 fumarate salt is crystalline polymorphic Pattern 5 characterized by XRPD signals at 7.9°2θ, 15.7°2θ, 20.2°2θ, 21.6°2θ, and 23.7°2θ (±0.2°2θ; ±0.1°2θ; or ±0.0°2θ; Cu Kα1 radiation).

In some embodiments, crystalline polymorphic Pattern 5 is characterized by one, two, three, four, or five XRPD signals selected from those set forth in Table 38.

TABLE 38

Signal angle data of Compound 1 Pattern 5 Fumarate Salt (±0.2 °2θ; ±0.1 °2θ; or ±0.0 °2θ; Cu Kα1 radiation)

| Signal number | 2-θ (°) | d Value | Net Intensity (counts) | Gross Intensity (counts) | Rel. Intensity (%) |
|---|---|---|---|---|---|
| Signal #1 | 7.9 | 11.25 | 36879.1 | 37068.4 | 100.0 |
| Signal #2 | 15.7 | 5.63 | 4937.8 | 5117.8 | 13.4 |
| Signal #3 | 20.2 | 4.39 | 8240.2 | 8524.7 | 22.3 |
| Signal #4 | 21.6 | 4.11 | 8758.6 | 9090.9 | 23.7 |
| Signal #5 | 23.7 | 3.76 | 6271.1 | 6582.0 | 17.0 |

Compound 1 Fumarate—Pattern 6

In some embodiments, the compound 1 fumarate salt is Pattern 6 crystalline polymorph. In some embodiments, the Pattern 6 crystalline polymorph is characterized by the XRPD signals set for the below in Table 39. In some embodiments, the Pattern 6 crystalline polymorph XRPD pattern is substantially similar to that shown in FIG. 71.

In some embodiments, the compound 1 fumarate salt is crystalline polymorphic Pattern 6 characterized by an XRPD signal at 19.3°2θ (±0.2°2θ; ±0.1°2θ; or ±0.0°2θ; Cu Kα1 radiation).

In some embodiments, the compound 1 fumarate salt is crystalline polymorphic Pattern 6 characterized by XRPD signals at 8.2°2θ and 19.3°2θ (±0.2°2θ; ±0.1°2θ; or ±0.0°2θ; Cu Kα1 radiation).

In some embodiments, the compound 1 fumarate salt is crystalline polymorphic Pattern 6 characterized by two or more, or three or more XRPD signals selected from the group consisting of 8.2°2θ, 19.3°2θ, and 20.2°2θ (±0.2°2θ; ±0.1°2θ; or ±0.0°2θ; Cu Kα1 radiation). In some embodiments, the compound 1 fumarate salt is crystalline polymorphic Pattern 6 characterized by XRPD signals at 8.2°2θ, 19.3°2θ, and 20.2°2θ (±0.2°2θ; ±0.1°2θ; or ±0.0°2θ; Cu Kα1 radiation).

In some embodiments, the compound 1 fumarate salt is crystalline polymorphic Pattern 6 characterized by two or more, or three or more XRPD signals selected from the group consisting of 8.2°2θ, 19.3°2θ, 20.2°2θ, and 21.7°2θ (±0.2°2θ; ±0.1°2θ; or ±0.0°2θ; Cu Kα1 radiation).

In some embodiments, the compound 1 fumarate salt is crystalline polymorphic Pattern 6 characterized by XRPD signals at 8.2°2θ, 19.3°2θ, 20.2°2θ, and 21.7°2θ (±0.2°2θ; ±0.1°2θ, or ±0.0°2θ; Cu Kα1 radiation).

In some embodiments, the compound 1 fumarate salt is crystalline polymorphic Pattern 6 characterized by two or more, or three or more XRPD signals selected from the group consisting of 8.2°2θ, 19.3°2θ, 20.2°2θ, 21.7°2θ, and 23.2°2θ (±0.2°2θ; ±0.1°2θ; or ±0.0°2θ; Cu Kα1 radiation).

In some embodiments, the compound 1 fumarate salt is crystalline polymorphic Pattern 6 characterized by XRPD signals at 8.2°2θ, 19.3°2θ, 20.2°2θ, 21.7°2θ, and 23.2°2θ (±0.2°2θ; ±0.1°2θ; or ±0.0°2θ; Cu Kα1 radiation).

In some embodiments, the compound 1 fumarate salt is crystalline polymorphic Pattern 6 characterized by two or more, or three or more XRPD signals selected from the group consisting of 8.2°2θ, 19.3°2θ, 20.2°2θ, 21.7°2θ, 23.2°2θ, and 23.8°2θ (±0.2°2θ; ±0.1°2θ; or ±0.0°2θ; Cu Kα1 radiation). In some embodiments, the compound 1 fumarate salt is crystalline polymorphic Pattern 6 characterized by XRPD signals at 8.2°2θ, 19.3°2θ, 20.2°2θ, 21.7°2θ, 23.2°2θ, and 23.8°2θ (±0.2°2θ; ±0.1°2θ; or ±0.0°2θ; Cu Kα1 radiation).

In some embodiments, the compound 1 fumarate salt is crystalline polymorphic Pattern 6 characterized by two or more, or three or more XRPD signals selected from the group consisting of 8.2°2θ, 18.4°2θ, 19.3°2θ, 20.2°2θ, 21.7°2θ, 23.2°2θ, and 23.8°2θ (±0.2°2θ; ±0.1°2θ; or ±0.0°2θ; Cu Kα1 radiation). In some embodiments, the compound 1 fumarate salt is crystalline polymorphic Pattern 6 characterized by XRPD signals at 8.2°2θ, 18.4°2θ, 19.3°2θ, 20.2°2θ, 21.7°2θ, 23.2°2θ, and 23.8°2θ (±0.2°2θ; ±0.1°2θ; or ±0.0°2θ; Cu Kα1 radiation).

In some embodiments, the compound 1 fumarate salt is crystalline polymorphic Pattern 6 characterized by two or more, or three or more XRPD signals selected from the group consisting of 8.2°2θ, 12.3°2θ, 18.4°2θ, 19.3°2θ, 20.2°2θ, 21.7°2θ, 23.2°2θ, and 23.8°2θ (±0.2°2θ; ±0.1°2θ; or ±0.0°2θ; Cu Kα1 radiation). In some embodiments, the compound 1 fumarate salt is crystalline polymorphic Pattern 6 characterized by XRPD signals at 8.2°2θ, 12.3°2θ, 18.4°2θ, 19.3°2θ, 20.2°2θ, 21.7°2θ, 23.2°2θ, and 23.8°2θ (±0.2°2θ; ±0.1°2θ; or ±0.0°2θ; Cu Kα1 radiation).

In some embodiments, the compound 1 fumarate salt is crystalline polymorphic Pattern 6 characterized by two or more, or three or more XRPD signals selected from the group consisting of 8.2°2θ, 12.3°2θ, 14.9°2θ, 18.4°2θ, 19.3°2θ, 20.2°2θ, 21.7°2θ, 23.2°2θ, and 23.8°2θ (±0.2 20°2θ; ±0.1°2θ; or ±0.0°2θ; Cu Kα1 radiation). In some embodiments, the compound 1 fumarate salt is crystalline polymorphic Pattern 6 characterized by XRPD signals at 8.2°2θ, 12.3°2θ, 14.9°2θ, 18.4°2θ, 19.3°2θ, 20.2°2θ, 21.7°2θ, 23.2°2θ, and 23.8°2θ (±0.2°2θ; ±0.1°2θ; or ±0.0°2θ; Cu Kα1 radiation).

In some embodiments, the compound 1 fumarate salt is crystalline polymorphic Pattern 6 characterized by two or more, or three or more XRPD signals selected from the group consisting of 8.2°2θ, 12.3°2θ, 14.9°2θ, 18.4°2θ, 19.3°2θ, 20.2°2θ, 20.9°2θ, 21.7°2θ, 23.2°2θ, and 23.8°2θ (±0.2°2θ; ±0.1°2θ; or ±0.0°2θ; Cu Kα1 radiation). In some embodiments, the compound 1 fumarate salt is crystalline polymorphic Pattern 6 characterized by XRPD signals at 8.2°2θ, 12.3°2θ, 14.9°2θ, 18.4°2θ, 19.3°2θ, 20.2°2θ, 20.9°2θ, 21.7°2θ, 23.2°2θ, and 23.8°2θ (±0.2°2θ; ±0.1°2θ; or ±0.0°2θ; Cu Kα1 radiation).

In some embodiments, the compound 1 fumarate salt is crystalline polymorphic Pattern 6 characterized by two or more, or three or more XRPD signals selected from the group consisting of 8.2°2θ, 12.3°2θ, 14.9°2θ, 18.4°2θ, 19.3°2θ, 20.2°2θ, 20.9°2θ, 21.7°2θ, 23.2°2θ, 23.8°2θ, and 26.1°2θ (±0.2°2θ; ±0.1°2θ; or ±0.0°2θ; Cu Kα1 radiation).

In some embodiments, the compound 1 fumarate salt is crystalline polymorphic Pattern 6 characterized by XRPD signals at 8.2°2θ, 12.3°2θ, 14.9°2θ, 18.4°2θ, 19.3°2θ, 20.2°2θ, 20.9°2θ, 21.7°2θ, 23.2°2θ, 23.8°2θ, and 26.1°2θ (±0.2°2θ; ±0.1°2θ; or ±0.0°2θ; Cu Kα1 radiation).

In some embodiments, the compound 1 fumarate salt is crystalline polymorphic Pattern 6 characterized by two or more, or three or more XRPD signals selected from the group consisting of 8.2°2θ, 12.3°2θ, 14.9°2θ, 18.4°2θ, 19.3°2θ, 20.2°2θ, 20.9°2θ, 21.7°2θ, 22.4°2θ, 23.2°2θ, 23.8°2θ, and 26.1°2θ (±0.2°2θ; ±0.1°2θ; or ±0.0°2θ; Cu Kα1 radiation). In some embodiments, the compound 1 fumarate salt is crystalline polymorphic Pattern 6 characterized by XRPD signals at 8.2°2θ, 12.3°2θ, 14.9°2θ, 18.4°2θ, 19.3°2θ, 20.2°2θ, 20.9°2θ, 21.7°2θ, 22.4°2θ, 23.2°2θ, 23.8°2θ, and 26.1°2θ (±0.2°2θ; ±0.1°2θ; or ±0.0°2θ; Cu Kα1 radiation).

In some embodiments, the compound 1 fumarate salt is crystalline polymorphic Pattern 6 characterized by two or more, or three or more XRPD signals selected from the group consisting of 8.2°2θ, 12.3°2θ, 13.4°2θ, 14.9°2θ, 18.4°2θ, 19.3°2θ, 20.2°2θ, 20.9°2θ, 21.7°2θ, 22.4°2θ, 23.2°2θ, 23.8°2θ, and 26.1°2θ (±0.2°2θ; ±0.1°2θ; or ±0.0°2θ; Cu Kα1 radiation). In some embodiments, the compound 1 fumarate salt is crystalline polymorphic Pattern 6 characterized by XRPD signals at 8.2°2θ, 12.3°2θ, 13.4°2θ, 14.9°2θ, 18.4°2θ, 19.3°2θ, 20.2°2θ, 20.9°2θ, 21.7°2θ, 22.4°2θ, 23.2°2θ, 23.8°2θ, and 26.1°2θ (±0.2°2θ; ±0.1°2θ; or ±0.0°2θ; Cu Kα1 radiation).

In some embodiments, the compound 1 fumarate salt is crystalline polymorphic Pattern 6 characterized by two or more, or three or more XRPD signals selected from the group consisting of 8.2°2θ, 12.3°2θ, 13.4°2θ, 14.9°2θ, 18.4°2θ, 19.3°2θ, 20.2°2θ, 20.9°2θ, 21.7°2θ, 22.4°2θ, 23.2°2θ, 23.8°2θ, 26.1°2θ, and 29.1°2θ (±0.2°2θ; ±0.1°2θ; or ±0.0°2θ; Cu Kα1 radiation). In some embodiments, the compound 1 fumarate salt is crystalline polymorphic Pattern 6 characterized by XRPD signals at 8.2°2θ, 12.3°2θ, 13.4°2θ, 14.9°2θ, 18.4°2θ, 19.3°2θ, 20.2°2θ, 20.9°2θ, 21.7°2θ, 22.4°2θ, 23.2°2θ, 23.8°2θ, 26.1°2θ, and 29.1°2θ (±0.2°2θ; ±0.1°2θ; or ±0.0°2θ; Cu Kα1 radiation).

In some embodiments, the compound 1 fumarate salt is crystalline polymorphic Pattern 6 characterized by two or more, or three or more XRPD signals selected from the group consisting of 8.2°2θ, 12.3°2θ, 13.4°2θ, 14.9°2θ, 16.7°2θ, 18.4°2θ, 19.3°2θ, 20.2°2θ, 20.9°2θ, 21.7°2θ, 22.4°2θ, 23.2°2θ, 23.8°2θ, 26.1°2θ, and 29.1°2θ (±0.2°2θ; ±0.1°2θ; or ±0.0°2θ; Cu Kα1 radiation). In some embodiments, the compound 1 fumarate salt is crystalline polymorphic Pattern 6 characterized by XRPD signals at 8.2°2θ, 12.3°2θ, 13.4°2θ, 14.9°2θ, 16.7°2θ, 18.4°2θ, 19.3°2θ, 20.2°2θ, 20.9°2θ, 21.7°2θ, 22.4°2θ, 23.2°2θ, 23.8°2θ, 26.1°2θ, and 29.1°2θ (±0.2°2θ; ±0.1°2θ; or 0.0°2θ; Cu Kα1 radiation).

In some embodiments, the compound 1 fumarate salt is crystalline polymorphic Pattern 6 characterized by two or more, or three or more XRPD signals selected from the group consisting of 8.2°2θ, 12.3°2θ, 13.4°2θ, 13.9°2θ, 14.9°2θ, 16.7°2θ, 18.4°2θ, 19.3°2θ, 20.2°2θ, 20.9°2θ, 21.7°2θ, 22.4°2θ, 23.2°2θ, 23.8°2θ, 26.1°2θ, and 29.1°2θ (±0.2°2θ; ±0.1°2θ; or ±0.0°2θ; Cu Kα1 radiation). In some embodiments, the compound 1 fumarate salt is crystalline polymorphic Pattern 6 characterized by XRPD signals at 8.2°2θ, 12.3°2θ, 13.4°2θ, 13.9°2θ, 14.9°2θ, 16.7°2θ, 18.4°2θ, 19.3°2θ, 20.2°2θ, 20.9°2θ, 21.7°2θ, 22.4°2θ, 23.2°2θ, 23.8°2θ, 26.1°2θ, and 29.1°2θ (±0.2°2θ; ±0.1°2θ; or ±0.0°2θ; Cu Kα1 radiation).

In some embodiments, the compound 1 fumarate salt is crystalline polymorphic Pattern 6 characterized by two or more, or three or more XRPD signals selected from the group consisting of 8.2°2θ, 12.3°2θ, 13.4°2θ, 13.9°2θ, 14.9°2θ, 16.7°2θ, 18.4°2θ, 19.3°2θ, 20.2°2θ, 20.9°2θ, 21.7°2θ, 22.4°2θ, 23.2°2θ, 23.8°2θ, 24.4°2θ, 26.1°2θ, and 29.1°2θ (±0.2°2θ; ±0.1°2θ; or ±0.0°2θ; Cu Kα1 radiation). In some embodiments, the compound 1 fumarate salt is crystalline polymorphic Pattern 6 characterized by XRPD signals at 8.2°2θ, 12.3°2θ, 13.4°2θ, 13.9°2θ, 14.9°2θ, 16.7°2θ, 18.4°2θ, 19.3°2θ, 20.2°2θ, 20.9°2θ, 21.7°2θ, 22.4°2θ, 23.2°2θ, 23.8°2θ, 24.4°2θ, 26.1°2θ, and 29.1°2θ (±0.2°2θ; ±0.1°2θ; or ±0.0°2θ; Cu Kα1 radiation).

In some embodiments, the compound 1 fumarate salt is crystalline polymorphic Pattern 6 characterized by two or more, or three or more XRPD signals selected from the group consisting of 8.2°2θ, 12.3°2θ, 13.4°2θ, 13.9°2θ, 14.9°2θ, 16.7°2θ, 18.4°2θ, 19.3°2θ, 20.2°2θ, 20.9°2θ, 21.7°2θ, 22.4°2θ, 23.2°2θ, 23.8°2θ, 24.4°2θ, 25.1°2θ, 26.1°2θ, and 29.1°2θ (±0.2°2θ; ±0.1°2θ; or ±0.0°2θ; Cu Kα1 radiation). In some embodiments, the compound 1 fumarate salt is crystalline polymorphic Pattern 6 characterized by XRPD signals at 8.2°2θ, 12.3°2θ, 13.4°2θ, 13.9°2θ, 14.9°2θ, 16.7°2θ, 18.4°2θ, 19.3°2θ, 20.2°2θ, 20.9°2θ, 21.7°2θ, 22.4°2θ, 23.2°2θ, 23.8°2θ, 24.4°2θ, 25.1°2θ, 26.1°2θ, and 29.1°2θ (±0.2°2θ; ±0.1°2θ; or ±0.0°2θ; Cu Kα1 radiation).

In some embodiments, the compound 1 fumarate salt is crystalline polymorphic Pattern 6 characterized by two or more, or three or more XRPD signals selected from the group consisting of 8.2°2θ, 12.3°2θ, 13.4°2θ, 13.9°2θ, 14.9°2θ, 16.7°2θ, 18.4°2θ, 19.3°2θ, 20.2°2θ, 20.9°2θ, 21.7°2θ, 22.4°2θ, 23.2°2θ, 23.8°2θ, 24.4°2θ, 25.1°2θ, 26.1°2θ, 29.1°2θ, and 29.8°2θ (±0.2°2θ; ±0.1°2θ; or ±0.0°2θ; Cu Kα1 radiation). In some embodiments, the compound 1 fumarate salt is crystalline polymorphic Pattern 6 characterized by XRPD signals at 8.2°2θ, 12.3°2θ, 13.4°2θ, 13.9°2θ, 14.9°2θ, 16.7°2θ, 18.4°2θ, 19.3°2θ, 20.2°2θ, 20.9°2θ, 21.7°2θ, 22.4°2θ, 23.2°2θ, 23.8°2θ, 24.4°2θ, 25.1°2θ, 26.1°2θ, 29.1°2θ, and 29.8°2θ (±0.2°2θ; ±0.1°2θ; or ±0.0°2θ; Cu Kα1 radiation).

In some embodiments, the compound 1 fumarate salt is crystalline polymorphic Pattern 6 characterized by two or more, or three or more XRPD signals selected from the group consisting of 8.2°2θ, 12.3°2θ, 13.4°2θ, 13.9°2θ, 14.9°2θ, 16.7°2θ, 17.2°2θ, 18.4°2θ, 19.3°2θ, 20.2°2θ, 20.9°2θ, 21.7°2θ, 22.4°2θ, 23.2°2θ, 23.8°2θ, 24.4°2θ, 25.1°2θ, 26.1°2θ, 29.1°2θ, and 29.8°2θ (±0.2°2θ; ±0.1°2θ; or ±0.0°2θ; Cu Kα1 radiation). In some embodiments, the compound 1 fumarate salt is crystalline polymorphic Pattern 6 characterized by XRPD signals at 8.2°2θ, 12.3°2θ, 13.4°2θ, 13.9°2θ, 14.9°2θ, 16.7°2θ, 17.2°2θ, 18.4°2θ, 19.3°2θ, 20.2°2θ, 20.9°2θ, 21.7°2θ, 22.4°2θ, 23.2°2θ, 23.8°2θ, 24.4°2θ, 25.1°2θ, 26.1°2θ, 29.1°2θ, and 29.8°2θ (±0.2°2θ; ±0.1°2θ; or ±0.0°2θ; Cu Kα1 radiation).

In some embodiments, the compound 1 fumarate salt is crystalline polymorphic Pattern 6 characterized by two or more, or three or more XRPD signals selected from the group consisting of 8.2°2θ, 12.3°2θ, 13.4°2θ, 13.9°2θ, 14.9°2θ, 16.7°2θ, 17.2°2θ, 18.4°2θ, 19.3°2θ, 20.2°2θ, 20.9°2θ, 21.7°2θ, 22.4°2θ, 23.2°2θ, 23.8°2θ, 24.4°2θ, 25.1°2θ, 26.1°2θ, 27.6°2θ, 29.1°2θ, and 29.8°2θ (±0.2°2θ; ±0.1°2θ; or ±0.0°2θ; Cu Kα1 radiation). In some embodiments, the compound 1 fumarate salt is crystalline polymorphic Pattern 6 characterized by XRPD signals at 8.2°2θ, 12.3°2θ, 13.4°2θ, 13.9°2θ, 14.9°2θ, 16.7°2θ, 17.2°2θ, 18.4°2θ, 19.3°2θ, 20.2°2θ, 20.9°2θ, 21.7°2θ, 22.4°2θ, 23.2°2θ, 23.8°2θ, 24.4°2θ, 25.1°2θ, 26.1°2θ, 27.6°2θ, 29.1°2θ, and 29.8°2θ (±0.2°2θ; ±0.1°2θ; or ±0.0°2θ; Cu Kα1 radiation).

In some embodiments, crystalline polymorphic Pattern 6 is characterized by one, two, three, four, five, six, seven, eight, nine, ten, eleven, twelve, thirteen, fourteen, fifteen, sixteen, seventeen, eighteen, nineteen, twenty, or twenty-one XRPD signals selected from those set forth in Table 39.

TABLE 39

Crystalline compound 1 fumarate pattern 6 XRPD signals (±0.2 °2θ; ±0.1 °2θ; or ±0.0 °2θ; Cu Kα1 radiation)

| Signal number | 2-θ (°) | d Value | Net Intensity (counts) | Gross Intensity (counts) | Rel. Intensity (%) |
|---|---|---|---|---|---|
| Signal #1 | 8.2 | 10.83 | 1218.4 | 1356.9 | 86.3 |
| Signal #2 | 12.3 | 7.17 | 604.7 | 762.0 | 42.8 |
| Signal #3 | 13.4 | 6.61 | 262.3 | 441.1 | 18.6 |
| Signal #4 | 13.9 | 6.35 | 229.6 | 417.8 | 16.3 |
| Signal #5 | 14.9 | 5.94 | 553.3 | 751.8 | 39.2 |
| Signal #6 | 16.7 | 5.29 | 253.0 | 511.7 | 17.9 |
| Signal #7 | 17.2 | 5.16 | 154.3 | 428.8 | 10.9 |
| Signal #8 | 18.4 | 4.82 | 633.2 | 944.9 | 44.9 |
| Signal #9 | 19.3 | 4.60 | 1411.6 | 1743.2 | 100.0 |
| Signal #10 | 20.2 | 4.39 | 1172.5 | 1517.9 | 83.1 |
| Signal #11 | 20.9 | 4.24 | 331.0 | 682.0 | 23.4 |
| Signal #12 | 21.7 | 4.09 | 860.6 | 1212.8 | 61.0 |
| Signal #13 | 22.4 | 3.97 | 294.4 | 643.5 | 20.9 |
| Signal #14 | 23.2 | 3.82 | 695.7 | 1035.9 | 49.3 |
| Signal #15 | 23.8 | 3.74 | 682.1 | 1013.9 | 48.3 |
| Signal #16 | 24.4 | 3.65 | 227.3 | 546.0 | 16.1 |
| Signal #17 | 25.1 | 3.55 | 203.8 | 505.8 | 14.4 |
| Signal #18 | 26.1 | 3.41 | 315.5 | 595.7 | 22.3 |
| Signal #19 | 27.6 | 3.23 | 146.0 | 389.1 | 10.3 |
| Signal #20 | 29.1 | 3.07 | 260.8 | 461.9 | 18.5 |
| Signal #21 | 29.8 | 3.00 | 187.4 | 376.3 | 13.3 |

Compound 1 HCl Salt

In some embodiments, the compound 1 salt is a compound 1 HCl salt. In some embodiments, the compound 1 HCl salt is amorphous. In some embodiments, the compound 1 HCl salt is crystalline. In some embodiments, the compound 1 HCl salt is a 1:1 compound 1:HCl salt. In some embodiments, the compound 1 HCl salt is a 2:1 compound 1:HCl salt.

Amorphous Compound 1 HCl Salts

In some embodiments, the compound 1 HCl salt is an amorphous compound 1 HCl salt characterized by a glass temperature (Tg) of about 37° C. In some embodiments, the amorphous compound 1 HCl salt is characterized by a XRPD pattern that is substantially similar to that shown in FIG. 369. In some embodiments, the amorphous compound 1 HCl salt is characterized by a DSC profile that is substantially similar to that shown in any one of FIG. 373. In some embodiments, the amorphous compound 1 HCl salt is characterized by a TGA profile that is substantially similar to that shown in any one of FIG. 377. In some embodiments, the amorphous compound 1 HCl salt is characterized by a $^1$H NMR spectrum that is substantially similar to that shown in FIG. 368.

Crystalline Compound 1 HCl Salts

In some embodiments, the compound 1 HCl salt is a crystalline polymorph. In some embodiments, the crystalline polymorph is a compound 1 HCl Form A polymorph. In some embodiments, the crystalline polymorph is a compound 1 HCl Form B polymorph. In some embodiments, the crystalline polymorph is characterized by the XRPD signals set for the below in Tables 40-42 or 123-126. In some embodiments, the crystalline polymorph XRPD pattern is substantially similar to that shown in FIG. 167, 196, 220, or 391. In some embodiments, the crystalline polymorph $^1$H-NMR spectrum is substantially similar to that shown in FIG. 189. In some embodiments, the crystalline polymorph DVS is substantially similar to that shown in FIG. 191. In some embodiments, the crystalline polymorph TGA spectrum is substantially similar to that shown in FIG. 195, 218, or 222. In some embodiments, the crystalline compound 1 HCl DSC spectrum is substantially similar to that shown in any one of FIG. 190, 217, or 221.

In some embodiments, the crystalline compound 1 HCl is a crystalline polymorphic form, e.g., Form A, characterized by DSC having an onset at about 200.03° C.° C. In some embodiments, the crystalline compound 1 fumarate Form A is a crystalline polymorphic form characterized by TGA having an onset at about 243.1° C.

In some embodiments, the compound 1 HCl salt is a crystalline Form A polymorph characterized by an XRPD signal at 24.9°2θ (±0.2°2θ; ±0.1°2θ; or ±0.0°2θ; Cu Kα1 radiation).

In some embodiments, the compound 1 HCl salt is a crystalline polymorph characterized by XRPD signals at 21.7°2θ, and 24.9°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting of 18.0°2θ, 21.7°2θ, and 24.9°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 18.0°2θ, 21.7°2θ, and 24.9°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting of 18.0°2θ, 21.7°2θ, 24.9°2θ, and 29.0°2θ (±0.2°2θ; ±0.1°2θ; or ±0.0°2θ; Cu Kα1 radiation).

In some embodiments, the compound 1 HCl salt is a crystalline Form A polymorph characterized by XRPD signals at 18.0°2θ, 21.7°2θ, 24.9°2θ, and 29.0°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting of 17.8°2θ, 18.0°2θ, 21.7°2θ, 24.9°2θ, and 29.0°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 17.8°2θ, 18.0°2θ, 21.7°2θ, 24.9°2θ, and 29.0°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting of 17.8°2θ, 18.0°2θ, 18.6°2θ, 21.7°2θ, 24.9°2θ, and 29.0°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 17.8°2θ, 18.0°2θ, 18.6°2θ, 21.7°2θ, 24.9°2θ, and 29.0°2θ (±0.2°2θ; ±0.1°2θ; or 0.0°2θ; Cu Kα1 radiation).

In some embodiments, the compound 1 HCl salt is a crystalline Form A polymorph characterized by two or more, or three or more XRPD signals selected from the group consisting of 12.4°2θ, 17.8°2θ, 18.0°2θ, 18.6°2θ, 21.7°2θ, 24.9°2θ, and 29.0°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 12.4°2θ, 17.8°2θ, 18.0°2θ, 18.6°2θ, 21.7°2θ, 24.9°2θ, and 29.0°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting of 12.4°2θ, 17.8°2θ, 18.0°2θ, 18.6°2θ, 21.7°2θ, 24.9°2θ, 25.9°2θ, and 29.0°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 12.4°2θ, 17.8°2θ, 18.0°2θ, 18.6°2θ, 21.7°2θ, 24.9°2θ, 25.9°2θ, and 29.0°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting of 12.4°2θ, 17.8°2θ, 18.0°2θ, 18.6°2θ, 21.7°2θ, 24.9°2θ, 25.5°2θ, 25.9°2θ, and 29.0°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 12.4°2θ, 17.8°2θ, 18.0°2θ, 18.6°2θ, 21.7°2θ, 24.9°2θ, 25.5°2θ, 25.9°2θ, and 29.0°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting 20 of 12.4°2θ, 13.5°2θ, 17.8°2θ, 18.0°2θ, 18.6°2θ, 21.7°2θ, 24.9°2θ, 25.5°2θ, 25.9°2θ, and 29.0°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 12.4°2θ, 13.5°2θ, 17.8°2θ, 18.0°2θ, 18.6°2θ, 21.7°2θ, 24.9°2θ, 25.5°2θ, 25.9°2θ, and 29.0°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting of 12.4°2θ, 13.5°2θ, 17.8°2θ, 18.0°2θ, 18.6°2θ, 21.7°2θ, 24.9°2θ, 25.5°2θ, 25.9°2θ, 27.3°2θ, and 29.0°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 12.4°2θ, 13.5°2θ, 17.8°2θ, 18.0°2θ, 18.6°2θ, 21.7°2θ, 24.9°2θ, 25.5°2θ, 25.9°2θ, 27.3°2θ, and 29.0°2θ (±0.2°2θ; ±0.1°2θ; or 0.0°2θ; Cu Kα1 radiation).

In some embodiments, the compound 1 HCl salt is a crystalline Form A polymorph characterized by two or more, or three or more XRPD signals selected from the group consisting of 12.4°2θ, 13.5°2θ, 17.8°2θ, 18.0°2θ, 18.6°2θ, 20.0°2θ, 21.7°2θ, 24.9°2θ, 25.5°2θ, 25.9°2θ, 27.3°2θ, and 29.0°2θ (±0.2°2θ; ±0.1°2θ; or 0.0°2θ; Cu Kα1 radiation). In some embodiments, the compound 1 HCl salt is a crystalline Form A polymorph characterized by XRPD signals at 12.4°2θ, 13.5°2θ, 17.8°2θ, 18.0°2θ, 18.6°2θ, 20.0°2θ, 21.7°2θ, 24.9°2θ, 25.5°2θ, 25.9°2θ, 27.3°2θ, and 29.0°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting 10 of 12.4°2θ, 13.5°2θ, 17.8°2θ, 18.0°2θ, 18.6°2θ, 20.0°2θ, 21.7°2θ, 24.9°2θ, 25.5°2θ, 25.9°2θ, 27.3°2θ, 29.0°2θ, and 30.3°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 12.4°2θ, 13.5°2θ, 17.8°2θ, 18.0°2θ, 18.6°2θ, 20.0°2θ, 21.7°2θ, 24.9°2θ, 25.5°2θ, 25.9°2θ, 27.3°2θ, 29.0°2θ, and 30.3°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting of 12.4°2θ, 13.5°2θ, 17.8°2θ, 18.0°2θ, 18.6°2θ, 20.0°2θ, 20.4°2θ, 21.7°2θ, 24.9°2θ, 25.5°2θ, 25.9°2θ, 27.3°2θ, 29.0°2θ, and 30.3°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 12.4°2θ, 13.5°2θ, 17.8°2θ, 18.0°2θ, 18.6°2θ, 20.0°2θ, 20.4°2θ, 21.7°2θ, 24.9°2θ, 25.5°2θ, 25.9°2θ, 27.3°2θ, 29.0°2θ, and 30.3°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting 25 of 12.4°2θ, 13.5°2θ, 17.5°2θ, 17.8°2θ, 18.0°2θ, 18.6°2θ, 20.0°2θ, 20.4°2θ, 21.7°2θ, 24.9°2θ, 25.5°2θ, 25.9°2θ, 27.3°2θ, 29.0°2θ, and 30.3°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 12.4°2θ, 13.5°2θ, 17.5°2θ, 17.8°2θ, 18.0°2θ, 18.6°2θ, 20.0°2θ, 20.4°2θ, 21.7°2θ, 24.9°2θ, 25.5°2θ, 25.9°2θ, 27.3°2θ, 29.0°2θ, and 30.3°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting of 12.4°2θ, 13.5°2θ, 15.3°2θ, 17.5°2θ, 17.8°2θ, 18.0°2θ, 18.6°2θ, 20.0°2θ, 20.4°2θ, 21.7°2θ, 24.9°2θ, 25.5°2θ, 25.9°2θ, 27.3°2θ, 29.0°2θ, and 30.3°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 12.4°2θ, 13.5°2θ, 15.3°2θ, 17.5°2θ, 17.8°2θ, 18.0°2θ, 18.6°2θ, 20.0°2θ, 20.4°2θ, 21.7°2θ, 24.9°2θ, 25.5°2θ, 25.9°2θ, 27.3°2θ, 29.0°2θ, and 30.3°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting of 12.4°2θ, 13.5°2θ, 15.3°2θ, 17.5°2θ, 17.8°2θ, 18.0°2θ, 18.6°2θ, 20.0°2θ, 20.4°2θ, 21.7°2θ, 24.9°2θ, 25.5°2θ, 25.9°2θ, 27.3°2θ, 28.4°2θ, 29.0°2θ, and 30.3°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 12.4°2θ, 13.5°2θ, 15.3°2θ, 17.5°2θ, 17.8°2θ, 18.0°2θ, 18.6°2θ, 20.0°2θ, 20.4°2θ, 21.7°2θ, 24.9°2θ, 25.5°2θ, 25.9°2θ, 27.3°2θ, 28.4°2θ, 29.0°2θ, and 30.3°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting of 12.4°2θ, 13.5°2θ, 14.2°2θ, 15.3°2θ, 17.5°2θ, 17.8°2θ, 18.0°2θ, 18.6°2θ, 20.0°2θ, 20.4°2θ, 21.7°2θ, 24.9°2θ, 25.5°2θ, 25.9°2θ, 27.3°2θ, 28.4°2θ, 29.0°2θ, and 30.3°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 12.4°2θ, 13.5°2θ, 14.2°2θ, 15.3°2θ, 17.5°2θ, 17.8°2θ, 18.0°2θ, 18.6°2θ, 20.0°2θ, 20.4°2θ, 21.7°2θ, 24.9°2θ, 25.5°2θ, 25.9°2θ, 27.3°2θ, 28.4°2θ, 29.0°2θ, and 30.3°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting of 12.4°2θ, 13.5°2θ, 14.2°2θ, 15.3°2θ, 17.5°2θ, 17.8°2θ, 18.0°2θ, 18.6°2θ, 20.0°2θ, 20.4°2θ, 21.7°2θ, 24.9°2θ, 25.5°2θ, 25.9°2θ, 27.3°2θ, 28.0°2θ, 28.4°2θ, 29.0°2θ, and 30.3°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 12.4°2θ, 13.5°2θ, 14.2°2θ, 15.3°2θ, 17.5°2θ, 17.8°2θ, 18.0°2θ, 18.6°2θ, 20.0°2θ, 20.4°2θ, 21.7°2θ, 24.9°2θ, 25.5°2θ, 25.9°2θ, 27.3°2θ, 28.0°2θ, 28.4°2θ, 29.0°2θ, and 30.3°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting of 12.4°2θ, 13.5°2θ, 14.2°2θ, 15.3°2θ, 17.5°2θ, 17.8°2θ, 18.0°2θ, 18.6°2θ, 20.0°2θ, 20.4°2θ, 21.7°2θ, 24.9°2θ, 25.5°2θ, 25.9°2θ, 27.3°2θ, 28.0°2θ, 28.4°2θ, 29.0°2θ, 30.3°2θ, and 32.2°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 12.4°2θ, 13.5°2θ, 14.2°2θ, 15.3°2θ, 17.5°2θ, 17.8°2θ, 18.0°2θ, 18.6°2θ, 20.0°2θ, 20.4°2θ, 21.7°2θ, 24.9°2θ, 25.5°2θ, 25.9°2θ, 27.3°2θ, 28.0°2θ, 28.4°2θ, 29.0°2θ, 30.3°2θ, and 32.2°2θ (±0.2°2θ; ±0.1°2θ; or ±0.0°2θ; Cu Kα1 radiation).

In some embodiments, the crystalline polymorph is characterized by one, two, three, four, five, six, seven, eight, nine, ten, eleven, twelve, thirteen, fourteen, fifteen, sixteen, seventeen, eighteen, nineteen, or twenty XRPD signals selected from those set forth in Table 40.

TABLE 40

Crystalline compound 1 HCl XRPD Form A signals (±0.2 °2θ; ±0.1 °2θ; or ±0.0 °2θ; Cu Kα1 radiation).

| Signal number | 2-θ (°) | d Value | Net Intensity (counts) | Gross Intensity (counts) | Rel. Intensity (%) |
|---|---|---|---|---|---|
| Signal #1 | 12.4 | 7.15 | 997.6 | 1051.0 | 61.6 |
| Signal #2 | 13.5 | 6.53 | 592.0 | 648.2 | 36.6 |
| Signal #3 | 14.2 | 6.22 | 177.2 | 229.8 | 10.9 |
| Signal #4 | 15.3 | 5.78 | 186.5 | 236.2 | 11.5 |
| Signal #5 | 17.5 | 5.06 | 356.2 | 410.8 | 22.0 |
| Signal #6 | 17.8 | 4.98 | 1166.0 | 1223.1 | 72.0 |
| Signal #7 | 18.0 | 4.92 | 1255.0 | 1313.7 | 77.5 |
| Signal #8 | 18.6 | 4.76 | 1145.3 | 1206.2 | 70.8 |
| Signal #9 | 20.0 | 4.45 | 446.4 | 508.9 | 27.6 |
| Signal #10 | 20.4 | 4.34 | 358.6 | 423.1 | 22.2 |
| Signal #11 | 21.7 | 4.09 | 1350.4 | 1413.9 | 83.4 |
| Signal #12 | 24.9 | 3.58 | 1618.4 | 1693.7 | 100.0 |
| Signal #13 | 25.5 | 3.50 | 612.2 | 690.3 | 37.8 |
| Signal #14 | 25.9 | 3.44 | 801.7 | 880.2 | 49.5 |
| Signal #15 | 27.3 | 3.26 | 531.1 | 613.3 | 32.8 |
| Signal #16 | 28.0 | 3.18 | 173.8 | 259.7 | 10.7 |
| Signal #17 | 28.4 | 3.14 | 183.1 | 269.4 | 11.3 |
| Signal #18 | 29.0 | 3.08 | 1224.2 | 1309.0 | 75.6 |
| Signal #19 | 30.3 | 2.95 | 398.8 | 472.4 | 24.6 |
| Signal #20 | 32.2 | 2.78 | 162.7 | 220.8 | 10.1 |

In some embodiments, the compound 1 HCl salt is a crystalline Form A polymorph characterized by an XRPD signal at 18.1°2θ (±0.2°2θ; ±0.1°2θ; or ±0.0°2θ; Cu Kα1 radiation).

In some embodiments, the compound 1 HCl salt is a crystalline Form A polymorph characterized by XRPD signals at 18.1°2θ and 21.7°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting of 17.8°2θ, 18.1°2θ, and 21.7°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 17.8°2θ, 18.1°2θ, and 21.7°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting of 17.8°2θ, 18.1°2θ, 21.7°2θ, and 29.0°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 17.8°2θ, 18.1°2θ, 21.7°2θ, and 29.0°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting of 17.8°2θ, 18.1°2θ, 21.7°2θ, 24.9°2θ, and 29.0°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 17.8°2θ, 18.1°2θ, 21.7°2θ, 24.9°2θ, and 29.0°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting of 17.8°2θ, 18.1°2θ, 18.7°2θ, 21.7°2θ, 24.9°2θ, and 29.0°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 17.8°2θ, 18.1°2θ, 18.7°2θ, 21.7°2θ, 24.9°2θ, and 29.0°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting of 12.4°2θ, 17.8°2θ, 18.1°2θ, 18.7°2θ, 21.7°2θ, 24.9°2θ, and 29.0°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 12.4°2θ, 17.8°2θ, 18.1°2θ, 18.7°2θ, 21.7°2θ, 24.9°2θ, and 29.0°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting of 12.4°2θ, 17.8°2θ, 18.1°2θ, 18.7°2θ, 21.7°2θ, 24.9°2θ, 25.9°2θ, and 29.0°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 12.4°2θ, 17.8°2θ, 18.1°2θ, 18.7°2θ, 20.0°2θ, 21.7°2θ, 24.9°2θ, 25.9°2θ, and 29.0°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting 30 of 12.4°2θ, 17.8°2θ, 18.1°2θ, 18.7°2θ, 20.0°2θ, 21.7°2θ, 24.9°2θ, 25.9°2θ, 27.4°2θ, and 29.0°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 12.4°2θ, 17.8°2θ, 18.1°2θ, 18.7°2θ, 20.0°2θ, 21.7°2θ, 24.9°2θ, 25.9°2θ, 27.4°2θ, and 29.0°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting of 12.4°2θ, 13.6°2θ, 17.8°2θ, 18.1°2θ, 18.7°2θ, 20.0°2θ, 21.7°2θ, 24.9°2θ, 25.9°2θ, 27.4°2θ, and 29.0°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 12.4°2θ, 13.6°2θ, 17.8°2θ, 18.1°2θ, 18.7°2θ, 20.0°2θ, 21.7°2θ, 24.9°2θ, 25.9°2θ, 27.4°2θ, and 29.0°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting of 12.4°2θ, 13.6°2θ, 17.8°2θ, 18.1°2θ, 18.7°2θ, 20.0°2θ, 20.5°2θ, 21.7°2θ, 24.9°2θ, 25.9°2θ, 27.4°2θ, and 29.0°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 12.4°2θ, 13.6°2θ, 17.8°2θ, 18.1°2θ, 18.7°2θ, 20.0°2θ, 20.5°2θ, 21.7°2θ, 24.9°2θ, 25.9°2θ, 27.4°2θ, and 29.0°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting 20 of 12.4°2θ, 13.6°2θ, 17.6°2θ, 17.8°2θ, 18.1°2θ, 18.7°2θ, 20.0°2θ, 20.5°2θ, 21.7°2θ, 24.9°2θ, 25.9°2θ, 27.4°2θ, and 29.0°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 12.4°2θ, 13.6°2θ, 17.6°2θ, 17.8°2θ, 18.1°2θ, 18.7°2θ, 20.0°2θ, 20.5°2θ, 21.7°2θ, 24.9°2θ, 25.9°2θ, 27.4°2θ, and 29.0°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting of 12.4°2θ, 13.6°2θ, 17.6°2θ, 17.8°2θ, 18.1°2θ, 18.7°2θ, 20.0°2θ, 20.5°2θ, 21.7°2θ, 24.9°2θ, 25.5°2θ, 25.9°2θ, 27.4°2θ, and 29.0°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 12.4°2θ, 13.6°2θ, 17.6°2θ, 17.8°2θ, 18.1°2θ, 18.7°2θ, 20.0°2θ, 20.5°2θ, 21.7°2θ, 24.9°2θ, 25.5°2θ, 25.9°2θ, 27.4°2θ, and 29.0°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting of 12.4°2θ, 13.6°2θ, 17.6°2θ, 17.8°2θ, 18.1°2θ, 18.7°2θ, 20.0°2θ, 20.5°2θ, 21.7°2θ, 23.1°2θ, 24.9°2θ, 25.5°2θ, 25.9°2θ, 27.4°2θ, and 29.0°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 12.4°2θ, 13.6°2θ, 17.6°2θ, 17.8°2θ, 18.1°2θ, 18.7°2θ, 20.0°2θ, 20.5°2θ, 21.7°2θ, 23.1°2θ, 24.9°2θ, 25.5°2θ, 25.9°2θ, 27.4°2θ, and 29.0°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting of 12.4°2θ, 13.6°2θ, 17.6°2θ, 17.8°2θ, 18.1°2θ, 18.7°2θ, 20.0°2θ, 20.5°2θ, 21.7°2θ, 23.1°2θ, 24.9°2θ, 25.5°2θ, 25.9°2θ, 27.4°2θ, 29.0°2θ, and 30.3°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 12.4°2θ, 13.6°2θ, 17.6°2θ, 17.8°2θ, 18.1°2θ, 18.7°2θ, 20.0°2θ, 20.5°2θ, 21.7°2θ, 23.1°2θ, 24.9°2θ, 25.5°2θ, 25.9°2θ, 27.4°2θ, 29.0°2θ, and 30.3°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting of 12.4°2θ, 13.6°2θ, 15.3°2θ, 17.6°2θ, 17.8°2θ, 18.1°2θ, 18.7°2θ, 20.0°2θ, 20.5°2θ, 21.7°2θ, 23.1°2θ, 24.9°2θ, 25.5°2θ, 25.9°2θ, 27.4°2θ, 29.0°2θ, and 30.3°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 12.4°2θ, 13.6°2θ, 15.3°2θ, 17.6°2θ, 17.8°2θ, 18.1°2θ, 18.7°2θ, 20.0°2θ, 20.5°2θ, 21.7°2θ, 23.1°2θ, 24.9°2θ, 25.5°2θ, 25.9°2θ, 27.4°2θ, 29.0°2θ, and 30.3°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting of 6.4°2θ, 12.4°2θ, 13.6°2θ, 15.3°2θ, 17.6°2θ, 17.8°2θ, 18.1°2θ, 18.7°2θ, 20.0°2θ, 20.5°2θ, 21.7°2θ, 23.1°2θ, 24.9°2θ, 25.5°2θ, 25.9°2θ, 27.4°2θ, 29.0°2θ, and 30.3°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 6.4°2θ, 12.4°2θ, 13.6°2θ, 15.3°2θ, 17.6°2θ, 17.8°2θ, 18.1°2θ, 18.7°2θ, 20.0°2θ, 20.5°2θ, 21.7°2θ, 23.1°2θ, 24.9°2θ, 25.5°2θ, 25.9°2θ, 27.4°2θ, 29.0°2θ, and 30.3°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting of 6.4°2θ, 12.4°2θ, 13.6°2θ, 15.3°2θ, 17.6°2θ, 17.8°2θ, 18.1°2θ, 18.7°2θ, 20.0°2θ, 20.5°2θ, 21.7°2θ, 23.1°2θ, 24.9°2θ, 25.5°2θ, 25.9°2θ, 27.4°2θ, 29.0°2θ, 30.1°2θ, and 30.3°2θ (±0.2°2θ; ±0.1°2θ; or 0.0°2θ; Cu Kα1 radiation). In some embodiments, the compound 1 HCl salt is a crystalline Form A polymorph characterized by XRPD signals at 6.4°2θ, 12.4°2θ, 13.6°2θ, 15.3°2θ, 17.6°2θ, 17.8°2θ, 18.1°2θ, 18.7°2θ, 20.0°2θ, 20.5°2θ, 21.7°2θ, 23.1°2θ, 24.9°2θ, 25.5°2θ, 25.9°2θ, 27.4°2θ, 29.0°2θ, 30.1°2θ, and 30.3°2θ (±0.2°2θ; ±0.1°2θ; or ±0.0°2θ; Cu Kα1 radiation).

In some embodiments, the crystalline polymorph is characterized by one, two, three, four, five, six, seven, eight, nine, ten, eleven, twelve, thirteen, fourteen, fifteen, sixteen, seventeen, eighteen, or nineteen XRPD signals selected from those set forth in Table 41.

TABLE 41

Crystalline compound 1 Form A HCl XRPD signals (±0.2 °2θ; ±0.1 °2θ; or ±0.0 °2θ; Cu Kα1 radiation)

| Signal number | 2-θ (°) | d Value | Net Intensity (counts) | Gross Intensity (counts) | Rel. Intensity (%) |
|---|---|---|---|---|---|
| Signal #1 | 6.4 | 13.90 | 229.6 | 376.1 | 10.2 |
| Signal #2 | 12.4 | 7.14 | 1064.3 | 1145.9 | 47.1 |
| Signal #3 | 13.6 | 6.52 | 504.4 | 585.1 | 22.3 |
| Signal #4 | 15.3 | 5.77 | 246.8 | 316.6 | 10.9 |
| Signal #5 | 17.6 | 5.05 | 465.8 | 540.2 | 20.6 |
| Signal #6 | 17.8 | 4.97 | 1754.3 | 1832.6 | 77.7 |
| Signal #7 | 18.1 | 4.91 | 2258.6 | 2339.8 | 100.0 |
| Signal #8 | 18.7 | 4.75 | 1128.1 | 1213.9 | 49.9 |
| Signal #9 | 20.0 | 4.44 | 606.5 | 695.9 | 26.9 |
| Signal #10 | 20.5 | 4.33 | 499.2 | 588.5 | 22.1 |
| Signal #11 | 21.7 | 4.09 | 1883.4 | 1966.3 | 83.4 |
| Signal #12 | 23.1 | 3.85 | 281.4 | 365.0 | 12.5 |
| Signal #13 | 24.9 | 3.57 | 1364.6 | 1464.1 | 60.4 |
| Signal #14 | 25.5 | 3.49 | 297.3 | 397.3 | 13.2 |
| Signal #15 | 25.9 | 3.44 | 946.9 | 1045.3 | 41.9 |
| Signal #16 | 27.4 | 3.25 | 531.4 | 627.4 | 23.5 |
| Signal #17 | 29.0 | 3.08 | 1378.2 | 1476.4 | 61.0 |
| Signal #18 | 30.1 | 2.97 | 215.2 | 307.2 | 9.5 |
| Signal #19 | 30.3 | 2.95 | 258.8 | 349.8 | 11.5 |

In some embodiments, the compound 1 HCl salt is a crystalline Form A polymorph characterized by an XRPD at 18.1°2θ (±0.2°2θ; ±0.1°2θ; or ±0.0°2θ; Cu Kα1 radiation).

In some embodiments, the compound 1 HCl salt is a crystalline Form A polymorph characterized by XRPD signals at 18.1°2θ and 24.9°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting of 12.4°2θ, 18.1°2θ, and 24.9°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 12.4°2θ, 18.1°2θ, and 24.9°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting of 12.4°2θ, 18.1°2θ, 21.8°2θ, and 24.9°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 12.4°2θ, 18.1°2θ, 21.8°2θ, and 24.9°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting of 12.4°2θ, 18.1°2θ, 18.7°2θ, 21.8°2θ, and 24.9°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 12.4°2θ, 18.1°2θ, 18.7°2θ, 21.8°2θ, and 24.9°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting of 12.4°2θ, 17.9°2θ, 18.1°2θ, 18.7°2θ, 21.8°2θ, and 24.9°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 12.4°2θ, 17.9°2θ, 18.1°2θ, 18.7°2θ, 21.8°2θ, and 24.9°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting of 12.4°2θ, 17.9°2θ, 18.1°2θ, 18.7°2θ, 21.8°2θ, 24.9°2θ, and 25.9°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 12.4°2θ, 17.9°2θ, 18.1°2θ, 18.7°2θ, 21.8°2θ, 24.9°2θ, and 25.9°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting of 12.4°2θ, 17.9°2θ, 18.1°2θ, 18.7°2θ, 21.8°2θ, 24.9°2θ, 25.9°2θ, and 29.0°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 12.4°2θ, 17.9°2θ, 18.1°2θ, 18.7°2θ, 21.8°2θ, 24.9°2θ, 25.9°2θ, and 29.0°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting of 12.4°2θ, 13.6°2θ, 17.9°2θ, 18.1°2θ, 18.7°2θ, 21.8°2θ, 24.9°2θ, 25.9°2θ, and 29.0°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 12.4°2θ, 13.6°2θ, 17.9°2θ, 18.1°2θ, 18.7°2θ, 21.8°2θ, 24.9°2θ, 25.9°2θ, and 29.0°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting 30 of 12.4°2θ, 12.8°2θ, 13.6°2θ, 17.9°2θ, 18.1°2θ, 18.7°2θ, 21.8°2θ, 24.9°2θ, 25.9°2θ, and 29.0°2θ (±0.2°2θ, ±0.1°2θ; or ±0.0°2θ; Cu Kα1 radiation). In some embodiments, the compound 1 HCl salt is a crystalline Form A polymorph characterized by XRPD signals at 12.4°2θ, 12.8°2θ, 13.6°2θ, 17.9°2θ, 18.1°2θ, 18.7°2θ, 21.8°2θ, 24.9°2θ, 25.9°2θ, and 29.0°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting of 12.4°2θ, 12.8°2θ, 13.6°2θ, 17.6°2θ, 17.9°2θ, 18.1°2θ, 18.7°2θ, 21.8°2θ, 24.9°2θ, 25.9°2θ, and 29.0°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 12.4°2θ, 12.8°2θ, 13.6°2θ, 17.6°2θ, 17.9°2θ, 18.1°2θ, 18.7°2θ, 21.8°2θ, 24.9°2θ, 25.9°2θ, and 29.0°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting of 12.4°2θ, 12.8°2θ, 13.6°2θ, 17.6°2θ, 17.9°2θ, 18.1°2θ, 18.7°2θ, 21.8°2θ, 23.1°2θ, 24.9°2θ, 25.9°2θ, 29.0°2θ, and 30.4°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 12.4°2θ, 12.8°2θ, 13.6°2θ, 17.6°2θ, 17.9°2θ, 18.1°2θ, 18.7°2θ, 21.8°2θ, 23.1°2θ, 24.9°2θ, 25.9°2θ, 29.0°2θ, and 30.4°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting of 12.4°2θ, 12.8°2θ, 13.6°2θ, 17.6°2θ, 17.9°2θ, 18.1°2θ, 18.7°2θ, 20.0°2θ, 21.8°2θ, 23.1°2θ, 24.9°2θ, 25.9°2θ, 29.0°2θ, and 30.4°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 12.4°2θ, 12.8°2θ, 13.6°2θ, 17.6°2θ, 17.9°2θ, 18.1°2θ, 18.7°2θ, 20.0°2θ, 21.8°2θ, 23.1°2θ, 24.9°2θ, 25.9°2θ, 29.0°2θ, and 30.4°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting of 12.4°2θ, 12.8°2θ, 13.6°2θ, 17.6°2θ, 17.9°2θ, 18.1°2θ, 18.7°2θ, 20.0°2θ, 21.8°2θ, 23.1°2θ, 24.9°2θ, 25.5°2θ, 25.9°2θ, 29.0°2θ, and 30.4°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 12.4°2θ, 12.8°2θ, 13.6°2θ, 17.6°2θ, 17.9°2θ, 18.1°2θ, 18.7°2θ, 20.0°2θ, 21.8°2θ, 23.1°2θ, 24.9°2θ, 25.5°2θ, 25.9°2θ, 29.0°2θ, and 30.4°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting of 12.4°2θ, 12.8°2θ, 13.6°2θ, 17.6°2θ, 17.9°2θ, 18.1°2θ, 18.7°2θ, 20.0°2θ, 21.8°2θ, 23.1°2θ, 24.9°2θ, 25.5°2θ, 25.9°2θ, 27.4°2θ, 29.0°2θ, and 30.4°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 12.4°2θ, 12.8°2θ, 13.6°2θ, 17.6°2θ, 17.9°2θ, 18.1°2θ, 18.7°2θ, 20.0°2θ, 21.8°2θ, 23.1°2θ, 24.9°2θ, 25.5°2θ, 25.9°2θ, 27.4°2θ, 29.0°2θ, and 30.4°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting of 12.4°2θ, 12.8°2θ, 13.6°2θ, 17.6°2θ, 17.9°2θ, 18.1°2θ, 18.7°2θ, 20.0°2θ, 20.5°2θ, 21.8°2θ, 23.1°2θ, 24.9°2θ, 25.5°2θ, 25.9°2θ, 27.4°2θ, 29.0°2θ, and 30.4°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 12.4°2θ, 12.8°2θ, 13.6°2θ, 17.6°2θ, 17.9°2θ, 18.1°2θ, 18.7°2θ, 20.0°2θ, 20.5°2θ, 21.8°2θ, 23.1°2θ, 24.9°2θ, 25.5°2θ, 25.9°2θ, 27.4°2θ, 29.0°2θ, and 30.4°2θ (±0.2°2θ; ±0.1°2θ; or ±0.0°2θ; Cu Kα1 radiation).

In some embodiments, the crystalline polymorph is characterized by one, two, three, four, five, six, seven, eight, nine, ten, eleven, twelve, thirteen, fourteen, fifteen, sixteen, or seventeen XRPD signals selected from those set forth in Table 42.

TABLE 42

Crystalline compound 1 Form A HCl XRPD signals (±0.2 °2θ; ±0.1 °2θ; or ±0.0 °2θ; Cu Kα1 radiation)

| Signal number | 2-θ (°) | d Value | Net Intensity (counts) | Gross Intensity (counts) | Rel. Intensity (%) |
|---|---|---|---|---|---|
| Signal #1 | 12.4 | 7.12 | 5423.8 | 5508.1 | 85.0 |
| Signal #2 | 12.8 | 6.92 | 912.2 | 1000.4 | 14.3 |
| Signal #3 | 13.6 | 6.50 | 1573.4 | 1662.5 | 24.7 |
| Signal #4 | 17.6 | 5.04 | 889.5 | 984.1 | 13.9 |
| Signal #5 | 17.9 | 4.96 | 1853.6 | 1953.2 | 29.0 |
| Signal #6 | 18.1 | 4.90 | 6381.3 | 6483.4 | 100.0 |
| Signal #7 | 18.7 | 4.74 | 1898.7 | 2003.9 | 29.8 |
| Signal #8 | 20.0 | 4.43 | 763.8 | 865.4 | 12.0 |
| Signal #9 | 20.5 | 4.33 | 641.1 | 737.4 | 10.0 |
| Signal #10 | 21.8 | 4.08 | 3020.6 | 3118.6 | 47.3 |
| Signal #11 | 23.1 | 3.84 | 856.4 | 956.5 | 13.4 |
| Signal #12 | 24.9 | 3.57 | 5686.6 | 5817.0 | 89.1 |
| Signal #13 | 25.5 | 3.49 | 703.0 | 837.8 | 11.0 |
| Signal #14 | 25.9 | 3.44 | 1773.3 | 1908.1 | 27.8 |
| Signal #15 | 27.4 | 3.25 | 645.9 | 774.1 | 10.1 |
| Signal #16 | 29.0 | 3.07 | 1730.4 | 1850.8 | 27.1 |
| Signal #17 | 30.4 | 2.94 | 802.0 | 907.1 | 12.6 |

In some embodiments, the compound 1 HCl salt is a crystalline Form A polymorph characterized an XRPD signal at 18.0°2θ (±0.2°2θ; ±0.1°2θ; or ±0.0°2θ; Cu Kα1 radiation).

In some embodiments, the compound 1 HCl salt is a crystalline Form A polymorph characterized by XRPD signals at 18.0°2θ, and 29.0°2θ (±0.2°2θ; ±0.1°2θ, or ±0.0°2θ; Cu Kα1 radiation).

In some embodiments, the compound 1 HCl salt is a crystalline Form A polymorph characterized by two or more, or three or more XRPD signals selected from the group consisting of 17.8°2θ, 18.0°2θ, and 29.0°2θ (±0.2°2θ, ±0.1°2θ, or ±0.0°2θ; Cu Kα1 radiation). In some embodiments, the compound 1 HCl salt is a crystalline Form A polymorph characterized by XRPD signals at 17.8°2θ, 18.0°2θ, and 29.0°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting of 12.3°2θ, 17.8°2θ, 18.0°2θ, and 29.0°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 12.3°2θ, 17.8°2θ, 18.0°2θ, and 29.0°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting of 12.3°2θ, 17.8°2θ, 18.0°2θ, 25.8°2θ, and 29.0°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 12.3°2θ, 17.8°2θ, 18.0°2θ, 25.8°2θ, and 29.0°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting of 12.3°2θ, 17.8°2θ, 18.0°2θ, 24.8°2θ, 25.8°2θ, and 29.0°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 12.3°2θ, 17.8°2θ, 18.0°2θ, 24.8°2θ, 25.8°2θ, and 29.0°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting of 12.3°2θ, 17.5°2θ, 17.8°2θ, 18.0°2θ, 24.8°2θ, 25.8°2θ, and 29.0°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 12.3°2θ, 17.5°2θ, 17.8°2θ, 18.0°2θ, 24.8°2θ, 25.8°2θ, and 29.0°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting of 12.3°2θ, 17.5°2θ, 17.8°2θ, 18.0°2θ, 21.7°2θ, 24.8°2θ, 25.8°2θ, and 29.0°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 12.3°2θ, 17.5°2θ, 17.8°2θ, 18.0°2θ, 21.7°2θ, 24.8°2θ, 25.8°2θ, and 29.0°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting of 12.3°2θ, 17.5°2θ, 17.8°2θ, 18.0°2θ, 18.6°2θ, 21.7°2θ, 24.8°2θ, 25.8°2θ, and 29.0°2θ (±0.2°2θ; 0.1°2θ; or ±0.0°2θ; Cu Kα1 radiation). In some embodiments, the compound 1 HCl salt is a crystalline Form A polymorph characterized by XRPD signals at 12.3°2θ, 17.5°2θ, 17.8°2θ, 18.0°2θ, 18.6°2θ, 21.7°2θ, 24.8°2θ, 25.8°2θ, and 29.0°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting of 12.3°2θ, 17.5°2θ, 17.8°2θ, 18.0°2θ, 18.6°2θ, 20.0°2θ, 21.7°2θ, 24.8°2θ, 25.8°2θ, and 29.0°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 12.3°2θ, 17.5°2θ, 17.8°2θ, 18.0°2θ, 18.6°2θ, 20.0°2θ, 21.7°2θ, 24.8°2θ, 25.8°2θ, and 29.0°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting of 12.3°2θ, 17.5°2θ, 17.8°2θ, 18.0°2θ, 18.6°2θ, 20.0°2θ, 21.7°2θ, 24.8°2θ, 25.8°2θ, 27.3°2θ, and 29.0°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 12.3°2θ, 17.5°2θ, 17.8°2θ, 18.0°2θ, 18.6°2θ, 20.0°2θ, 21.7°2θ, 24.8°2θ, 25.8°2θ, 27.3°2θ, and 29.0°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting of 12.3°2θ, 13.5°2θ, 17.5°2θ, 17.8°2θ, 18.0°2θ, 18.6°2θ, 20.0°2θ, 21.7°2θ, 24.8°2θ, 25.8°2θ, 27.3°2θ, and 29.0°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 12.3°2θ, 13.5°2θ, 17.5°2θ, 17.8°2θ, 18.0°2θ, 18.6°2θ, 20.0°2θ, 21.7°2θ, 24.8°2θ, 25.8°2θ, 27.3°2θ, and 29.0°2θ (±0.2°2θ; 0.1°2θ; or ±0.0°2θ; Cu Kα1 radiation). In some embodiments, the compound 1 HCl salt is a crystalline Form A polymorph characterized by two or more, or three or more XRPD signals selected from the group consisting of 12.3°2θ, 13.5°2θ, 17.5°2θ, 17.8°2θ, 18.0°2θ, 18.6°2θ, 20.0°2θ, 20.4°2θ, 21.7°2θ, 24.8°2θ, 25.8°2θ, 27.3°2θ, and 29.0°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 12.3°2θ, 13.5°2θ, 17.5°2θ, 17.8°2θ, 18.0°2θ, 18.6°2θ, 20.0°2θ, 20.4°2θ, 21.7°2θ, 24.8°2θ, 25.8°2θ, 27.3°2θ, and 29.0°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting 10 of 12.3°2θ, 13.5°2θ, 17.5°2θ, 17.8°2θ, 18.0°2θ, 18.6°2θ, 20.0°2θ, 20.4°2θ, 21.7°2θ, 24.8°2θ, 25.8°2θ, 27.3°2θ, 29.0°2θ, and 30.3°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 12.3°2θ, 13.5°2θ, 17.5°2θ, 17.8°2θ, 18.0°2θ, 18.6°2θ, 20.0°2θ, 20.4°2θ, 21.7°2θ, 24.8°2θ, 25.8°2θ, 27.3°2θ, 29.0°2θ, and 30.3°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting of 12.3°2θ, 13.5°2θ, 17.5°2θ, 17.8°2θ, 18.0°2θ, 18.6°2θ, 20.0°2θ, 20.4°2θ, 21.7°2θ, 24.8°2θ, 25.8°2θ, 27.3°2θ, 29.0°2θ, 30.3°2θ, and 34.4°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 12.3°2θ, 13.5°2θ, 17.5°2θ, 17.8°2θ, 18.0°2θ, 18.6°2θ, 20.0°2θ, 20.4°2θ, 21.7°2θ, 24.8°2θ, 25.8°2θ, 27.3°2θ, 29.0°2θ, 30.3°2θ, and 34.4°2θ (±0.2°2θ; ±0.1°2θ; or ±0.0°2θ; Cu Kα1 radiation).

In some embodiments, the crystalline polymorph is characterized by one, two, three, four, five, six, seven, eight, nine, ten, eleven, twelve, thirteen, fourteen, or fifteen XRPD signals selected from those set forth in Table 123.

TABLE 123

Crystalline Compound 1 HCl Form A XRPD signals (±0.2 °2θ; ±0.1 °2θ; or ±0.0 °2θ; Cu Kα1 radiation)

| Signal number | 2-θ (°) | d Value | Net Intensity (counts) | Gross Intensity (counts) | Rel. Intensity (%) |
|---|---|---|---|---|---|
| Signal #1 | 12.3 | 7.16 | 945.3 | 993.8 | 34.1 |
| Signal #2 | 13.5 | 6.54 | 409.1 | 456.4 | 14.8 |
| Signal #3 | 17.5 | 5.06 | 852.4 | 905.5 | 30.8 |
| Signal #4 | 17.8 | 4.98 | 1125.8 | 1182.2 | 40.6 |
| Signal #5 | 18.0 | 4.92 | 2771.3 | 2829.9 | 100.0 |
| Signal #6 | 18.6 | 4.76 | 641.5 | 703.1 | 23.1 |
| Signal #7 | 20.0 | 4.45 | 499.5 | 561.3 | 18.0 |
| Signal #8 | 20.4 | 4.35 | 378.4 | 438.3 | 13.7 |
| Signal #9 | 21.7 | 4.10 | 811.7 | 869.3 | 29.3 |
| Signal #10 | 24.8 | 3.58 | 868.5 | 943.1 | 31.3 |
| Signal #11 | 25.8 | 3.45 | 887.3 | 961.0 | 32.0 |
| Signal #12 | 27.3 | 3.26 | 485.6 | 556.7 | 17.5 |
| Signal #13 | 29.0 | 3.08 | 1809.7 | 1885.0 | 65.3 |
| Signal #14 | 30.3 | 2.95 | 293.2 | 361.2 | 10.6 |
| Signal #15 | 34.4 | 2.60 | 292.0 | 350.2 | 10.5 |

In some embodiments, the compound 1 HCl salt is a crystalline Form B polymorph characterized a XRPD signal at 18.2°2θ (±0.2°2θ; ±0.1°2θ; or ±0.0°2θ; Cu Kα1 radiation).

In some embodiments, the compound 1 HCl salt is a crystalline Form B polymorph characterized by XRPD signals at 18.2°2θ and 25.0°2θ (±0.2°2θ; ±0.1°2θ; or ±0.0°2θ; Cu Kα1 radiation).

In some embodiments, the compound 1 HCl salt is a crystalline Form B polymorph characterized by two or more, or three or more XRPD signals selected from the group consisting of 18.2°2θ, 25.0 20, and 26.0°2θ (±0.2°2θ; ±0.1°2θ; or ±0.0°2θ; Cu Kα1 radiation). In some embodiments, the compound 1 HCl salt is a crystalline Form B polymorph characterized by XRPD signals at 18.2°2θ, 25.0°2θ, and 26.0°2θ (±0.2 20; 0.1°2θ; or ±0.0°2θ; Cu Kα1 radiation).

In some embodiments, the compound 1 HCl salt is a crystalline Form B polymorph characterized by two or more, or three or more XRPD signals selected from the group consisting of 18.2°2θ, 21.9°2θ, 25.0°2θ, and 26.0°2θ (±0.2°2θ; ±0.1°2θ; or ±0.0°2θ; Cu Kα1 radiation).

In some embodiments, the compound 1 HCl salt is a crystalline Form B polymorph characterized by XRPD signals at 18.2°2θ, 21.9°2θ, 25.0°2θ, and 26.0°2θ (±0.2°2θ; ±0.1°2θ; or ±0.0°2θ; Cu Kα1 radiation).

In some embodiments, the compound 1 HCl salt is a crystalline Form B polymorph characterized by two or more, or three or more XRPD signals selected from the group consisting of 12.9°2θ, 18.2°2θ, 21.9°2θ, 25.0°2θ, and 26.0°2θ (±0.2°2θ; ±0.1°2θ; or ±0.0°2θ; Cu Kα1 radiation). In some embodiments, the compound 1 HCl salt is a crystalline Form B polymorph characterized by XRPD signals at 12.9°2θ, 18.2°2θ, 21.9°2θ, 25.0°2θ, and 26.0°2θ (±0.2°2θ; ±0.1°2θ; or ±0.0°2θ; Cu Kα1 radiation).

In some embodiments, the compound 1 HCl salt is a crystalline Form B polymorph characterized by two or more, or three or more XRPD signals selected from the group consisting of 12.5°2θ, 12.9°2θ, 18.2°2θ, 21.9°2θ, 25.0°2θ, and 26.0°2θ (±0.2°2θ; ±0.1°2θ; or ±0.0°2θ; Cu Kα1 radiation). In some embodiments, the compound 1 HCl salt is a crystalline Form B polymorph characterized by XRPD signals at 12.5°2θ, 12.9°2θ, 18.2°2θ, 21.9°2θ, 25.0°2θ, and 26.0°2θ (±0.2°2θ; ±0.1°2θ; or ±0.0°2θ; Cu Kα1 radiation).

In some embodiments, the compound 1 HCl salt is a crystalline Form B polymorph characterized by two or more, or three or more XRPD signals selected from the group consisting of 12.5°2θ, 12.9°2θ, 18.0°2θ, 18.2°2θ, 21.9°2θ, 25.0°2θ, and 26.0°2θ (±0.2°2θ; ±0.1°2θ; or ±0.0°2θ; Cu Kα1 radiation). In some embodiments, the compound 1 HCl salt is a crystalline Form B polymorph characterized by XRPD signals at 12.5°2θ, 12.9°2θ, 18.0°2θ, 18.2°2θ, 21.9°2θ, 25.0°2θ, and 26.0°2θ (±0.2°2θ; ±0.1°2θ; or ±0.0°2θ; Cu Kα1 radiation).

In some embodiments, the compound 1 HCl salt is a crystalline Form B polymorph characterized by two or more, or three or more XRPD signals selected from the group consisting of 12.5°2θ, 12.9°2θ, 18.0°2θ, 18.2°2θ, 20.6°2θ, 21.9°2θ, 25.0°2θ, and 26.0°2θ (±0.2°2θ; ±0.1°2θ; or ±0.0°2θ; Cu Kα1 radiation). In some embodiments, the compound 1 HCl salt is a crystalline Form B polymorph characterized by XRPD signals at 12.5°2θ, 12.9°2θ, 18.0°2θ, 18.2 30°2θ, 20.6°2θ, 21.9°2θ, 25.0°2θ, and 26.0°2θ (±0.2°2θ; ±0.1°2θ; or ±0.0°2θ; Cu Kα1 radiation).

In some embodiments, the compound 1 HCl salt is a crystalline Form B polymorph characterized by two or more, or three or more XRPD signals selected from the group consisting of 12.5°2θ, 12.9°2θ, 18.0°2θ, 18.2°2θ, 20.6°2θ, 21.9°2θ, 25.0°2θ, 26.0°2θ, and 29.1°2θ (±0.2°2θ; ±0.1°2θ; or ±0.0°2θ; Cu Kα1 radiation). In some embodiments, the compound 1 HCl salt is a crystalline Form B polymorph characterized by XRPD signals at 12.5°2θ, 12.9°2θ, 18.0°2θ, 18.2°2θ, 20.6°2θ, 21.9°2θ, 25.0°2θ, 26.0°2θ, and 29.1°2θ (±0.2°2θ; ±0.1°2θ; or ±0.0°2θ; Cu Kα1 radiation).

In some embodiments, the compound 1 HCl salt is a crystalline Form B polymorph characterized by two or more, or three or more XRPD signals selected from the group consisting of 6.5°2θ, 12.5°2θ, 12.9°2θ, 18.0°2θ, 18.2°2θ, 20.6°2θ, 21.9°2θ, 25.0°2θ, 26.0°2θ, and 29.1°2θ (±0.2°2θ; ±0.1°2θ; or ±0.0°2θ; Cu Kα1 radiation). In some embodiments, the compound 1 HCl salt is a crystalline Form B polymorph characterized by XRPD signals at 6.5°2θ, 12.5°2θ, 12.9°2θ, 18.0°2θ, 18.2°2θ, 20.6°2θ, 21.9°2θ, 25.0°2θ, 26.0°2θ, and 29.1°2θ (±0.2°2θ; ±0.1°2θ; or ±0.0°2θ; Cu Kα1 radiation).

In some embodiments, the compound 1 HCl salt is a crystalline Form B polymorph characterized by two or more, or three or more XRPD signals selected from the group consisting of 6.4°2θ, 6.5°2θ, 12.5°2θ, 12.9°2θ, 18.0°2θ, 18.2°2θ, 20.6°2θ, 21.9°2θ, 25.0°2θ, 26.0°2θ, and 29.1°2θ (±0.2°2θ; ±0.1°2θ; or ±0.0°2θ; Cu Kα1 radiation). In some embodiments, the compound 1 HCl salt is a crystalline Form B polymorph characterized by XRPD signals at 6.4°2θ, 6.5°2θ, 12.5°2θ, 12.9°2θ, 18.0°2θ, 18.2°2θ, 20.6°2θ, 21.9°2θ, 25.0°2θ, 26.0°2θ, and 29.1°2θ (±0.2°2θ; ±0.1°2θ; or ±0.0°2θ; Cu Kα1 radiation).

In some embodiments, the compound 1 HCl salt is a crystalline Form B polymorph characterized by two or more, or three or more XRPD signals selected from the group consisting of 6.4°2θ, 6.5°2θ, 12.5°2θ, 12.9°2θ, 18.0°2θ, 18.2°2θ, 20.6°2θ, 21.9°2θ, 25.0°2θ, 25.6°2θ, 26.0°2θ, and 29.1°2θ (±0.2°2θ; ±0.1°2θ; or ±0.0°2θ; Cu Kα1 radiation). In some embodiments, the compound 1 HCl salt is a crystalline Form B polymorph characterized by XRPD signals at 6.4°2θ, 6.5°2θ, 12.5°2θ, 12.9°2θ, 18.0°2θ, 18.2°2θ, 20.6°2θ, 21.9°2θ, 25.0°2θ, 25.6°2θ, 26.0°2θ, and 29.1°2θ (±0.2°2θ; ±0.1°2θ; or ±0.0°2θ; Cu Kα1 radiation).

In some embodiments, the compound 1 HCl salt is a crystalline Form B polymorph characterized by two or more, or three or more XRPD signals selected from the group consisting of 6.4°2θ, 6.5°2θ, 12.5°2θ, 12.9°2θ, 18.0°2θ, 18.2°2θ, 20.6°2θ, 21.9°2θ, 25.0°2θ, 25.6°2θ, 26.0°2θ, 29.1°2θ, and 34.6°2θ (±0.2°2θ; ±0.1°2θ; or ±0.0°2θ; Cu Kα1 radiation). In some embodiments, the compound 1 HCl salt is a crystalline Form B polymorph characterized by XRPD signals at 6.4°2θ, 6.5°2θ, 12.5°2θ, 12.9°2θ, 18.0°2θ, 18.2°2θ, 20.6°2θ, 21.9°2θ, 25.0°2θ, 25.6°2θ, 26.0°2θ, 29.1°2θ, and 34.6°2θ (±0.2°2θ; ±0.1°2θ; or ±0.0°2θ; Cu Kα1 radiation).

In some embodiments, the compound 1 HCl salt is a crystalline Form B polymorph characterized by two or more, or three or more XRPD signals selected from the group consisting of 6.4°2θ, 6.5°2θ, 12.5°2θ, 12.9°2θ, 18.0°2θ, 18.2°2θ, 20.6°2θ, 21.9°2θ, 25.0°2θ, 25.6°2θ, 26.0°2θ, 29.1°2θ, 34.6°2θ, and 37.8°2θ (±0.2°2θ; ±0.1°2θ; or ±0.0°2θ; Cu Kα1 radiation). In some embodiments, the compound 1 HCl salt is a crystalline Form B polymorph characterized by XRPD signals at 6.4°2θ, 6.5°2θ, 12.5°2θ, 12.9°2θ, 18.0°2θ, 18.2°2θ, 20.6°2θ, 21.9°2θ, 25.0°2θ, 25.6°2θ, 26.0°2θ, 29.1°2θ, 34.6°2θ, and 37.8°2θ (±0.2°2θ; ±0.1°2θ; or ±0.0°2θ; Cu Kα1 radiation).

In some embodiments, the compound 1 HCl salt is a crystalline Form B polymorph characterized by two or more, or three or more XRPD signals selected from the group consisting of 6.4°2θ, 6.5°2θ, 12.5°2θ, 12.9°2θ, 18.0°2θ, 18.2°2θ, 18.8°2θ, 20.6°2θ, 21.9°2θ, 25.0°2θ, 25.6°2θ, 26.0°2θ, 29.1°2θ, 34.6°2θ, and 37.8°2θ (±0.2°2θ; ±0.1°2θ; or ±0.0°2θ; Cu Kα1 radiation). In some embodiments, the compound 1 HCl salt is a crystalline Form B polymorph characterized by XRPD signals at 6.4°2θ, 6.5°2θ, 12.5°2θ, 12.9°2θ, 18.0°2θ, 18.2°2θ, 18.8°2θ, 20.6°2θ, 21.9°2θ, 25.0°2θ, 25.6°2θ, 26.0°2θ, 29.1°2θ, 34.6°2θ, and 37.8°2θ (±0.2°2θ; ±0.1°2θ; or ±0.0°2θ; Cu Kα1 radiation).

In some embodiments, the compound 1 HCl salt is a crystalline Form B polymorph characterized by two or more, or three or more XRPD signals selected from the group consisting of 6.4°2θ, 6.5°2θ, 12.5°2θ, 12.9°2θ, 18.0°2θ, 18.2°2θ, 18.8°2θ, 20.6°2θ, 21.9°2θ, 23.2°2θ, 25.0°2θ, 25.6°2θ, 26.0°2θ, 29.1°2θ, 34.6°2θ, and 37.8°2θ (±0.2°2θ; ±0.1°2θ; or ±0.0°2θ; Cu Kα1 radiation). In some embodiments, the compound 1 HCl salt is a crystalline Form B polymorph characterized by XRPD signals at 6.4°2θ, 6.5°2θ, 12.5°2θ, 12.9°2θ, 18.0°2θ, 18.2°2θ, 18.8°2θ, 20.6°2θ, 21.9°2θ, 23.2°2θ, 25.0°2θ, 25.6°2θ, 26.0°2θ, 29.1°2θ, 34.6°2θ, and 37.8°2θ (±0.2°2θ; ±0.1°2θ; or ±0.0°2θ; Cu Kα1 radiation).

In some embodiments, the compound 1 HCl salt is a crystalline Form B polymorph characterized by two or more, or three or more XRPD signals selected from the group consisting of 6.4°2θ, 6.5°2θ, 12.5°2θ, 12.9°2θ, 18.0°2θ, 18.2°2θ, 18.8°2θ, 20.6°2θ, 21.9°2θ, 23.2°2θ, 25.0°2θ, 25.6°2θ, 26.0°2θ, 29.1°2θ, 32.4°2θ, 34.6°2θ, and 37.8°2θ (±0.2°2θ; ±0.1°2θ; or ±0.0°2θ; Cu Kα1 radiation). In some embodiments, the compound 1 HCl salt is a crystalline Form B polymorph characterized by XRPD signals at 6.4°2θ, 6.5°2θ, 12.5°2θ, 12.9°2θ, 18.0°2θ, 18.2°2θ, 18.8°2θ, 20.6°2θ, 21.9°2θ, 23.2°2θ, 25.0°2θ, 25.6°2θ, 26.0°2θ, 29.1°2θ, 32.4°2θ, 34.6°2θ, and 37.8°2θ (±0.2°2θ; ±0.1°2θ; or ±0.0°2θ; Cu Kα1 radiation).

In some embodiments, the compound 1 HCl salt is a crystalline Form B polymorph characterized by two or more, or three or more XRPD signals selected from the group consisting of 6.4°2θ, 6.5°2θ, 12.5°2θ, 12.9°2θ, 18.0°2θ, 18.2°2θ, 18.8°2θ, 20.6°2θ, 21.9°2θ, 23.2°2θ, 25.0°2θ, 25.6°2θ, 26.0°2θ, 28.6°2θ, 29.1°2θ, 32.4°2θ, 34.6°2θ, and 37.8°2θ (±0.2°2θ; ±0.1°2θ; or ±0.0°2θ; Cu Kα1 radiation). In some embodiments, the compound 1 HCl salt is a crystalline Form B polymorph characterized by XRPD signals at 6.4°2θ, 6.5°2θ, 12.5°2θ, 12.9°2θ, 18.0°2θ, 18.2°2θ, 18.8°2θ, 20.6°2θ, 21.9°2θ, 23.2°2θ, 25.0°2θ, 25.6°2θ, 26.0°2θ, 28.6°2θ, 29.1°2θ, 32.4°2θ, 34.6°2θ, and 37.8°2θ (±0.2°2θ; ±0.1°2θ; or ±0.0°2θ; Cu Kα1 radiation).

In some embodiments, the compound 1 HCl salt is a crystalline Form B polymorph characterized by two or more, or three or more XRPD signals selected from the group consisting of 6.4°2θ, 6.5°2θ, 12.5°2θ, 12.9°2θ, 17.8°2θ, 18.0°2θ, 18.2°2θ, 18.8°2θ, 20.6°2θ, 21.9°2θ, 23.2°2θ, 25.0°2θ, 25.6°2θ, 26.0°2θ, 28.6°2θ, 29.1°2θ, 32.4°2θ, 34.6°2θ, and 37.8°2θ (±0.2°2θ; ±0.1°2θ; or 0.0°2θ; Cu Kα1 radiation). In some embodiments, the compound 1 HCl salt is a crystalline Form B polymorph characterized by XRPD signals at 6.4°2θ, 6.5°2θ, 12.5°2θ, 12.9°2θ, 17.8°2θ, 18.0°2θ, 18.2°2θ, 18.8°2θ, 20.6°2θ, 21.9°2θ, 23.2°2θ, 25.0°2θ, 25.6°2θ, 26.0°2θ, 28.6°2θ, 29.1°2θ, 32.4°2θ, 34.6°2θ, and 37.8°2θ (±0.2°2θ; ±0.1°2θ; or ±0.0°2θ; Cu Kα1 radiation).

In some embodiments, the compound 1 HCl salt is a crystalline Form B polymorph characterized by two or more, or three or more XRPD signals selected from the group consisting of 6.4°2θ, 6.5°2θ, 12.5°2θ, 12.9°2θ, 17.8°2θ, 18.0°2θ, 18.2°2θ, 18.8°2θ, 20.6°2θ, 21.9°2θ, 23.2°2θ, 25.0°2θ, 25.6°2θ, 26.0°2θ, 27.6°2θ, 28.6°2θ, 29.1°2θ, 32.4°2θ, 34.6°2θ, and 37.8°2θ (±0.2°2θ; ±0.1°2θ; or ±0.0°2θ; Cu Kα1 radiation). In some embodiments, the compound 1 HCl salt is a crystalline Form B polymorph characterized by XRPD signals at 6.4°2θ, 6.5°2θ, 12.5°2θ, 12.9°2θ, 17.8°2θ, 18.0°2θ, 18.2°2θ, 18.8°2θ, 20.6°2θ, 21.9°2θ, 23.2°2θ, 25.0°2θ, 25.6°2θ, 26.0°2θ, 27.6°2θ, 28.6°2θ, 29.1°2θ, 32.4°2θ, 34.6°2θ, and 37.8°2θ (±0.2°2θ; ±0.1°2θ; or ±0.0°2θ; Cu Kα1 radiation).

In some embodiments, the compound 1 HCl salt is a crystalline Form B polymorph characterized by two or more, or three or more XRPD signals selected from the group consisting of 6.4°2θ, 6.5°2θ, 12.5°2θ, 12.9°2θ, 17.8°2θ, 18.0°2θ, 18.2°2θ, 18.8°2θ, 20.1°2θ, 20.6°2θ, 21.9°2θ, 23.2°2θ, 25.0°2θ, 25.6°2θ, 26.0°2θ, 27.6°2θ, 28.6°2θ, 29.1°2θ, 32.4°2θ, 34.6°2θ, and 37.8°2θ (±0.2°2θ; ±0.1°2θ; or ±0.0°2θ; Cu Kα1 radiation). In some embodiments, the compound 1 HCl salt is a crystalline Form B polymorph characterized by XRPD signals at 6.4°2θ, 6.5°2θ, 12.5°2θ, 12.9°2θ, 17.8°2θ, 18.0°2θ, 18.2°2θ, 18.8°2θ, 20.1°2θ, 20.6°2θ, 21.9°2θ, 23.2°2θ, 25.0°2θ, 25.6°2θ, 26.0°2θ, 27.6°2θ, 28.6°2θ, 29.1°2θ, 32.4°2θ, 34.6°2θ, and 37.8°2θ (±0.2°2θ; ±0.1°2θ; or ±0.0°2θ; Cu Kα1 radiation).

In some embodiments, the crystalline polymorph is characterized by one, two, three, four, five, six, seven, eight, nine, ten, eleven, twelve, thirteen, fourteen, fifteen, sixteen, seventeen, eighteen, nineteen, twenty, or twenty-one XRPD signals selected from those set forth in Table 124.

TABLE 124

Crystalline Compound 1 HCl Form B XRPD signals (±0.2 °2θ; ±0.1 °2θ; or ±0.0 °2θ; Cu Kα1 radiation)

| Signal number | 2-θ (°) | d Value | Net Intensity (counts) | Gross Intensity (counts) | Rel. Intensity (%) |
|---|---|---|---|---|---|
| Signal #1 | 6.4 | 13.74 | 557.1 | 685.3 | 17.4 |
| Signal #2 | 6.5 | 13.59 | 606.8 | 733.5 | 18.9 |
| Signal #3 | 12.5 | 7.06 | 695.3 | 774.8 | 21.7 |
| Signal #4 | 12.9 | 6.86 | 866.4 | 947.3 | 27.0 |
| Signal #5 | 17.8 | 4.99 | 387.4 | 466.1 | 12.1 |
| Signal #6 | 18.0 | 4.92 | 670.4 | 753.0 | 20.9 |
| Signal #7 | 18.2 | 4.87 | 3205.8 | 3290.5 | 100.0 |
| Signal #8 | 18.8 | 4.72 | 450.4 | 539.4 | 14.0 |
| Signal #9 | 20.1 | 4.41 | 331.2 | 421.3 | 10.3 |
| Signal #10 | 20.6 | 4.30 | 668.6 | 757.0 | 20.9 |
| Signal #11 | 21.9 | 4.06 | 951.4 | 1037.9 | 29.7 |
| Signal #12 | 23.2 | 3.82 | 432.5 | 521.0 | 13.5 |
| Signal #13 | 25.0 | 3.55 | 1538.0 | 1646.9 | 48.0 |
| Signal #14 | 25.6 | 3.47 | 548.1 | 657.9 | 17.1 |
| Signal #15 | 26.0 | 3.42 | 1311.6 | 1419.7 | 40.9 |
| Signal #16 | 27.6 | 3.23 | 382.9 | 484.6 | 11.9 |
| Signal #17 | 28.6 | 3.12 | 393.4 | 493.6 | 12.3 |
| Signal #18 | 29.1 | 3.06 | 612.6 | 706.9 | 19.1 |
| Signal #19 | 32.4 | 2.76 | 395.3 | 480.3 | 12.3 |
| Signal #20 | 34.6 | 2.59 | 513.3 | 598.2 | 16.0 |
| Signal #21 | 37.8 | 2.38 | 466.9 | 545.6 | 14.6 |

In some embodiments, the compound 1 HCl salt is a crystalline Form B polymorph characterized a XRPD signal at 18.3°2θ (±0.2°2θ; ±0.1°2θ; or ±0.0°2θ; Cu Kα1 radiation).

In some embodiments, the compound 1 HCl salt is a crystalline Form B polymorph characterized by XRPD signals at 18.3°2θ and 25.1°2θ (±0.2°2θ; ±0.1°2θ; or ±0.0°2θ; Cu Kα1 radiation).

In some embodiments, the compound 1 HCl salt is a crystalline Form B polymorph characterized by two or more, or three or more XRPD signals selected from the group consisting of 18.0°2θ, 18.3°2θ, and 25.1°2θ (±0.2°2θ; 0.1°2θ; or 0.0°2θ; Cu Kα1 radiation). In some embodiments, the compound 1 HCl salt is a crystalline Form B polymorph characterized by XRPD signals at 18.0°2θ, 18.3°2θ, and 25.1°2θ (±0.2°2θ; ±0.1°2θ; or ±0.0°2θ; Cu Kα1 radiation).

In some embodiments, the compound 1 HCl salt is a crystalline Form B polymorph characterized by two or more, or three or more XRPD signals selected from the group consisting of 18.0°2θ, 18.3°2θ, 25.0°2θ, and 25.1°2θ (±0.2°2θ; ±0.1°2θ; or ±0.0°2θ; Cu Kα1 radiation).

In some embodiments, the compound 1 HCl salt is a crystalline Form B polymorph characterized by XRPD signals at 18.0°2θ, 18.3°2θ, 25.0°2θ, and 25.1°2θ (±0.2°2θ; ±0.1°2θ; or ±0.0°2θ; Cu Kα1 radiation).

In some embodiments, the compound 1 HCl salt is a crystalline Form B polymorph characterized by two or more, or three or more XRPD signals selected from the group consisting of 12.5°2θ, 18.0°2θ, 18.3°2θ, 25.0°2θ, and 25.1°2θ (±0.2°2θ; ±0.1°2θ; or ±0.0°2θ; Cu Kα1 radiation).

In some embodiments, the compound 1 HCl salt is a crystalline Form B polymorph characterized by XRPD signals at 12.5°2θ, 18.0°2θ, 18.3°2θ, 25.0°2θ, and 25.1°2θ (±0.2°2θ; ±0.1°2θ; or ±0.0°2θ; Cu Kα1 radiation).

In some embodiments, the compound 1 HCl salt is a crystalline Form B polymorph characterized by two or more, or three or more XRPD signals selected from the group consisting of 12.5°2θ, 12.6°2θ, 18.0°2θ, 18.3°2θ, 25.0°2θ, and 25.1°2θ (±0.2°2θ; ±0.1°2θ; or ±0.0°2θ; Cu Kα1 radiation). In some embodiments, the compound 1 HCl salt is a crystalline Form B polymorph characterized by XRPD signals at 12.5°2θ, 12.6°2θ, 18.0°2θ, 18.3°2θ, 25.0°2θ, and 25.1°2θ (±0.2°2θ; ±0.1°2θ; or ±0.0°2θ, Cu Kα1 radiation).

In some embodiments, the compound 1 HCl salt is a crystalline Form B polymorph characterized by two or more, or three or more XRPD signals selected from the group consisting of 12.5°2θ, 12.6°2θ, 13.0°2θ, 18.0°2θ, 18.3°2θ, 25.0°2θ, and 25.1°2θ (±0.2°2θ; ±0.1°2θ; or ±0.0°2θ; Cu Kα1 radiation). In some embodiments, the compound 1 HCl salt is a crystalline Form B polymorph characterized by XRPD signals at 12.5°2θ, 12.6°2θ, 13.0°2θ, 18.0°2θ, 18.3°2θ, 25.0°2θ, and 25.1°2θ (±0.2°2θ; ±0.1°2θ; or ±0.0°2θ; Cu Kα1 radiation).

In some embodiments, the compound 1 HCl salt is a crystalline Form B polymorph characterized by two or more, or three or more XRPD signals selected from the group consisting of 12.5°2θ, 12.6°2θ, 13.0°2θ, 18.0°2θ, 18.3°2θ, 25.0°2θ, 25.1°2θ, and 39.2°2θ (±0.2°2θ; ±0.1°2θ; or ±0.0°2θ; Cu Kα1 radiation). In some embodiments, the compound 1 HCl salt is a crystalline Form B polymorph characterized by XRPD signals at 12.5°2θ, 12.6°2θ, 13.0°2θ, 18.0°2θ, 18.3°2θ, 25.0°2θ, 25.1°2θ, and 39.2°2θ (±0.2°2θ; ±0.1°2θ; or ±0.0°2θ; Cu Kα1 radiation).

In some embodiments, the compound 1 HCl salt is a crystalline Form B polymorph characterized by two or more, or three or more XRPD signals selected from the group consisting of 12.5°2θ, 12.6°2θ, 13.0°2θ, 18.0°2θ, 18.3°2θ, 25.0°2θ, 25.1°2θ, 27.6°2θ, and 39.2°2θ (±0.2°2θ; ±0.1°2θ; or ±0.0°2θ; Cu Kα1 radiation). In some embodiments, the compound 1 HCl salt is a crystalline Form B polymorph characterized by XRPD signals at 12.5°2θ, 12.6°2θ, 13.0°2θ, 18.0°2θ, 18.3°2θ, 25.0°2θ, 25.1°2θ, 27.6°2θ, and 39.2°2θ (±0.2°2θ; ±0.1°2θ; or ±0.0°2θ; Cu Kα1 radiation).

In some embodiments, the compound 1 HCl salt is a crystalline Form B polymorph characterized by two or more, or three or more XRPD signals selected from the group consisting of 12.5°2θ, 12.6°2θ, 13.0°2θ, 18.0°2θ, 18.3°2θ, 22.0°2θ, 25.0°2θ, 25.1°2θ, 27.6°2θ, and 39.2°2θ (±0.2°2θ; ±0.1°2θ; or ±0.0°2θ; Cu Kα1 radiation). In some embodiments, the compound 1 HCl salt is a crystalline Form B polymorph characterized by XRPD signals at 12.5°2θ, 12.6°2θ, 13.0°2θ, 18.0°2θ, 18.3°2θ, 22.0°2θ, 25.0°2θ, 25.1°2θ, 27.6°2θ, and 39.2°2θ (±0.2°2θ; ±0.1°2θ; or ±0.0°2θ; Cu Kα1 radiation).

In some embodiments, the compound 1 HCl salt is a crystalline Form B polymorph characterized by two or more, or three or more XRPD signals selected from the group consisting of 12.5°2θ, 12.6°2θ, 13.0°2θ, 18.0°2θ, 18.3°2θ, 22.0°2θ, 25.0°2θ, 25.1°2θ, 27.6°2θ, 29.2°2θ, and 39.2°2θ (±0.2°2θ; ±0.1°2θ; or ±0.0°2θ; Cu Kα1 radiation). In some embodiments, the compound 1 HCl salt is a crystalline Form B polymorph characterized by XRPD signals at 12.5°2θ, 12.6°2θ, 13.0°2θ, 18.0°2θ, 18.3°2θ, 22.0°2θ, 25.0°2θ, 25.1°2θ, 27.6°2θ, 29.2°2θ, and 39.2°2θ (±0.2°2θ; ±0.1°2θ; or ±0.0°2θ; Cu Kα1 radiation).

In some embodiments, the compound 1 HCl salt is a crystalline Form B polymorph characterized by two or more, or three or more XRPD signals selected from the group consisting of 6.7°2θ, 12.5°2θ, 12.6°2θ, 13.0°2θ, 18.0°2θ, 18.3°2θ, 22.0°2θ, 25.0°2θ, 25.1°2θ, 27.6°2θ, 29.2°2θ, and 39.2°2θ (±0.2°2θ; ±0.1°2θ; or ±0.0°2θ; Cu Kα1 radiation). In some embodiments, the compound 1 HCl salt is a crystalline Form B polymorph characterized by XRPD signals at 6.7°2θ, 12.5°2θ, 12.6°2θ, 13.0°2θ, 18.0°2θ, 18.3°2θ, 22.0°2θ, 25.0°2θ, 25.1°2θ, 27.6°2θ, 29.2°2θ, and 39.2°2θ (±0.2°2θ; ±0.1°2θ; or ±0.0°2θ; Cu Kα1 radiation).

In some embodiments, the compound 1 HCl salt is a crystalline Form B polymorph characterized by two or more, or three or more XRPD signals selected from the group consisting of 6.7°2θ, 12.5°2θ, 12.6°2θ, 13.0°2θ, 18.0°2θ, 18.3°2θ, 22.0°2θ, 25.0°2θ, 25.1°2θ, 27.6°2θ, 29.2°2θ, 32.5°2θ, and 39.2°2θ (±0.2°2θ; ±0.1°2θ; or ±0.0°2θ; Cu Kα1 radiation). In some embodiments, the compound 1 HCl salt is a crystalline Form B polymorph characterized by XRPD signals at 6.7°2θ, 12.5°2θ, 12.6°2θ, 13.0°2θ, 18.0°2θ, 18.3°2θ, 22.0°2θ, 25.0°2θ, 25.1°2θ, 27.6°2θ, 29.2°2θ, 32.5°2θ, and 39.2°2θ (±0.2°2θ; ±0.1°2θ; or ±0.0°2θ; Cu Kα1 radiation).

In some embodiments, the compound 1 HCl salt is a crystalline Form B polymorph characterized by two or more, or three or more XRPD signals selected from the group consisting of 6.7°2θ, 12.5°2θ, 12.6°2θ, 13.0°2θ, 18.0°2θ, 18.3°2θ, 22.0°2θ, 25.0°2θ, 25.1°2θ, 27.6°2θ, 29.2°2θ, 30.6°2θ, 32.5°2θ, and 39.2°2θ (±0.2°2θ; ±0.1°2θ; or ±0.0°2θ; Cu Kα1 radiation). In some embodiments, the compound 1 HCl salt is a crystalline Form B polymorph characterized by XRPD signals at 6.7°2θ, 12.5°2θ, 12.6°2θ, 13.0°2θ, 18.0°2θ, 18.3°2θ, 22.0°2θ, 25.0°2θ, 25.1°2θ, 27.6°2θ, 29.2°2θ, 30.6°2θ, 32.5°2θ, and 39.2°2θ (±0.2°2θ; ±0.1°2θ; or ±0.0°2θ; Cu Kα1 radiation).

In some embodiments, the compound 1 HCl salt is a crystalline Form B polymorph characterized by two or more, or three or more XRPD signals selected from the group consisting of 6.7°2θ, 12.5°2θ, 12.6°2θ, 13.0°2θ, 18.0°2θ, 18.3°2θ, 22.0°2θ, 25.0°2θ, 25.1°2θ, 26.1°2θ, 27.6°2θ, 29.2°2θ, 30.6°2θ, 32.5°2θ, and 39.2°2θ (±0.2°2θ; ±0.1°2θ; or ±0.0°2θ; Cu Kα1 radiation). In some embodiments, the compound 1 HCl salt is a crystalline Form B polymorph characterized by XRPD signals at 6.7°2θ, 12.5°2θ, 12.6°2θ, 13.0°2θ, 18.0°2θ, 18.3°2θ, 22.0°2θ, 25.0°2θ, 25.1°2θ, 26.1°2θ, 27.6°2θ, 29.2°2θ, 30.6°2θ, 32.5°2θ, and 39.2°2θ (±0.2°2θ; ±0.1°2θ; or ±0.0°2θ; Cu Kα1 radiation).

In some embodiments, the compound 1 HCl salt is a crystalline Form B polymorph characterized by two or more, or three or more XRPD signals selected from the group consisting of 6.7°2θ, 12.5°2θ, 12.6°2θ, 13.0°2θ, 18.0°2θ, 18.3°2θ, 22.0°2θ, 25.0°2θ, 25.1°2θ, 26.0°2θ, 26.1°2θ, 27.6°2θ, 29.2°2θ, 30.6°2θ, 32.5°2θ, and 39.2°2θ (±0.2°2θ; ±0.1°2θ; or ±0.0°2θ; Cu Kα1 radiation). In some embodiments, the compound 1 HCl salt is a crystalline Form B polymorph characterized by XRPD signals at 6.7°2θ, 12.5°2θ, 12.6°2θ, 13.0°2θ, 18.0°2θ, 18.3°2θ, 22.0°2θ, 25.0°2θ, 25.1°2θ, 26.0°2θ, 26.1°2θ, 27.6°2θ, 29.2°2θ, 30.6°2θ, 32.5°2θ, and 39.2°2θ (±0.2°2θ; ±0.1°2θ; or ±0.0°2θ; Cu Kα1 radiation).

In some embodiments, the compound 1 HCl salt is a crystalline Form B polymorph characterized by two or more, or three or more XRPD signals selected from the group consisting of 6.7°2θ, 12.5°2θ, 12.6°2θ, 13.0°2θ, 18.0°2θ, 18.3°2θ, 18.9°2θ, 22.0°2θ, 25.0°2θ, 25.1°2θ, 26.0°2θ, 26.1°2θ, 27.6°2θ, 29.2°2θ, 30.6°2θ, 32.5°2θ, and 39.2°2θ (±0.2°2θ; ±0.1°2θ; or ±0.0°2θ; Cu Kα1 radiation). In some embodiments, the compound 1 HCl salt is a crystalline Form B polymorph characterized by XRPD signals at 6.7°2θ, 12.5°2θ, 12.6°2θ, 13.0°2θ, 18.0°2θ, 18.3°2θ, 18.9°2θ, 22.0°2θ, 25.0°2θ, 25.1°2θ, 26.0°2θ, 26.1°2θ, 27.6°2θ, 29.2°2θ, 30.6°2θ, 32.5°2θ, and 39.2°2θ (±0.2°2θ; ±0.1°2θ; or ±0.0°2θ; Cu Kα1 radiation).

In some embodiments, the compound 1 HCl salt is a crystalline Form B polymorph characterized by two or more, or three or more XRPD signals selected from the group consisting of 6.7°2θ, 12.5°2θ, 12.6°2θ, 13.0°2θ, 13.9°2θ, 18.0°2θ, 18.3°2θ, 18.9°2θ, 22.0°2θ, 25.0°2θ, 25.1°2θ, 26.0°2θ, 26.1°2θ, 27.6°2θ, 29.2°2θ, 30.6°2θ, 32.5°2θ, and 39.2°2θ (±0.2°2θ; ±0.1°2θ; or ±0.0°2θ; Cu Kα1 radiation). In some embodiments, the compound 1 HCl salt is a 30 crystalline Form B polymorph characterized by XRPD signals at 6.7°2θ, 12.5°2θ, 12.6°2θ, 13.0°2θ, 13.9°2θ, 18.0°2θ, 18.3°2θ, 18.9°2θ, 22.0°2θ, 25.0°2θ, 25.1°2θ, 26.0°2θ, 26.1°2θ, 27.6°2θ, 29.2°2θ, 30.6°2θ, 32.5°2θ, and 39.2°2θ (±0.2°2θ; ±0.1°2θ; or ±0.0°2θ; Cu Kα1 radiation).

In some embodiments, the crystalline polymorph is characterized by one, two, three, four, five, six, seven, eight, nine, ten, eleven, twelve, thirteen, fourteen, fifteen, sixteen, seventeen, or eighteen XRPD signals selected from those set forth in Table 125.

TABLE 125

Crystalline Compound 1 HCl Form B XRPD signals (±0.2 °2θ; ±0.1 °2θ; or ±0.0 °2θ; Cu Kα1 radiation)

| Signal number | 2-θ (°) | d Value | Net Intensity (counts) | Gross Intensity (counts) | Rel. Intensity (%) |
|---|---|---|---|---|---|
| Signal #1 | 6.7 | 13.26 | 725.9 | 814.9 | 24.8 |
| Signal #2 | 12.5 | 7.10 | 1141.3 | 1214.3 | 39.0 |
| Signal #3 | 12.6 | 7.02 | 1096.8 | 1171.4 | 37.5 |
| Signal #4 | 13.0 | 6.80 | 931.4 | 1009.9 | 31.9 |
| Signal #5 | 13.9 | 6.39 | 311.2 | 391.5 | 10.6 |
| Signal #6 | 18.0 | 4.94 | 1333.1 | 1405.3 | 45.6 |
| Signal #7 | 18.3 | 4.84 | 2923.0 | 2999.0 | 100.0 |
| Signal #8 | 18.9 | 4.68 | 397.2 | 476.3 | 13.6 |
| Signal #9 | 22.0 | 4.04 | 757.0 | 828.5 | 25.9 |
| Signal #10 | 25.0 | 3.56 | 1292.2 | 1393.2 | 44.2 |
| Signal #11 | 25.1 | 3.54 | 1715.1 | 1818.7 | 58.7 |
| Signal #12 | 26.0 | 3.43 | 405.0 | 516.3 | 13.9 |
| Signal #13 | 26.1 | 3.4 | 480.6 | 592.5 | 16.4 |
| Signal #14 | 27.6 | 3.22 | 838.7 | 951.9 | 28.7 |
| Signal #15 | 29.2 | 3.05 | 743.9 | 850.1 | 25.5 |
| Signal #16 | 30.6 | 2.92 | 551.3 | 648.2 | 18.9 |
| Signal #17 | 32.5 | 2.76 | 614.5 | 696.6 | 21.0 |
| Signal #18 | 39.2 | 2.30 | 845.3 | 915.1 | 28.9 |

In some embodiments, the compound 1 HCl salt is a crystalline Form A polymorph characterized by a XRPD signal at 18.1°2θ (±0.2°2θ; ±0.1°2θ; or ±0.0°2θ; Cu Kα1 radiation).

In some embodiments, the compound 1 HCl salt is a crystalline Form A polymorph characterized by XRPD signals at 18.1°2θ, and 21.8°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting of 17.9°2θ, 18.1°2θ, and 21.8°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 17.9°2θ, 18.1°2θ, and 21.8°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting of 17.9°2θ, 18.1°2θ, 21.8°2θ, and 24.9°2θ (±0.2°2θ; ±0.1°2θ; or 0.0°2θ; Cu Kα1 radiation).

In some embodiments, the compound 1 HCl salt is a crystalline Form A polymorph characterized by XRPD signals at 17.9°2θ, 18.1°2θ, 21.8°2θ, and 24.9°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting of 17.9°2θ, 18.1°2θ, 21.8°2θ, 24.9°2θ, and 29.0°2θ (±0.2°2θ; ±0.1°2θ; or ±0.0°2θ; Cu Kα1 radiation).

In some embodiments, the compound 1 HCl salt is a crystalline Form A polymorph characterized by XRPD signals at 17.9°2θ, 18.1°2θ, 21.8°2θ, 24.9°2θ, and 29.0°2θ (±0.2 20; 20±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting of 17.9°2θ, 18.1°2θ, 18.7°2θ, 21.8°2θ, 24.9°2θ, and 29.0°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 17.9°2θ, 18.1°2θ, 18.7°2θ, 21.8°2θ, 24.9°2θ, and 29.0°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting of 12.4°2θ, 17.9°2θ, 18.1°2θ, 18.7°2θ, 21.8°2θ, 24.9°2θ, and 29.0°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 12.4°2θ, 17.9°2θ, 18.1°2θ, 18.7°2θ, 21.8°2θ, 24.9°2θ, and 29.0°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting of 12.4°2θ, 17.9°2θ, 18.1°2θ, 18.7°2θ, 21.8°2θ, 24.9°2θ, 25.9°2θ, and 29.0°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 12.4°2θ, 17.9°2θ, 18.1°2θ, 18.7°2θ, 21.8°2θ, 24.9°2θ, 25.9°2θ, and 29.0°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting of 12.4°2θ, 17.9°2θ, 18.1°2θ, 18.7°2θ, 20.0°2θ, 21.8°2θ, 24.9°2θ, 25.9°2θ, and 29.0°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 12.4°2θ, 17.9°2θ, 18.1°2θ, 18.7°2θ, 20.0°2θ, 21.8°2θ, 24.9°2θ, 25.9°2θ, and 29.0°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting of 12.4°2θ, 17.9°2θ, 18.1°2θ, 18.7°2θ, 20.0°2θ, 21.8°2θ, 24.9°2θ, 25.9°2θ, 27.4°2θ, and 29.0°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 12.4°2θ, 17.9°2θ, 18.1°2θ, 18.7°2θ, 20.0°2θ, 21.8°2θ, 24.9°2θ, 25.9°2θ, 27.4°2θ, and 29.0°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting of 12.4°2θ, 13.6°2θ, 17.9°2θ, 18.1°2θ, 18.7°2θ, 20.0°2θ, 21.8°2θ, 24.9°2θ, 25.9°2θ, 27.4°2θ, and 29.0°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 12.4°2θ, 13.6°2θ, 17.9°2θ, 18.1°2θ, 18.7°2θ, 20.0°2θ, 21.8°2θ, 24.9°2θ, 25.9°2θ, 27.4°2θ, and 29.0°2θ (±0.2°2θ; ±0.1°2θ; or ±0.0°2θ. Cu Kα1 radiation).

In some embodiments, the compound 1 HCl salt is a crystalline Form A polymorph characterized by two or more, or three or more XRPD signals selected from the group consisting of 12.4°2θ, 13.6°2θ, 17.6°2θ, 17.9°2θ, 18.1°2θ, 18.7°2θ, 20.0°2θ, 21.8°2θ, 24.9°2θ, 25.9°2θ, 27.4°2θ, and 29.0°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 12.4°2θ, 13.6°2θ, 17.6°2θ, 17.9°2θ, 18.1°2θ, 18.7°2θ, 20.0°2θ, 21.8°2θ, 24.9°2θ, 25.9°2θ, 27.4°2θ, and 29.0°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting of 12.4°2θ, 13.6°2θ, 17.6°2θ, 17.9°2θ, 18.1°2θ, 18.7°2θ, 20.0°2θ, 20.5°2θ, 21.8°2θ, 24.9°2θ, 25.9°2θ, 27.4°2θ, and 29.0°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 12.4°2θ, 13.6°2θ, 17.6°2θ, 17.9°2θ, 18.1°2θ, 18.7°2θ, 20.0°2θ, 20.5°2θ, 21.8°2θ, 24.9°2θ, 25.9°2θ, 27.4°2θ, and 29.0°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting 15 of 12.4°2θ, 13.6°2θ, 17.6°2θ, 17.9°2θ, 18.1°2θ, 18.7°2θ, 20.0°2θ, 20.5°2θ, 21.8°2θ, 24.9°2θ, 25.9°2θ, 27.4°2θ, 29.0°2θ, and 30.3°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 12.4°2θ, 13.6°2θ, 17.6°2θ, 17.9°2θ, 18.1°2θ, 18.7°2θ, 20.0°2θ, 20.5°2θ, 21.8°2θ, 24.9°2θ, 25.9°2θ, 27.4°2θ, 29.0°2θ, and 30.3°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting of 12.4°2θ, 13.6°2θ, 15.4°2θ, 17.6°2θ, 17.9°2θ, 18.1°2θ, 18.7°2θ, 20.0°2θ, 20.5°2θ, 21.8°2θ, 24.9°2θ, 25.9°2θ, 27.4°2θ, 29.0°2θ, and 30.3°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 12.4°2θ, 13.6°2θ, 15.4°2θ, 17.6°2θ, 17.9°2θ, 18.1°2θ, 18.7°2θ, 20.0°2θ, 20.5°2θ, 21.8°2θ, 24.9°2θ, 25.9°2θ, 27.4°2θ, 29.0°2θ, and 30.3°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting of 12.4°2θ, 13.6°2θ, 15.4°2θ, 17.6°2θ, 17.9°2θ, 18.1°2θ, 18.7°2θ, 20.0°2θ, 20.5°2θ, 21.8°2θ, 24.9°2θ, 25.5°2θ, 25.9°2θ, 27.4°2θ, 28.5°2θ, 29.0°2θ, and 30.3°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 12.4°2θ, 13.6°2θ, 15.4°2θ, 17.6°2θ, 17.9°2θ, 18.1°2θ, 18.7°2θ, 20.0°2θ, 20.5°2θ, 21.8°2θ, 24.9°2θ, 25.5°2θ, 25.9°2θ, 27.4°2θ, 28.5°2θ, 29.0°2θ, and 30.3°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting of 12.4°2θ, 13.6°2θ, 15.4°2θ, 17.6°2θ, 17.9°2θ, 18.1°2θ, 18.7°2θ, 20.0°2θ, 20.5°2θ, 21.8°2θ, 23.1°2θ, 24.9°2θ, 25.5°2θ, 25.9°2θ, 27.4°2θ, 28.5°2θ, 29.0°2θ, and 30.3°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 12.4°2θ, 13.6°2θ, 15.4°2θ, 17.6°2θ, 17.9°2θ, 18.1°2θ, 18.7°2θ, 20.0°2θ, 20.5°2θ, 21.8°2θ, 23.1°2θ, 24.9°2θ, 25.5°2θ, 25.9°2θ, 27.4°2θ, 28.5°2θ, 29.0°2θ, and 30.3°2θ (±0.2°2θ; ±0.1°2θ; or ±0.0°2θ; Cu Kα1 radiation).

In some embodiments, the compound 1 HCl salt is a crystalline Form A polymorph characterized by two or more, or three or more XRPD signals selected from the group consisting of 12.4°2θ, 13.6°2θ, 15.4°2θ, 17.6°2θ, 17.9°2θ, 18.1°2θ, 18.7°2θ, 20.0°2θ, 20.5°2θ, 21.8°2θ, 23.1°2θ, 24.9°2θ, 25.5°2θ, 25.9°2θ, 27.4°2θ, 28.5°2θ, 29.0°2θ, 30.1°2θ, and 30.3°2θ (±0.2°2θ; ±0.1°2θ; or ±0.0°2θ; Cu Kα1 radiation). In some embodiments, the compound 1 HCl salt is a crystalline Form A polymorph characterized by XRPD signals at 12.4°2θ, 13.6°2θ, 15.4°2θ, 17.6°2θ, 17.9°2θ, 18.1°2θ, 18.7°2θ, 20.0°2θ, 20.5°2θ, 21.8°2θ, 23.1°2θ, 24.9°2θ, 25.5°2θ, 25.9°2θ, 27.4°2θ, 28.5°2θ, 29.0°2θ, 30.1°2θ, and 30.3°2θ (±0.2°2θ; ±0.1°2θ; or ±0.0°2θ; Cu Kα1 radiation).

In some embodiments, the crystalline polymorph is characterized by one, two, three, four, five, six, seven, eight, nine, ten, eleven, twelve, thirteen, fourteen, fifteen, sixteen, seventeen, eighteen, or nineteen XRPD signals selected from those set forth in Table 126.

TABLE 126

Crystalline Compound 1 HCl Form A XRPD signals (±0.2 °2θ; ±0.1 °2θ; or ±0.0 °2θ; Cu Kα1 radiation)

| Signal number | 2-θ (°) | d Value | Net Intensity (counts) | Gross Intensity (counts) | Rel. Intensity (%) |
|---|---|---|---|---|---|
| Signal #1 | 12.4 | 7.12 | 873.8 | 939.5 | 54.4 |
| Signal #2 | 13.6 | 6.51 | 451.8 | 519.6 | 28.1 |
| Signal #3 | 15.4 | 5.76 | 213.0 | 277.9 | 13.3 |
| Signal #4 | 17.6 | 5.04 | 444.6 | 521.5 | 27.7 |
| Signal #5 | 17.9 | 4.96 | 1536.3 | 1618.6 | 95.7 |

TABLE 126-continued

Crystalline Compound 1 HCl Form A XRPD signals (±0.2 °2θ; ±0.1 °2θ; or ±0.0 °2θ; Cu Kα1 radiation)

| Signal number | 2-θ (°) | d Value | Net Intensity (counts) | Gross Intensity (counts) | Rel. Intensity (%) |
|---|---|---|---|---|---|
| Signal #6 | 18.1 | 4.90 | 1605.9 | 1691.9 | 100.0 |
| Signal #7 | 18.7 | 4.74 | 974.0 | 1068.1 | 60.7 |
| Signal #8 | 20.0 | 4.43 | 466.8 | 568.0 | 29.1 |
| Signal #9 | 20.5 | 4.33 | 328.2 | 428.2 | 20.4 |
| Signal #10 | 21.8 | 4.08 | 1568.5 | 1663.9 | 97.7 |
| Signal #11 | 23.1 | 3.84 | 188.4 | 279.0 | 11.7 |
| Signal #12 | 24.9 | 3.57 | 1411.8 | 1521.1 | 87.9 |
| Signal #13 | 25.5 | 3.49 | 210.9 | 323.6 | 13.1 |
| Signal #14 | 25.9 | 3.44 | 822.4 | 935.9 | 51.2 |
| Signal #15 | 27.4 | 3.25 | 466.6 | 581.2 | 29.1 |
| Signal #16 | 28.5 | 3.13 | 212.1 | 326.3 | 13.2 |
| Signal #17 | 29.0 | 3.07 | 1312.1 | 1422.8 | 81.7 |
| Signal #18 | 30.1 | 2.96 | 188.3 | 286.9 | 11.7 |
| Signal #19 | 30.3 | 2.95 | 241.5 | 337.6 | 15.0 |

Calculated XRPD profile of Crystalline Compound 1 HCl Salt Form A In some embodiments, the crystalline compound 1 HCl salt is characterized by a set of XRPD signals that are calculated. In some embodiments, the calculated set of XRPD signals is described in Table 114. A calculated XRPD profile for crystalline compound 1 HCl salt is provided (FIG. 353) and is overlaid with an experimentally observed XRPD profile for crystalline compound 1 HCl salt (FIG. 354).

TABLE 114

Calculated Crystalline Compound 1 Form A HCl XRPD signals (±0.2 °2θ; ±0.1 °2θ; or ±0.0 °2θ; Cu Kα1 radiation)

| Signal number | 2-θ (°) | d Value | Net Intensity (counts) | Gross Intensity (counts) | Rel. Intensity (%) |
|---|---|---|---|---|---|
| Signal #1 | 6.4 | 13.75 | 1619.4 | 1633.5 | 16.6 |
| Signal #2 | 12.5 | 7.10 | 4605.9 | 4645.5 | 47.1 |
| Signal #3 | 13.7 | 6.48 | 2941.3 | 2986.8 | 30.1 |
| Signal #4 | 15.4 | 5.73 | 1198.2 | 1221.5 | 12.3 |
| Signal #5 | 17.7 | 5.02 | 2805.6 | 2858.3 | 28.7 |
| Signal #6 | 18.0 | 4.94 | 8170.4 | 8229.6 | 83.6 |
| Signal #7 | 18.2 | 4.86 | 8984.2 | 9047.9 | 91.9 |
| Signal #8 | 18.8 | 4.71 | 6186.9 | 6254.6 | 63.3 |
| Signal #9 | 20.2 | 4.40 | 2901.3 | 2970.4 | 29.7 |
| Signal #10 | 20.7 | 4.29 | 2536.0 | 2610.0 | 25.9 |
| Signal #11 | 21.9 | 4.05 | 9775.1 | 9851.1 | 100.0 |
| Signal #12 | 25.1 | 3.55 | 8181.6 | 8272.5 | 83.7 |
| Signal #13 | 25.7 | 3.47 | 1700.3 | 1795.3 | 17.4 |
| Signal #14 | 26.1 | 3.41 | 6545.6 | 6638.8 | 67.0 |
| Signal #15 | 27.5 | 3.24 | 2577.1 | 2668.1 | 26.4 |
| Signal #16 | 27.7 | 3.22 | 2483.7 | 2579.4 | 25.4 |
| Signal #17 | 28.3 | 3.15 | 1085.9 | 1189.6 | 11.1 |
| Signal #18 | 28.7 | 3.11 | 1326.3 | 1431.9 | 13.6 |
| Signal #19 | 28.8 | 3.09 | 1146.4 | 1251.9 | 11.7 |
| Signal #20 | 29.2 | 3.05 | 9176.3 | 9279.5 | 93.9 |
| Signal #21 | 29.4 | 3.03 | 1181.7 | 1282.7 | 12.1 |
| Signal #22 | 30.3 | 2.95 | 1526.2 | 1609.3 | 15.6 |
| Signal #23 | 30.5 | 2.93 | 1294.4 | 1373.5 | 13.2 |
| Signal #24 | 30.7 | 2.91 | 1384.8 | 1458.2 | 14.2 |
| Signal #25 | 33.9 | 2.65 | 1308.3 | 1346.6 | 13.4 |
| Signal #26 | 34.8 | 2.58 | 1271.3 | 1313.6 | 13.0 |
| Signal #27 | 47.4 | 1.92 | 1085.5 | 1133.8 | 11.1 |

Compound 1 Maleate Salt

In some embodiments, the compound 1 salt is a compound 1 maleate salt. In some embodiments, the compound 1 maleate salt is amorphous. In some embodiments, the compound 1 maleate salt is crystalline. In some embodiments, the compound 1 maleate salt is a 1:1 compound 1:maleate salt. In some embodiments, the compound 1 maleate salt is a 2:1 compound 1:maleate salt.

In some embodiments, the compound 1 maleate salt is a crystalline polymorph. In some embodiments, the crystalline polymorph is characterized by the XRPD signals set for the below in Tables 43 and 44. In some embodiments, the crystalline polymorph XRPD pattern is substantially similar to that shown in FIG. 205 or 168. In some embodiments, the crystalline polymorph $^1$H-NMR spectrum is substantially similar to that shown in FIG. 198. In some embodiments, the crystalline polymorph DVS is substantially similar to that shown in FIG. 200. In some embodiments, the crystalline polymorph TGA spectrum is substantially similar to that shown in FIG. 227. In some embodiments, the crystalline compound 1 benzoate DSC spectrum is substantially similar to that shown in any one of FIG. 199 or 226.

In some embodiments, the crystalline compound 1 maleate Is a crystalline polymorphic form characterized by DSC having a melting signal at about 60.2° C. In some embodiments, the crystalline compound 1 fumarate Form A Is a crystalline polymorphic form characterized by TGA having an onset at about 200.0° C.

In some embodiments, the compound 1 maleate salt is a crystalline polymorph 15 characterized by an XRPD signal at 23.7°2θ (±0.2°2θ; ±0.1°2θ; or ±0.0°2θ; Cu Kα1 radiation).

In some embodiments, the compound 1 maleate salt is a crystalline polymorph characterized by XRPD signals at 21.6°2θ, and 23.7°2θ (±0.2°2θ; ±0.1°2θ; or ±0.0°2θ; Cu Kα1 radiation).

In some embodiments, the compound 1 maleate salt is a crystalline polymorph characterized by two or more, or three or more XRPD signals selected from the group consisting of 21.6°2θ, 23.7 20, and 26.0°2θ (±0.2°2θ; ±0.1°2θ; or ±0.0°2θ; Cu Kα1 radiation). In some embodiments, the compound 1 maleate salt is a crystalline polymorph characterized by XRPD signals at 21.6°2θ, 23.7°2θ, and 26.0°2θ (±0.2 20; 0.1°2θ; or ±0.0°2θ; Cu Kα1 radiation).

In some embodiments, the compound 1 maleate salt is a crystalline polymorph characterized by two or more, or three or more XRPD signals selected from the group consisting of 21.6°2θ, 23.7°2θ, 26.0°2θ, and 26.5°2θ (±0.2°2θ; ±0.1°2θ; or ±0.0°2θ; Cu Kα1 radiation).

In some embodiments, the compound 1 maleate salt is a crystalline polymorph characterized by XRPD signals at 21.6°2θ, 23.7°2θ, 26.0°2θ, and 26.5°2θ (±0.2°2θ; ±0.1°2θ; or ±0.0°2θ; Cu Kα1 radiation).

In some embodiments, the compound 1 maleate salt is a crystalline polymorph characterized by two or more, or three or more XRPD signals selected from the group consisting of 19.2°2θ, 21.6°2θ, 23.7°2θ, 26.0°2θ, and 26.5°2θ (±0.2°2θ; ±0.1°2θ; or ±0.0°2θ; Cu Kα1 radiation). In some embodiments, the compound 1 maleate salt is a crystalline polymorph characterized by XRPD signals at 19.2°2θ, 21.6°2θ, 23.7°2θ, 26.0°2θ, and 26.5°2θ (±0.2°2θ; ±0.1°2θ; or ±0.0°2θ; Cu Kα1 radiation).

In some embodiments, the compound 1 maleate salt is a crystalline polymorph characterized by two or more, or three or more XRPD signals selected from the group consisting of 11.8°2θ, 19.2°2θ, 21.6°2θ, 23.7°2θ, 26.0°2θ, and 26.5°2θ (±0.2°2θ; ±0.1°2θ; or ±0.0°2θ; Cu Kα1 radiation). In some embodiments, the compound 1 maleate salt is a crystalline polymorph characterized by XRPD signals at 11.8°2θ, 19.2°2θ, 21.6°2θ, 23.7°2θ, 26.0°2θ, and 26.5°2θ (±0.2°2θ; ±0.1°2θ; or ±0.0°2θ; Cu Kα1 radiation).

In some embodiments, the compound 1 maleate salt is a crystalline polymorph characterized by two or more, or three or more XRPD signals selected from the group consisting of 9.4°2θ, 11.8°2θ, 19.2°2θ, 21.6°2θ, 23.7°2θ, 26.0°2θ, and 26.5°2θ (±0.2°2θ; ±0.1°2θ; or ±0.0°2θ; Cu Kα1 radiation). In some embodiments, the compound 1 maleate salt is a crystalline polymorph characterized by XRPD signals at 9.4°2θ, 11.8°2θ, 19.2°2θ, 21.6°2θ, 23.7°2θ, 26.0°2θ, and 26.5°2θ (±0.2 2θ; 0.1°2θ; or ±0.0°2θ; Cu Kα1 radiation).

In some embodiments, the compound 1 maleate salt is a crystalline polymorph characterized by two or more, or three or more XRPD signals selected from the group consisting of 9.4°2θ, 11.8°2θ, 18.6°2θ, 19.2°2θ, 21.6°2θ, 23.7°2θ, 26.0°2θ, and 26.5°2θ (±0.2°2θ; ±0.1°2θ; or ±0.0°2θ; Cu Kα1 radiation). In some embodiments, the compound 1 maleate salt is a crystalline polymorph characterized by XRPD signals at 9.4°2θ, 11.8°2θ, 18.6°2θ, 19.2°2θ, 21.6°2θ, 23.7°2θ, 26.0°2θ, and 26.5°2θ (±0.2°2θ; ±0.1°2θ; or ±0.0°2θ; Cu Kα1 radiation).

In some embodiments, the compound 1 maleate salt is a crystalline polymorph characterized by two or more, or three or more XRPD signals selected from the group consisting of 9.4°2θ, 11.8°2θ, 18.6°2θ, 19.2°2θ, 21.6°2θ, 23.7°2θ, 25.0°2θ, 26.0°2θ, and 26.5°2θ (±0.2°2θ; ±0.1°2θ; or ±0.0°2θ; Cu Kα1 radiation). In some embodiments, the compound 1 maleate salt is a crystalline polymorph characterized by XRPD signals at 9.4°2θ, 11.8°2θ, 18.6°2θ, 19.2°2θ, 21.6°2θ, 23.7°2θ, 25.0°2θ, 26.0°2θ, and 26.5°2θ (±0.2°2θ; ±0.1°2θ; or ±0.0°2θ; Cu Kα1 radiation).

In some embodiments, the compound 1 maleate salt is a crystalline polymorph characterized by two or more, or three or more XRPD signals selected from the group consisting of 9.4°2θ, 11.8°2θ, 18.6°2θ, 19.2°2θ, 20.9°2θ, 21.6°2θ, 23.7°2θ, 25.0°2θ, 26.0°2θ, and 26.5°2θ (±0.2°2θ; ±0.1°2θ; or ±0.0°2θ; Cu Kα1 radiation). In some embodiments, the compound 1 maleate salt is a crystalline polymorph characterized by XRPD signals at 9.4°2θ, 11.8°2θ, 18.6°2θ, 19.2°2θ, 20.9°2θ, 21.6°2θ, 23.7°2θ, 25.0°2θ, 26.0°2θ, and 26.5°2θ (±0.2°2θ; ±0.1°2θ; or ±0.0°2θ; Cu Kα1 radiation).

In some embodiments, the compound 1 maleate salt is a crystalline polymorph characterized by two or more, or three or more XRPD signals selected from the group consisting of 9.4°2θ, 11.8°2θ, 16.9°2θ, 18.6°2θ, 19.2°2θ, 20.9°2θ, 21.6°2θ, 23.7°2θ, 25.0°2θ, 26.0°2θ, and 26.5°2θ (±0.2°2θ; ±0.1°2θ; or ±0.0°2θ. Cu Kα1 radiation). In some embodiments, the compound 1 maleate salt is a crystalline polymorph characterized by XRPD signals at 9.4°2θ, 11.8°2θ, 16.9°2θ, 18.6°2θ, 19.2°2θ, 20.9°2θ, 21.6°2θ, 23.7°2θ, 25.0°2θ, 26.0°2θ, and 26.5°2θ (±0.2°2θ; ±0.1°2θ; or ±0.0°2θ; Cu Kα1 radiation).

In some embodiments, the compound 1 maleate salt is a crystalline polymorph characterized by two or more, or three or more XRPD signals selected from the group consisting of 9.4°2θ, 11.8°2θ, 16.9°2θ, 18.6°2θ, 19.2°2θ, 20.9°2θ, 21.6°2θ, 22.2°2θ, 23.7°2θ, 25.0°2θ, 26.0°2θ, and 26.5°2θ (±0.2°2θ; ±0.1°2θ; or ±0.0°2θ; Cu Kα1 radiation). In some embodiments, the compound 1 maleate salt is a crystalline polymorph characterized by XRPD signals at 9.4°2θ, 11.8°2θ, 16.9°2θ, 18.6°2θ, 19.2°2θ, 20.9°2θ, 21.6°2θ, 22.2°2θ, 23.7°2θ, 25.0°2θ, 26.0°2θ, and 26.5°2θ (±0.2°2θ; ±0.1°2θ; or ±0.0°2θ; Cu Kα1 radiation).

In some embodiments, the compound 1 maleate salt is a crystalline polymorph characterized by two or more, or three or more XRPD signals selected from the group consisting of 9.4°2θ, 10.9°2θ, 11.8°2θ, 16.9°2θ, 18.6°2θ, 19.2°2θ, 20.9°2θ, 21.6°2θ, 22.2°2θ, 23.7°2θ, 25.0°2θ, 26.0°2θ, and 26.5°2θ (±0.2°2θ; ±0.1°2θ; or ±0.0°2θ; Cu Kα1 radiation). In some embodiments, the compound 1 maleate salt is a crystalline polymorph characterized by XRPD signals at 9.4°2θ, 10.9°2θ, 11.8°2θ, 16.9°2θ, 18.6°2θ, 19.2°2θ, 20.9°2θ, 21.6°2θ, 22.2°2θ, 23.7°2θ, 25.0°2θ, 26.0°2θ, and 26.5°2θ (±0.2°2θ; ±0.1°2θ; or ±0.0°2θ; Cu Kα1 radiation).

In some embodiments, crystalline polymorph is characterized by one, two, three, four, five, six, seven, eight, nine, ten, eleven, twelve, or thirteen XRPD signals selected from those set forth in Table 43.

TABLE 43

Crystalline Compound 1 Maleate Salt XRPD signals (±0.2 °2θ; ±0.1 °2θ; or ±0.0 °2θ; Cu Kα1 radiation)

| Signal number | 2-θ (°) | d Value | Net Intensity (counts) | Gross Intensity (counts) | Rel. Intensity (%) |
| --- | --- | --- | --- | --- | --- |
| Signal #1 | 9.4 | 9.36 | 781.7 | 842.9 | 22.8 |
| Signal #2 | 10.9 | 8.14 | 349.7 | 414.9 | 10.2 |
| Signal #3 | 11.8 | 7.50 | 1028.1 | 1095.8 | 30.0 |
| Signal #4 | 16.9 | 5.24 | 436.3 | 526.4 | 12.7 |
| Signal #5 | 18.6 | 4.76 | 709.5 | 825.6 | 20.7 |
| Signal #6 | 19.2 | 4.63 | 1126.1 | 1246.0 | 32.9 |
| Signal #7 | 20.9 | 4.25 | 436.9 | 573.5 | 12.8 |
| Signal #8 | 21.6 | 4.11 | 2203.6 | 2358.5 | 64.3 |
| Signal #9 | 22.2 | 4.00 | 397.3 | 561.8 | 11.6 |
| Signal #10 | 23.7 | 3.75 | 3426.3 | 3617.2 | 100.0 |
| Signal #11 | 25.0 | 3.55 | 587.5 | 785.4 | 17.1 |
| Signal #12 | 26.0 | 3.42 | 1321.4 | 1510.2 | 38.6 |
| Signal #13 | 26.5 | 3.37 | 1149.3 | 1330.8 | 33.5 |

In some embodiments, the compound 1 maleate salt is a crystalline polymorph characterized by an XRPD signal at 19.1°2θ (±0.2°2θ; ±0.1°2θ; or ±0.0°2θ; Cu Kα1 radiation).

In some embodiments, the compound 1 maleate salt is a crystalline polymorph characterized by XRPD signals at 19.1°2θ, and 23.7°2θ (±0.2°2θ; ±0.1°2θ; or ±0.0°2θ; Cu Kα1 radiation).

In some embodiments, the compound 1 maleate salt is a crystalline polymorph characterized by two or more, or three or more XRPD signals selected from the group consisting of 19.1°2θ, 23.7°2θ, and 26.4°2θ (±0.2°2θ; ±0.1°2θ; or ±0.0°2θ; Cu Kα1 radiation). In some embodiments, the compound 1 maleate salt is a crystalline polymorph characterized by XRPD signals at 19.1°2θ, 23.7°2θ, and 26.4°2θ (±0.2°2θ, ±0.1°2θ, or ±0.0°2θ Cu Kα1 radiation).

In some embodiments, the compound 1 maleate salt is a crystalline polymorph characterized by two or more, or three or more XRPD signals selected from the group consisting of 18.5°2θ, 19.1°2θ, 23.7°2θ, and 26.4°2θ (±0.2°2θ; ±0.1°2θ; or ±0.0°2θ; Cu Kα1 radiation).

In some embodiments, the compound 1 maleate salt is a crystalline polymorph characterized by XRPD signals at 18.5°2θ, 19.1°2θ, 23.7°2θ, and 26.4°2θ (±0.2°2θ; ±0.1°2θ; or ±0.0°2θ; Cu Kα1 radiation).

In some embodiments, the compound 1 maleate salt is a crystalline polymorph characterized by two or more, or three or more XRPD signals selected from the group consisting of 18.5°2θ, 19.1°2θ, 21.6°2θ, 23.7°2θ, and 26.4°2θ (±0.2°2θ; ±0.1°2θ; or ±0.0°2θ; Cu Kα1 radiation). In some embodiments, the compound 1 maleate salt is a crystalline polymorph characterized by XRPD signals at 18.5°2θ, 19.1°2θ, 21.6°2θ, 23.7°2θ, and 26.4°2θ (±0.2°2θ; ±0.1°2θ; or ±0.0°2θ; Cu Kα1 radiation).

In some embodiments, the compound 1 maleate salt is a crystalline polymorph characterized by two or more, or three or more XRPD signals selected from the group consisting of 18.5°2θ, 19.1°2θ, 20.8°2θ, 21.6°2θ, 23.7°2θ, and 26.4°2θ (±0.2°2θ; ±0.1°2θ; or ±0.0°2θ; Cu Kα1 radiation). In some embodiments, the compound 1 maleate salt is a crystalline polymorph characterized by XRPD signals at 18.5°2θ, 19.1°2θ, 20.8°2θ, 21.6°2θ, 23.7°2θ, and 26.4°2θ (±0.2°2θ; ±0.1°2θ; or ±0.0°2θ; Cu Kα1 radiation).

In some embodiments, the compound 1 maleate salt is a crystalline polymorph characterized by two or more, or three or more XRPD signals selected from the group consisting of 18.5°2θ, 19.1°2θ, 20.8°2θ, 21.6°2θ, 23.7°2θ, 26.0°2θ, and 26.4°2θ (±0.2°2θ; ±0.1°2θ; or ±0.0°2θ; Cu Kα1 radiation). In some embodiments, the compound 1 maleate salt is a crystalline polymorph characterized by XRPD signals at 18.5°2θ, 19.1°2θ, 20.8°2θ, 21.6°2θ, 23.7°2θ, 26.0°2θ, and 26.4°2θ (±0.2°2θ; ±0.1°2θ; or ±0.0°2θ; Cu Kα1 radiation).

In some embodiments, the compound 1 maleate salt is a crystalline polymorph characterized by two or more, or three or more XRPD signals selected from the group consisting of 16.7°2θ, 18.5°2θ, 19.1°2θ, 20.8°2θ, 21.6°2θ, 23.7°2θ, 26.0°2θ, and 26.4°2θ (±0.2°2θ; ±0.1°2θ; or ±0.0°2θ; Cu Kα1 radiation). In some embodiments, the compound 1 maleate salt is a crystalline polymorph characterized by XRPD signals at 16.7°2θ, 18.5°2θ, 19.1°2θ, 20.8°2θ, 21.6°2θ, 23.7°2θ, 26.0°2θ, and 26.4°2θ (±0.2°2θ; ±0.1°2θ; or ±0.0°2θ; Cu Kα1 radiation).

In some embodiments, the compound 1 maleate salt is a crystalline polymorph characterized by two or more, or three or more XRPD signals selected from the group consisting of 16.7°2θ, 18.5°2θ, 19.1°2θ, 20.8°2θ, 21.6°2θ, 22.2°2θ, 23.7°2θ, 26.0°2θ, and 26.4°2θ (±0.2°2θ; ±0.1°2θ; or ±0.0°2θ; Cu Kα1 radiation). In some embodiments, the compound 1 maleate salt is a crystalline polymorph characterized by XRPD signals at 16.7°2θ, 18.5°2θ, 19.1°2θ, 20.8°2θ, 21.6°2θ, 22.2°2θ, 23.7°2θ, 26.0°2θ, and 26.4°2θ (±0.2°2θ; ±0.1°2θ; or ±0.0°2θ; Cu Kα1 radiation).

In some embodiments, the compound 1 maleate salt is a crystalline polymorph characterized by two or more, or three or more XRPD signals selected from the group consisting of 16.7°2θ, 18.5°2θ, 19.1°2θ, 20.8°2θ, 21.6°2θ, 22.2°2θ, 23.7°2θ, 24.1°2θ, 26.0°2θ, and 26.4°2θ (±0.2°2θ; ±0.1°2θ; or ±0.0°2θ; Cu Kα1 radiation). In some embodiments, the compound 1 maleate salt is a crystalline polymorph characterized by XRPD signals at 16.7°2θ, 18.5°2θ, 19.1°2θ, 20.8°2θ, 21.6°2θ, 22.2°2θ, 23.7°2θ, 24.1°2θ, 26.0°2θ, and 26.4°2θ (±0.2°2θ; ±0.1°2θ; or ±0.0°2θ; Cu Kα1 radiation).

In some embodiments, the compound 1 maleate salt is a crystalline polymorph characterized by two or more, or three or more XRPD signals selected from the group consisting of 11.8°2θ, 16.7°2θ, 18.5°2θ, 19.1°2θ, 20.8°2θ, 21.6°2θ, 22.2°2θ, 23.7°2θ, 24.1°2θ, 26.0°2θ, and 26.4°2θ (±0.2°2θ; ±0.1°2θ; or ±0.0°2θ; Cu Kα1 radiation). In some embodiments, the compound 1 maleate salt is a crystalline polymorph characterized by XRPD signals at 11.8°2θ, 16.7°2θ, 18.5°2θ, 19.1°2θ, 20.8°2θ, 21.6°2θ, 22.2°2θ, 23.7°2θ, 24.1°2θ, 26.0°2θ, and 26.4°2θ (±0.2°2θ; ±0.1°2θ; or ±0.0°2θ; Cu Kα1 radiation).

In some embodiments, the compound 1 maleate salt is a crystalline polymorph characterized by two or more, or three or more XRPD signals selected from the group consisting of 11.8°2θ, 16.7°2θ, 18.5°2θ, 19.1°2θ, 20.8°2θ, 21.6°2θ, 22.2°2θ, 23.7°2θ, 24.1°2θ, 26.0°2θ, 26.4°2θ, and 30.2°2θ (±0.2°2θ; ±0.1°2θ; or ±0.0°2θ; Cu Kα1 radiation). In some embodiments, the compound 1 maleate salt is a crystalline polymorph characterized by XRPD signals at 1.8°2θ, 16.7°2θ, 18.5°2θ, 19.1°2θ, 20.8°2θ, 21.6°2θ, 22.2°2θ, 23.7°2θ, 24.1°2θ, 26.0°2θ, 26.4°2θ and 30.2°2θ (±0.2°2θ; ±0.1°2θ; or ±0.0°2θ; Cu Kα1 radiation).

In some embodiments, the compound 1 maleate salt is a crystalline polymorph characterized by two or more, or three or more XRPD signals selected from the group consisting of 11.8°2θ, 16.7°2θ, 18.5°2θ, 19.1°2θ, 20.8°2θ, 21.6°2θ, 22.2°2θ, 23.7°2θ, 24.1°2θ, 26.0°2θ, 26.4°2θ, 28.2°2θ, and 30.2°2θ (±0.2°2θ; ±0.1°2θ; or ±0.0°2θ; Cu Kα1 radiation). In some embodiments, the compound 1 maleate salt is a crystalline polymorph characterized by XRPD signals at 11.8°2θ, 16.7°2θ, 18.5°2θ, 19.1°2θ, 20.8°2θ, 21.6°2θ, 22.2°2θ, 23.7°2θ, 24.1°2θ, 26.0°2θ, 26.4°2θ, 28.2°2θ, and 30.2°2θ (±0.2°2θ; ±0.1°2θ; or ±0.0°2θ; Cu Kα1 radiation).

In some embodiments, the compound 1 maleate salt is a crystalline polymorph characterized by two or more, or three or more XRPD signals selected from the group consisting of 11.8°2θ, 16.7°2θ, 16.8°2θ, 18.5°2θ, 19.1°2θ, 20.8°2θ, 21.6°2θ, 22.2°2θ, 23.7°2θ, 24.1°2θ, 26.0°2θ, 26.4°2θ, 28.2°2θ, and 30.2°2θ (±0.2°2θ; ±0.1°2θ; or ±0.0°2θ; Cu Kα1 radiation). In some embodiments, the compound 1 maleate salt is a crystalline polymorph characterized by XRPD signals at 11.8°2θ, 16.7°2θ, 16.8°2θ, 18.5°2θ, 19.1°2θ, 20.8°2θ, 21.6°2θ, 22.2°2θ, 23.7°2θ, 24.1°2θ, 26.0°2θ, 26.4°2θ, 28.2°2θ, and 30.2°2θ (±0.2°2θ; ±0.1°2θ; or ±0.0°2θ; Cu Kα1 radiation).

In some embodiments, the compound 1 maleate salt is a crystalline polymorph characterized by two or more, or three or more XRPD signals selected from the group consisting 15 of 11.8°2θ, 16.7°2θ, 16.8°2θ, 18.5°2θ, 19.1°2θ, 20.8°2θ, 21.6°2θ, 22.2°2θ, 23.7°2θ, 24.1°2θ, 24.9°2θ, 26.0°2θ, 26.4°2θ, 28.2°2θ, and 30.2°2θ (±0.2°2θ; ±0.1°2θ; or ±0.0°2θ; Cu Kα1 radiation). In some embodiments, the compound 1 maleate salt is a crystalline polymorph characterized by XRPD signals at 11.8°2θ, 16.7°2θ, 16.8°2θ, 18.5°2θ, 19.1°2θ, 20.8°2θ, 21.6°2θ, 22.2°2θ, 23.7°2θ, 24.1°2θ, 24.9°2θ, 26.0°2θ, 26.4°2θ, 28.2°2θ, and 30.2°2θ (±0.2°2θ; ±0.1°2θ; or ±0.0°2θ; Cu Kα1 radiation).

In some embodiments, the compound 1 maleate salt is a crystalline polymorph characterized by two or more, or three or more XRPD signals selected from the group consisting of 9.4°2θ, 11.8°2θ, 16.7°2θ, 16.8°2θ, 18.5°2θ, 19.1°2θ, 20.8°2θ, 21.6°2θ, 22.2°2θ, 23.7°2θ, 24.1°2θ, 24.9°2θ, 26.0°2θ, 26.4°2θ, 28.2°2θ, and 30.2°2θ (±0.2°2θ; ±0.1°2θ; or ±0.0°2θ; Cu Kα1 radiation). In some embodiments, the compound 1 maleate salt is a crystalline polymorph characterized by XRPD signals at 9.4°2θ, 11.8°2θ, 16.7°2θ, 16.8°2θ, 18.5°2θ, 19.1°2θ, 20.8°2θ, 21.6°2θ, 22.2°2θ, 23.7°2θ, 24.1°2θ, 24.9°2θ, 26.0°2θ, 26.4°2θ, 28.2°2θ, and 30.2°2θ (±0.2°2θ; ±0.1°2θ; or ±0.0°2θ; Cu Kα1 radiation).

In some embodiments, the compound 1 maleate salt is a crystalline polymorph characterized by two or more, or three or more XRPD signals selected from the group consisting of 9.4°2θ, 11.8°2θ, 16.7°2θ, 16.8°2θ, 17.7°2θ, 18.5°2θ, 19.1°2θ, 20.8°2θ, 21.6°2θ, 22.2°2θ, 23.7°2θ, 24.1°2θ, 24.9°2θ, 26.0°2θ, 26.4°2θ, 28.2°2θ, and 30.2°2θ (±0.2°2θ; ±0.1°2θ; or 0.0°2θ; Cu Kα1 radiation). In some embodiments, the compound 1 maleate salt is a crystalline polymorph characterized by XRPD signals at 9.4°2θ, 11.8°2θ, 16.7°2θ, 16.8°2θ, 17.7°2θ 18.5°2θ, 19.1°2θ, 20.8°2θ, 21.6°2θ, 22.2°2θ, 23.7°2θ, 24.1°2θ, 24.9°2θ, 26.0°2θ, 26.4°2θ, 28.2°2θ, and 30.2°2θ (±0.2°2θ; ±0.1°2θ, or ±0.0°2θ; Cu Kα1 radiation).

In some embodiments the crystalline polymorph is characterized by one, two, three, four, five, six, seven, eight, nine, ten, eleven, twelve, thirteen, fourteen, fifteen, sixteen, or seventeen XRPD signals selected from those set forth in Table 44.

TABLE 44

Crystalline Compound 1 Maleate Salt XRPD Signals (±0.2 °2θ; ±0.1 °2θ; or ±0.0 °2θ; Cu Kα1 radiation)

| Signal number | 2-θ (°) | d Value | Net Intensity (counts) | Gross Intensity (counts) | Rel. Intensity (%) |
|---|---|---|---|---|---|
| Signal #1 | 9.4 | 9.39 | 205.8 | 279.4 | 11.2 |
| Signal #2 | 11.8 | 7.52 | 367.2 | 434.2 | 19.9 |
| Signal #3 | 16.7 | 5.32 | 506.8 | 581.9 | 27.5 |
| Signal #4 | 16.8 | 5.29 | 269.0 | 345.6 | 14.6 |
| Signal #5 | 17.7 | 4.99 | 187.4 | 275.8 | 10.2 |
| Signal #6 | 18.5 | 4.78 | 1074.6 | 1169.4 | 58.3 |
| Signal #7 | 19.1 | 4.64 | 1843.6 | 1940.4 | 100.0 |
| Signal #8 | 20.8 | 4.26 | 584.1 | 695.0 | 31.7 |
| Signal #9 | 21.6 | 4.12 | 771.4 | 888.1 | 41.8 |
| Signal #10 | 22.2 | 4.01 | 396.4 | 514.1 | 21.5 |
| Signal #11 | 23.7 | 3.76 | 1531.8 | 1650.8 | 83.1 |
| Signal #12 | 24.1 | 3.69 | 370.3 | 491.9 | 20.1 |
| Signal #13 | 24.9 | 3.57 | 257.3 | 379.0 | 14.0 |
| Signal #14 | 26.0 | 3.42 | 507.9 | 627.6 | 27.5 |
| Signal #15 | 26.4 | 3.37 | 1307.7 | 1426.1 | 70.9 |
| Signal #16 | 28.2 | 3.17 | 284.8 | 395.6 | 15.4 |
| Signal #17 | 30.2 | 2.96 | 295.1 | 395.7 | 16.0 |

Crystalline Compound 1 Benzoate Salt

In some embodiments, the compound 1 salt is a compound 1 benzoate salt. In some embodiments, the compound 1 benzoate salt is amorphous. In some embodiments, the compound 1 benzoate salt is crystalline. In some embodiments, the compound 1 benzoate salt is a 1:1 compound 1:benzoate salt. In some embodiments, the compound 1 benzoate salt is a 2:1 compound 1:benzoate salt.

In some embodiments, the compound 1 benzoate salt is a crystalline polymorph. In some embodiments, the crystalline polymorph is characterized by the XRPD signals set for the below in Table 46. In some embodiments, the crystalline polymorph XRPD pattern is substantially similar to that shown in FIG. 169. In some embodiments, the crystalline polymorph $^1$H-NMR spectrum is substantially similar to that shown in 207. In some embodiments, the crystalline polymorph DVS is substantially similar to that shown in FIG. 209. In some embodiments, the crystalline polymorph TGA spectrum is substantially similar to that shown in FIG. 231 or 213. In some embodiments, the crystalline compound 1 benzoate DSC spectrum is substantially similar to that shown in any one of FIG. 208 or 230.

In some embodiments, the crystalline compound 1 benzoate is a crystalline polymorphic form characterized by DSC having a melting signal at about 101.0° C. In some embodiments, the crystalline compound 1 fumarate Form A Is a crystalline polymorphic form characterized by TGA 20 having an onset at about 102.2° C.

In some embodiments, the compound 1 benzoate salt is a crystalline polymorph characterized by an XRPD signal at 17.5°2θ (±0.2°2θ; ±0.1°2θ; or ±0.0°2θ; Cu Kα1 radiation).

In some embodiments, the compound 1 benzoate salt is a crystalline polymorph characterized by XRPD signals at 14.5°2θ, and 17.5°2θ (±0.2°2θ; ±0.1°2θ; or ±0.0°2θ; Cu Kα1 radiation).

In some embodiments, the compound 1 benzoate salt is a crystalline polymorph characterized by two or more, or three or more XRPD signals selected from the group consisting of 14.5°2θ, 17.5°2θ, and 18.6°2θ (±0.2°2θ; ±0.1°2θ; or ±0.0°2θ; Cu Kα1 radiation). In some embodiments, the compound 1 benzoate salt is a crystalline polymorph characterized by XRPD signals at 14.5°2θ, 17.5°2θ, and 18.6°2θ (±0.2°2θ; ±0.1°2θ; or ±0.0°2θ; Cu Kα1 radiation).

In some embodiments, the compound 1 benzoate salt is a crystalline polymorph characterized by two or more, or three or more XRPD signals selected from the group consisting of 13.8°2θ, 14.5°2θ, 17.5°2θ, and 18.6°2θ (±0.2°2θ; ±0.1°2θ; or ±0.0°2θ; Cu Kα1 radiation). In some embodiments, the compound 1 benzoate salt is a crystalline polymorph characterized by XRPD signals at 13.8°2θ, 14.5°2θ, 17.5°2θ, and 18.6°2θ (±0.2°2θ; ±0.1°2θ; or ±0.0°2θ; Cu Kα1 radiation).

In some embodiments, the compound 1 benzoate salt is a crystalline polymorph characterized by two or more, or three or more XRPD signals selected from the group consisting of 13.8°2θ, 14.5°2θ, 17.5°2θ, 18.6°2θ, and 19.2°2θ (±0.2°2θ; ±0.1°2θ; or ±0.0°2θ; Cu Kα1 radiation). In some embodiments, the compound 1 benzoate salt is a crystalline polymorph characterized by XRPD signals at 13.8°2θ, 14.5°2θ, 17.5°2θ, 18.6°2θ, and 19.2°2θ (±0.2°2θ; ±0.1°2θ; or ±0.0°2θ; Cu Kα1 radiation).

In some embodiments, the compound 1 benzoate salt is a crystalline polymorph characterized by two or more, or three or more XRPD signals selected from the group consisting of 7.8°2θ, 13.8°2θ, 14.5°2θ, 17.5°2θ, 18.6°2θ, and 19.2°2θ (±0.2°2θ; ±0.1°2θ; or ±0.0°2θ; Cu Kα1 radiation). In some embodiments, the compound 1 benzoate salt is a crystalline polymorph characterized by XRPD signals at 7.8°2θ, 13.8°2θ, 14.5°2θ, 17.5°2θ, 18.6°2θ, and 19.2°2θ (±0.2°2θ; ±0.1°2θ; or ±0.0°2θ; Cu Kα1 radiation).

In some embodiments, the compound 1 benzoate salt is a crystalline polymorph characterized by two or more, or three or more XRPD signals selected from the group consisting of 7.8°2θ, 13.8°2θ, 14.5°2θ, 17.5°2θ, 18.6°2θ, 19.2°2θ, and 25.3°2θ (±0.2°2θ; ±0.1°2θ; or ±0.0°2θ; Cu Kα1 radiation). In some embodiments, the compound 1 benzoate salt is a crystalline polymorph characterized by XRPD signals at 7.8°2θ, 13.8°2θ, 14.5°2θ, 17.5°2θ, 18.6°2θ, 19.2°2θ, and 25.3°2θ (±0.2°2θ; ±0.1°2θ; or ±0.0°2θ; Cu Kα1 radiation).

In some embodiments, the compound 1 benzoate salt is a crystalline polymorph characterized by two or more, or three or more XRPD signals selected from the group consisting of 7.8°2θ, 13.8°2θ, 14.5°2θ, 1 5.5°2θ, 17.5°2θ, 18.6°2θ, 19.2°2θ, and 25.3°2θ (±0.2°2θ; ±0.1°2θ; or ±0.0°2θ; Cu Kα1 radiation). In some embodiments, the compound 1 benzoate salt is a crystalline polymorph characterized by XRPD signals at 7.8°2θ, 13.8°2θ, 14.5°2θ, 15.5°2θ, 17.5°2θ, 18.6°2θ, 19.2°2θ, and 25.3°2θ (±0.2°2θ; ±0.1°2θ; or ±0.0°2θ; Cu Kα1 radiation).

In some embodiments, the compound 1 benzoate salt is a crystalline polymorph characterized by two or more, or three or more XRPD signals selected from the group consisting of 7.8°2θ, 13.8°2θ, 14.5°2θ, 15.5°2θ, 17.5°2θ, 18.6°2θ, 19.2°2θ, 25.2°2θ, and 25.3°2θ (±0.2°2θ; ±0.1°2θ; or ±0.0°2θ; Cu Kα1 radiation). In some embodiments, the compound 1 benzoate salt is a crystalline polymorph characterized by XRPD signals at 7.8°2θ, 13.8°2θ, 14.5°2θ, 15.5°2θ, 17.5°2θ, 18.6°2θ, 19.2°2θ, 25.2°2θ, and 25.3°2θ (±0.2°2θ; ±0.1°2θ; or ±0.0°2θ; Cu Kα1 radiation).

In some embodiments, the compound 1 benzoate salt is a crystalline polymorph characterized by two or more, or three or more XRPD signals selected from the group consisting of 7.8°2θ, 12.5°2θ, 13.8°2θ, 14.5°2θ, 15.5°2θ, 17.5°2θ, 18.6°2θ, 19.2°2θ, 25.2°2θ, and 25.3°2θ (±0.2°2θ; ±0.1°2θ; or ±0.0°2θ; Cu Kα1 radiation). In some embodiments, the compound 1 benzoate salt is a crystalline polymorph characterized by XRPD signals at 7.8°2θ, 12.5°2θ, 13.8°2θ, 14.5°2θ, 15.5°2θ, 17.5°2θ, 18.6°2θ, 19.2°2θ, 25.2°2θ, and 25.3°2θ (±0.2°2θ; ±0.1°2θ; or ±0.0°2θ; Cu Kα1 radiation).

In some embodiments, the compound 1 benzoate salt is a crystalline polymorph characterized by two or more, or three or more XRPD signals selected from the group consisting of 7.8°2θ, 12.5°2θ, 13.8°2θ, 14.5°2θ, 15.5°2θ, 17.5°2θ, 18.6°2θ, 19.2°2θ, 19.7°2θ, 25.2°2θ, and 25.3°2θ (±0.2°2θ; ±0.1°2θ; or ±0.0°2θ; Cu Kα1 radiation). In some embodiments, the compound 1 benzoate salt is a crystalline polymorph characterized by XRPD signals at 7.8°2θ, 12.5°2θ, 13.8°2θ, 14.5°2θ, 15.5°2θ, 17.5°2θ, 18.6°2θ, 19.2°2θ, 19.7°2θ, 25.2°2θ, and 25.3°2θ (±0.2°2θ; ±0.1°2θ; or ±0.0°2θ; Cu Kα1 radiation).

In some embodiments, the compound 1 benzoate salt is a crystalline polymorph characterized by two or more, or three or more XRPD signals selected from the group consisting of 7.8°2θ, 12.5°2θ, 13.8°2θ, 14.5°2θ, 15.5°2θ, 17.5°2θ, 18.6°2θ, 19.2°2θ, 19.7°2θ, 23.7°2θ, 25.2°2θ, and 25.3°2θ (±0.2°2θ; ±0.1°2θ; or ±0.0°2θ; Cu Kα1 radiation). In some embodiments, the compound 1 benzoate salt is a crystalline polymorph characterized by XRPD signals at 7.8°2θ, 12.5°2θ, 13.8°2θ, 14.5°2θ, 15.5°2θ, 17.5°2θ, 18.6°2θ, 19.2°2θ, 19.7°2θ, 23.7°2θ, 25.2°2θ, and 25.3°2θ (±0.2°2θ; ±0.1°2θ; or ±0.0°2θ; Cu Kα1 radiation).

In some embodiments, the compound 1 benzoate salt is a crystalline polymorph characterized by two or more, or three or more XRPD signals selected from the group consisting of 7.8°2θ, 12.5°2θ, 13.8°2θ, 14.5°2θ, 15.5°2θ, 17.5°2θ, 18.6°2θ, 19.2°2θ, 19.7°2θ, 20.6°2θ, 23.7°2θ, 25.2°2θ, and 25.3°2θ (±0.2°2θ; ±0.1°2θ; or ±0.0°2θ; Cu Kα1 radiation). In some embodiments, the compound 1 benzoate salt is a crystalline polymorph characterized by XRPD signals at 7.8 0.20, 12.5°2θ 13.8°2θ, 14.5°2θ, 15.5°2θ, 17.5°2θ, 18.6°2θ, 19.2°2θ, 19.7°2θ, 20.6°2θ, 23.7°2θ, 25.2°2θ, and 25.3°2θ (±0.2°2θ; ±0.1°2θ; or ±0.0°2θ; Cu Kα1 radiation).

In some embodiments, crystalline polymorph is characterized by one, two, three, four, five, six, seven, eight, ten, eleven, twelve, or thirteen XRPD signals selected from those set forth in Table 45.

TABLE 45

Crystalline compound 1 benzoate salt XRPD signals (±0.2 °2θ; ±0.1 °2θ; or ±0.0 °2θ; Cu Kα1 radiation)

| Signal number | 2-θ (°) | d Value | Net Intensity (counts) | Gross Intensity (counts) | Rel. Intensity (%) |
|---|---|---|---|---|---|
| Signal #1 | 7.8 | 11.28 | 1803.2 | 1921.3 | 19.9 |
| Signal #2 | 12.5 | 7.08 | 1379.5 | 1497.4 | 15.2 |
| Signal #3 | 13.8 | 6.43 | 2438.3 | 2595.4 | 26.9 |
| Signal #4 | 14.5 | 6.10 | 2985.8 | 3166.9 | 33.0 |
| Signal #5 | 15.5 | 5.72 | 1578.8 | 1782.4 | 17.4 |
| Signal #6 | 17.5 | 5.07 | 9059.3 | 9310.6 | 100.0 |
| Signal #7 | 18.6 | 4.76 | 2469.9 | 2748.9 | 27.3 |
| Signal #8 | 19.2 | 4.62 | 2112.2 | 2395.9 | 23.3 |
| Signal #9 | 19.7 | 4.50 | 1262.4 | 1544.5 | 13.9 |
| Signal #10 | 20.6 | 4.31 | 978.6 | 1246.4 | 10.8 |
| Signal #11 | 23.7 | 3.76 | 1206.2 | 1416.9 | 13.3 |
| Signal #12 | 25.2 | 3.53 | 1563.8 | 1783.7 | 17.3 |
| Signal #13 | 25.3 | 3.52 | 1618.8 | 1838.4 | 17.9 |

In some embodiments, the compound 1 benzoate salt is a crystalline polymorph characterized by an XRPD signal at 17.5°2θ (±0.2°2θ; ±0.1°2θ; or ±0.0°2θ; Cu Kα1 radiation).

In some embodiments, the compound 1 benzoate salt is a crystalline polymorph characterized by XRPD signals at 7.8°2θ and 17.5°2θ (±0.2°2θ; ±0.1°2θ; or ±0.0°2θ; Cu Kα1 radiation).

In some embodiments, the compound 1 benzoate salt is a crystalline polymorph characterized by two or more, or three or more XRPD signals selected from the group consisting of 7.8°2θ, 17.5°2θ, and 19.1°2θ (±0.2°2θ; ±0.1°2θ; or ±0.0°2θ; Cu Kα1 radiation). In some embodiments, the compound 1 benzoate salt is a crystalline polymorph characterized by XRPD signals at 7.8°2θ, 17.5°2θ, and 19.1°2θ (±0.2°2θ; ±0.1°2θ; or ±0.0°2θ; Cu Kα1 radiation).

In some embodiments, the compound 1 benzoate salt is a crystalline polymorph characterized by two or more, or three or more XRPD signals selected from the group consisting of 7.8°2θ, 14.5°2θ, 17.5°2θ, and 19.1°2θ (±0.2°2θ; ±0.1°2θ; or ±0.0°2θ; Cu Kα1 radiation).

In some embodiments, the compound 1 benzoate salt is a crystalline polymorph characterized by XRPD signals at 7.8°2θ, 14.5°2θ, 17.5°2θ, and 19.1°2θ (±0.2°2θ; ±0.1°2θ; or ±0.0°2θ; Cu Kα1 radiation).

In some embodiments, the compound 1 benzoate salt is a crystalline polymorph characterized by two or more, or three or more XRPD signals selected from the group consisting of 7.8°2θ, 14.5°2θ, 17.5°2θ, 19.1°2θ, and 20.5°2θ (±0.2°2θ; ±0.1°2θ; or ±0.0°2θ; Cu Kα1 radiation). In some embodiments, the compound 1 benzoate salt is a crystalline polymorph characterized by XRPD signals at 7.8°2θ, 14.5°2θ, 17.5°2θ, 19.1°2θ, and 20.5°2θ (±0.2°2θ; ±0.1°2θ; or ±0.0°2θ; Cu Kα1 radiation).

In some embodiments, the compound 1 benzoate salt is a crystalline polymorph characterized by two or more, or three or more XRPD signals selected from the group consisting of 7.8°2θ, 14.5°2θ, 17.5°2θ, 19.1°2θ, 20.5°2θ, and 23.6°2θ (±0.2°2θ; ±0.1°2θ; or ±0.0°2θ; Cu Kα1 radiation). In some embodiments, the compound 1 benzoate salt is a crystalline polymorph characterized by XRPD signals at 7.8°2θ, 14.5°2θ, 17.5°2θ, 19.1°2θ, 20.5°2θ, and 23.6°2θ (±0.2°2θ; ±0.1°2θ; or ±0.0°2θ; Cu Kα1 radiation).

In some embodiments, the compound 1 benzoate salt is a crystalline polymorph characterized by two or more, or three or more XRPD signals selected from the group consisting of 7.8°2θ, 14.5°2θ, 17.5°2θ, 19.1°2θ, 20.5°2θ, 23.6°2θ, and 25.3°2θ (±0.2°2θ; ±0.1°2θ; or ±0.0°2θ; Cu Kα1 radiation). In some embodiments, the compound 1 benzoate salt is a crystalline polymorph characterized by XRPD signals at 7.8°2θ, 14.5°2θ, 17.5°2θ, 19.1°2θ, 20.5°2θ, 23.6°2θ, and 25.3°2θ (±0.2°2θ; ±0.1°2θ; or ±0.0°2θ; Cu Kα1 radiation).

In some embodiments, the compound 1 benzoate salt is a crystalline polymorph characterized by two or more, or three or more XRPD signals selected from the group consisting of 7.8°2θ, 14.5°2θ, 17.5°2θ, 18.6°2θ, 19.1°2θ, 20.5°2θ, 23.6°2θ, and 25.3°2θ (±0.2°2θ; ±0.1°2θ; or ±0.0°2θ; Cu Kα1 radiation). In some embodiments, the compound 1 benzoate salt is a crystalline polymorph characterized by XRPD signals at 7.8°2θ, 14.5°2θ, 17.5°2θ, 18.6°2θ, 19.1°2θ, 20.5°2θ, 23.6°2θ, and 25.3°2θ (±0.2°2θ; ±0.1°2θ; or ±0.0°2θ; Cu Kα1 radiation).

In some embodiments, the compound 1 benzoate salt is a crystalline polymorph characterized by two or more, or three or more XRPD signals selected from the group consisting of 7.8°2θ, 13.7°2θ, 14.5°2θ, 17.5°2θ, 18.6°2θ, 19.1°2θ, 20.5°2θ, 23.6°2θ, and 25.3°2θ (±0.2°2θ; ±0.1°2θ; or ±0.0°2θ; Cu Kα1 radiation). In some embodiments, the compound 1 benzoate salt is a crystalline polymorph characterized by XRPD signals at 7.8°2θ, 13.7°2θ, 14.5°2θ, 17.5°2θ, 18.6°2θ, 19.1°2θ, 20.5°2θ, 23.6°2θ, and 25.3°2θ (±0.2°2θ; ±0.1°2θ; or ±0.0°2θ; Cu Kα1 radiation).

In some embodiments, the compound 1 benzoate salt is a crystalline polymorph characterized by two or more, or three or more XRPD signals selected from the group consisting of 7.8°2θ, 13.7°2θ, 14.5°2θ, 17.5°2θ, 18.6°2θ, 19.1°2θ, 20.5°2θ, 21.4°2θ, 23.6°2θ, and 25.3°2θ (±0.2°2θ; ±0.1°2θ;

or ±0.0°2θ; Cu Kα1 radiation). In some embodiments, the compound 1 benzoate salt is a crystalline polymorph characterized by XRPD signals at 7.8°2θ, 13.7°2θ, 14.5°2θ, 17.5°2θ, 18.6°2θ, 19.1°2θ, 20.5°2θ, 21.4°2θ, 23.6°2θ, and 25.3°2θ (±0.2°2θ; ±0.1°2θ; or ±0.0°2θ; Cu Kα1 radiation).

In some embodiments, the compound 1 benzoate salt is a crystalline polymorph characterized by two or more, or three or more XRPD signals selected from the group consisting of 7.8°2θ, 13.7°2θ, 14.5°2θ, 17.5°2θ, 18.6°2θ, 19.1°2θ, 20.5°2θ, 21.4°2θ, 23.6°2θ, 25.3°2θ, and 25.9°2θ (±0.2°2θ; ±0.1°2θ; or ±0.0°2θ; Cu Kα1 radiation). In some embodiments, the compound 1 benzoate salt is a crystalline polymorph characterized by XRPD signals at 7.8°2θ, 13.7°2θ, 14.5°2θ, 17.5°2θ, 18.6°2θ, 19.1°2θ, 20.5°2θ, 21.4°2θ, 23.6°2θ, 25.3°2θ, and 25.9°2θ (±0.2°2θ; ±0.1°2θ, or ±0.0°2θ; Cu Kα1 radiation).

In some embodiments, the compound 1 benzoate salt is a crystalline polymorph characterized by two or more, or three or more XRPD signals selected from the group consisting of 7.8°2θ, 13.7°2θ, 14.5°2θ, 15.7°2θ, 17.5°2θ, 18.6°2θ, 19.1°2θ, 20.5°2θ, 21.4°2θ, 23.6°2θ, 25.3°2θ, and 25.9°2θ (±0.2°2θ; ±0.1°2θ; or ±0.0°2θ; Cu Kα1 radiation). In some embodiments, the compound 1 benzoate salt is a crystalline polymorph characterized by XRPD signals at 7.8°2θ, 13.7°2θ, 14.5°2θ, 15.7°2θ, 17.5°2θ, 18.6°2θ, 19.1°2θ, 20.5°2θ, 21.4°2θ, 23.6°2θ, 25.3°2θ, and 25.9°2θ (±0.2°2θ; ±0.1°2θ; or ±0.0°2θ; Cu Kα1 radiation).

In some embodiments, the compound 1 benzoate salt is a crystalline polymorph characterized by two or more, or three or more XRPD signals selected from the group consisting of 7.8°2θ, 13.7°2θ, 14.5°2θ, 15.7°2θ, 17.5°2θ, 18.6°2θ, 19.1°2θ, 19.7°2θ, 20.5°2θ, 21.4°2θ, 23.6°2θ, 25.3°2θ, and 25.9°2θ (±0.2°2θ; ±0.1°2θ; or ±0.0°2θ; Cu Kα1 radiation). In some embodiments, the compound 1 benzoate salt is a crystalline polymorph characterized by XRPD signals at 7.8°2θ, 13.7°2θ, 14.5°2θ, 15.7°2θ, 17.5°2θ, 18.6°2θ, 19.1°2θ, 19.7°2θ, 20.5°2θ, 21.4°2θ, 23.6°2θ, 25.3°2θ, and 25.9°2θ (±0.2°2θ; ±0.1°2θ; or ±0.0°2θ; Cu Kα1 radiation).

In some embodiments, the compound 1 benzoate salt is a crystalline polymorph characterized by two or more, or three or more XRPD signals selected from the group consisting of 7.8°2θ, 12.5°2θ, 13.7°2θ, 14.5°2θ, 15.7°2θ, 17.5°2θ, 18.6°2θ, 19.1°2θ, 19.7°2θ, 20.5°2θ, 21.4°2θ, 23.6°2θ, 25.3°2θ, and 25.9°2θ (±0.2°2θ; ±0.1°2θ; or ±0.0°2θ; Cu Kα1 radiation). In some embodiments, the compound 1 benzoate salt is a crystalline polymorph characterized by XRPD signals at 7.8°2θ, 12.5°2θ, 13.7°2θ, 14.5°2θ, 15.7°2θ, 17.5°2θ, 18.6°2θ, 19.1°2θ, 19.7°2θ, 20.5°2θ, 21.4°2θ, 23.6°2θ, 25.3°2θ, and 25.9°2θ (±0.2°2θ; ±0.1°2θ; or ±0.0°2θ; Cu Kα1 radiation).

In some embodiments, crystalline compound 1 benzoate is characterized by one, two, three, four, five, six, seven, eight, nine, ten, eleven, twelve, thirteen, or fourteen XRPD signals selected from those set forth in Table 46.

TABLE 46

Crystalline compound 1 Benzoate XRPD signals (±0.2 °2θ; ±0.1 °2θ; or ±0.0 °2θ; Cu Kα1 radiation)

| Signal number | 2-θ (°) | d Value | Net Intensity (counts) | Gross Intensity (counts) | Rel. Intensity (%) |
|---|---|---|---|---|---|
| Signal #1 | 7.8 | 11.30 | 2104.9 | 2228.3 | 54.0 |
| Signal #2 | 12.5 | 7.10 | 405.5 | 501.7 | 10.4 |
| Signal #3 | 13.7 | 6.45 | 473.3 | 590.7 | 12.1 |
| Signal #4 | 14.5 | 6.11 | 1286.0 | 1416.0 | 33.0 |

TABLE 46-continued

Crystalline compound 1 Benzoate XRPD signals (±0.2 °2θ; ±0.1 °2θ; or ±0.0 °2θ; Cu Kα1 radiation)

| Signal number | 2-θ (°) | d Value | Net Intensity (counts) | Gross Intensity (counts) | Rel. Intensity (%) |
|---|---|---|---|---|---|
| Signal #5 | 15.7 | 5.66 | 426.6 | 579.4 | 10.9 |
| Signal #6 | 17.5 | 5.08 | 3901.0 | 4093.7 | 100.0 |
| Signal #7 | 18.6 | 4.77 | 573.2 | 789.6 | 14.7 |
| Signal #8 | 19.1 | 4.63 | 1533.8 | 1756.2 | 39.3 |
| Signal #9 | 19.7 | 4.50 | 416.8 | 640.9 | 10.7 |
| Signal #10 | 20.5 | 4.32 | 888.8 | 1108.0 | 22.8 |
| Signal #11 | 21.4 | 4.16 | 445.7 | 651.8 | 11.4 |
| Signal #12 | 23.6 | 3.76 | 829.9 | 995.4 | 21.3 |
| Signal #13 | 25.3 | 3.52 | 816.4 | 987.0 | 20.9 |
| Signal #14 | 25.9 | 3.43 | 436.4 | 598.7 | 11.2 |

Compound 1 Tosylate Salt

In some embodiments, the compound 1 salt is a compound 1 tosylate salt. In some embodiments, the compound 1 tosylate salt is amorphous. In some embodiments, the compound 1 tosylate salt is crystalline. In some embodiments, the compound 1 tosylate salt is a 1:1 compound 1:tosylate salt. In some embodiments, the compound 1 tosylate salt is a 2:1 compound 1:tosylate salt.

In some embodiments, the compound 1 tosylate salt is a crystalline polymorph. In some embodiments, the crystalline polymorph is characterized by the XRPD signals set for the below in Table 113. In some embodiments, the crystalline polymorph XRPD pattern is substantially similar to that shown in FIG. 170. In some embodiments, the crystalline polymorph TGA spectrum is substantially similar to that shown in FIG. 235. In some embodiments, the crystalline compound 1 tosylate DSC spectrum is substantially similar to that shown in FIG. 234.

In some embodiments, the crystalline compound 1 tosylate is a crystalline polymorphic form characterized by DSC having a melting signal at about 137.7° C.

In some embodiments, the compound 1 tosylate salt is a crystalline polymorph characterized by an XRPD signal at 19.8°2θ (±0.2°2θ; ±0.1°2θ; or ±0.0°2θ; Cu Kα1 radiation).

In some embodiments, the compound 1 tosylate salt is a crystalline polymorph characterized by XRPD signals at 19.5°2θ, and 19.8°2θ (±0.2°2θ; ±0.1°2θ; or ±0.0°2θ; Cu Kα1 radiation).

In some embodiments, the compound 1 tosylate salt is a crystalline polymorph characterized by two or more, or three or more XRPD signals selected from the group consisting of 19.5°2θ, 19.8°2θ, and 25.5°2θ (±0.2°2θ; ±0.1°2θ; or ±0.0°2θ; Cu Kα1 radiation). In some embodiments, the compound 1 tosylate salt is a crystalline polymorph characterized by XRPD signals at 19.5°2θ, 19.8°2θ, and 25.5°2θ (±0.2°2θ; ±0.1°2θ; or ±0.0°2θ; Cu Kα1 radiation).

In some embodiments, the compound 1 tosylate salt is a crystalline polymorph characterized by two or more, or three or more XRPD signals selected from the group consisting of 15.3°2θ, 19.5°2θ, 19.8°2θ, and 25.5°2θ (±0.2°2θ; ±0.1°2θ; or ±0.0°2θ; Cu Kα1 radiation).

In some embodiments, the compound 1 tosylate salt is a crystalline polymorph characterized by XRPD signals at 15.3°2θ, 19.5°2θ, 19.8°2θ, and 25.5°2θ (±0.2°2θ; ±0.1°2θ, or ±0.0°2θ; Cu Kα1 radiation).

In some embodiments, the compound 1 tosylate salt is a crystalline polymorph characterized by two or more, or three or more XRPD signals selected from the group consisting of 14.5°2θ, 15.3°2θ, 19.5°2θ, 19.8°2θ, and 25.5°2θ (±0.2°2θ; ±0.1°2θ; or ±0.0°2θ; Cu Kα1 radiation). In some embodiments, the compound 1 tosylate salt is a crystalline polymorph characterized by XRPD signals at 14.5°2θ, 15.3°2θ, 19.5°2θ, 19.8°2θ, and 25.5°2θ (±0.2°2θ; ±0.1°2θ, or ±0.0°2θ; Cu Kα1 radiation).

In some embodiments, the compound 1 tosylate salt is a crystalline polymorph characterized by two or more, or three or more XRPD signals selected from the group consisting of 14.5°2θ, 15.3°2θ, 16.5°2θ, 19.5°2θ, 19.8°2θ, and 25.5°2θ (±0.2°2θ; ±0.1°2θ; or ±0.0°2θ; Cu Kα1 radiation). In some embodiments, the compound 1 tosylate salt is a crystalline polymorph characterized by XRPD signals at 14.5°2θ, 15.3°2θ, 16.5°2θ, 19.5°2θ, 19.8°2θ, and 25.5°2θ (±0.2°2θ; ±0.1°2θ; or ±0.0°2θ; Cu Kα1 radiation).

In some embodiments, the compound 1 tosylate salt is a crystalline polymorph characterized by two or more, or three or more XRPD signals selected from the group consisting of 14.5°2θ, 15.3°2θ, 16.3°2θ, 16.5°2θ, 19.5°2θ, 19.8°2θ, and 25.5°2θ (±0.2°2θ; ±0.1°2θ; or ±0.0°2θ; Cu Kα1 radiation). In some embodiments, the compound 1 tosylate salt is a crystalline polymorph characterized by XRPD signals at 14.5°2θ, 15.3°2θ, 16.3°2θ, 16.5°2θ, 19.5°2θ, 19.8°2θ, and 25.5°2θ (±0.2°2θ; ±0.1°2θ; or ±0.0°2θ; Cu Kα1 radiation).

In some embodiments, the compound 1 tosylate salt is a crystalline polymorph characterized by two or more, or three or more XRPD signals selected from the group consisting of 14.5°2θ, 15.3°2θ, 16.3°2θ, 16.5°2θ, 19.5°2θ, 19.8°2θ, 23.3°2θ, and 25.5°2θ (±0.2°2θ; ±0.1°2θ; or ±0.0°2θ, Cu Kα1 radiation). In some embodiments, the compound 1 tosylate salt is a crystalline polymorph characterized by XRPD signals at 14.5°2θ, 15.3°2θ, 16.3°2θ, 16.5°2θ, 19.5°2θ, 19.8°2θ, 23.3°2θ, and 25.5°2θ (±0.2°2θ; ±0.1°2θ; or ±0.0°2θ; Cu Kα1 radiation).

In some embodiments, the compound 1 tosylate salt is a crystalline polymorph characterized by two or more, or three or more XRPD signals selected from the group consisting of 10.3°2θ, 14.5°2θ, 15.3°2θ, 16.3°2θ, 16.5°2θ, 19.5°2θ, 19.8°2θ, 23.3°2θ, and 25.5°2θ (±0.2°2θ; ±0.1°2θ; or ±0.0°2θ; Cu Kα1 radiation). In some embodiments, the compound 1 tosylate salt is a crystalline polymorph characterized by XRPD signals at 10.3°2θ, 14.5°2θ, 15.3°2θ, 16.3°2θ, 16.5°2θ, 19.5°2θ, 19.8°2θ, 23.3°2θ, and 25.5°2θ (±0.2°2θ; ±0.1°2θ; or ±0.0°2θ; Cu Kα1 radiation).

In some embodiments, the compound 1 tosylate salt is a crystalline polymorph characterized by two or more, or three or more XRPD signals selected from the group consisting of 10.3°2θ, 14.5°2θ, 15.3°2θ, 16.3°2θ, 16.5°2θ, 19.5°2θ, 19.8°2θ, 20.6°2θ, 23.3°2θ, and 25.5°2θ (±0.2°2θ; ±0.1°2θ; or ±0.0°2θ; Cu Kα1 radiation). In some embodiments, the compound 1 tosylate salt is a crystalline polymorph characterized by XRPD signals at 10.3°2θ, 14.5°2θ, 15.3°2θ, 16.3°2θ, 16.5°2θ, 19.5°2θ, 19.8°2θ, 20.6°2θ, 23.3°2θ, and 25.5°2θ (±0.2°2θ; ±0.1°2θ; or ±0.0°2θ; Cu Kα1 radiation).

In some embodiments, the compound 1 tosylate salt is a crystalline polymorph characterized by two or more, or three or more XRPD signals selected from the group consisting of 10.3°2θ, 14.5°2θ, 15.3°2θ, 16.3°2θ, 16.5°2θ, 19.5°2θ, 19.8°2θ, 20.6°2θ, 22.9°2θ, 23.3°2θ, and 25.5°2θ (±0.2°2θ. 0.1°2θ; or ±0.0°2θ; Cu Kα1 radiation). In some embodiments, the compound 1 tosylate salt is a crystalline polymorph characterized by XRPD signals at 10.3°2θ, 14.5°2θ, 15.3°2θ, 16.3°2θ, 16.5°2θ, 19.5°2θ, 19.8°2θ, 20.6°2θ, 22.9°2θ, 23.3°2θ, and 25.5°2θ (±0.2°2θ; ±0.1°2θ; or ±0.0°2θ; Cu Kα1 radiation).

In some embodiments, the compound 1 tosylate salt is a crystalline polymorph characterized by two or more, or three or more XRPD signals selected from the group consisting of 10.3°2θ, 14.5°2θ, 15.3°2θ, 16.3°2θ, 16.5°2θ, 19.5°2θ, 19.8°2θ, 20.6°2θ, 22.9°2θ, 23.3°2θ, 25.5°2θ, and 30.3°2θ (±0.2°2θ; ±0.1°2θ; or ±0.0°2θ; Cu Kα1 radiation). In some embodiments, the compound 1 tosylate salt is a crystalline polymorph characterized by XRPD signals at 10.3°2θ, 14.5°2θ, 15.3°2θ, 16.3°2θ, 16.5°2θ, 19.5°2θ, 19.8°2θ, 20.6°2θ, 22.9°2θ, 23.3°2θ, 25.5°2θ, and 30.3°2θ (±0.2°2θ; ±0.1°2θ; or ±0.0°2θ; Cu Kα1 radiation).

In some embodiments, the compound 1 tosylate salt is a crystalline polymorph characterized by two or more, or three or more XRPD signals selected from the group consisting of 10.3°2θ, 14.5°2θ, 15.3°2θ, 16.3°2θ, 16.5°2θ, 19.5°2θ, 19.8°2θ, 20.6°2θ, 22.9°2θ, 23.3°2θ, 25.5°2θ, 26.2°2θ, and 30.3°2θ (±0.2°2θ; ±0.1°2θ; or ±0.0°2θ; Cu Kα1 radiation). In some embodiments, the compound 1 tosylate salt is a crystalline polymorph characterized by XRPD signals at 10.3°2θ, 14.5°2θ, 15.3°2θ, 16.3°2θ, 16.5°2θ, 19.5°2θ, 19.8°2θ, 20.6°2θ, 22.9°2θ, 23.3°2θ, 25.5°2θ, 26.2°2θ, and 30.3°2θ (±0.2°2θ; ±0.1°2θ; or ±0.0°2θ; Cu Kα1 radiation).

In some embodiments, the compound 1 tosylate salt is a crystalline polymorph characterized by two or more, or three or more XRPD signals selected from the group consisting of 10.3°2θ, 14.5°2θ, 15.3°2θ, 16.3°2θ, 16.5°2θ, 19.5°2θ, 19.8°2θ, 20.6°2θ, 22.9°2θ, 23.3°2θ, 25.5°2θ, 26.2°2θ, 29.4°2θ, and 30.3°2θ (±0.2°2θ; ±0.1°2θ; or ±0.0°2θ; Cu Kα1 radiation). In some embodiments, the compound 1 tosylate salt is a crystalline polymorph characterized by XRPD signals at 10.3°2θ, 14.5°2θ, 15.3°2θ, 16.3°2θ, 16.5°2θ, 19.5°2θ, 19.8°2θ, 20.6°2θ, 22.9°2θ, 23.3°2θ, 25.5°2θ, 26.2°2θ, 29.4°2θ, and 30.3°2θ (±0.2°2θ; ±0.1°2θ; or ±0.0°2θ; Cu Kα1 radiation).

In some embodiments, the compound 1 tosylate salt is a crystalline polymorph characterized by two or more, or three or more XRPD signals selected from the group consisting of 10.3°2θ, 14.5°2θ, 15.3°2θ, 16.3°2θ, 16.5°2θ, 19.5°2θ, 19.8°2θ, 20.6°2θ, 22.9°2θ, 23.3°2θ, 25.5°2θ, 26.2°2θ, 26.6°2θ, 29.4°2θ, and 30.3°2θ (±0.2°2θ; ±0.1°2θ; or ±0.0°2θ; Cu Kα1 radiation). In some embodiments, the compound 1 tosylate salt is a crystalline polymorph characterized by XRPD signals at 10.3°2θ, 14.5°2θ, 15.3°2θ, 16.3°2θ, 16.5°2θ, 19.5°2θ, 19.8°2θ, 20.6°2θ, 22.9°2θ, 23.3°2θ, 25.5°2θ, 26.2°2θ, 26.6°2θ, 29.4°2θ, and 30.3°2θ (±0.2°2θ; ±0.1°2θ; or 0.0°2θ. Cu Kα1 radiation).

In some embodiments, the compound 1 tosylate salt is a crystalline polymorph characterized by two or more, or three or more XRPD signals selected from the group consisting of 10.3°2θ, 14.5°2θ, 15.3°2θ, 16.3°2θ, 16.5°2θ, 19.5°2θ, 19.8°2θ, 20.6°2θ, 20.7°2θ, 22.9°2θ, 23.3°2θ, 25.5°2θ, 26.2°2θ, 26.6°2θ, 29.4°2θ, and 30.3°2θ (±0.2°2θ; ±0.1°2θ; or ±0.0°2θ; Cu Kα1 radiation). In some embodiments, the compound 1 tosylate salt is a crystalline polymorph characterized by XRPD signals at 10.3°2θ, 14.5°2θ, 15.3°2θ, 16.3°2θ, 16.5°2θ, 19.5°2θ, 19.8°2θ, 20.6°2θ, 20.7°2θ, 22.9°2θ, 23.3°2θ, 25.5°2θ, 26.2°2θ, 26.6°2θ, 29.4°2θ, and 30.3°2θ (±0.2°2θ; ±0.1°2θ; or ±0.0°2θ; Cu Kα1 radiation).

In some embodiments, the compound 1 tosylate salt is a crystalline polymorph characterized by two or more, or three or more XRPD signals selected from the group consisting of 10.3°2θ, 14.5°2θ, 15.3°2θ, 16.3°2θ, 16.5°2θ, 18.2°2θ, 19.5°2θ, 19.8°2θ, 20.6°2θ, 20.7°2θ, 22.9°2θ, 23.3°2θ, 25.5°2θ, 26.2°2θ, 26.6°2θ, 29.4°2θ, and 30.3°2θ (±0.2°2θ; ±0.1°2θ; or ±0.0°2θ; Cu Kα1 radiation). In some embodiments, the compound 1 tosylate salt is a crystalline polymorph characterized by XRPD signals at 10.3°2θ, 14.5°2θ, 15.3°2θ, 16.3°2θ, 16.5°2θ, 18.2°2θ, 19.5°2θ, 19.8°2θ, 20.6°2θ, 20.7°2θ, 22.9°2θ, 23.3°2θ, 25.5°2θ, 26.2°2θ, 26.6°2θ, 29.4°2θ, and 30.3°2θ (±0.2°2θ; ±0.1°2θ; or ±0.0°2θ; Cu Kα1 radiation).

In some embodiments, the compound 1 tosylate salt is a crystalline polymorph characterized by two or more, or three or more XRPD signals selected from the group consisting of 10.3°2θ, 14.5°2θ, 15.3°2θ, 16.3°2θ, 16.5°2θ, 18.2°2θ, 19.5°2θ, 19.8°2θ, 20.6°2θ, 20.7°2θ, 22.9°2θ, 23.3°2θ, 25.5°2θ, 26.0°2θ, 26.2°2θ, 26.6°2θ, 29.4°2θ, and 30.3°2θ (±0.2°2θ; ±0.1°2θ; or ±0.0°2θ; Cu Kα1 radiation). In some embodiments, the compound tosylate salt is a crystalline polymorph characterized by XRPD signals at 10.3°2θ, 14.5°2θ, 15.3°2θ, 16.3°2θ, 16.5°2θ 18.2°2θ, 19.5°2θ, 19.8°2θ, 20.6°2θ, 20.7°2θ, 22.9°2θ, 23.3°2θ, 25.5°2θ, 26.0°2θ, 26.2°2θ, 26.6°2θ, 29.4°2θ, and 30.3°2θ (±0.2°2θ; ±0.1°2θ; or ±0.0°2θ; Cu Kα1 radiation).

In some embodiments, crystalline polymorph is characterized by one, two, three, four, five, six, seven, eight, nine, ten, eleven, twelve, thirteen, fourteen, fifteen, sixteen, seventeen, or eighteen XRPD signals selected from those set forth in Table 113.

TABLE 113

Crystalline compound 1 tosylate XRPD signals (±0.2°2θ; ±0.1 °2θ; or ±0.0 °2θ; Cu Kα1 radiation)

| Signal number | 2-θ (°) | d Value | Net Intensity (counts) | Gross Intensity (counts) | Rel. Intensity (%) |
|---|---|---|---|---|---|
| Signal #1 | 10.3 | 8.55 | 474.8 | 585.9 | 19.3 |
| Signal #2 | 14.5 | 6.11 | 1370.5 | 1504.6 | 55.7 |
| Signal #3 | 15.3 | 5.79 | 1520.3 | 1671.6 | 61.8 |
| Signal #4 | 16.3 | 5.43 | 748.3 | 911.8 | 30.4 |
| Signal #5 | 16.5 | 5.36 | 822.5 | 987.1 | 33.4 |
| Signal #6 | 18.2 | 4.87 | 268.3 | 454.0 | 10.9 |
| Signal #7 | 19.5 | 4.55 | 2407.4 | 2609.4 | 97.8 |
| Signal #8 | 19.8 | 4.48 | 2460.8 | 2664.7 | 100.0 |
| Signal #9 | 20.6 | 4.31 | 459.0 | 663.0 | 18.7 |
| Signal #10 | 20.7 | 4.28 | 298.7 | 502.0 | 12.1 |
| Signal #11 | 22.9 | 3.88 | 432.4 | 618.5 | 17.6 |
| Signal #12 | 23.3 | 3.81 | 559.6 | 738.7 | 22.7 |
| Signal #13 | 25.5 | 3.49 | 1731.4 | 1899.3 | 70.4 |
| Signal #14 | 26.0 | 3.43 | 259.7 | 422.1 | 10.6 |
| Signal #15 | 26.2 | 3.40 | 347.4 | 506.1 | 14.1 |
| Signal #16 | 26.6 | 3.35 | 299.5 | 452.0 | 12.2 |
| Signal #17 | 29.4 | 3.04 | 321.5 | 470.6 | 13.1 |
| Signal #18 | 30.3 | 2.95 | 372.0 | 509.4 | 15.1 |

Compound 1 Tartrate Salt

In some embodiments, the compound 1 salt is a compound 1 tartrate salt. In some embodiments, the compound 1 tartrate salt is amorphous. In some embodiments, the compound 1 tartrate salt is crystalline. In some embodiments, the compound 1 tartrate salt is a 1:1 compound 1:tartrate salt. In some embodiments, the compound 1 tartrate salt is a 2:1 compound 1:tartrate salt.

In some embodiments, the compound 1 tartrate salt is a crystalline polymorph. In some embodiments, the crystalline polymorph is characterized by the XRPD signals set for the below in Table 47. In some embodiments, the crystalline polymorph XRPD pattern is substantially similar to that shown in FIG. 171. In some embodiments, the crystalline polymorph TGA spectrum is substantially similar to that shown in FIG. 239.

In some embodiments, the crystalline compound 1 tartrate is a crystalline polymorphic form characterized by DSC having a melting signal at about 115.5° C.

In some embodiments, the compound 1 tartrate salt is a crystalline polymorph characterized by an XRPD signal at 17.5°2θ (±0.2°2θ; ±0.1°2θ; or ±0.0°2θ; Cu Kα1 radiation).

In some embodiments, the compound 1 tartrate salt is a crystalline polymorph characterized by XRPD signals at 4.3°2θ, and 17.5°2θ (±0.2°2θ; ±0.1°2θ; or ±0.0°2θ; Cu Kα1 radiation).

In some embodiments, the compound 1 tartrate salt is a crystalline polymorph characterized by two or more, or three or more XRPD signals selected from the group consisting of 4.3°2θ, 17.5°2θ, and 19.3°2θ (±0.2°2θ; ±0.1°2θ; or ±0.0°2θ; Cu Kα1 radiation). In some embodiments, the compound 1 tartrate salt is a crystalline polymorph characterized by XRPD signals at 4.3°2θ, 17.5°2θ, and 19.3°2θ (±0.2°2θ; ±0.1°2θ; or ±0.0°2θ; Cu Kα1 radiation).

In some embodiments, the compound 1 tartrate salt is a crystalline polymorph characterized by two or more, or three or more XRPD signals selected from the group consisting of 4.3°2θ, 17.5°2θ, 19.3°2θ, and 20.1°2θ (±0.2°2θ; ±0.1°2θ; or ±0.0°2θ; Cu Kα1 radiation). In some embodiments, the compound 1 tartrate salt is a crystalline polymorph characterized by XRPD signals at 4.3°2θ, 17.5°2θ, 19.3°2θ, and 20.1°2θ (±0.2°2θ; ±0.1°2θ; or ±0.0°2θ; Cu Kα1 radiation).

In some embodiments, the compound 1 tartrate salt is a crystalline polymorph characterized by two or more, or three or more XRPD signals selected from the group consisting of 4.3°2θ, 14.5°2θ, 17.5°2θ, 19.3°2θ, and 20.1°2θ (±0.2°2θ; ±0.1°2θ; or ±0.0°2θ; Cu Kα1 radiation). In some embodiments, the compound 1 tartrate salt is a crystalline polymorph characterized by XRPD signals at 4.3°2θ, 14.5°2θ, 17.5°2θ, 19.3°2θ, and 20.1°2θ (±0.2°2θ; ±0.1°2θ; or ±0.0°2θ; Cu Kα1 radiation).

In some embodiments, the compound 1 tartrate salt is a crystalline polymorph characterized by two or more, or three or more XRPD signals selected from the group consisting of 4.3°2θ, 14.5°2θ, 17.5°2θ, 19.3°2θ, 20.1°2θ, and 21.0°2θ (±0.2°2θ; ±0.1°2θ; or 0.0°2θ; Cu Kα1 radiation).

In some embodiments, the compound 1 tartrate salt is a crystalline polymorph characterized by XRPD signals at 4.3°2θ, 14.5°2θ, 17.5°2θ, 19.3°2θ, 20.1°2θ, and 21.0°2θ, (±0.2°2θ; ±0.1°2θ; or ±0.0°2θ; Cu Kα1 radiation).

In some embodiments, the compound 1 tartrate salt is a crystalline polymorph characterized by two or more, or three or more XRPD signals selected from the group consisting of 4.3°2θ, 14.5°2θ, 17.5°2θ, 19.3°2θ, 20.1°2θ, 21.0°2θ, and 23.7°2θ (±0.2°2θ; ±0.1°2θ; or ±0.0°2θ; Cu Kα1 radiation). In some embodiments, the compound 1 tartrate salt is a crystalline polymorph characterized by XRPD signals at 4.3°2θ, 14.5°2θ, 17.5°2θ, 19.3°2θ, 20.1°2θ, 21.0°2θ, and 23.7°2θ (±0.2°2θ; ±0.1°2θ; or ±0.0°2θ; Cu Kα1 radiation).

In some embodiments, the compound 1 tartrate salt is a crystalline polymorph characterized by two or more, or three or more XRPD signals selected from the group consisting of 4.3°2θ, 14.5°2θ, 17.5°2θ, 18.7°2θ, 19.3°2θ, 20.1°2θ, 21.0°2θ, and 23.7°2θ (±0.2°2θ; ±0.1°2θ; or ±0.0°2θ; Cu Kα1 radiation). In some embodiments, the compound 1 tartrate salt is a crystalline polymorph characterized by XRPD signals at 4.3°2θ, 14.5°2θ, 17.5°2θ, 18.7°2θ, 19.3°2θ, 20.1°2θ, 21.0°2θ, and 23.7°2θ (±0.2°2θ; ±0.1°2θ; or ±0.0°2θ; Cu Kα1 radiation).

In some embodiments, the compound 1 tartrate salt is a crystalline polymorph characterized by two or more, or three or more XRPD signals selected from the group consisting of 4.3°2θ, 14.5°2θ, 17.5°2θ, 18.7°2θ, 19.3°2θ, 20.1°2θ, 21.0°2θ, 23.3°2θ, and 23.7°2θ (±0.2°2θ; ±0.1°2θ; or ±0.0°2θ; Cu Kα1 radiation). In some embodiments, the compound 1 tartrate salt is a crystalline polymorph characterized by XRPD signals at 4.3°2θ, 14.5°2θ, 17.5°2θ, 18.7°2θ, 19.3°2θ, 20.1°2θ, 21.0°2θ, 23.3°2θ, and 23.7°2θ (±0.2°2θ; ±0.1°2θ; or ±0.0°2θ; Cu Kα1 radiation).

In some embodiments, the compound 1 tartrate salt is a crystalline polymorph characterized by two or more, or three or more XRPD signals selected from the group consisting of 4.3°2θ, 14.5°2θ, 17.5°2θ, 18.7°2θ, 19.3°2θ, 20.1°2θ, 21.0°2θ, 23.3°2θ, 23.7°2θ, and 31.8°2θ (±0.2°2θ; ±0.1°2θ; or 0.0°2θ; Cu Kα1 radiation). In some embodiments, the compound 1 tartrate salt is a crystalline polymorph characterized by XRPD signals at 4.3°2θ, 14.5°2θ, 17.5°2θ, 18.7°2θ, 19.3°2θ, 20.1°2θ, 21.0°2θ, 23.3°2θ, 23.7°2θ, and 31.8°2θ (±0.2°2θ; ±0.1°2θ, or 0.0°2θ; Cu Kα1 radiation).

In some embodiments, the compound 1 tartrate salt is a crystalline polymorph characterized by two or more, or three or more XRPD signals selected from the group consisting of 4.3°2θ, 14.5°2θ, 17.5°2θ, 18.7°2θ, 19.3°2θ, 20.1°2θ, 21.0°2θ, 23.3°2θ, 23.7°2θ, 27.5°2θ, and 31.8°2θ (±0.2°2θ; ±0.1°2θ; or ±0.0°2θ; Cu Kα1 radiation). In some embodiments, the compound 1 tartrate salt is a crystalline polymorph characterized by XRPD signals at 4.3°2θ, 14.5°2θ, 17.5°2θ, 18.7°2θ, 19.3°2θ, 20.1°2θ, 21.0°2θ, 23.3°2θ, 23.7°2θ, 27.5°2θ, and 31.8°2θ (±0.2°2θ; ±0.1°2θ; or ±0.0°2θ; Cu Kα1 radiation).

In some embodiments, the compound 1 tartrate salt is a crystalline polymorph characterized by two or more, or three or more XRPD signals selected from the group consisting of 4.3°2θ, 14.5°2θ, 17.5°2θ, 18.7°2θ, 19.3°2θ, 20.1°2θ, 21.0°2θ, 23.3°2θ, 23.7°2θ, 27.5°2θ, 31.8°2θ, and 38.9°2θ (±0.2°2θ; ±0.1°2θ; or ±0.0°2θ; Cu Kα1 radiation). In some embodiments, the compound 1 tartrate salt is a crystalline polymorph characterized by XRPD signals at 4.3°2θ, 14.5°2θ, 17.5°2θ, 18.7°2θ, 19.3°2θ, 20.1°2θ, 21.0°2θ, 23.3°2θ, 23.7°2θ, 27.5°2θ, 31.8°2θ, and 38.9°2θ (±0.2°2θ; ±0.1°2θ; or ±0.0°2θ; Cu Kα1 radiation).

In some embodiments, the compound 1 tartrate salt is a crystalline polymorph characterized by two or more, or three or more XRPD signals selected from the group consisting of 4.3°2θ, 13.1°2θ, 14.5°2θ, 17.5°2θ, 18.7°2θ, 19.3°2θ, 20.1°2θ, 21.0°2θ, 23.3°2θ, 23.7°2θ, 27.5°2θ, 31.8°2θ, and 38.9°2θ (±0.2°2θ; ±0.1°2θ; or ±0.0°2θ; Cu Kα1 radiation). In some embodiments, the compound 1 tartrate salt is a crystalline polymorph characterized by XRPD signals at 4.3°2θ, 13.1°2θ, 14.5°2θ, 17.5°2θ, 18.7°2θ, 19.3°2θ, 20.1°2θ, 21.0°2θ, 23.3°2θ, 23.7°2θ, 27.5°2θ, 31.8°2θ, and 38.9°2θ (±0.2 2θ; 0.1°2θ; or ±0.0°2θ; Cu Kα1 radiation).

In some embodiments, the compound 1 tartrate salt is a crystalline polymorph characterized by two or more, or three or more XRPD signals selected from the group consisting of 4.3°2θ, 13.1°2θ, 14.5°2θ, 17.5°2θ, 18.7°2θ, 19.3°2θ, 20.1°2θ, 21.0°2θ, 23.3°2θ, 23.7°2θ, 27.5°2θ, 29.7°2θ, 31.8°2θ, and 38.9°2θ (±0.2°2θ; ±0.1°2θ; or ±0.0°2θ; Cu Kα1 radiation). In some embodiments, the compound 1 tartrate salt is a crystalline polymorph characterized by XRPD signals at 4.3°2θ, 13.1°2θ, 14.5°2θ, 17.5°2θ, 18.7°2θ, 19.3°2θ, 20.1°2θ, 21.0°2θ, 23.3°2θ, 23.7°2θ, 27.5°2θ, 29.7°2θ, 31.8°2θ, and 38.9°2θ (±0.2°2θ; ±0.1°2θ; or ±0.0°2θ; Cu Kα1 radiation).

In some embodiments, the compound 1 tartrate salt is a crystalline polymorph characterized by two or more, or three or more XRPD signals selected from the group consisting of 4.3°2θ, 13.1°2θ, 14.5°2θ, 17.5°2θ, 18.7°2θ, 19.3°2θ, 20.1°2θ, 21.0°2θ, 23.3°2θ, 23.7°2θ, 27.5°2θ, 28.0°2θ, 29.7°2θ, 31.8°2θ, and 38.9°2θ (±0.2°2θ; ±0.1°2θ; or ±0.0°2θ; Cu Kα1 radiation). In some embodiments, the compound 1 tartrate salt is a crystalline polymorph characterized by XRPD signals at 4.3°2θ, 13.1°2θ, 14.5°2θ, 17.5°2θ, 18.7°2θ, 19.3°2θ, 20.1°2θ, 21.0°2θ, 23.3°2θ, 23.7°2θ, 27.5°2θ, 28.0°2θ, 29.7°2θ, 31.8°2θ, and 38.9°2θ (±0.2°2θ; ±0.1°2θ; or ±0.0°2θ; Cu Kα1 radiation).

In some embodiments, the compound 1 tartrate salt is a crystalline polymorph characterized by two or more, or three or more XRPD signals selected from the group consisting of 4.3°2θ, 13.1°2θ, 14.5°2θ, 16.9°2θ, 17.5°2θ, 18.7°2θ, 19.3°2θ, 20.1°2θ, 21.0°2θ, 23.3°2θ, 23.7°2θ, 27.5°2θ, 28.0°2θ, 29.7°2θ, 31.8°2θ, and 38.9°2θ (±0.2°2θ; ±0.1°2θ; or ±0.0°2θ; Cu Kα1 radiation).

In some embodiments, the compound 1 tartrate salt is a crystalline polymorph characterized by XRPD signals at 4.3°2θ, 13.1°2θ, 14.5°2θ, 16.9°2θ, 17.5°2θ, 18.7°2θ, 19.3°2θ, 20.1°2θ, 21.0°2θ, 23.3°2θ, 23.7°2θ, 27.5°2θ, 28.0°2θ, 29.7°2θ, 31.8°2θ, and 38.9°2θ (±0.2°2θ; ±0.1°2θ; or ±0.0°2θ; Cu Kα1 radiation).

In some embodiments, the compound 1 tartrate salt is a crystalline polymorph characterized by two or more, or three or more XRPD signals selected from the group consisting of 4.3°2θ, 13.1°2θ, 14.5°2θ, 16.9°2θ, 17.5°2θ, 18.7°2θ, 19.3°2θ, 20.1°2θ, 21.0°2θ, 21.8°2θ, 23.3°2θ, 23.7°2θ, 27.5°2θ, 28.0°2θ, 29.7°2θ, 31.8°2θ, and 38.9°2θ (±0.2°2θ; ±0.1°2θ; or ±0.0°2θ; Cu Kα1 radiation). In some embodiments, the compound 1 tartrate salt is a crystalline polymorph characterized by XRPD signals at 4.3°2θ, 13.1°2θ, 14.5°2θ, 16.9°2θ, 17.5°2θ, 18.7°2θ, 19.3°2θ, 20.1°2θ, 21.0°2θ, 21.8°2θ, 23.3°2θ, 23.7°2θ, 27.5°2θ, 28.0°2θ, 29.7°2θ, 31.8°2θ, and 38.9°2θ (±0.2°2θ; ±0.1°2θ; or ±0.0°2θ; Cu Kα1 radiation).

In some embodiments, the compound 1 tartrate salt is a crystalline polymorph characterized by two or more, or three or more XRPD signals selected from the group consisting of 4.3°2θ, 13.1°2θ, 14.5°2θ, 16.9°2θ, 17.5°2θ, 18.7°2θ, 19.3°2θ, 20.1°2θ, 21.0°2θ, 21.8°2θ, 23.3°2θ, 23.7°2θ, 24.8°2θ, 27.5°2θ, 28.0°2θ, 29.7°2θ, 31.8°2θ, and 38.9°2θ (±0.2°2θ; ±0.1°2θ; or ±0.0°2θ; Cu Kα1 radiation). In some embodiments, the compound 1 tartrate salt is a crystalline polymorph characterized by XRPD signals at 4.3°2θ, 13.1°2θ, 14.5°2θ, 16.9°2θ, 17.5°2θ, 18.7°2θ, 19.3°2θ, 20.1°2θ, 21.0°2θ, 21.8°2θ, 23.3°2θ, 23.7°2θ, 24.8°2θ, 27.5°2θ, 28.0°2θ, 29.7°2θ, 31.8°2θ, and 38.9°2θ (±0.2°2θ; ±0.1°2θ; or ±0.0°2θ; Cu Kα1 radiation).

In some embodiments, the compound 1 tartrate salt is a crystalline polymorph characterized by two or more, or three or more XRPD signals selected from the group consisting of 4.3°2θ, 13.1°2θ, 14.5°2θ, 16.9°2θ, 17.5°2θ, 18.7°2θ, 19.3°2θ, 20.1°2θ, 21.0°2θ, 21.8°2θ, 23.3°2θ, 23.7°2θ, 24.8°2θ, 26.8°2θ, 27.5°2θ, 28.0°2θ, 29.7°2θ, 31.8°2θ, and 38.9°2θ (±0.2°2θ; ±0.1°2θ; or ±0.0°2θ; Cu Kα1 radiation). In some embodiments, the compound 1 tartrate salt is a crystalline polymorph characterized by XRPD signals at 4.3°2θ, 13.1°2θ, 14.5°2θ, 16.9°2θ, 17.5°2θ, 18.7°2θ, 19.3°2θ, 20.1°2θ, 21.0°2θ, 21.8°2θ, 23.3°2θ, 23.7°2θ, 24.8°2θ, 26.8°2θ, 27.5°2θ, 28.0°2θ, 29.7°2θ, 31.8°2θ, and 38.9°2θ (±0.2°2θ; ±0.1°2θ; or ±0.0°2θ; Cu Kα1 radiation).

In some embodiments, the compound 1 tartrate salt is a crystalline polymorph characterized by two or more, or three or more XRPD signals selected from the group consisting of 4.3°2θ, 13.1°2θ, 14.5°2θ, 16.9°2θ, 17.5°2θ, 18.7°2θ, 19.3°2θ, 20.1°2θ, 21.0°2θ, 21.8°2θ, 23.3°2θ, 23.7°2θ, 24.8°2θ, 26.8°2θ, 27.5°2θ, 28.0°2θ, 29.7°2θ, 31.8°2θ, 36.1°2θ, and 38.9°2θ (±0.2°2θ; ±0.1°2θ; or ±0.0°2θ; Cu Kα1 radiation). In some embodiments, the compound 1 tartrate salt is a crystalline polymorph characterized by XRPD signals at 4.3°2θ, 13.1°2θ, 14.5°2θ, 16.9°2θ, 17.5°2θ, 18.7°2θ, 19.3°2θ, 20.1°2θ, 21.0°2θ, 21.8°2θ, 23.3°2θ, 23.7°2θ, 24.8°2θ, 26.8°2θ, 27.5°2θ, 28.0°2θ, 29.7°2θ, 31.8°2θ, 36.1°2θ, and 38.9°2θ (±0.2°2θ; ±0.1°2θ; or ±0.0°2θ; Cu Kα1 radiation).

In some embodiments, the compound 1 tartrate salt is a crystalline polymorph characterized by two or more, or three or more XRPD signals selected from the group consisting of 4.3°2θ, 13.1°2θ, 14.5°2θ, 16.9°2θ, 17.5°2θ, 18.7°2θ, 19.3°2θ, 20.1°2θ, 21.0°2θ, 21.8°2θ, 23.3°2θ, 23.7°2θ, 24.8°2θ, 26.8°2θ, 27.5°2θ, 28.0°2θ, 29.1°2θ, 29.7°2θ, 31.8°2θ, 36.1°2θ, and 38.9°2θ (±0.2°2θ; ±0.1°2θ; or ±0.0°2θ; Cu Kα1 radiation). In some embodiments, the compound 1 tartrate salt is a crystalline polymorph characterized by XRPD signals at 4.3°2θ, 13.1°2θ, 14.5°2θ, 16.9°2θ, 17.5°2θ, 18.7°2θ, 19.3°2θ, 20.1°2θ, 21.0°2θ, 21.8°2θ, 23.3°2θ, 23.7°2θ, 24.8°2θ, 26.8°2θ, 27.5°2θ, 28.0°2θ, 29.1°2θ, 29.7°2θ, 31.8°2θ, 36.1°2θ, and 38.9°2θ (±0.2°2θ; ±0.1°2θ; or ±0.0°2θ; Cu Kα1 radiation).

In some embodiments, the compound 1 tartrate salt is a crystalline polymorph characterized by two or more, or three or more XRPD signals selected from the group consisting of 4.3°2θ, 13.1°2θ, 14.5°2θ, 16.9°2θ, 17.5°2θ, 18.7°2θ, 19.3°2θ, 20.1°2θ, 21.0°2θ, 21.8°2θ, 23.3°2θ, 23.7°2θ, 24.8°2θ, 26.8°2θ, 27.5°2θ, 28.0°2θ, 29.1°2θ, 29.7°2θ, 31.8°2θ, 35.0°2θ, 36.1°2θ, and 38.9°2θ (±0.2°2θ; ±0.1°2θ; or ±0.0°2θ; Cu Kα1 radiation). In some embodiments, the compound 1 tartrate salt is a crystalline polymorph characterized by XRPD signals at 4.3°2θ, 13.1°2θ, 14.5°2θ, 16.9°2θ, 17.5°2θ, 18.7°2θ, 19.3°2θ, 20.1°2θ, 21.0°2θ, 21.8°2θ, 23.3°2θ, 23.7°2θ, 24.8°2θ, 26.8°2θ, 27.5°2θ, 28.0°2θ, 29.1°2θ, 29.7°2θ, 31.8°2θ, 35.0°2θ, 36.1°2θ, and 38.9°2θ (±0.2°2θ; ±0.1°2θ; or ±0.0°2θ; Cu Kα1 radiation).

In some embodiments, the compound 1 tartrate salt is a crystalline polymorph characterized by two or more, or three or more XRPD signals selected from the group consisting of 4.3°2θ, 13.1°2θ, 14.5°2θ, 16.9°2θ, 17.5°2θ, 18.7°2θ, 19.3°2θ, 20.1°2θ, 21.0°2θ, 21.8°2θ, 23.3°2θ, 23.7°2θ, 24.8°2θ, 26.8°2θ, 27.5°2θ, 28.0°2θ, 29.1°2θ, 29.7°2θ, 30.8°2θ, 31.8°2θ, 35.0°2θ, 36.1°2θ, and 38.9°2θ (±0.2°2θ; ±0.1°2θ; or ±0.0°2θ; Cu Kα1 radiation). In some embodiments, the compound 1 tartrate salt is a crystalline polymorph characterized by XRPD signals at 4.3°2θ, 13.1°2θ, 14.5°2θ, 16.9°2θ, 17.5°2θ, 18.7°2θ, 19.3°2θ, 20.1°2θ, 21.0°2θ, 21.8°2θ, 23.3°2θ, 23.7°2θ, 24.8°2θ, 26.8°2θ, 27.5°2θ, 28.0°2θ, 29.1°2θ, 29.7°2θ, 30.8°2θ, 31.8°2θ, 35.0°2θ, 36.1°2θ, and 38.9°2θ (±0.2°2θ; ±0.1°2θ; or ±0.0°2θ; Cu Kα1 radiation).

In some embodiments, the compound 1 tartrate salt is a crystalline polymorph characterized by two or more, or three or more XRPD signals selected from the group consisting of 4.3°2θ, 8.7°2θ, 13.1°2θ, 14.5°2θ, 16.9°2θ, 17.5°2θ, 18.7°2θ, 19.3°2θ, 20.1°2θ, 21.0°2θ, 21.8°2θ, 23.3°2θ, 23.7°2θ, 24.8°2θ, 26.8°2θ, 27.5°2θ, 28.0°2θ, 29.1°2θ, 29.7°2θ, 30.8°2θ, 31.8°2θ, 35.0°2θ, 36.1°2θ, and 38.9°2θ (±0.2°2θ; ±0.1°2θ; or ±0.0°2θ; Cu Kα1 radiation). In some embodiments, the compound 1 tartrate salt is a crystalline polymorph characterized by XRPD signals at 4.3°2θ, 8.7°2θ, 13.1°2θ, 14.5°2θ, 16.9°2θ, 17.5°2θ, 18.7°2θ, 19.3°2θ, 20.1°2θ, 21.0°2θ, 21.8°2θ, 23.3°2θ, 23.7°2θ, 24.8°2θ, 26.8°2θ, 27.5°2θ, 28.0°2θ, 29.1°2θ, 29.7°2θ, 30.8°2θ, 31.8°2θ, 35.0°2θ, 36.1°2θ, and 38.9°2θ (±0.2°2θ; ±0.1°2θ; or ±0.0°2θ; Cu Kα1 radiation).

In some embodiments, the compound 1 tartrate salt is a crystalline polymorph characterized by two or more, or three or more XRPD signals selected from the group consisting of 4.3°2θ, 8.7°2θ, 13.1°2θ, 14.5°2θ, 16.9°2θ, 17.5°2θ, 18.7°2θ, 19.3°2θ, 20.1°2θ, 21.0°2θ, 21.8°2θ, 23.3°2θ, 23.7°2θ, 24.8°2θ, 26.8°2θ, 27.5°2θ, 28.0°2θ, 29.1°2θ, 29.7°2θ, 30.8°2θ, 31.8°2θ, 35.0°2θ, 36.1°2θ, 37.6°2θ, and 38.9°2θ (±0.2°2θ; ±0.1°2θ; or ±0.0°2θ; Cu Kα1 radiation). In some embodiments, the compound 1 tartrate salt is a crystalline polymorph characterized by XRPD signals at 4.3°2θ, 8.7°2θ, 13.1°2θ, 14.5°2θ, 16.9°2θ, 17.5°2θ, 18.7°2θ, 19.3°2θ, 20.1°2θ, 21.0°2θ, 21.8°2θ, 23.3°2θ, 23.7°2θ, 24.8°2θ, 26.8°2θ, 27.5°2θ, 28.0°2θ, 29.1°2θ, 29.7°2θ, 30.8°2θ, 31.8°2θ, 35.0°2θ, 36.1°2θ, 37.6°2θ, and 38.9°2θ (±0.2°2θ; ±0.1°2θ; or ±0.0°2θ; Cu Kα1 radiation).

In some embodiments, the compound 1 tartrate salt is a crystalline polymorph characterized by two or more, or three or more XRPD signals selected from the group consisting of 4.3°2θ, 8.7°2θ, 13.1°2θ, 14.5°2θ, 16.9°2θ, 17.5°2θ, 18.7°2θ, 19.3°2θ, 20.1°2θ, 21.0°2θ, 21.8°2θ, 23.3°2θ, 23.7°2θ, 24.8°2θ, 26.8°2θ, 27.5°2θ, 28.0°2θ, 29.1°2θ, 29.2°2θ, 29.7°2θ, 30.8°2θ, 31.8°2θ, 35.0°2θ, 36.1°2θ, 37.6°2θ, and 38.9°2θ (±0.2°2θ; ±0.1°2θ; or ±0.0°2θ; Cu Kα1 radiation). In some embodiments, the compound 1 tartrate salt is a crystalline polymorph characterized by XRPD signals at 4.3°2θ, 8.7°2θ, 13.1°2θ, 14.5°2θ, 16.9°2θ, 17.5°2θ, 18.7°2θ, 19.3°2θ, 20.1°2θ, 21.0°2θ, 21.8°2θ, 23.3°2θ, 23.7°2θ, 24.8°2θ, 26.8°2θ, 27.5°2θ, 28.0°2θ, 29.1°2θ, 29.2°2θ, 29.7°2θ, 30.8°2θ, 31.8°2θ, 35.0°2θ, 36.1°2θ, 37.6°2θ, and 38.9°2θ (±0.2°2θ; ±0.1°2θ; or ±0.0°2θ; Cu Kα1 radiation).

In some embodiments, the compound 1 tartrate salt is a crystalline polymorph characterized by two or more, or three or more XRPD signals selected from the group consisting of 4.3°2θ, 8.7°2θ, 13.1°2θ, 14.5°2θ, 16.9°2θ, 17.5°2θ, 18.7°2θ, 19.3°2θ, 20.1°2θ, 21.0°2θ, 21.8°2θ, 23.3°2θ, 23.7°2θ, 24.8°2θ, 26.8°2θ, 27.5°2θ, 28.0°2θ, 29.1°2θ, 29.2°2θ, 29.7°2θ, 30.8°2θ, 31.8°2θ, 33.3°2θ, 35.0°2θ, 36.1°2θ, 37.6°2θ, and 38.9°2θ (±0.2°2θ; ±0.1°2θ; or ±0.0°2θ; Cu Kα1 radiation). In some embodiments, the compound 1 tartrate salt is a crystalline polymorph characterized by XRPD signals at 4.3°2θ, 8.7°2θ, 13.1°2θ, 14.5°2θ, 16.9°2θ, 17.5°2θ, 18.7°2θ, 19.3°2θ, 20.1°2θ, 21.0°2θ, 21.8°2θ, 23.3°2θ, 23.7°2θ, 24.8°2θ, 26.8°2θ, 27.5°2θ, 28.0°2θ, 29.1°2θ, 29.2°2θ, 29.7°2θ, 30.8°2θ, 31.8°2θ, 33.3°2θ, 35.0°2θ, 36.1°2θ, 37.6°2θ, and 38.9°2θ (±0.2°2θ; ±0.1°2θ; or ±0.0°2θ; Cu Kα1 radiation).

In some embodiments, the compound 1 tartrate salt is a crystalline polymorph characterized by two or more, or three or more XRPD signals selected from the group consisting of 4.3°2θ, 8.7°2θ, 13.1°2θ, 14.5°2θ, 16.2°2θ, 16.9°2θ, 17.5°2θ, 18.7°2θ, 19.3°2θ, 20.1°2θ, 21.0°2θ, 21.8°2θ, 23.3°2θ, 23.7°2θ, 24.8°2θ, 26.8°2θ, 27.5°2θ, 28.0°2θ, 29.1°2θ, 29.2°2θ, 29.7°2θ, 30.8°2θ, 31.8°2θ, 33.3°2θ, 35.0°2θ, 36.1°2θ, 37.6°2θ, and 38.9°2θ (±0.2°2θ; ±0.1°2θ; or ±0.0°2θ; Cu Kα1 radiation). In some embodiments, the compound 1 tartrate salt is a crystalline polymorph characterized by XRPD signals a 4.3°2θ, 8.7°2θ, 13.1°2θ, 14.5°2θ, 16.2°2θ, 16.9°2θ, 17.5°2θ, 18.7°2θ, 19.3°2θ, 20.1°2θ, 21.0°2θ, 21.8°2θ, 23.3°2θ, 23.7°2θ, 24.8°2θ, 26.8°2θ, 27.5°2θ, 28.0°2θ, 29.1°2θ, 29.2°2θ, 29.7°2θ, 30.8°2θ, 31.8°2θ, 33.3°2θ, 35.0°2θ, 36.1°2θ, 37.6°2θ, and 38.9°2θ (0.2°2θ; ±0.1°2θ; or ±0.0°2θ; Cu Kα1 radiation).

In some embodiments, crystalline polymorphic Pattern 6 is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, or twenty-eight XRPD signals selected from those set forth in Table 47.

TABLE 47

Crystalline compound 1 tartrate salt XRPD signals (±0.2 °2θ; ±0.1 °2θ; or ±0.0 °2θ; Cu Kα1 radiation)

| Signal number | 2-θ (°) | d Value | Net Intensity (counts) | Gross Intensity (counts) | Rel. Intensity (%) |
|---|---|---|---|---|---|
| Signal #1 | 4.3 | 20.31 | 1458.7 | 1808.7 | 100.0 |
| Signal #2 | 8.7 | 10.15 | 178.6 | 254.9 | 12.2 |
| Signal #3 | 13.1 | 6.77 | 424.0 | 496.7 | 29.1 |
| Signal #4 | 14.5 | 6.12 | 996.2 | 1070.0 | 68.3 |
| Signal #5 | 16.2 | 5.46 | 152.5 | 237.5 | 10.5 |
| Signal #6 | 16.9 | 5.25 | 314.4 | 408.3 | 21.6 |
| Signal #7 | 17.5 | 5.08 | 1369.8 | 1470.4 | 93.9 |
| Signal #8 | 18.7 | 4.74 | 796.1 | 911.6 | 54.6 |
| Signal #9 | 19.3 | 4.59 | 1183.0 | 1304.7 | 81.1 |
| Signal #10 | 20.1 | 4.42 | 1036.2 | 1161.4 | 71.0 |
| Signal #11 | 21.0 | 4.23 | 932.6 | 1055.0 | 63.9 |
| Signal #12 | 21.8 | 4.07 | 252.4 | 367.9 | 17.3 |
| Signal #13 | 23.3 | 3.81 | 631.1 | 733.7 | 43.3 |
| Signal #14 | 23.7 | 3.75 | 904.7 | 1005.0 | 62.0 |
| Signal #15 | 24.8 | 3.59 | 226.3 | 317.1 | 15.5 |
| Signal #16 | 26.8 | 3.33 | 207.9 | 302.9 | 14.2 |
| Signal #17 | 27.5 | 3.24 | 489.9 | 588.4 | 33.6 |
| Signal #18 | 28.0 | 3.18 | 336.8 | 435.0 | 23.1 |
| Signal #19 | 29.1 | 3.07 | 192.9 | 292.4 | 13.2 |
| Signal #20 | 29.2 | 3.06 | 166.1 | 265.7 | 11.4 |
| Signal #21 | 29.7 | 3.01 | 396.7 | 495.3 | 27.2 |
| Signal #22 | 30.8 | 2.90 | 185.8 | 282.0 | 12.7 |
| Signal #23 | 31.8 | 2.81 | 524.1 | 618.5 | 35.9 |
| Signal #24 | 33.3 | 2.69 | 165.3 | 251.7 | 11.3 |
| Signal #25 | 35.0 | 2.56 | 191.9 | 278.2 | 13.2 |
| Signal #26 | 36.1 | 2.48 | 195.9 | 288.5 | 13.4 |
| Signal #27 | 37.6 | 2.39 | 168.8 | 276.4 | 11.6 |
| Signal #28 | 38.9 | 2.31 | 455.6 | 592.5 | 31.2 |

Compound 1 HBr Salt

In some embodiments, the compound 1 salt is a compound 1 HBr salt. In some embodiments, the compound 1 HBr salt is amorphous. In some embodiments, the compound 1 HBr salt is crystalline. In some embodiments, the compound 1 HBr salt is a 1:1 compound 1: HBr salt. In some embodiments, the compound 1 HBr salt is a 2:1 compound 1:HBr salt.

In some embodiments, the compound 1 HBr salt is a crystalline polymorph. In some embodiments, the crystalline polymorph is characterized by the XRPD signals set for the below in Table 48. In some embodiments, the crystalline polymorph XRPD pattern is substantially similar to that shown in FIG. 172. In some embodiments, the crystalline polymorph TGA spectrum is substantially similar to that shown in 242. In some embodiments, the crystalline polymorph DSC spectrum is substantially similar to that shown in any one of FIG. 241.

In some embodiments, the crystalline compound 1 HBr salt is a crystalline polymorphic form characterized by DSC having a melting signal at about 194.8° C. In some embodiments, the crystalline compound 1 HBr salt is a crystalline polymorphic form characterized by TGA having an onset at about 253.7° C.

In some embodiments, the compound 1 HBr salt is a crystalline polymorph characterized by two an XRPD signal at 21.6°2θ (±0.2°2θ; ±0.1°2θ; or ±0.0°2θ; Cu Kα1 radiation).

In some embodiments, the compound 1 HBr salt is a crystalline polymorph characterized by XRPD signals at 18.1°2θ, and 21.6°2θ (±0.2°2θ; ±0.1°2θ; or ±0.0°2θ; Cu Kα1 radiation).

In some embodiments, the compound 1 HBr salt is a crystalline polymorph characterized by two or more, or three or more XRPD signals selected from the group consisting of 12.2°2θ, 18.1°2θ, and 21.6°2θ (±0.2°2θ; ±0.1°2θ; or ±0.0°2θ; Cu Kα1 radiation). In some embodiments, the compound 1 HBr salt is a crystalline polymorph characterized by XRPD signals at 12.2°2θ, 18.1°2θ, and 21.6°2θ (±0.2°2θ; ±0.1°2θ; or ±0.0°2θ; Cu Kα1 radiation).

In some embodiments, the compound 1 HBr salt is a crystalline polymorph characterized by two or more, or three or more XRPD signals selected from the group consisting of 12.2°2θ, 18.1°2θ, 21.6°2θ, and 28.5°2θ (±0.2°2θ; ±0.1°2θ; or ±0.0°2θ; Cu Kα1 radiation). In some embodiments, the compound 1 HBr salt is a crystalline polymorph characterized by XRPD signals at 12.2°2θ, 18.1°2θ, 21.6°2θ, and 28.5°2θ (±0.2°2θ; ±0.1°2θ; or ±0.0°2θ; Cu Kα1 radiation).

In some embodiments, the compound 1 HBr salt is a crystalline polymorph characterized by two or more, or three or more XRPD signals selected from the group consisting of 12.2°2θ, 18.1°2θ, 21.6°2θ, 24.4°2θ, and 28.5°2θ (±0.2°2θ; ±0.1°2θ; or ±0.0°2θ; Cu Kα1 radiation). In some embodiments, the compound 1 HBr salt is a crystalline polymorph characterized by XRPD signals at 12.2°2θ, 18.1°2θ, 21.6°2θ, 24.4°2θ, and 28.5°2θ (±0.2°2θ; ±0.1°2θ; or ±0.0°2θ; Cu Kα1 radiation).

In some embodiments, the compound 1 HBr salt is a crystalline polymorph characterized by two or more, or three or more XRPD signals selected from the group consisting of 12.2°2θ, 17.5°2θ, 18.1°2θ, 21.6°2θ, 24.4°2θ, and 28.5°2θ (±0.2°2θ; ±0.1°2θ; or ±0.0°2θ; Cu Kα1 radiation). In some embodiments, the compound 1 HBr salt is a crystalline polymorph characterized by XRPD signals at 12.2°2θ, 17.5°2θ, 18.1°2θ, 21.6°2θ, 24.4°2θ, and 28.5°2θ (±0.2°2θ; ±0.1°2θ; or ±0.0°2θ; Cu Kα1 radiation).

In some embodiments, the compound 1 HBr salt is a crystalline polymorph characterized by two or more, or three or more XRPD signals selected from the group consisting of 12.2°2θ, 17.5°2θ, 18.1°2θ, 21.6°2θ, 24.4°2θ, 27.0°2θ, and 28.5°2θ (±0.2°2θ; ±0.1°2θ; or ±0.0°2θ; Cu Kα1 radiation). In some embodiments, the compound 1 HBr salt is a crystalline polymorph characterized by XRPD signals at 12.2°2θ, 17.5°2θ, 18.1°2θ, 21.6°2θ, 24.4°2θ, 27.0°2θ, and 28.5°2θ (±0.2°2θ; ±0.1°2θ; or ±0.0°2θ; Cu Kα1 radiation).

In some embodiments, the compound 1 HBr salt is a crystalline polymorph characterized by two or more, or three or more XRPD signals selected from the group consisting of 12.2°2θ, 17.5°2θ, 18.1°2θ, 21.6°2θ, 24.4°2θ, 25.5°2θ, 27.0°2θ, and 28.5°2θ (±0.2°2θ; ±0.1°2θ; or ±0.0°2θ; Cu Kα1 radiation). In some embodiments, the compound 1 HBr salt is a crystalline polymorph characterized by XRPD signals at 12.2°2θ, 17.5°2θ, 18.1°2θ, 21.6°2θ, 24.4°2θ, 25.5°2θ, 27.0°2θ, and 28.5°2θ (±0.2°2θ; ±0.1°2θ; or ±0.0°2θ; Cu Kα1 radiation).

In some embodiments, the compound 1 HBr salt is a crystalline polymorph characterized 10 by two or more, or three or more XRPD signals selected from the group consisting of 12.2°2θ, 17.5°2θ, 18.1°2θ, 18.4°2θ, 21.6°2θ, 24.4°2θ, 25.5°2θ, 27.0°2θ, and 28.5°2θ (±0.2°2θ; ±0.1°2θ; or ±0.0°2θ; Cu Kα1 radiation). In some embodiments, the compound 1 HBr salt is a crystalline polymorph characterized by XRPD signals at 12.2°2θ, 17.5°2θ, 18.1°2θ, 18.4°2θ, 21.6°2θ, 24.4°2θ, 25.5°2θ, 27.0°2θ, and 28.5°2θ (±0.2°2θ; ±0.1°2θ; or ±0.0°2θ; Cu Kα1 radiation).

In some embodiments, the compound 1 HBr salt is a crystalline polymorph characterized by two or more, or three or more XRPD signals selected from the group consisting of 12.2°2θ, 17.5°2θ, 18.1°2θ, 18.4°2θ, 21.6°2θ, 24.4°2θ, 25.5°2θ, 26.1°2θ, 27.0°2θ, and 28.5°2θ (±0.2°2θ; ±0.1°2θ; or ±0.0°2θ; Cu Kα1 radiation). In some embodiments, the compound 1 HBr salt is a crystalline polymorph characterized by XRPD signals at 12.2°2θ, 17.5°2θ, 18.1°2θ, 18.4°2θ, 21.6°2θ, 24.4°2θ, 25.5°2θ, 26.1°2θ, 27.0°2θ, and 28.5°2θ (±0.2°2θ; ±0.1°2θ; or ±0.0°2θ; Cu Kα1 radiation).

In some embodiments, the compound 1 HBr salt is a crystalline polymorph characterized by two or more, or three or more XRPD signals selected from the group consisting of 12.2°2θ, 17.5°2θ, 18.1°2θ, 18.4°2θ, 21.6°2θ, 24.4°2θ, 25.5°2θ, 26.1°2θ, 27.0°2θ, 28.4°2θ, and 28.5°2θ (±0.2°2θ; ±0.1°2θ; or ±0.0°2θ; Cu Kα1 radiation). In some embodiments, the compound 1 HBr salt is a crystalline polymorph characterized by XRPD signals at 12.2°2θ, 17.5°2θ, 18.1°2θ, 18.4°2θ, 21.6°2θ, 24.4°2θ, 25.5°2θ, 26.1°2θ, 27.0°2θ, 28.4°2θ, and 28.5°2θ (±0.2°2θ; ±0.1°2θ; or ±0.0°2θ; Cu Kα1 radiation).

In some embodiments, the compound 1 HBr salt is a crystalline polymorph characterized by two or more, or three or more XRPD signals selected from the group consisting of 12.2°2θ, 17.5°2θ, 18.1°2θ, 18.4°2θ, 20.6°2θ, 21.6°2θ, 24.4°2θ, 25.5°2θ, 26.1°2θ, 27.0°2θ, 28.4°2θ, and 28.5°2θ (±0.2°2θ; ±0.1°2θ; or ±0.0°2θ; Cu Kα1 radiation). In some embodiments, the compound 1 HBr salt is a crystalline polymorph characterized by XRPD signals at 12.2°2θ, 17.5°2θ, 18.1°2θ, 18.4°2θ, 20.6°2θ, 21.6°2θ, 24.4°2θ, 25.5°2θ, 26.1°2θ, 27.0°2θ, 28.4°2θ, and 28.5°2θ (±0.2°2θ; ±0.1°2θ; or ±0.0°2θ; Cu Kα1 radiation).

In some embodiments, the compound 1 HBr salt is a crystalline polymorph characterized by two or more, or three or more XRPD signals selected from the group consisting of 12.2°2θ, 13.0°2θ, 17.5°2θ, 18.1°2θ, 18.4°2θ, 20.6°2θ, 21.6°2θ, 24.4°2θ, 25.5°2θ, 26.1°2θ, 27.0°2θ, 28.4°2θ, and 28.5°2θ (±0.2°2θ; ±0.1°2θ; or ±0.0°2θ; Cu Kα1 radiation). In some embodiments, 10 the compound 1 HBr salt is a crystalline polymorph characterized by XRPD signals at 12.2°2θ, 13.0°2θ, 17.5°2θ, 18.1°2θ, 18.4°2θ, 20.6°2θ, 21.6°2θ, 24.4°2θ, 25.5°2θ, 26.1°2θ, 27.0°2θ, 28.4°2θ, and 28.5°2θ (±0.2 20; 0.1°2θ; or ±0.0°2θ; Cu Kα1 radiation).

In some embodiments, the compound 1 HBr salt is a crystalline polymorph characterized by two or more, or three or more XRPD signals selected from the group consisting of 12.2°2θ, 13.0°2θ, 17.5°2θ, 18.1°2θ, 18.4°2θ, 20.6°2θ, 21.6°2θ, 23.3°2θ, 24.4°2θ, 25.5°2θ, 26.1°2θ, 27.0°2θ, 28.4°2θ, and 28.5°2θ (±0.2°2θ; ±0.1°2θ; or ±0.0°2θ; Cu Kα1 radiation). In some embodiments, the compound 1 HBr salt is a crystalline polymorph characterized by XRPD signals at 12.2°2θ, 13.0°2θ, 17.5°2θ, 18.1°2θ, 18.4°2θ, 20.6°2θ, 21.6°2θ, 23.3°2θ, 24.4°2θ, 25.5°2θ, 26.1°2θ, 27.0°2θ, 28.4°2θ, and 28.5°2θ (±0.2°2θ; ±0.1°2θ; or ±0.0°2θ; Cu Kα1 radiation).

In some embodiments, the compound 1 HBr salt is a crystalline polymorph characterized by two or more, or three or more XRPD signals selected from the group consisting of 6.5°2θ, 12.2°2θ, 13.0°2θ, 17.5°2θ, 18.1°2θ, 18.4°2θ, 20.6°2θ, 21.6°2θ, 23.3°2θ, 24.4°2θ, 25.5°2θ, 26.1°2θ, 27.0°2θ, 28.4°2θ, and 28.5°2θ (±0.2°2θ; ±0.1°2θ; or ±0.0°2θ; Cu Kα1 radiation). In some embodiments, the compound 1 HBr salt is a crystalline polymorph characterized by XRPD signals at 6.5°2θ, 12.2°2θ, 13.0°2θ, 17.5°2θ, 18.1°2θ, 18.4°2θ, 20.6°2θ, 21.6°2θ, 23.3°2θ, 24.4°2θ, 25.5°2θ, 26.1°2θ, 27.0°2θ, 28.4°2θ, and 28.5°2θ (±0.2°2θ; ±0.1°2θ; or ±0.0°2θ; Cu Kα1 radiation).

In some embodiments, the compound 1 HBr salt is a crystalline polymorph characterized by two or more, or three or more XRPD signals selected from the group consisting of 6.5°2θ, 12.2°2θ, 13.0°2θ, 17.5°2θ, 18.1°2θ, 18.4°2θ, 20.6°2θ, 21.6°2θ, 23.3°2θ, 23.7°2θ, 24.4°2θ, 25.5°2θ, 26.1°2θ, 27.0°2θ, 28.4°2θ, and 28.5°2θ (±0.2°2θ; ±0.1°2θ; or ±0.0°2θ; Cu Kα1 radiation). In some embodiments, the compound 1 HBr salt is a crystalline polymorph characterized by XRPD signals at 6.5°2θ, 12.2°2θ, 13.0°2θ, 17.5°2θ, 18.1°2θ, 18.4°2θ, 20.6°2θ, 21.6°2θ, 23.3°2θ, 23.7°2θ, 24.4°2θ, 25.5°2θ, 26.1°2θ, 27.0°2θ, 28.4°2θ, and 28.5°2θ (±0.2°2θ; ±0.1°2θ; or ±0.0°2θ; Cu Kα1 radiation).

In some embodiments, the compound 1 HBr salt is a crystalline polymorph characterized by two or more, or three or more XRPD signals selected from the group consisting of 6.5°2θ, 12.2°2θ, 13.0°2θ, 17.5°2θ, 18.1°2θ, 18.4°2θ, 20.6°2θ, 21.6°2θ, 22.9°2θ, 23.3°2θ, 23.7°2θ, 24.4°2θ, 25.5°2θ, 26.1°2θ, 27.0°2θ, 28.4°2θ, and 28.5°2θ (±0.2°2θ; ±0.1°2θ; or ±0.0°2θ; Cu Kα1 radiation). In some embodiments, the compound 1 HBr salt is a crystalline polymorph characterized by XRPD signals at 6.5°2θ, 12.2°2θ, 13.0°2θ, 17.5°2θ, 18.1°2θ, 18.4°2θ, 20.6°2θ, 21.6°2θ, 22.9°2θ, 23.3°2θ, 23.7°2θ, 24.4°2θ, 25.5°2θ, 26.1°2θ, 27.0°2θ, 28.4°2θ, and 28.5°2θ (±0.2°2θ; ±0.1°2θ; or ±0.0°2θ; Cu Kα1 radiation).

In some embodiments, the compound 1 HBr salt is a crystalline polymorph characterized by two or more, or three or more XRPD signals selected from the group consisting of 6.5°2θ, 12.2°2θ, 13.0°2θ, 17.5°2θ, 18.1°2θ, 18.4°2θ, 19.8°2θ, 20.6°2θ, 21.6°2θ, 22.9°2θ, 23.3°2θ, 23.7°2θ, 24.4°2θ, 25.5°2θ, 26.1°2θ, 27.0°2θ, 28.4°2θ, and 28.5°2θ (±0.2°2θ; ±0.1°2θ; or ±0.0°2θ; Cu Kα1 radiation). In some embodiments, the compound 1 HBr salt is a crystalline polymorph characterized by XRPD signals at 6.5°2θ, 12.2°2θ, 13.0°2θ, 17.5°2θ, 18.1°2θ, 18.4°2θ, 19.8°2θ, 20.6°2θ, 21.6°2θ, 22.9°2θ, 23.3°2θ, 23.7°2θ, 24.4°2θ, 25.5°2θ, 26.1°2θ, 27.0°2θ, 28.4°2θ, and 28.5°2θ (±0.2°2θ; ±0.1°2θ; or ±0.0°2θ; Cu Kα1 radiation).

In some embodiments, the compound 1 HBr salt is a crystalline polymorph characterized by two or more, or three or more XRPD signals selected from the group consisting of 6.5°2θ, 12.2°2θ, 13.0°2θ, 14.2°2θ, 17.5°2θ, 18.1°2θ, 18.4°2θ, 19.8°2θ, 20.6°2θ, 21.6°2θ, 22.9°2θ, 23.3°2θ, 23.7°2θ, 24.4°2θ, 25.5°2θ, 26.1°2θ, 27.0°2θ, 28.4°2θ, and 28.5°2θ (±0.2°2θ; ±0.1°2θ; or ±0.0°2θ; Cu Kα1 radiation). In some embodiments, the compound 1 HBr salt is a crystalline polymorph characterized by XRPD signals at 6.5°2θ, 12.2°2θ, 13.0°2θ, 14.2°2θ, 17.5°2θ, 18.1°2θ, 18.4°2θ, 19.8°2θ, 20.6°2θ, 21.6°2θ, 22.9°2θ, 23.3°2θ, 23.7°2θ, 24.4°2θ, 25.5°2θ, 26.1°2θ, 27.0°2θ, 28.4°2θ, and 28.5°2θ (±0.2°2θ; ±0.1°2θ; or ±0.0°2θ; Cu Kα1 radiation).

In some embodiments, the compound 1 HBr salt is a crystalline polymorph characterized by two or more, or three or more XRPD signals selected from the group consisting of 6.5°2θ, 12.2°2θ, 13.0°2θ, 14.2°2θ, 17.5°2θ, 18.1°2θ, 18.4°2θ, 19.8°2θ, 20.6°2θ, 21.6°2θ, 22.9°2θ, 23.3°2θ, 23.7°2θ, 24.4°2θ, 25.5°2θ, 26.1°2θ, 27.0°2θ, 28.4°2θ, 28.5°2θ, and 34.9°2θ (±0.2°2θ; ±0.1°2θ; or ±0.0°2θ; Cu Kα1 radiation). In some embodiments, the compound 1 HBr salt is a crystalline polymorph characterized by XRPD signals at 6.5°2θ, 12.2°2θ, 13.0°2θ, 14.2°2θ, 17.5°2θ, 18.1°2θ, 18.4°2θ, 19.8°2θ, 20.6°2θ, 21.6°2θ, 22.9°2θ, 23.3°2θ, 23.7°2θ, 24.4°2θ, 25.5°2θ, 26.1°2θ, 27.0°2θ, 28.4°2θ, 28.5°2θ, and 34.9°2θ (±0.2°2θ; ±0.1°2θ; or ±0.0°2θ; Cu Kα1 radiation).

In some embodiments, the compound 1 HBr salt is a crystalline polymorph characterized by two or more, or three or more XRPD signals selected from the group consisting of 6.5°2θ, 12.2°2θ, 13.0°2θ, 14.2°2θ, 17.5°2θ, 18.1°2θ, 18.4°2θ, 19.8°2θ, 20.6°2θ, 21.6°2θ, 22.9°2θ, 23.3°2θ, 23.7°2θ, 24.4°2θ, 25.5°2θ, 26.1°2θ, 27.0°2θ, 28.4°2θ, 28.5°2θ, 30.1°2θ, and 34.9°2θ (±0.2°2θ; ±0.1°2θ; or ±0.0°2θ; Cu Kα1 radiation). In some embodiments, the compound 1 HBr salt is a crystalline polymorph characterized by XRPD signals at 6.5°2θ, 12.2°2θ, 13.0°2θ, 14.2°2θ, 17.5°2θ, 18.1°2θ, 18.4°2θ, 19.8°2θ, 20.6°2θ, 21.6°2θ, 22.9°2θ, 23.3°2θ, 23.7°2θ, 24.4°2θ, 25.5°2θ, 26.1°2θ, 27.0°2θ, 28.4°2θ, 28.5°2θ, 30.1°2θ, and 34.9°2θ (±0.2°2θ; ±0.1°2θ; or ±0.0°2θ; Cu Kα1 radiation).

In some embodiments, the compound 1 HBr salt is a crystalline polymorph characterized by two or more, or three or more XRPD signals selected from the group consisting of 6.5°2θ, 12.2°2θ, 13.0°2θ, 14.2°2θ, 17.5°2θ, 18.1°2θ, 18.4°2θ, 19.8°2θ, 20.6°2θ, 21.6°2θ, 22.9°2θ, 23.3°2θ, 23.7°2θ, 24.4°2θ, 25.5°2θ, 26.1°2θ, 27.0°2θ, 27.5°2θ, 28.4°2θ, 28.5°2θ, 30.1°2θ, and 34.9°2θ (±0.2°2θ; ±0.1°2θ; or ±0.0°2θ; Cu Kα1 radiation). In some embodiments, the compound 1 HBr salt is a crystalline polymorph characterized by XRPD signals at 6.5°2θ, 12.2°2θ, 13.0°2θ, 14.2°2θ, 17.5°2θ, 18.1°2θ, 18.4°2θ, 19.8°2θ, 20.6°2θ, 21.6°2θ, 22.9°2θ, 23.3°2θ, 23.7°2θ, 24.4°2θ, 25.5°2θ, 26.1°2θ, 27.0°2θ, 27.5°2θ, 28.4°2θ, 28.5°2θ, 30.1°2θ, and 34.9°2θ (±0.2°2θ; ±0.1°2θ; or ±0.0°2θ; Cu Kα1 radiation).

In some embodiments, the compound 1 HBr salt is a crystalline polymorph characterized by two or more, or three or more XRPD signals selected from the group consisting of 6.5°2θ, 12.2°2θ, 13.0°2θ, 14.2°2θ, 17.5°2θ, 18.1°2θ, 18.4°2θ, 19.8°2θ, 20.6°2θ, 21.6°2θ, 22.9°2θ, 23.3°2θ, 23.7°2θ, 24.4°2θ, 25.5°2θ, 26.1°2θ, 27.0°2θ, 27.5°2θ, 28.4°2θ, 28.5°2θ, 30.1°2θ, 33.3°2θ, and 34.9°2θ (±0.2°2θ; ±0.1°2θ; or ±0.0°2θ; Cu Kα1 radiation). In some embodiments, the compound 1 HBr salt is a crystalline polymorph characterized by XRPD signals at 6.5°2θ, 12.2°2θ, 13.0°2θ, 14.2°2θ, 17.5°2θ, 18.1°2θ, 18.4°2θ, 19.8°2θ, 20.6°2θ, 21.6°2θ, 22.9°2θ, 23.3°2θ, 23.7°2θ, 24.4°2θ, 25.5°2θ, 26.1°2θ, 27.0°2θ, 27.5°2θ, 28.4°2θ, 28.5°2θ, 30.1°2θ, 33.3°2θ, and 34.9°2θ (±0.2°2θ; ±0.1°2θ; or ±0.0°2θ; Cu Kα1 radiation).

In some embodiments, the compound 1 HBr salt is a crystalline polymorph characterized by two or more, or three or more XRPD signals selected from the group consisting of 6.5°2θ, 12.2°2θ, 13.0°2θ, 14.2°2θ, 17.5°2θ, 18.1°2θ, 18.4°2θ, 19.8°2θ, 20.6°2θ, 21.6°2θ, 22.9°2θ, 23.3°2θ, 23.7°2θ, 24.4°2θ, 25.5°2θ, 26.1°2θ, 26.8°2θ, 27.0°2θ, 27.5°2θ, 28.4°2θ, 28.5°2θ, 30.1°2θ, 33.3°2θ, and 34.9°2θ (±0.2°2θ; ±0.1°2θ; or ±0.0°2θ; Cu Kα1 radiation). In some embodiments, the compound 1 HBr salt is a crystalline polymorph characterized by XRPD signals at 6.5°2θ, 12.2°2θ, 13.0°2θ, 14.2°2θ, 17.5°2θ, 18.1°2θ, 18.4°2θ, 19.8°2θ, 20.6°2θ, 21.6°2θ, 22.9°2θ, 23.3°2θ, 23.7°2θ, 24.4°2θ, 25.5°2θ, 26.1°2θ, 26.8°2θ, 27.0°2θ, 27.5°2θ, 28.4°2θ, 28.5°2θ, 30.1°2θ, 33.3°2θ, and 34.9°2θ (±0.2°2θ; ±0.1°2θ; or ±0.0°2θ; Cu Kα1 radiation).

In some embodiments, the compound 1 HBr salt is a crystalline polymorph characterized by two or more, or three or more XRPD signals selected from the group consisting of 6.5°2θ, 12.2°2θ, 13.0°2θ, 14.2°2θ, 17.5°2θ, 18.1°2θ, 18.4°2θ, 19.8°2θ, 20.6°2θ, 21.6°2θ, 22.9°2θ, 23.3°2θ, 23.7°2θ, 24.4°2θ, 25.5°2θ, 26.1°2θ, 26.8°2θ, 27.0°2θ, 27.5°2θ, 28.4°2θ, 28.5°2θ, 29.6°2θ, 30.1°2θ, 33.3°2θ, and 34.9°2θ (±0.2°2θ; ±0.1°2θ; or 0.0°2θ; Cu Kα1 radiation). In some embodiments, the compound 1 HBr salt is a crystalline polymorph characterized by XRPD signals at 6.5°2θ, 12.2°2θ, 13.0°2θ, 14.2°2θ, 17.5°2θ, 18.1°2θ, 18.4°2θ, 19.8°2θ, 20.6°2θ, 21.6°2θ, 22.9°2θ, 23.3°2θ, 23.7°2θ, 24.4°2θ, 25.5°2θ, 26.1°2θ, 26.8°2θ, 27.0°2θ, 27.5°2θ, 28.4°2θ, 28.5°2θ, 29.6°2θ, 30.1°2θ, 33.3°2θ, and 34.9°2θ (±0.2°2θ; ±0.1°2θ; or ±0.0°2θ; Cu Kα1 radiation).

In some embodiments, crystalline polymorph is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, or twenty-five XRPD signals selected from those set forth in Table 48.

TABLE 48

Crystalline compound 1 HBr salt XRPD signals (±0.2 °2θ; ±0.1 °2θ; or ±0.0 °2θ; Cu Kα1 radiation)

| Signal number | 2-θ (°) | d Value | Net Intensity (counts) | Gross Intensity (counts) | Rel. Intensity (%) |
|---|---|---|---|---|---|
| Signal #1 | 6.5 | 13.52 | 373.9 | 537.6 | 18.7 |
| Signal #2 | 12.2 | 7.25 | 1330.8 | 1467.7 | 66.5 |
| Signal #3 | 13.0 | 6.78 | 529.7 | 675.6 | 26.5 |
| Signal #4 | 14.2 | 6.25 | 295.9 | 446.3 | 14.8 |
| Signal #5 | 17.5 | 5.06 | 1145.4 | 1336.0 | 57.2 |
| Signal #6 | 18.1 | 4.89 | 1961.2 | 2161.6 | 98.0 |
| Signal #7 | 18.4 | 4.83 | 642.7 | 846.1 | 32.1 |
| Signal #8 | 19.8 | 4.48 | 338.9 | 562.2 | 16.9 |
| Signal #9 | 20.6 | 4.31 | 561.7 | 801.2 | 28.1 |
| Signal #10 | 21.6 | 4.11 | 2000.9 | 2252.2 | 100.0 |
| Signal #11 | 22.9 | 3.89 | 347.3 | 603.0 | 17.4 |
| Signal #12 | 23.3 | 3.82 | 396.1 | 653.6 | 19.8 |
| Signal #13 | 23.7 | 3.74 | 358.0 | 615.5 | 17.9 |
| Signal #14 | 24.4 | 3.64 | 1251.6 | 1513.3 | 62.6 |
| Signal #15 | 25.5 | 3.49 | 652.7 | 926.6 | 32.6 |
| Signal #16 | 26.1 | 3.41 | 576.3 | 852.6 | 28.8 |
| Signal #17 | 26.8 | 3.32 | 209.7 | 485.6 | 10.5 |
| Signal #18 | 27.0 | 3.30 | 689.4 | 964.8 | 34.5 |
| Signal #19 | 27.5 | 3.24 | 224.5 | 496.7 | 11.2 |
| Signal #20 | 28.5 | 3.13 | 1318.0 | 1576.8 | 65.9 |
| Signal #21 | 28.4 | 3.14 | 571.0 | 832.0 | 28.5 |
| Signal #22 | 29.6 | 3.02 | 206.5 | 441.2 | 10.3 |
| Signal #23 | 30.1 | 2.97 | 240.0 | 458.6 | 12.0 |
| Signal #24 | 33.3 | 2.69 | 222.8 | 402.1 | 11.1 |
| Signal #25 | 34.9 | 2.57 | 255.6 | 440.7 | 12.8 |

Compound 1 Galactarate Salt

In some embodiments, the compound 1 salt is a compound 1 Galactarate salt. In some embodiments, the compound 1 Galactarate salt is amorphous. In some embodiments, the compound 1 Galactarate salt is crystalline. In some embodiments, the compound 1 Galactarate salt is a 1:1 compound 1:Galactarate salt. In some embodiments, the compound 1 Galactarate salt is a 2:1 compound 1:Galactarate salt.

In some embodiments, the compound 1 galactarate salt is a crystalline polymorph. In some embodiments, the crystalline polymorph is characterized by the XRPD signals set for the below in Table 49. In some embodiments, the crystalline polymorph XRPD pattern is substantially similar to that shown in FIG. 173. In some embodiments, the crystalline polymorph DSC spectrum is substantially similar to that shown in FIG. 245.

In some embodiments, the crystalline compound 1 galactarate is a crystalline polymorphic form characterized by DSC having a melting signal at about 167.5° C. In some embodiments, the compound 1 Galactarate salt is a crystalline polymorph characterized by an XRPD signal at 19.6°2θ (±0.2°2θ; ±0.1°2θ; or ±0.0°2θ; Cu Kα1 radiation).

In some embodiments, the compound 1 Galactarate salt is a crystalline polymorph characterized by XRPD signals at 5.2°2θ and 19.6°2θ (±0.2°2θ; ±0.1°2θ; or ±0.0°2θ; Cu Kα1 radiation).

In some embodiments, the compound 1 Galactarate salt is a crystalline polymorph characterized by two or more, or three or more XRPD signals selected from the group consisting of 5.2°2θ, 15.9°2θ, and 19.6°2θ (±0.2°2θ; ±0.1°2θ; or ±0.0°2θ; Cu Kα1 radiation). In some embodiments, the compound 1 Galactarate salt is a crystalline polymorph characterized by XRPD signals at 5.2°2θ, 15.9°2θ, and 19.6°2θ (±0.2°2θ; ±0.1°2θ; or ±0.0°2θ; Cu Kα1 radiation).

In some embodiments, the compound 1 Galactarate salt is a crystalline polymorph characterized by two or more, or three or more XRPD signals selected from the group consisting of 5.2°2θ, 15.9°2θ, 19.6°2θ, and 30.7°2θ (±0.2°2θ; ±0.1°2θ; or ±0.0°2θ; Cu Kα1 radiation).

In some embodiments, the compound 1 Galactarate salt is a crystalline polymorph characterized by XRPD signals at 5.2°2θ, 15.9°2θ, 19.6°2θ, and 30.7°2θ (±0.2°2θ; ±0.1°2θ; or ±0.0°2θ; Cu Kα1 radiation).

In some embodiments, the compound 1 Galactarate salt is a crystalline polymorph characterized by two or more, or three or more XRPD signals selected from the group consisting of 5.2°2θ, 15.9°2θ, 17.9°2θ, 19.6°2θ, and 30.7°2θ (±0.2°2θ; ±0.1°2θ; or ±0.0°2θ; Cu Kα1 radiation). In some embodiments, the compound 1 Galactarate salt is a crystalline polymorph characterized by XRPD signals at 5.2°2θ, 15.9°2θ, 17.9°2θ, 19.6°2θ, and 30.7°2θ (±0.2°2θ; ±0.1°2θ; or ±0.0°2θ; Cu Kα1 radiation).

In some embodiments, the compound 1 Galactarate salt is a crystalline polymorph characterized by two or more, or three or more XRPD signals selected from the group consisting of 5.2°2θ, 15.9°2θ, 16.4°2θ, 17.9°2θ, 19.6°2θ, and 30.7°2θ (±0.2°2θ; ±0.1°2θ; or ±0.0°2θ; Cu Kα1 radiation). In some embodiments, the compound 1 Galactarate salt is a crystalline polymorph characterized by XRPD signals at 5.2°2θ, 15.9°2θ, 16.4°2θ, 17.9°2θ, 19.6°2θ, and 30.7°2θ (±0.2°2θ; ±0.1°2θ; or ±0.0°2θ; Cu Kα1 radiation).

In some embodiments, the compound 1 Galactarate salt is a crystalline polymorph characterized by two or more, or three or more XRPD signals selected from the group consisting of 5.2°2θ, 15.9°2θ, 16.4°2θ, 17.9°2θ, 19.6°2θ, 20.4°2θ, and 30.7°2θ (±0.2°2θ; ±0.1°2θ; or ±0.0°2θ; Cu Kα1 radiation). In some embodiments, the compound 1 Galactarate salt is a crystalline polymorph characterized by XRPD signals at 5.2°2θ, 15.9°2θ, 16.4°2θ, 17.9°2θ, 19.6°2θ, 20.4°2θ, and 30.7°2θ (±0.2°2θ; ±0.1°2θ; or ±0.0°2θ; Cu Kα1 radiation).

In some embodiments, the compound 1 Galactarate salt is a crystalline polymorph characterized by two or more, or three or more XRPD signals selected from the group consisting of 5.2°2θ, 15.9°2θ, 16.4°2θ, 17.9°2θ, 19.6°2θ, 20.4°2θ, 25.2°2θ, and 30.7°2θ (±0.2°2θ; ±0.1°2θ; or ±0.0°2θ; Cu Kα1 radiation). In some embodiments, the compound 1 Galactarate salt is a crystalline polymorph characterized by XRPD signals at 5.2°2θ, 15.9°2θ, 16.4°2θ, 17.9°2θ, 19.6°2θ, 20.4°2θ, 25.2°2θ, and 30.7°2θ (±0.2°2θ; ±0.1°2θ; or ±0.0°2θ; Cu Kα1 radiation).

In some embodiments, the compound 1 Galactarate salt is a crystalline polymorph characterized by two or more, or three or more XRPD signals selected from the group consisting of 5.2°2θ, 12.1°2θ, 15.9°2θ, 16.4°2θ, 17.9°2θ, 19.6°2θ, 20.4°2θ, 25.2°2θ, and 30.7°2θ (±0.2°2θ; ±0.1°2θ; or ±0.0°2θ; Cu Kα1 radiation). In some embodiments, the compound 1 Galactarate salt is a crystalline polymorph characterized by XRPD signals at 5.2°2θ, 12.1°2θ, 15.9°2θ, 16.4°2θ, 17.9°2θ, 19.6°2θ, 20.4°2θ, 25.2°2θ, and 30.7°2θ (±0.2°2θ; ±0.1°2θ; or ±0.0°2θ; Cu Kα1 radiation).

In some embodiments, the compound 1 Galactarate salt is a crystalline polymorph characterized by two or more, or three or more XRPD signals selected from the group consisting of 5.2°2θ, 12.1°2θ, 15.9°2θ, 16.4°2θ, 17.9°2θ, 19.6°2θ, 20.4°2θ, 25.2°2θ, 30.7°2θ, and 34.4°2θ (±0.2°2θ; ±0.1°2θ; or ±0.0°2θ; Cu Kα1 radiation). In some embodiments, the compound 1 Galactarate salt is a crystalline polymorph characterized by XRPD signals at 5.2°2θ, 12.1°2θ, 15.9°2θ, 16.4°2θ, 17.9°2θ, 19.6°2θ, 20.4°2θ, 25.2°2θ, 30.7°2θ, and 34.4°2θ (±0.2°2θ; ±0.1°2θ; or ±0.0°2θ; Cu Kα1 radiation).

In some embodiments, the compound 1 Galactarate salt is a crystalline polymorph characterized by two or more, or three or more XRPD signals selected from the group consisting of 5.2°2θ, 12.1°2θ, 15.9°2θ, 16.4°2θ, 17.9°2θ, 19.6°2θ, 20.4°2θ, 25.2°2θ, 30.7°2θ, 34.4°2θ, and 37.6°2θ (±0.2°2θ; ±0.1°2θ; or ±0.0°2θ; Cu Kα1 radiation). In some embodiments, the compound 1 Galactarate salt is a crystalline polymorph characterized by XRPD signals at 5.2°2θ, 12.1°2θ, 15.9°2θ, 16.4°2θ, 17.9°2θ, 19.6°2θ, 20.4°2θ, 25.2°2θ, 30.7°2θ, 34.4°2θ, and 37.6°2θ (±0.2°2θ; ±0.1°2θ; or ±0.0°2θ. Cu Kα1 radiation).

In some embodiments, the compound 1 Galactarate salt is a crystalline polymorph characterized by two or more, or three or more XRPD signals selected from the group consisting of 5.2°2θ, 12.1°2θ, 15.9°2θ, 16.4°2θ, 17.9°2θ, 19.6°2θ, 20.4°2θ, 22.4°2θ, 25.2°2θ, 30.7°2θ, 34.4°2θ, and 37.6°2θ (±0.2°2θ; ±0.1°2θ; or ±0.0°2θ; Cu Kα1 radiation). In some embodiments, the compound 1 Galactarate salt is a crystalline polymorph characterized by XRPD signals at 5.2°2θ, 12.1°2θ, 15.9°2θ, 16.4°2θ, 17.9°2θ, 19.6°2θ, 20.4°2θ, 22.4°2θ, 25.2°2θ, 30.7°2θ, 34.4°2θ, and 37.6°2θ (±0.2°2θ; ±0.1°2θ; or ±0.0°2θ; Cu Kα1 radiation).

In some embodiments, the compound 1 Galactarate salt is a crystalline polymorph characterized by two or more, or three or more XRPD signals selected from the group consisting of 5.2°2θ, 12.1°2θ, 15.9°2θ, 16.4°2θ, 17.9°2θ, 19.6°2θ, 20.4°2θ, 21.5°2θ, 22.4°2θ, 25.2°2θ, 30.7°2θ, 34.4°2θ, and 37.6°2θ (±0.2°2θ; ±0.1°2θ; or ±0.0°2θ; Cu Kα1 radiation). In some embodiments, the compound 1 Galactarate salt is a crystalline polymorph characterized by XRPD signals at 5.2°2θ, 12.1°2θ, 15.9°2θ, 16.4°2θ, 17.9°2θ, 19.6°2θ, 20.4°2θ, 21.5°2θ, 22.4°2θ, 25.2°2θ, 30.7°2θ, 34.4°2θ, and 37.6°2θ (±0.2°2θ; ±0.1°2θ; or ±0.0°2θ; Cu Kα1 radiation).

In some embodiments, the compound 1 Galactarate salt is a crystalline polymorph characterized by two or more, or three or more XRPD signals selected from the group consisting of 5.2°2θ, 12.1°2θ, 13.0°2θ, 15.9°2θ, 16.4°2θ, 17.9°2θ, 19.6°2θ, 20.4°2θ, 21.5°2θ, 22.4°2θ, 25.2°2θ, 30.7°2θ, 34.4°2θ, and 37.6°2θ (±0.2°2θ; ±0.1°2θ; or ±0.0°2θ; Cu Kα1 radiation). In some embodiments, the compound 1 Galactarate salt is a crystalline polymorph characterized by XRPD signals at 5.2°2θ, 12.1°2θ, 13.0°2θ, 15.9°2θ, 16.4°2θ, 17.9°2θ, 19.6°2θ, 20.4°2θ, 21.5°2θ, 22.4°2θ, 25.2°2θ, 30.7°2θ, 34.4°2θ, and 37.6°2θ (±0.2°2θ; ±0.1°2θ; or ±0.0°2θ; Cu Kα1 radiation).

In some embodiments, the compound 1 Galactarate salt is a crystalline polymorph characterized by two or more, or three or more XRPD signals selected from the group consisting of 5.2°2θ, 12.1°2θ, 13.0°2θ, 15.9°2θ, 16.4°2θ, 17.9°2θ, 19.6°2θ, 20.4°2θ, 21.5°2θ, 22.4°2θ, 24.9°2θ, 25.2°2θ, 30.7°2θ, 34.4°2θ, and 37.6°2θ (±0.2°2θ; ±0.1°2θ; or ±0.0°2θ; Cu Kα1 radiation). In some embodiments, the compound 1 Galactarate salt is a crystalline polymorph characterized by XRPD signals at 5.2°2θ, 12.1°2θ, 13.0°2θ, 15.9°2θ, 16.4°2θ, 17.9°2θ, 19.6°2θ, 20.4°2θ, 21.5°2θ, 22.4°2θ, 24.9°2θ, 25.2°2θ, 30.7°2θ, 34.4°2θ, and 37.6°2θ (±0.2°2θ; ±0.1°2θ; or ±0.0°2θ; Cu Kα1 radiation).

In some embodiments, the compound 1 Galactarate salt is a crystalline polymorph characterized by two or more, or three or more XRPD signals selected from the group consisting of 5.2°2θ, 12.1°2θ, 13.0°2θ, 15.9°2θ, 16.4°2θ, 17.9°2θ, 19.6°2θ, 20.4°2θ, 21.5°2θ, 22.4°2θ, 24.9°2θ, 25.2°2θ, 26.7°2θ, 30.7°2θ, 34.4°2θ, and 37.6°2θ (±0.2°2θ; ±0.1°2θ; or ±0.0°2θ; Cu Kα1 radiation). In some embodiments, the compound 1 Galactarate salt is a crystalline polymorph characterized by XRPD signals at 5.2°2θ, 12.1°2θ, 13.0°2θ, 15.9°2θ, 16.4°2θ, 17.9°2θ, 19.6°2θ, 20.4°2θ, 21.5°2θ, 22.4°2θ, 24.9°2θ, 25.2°2θ, 26.7°2θ, 30.7°2θ, 34.4°2θ, and 37.6°2θ (±0.2°2θ; ±0.1°2θ; or ±0.0°2θ; Cu Kα1 radiation).

In some embodiments, the compound 1 Galactarate salt is a crystalline polymorph characterized by two or more, or three or more XRPD signals selected from the group consisting of 5.2°2θ, 12.1°2θ, 13.0°2θ, 15.9°2θ, 16.4°2θ, 17.9°2θ, 19.6°2θ, 20.4°2θ, 21.5°2θ, 22.4°2θ, 24.9°2θ, 25.2°2θ, 26.7°2θ, 30.7°2θ, 34.4°2θ, 34.8°2θ, and 37.6°2θ (±0.2°2θ; ±0.1°2θ; or ±0.0°2θ; Cu Kα1 radiation). In some embodiments, the compound 1 Galactarate salt is a crystalline polymorph characterized by XRPD signals at 5.2°2θ, 12.1°2θ, 13.0°2θ, 15.9°2θ, 16.4°2θ, 17.9°2θ, 19.6°2θ, 20.4°2θ, 21.5°2θ, 22.4°2θ, 24.9°2θ, 25.2°2θ, 26.7°2θ, 30.7°2θ, 34.4°2θ, 34.8°2θ, and 37.6°2θ (±0.2°2θ; ±0.1°2θ; or ±0.0°2θ; Cu Kα1 radiation).

In some embodiments, crystalline polymorph is characterized by one, two, three, four, five, six, seven, eight, nine, ten, eleven, twelve, thirteen, fourteen, fifteen, sixteen, or seventeen XRPD signals selected from those set forth in Table 49.

TABLE 49

Crystalline compound 1 galactarate salt XRPD Signals (±0.2 °2θ; ±0.1 °2θ; or ±0.0 °2θ; Cu Kα1 radiation)

| Signal number | 2-θ (°) | d Value | Net Intensity (counts) | Gross Intensity (counts) | Rel. Intensity (%) |
|---|---|---|---|---|---|
| Signal #1 | 5.2 | 16.87 | 1950.2 | 2243.8 | 71.8 |
| Signal #2 | 12.1 | 7.29 | 502.7 | 599.3 | 18.5 |
| Signal #3 | 13.0 | 6.83 | 329.3 | 430.9 | 12.1 |
| Signal #4 | 15.9 | 5.58 | 1262.9 | 1383.7 | 46.5 |
| Signal #5 | 16.4 | 5.41 | 720.1 | 848.3 | 26.5 |
| Signal #6 | 17.9 | 4.94 | 898.0 | 1036.9 | 33.1 |
| Signal #7 | 19.6 | 4.52 | 2715.8 | 2871.7 | 100.0 |
| Signal #8 | 20.4 | 4.36 | 646.7 | 806.9 | 23.8 |
| Signal #9 | 21.5 | 4.14 | 334.3 | 489.7 | 12.3 |
| Signal #10 | 22.4 | 3.97 | 414.3 | 554.8 | 15.3 |
| Signal #11 | 24.9 | 3.57 | 328.2 | 465.1 | 12.1 |
| Signal #12 | 25.2 | 3.54 | 619.9 | 757.6 | 22.8 |
| Signal #13 | 26.7 | 3.33 | 280.4 | 407.8 | 10.3 |

TABLE 49-continued

Crystalline compound 1 galactarate salt XRPD Signals (±0.2 °2θ; ±0.1 °2θ; or ±0.0 °2θ; Cu Kα1 radiation)

| Signal number | 2-θ (°) | d Value | Net Intensity (counts) | Gross Intensity (counts) | Rel. Intensity (%) |
|---|---|---|---|---|---|
| Signal #14 | 30.7 | 2.91 | 1036.2 | 1154.4 | 38.2 |
| Signal #15 | 34.4 | 2.60 | 478.6 | 607.2 | 17.6 |
| Signal #16 | 34.8 | 2.58 | 278.6 | 404.8 | 10.3 |
| Signal #17 | 37.6 | 2.39 | 434.3 | 564.2 | 16.0 |

Compound 1 Succinate Salt

In some embodiments, the compound 1 salt is a compound 1 Succinate salt. In some embodiments, the compound 1 Succinate salt is amorphous. In some embodiments, the compound 1 Succinate salt is crystalline. In some embodiments, the compound 1 Succinate salt is a 1:1 compound 1:Succinate salt. In some embodiments, the compound 1 Succinate salt is a 2:1 compound 1:Succinate salt.

In some embodiments, the compound 1 Succinate salt is a crystalline polymorph. In some embodiments, the crystalline polymorph is characterized by the XRPD signals set for the below in Table 50. In some embodiments, the crystalline polymorph XRPD pattern is substantially similar to that shown in FIG. 174. In some embodiments, the crystalline polymorph DSC spectrum is substantially similar to that shown in FIG. 248.

In some embodiments, the crystalline compound 1 succinate is a crystalline polymorphic form characterized by DSC having a melting signal at about 89.8° C.

In some embodiments, the compound 1 Succinate salt is a crystalline polymorph characterized by an XRPD signal at 18.2°2θ (±0.2°2θ; ±0.1°2θ; or ±0.0°2θ; Cu Kα1 radiation).

In some embodiments, the compound 1 Succinate salt is a crystalline polymorph characterized by XRPD signals at 18.2°2θ and 19.3°2θ (±0.2°2θ; ±0.1°2θ; or ±0.0°2θ; Cu Kα1 radiation).

In some embodiments, the compound 1 Succinate salt is a crystalline polymorph characterized by two or more, or three or more XRPD signals selected from the group consisting of 18.2°2θ, 19.3°2θ, and 22.0°2θ (±0.2°2θ; ±0.1°2θ; or ±0.0°2θ; Cu Kα1 radiation). In some embodiments, the compound 1 Succinate salt is a crystalline polymorph characterized by XRPD 15 signals at 18.2°2θ, 19.3°2θ, and 22.0°2θ (±0.2°2θ; ±0.1°2θ; or ±0.0°2θ; Cu Kα1 radiation).

In some embodiments, the compound 1 Succinate salt is a crystalline polymorph characterized by two or more, or three or more XRPD signals selected from the group consisting of 18.2°2θ, 19.3°2θ, 20.0°2θ, and 22.0°2θ (±0.2°2θ; ±0.1°2θ; or ±0.0°2θ; Cu Kα1 radiation).

In some embodiments, the compound 1 Succinate salt is a crystalline polymorph characterized by XRPD signals at 18.2°2θ, 19.3°2θ, 20.0°2θ, and 22.0°2θ (±0.2°2θ; ±0.1°2θ; or ±0.0°2θ; Cu Kα1 radiation).

In some embodiments, the compound 1 Succinate salt is a crystalline polymorph characterized by two or more, or three or more XRPD signals selected from the group consisting of 18.2°2θ, 19.3°2θ, 20.0°2θ, 22.0°2θ, and 26.1°2θ (±0.2°2θ; ±0.1°2θ; or ±0.0°2θ; Cu Kα1 radiation). In some embodiments, the compound 1 Succinate salt is a crystalline polymorph characterized by XRPD signals at 18.2°2θ, 19.3°2θ, 20.0°2θ, 22.0°2θ, and 26.1°2θ (±0.2°2θ; ±0.1°2θ; or ±0.0°2θ; Cu Kα1 radiation).

In some embodiments, the compound 1 Succinate salt is a crystalline polymorph characterized by two or more, or three or more XRPD signals selected from the group consisting of 17.7°2θ, 18.2°2θ, 19.3°2θ, 20.0°2θ, 22.0°2θ, and 26.1°2θ (±0.2°2θ; ±0.1°2θ; or ±0.0°2θ; Cu Kα1 radiation). In some embodiments, the compound 1 Succinate salt is a crystalline polymorph characterized by XRPD signals at 17.7°2θ, 18.2°2θ, 19.3°2θ, 20.0°2θ, 22.0°2θ, and 26.1°2θ (±0.2°2θ; ±0.1°2θ; or ±0.0°2θ; Cu Kα1 radiation).

In some embodiments, the compound 1 Succinate salt is a crystalline polymorph characterized by two or more, or three or more XRPD signals selected from the group consisting of 12.7°2θ, 17.7°2θ, 18.2°2θ, 19.3°2θ, 20.0°2θ, 22.0°2θ, and 26.1°2θ (±0.2°2θ; ±0.1°2θ; or ±0.0°2θ; Cu Kα1 radiation). In some embodiments, the compound 1 Succinate salt is a crystalline polymorph characterized by XRPD signals at 12.7°2θ, 17.7°2θ, 18.2°2θ, 19.3°2θ, 20.0°2θ, 22.0°2θ, and 26.1°2θ (±0.2°2θ; ±0.1°2θ; or ±0.0°2θ; Cu Kα1 radiation).

In some embodiments, the compound 1 Succinate salt is a crystalline polymorph characterized by two or more, or three or more XRPD signals selected from the group consisting of 12.7°2θ, 17.7°2θ, 18.2°2θ, 19.3°2θ, 20.0°2θ, 22.0°2θ, 24.1°2θ, and 26.1°2θ (±0.2°2θ; ±0.1°2θ; or ±0.0°2θ; Cu Kα1 radiation). In some embodiments, the compound 1 Succinate salt is a crystalline polymorph characterized by XRPD signals at 12.7°2θ, 17.7°2θ, 18.2°2θ, 19.3°2θ, 20.0°2θ, 22.0°2θ, 24.1°2θ, and 26.1°2θ (±0.2°2θ; ±0.1°2θ; or ±0.0°2θ; Cu Kα1 radiation).

In some embodiments, the compound 1 Succinate salt is a crystalline polymorph characterized by two or more, or three or more XRPD signals selected from the group consisting of 12.7°2θ, 17.7°2θ, 18.2°2θ, 19.3°2θ, 20.0°2θ, 22.0°2θ, 24.1°2θ, 26.1°2θ, and 28.2°2θ (±0.2°2θ; ±0.1°2θ; or ±0.0°2θ; Cu Kα1 radiation). In some embodiments, the compound 1 Succinate salt is a crystalline polymorph characterized by XRPD signals at 12.7°2θ, 17.7°2θ, 18.2°2θ, 19.3°2θ, 20.0°2θ, 22.0°2θ, 24.1°2θ, 26.1°2θ, and 28.2°2θ (±0.2°2θ; ±0.1°2θ; or ±0.0°2θ; Cu Kα1 radiation).

In some embodiments, the compound 1 Succinate salt is a crystalline polymorph characterized by two or more, or three or more XRPD signals selected from the group consisting of 12.7°2θ, 17.7°2θ, 18.2°2θ, 19.3°2θ, 20.0°2θ, 22.0°2θ, 24.1°2θ, 26.1°2θ, 28.2°2θ, and 31.4°2θ (±0.2°2θ; ±0.1°2θ; or ±0.0°2θ; Cu Kα1 radiation). In some embodiments, the compound 1 Succinate salt is a crystalline polymorph characterized by XRPD signals at 12.7°2θ, 17.7°2θ, 18.2°2θ, 19.3°2θ, 20.0°2θ, 22.0°2θ, 24.1°2θ, 26.1°2θ, 28.2°2θ, and 31.4°2θ (±0.2°2θ; ±0.1°2θ; or ±0.0°2θ; Cu Kα1 radiation).

In some embodiments, the compound 1 Succinate salt is a crystalline polymorph characterized by two or more, or three or more XRPD signals selected from the group consisting of 12.7°2θ, 17.7°2θ, 18.2°2θ, 19.3°2θ, 20.0°2θ, 22.0°2θ, 24.1°2θ, 26.1°2θ, 27.5°2θ, 28.2°2θ, and 31.4°2θ (±0.2°2θ; ±0.1°2θ; or ±0.0°2θ; Cu Kα1 radiation). In some embodiments, the compound 1 Succinate salt is a crystalline polymorph characterized by XRPD signals at 12.7°2θ, 17.7°2θ, 18.2°2θ, 19.3°2θ, 20.0°2θ, 22.0°2θ, 24.1°2θ, 26.1°2θ, 27.5°2θ, 28.2°2θ, and 31.4°2θ (±0.2°2θ; ±0.1°2θ; or ±0.0°2θ; Cu Kα1 radiation).

In some embodiments, the compound 1 Succinate salt is a crystalline polymorph characterized by two or more, or three or more XRPD signals selected from the group consisting of 12.7°2θ, 17.7°2θ, 18.2°2θ, 19.3°2θ, 20.0°2θ, 22.0°2θ, 24.1°2θ, 24.7°2θ, 26.1°2θ, 27.5°2θ, 28.2°2θ, and 31.4°2θ (±0.2°2θ; ±0.1°2θ; or ±0.0°2θ; Cu Kα1 radiation).

In some embodiments, the compound 1 Succinate salt is a crystalline polymorph characterized by two or more, or three or more XRPD signals selected from the group consisting of 12.7°2θ, 13.9°2θ, 17.7°2θ, 18.2°2θ, 19.3°2θ, 20.0°2θ, 22.0°2θ, 24.1°2θ, 24.7°2θ, 26.1°2θ, 27.5°2θ, 28.2°2θ, and 31.4°2θ (±0.2°2θ; ±0.1°2θ; or ±0.0°2θ; Cu Kα1 radiation). In some embodiments, the compound 1 Succinate salt is a crystalline polymorph characterized by XRPD signals at 12.7°2θ, 13.9°2θ, 17.7°2θ, 18.2°2θ, 19.3°2θ, 20.0°2θ, 22.0°2θ, 24.1°2θ, 24.7°2θ, 26.1°2θ, 27.5°2θ, 28.2°2θ, and 31.4°2θ (±0.2°2θ; ±0.1°2θ; or ±0.0°2θ; Cu Kα1 radiation).

In some embodiments, the compound 1 Succinate salt is a crystalline polymorph characterized by two or more, or three or more XRPD signals selected from the group consisting of 12.7°2θ, 13.9°2θ, 17.7°2θ, 18.2°2θ, 19.3°2θ, 20.0°2θ, 22.0°2θ, 24.1°2θ, 24.7°2θ, 25.5°2θ, 26.1°2θ, 27.5°2θ, 28.2°2θ, and 31.4°2θ (±0.2°2θ; ±0.1°2θ; or ±0.0°2θ; Cu Kα1 radiation). In some embodiments, the compound 1 Succinate salt is a crystalline polymorph characterized by XRPD signals at 12.7°2θ, 13.9°2θ, 17.7°2θ, 18.2°2θ, 19.3°2θ, 20.0°2θ, 22.0°2θ, 24.1°2θ, 24.7°2θ, 25.5°2θ, 26.1°2θ, 27.5°2θ, 28.2°2θ, and 31.4°2θ (±0.2°2θ; ±0.1°2θ; or ±0.0°2θ; Cu Kα1 radiation).

In some embodiments, the compound 1 Succinate salt is a crystalline polymorph characterized by two or more, or three or more XRPD signals selected from the group consisting of 12.7°2θ, 13.9°2θ, 17.7°2θ, 18.2°2θ, 19.3°2θ, 20.0°2θ, 22.0°2θ, 23.7°2θ, 24.1°2θ, 24.7°2θ, 25.5°2θ, 26.1°2θ, 27.5°2θ, 28.2°2θ, and 31.4°2θ (±0.2°2θ; ±0.1°2θ; or ±0.0°2θ; Cu Kα1 radiation). In some embodiments, the compound 1 Succinate salt is a crystalline polymorph characterized by XRPD signals at 12.7°2θ, 13.9°2θ, 17.7°2θ, 18.2°2θ, 19.3°2θ, 20.0°2θ, 22.0°2θ, 23.7°2θ, 24.1°2θ, 24.7°2θ, 25.5°2θ, 26.1°2θ, 27.5°2θ, 28.2°2θ, and 31.4°2θ (±0.2°2θ; ±0.1°2θ; or ±0.0°2θ; Cu Kα1 radiation).

In some embodiments, the compound 1 Succinate salt is a crystalline polymorph characterized by two or more, or three or more XRPD signals selected from the group consisting of 12.7°2θ, 13.9°2θ, 17.7°2θ, 18.2°2θ, 19.3°2θ, 20.0°2θ, 21.3°2θ, 22.0°2θ, 23.7°2θ, 24.1°2θ, 24.7°2θ, 25.5°2θ, 26.1°2θ, 27.5°2θ, 28.2°2θ, and 31.4°2θ (±0.2°2θ; ±0.1°2θ; or ±0.0°2θ; Cu Kα1 radiation). In some embodiments, the compound 1 Succinate salt is a crystalline polymorph characterized by XRPD signals at 12.7°2θ, 13.9°2θ, 17.7°2θ, 18.2°2θ, 19.3°2θ, 20.0°2θ, 21.3°2θ, 22.0°2θ, 23.7°2θ, 24.1°2θ, 24.7°2θ, 25.5°2θ, 26.1°2θ, 27.5°2θ, 28.2°2θ, and 31.4°2θ (±0.2°2θ; ±0.1°2θ; or ±0.0°2θ; Cu Kα1 radiation).

In some embodiments, the compound 1 Succinate salt is a crystalline polymorph characterized by two or more, or three or more XRPD signals selected from the group consisting of 12.7°2θ, 13.9°2θ, 17.3°2θ, 17.7°2θ, 18.2°2θ, 19.3°2θ, 20.0°2θ, 21.3°2θ, 22.0°2θ, 23.7°2θ, 24.1°2θ, 24.7°2θ, 25.5°2θ, 26.1°2θ, 27.5°2θ, 28.2°2θ, and 31.4°2θ (±0.2°2θ; ±0.1°2θ; or ±0.0°2θ; Cu Kα1 radiation). In some embodiments, the compound 1 Succinate salt is a crystalline polymorph characterized by XRPD signals at 12.7°2θ, 13.9°2θ, 17.3°2θ, 17.7°2θ, 18.2°2θ, 19.3°2θ, 20.0°2θ, 21.3°2θ, 22.0°2θ, 23.7°2θ, 24.1°2θ, 24.7°2θ, 25.5°2θ, 26.1°2θ, 27.5°2θ, 28.2°2θ, and 31.4°2θ (±0.2°2θ; ±0.1°2θ; or ±0.0°2θ; Cu Kα1 radiation).

In some embodiments, the compound 1 Succinate salt is a crystalline polymorph characterized by two or more, or three or more XRPD signals selected from the group consisting of 12.7°2θ, 13.9°2θ, 17.3°2θ, 17.7°2θ, 18.2°2θ, 19.3°2θ, 20.0°2θ, 21.2°2θ, 21.3°2θ, 22.0°2θ, 23.7°2θ, 24.1°2θ, 24.7°2θ, 25.5°2θ, 26.1°2θ, 27.5°2θ, 28.2°2θ, and 31.4°2θ (±0.2°2θ; ±0.1°2θ; or ±0.0°2θ; Cu Kα1 radiation). In some embodiments, the compound 1 Succinate salt is a crystalline polymorph characterized by XRPD signals at 12.7°2θ, 13.9°2θ, 17.3°2θ, 17.7°2θ, 18.2°2θ, 19.3°2θ, 20.0°2θ, 21.2°2θ, 21.3°2θ, 22.0°2θ, 23.7°2θ, 24.1°2θ, 24.7°2θ, 25.5°2θ, 26.1°2θ, 27.5°2θ, 28.2°2θ, and 31.4°2θ (±0.2°2θ; ±0.1°2θ; or ±0.0°2θ; Cu Kα1 radiation).

In some embodiments, the crystalline polymorph is characterized by one, two, three, four, five, six, seven, eight, nine, ten, eleven, twelve, thirteen, fourteen, fifteen, sixteen, seventeen, or eighteen XRPD signals selected from those set forth in Table 50.

TABLE 50

Crystalline Compound 1 succinate salt XRPD Signals (±0.2 °2θ; ±0.1 °2θ; or ±0.0 °2θ; Cu Kα1 radiation)

| Signal number | 2-θ (°) | d Value | Net Intensity (counts) | Gross Intensity (counts) | Rel. Intensity (%) |
|---|---|---|---|---|---|
| Signal #1 | 12.7 | 6.99 | 831.7 | 923.5 | 25.5 |
| Signal #2 | 13.9 | 6.39 | 453.7 | 556.2 | 13.9 |
| Signal #3 | 17.3 | 5.11 | 373.2 | 516.0 | 11.4 |
| Signal #4 | 17.7 | 5.01 | 900.9 | 1056.3 | 27.6 |
| Signal #5 | 18.2 | 4.86 | 3265.5 | 3436.0 | 100.0 |
| Signal #6 | 19.3 | 4.60 | 2015.8 | 2206.0 | 61.7 |
| Signal #7 | 20.0 | 4.43 | 1259.7 | 1456.3 | 38.6 |
| Signal #8 | 21.2 | 4.18 | 330.1 | 522.5 | 10.1 |
| Signal #9 | 21.3 | 4.17 | 385.4 | 577.3 | 11.8 |
| Signal #10 | 22.0 | 4.04 | 1262.6 | 1444.0 | 38.7 |
| Signal #11 | 23.7 | 3.75 | 395.2 | 588.9 | 12.1 |
| Signal #12 | 24.1 | 3.68 | 795.7 | 997.0 | 24.4 |
| Signal #13 | 24.7 | 3.60 | 456.4 | 663.3 | 14.0 |
| Signal #14 | 25.5 | 3.50 | 424.8 | 635.7 | 13.0 |
| Signal #15 | 26.1 | 3.41 | 1066.7 | 1277.3 | 32.7 |
| Signal #16 | 27.5 | 3.24 | 500.9 | 692.9 | 15.3 |
| Signal #17 | 28.2 | 3.16 | 771.5 | 945.2 | 23.6 |
| Signal #18 | 31.4 | 2.85 | 646.3 | 803.5 | 19.8 |

Compound 1 Citrate Salt

In some embodiments, the compound 1 salt is a compound 1 Citrate salt. In some embodiments, the compound 1 Citrate salt is amorphous. In some embodiments, the compound 1 Citrate salt is crystalline. In some embodiments, the compound 1 Citrate salt is a 1:1 compound 1 Citrate salt. In some embodiments, the compound 1 Citrate salt is a 2:1 compound 1:Citrate salt.

In some embodiments, the compound 1 Citrate salt is a crystalline polymorph. In some embodiments, the crystalline polymorph is characterized by the XRPD signals set for the below in Table 51. In some embodiments, the crystalline polymorph XRPD pattern is substantially similar to that shown in FIG. 257. In some embodiments, the crystalline polymorph DSC spectrum is substantially similar to that shown in FIG. 258.

In some embodiments, the crystalline compound 1 citrate is a crystalline polymorphic form characterized by DSC having a melting signal at about 182.8° C.

In some embodiments, the compound 1 Citrate salt is a crystalline polymorph characterized by an XRPD signal at 23.9°2θ (±0.2°2θ; ±0.1°2θ; or ±0.0°2θ; Cu Kα1 radiation).

In some embodiments, the compound 1 Citrate salt is a crystalline polymorph characterized by XRPD signals at 18.2°2θ, and 23.9°2θ (±0.2°2θ; ±0.1°2θ; or ±0.0°2θ; Cu Kα1 radiation).

In some embodiments, the compound 1 Citrate salt is a crystalline polymorph characterized by two or more, or three or more XRPD signals selected from the group consisting of 18.2°2θ, 23.9°2θ, and 26.2°2θ (±0.2°2θ; ±0.1°2θ; or ±0.0°2θ; Cu Kα1 radiation). In some embodiments, the compound 1 Citrate salt is a crystalline polymorph characterized by XRPD signals at 18.2°2θ, 23.9°2θ, and 26.2°2θ (±0.2°2θ; ±0.1°2θ; or ±0.0°2θ; Cu Kα1 radiation).

In some embodiments, the compound 1 Citrate salt is a crystalline polymorph characterized by two or more, or three or more XRPD signals selected from the group consisting of 18.0°2θ, 18.2°2θ, 23.9°2θ, and 26.2°2θ (±0.2°2θ; ±0.1°2θ; or ±0.0°2θ; Cu Kα1 radiation). In some embodiments, the compound 1 Citrate salt is a crystalline polymorph characterized by XRPD signals at 18.0°2θ, 18.2°2θ, 23.9°2θ, and 26.2°2θ (±0.2°2θ; ±0.1°2θ; or ±0.0°2θ; Cu Kα1 radiation).

In some embodiments, the compound 1 Citrate salt is a crystalline polymorph characterized by two or more, or three or more XRPD signals selected from the group consisting of 18.0°2θ, 18.2°2θ, 19.6°2θ, 23.9°2θ, and 26.2°2θ (±0.2°2θ; ±0.1°2θ; or ±0.0°2θ; Cu Kα1 radiation). In some embodiments, the compound 1 Citrate salt is a crystalline polymorph characterized by XRPD signals at 18.0°2θ, 18.2°2θ, 19.6°2θ, 23.9°2θ, and 26.2°2θ (±0.2°2θ; ±0.1°2θ; or ±0.0°2θ; Cu Kα1 radiation).

In some embodiments, the compound 1 Citrate salt is a crystalline polymorph characterized by two or more, or three or more XRPD signals selected from the group consisting of 18.0°2θ, 18.2°2θ, 19.6°2θ, 23.9°2θ, 26.1°2θ, and 26.2°2θ (±0.2°2θ; ±0.1°2θ; or ±0.0°2θ; Cu Kα1 radiation). In some embodiments, the compound 1 Citrate salt is a crystalline polymorph characterized by XRPD signals at 18.0°2θ, 18.2°2θ, 19.6°2θ, 23.9°2θ, 26.1°2θ, and 26.2°2θ (±0.2°2θ; ±0.1°2θ; or ±0.0°2θ; Cu Kα1 radiation).

In some embodiments, the compound 1 Citrate salt is a crystalline polymorph characterized by two or more, or three or more XRPD signals selected from the group consisting of 18.0°2θ, 18.2°2θ, 19.6°2θ, 23.9°2θ, 26.1°2θ, 26.2°2θ, and 28.9°2θ (±0.2°2θ; ±0.1°2θ; or ±0.0°2θ; Cu Kα1 radiation). In some embodiments, the compound 1 Citrate salt is a crystalline polymorph characterized by XRPD signals at 18.0°2θ, 18.2°2θ, 19.6°2θ, 23.9°2θ, 26.1°2θ, 26.2°2θ, and 28.9°2θ (±0.2°2θ; ±0.1°2θ, or ±0.0°2θ; Cu Kα1 radiation).

In some embodiments, the compound 1 Citrate salt is a crystalline polymorph characterized by two or more, or three or more XRPD signals selected from the group consisting of 18.0°2θ, 18.2°2θ, 19.6°2θ, 23.9°2θ, 26.1°2θ, 26.2°2θ, 28.9°2θ, and 31.4°2θ (±0.2°2θ; ±0.1°2θ; or ±0.0°2θ; Cu Kα1 radiation). In some embodiments, the compound 1 Citrate salt is a crystalline polymorph characterized by XRPD signals at 18.0°2θ, 18.2°2θ, 19.6°2θ, 23.9°2θ, 26.1°2θ, 26.2°2θ, 28.9°2θ, and 31.4°2θ (±0.2°2θ; ±0.1°2θ; or ±0.0°2θ; Cu Kα1 radiation).

In some embodiments, the compound 1 Citrate salt is a crystalline polymorph characterized by two or more, or three or more XRPD signals selected from the group consisting of 18.0°2θ, 18.2°2θ, 19.6°2θ, 23.9°2θ, 26.1°2θ, 26.2°2θ, 28.9°2θ, 31.4°2θ, and 36.2°2θ (±0.2°2θ; ±0.1°2θ; or ±0.0°2θ; Cu Kα1 radiation). In some embodiments, the compound 1 Citrate salt is a crystalline polymorph characterized by XRPD signals at 18.0°2θ, 18.2°2θ, 19.6°2θ, 23.9°2θ, 26.1°2θ, 26.2°2θ, 28.9°2θ, 31.4°2θ, and 36.2°2θ (±0.2°2θ; ±0.1°2θ; or ±0.0°2θ; Cu Kα1 radiation).

In some embodiments, the compound 1 Citrate salt is a crystalline polymorph characterized by two or more, or three or more XRPD signals selected from the group consisting of 18.0°2θ, 18.2°2θ, 19.6°2θ, 23.9°2θ, 26.1°2θ, 26.2°2θ, 28.9°2θ, 31.4°2θ, 36.2°2θ, and 37.0°2θ (±0.2°2θ; ±0.1°2θ; or ±0.0°2θ; Cu Kα1 radiation). In some embodiments, the compound 1 Citrate salt is a crystalline polymorph characterized by XRPD signals at 18.0°2θ, 18.2°2θ, 19.6°2θ, 23.9°2θ, 26.1°2θ, 26.2°2θ, 28.9°2θ, 31.4°2θ, 36.2°2θ, and 37.0°2θ (±0.2°2θ; ±0.1°2θ; or 0.0°2θ; Cu Kα1 radiation).

In some embodiments, the compound 1 Citrate salt is a crystalline polymorph characterized by two or more, or three or more XRPD signals selected from the group consisting of 14.2°2θ, 18.0°2θ, 18.2°2θ, 19.6°2θ, 23.9°2θ, 26.1°2θ, 26.2°2θ, 28.9°2θ, 31.4°2θ, 36.2°2θ, and 37.0°2θ (±0.2°2θ; ±0.1°2θ; or ±0.0°2θ; Cu Kα1 radiation). In some embodiments, the compound 1 Citrate salt is a crystalline polymorph characterized by XRPD signals at 14.2°2θ, 18.0°2θ, 18.2°2θ, 19.6°2θ, 23.9°2θ, 26.1°2θ, 26.2°2θ, 28.9°2θ, 31.4°2θ, 36.2°2θ, and 37.0°2θ (±0.2°2θ; ±0.1°2θ; or ±0.0°2θ; Cu Kα1 radiation).

In some embodiments, the compound 1 Citrate salt is a crystalline polymorph characterized by two or more, or three or more XRPD signals selected from the group consisting of 14.2°2θ, 18.0°2θ, 18.2°2θ, 19.6°2θ, 23.9°2θ, 26.1°2θ, 26.2°2θ, 28.9°2θ, 31.4°2θ, 33.7°2θ, 36.2°2θ, and 37.0°2θ (±0.2°2θ; ±0.1°2θ; or ±0.0°2θ; Cu Kα1 radiation). In some embodiments, the compound 1 Citrate salt is a crystalline polymorph characterized by XRPD signals at 14.2°2θ, 18.0°2θ, 18.2°2θ, 19.6°2θ, 23.9°2θ, 26.1°2θ, 26.2°2θ, 28.9°2θ, 31.4°2θ, 33.7°2θ, 36.2°2θ, and 37.0°2θ (±0.2°2θ; ±0.1°2θ; or ±0.0°2θ; Cu Kα1 radiation).

In some embodiments, the compound 1 Citrate salt is a crystalline polymorph characterized by two or more, or three or more XRPD signals selected from the group consisting of 14.2°2θ, 18.0°2θ, 18.2°2θ, 19.6°2θ, 23.9°2θ, 26.1°2θ, 26.2°2θ, 28.9°2θ, 31.1°2θ, 31.4°2θ, 33.7°2θ, 36.2°2θ, and 37.0°2θ (±0.2°2θ; ±0.1°2θ; or ±0.0°2θ; Cu Kα1 radiation). In some embodiments, the compound 1 Citrate salt is a crystalline polymorph characterized by XRPD signals at 14.2°2θ, 18.0°2θ, 18.2°2θ, 19.6°2θ, 23.9°2θ, 26.1°2θ, 26.2°2θ, 28.9°2θ, 31.1°2θ, 31.4°2θ, 33.7°2θ, 36.2°2θ, and 37.0°2θ (±0.2°2θ; ±0.1°2θ; or ±0.0°2θ; Cu Kα1 radiation).

In some embodiments, the compound 1 Citrate salt is a crystalline polymorph characterized by two or more, or three or more XRPD signals selected from the group consisting of 14.2°2θ, 18.0°2θ, 18.2°2θ, 19.6°2θ, 23.9°2θ, 26.1°2θ, 26.2°2θ, 28.9°2θ, 31.1°2θ, 31.4°2θ, 33.7°2θ, 36.2°2θ, 37.0°2θ, and 37.6°2θ (±0.2°2θ; ±0.1°2θ; or ±0.0°2θ; Cu Kα1 radiation). In some embodiments, the compound 1 Citrate salt is a crystalline polymorph characterized by XRPD signals at 14.2°2θ, 18.0°2θ, 18.2°2θ, 19.6°2θ, 23.9°2θ, 26.1°2θ, 26.2°2θ, 28.9°2θ, 31.1°2θ, 31.4°2θ, 33.7°2θ, 36.2°2θ, 37.0°2θ, and 37.6°2θ (±0.2°2θ; ±0.1°2θ; or ±0.0°2θ; Cu Kα1 radiation).

In some embodiments, the compound 1 Citrate salt is a crystalline polymorph characterized by two or more, or three or more XRPD signals selected from the group consisting of 14.2°2θ, 14.4°2θ, 18.0°2θ, 18.2°2θ, 19.6°2θ, 23.9°2θ, 26.1°2θ, 26.2°2θ, 28.9°2θ, 31.1°2θ, 31.4°2θ, 33.7°2θ, 36.2°2θ, 37.0°2θ, and 37.6°2θ (±0.2°2θ; ±0.1°2θ; or ±0.0°2θ; Cu Kα1 radiation). In some embodiments, the compound 1 Citrate salt is a crystalline polymorph characterized by XRPD signals at 14.2°2θ, 14.4°2θ, 18.0°2θ, 18.2°2θ, 19.6°2θ, 23.9°2θ, 26.1°2θ, 26.2°2θ, 28.9°2θ, 31.1°2θ, 31.4°2θ, 33.7°2θ, 36.2°2θ, 37.0°2θ, and 37.6°2θ (±0.2°2θ; ±0.1°2θ; or ±0.0°2θ; Cu Kα1 radiation).

In some embodiments, the compound 1 Citrate salt is a crystalline polymorph characterized by two or more, or three or more XRPD signals selected from the group consisting of 14.2°2θ, 14.4°2θ, 18.0°2θ, 18.2°2θ, 19.6°2θ, 23.9°2θ, 26.1°2θ, 26.2°2θ, 27.6°2θ, 28.9°2θ, 31.1°2θ, 31.4°2θ, 33.7°2θ, 36.2°2θ, 37.0°2θ, and 37.6°2θ (±0.2°2θ; ±0.1°2θ; or ±0.0°2θ; Cu Kα1 radiation). In some embodiments, the compound 1 Citrate salt is a crystalline polymorph characterized by XRPD signals at 14.2°2θ, 14.4°2θ, 18.0°2θ, 18.2°2θ, 19.6°2θ, 23.9°2θ, 26.1°2θ, 26.2°2θ, 27.6°2θ, 28.9°2θ, 31.1°2θ, 31.4°2θ, 33.7°2θ, 36.2°2θ, 37.0°2θ, and 37.6°2θ (±0.2°2θ; ±0.1°2θ; or ±0.0°2θ; Cu Kα1 radiation).

In some embodiments, crystalline polymorph is characterized by one, two, three, four, five, six, seven, eight, nine, ten, eleven, twelve, thirteen, fourteen, fifteen, or sixteen XRPD signals selected from those set forth in Table 51.

TABLE 51

Crystalline compound 1 citrate salt XRPD Signals (±0.2 °2θ; ±0.1 °2θ; or ±0.0 °2θ; Cu Kα1 radiation)

| Signal number | 2-θ (°) | d Value | Net Intensity (counts) | Gross Intensity (counts) | Rel. Intensity (%) |
|---|---|---|---|---|---|
| Signal #1 | 14.2 | 6.23 | 219.3 | 419.7 | 27.4 |
| Signal #2 | 14.4 | 6.13 | 114.1 | 320.5 | 14.2 |
| Signal #3 | 18.0 | 4.93 | 532.8 | 804.9 | 66.5 |
| Signal #4 | 18.2 | 4.86 | 741.7 | 1015.9 | 92.6 |
| Signal #5 | 19.6 | 4.54 | 446.3 | 723.9 | 55.7 |
| Signal #6 | 23.9 | 3.72 | 801.3 | 1023.6 | 100.0 |
| Signal #7 | 26.1 | 3.41 | 281.9 | 491.4 | 35.2 |
| Signal #8 | 26.2 | 3.40 | 594.1 | 803.6 | 74.1 |
| Signal #9 | 27.6 | 3.23 | 45.3 | 254.3 | 5.6 |
| Signal #10 | 28.9 | 3.08 | 278.2 | 485.1 | 34.7 |
| Signal #11 | 31.1 | 2.87 | 125.3 | 318.2 | 15.6 |
| Signal #12 | 31.4 | 2.85 | 261.8 | 453.8 | 32.7 |
| Signal #13 | 33.7 | 2.66 | 152.3 | 344.1 | 19.0 |
| Signal #14 | 36.2 | 2.48 | 254.1 | 446.7 | 31.7 |
| Signal #15 | 37.0 | 2.43 | 222.4 | 410.4 | 27.8 |
| Signal #16 | 37.6 | 2.39 | 118.7 | 300.0 | 14.8 |

Compound 1 Malate Salt

In some embodiments, the compound 1 salt is a compound 1 Malate salt. In some embodiments, the compound 1 Malate salt is amorphous. In some embodiments, the compound 1 Malate salt is crystalline. In some embodiments, the compound 1 Malate salt is a 1:1 compound 1:Malate salt. In some embodiments, the compound 1 Malate salt is a 2:1 compound 1:Malate salt.

In some embodiments, the compound 1 Malate salt is a crystalline polymorph. In some embodiments, the crystalline polymorph is characterized by the XRPD signals set for the below in Table 52. In some embodiments, the crystalline polymorph XRPD pattern is substantially similar to that shown in FIG. 261. In some embodiments, the crystalline polymorph DSC spectrum is substantially similar to that shown in any one of FIG. 262.

In some embodiments, the crystalline compound 1 malate is a crystalline polymorphic form characterized by DSC having a melting signal at about 193.5° C.

In some embodiments, the compound 1 Malate salt is a crystalline polymorph characterized by an XRPD signal at 19.3°2θ (±0.2°2θ; ±0.1°2θ; or ±0.0°2θ; Cu Kα1 radiation).

In some embodiments, the compound 1 Malate salt is a crystalline polymorph characterized by XRPD signals at 19.3°2θ and 24.4°2θ (±0.2°2θ; ±0.1°2θ; or ±0.0°2θ; Cu Kα1 radiation).

In some embodiments, the compound 1 Malate salt is a crystalline polymorph characterized by two or more, or three or more XRPD signals selected from the group consisting of 19.3°2θ, 24.4°2θ, and 29.4°2θ (±0.2°2θ; ±0.1°2θ; or ±0.0°2θ; Cu Kα1 radiation). In some embodiments, the compound 1 Malate salt is a crystalline polymorph characterized by XRPD signals at 19.3°2θ, 24.4°2θ, and 29.4°2θ (±0.2 2θ; 0.1°2θ; or ±0.0°2θ; Cu Kα1 radiation).

In some embodiments, the compound 1 Malate salt is a crystalline polymorph characterized by two or more, or three or more XRPD signals selected from the group consisting of 19.3°2θ, 21.0°2θ, 24.4°2θ, and 29.4°2θ (±0.2°2θ; ±0.1°2θ; or ±0.0°2θ; Cu Kα1 radiation). In some embodiments, the compound 1 Malate salt is a crystalline polymorph characterized by XRPD signals at 19.3°2θ, 21.0°2θ, 24.4°2θ, and 29.4°2θ (±0.2°2θ; ±0.1°2θ; or ±0.0°2θ; Cu Kα1 radiation).

In some embodiments, the compound 1 Malate salt is a crystalline polymorph characterized by two or more, or three or more XRPD signals selected from the group consisting of 19.3°2θ, 21.0°2θ, 24.4°2θ, 29.4°2θ, and 37.7°2θ (±0.2°2θ; ±0.1°2θ; or ±0.0°2θ; Cu Kα1 radiation). In some embodiments, the compound 1 Malate salt is a crystalline polymorph characterized by XRPD signals at 19.3°2θ, 21.0°2θ, 24.4°2θ, 29.4°2θ, and 37.7°2θ (±0.2°2θ; ±0.1°2θ; or ±0.0°2θ; Cu Kα1 radiation).

In some embodiments, the compound 1 Malate salt is a crystalline polymorph characterized by two or more, or three or more XRPD signals selected from the group consisting of 19.3°2θ, 20.9°2θ, 21.0°2θ, 24.4°2θ, 29.4°2θ, and 37.7°2θ (±0.2°2θ; ±0.1°2θ; or ±0.0°2θ; Cu Kα1 radiation). In some embodiments, the compound 1 Malate salt is a crystalline polymorph characterized by XRPD signals at 19.3°2θ, 20.9°2θ, 21.0°2θ, 24.4°2θ, 29.4°2θ, and 37.7°2θ (±0.2°2θ; ±0.1°2θ; or ±0.0°2θ; Cu Kα1 radiation).

In some embodiments, the compound 1 Malate salt is a crystalline polymorph characterized by two or more, or three or more XRPD signals selected from the group consisting of 19.3°2θ, 20.9°2θ, 21.0°2θ, 24.4°2θ, 29.4°2θ, 29.7°2θ, and 37.7°2θ (±0.2°2θ; ±0.1°2θ; or ±0.0°2θ; Cu Kα1 radiation). In some embodiments, the compound 1 Malate salt is a crystalline polymorph characterized by XRPD signals at 19.3°2θ, 20.9°2θ, 21.0°2θ, 24.4°2θ, 29.4°2θ, 29.7°2θ, and 37.7°2θ (±0.2°2θ; ±0.1°2θ; or ±0.0°2θ; Cu Kα1 radiation).

In some embodiments, the compound 1 Malate salt is a crystalline polymorph characterized by two or more, or three or more XRPD signals selected from the group consisting of 19.3°2θ, 20.9°2θ, 21.0°2θ, 22.3°2θ, 24.4°2θ, 29.4°2θ, 29.7°2θ, and 37.7°2θ (±0.2°2θ; ±0.1°2θ; or ±0.0°2θ; Cu Kα1 radiation). In some embodiments, the compound 1 Malate salt is a crystalline polymorph characterized by XRPD signals at 19.3°2θ, 20.9°2θ, 21.0°2θ, 22.3°2θ, 24.4°2θ, 29.4°2θ, 29.7°2θ, and 37.7°2θ (±0.2°2θ; ±0.1°2θ; or ±0.0°2θ; Cu Kα1 radiation).

In some embodiments, the compound 1 Malate salt is a crystalline polymorph characterized by two or more, or three or more XRPD signals selected from the group consisting of 19.3°2θ, 20.9°2θ, 21.0°2θ, 22.3°2θ, 24.4°2θ, 29.4°2θ, 29.7°2θ, 30.2°2θ, and 37.7°2θ (±0.2°2θ; ±0.1°2θ; or ±0.0°2θ; Cu Kα1 radiation). In some embodiments, the compound 1 Malate salt is a crystalline polymorph characterized by XRPD signals at 19.3°2θ, 20.9°2θ, 21.0°2θ, 22.3°2θ, 24.4°2θ, 29.4°2θ, 29.7°2θ, 30.2°2θ, and 37.7°2θ (±0.2°2θ; ±0.1°2θ; or ±0.0°2θ; Cu Kα1 radiation).

In some embodiments, the compound 1 Malate salt is a crystalline polymorph characterized by two or more, or three or more XRPD signals selected from the group consisting of 19.3°2θ, 20.9°2θ, 21.0°2θ, 22.3°2θ, 24.4°2θ, 29.4°2θ, 29.7°2θ, 30.2°2θ, 34.1°2θ, and 37.7°2θ (±0.2°2θ; ±0.1°2θ; or ±0.0°2θ; Cu Kα1 radiation). In some embodiments, the compound 1 Malate salt is a crystalline polymorph characterized by XRPD signals at 19.3°2θ, 20.9°2θ, 21.0°2θ, 22.3°2θ, 24.4°2θ, 29.4°2θ, 29.7°2θ, 30.2°2θ, 34.1°2θ, and 37.7°2θ (±0.2°2θ; ±0.1°2θ; or ±0.0°2θ; Cu Kα1 radiation).

In some embodiments, the compound 1 Malate salt is a crystalline polymorph characterized by two or more, or three or more XRPD signals selected from the group consisting of 7.5°2θ, 19.3°2θ, 20.9°2θ, 21.0°2θ, 22.3°2θ, 24.4°2θ, 29.4°2θ, 29.7°2θ, 30.2°2θ, 34.1°2θ, and 37.7°2θ (±0.2°2θ; ±0.1°2θ; or ±0.0°2θ; Cu Kα1 radiation). In some embodiments, the compound 1 Malate salt is a crystalline polymorph characterized by XRPD signals at 7.5°2θ, 19.3°2θ, 20.9°2θ, 21.0°2θ, 22.3°2θ, 24.4°2θ, 29.4°2θ, 29.7°2θ, 30.2°2θ, 34.1°2θ, and 37.7°2θ (±0.2°2θ; ±0.1°2θ; or ±0.0°2θ; Cu Kα1 radiation).

In some embodiments, the compound 1 Malate salt is a crystalline polymorph characterized by two or more, or three or more XRPD signals selected from the group consisting of 7.5°2θ, 19.3°2θ, 20.9°2θ, 21.0°2θ, 22.3°2θ, 24.4°2θ, 27.7°2θ, 29.4°2θ, 29.7°2θ, 30.2°2θ, 34.1°2θ, and 37.7°2θ (±0.2°2θ; ±0.1°2θ; or ±0.0°2θ; Cu Kα1 radiation). In some embodiments, the compound 1 Malate salt is a crystalline polymorph characterized by XRPD signals at 7.5°2θ, 19.3°2θ, 20.9°2θ, 21.0°2θ, 22.3°2θ, 24.4°2θ, 27.7°2θ, 29.4°2θ, 29.7°2θ, 30.2°2θ, 34.1°2θ, and 37.7°2θ (±0.2°2θ; ±0.1°2θ; or 0.0°2θ; Cu Kα1 radiation).

In some embodiments, the compound 1 Malate salt is a crystalline polymorph characterized by two or more, or three or more XRPD signals selected from the group consisting of 7.5°2θ, 19.3°2θ, 20.9°2θ, 21.0°2θ, 22.3°2θ, 24.4°2θ, 27.7°2θ, 29.4°2θ, 29.7°2θ, 30.2°2θ, 34.1°2θ, 37.0°2θ, and 37.7°2θ (±0.2°2θ; ±0.1°2θ; or ±0.0°2θ; Cu Kα1 radiation). In some embodiments, the 30 compound 1 Malate salt is a crystalline polymorph characterized by XRPD signals at 7.5°2θ, 19.3°2θ, 20.9°2θ, 21.0°2θ, 22.3°2θ, 24.4°2θ, 27.7°2θ, 29.4°2θ, 29.7°2θ, 30.2°2θ, 34.1°2θ, 37.0°2θ, and 37.7°2θ (±0.2°2θ; ±0.1°2θ; or ±0.0°2θ; Cu Kα1 radiation).

In some embodiments, the crystalline polymorph is characterized by one, two, three, four, five, six, seven, eight, nine, ten, eleven, twelve, or thirteen XRPD signals selected from those set forth in Table 52.

TABLE 52

Crystalline compound 1 malate salt XRPD Signals (±0.2 °2θ; ±0.1 °2θ; or ±0.0 °2θ; Cu Kα1 radiation)

| Name | Angle | d Value | Net Intensity | Gross Intensity | Rel. Intensity (%) |
| --- | --- | --- | --- | --- | --- |
| Signal #1 | 7.5 | 11.72 | 116.6 | 232.9 | 13.0 |
| Signal #3 | 19.3 | 4.58 | 894.5 | 1074.7 | 100.0 |
| Signal #5 | 20.9 | 4.26 | 180.2 | 360.7 | 20.1 |
| Signal #6 | 21.0 | 4.23 | 187.8 | 367.8 | 21.0 |
| Signal #7 | 22.3 | 3.98 | 153.2 | 319.1 | 17.1 |
| Signal #8 | 24.4 | 3.65 | 690.1 | 834.8 | 77.1 |
| Signal #9 | 27.7 | 3.22 | 101.4 | 218.1 | 11.3 |
| Signal #10 | 29.4 | 3.04 | 278.4 | 386.6 | 31.1 |
| Signal #11 | 29.7 | 3.01 | 156.0 | 263.5 | 17.4 |
| Signal #12 | 30.2 | 2.96 | 140.0 | 245.0 | 15.7 |
| Signal #13 | 34.1 | 2.63 | 128.6 | 223.9 | 14.4 |
| Signal #15 | 37.0 | 2.42 | 94.7 | 198.5 | 10.6 |
| Signal #16 | 37.7 | 2.39 | 183.8 | 285.1 | 20.5 |

Compound 1 Glucuronate Salt

In some embodiments, the compound 1 salt is a compound 1 Glucuronate salt. In some embodiments, the compound 1 Glucuronate salt is amorphous. In some embodiments, the compound 1 Glucuronate salt is crystalline. In some embodiments, the compound 1 Glucuronate salt is a 1:1 compound 1:Glucuronate salt. In some embodiments, the compound 1 Glucuronate 15 salt is a 2:1 compound 1:Glucuronate salt.

In some embodiments, the compound 1 Glucuronate salt is a crystalline polymorph. In some embodiments, the crystalline polymorph is characterized by the XRPD signals set for the below in Table 53. In some embodiments, the crystalline polymorph XRPD pattern is substantially similar to that shown in FIG. 259. In some embodiments, the crystalline polymorph DSC spectrum is substantially similar to that shown in FIG. 260.

In some embodiments, the crystalline compound 1 glucuronate is a crystalline polymorphic form characterized by DSC having a melting signal at about 131.8° C.

In some embodiments, the compound 1 Glucuronate salt is a crystalline polymorph characterized an XRPD signal at 20.0°2θ (±0.2°2θ; ±0.1°2θ; or ±0.0°2θ; Cu Kα1 radiation).

In some embodiments, the compound 1 Glucuronate salt is a crystalline polymorph characterized by XRPD signals at 20.0°2θ and 20.5°2θ (±0.2°2θ; ±0.1°2θ; or 0.0°2θ; Cu Kα1 radiation).

In some embodiments, the compound 1 Glucuronate salt is a crystalline polymorph characterized by two or more, or three or more XRPD signals selected from the group consisting of 20.0°2θ, 20.5°2θ, and 22.5°2θ (±0.2°2θ; ±0.1°2θ; or ±0.0°2θ; Cu Kα1 radiation). In some embodiments, the compound 1 Glucuronate salt is a crystalline polymorph characterized by XRPD signals at 20.0°2θ, 20.5°2θ, and 22.5°2θ (±0.2°2θ; ±0.1°2θ; or ±0 0°2θ; Cu Kα1 radiation).

In some embodiments, the compound 1 Glucuronate salt is a crystalline polymorph characterized by two or more, or three or more XRPD signals selected from the group consisting 20 of 20.0°2θ, 20.5°2θ, 22.5°2θ, and 24.4°2θ (±0.2°2θ; ±0.1°2θ; or 0.0°2θ; Cu Kα1 radiation).

In some embodiments, the compound 1 Glucuronate salt is a crystalline polymorph characterized by XRPD signals at 20.0°2θ, 20.5°2θ, 22.5°2θ, and 24.4°2θ (±0.2°2θ; ±0.1°2θ; or ±0.0°2θ; Cu Kα1 radiation).

In some embodiments, the compound 1 Glucuronate salt is a crystalline polymorph characterized by two or more, or three or more XRPD signals selected from the group consisting of 17.7°2θ, 20.0°2θ, 20.5°2θ, 22.5°2θ, and 24.4°2θ (±0.2°2θ; ±0.1°2θ; or ±0.0°2θ; Cu Kα1 radiation). In some embodiments, the compound 1 Glucuronate salt is a crystalline polymorph characterized by XRPD signals at 17.7°2θ, 20.0°2θ, 20.5°2θ, 22.5°2θ, and 24.4°2θ (±0.2°2θ; ±0.1°2θ; or ±0.0°2θ; Cu Kα1 radiation).

In some embodiments, the compound 1 Glucuronate salt is a crystalline polymorph characterized by two or more, or three or more XRPD signals selected from the group consisting of 17.7°2θ, 20.0°2θ, 20.5°2θ, 22.5°2θ, 24.4°2θ, and 26.1°2θ (±0.2°2θ; ±0.1°2θ; or ±0.0°2θ; Cu Kα1 radiation). In some embodiments, the compound 1 Glucuronate salt is a crystalline polymorph characterized by XRPD signals at 17.7°2θ, 20.0°2θ, 20.5°2θ, 22.5°2θ, 24.4°2θ, and 26.1°2θ (±0.2°2θ; ±0.1°2θ; or ±0.0°2θ; Cu Kα1 radiation).

In some embodiments, the compound 1 Glucuronate salt is a crystalline polymorph characterized by two or more, or three or more XRPD signals selected from the group consisting of 17.7°2θ, 20.0°2θ, 20.5°2θ, 22.5°2θ, 24.4°2θ, 26.1°2θ, and 30.6°2θ (±0.2°2θ; ±0.1°2θ; or ±0.0°2θ; Cu Kα1 radiation). In some embodiments, the compound 1 Glucuronate salt is a crystalline polymorph characterized by XRPD signals at 17.7°2θ, 20.0°2θ, 20.5°2θ, 22.5°2θ, 24.4°2θ, 26.1°2θ, and 30.6°2θ (±0.2°2θ; ±0.1°2θ; or ±0.0°2θ; Cu Kα1 radiation).

In some embodiments, the compound 1 Glucuronate salt is a crystalline polymorph characterized by two or more, or three or more XRPD signals selected from the group consisting of 15.1°2θ, 17.7°2θ, 20.0°2θ, 20.5°2θ, 22.5°2θ, 24.4°2θ, 26.1°2θ, and 30.6°2θ (±0.2°2θ; ±0.1°2θ; or ±0.0°2θ; Cu Kα1 radiation). In some embodiments, the compound 1 Glucuronate salt is a crystalline polymorph characterized by XRPD signals at 15.1°2θ, 17.7°2θ, 20.0°2θ, 20.5°2θ, 22.5°2θ, 24.4°2θ, 26.1°2θ, and 30.6°2θ (±0.2°2θ; ±0.1°2θ; or ±0.0°2θ; Cu Kα1 radiation).

In some embodiments, the compound 1 Glucuronate salt is a crystalline polymorph characterized by two or more, or three or more XRPD signals selected from the group consisting of 15.1°2θ, 17.7°2θ, 20.0°2θ, 20.5°2θ, 22.5°2θ, 24.4°2θ, 26.1°2θ, 30.6°2θ, and 35.5°2θ (±0.2°2θ; ±0.1°2θ; or ±0.0°2θ; Cu Kα1 radiation). In some embodiments, the compound 1 Glucuronate salt is a crystalline polymorph characterized by XRPD signals at 15.1°2θ, 17.7°2θ, 20.0°2θ, 20.5°2θ, 22.5°2θ, 24.4°2θ, 26.1°2θ, 30.6°2θ, and 35.5°2θ (±0.2°2θ; ±0.1°2θ; or ±0.0°2θ; Cu Kα1 radiation).

In some embodiments, the compound 1 Glucuronate salt is a crystalline polymorph characterized by two or more, or three or more XRPD signals selected from the group consisting of 15.1°2θ, 17.7°2θ, 20.0°2θ, 20.5°2θ, 22.5°2θ, 24.4°2θ, 25.5°2θ, 26.1°2θ, 30.6°2θ, and 35.5°2θ (±0.2°2θ; ±0.1°2θ; or ±0.0°2θ; Cu Kα1 radiation). In some embodiments, the compound 1 Glucuronate salt is a crystalline polymorph characterized by XRPD signals at 15.1°2θ, 17.7°2θ, 20.0°2θ, 20.5°2θ, 22.5°2θ, 24.4°2θ, 25.5°2θ, 26.1°2θ, 30.6°2θ, and 35.5°2θ (±0.2°2θ; ±0.1°2θ; or ±0.0°2θ; Cu Kα1 radiation).

In some embodiments, crystalline polymorph is characterized by one, two, three, four, five, six, seven, eight, nine, ten, eleven, or twelve XRPD signals selected from those set forth in Table 53.

TABLE 53

Crystalline compound 1 glucuronate salt XRPD Signals (±0.2 °2θ; ±0.1 °2θ; or ±0.0 °2θ; Cu Kα1 radiation)

| Signal number | 2-θ (°) | d Value | Net Intensity (counts) | Gross Intensity (counts) | Rel. Intensity (%) |
|---|---|---|---|---|---|
| Signal #1 | 15.1 | 5.88 | 198.3 | 591.0 | 23.6 |
| Signal #2 | 17.7 | 4.99 | 242.2 | 716.3 | 28.8 |
| Signal #3 | 20.0 | 4.43 | 841.9 | 1343.6 | 100.0 |
| Signal #4 | 20.5 | 4.34 | 445.4 | 947.9 | 52.9 |
| Signal #5 | 22.5 | 3.95 | 366.5 | 854.6 | 43.5 |
| Signal #6 | 24.4 | 3.65 | 303.9 | 752.1 | 36.1 |
| Signal #7 | 25.5 | 3.50 | 106.7 | 522.0 | 12.7 |
| Signal #8 | 26.1 | 3.41 | 240.8 | 631.7 | 28.6 |
| Signal #9 | 30.6 | 2.92 | 212.1 | 480.9 | 25.2 |
| Signal #10 | 35.5 | 2.53 | 140.2 | 368.4 | 16.7 |
| Signal #11 | 35.5 | 2.53 | 118.7 | 346.8 | 14.1 |
| Signal #12 | 35.5 | 2.53 | 115.6 | 343.4 | 13.7 |

Compound 1 Ascorbate Salt

In some embodiments, the compound 1 salt is a compound 1 Ascorbate salt. In some embodiments, the compound 1 Ascorbate salt is amorphous. In some embodiments, the compound 1 Ascorbate salt is crystalline. In some embodiments, the compound 1 Ascorbate salt is a 1:1 compound 1:Ascorbate salt. In some embodiments, the compound 1 Ascorbate salt is a 2:1 compound 1:Ascorbate salt.

In some embodiments, the compound 1 ascorbate salt is a crystalline polymorph. In some embodiments, the crystalline polymorph is characterized by the XRPD signals set for the below in Table 54. In some embodiments, the crystalline polymorph XRPD pattern is substantially similar to that shown in FIG. 265. In some embodiments, the polymorph DSC spectrum is substantially similar to that shown in FIG. 266.

In some embodiments, the crystalline compound 1 ascorbate is a crystalline polymorphic form characterized by DSC having a melting signal at about 157.0° C.

In some embodiments, the compound 1 Ascorbate salt is a crystalline polymorph characterized by an XRPD signal at 34.8°2θ (±0.2°2θ; ±0.1°2θ; or ±0.0°2θ; Cu Kα1 radiation).

In some embodiments, the compound 1 Ascorbate salt is a crystalline polymorph characterized by XRPD signals at 10.5°2θ and 34.8°2θ (±0.2°2θ; ±0.1°2θ; or ±0.0°2θ; Cu Kα1 radiation).

In some embodiments, the compound 1 Ascorbate salt is a crystalline polymorph characterized by two or more, or three or more XRPD signals selected from the group consisting of 10.5°2θ, 19.9°2θ, and 34.8°2θ (±0.2°2θ; ±0.1°2θ; or ±0.0°2θ; Cu Kα1 radiation). In some embodiments, the compound 1 Ascorbate salt is a crystalline polymorph characterized by XRPD signals at 10.5°2θ, 19.9°2θ, and 34.8°2θ (±0.2 2θ; 0.1°2θ; or ±0.0°2θ; Cu Kα1 radiation).

In some embodiments, the compound 1 Ascorbate salt is a crystalline polymorph characterized by two or more, or three or more XRPD signals selected from the group consisting of 10.5°2θ, 19.9°2θ, 30.1°2θ, and 34.8°2θ (±0.2°2θ; ±0.1°2θ; or ±0.0°2θ; Cu Kα1 radiation).

In some embodiments, the compound 1 Ascorbate salt is a crystalline polymorph characterized by XRPD signals at 10.5°2θ, 19.9°2θ, 30.1°2θ, and 34.8°2θ (±0.2°2θ; ±0.1°2θ; or ±0.0°2θ; Cu Kα1 radiation).

In some embodiments, the compound 1 Ascorbate salt is a crystalline polymorph characterized by two or more, or three or more XRPD signals selected from the group consisting of 10.5°2θ, 19.9°2θ, 28.1°2θ, 30.1°2θ, and 34.8°2θ (±0.2°2θ; ±0.1°2θ; or ±0.0°2θ; Cu Kα1 radiation). In some embodiments, the compound 1 Ascorbate salt is a crystalline polymorph characterized by XRPD signals at 10.5°2θ, 19.9°2θ, 28.1°2θ, 30.1°2θ, and 34.8°2θ (±0.2°2θ; ±0.1°2θ; or ±0.0°2θ; Cu Kα1 radiation).

In some embodiments, the compound 1 Ascorbate salt is a crystalline polymorph characterized by two or more, or three or more XRPD signals selected from the group consisting of 10.5°2θ, 17.5°2θ, 19.9°2θ, 28.1°2θ, 30.1°2θ, and 34.8°2θ (±0.2°2θ; ±0.1°2θ; or ±0.0°2θ; Cu Kα1 radiation). In some embodiments, the compound 1 Ascorbate salt is a crystalline polymorph characterized by XRPD signals at 10.5°2θ, 17.5°2θ, 19.9°2θ, 28.1°2θ, 30.1°2θ, and 34.8°2θ (±0.2°2θ; ±0.1°2θ; or ±0.0°2θ; Cu Kα1 radiation).

In some embodiments, the compound 1 Ascorbate salt is a crystalline polymorph characterized by two or more, or three or more XRPD signals selected from the group consisting of 10.5°2θ, 17.5°2θ, 19.9°2θ, 25.3°2θ, 28.1°2θ, 30.1°2θ, and 34.8°2θ (±0.2°2θ; ±0.1°2θ; or ±0.0°2θ; Cu Kα1 radiation). In some embodiments, the compound 1 Ascorbate salt is a crystalline polymorph characterized by XRPD signals at 10.5°2θ, 17.5°2θ, 19.9°2θ, 25.3°2θ, 28.1°2θ, 30.1°2θ, and 34.8°2θ (±0.2°2θ; ±0.1°2θ; or ±0.0°2θ; Cu Kα1 radiation).

In some embodiments, the compound 1 Ascorbate salt is a crystalline polymorph characterized by two or more, or three or more XRPD signals selected from the group consisting of 10.5°2θ, 17.5°2θ, 19.9°2θ, 21.1°2θ, 25.3°2θ, 28.1°2θ, 30.1°2θ, and 34.8°2θ (±0.2°2θ: ±0.1°2θ; or ±0.0°2θ; Cu Kα1 radiation). In some embodiments, the compound 1 Ascorbate salt is a crystalline polymorph characterized by XRPD signals at 10.5°2θ, 17.5°2θ, 19.9°2θ, 21.1°2θ, 25.3°2θ, 28.1°2θ, 30.1°2θ, and 34.8°2θ (±0.2°2θ; ±0.1°2θ; or ±0.0°2θ; Cu Kα1 radiation).

In some embodiments, the compound 1 Ascorbate salt is a crystalline polymorph characterized by two or more, or three or more XRPD signals selected from the group consisting of 10.5°2θ, 16.1°2θ, 17.5°2θ, 19.9°2θ, 21.1°2θ, 25.3°2θ, 28.1°2θ, 30.1°2θ, and 34.8°2θ (±0.2°2θ; ±0.1°2θ; or ±0.0°2θ; Cu Kα1 radiation). In some embodiments, the compound 1 Ascorbate salt is a crystalline polymorph characterized by XRPD signals at 10.5°2θ, 16.1°2θ, 17.5°2θ, 19.9°2θ, 21.1°2θ, 25.3°2θ, 28.1°2θ, 30.1°2θ, and 34.8°2θ (±0.2°2θ; ±0.1°2θ; or ±0.0°2θ; Cu Kα1 radiation).

In some embodiments, crystalline polymorph is characterized by one, two, three, four, five, six, seven, eight, nine, or ten XRPD signals selected from those set forth in Table 54.

TABLE 54

Crystalline compound 1 ascorbate salt XRPD signals (±0.2 °2θ; ±0.1 °2θ; or ±0.0 °2θ; Cu Kα1 radiation)

| Signal number | 2-θ (°) | d Value | Net Intensity (counts) | Gross Intensity (counts) | Rel. Intensity (%) |
|---|---|---|---|---|---|
| Signal #1 | 10.5 | 8.40 | 4549.3 | 4722.9 | 59.2 |
| Signal #2 | 16.1 | 5.49 | 967.6 | 1276.6 | 12.6 |
| Signal #3 | 17.5 | 5.06 | 1284.7 | 1640.2 | 16.7 |
| Signal #4 | 19.9 | 4.46 | 3172.9 | 3547.3 | 41.3 |
| Signal #5 | 21.1 | 4.20 | 1064.9 | 1416.0 | 13.9 |
| Signal #6 | 25.3 | 3.51 | 1086.3 | 1333.6 | 14.1 |
| Signal #7 | 28.1 | 3.18 | 1363.4 | 1604.6 | 17.7 |
| Signal #8 | 28.1 | 3.17 | 2409.3 | 2649.7 | 31.3 |
| Signal #9 | 30.1 | 2.97 | 2601.5 | 2831.9 | 33.8 |
| Signal #10 | 34.8 | 2.57 | 7687.5 | 7907.7 | 100.0 |

Compound 1 Sulfate Salt

In some embodiments, the compound 1 salt is a compound 1 sulfate salt. In some embodiments, the compound 1 sulfate salt is amorphous. In some embodiments, the compound 1 sulfate salt is crystalline. In some embodiments, the compound 1 sulfate salt is a 1:1 compound 1 sulfate salt. In some embodiments, the compound 1 sulfate salt is a 2:1 compound 1:sulfate salt.

In some embodiments, the compound 1 ascorbate salt is a crystalline polymorph. In some embodiments, the crystalline polymorph XRPD pattern is substantially similar to that shown in FIG. 249. In some embodiments, the polymorph DSC spectrum is substantially similar to that shown in FIG. 250. In some embodiments, the polymorph TGA profile is substantially similar to that shown in FIG. 251.

Compound 1 Mesylate Salt

In some embodiments, the compound 1 salt is a compound 1 mesylate salt. In some embodiments, the compound 1 mesylate salt is amorphous. In some embodiments, the compound 1 mesylate salt is crystalline. In some embodiments, the compound 1 mesylate salt is a 1:1 compound 1:mesylate salt. In some embodiments, the compound 1 mesylate salt is a 2:1 compound 1:mesylate salt.

In some embodiments, the compound 1 mesylate salt is a crystalline polymorph. In some embodiments, the crystalline polymorph XRPD pattern is substantially similar to that shown in FIG. 253. In some embodiments, the polymorph DSC spectrum is substantially similar to that shown in FIG. 254 or 255.

Compound 1 Esylate Salt

In some embodiments, the compound 1 salt is a compound 1 esylate salt. In some embodiments, the compound 1 esylate salt is amorphous. In some embodiments, the compound 1 esylate salt is crystalline. In some embodiments, the compound 1 esylate salt is a 1:1 compound 1:esylate salt. In some embodiments, the compound 1 esylate salt is a 2:1 compound 1:esylate salt.

In some embodiments, the compound 1 esylate salt is a crystalline polymorph. In some embodiments, the crystalline polymorph XRPD pattern is substantially similar to that shown in FIG. 252.

Compound 1 Phosphate Salt

In some embodiments, the compound 1 salt is a compound 1 phosphate salt. In some embodiments, the compound 1 phosphate salt is amorphous. In some embodiments, the compound 1 phosphate salt is crystalline. In some embodiments, the compound 1 phosphate salt is a 1:1 compound 1:phosphate salt. In some embodiments, the compound 1 phosphate salt is a 2:1 compound 1:phosphate salt.

In some embodiments, the compound 1 phosphate salt is a crystalline polymorph. In some embodiments, the crystalline polymorph XRPD pattern is substantially similar to that shown in FIG. 257.

Compound 1 Edisylate Salt

In some embodiments, the compound 1 salt is a compound 1 edisylate salt. In some embodiments, the compound 1 edisylate salt is amorphous. In some embodiments, the compound 1 edisylate salt is crystalline. In some embodiments, the compound 1 edisylate salt is a 1:1 compound 1:edisylate salt. In some embodiments, the compound 1 edisylate salt is a 2:1 compound 1:edisylate salt.

In some embodiments, the compound 1 phosphate salt is a crystalline polymorph. In some embodiments, the crystalline polymorph XRPD pattern is substantially similar to that shown in FIG. 267.

Compound 1 Adipate Salt

In some embodiments, the compound 1 salt is a compound 1 edisylate salt. In some embodiments, the compound 1 edisylate salt is amorphous. In some embodiments, the compound 1 edisylate salt is crystalline. In some embodiments, the compound 1 edisylate salt is a 1:1 compound 1:edisylate salt. In some embodiments, the compound 1 edisylate salt is a 2:1 compound 1:edisylate salt.

In some embodiments, the compound 1 phosphate salt is a crystalline polymorph. In some embodiments, the crystalline polymorph XRPD pattern is substantially similar to that shown in FIG. 268.

Pharmaceutical Compositions and Formulations

In some embodiments, the present disclosure provides a pharmaceutical composition comprising one or more of the disclosed solid forms of (R)-1-(5-methoxy-1H-indol-1-yl)-N,N-dimethylpropan-2-amine fumarate, and a pharmaceutically acceptable excipient. Such compositions are suitable for administration to a subject, such as a human subject.

The presently disclosed pharmaceutical compositions can be prepared in a wide variety of oral, parenteral, such as intravenous, and topical dosage forms. Oral preparations include tablets, pills, powder, capsules, lozenges, cachets, slurries, suspensions, etc., suitable for ingestion by the patient. The compositions of the present invention can also be administered as solutions, orally or parenterally, such as by injection, that is, intravenously, intramuscularly, intracutaneously, subcutaneously, intraduodenally, or intraperitoneally. Also, the compositions described herein can be administered by inhalation, for example, intranasally. Additionally, the compositions of the present invention can be administered transdermally. The compositions of this invention can also be administered by intraocular, intravaginal, and intrarectal routes including suppositories, insufflation, powders and aerosol formulations (for examples of steroid inhalants, see Rohatagi, *J. Clin. Pharmacol.* 35:1187-1193, 1995, Tjwa, *Ann. Allergy Asthma Immunol.* 75:107-111, 1995). Accordingly, the present disclosure also provides pharmaceutical compositions including a pharmaceutically acceptable carrier or excipient and the solid form of the compounds of the present disclosure.

For preparing pharmaceutical compositions from the compounds disclosed herein, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Mack Publishing Co, Easton PA ("Remington's").

In powders, the carrier is a finely divided solid, which is in a mixture with the finely divided active component. In tablets, the active component is mixed with the carrier having the necessary binding properties in suitable proportions and compacted in the shape and size desired. The powders and tablets preferably contain from 5% to 70% or 10% to 70% of the compounds of the present disclosure.

Suitable solid excipients include, but are not limited to, magnesium carbonate; magnesium stearate; talc; pectin; dextrin; starch; tragacanth; a low melting wax; cocoa butter; carbohydrates; sugars including, but not limited to, lactose, sucrose, mannitol, or sorbitol, starch from corn, wheat, rice, potato, or other plants; cellulose such as methyl cellulose, hydroxypropylmethyl-cellulose, or sodium carboxymethyl-cellulose; and gums including arabic and tragacanth; as well as proteins including, but not limited to, gelatin and collagen.

If desired, disintegrating or solubilizing agents may be added, such as the cross-linked polyvinyl pyrrolidone, agar, alginic acid, or a salt thereof, such as sodium alginate.

For preparing suppositories, a low melting wax, such as a mixture of fatty acid glycerides or cocoa butter, is first melted and the compounds of the present invention are dispersed homogeneously therein, as by stirring. The molten homogeneous mixture is then poured into convenient sized molds, allowed to cool, and thereby to solidify.

Liquid form preparations include suspensions, for example, aqueous solutions and water or water/propylene glycol suspensions.

Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include suspensions. These preparations may contain, in addition to the active component, colorants, flavors, stabilizers, buffers, artificial and natural sweeteners, dispersants, thickeners, solubilizing agents, and the like.

Oil suspensions can be formulated by suspending the compound of the present invention in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The compositions of the present disclosure can also be delivered as microspheres for slow release in the body. For example, microspheres can be formulated for administration via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). Both transdermal and intradermal routes afford constant delivery for weeks or months.

In some embodiments, the pharmaceutical compositions of the present disclosure can be formulated for parenteral administration, such as intravenous (IV) administration or administration into a body cavity or lumen of an organ. The formulations for administration will commonly comprise a solution or suspension of the compositions of the present disclosure dissolved or suspended in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose, any bland fixed oil can be employed including synthetic mono- or diglycerides. In addition, fatty acids such as oleic acid can likewise be used in the preparation of injectables. These solutions or suspensions are sterile and generally free of undesirable matter. These formulations may be sterilized by conventional, well known sterilization techniques. The formulations may contain pharmaceutically acceptable auxiliary substances as required to approximate physiological conditions such as pFI adjusting and buffering agents, toxicity adjusting agents, e.g., sodium acetate, sodium chloride, potassium chloride, calcium chloride, sodium lactate and the like. The concentration of the compositions of the present disclosure in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In some embodiments, the formulations of the compositions of the present disclosure can be delivered by the use of liposomes which fuse with the cellular membrane or are endocytosed, for example, by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

Administration:

The compositions of the present disclosure can be administered by any suitable means, including oral, parenteral and topical methods. Transdermal administration methods, by a topical route, can be formulated as applicator sticks, suspensions, creams, ointments, pastes, jellies, paints, powders, and aerosols.

The pharmaceutical preparation is preferably in unit dosage form. In such form the preparation is subdivided into unit doses containing appropriate quantities of the compounds of the present invention. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The compound of the present invention can be present in any suitable amount, and can depend on various factors including, but not limited to, weight and age of the subject, state of the disease, and the like as is known to those of ordinary skill in the art. Suitable dosage ranges for the compounds disclosed herein include from about 0.1 mg to about 10,000 mg, or about 1 mg to about 1000 mg, or about 10 mg to about 750 mg, or about 25 mg to about 500 mg, or about 50 mg to about 250 mg. Suitable dosages for the compound of the present invention include about 1 mg, 5, 10, 20, 30, 40, 50, 60, 70, 80, 90, 100, 200, 300, 400, 500, 600, 700, 800, 900 or 1000 mg.

The compounds disclosed herein can be administered at any suitable frequency, interval and duration. For example, the compounds can be administered once an hour, or two, three or more times an hour, once a day, or two, three, or more times per day, or once every 2, 3, 4, 5, 6, or 7 days, so as to provide the preferred dosage level. When the compound of the present invention is administered more than once a day, representative intervals include 5, 10, 15, 20, 30, 45 and 60 minutes, as well as 1, 2, 4, 6, 8, 10, 12, 16, 20, and 24 hours. The compound of the present invention can be administered once, twice, or three or more times, for an hour, for 1 to 6 hours, for 1 to 12 hours, for 1 to 24 hours, for 6 to 12 hours, for 12 to 24 hours, for a single day, for 1 to 7 days, for a single week, for 1 to 4 weeks, for a month, for 1 to 12 months, for a year or more, or even indefinitely.

The composition can also contain other compatible therapeutic agents. The compounds described herein can be used in combination with one another, with other active agents known to be useful in modulating a glucocorticoid receptor, or with adjunctive agents that may not be effective alone, but may contribute to the efficacy of the active agent.

The compounds of the present invention can be co-administered with a second active agent. Co-administration includes administering the compound of the present invention and active agent within 0.5, 1, 2, 4, 6, 8, 10, 12, 16, 20, or 24 hours of each other. Co-administration also includes administering the compound of the present invention and active agent simultaneously, approximately simultaneously (e.g., within about 1, 5, 10, 15, 20, or 30 minutes of each other), or sequentially in any order. Moreover, the compound of the present disclosure and the active agent can each be administered once a day, or two, three, or more times per day so as to provide the preferred dosage level per day.

In some embodiments, co-administration can be accomplished by co-formulation, such as by preparing a single pharmaceutical composition including both the compound of the present disclosure and a second active agent. In other embodiments, the compound of the present disclosure and the second active agent can be formulated separately.

The disclosed compounds and the second active agent can be present in the compositions of the present disclosure in any suitable weight ratio, such as from about 1:100 to about 100:1 (w/w), or about 1:50 to about 50:1, or about 1:25 to about 25:1, or about 1:10 to about 10:1, or about 1:5 to about 5:1 (w/w). The compound of the present disclosure and the second active agent can be present in any suitable weight ratio, such as about 1:100 (w/w), 1:50, 1:25, 1:10, 1:5, 1:4, 1:3, 1:2, 1:1, 2:1, 3:1, 4:1, 5:1, 10:1, 25:1, 50:1 or 100:1 (w/w). Other dosages and dosage ratios of the compound of the present disclosure and the active agent are suitable in the compositions and methods disclosed herein.

Methods of Treatment

The solid forms of the compounds of the present disclosure, e.g., of compound 1, can be used for increasing neuronal plasticity. The compounds of the present disclosure can also be used to treat any brain disorder The solid forms of the present disclosure can also be used for increasing at least one of translation, transcription or secretion of neurotrophic factors.

In some embodiments, a compound of the present disclosure is used to treat neurological diseases. In some embodiments, the compounds have, for example, anti-addictive properties, antidepressant properties, anxiolytic properties, or a combination thereof. In some embodiments, the neurological disease is a neuropsychiatric disease. In some embodiments, the neuropsychiatric disease is a mood or anxiety disorder. In some embodiments, the neurological disease is a migraine, headaches (e.g., cluster headache), post-traumatic stress disorder (PTSD), anxiety, depression, neurodegenerative disorder, Alzheimer's disease, Parkinson's disease, psychological disorder, treatment resistant depression, suicidal ideation, major depressive disorder, bipolar disorder, schizophrenia, stroke, traumatic brain injury, and addiction (e.g., substance use disorder). In some embodiments, the neurological disease is a migraine or cluster headache. In some embodiments, the neurological disease is a neurodegenerative disorder, Alzheimer's disease, or Parkinson's disease. In some embodiments, the neurological disease is a psychological disorder, treatment resistant depression, suicidal ideation, major depressive disorder, bipolar disorder, schizophrenia, post-traumatic stress disorder (PTSD), addiction (e.g., substance use disorder), depression, or anxiety. In some embodiments, the neuropsychiatric disease is a psychological disorder, treatment resistant depression, suicidal ideation, major depressive disorder, bipolar disorder, schizophrenia, post-traumatic stress disorder (PTSD), addiction (e.g., substance use disorder), depression, or anxiety. In some embodiments, the neuropsychiatric disease or neurological disease is post-traumatic stress disorder (PTSD), addiction (e.g., substance use disorder), schizophrenia, depression, or anxiety. In some embodiments, the neuropsychiatric disease or neurological disease is addiction (e.g., substance use disorder). In some embodiments, the neuropsychiatric disease or neurological disease is depression. In some embodiments, the neuropsychiatric disease or neurological disease is anxiety. In some embodiments, the neuropsychiatric disease or neurological disease is post-traumatic stress disorder (PTSD). In some embodiments, the neurological disease is stroke or traumatic brain injury. In some embodiments, the neuropsychiatric disease or neurological disease is schizophrenia.

In some embodiments, a compound of the present disclosure is used for increasing neuronal plasticity. In some embodiments, the compounds described herein are used for treating a brain disorder. In some embodiments, the compounds described herein are used for increasing at least one of translation, transcription, or secretion of neurotrophic factors.

In some embodiments, the present disclosure provides a method of treating a disease, including administering to a subject in need thereof, a therapeutically effective amount of a compound of the present disclosure. In some embodiments, the disease is a musculoskeletal pain disorder including fibromyalgia, muscle pain, joint stiffness, osteoarthritis, rheumatoid arthritis, muscle cramps. In some embodiments, the present invention provides a method of treating a disease of women's reproductive health including premenstrual dysphoric disorder (PMDD), premenstrual syndrome (PMS), post-partum depression, and menopause.

In some embodiments, the compounds of the present disclosure have activity as $5\text{-HT}_{2A}$ modulators. In some embodiments, the compounds of the present disclosure elicit a biological response by activating the $5\text{-HT}_{2A}$ receptor (e.g., allosteric modulation or modulation of a biological target that activates the $5\text{-HT}_{2A}$ receptor). $5\text{-HT}_{2A}$ agonism has been correlated with the promotion of neural plasticity (Ly et al., 2018). $5\text{-HT}_{2A}$ antagonists abrogate the neuritogenesis and spinogenesis effects of hallucinogenic compounds with $5\text{-HT}_{2A}$ agonist activity, for example, DMT, LSD, and DOI. In some embodiments, the compounds of the present disclosure are $5\text{-HT}_{2A}$ modulators and promote neural plasticity (e.g., cortical structural plasticity). In some embodiments, the compounds of the present disclosure are selective $5\text{-HT}_{2A}$ modulators and promote neural plasticity (e.g., cortical structural plasticity). In some embodiments, promotion of neural plasticity includes, for example, increased dendritic spine growth, increased synthesis of synaptic proteins, strengthened synaptic responses, increased dendritic arbor complexity, increased dendritic branch content, increased spinogenesis, increased neuritogenesis, or any combination thereof. In some embodiments, increased neural plasticity includes, for example, increased cortical structural plasticity in the anterior parts of the brain.

In some embodiments, the $5\text{-HT}_{2A}$ modulators (e.g., $5\text{-HT}_{2A}$ agonists) are non-hallucinogenic. In some embodiments, non-hallucinogenic $5\text{-HT}_{2A}$ modulators (e.g., $5\text{-HT}_{2A}$ agonists) are used to treat neurological diseases, which modulators do not elicit dissociative side-effects. In some embodiments, the hallucinogenic potential of the compounds described herein is assessed in vitro. In some embodiments, the hallucinogenic potential assessed in vitro of the compounds described herein is compared to the hallucinogenic potential assessed in vitro of hallucinogenic homologs. In some embodiments, the compounds described herein elicit less hallucinogenic potential in vitro than the hallucinogenic homologs.

In some embodiments, serotonin receptor modulators, such as modulators of serotonin receptor 2A (5-$HT_{2A}$ modulators, e.g., 5-$HT_{2A}$ agonists), are used to treat a brain disorder. The presently disclosed compounds can function as 5-$HT_{2A}$ agonists alone, or in combination with a second therapeutic agent that also is a 5-$HT_{2A}$ modulator. In such cases the second therapeutic agent can be an agonist or an antagonist. In some instances, it may be helpful administer a 5-$HT_{2A}$ antagonist in combination with a compound of the present disclosure to mitigate undesirable effects of 5-$HT_{2A}$ agonism, such as potential hallucinogenic effects. Serotonin receptor modulators useful as second therapeutic agents for combination therapy as described herein are known to those of skill in the art and include, without limitation, ketanserin, volinanserin (MDL-100907), eplivanserin (SR-46349), pimavanserin (ACP-103), glemanserin (MDL-11939), ritanserin, flibanserin, nelotanserin, blonanserin, mianserin, mirtazapine, roluperiodone (CYR-101, MIN-101), quetiapine, olanzapine, altanserin, acepromazine, nefazodone, risperidone, pruvanserin, AC-90179, AC-279, adatanserin, fananserin, HY10275, benanserin, butanserin, manserin, iferanserin, lidanserin, pelanserin, seganserin, tropanserin, lorcaserin, ICI-169369, methiothepin, 10 methysergide, trazodone, cinitapride, cyproheptadine, brexpiprazole, cariprazine, agomelatine, setoperone, 1-(1-Naphthyl)piperazine, LY-367265, pirenperone, metergoline, deramciclane, amperozide, cinanserin, LY-86057, GSK-215083, cyamemazine, mesulergine, BF-1, LY-215840, sergolexole, spiramide, LY-53857, amesergide, LY-108742, pipamperone, LY-314228, 5-I-R91150, 5-MeO-NBpBrT, 9-Aminomethyl-9,10-dihydroanthracene, niaprazine, SB-215505, SB-204741, SB-206553, SB-242084, LY-272015, SB-243213, SB-200646, RS-102221, zotepine, clozapine, chlorpromazine, sertindole, iloperidone, paliperidone, asenapine, amisulpride, aripiprazole, lurasidone, ziprasidone, lumateperone, perospirone, mosapramine, AMDA (9-Aminomethyl-9,10-dihydroanthracene), methiothepin, an extended-release form of olanzapine (e.g., ZYPREXA RELPREVV), an extended-release form of quetiapine, an extended-release form of risperidone (e.g., Risperdal Consta), an extended-release form of paliperidone (e.g., Invega Sustenna and Invega Trinza), an extended-release form of fluphenazine decanoate including Prolixin Decanoate, an extended-release form of aripiprazole lauroxil including Aristada, and an extended-release form of aripiprazole including Abilify Maintena, or a pharmaceutically acceptable salt, solvate, metabolite, deuterated analog, derivative, prodrug, or combinations thereof. In some embodiments, the serotonin receptor modulator used as a second therapeutic is pimavanserin or a pharmaceutically acceptable salt, solvate, metabolite, derivative, or prodrug thereof. In some embodiments, the serotonin receptor modulator is administered prior to a compound disclosed herein, such as about three or about one hours prior to administration of a compound disclosed herein. In some embodiments, the serotonin receptor modulator is administered at most about one hour prior to the presently disclosed compound. Thus, in some embodiments of combination therapy with the presently disclosed compounds, the second therapeutic agent is a serotonin receptor modulator. In some embodiments the second therapeutic agent serotonin receptor modulator is provided at a dose of from about 10 mg to about 350 mg. In some embodiments, the serotonin receptor modulator is provided at a dose of from about 20 mg to about 200 mg. In some embodiments, the serotonin receptor modulator is provided at a dose of from about 10 mg to about 100 mg. In certain such embodiments, the compound of the present disclosure is provided at a dose of from about 10 mg to about 100 mg, or from about 20 to about 200 mg, or from about 15 to about 300 mg, and the serotonin receptor modulator is provided at a dose of about 10 mg to about 100 mg.

In some embodiments, non-hallucinogenic 5-$HT2_A$ modulators (e.g., 5-$HT2_A$ agonists) are used to treat neurological diseases. In some embodiments, the neurological diseases comprise decreased neural plasticity, decreased cortical structural plasticity, decreased 5-$HT_{2A}$ receptor content, decreased dendritic arbor complexity, loss of dendritic spines, decreased dendritic branch content, decreased spinogenesis, decreased neuritogenesis, retraction of neurites, or any combination thereof.

In some embodiments, non-hallucinogenic 5-$HT_{2A}$ modulators (e.g., 5-$HT_{2A}$ agonists) are used for increasing neuronal plasticity. In some embodiments, non-hallucinogenic 5-$HT_{2A}$ modulators (e.g., 5-$HT_{2A}$ agonists) are used for treating a brain disorder. In some embodiments, non-hallucinogenic 5-$HT_{2A}$ modulators (e.g., 5-FIT2A agonists) are used for increasing at least one of translation, transcription, or secretion of neurotrophic factors.

In some embodiments the presently disclosed compounds are given to patients in a low dose that is lower than would produce noticeable psychedelic effects but high enough to provide a therapeutic benefit. This dose range is predicted to be between 200 ug (micrograms) and 2 mg.

Methods for Increasing Neuronal Plasticity

Neuronal plasticity refers to the ability of the brain to change structure and/or function throughout a subject's life. New neurons can be produced and integrated into the central nervous system throughout the subject's life. Increasing neuronal plasticity includes, but is not limited to, promoting neuronal growth, promoting neuritogenesis, promoting synaptogenesis, promoting dendritogenesis, increasing dendritic arbor complexity, increasing dendritic spine density, and increasing excitatory synapsis in the brain. In some embodiments, increasing neuronal plasticity comprises promoting neuronal growth, promoting neuritogenesis, promoting synaptogenesis, promoting dendritogenesis, increasing dendritic arbor complexity, and increasing dendritic spine density.

In some embodiments, increasing neuronal plasticity by treating a subject with one or more of the disclosed compounds can treat neurodegenerative disorder, Alzheimer's, Parkinson's disease, psychological disorder, depression, addiction, anxiety, post-traumatic stress disorder, treatment resistant depression, suicidal ideation, major depressive disorder, bipolar disorder, schizophrenia, stroke, traumatic brain injury, or substance use disorder.

In some embodiments, the present disclosure provides methods for increasing neuronal plasticity, comprising contacting a neuronal cell with a compound of the present disclosure. In some embodiments, increasing neuronal plasticity improves a brain disorder described herein.

In some embodiments, a compound of the present disclosure is used to increase neuronal plasticity. In some embodiments, the compounds used to increase neuronal plasticity have, for example, anti-addictive properties, antidepressant properties, anxiolytic properties, or a combination thereof. In some embodiments, decreased neuronal plasticity is associated with a neuropsychiatric disease. In some embodiments, the neuropsychiatric disease is a mood or anxiety disorder. In some embodiments, the neuropsychiatric disease includes, for example, migraine, cluster headache, post-traumatic stress disorder (PTSD), schizophrenia, anxiety, depression, and addiction (e.g., substance abuse disorder). In some embodiments, brain disorders include, for example, migraines, addiction (e.g., substance use disorder), depression, and anxiety.

In some embodiments, the experiment or assay to determine increased neuronal plasticity of any compound of the present disclosure is a phenotypic assay, a dendritogenesis assay, a spinogenesis assay, a synaptogenesis assay, a Sholl analysis, a concentration-response experiment, a 5-HT$_{2A}$ agonist assay, a 5-HT$_{2A}$ antagonist assay, a 5-HT$_{2A}$ binding assay, or a 5-HT$_{2A}$ blocking experiment (e.g., ketanserin blocking experiments). In some embodiments, the experiment or assay to determine the hallucinogenic potential of any compound of the present invention is a mouse head-twitch response (HTR) assay.

In some embodiments, the present disclosure provides a method for increasing neuronal plasticity, comprising contacting a neuronal cell with a compound disclosed herein.

Methods of Treating a Brain Disorder

In some embodiments, the present disclosure provides a method of treating a disease, including administering to a subject in need thereof, a therapeutically effective amount of a compound of the present disclosure. In some embodiments, the disease is a musculoskeletal pain disorder including fibromyalgia, muscle pain, joint stiffness, osteoarthritis, rheumatoid arthritis, muscle cramps. In some embodiments, the present disclosure provides a method of treating a disease of women's reproductive health including premenstrual dysphoric disorder (PMDD), premenstrual syndrome (PMS), post-partum depression, and menopause. In some embodiments, the present disclosure provides a method of treating a brain disorder, including administering to a subject in need thereof, a therapeutically effective amount of a compound of the present disclosure. In some embodiments, the present disclosure provides a method of treating a brain disorder with combination therapy, including administering to a subject in need thereof, a therapeutically effective amount of a compound of the present disclosure and at least one additional therapeutic agent.

In some embodiments, 5-HT$_{2A}$ modulators (e.g., 5-HT$_{2A}$ agonists) are used to treat a brain disorder. In some embodiments, the brain disorders comprise decreased neural plasticity, decreased cortical structural plasticity, decreased 5-HT$_{2A}$ receptor content, decreased dendritic arbor complexity, loss of dendritic spines, decreased dendritic branch content, decreased spinogenesis, decreased neuritogenesis, retraction of neurites, or any combination thereof.

In some embodiments, a compound of the present disclosure is used to treat brain disorders. In some embodiments, the compounds have, for example, anti-addictive properties, antidepressant properties, anxiolytic properties, or a combination thereof. In some embodiments, the brain disorder is a neuropsychiatric disease. In some embodiments, the neuropsychiatric disease is a mood or anxiety disorder. In some embodiments, brain disorders include, for example, migraine, cluster headache, post-traumatic stress disorder (PTSD), anxiety, depression, panic disorder, suicidality, schizophrenia, and addiction (e.g., substance abuse disorder). In some embodiments, brain disorders include, for example, migraines, addiction (e.g., substance use disorder), depression, and anxiety.

In some embodiments, the present disclosure provides a method of treating a brain disorder, comprising administering to a subject in need thereof a therapeutically effective amount of a compound disclosed herein.

In some embodiments, the brain disorder is a neurodegenerative disorder, Alzheimer's, Parkinson's disease, psychological disorder, depression, addiction, anxiety, post-traumatic stress disorder, treatment resistant depression, suicidal ideation, major depressive disorder, bipolar disorder, schizophrenia, stroke, traumatic brain injury, or substance use disorder.

In some embodiments, the brain disorder is a neurodegenerative disorder, Alzheimer's, or Parkinson's disease. In some embodiments, the brain disorder is a psychological disorder, depression, addiction, anxiety, or a post-traumatic stress disorder. In some embodiments, the brain disorder is depression. In some embodiments, the brain disorder is addiction. In some embodiments, the brain disorder is treatment resistant depression, suicidal ideation, major depressive disorder, bipolar disorder, schizophrenia, stroke, traumatic brain injury or substance use disorder. In some embodiments, the brain disorder is treatment resistant depression, suicidal ideation, major depressive disorder, bipolar disorder, schizophrenia, or substance use disorder. In some embodiments, the brain disorder is stroke or traumatic brain injury. In some embodiments, the brain disorder is treatment resistant depression, suicidal ideation, major depressive disorder, bipolar disorder, or substance use disorder. In some embodiments, the brain disorder is schizophrenia. In some embodiments, the brain disorder is alcohol use disorder.

In some embodiments, the method further comprises administering one or more additional therapeutic agent that is lithium, olanzapine (Zyprexa), quetiapine (Seroquel), risperidone (Risperdal), ariprazole (Abilify), ziprasidone (Geodon), clozapine (Clozaril), divalproex sodium (Depakote), lamotrigine (Lamictal), valproic acid (Depakene), carbamazepine (Equetro), topiramate (Topamax), levomilnacipran (Fetzima), duloxetine (Cymbalta, Yentreve), venlafaxine (Effexor), citalopram (Celexa), fluvoxamine (Luvox), escitalopram (Lexapro), fluoxetine (Prozac), paroxetine (Paxil), sertraline (Zoloft), clomipramine (Anafranil), amitriptyline (Elavil), desipramine (Norpramin), imipramine (Tofranil), nortriptyline (Pamelor), phenelzine (Nardil), tranylcypromine (Parnate), diazepam (Valium), alprazolam (Xanax), or clonazepam (Klonopin).

In certain embodiments of the method for treating a brain disorder with a solid form disclosed herein, a second therapeutic agent that is an empathogenic agent is administered. Examples of suitable empathogenic agents for use in combination with the present solid forms include phenethylamines, such as 3,4-methylene-dioxymethamphetamine (MDMA), and analogs thereof. Other suitable empathogenic agents for use in combination with the presently disclosed compounds include, without limitation,
N-Allyl-3,4-methylenedioxy-amphetamine (MDAL)
N-Butyl-3,4-methylenedioxyamphetamine (MDBU)
N-Benzyl-3,4-methylenedioxyamphetamine (MDBZ)
N-Cyclopropylmethyl-3,4-methylenedioxyamphetamine (MDCPM)
N,N-Dimethyl-3,4-methylenedioxyamphetamine (MDDM)
N-Ethyl-3,4-methylenedioxyamphetamine (MDE; MDEA)
N-(2-Hydroxyethyl)-3,4-methylenedioxy amphetamine (MDHOET)

N-Isopropyl-3,4-methylenedioxyamphetamine (MDLP)
N-Methyl-3,4-ethylenedioxyamphetamine (MDMC)
N-Methoxy-3,4-methylenedioxyamphetamine (MDMEO)
N-(2-Methoxyethyl)-3,4-methylenedioxyamphetamine (MDMEOET)
alpha,alpha,N-Trimethyl-3,4-methylenedioxyphenethylamine (MDMP;
3,4-Methylenedioxy-N-methylphentermine)
N-Hydroxy-3,4-methylenedioxyamphetamine (MDOH)
3,4-Methylenedioxyphenethylamine (MDPEA)
alpha,alpha-Dimethyl-3,4-methylenedioxyphenethylamine (MDPH; 3,4-methylenedioxyphentermine)
N-Propargyl-3,4-methylenedioxyamphetamine (MDPL)
Methylenedioxy-2-aminoindane (MDAI)
1,3-Benzodioxolyl-N-methylbutanamine (MBDB),
3,4-methylenedioxy-N-methyl-α-ethylphenylethylamine
3,4-Methylenedioxyamphetamine MDA
Methylone (also known as "3,4-methylenedioxy-N-methylcathinone
Ethylone, also known as 3,4-methylenedioxy-N-ethylcathinone
GHB or Gamma Hydroxybutyrate or sodium oxybate
N-Propyl-3,4-methylenedioxyamphetamine (MDPR), and the like.

In some embodiments, the compounds of the present disclosure are used in combination with the standard of care therapy for a neurological disease described herein. Non-limiting examples of the standard of care therapies, may include, for example, lithium, olanzapine, quetiapine, risperidone, aripirazole, ziprasidone, clozapine, divalproex sodium, lamotrigine, valproic acid, carbamazepine, topiramate, levomilnacipran, duloxetine, venlafaxine, citalopram, fluvoxamine, escitalopram, fluoxetine, paroxetine, sertraline, clomipramine, amitriptyline, desipramine, imipramine, nortriptyline, phenelzine, tranylcypromine, diazepam, alprazolam, clonazepam, or any combination thereof. Nonlimiting examples of standard of care therapy for depression are sertraline, fluoxetine, escitalopram, venlafaxine, or aripiprazole. Non-limiting examples of standard of care therapy for depression are citralopram, escitalopram, fluoxetine, paroxetine, diazepam, or sertraline. Additional examples of standard of care therapeutics are known to those of ordinary skill in the art.

Methods of Increasing at Least One of Translation, Transcription, or Secretion of Neurotrophic Factors Neurotrophic factors refers to a family of soluble peptides or proteins which support the survival, growth, and differentiation of developing and mature neurons. Increasing at least one of translation, transcription, or secretion of neurotrophic factors can be useful for, but not limited to, increasing neuronal plasticity, promoting neuronal growth, promoting neuritogenesis, promoting synaptogenesis, promoting dendritogenesis, increasing dendritic arbor complexity, increasing dendritic spine density, and increasing excitatory synapsis in the brain. In some embodiments, increasing at least one of translation, transcription, or secretion of neurotrophic factors can increasing neuronal plasticity. In some embodiments, increasing at least one of translation, transcription, or secretion of neurotrophic factors can promoting neuronal growth, promoting neuritogenesis, promoting synaptogenesis, promoting dendritogenesis, increasing dendritic arbor complexity, and/or increasing dendritic spine density.

In some embodiments, 5-HT$_{2A}$ modulators (e.g., 5-HT$_{2A}$ agonists) are used to increase at least one of translation, transcription, or secretion of neurotrophic factors. In some embodiments, a compound of the present disclosure is used to increase at least one of translation, transcription, or secretion of neurotrophic factors. In some embodiments, increasing at least one of translation, transcription or secretion of neurotrophic factors treats a migraine, headaches (e.g., cluster headache), post-traumatic stress disorder (PTSD), anxiety, depression, neurodegenerative disorder, Alzheimer's disease, Parkinson's disease, psychological disorder, treatment resistant depression, suicidal ideation, major depressive disorder, bipolar disorder, schizophrenia, stroke, traumatic brain injury, and addiction (e.g., substance use disorder).

In some embodiments, the experiment or assay used to determine increase translation of neurotrophic factors includes ELISA, western blot, immunofluorescence assays, proteomic experiments, and mass spectrometry. In some embodiments, the experiment or assay used to determine increase transcription of neurotrophic factors includes gene expression assays, PCR, and microarrays. In some embodiments, the experiment or assay used to determine increase secretion of neurotrophic factors includes ELISA, western blot, immunofluorescence assays, proteomic experiments, and mass spectrometry.

In some embodiments, the present disclosure provides a method for increasing at least one of translation, transcription or secretion of neurotrophic factors, comprising contacting a neuronal cell with a compound disclosed herein.

EXAMPLES

Example 1

Polymorph Production

The active pharmaceutical ingredient (API), (R)-1-(5-methoxy-1H-indol-1-yl)-N,N-dimethylpropan-2-amine fumarate, is characterized to evaluate its physical properties. The evaluation is performed by X-ray powder diffraction (XRPD), polarized light microscopy (PLM), differential scanning calorimetry (DSC), thermogravimetry (TG), dynamic vapor sorption/desorption (DVS), and/or solubility testing in organic solvents, water, and mixed solvent systems. XRPD data is used to assess crystallinity. PLM data is used to evaluate crystallinity and particle size/morphology. DSC data is used to evaluate melting point, thermal stability, and crystalline form conversion. TG data is used to evaluate if the API is a solvate or hydrate, and to evaluate thermal stability. DVS data is used to evaluate hygroscopicity of the API and if hydrates can be formed at high relative humidity. About 10 to 15 solvents may be selected from the list below, based on their properties (polarity, dielectric constant and dipole moment).

TABLE 55

| Solvents | |
| --- | --- |
| acetic acid | n-heptane |
| acetone | n-hexane |
| acetonitrile | 1,1,1,3,3,3-hexafluoro-2-propanol |
| benzyl alcohol | isobutanol (2-methyl-1-propanol) |
| 1-butanol | isopentanol (3-methyl-1-butanol) |
| 2-butanol | isopropyl alcohol (2-propanol) |
| butyl acetate | isopropylbenzene (cumene) |
| t-butyl methyl ether | methanol |
| chlorobenzene | methoxybenzene (anisole) |
| chloroform | methyl acetate |
| di(ethylene glycol) | methyl ethyl ketone (2-butanone ) |
| dichloromethane | methyl isobutyl ketone |
| diethyl ether | nitromethane |
| diethylamine | N-methyl-2-pyrrolidone (NMP) |

TABLE 55-continued

| Solvents | |
|---|---|
| Dimethylacetamide (DMA) | 1-octanol |
| diisopropyl ether | 1-pentanol |
| N,N-dimethyl-formamide (DMF) | 1-propanol |
| dimethyl sulfoxide | perfluorohexane |
| 1,4-dioxane | propyl acetate |
| 1,2-ethanediol (ethylene glycol) | 1,1,2,2-tetrachloroethane |
| ethanol | tetrahydrofuran |
| ethanolamine | toluene |
| 2-ethoxyethanol (Cellusolve) | 1,1,1-trichloroethane |
| ethyl acetate | 2,2,2-trifluoroethanol |
| ethyl formate | water |
| formic acid | o-xylene (1,2-dimethylbenzene) |
| glycerol | p-xylene (1,4-dimethylbenzene) |

The information obtained is used for designing the subsequent polymorph screen. Solvents are used as a single solvent or as solvent mixtures, some containing water. The techniques used for the polymorph screen are chosen based on the solvent selected and properties of the API. The following techniques (or a combination of techniques) may be used for the polymorph screening:

- API is dissolved in a solvent or mixture of solvents, and the solvents are evaporated at different rates (slow evaporation or fast evaporation) and at different temperatures (ambient or elevated).
- API is dissolved in a solvent or mixture of solvents (at ambient temperature or an elevated temperature), and the final solution is cooled (between −78° C. to 20° C.). The cooling method can be a fast cooling (by plunging the sample to an ice bath or a dry ice/acetone bath), or slow cooling. The solids formed will be recovered by filtration and dried (air dried or vacuum dried).
- API is dissolved in a solvent or mixture of solvents, and an antisolvent is added to precipitate the salt. The solids formed will be recovered by filtration and dried (air dried or vacuum dried).
- API is added to a solvent or mixture of solvents, where the API is not fully dissolved. The slurry will be agitated at different temperatures for a number of days. The solids formed will be recovered by filtration and (air dried or vacuum dried).
- API is milled (by mechanical milling or by mortar and pestle), with a drop of solvent, or without any solvent.
- API is melted and cooled (at different cooling rates, fast and slow, and cooled to different temperatures) to obtain solids.
- API is suspended in a solvent or mixture of solvents, and the slurry is placed in a heating/cooling cycle for multiple cycles. The remaining solids after the final cooling cycle will be filtered and (air dried or vacuum dried).
- API is processed to obtain an amorphous form (by melting, milling, solvent evaporation, spray drying or lyophilization). The amorphous form will then be exposed to elevated humidity (or elevated temperature, or combination thereof), or to solvent vapors for extended period of days.
- API is exposed to elevated humidity (or elevated temperature, or combination thereof), or to solvent vapors for extended period of days.
- Two or more polymorphs of the API are mixed in a solvent or solvent systems (some solvent mixtures containing variable amount of water) to obtain a slurry, and the slurry will be agitated (at various temperatures) for an extended period of time (days). The solvent system used can be pre-saturated with the API. The final solids will be filtered and dried (air dried or vacuum dried).
- API is heated to a specific temperature and cooled (at ambient conditions or in a dry box).

The solids obtained are analyzed by XRPD to determine if they are crystalline and, if so, by DSC to see the melting point and by TG to see if they are hydrated/solvated, and by $^1$H NMR spectroscopy to ensure chemical integrity. KF water titration is performed on forms that are hydrated. DVS analysis is performed to evaluate hygroscopicity of the form and if hydrated form is present. In particular variable temperature analyses, including variable temperature XRPD, are performed to assess the stability of each physical form as well as its crystallinity.

Differential scanning calorimetry (DSC) thermograms are obtained using a DSC Q 100 (TA Instruments, New Castle, DE). The temperature axis and cell constant of the DSC cell are calibrated with indium (10 mg, 99.9% pure, melting point 156.6° C., heat of fusion 28.4 J/g). Samples (2.0-5.0 mg) are weighed in aluminum pans on an analytical balance. Aluminum pans without lids are used for the analysis. The samples are equilibrated at 25° C. and heated to 250-300° C. at a heating rate of 10° C./min under continuous nitrogen flow. TG analysis of the samples is performed with a Q 50 (TA Instruments, New Castle, DE). Samples (2.0-5.0 mg) are analyzed in open aluminum pans under a nitrogen flow (50 mL/min) at 25° C. to 210° C. with a heating rate of 10° C./min.

The sample for moisture analysis is allowed to dry at 25° C. for up to 4 hours under a stream of dry nitrogen. The relative humidity is then increased stepwise from 10 to 90% relative humidity (adsorption scan) allowing the sample to equilibrate for a maximum of four hours before weighing and moving on to the next step. The desorption scan is measured from 85 to 0% relative humidity with the same equilibration time. The sample is then dried under a stream of dry nitrogen at 80° C. for 2 hours or until no weight loss is observed.

X-ray powder diffraction data are collected using a Miniflex Tabletop XRD system (Rigaku/MSC, The Woodlands, TX) from 5° to 45°2θ with steps of 0.1°, and the measuring time is 1.0 second/step. All samples are ground to similar size before exposure to radiation. The powder samples are illuminated using CuKα radiation (λ=1.54056 Å) at 30 kV and 15 mA.

Variable temperature XRPD data are collected using a Huber Imaging Plate Guinier Camera 670 employing Ni-filtered CuKα$_1$ radiation (λ=1.5405981 Å) produced at 40 kV and 20 mA by a Philips PW1120/00 generator fitted with a Huber long fine-focus tube PW2273/20 and a Huber Guinier Monochromator Series 611/15. The original powder is packed into a Lindemann capillary (Hilgenberg, Germany) with an internal diameter of 1 mm and a wall thickness of 0.01 mm. The sample is heated at an average rate of 5 Kmi$^{n-1}$ using a Huber High Temperature Controller HTC 9634 unit with the capillary rotation device 670.2. The temperature is held constant at selected intervals for 10 min while the sample is exposed to X-rays and multiple scans are recorded. A 2θ-range of 4.00-100.0° is used with a step size of 0.0050°2θ.

In certain embodiments wherein the solid form is a solvate, such as a hydrate, the DSC thermogram reveals endothermic transitions. In accordance with the observed DSC transitions, TGA analysis indicates stages of weight change corresponding to desolvation or dehydration and/or melting of the sample. In the case of hydrates, these results are in harmony with Karl Fisher titration data which indicate the water content of the sample.

The moisture sorption profile of a sample can be generated to assess the stability of a solid form is stable over a range of relative humidities. In certain embodiments, the change in moisture content over 10.0 to 95.0% relative humidity is small. In other embodiments the change in moisture content over 10.0 to 95.0% relative humidity is reversible.

In certain embodiments, the XRPD pattern of a sample of solid form indicates that the sample has a well-defined crystal structure and a high degree of crystallinity.

Example 2

Evaluation of Metabolic Stability in Human Liver Microsomes
Microsomal Assay: Human liver microsomes (20 mg/mL) are obtained. β-nicotinamide adenine dinucleotide phosphate, reduced form (NADPH), magnesium chloride ($MgCl_2$), and dimethyl sulfoxide (DMSO) are purchased from Sigma-Aldrich.
Determination of Metabolic Stability: 7.5 mM stock preparations of test compounds of the disclosed compounds are prepared in a suitable solvent, such as DMSO. The 7.5 mM stock preparations are diluted to 12.5-50 µM in acetonitrile (ACN). The 20 mg/mL human liver microsomes are diluted to 0.625 mg/mL in 0.1 M potassium phosphate buffer, pH 7.4, containing 3 mM $MgCl_2$. The diluted microsomes are added to wells of a 96-well deep-well polypropylene plate in triplicate. A 10 pL aliquot of the 12.5-50 µM test compound is added to the microsomes and the mixture is pre-warmed for 10 minutes. Reactions are initiated by addition of pre-warmed NADPH solution. The final reaction volume is 0.5 mL and contains 4.0 mg/mL human liver microsomes, 0.25 µM test compound, and 2 mM NADPH in 0.1 M potassium phosphate buffer, pH 7.4, and 3 mM $MgCl_2$. The reaction mixtures are incubated at 37° C., and 50 pL aliquots are removed at 0, 5, 10, 20, and 30 minutes and added to shallow-well 96-well plates which contain 50 pL of ice-cold ACN (acetonitrile) with internal standard to stop the reactions. The plates are stored at 4° C. for 20 minutes after which 100 pL of water is added to the wells of the plate before centrifugation to pellet precipitated proteins. Supernatants are transferred to another 96-well plate and analyzed for amounts of parent remaining by LC-MS/MS using an Applied Bio-systems API 4000 mass spectrometer. The same procedure is followed for the non-deuterated counterpart of the compound and the positive control, 7-ethoxycoumarin (1 µM). Testing is done in triplicate.

Data analysis: The in vitro $T_{1/2}$s for test compounds are calculated from the slopes of the linear regression of % parent remaining (ln) vs incubation time relationship.

$$\text{in vitro } T_{1/2} = 0.693/k$$

k=-[slope of linear regression of % parent remaining (ln) vs incubation time]
The apparent intrinsic clearance is calculated using the following equation:

$$CL_{inc}(\text{mL/min/kg}) = (0.693/\text{in vitro } T)(\text{Incubation Volume/mg of microsomes})(45 \text{ mg microsomes/gram of liver})(20 \text{ gm of liver/kg b.w.})$$

Data analysis is performed using Microsoft Excel Software.
In these experiments, values equal to or more than a 15% increase in half-life are considered to be a significant difference if the apparent intrinsic clearance ratio (comparator compound/new solid form) is >1.15 or <0.85, then there is considered to be significant differentiation.

Example 3

Oral Bioavailability in Rats
Pharmacokinetics of test articles following a single intravenous or oral administration in rats: A pharmacokinetic (PK) study is performed in three male Sprague-Dawley (SD) rats following intravenous (IV) and oral (PO) administration of a compound disclosed herein. Test compounds are measured in plasma.
A detailed description of the in vivo methods.
Rat Strain
Rats used in these studies are supplied by Charles River (Margate UK) and are specific pathogen free. The strain of rats is Sprague Dawley. Male rats are 175-225 g on receipt and are allowed to acclimatize for 5-7 days.
Animal Housing
Rats are group housed in sterilised individual ventilated cages that expose the animals at all times to HEPA filtered sterile air. Animals will have free access to food and water (sterile) and will have sterile aspen chip bedding (at least once weekly). The room temperature is 22° C.+/−1° C., with a relative humidity of 60% and maximum background noise of 56 dB. Rats are exposed to 12-hour light/dark cycles.
Treatment
The test articles are administered in a suitable dose volume for intravenous (IV) or (PO) for oral routes of administration.
Single IV/PO Dose Pharmacokinetics Study in Rats
Each test article is administered as a single IV bolus (via a lateral tail-vein) or a single oral gavage in cohorts of 3 rats per route. Following dose administrations, a 100 µL whole blood sample (EDTA) is collected via the tail-vein at time-points described in Table 1. The blood is centrifuged to separate plasma. Approximately 40 µL of plasma is dispensed per time-point, per rat, in a 96 well plate and frozen until analysis. Bioanalysis is carried out on plasma samples.
Dose Formulation Samples
Dose formulation samples are diluted in two steps with 50:50 (v/v) methanol/water to an appropriate concentration, then diluted 10:90 (v/v) with control matrix to match to the calibration standard in plasma.
Sample Extraction Procedure
Calibration and QC standards, incurred samples, blank matrix and dose formulation samples are extracted by protein precipitation, via the addition of a bespoke acetonitrile (ACN)-based Internal Standard (IS) solution, containing several compounds and including Metoprolol and Rosuvastatin, both of which are monitored for during analysis. Following centrifugation, a 40 µL aliquot of supernatant is diluted by the addition of 80 µL water. The prepared sample extracts are analysed by LC-MS/MS. In one embodiment, the oral bioavailability of a disclosed crystalline solid form is superior to an amorphous or known crystalline form.

Example 4

Solubility Results and Crystallization of Fumarate Salt
Assessment of solubility according to Example 1 demonstrated that the fumarate salt is soluble in many solvents at least at the 5 vol (200 mg/mL) concentration, including acetone, acetonitrile, butanol, dichloromethane, ethanol, methanol, methyl ethyl ketone, tetrahydrofuran and water at 20 degrees Celsius; in isopropyl alcohol (IPA) and dioxane at 40 degrees Celsius, and in 2-methyl tetrahydrofuran (2-MeTHF) at reflux. The salt compound also dissolved in refluxing methylisobutyketone (MIBK) at 15 vol concentration. Consistent with Example 1, the solutions formed were cooled and the IPA, 2-MeTHF and MIBK solutions yielded solid material on cooling. The solid product obtained from MIBK was analyzed by XRPD, TG and $^1$H NMR—the XRPD diffractogram is provided as FIG. 1 and the $^1$H NMR spectrum is provided as FIG. 2.

Example 5

Production of the Hemifumarate Salt

Figure 3:
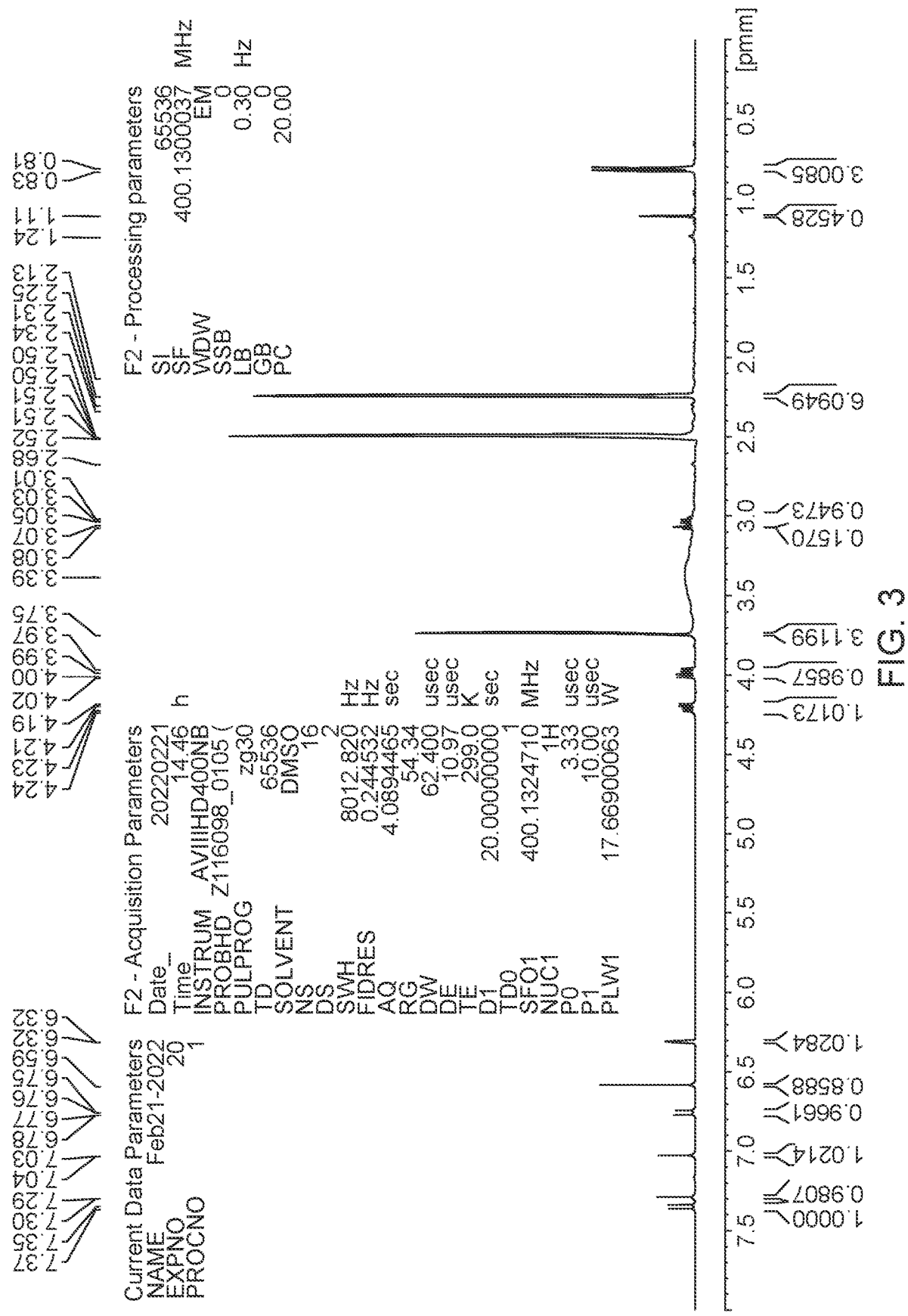
FIG. 3 provides an $^1$H NMR spectrum for crystalline compound 1 hemifumarate Form I/Pattern 2.
Figure 4:
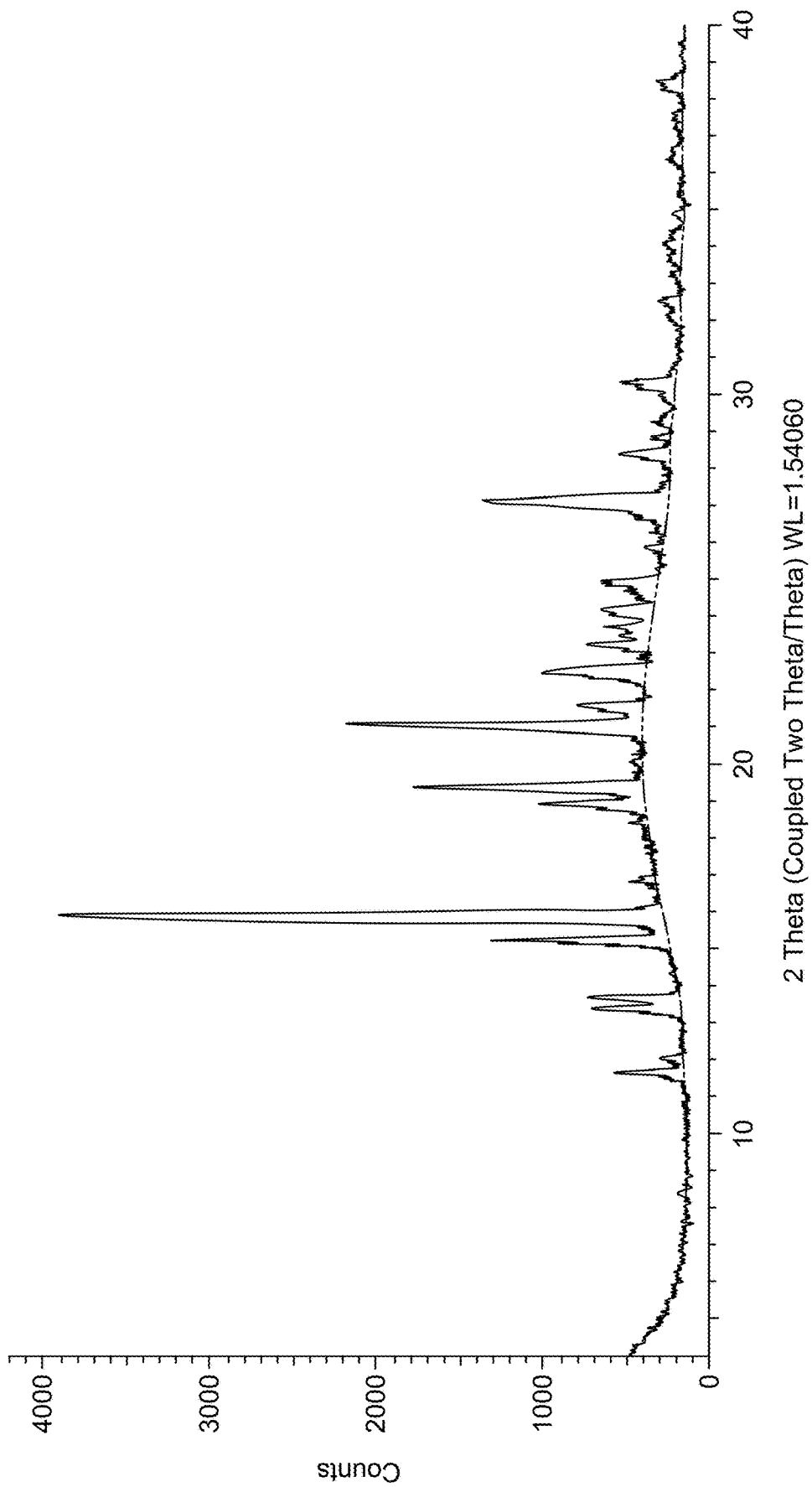
FIG. 4 provides an XRPD diffractogram for crystalline Compound 1 hemifumarate Form I/Pattern 2. XRPD signals observed in this diffractogram are characterized in Table 33.

This example describes the production of (R)-1-(5-methoxy-1H-indol-1-yl)-N,N-dimethylpropan-2-amine hemifumarate. (R)-1-(5-methoxy-1H-indol-1-yl)-N,N-dimethylpropan-2-amine fumarate and free base compound in equimolar amounts were dissolved in 10 vol methanol with heating. The resultant solution was concentrated to dryness and the solid residue was analyzed by $^1$H NMR, XRPD and DSC. The $^1$H NMR spectrum for the hemifumarate product is provided as FIG. 3. This sample comprised crystalline material having Pattern 2, as illustrated in FIG. 4.

Example 6

Production of Compound 1 Fumarate and Hemifumarate Solid Forms

Figure 5:
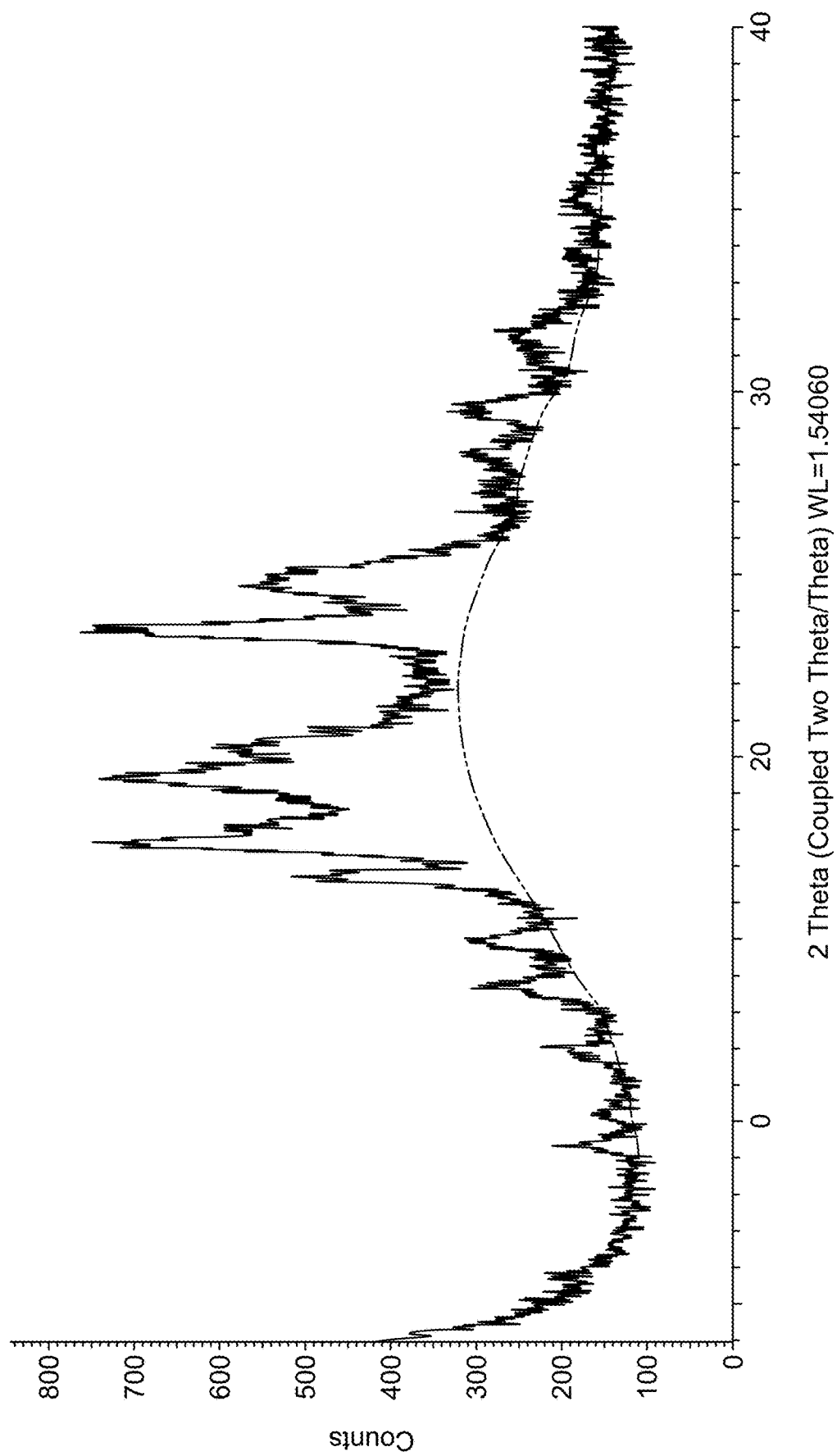
FIG. 5 provides an XRPD diffractogram for a sample produced according to Example 5 comprising crystalline Compound 1·monofumarate Form B/Pattern 3b. XRPD signals observed in this diffractogram are characterized in Table 32.
Figure 6:
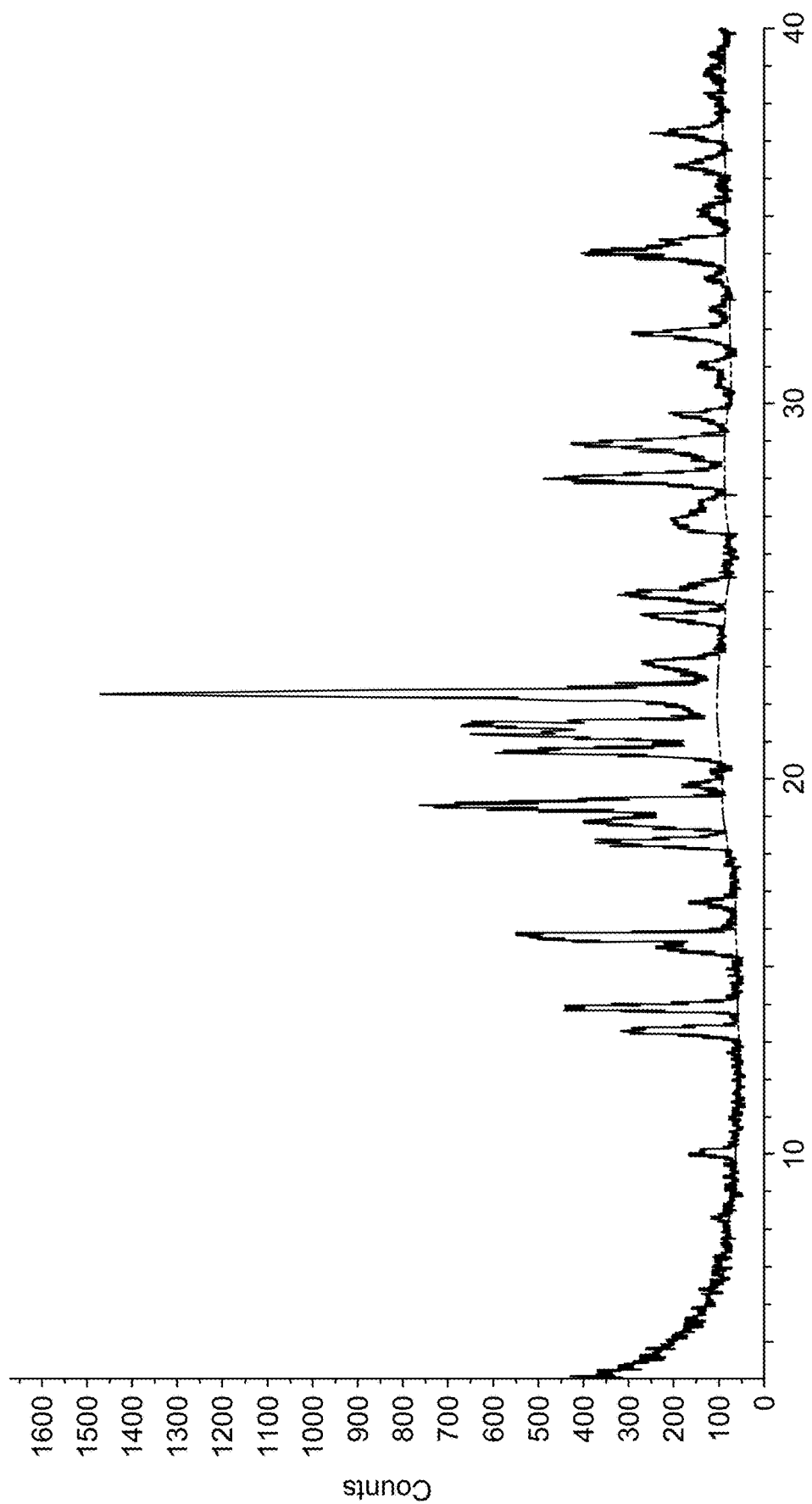
FIG. 6 provides an XRPD diffractogram for a sample produced according to Example 5 comprising crystalline Compound 1·monofumarate Pattern 1. XRPD signals observed in this diffractogram are characterized in Table 5.
Figure 8:
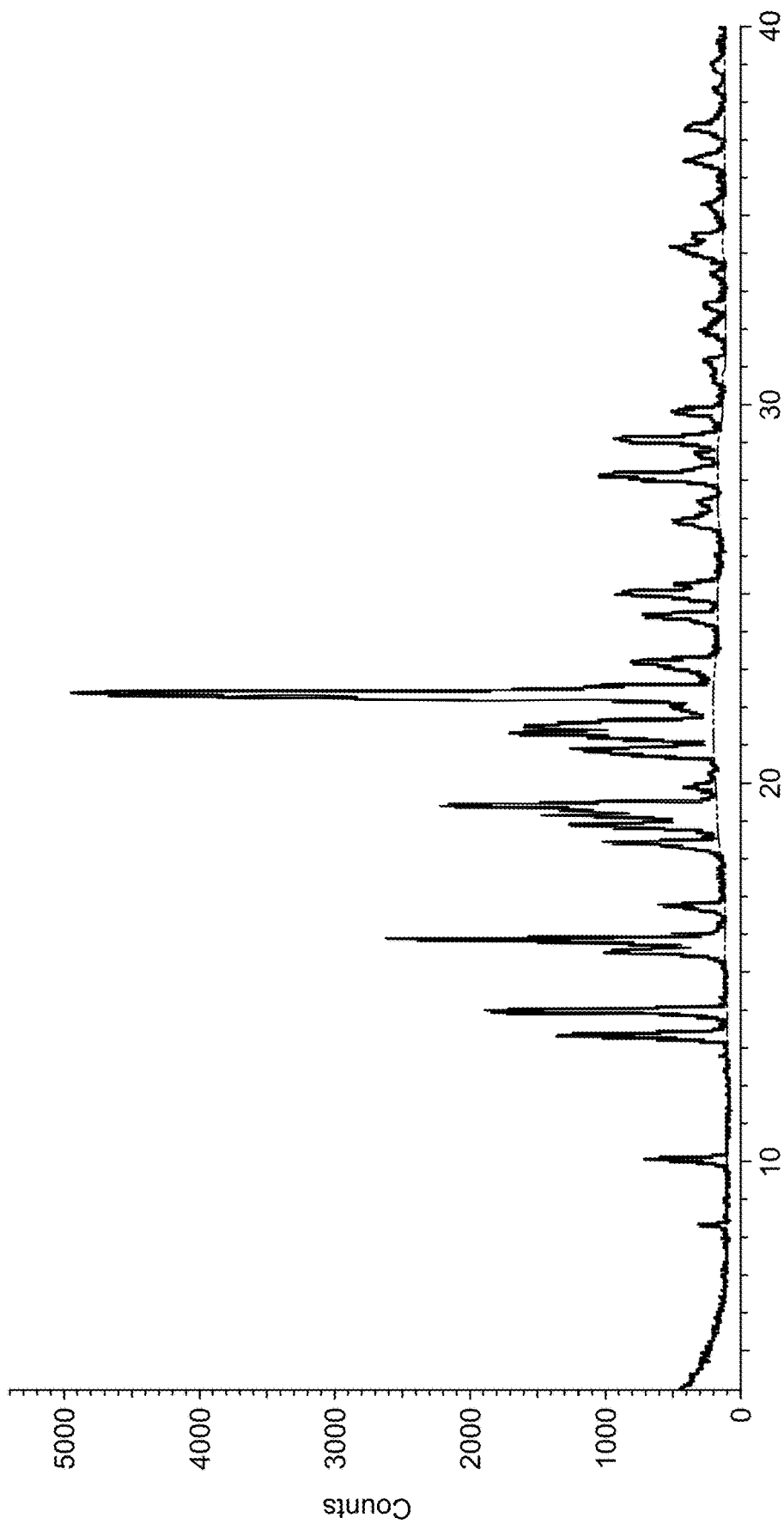
FIG. 8 provides an XRPD diffractogram for a sample comprising crystalline Compound 1 monofumarate Pattern 1. XRPD signals observed in this diffractogram are characterized in Table 6.
Figure 9:
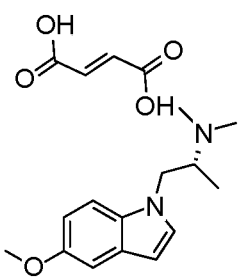
FIG. 9 shows the chemical structure of compound 1

This example describes the production of Compound 1 fumarate solid forms using suspension (slurry) equilibration consistent with Example 1. Stable suspensions were observed after stirring for 3-7 days at 20° C. in five solvents: Stirring of the fumarate salt with MTBE (methyl-t-butyl ether), ethyl acetate, isopropyl acetate, methyl ethyl ketone and 2-methyl tetrahydrofuran yielded solid forms. The solid forms were isolated from these five solvents via centrifugation and were characterized by XRPD, TGA, DSC and $^1$H NMR. Isolation from MTBE according to this example yielded Compound 1 fumarate comprising Pattern 3b as illustrated in FIG. 5. Isolation from isopropyl acetate yielded pattern 3a when wet and upon drying Pattern 1 as illustrated in FIG. 6. Isolation from ethyl acetate gave the same Patterns as from isopropyl acetate. Isolation from methyl ethyl ketone yielded material having XRPD Pattern 6, which, upon drying under nitrogen yielded material having Pattern 1 as illustrated in FIG. 8. Isolation from 2-methyl THF yielded a solid sample comprising crystalline material of Pattern 1.

Figure 7:
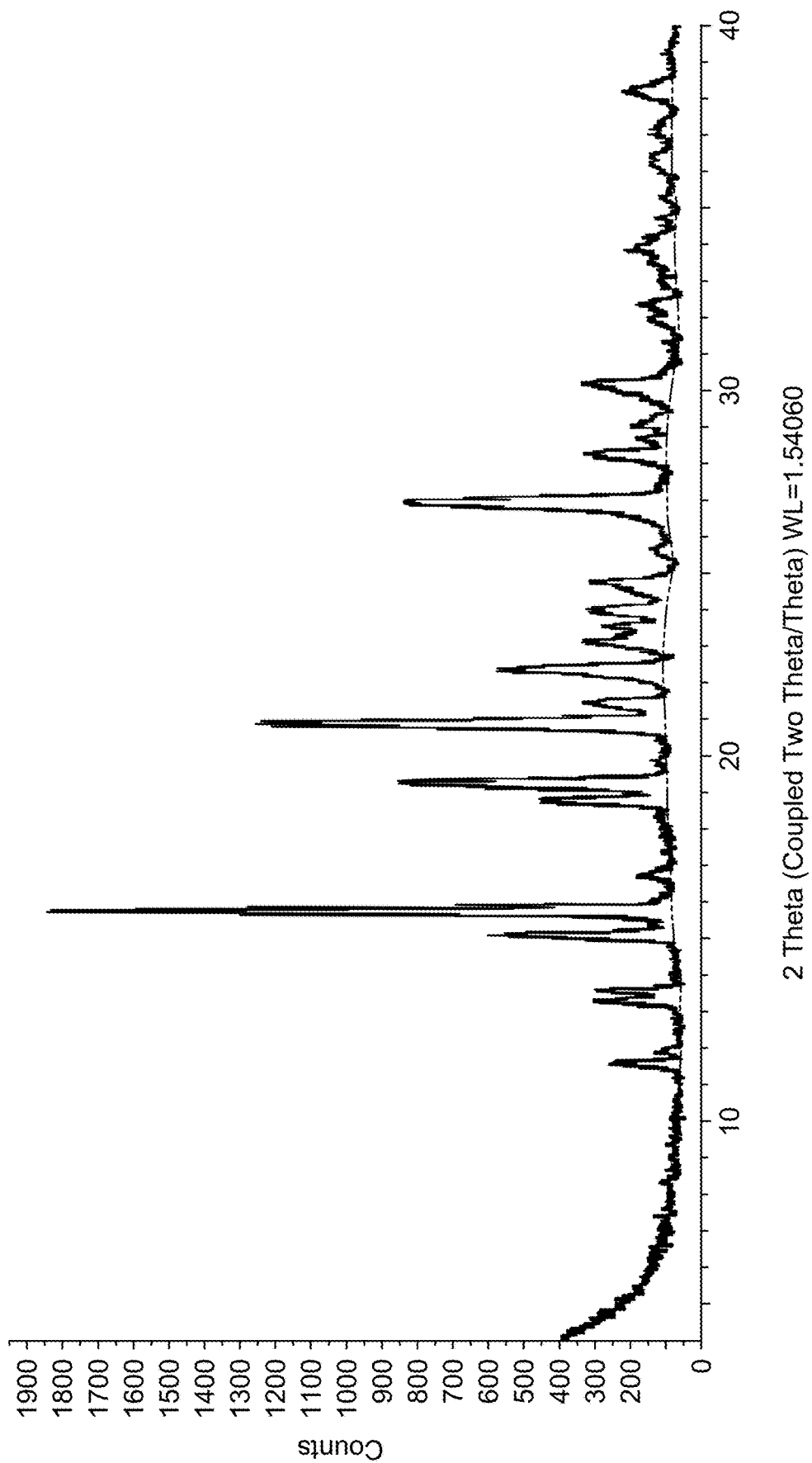
FIG. 7 provides an XRPD diffractogram for a sample comprising crystalline Compound 1·hemifumarate Form II/Pattern 4. XRPD signals observed in this diffractogram are characterized in Table 35.

Hemifumarate prepared according to Example 5 was suspended in MTBE and stirred, yielding, following isolation via centrifugation and drying, crystalline hemifumarate of Pattern 4 as illustrated in FIG. 7.

Example 7 Screening for Crystalline Polymorphs of Compound 1 Fumarate Salt

Summary

Compound 1 was supplied as the amorphous Compound 1·Fumarate salt form (batch: 1). The fumarate stoichiometry was 1.0 API to 1.0 fumaric acid. Fumaric acid is a 1,4-dicarboxylic acid and is mono-salified; hence, the salt as supplied, is technically a hydrogen fumarate acid salt. There was a risk that compound 1·Fumarate may re-proportionate into compound 1·0.5Fumarate±0.5 fumaric acid; or disproportionate into discrete non-ionised entities, i.e., compound 1·Native+fumaric acid. Therefore, any manufacturing crystallisation involved complete dissolution of each precursor, otherwise there was a risk that regions of compound 1·Fumarate, compound 1·0.5Fumarate, non-ionised compound 1 and non-ionised fumaric acid may occur in the solid 20 phase. Chemically, the pendant, dimethyl amine of compound 1, is incapable of Michael addition to the fumaric acid counter ion. Cleavage of the methoxy substituent on the indole ring of compound 1, was judged unlikely; however, may only occur at v. low pH. Esterification of the fumaric acid counterion by several alcohols was possible. Researchers were cognizant of this and monitored accordingly by $^1$H NMR.

Important Findings Summary

Compound 1·MonoFumarate Form A (previously assigned Pattern #1) was the stable form that was selected to be incorporated into the salt screen stability evaluation panel.

Monofumarate Form A was a single phase and was accessible via crystallisation from multiple solvents.

Compound 1·MonoFumarate Form B (previously Pattern #3b), exhibited a shallow melt event and is most likely a metastable phase; several attempts were made to re-prepare Form B and Form A was always generated instead.

Two forms of Compound 1·0.5Fumarate (hemi-salt) were identified, these were assigned Form I and Form II.

The remainder of the products were classified 'Patterns' and corresponded to mixed phases that exhibited multiple thermal events.

Analytical data collected for Monofumarate Form A, Hemifumarate Form I, Monofumarate Form B, and Hemifumarate Form II are summarized in

TABLE 56

Pattern summary table

| Final solvent contact | Initial designation by XRPD Pattern | Solvent content (% w/w) | $^{1H}$NMR API molecular i.d. | Stoichiometry Compund 1 to Fumaric acid | TGA (% Δwt.) | TGA (comment) | DSC Single melt event? | Thermal events | Form assignment |
|---|---|---|---|---|---|---|---|---|---|
| Stirred in iPAC | Pattern #1 | iPAC (0.5) | Consistent with compound 1 | 1 to 1 | Ablated (−59.4% w/w, 208.6° C.) | Anhydrous | Yes | −50.05 Jĝ−1 (110.98° C.), −218.11 Jĝ−1 (198.22° C.) | Form A |
| Stirred in tBME | Pattern #2 | tBME (1.3) MeOH (0.5) | Consistent with compound 1 | 2 to 1 | Ablated (−65.5% w/w, 200.4° C.) | Anhydrous | No, one sharp endotherm early on | −52.66 Jĝ−1 (91.5° C.), −256.86 | Form I |

TABLE 56-continued

Pattern summary table

| Final solvent contact | Initial designation by XRPD Pattern | Solvent | API content (% w/w) | ¹H NMR API molecular i.d. | Stoichiometry Compund 1 to Fumaric acid | TGA TGA (% Δwt.) | TGA (comment) | DSC Single melt event? | Thermal events | Form assignment |
|---|---|---|---|---|---|---|---|---|---|---|
| | | | | | | | | with a broad peak later | Jg^−1 (248.07° C.) | |
| Stirred in tBME | Pattern #3b | tBME (0.1) | | Consistent with compound 1 | 1 to 1 | Ablated (−62.7% w/w, 208.7° C.) | Anhydrous | Yes, but shallow and broad | −22.04 Jg^−1 (56.3° C.), | Form B |
| Stirred in tBME | Pattern #4 | tBME (n.d.) | | Consistent with compound 1 | 2 to 1 | Ablated (−69.5% w/w, 216.4° C.) | Anhydrous | Yes | −5.41 Jg^−1 (90.46° C.) | Form II |

No evidence for hydrate formation was observed, including several weeks at 40° C./75% RH and aqueous slurries.
DVS mass per unit time equlibrated @ dm/dt (0.0002%/min) on Form A was performed (specimen was deliquescent by DVS).
SCZRD of Form A was solved and reported.

TABLE 56

Pattern summary table

| Final solvent contact | Initial designation by XRPD Pattern | Solvent | API content (% w/w) | ¹H NMR API molecular i.d. | Stoichiometry Compound 1 to Fumaric acid | TGA TGA (% Δwt.) | TGA (comment) | DSC Single melt event? | Thermal events | Form assignment |
|---|---|---|---|---|---|---|---|---|---|---|
| Stirred in iPAC | Pattern #1 | iPAC (0.5) | | Consistent with compound 1 | 1 to 1 | Ablated (−59.4% w/w, 208.6° C.) | Anhydrous | Yes | −50.05 Jg^−1 (110.98° C.), −218.11 Jg^−1 (198.22° C.) | Form A |
| Stirred in tBMR | Pattern #2 | tBME (1.3) MeOH (0.5) | | Consistent with compound 1 | 2 to 1 | Ablated (−65.5% w/w, 200.4° C.) | Anhydrous | No, one sharp endotherm early on with a broad peak later | −52.66 Jg^−1 (91.5° C.), −256.86 Jg^−1 (248.07° C.) | Form I |
| Stirred in tBME | Pattern #3b | tBME (0.1) | | Consistent with compound 1 | 1 to 1 | Ablated (−62.7% w/w, 208.7° C.) | Anhydrous | Yes, but shallow and broad | −22.04 Jg^−1 (56.3° C.), | Form B |
| Stirred in tBME | Pattern #4 | tBME (n.d.) | | Consistent with compound 1 | 2 to 1 | Ablated (−69.5% w/w, 216.4° C.) | Anhydrous | Yes | −5.41 Jg^−1 (90.46° C.), | Form II |

TABLE 57

Summary of the powder patterns identified during polymorph screen and accompained by their analytical data.

| Designation | Solvent | DSC Event | Thermal measurements | TGA % Δwt | TGA Comment | ¹H NMR (stoich.) | ¹H NMR (solvent) | Form Assignment |
|---|---|---|---|---|---|---|---|---|
| Amorphous | DCM & THF | Complex thermal profile | Integral −1.12 Jg^−1 Onset 120.22° C. Peak 122.00° C. Endset 125.46° C. | −4.2%, 120° C.; (−53.0% w/w, 218.8° C.) | Stepped baseline (de-solvation) | 1 to 1 (API to fumarate) | DCM (1.2% w/w) + THF (1.5% w/w) | Amorphous |
| PATTERN #1 | Various (e.g. iPAc, | Single melt | Integral −50.02 Jg^−1 Onset 110.98° C. | Ablated (−59.4% | Flat baseline | 1 to 1 (API to | iPrOAc (0.5% | Form A |

TABLE 57-continued

Summary of the powder patterns identified during polymorph screen and accompained by their analytical data.

| | | | DSC | | TGA | | ¹H NMR | ¹H NMR | |
| | | | | Thermal | | | ¹H NMR | ¹H NMR | Form |
| Designation | Solvent | Event | | measurements | % Δwt | Comment | (stoich.) | (solvent) | Assignment |
|---|---|---|---|---|---|---|---|---|---|
| | acetone, 2Me-THF, CPME, MEK) | | Peak Endset | 116.17° C. 118.11° C. | w/w, 208.6° C.) | (anhydrous) | fumarate) | w/w) | |
| PATTERN #2 | IPA | Single melt | Integral Onset Peak Endset | −52.66 Jg^−1 87.48° C. 91.50° C. 94.55° C. | Ablated (−65.5% w/w, 200.4° C.) | Flat baseline (anhydrous) | 2 to 1 (API to fumarate) | tBME (1.3% w/w), methanol (0.5% w/w) | Form I |
| PATTERN #3a | EtOAc | — | — | — | — | — | — | — | N/A (Pattern #3a) |
| ⌇ | EtOAc | Small secondary and main single melt | Integral Onset Peak Endset | −10.53 Jg^−1 67.88° C. 76.50° C. 81.04° C. | Ablated (−60.7% w/w, 208.5° C.) | Flat baseline (anhydrous) | 1 to 1 (API to fumarate) | etOAC (0.6% w/w) | Form A |
| | EtOAc | | Integral Onset Peak Endset | −35.88 Jg^−1 112.05° C. 114.33° C. 117.58° C. | | | | | |
| PATTERN #3b | tBME | Single event | Integral Onset Peak Endset | −22.04 Jg^−1 56.30° C. 66.17° C. 71.17° C. | Ablated (−62.7% w/w, 208.4° C.) | Flat baseline (anhydrous) | 1 to 1 (API to fumarate) | tBME (0.1% w/w) | Form B (disordered; attempts to reprepare gave Form A) |
| PATTERN #4 | tBME | Single melt | Integral Onset Peak Endset | −56.11 Jg^−1 90.46° C. 97.17° C. 101.96° C. | Ablated (−69.4% w/w, 216.4° C.) | Flat baseline (anhydrous) | 2 to 1 (API to fumarate) | Methonal n.d., tBME (0.06% w/w) | Form II |
| PATTERN #5 | MIBK (20.0 vol), crystallised on cooling. | — | — | — | — | — | — | — | N/A (Pattern #5) |
| ⌇ | Oven dried T1 and converted to T2 when dried. | — | — | — | De-solv. (−12.7% w/w, 126.2° C.); Ablated (−60.1% w/w, 218.0° C.) | Stepped baseline (de-solvation) | 1 to 1 (API to fumarate); hemi-solvate | MIBK (11.1% w/w); (22.3% w/w th., unary solvate) | Not analysed (attempts to reprepare gave Form A) |
| PATTERN #6 | MEK | — | — | — | — | — | — | — | N/A (Pattern #6) |
| ⌇ | MEK | Single melt | — Onset Peak Endset | — 113.23° C. 116.61° C. 119.49° C. | Ablated (−75.2% w/w, 210° C.) | Anhydrous | 1 to 1 (API to fumarate) | MEK (0.18% w/w) | Form A |

TABLE 58

Summary of Characterization Data for the Form A crystalline fumarate salt of compound 1

| Provenances of reference batches | Compound 1.MonoFumarate (Form A, Pattern #1) |
|---|---|
| Batch 1. obtained from suspension equilibration of amorphous compound 1 in MEK (2.5 vol) at 20° C. The product was isolated by filtration and oven-dried under vacuum over 20 h at 40° C. Refer to FIGS. 12, 24, 25, 26, 27, 51, | Molecular weight: 348.399 gmol$^{-1}$<br>Exact molecular weight: 348.168<br>Molecular formula: $C_{18}H_{24}N_2O_5$<br>Unary fumarate: 33.3% w/w th., fumaric acid (i.e., 1.0 mol of API to 1.0 mol fumaric acid)<br>Nature of hydrogen bonding: Hydrogen-bond between oxygen atoms O5 and O3 of fumaric acid 2.590A. Salified between N2 and O2 2.656A.<br>Crystal system 100(2): orthorhombic<br>Space group 100(2): P2$_1$2$_1$2$_1$<br>Unit cell 100(2) K: a = 9.03500(10) Å, b = 9.44030(10) Å, c = 21.0000(2) Å, a = b = g = 90°, V = 1791.16(3) Å$^3$ |

TABLE 58-continued

Summary of Characterization Data for the Form A crystalline fumarate salt of compound 1

Figure 103:
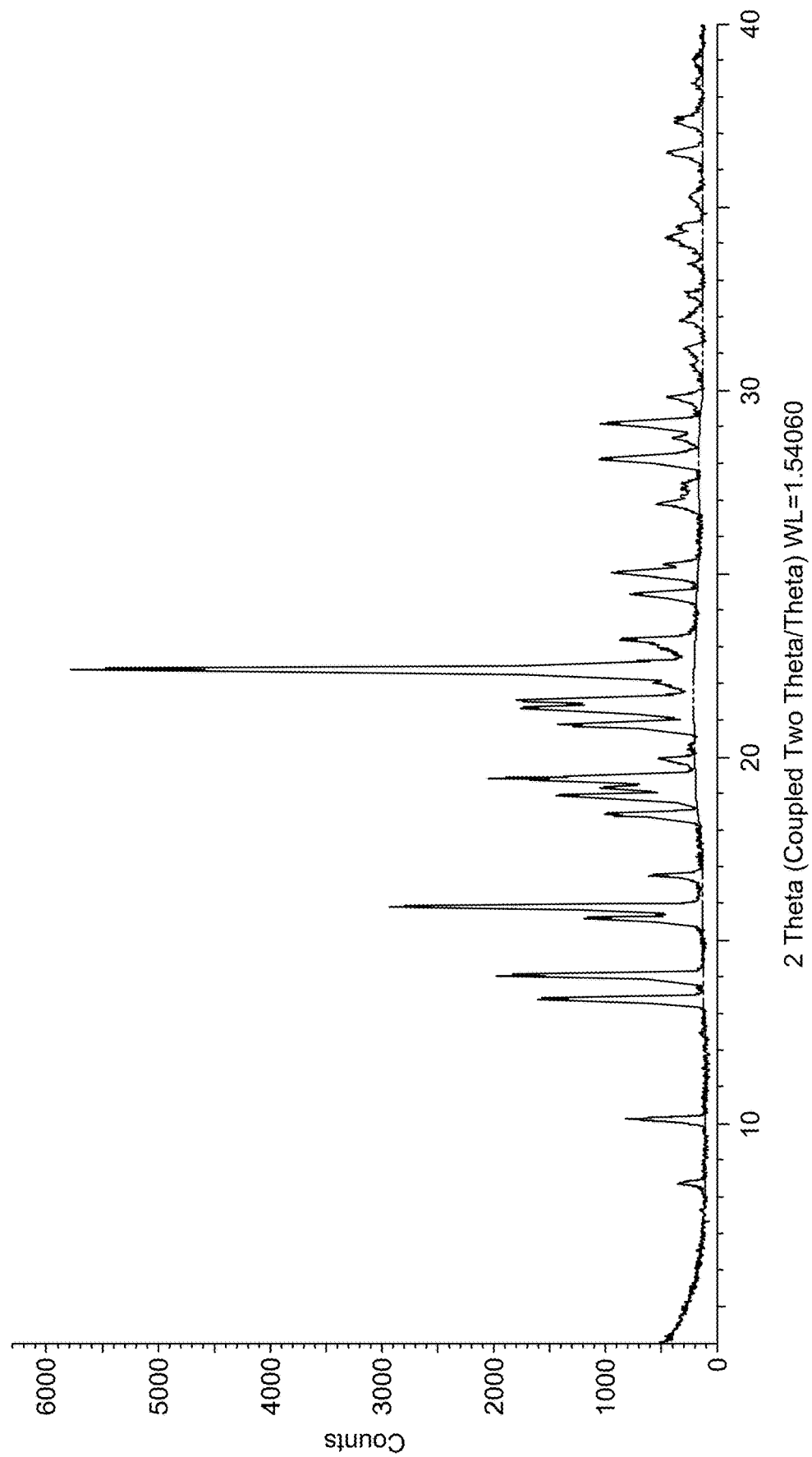
FIG. 103 shows a XRPD profile of crystalline compound 1 monofumarate Form A.
Figure 104:
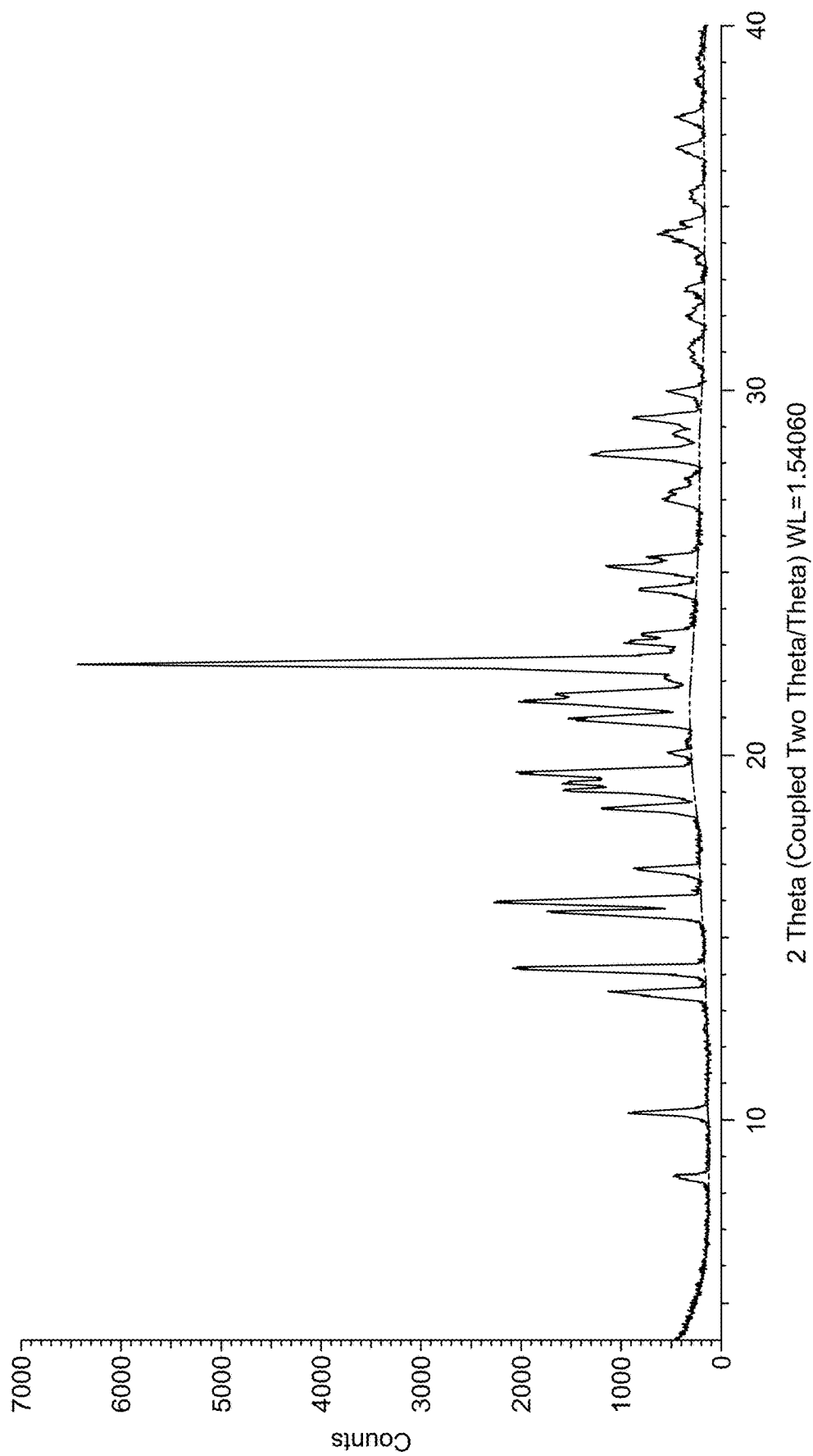
FIG. 104 shows a XRPD profile of crystalline compound 1 monofumarate (Pattern #1, Form A)
Figure 105:
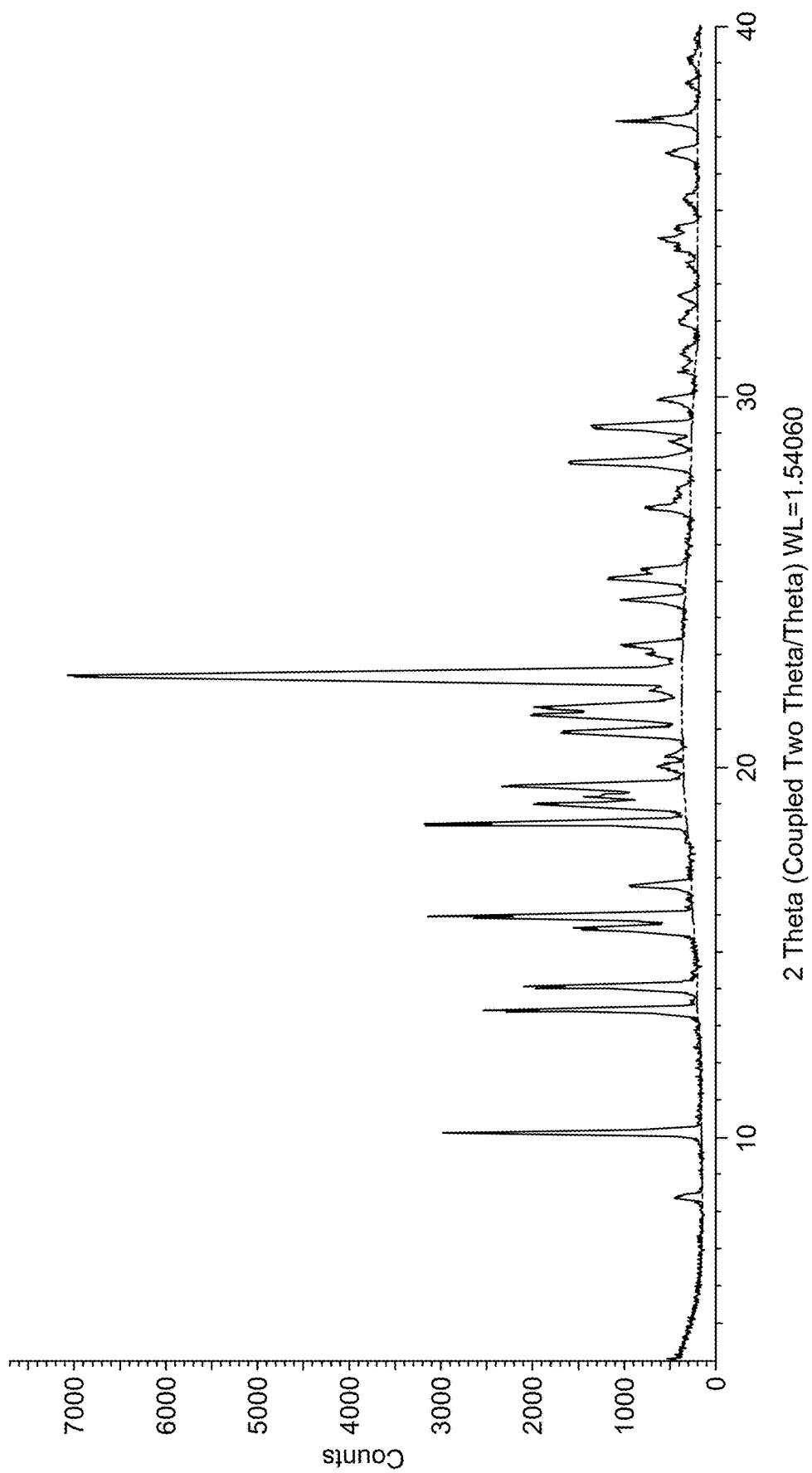
FIG. 105 shows a XRPD profile of crystalline compound 1 monofumarate (Pattern #1, Form A)
Figure 106:
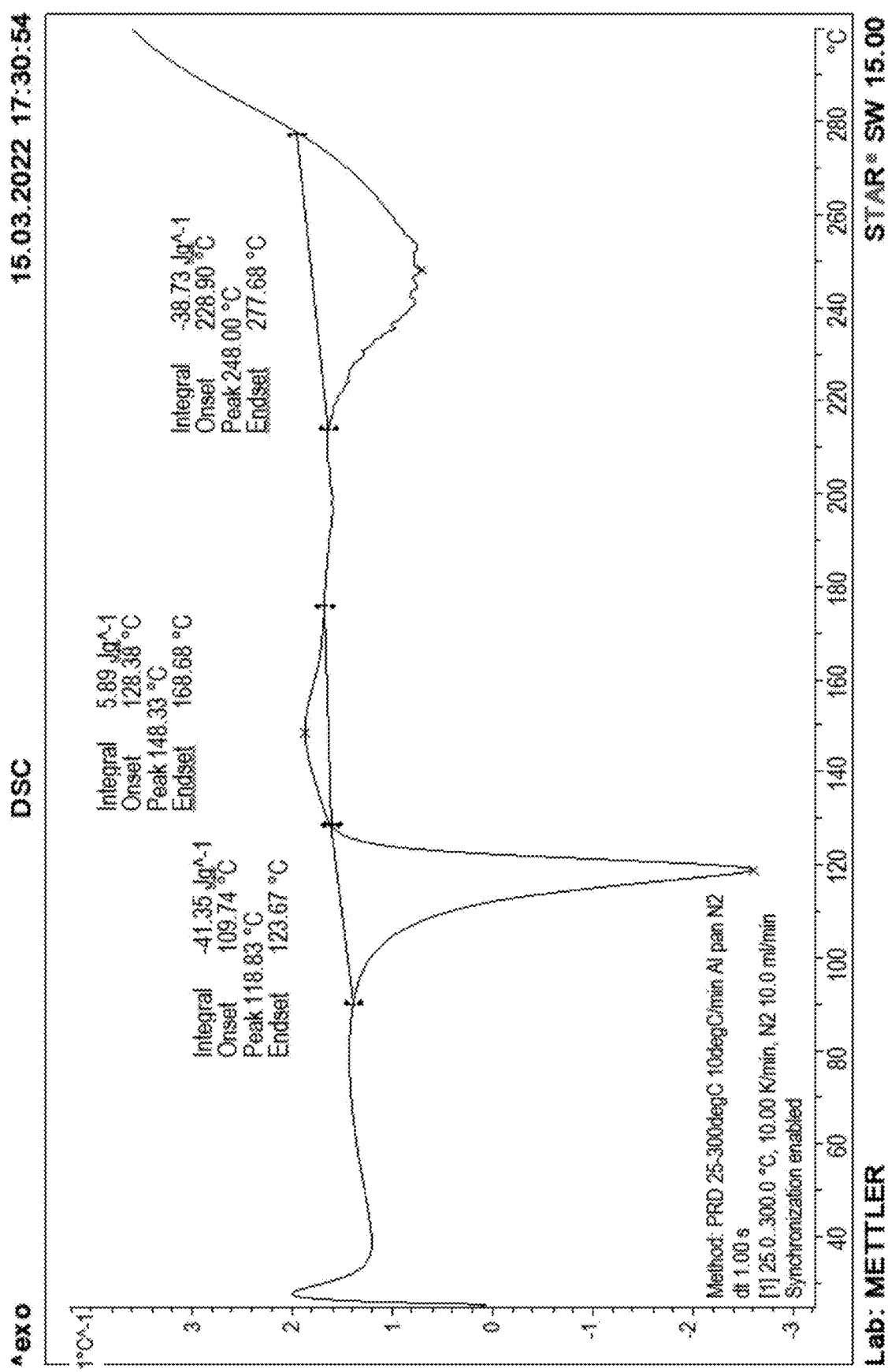
FIG. 106 shows a DSC profile of crystalline compound 1 monofumarate, analysis was acquired at a ramp rate of +10° C./minute.
Figure 107:
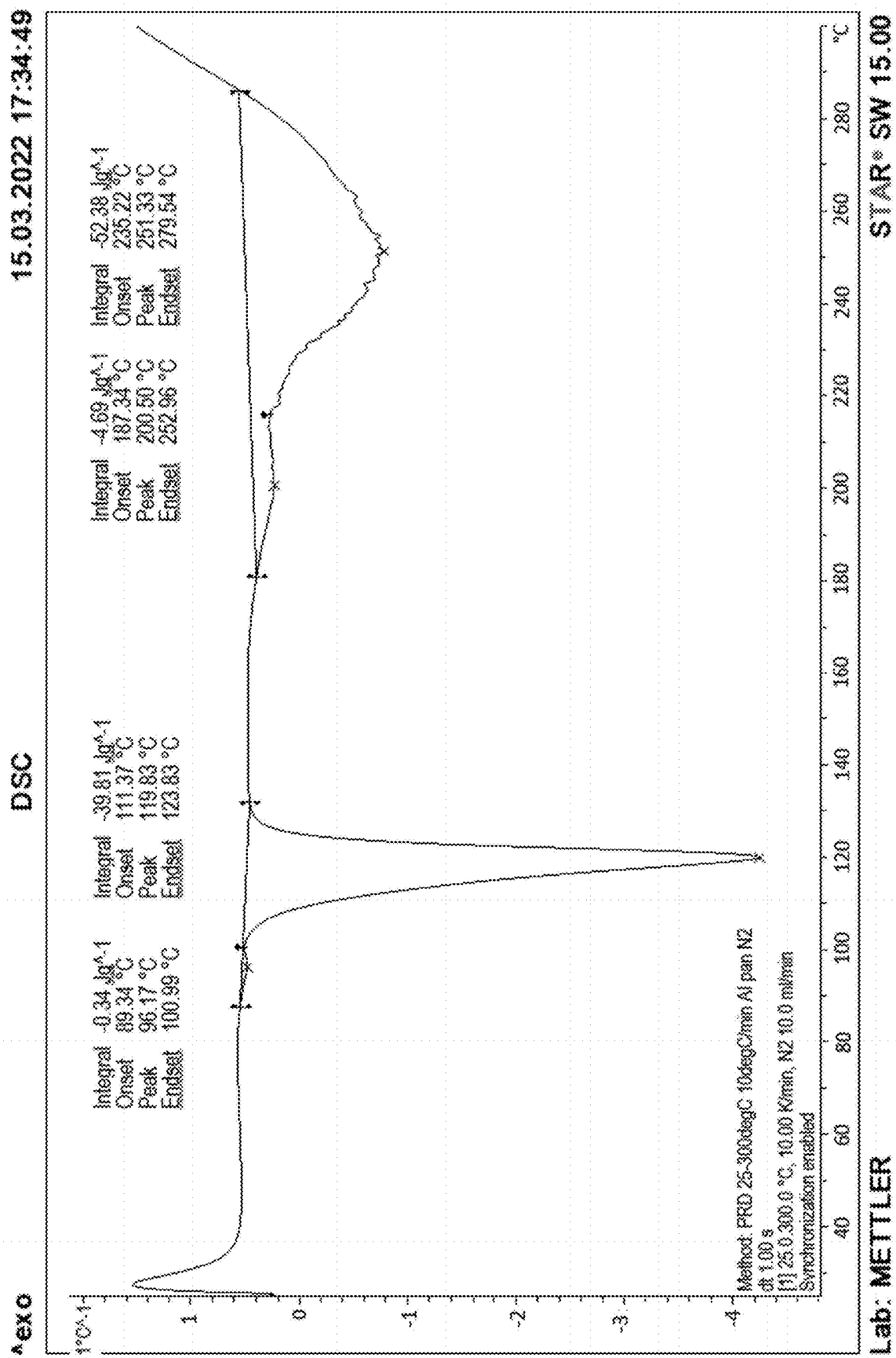
FIG. 107 shows a DSC profile of crystalline compound 1 monofumarate, analysis was acquired at a ramp rate of +10° C./minute.
Figure 108:
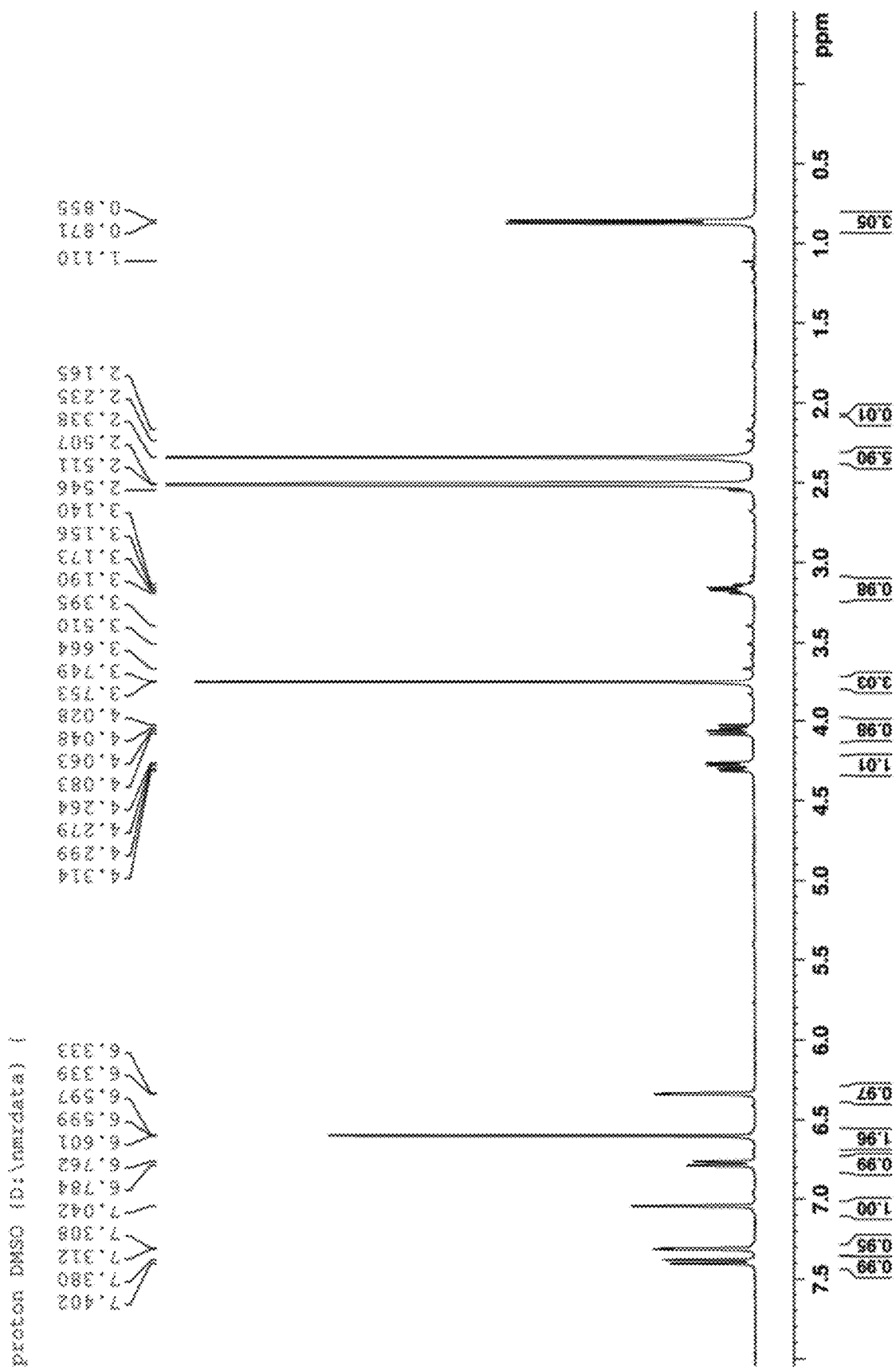
FIG. 108 shows a $^1$H NMR spectrum of crystalline compound 1 monofumarate, spectrum was acquired in DMSO-$d_6$ and calibrated to the non-deuterated solvent residual at 2.50 ppm. MEK and tBME n.d.
Figure 109:
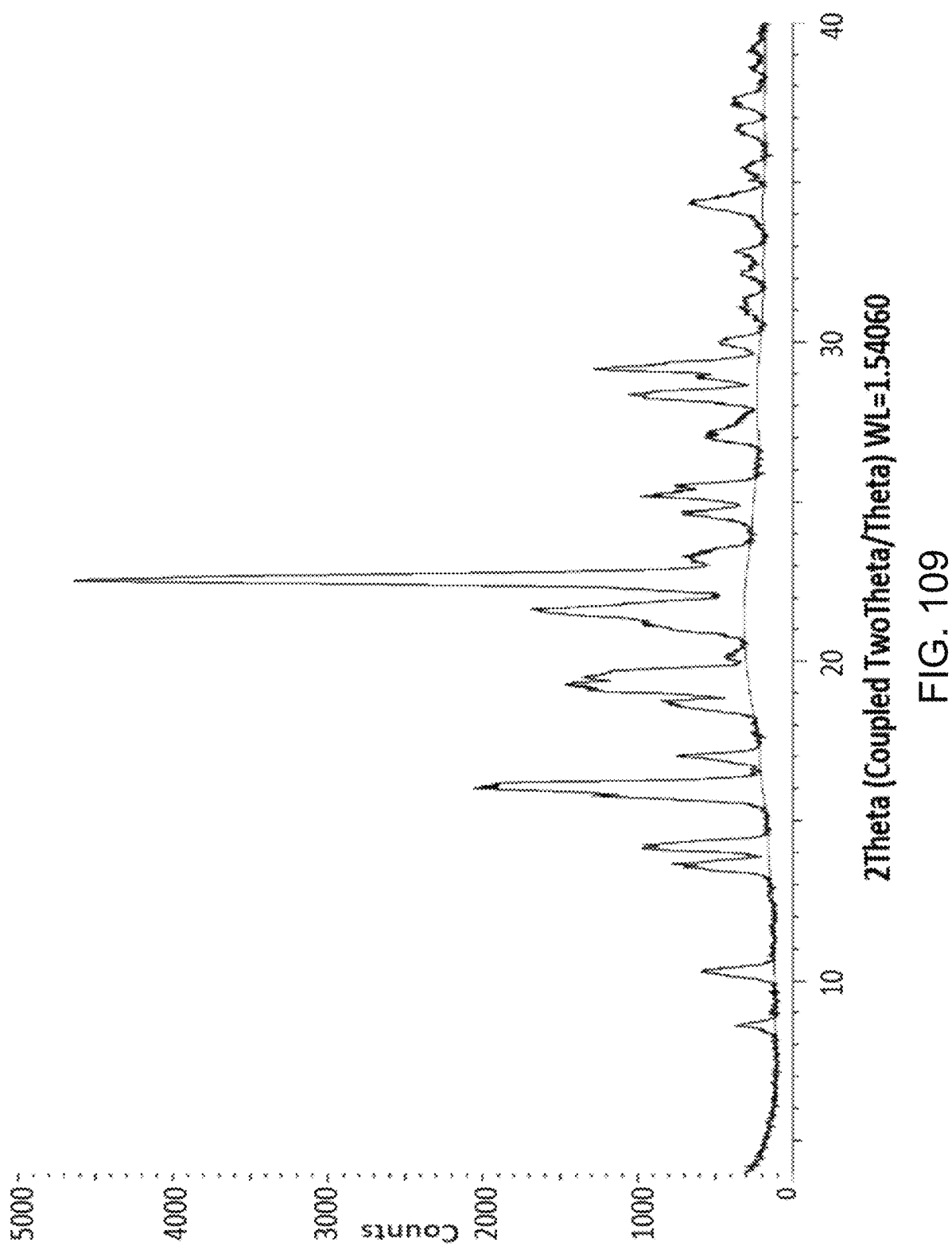
FIG. 109 shows a XRPD profile of crystalline compound 1 monofumarate (Pattern #1, Form A)
Figure 110:
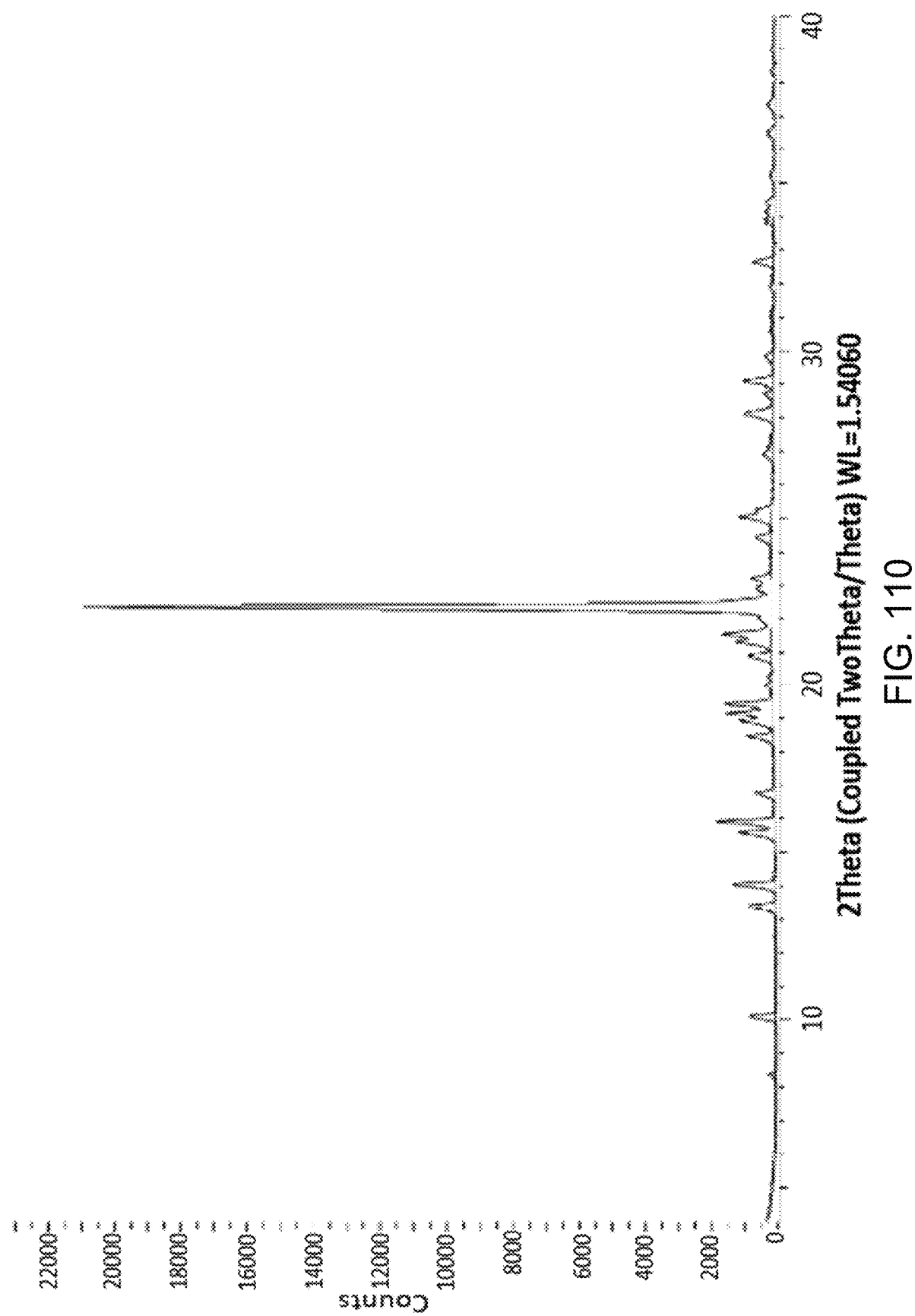
FIG. 110 shows a XRPD profile of crystalline compound 1 monofumarate (Pattern #1)
Figure 111:
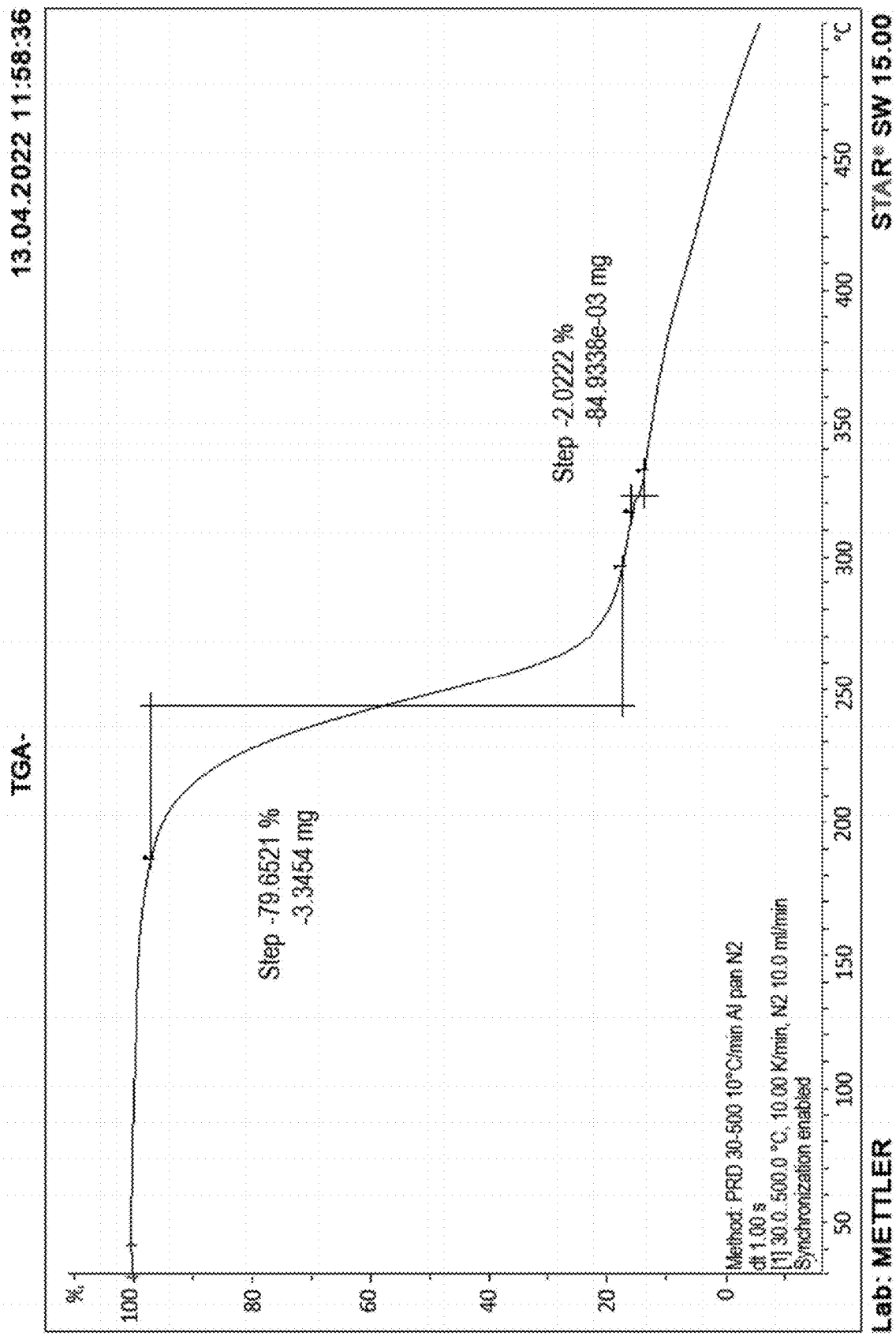
FIG. 111 shows a TGA thermogram of crystalline compound monofumarate, analysis was acquired at a ramp rate of +10° C./minute.
Figure 112:
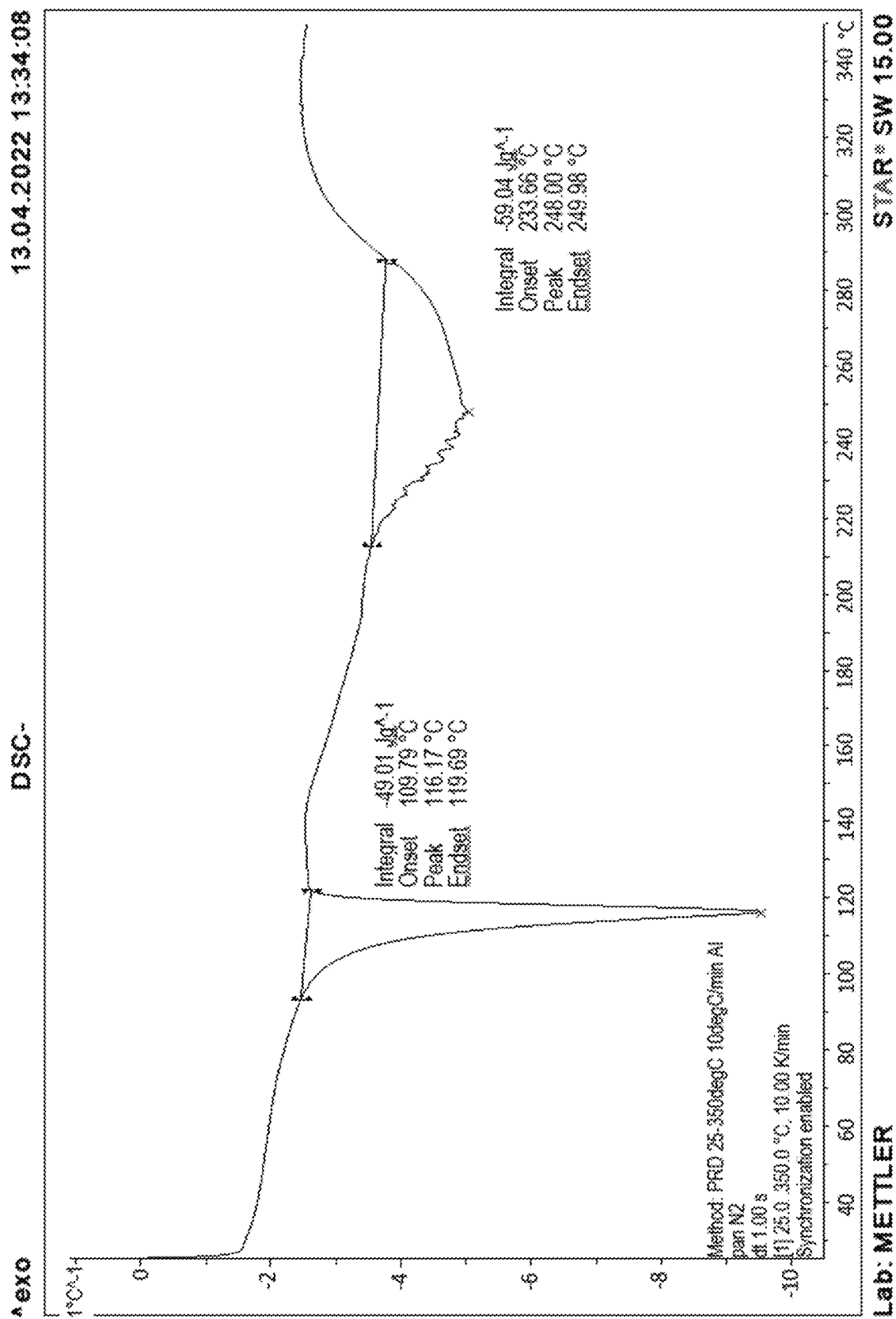
FIG. 112 shows a DSC profile of crystalline compound 1 monofumarate, analysis was acquired at a ramp rate of +10° C./minute.
Figure 113:
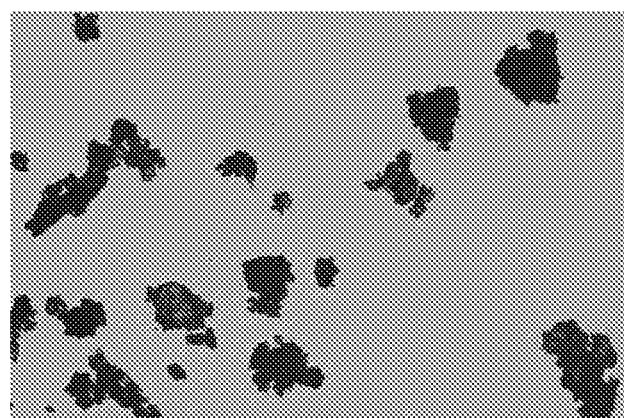
FIG. 113 shows a magnified image of crystalline compound 1 monofumarate, normal polarised (magnification× 2).
Figure 114:
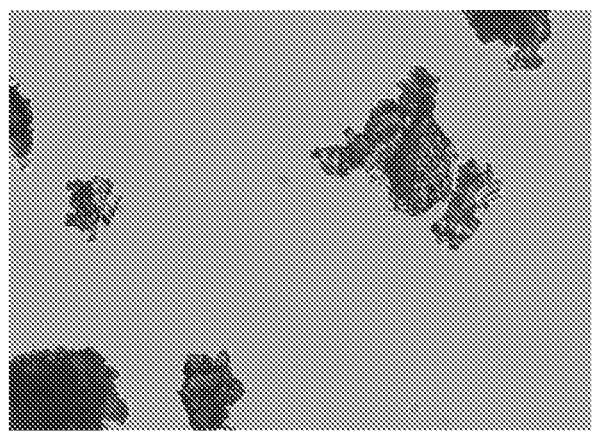
FIG. 114 shows a magnified image of crystalline compound 1 monofumarate, normal polarised (magnification× 5).
Figure 115:
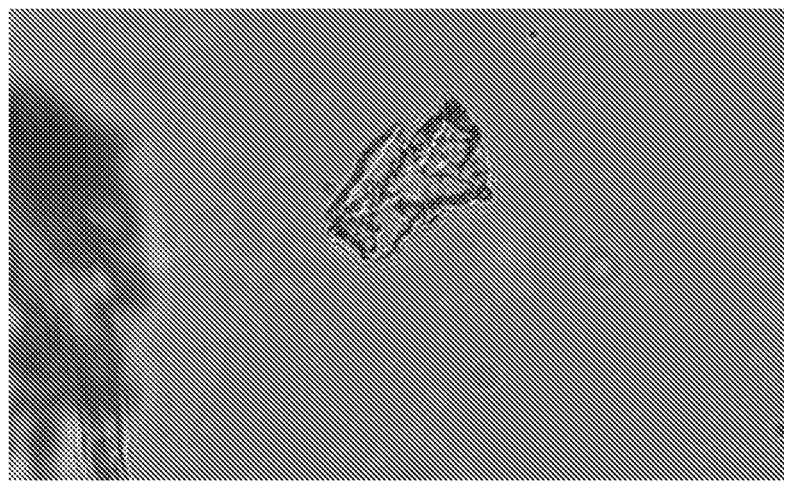
FIG. 115 crystalline compound 1 monofumarate, normal polarized (magnification×25).
Figure 116:
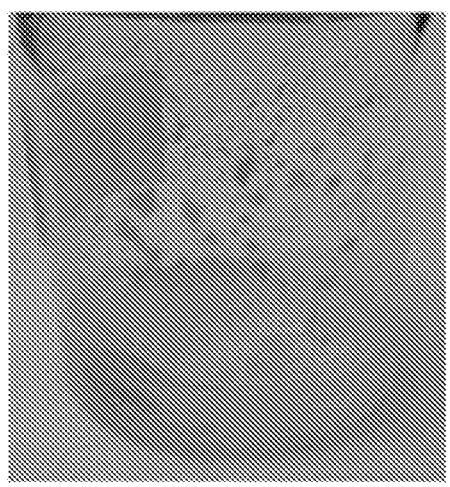
FIG. 116 shows the result of vapor diffusion experiment in MEK with tBME as diffusant solvent (t=92 h)
Figure 117:
FIG. 117 shows the results of vapor diffusion experiment with butanol as solvent and heptane as diffusion solvent (t=92 h).
Figure 118:
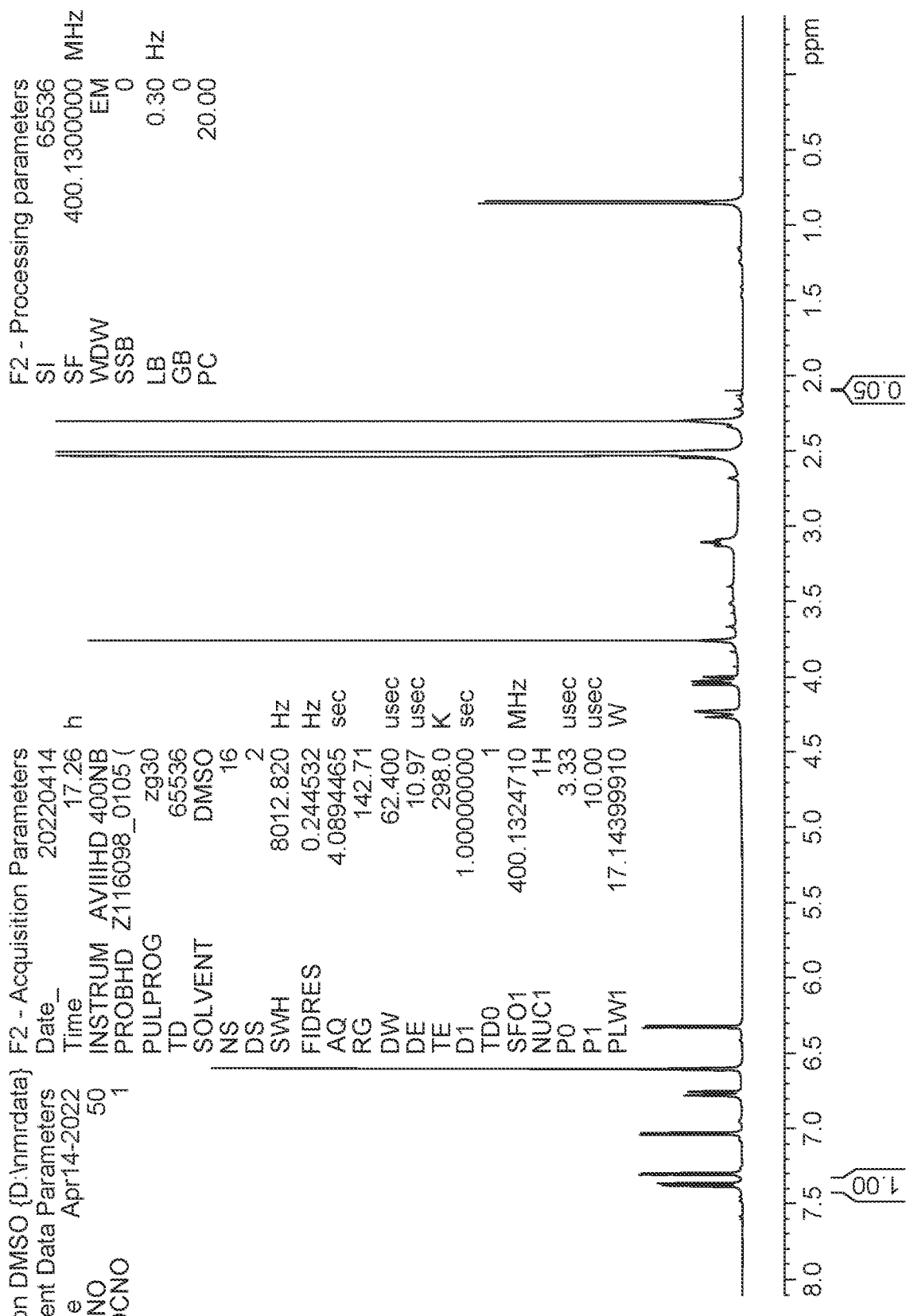
FIG. 118 shows a $^1$H NMR spectrum of crystalline compound 1 monofumarate, spectrum was acquired in DMSO-$d_6$ and calibrated to the non-deuterated solvent residual at 2.50 ppm. Acetone content, 0.3% w/w.
Figure 119:
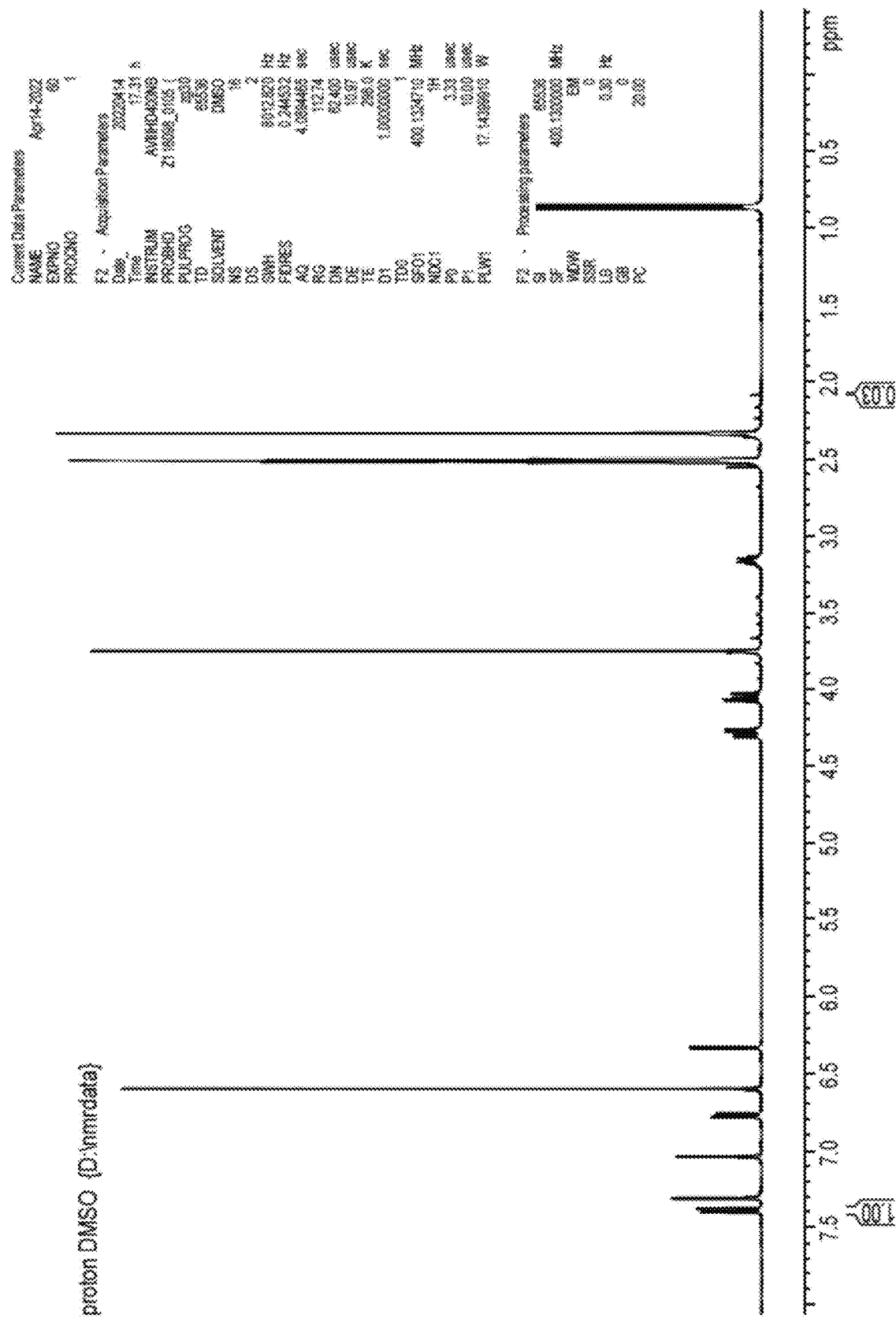
FIG. 119 shows a $^1$H NMR spectrum of crystalline compound 1 monofumarate, spectrum was acquired in DMSO-$d_6$ and calibrated to the non-deuterated solvent residual at 2.50 ppm. MeCN content, 0.1% w/w.
Figure 120:
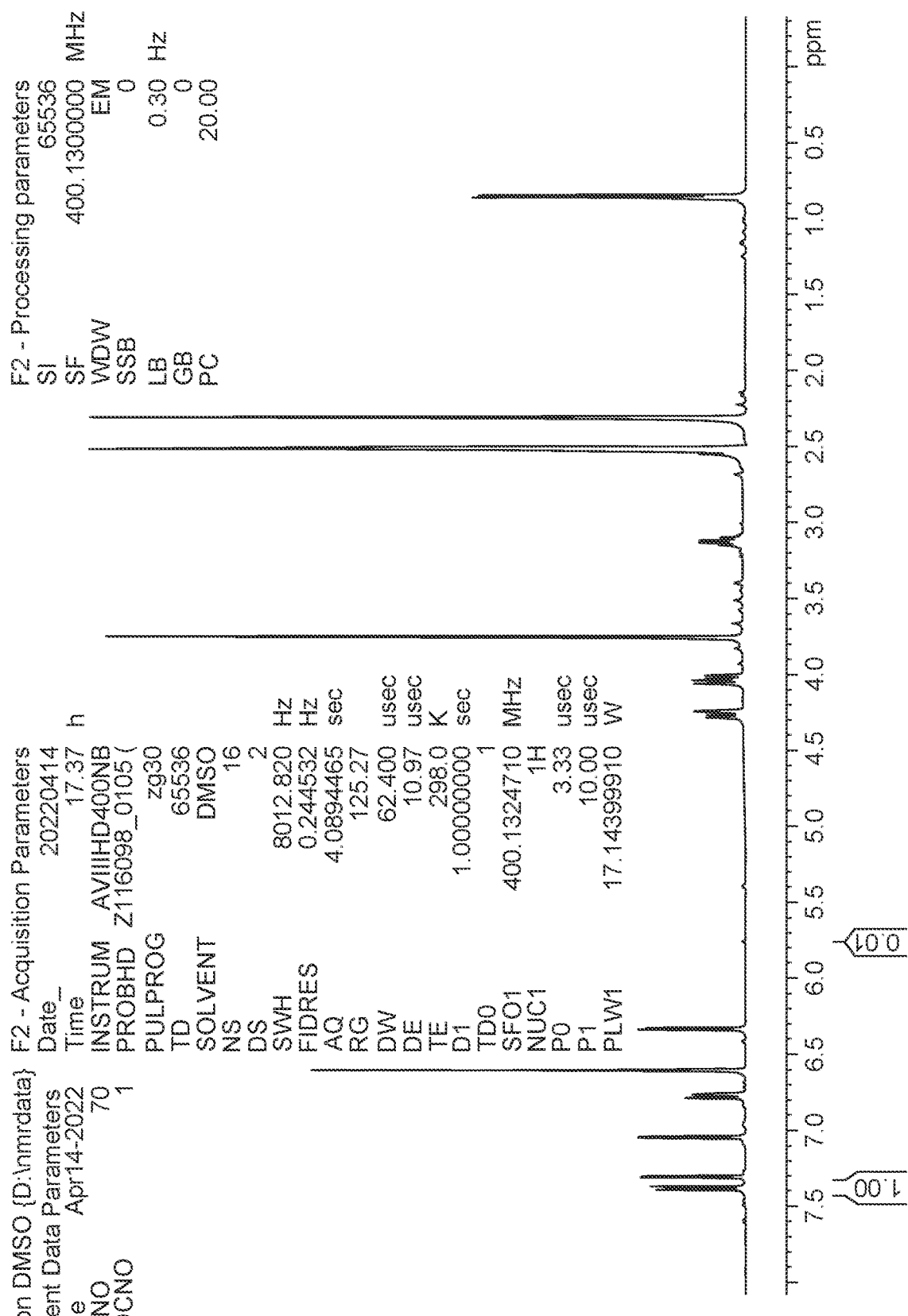
FIG. 120 shows a $^1$H NMR spectrum of crystalline compound 1 monofumarate, spectrum was acquired in DMSO-d$_6$ and calibrated to the non-deuterated solvent residual at 2.50 ppm. DCM content, 0.9% w/w.
Figure 121:
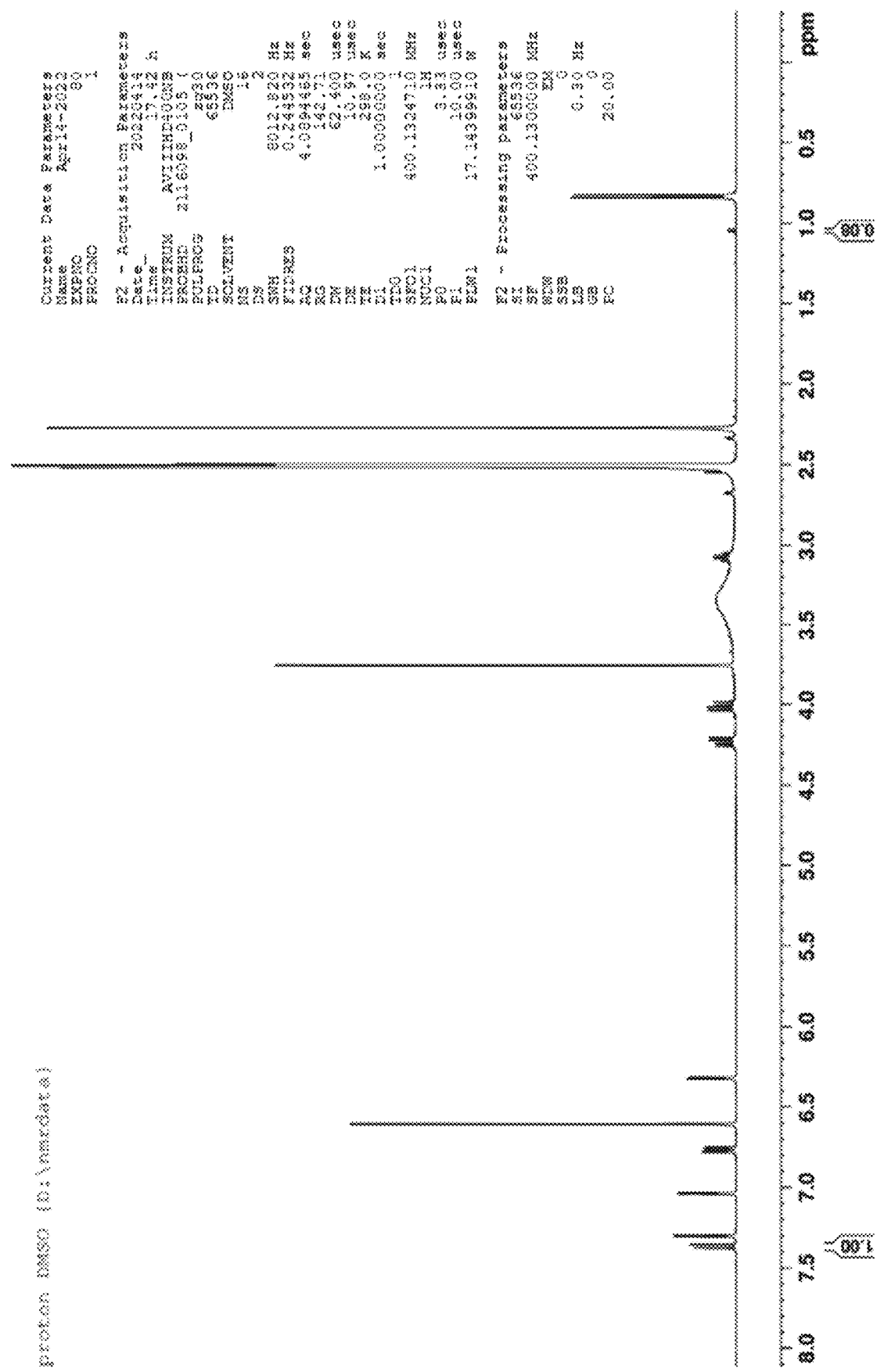
Figure 122:
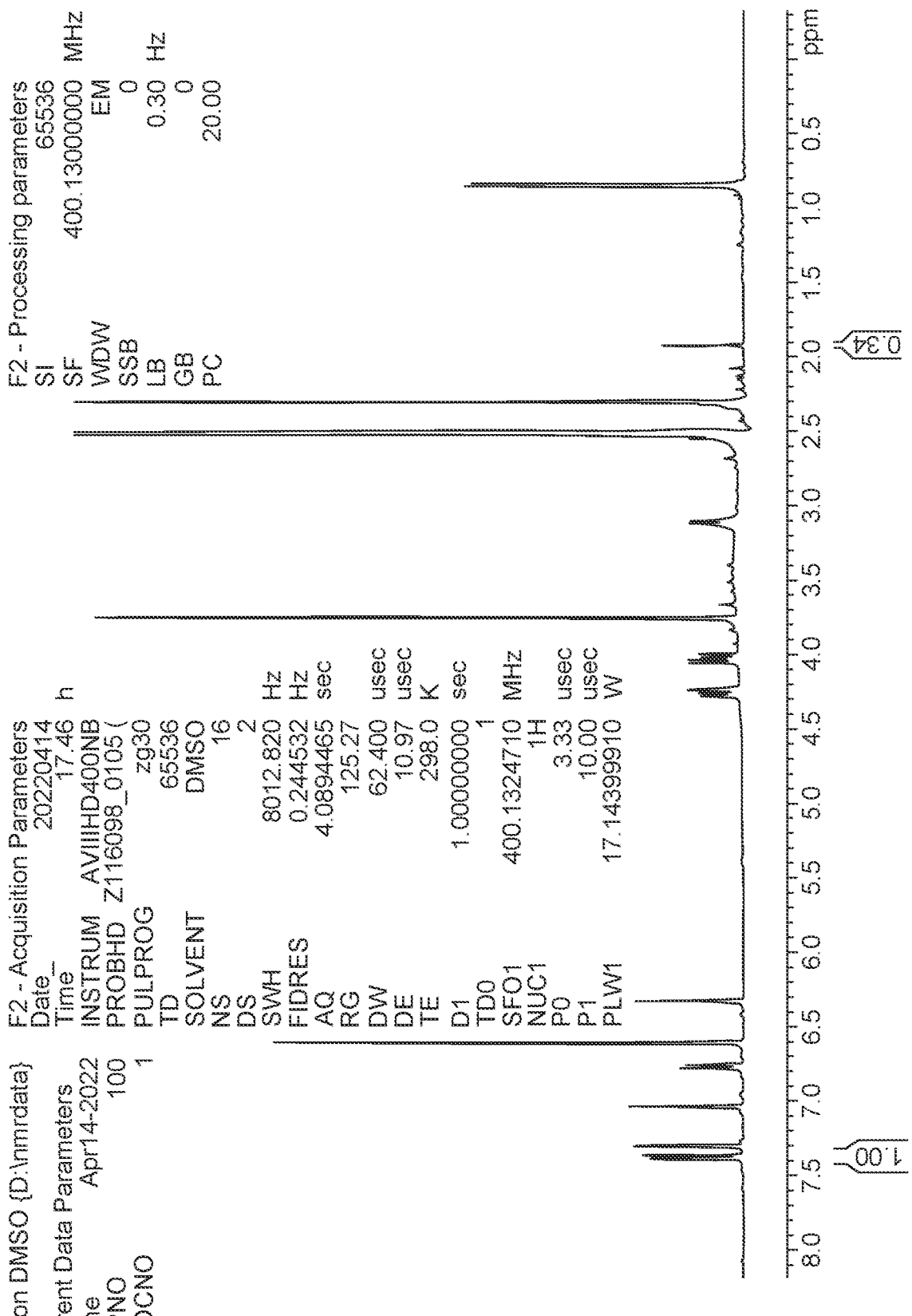
Figure 123:
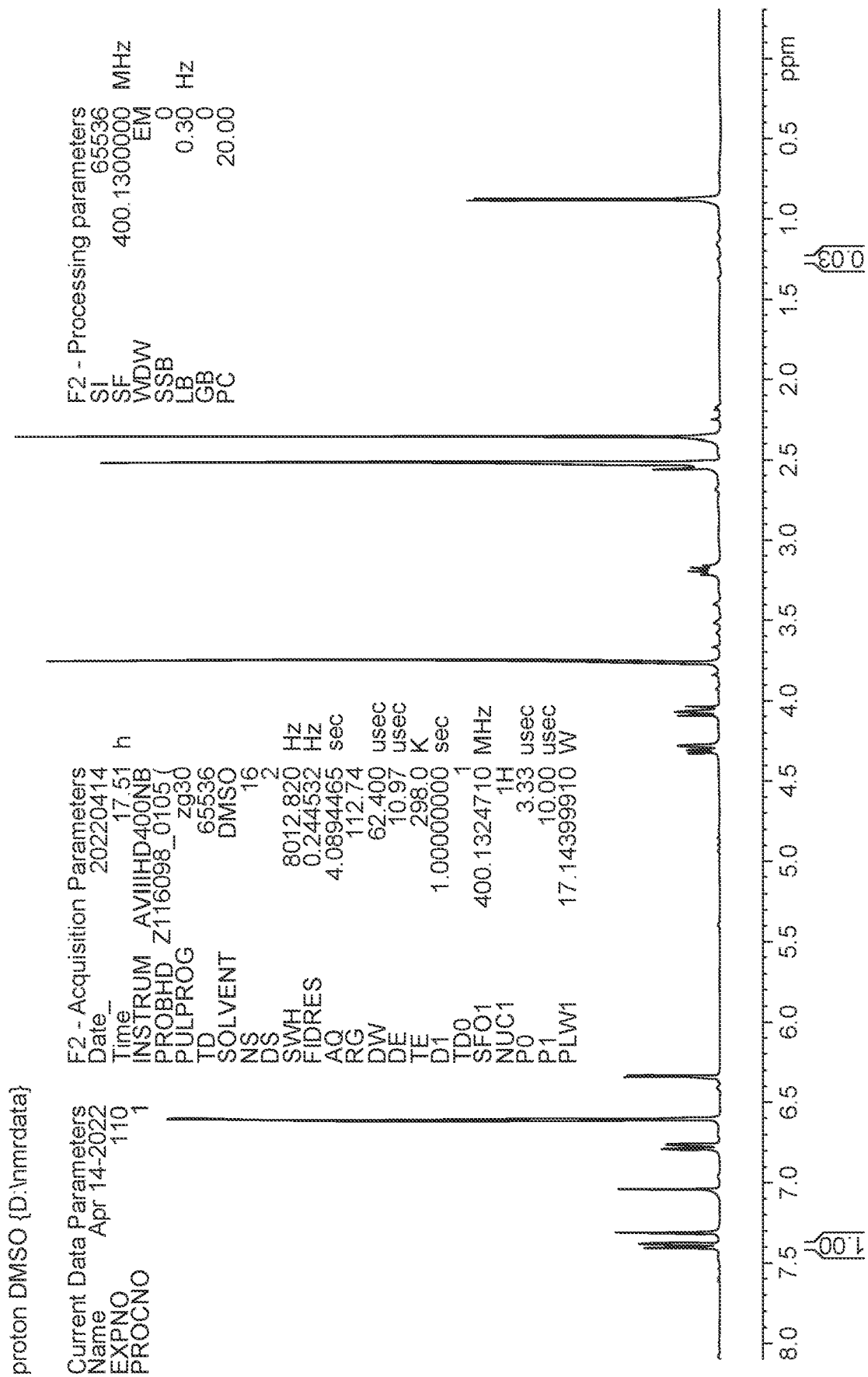
Figure 124:
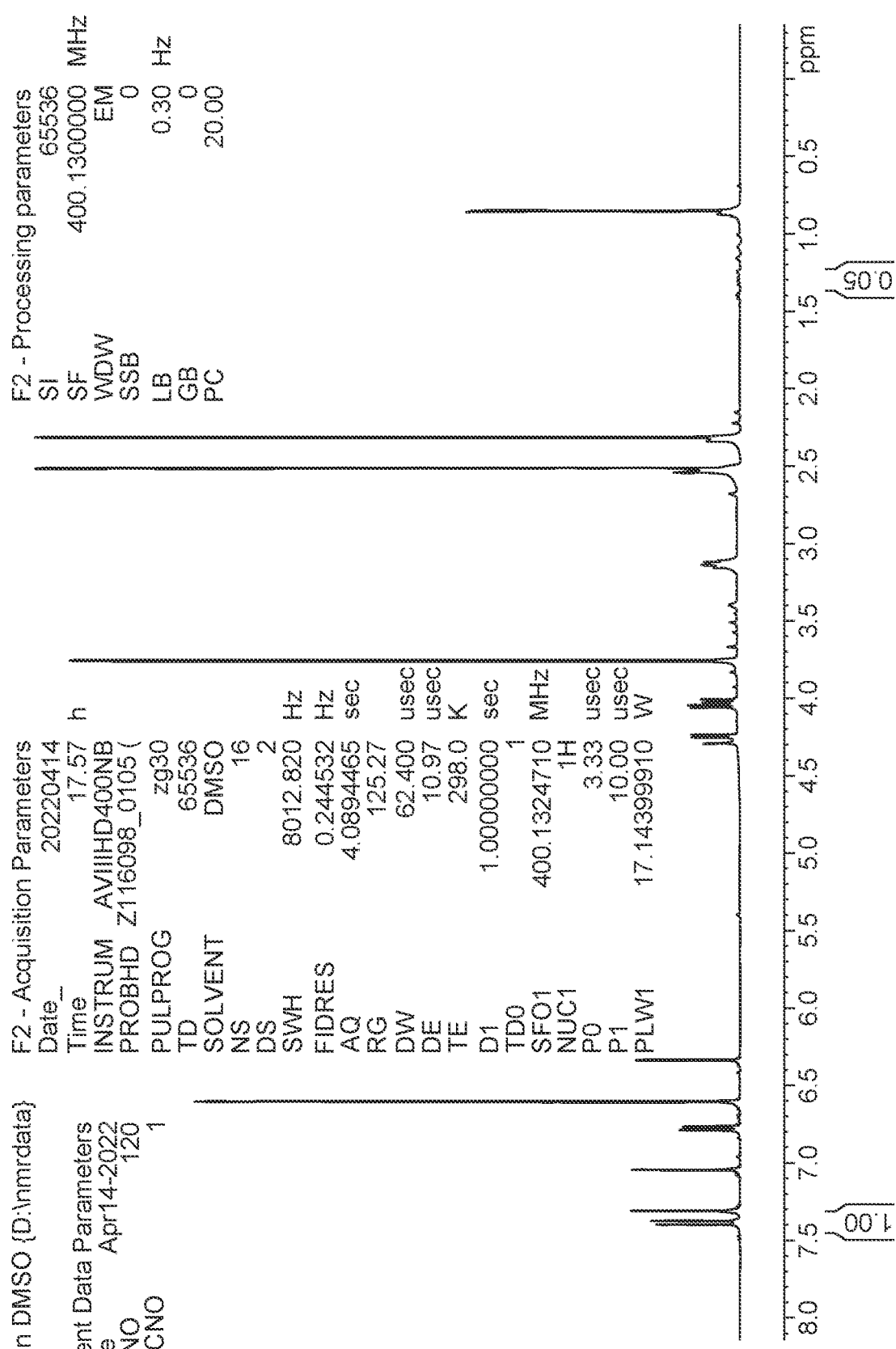
Figure 125:
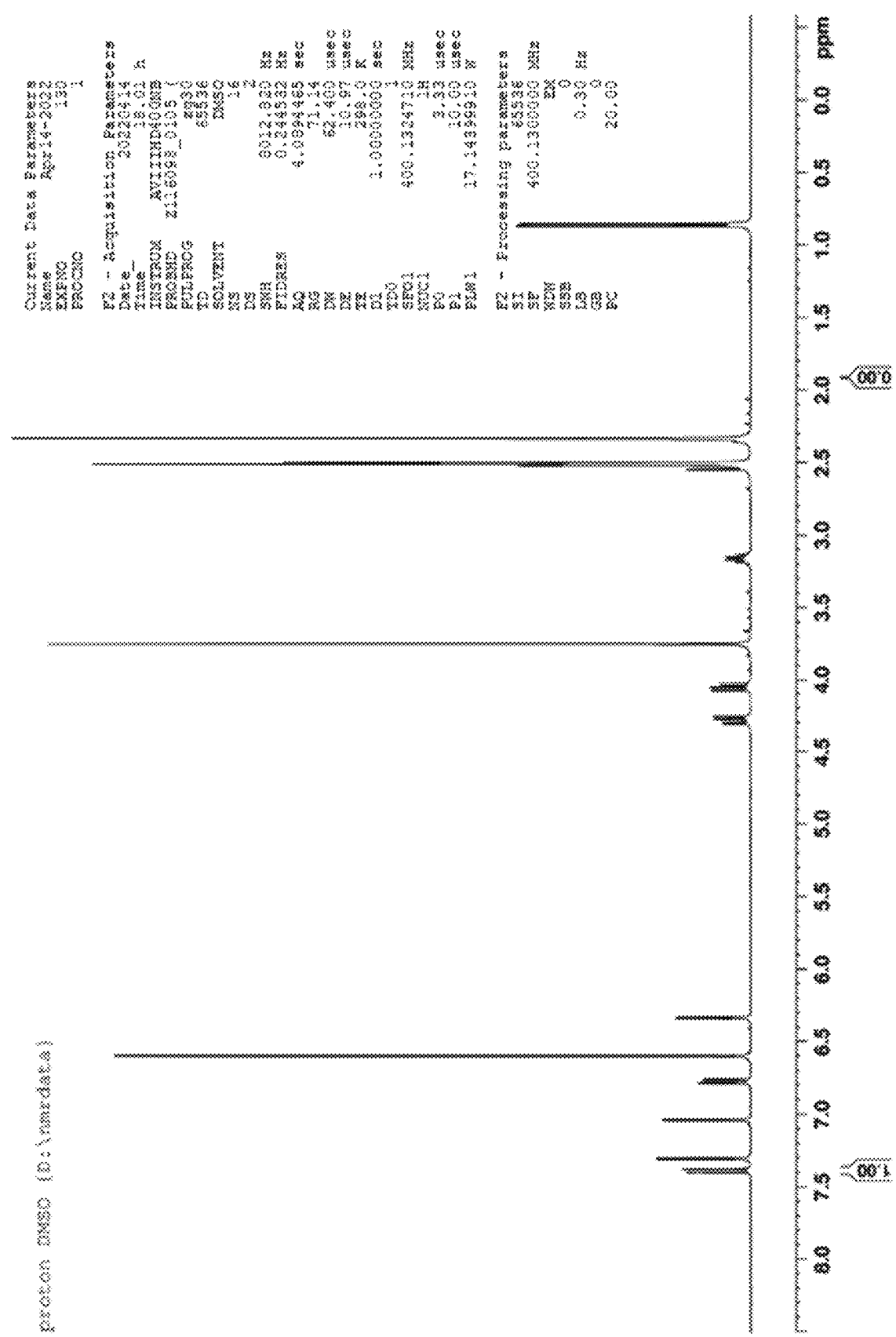
Figure 126:
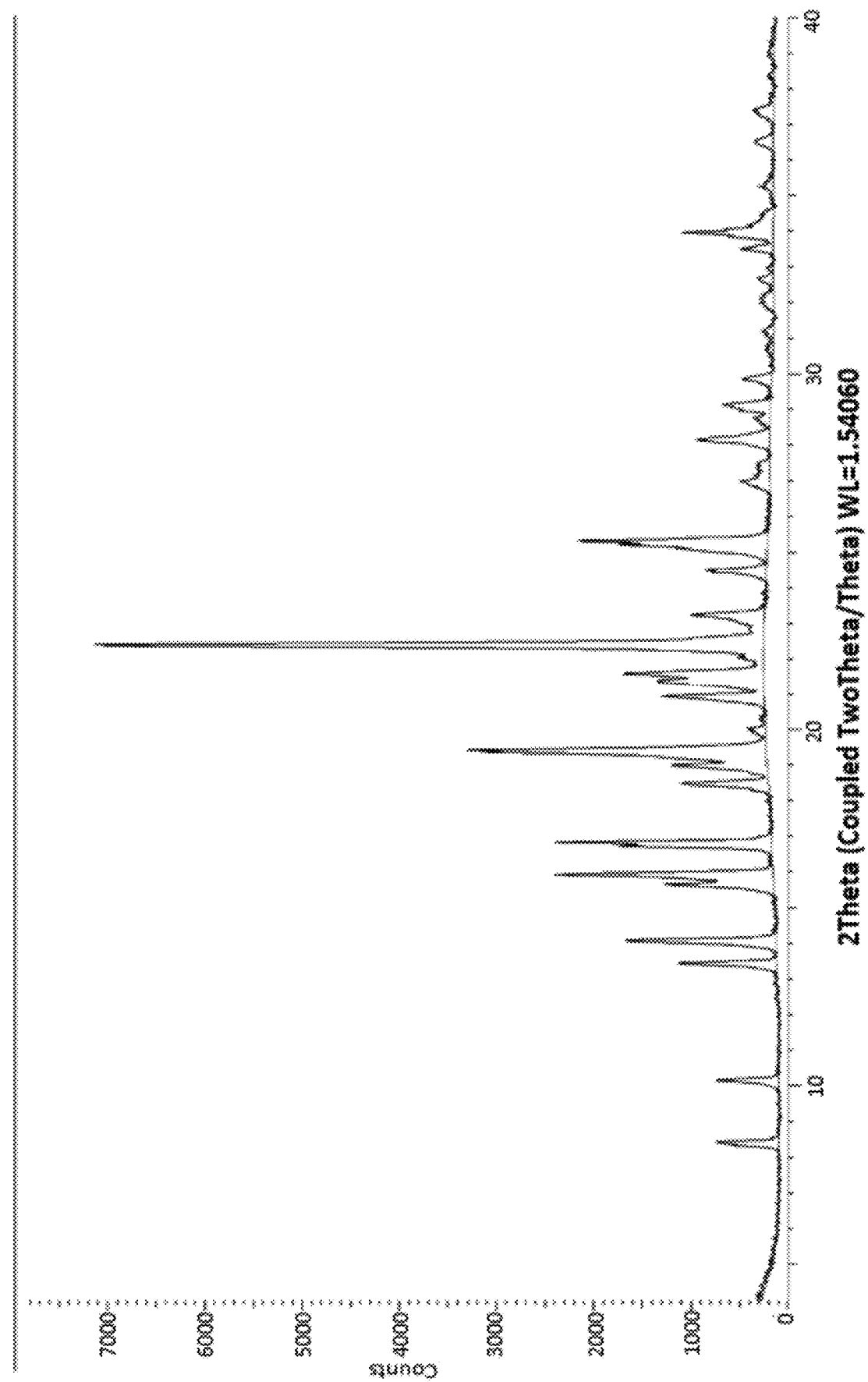
Figure 127:
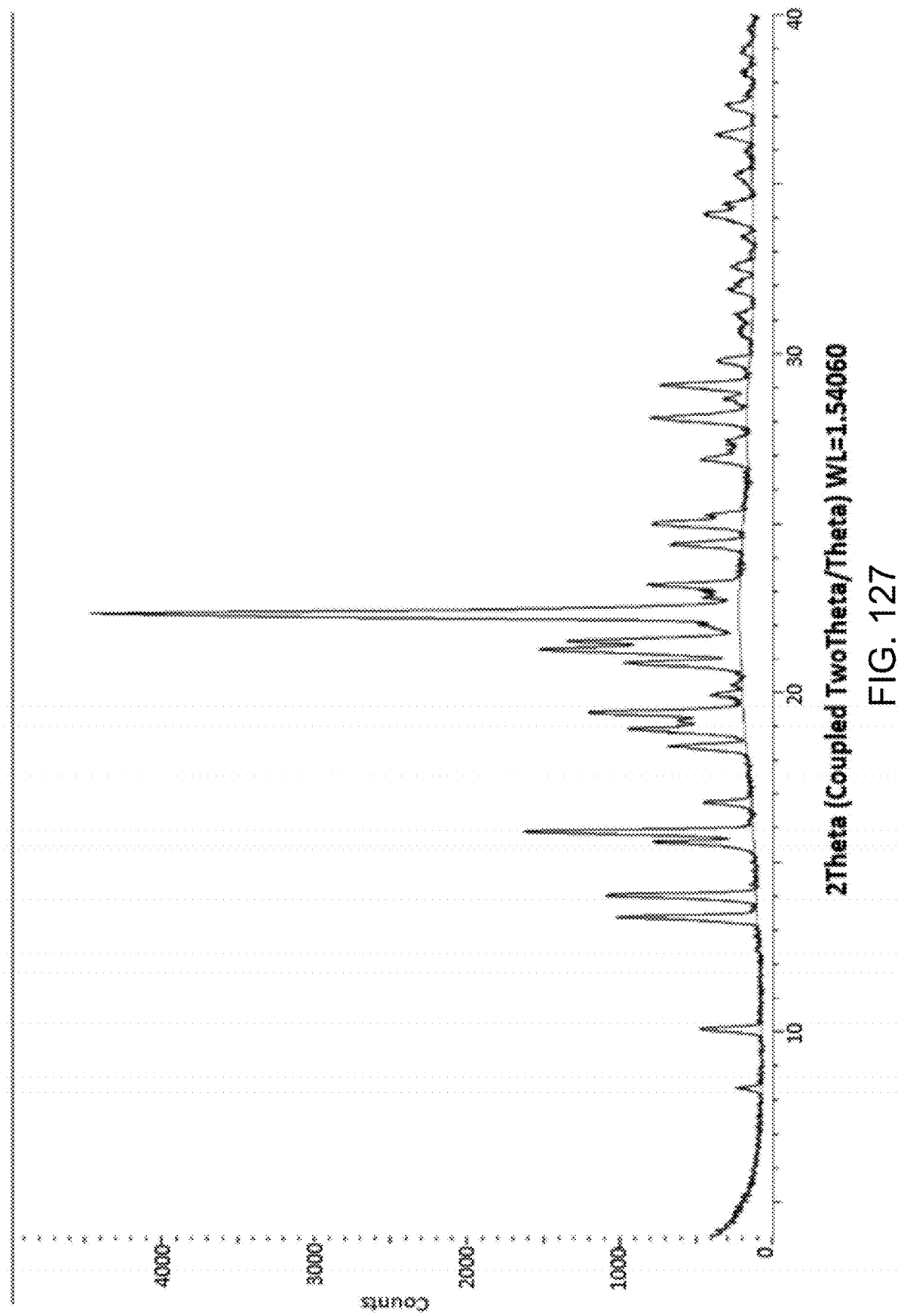
Figure 128:
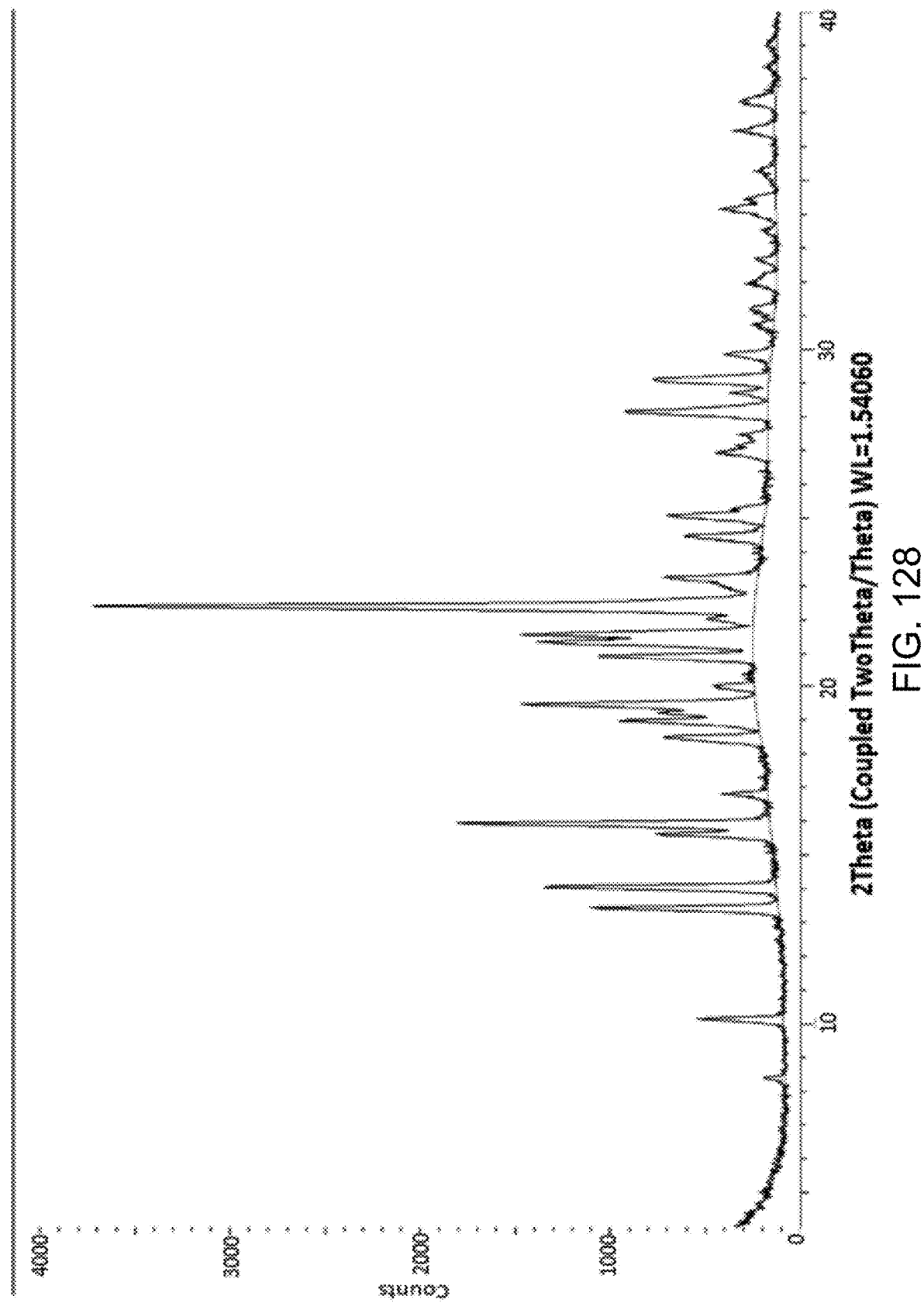
Figure 129:
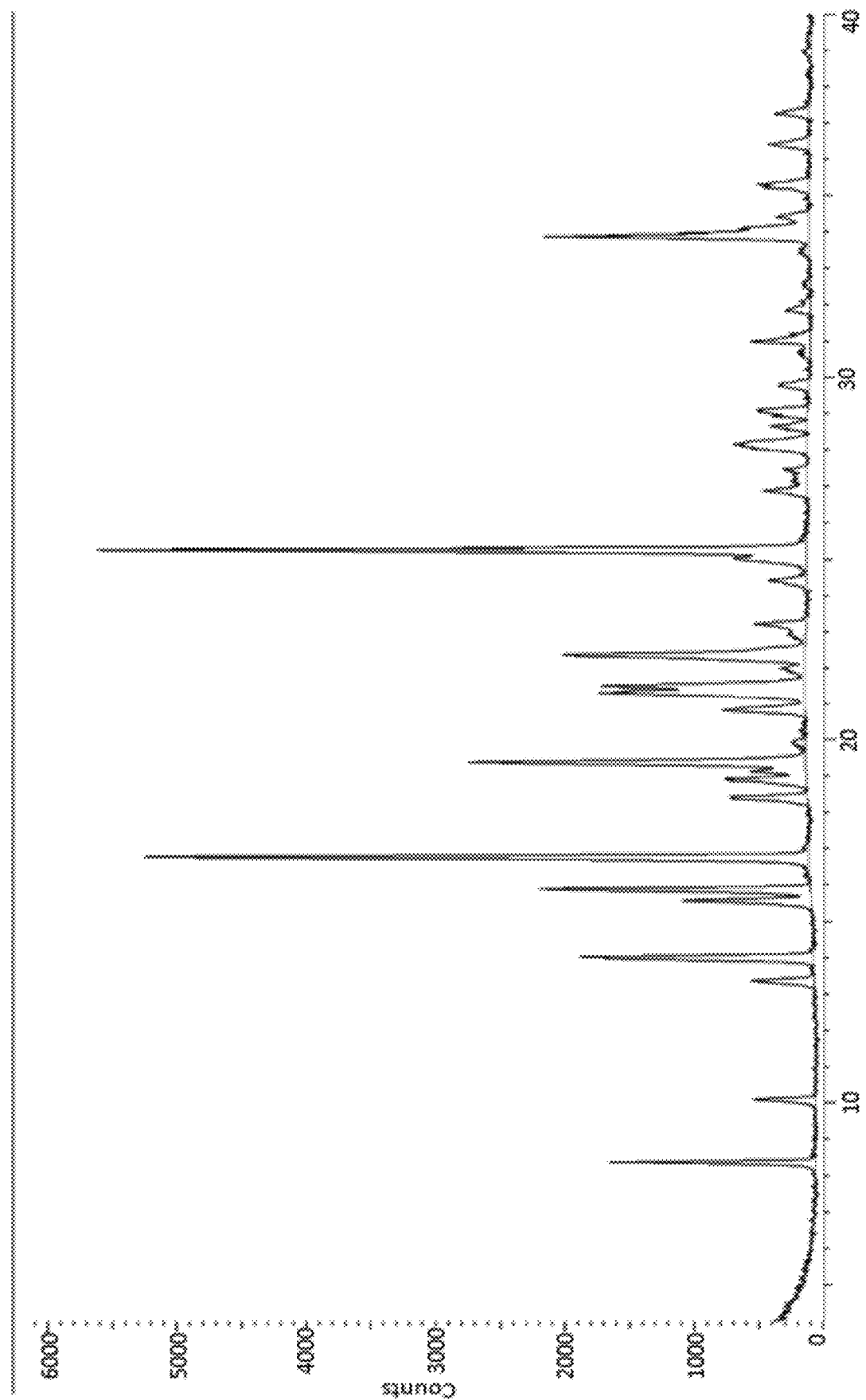
Figure 130:
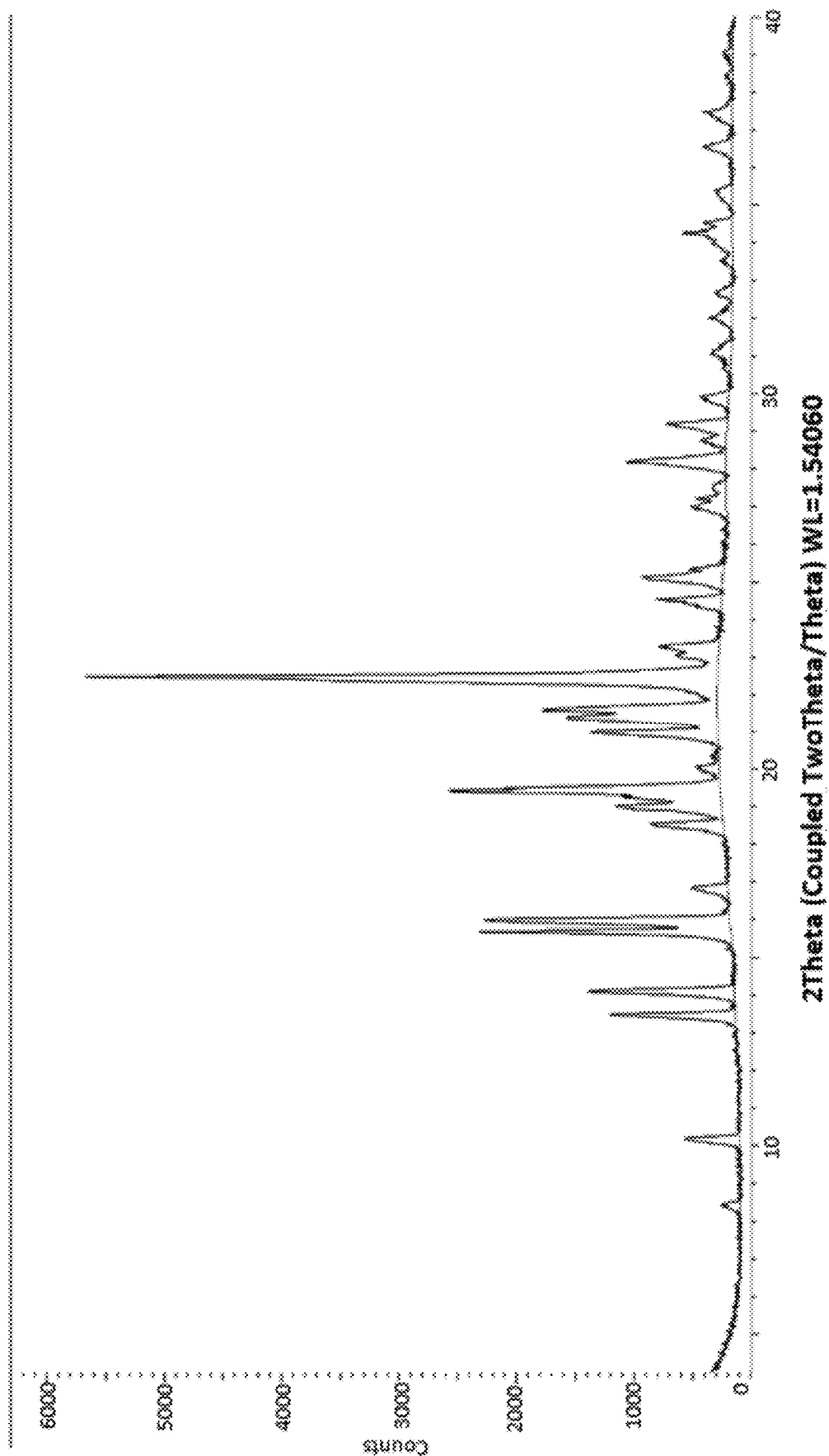
Figure 131:
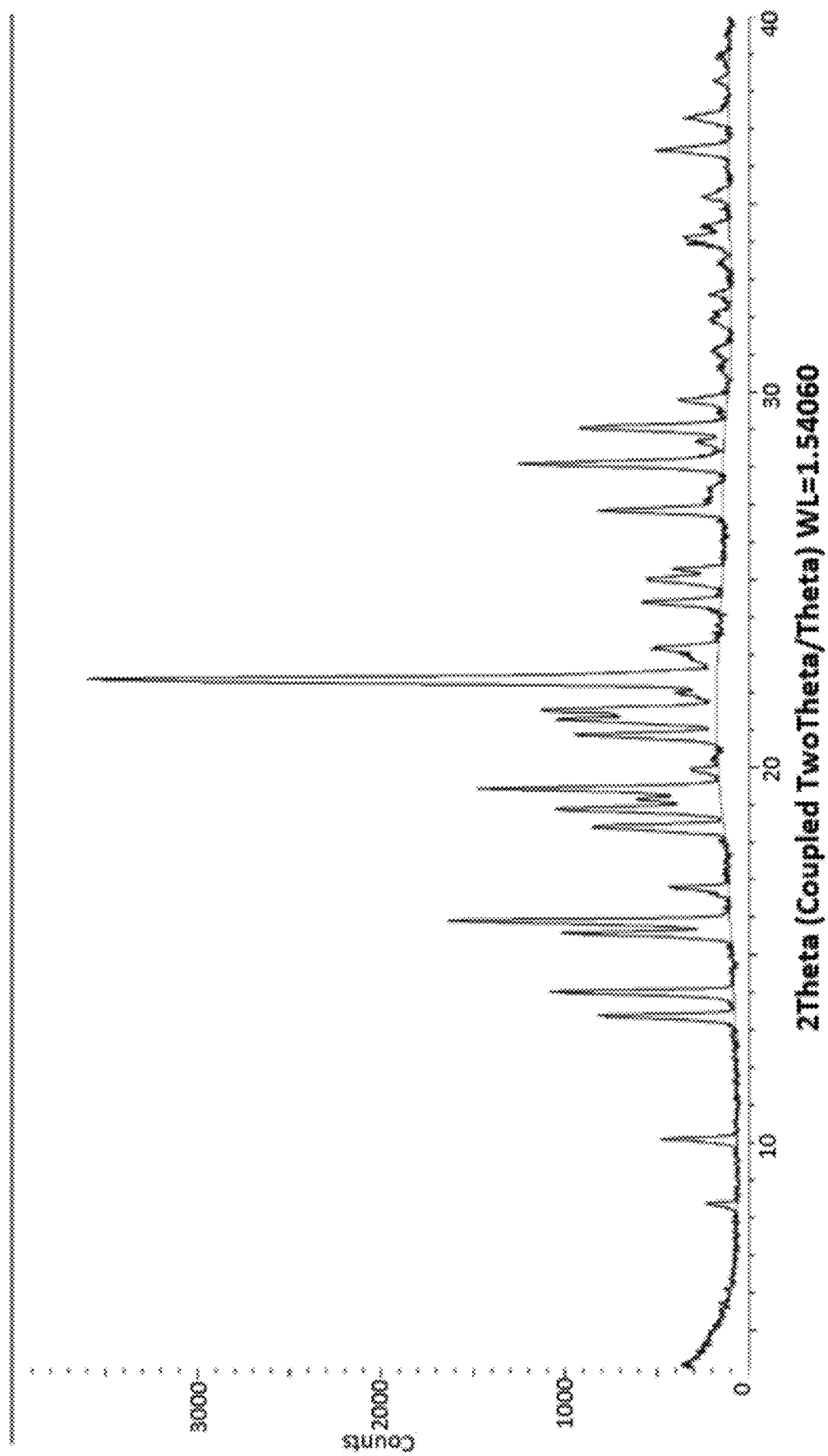
Figure 132:
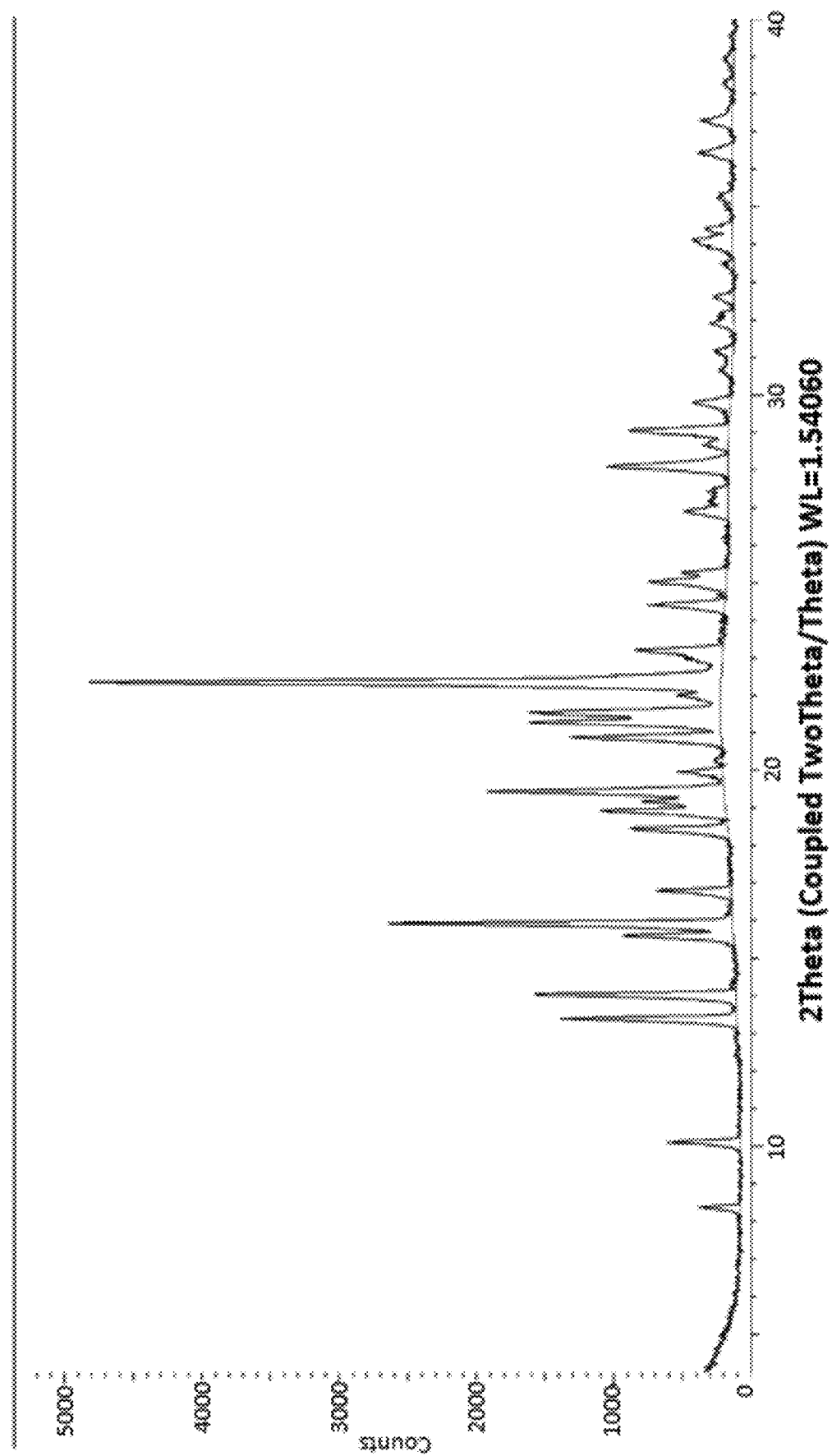

| Provenances of reference batches | Compound 1.MonoFumarate (Form A, Pattern #1) |
|---|---|
| 54, 55, 156, 157, 158, 159, 160, and 161-166 for characterization. Batches 2-6: ( ), obtained from suspension equilibration of compound 1 in EtOAc, iPAc, MEK and 2-Me THF, respectively (5 vol) at 20° C. and isolated by centrifuging and oven-drying under vacuum over 20 h at 40° C. Refer to FIGS. 24, 62, 63, 64, 65, 66, 69, 72, 73, 79, 80, 75, 82, and 84 for characterization data. Batch 3: obtained from heat-up, cool-down crystallisations of amorphous compound 1 batch 1 and isolated by centrifuging and oven-drying under vacuum over 20 h at 40° C. Refer to FIG. 103 for characterization data. | Asymmetric unit: contained one molecule of API and one molecule of fumaric acid (crystal bonded). XRPD: 10.1°, 13.4°, 14.1°, 15.6°, 15.9°, 18.5°, 19.0°, 19.2°, 19.5°, 20.9°, 21.4°, 21.6°, 22.4°, 25.1°, 28.2°, 29.1°(2θ, 1 d.p). DSC: onset 114.4° C. (−72.7 Jg$^{-1}$, endotherm, melt) TGA: onset 207.9° C. (−67.2% w/w, ablation). DVS 90 to 0 to 90% RH (dm/dt <0.002%): 0.0 (0.00%), 5.0 (0.021%), 10.0 (0.047%), 15.0 (0.068%), 20.0 (0.088%), 25.0 (0.107%), 30.0 (0.125%), 40.0 (0.173%), 50.0 (0.242%), 60.0 (0.366%), 70.0 (0.590%), 80.0 (0.174%), 90.0 (9.440%), 90.0 (9.440%), 80.0 (2.087%), 70.0 (0.885%), 60.0 (0.619%), 50.0 (0.476%), 40.0 (0.374%), 30.0 (0.279%), 25.0 (0.238%), 20.0 (0.201%), 15.0 (0.169%), 10.0 (0.141%), 5.0 (0.113%), 0.0 (0.085%). UV chromatographic purity: 98.37% area (212 nm), (refer to FIG. 160. $^1$H NMR: (DMSO-d$_6$, 400 MHZ); δ 7.4 (d, J = 9.0 Hz, 1 H), 7.3 (s, 1 H), 7.0 (s, 1 H), 6.8 (dt, J = 8.9, 3.8, 1.7 Hz, 1 H), 6.6 (s, 2 H), 6.3 (td, J = 3.11 1.5, 0.8, 1 H), 4.3 (dd, J = 13.9, 6.4 Hz, 1 H), 4.0 (dd, J = 13.9, 6.4 Hz, 1 H), 3.8 (s, 3 H), 3.1 (p, J = 33.8, 20.8, 11.2, 7.2 Hz, 1 H), 2.3 (s, 1 H), 0.8 (dd, J = 6.6, 0.8 Hz, 3 H) conforms to the molecular structure (Σ22H$^1$), (refer to FIG. 156). Appearance: refer to FIG. 161 to FIG. 164. Solubility in SIF buffers: Soluble in FaSSIF, FeSSIF and FaSSGF at 37° C. up to 24 h. |

Qualitative Solubility Screen

[1] The molecular formula (C$_{18}$H$_{24}$N$_2$O$_5$) includes the carboxylic acid protons includes the carboxylic acid protons, however, they co-resonate with water.

Compound 1·Fumarate was soluble in many of the common solvents assessed (predominantly Classes 2 and 3 solvents) at 5.0 vol (200 mg/ml), 10.0 vol, 15.0 vol and 20.0 vol (refer to Table). Solids were isolated on cooling from isopropanol (IPA, 5.0 vol), 2-MeTHF (5.0 vol) and methylisobutylketone (MIBK, 15.0 vol). The products from IPA and 2-MeTHF were gums, and not pursued further.

Figure 10:
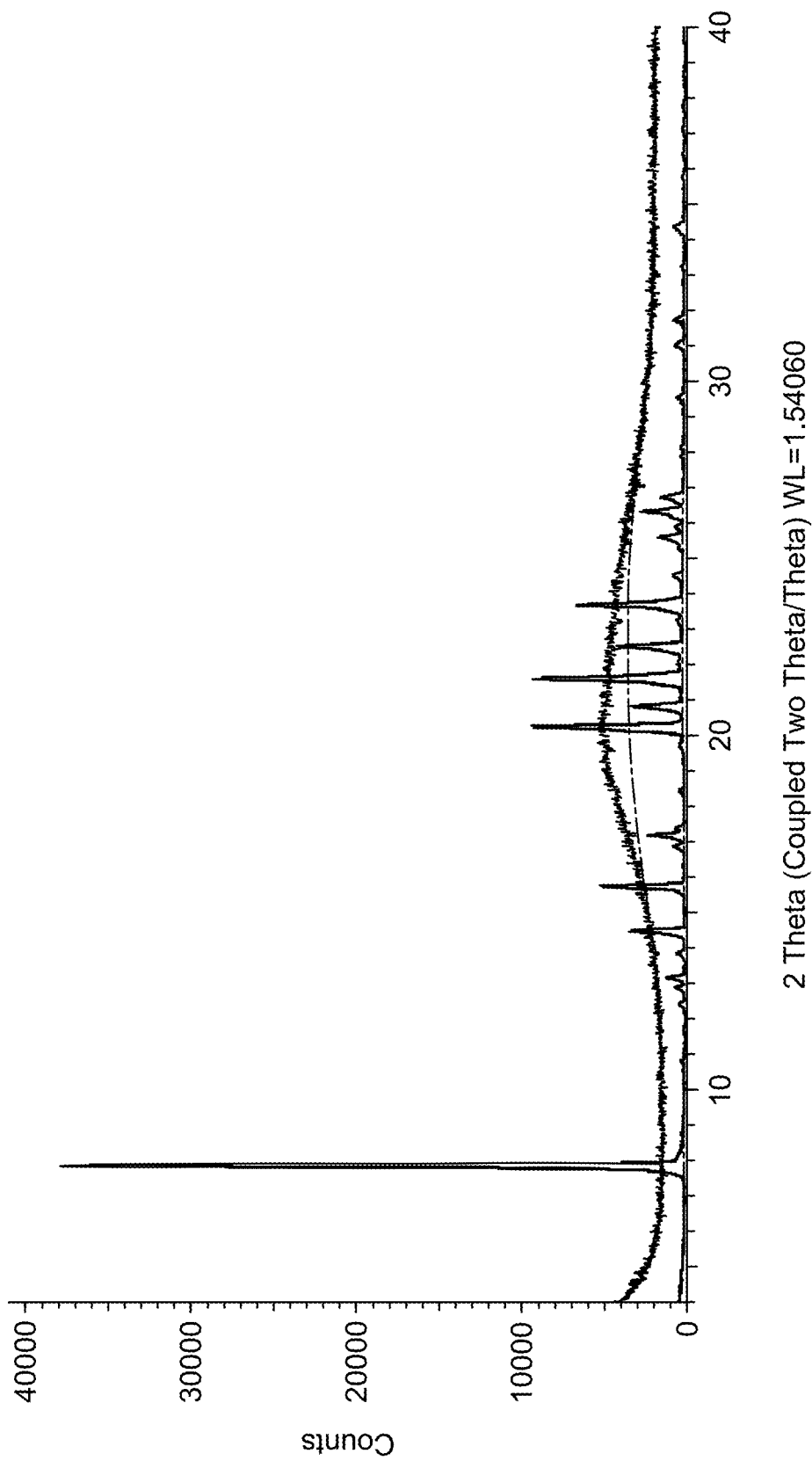
FIG. 10 shows the overlay of XRPD profiles of amorphous compound 1 (top) and the compound 1 crystalline Pattern 5 fumarate salt, which was crystalized from amorphous compound 1 in MIBK.
Figure 11:
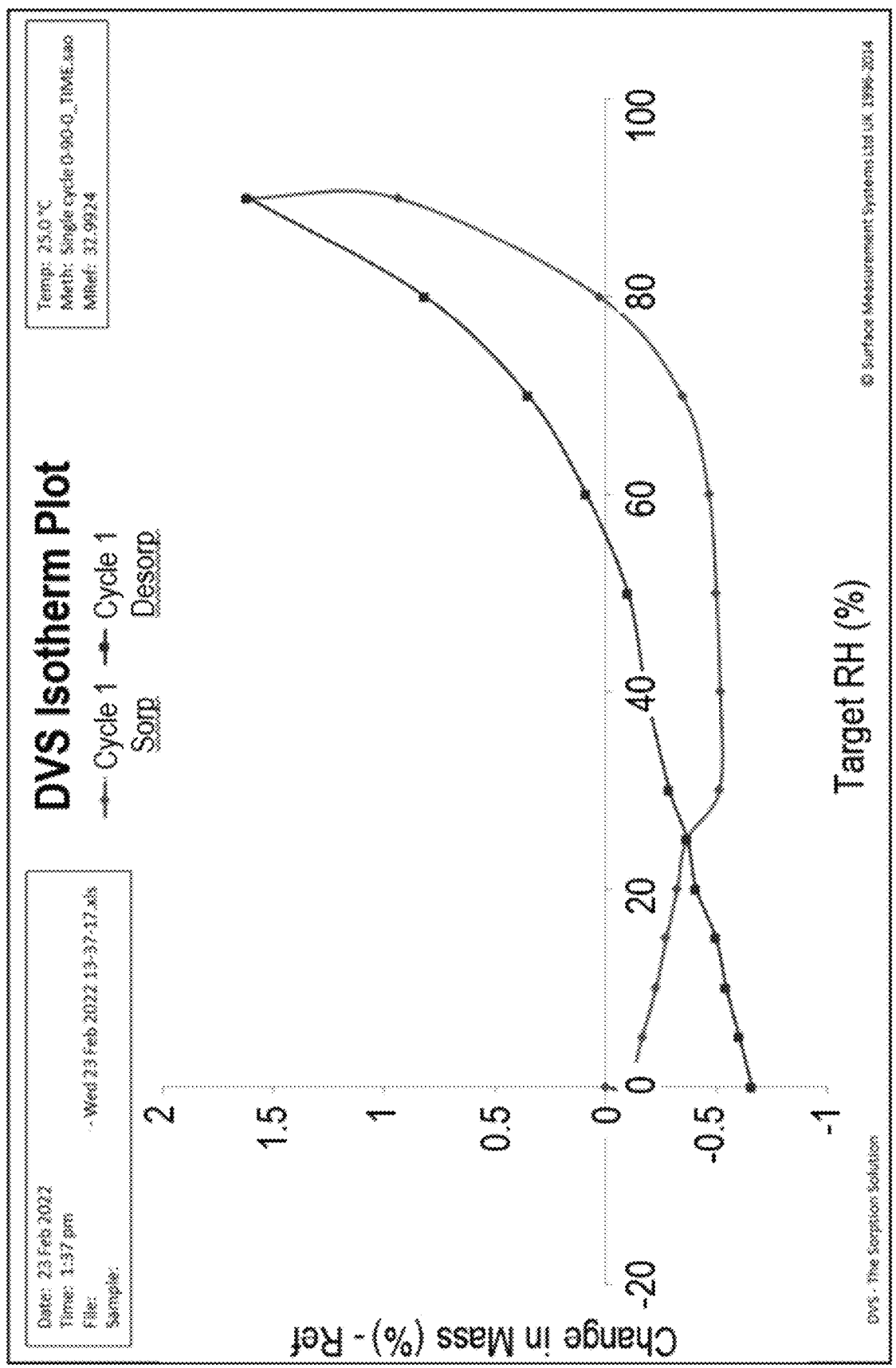
FIG. 11 shows the DVS isotherm plot of amorphous compound 1, obtained with 0% to 90% to 0% RH vs. time. Fixed time of 60 min between % RH steps, 27 h for 1 cycle.
Figure 39:
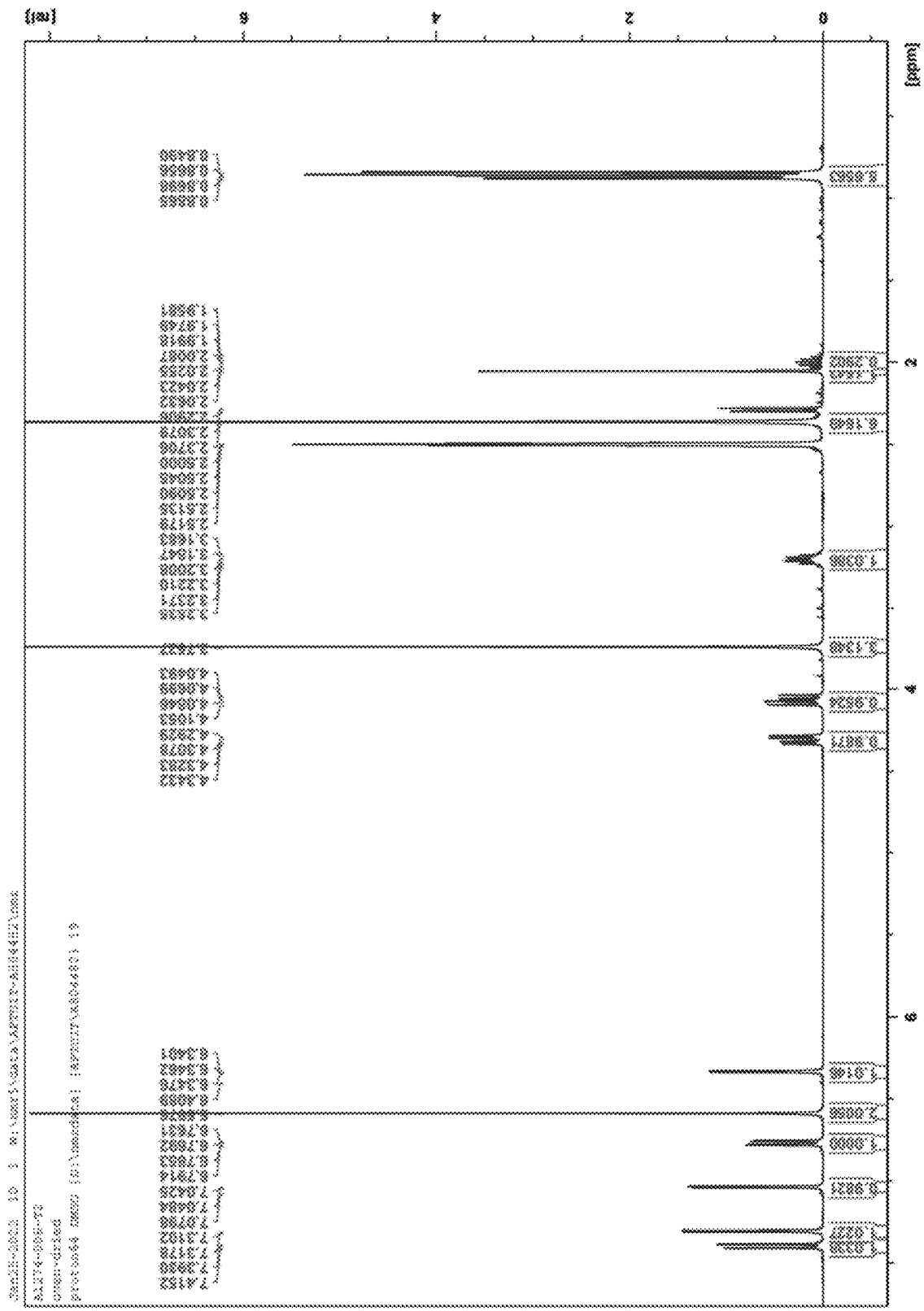
FIG. 39 shows a $^1$H NMR spectrum of crystalline compound 1 fumarate, spectrum was acquired in DMSO-$d_6$ and calibrated to the non-deuterated solvent residual at 2.50 ppm. API to Fumaric acid, 1.0 to 1.0. MIBK content, 11.0% w/w.
Figure 40:
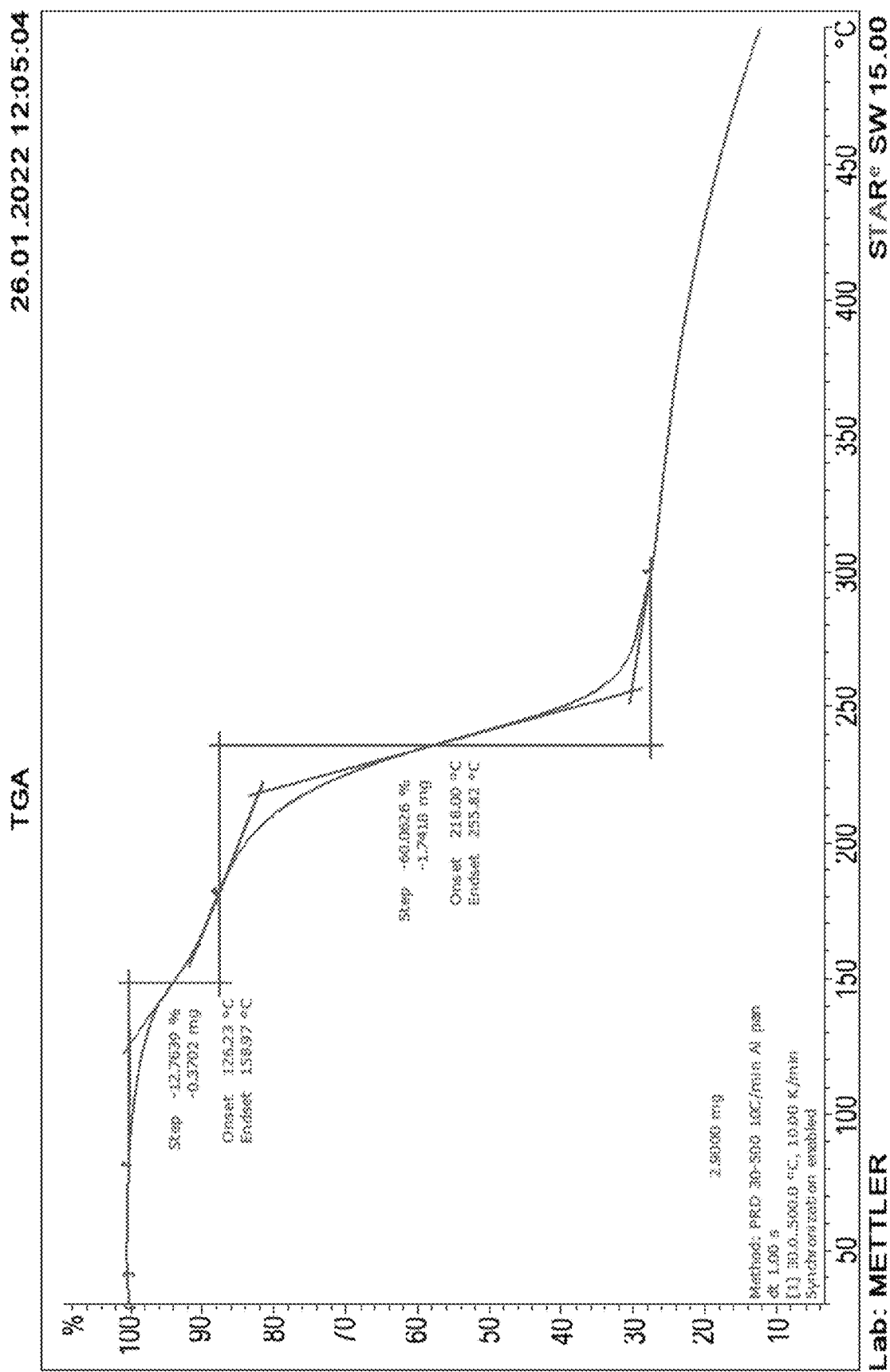
FIG. 40 shows a TGA profile of crystalline compound 1 fumarate.
Figure 41:
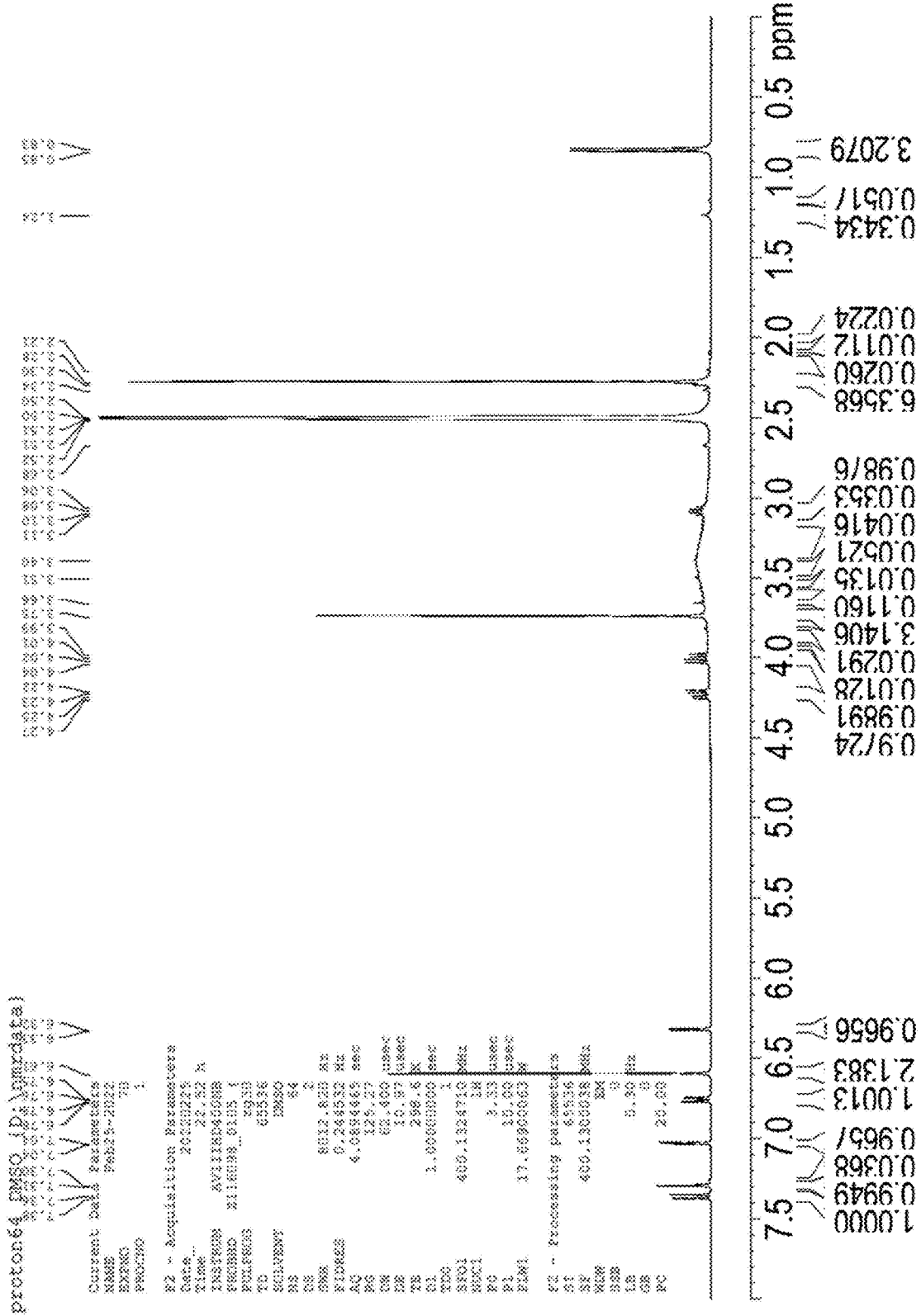
FIG. 41 shows an $^1$H NMR spectrum of amorphous compound 1 fumarate (t=5 w, open vial), spectrum was acquired in DMSO-$d_6$ and calibrated to the non-deuterated solvent residual at 2.50 ppm.
Figure 42:
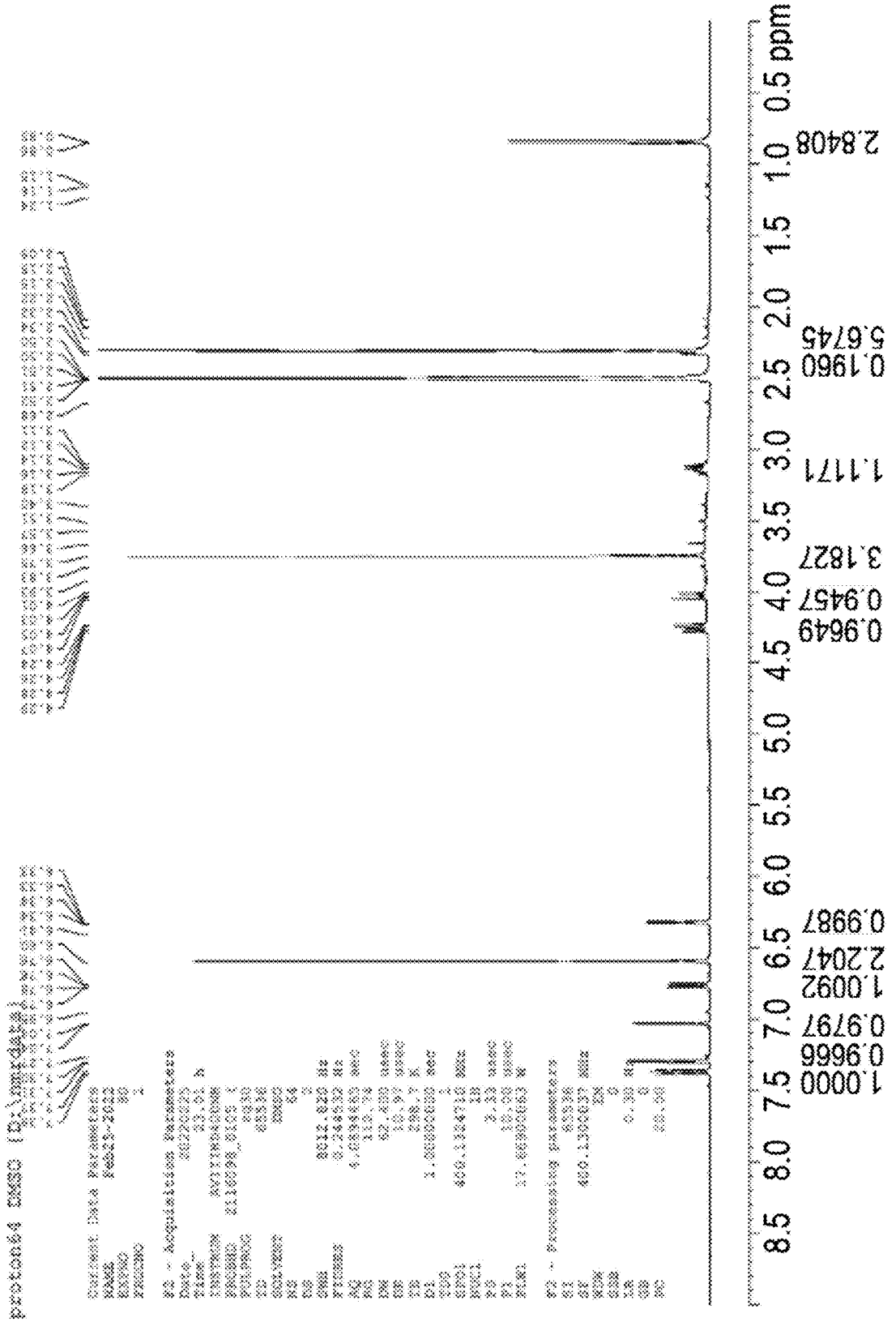
FIG. 42 shows an $^1$H NMR spectrum of amorphous compound 1 fumarate (t=5 w, open vial), spectrum was acquired in DMSO-$d_6$ and calibrated to the non-deuterated solvent residual at 2.50 ppm.
Figure 43:
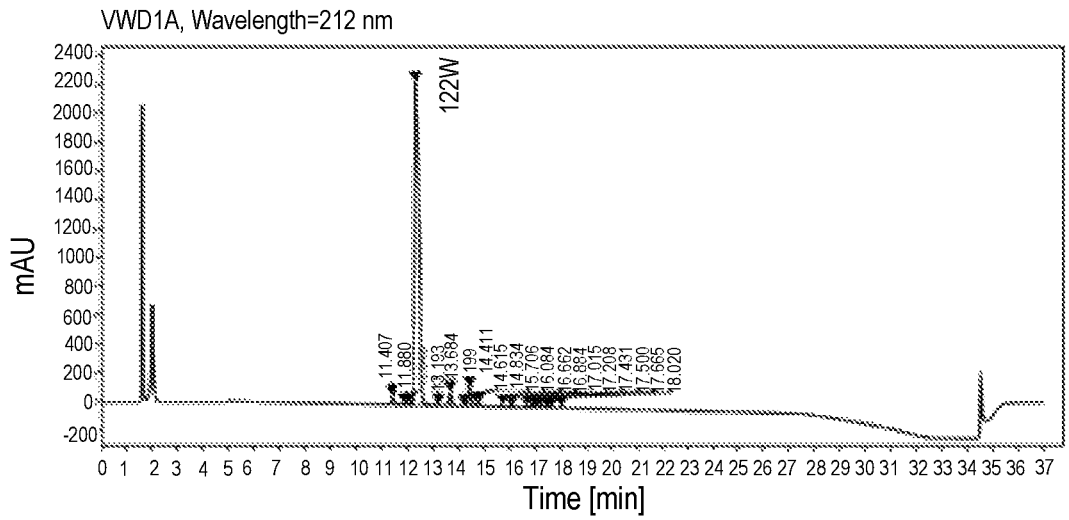
FIG. 43 shows the HPLC profile of amorphous compound 1 fumarate after being stored in a wide-necked, open vial for two weeks at 75% RH at 40° C.
Figure 44:
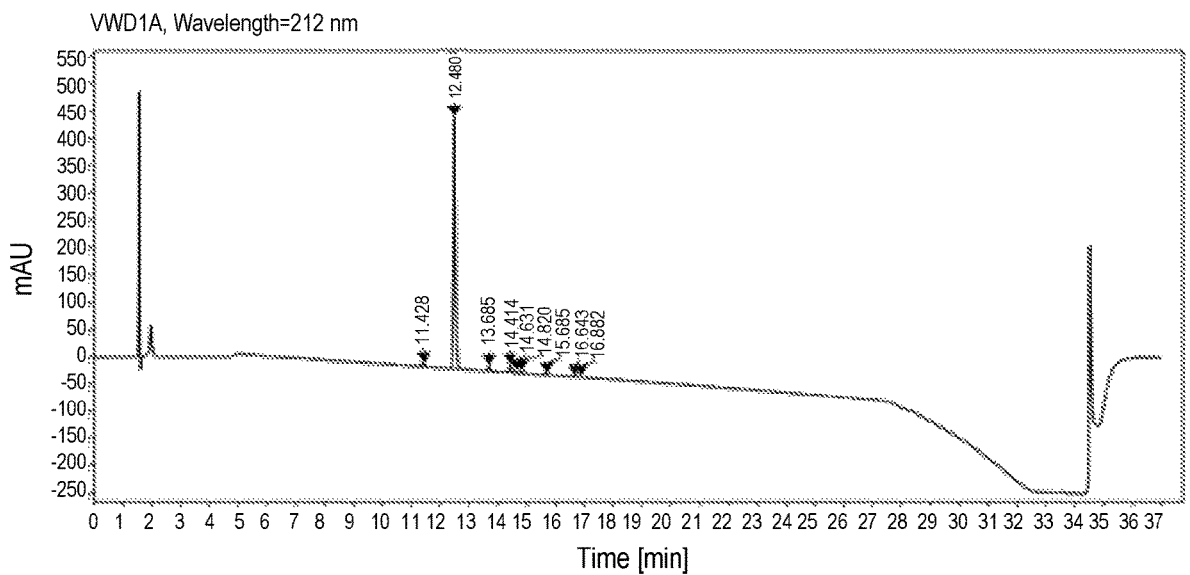
FIG. 44 shows the HPLC profile of amorphous compound 1 fumarate after being stored in a wide-necked, open vial for three weeks at 75% RH at 40° C.
Figure 45:
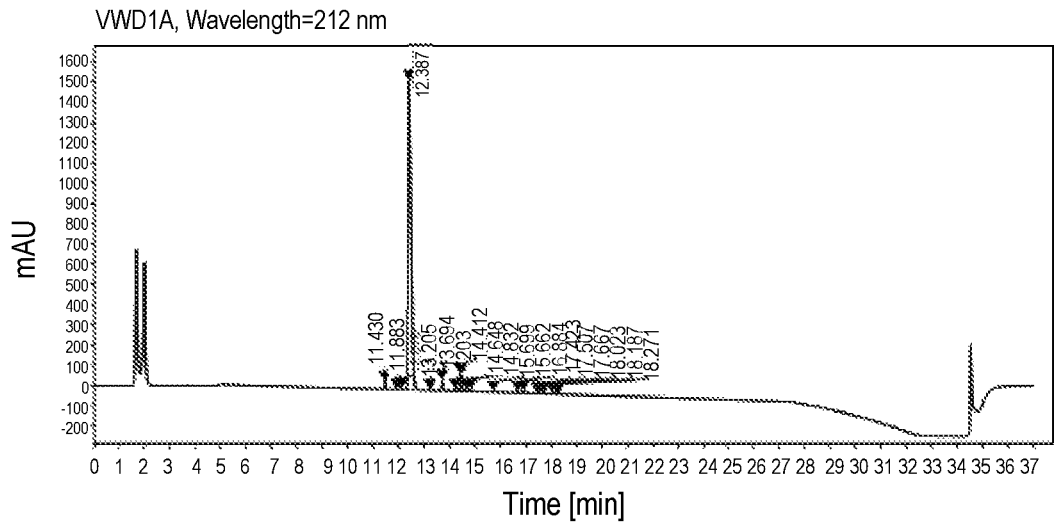
FIG. 45 shows the HPLC profile of amorphous compound 1 fumarate after being stored in a wide-necked, open vial for four weeks at 75% RH at 40° C.
Figure 46:
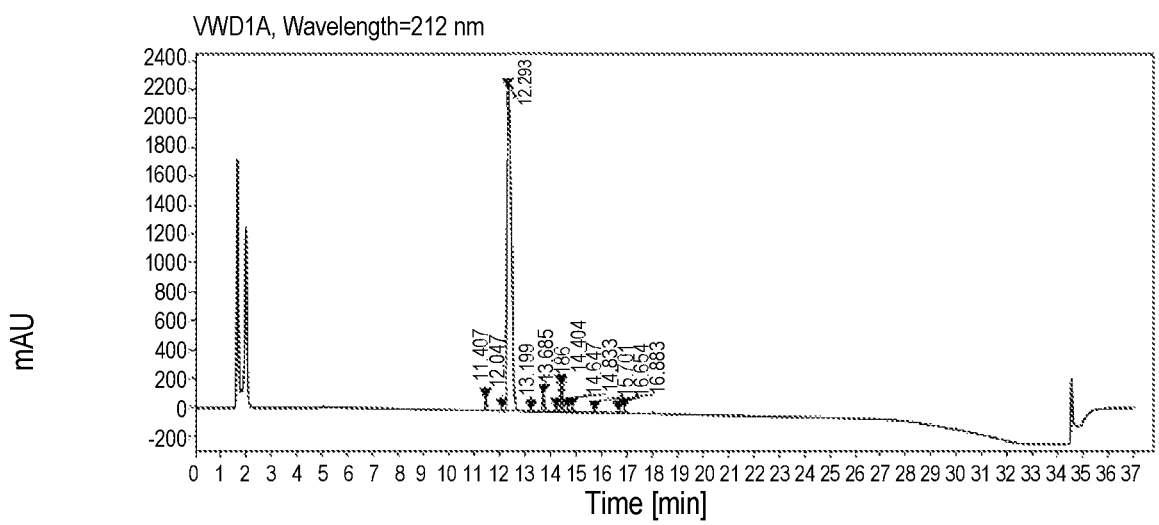
FIG. 46 shows the HPLC profile of amorphous compound 1 fumarate after being stored in a wide-necked, open vial for five weeks at 75% RH at 40° C.
Figure 47:
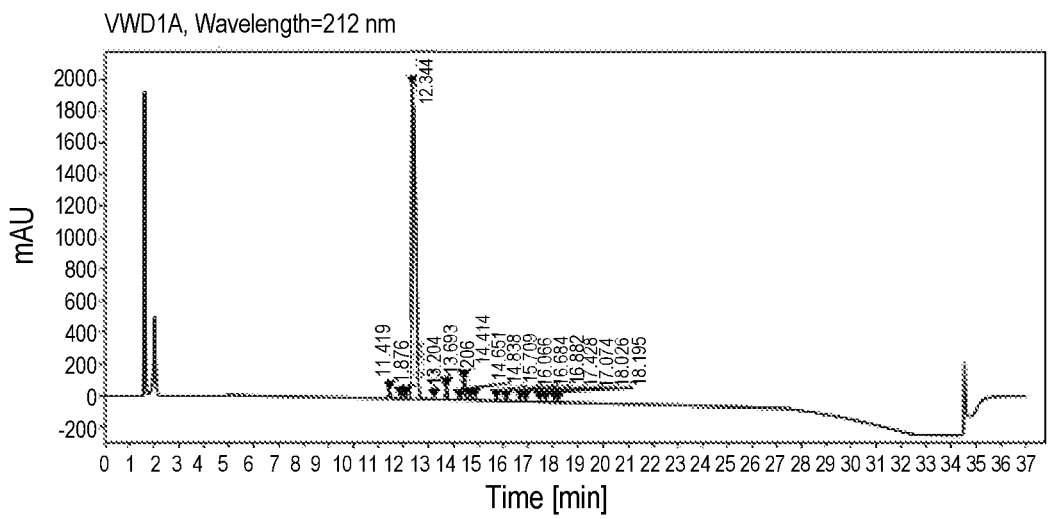
FIG. 47 shows the HPLC profile of amorphous compound 1 fumarate after being stored in a wide-necked, open vial and then inside double polyethlene bags, tied tightly with cable ties for two weeks at 75% RH at 40° C.
Figure 48:
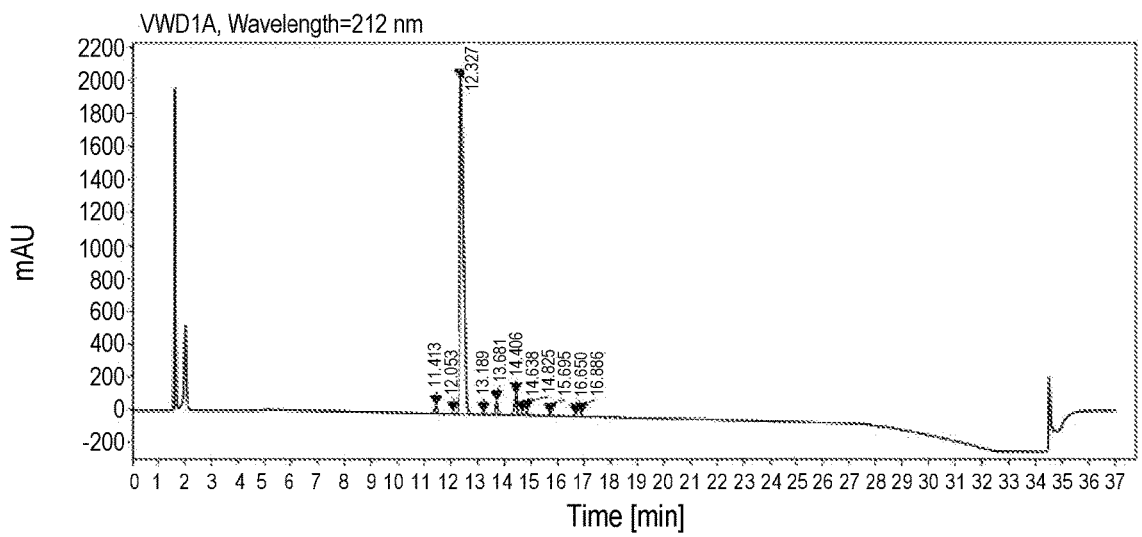
FIG. 48 shows the HPLC profile of amorphous compound 1 fumarate after being stored in a wide-necked, open vial and then inside double polyethlene bags, tied tightly with cable ties for three weeks at 75% RH at 40° C.
Figure 49:
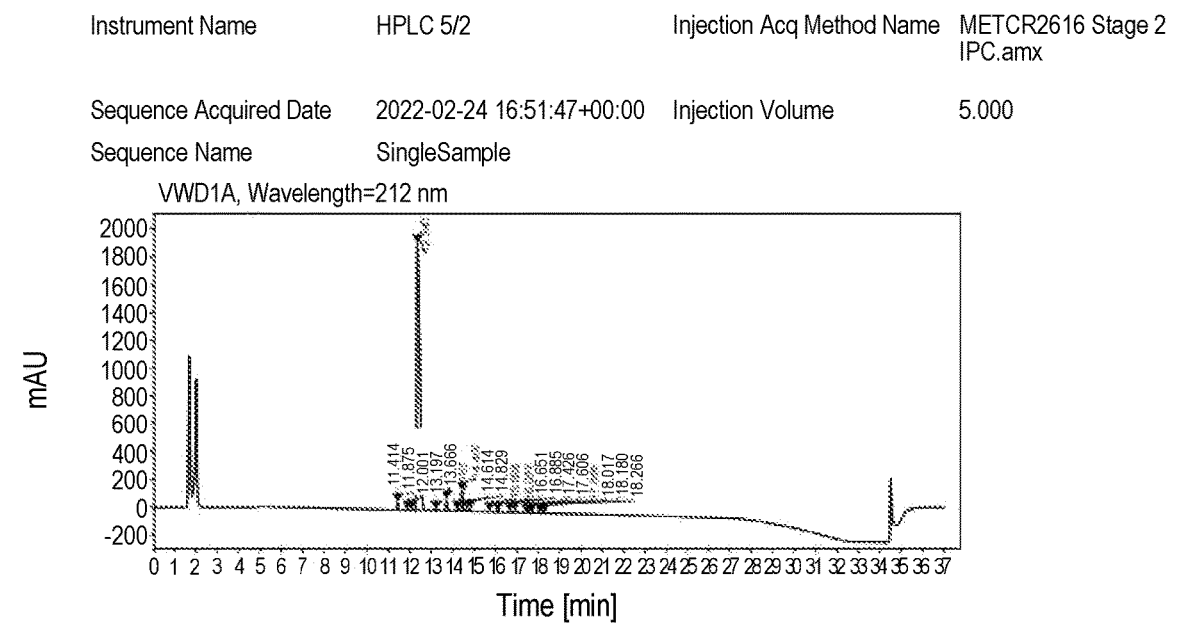
FIG. 49 shows the HPLC profile of amorphous compound 1 fumarate after being stored in a wide-necked, open vial and then inside double polyethlene bags, tied tightly with cable ties for four weeks at 75% RH at 40° C.
Figure 50:
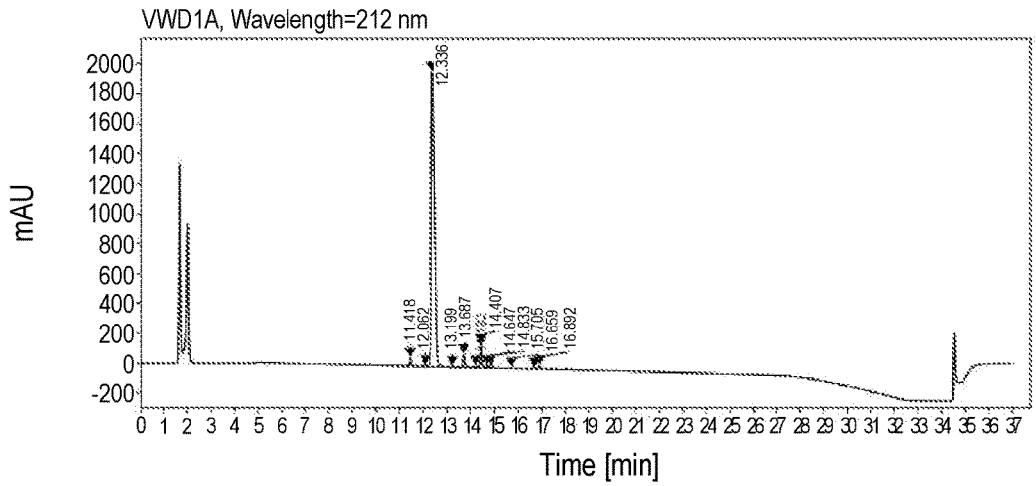
FIG. 50 shows the HPLC profile of amorphous compound 1 fumarate (t=5 w).
Figure 51:
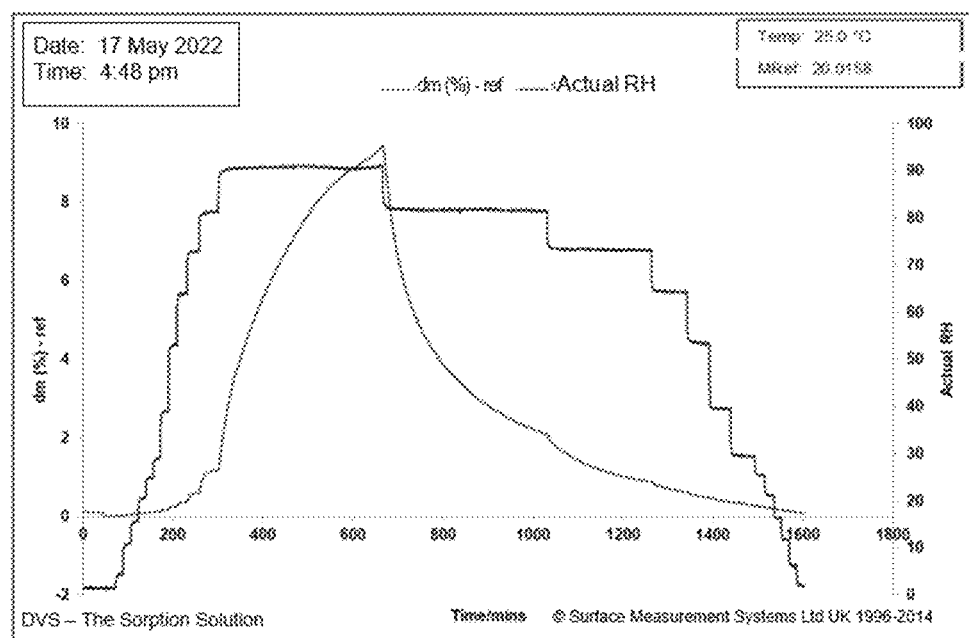
FIG. 51 shows DVS data for amorphous compound 1 fumarate.
Figure 52:
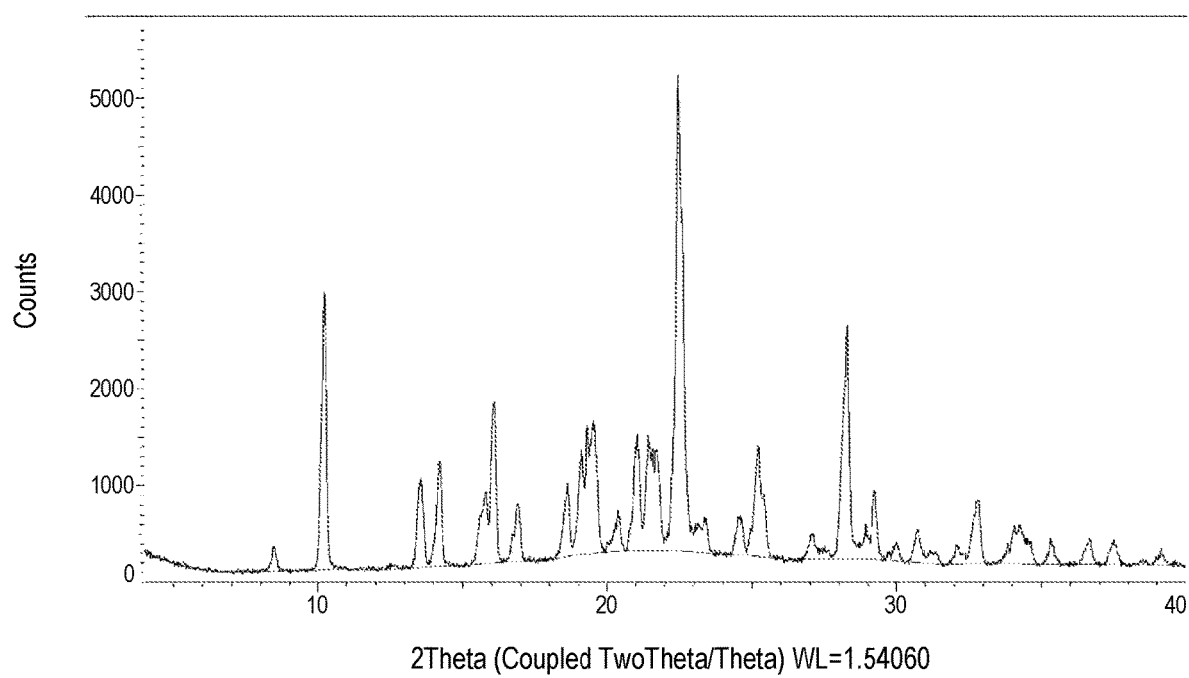
FIG. 52 shows a XPRD profile of crystalline compound 1 monofumarate Form A post-DVS.
Figure 53:
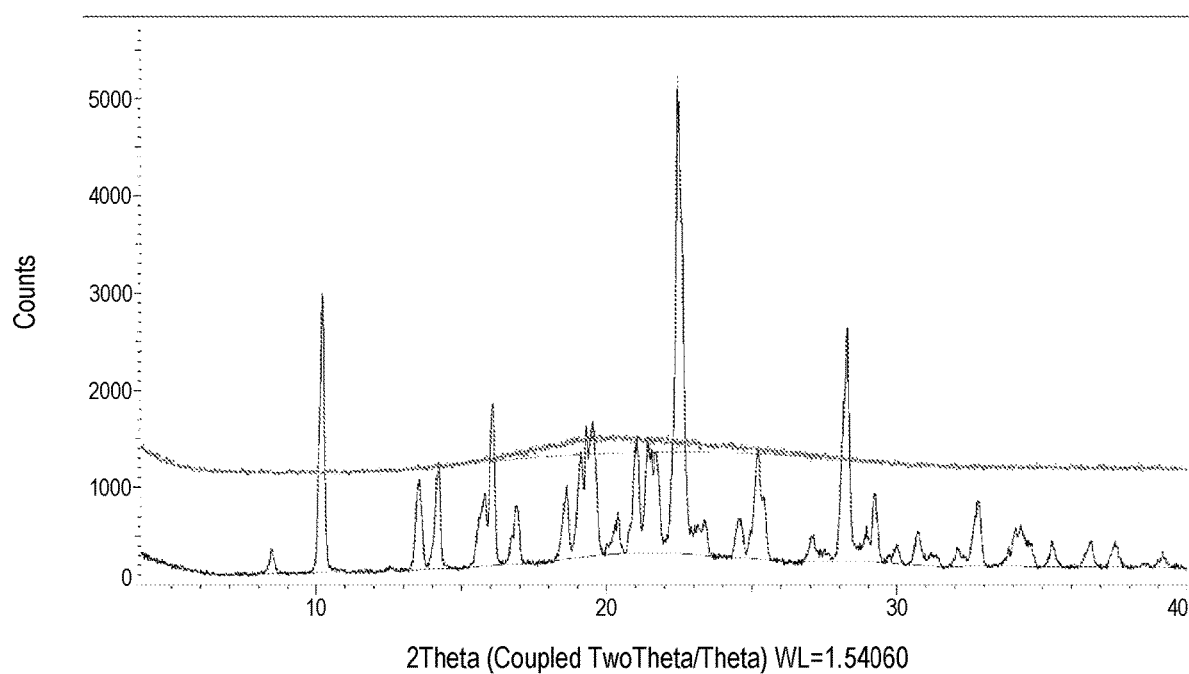
FIG. 53 shows an overlay of the XRPD profile of amorphous compound 1 pre-DVS analysis (top) and crystalline compound monofumarate Form A measured after the DVS-analysis (bottom).
Figure 54:
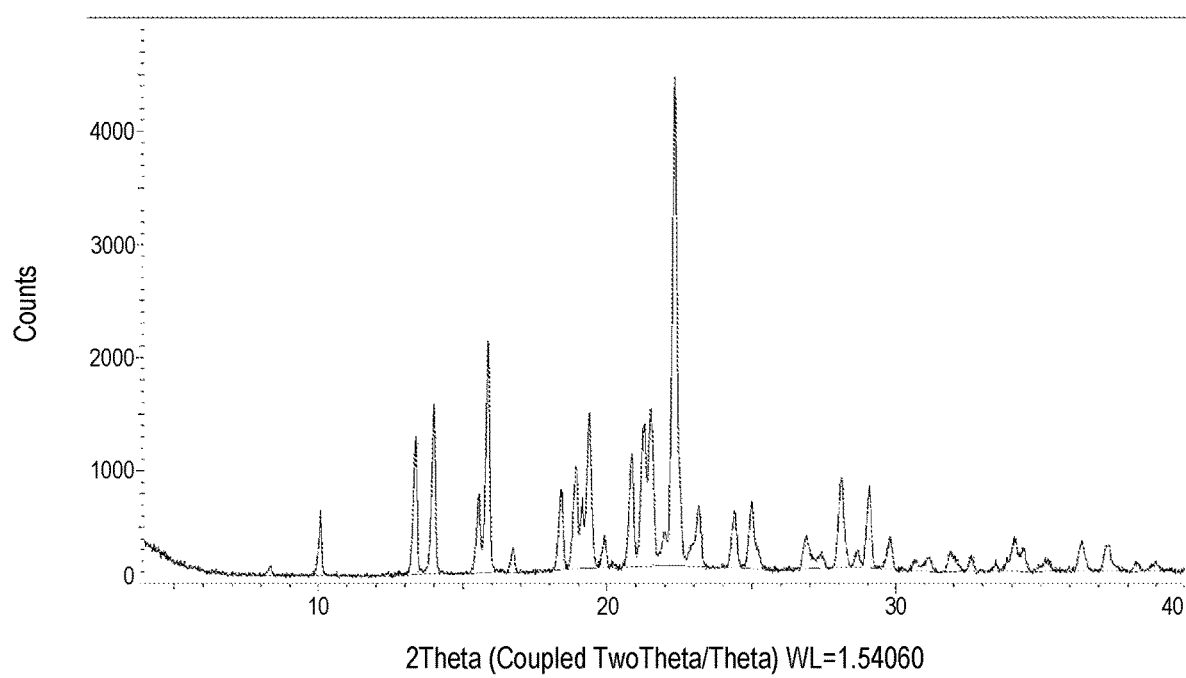
FIG. 54 shows a XRPD profile of crystalline compound 1 monofumarate Form A obtained post-DVS analysis.
Figure 55:
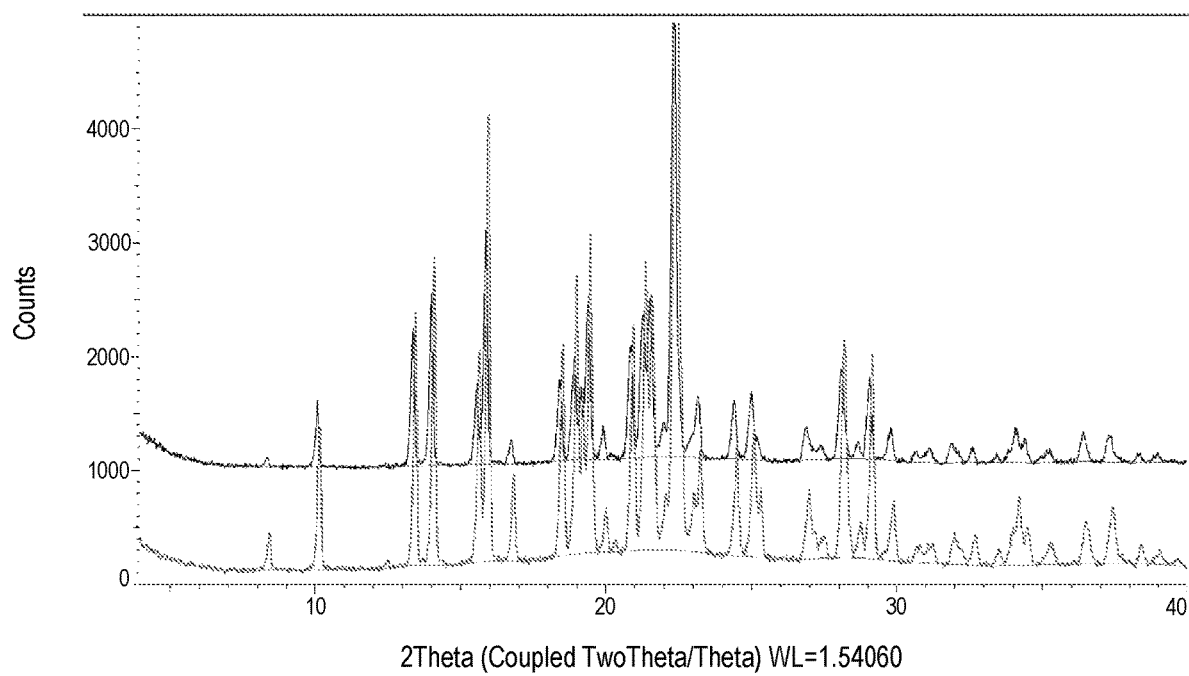
FIG. 55 shows an overlay of the XRPD profile of crystalline compound 1 monofumarate Form A obtained pre-DVS analysis (top) and post-DVS analysis (bottom).

The product from MIBK was analyzed by XRPD, TGA and $^1$H NMR (refer to FIG. 10, FIG. 39, and FIG. 40). Specimen isolated after crystallization from MIBK was most likely the crystalline hemi-solvate version, Compound 1 Fumarate with 0.5MIBK.

TABLE 59

Solubility screen of Compound 1•Fumarate

| | | 5 vol | | | | 10, 15 & 20 vol | | | |
|---|---|---|---|---|---|---|---|---|---|
| | | Solution at | | | Solid on | Solution at | | | Solid on |
| Solvent | ICH Class | 20° C. | 40° C. | reflux | cooling | 20° C. | 40° C. | reflux | cooling |
| Acetone | 3 | ✓ | — | — | — | — | — | — | — |
| MeCN | 2 | ✓ | — | — | — | — | — | — | — |
| Butanol | 3 | ✓ | — | — | — | — | — | — | — |
| tBME | 3 | x | x | x | — | x | x | x | — |
| DCM | 2 | ✓ | — | — | — | — | — | — | — |
| Et$_2$O | 3 | x | x | x | — | x | x | x | — |
| Ethanol | 3 | ✓ | — | — | — | — | — | — | — |
| EtOAc | 3 | x | x | x | — | x | x | x | — |
| IPA | 3 | x | ✓ | — | Yes | — | — | — | — |
| iPrOAc | 3 | x | x | x | — | x | x | x | — |
| Methanol | 2 | ✓ | — | — | — | — | — | — | — |
| MEK | 3 | ✓ | — | — | — | — | — | — | — |
| 2-MeTHF | 3 | x | x | ✓ | Yes | — | — | — | — |
| THF | 2 | ✓ | — | — | — | — | — | — | — |
| Toluene | 2 | x | x | x | — | x | x | x | — |
| Water | # | ✓ | — | — | — | — | — | — | — |
| Dioxane | 3 | x | ✓ | — | No | — | — | — | — |
| CPME | 3 | x | x | x | — | x | x | x | — |
| Heptane | 3 | x | x | x | — | x | x | x | — |
| MIBK | 3 | x | x | x | — | x | x | ✓ | Yes |

Stability Examination of Amorphous Compound 1 Batch 1 at 40° C./75% RH

Two equal portions of amorphous compound 1 Fumarate (batch 1, CP 93.84% area) were weighed out, one of which was placed inside an open vial, while the other was double polyethene bagged, each bag was tied tightly with cable ties. Both samples were maintained at 75% RH at 40° C. and monitored by HPLC at time points t=1 h, 3 h, 24 h, 48 h, 7 d, 2 w, 3 w, 4 w and 5 w.

Under the conditions evaluated during this study, XRPD analysis could not be performed as compound 1 Fumarate turned to an oily residue within 3 h under both conditions. No crystallisation was observed after this time, chemical purity had decreased by approximately 2% area at the 5 week time point, indicating good stability of the amorphous phase under these conditions, over this time.

DVS Analyses

There are two main methods to use, one is by time where the equilibration is given by a fixed time, i.e., 1 hour per step and is appropriate for an unknown phase. The second, is by mass per time unit (dm/dt) of 0.002%/min; that is when the difference in weight is less than 0.002%, the instrument moves onto the next step. For unknown hygroscopicity, the method by time is indicated because it gives an idea of water affinity without wasting much time. Ideally the analyses are repeated using the mass equilibration method to confirm. By experience for hygroscopic samples, the analysis can continue for days. For non-hygroscopic samples the difference between the two methods may not be significant.

Figure 12:
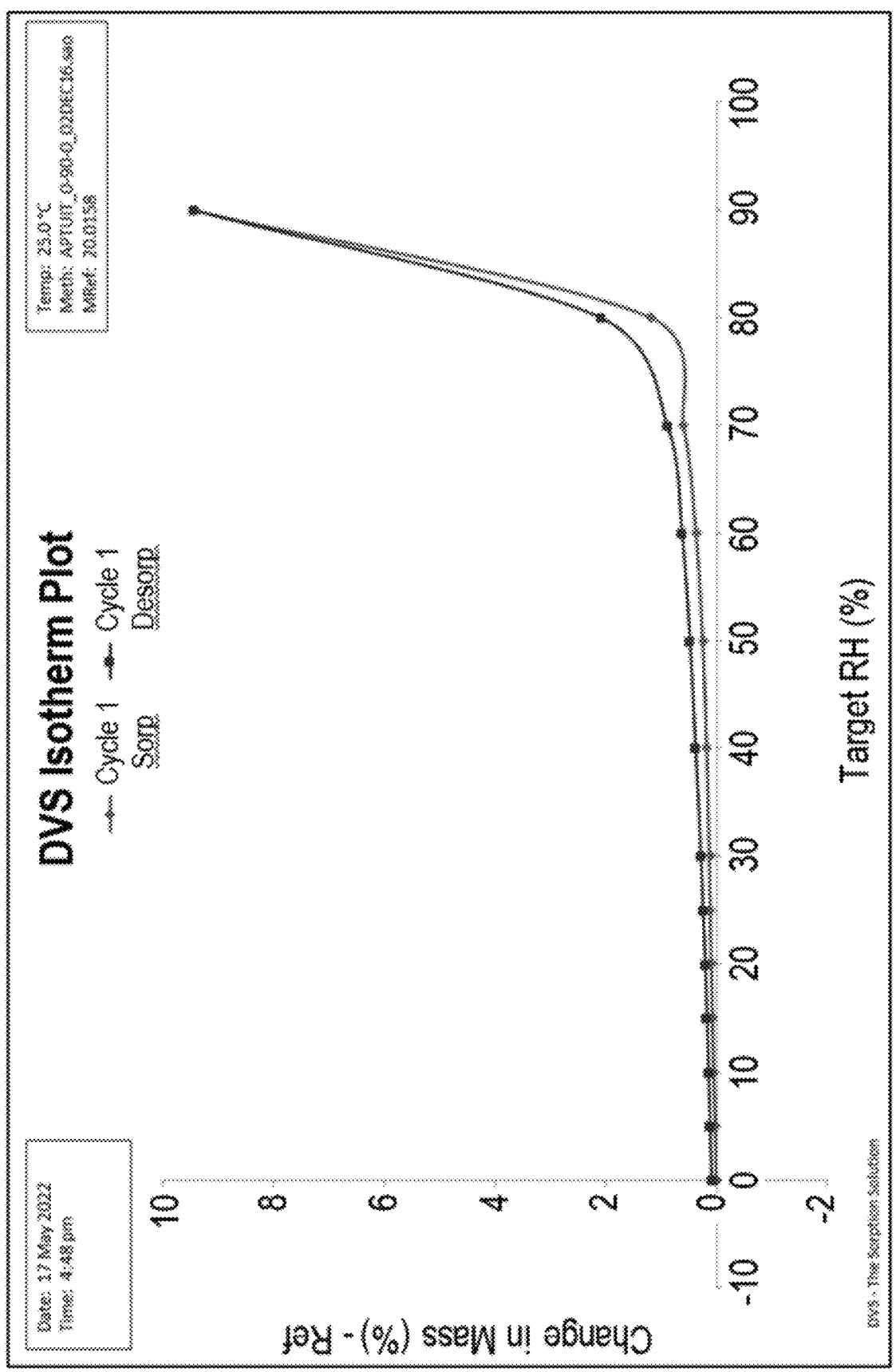
FIG. 12 shows the mass equilibrated DVS isotherm plot of the compound 1 crystalline Form A monofumarate salt. Mass equilibrated dm/dt 0.0002% in between % RH steps.

Consequently, amorphous batch 1 was analyzed by the fixed time method and once compound 1 fumarate crystalline polymorphic Form A was generated the analyses was repeated as mass per unit time equilibrated @dm/dt (0.0002%/min) and is given below (refer to FIG. 12). DVS data of compound 1 fumarate crystalline polymorphic Form A showed deliquescent type isotherm, gained ca. 1% w/w at 70% RH after which, pronounced mono, multilayer sorption and probable deliquescence occurred >80% RH.

Re-Proportionation Examination

Figure 13:
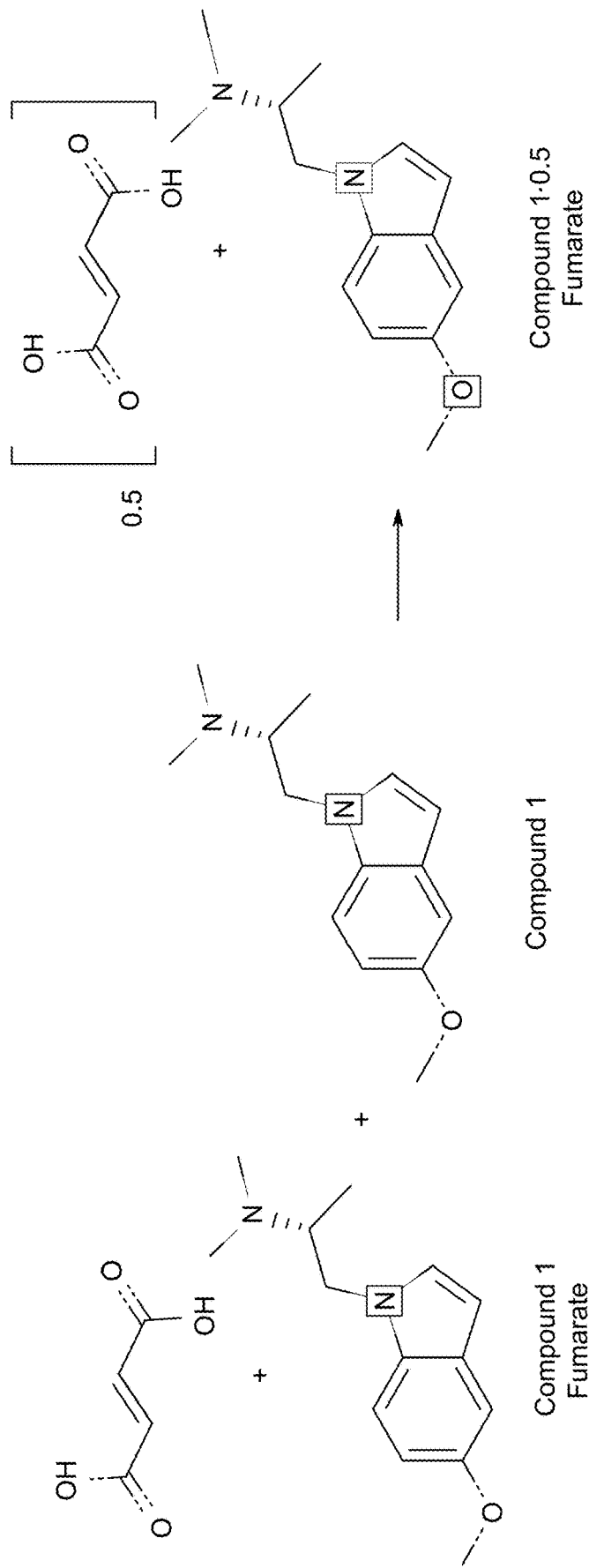
FIG. 13 shows a chemical scheme for re-proportionation of compound 1 fumarate.

The activated compound 1·0.5Fumarate was equilibrated in tBME (initially gum and converted to stable suspension), to determine if the hemi-salt was metastable w.r.t. the unary salt, and spontaneously reverted into compound 1·Fumarate under suspension equilibration conditions. The output from this experiment was consistent with compound 1·0.5Fumarate, concluding that re-proportionation did not occur (i.e., 2compound 1·0.5Fum→compound 1·Fum+compound 1, refer to FIG. 13).

Competitive Re-Proportionation of Unary and Hemi Salts

Figure 14:
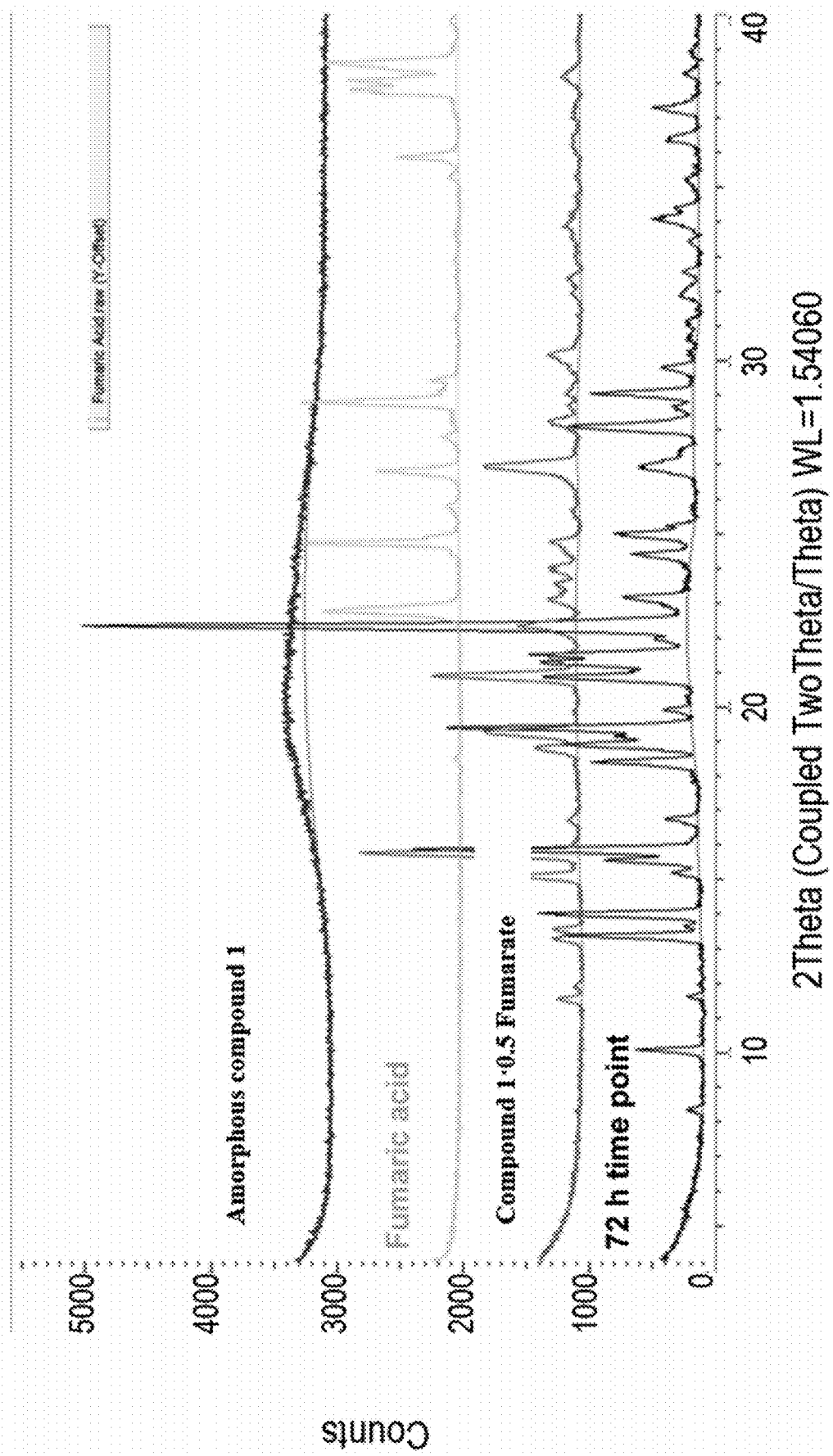
FIG. 14 shows the overlaid XRPD profiles of amorphous compound 1 (top), crystalline fumaric acid (second from top), crystalline compound 1 hemi-fumarate Form II/Pattern 4, and crystalline compound 1 monofumarate Form A, which was measured at the 72-hour timepoint of the competitive re-proportionation experiment described in Example 7.

The powder diffraction pattern of the material isolated from competitive re-proportionation experiments was consistent with Form A, a unary fumarate, i.e. indicating that unary compound 1 fumarate salts were favoured over hemi compound 1 fumarate salts under competitive suspension equilibration conditions (refer to FIG. 14). Therefore, if an under charge of fumaric acid generated a mixture of hemi fumarate and unary fumarate, then the mixed phase should convert to single phase composition of unary fumarate salt and compound 1 free base (in solution) during aging (refer to FIG. 15).

Suspension Equilibration at 20 and 40° C.

Suspension equilibration is a thermodynamic dwelling technique, designed to promote the evolution of the API into a more stable phase. Amorphous compound 1 fumarate was subjected to this technique at ambient temperature (20° C.) and at elevated temperature (40° C.), in a diverse range of solvents.

Amorphous compound 1 fumarate underwent suspension equilibration in 19 single solvents at two different temperature set points (20 and 40° C.). The products were isolated by centrifugation and analysed wet by XRPD. After drying, the samples were reanalyzed.

At 20° C., dissolution or gumming was initially observed in the presence of most solvents; after several days, five of the gums had mobilised to give stable suspensions (refer to entries, Table 61). The products were isolated via centrifugation and the wet pellets were analysed by XRPD, oven dried and reanalysed by XRPD, TGA, DSC and $^1$H NMR.

The companion screen performed at 40° C., yielded no hits. Consequently, the screen was repeated in the presence of an appropriate polarity modifier (either heptane or tBME), to ensure activity of the solvent was maintained while generating stable suspensions from the onset (refer to Table 62). XRPD analysis of both wet and oven dried pellets showed monofumarate Form A (FIG. 74-77).

TABLE 60

Solubility screen of amorphous compound 1 fumarate

| Conditions | HPLC (% area) | XRPD t = 3 h | XRPD t = 24 h | XRPD t = 48 h | XRPD t = 7 days | XRPD t = 2 w | HPLC (% area) | XRPD t = 3 w | HPLC (% area) | XRPD t = 4 w | HPLC (% area) | XRPD t = 5 w | HPLC (% area) |
|---|---|---|---|---|---|---|---|---|---|---|---|---|---|
| Open-necked, wide via at 75% RH/ 40° C. for 5 weeks | 93.84 | Highly/ hygro- scopic/ oily residue | Highly/ hygro- scopic/ oily residue | Highly/ hygro- scopic/ oily residue | Highly/ hygro- scopic/ oily residue | Highly/ hygro- scopic/ oily residue | 91.24 | Highly/ hygro- scopic/ oily residue | 94.17 | Highly/ hygro- scopic/ oily residue | 91.86 | Highly/ hygro- scopic/ oily residue | 91.57 |
| Sealed PK0056 electrostatic bags at 75% RH/ 40° C. for 5 weeks | | Highly/ hygro- scopic/ oily residue | Highly/ hygro- scopic/ oily residue | Highly/ hygro- scopic/ oily residue | Highly/ hygro- scopic/ oily residue | Highly/ hygro- scopic/ oily residue | 91.21 | Highly/ hygro- scopic/ oily residue | 91.94 | Highly/ hygro- scopic/ oily residue | 90.9 | Highly/ hygro- scopic/ oily residue | 91.3 |

TABLE 61

Summary of results of suspension equilibration study at 20° C. (orange colour indicated form change after oven drying). Compound 1 monofumarate was the input.

| Solvent (5 vol) | Obs. (t = 0, @ 20° C.) | Obs. (t = 1 d, @ 20° C.) | Obs. (t = 3 d, @ 20° C.) | Obs. (t = 7 d, @ 20° C.) | Yield % | XRPD (wet) | XRPD (post nitrogen dried) | DSC | TGA | $^1$H NMR (solvent content, % w/w) |
|---|---|---|---|---|---|---|---|---|---|---|
| Acetone | Solution | Solution | Solution | Solution | — | — | — | — | — | — |
| MeCN | Solution | Solution | Solution | Solution | — | — | — | — | — | — |
| tBME | Gum | Feint suspension + gum | Suspension | White suspension | Quant. | Pattern #3b | Pattern #3b | Integral: −22.04 Jg^−1 Onset: 56.30° C. | flat baseline Step: −62.7138% Onset: 208.43° C. | 0.1 |
| Chlorobenzane | Gum | Gum | Gum | Gum and feint suspension | — | — | — | — | — | — |
| DCM | Feint suspension | Gum | Gum | Feint suspension | — | — | — | — | — | — |
| Ethanol | Solution | Solution | Solution | Solution | — | — | — | — | — | — |
| Ethyl acetate | Gum | Suspension + oil | Suspension | Suspension | Quant. | Pattern #3a | Pattern #1 | Integral: −35.88 Jg^−1 Onset: 112.05° C. | flat basline Step: −60.7231% Onset: 208.47° C. | 0.1 |
| Ethyl Formate | Gum | Feint suspension | Feint suspension | Feint suspension | — | — | — | — | — | — |
| Heptane | Gum | Feint suspension | Feint suspension | Gum and feint suspension | — | — | — | — | — | — |
| Isopropyl acetate | Gum | Gum | Suspension | Suspension and gum | Quant. | Pattern #3a | Pattern #1 | Integral: −50.02 Jg^−1 Onset: 110.98° C. | flat baseline Step: −59.4072% Onset: 208.64° C. | 0.5 |
| Methonal | Solution | Solution | Solution | Solution | — | — | — | — | — | — |
| Methyl acetate | Oil | Feint suspension + oil | Feint suspension | Feint suspension | — | — | — | — | — | — |
| Methyl-ethyl ketone | Solution | Solution | Solution | Suspension | Quant. | Pattern #6 | Pattern #1 | Integral: −39.80 Jg^−1 Onset: 113.34° C. | flat baseline Step: −75.1831% Onset: 210.71° C. | 0.2 |
| 2-Methyl THF | Gum | Solution | Suspension | Suspension | Quant. | Pattern #1 | Pattern #1 | Integral: −53.85 Jg^−1 Onset: 110.53° C. | flat baseline Step: −67.2919% Onset: 208.72° C. | n.d. |
| Nitromethane | Solution | Solution | Solution | Solution | — | — | — | — | — | — |
| 2-Propanol | Gum | Solution | Solution | Solution | — | — | — | — | — | — |
| Tetrahydrofuran | Solution | Solution | Solution | Solution | — | — | — | — | — | — |
| Toluene | Gum | Gum | Gum | Gum | — | — | — | — | — | — |
| Water | Feint suspension | Solution | Solution | Solution | — | — | — | — | — | — |

TABLE 62

Summary of results of suspension equilibration study at 40° C.

| Precipitant solvent (7 parts, 10 vol total) | Co-Solvent (3 part, 10 vol total) | Key chemical functional groups | Observations (t = 0 @ 40° C.) | Observations (t = 1 d) @ 40° C.) | Observations (t = 3 d) @ 40° C.) | Observations (t = 7 d @ 40° C.) | XRPD (wet) | XRPD (post oven dried) |
|---|---|---|---|---|---|---|---|---|
| Heptane | Acetone | Symmetrical ketone | Gum | Gum | Gum/oil | Gum | Pattern #1 | Pattern #1 |
| Heptane | Acetonitrile | Simple dipolar-aprotic nitrile | Oil (biphasic) | Oil (biphasic) | Oil (biphasic) | Oil (biphasic) | — | — |
| Heptane | tert-Butylmethyl ether | Branched aliphatic methoxyether | Gum | Gum | Gum | Oil/gum | — | — |

TABLE 62-continued

Summary of results of suspension equilibration study at 40° C.

| Precipitant solvent (7 parts, 10 vol total) | Co-Solvent (3 part, 10 vol total) | Key chemical functional groups | Observations (t = 0 @ 40° C.) | Observations (t = 1 d) @ 40° C.) | Observations (t = 3 d) @ 40° C.) | Observations (t = 7 d @ 40° C.) | XRPD (wet) | XRPD (post oven dried) |
|---|---|---|---|---|---|---|---|---|
| Heptane | Chlorobenzene | Aromatic halide | Gum | Gum | Gum + very feint suspension | Gum + very feint suspension | Pattern #1 | Pattern #1 |
| Heptane | Dichloromethane | Chlorinated hydrocarbon | Gum + Feint suspension | Gum + feint suspension | Gum + very feint suspension | Gum + feint suspension | Pattern #1 | Pattern #1 |
| Heptane | Ethanol | Linear aliphatic alcohol | Gum + Feint suspension | Gum + feint suspension | Suspension | Suspension (sticky) | Pattern #1 | Pattern #1 |
| Heptane | Ethyl acetate | Aliphatic ester | Gum | Gum | Gum | Oil/gum | — | — |
| Heptane | Ethyl formate | Aldehyde aliphatic ester | Gum + Feint suspension | Gum + feint suspension | Gum | Suspension (sticky) | Pattern #1 | Pattern #1 |
| Heptane | Heptane | Linear alkane | Gum | Gum | Gum + very feint suspension | Gum + feint suspension | Pattern #1 | Pattern #1 |
| Heptane | Isopropyl acetate | Branched aliphatic ester | Gum | Gum + feint suspension | Gum + feint suspension | Gum + feint suspension | Pattern #1 | Pattern #1 |
| Heptane | Methanol | Simple aliphatic alcohol | Oil (biphasic) | Oil (biphasic) | Biphasic (oil) | Oil (biphasic) | Pattern #1 | Pattern #1 |
| Heptane | Methyl acetate | Simple aliphatic ester | Gum + Feint suspension | Gum + feint suspension | Gum + feint suspension | Suspension (sticky) | Pattern #1 | Pattern #1 |
| Heptane | Methylethyl ketone | Asymmetric dialkyl ketone | Gum | Gum + feint suspension | Gum + feint suspension | Gum + feint suspension | Pattern #1 | Pattern #1 |
| Heptane | 2-Methyl THF | Asymmetric cyclic ether | Gum | Gum + feint suspension | Gum + feint suspension | Gum + feint suspension | Pattern #1 | Pattern #1 |
| Heptane | Nitromethane | Dipolar aprotic nitro | Oil (biphasic) | Oil (biphasic) | Oil (biphasic) | Biphasic (hazy) | — | — |
| Heptane | 2-Propanol | Branched aliphatic alcohol | Gum + Feint suspension | Gum + feint suspension | Suspension | Suspension (sticky) | Pattern #1 | Pattern #1 |
| Heptane | Tetrahydrofuran | Symmetric cyclic ether | Gum | Gum + feint suspension | Gum + feint suspension | Gum + feint suspension | Pattern #1 | Pattern #1 |
| Heptane | Toluene | Alkyl aromatic hydrocarbon | Gum | Gum | Gum + feint suspension | Gum + feint suspension | Pattern #1 | Pattern #1 |
| Heptane | Water | Dihydrogen oxide | Oil (biphasic) | Oil (biphasic) | Oil (biphasic) | Oil (biphasic) | — | — |

Thermocycling

Thermocycling in different solvents can promote the formation of alternative polymorphic forms. compound 1·Fumarate was heated and cooled between 20° C. and 75% of the relevant solvent b.p. at 0.5° C./minute, for 5 consecutive cycles; a 10-minute dwell was incorporated at each inflection (refer to Table 63). Thermocycling is ripening technique that encourages particle size enlargement and promotes the evolution of the API into a stable phase. Smaller, less stable particles dissolve as the upper temperature boundary is approached, leaving larger stable particles behind; during cooling the concentrated supernatant de-supersaturates resulting in growth in the presence of the larger particles; after thermocycling, the particles should be larger and fewer in number. The products were analysed both wet and dry to determine if form changes had occurred, all products were consistent with monofumarate Form A (refer to FIGS. 16-19 and FIGS. 88-102).

TABLE 63

Thermocycling data summary-All products (wet and Dry) were consistent with Pattern #1, Form A

| Input weight (mg) | Solvent A | Solvent B | Solvent ratio | Output (mg) | Yield (%) | XRPD crystallinity[2] (wet, %) | XRPD crystallinity[2] (dry, %) | DSC | $^1$H NMR (solvent content, % w/w) |
|---|---|---|---|---|---|---|---|---|---|
| 75.6 | MEK | Heptane | (1 to 1) | 61.3 | 81.1 | 83.4 | 83.2 | 116.95° C. | 3.3 |
| 75.8 | tBME | — | 100.0% | 49.5 | 65.3 | 79.0 | 81.0 | 115.33° C., 251.17° C. | 0.2 |
| 75.1 | iPAC | — | 100.0% | 59.2 | 78.8 | 80.7 | 82.7 | 116.83° C., 251.83° C. | 1.3 |
| 75.8 | Toluene | — | 100.0% | 49.1 | 64.8 | 52.4 | 68.1 | 105.50° C., 174.83° C., 251.26° C. | 5.0 |

[2]XRPD crysallinity is computed from the powder pattern and takes it to account the contribution from crystalline peaks and amorphous. Not based on the measurements of physical calibrants and it is calculated by the software.

Heal-Up/Cool Down (HUCD) Crystallization in Different Solvents

Crystallisation from different solvents can be a useful method to investigate alternative polymorphic forms. This crystallisation screen of compound 1·Fumarate could also be used to identify potential conditions for future scale-up crystallisations to control the form outcome. Amorphous compound 1 fumarate (batch 1) was crystallised from several solvents (refer to Table 64). Only entries N1 AND N2 remained in solution when cooled down. The XRPD diffractograms of the rest, which delivered solids, matched monofumarate Form A when oven dried (FIG. 103).

TABLE 64

Summary of HUCD experiment with Compound 1 monofumarate as input

| Input weight (mg) | Precipitant solvent (5 vol) | Co-Solvents | Co-solvent (volumes added, µl) | Key chemical functional groups | b.p. (° C.) | ICH Classes | Observations (t = 0 @ T = 20° C.) | Observations (t = 3 d @ 20° C.) | Form XRPD (moist) | Form XRPD (oven dried) | Tare | Gross | Net | Yield % |
|---|---|---|---|---|---|---|---|---|---|---|---|---|---|---|
| 75.8 | Heptane | Acetone | 200 | Symmetrical ketone | 56 | 3 | suspension | suspension | N/A | Pattern 1 | 1.003 | 1.0597 | 56.7 | 74.8% |
| 74.8 | Heptane | Acetonitrile | 80 | Simple dipolar-aprotic nitrile | 82 | 2 | 2-phase solution | 2-phase solution | N/A | N/A | 1.0077 | N/A | N/A | N/A |
| 76.2 | Heptane | Butanol | 100 | Linear aliphatic alcohol | 118 | 3 | suspension | suspension | N/A | Pattern 1 | 1.001 | 1.047 | 46 | 60.4% |
| 75.1 | Heptane | tert-Butyl-methyl ether | 300 | Branched aliphatic methoxy ether | 55 | 3 | oil/white solid | oil/white solid | N/A | Pattern 1 | 1.0013 | 1.0485 | 47.2 | 62.8% |
| 76.9 | Heptane | Dichloromethane | 160 | Chlorinated hydrocarbon | 40 | 2 | suspension | suspension | N/A | Pattern 1 | 1.0012 | 1.0502 | 49 | 63.7% |
| 76.9 | Heptane | Ethanol | 180 | Linear aliphatic alcohol | 78 | 3 | suspension | suspension | N/A | Pattern 1 | 1.0096 | 1.0498 | 40.2 | 52.3% |
| 77.1 | Heptane | Ehtyl acetate | 420 | Aliphatic ester | 75 | 3 | suspension | suspension | N/A | Pattern 1 | 1.0089 | 1.0505 | 41.6 | 54.0% |
| 75.1 | Heptane | Diethyl ether | 800 | Linear ether | 54 | 3 | gum | gum | N/A | Pattern 1 | 1.0064 | 1.0523 | 45.9 | 61.1% |
| 74.3 | Heptane | Isopropyl acetate | 660 | Branched aliphatic ester | 87 | 3 | suspension | suspension | N/A | Pattern 1 | 1.0037 | 1.0372 | 33.5 | 45.1% |
| 74.1 | Heptane | Dioxane | 240 | Symmetric cyclic ester | 101 | 3 | suspension | suspension | N/A | Pattern 1 | 1.0081 | 1.03742 | 29.1 | 39.3% |
| 80.0 | Heptane | Methylethyl ketone | 100 | Asymmetric dialkyl ketone | 80 | 3 | suspension | suspension | N/A | Pattern 1 | 1.0052 | 1.0544 | 49.2 | 61.5% |
| 76.2 | Heptane | 2-Methyl THF | 380 | Asymmetric cyclic ether | 80 | # | suspension | suspension | N/A | Pattern 1 | 1.0121 | 1.0687 | 56.6 | 74.3% |
| 82.5 | Heptane | 2-Propanol | 120 | Branched aliphatic alcohol | 83 | 3 | suspension | suspension | N/A | Pattern 1 | 1.011 | 1.0404 | 29.4 | 35.6% |
| 77.1 | Heptane | CPME | 800 | Symmetric cyclic ester | 106 | # | gum | gum | N/A | Pattern 1 | 1.0059 | 1.0636 | 57.7 | 74.8% |
| 74.4 | Heptane | Tetrahydrofuran | 300 | Symmetric cyclic ester | 66 | 2 | suspension | suspension | N/A | Pattern 1 | 0.9989 | 1.0404 | 42.5 | 57.1% |
| 78.0 | — | Toluene | 800 | Alkyl aromatic hydrocarbon | 111 | 2 | gum | gum | N/A | Pattern 1 | 1.0111 | 1.0758 | 64.7 | 82.9% |
| 79.6 | Water | Ethanol | 80 | Water | 100 | # | solution | solution | N/A | N/A | N/A | N/A | N/A | N/A |
| 90.0 | Heptane | MIBK | 420 | Asymmetric dialkyl ketone | 116 | # | suspension | suspension | N/A | Pattern 1 | 1.0038 | 1.0515 | 47.7 | 53.0% |

Vapor Diffusion

Vapor diffusion is a slower thermodynamic crystallization technique and good for generating single crystals suitable for single crystal X-ray diffraction (SCXRD). The technique consisted of a solution of amorphous compound 1 fumarate in the relevant non-diffusant solvent, placed inside a small, wide-necked vessel. The wide-necked vessel was then placed inside a larger jar, and the appropriate diffusant solvent was added to the larger jar, to form a moat of diffusant around the smaller vessel.

As the diffusant solvent gradually evaporated, the composition of the non-diffusant solvent changed and in doing so, promoted de-supersaturation and crystallization of compound 1·Fumarate. After 14 days, entry N and entry N remained in full solution, while entry N exhibited a gummy solid which dissolved when worked up. The stable, target form (Pattern #1, monofumarate Form A) was crystallized from MEK with tBME as the diffusant solvent (entry N, refer to Table 65). Microscopy showed mainly aggregations of crystals with very few individual crystals (FIGS. 108-117).

TABLE 65

Summary of vapor diffusion experiment

| Input weight (mg) | Solvent A | Solvent volume (ml) | Solvent B | Co-solvent volume added (ml) | Output (mg) | Yield (% th) | XRPD (wet) | XRPD (dry) |
|---|---|---|---|---|---|---|---|---|
| 75.7 | Water | 0.375 | Acetone | 6.0 | — | — | — | — |
| 76.2 | MEK | 0.375 | tBME | 6.0 | 57.8 | 75.9 | Pattern #1 Form A | Pattern #1 Form A |
| 75.4 | BuOH | 0.375 | Heptane | 6.0 | — | — | — | — |
| 74.4 | MEK | 0.475 | Water | 6.0 | — | — | — | — |

Evaporation Screen

An evaporation screen of compound 1 Fumarate was performed to determine if alternative polymorphic forms were generated by evaporative crystallization (refer to Table 66). Condition-D (methanol) and Condition-F (DMSO) achieved full dissolution at 20° C. Condition-E (DCM), Condition-I (2-MTHF) and Condition-M (MIBK) did not achieve full dissolution despite heating to reflux and sonication.[3] The rest were dissolved after heating to reflux or sonication.

[3] The products from these solvents were still analysed.

Condition-A, condition-D, and condition-J formed oils upon full evaporation of solvent after 6 days. Condition-E, condition-I and condition-L showed precipitate but did not go into full solution at the start of the experiment. Condition-F, and condition-L were in full solution after 6 days. The outputs from this experiment all matched Pattern #1 (monofumarate Form A, FIGS. 118-151).

In Situ Hybidization Evaluation

An XRPD specimen of monofumarate Form A was prepared and treated with sequential aliquots of water. The overlaid XRPD diffractograms indicate that Form A underwent conversion into its amorphous form (refer to FIG. 23).

TABLE 66

Summary of evaporative screen experiment

| | Input weight (mg) | Solvent | Output (mg) | Yield (%) | XRPD (wet) | XRPD (dry) | $^1$H NMR (solvent content, % w/w) |
|---|---|---|---|---|---|---|---|
| A | 51.3 | EtOH | — | — | — | — | — |
| B | 49.1 | Acetone | 37.5 | 76.4 | Pattern #1 Form A | Pattern #1 Form A | 0.26 |
| C | 51.1 | MeCN | 25.1 | 49.1 | | Pattern #1 Form A | 0.12 |
| D | 50.3 | MeOH | — | — | — | — | — |
| E | 50.3 | DCM | 24.2 | 48.1 | Pattern #1 Form A | Pattern #1 Form A | 0.86 |
| F | 49.2 | DMSO | — | — | — | — | — |
| G | 50.5 | IPA | 15.2 | 30.1 | Pattern #1 Form A | Pattern #1 Form A | 0.22 |

TABLE 66-continued

Summary of evaporative screen experiment

| | Input weight (mg) | Solvent | Output (mg) | Yield (%) | XRPD (wet) | XRPD (dry) | $^1$H NMR (solvent content, % w/w) |
|---|---|---|---|---|---|---|---|
| H | 50.8 | MEK | 38.6 | 76.0 | Pattern #1 Form A | Pattern #1 Form A | 2.32 |
| I | 50.3 | 2-MeTHF | 36.8 | 73.2 | Pattern #1 Form A | Pattern #1 Form A | 0.22 |
| J | 51 | THF | — | — | — | — | — |
| K | 50 | BuOH | 36.4 | 72.8 | Pattern #1 Form A | Pattern #1 Form A | 0.51 |
| L | 50.1 | Water | — | — | — | — | — |
| M | 50.9 | MIBK | 31.6 | 62.1 | Pattern #1 Form A | Pattern #1 Form A | 0.44 |
| N | 49.6 | Dioxane | — | — | — | — | — |

Conversion to the Target Form: Suspension Equilibration in MEK at 20° C.

XRPD analysis of the output matched the previously obtained stable form (Pattern #1, Form A, refer to FIG. 24), confirming successful conversion to the desired form. This batch was used in the salt screen studies performed on amorphous compound 1.

Attempted Re-Preparation of Form B: Suspension in tBME at 20° C.

Figure 25:
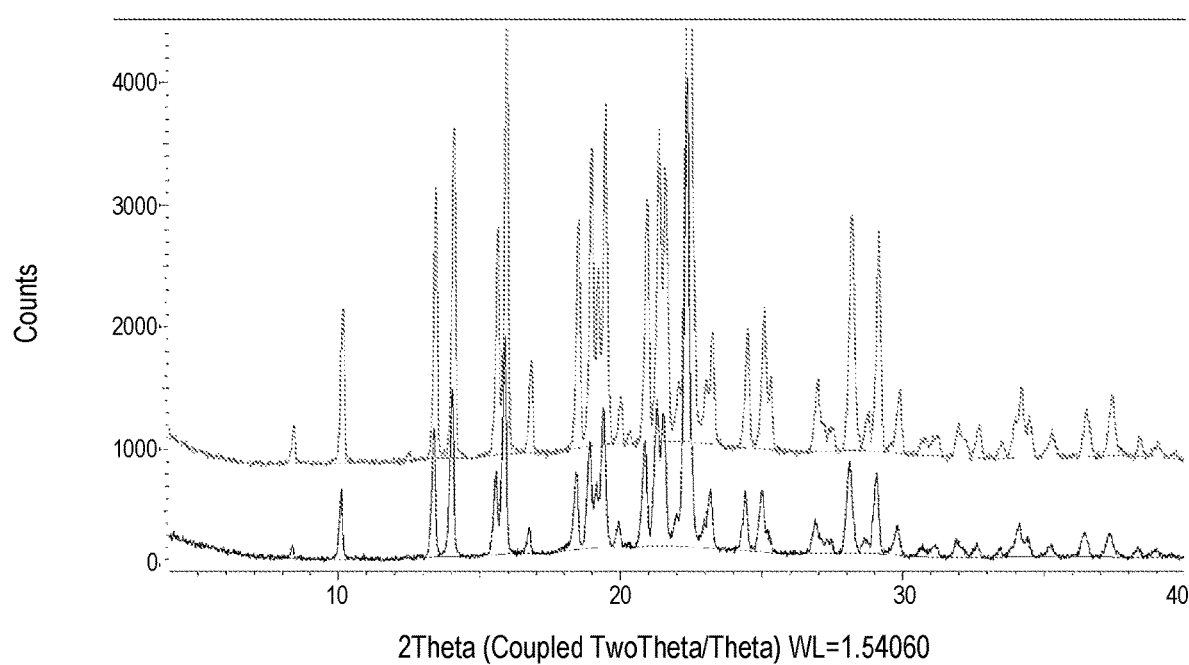
FIG. 25 shows the XRPD diffractogram overlay of crystalline compound 1 monofumarate Form A produced by suspension equilibrium in tBME at 20° C. for 4 days (top) and a reference sample of crystalline compound 1 monofumarate Form A (bottom).

The initial trial to re-prepare monofumarate Form B was performed by dissolving compound 1 Fumarate in tBME (5.0 vol) at 40° C. and was unsuccessful and instead delivered monofumarate Form A after stirring at 20° C. for 4 days (refer to FIG. 25, FIG. 347). The experiment was repeated by applying the same conditions for ca. 18 h, however, the output matched monofumarate Form A (refer to FIG. 26, FIG. 348, FIG. 349). The third attempt involved dissolution of Compound 1 Fumarate in MeOH (4.5 vol), followed by the charge tBME as an anti-solvent to enforce the formation of to deliver the kinetic form out of solution. Unfortunately, the powder diffraction pattern of the obtained material was consistent with monofumarate Form A (refer to FIG. 27).

Competitive Suspension Equilibration (Form A and Form B)

All three attempts to generate monofumarate Form B in tBME failed, and gave monofumarate Form A. These three experiments (attempted isolation of monofumarate Form B from tBME, iPAc, and toluene, which instead led to the isolation of monofumarate Form A) verified the relative stability of Form A relative to Form B (FIG. 17-19, FIG. 343-348).

Crystallization Experiments to Grow a Single Crystal of Monofumarate Form A

A single crystal of Form A was prepared by dissolution in DCM followed by evaporation and was submitted to the UK National Crystallography Service.

Figure 28:
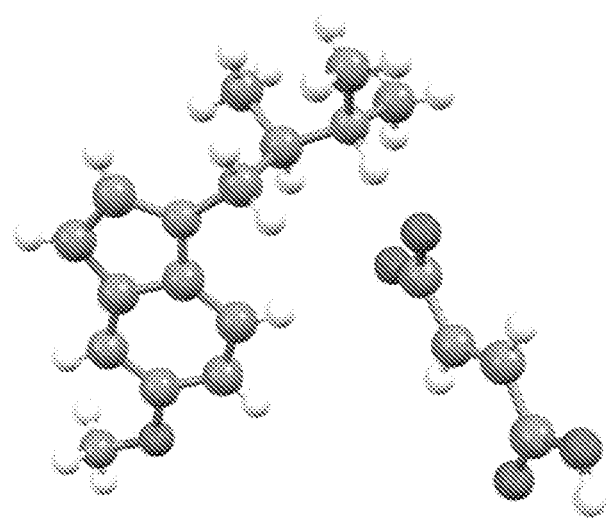
FIG. 28 shows the single-crystal structure of crystalline compound 1 monofumarate Form A.
Figure 29:
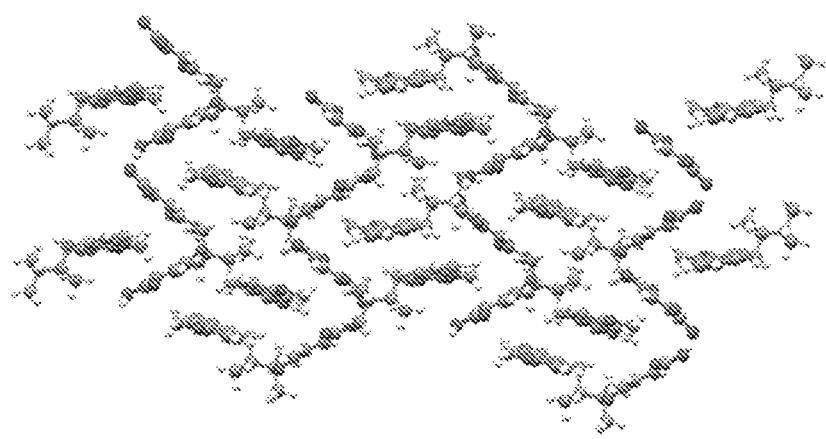
FIG. 29 shows the packing of the crystal lattice of crystalline compound 1 monofumarate Form A.

The unit cell contained 1 API molecule and 1 fumarate. Crystal Data of monofumarate Form A (refer to FIG. 28): $C_{18}H_{24}N_2O_5$, $M_r$=348.39, orthorhombic, $P2_12_12_1$ (No. 19), a=9.03500(10) Å, b=9.44030(10) Å, c=21.0000(2) Å, a=b=g=90°, V=1791.16(3) Å$^3$, T=100(2) K, Z=4, Z'=1, m(Cu Kα)=0.782 mm$^1$, 18799 reflections measured, 3737 unique ($R_{int}$=0.0414) which were used in all calculations. The final wR$_2$ was 0.0750 (all data) and R$_1$ was 0.0292 (1≥2 s(I)).

Figure 30:
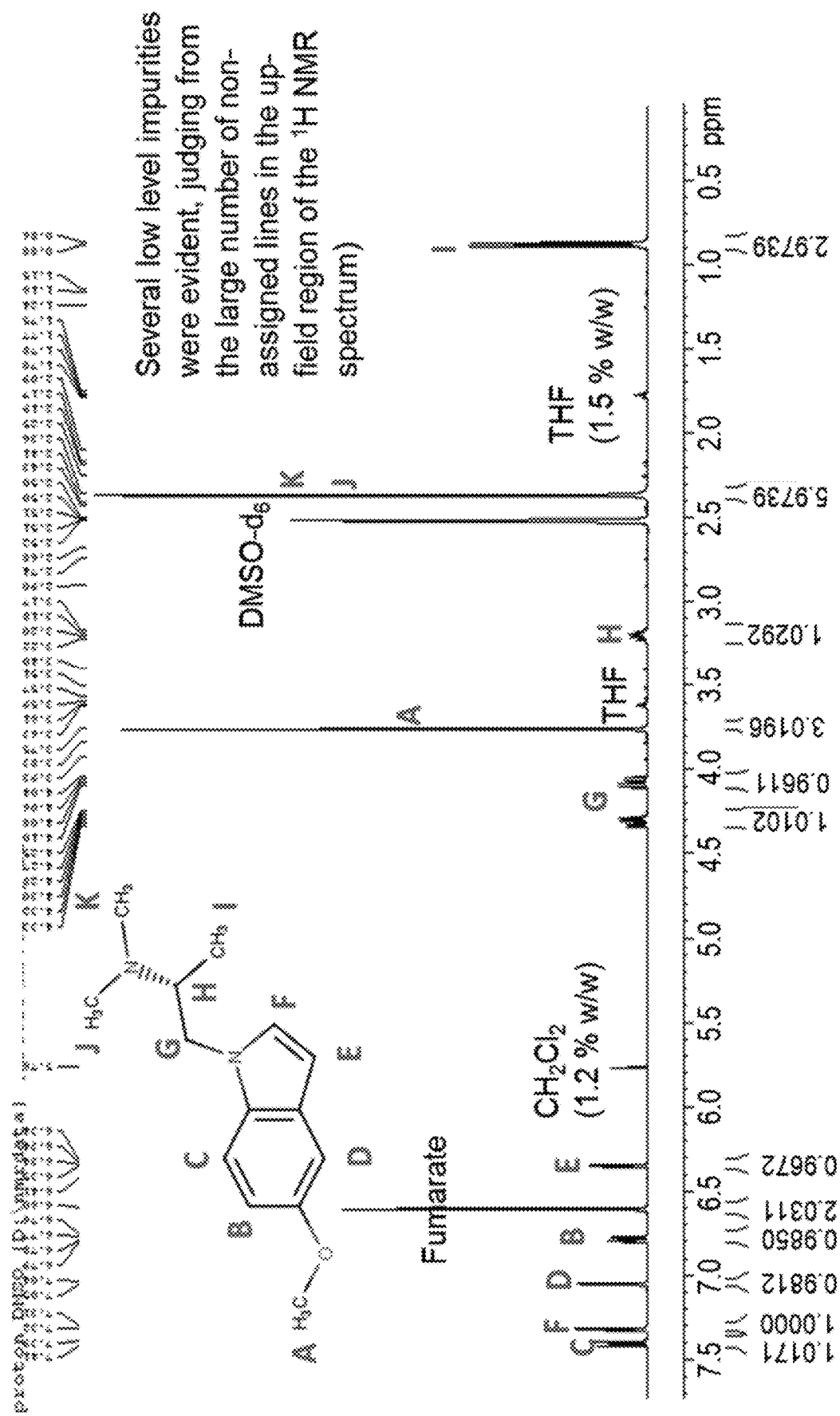
FIG. 30 shows the $^1$H NMR spectrum of amorphous compound 1 Fumarate. The spectrum was acquired in DMSO-do and calibrated to the non-deuterated solvent residual at 2.50 ppm. API to Fumaric acid, 1.0 to 1.0.
Figure 31:
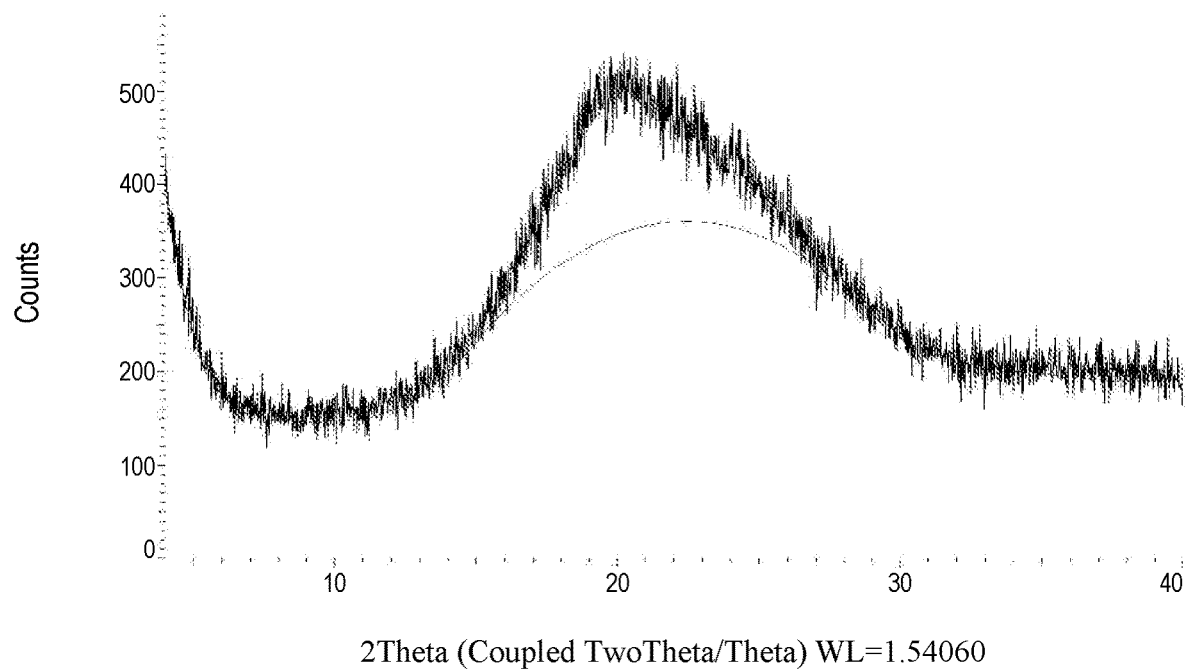
FIG. 31 shows the XRPD profile of amorphous compound 1.
Figure 32:
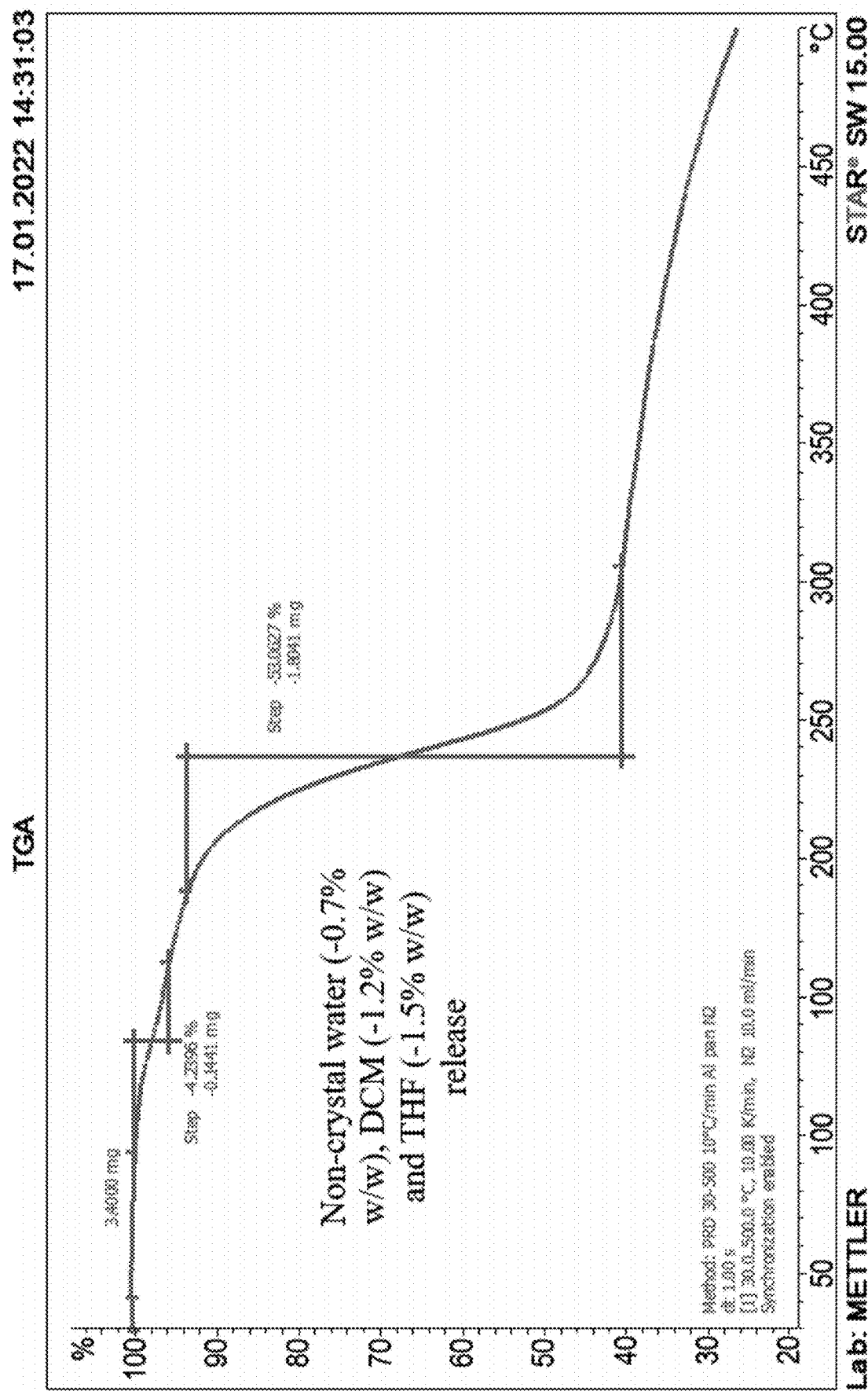
FIG. 32 shows the TGA thermogram of amorphous compound 1, analysis was acquired at a ramp rate of +10° C./minute.
Figure 33:
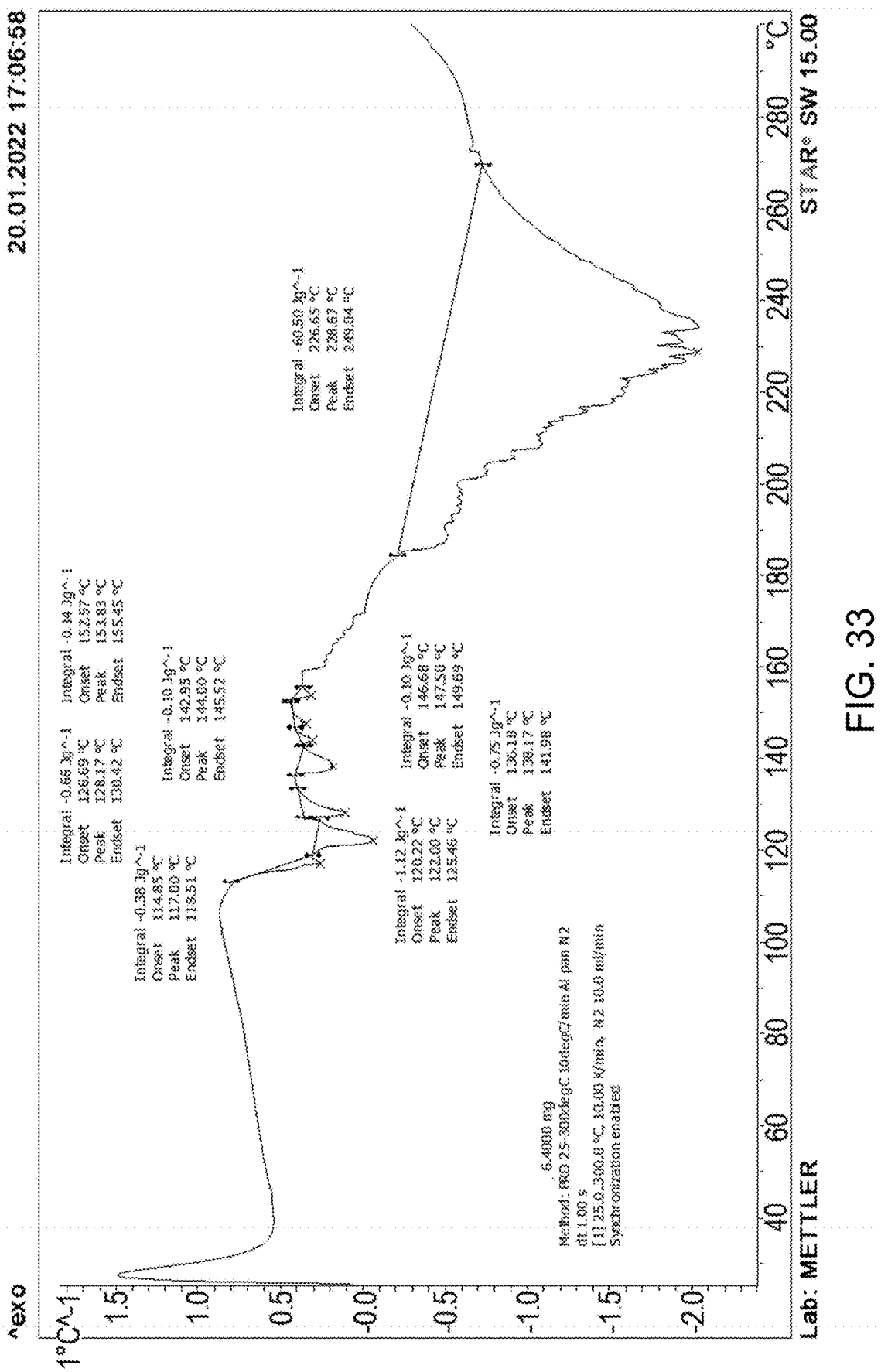
FIG. 33 shows the DSC profile of amorphous compound 1, analysis was acquired at a ramp rate of +10° C./minute.
Figure 34:
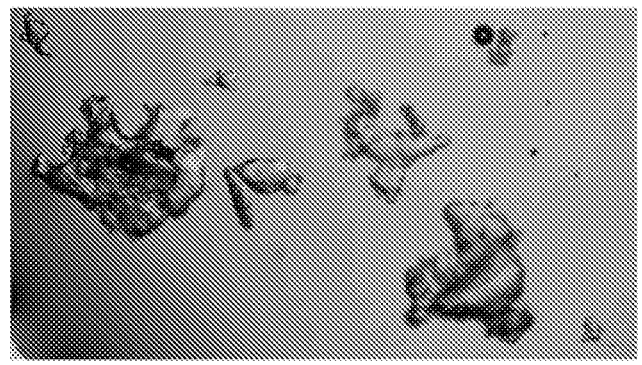
FIG. 34 is an image of a sample of amorphous compound 1, normal polarized (magnification×2).
Figure 35:
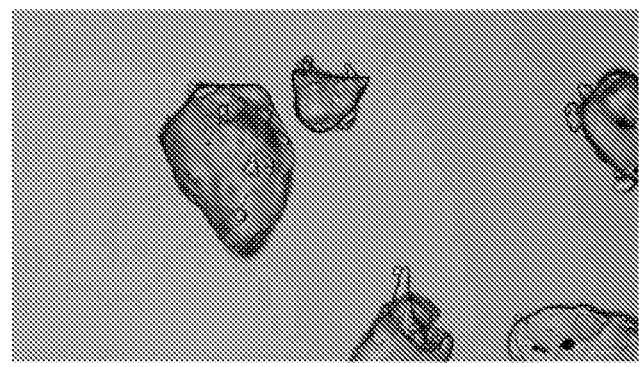
FIG. 35 is an image of a sample of amorphous compound 1, cross polarized (magnification×2).
Figure 36:
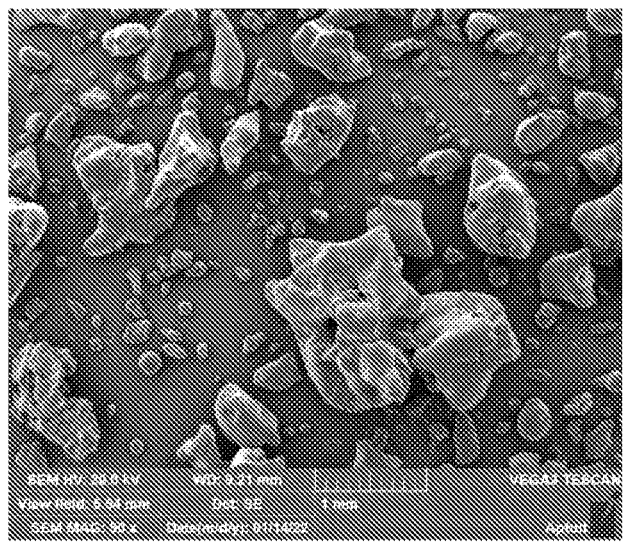
FIG. 36 is an image of a sample of amorphous compound 1 (magnification×50, wide field)
Figure 37:
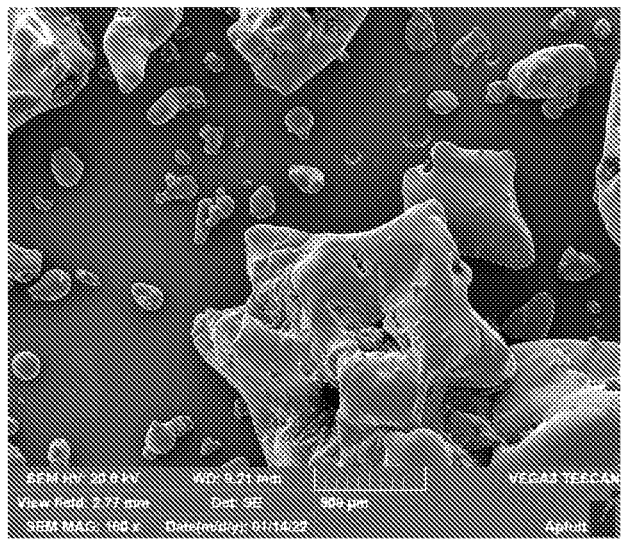
FIG. 37 is an image of a sample of amorphous compound 1 (magnification×100, res.).
Figure 38:
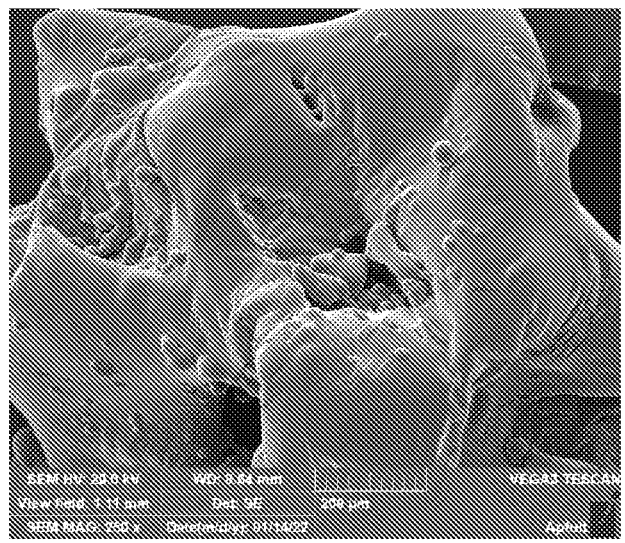
FIG. 38 is an image of a sample of amorphous compound 1 (magnification×250, res.).

According to the crystal structure obtained, hydrogen-bond between oxygen atoms 05 and O3 of fumaric acid 2.590 A. Salified between N2 and O2 2.656 A. Extensive hydrogen bonding structure, each fumarate molecule hydrogen bonds between 1 API and 2 separate fumarate molecules creating a chain between molecules throughout the structure (refer to FIG. 338). Void space analysis indicates a maximum radius of 0.93 Å, too small for solvent molecules to be present in the structure (refer to FIG. 30).

Conclusions

Monofumarate Form A (1.0 to 1.0 fumarate salt), hemifumarate Form I (1.0 to 0.5 fumarate salt), monofumarate Form B (1.0 to 1.0 salt), hemifumarate Form II (1.0 to 0.5 fumarate salt), in conjunction with Pattern #3a, Pattern #5 and Pattern #6 were generated. Form A was definitively characterised, including single crystal structure determination. In certain cases, it was not possible to obtain full characterisation of certain forms due to their metastability. Form A was the stable monotropic form.

Compound 1·MonoFumarate Form A (previously assigned Pattern #1) was found to be the stable form and was selected to be progressed into the salt screen. Monofumarate Form A was generated even when conditions for monofumarate Form B formation were applied. The considerable difficulties encountered in attempting to re-prepare the subordinate phases meant that no formal competitive suspension equilibration slurries were carried out and served to demonstrate that monofumarate Form A was most likely, the most stable form. The fumarate salt form is also capable of disproportionation (i.e., separation into non-ionised versions of the API and fumaric acid) and re-proportionation (conversion into the hemi fumarate and non-ionised fumaric acid, Forms I and II were identified) under certain conditions. Preliminary stability evaluation of Compound 1 Fumarate, included several weeks at 40° C./75% RH and showed no evidence for hydrate formation or degradation.

Summary of Forms

Monofumarate Form A (Pattern #1)

Preparation

Monofumarate Form A (Pattern #1) was prepared in various solvents e.g. iPAc, acetone, 2Me-THF, CPME or MEK.

Characterization Data

XRPD: an exemplary XRPD profile for Form A is shown in FIG. 6.

The XRPD peak pattern of crystalline compound 1 fumarate Form A was calculated. The calculated peaks are shown in Table 115.

TABLE 115

Calculated XRPD signals for crystalline compound 1 monofumarate, Pattern #1, Form A.

| Signal number | 2-θ (°) | d Value | Net Intensity (counts) | Gross Intensity (counts) | Rel. Intensity (%) |
|---|---|---|---|---|---|
| Signal #1 | 10.3 | 8.61 | 1126.6 | 1139.1 | 11.5 |
| Signal #2 | 13.6 | 6.53 | 2683.7 | 2720.5 | 27.4 |
| Signal #3 | 14.2 | 6.23 | 3675.4 | 3715.5 | 37.5 |
| Signal #4 | 15.7 | 5.62 | 1512.1 | 1550.0 | 15.4 |
| Signal #5 | 16.0 | 5.53 | 4660.4 | 4697.7 | 47.5 |
| Signal #6 | 18.8 | 4.72 | 1197.4 | 1238.8 | 12.2 |
| Signal #7 | 19.3 | 4.60 | 2498.7 | 2550.3 | 25.5 |
| Signal #8 | 19.5 | 4.54 | 2989.3 | 3044.4 | 30.5 |
| Signal #9 | 21.2 | 4.18 | 2615.2 | 2686.7 | 26.7 |
| Signal #10 | 21.7 | 4.09 | 3301.8 | 3377.4 | 33.7 |
| Signal #11 | 22.7 | 3.91 | 9809.5 | 9879.0 | 100.0 |
| Signal #12 | 23.4 | 3.80 | 1482.8 | 1536.3 | 15.1 |
| Signal #13 | 24.8 | 3.59 | 1286.3 | 1315.4 | 13.1 |
| Signal #14 | 25.3 | 3.52 | 983.5 | 1011.2 | 10.0 |
| Signal #15 | 28.7 | 3.11 | 1676.0 | 1727.6 | 17.1 |
| Signal #16 | 29.6 | 3.01 | 2058.9 | 2112.0 | 21.0 |

Figure 64:
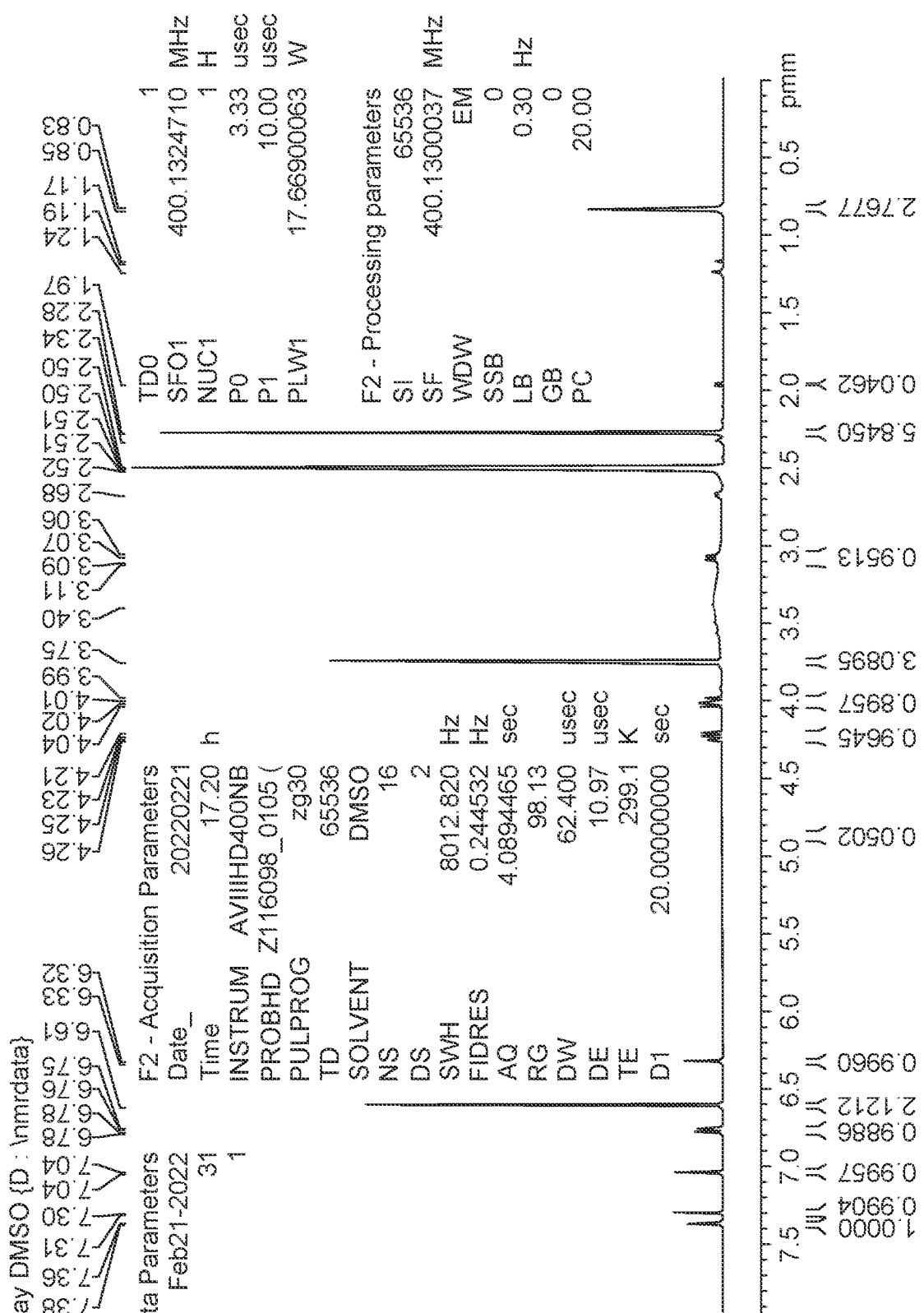
FIG. 64 shows a $^1$H NMR spectrum of crystalline compound 1 fumarate Form A, spectrum was acquired in DMSO-$d_6$ and calibrated to the non-deuterated solvent residual at 2.50 ppm. API to Fumaric acid, 1.0 to 1.0. IPAc content, 0.5% w/w.
Figure 65:
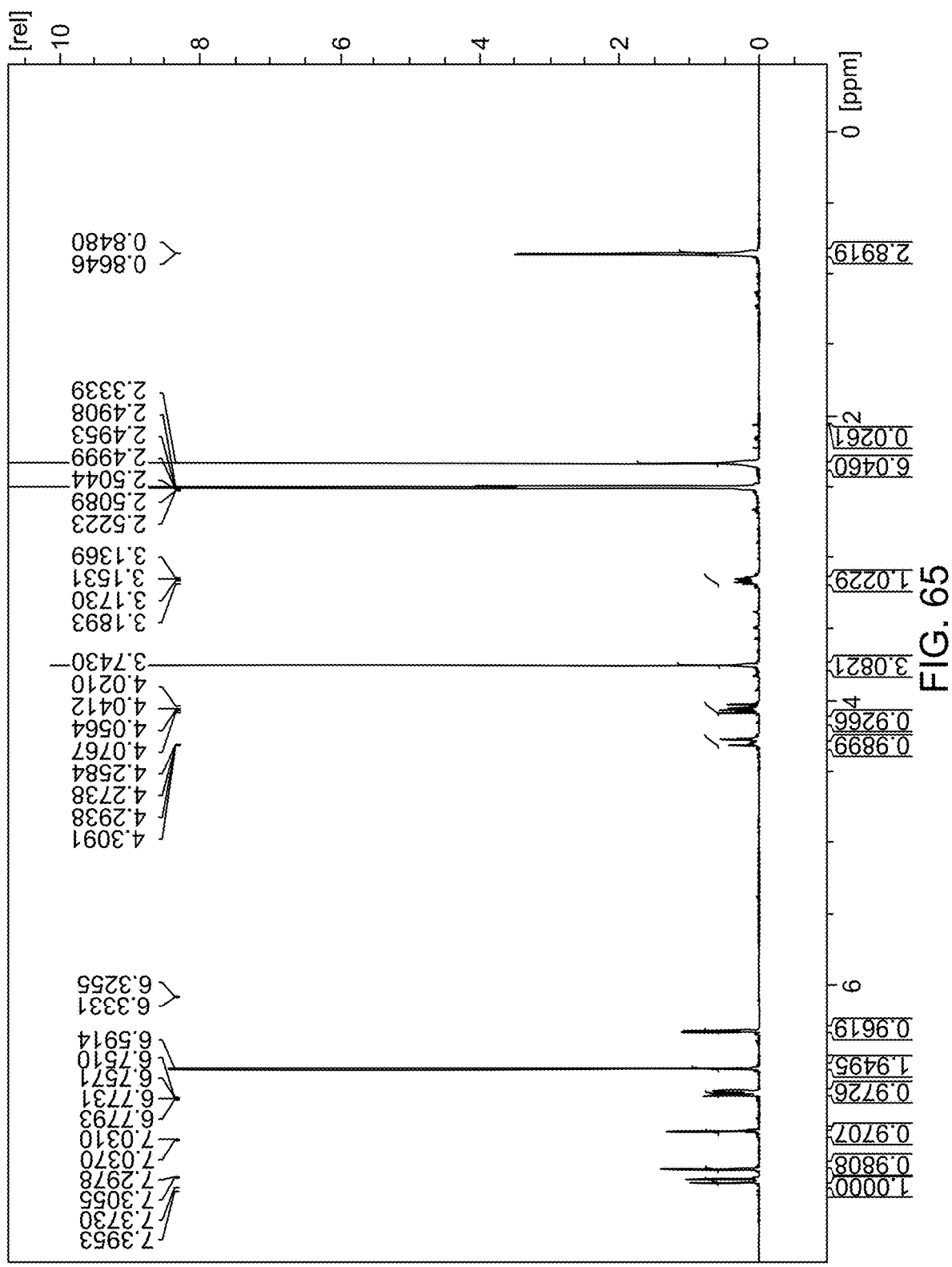
FIG. 65 shows a $^1$H NMR spectrum of crystalline compound 1 monofumarate Form A, spectrum was acquired in DMSO-$d_6$ and calibrated to the non-deuterated solvent residual at 2.50 ppm. API to Fumaric acid, 1.0 to 1.0. MEK content, 0.2% w/w.
Figure 66:
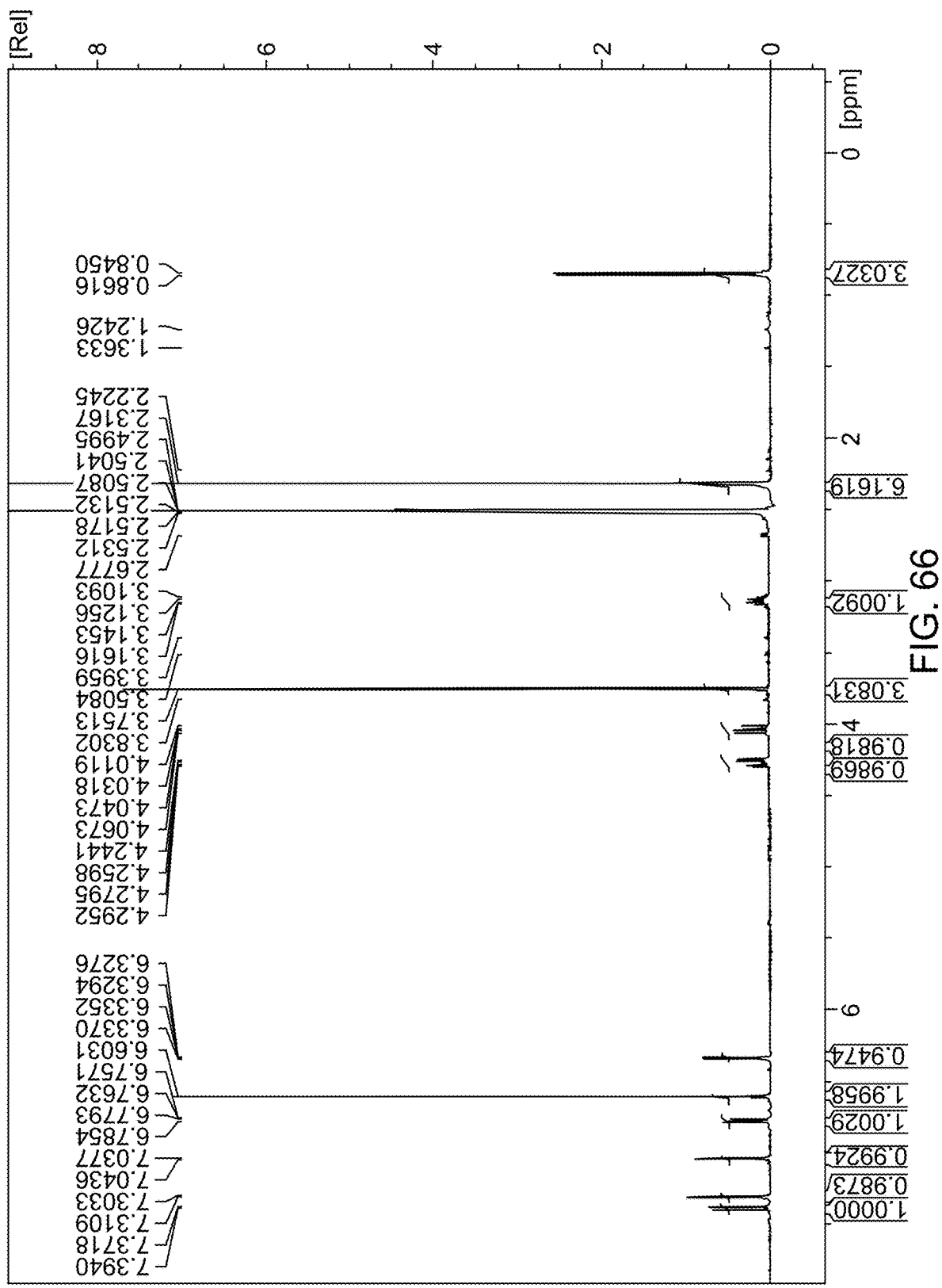
FIG. 66 shows a $^1$H NMR spectrum of crystalline compound 1 monofumarate Form A, spectrum was acquired in DMSO-$d_6$ and calibrated to the non-deuterated solvent residual at 2.50 ppm. API to Fumaric acid, 1.0 to 1.0. MEK content, 0.2% w/w.
Figure 80:
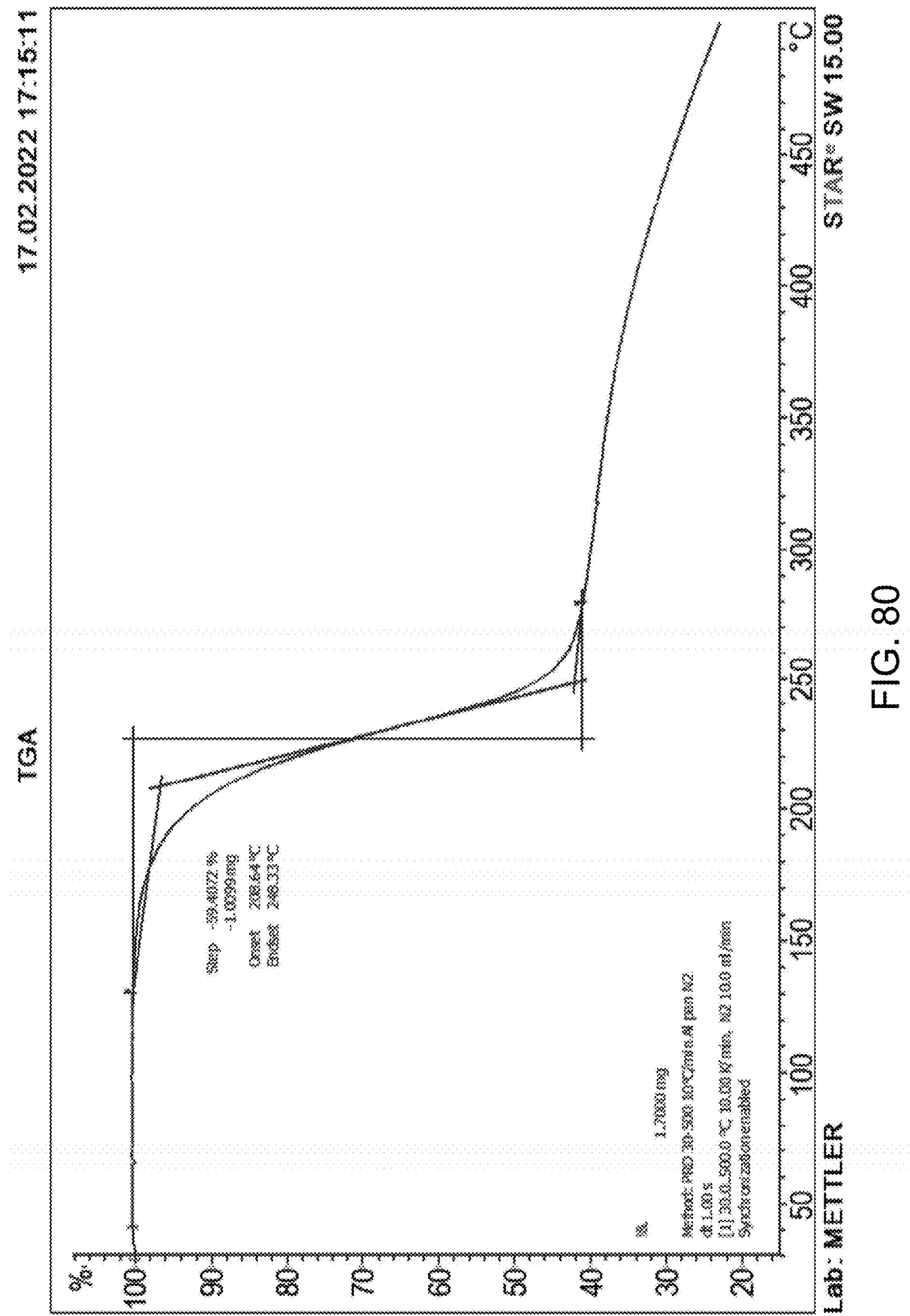
FIG. 80 shows a TGA thermogram of crystalline compound 1 monofumarate Form A, analysis was acquired at a ramp rate of +10° C./minute.
Figure 81:
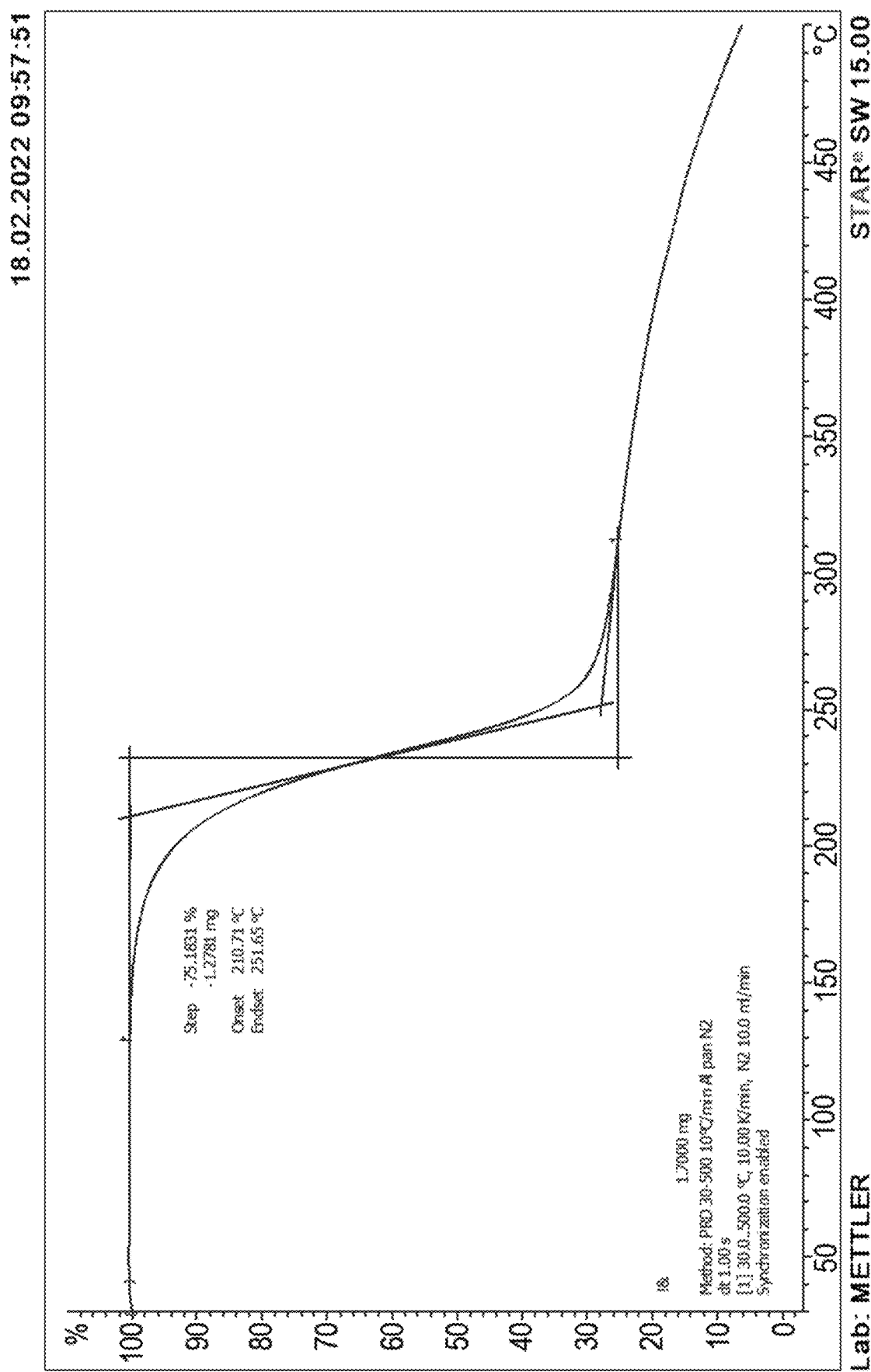
FIG. 81 shows a TGA thermogram of crystalline compound 1 monofumarate Form A, analysis was acquired at a ramp rate of +10° C./minute.
Figure 82:
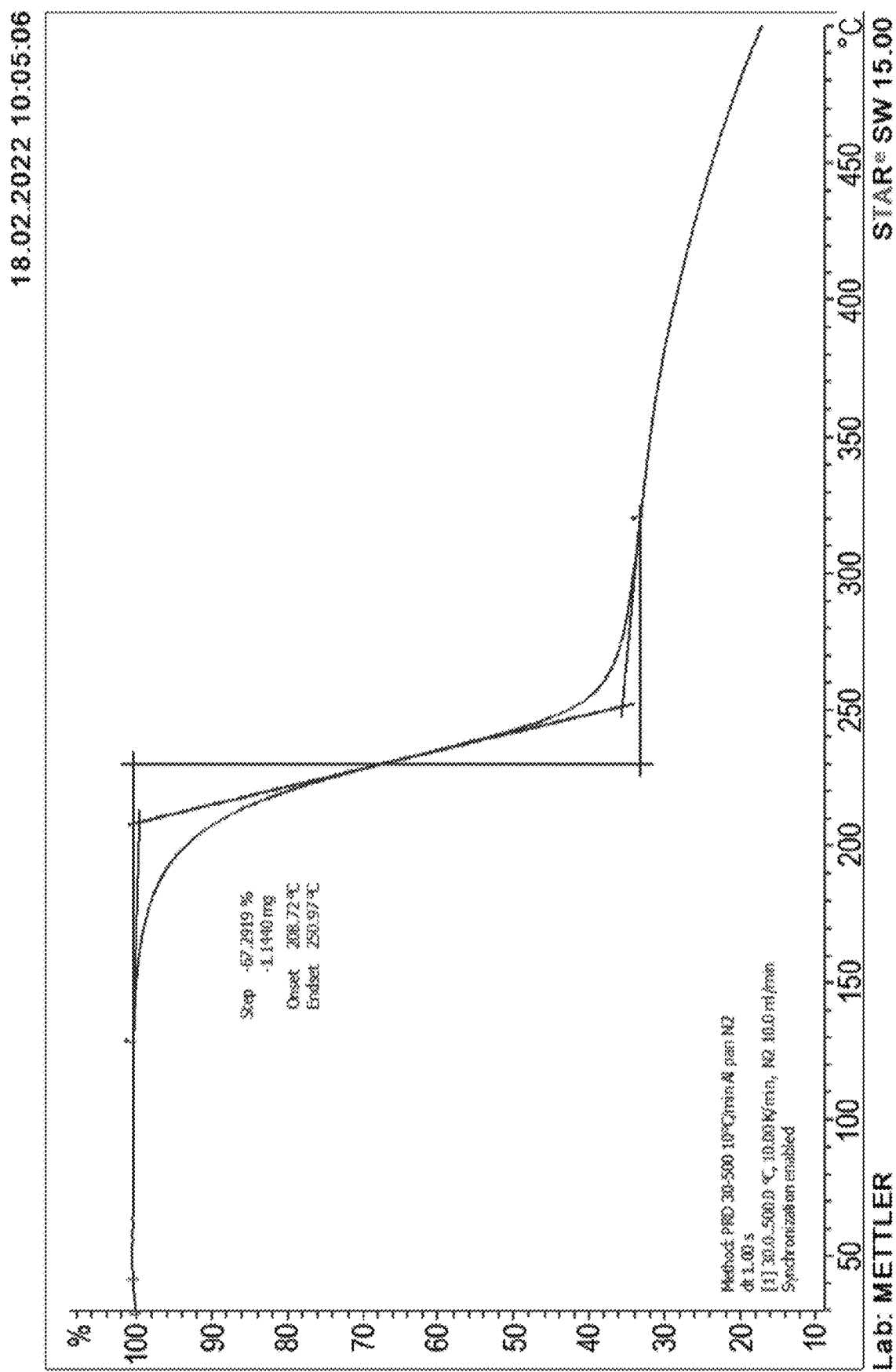
FIG. 82 shows a TGA thermogram of crystalline compound 1 monofumarate Form A, analysis was acquired at a ramp rate of +10° C./minute.
Figure 85:
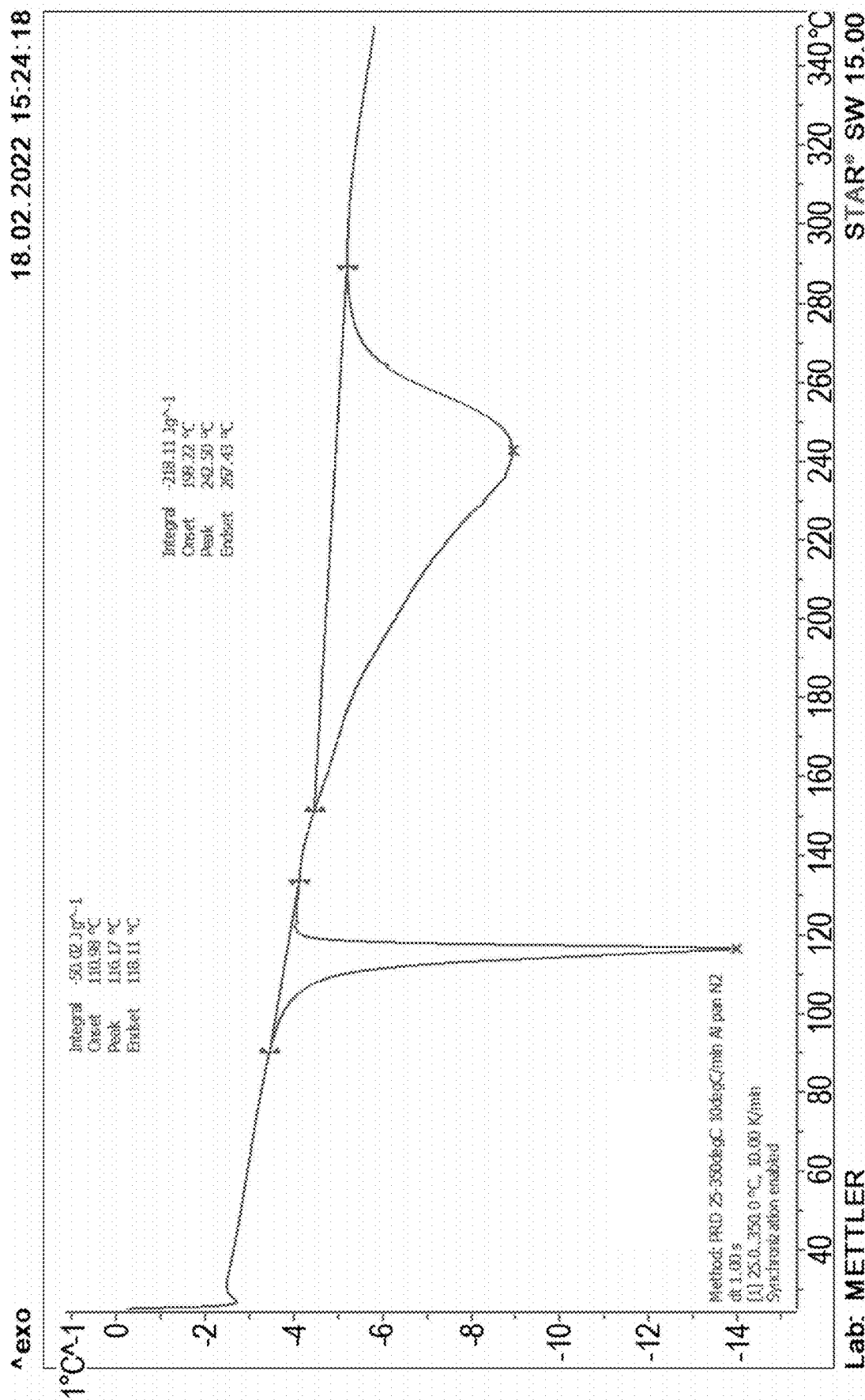
FIG. 85 shows a DSC profile of crystalline compound 1 monofumarate Form A, analysis was acquired at a ramp rate of +10° C./minute.
Figure 86:
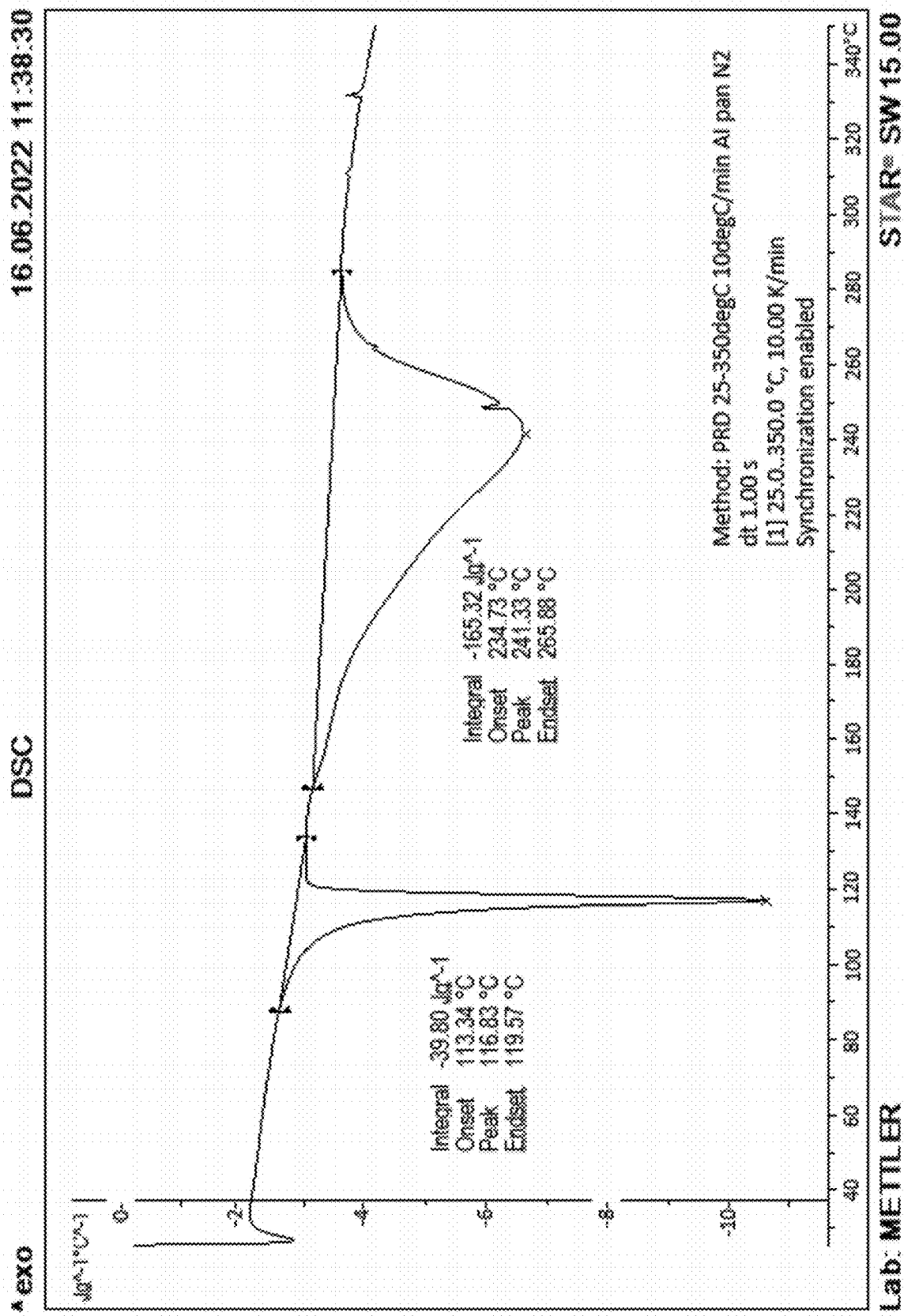
FIG. 86 shows a DSC profile of crystalline compound 1 monofumarate Form A, analysis was acquired at a ramp rate of +10° C./minute.
Figure 87:
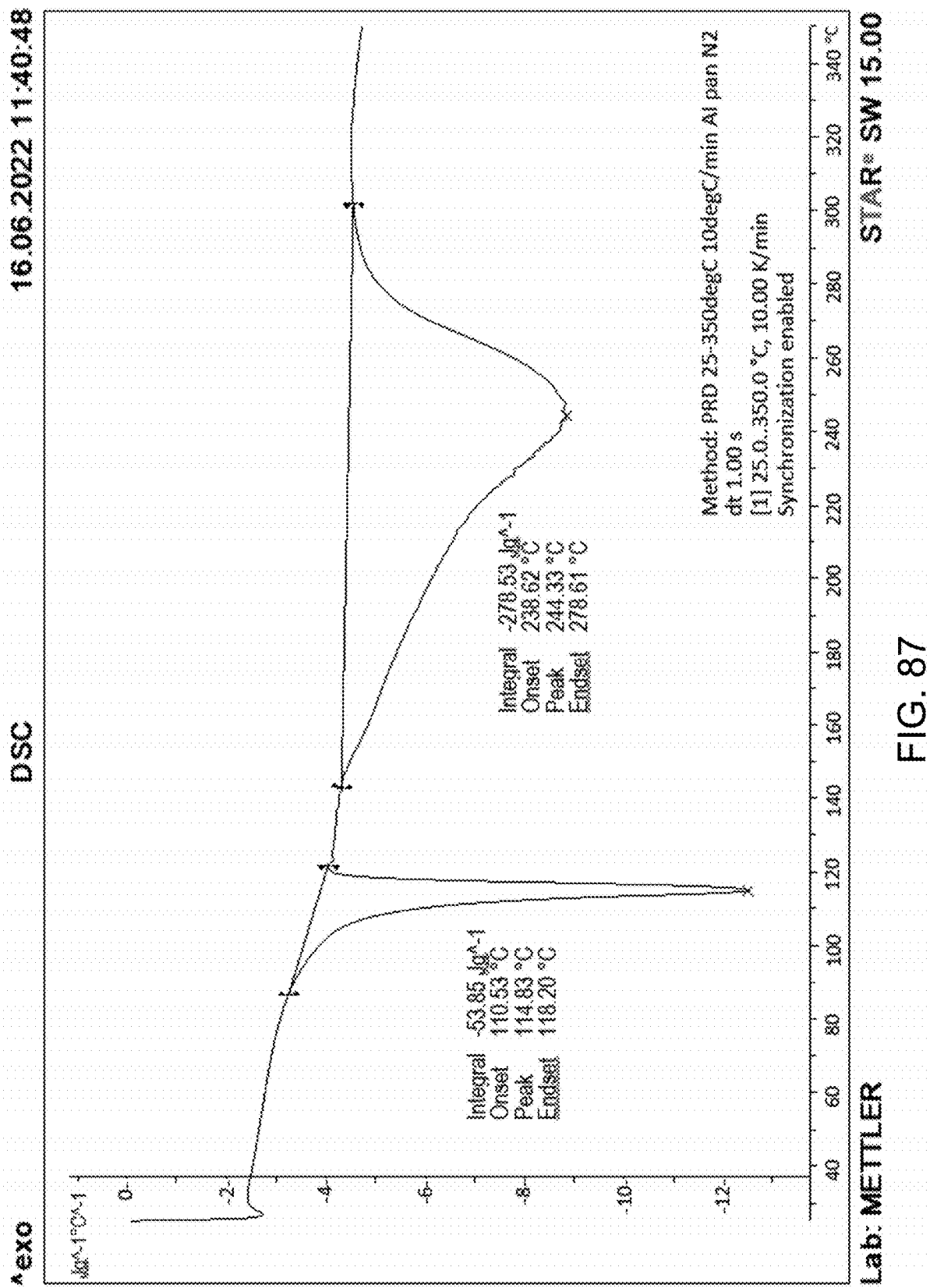
FIG. 87 shows a DSC profile of crystalline compound 1 monofumarate Form A, analysis was acquired at a ramp rate of +10° C./minute.
Figure 88:
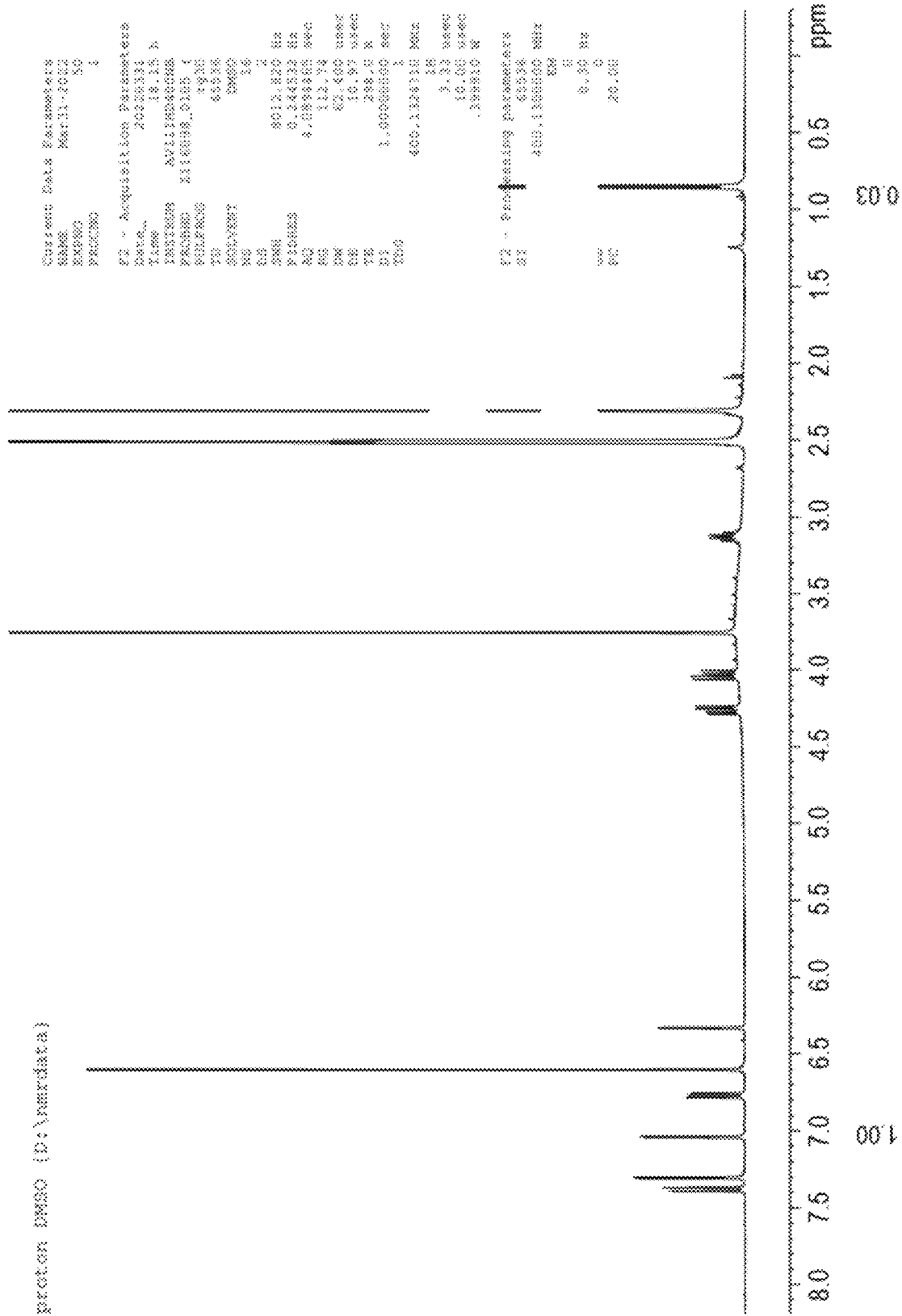
FIG. 88 shows a $^1$H NMR spectrum of crystalline compound 1 monofumarate Form A, spectrum was acquired in DMSO-$d_6$ and calibrated to the non-deuterated solvent residual at 2.50 ppm. MEK content, 3.3% w/w.
Figure 89:
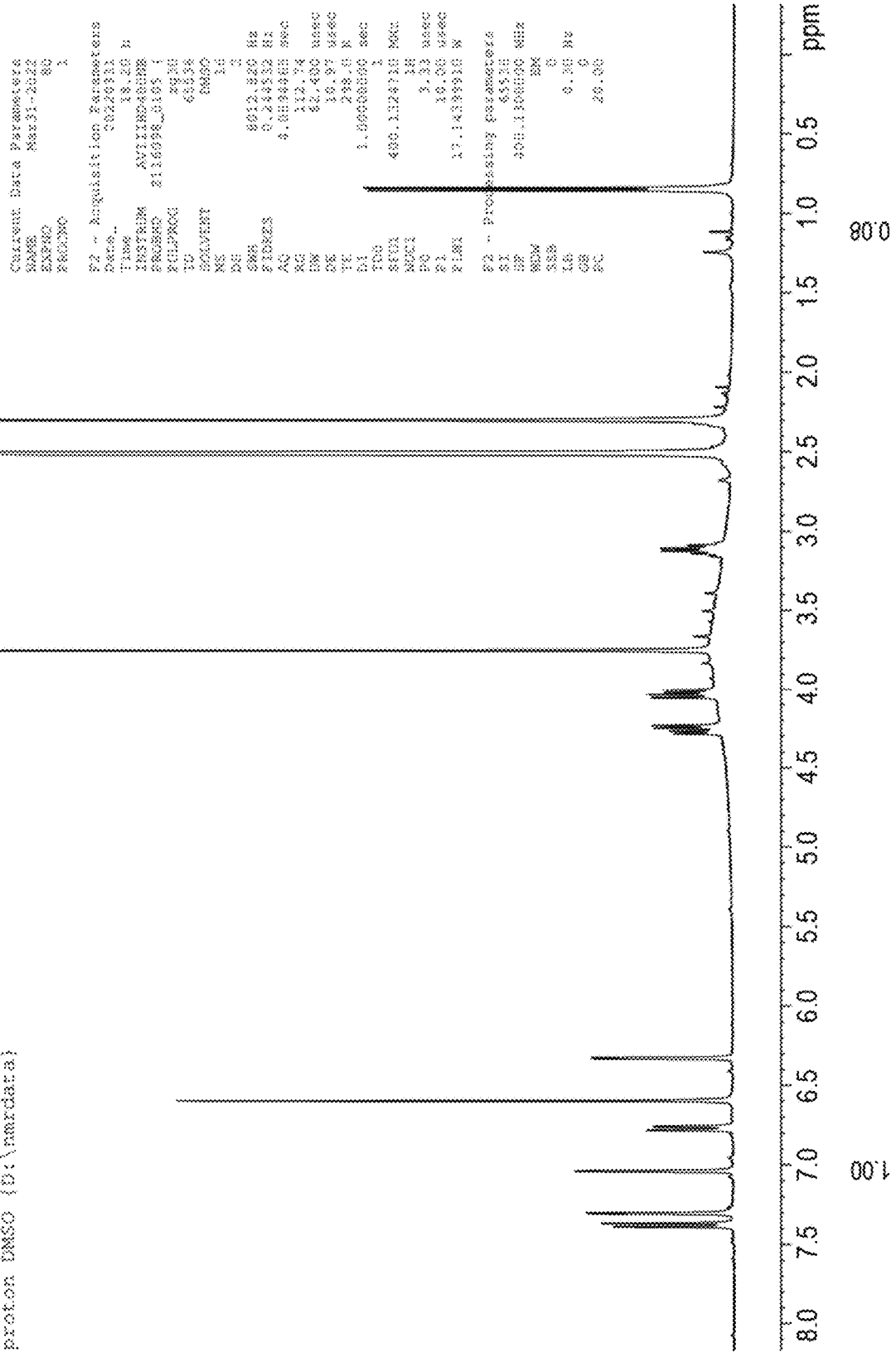
FIG. 89 shows a $^1$H NMR spectrum of crystalline compound 1 monofumarate Form A, spectrum was acquired in DMSO-$d_6$ and calibrated to the non-deuterated solvent residual at 2.50 ppm. tBME content, 0.2% w/w.
Figure 90:
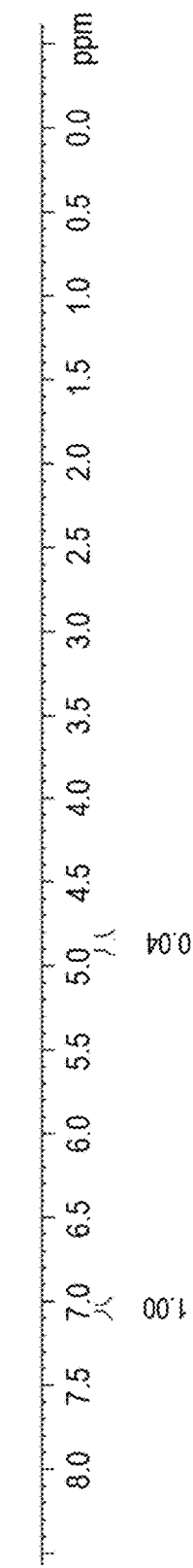
FIG. 90 shows a $^1$H NMR spectrum of crystalline compound 1 monofumarate Form A, spectrum was acquired in DMSO-$d_6$ and calibrated to the non-deuterated solvent residual at 2.50 ppm. iPAc content, 1.3% w/w.
Figure 91:
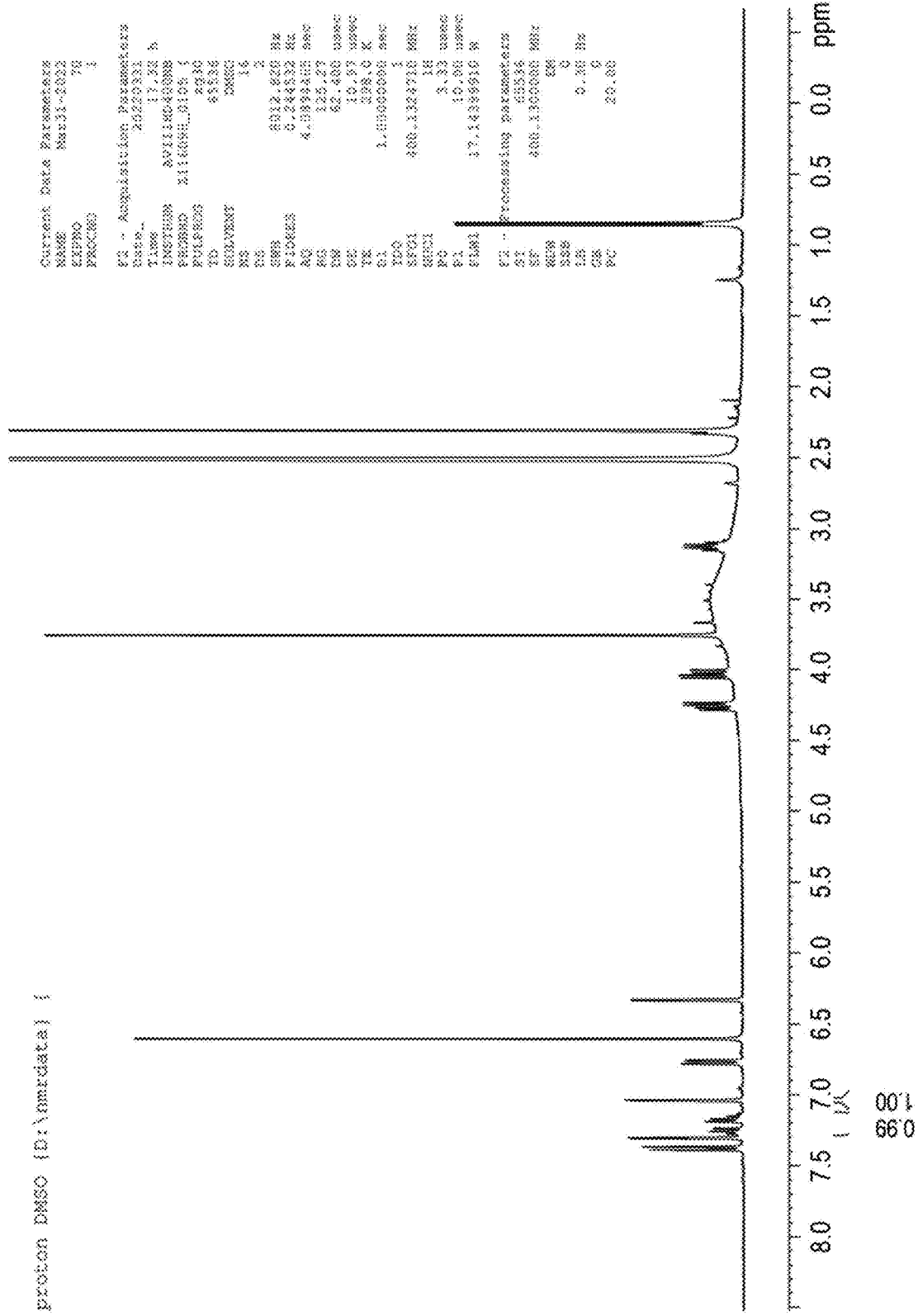
FIG. 91 shows a $^1$H NMR spectrum of crystalline compound 1 monofumarate Form A, spectrum was acquired in DMSO-$d_6$ and calibrated to the non-deuterated solvent residual at 2.50 ppm. iPAc content, 1.3% w/w.
Figure 92:
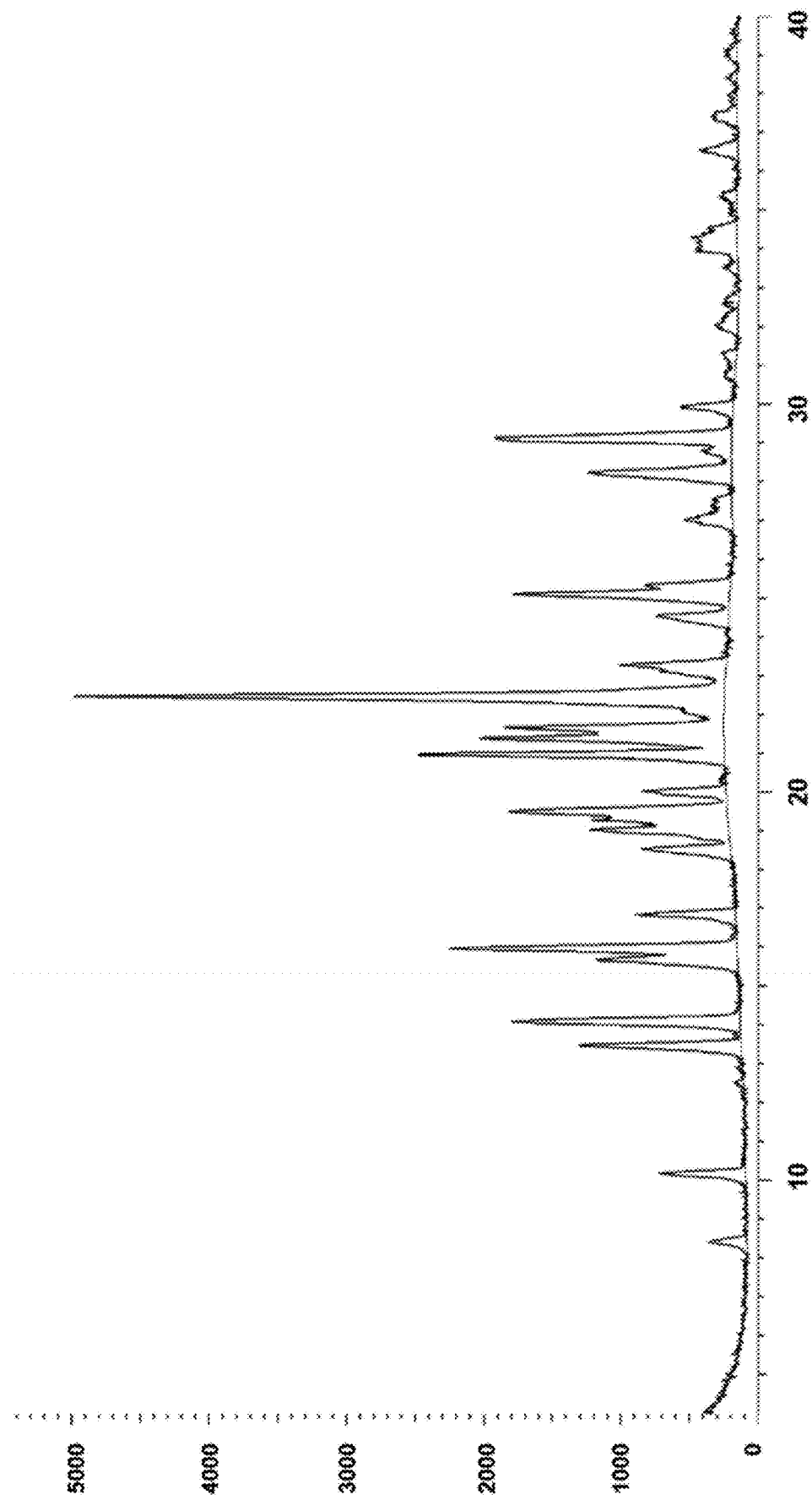
FIG. 92 shows a XRPD profile of crystalline compound 1 monofumarate Form A (Pattern #1, Form A).
Figure 93:
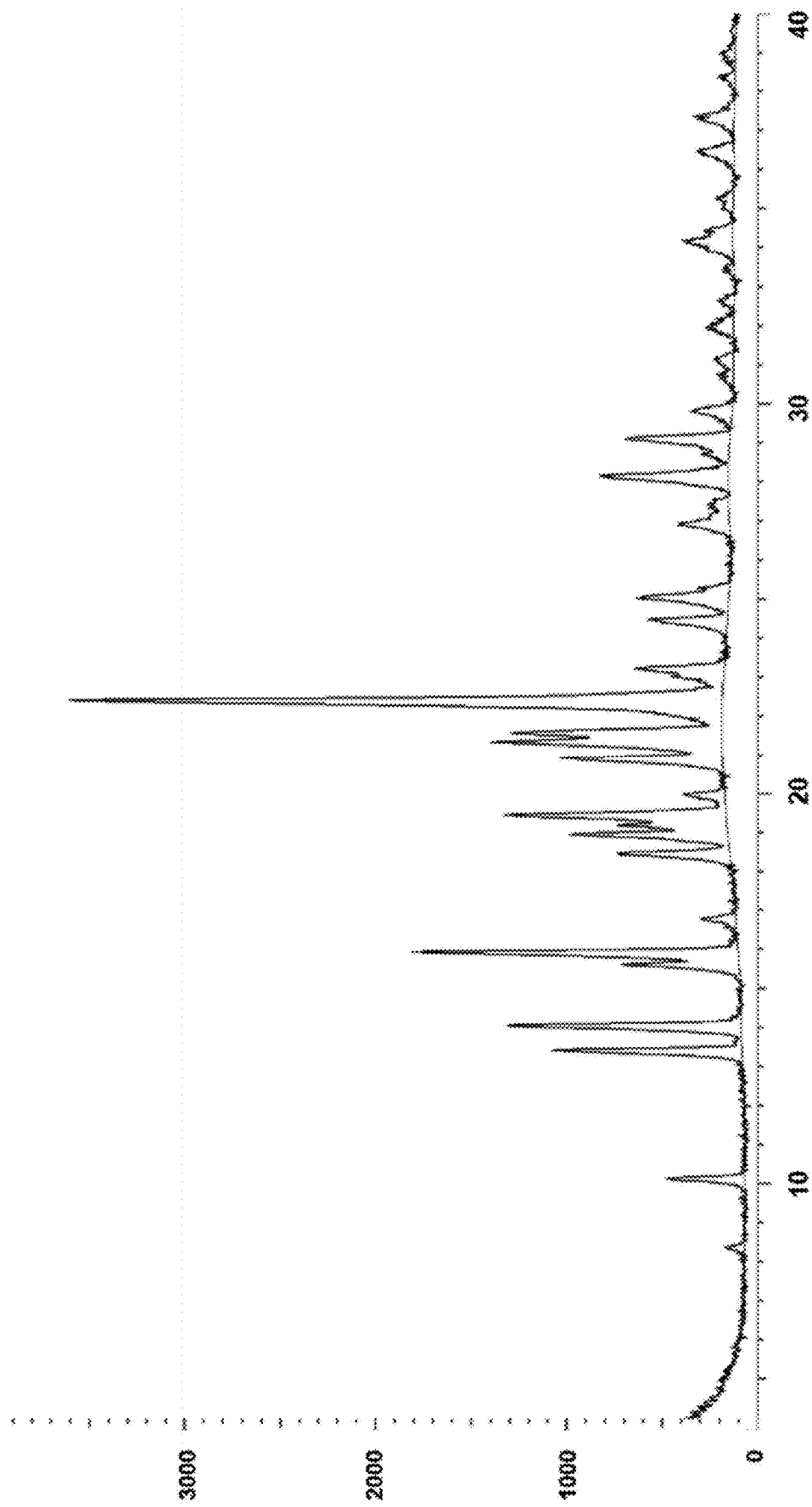
FIG. 93 shows a XRPD profile of crystalline compound 1 monofumarate Form A
Figure 94:
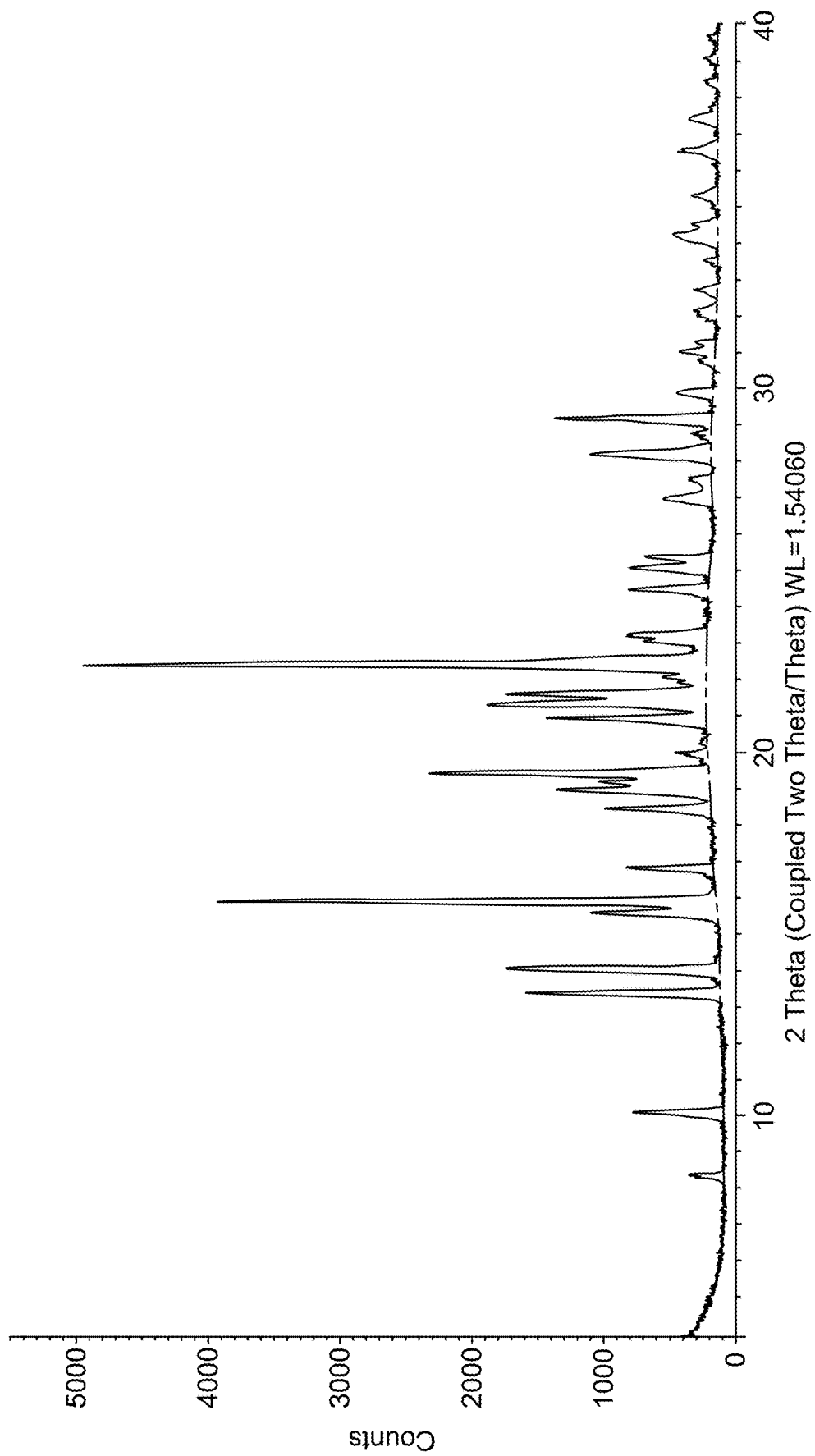
FIG. 94 shows a XRPD profile of crystalline compound 1 monofumarate Form A (Pattern #1, Form A)
Figure 95:
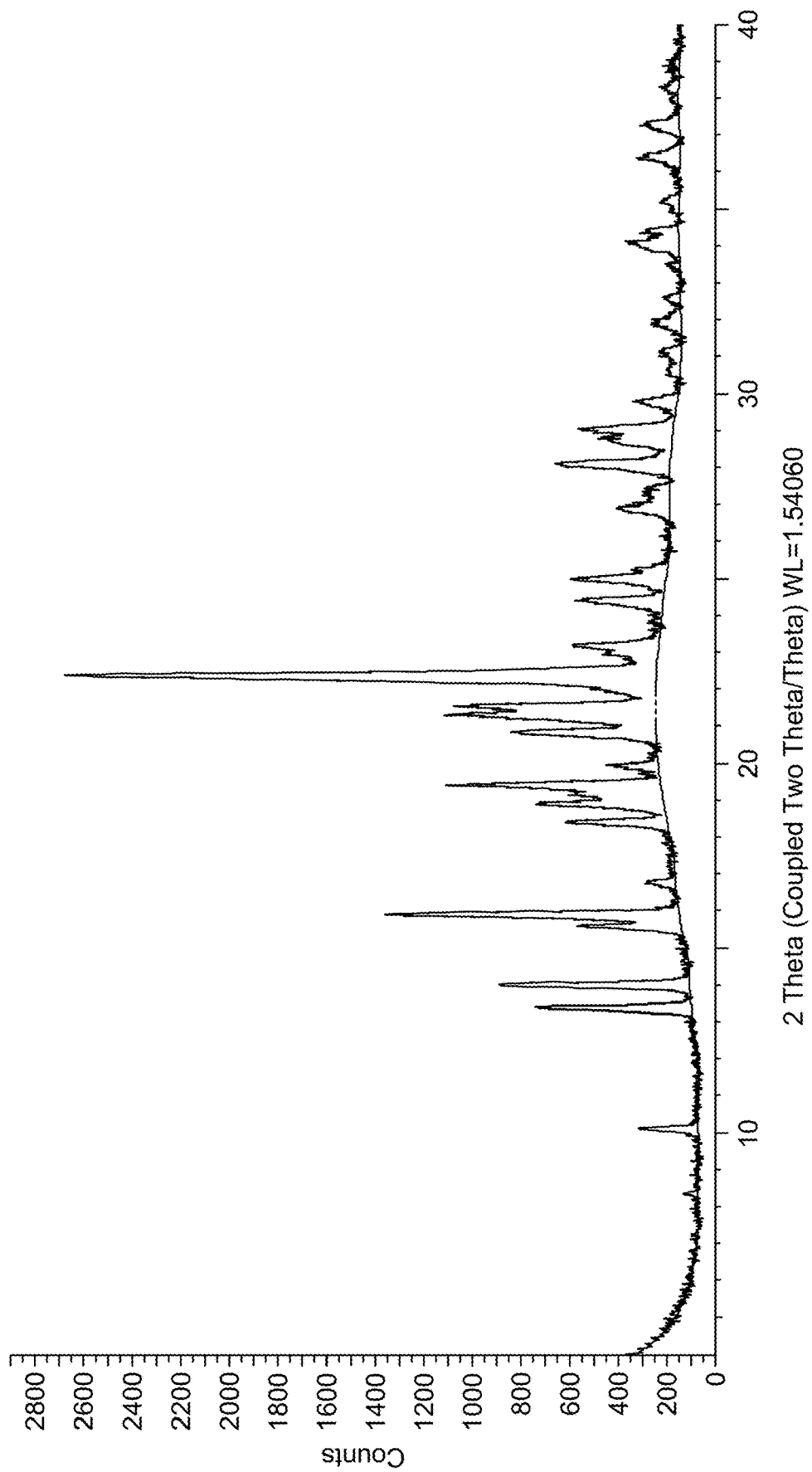
FIG. 95 shows a XRPD profile of crystalline compound 1 monofumarate Form A (Pattern #1, Form A)
Figure 96:
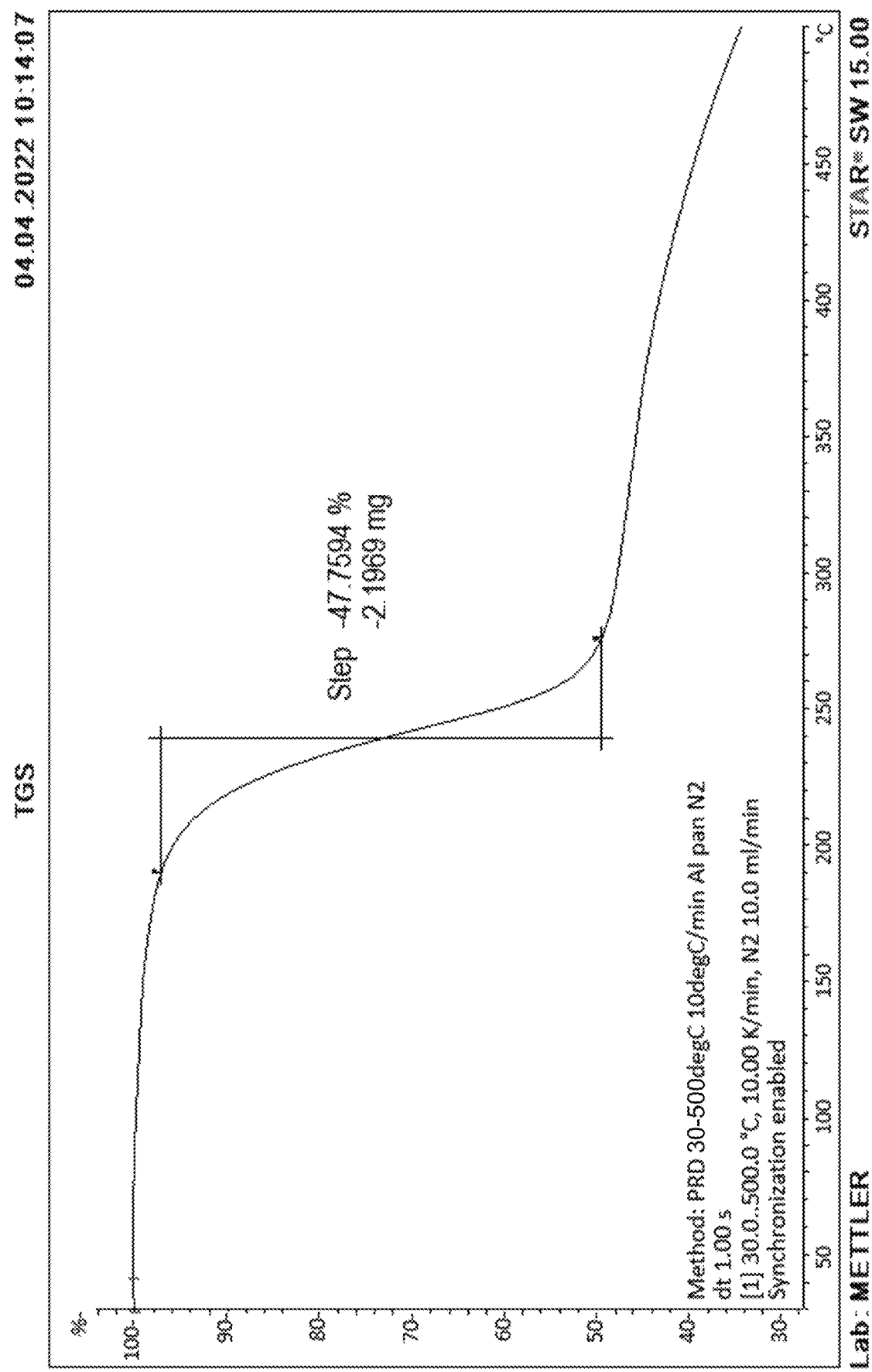
FIG. 96 shows a TGA thermogram of crystalline compound 1 monofumarate Form A, analysis was acquired at a ramp rate of +10° C./minute.
Figure 97:
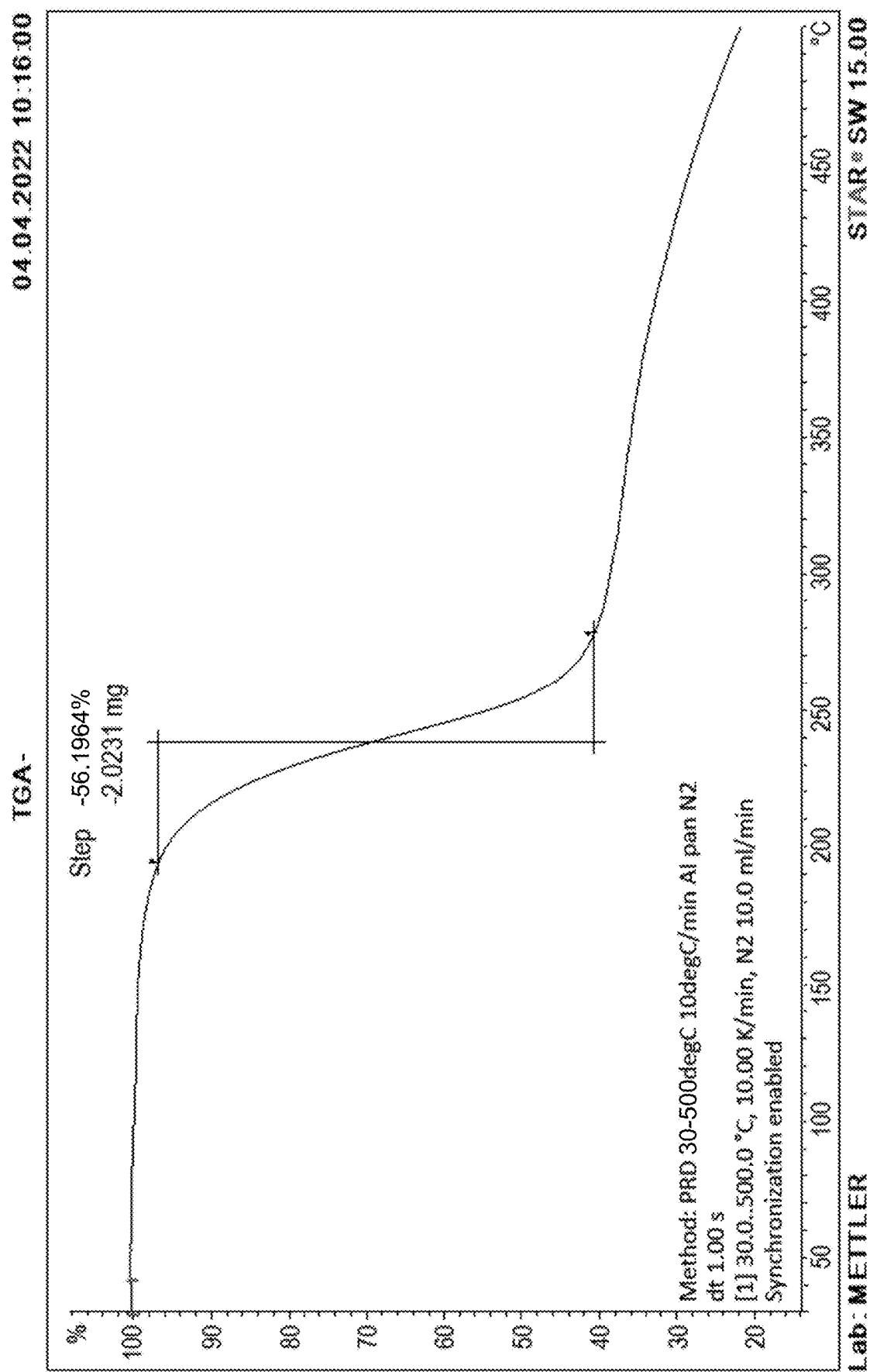
FIG. 97 shows a TGA thermogram of crystalline compound 1 monofumarate Form A, analysis was acquired at a ramp rate of +10° C./minute.
Figure 98:
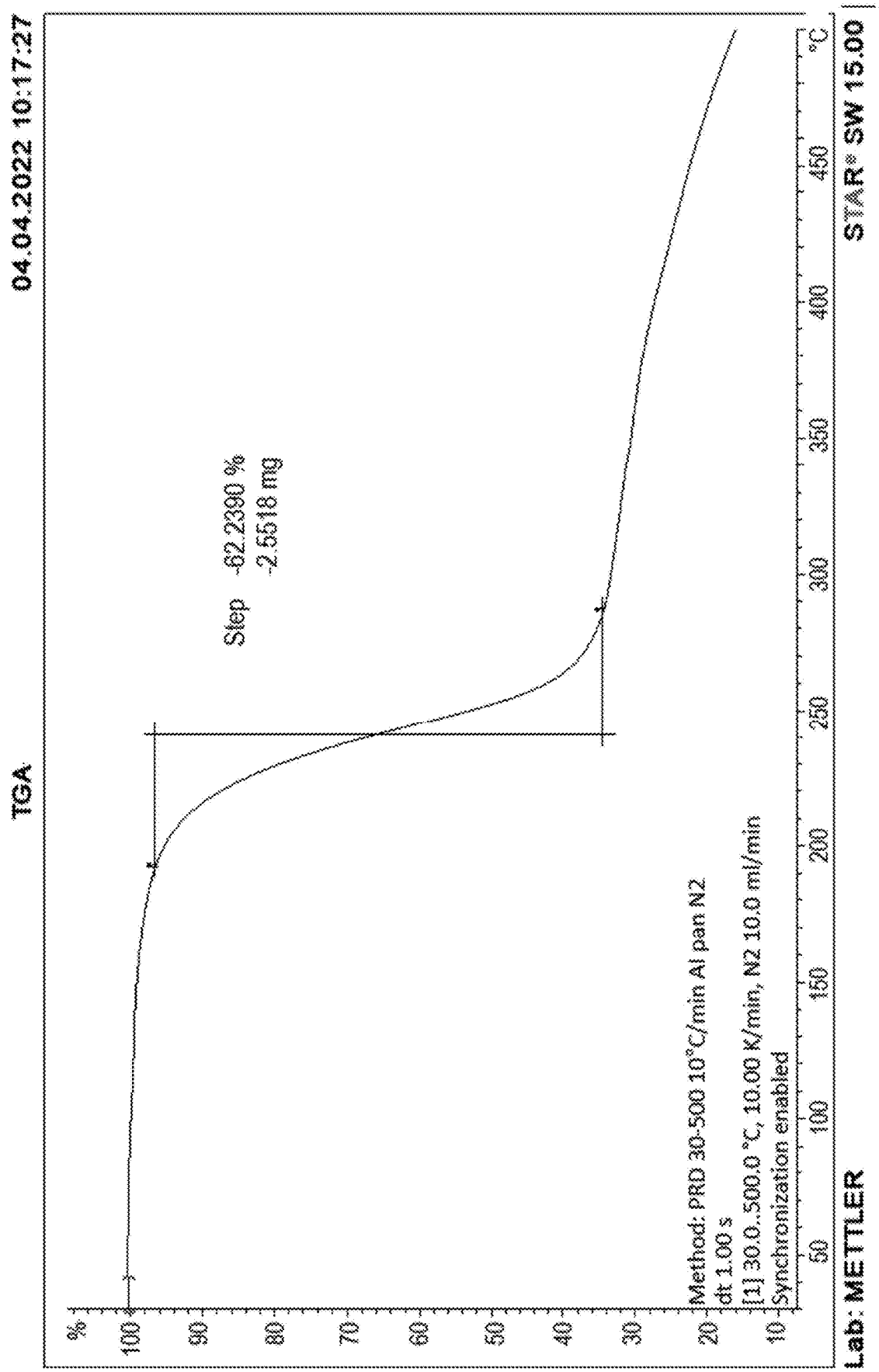
FIG. 98 TGA thermogram of crystalline compound 1 monofumarate Form A, analysis was acquired at a ramp rate of +10° C./minute.
Figure 99:
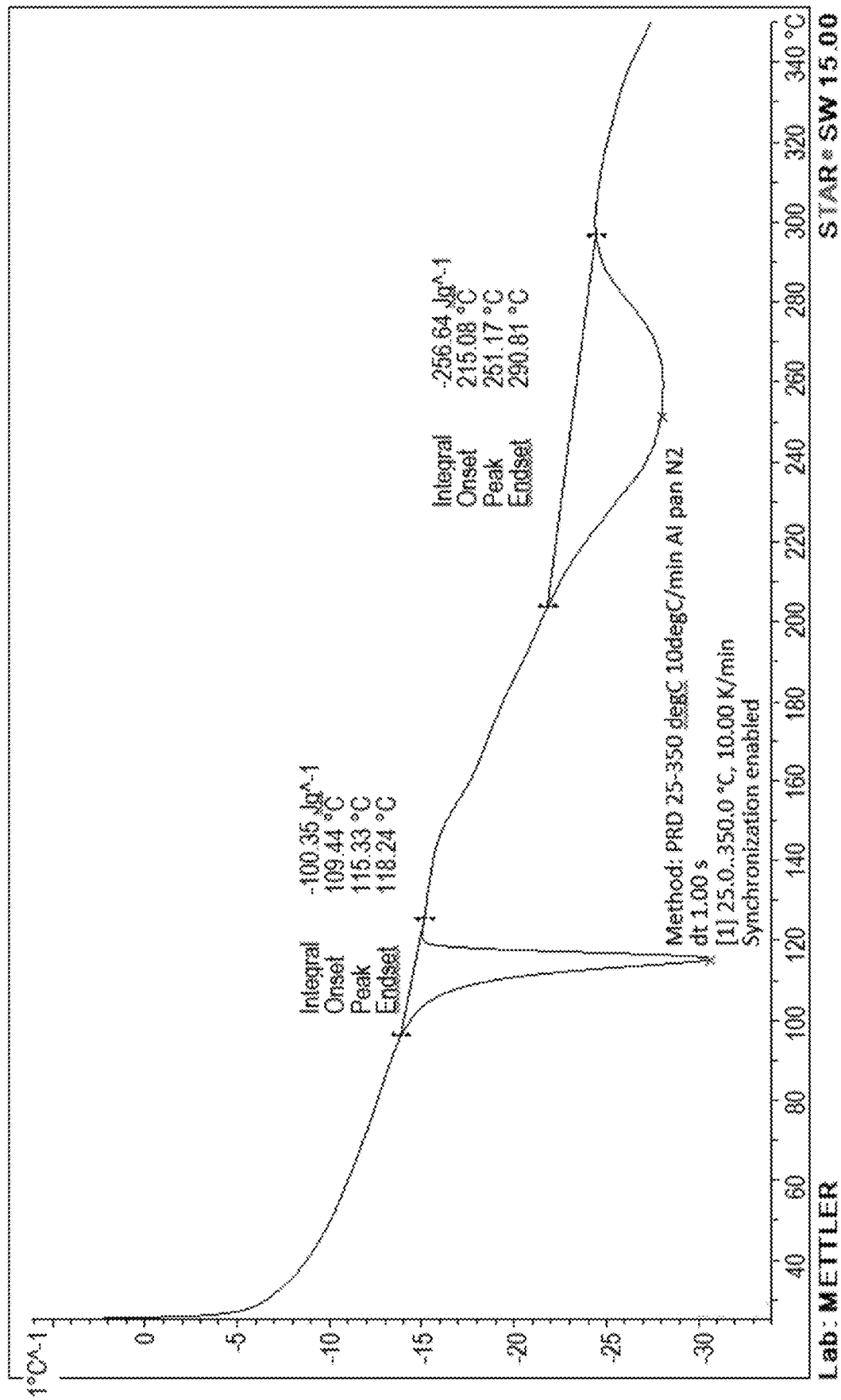
FIG. 99 shows a DSC profile of crystalline compound 1 monofumarate Form A, analysis was acquired at a ramp rate of +10° C./minute.
Figure 100:
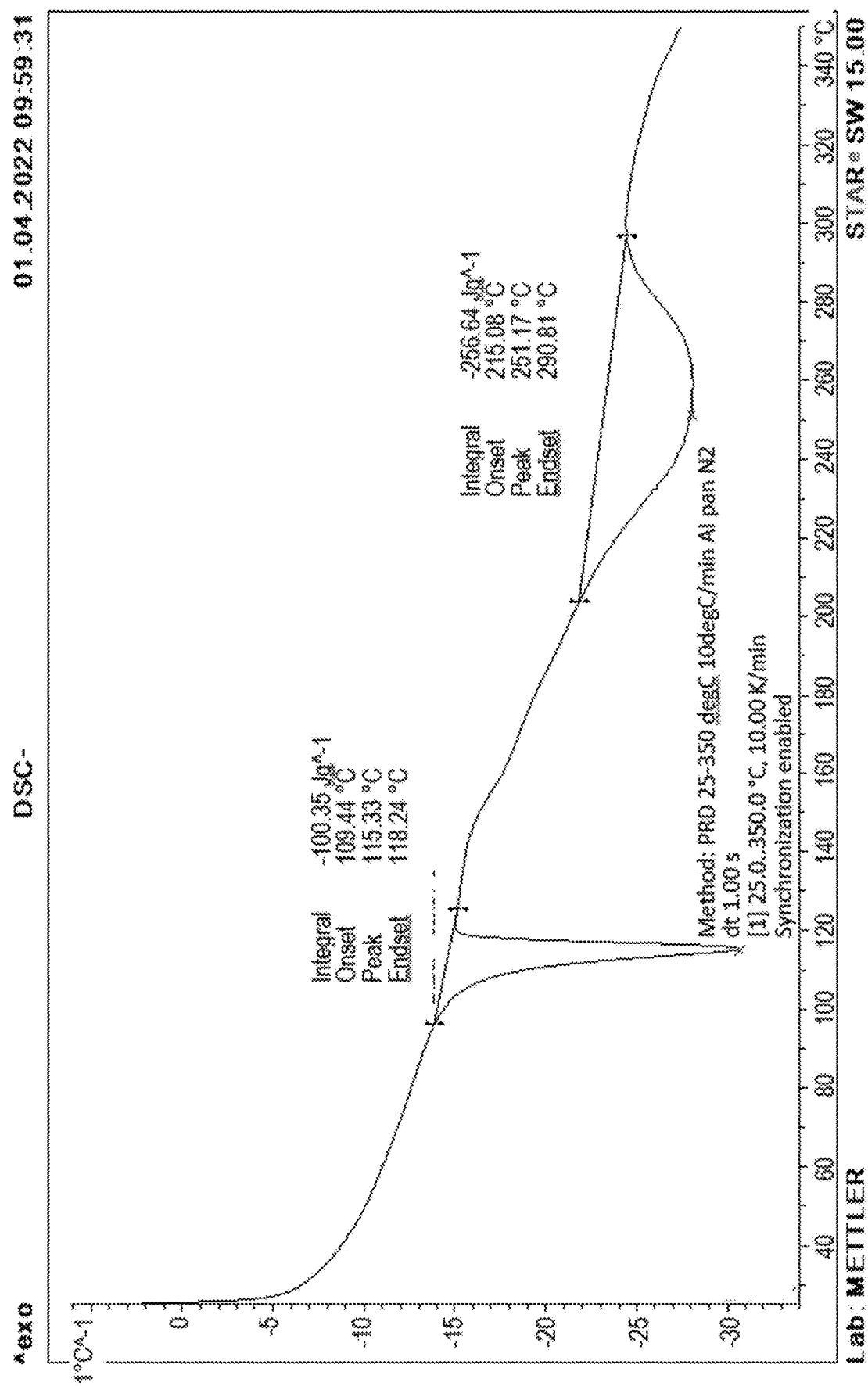
FIG. 100 shows a DSC profile of crystalline compound 1 monofumarate Form A, analysis was acquired at a ramp rate of +10° C./minute.
Figure 101:
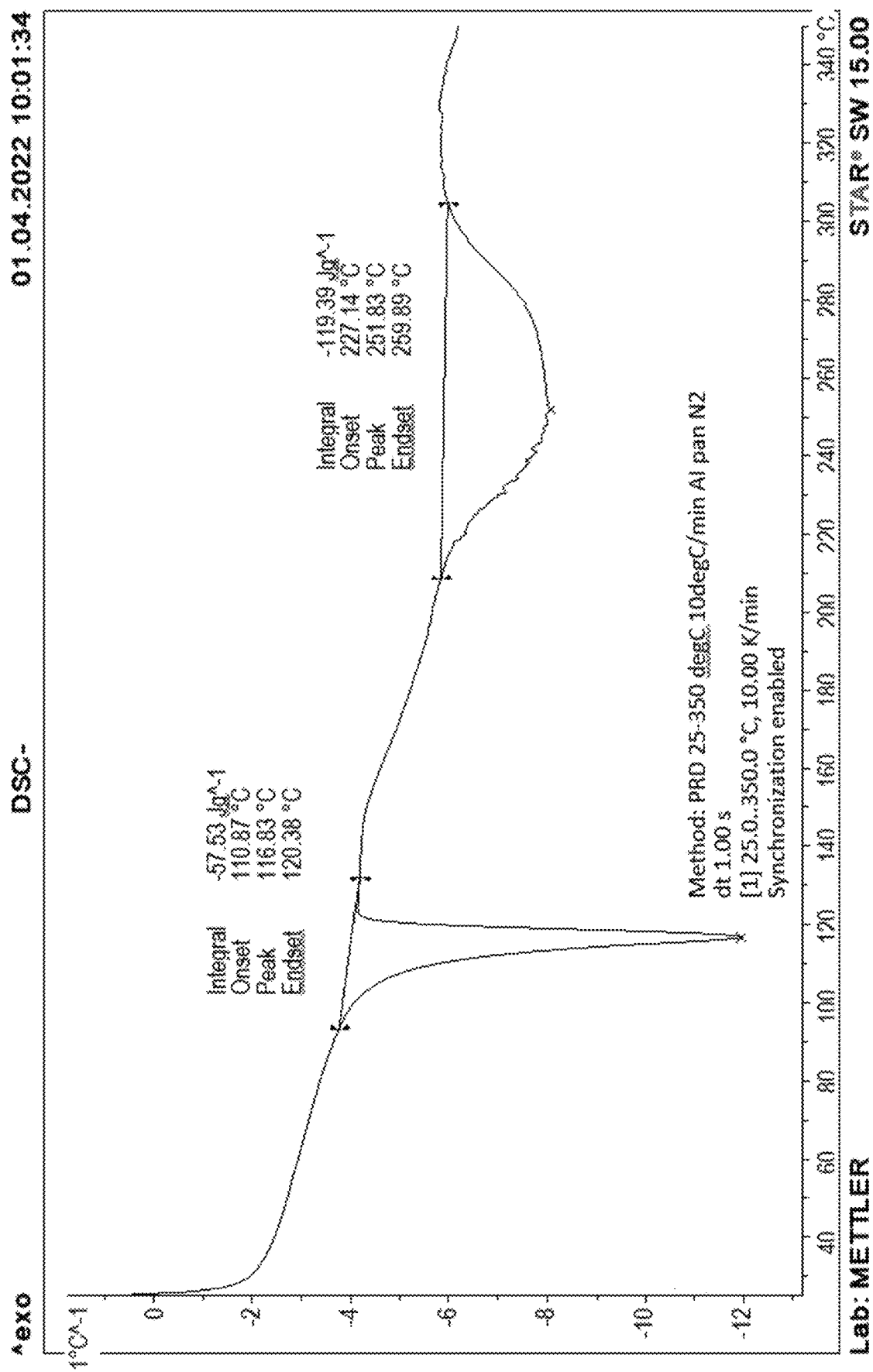
FIG. 101 shows a DSC profile of crystalline compound 1 monofumarate Form A, analysis was acquired at a ramp rate of +10° C./minute.
Figure 102:
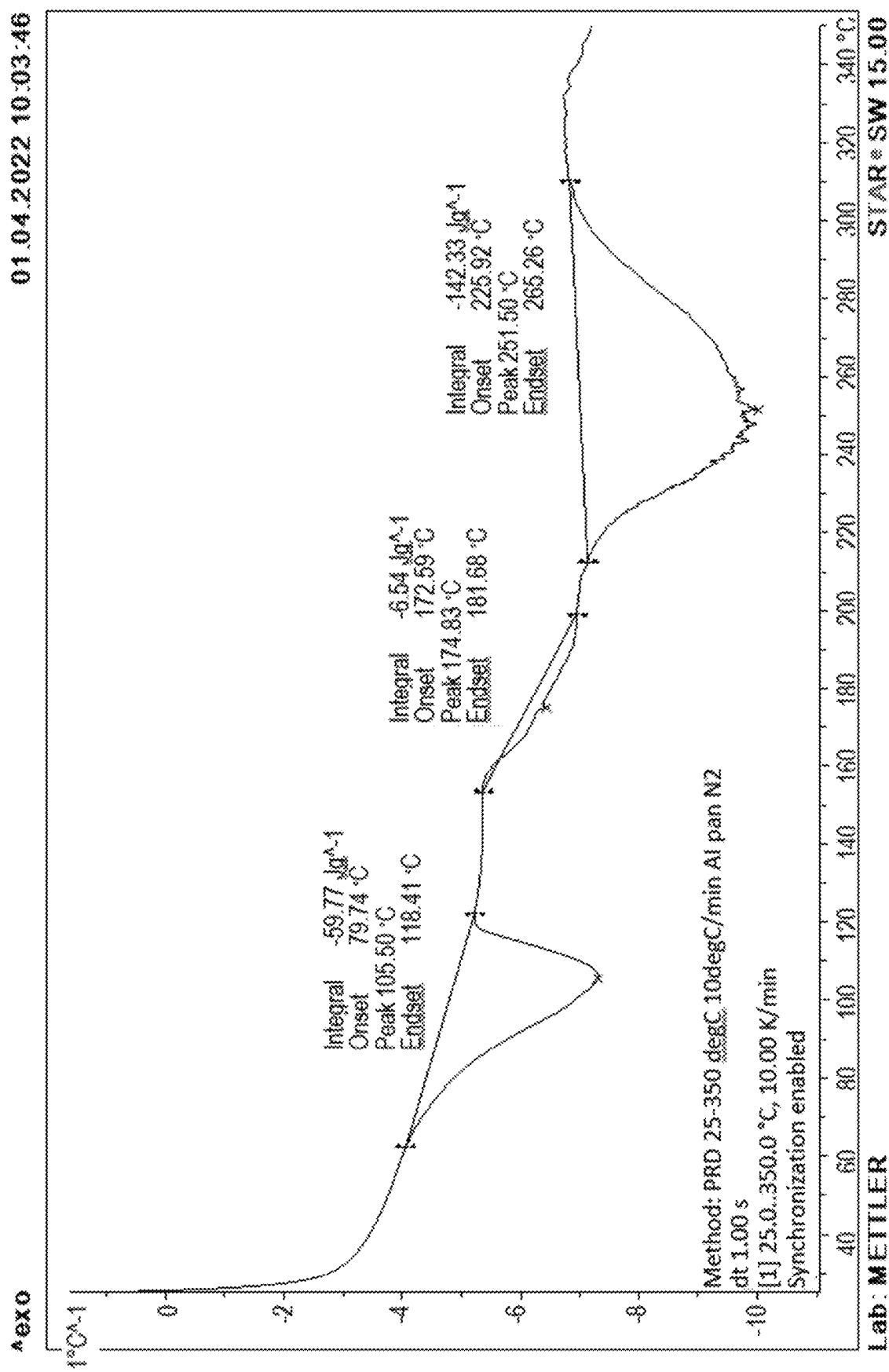
FIG. 102 shows a DSC profile of crystalline compound 1 monofumarate Form A, analysis was acquired at a ramp rate of +10° C./minute.

DSC: An exemplary DSC profile for Form A is shown in FIG. 85.
TGA: An exemplary TGA profile for Form A is shown in FIG. 80.
$^1$H NMR: An exemplary $^1$H NMR spectrum for monofumarate Form A is shown in FIG. 64. The $^1$H NMR shows 1:1 stoichiometry of compound and fumarate.

Figure 1:
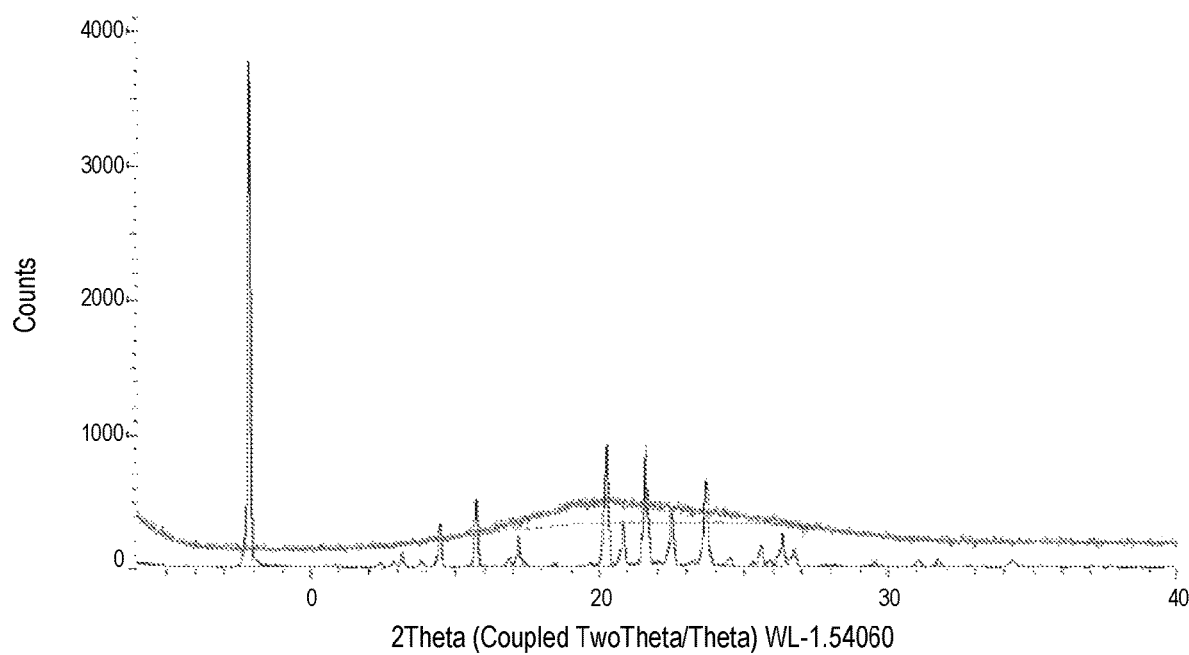
FIG. 1 provides an XRPD diffractogram of crystalline Compound 1 fumarate, pattern 5, isolated from MIBK according to Example 4 overlaid with an XRPD diffractogram for the amorphous fumarate salt. XRPD signals observed in the pattern 5 diffractogram are characterized in Table 38.
Figure 2:
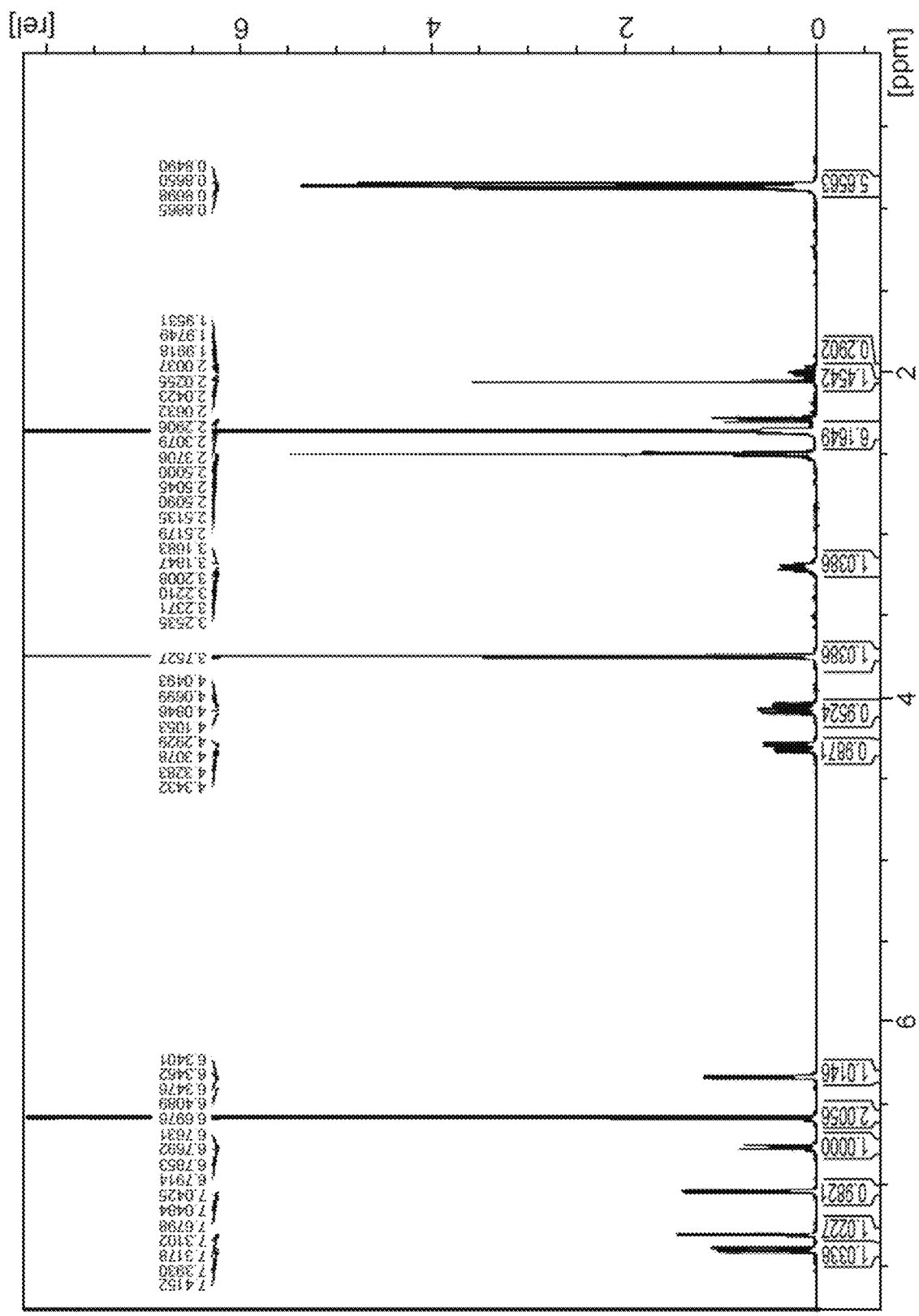
FIG. 2 provides an $^1$H NMR spectrum for the Compound 1 fumarate, pattern 5, crystalline form produced according to Example 4.
Figure 57:
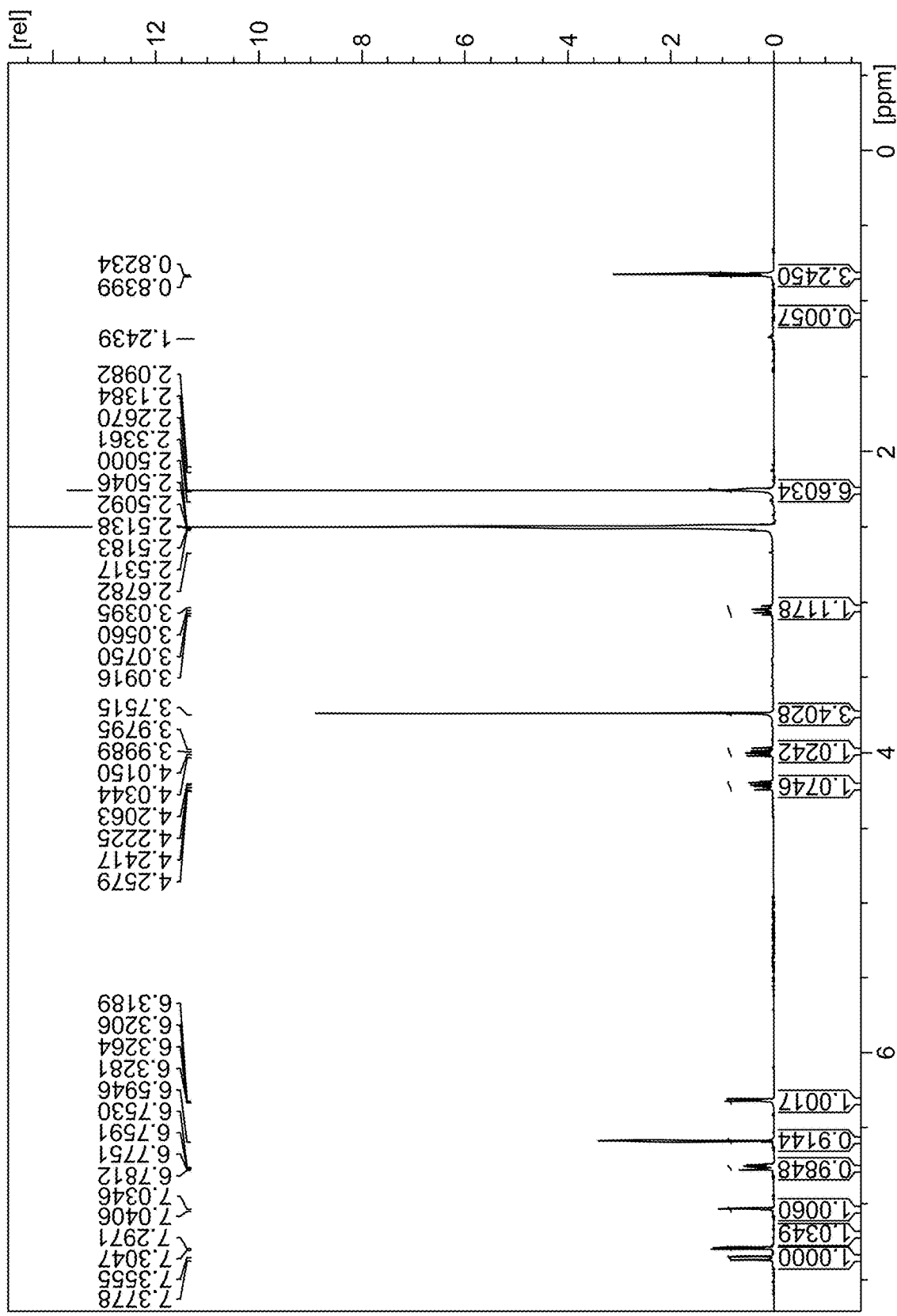
FIG. 57 shows a $^1$H NMR spectrum of crystalline compound 1 hemi-fumarate Form II (oven-dried after equilibration), spectrum was acquired in DMSO-$d_6$ and calibrated to the non-deuterated solvent residual at 2.50 ppm. API to Fumaric acid. 2.0 to 1.0.
Figure 59:
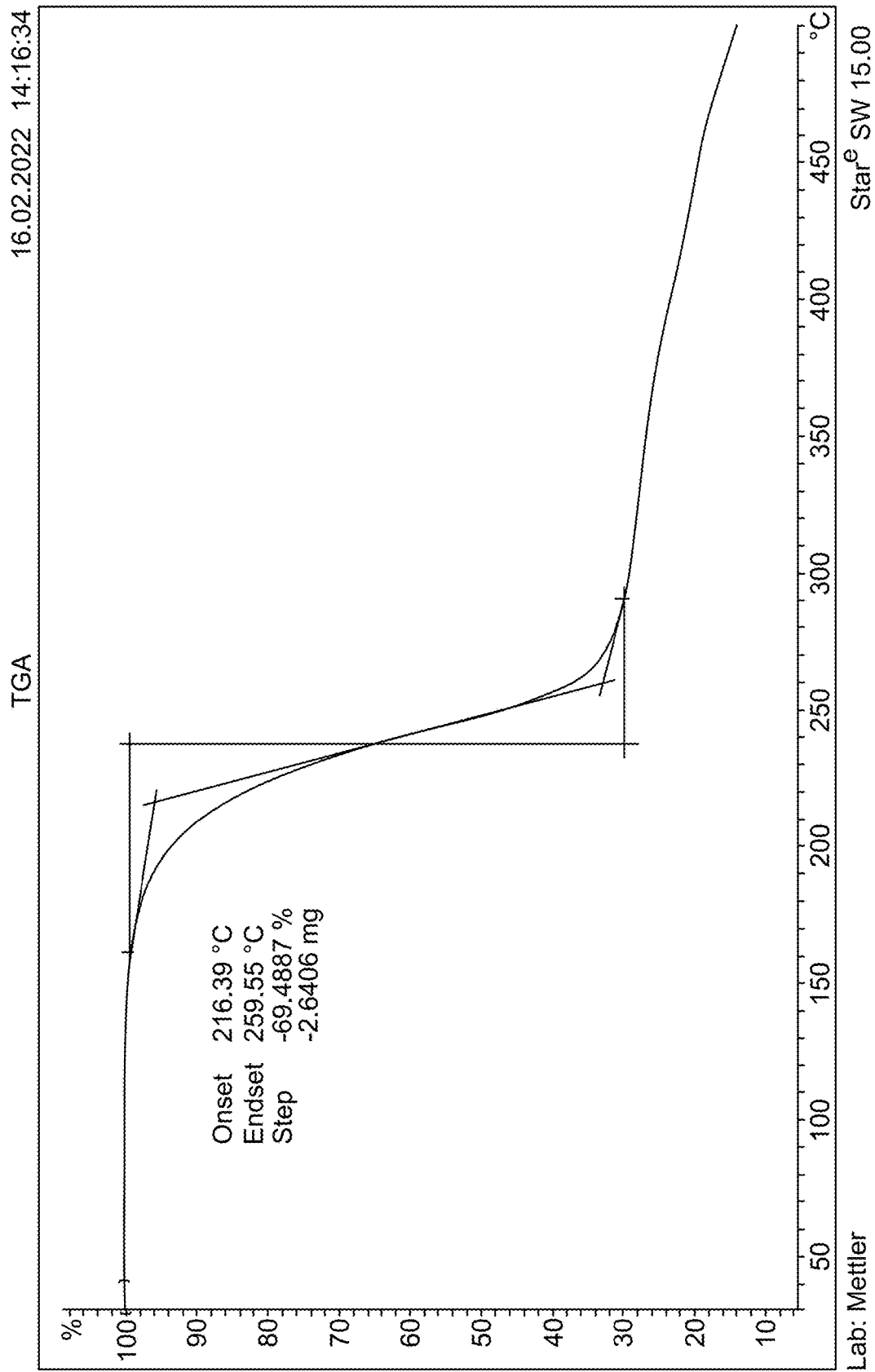
FIG. 59 shows a TGA thermogram of crystalline compound 1 hemi-fumarate Form II, analysis was acquired at a ramp rate of +10° C./minute.
Figure 60:
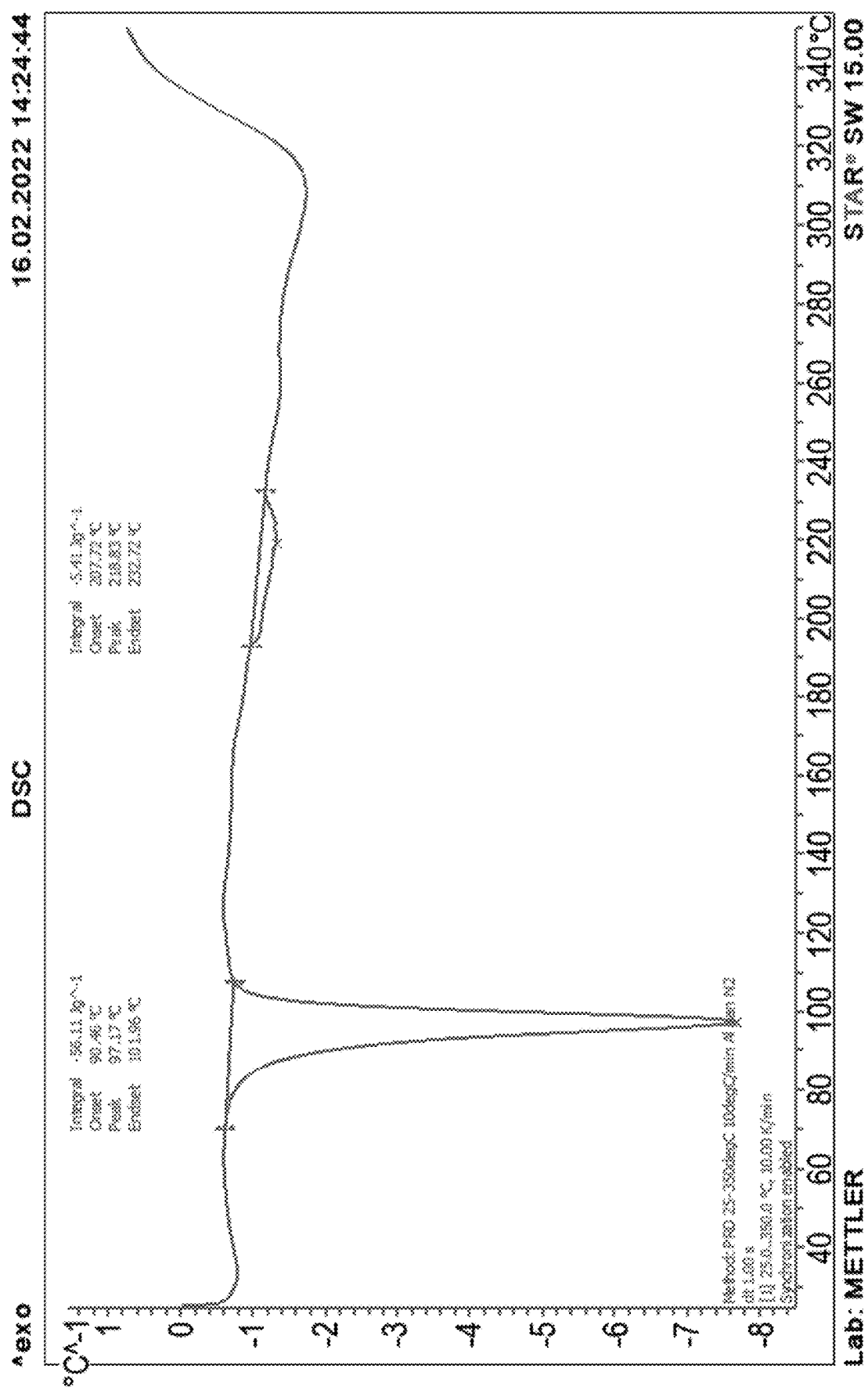
FIG. 60 shows a DSC profile of crystalline compound 1 hemi-fumarate Form II, analysis was acquired at a ramp rate of +10° C./minute.
Figure 61:
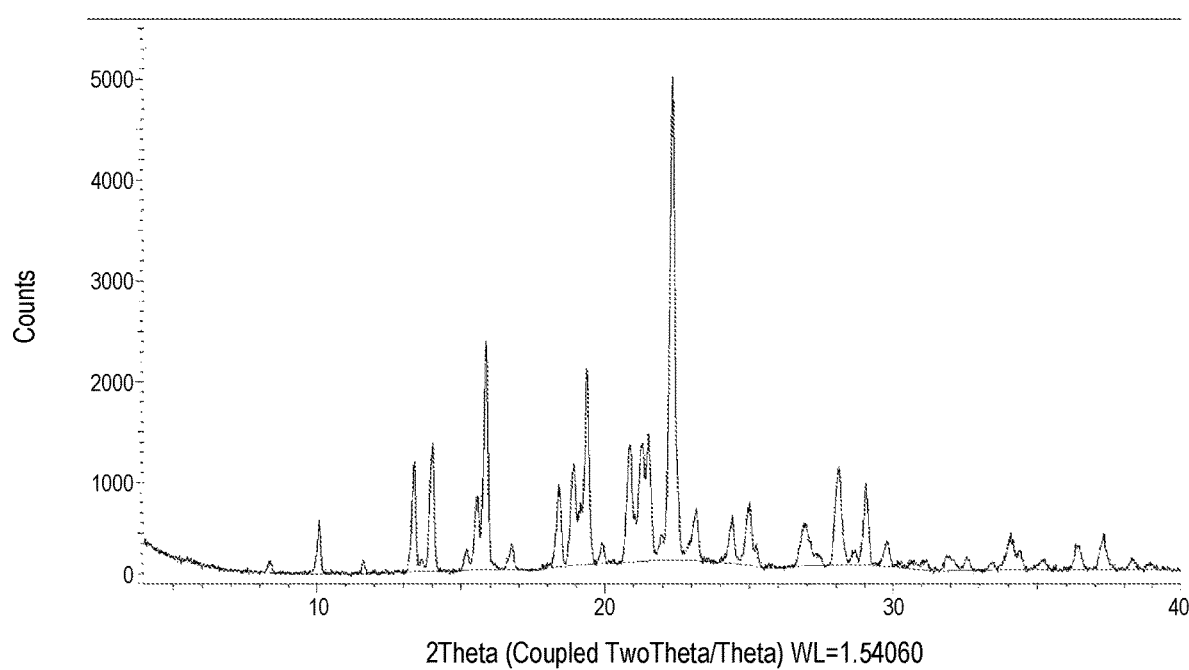
FIG. 61 shows a XRPD profile of crystalline compound 1 monofumarate Form A (wet pellet, Pattern #1, Form A).
Figure 62:
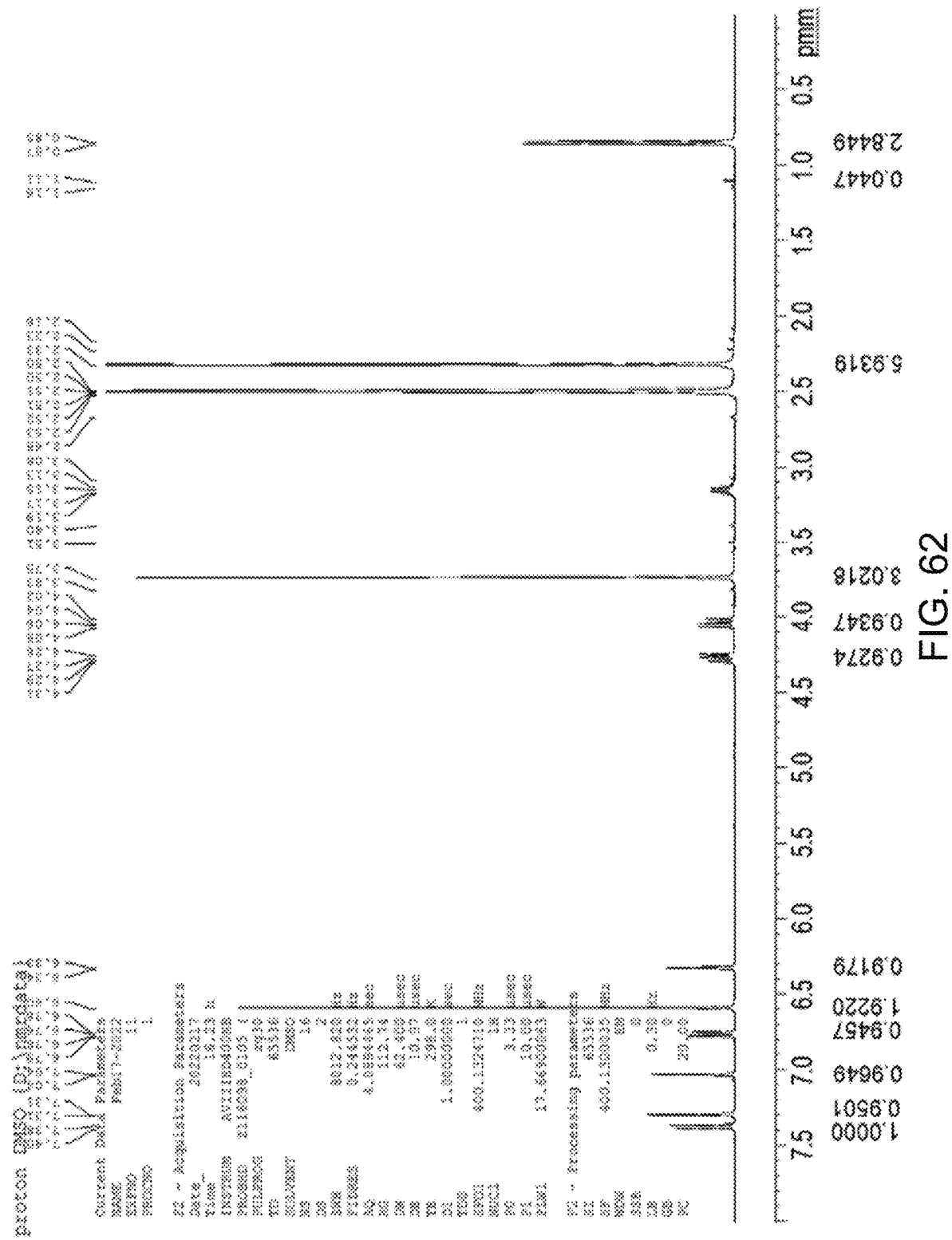
FIG. 62 shows a $^1$H NMR spectrum of crystalline compound 1 monofumarate pattern #3b, spectrum was acquired in DMSO-$d_6$ and calibrated to the non-deuterated solvent residual at 2.50 ppm. API to Fumaric acid, 1.0 to 1.0. tBME content, 0.1% w/w.
Figure 63:
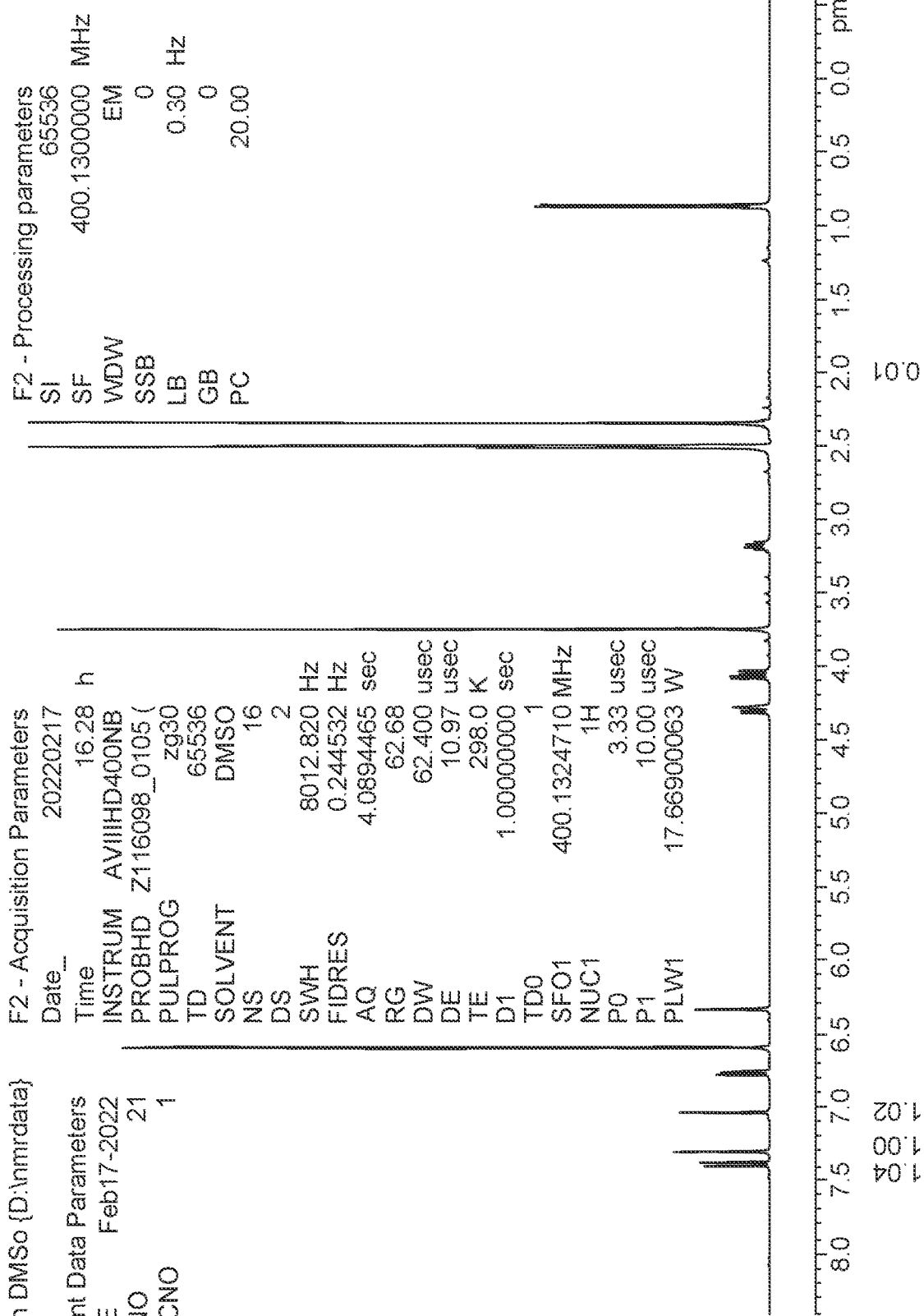
FIG. 63 shows a $^1$H NMR spectrum of crystalline compound 1 monofumarate Form A, spectrum was acquired in DMSO-$d_6$ and calibrated to the non-deuterated solvent residual at 2.50 ppm. API to Fumaric acid, 1.0 to 1.0. EtOAc content, 0.1% w/w.
Figure 68:
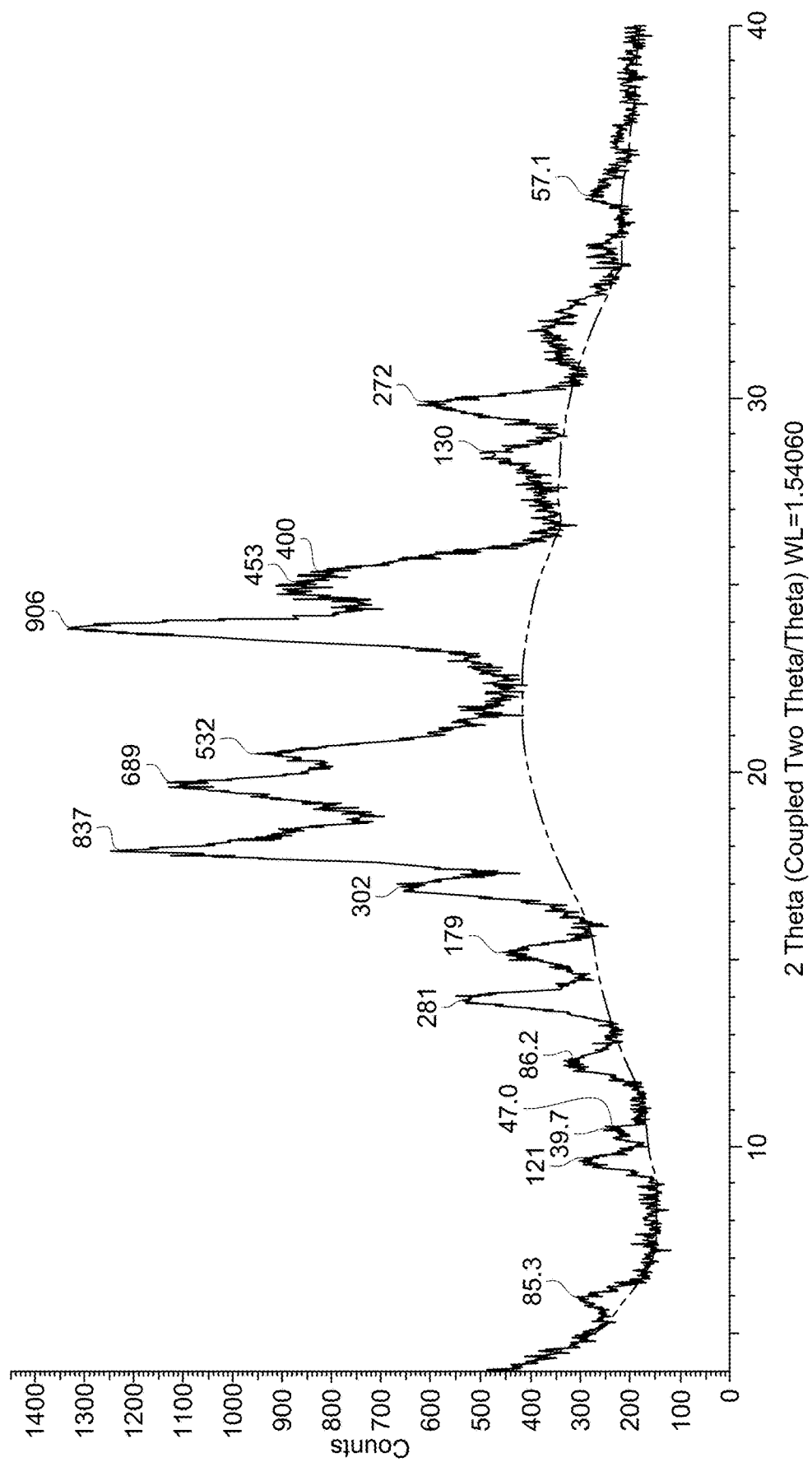
FIG. 68 shows a XRPD profile of crystalline compound 1 fumarate Pattern #3a (wet pellet, Pattern #3a)
Figure 69:
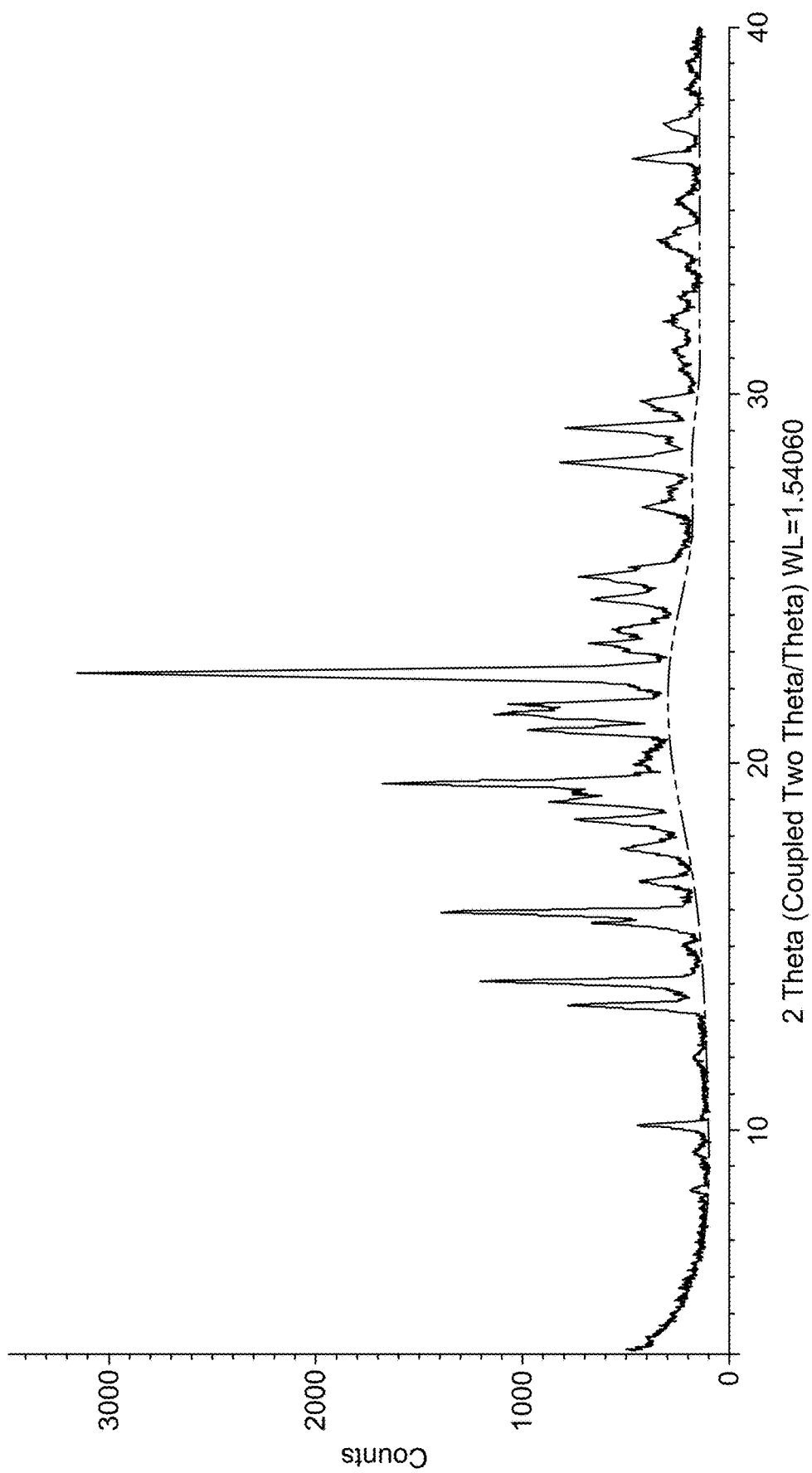
FIG. 69 shows a XRPD profile of crystalline compound 1 monofumarate Form A (oven dried, Pattern #1).
Figure 71:
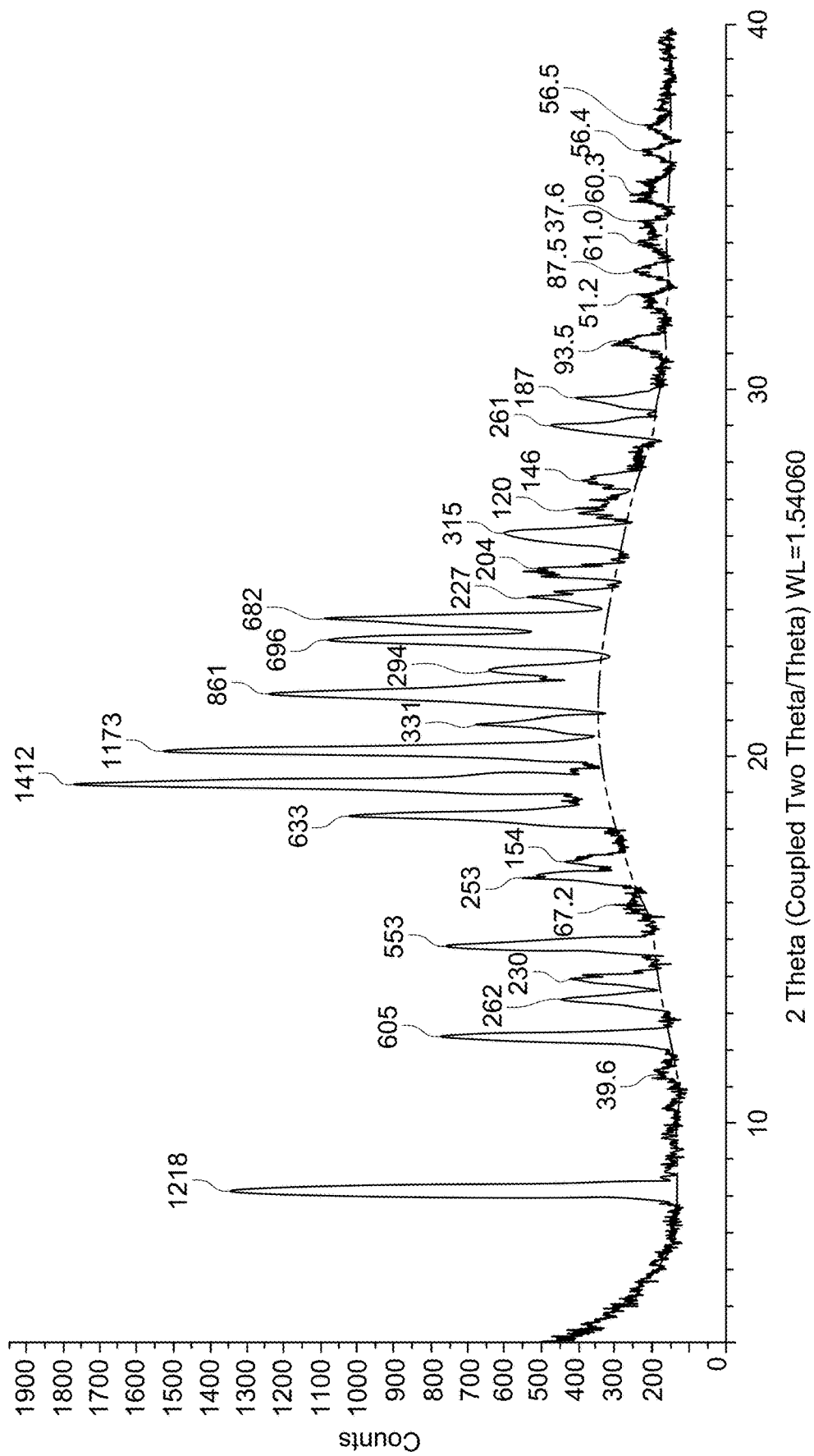
FIG. 71 shows a XRPD profile of crystalline compound 1 fumarate pattern 6 (wet pellet, Pattern #6).
Figure 72:
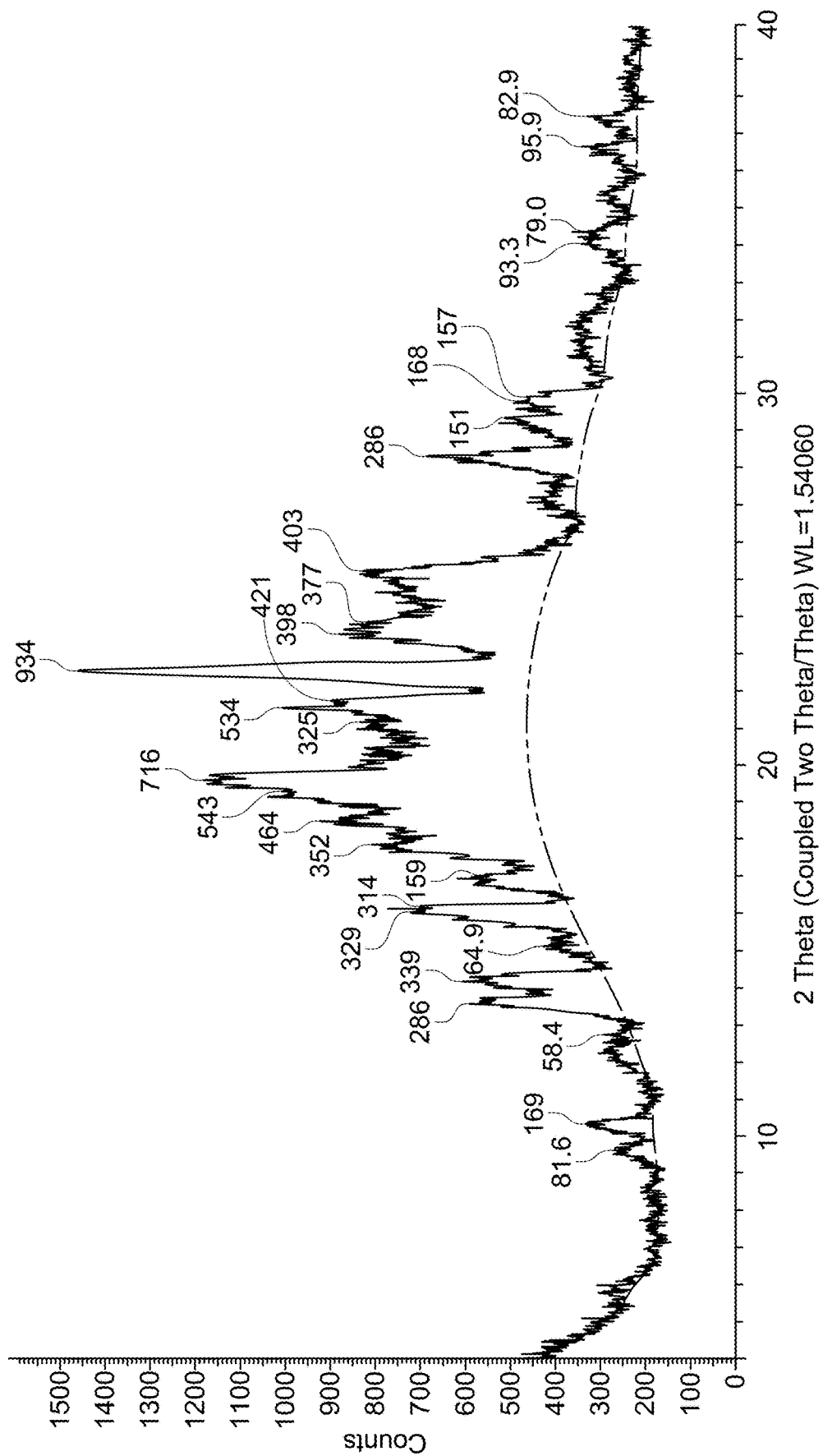
FIG. 72 shows XRPD profile of crystalline compound monofumarate Form A (wet pellet, Pattern #1, Form A.
Figure 73:
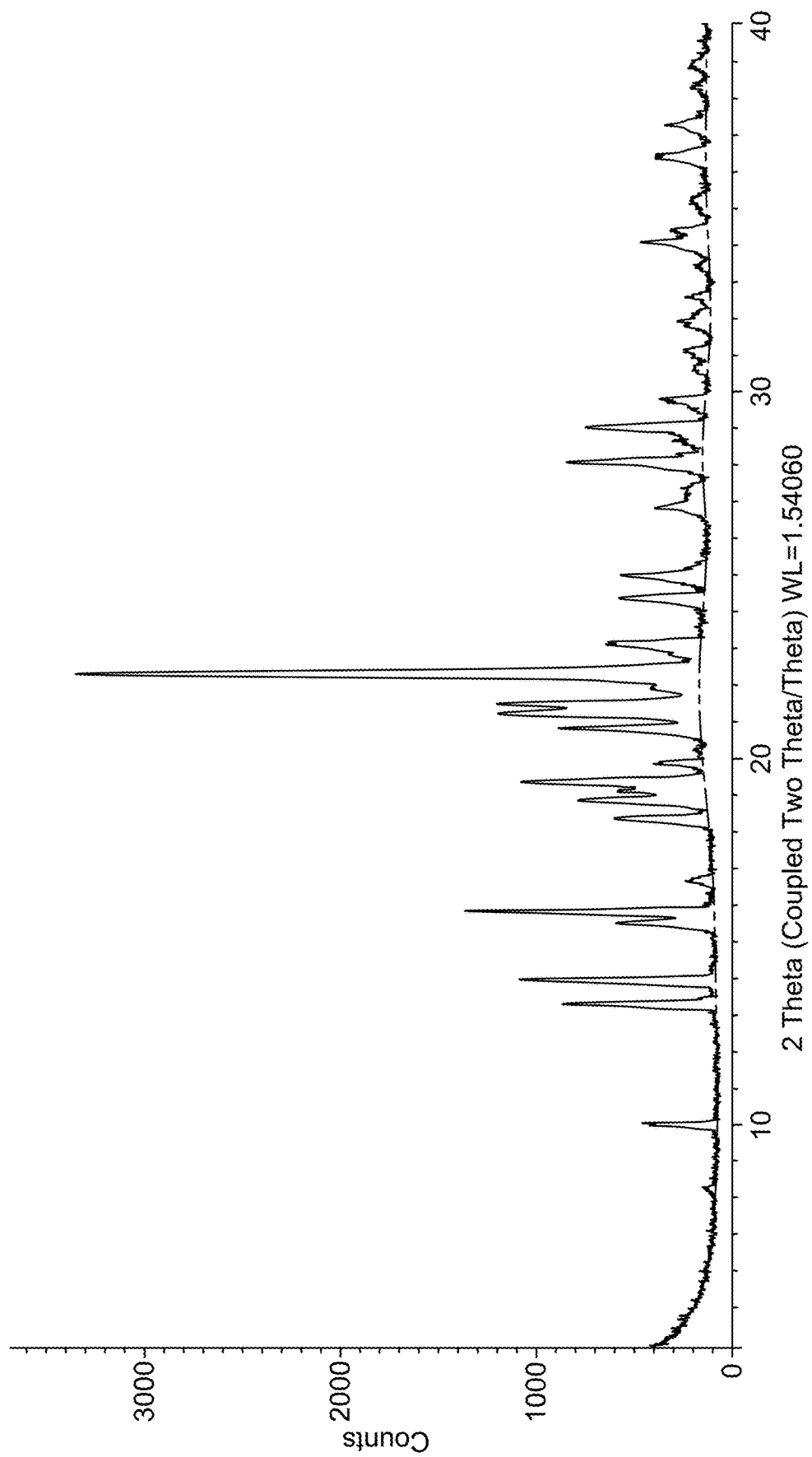
FIG. 73 shows a XRPD profile of crystalline compound 1 monofumarate Form A (wet pellet, Pattern #1, Form A).
Figure 74:
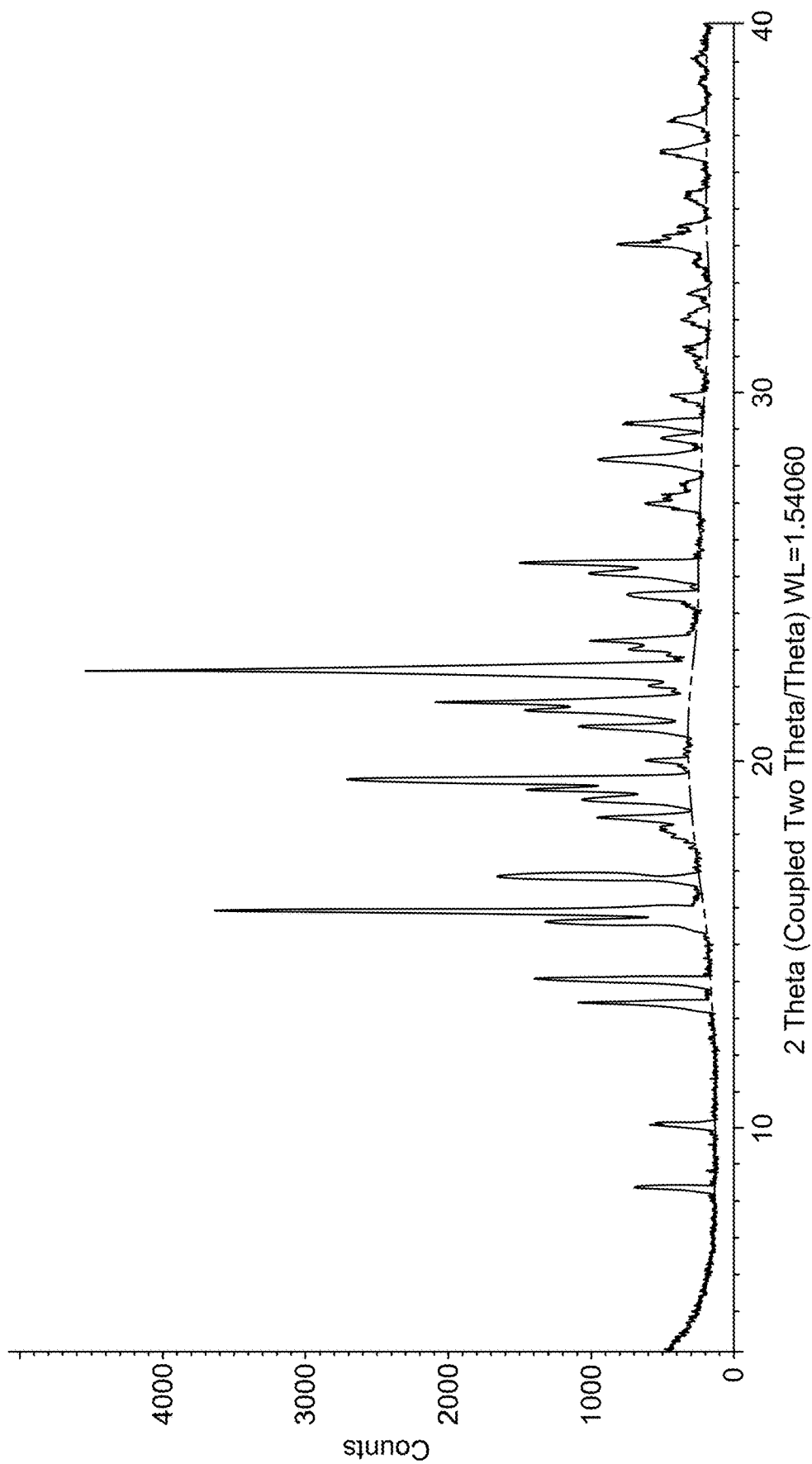
FIG. 74 shows a XRPD profile of crystalline compound 1 monofumarate Form A (wet pellet, Pattern #1, Form A).
Figure 75:
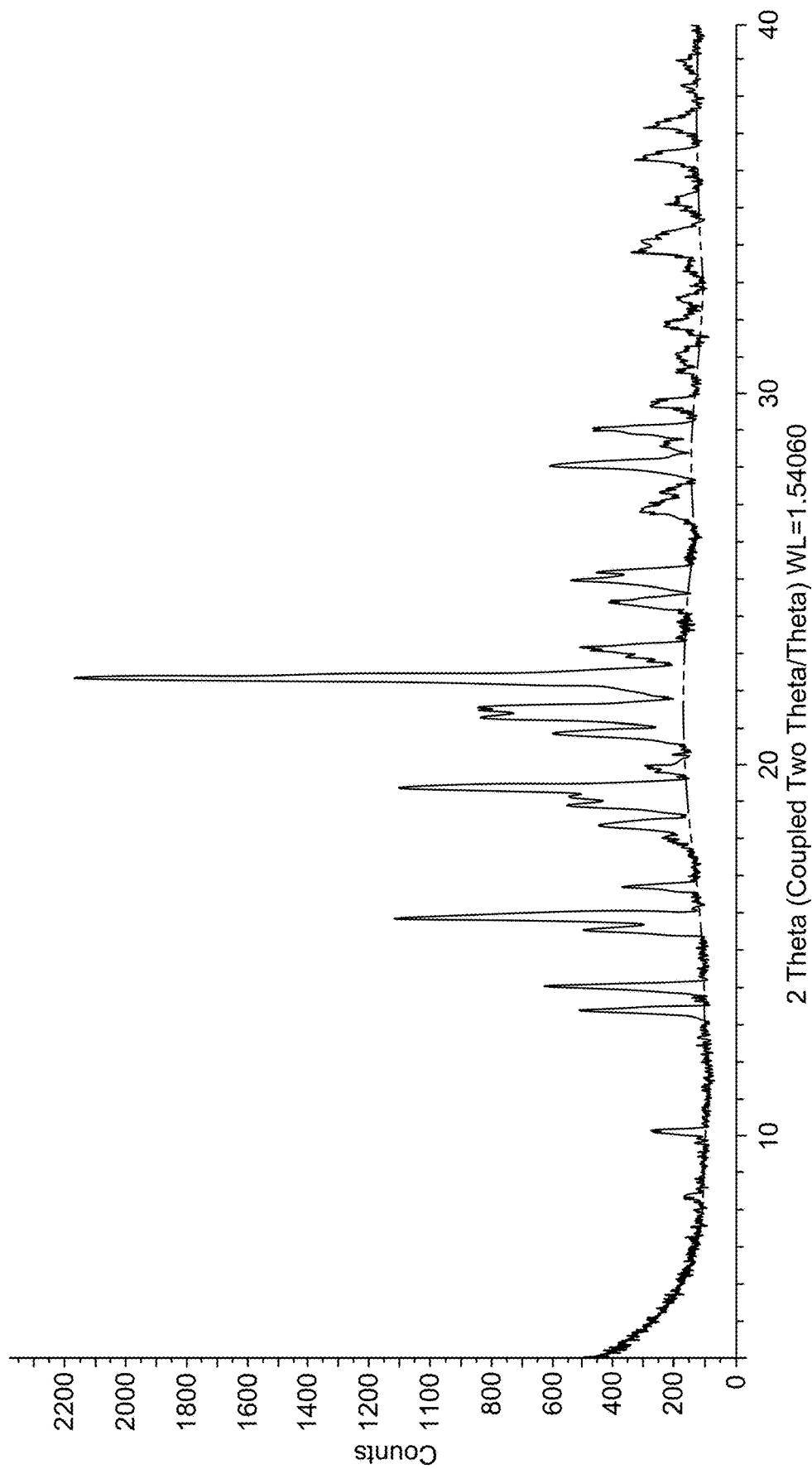
FIG. 75 shows a XRPD profile of crystalline compound 1 monofumarate Form A (oven dried).
Figure 76:
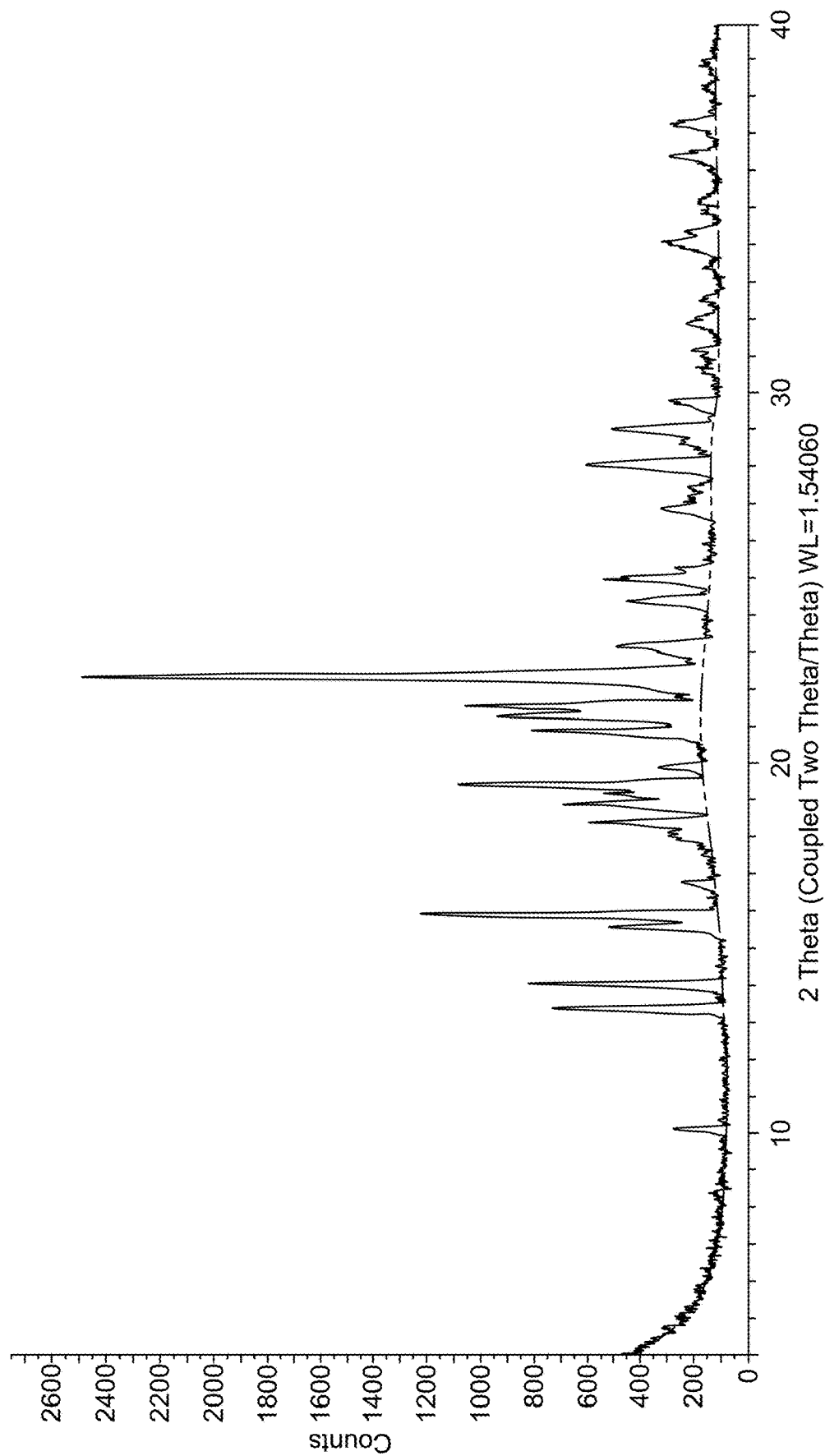
FIG. 76 shows a XRPD profile of crystalline compound 1 monofumarate Form A (wet pellet).
Figure 77:
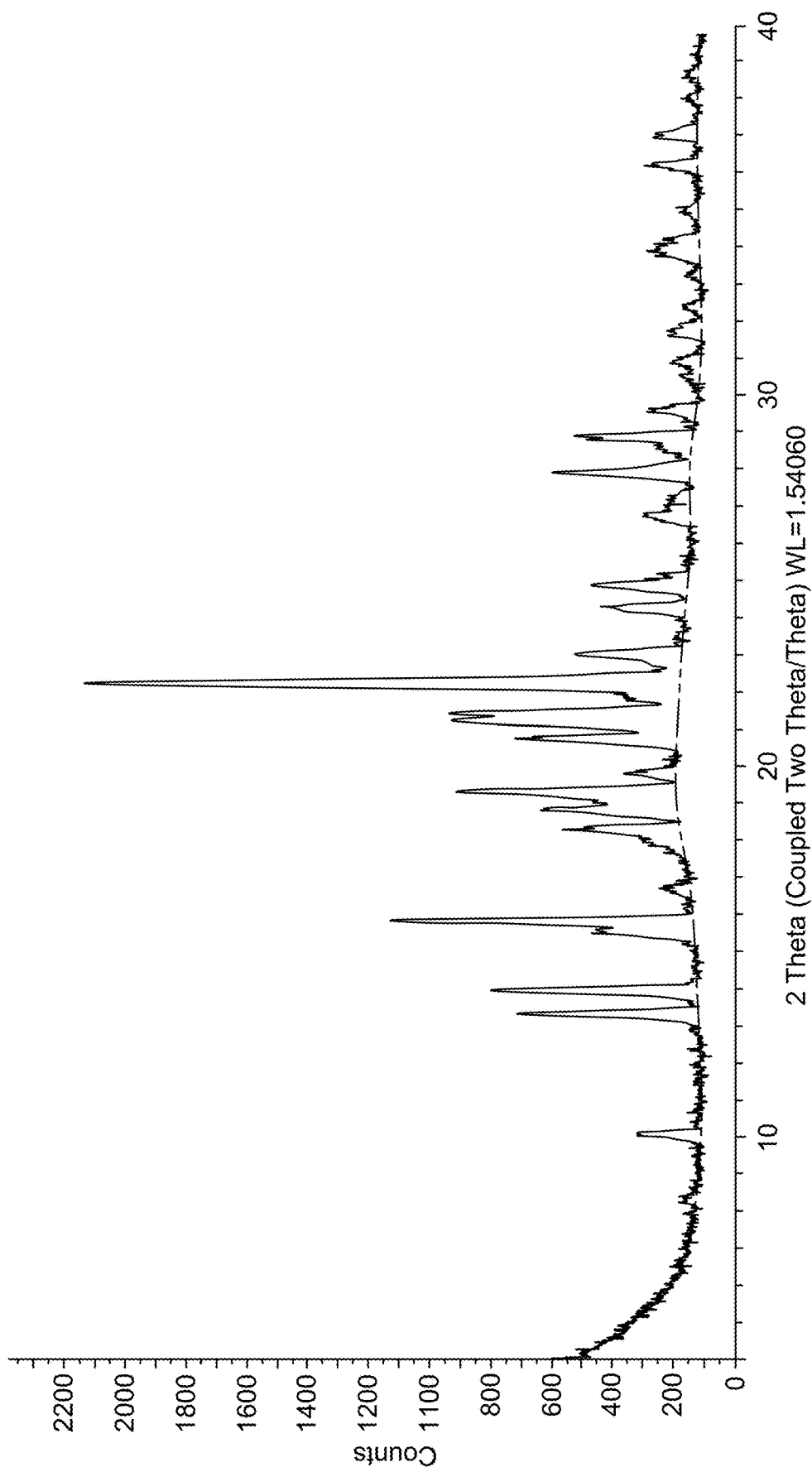
FIG. 77 shows a XRPD profile of crystalline compound 1 monofumarate Form A (oven dried).
Figure 78:
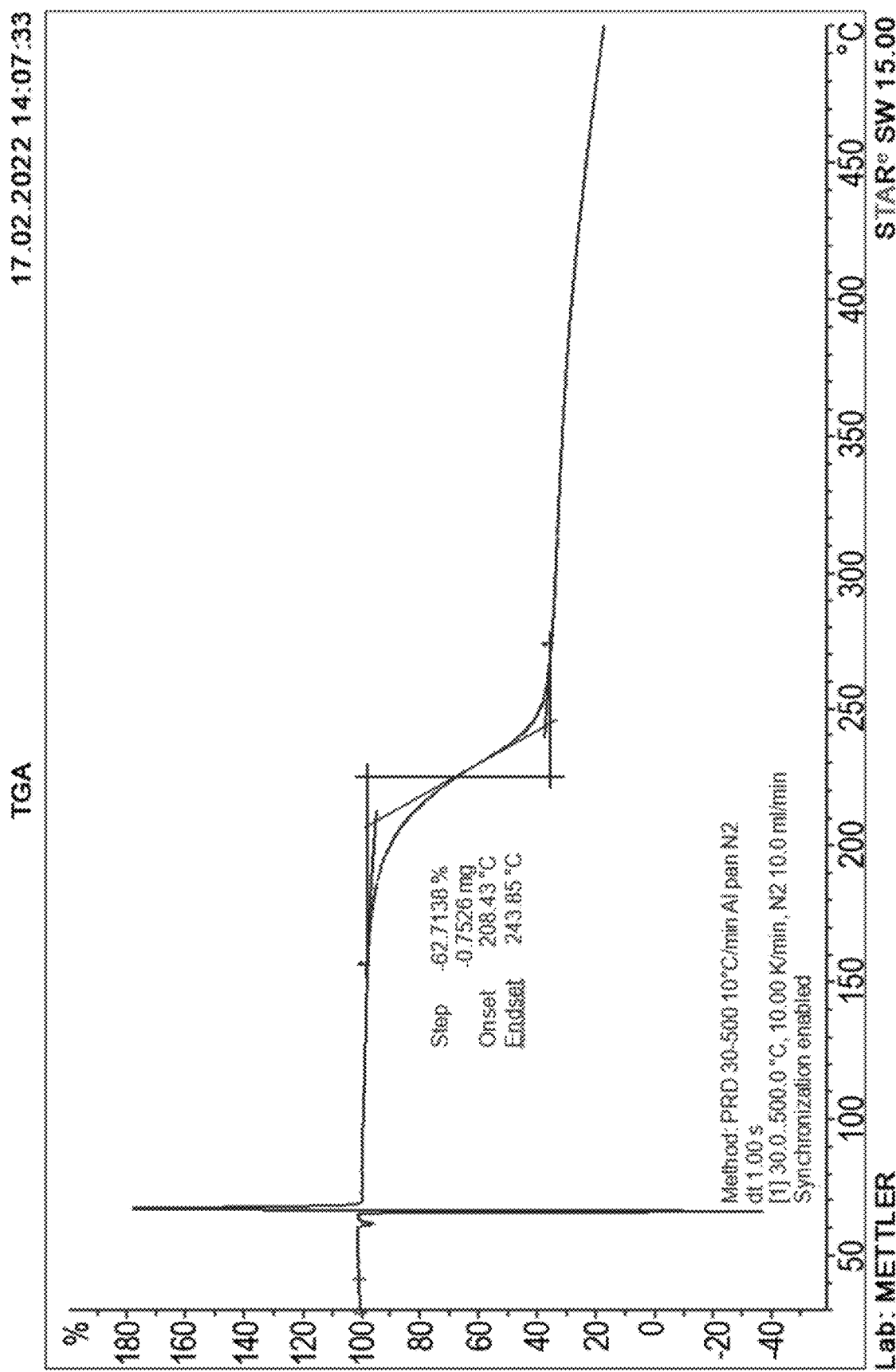
FIG. 78 shows a TGA thermogram of crystalline compound 1 monofumarate Form B, Pattern 3b, analysis was acquired at a ramp rate of +10° C./minute.
Figure 79:
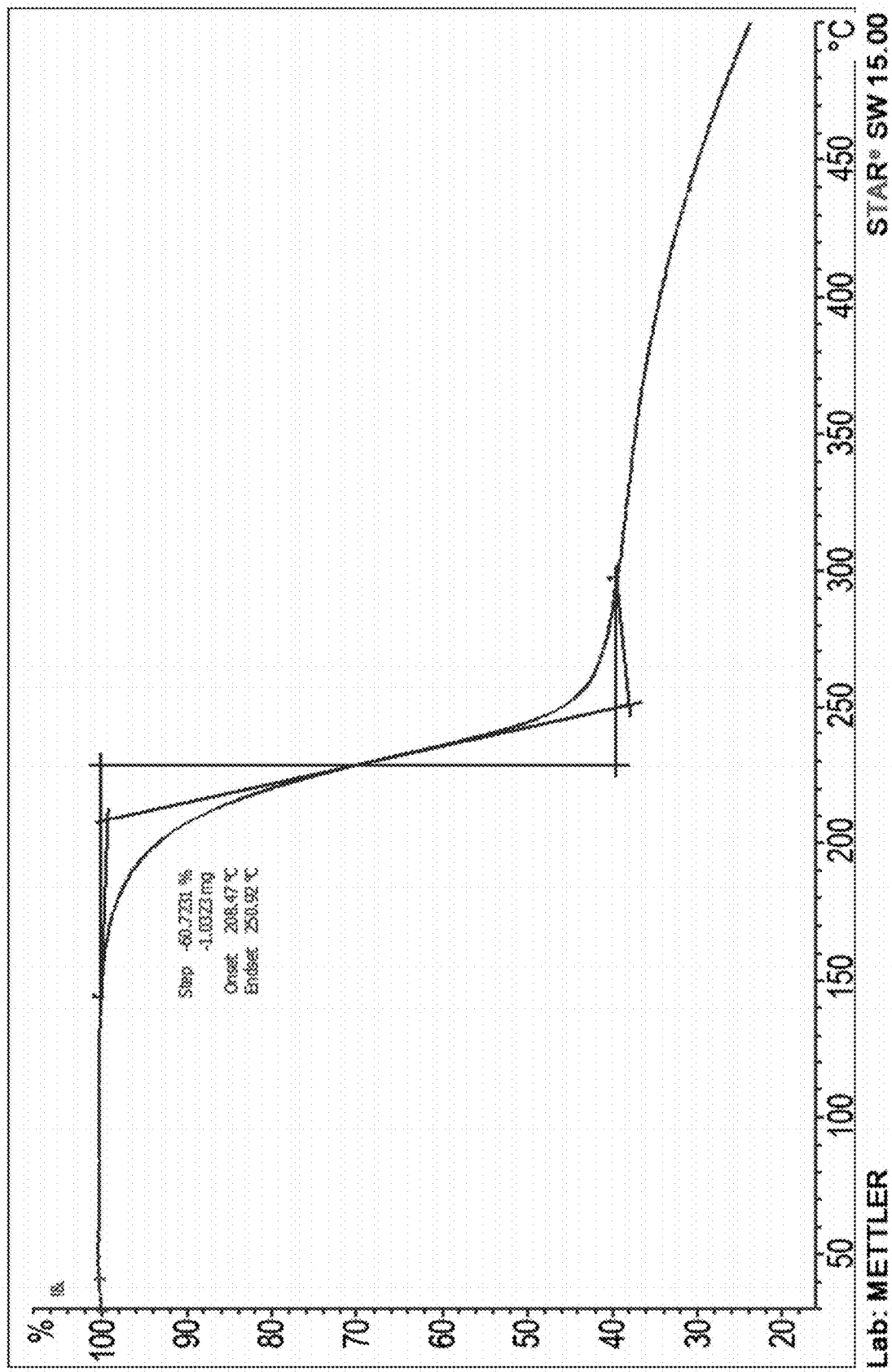
FIG. 79 shows a TGA thermogram of crystalline compound 1 monofumarate Form A, analysis was acquired at a ramp rate of +10° C./minute.
Figure 83:
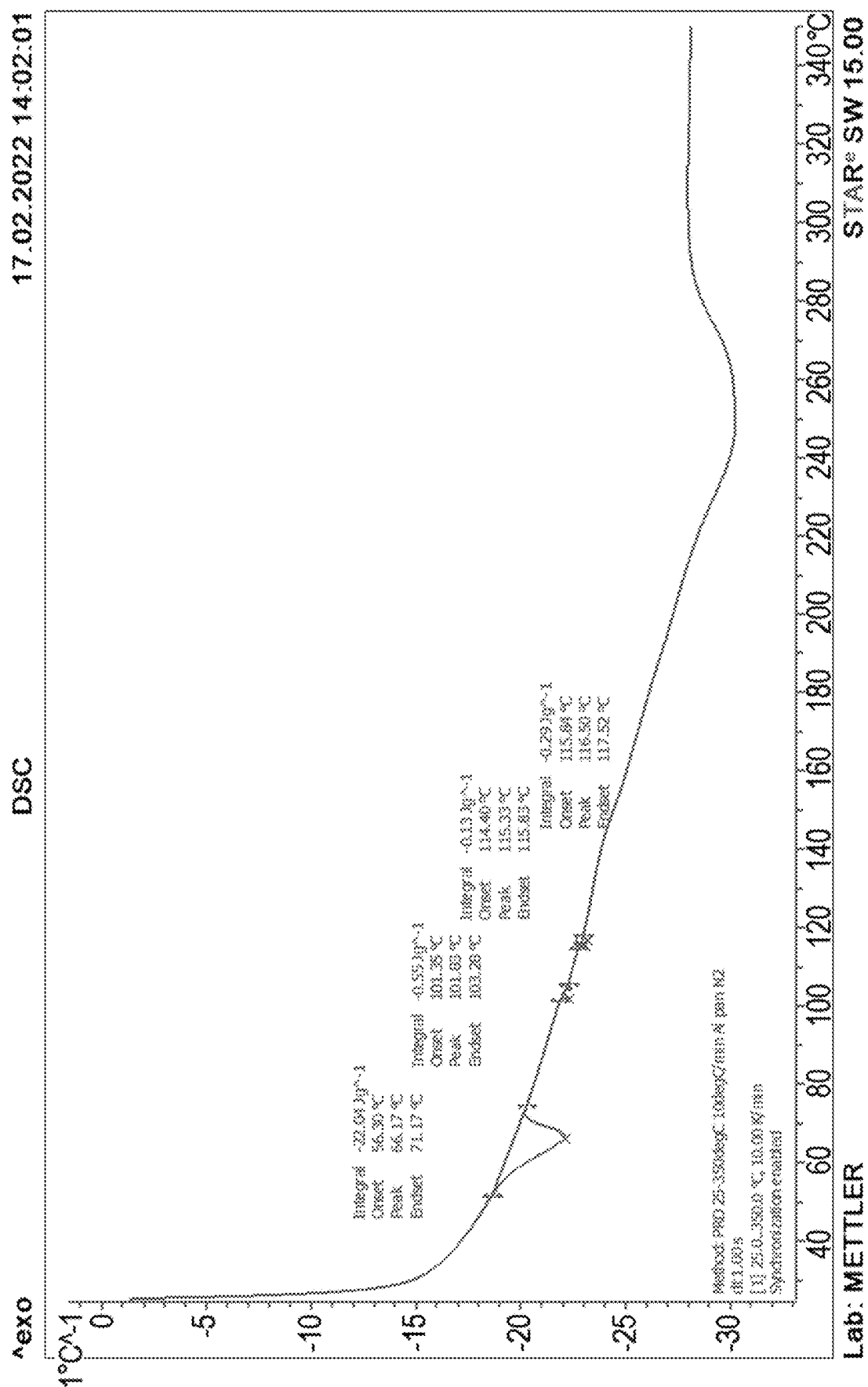
FIG. 83 shows a DSC profile of compound 1 monofumarate Form B, pattern 3b, analysis was acquired at a ramp rate of +10° C./minute.
Figure 84:
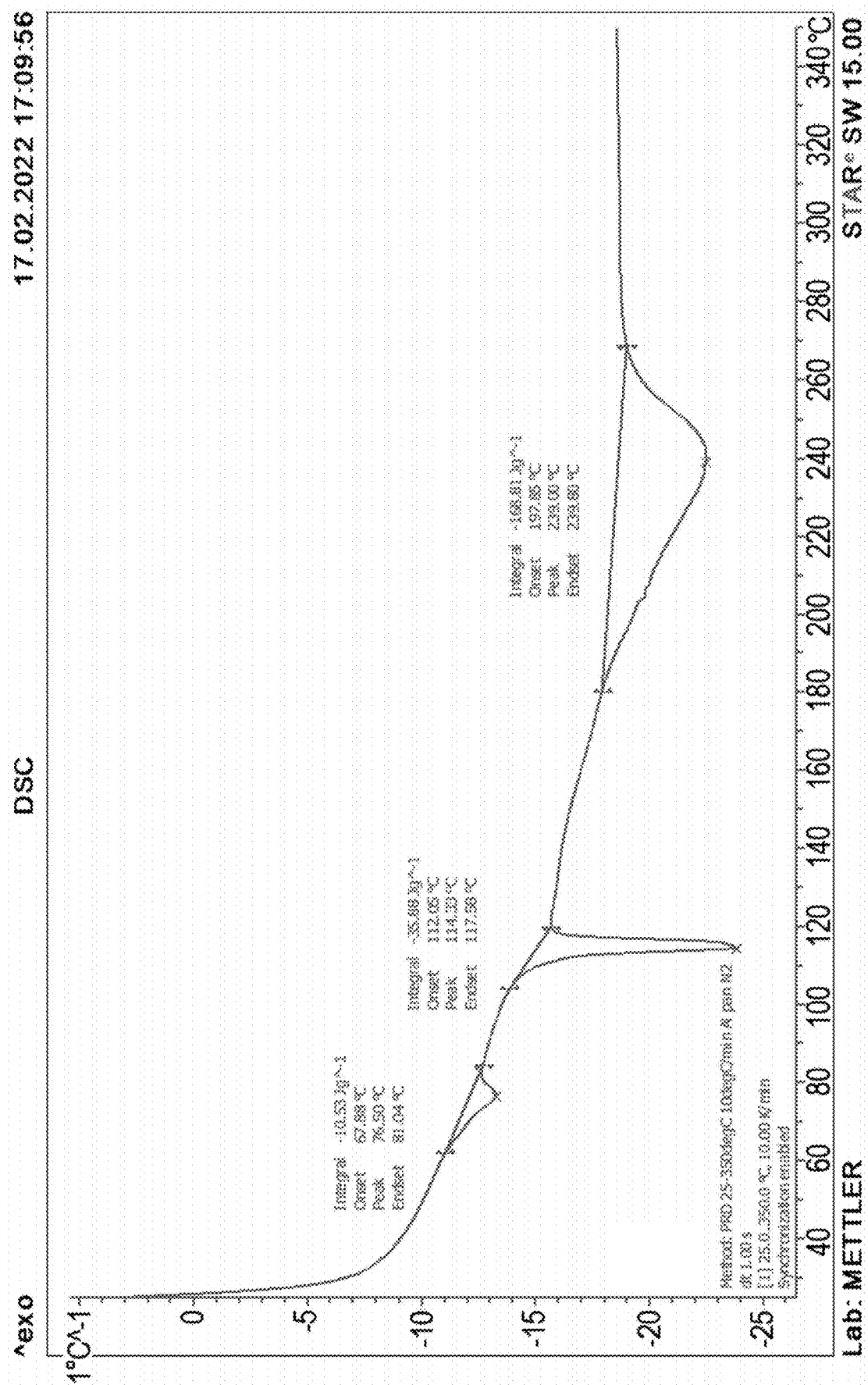
FIG. 84 shows a DSC profile of 8 crystalline compound 1 monofumarate Form A, analysis was acquired at a ramp rate of +10° C./minute.

Monofumarate Form B (Pattern #3b)
Preparation
Monofumarate Form B (Pattern #3b) was prepared in tBME.
Characterization Data
XRPD: An exemplary XRPD profile for monofumarate Form B is shown in FIG. 5.
DSC: An exemplary DSC profile for monofumarate Form B is shown in FIG. 83.
TGA: An exemplary TGA profile for monofumarate Form B is shown in FIG. 78.
$^1$H NMR: An exemplary $^1$H NMR spectrum for monofumarate Form B is shown in FIG. 62. The
$^1$H NMR shows a 1:1 stoichiometry of compound and fumarate.
Pattern #3a
Preparation
Pattern #3a was prepared in ethyl acetate.
Characterization Data
XRPD: An exemplary XRPD profile for Pattern #3a is shown in FIG. 68. Upon drying Pattern #3a transformed into Form A. An XRPD pattern for material that was Pattern #3a and transformed into Form A after heating is shown in FIG. 69.
Hemifumarate Form I (Pattern #2)
Preparation
Hemifumarate Form I (Pattern #2) was prepared in IPA.
Characterization Data
XRPD: An exemplary XRPD profile for hemifumarate Form I is shown in FIG. 4.
DSC: An exemplary DSC profile for hemifumarate Form I is shown in FIG. 340.
TGA: An exemplary TGA profile for hemifumarate Form I is shown in FIG. 341.
$^1$H NMR: An exemplary $^1$H NMR spectrum for hemifumarate Form I is shown in FIG. 3. The $^1$H
NMR shows a 2:1 stoichiometry of compound and fumarate.
Hemifumarate Form II (Pattern #4)
Preparation
Hemifumarate Form II (Pattern #4) was prepared in tBME.
Characterization Data
XRPD: An exemplary XRPD profile for hemifumarate Form II is shown in FIG. 7.
DSC: An exemplary DSC profile for hemifumarate Form II is shown in FIG. 60.
TGA: An exemplary TGA profile for hemifumarate Form II is shown in FIG. 59.
$^1$H NMR: An exemplary $^1$H NMR spectrum for Form II is shown in FIG. 57. The $^1$H NMR shows a 2:1 stoichiometry of compound and fumarate.
Pattern #5
Preparation
Pattern #5 was prepared in MIBK.
Characterization Data
XRPD: An exemplary XRPD profile for Pattern #5 is shown in FIG. 1.
DSC: An exemplary DSC profile for Pattern #5 is shown in FIG. 40.
$^1$H NMR: An exemplary $^1$H NMR spectrum for Pattern #5 is shown in FIG. 39. The $^1$H NMR shows a 1:1 stoichiometry of compound and fumarate.
Pattern #6
Preparation
Pattern #6 was prepared in MEK.
Characterization Data
XRPD: An exemplary XRPD profile for Pattern #6 is shown in FIG. 71.
Upon drying, Pattern #6 transformed into Form A.
Instrumental
DSC
A Mettler Toledo DSC 3 instrument was used for the thermal analysis operating with STARe™ software. The analysis was conducted in 40 µl open aluminium pans, under nitrogen and sample sizes ranged from 1 to 10 mg. Typical analysis method was 20 to 250° C. at 10° C./minute.
Alternatively, a Mettler Toledo DSC 821 instrument was used for the thermal analysis operating with STARe™ software. The analysis was conducted in 40 µl open aluminium pans, under nitrogen and sample sizes ranged from 1 to 10 mg. Typical analysis method was 20 to 250° C. at 10° C./minute.
FT-IR
FT-IR Spectra were acquired using a PerkinElmer Frontier FT-IR spectrometer. Samples were analysed directly using a universal ATR attachment in the Mid and Far frequency ranges; 4000 to 30 cm$^{-1}$. Spectra were processed using Spectrum software. Standard KBr windows are used for mid-IR applications; polyethylene and polyethylene/diamond windows are used for operation in the far-IR. Further capabilities of the instrument include a liquid flow cell with ZnSe windows used for rapid monitoring of reactions. This couples with time-based software that allows time-resolved measurements to be taken.
LC-MS
Routine Liquid Chromatography-Mass Spectrometry (LC-MS) data were collected using the Agilent 1260 Infinity II interfaced with 1260 Infinity II DAD HS and Agilent series 1260 Infinity II binary pump.
The instrument used a single quadrupole InfinityLab MSD. The instrument was calibrated up to 2000 Da.
$^1$H NMR
$^1$H NMR Spectra were acquired using a Bruker 400 MHz spectrometer and data was processed using Topspin. Samples were prepared in DMSO-$d_6$ at typical concentrations of 10 to 20 mg/mL and up to 50 mg/mL for $^1$H NMR w/w assay and calibrated to the corresponding non-deuterated solvent residual at 2.50 ppm.

$^1$H NMR w/w Assay

Assays (w/w) of API by $^1$H NMR spectroscopy were measured by the project chemist. Internal standard 2,3,5,6-terachloronitrobenzene (TCNB), (ca. 20 mg, F.W. 260.89) were dissolved in DMSO-$d_6$ (2.0 mL) and the $^1$H NMR spectrum was acquired using an extended relaxation method.

Thermal Gravimetric Analysis

A Mettler Toledo TGA 2 instrument was used to measure the weight loss as a function of temperature from 25 to 500° C. The scan rate was typically 5 or 10° C. per minute. Experiments and analysis were carried out using the STARe™ software. The analysis was conducted in 100 µL open aluminium pans, under nitrogen and sample sizes ranged from 1 to 10 mg.

XRPD Analysis

X-Ray powder diffraction (XRPD) analysis was carried out using a Bruker D2 Phaser powder diffractometer equipped with a LynxEye detector. The specimens underwent minimum preparation but, if necessary, they were lightly milled in a pestle and mortar before acquisition. The specimens were located at the centre of a silicon sample holder within a 5 mm pocket (ca. 5 to 10 mg).

The samples were continuously spun during data collection and scanned using a step size of 0.02°2-theta (2θ) between the range of 4° to 40°2-theta. Data was acquired using either 3- or 20-minutes acquisition methods. Data was processed using Bruker Diffrac.Suite.

Peak tables report only peaks >10%.

Relative intensity values in peak tables were calculated using the Net. intensity values.

Background curvature is automatically calculated over 4 to 40°2-theta by the Brucker EVA software.

HPLC

HPLC data was acquired using an Agilent HPLC instrument. Samples were diluted to 1 mg/mL concentration in $H_2O$/DMSO (1/1, v/v).

Method parameters:
  Column: Halo C18, 150×4.6 mm, 2.71 µm
  Inj. volume: 5 µL
  Detection: UV @ 212 nm
  Mobile Phase A: 0.1% TFA in water/acetonitrile 95/5 v/v
  Mobile Phase B: 0.05% TFA in water/acetonitrile 5/95 v/v

TABLE 67

HPLC Parameters

| Time | % A | % B |
|---|---|---|
| 0.0 | 100 | 0 |
| 2.0 | 100 | 0 |
| 25.0 | 50 | 50 |
| 30.0 | 0 | 100 |
| 32.0 | 0 | 100 |
| 32.1 | 100 | 0 |
| 37.0 | 100 | 0 |

Flow rate: 1 mL/min
Column temperature: 30° C.
Run time: 37 minutes
Integration time: 32 minutes
Wash vial or syringe wash: Sample diluent

DVS

The moisture sorption properties of the feed API were analysed by DVS Intrinsic instrument (Surface Measurement System). Approximately 20 to 50 mg of API was weighed onto an aluminium pan and loaded into the instrument equilibrated at 25° C. The sample was equilibrated under a dry atmosphere (0% relative humidity) for 60 minutes, before increasing the humidity from 0% to 30% at 5%4 step increment and from 30% to 90% at 10% step increment. A desorption cycle was also applied from 90% to 30% (10% step decrement) and from 30% to 0% (5% step decrement). A rate of change in mass per time unit (dm/dt) of 0.002%/min was set as the equilibrium parameter. Kinetic and isotherm graphs were calculated.

TABLE 68

Solvents used in the solubility screen

| Solvents | b.p. (° C.) | ICH Classes |
|---|---|---|
| Acetone | 56 | 3 |
| Acetonitrile | 82 | 2 |
| tert-Butylmethyl ether | 55 | 3 |
| Dichloromethane | 40 | 2 |
| DMSO | | |
| Ethanol | 78 | 3 |
| Ethyl acetate | 75 | 3 |
| 2-Propanol | 83 | 3 |
| iPrOAc | 87 | 3 |
| Methanol | 65 | 2 |
| Methylethyl ketone | 80 | 3 |
| 2-Methyl THF | 80 | # |
| Tetrahydrofuran | 66 | 2 |
| Toluene | 111 | 2 |
| Water | 100 | # |

Procedures—Qualitative Solubility Screen

Compound 1 Fumarate (batch 1, 25 mg, 1 wt) was weighed out in 20 separate vials to qualitatively examine the solubility in an array of diverse solvents. The solubility was tested initially at 5 vol at 20° C., 40° C. and reflux. If insoluble at 5 vol, the solvent quantity was increased to 10 vol, 15 vol and 20 vol of the respective solvent. The suspensions that occurred upon cooling down were centrifuged and the solvent wet pellets were analysed by XRPD. The insoluble suspensions were additionally worked up for XRPD analysis. The resultant powder patterns were subsequently cross-referenced against the input supplied material.

Procedures—Stability Examination of Supplied Material at 40 V 75% RH compound 1·Fumarate (batch 1, 100 mg) was placed inside a wide-necked, open vial (suffix -A) Compound 1‰Fumarate (batch 1, 100 mg) was placed inside a wide-necked, open vial and then inside double polyethene bags (SPC/PK/0052), tied tightly with cable ties (suffix -B). Both samples were maintained under equilibrium humidity of 75% RH at 40° C. and monitored, initially at hourly and then weekly time points.

Procedures—Re-Proportionation Examination

Figure 56:
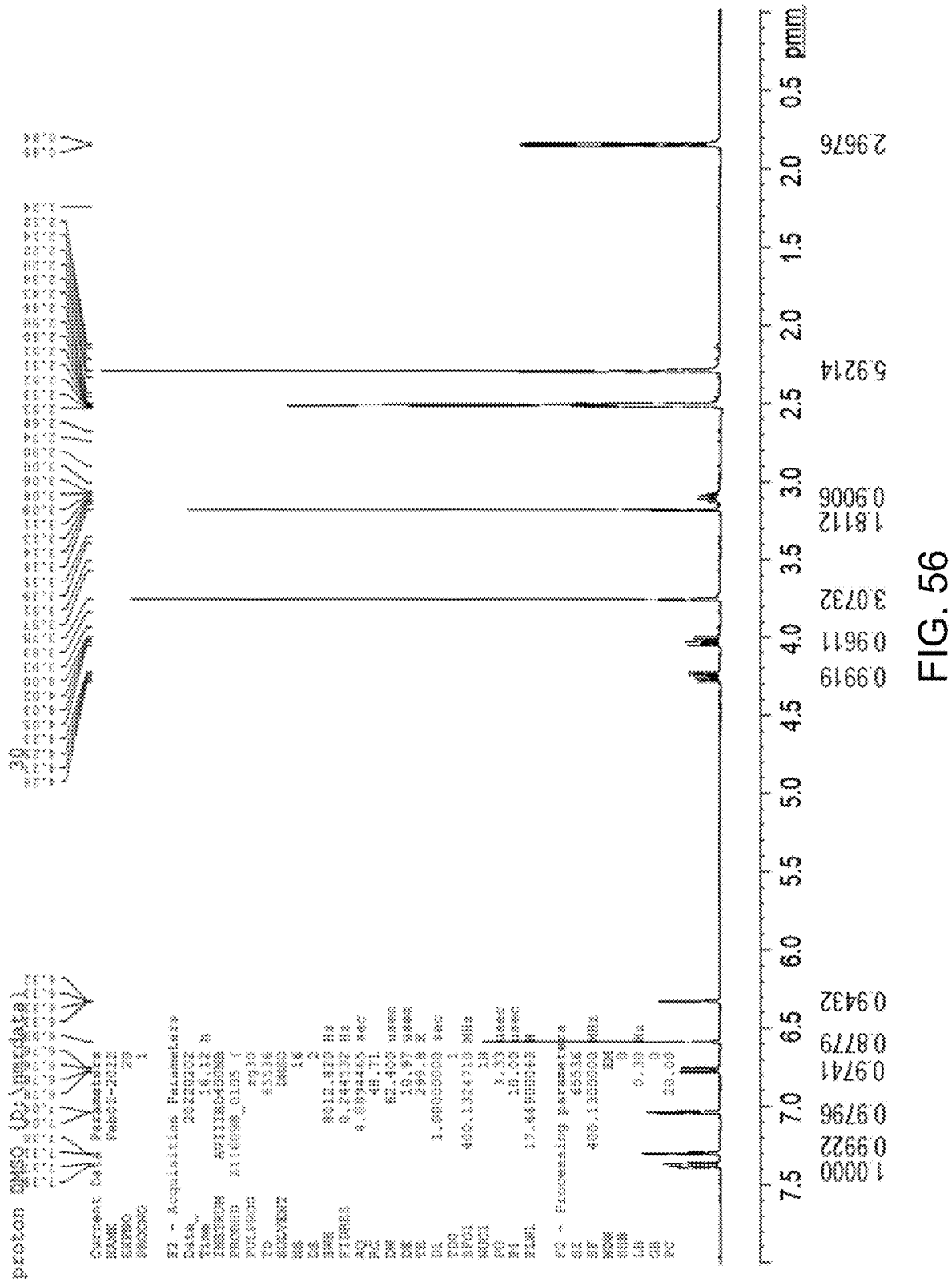
FIG. 56 shows a $^1$H NMR spectrum of crystalline compound 1 hemi-fumarate Form II (preparation of hemifumarate in methanol), spectrum was acquired in DMSO-$d_6$ and calibrated to the non-deuterated solvent residual at 2.50 ppm. API to Fumaric acid, 2.0 to 1.0.
Figure 58:
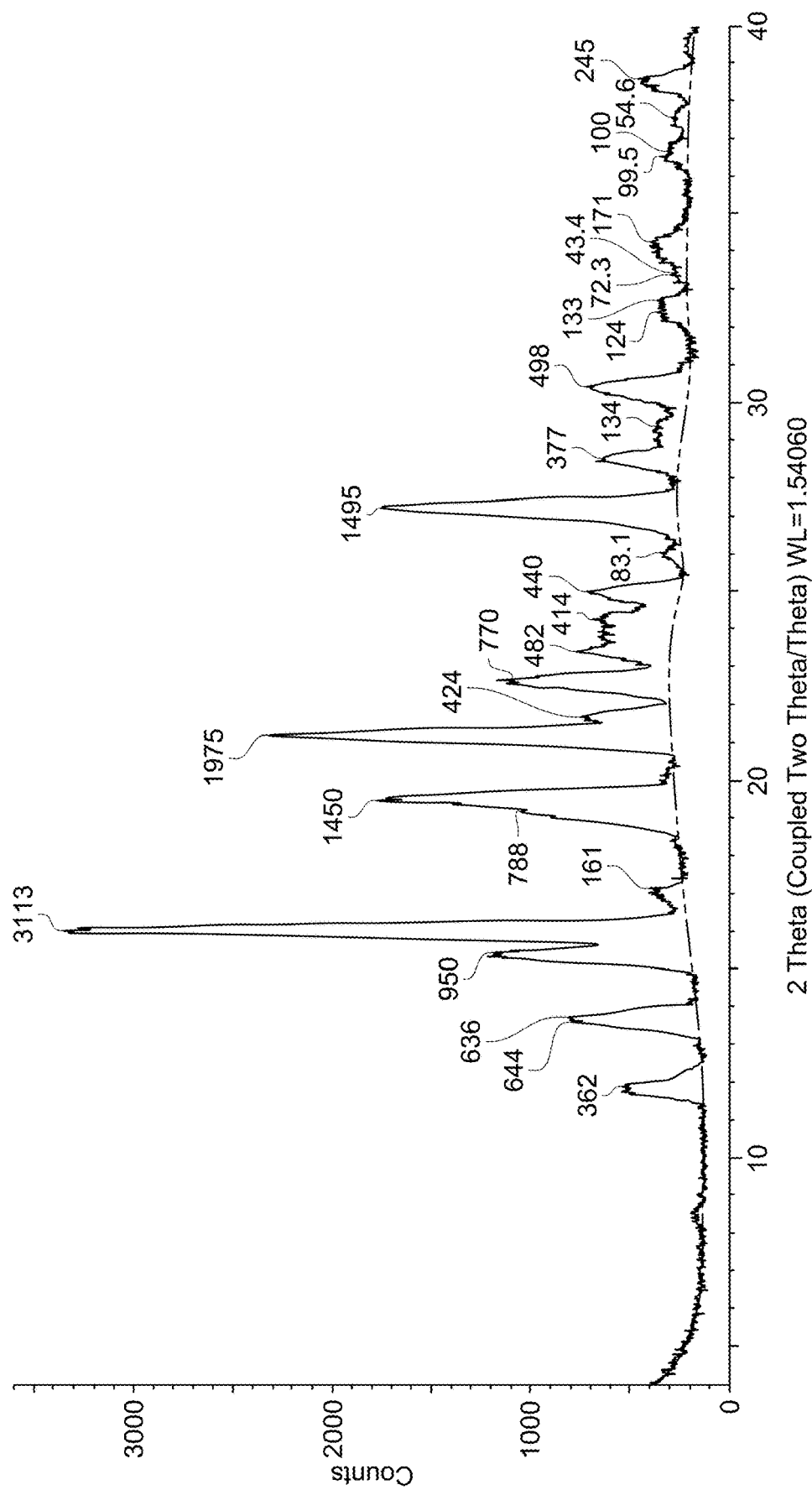
FIG. 58 shows a XRPD profile of crystalline compound 1 hemi-fumarate Form I (wet pellet).

Amorphous compound 1 (70.8 mg, 1 wt) and fumaric acid (17.7 mg, 0.25 wt, 0.5 eq.) were dissolved in methanol (500 µL, 7.0 vol) at temperature. The solution was concentrated to dryness and the residue (was analysed by $^1$H NMR spectroscopy, XRPD and DSC, to confirm the chemical composition and salt stoichiometry (FIGS. 56-58). The material 1 was subjected in a suspension equilibration experiment in tBME (3.5 vol) at 20° C. for ca. 24 h prior to centrifuging and oven drying at 40° C. under vacuum.

Procedures—Competitive Re-Proportionation of Unary and Hemi Salt Forms.

Figure 15:
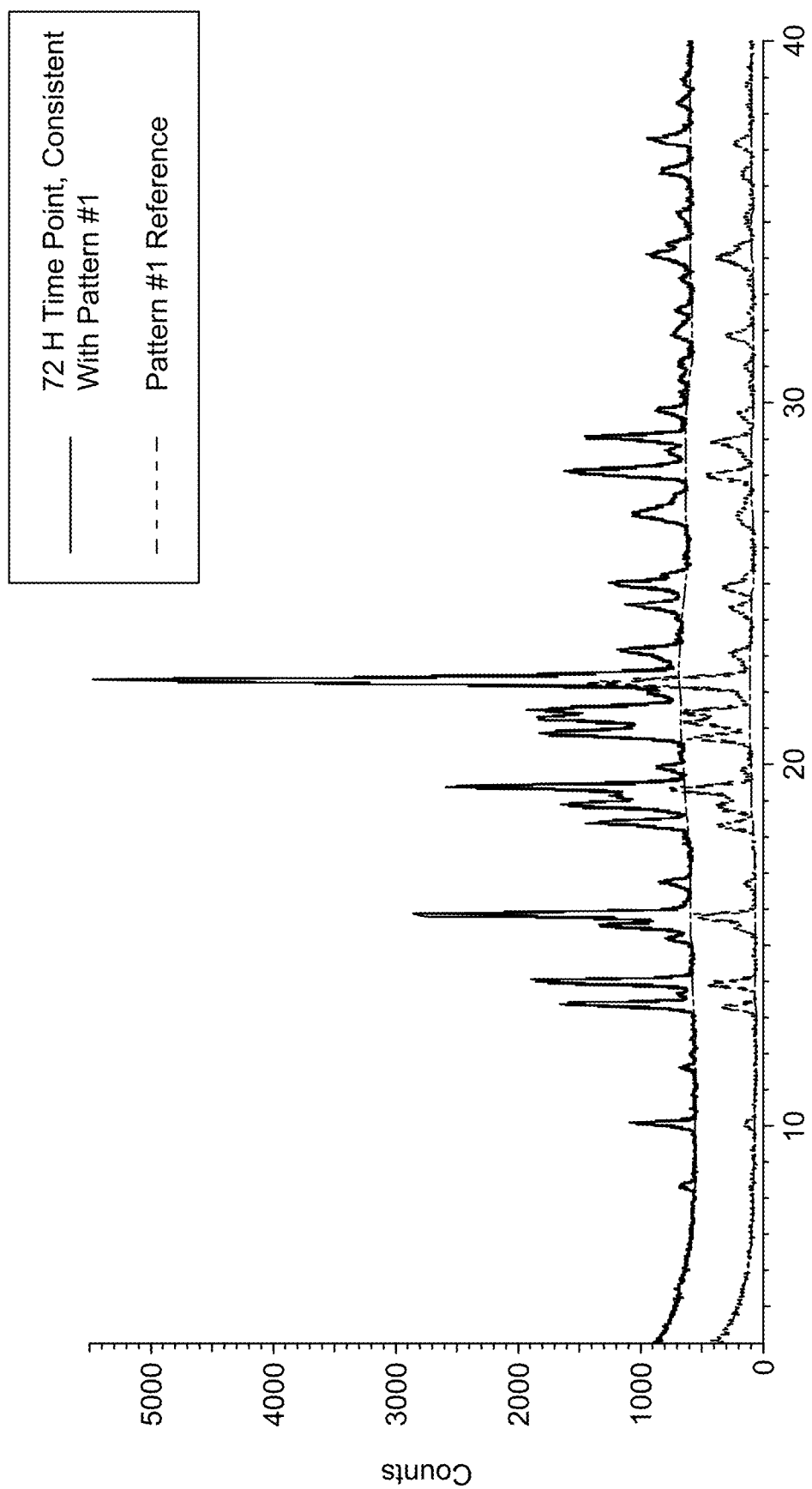
FIG. 15 shows the overlaid XRPD profiles for the crystalline compound 1 monofumarate Form A measured at the 72-hour timepoint of the competitive re-proportionation experiment described in Example 7 and a reference sample of crystalline compound 1 monofumarate Form A.
Figure 16:
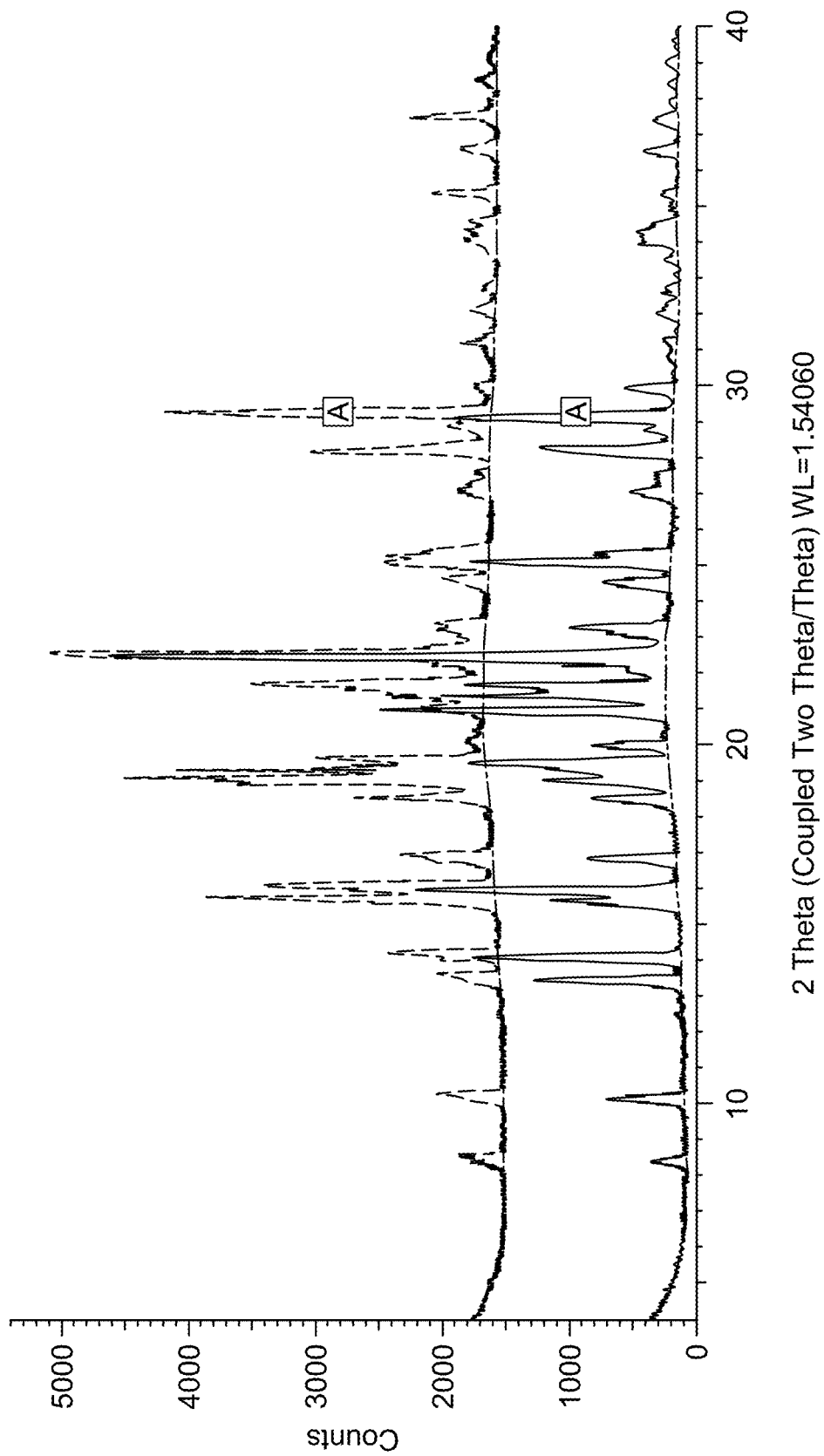
FIG. 16 shows the overlaid XRPD profiles of wet (top) and dried (bottom) crystalline compound 1 monofumarate Form A, isolated from MEK:heptane 1:1.
Figure 17:
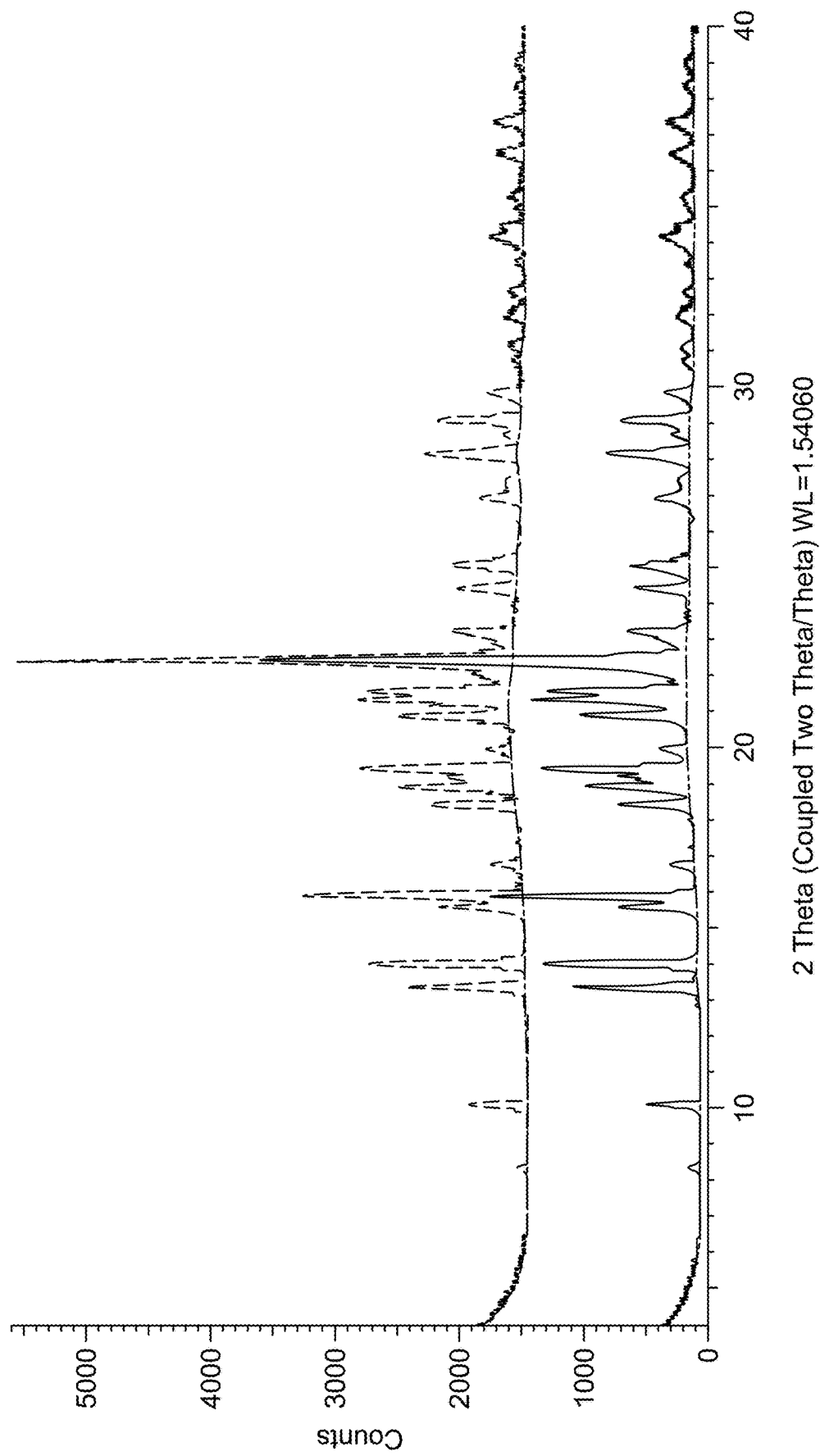
FIG. 17 shows the overlaid XRPD profiles of wet (top) and dried (bottom) crystalline compound 1 monofumarate Form A, isolated from tBME.
Figure 18:
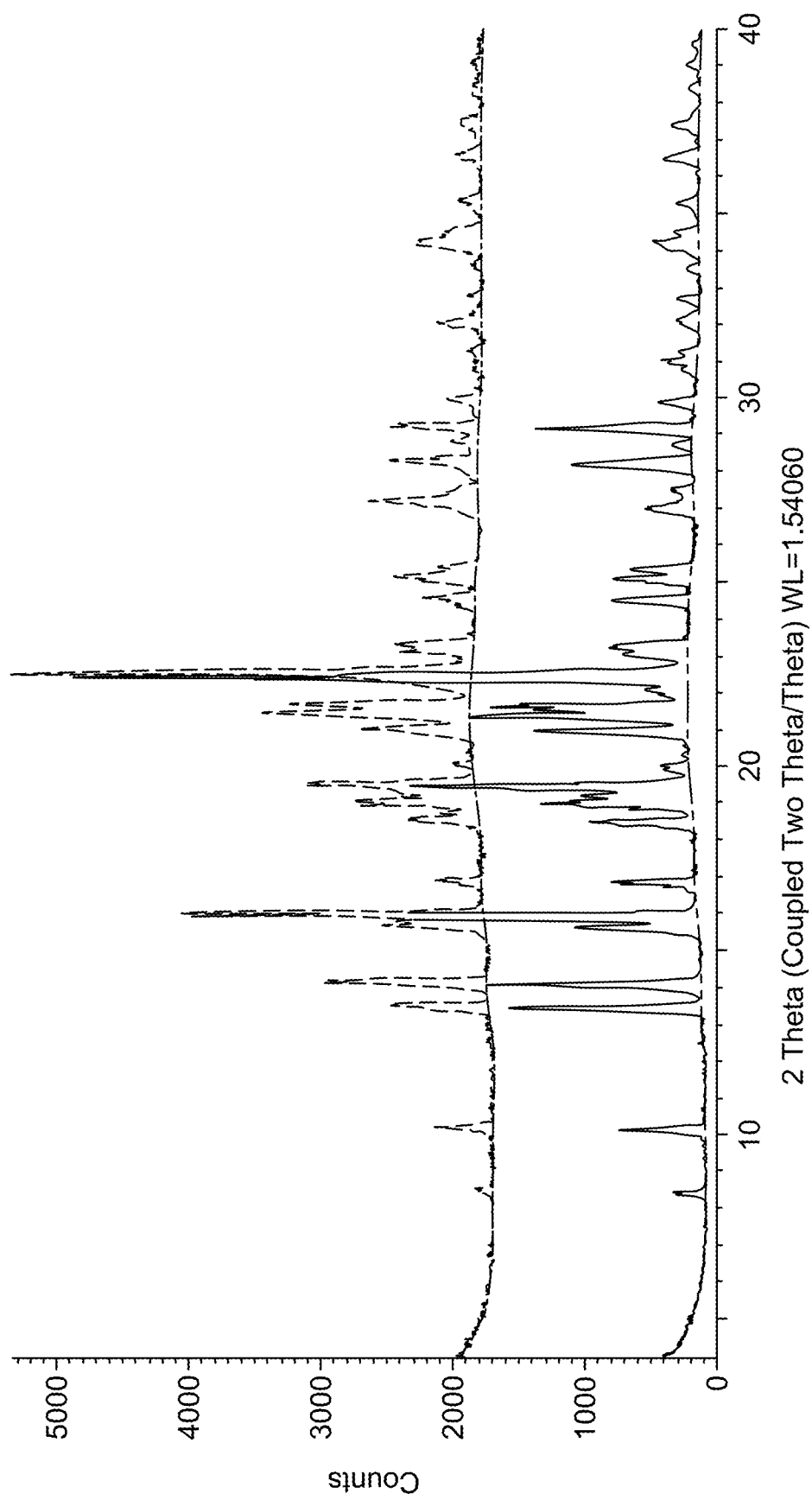
FIG. 18 shows the overlaid XRPD profiles of wet (top) and dried (bottom) crystalline compound 1 monofumarate Form A, isolated from iPAc.
Figure 19:
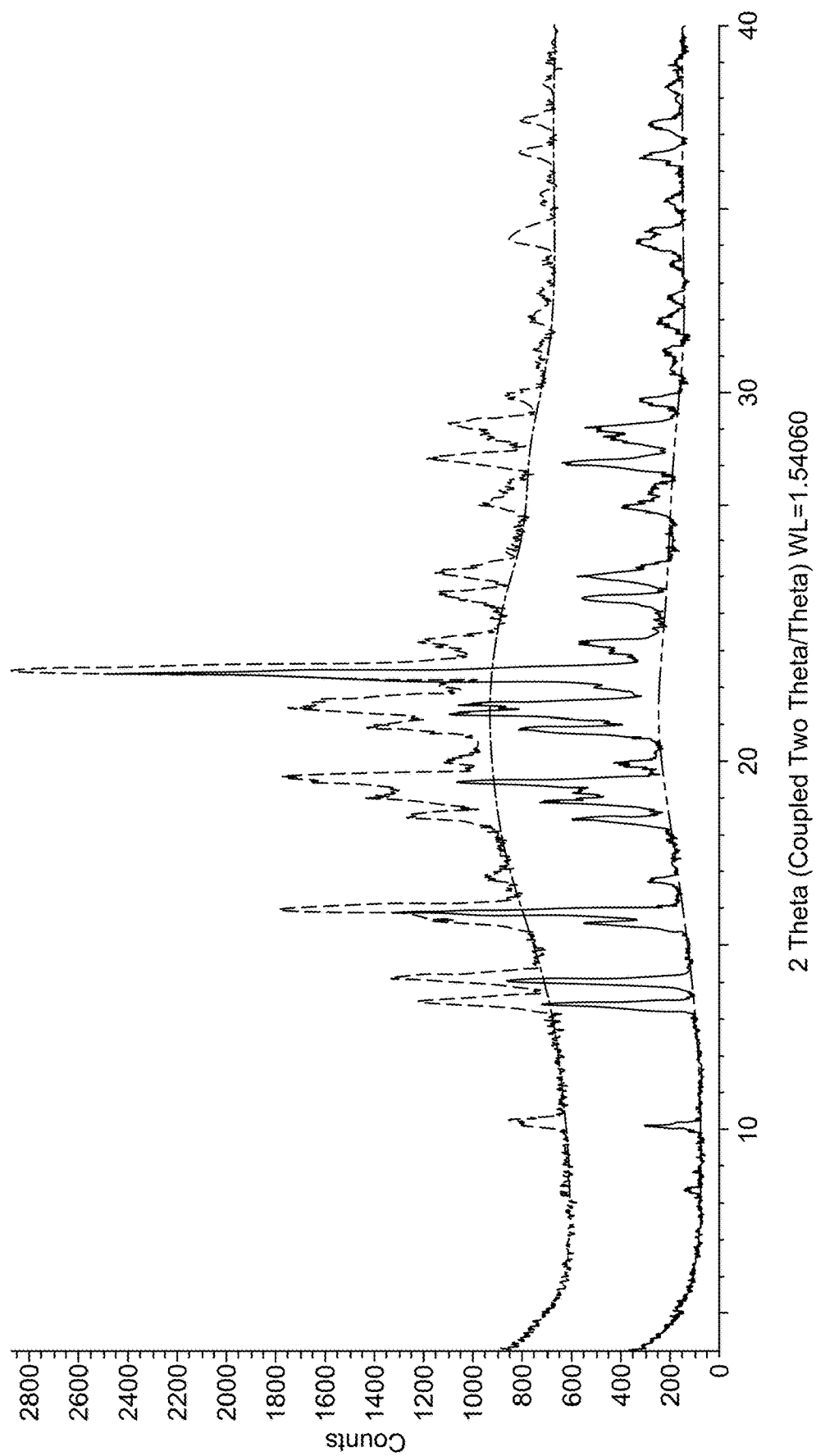
FIG. 19 shows the overlaid XRPD profiles of wet (top) and dried (bottom) crystalline compound 1 monofumarate Form A, isolated from toluene.
Figure 20:
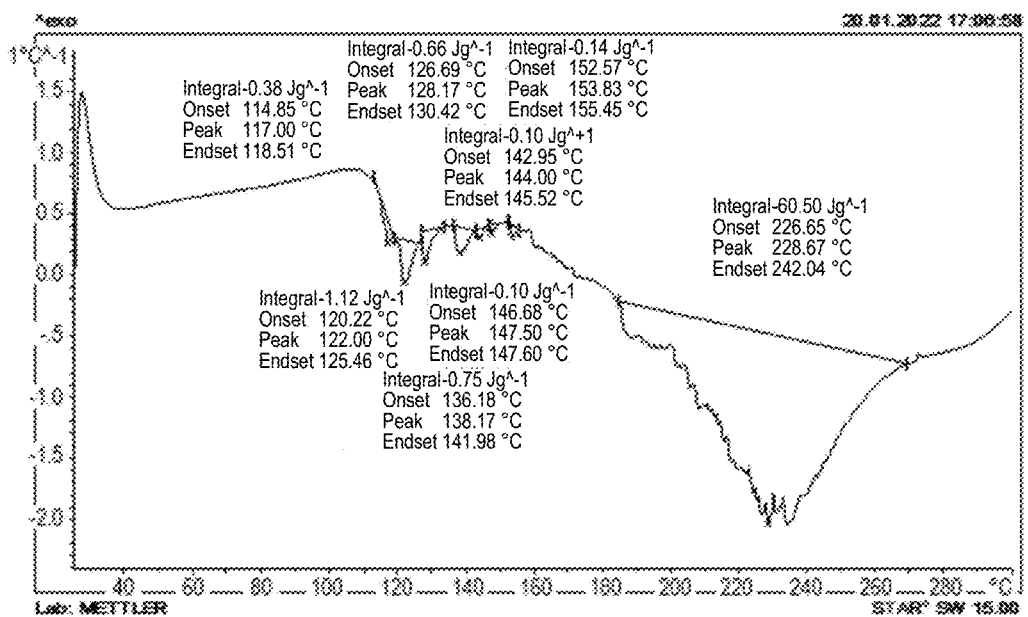
FIG. 20 shows DSC thermograms of samples of compound 1 fumarate before and after neat grinding (NG) and liquid assisted grinding (LAG) conditions. NG and LAG of amorphous compound 1 both resulted in the formation of crystalline compound 1 monofumarate Form A.
Figure 20:
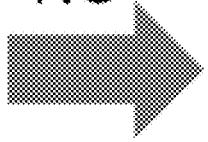
Figure 20:
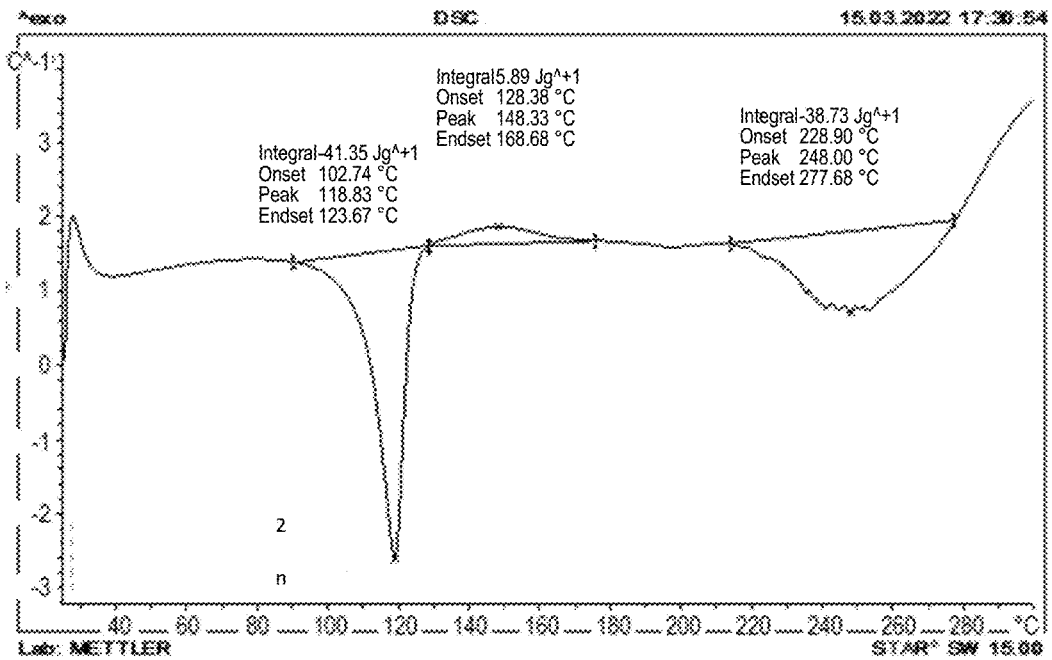
Figure 21:
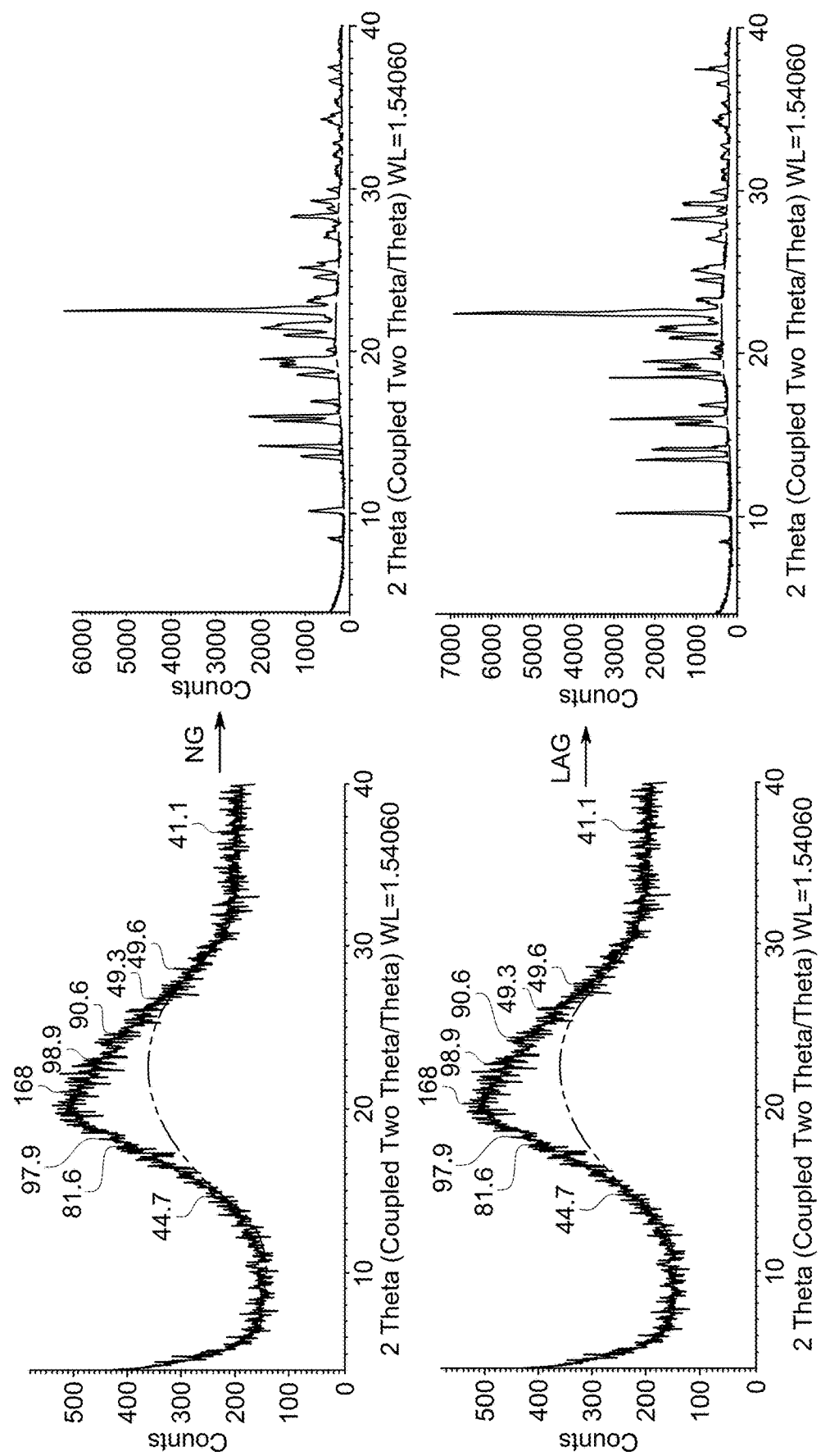
FIG. 21 shows XRPD profiles of samples of compound 1 fumarate before and after neat grinding (NG) and liquid assisted grinding (LAG) conditions. NG and LAG of amorphous compound 1 both resulted in the formation of crystalline compound 1 monofumarate Form A.
Figure 22:
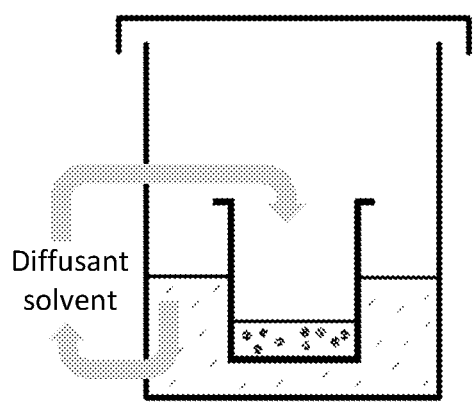
FIG. 22 shows an illustration of the vapor diffusion experiment apparatus set up.

Equimolecular quantities of compound 1 Fumarate (35 mg, 1 wt) and compound 1 0.5Fumarate (35 mg, 1 wt) were stirred in tBME (250 µl, 7.0 vol) at 20° C. for 72 h. The product was isolated via centrifugation and analyzed by XRPD (FIGS. 14 and 15).

Procedures—Suspension Equilibrations at 20 and 40 V

Separate portions of compound 1 (ca 50 mg, 1.0 wt.) were charged to separate vessels. The appropriate solvents (e.g. 250 µl, 5.0 vol), as described in Table and Table were charged to the vessels and the mixtures were stirred for several days at their relevant temperatures e.g. 20 to 40° C. After this time the products were cooled, isolated by centrifugation, analyzed as wet pellet by XRPD and dried under reduced pressure at 40° C. and re-analyzed by XRPD and companion analyses for evidence of alternative crystalline forms (FIGS. 74-77).

Procedures—Thermocycling

Compound 1 Fumarate (75 mg, 1 wt) was weighed out in to 4 separate vials and the corresponding solvents (750 ul, 10 vol) from Table were charged.

The suspensions underwent constant amplitude thermocycling at ±0.5° C./min up to 75% of the relevant solvent b.p. and −0.5° C./min down to 20° C. The thermocycle was repeated 5 times (FIGS. 16-19 and 88-102).

TABLE 69

Thermocycle experiment setup description starting from amorphous compound 1

| Input weight (mg) | Solvent A | Solvent B | Solvent ratio | b.p. (° C.) | Thermocycle peak T (° C.) |
|---|---|---|---|---|---|
| 75.6 | MEK | Heptane | (1 to 1) | ca. 90 | 68 |
| 75.8 | tBME | — | 100.0% | 55 | 41 |
| 75.1 | iPAC | — | 100.0% | 89 | 67 |
| 75.8 | Tolune | — | 100.0% | 110 | 82 |

Procedures—Heat-Up Cool Down (HUCD) Crystallization in Different Solvents

Separate portions of compound 1 Fumarate (75 mg, 1.0 wt.) were charged to separate vessels. The appropriate solvents (750 µl) were charged to the relevant vessels and subsequent charges of the appropriate co-solvent were made to accomplish dissolution. The solutions were cooled to 18 to 23° C. and allowed to stand undisturbed, until crystallization was judged complete. After this time the products were isolated by centrifugation, washed with recycled maturation solvent, dried under reduced pressure at 40° C. and analyzed by XRPD for evidence of alternative crystalline forms (FIG. 103).

Procedures—Mechanochemistry (LAG)

Compound 1·Fumarate (EXP-21-IS3344, 75 mg) and one ball-bearing (7.0 mm, 1.4 g) were placed inside a steel vessel (1.5 ml), and attached to a Retsch MM 500, VARIO mixer-mill. The vessel was oscillated at 500 rpm for 30 minutes, under neat grinding condition (NG, suffix -A) and liquid assisted grinding condition (LAG, methanol η=0.5, suffix -B).

Procedures—Vapor Diffusion Screen

Compound 1 Fumarate (4×75 mg) was weighed out in to 4 separate snap-top vials and Solvent A (375 ul) was charged to each vial. Gentle warming was applied to ensure full dissolution and the vials (open) were placed inside amber jars vials that contained 6 ml of Solvent B. The 4 jars that contained the vials were left standing at 20° C., to allow slow movement of the diffusant solvent from the outer jar into the solvent inside the smaller, open wide-necked vessel and promote crystallization by altering the solvent composition.

TABLE 70

Vapor diffusion expriment setup description

| Input weight (mg) | Solvent A | Solvent Volume (ml) | Solvent B | Co-Solvent volume added (ml) |
|---|---|---|---|---|
| 75.7 | Water | 0.375 | Acetone | 6.0 |
| 76.2 | MEK | 0.375 | tBME | 6.0 |
| 75.4 | BuOH | 0.375 | Heptane | 6.0 |
| 74.4 | MEK | 0.475 | Water | 6.0 |

Procedures—Evaporation Screen

Crystallisation of the API was examined by changing the composition of the crystallisation solvent by evaporation of a volatile diluent. This technique is useful for generating kinetic forms and solvates. Separate portions of compound 1·Fumarate (ca 50 mg, 1.0 wt.) were charged to separate vessels. The appropriate solvents (1 ml, 20.0 vol) were charged to the relevant vessels full dissolution was accomplished at 20° C. The products were analysed by XRPD and companion analyses, for evidence of alternative crystalline forms (FIG. 118-151).

Procedures—In-Situ Hydration Evaluation

Figure 23:
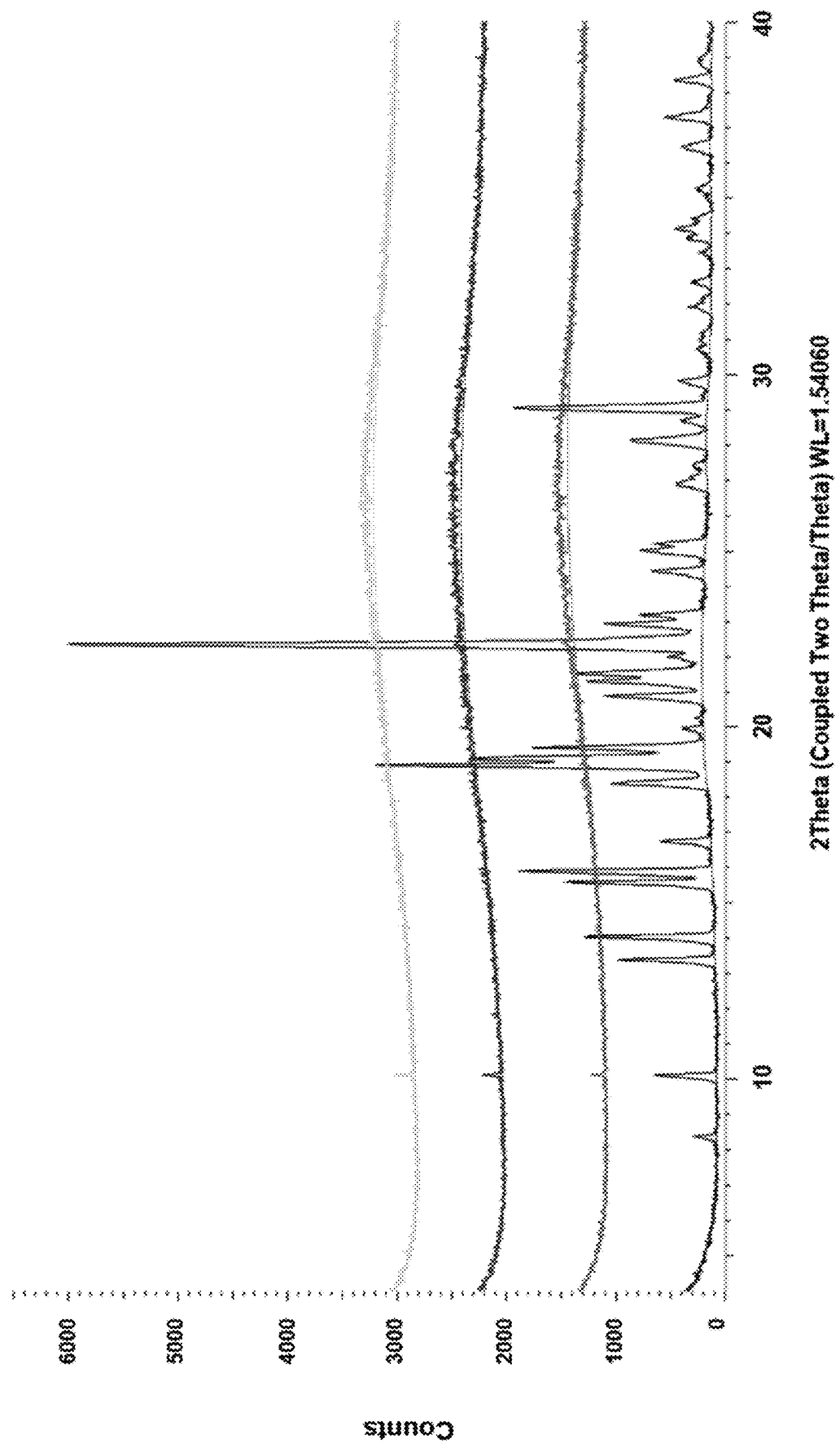
FIG. 23 shows the XRPD diffractogram overlay of crystalline compound 1 monofumarate Form A prior to treatment with water, as described in the in-situ hydration experiments in Example 7, (bottom), the resultant material at 9 minutes (second from bottom), the resultant material at 18 minutes (second from top), and the resultant material at 27 minutes (top).
Figure 24:
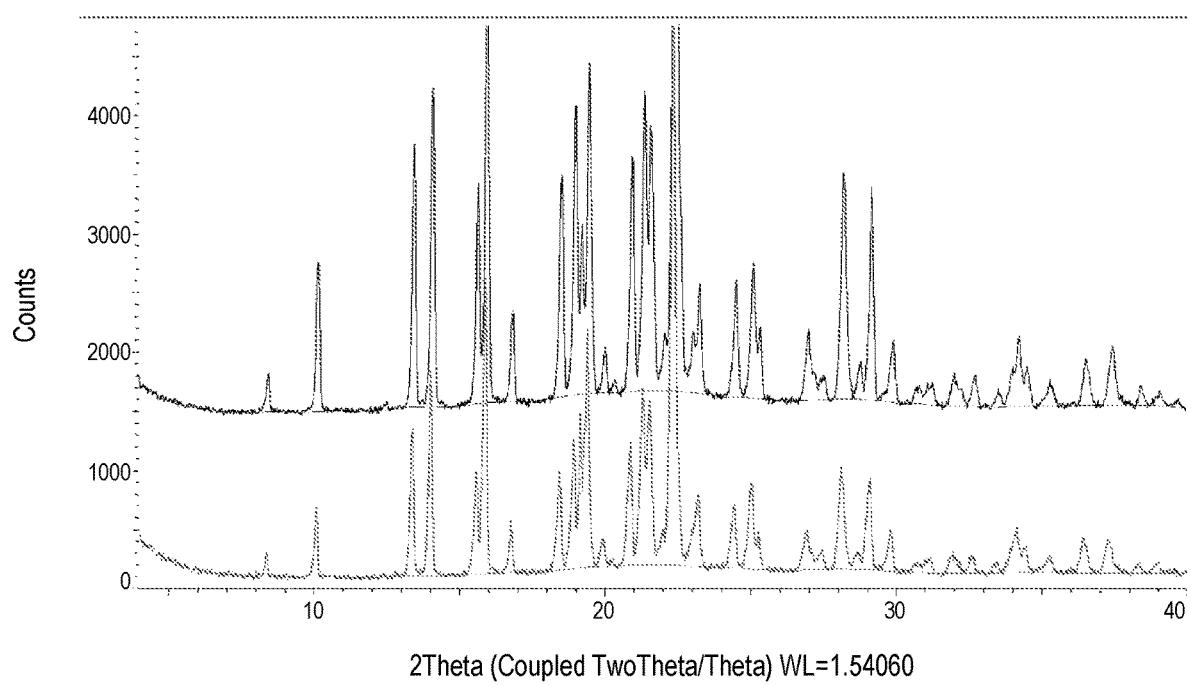
FIG. 24 shows the XRPD diffractogram overlay of crystalline compound 1 monofumarate Form A produced by suspension equilibrium in MEK at 20° C. (top) and a reference sample of crystalline compound 1 monofumarate Form A (bottom).

An XRPD plate was made up with a small amount of compound 1·Fumarate (batch 1, 5 mg, 1.0 wt) and analysed by XRPD on the 9-minute method and labelled as T=0. After the run, the sample was charged with purified water (10 µL, 2.0 vol) and analysed again by XRPD, labelled as T=9. This was repeated twice more for T=18 and T=27. The sample was left to stand under ambient conditions (15-25° C., ambient humidity, and pressure) in the fume hood for 33 h (FIG. 23).

Procedures—Form Control: Suspension Equilibration in MEK at 20° C.

Compound 1 Fumarate (1.0 g, 1 wt) was suspended in MEK (2.5 ml, 2.5 vol) at 20° C. for ca 24 h. The suspension was filtered through a sintered funnel and the filter cake was dried under nitrogen flow for ca. 3 h prior to oven-drying under vacuum at 40° C. for ca. 24 h. The product was collected as a light-yellow solid (635.7 mg, 63% yield uncorr.).

Procedures—Preparation of Form B: Suspension in IBME at 20° C.

Attempt #1: compound 1 fumarate (batch 1, 100.0 mg, 1.0 wt) was suspended in tBME (500 ul, 5.0 vol) at 20° C. and stirred for ca. 4 days. The resultant solids were filtered and analysed as a wet pellet by XRPD (FIG. 25).

Figure 26:
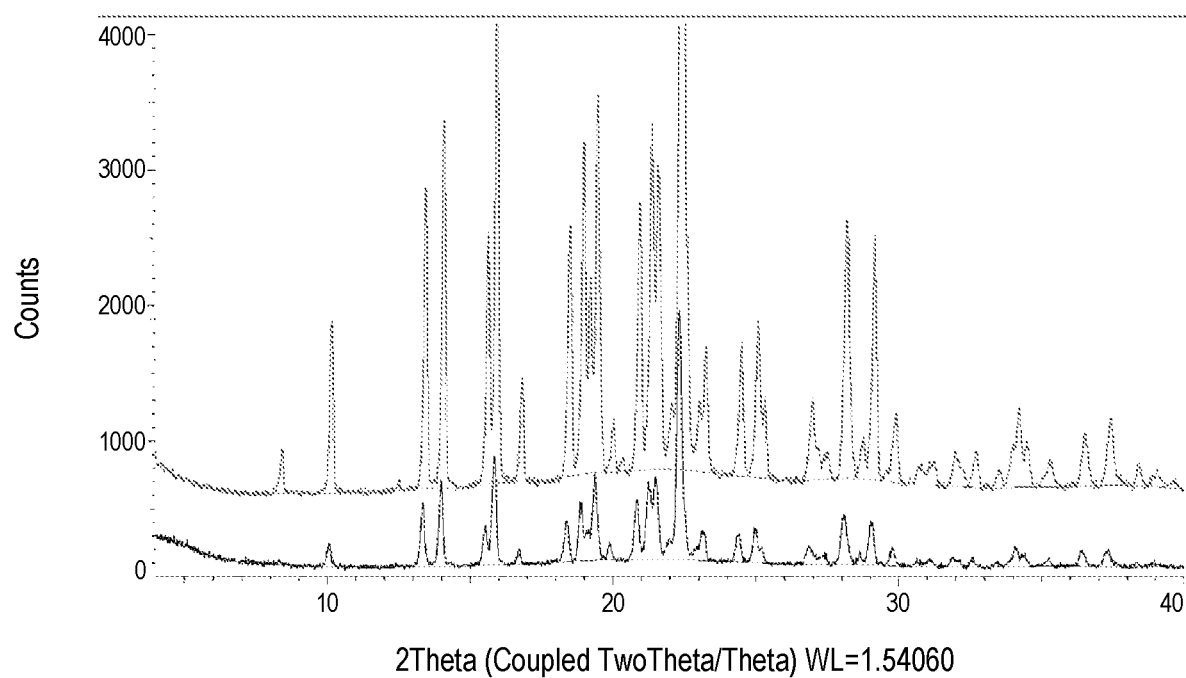
FIG. 26 shows the XRPD diffractogram overlay of crystalline compound 1 monofumarate Form A produced by stirring in tBME at 20° C. for 18 hours (top) and a reference sample of crystalline compound 1 fumarate Form A (bottom).

Attempt #2: compound 1 fumarate (batch 1, 75.0 mg, 1 wt) was in tBME (375 ul, 5.0 vol) at 20° C. for ca. 18 h. and was isolated by suction filtration and dried under sustained nitrogen flux at 20° C., over 20 h and analyzed by XRPD. The diffractogram matched a v. disordered Form A (FIG. 26).

Figure 27:
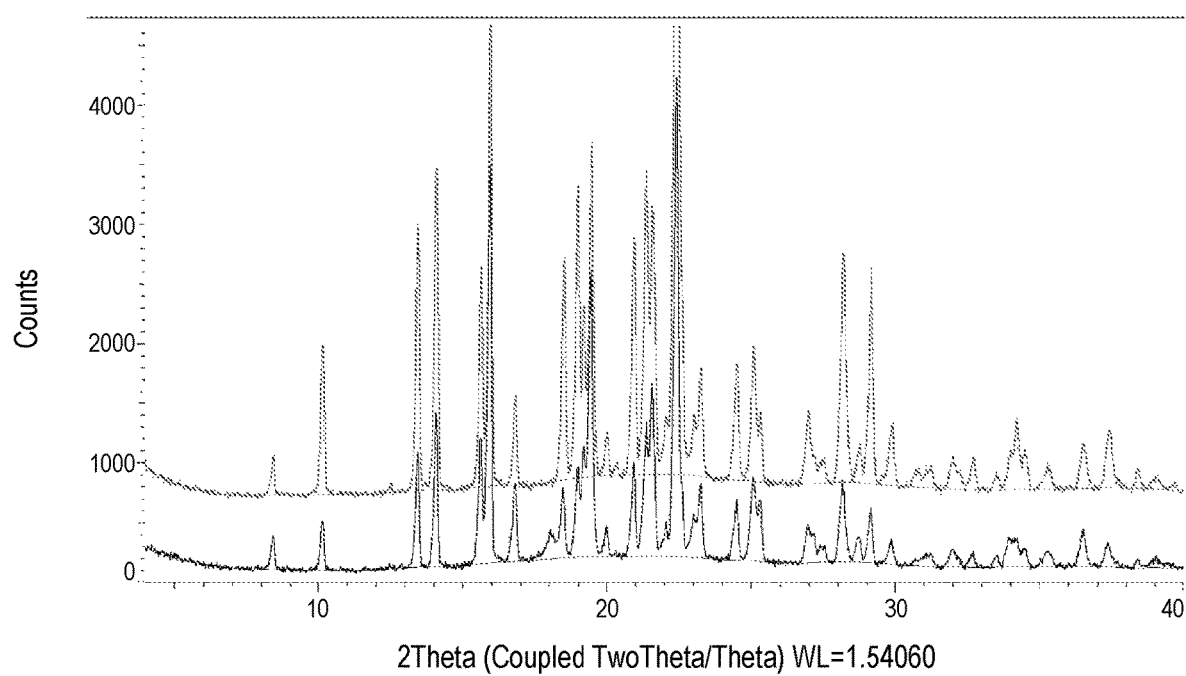
FIG. 27 shows the XRPD diffractogram overlay of crystalline compound 1 monofumarate Form A produced by dissolving amorphous compound 1 in methanol followed by charging with tBME as anti-solvent (top) and a reference sample of crystalline compound 1 fumarate Form A (bottom).

Attempt #3: Compound 1 fumarate (75.0 mg, 1 wt) was dissolved in methanol (338 ul, 4.5 vol) and tBME (500 ul, 5.0 vol) was charged in one portion to achieve rapid (kinetic) precipitation (observation: feint suspension). The resultant solids were isolated by suction filtration, pulled free of surplus solvents, and analysed by XRPD. All three outputs above matched Form A (FIG. 27).

Procedures—Crystallization Experiments to Grow Single Crystal of Form A

Amorphous compound 1·Fumarate (batch 1, 57.1 mg, 1.0 wt) was dissolved in DCM (5.0 ml, 87.6 vol) and was evaporated to give a solid sample of Form A.

A crystalline sample of Form A which had been recrystallised from DCM, was isolated and submitted by Aptuit. A small portion of this sample was suspended in perfluoro ether oil and a suitable colourless block-shaped crystal with dimensions 0.18×0.09×0.09 mm$^3$ was selected. This crystal was mounted on a MITIGEN holder oil on a Rigaku 007HF diffractometer with HF Varimax confocal mirrors, an UG2 goniometer and HyPix 6000HE detector. The crystal was kept at a steady T=100(2) K during data collection. The structure was solved with the ShelXT 2014/5 (Sheldrick, 2014) solution program using dual methods and by using Olex2 1.5 (Dolomanov et al., 2009) as the graphical interface. The model was refined with ShelXL 2014/7 (Sheldrick, 2015) using full matrix least squares minimisation on F$^2$.

X-ray data were collected upon a colourless block-shaped crystal with dimensions 0.18×0.09×0.09 mm$^3$, which was mounted on a MITIGEN holder oil. X-ray diffraction data were collected using a Rigaku 007HF diffractometer with HF Varimax confocal mirrors, an UG2 goniometer and HyPix 6000HE detector equipped with an Oxford Cryosystems low-temperature device, operating at T=100(2) K.

Data were measured using profile data from w-scans of 0.5° per frame for 1.0/0.2 s using Cu K$_\alpha$ radiation (Rotating anode, 40.0 kV, 30.0 mA). The total number of runs and images was based on the strategy calculation from the program CrysAlisPro 1.171.42.61a (Rigaku OD, 2022). The maximum resolution achieved was Q=76.947°.

Cell parameters were retrieved using the CrysAlisPro 1.171.42.61a (Rigaku OD, 2022) software and refined using CrysAlisPro 1.171.42.61a (Rigaku OD, 2022) on 15272 reflections, 81% of the observed reflections. Data reduction was performed using the CrysAlisPro 1.171.42.61a (Rigaku OD, 2022) software which corrects for Lorentz polarisation. The final completeness is 100.00% (IUCr) out to 76.947° in Q.

A multi-scan absorption correction was performed using CrysAlisPro 1.171.42.61a (Rigaku Oxford Diffraction, 2022) Empirical absorption correction using spherical harmonics, implemented in SCALE3 ABSPACK scaling algorithm. The absorption coefficient m of this material is 0.782 mm$^{-1}$ at this wavelength (I=1.54184 Å) and the minimum and maximum transmissions are 0.640 and 1.000.

The structure was solved in the space group P2$_1$2$_1$2$_1$ (#19) by using dual methods using the ShelXT 2014/5 (Sheldrick, 2014) structure solution program and refined by full matrix least squares minimisation on P using version 2014/7 of ShelXL 2014/7 (Sheldrick, 2015). All non-hydrogen atoms were refined anisotropically. The position of the O—H atom H5A and the N—H atom H2 were located from the electron difference map and refined with their thermal parameters linked to their parent atoms. The positions of the remaining H atoms were calculated geometrically and refined using the riding model.

There was a single molecule in the asymmetric unit, which is represented by the reported sum formula. In other words: Z is 4 and Z' is 1.

Characterization Data:
Amorphous Compound 1·Fumarate (Batch 1)

TABLE 71

Batch used for the crystallisation development experiments.

| Batch references | HPLC (% area) | Q $^1$H NMR (% w/w) | KF (% w/w water) | XRPD assignment |
|---|---|---|---|---|
| Batch 1 | 93.83 | 96.9 | 0.7 | Amorphous |

Chemical Data:
IUPAC Name:
  (2E)-but-2-enedioic acid; [(2R)-1-(5-methoxy-1H-indol-1-yl) propan-2-yl] dimethylamine
Mass: 348.40
Exact mass: 348.17
Formula: $C_{18}H_{24}N_2O_5$
Composition: C (62.1%), H (6.91%), N (8.0%), O (23.0%)
Single Crystal Experiment Data:

TABLE 72

Single Crystal Data

| Compound | |
|---|---|
| Formula | $C_{18}H_{24}N_2O_5$ |
| D$_{calc.}$/g cm$^{-3}$ | 1.292 |
| m/mm$^{-1}$ | 0.782 |
| Formula Weight | 348.39 |
| Colour | colourless |
| Shape | block-shaped |
| Size/mm$^3$ | 0.18 × 0.09 × 0.09 |
| T/K | 100(2) |
| Crystal System | orthorhombic |
| Flack Parameter | −0.01(6) |
| Hooft Parameter | −0.02(6) |
| Space Group | P2$_1$2$_1$2$_1$ |
| a/Å | 9.03500(10) |
| b/Å | 9.44030(10) |
| c/Å | 21.0000(2) |
| a/° | 90 |
| b/° | 90 |
| g/° | 90 |
| V/Å$^3$ | 1791.16(3) |
| Z | 4 |
| Z' | 1 |
| Wavelength/Å | 1.54184 |
| Radiation type | Cu K$_\alpha$ |
| Q$_{min}$/° | 4.210 |
| Q$_{max}$/° | 76.947 |
| Measured Refl's. | 18799 |
| Indep't Refl's | 3737 |
| Refl's I ≥ 2 s(I) | 3628 |
| R$_{int}$ | 0.0414 |
| Parameters | 236 |
| Restraints | 0 |
| Largest Signal | 0.126 |
| Deepest Hole | −0.213 |
| GooF | 1.055 |
| wR$_2$ (all data) | 0.0750 |
| wR$_2$ | 0.0739 |
| R$_1$ (all data) | 0.0303 |
| R$_1$ | 0.0292 |

TABLE 73

Single Crystal Reflections and Refinement

| Reflections | d min (Cu\a) 2 θ = 153.9° | 0.79 | 1/σ (I) | 34.1 | Rint | 4.14% | Full 135.4° 99% to 153.9° | 100 |
|---|---|---|---|---|---|---|---|---|
| Refinement: | Shift | −0.001 | Max peak | 0.1 | Min Peak | −0.2 | GooF | 1.055 Hooft −0.2(6) |

TABLE 74

Single Crystal Reflection Statistics

| | | | |
|---|---|---|---|
| Total reflections (after filtering) | 18868 | Unique reflections | 3737 |
| Completeness | 0.987 | Mean I/s | 25.56 |
| $hkl_{max}$ collected | (11, 11, 25) | $hkl_{min}$ collected | (−10, −10, −26) |
| $hkl_{max}$ used | (11, 11, 26) | $hkl_{min}$ used | (−11, 0, 0) |
| Lim $d_{max}$ collected | 100.0 | Lim $d_{min}$ collected | 0.77 |
| $d_{max}$ used | 21.0 | $d_{min}$ used | 0.79 |
| Friedel pairs | 1842 | Friedel pairs merged | 0 |
| Inconsistent equivalents | 0 | $R_{int}$ | 0.0414 |
| $R_{sigma}$ | 0.0293 | Intensity transformed | 0 |
| Omitted reflections | 0 | Omitted by user (OMIT hkl) | 0 |
| Multiplicity | (4063, 1985, 1324, 726, 387, 199, 86, 24, 4) | Maximum multiplicity | 15 |
| Removed systematic absences | 69 | Filtered off (Shel/OMIT) | 0 |

TABLE 75

Fractional Atomic Coordinates (×10⁴) and Equivalent Isotropic Displacement Parameters (Å² × 10³) for 2022NCSC0333b. $U_{eq}$ is defined as ⅓ of the trace of the orthogonalised $U_{ij}$.

| Atom | x | y | z | $U_{eq}$ |
|---|---|---|---|---|
| O1 | 11107.9(13) | 3999.9(14) | 3816.7(6) | 25.3(3) |
| N1 | 5415.0(15) | 3970.2(15) | 4744.0(6) | 19.7(3) |
| N2 | 4264.3(15) | 6096.0(14) | 6174.4(6) | 18.8(3) |
| C1 | 11332(2) | 3788(2) | 3149.2(8) | 27.3(4) |
| C2 | 8461.4(18) | 3617.6(16) | 3655.1(7) | 19.0(3) |
| C3 | 9665.4(18) | 3967.8(16) | 4029.4(8) | 19.7(3) |
| C4 | 9504.7(19) | 4317.5(17) | 4679.8(8) | 21.1(3) |
| C5 | 8133.2(19) | 4359.5(17) | 4965.6(8) | 20.5(3) |
| C6 | 6905.7(18) | 4021.0(16) | 4589.9(7) | 18.0(3) |
| C7 | 7050.2(18) | 3636.2(17) | 3941.5(7) | 18.1(3) |
| C8 | 5590.8(19) | 3337.2(17) | 3715.8(8) | 21.1(3) |
| C9 | 4640.5(19) | 3552.1(18) | 4211.4(8) | 22.1(3) |
| C10 | 4786.1(19) | 4265.8(17) | 5364.0(7) | 20.2(3) |
| C11 | 4620.1(18) | 5868.1(17) | 5478.5(7) | 19.1(3) |
| C12 | 3512(2) | 6551.6(19) | 5033.4(8) | 27.1(4) |
| C13 | 2818.6(19) | 5498.2(19) | 6384.7(8) | 24.5(3) |
| C14 | 4381(2) | 7621.5(17) | 6354.9(9) | 26.3(4) |
| O2 | 6248.1(14) | 4864.2(13) | 6925.7(6) | 24.9(3) |
| O3 | 7694.7(13) | 6221.5(13) | 6317.8(5) | 23.5(3) |
| O4 | 11445.5(14) | 3608.9(15) | 7643.4(6) | 29.1(3) |
| O5 | 10027.7(14) | 2797.4(13) | 8440.4(6) | 24.1(3) |
| C15 | 7498.8(19) | 5322.0(17) | 6755.1(8) | 20.5(3) |
| C16 | 8849.5(19) | 4736.7(17) | 7070.8(8) | 21.9(3) |
| C17 | 8861.0(18) | 4106.8(17) | 7634.8(8) | 21.3(3) |
| C18 | 10253.1(19) | 3506.4(17) | 7902.4(8) | 20.7(3) |

TABLE 76

Anisotropic Displacement Parameters (×10⁴) for 2022NCSC0333b. The anisotropic displacement factor exponent takes the form: $-2p^2[h^2a^{*2} \times U_{11}+ \ldots +2hka^* \times b^* \times U_{12}]$

| Atom | $U_{11}$ | $U_{22}$ | $U_{33}$ | $U_{23}$ | $U_{13}$ | $U_{12}$ |
|---|---|---|---|---|---|---|
| O1 | 17.5(5) | 33.7(6) | 24.6(6) | 0.4 (5) | 2.6 (5) | 0.6 (5) |
| N1 | 18.3(6) | 22.5(6) | 18.2(6) | −0.1 (5) | 1.6 (5) | −1.5 (5) |
| N2 | 18.1(6) | 18.8(6) | 19.3(6) | 0.6 (5) | 2.1 (5) | 0.9 (5) |
| C1 | 23.5(8) | 32.4(9) | 25.9(8) | 2.4 (7) | 5.5 (7) | 2.0 (7) |
| C2 | 20.3(8) | 18.1(7) | 18.7(7) | 0.6 (6) | 0.7 (6) | 2.0 (6) |
| C3 | 17.4(7) | 17.6(7) | 24.0(7) | 2.3 (6) | 1.1 (6) | 1.0 (6) |
| C4 | 20.6(8) | 21.5(7) | 21.4(7) | −0.4 (6) | −3.6 (6) | −0.7 (6) |
| C5 | 24.3(8) | 19.2(7) | 18.1(7) | −1.8 (6) | −1.3 (6) | 0.0 (6) |
| C6 | 19.0(7) | 15.6(6) | 19.5(7) | −0.1 (6) | 0.3 (6) | 0.9 (6) |
| C7 | 20.3(8) | 16.7(7) | 17.2(7) | 0.6 (6) | 0.1 (6) | 0.8 (6) |

TABLE 76-continued

Anisotropic Displacement Parameters (×10⁴) for 2022NCSC0333b. The anisotropic displacement factor exponent takes the form: $-2p^2[h^2a^{*2} \times U_{11}+ \ldots +2hka^* \times b^* \times U_{12}]$

| Atom | $U_{11}$ | $U_{22}$ | $U_{33}$ | $U_{23}$ | $U_{13}$ | $U_{12}$ |
|---|---|---|---|---|---|---|
| C8 | 23.0(8) | 22.6(7) | 17.9(7) | −0.8 (6) | −1.7 (6) | −2.7 (6) |
| C9 | 18.7(7) | 23.2(7) | 24.5(8) | 0.9 (6) | −1.6 (6) | −2.1 (6) |
| C10 | 21.9(7) | 20.3(7) | 18.3(7) | 1.6 (6) | 3.2 (6) | −0.3 (6) |
| C11 | 19.8(7) | 19.3(7) | 18.3(7) | 2.0 (6) | 3.3 (6) | 0.5 (6) |
| C12 | 33.7(10) | 24.3(8) | 23.5(8) | 3.8 (6) | −2.3 (7) | 3.8 (7) |
| C13 | 19.2(8) | 28.7(8) | 25.6(8) | 2.1 (7) | 6.7 (6) | 0.3 (6) |
| C14 | 31.6(9) | 20.2(7) | 27.3(8) | −3.1 (6) | 4.0 (7) | 1.5 (7) |
| O2 | 18.1(6) | 28.3(6) | 28.4(6) | 3.4 (5) | 0.4 (5) | −0.2 (5) |
| O3 | 22.9(6) | 27.5(6) | 20.2(5) | 1.8 (5) | −2.4 (4) | −2.7 (5) |
| O4 | 19.5(6) | 38.3(7) | 29.5(6) | 6.5 (6) | 0.5 (5) | −2.5 (5) |
| O5 | 23.4(6) | 25.8(6) | 23.0(6) | 2.6 (5) | 1.1 (5) | 2.1 (5) |
| C15 | 20.5(8) | 22.7(7) | 18.3(7) | −4.4 (6) | −0.3 (6) | 0.1 (6) |
| C16 | 18.3(8) | 24.6(7) | 22.8(7) | −1.0 (6) | 1.2 (6) | −1.1 (6) |
| C17 | 19.1(7) | 22.3(7) | 22.5(7) | −2.0 (6) | 1.4 (6) | −0.4 (6) |
| C18 | 21.6(8) | 20.5(7) | 20.2(7) | −2.5 (6) | −0.3 (6) | −2.1 (6) |

TABLE 77

Bond Lengths in Å for 2022NCSC0333b.

| c | Atom | Length/Å |
|---|---|---|
| O1 | C1 | 1.430(2) |
| O1 | C3 | 1.378(2 |
| N1 | C6 | 1.386(2) |
| N1 | C9 | 1.377(2) |
| N1 | C10 | 1.448(2) |
| N2 | C11 | 1.512(2) |
| N2 | C13 | 1.490(2) |
| N2 | C14 | 1.493(2) |
| C2 | C3 | 1.382(2) |
| C2 | C7 | 1.410(2) |
| C3 | C4 | 1.413(2) |
| C4 | C5 | 1.377(2) |
| C5 | C6 | 1.398(2) |
| C6 | C7 | 1.415(2) |
| C7 | C8 | 1.429(2) |
| C8 | C9 | 1.364(2) |
| C10 | C11 | 1.539(2) |
| C11 | C12 | 1.514(2) |
| O2 | C15 | 1.262(2) |
| O3 | C15 | 1.263(2) |
| O4 | C18 | 1.211(2) |
| O5 | C18 | 1.329(2) |
| C15 | C16 | 1.495(2) |
| C16 | C17 | 1.325(2) |
| C17 | C18 | 1.490(2) |

TABLE 78

Bond Lengths in Å for 2022NCSC0333b.

| Atom | Atom | Atom | Angle/° |
|---|---|---|---|
| C3 | O1 | C1 | 116.66(13) |
| C6 | N1 | C10 | 125.78(14) |
| C9 | N1 | C6 | 108.30(13) |
| C9 | N1 | C10 | 125.89(14) |
| C13 | N2 | C11 | 114.77(13) |
| C13 | N2 | C14 | 110.63(13) |
| C14 | N2 | C11 | 111.57(13) |
| C3 | C2 | C7 | 117.78(14) |
| O1 | C3 | C2 | 124.42(15) |
| O1 | C3 | C4 | 113.92(14) |
| C2 | C3 | C4 | 121.66(15) |
| C5 | C4 | C3 | 121.37(15) |
| C4 | C5 | C6 | 117.46(14) |
| N1 | C6 | C5 | 130.32(15) |
| N1 | C6 | C7 | 107.78(14) |

TABLE 78-continued

Bond Lengths in Å for 2022NCSC0333b.

| Atom | Atom | Atom | Angle/° |
|---|---|---|---|
| C5 | C6 | C7 | 121.90(15) |
| C2 | C7 | C6 | 119.81(15) |
| C2 | C7 | C8 | 133.65(14) |
| C6 | C7 | C8 | 106.54(14) |
| C9 | C8 | C7 | 107.35(14) |
| C8 | C9 | N1 | 110.02(15) |
| N1 | C10 | C11 | 111.61(13) |
| N2 | C11 | C10 | 108.16(12) |
| N2 | C11 | C12 | 113.29(13) |
| C12 | C11 | C10 | 112.76(14) |
| O2 | C15 | O3 | 124.20(16) |
| O2 | C15 | C16 | 118.60(15) |
| O3 | C15 | C16 | 117.16(15) |
| C17 | C16 | C15 | 124.65(16) |
| C16 | C17 | C18 | 120.96(15) |
| O4 | C18 | O5 | 123.96(16) |
| O4 | C18 | C17 | 123.47(15) |
| O5 | C18 | C17 | 112.51(14) |

TABLE 79

Torsion Angles in ° for 2022NCSC0333b.

| Atom | Atom | Atom | Atom | Angle/° |
|---|---|---|---|---|
| O1 | C3 | C4 | C5 | 178.87(15) |
| N1 | C6 | C7 | C2 | 179.16(14) |
| N1 | C6 | C7 | C8 | −0.66(17) |
| N1 | C10 | C11 | N2 | −168.45(13) |
| N1 | C10 | C11 | C12 | 65.47(18) |
| C1 | O1 | C3 | C2 | 6.3(2) |
| C1 | O1 | C3 | C4 | −174.23(14) |
| C2 | C3 | C4 | C5 | −1.7(2) |
| C2 | C7 | C8 | C9 | −179.29(17) |
| C3 | C2 | C7 | C6 | 0.7(2) |
| C3 | C2 | C7 | C8 | −179.53(17) |
| C3 | C4 | C5 | C6 | 1.0(2) |
| C4 | C5 | C6 | N1 | 179.84(16) |
| C4 | C5 | C6 | C7 | 0.5(2) |
| C5 | C6 | C7 | C2 | −1.4(2) |
| C5 | C6 | C7 | C8 | 178.79(15) |
| C6 | N1 | C9 | C8 | −0.28(19) |
| C6 | N1 | C10 | C11 | 80.99(19) |
| C6 | C7 | C8 | C9 | 0.50(18) |
| C7 | C2 | C3 | O1 | −179.83(15) |
| C7 | C2 | C3 | C4 | 0.8(2) |
| C7 | C8 | C9 | N1 | −0.14(19) |
| C9 | N1 | C6 | C5 | −178.81(16) |
| C9 | N1 | C6 | C7 | 0.59(18) |
| C9 | N1 | C10 | C11 | −100.96(19) |
| C10 | N1 | C6 | C5 | −0.5(3) |
| C10 | N1 | C6 | C7 | 178.92(14) |

TABLE 79-continued

Torsion Angles in ° for 2022NCSC0333b.

| Atom | Atom | Atom | Atom | Angle/° |
|---|---|---|---|---|
| C10 | N1 | C9 | C8 | −178.61(14) |
| C13 | N2 | C11 | C10 | −64.52(17) |
| C13 | N2 | C11 | C12 | 61.25(18) |
| C14 | N2 | C11 | C10 | 168.64(14) |
| C14 | N2 | C11 | C12 | −65.59(18) |
| O2 | C15 | C16 | C17 | −21.4(2) |
| O3 | C15 | C16 | C17 | 160.67(14) |
| C15 | C16 | C17 | C18 | 177.70(15) |
| C16 | C17 | C18 | O4 | 3.5(3) |
| C16 | C17 | C18 | O5 | −173.83(15) |

| Atom | x | y | z | Ueq |
|---|---|---|---|---|
| H1A | 10737 | 4449 | 2914 | 41 |
| H1B | 11054 | 2839 | 3037 | 41 |
| H1C | 12357 | 3935 | 3048 | 41 |
| H2 | 5110(30) | 5620(30) | 6430(12) | 33 |
| H5A | 10850(30) | 2250(30) | 8539(13) | 41 |
| H2A | 8578 | 3378 | 3228 | 23 |
| H4 | 10342 | 4524 | 4920 | 25 |
| H5 | 8028 | 4604 | 5392 | 25 |
| H8 | 5336 | 3049 | 3307 | 25 |
| H9 | 3620 | 3434 | 4192 | 27 |
| H10A | 5418 | 3865 | 5691 | 24 |
| H10B | 3823 | 3818 | 5396 | 24 |
| H11 | 5585 | 6305 | 5396 | 23 |
| H12A | 2549 | 6153 | 5107 | 41 |
| H12B | 3802 | 6382 | 4600 | 41 |
| H12C | 3482 | 7553 | 5111 | 41 |
| H13A | 2026 | 6012 | 6186 | 37 |
| H13B | 2735 | 5578 | 6839 | 37 |
| H13C | 2762 | 4519 | 6264 | 37 |

| Atom | Atom | Atom | Atom | Angle/° |
|---|---|---|---|---|
| H14A | 5323 | 7985 | 6221 | 39 |
| H14B | 4292 | 7714 | 6808 | 39 |
| H14C | 3604 | 8147 | 6151 | 39 |
| H16 | 9746 | 4820 | 6856 | 26 |
| H17 | 7987 | 4039 | 7867 | 26 |

TABLE 80

Hydrogen Bond information for 2022NCSC0333b.

| D | H | A | d(D—H)/Å | d(H—A)/Å | d(D—A)/Å | D—H—A/deg |
|---|---|---|---|---|---|---|
| N2 | H2 | O2 | 1.03(3) | 1.63(3) | 2.6559(19) | 171(2) |
| O5 | H5A | O3[1] | 0.93(3) | 1.66(3) | 2.5895(18) | 177(3) |

Example 8. Screening for Additional Salts and Polymorphs for Compound 1

TABLE 81

Abbreviations used in Example 8.

| | |
|---|---|
| $\varphi_i$ | Water activity coefficient |
| $a_w$ | Water activity |
| ASD | Amorphous solid dispersion |
| ca. | circa (Latin: approximately) |
| cf. | Confer/conferatur (Latin: to confer, to compare) |
| °C. | degree Celsius |
| CP | Chemical Purity |
| CP-MAS | Cross Polarised Magic Angle Spinning ($^{13}C$ NMR solid state technique) |
| Da | Dalton |
| DSC | Differential Scanning Calorimetry (measures changes in heat capacity) |
| DTA | Differential Thermal Analyses (measures changes in temperature) |
| DVS | Dynamic Vapour Sorption (used interchangeably with GVS) |
| e.g. | Exempli gratia (Latin: for example) |
| etc. | Et cetera (Latin: 'and others' or 'and so on') |
| FT-IR | Fourier Transformed, InfraRed spectroscopy (prefixed mid and far) |

TABLE 81-continued

Abbreviations used in Example 8.

| | |
|---|---|
| g | Gram (s) |
| GRAS | Generally Recognised As Safe |
| GVS | Gravimetric Vapour Sorption |
| h | Hour (s) |
| HPLC | High Performance Liquid Chromatography |
| HSM | Hot Stage Microscopy (thermal microscopy) |
| HUCD | Heat-up/cool-down crystallisation |
| i.e. | Id Est (Latin: that is) |
| IR | InfraRed Spectroscopy |
| J | Joule |
| Kelvin | Kelvin. SI unit of temperature, used interchangeably with ° C. to express increment/decrement of temperature set point (e.g. ramp rate on DSC thermogram 10 K/min); note K sign not prefixed by. |
| KF | Karl Fischer (determination of the water content by coulometric titration) |
| kg | Kilogram (s) |
| LAG | Liquid-Assisted grinding |
| LOD | Loss On Drying |
| mag | magnification |
| mAu | milli-Absorption units (chromatographic unit of signal height) |
| mAu*s | milli-Absorption units multiplied by second (chromatographic unit of signal area) |
| MET/CR | Aptuit chromatography method reference |
| min | Minute (s) |
| mg | Milligram (s) |
| ml | Millilitre (s) |
| mol | mole, amount of substance |
| N/A | Not Applicable |
| n.a. | not analysed |
| n.d. | not detected |
| NG | Neat grinding |
| nm | nanometre |
| NMR | Nuclear Magnetic Resonance |
| oab | on anhydrous basis |
| osfb | on solvent free basis |
| oasfb | on anhydrous solvent free basis |
| pH | -log [H$^+$] or pH = - log a$_{H}{}^+$ |
| pK$_a$ | -log (K$_a$), acid dissociation constant |
| pI | isoelectric point, quoted in unit pH |
| PLM | Polarised Light Microscopy |
| RelRT | Relative Retention Time (not be confused RT) |
| REP/ | Aptuit report (REP) reference |
| RFA | Request For Analysis (unique reference number) |
| RH | Relative Humidity (a$_w$ * 100) |
| RT | Room Temperature (ambient, typically: 18 to 23° C.) |
| s | Second (s) |
| SCXD | Single Crystal X-Ray Determination |
| SMPT | Solvent mediated phase transition |
| STA | Simulated Thermal Analysis (STA = TGA + DTA) |
| t | time in seconds, minutes, hour, days etc. (interval specified in parentheses); alias in common use tonne (t) |
| t | Tonne, metric unit of mass (1000 kg; 1 Mg), (compaction force in kg, suffixed in parentheses) |
| T | Temperature recorded in degrees Celsius (° C.); alias in common use, SI unit of magnetic flux density, also denoted T |
| MTBE | Methyl tert-butyl ether |
| TCNB | 2,3,5,6-Tetrachloronitrobenzene (C$_6$HCl$_4$NO$_2$, F.W. 260.89 gmol$^{-1}$) |
| TFE | Trifluoroethanol (solvent used for solvent drop grinding) |
| TGA | Thermogravimetric Analysis |
| th. | theoretical |
| UV | Ultra Violet |
| vol. | Volume or relative volume |
| vs. | versus |
| v/v | volume/volume |
| W | Watt |
| w/w | weight/weight |
| XRPD | X-Ray Powder Diffraction |

TABLE 82

Definitions of terms used in Example 8.

| | |
|---|---|
| Isostructural | Crystals are said to be isostructural if they have the same crystal structure but not necessarily the same cell dimensions nor the same |

TABLE 82-continued

Definitions of terms used in Example 8.

| | |
|---|---|
| | chemical composition (Kálmán, A., Párkányi, L. & Argay, G. (1993) Acta Cryst. B49, 1039-1049.) |
| Isomorphic | two crystalline solids are isomorphous if both have the same unit-cell dimensions and space group (source, vide supra). |
| Isomorphic desolvate | via solvent release from an isostructural solvate. |
| Native | Refers to an API in its native or non-ionised form. |
| Normal light | Light oscillating in all directions perpendicular to the axis to which the it travels. |
| Particle size | Expressed as a volume distribution, the range x10 >PSD< x90 captures the sizes of 80% of the particles. |
| Plane polarised light | Light passed through a polaroid filter which allows only light oscillating in one plane to be transmitted. |
| Polymorphism | Crystalline solid able to exhibit different crystalline phases. |
| Photomicrograph | Imaged captured of a small object under magnification through an optical microscope. |
| Pseudopolymorphism | Different crystal structure attributed to the incorporation of molecular water or solvent. |
| Solvates | Contains a molecule of solvent in the crystal lattice. |
| Thermogram | Differential scanning calorimetry trace: heat flow on y-ordinate (mW), time (minutes)/temperature (° C.) on x-ordinate. |

Summary

Non-ionised compound 1 (batch 1) was supplied as an amorphous, semi-solid.

The non-ionised form of compound 1 was screened against 19 common, Classes 1, 2 and 3 acidic counter-ions in selected solvents. The salt screen of the API delivered multiple hits and these hits were assessed based on the following desirable characteristics:

Flat baseline and single melt by DSC.
Flat baseline by TGA.
Unique powder diffraction pattern by XRPD.
Reduced impurity burden by $^1$H NMR.
Optically crystalline material under cross-polarised filter.

Based on the above criteria, several salts were selected for further experiments:

compound 1 HCl.
compound 1 Maleate.
compound 1 Benzoate.

This set of API salts underwent several physicochemical examinations consisting of:

Determination of solubility in fasted state simulated intestinal fluid (FaSSIF), fed state simulated intestinal fluid (FeSSIF) and fasted state simulated gastric fluid (FaSSGF) buffers and the pH adjusted after each time point and solid-phase, residue analyses.

Evaluation of stability at 40° C./75% RH for 10 days.
Analyses by DVS, under mass equilibrated condition.

The above studies were concluded and compound 1·HCl was nominated as the preferred salt form to be progressed into polymorph screening, the exhibited the following favourable outcomes:

Chemically and physically stable, during stability at 40° C./75% RH.
Freely soluble in the SIF buffers and disproportionation not observed.
Exhibited higher crystallographic quality, expected to give good impurity and solvent rejection during scale-up.

Project Design

The objective of the salt screen is to identify a more readily isolable form of each compound suitable for development scale-up.

Typically, for each salt screen, the activities detailed below were performed.

Full Physical Characterization of the Native Form of the API $^1$H-NMR spectroscopy was performed to confirm the identity and measure residual solvent content.

Q $^1$H-NMR spectroscopy assay (versus an internal standard) was performed to confirm w/w % composition.

Physical characterization of the API was performed and included:

DSC to provide an evaluation of transition activity, solvent release, melt and decomposition events; modulated DSC, where necessary, to deconvolute complex thermal transitions TGA, to provide alignment of key DSC events with weight loss transition activity $^1$H-NMR spectroscopy after key thermal events to confirm that chemical identity is unchanged (where relevant)

DVS (0% to 90% to 0%) and XRPD analysis after full cycle

XRPD analyses using 20-minute acquisition, performed first on the native form and second after pestle and mortar grinding to determine if the sample suffers from preferred orientation/strain effects and if grinding improves powder averaging Optical microscopy under cross-polarized filter, to provide an informal assessment of the presence of optically amorphous material Salt Screen Different counter-ions were screened based on the structure and calculated $pK_a$ of the API.

Once crystalline products were generated, the analyses and physical characterizations described above were performed:

Salt Selection

At this stage ca. 1 g of each front-runner salt form was prepared. Salt forms that offered significant solubility and stability advantages over the non-ionized API were prioritized. The following physicochemical evaluations were performed:

Determination of solubility in SIF buffers:
a HPLC calibration curve of the native API was prepared;
non-buffered aqueous solubility of the API was measured at the 1-, 3-, 6- and 20-hour time points; the residues were analyzed wet after centrifugation and dry after oven treatment and compared with the non-ionized versions of the API and counterion, and solubility was measured in FaSSIF, FeSSIF and FaSSGF buffers and the pH adjusted after each time point and solid-phase residues were analysed.

Evaluation of stability condition: 40° C./75% RH for 5 and 10 days.

Analyses by dynamic vapor sorption (DVS) and residue (post treatment).

Scale Up

Compound 1 HCl was subjected to polymorph screening.

TABLE 83

Characterization of crystalline compound 1 HCl salt

| Provenances of reference batches | Compound 1 HCl (Form A) |
|---|---|
| Preparation I:, obtained from heat-up/cool-down crystallization of amorphous compound 1 with hydrochloric acid (35% v/v aq.) in ethanol (2.0 vol) at 85° C. The product was isolated by centrifugation and was oven-dried under reduced pressure over 20 h at 40° C. (FIGs. 216-218, 220, 222) Preparation II: amorphous compound was crystallized from ethanol (2.0 vol), isolated by filtration, and dried under sustained nitrogen flux (<1 bar) over 20 h at 20° C. (FIGs. 179-182, 189-197, 270, 274, 280, and 286). | Molecular weight: 268.79 gmol$^{-1}$<br>Exact molecular weight: 268.1342<br>Molecular formula: $C_{14}H_{20}N_2O \cdot HCl$<br>Unary hydrochloride: 13.6% w/w th., hydrochloric acid (i.e., 1.0 mol API to 1.0 mol water)<br>XRPD: 12.4°, 13.5°, 14.2°, 15.3°, 17.5°, 17.8°, 18.0°, 18.6°, 19.9°, 20.4°, 21.7°, 24.9°, 25.4°, 25.9°, 27.3°, 28.0°, 28.4°, 29.0°, 90.3°, 32.2° (2θ, 1 d.p), (Refer to FIG. 182).<br>DSC: onset 205.7° C. (−99.7 Jg$^{-1}$, endotherm, melt), 221.9° C. (79.8 Jg$^{-1}$, exotherm, decomposition) (Refer to FIG. 180 and 190).<br>TGA: onset 243.3° C. (−71.9% w/w, ablation), 316.6° C. (−3.5% w/w, ablation), (Refer to FIG. 195).<br>DVS 0 to 90 to 0% RH (dm/dt <0.002%): 0.0 (0.00%), 5.0 (0.00%), 10.0 (0.02%), 15.0 (0.02%), 20.0 (0.03%), 25.0 (0.04%), 30.0 (0.05%), 40.0 (0.07%), 50.0 (0.10%), 60.0 (0.14%), 70.0 (0.19%), 80.0 (0.26%), 90.0 (0.46%), 90.0 (0.46%), 80.0 (0.29%), 70.0 (0.22%), 60.0 (0.17%), 50.0 (0.14%), 40.0 (0.10%), 30.0 (0.09%), 25.0 (0.07%), 20.0 (0.06%), 15.0 (0.05%), 10.0 (0.04%), 5.0 (0.03%), 0.0 (0.02%) (Refer to FIG. 191).<br>UV chromatographic purity: 99.60% area (254 nm), (Refer to FIG. 194).<br>$^1$H NMR: (DMSO-d6, 400 MHz); δ 11.2 (s, 1H), 7.6 (d, J = 8.9 Hz, 1H), 7.4 (d, J = 3.1 Hz, 1H), 7.1 (d, J = 2.4 Hz, 1H), 6.8 (dd, J = 8.9, 2.4 Hz, 1H), 6.4 (dd, J = 3.1, 0.6 Hz, 1H), 4.7 (dd, J = 13.7, 4.2 Hz, 1H), 4.3 (dd, J = 14.1, 9.8 Hz, 1H), 3.7 (s, 4H), 2.7 (dd, J = 19.2, 4.9 Hz, 6H), 1.1 (d, J = 6.6 Hz, 3H); ppm; conforms to the molecular structure (Σ21H), (refer to FIG. 179 and 189).<br>Residual solvents ICH Q3C (R8): (ethanol 0.02% w/w, ICH listed 5000 ppm).<br>Appearance: Refer to FIG. 192 and 193. |

TABLE 84

Characterization of crystalline compound 1 Maleate salt

| Provenances of reference batches | Compound 1 Maleate |
|---|---|
| Preparation I: (refer to FIGs. 206 and 223-227), obtained from heat-up/cool-down crystallization of EXP-21-IS3344 with maleic acid in ethanol (2.0 vol) at 85° C. The product was isolated by centrifugation and was oven-dried under reduced pressure over 20 h at 40° C. Preparation II: batch: Compound 1 maleate was crystallized from ethanol (2.0 vol), isolated by filtration, and dried under sustained nitrogen flux (<1 bar) over 20 h at 20° C. (FIGs. 176-178, 198, 199, 201-206, 271, 275, 282, and 290) | Molecular weight: 348.40 gmol$^{-1}$<br>Exact molecular weight: 348.168<br>Molecular formula: $C_{18}H_{24}N_2O_5$<br>Unary maleate: 33.3% w/w th., maleic acid (i.e., 1.0 mol of API to 1.0 mol water)<br>XRPD: 9.4°, 10.9°, 11.8°, 16.9°, 18.6°, 19.2°, 20.9°, 21.6°, 22.2°, 23.7°, 25.0°, 26.0°, 26.5° (2θ, 1 d.p), (Refer to Section FIG. 206, 168, 224, 205, and 271).<br>DSC: onset 54.7° C. (−1.0 Jg$^{-1}$, endotherm), 138.9° C. (−79.2 Jg$^{-1}$, endotherm, melt), 176.0° C. (20.2 Jg$^{-1}$, exotherm, decomposition) (Refer to FIG. 225, 226, 200, and 176-178).<br>TGA: onset 200.0° C. (−34.4% w/w, ablation), 240.4° C. (−33.7% w/w, ablation), (Refer to FIG. 227, 204, and 290).<br>DVS 0 to 90 to 0% RH (dm/dt <0.002%): 0.0 (0.00%), 5.0 (0.02%), 10.0 (0.05%), 15.0 (0.08%), 20.0 (0.11%), 25.0 (0.14%), 30.0 (0.18%), 40.0 (0.26%), 50.0 (0.42%), 60.0 (0.86%), 70.0 (1.38%), 80.0 (2.00%), 90.0 (3.44%), 90.0 (3.44%), 80.0 (2.03%), 70.0 (1.40%), (60.0 1.00%), 50.0 (0.70%), 40.0 (0.48%) 30.0 (0.30%), 25.0 (0.22%), 20.0 (0.15%), 15.0 (0.09%), 10.0 (0.03%), 5.0 (−0.03%), 0.0 (−0.07%) (Refer to FIG. 199).<br>UV chromatographic purity: 99.22% area (254 nm), (Refer to FIG. 203).<br>$^1$H NMR: (DMSO-d6, 400 MHZ); δ 7.5 (d, J = 8.9 Hz, 1H), 7.4 (d, J = 3.1 Hz, 1H), 7.1 (d, J = 2.4 Hz, 1H), 6.8 (dd, J = 8.9, 2.4 Hz, 1H), 6.4 (dd, J = 3.1, 0.6 Hz, 1H), 6.1 (s, 2H), 4.6 (dd, J = |

TABLE 84-continued

Characterization of crystalline compound 1 Maleate salt

| Provenances of reference batches | Compound 1 Maleate |
|---|---|
| | 14.3, 5.0 Hz, 1H), 4.3 (dd, J = 14.3, 9.2 Hz, 1H), 3.7 (s, 3H), 2.8 (s, 6H), 1.1 (d, J = 6.7 Hz., 3H); ppm; conforms to the molecular structure (Σ22H), (Refer to FIG. 223, 198, and 275). Residual solvents ICH Q3C (R8): (ethanol 0.2% w/w, ICH listed 5000 ppm). Appearance: Refer to FIG. 201 and 202. |

TABLE 85

Characterization of crystalline compound 1 Benzoate salt

| Provenances of reference batches | Compound 1·Benzoate |
|---|---|
| Preparation I (FIGs 215, 228-231) obtained from heat-up/cool-down crystallisation of amorphous compound 1 with benzoic acid in ethanol (2.0 vol) at 85° C. The product was isolated by centrifugation and was oven-dried under reduced pressure over 20 h at 40° C. Preparation II batch: compound 1 benzoate salt was crystallized from ethanol (2.0 vol), isolated by filtration, and dried under sustained nitrogen flux (<1 bar) over 20 h at 20° C. | Molecular weight: 354.45 gmol$^{-1}$<br>Exact molecular weight: 354.1943<br>Molecular formula: $C_{21}H_{26}N_2O_3$<br>Unary maleate: 34.5% w/w th., benzoic acid (i.e., 1.0 mol of API to 1.0 mol water)<br>XRPD: 7.8°, 12.5°, 13.7°, 14.5°, 15.5°, 17.5°, 18.6°, 19.2°, 19.7°, 20.6°, 23.7°, 25.2°, 25.3° (2θ, 1 d.p), (Refer to FIG. 215, 169, 229, 184, and 272).<br>DSC: onset 97.7° C. (−82.9 Jg$^{-1}$, endotherm, melt) (Refer to FIG. 230, 208, and 284).<br>TGA: onset 102.2° C. (−1.6% w/w, solvent release), 195.8° C. (−78.57% w/w, ablation), (refer to FIG. 231, 213, and 292.<br>DVS 0 to 90 to 0% RH (dm/dt <0.002%): 0.0 (−0.004%), 0.0 (−0.02%), 5.0 (0.02%), 10.0 (0.04%), 15.0 (0.06%), 20.0 (0.10%), 25.0 (0.10%), 30.0 (0.13%), 40.0 (0.19%), 50.0 (0.30%), 60.0 (0.42%), 70.0 (0.58%), 80.0 (0.89%), 90.0 (1.52%), 90.0 (1.52%), 80.0 (0.92%), 70.0 (0.61%), 60.0 (0.41%), 50.0 (0.20%), 40.0 (−0.19%) 30.0 (-0.16%), 25.0 (−0.19%), 20.0 (−0.25%), 15.0 (-0.29%), 10.0 (-0.34%), 5.0 (-0.39%), 0.0 (−0.47%) (Refer to FIG. 209).<br>UV chromatographic purity: 99.22% area (254 nm), (Refer to FIG. 212).<br>$^1$H NMR: (DMSO-d6, 400 MHZ), δ 7.9 (d, J = 8.2 Hz, 1 H), 7.6 (dt, J = 13.6, 6.8, 1.3 Hz, 1H), 7.5 (t, J = 15.2, 7.2 Hz, 1H), 7.4 (d, J = 8.9 Hz, 1H), 7.3 (d, J = 2.4 Hz, 1H), 7.0 (d, J = 2.0 Hz, 1H), 6.8 (dd, J = 9.3, 2.6 Hz, 1H), 6.3 (d, J = 2.9 Hz, 1H), 4.2 (dd, J = 14.2, 6.5 Hz, 1H), 4.0 (dd, J = 13.8, 7.5 Hz, 1H), 3.7 (s, 3H), 3.0 (sext, J = 33.8, 20.0, 13.8, 6.7, 6.6 Hz, 6H), 2.2 (s, 6H) 1.1 (d, J = 7.0 Hz, 3H); ppm; conforms to the molecular structure (Σ25H$^4$), (refer to FIG. 228 and 207).<br>Residual solvents ICH Q3C (R8): (ethanol 0.8% w/w, ICH listed 5000 ppm).<br>Appearance: Refer to FIGs. 210 and 211. |

Salt Screen

The objective of the salt screen was to identify a pharmaceutically acceptable crystalline salt form of the API. In addition, the elected salt form should exhibit appropriate physicochemical properties and should possess relevant toxicological considerations that are judged suitable for development scale-up. Additionally, a provisional process to access the elected salt form was evaluated.

Heat-Up Cool-Down Crystallization Salt Screen

Evidence of salt formation in the solid state was provided by the following analyses:

Presentation of a unique powder diffraction pattern, that exhibited significant differences from the powder patterns of compound 1 (non-ionised), the native acid counterion (also assumed non-ionised) and importantly, was non-congruent with the sum of their reflections.

Presence of integer stoichiometry of the counterion w.r.t. compound land a measurable change in the chemical shift of the relevant ionisable proton resonances.

Change in the value of melting point and ΔH fusion by DSC, compared to the values exhibited by compound 1 (non-ionised) and the acid counterion.

Three stable forms of salified compound 1 were identified (1.0 to 1.0 stoichiometry salts) for further experiments, specifically, HCl, Maleate and Benzoate compound 1 salts were selected for good crystallinity and little disordering by XRPD, a flat DSC baseline in conjunction with a single sharp melt event and negligible weight loss, prior to deflagration by TGA.

TABLE 87

Summary of results

| Salt forms | iPAC content (% w/w) | Salt Stoichiometry (API to counter ion) | Observations |
|---|---|---|---|
| Compound 1•HCl | ND | 1.0 to 1.0 | Highly crystalline, improvement in the impurity burden was observed in aryl and aliphatic regions. Single sharp melt event (204° C.) was observed. |
| Compound 1•Maleate | <0.1 | 1.0 to 1.0 | Exhibited sharp, single melt (144° C., cf. m.p. Maleic acid 135° C.) and small secondary endotherm, with onset 62° C. DSC thermocycle confirmed that the small event obs., is an irreversible transition<br>Compound 1•Native powder diffraction pattern was amorphous.<br>Several maleic acid reflections overlap with those from Compound 1•Maleate; however, based on the relative intensities, it is unlikely that the salt phase contains native, maleic acid.<br>A simple 1 to 1 admixture of the two salt precursors would give a uniform, additive XRPD. |
| Compound 1•Benzoate | 0.2 | 1.0 to 1.0 | Exhibited sharp, single endothermic event at 100° C. (benzoic acid 122° C.)<br>Compound 1•Native powder diffraction pattern was amorphous.<br>Benzoic acid reflections were distinct from Compound 1•Benzoate, it is unlikely that the salt phase contains native, benzoic acid.<br>A simple 1 to 1 admixture of the two salt precursors would give a uniform, additive XRPD. |
| Compound 1•Tosylate | 0.5 | 1.0 to 1.3 | Broad melt event (127° C.) was observed. 4-Toluene sulfonic acid m.p. 105 to 107° C.<br>Compound 1•Native, powder diffraction pattern was amorphous.<br>Compound 1•Tosylate exhibited a unique powder diffraction pattern that differed from native, 4-toluene sulfonic acid.<br>A simple 1 to 1 admixture of the two salt precursors would give an additive XRPD. |
| Compound 1•Tartrate | 1.1 | 1.0 to 1.4 | Exhibited sharp, single endothermic event at 107° C. (tartaric acid 169° C.)<br>Compound 1•Native, powder diffraction pattern was amorphous.<br>Compound 1•Tartrate exhibited a unique powder diffraction pattern that differed from native, Tartaric acid.<br>A simple 1 to 1 admixture of the two salt precursors would give an additive XRPD. |
| Compound 1•HBr | 3.7 | 1.0 to 1.0 | Crystalline, slightly increased background, increase in the impurity burden by $^1$H NMR was observed in aryl and aliphatic regions.<br>Bimodal melt (onsets 115 and 186° C.) and minor endothermic event (br. 106 to 126° C) was observed. |
| Compound 1•Galactarate | ND | 1.0 to 1.0 | Exhibited sharp, single endothermic event at 163 ° C. (Galactaric acid 230° C.).<br>Compound 1•Native powder diffraction pattern was amorphous.<br>Several reflections from galactaric acid were congruent with those present in A compound 1•Galactarate; the relative intensities were also similar, it is unlikely that the salt is a single phase and probably contains significant non-salified, galactaric acid. |
| Compound 1•Succinate | <0.1 | 1.0 to 1.7 | Exhibited broad, endothermic events with onsets 81 and 205° C. (succinic acid, m.p. 185° C.)<br>Compound 1•Native powder diffraction pattern was amorphous.<br>Several succinic acid reflections were coincident with Compound 1•Succinate reflections; hence, we cannot rule out the presence of non-salified succinic acid in the bulk phase; this finding is consistent with $^1$H NMR spectroscopy, that equated to over unity succinic acid composition.<br>A simple 1 to 1 admixture of the two salt precursors would give a uniform, additive XRPD; co-crystallisation would exhibit unique lattice parameters |

TABLE 88

Scale up to 1g

| Salt forms | Procedure | Observations |
|---|---|---|
| Comound 1•HCl | compound 1 free base (1.0 equiv.) and HCl (1.1 equiv) were dissolved in 2 vol of ethanol at 80° C. The clear red solution was left to cool down to ambient (solid was observed) before storing at sub-ambient for ca 18 h. The contents of the vial were filtered over a sintered funnel and was dried under vacuum and nitrogen flow for ca 3 h. The filter cake (0.96 g) was transferred in a tray and was submitted in an oven to dry under vacuum at 40° C. for ca 18 h. | 0.95 g of salt was isolated (82% yield) DSC, TGA, $^1$H NMR and XRPD were performed (FIGs. 179-182, 189-197, 270, 274, 280, and 286) |

TABLE 88-continued

Scale up to 1g

| Salt forms | Procedure | Observations |
|---|---|---|
| Compound 1 Maleate | 1.1 equiv. of maleic acid. compound 1 free base and maleic acid were dissolved in 2 vol of ethanol at 80° C. The clear yellow solution was left to cool down to ambient (solid was observed) before storing at sub-ambient for ca 18 h. | No solid was observed; therefore, the vial was transferred to the freezer for ca 96 h. Light yellow solid was observed after storing in the freezer for ca 96 h. 1.32 g of compound 1 maleate were collected (88% th yield) |
| Compound 1·Benzoate | 1.1 equiv. of benzoic acid. compound 1 free base and benzoic acid were dissolved in 2 vol of ethanol at 80° C. The clear yellow solution was left to cool down to ambient (solid was observed) before storing at sub-ambient for ca 18 h. | No solid was observed; therefore, the vial was transferred to the freezer for ca 96 h. No solid observed after storing in the freezer for ca. 96 h. Hence, the solution was concentrated to one half the original volume, and was then stored in a freezer for +5 days, prior to isolating by filtration and drying under steady nitrogen flux for ca 48 h. KF analysis of compound 1 benzoate showed 0.43% w/w water content. 1.5 g of compound 1Benzoate were collected (98% yield) |

Comparison of melting point onset and melt enthalpies is exhibited in Table 89. Discrepancies in m.p. were evident on the scaled-up samples. Some of the variability in fusion temperature is most likely attributed to particle non-homogeneity, poor crystallinity, and physical packing efficiency in the sample crucible; sample impurity burden may well have contributed.

A DSC specimen of compound 1-Maleate was examined because probable decomposition appeared to occur well after melting, the DSC was programmed as follows: 20' to 1700 to 200 to 300° C. The aim was to melt, crystallise and re-melt and assess the new onset temperature.

Both thermocycles showed a small melt at 40-65° C. This event was not repeated in the second thermocycle, indicating that event was irreversible and hence most likely attributed to loss of volatiles.

Both thermocycles had a consistent melt at 146° C., indicating that despite the slow cool the phase did not recrystallize after melting.

TABLE 89

Comparison between batches

| Counter ion | pKa 1 | pKa 2 | DSC (m.p. onset and enthalpy data) |
|---|---|---|---|
| Hydrochloric acid | −6.00 | N/A | 204.1° C. (−80.89 Jg^-1) 205.8° C. (−99.72 Jg^-1) |
| Maleic acid | 1.90 | 6.20 | 144.0° C. (−44.63 Jg^-1) 138.9° C. (−79.17 Jg^-1) |
| Benzoic acid | 4.20 | N/A | 100.06° C. (−55.31 Jg^-1) 97.8° C (−82.93 Jg^-1) |

Scale Up of Compound 1 HCl Salt to 5 g

The salification was performed via heat-up cool-down crystallization of compound 1·Native with aq. hydrochloric acid (35% v/v) from ethanol and afforded light pink crystals, (5.2 g, 88% th.) The product was analysed by XRPD, $^1$H NMR, TGA, DSC, HPLC, and PLM.

In summary, the scale-up of compound 1 HCl, performed as expected (refer to overlays with reference compound 1 HCl depicted in FIGS. 179-182.

Physicochemical Evaluation

An informal physicochemical evaluation of the nominated salts was performed to enable selection of the preferred salt form. Once the salt is selected, physicochemical properties are further evaluated as part of the DS activities.

Equilibrium Humidity Evaluation (40° C./75% RH for 10 Days)

At 40° C./75% RH the phases of the salt forms remained the same throughout.

The purity profiles of compound 1·HCl and compound 1·Benzoate were little changed at the 10-day stability time point.

TABLE 10

Summary of salts inputs

| Salt | Input (mg) |
|---|---|
| Fumarate salt | 100.2 |
| HCl salt | 100.7 |
| Maleate salt | 100.3 |
| Benzoate salt | 100.1 |

The color of each salt became more vivid after 5 and 10 days.

Compound 1 Fumarate and compound 1 Maleate showed a reduction in CP over the 10 day period.

TABLE 91

Stability of Compound 1 · Fumarate Form A at 40° C./75% RH for 10 days

| Comments | Area (mAu*) for reference RRT = 1.00 | 11.56 0.93 | 12.18 0.98 | 12.43 1.00 | 13.42 1.08 | 13.79 1.11 | 14.04 1.13 | 14.29 1.15 | 14.54 1.17 | 14.66 1.18 |
|---|---|---|---|---|---|---|---|---|---|---|
| Fumarate salt | 9682.01 | 0.36 | | 98.38 | | 0.79 | | 0.27 | 0.13 | |
| t = 5 d at 75% RH at 40° C. | 24968.48 | 0.64 | 0.05 | 96.82 | 0.05 | 1.06 | | 0.60 | 0.02 | 0.27 |
| t = 10 d at 75% RH at 40° C. | 24658.94 | 0.61 | 0.07 | 97.08 | 0.04 | 0.96 | 0.05 | 0.52 | | 0.09 |

| | Comments | 14.79 1.19 | 14.91 1.20 | 15.78 1.27 | 15.90 1.28 | 16.65 1.34 | 17.27 1.39 | 17.77 1.43 | 18.02 1.45 | 18.27 1.47 |
|---|---|---|---|---|---|---|---|---|---|---|
| | Fumarate salt | 0.08 | | | | | | | | |
| | t = 5 d at 75% RH at 40° C. | | 0.20 | 0.05 | 0.03 | | 0.10 | 0.06 | | 0.06 |
| | t = 10 d at 75% RH at 40° C. | 0.12 | 0.15 | 0.03 | 0.05 | 0.04 | 0.08 | 0.04 | 0.03 | 0.05 |

TABLE 92

Stability of Compound 1 · HCl at 40° C./75% RH for 10 days

| Comments | Area (mAu*) for reference RRT = 1.00 | 11.78 0.93 | 12.41 0.98 | 12.54 0.99 | 12.66 1.00 | 15.20 1.20 | 15.45 1.22 | 15.96 1.26 | 16.21 1.28 | 16.46 1.30 | 16.72 1.32 | 17.10 1.35 |
|---|---|---|---|---|---|---|---|---|---|---|---|---|
| HCl salt | 15871.84 | 0.01 | 0.02 | 0.01 | 99.60 | 0.01 | 0.11 | 0.16 | | 0.03 | 0.01 | 0.04 |
| t = 5 d at 75% RH at 40° C. | 25920.54 | 0.05 | 0.02 | | 99.42 | 0.02 | 0.42 | 0.02 | 0.02 | | | 0.04 |
| t = 10 d at 75% RH at 40° C. | 21464.89 | 0.05 | 0.01 | | 99.60 | | 0.31 | | | | | 0.02 |

TABLE 93

Stability of Compound 1 · Maleate at 40° C./75% RH for 10 days

| Comments | Area (mAu*) for reference RRT = 1.00 | 10.79 0.84 | 11.94 0.93 | 12.59 0.98 | 12.84 1.00 | 14.13 1.10 | 14.51 1.13 | 15.03 1.17 | 15.15 1.18 | 15.28 1.19 | 15.67 1.22 | 16.05 1.25 | 16.18 1.26 | 16.44 1.28 | 16.95 1.32 | 17.21 1.34 |
|---|---|---|---|---|---|---|---|---|---|---|---|---|---|---|---|---|
| Maleate salt | 11734.37 | | 0.03 | 0.06 | 99.22 | 0.28 | 0.14 | 0.02 | 0.03 | 0.08 | | 0.03 | | | | 0.11 |
| t = 5 d at 75% RH at 40° C. | 19221.84 | 0.31 | 0.05 | 0.03 | 99.09 | | 0.21 | | | 0.10 | | | | | | 0.22 |
| t = 10 d at 75% RH at 40° C. | 25936.47 | 0.65 | 0.06 | 0.05 | 98.30 | | 0.33 | | | 0.09 | 0.09 | 0.02 | 0.06 | 0.05 | 0.10 | 0.19 |

TABLE 94

Stability of Compound 1 · Benzoate at 40° C./75% RH for 10 days

| Comments | Area (mAu*) for reference RRT = 1.00 | 12.60 0.98 | 12.86 1.00 | 13.89 1.08 | 14.02 1.09 | 14.92 1.16 | 15.30 1.19 | 15.43 1.20 | 15.95 1.24 | 16.20 1.26 | 17.36 1.35 |
|---|---|---|---|---|---|---|---|---|---|---|---|
| Benzoate salt | 7191.18 | | 99.64 | | 0.03 | 0.03 | 0.10 | 0.02 | 0.06 | 0.01 | 0.10 |
| t = 5 d at 75% RH at 40° C. | 29686.77 | 0.04 | 99.64 | | | 0.03 | 0.10 | 0.02 | | 0.05 | 0.11 |
| t = 10 d at 75% RH at 40° C. | 24202.54 | 0.04 | 99.52 | 0.05 | | 0.04 | 0.13 | 0.02 | | 0.07 | 0.12 |

Solubility Determinations in SFI Buffers

The solubility of the salts below was determined in FaSSIF, FeSSIF and FaSSGF by reference to the calibration curve of amorphous compound 1.

Upon pH adjustment from 4.17 to 1.63, solid was observed in compound 1 benzoate (FIG. 184).

At t=24 h, the dry pellet was analysed by $^1$H NMR to determine whether disproportionation occurred.

Compound 1 Fumarate, HC; and Maleate salts were freely soluble in SIF buffers at the concentration tested (30 mg/ml) (FIG. 298).

Compound 3 Benzoate disproportionated in FaSSGF; $^1$H NMR analyses was performed on the isolated residue and confirmed disproportionation by the presence of non-ionised benzoic acid.

TABLE 95

| Summary of conditions | | | | |
|---|---|---|---|---|
| Input Masses (mg) | Input details | MW | Buffer | Buffer Charge (mL) |
| 150.8 | Compound 1•Fumarate | 348.40 | FaSSIF (pH6.5) | 5 |
| 150.5 | Compound 1•HCl | 268.79 | FaSSIF (pH6.5) | 5 |
| 150.3 | Compound 1•Maleate | 348.40 | FaSSIF (pH6.5) | 5 |
| 150.8 | Compound 1•Benzoate | 354.45 | FaSSIF (pH6.5) | 5 |
| 150.3 | Compound 1•Fumarate | 348.40 | FeSSIF (pH5.0) | 5 |
| 150.3 | Compound 1•HCl | 268.79 | FeSSIF (pH5.0) | 5 |
| 150.6 | Compound 1•Maleate | 348.40 | FeSSIF (pH5.0) | 5 |
| 150.1 | Compound 1•Benzoate | 354.45 | FeSSIF (pH5.0) | 5 |
| 150.5 | Compound 1•Fumarate | 348.40 | FaSSGF (pH1.6) | 5 |
| 150.0 | Compound 1•HCl | 268.79 | FaSSGF (pH1.6) | 5 |
| 150.4 | Compound 1•Maleate | 348.40 | FaSSGF (pH1.6) | 5 |
| 150.3 | Compound 1•Benzoate | 354.45 | FaSSGF (pH1.6) | 5 |

TABLE 96

| | | Trended HPLC data | | | | | | | | | | | | | | |
|---|---|---|---|---|---|---|---|---|---|---|---|---|---|---|---|---|
| | | RT | | | | | | | | | | | | | | |
| | | 11.45 | 11.70 | 12.34 | 12.72 | 13.61 | 13.86 | 14.88 | 15.01 | 15.13 | 15.77 | 15.90 | 16.15 | 16.28 | 16.79 | 16.91 |
| RRT—HPLC | Area | | | | | | | | RRT | | | | | | | |
| analysis (MET/CR/0000) Comments | (mAu*) for reference RRT = 1.00 | 0.90 | 0.92 | 0.97 | 1.00 | 1.07 | 1.09 | 1.17 | 1.18 Id Compound 1 | 1.19 | 1.24 | 1.25 | 1.27 | 1.28 | 1.32 | 1.33 |
| Compound 1.Benzoate | 7191.18 | | | | 99.64 | | 0.03 | 0.03 | 0.10 | 0.02 | 0.06 | | | 0.01 | | 0.10 |
| t = 1 h in FaSSGF | 14502.42 | 0.07 | 0.05 | | 99.28 | 0.04 | 0.06 | 0.04 | 0.15 | | | | 0.11 | 0.05 | | 0.15 |
| t = 3 h in FaSSGF | 5999.76 | | | 0.04 | 99.62 | 0.03 | | | 0.15 | | | | | | | 0.16 |
| t = 6 h in FaSSGF | 5818.12 | | | | 99.61 | | | | 0.12 | | 0.08 | 0.04 | | | 0.06 | 0.09 |
| t = 24 h in FaSSGF | 5782.24 | | | | 99.73 | | | | 0.15 | | | | | | 0.07 | 0.06 |

TABLE 97

Summary of SFI buffer experiment results

| SIF Buffer | Input | Weights input (mg) | Solubility (mg/ml) | t = 1 h @37° C. XRPD (wet) | t = 1 h @37° C. XRPD (dried) | t = 1 h @37° C. pH | t = 3 h @37° C. Solubility (mg/ml) | t = 3 h @37° C. XRPD (wet) | t = 3 h @37° C. XRPD (dried) | t = 3 h @37° C. pH | t = 6 h @37° C. Solubility (mg/ml) | t = 6 h @37° C. XRPD (wet) | t = 6 h @37° C. XRPD (dried) | t = 6 h @37° C. pH | t = 24 h @37° C. Solubility (mg/ml) | t = 24 h @37° C. XRPD (wet) | t = 24 h @37° C. XRPD (dried) | t = 24 h @37° C. pH |
|---|---|---|---|---|---|---|---|---|---|---|---|---|---|---|---|---|---|---|
| FaSSIF (ph 6.5) | Compound 1 · Fumarate | 150.8 | Solution, >30 mg/ml | N/A | N/A | 6.60 | Solution, >30 mg/ml | N/A | N/A | 6.40 | Solution, >30 mg/ml | N/A | N/A | 6.53 | Solution, >30 mg/ml | N/A | N/A | 6.52 |
| FaSSIF (ph 6.5) | Compound 1 · HCl | 150.5 | Solution, >30 mg/ml | N/A | N/A | 6.47 | Solution, >30 mg/ml | N/A | N/A | 6.50 | Solution, >30 mg/ml | N/A | N/A | 6.52 | Solution, >30 mg/ml | N/A | N/A | 6.50 |
| FaSSIF (ph 6.5) | Compound 1 · Maleate | 150.2 | Solution, >30 mg/ml | N/A | N/A | 6.47 | Solution, >30 mg/ml | N/A | N/A | 6.48 | Solution, >30 mg/ml | N/A | N/A | 6.47 | Solution, >30 mg/ml | N/A | N/A | 6.47 |
| FaSSIF (ph 6.5) | Compound 1 · Benzoate | 150.3 | Solution, >30 mg/ml | N/A | N/A | 6.55 | Solution, >30 mg/ml | N/A | N/A | 6.57 | Solution, >30 mg/ml | N/A | N/A | 6.50 | Solution, >30 mg/ml | N/A | N/A | 6.47 |
| FeSSIF (ph 5.0) | Compound 1 · Fumarate | 150.8 | Solution, >30 mg/ml | N/A | N/A | 5.00 | Solution, >30 mg/ml | N/A | N/A | 5.02 | Solution, >30 mg/ml | N/A | N/A | 5.02 | Solution, >30 mg/ml | N/A | N/A | 5.02 |
| FeSSIF (ph 5.0) | Compound 1 · HCl | 150.3 | Solution, >30 mg/ml | N/A | N/A | 4.98 | Solution, >30 mg/ml | N/A | N/A | 4.99 | Solution, >30 mg/ml | N/A | N/A | 4.99 | Solution, >30 mg/ml | N/A | N/A | 4.98 |
| FeSSIF (ph 5.0) | Compound 1 · Maleate | 150.6 | Solution, >30 mg/ml | N/A | N/A | 4.98 | Solution, >30 mg/ml | N/A | N/A | 4.98 | Solution, >30 mg/ml | N/A | N/A | 4.98 | Solution, >30 mg/ml | N/A | N/A | 4.95 |
| FeSSIF (ph 5.0) | Compound 1 · Benzoate | 150.1 | Solution, >30 mg/ml | N/A | N/A | 4.99 | Solution, >30 mg/ml | N/A | N/A | 4.99 | Solution, >30 mg/ml | N/A | N/A | 4.99 | Solution, >30 mg/ml | N/A | N/A | 4.98 |
| FaSSGF (ph 1.6) | Compound 1 · Fumarate | 150.5 | Solution, >30 mg/ml | N/A | N/A | 1.54 | Solution, >30 mg/ml | N/A | N/A | 1.56 | Solution, >30 mg/ml | N/A | N/A | 1.57 | Solution, >30 mg/ml | N/A | N/A | 1.55 |
| FaSSGF (ph 1.6) | Compound 1 · HCl | 150.0 | Solution, >30 mg/ml | N/A | N/A | 1.50 | Solution, >30 mg/ml | N/A | N/A | 1.63 | Solution, >30 mg/ml | N/A | N/A | 1.60 | Solution, >30 mg/ml | N/A | N/A | 1.62 |
| FaSSGF (ph 1.6) | Compound 1 · Maleate | 150.4 | Solution, >30 mg/ml | N/A | N/A | 1.54 | Solution, >30 mg/ml | N/A | N/A | 1.60 | Solution, >30 mg/ml | N/A | N/A | 1.59 | Solution, >30 mg/ml | N/A | N/A | 1.63 |
| FaSSGF (ph 1.6) | Compound 1 · Benzoate | 150.3 | 28.74 | Benzoic acid | Benzoic acid | 1.51 | 26.85 | Benzoic acid | Benzoic acid | 1.70 | 26.33 | Benzoic acid | Benzoic acid | 1.60 | 25.59 | Benzoic acid | Benzoic acid | 1.60 |

Dynamic Vapor Sorption (DVS)

Specimens were equilibrated at 0% RH for 60 min, prior to DVS analyses (stepped increment % RH up to 90% RH and stepped decrement % RH down to 0% RH.

DVS isotherms ranged from slightly hygroscopic (compound 1·HCl) to deliquescent (compound 1·Fumarate).

Fumarate DVS Results

Compound 1·Fumarate, deliquescent type isotherm, gained ca. 1% w/w at 70° RH after which, pronounced mono, multilayer sorption and probable deliquescence occurred >80% RH HCl DVS Results Compound 1·HCl, up to ca. 0.2% w/w at 70° RH (slightly hygroscopic isotherm) mono and multilayer sorption >80% RH up to ca. 0.5% w.w; exhibited small water affinity hysteresis. Compound 1·HCl was the best of the four salts.

Maleate DVS Results

Compound 1·-Maleate, hygroscopic, isotherm uptake ca. 3.5% w/w, small hysteresis, during desorption Benzoate DVS Results Compound 1·Benzoate, hygroscopic isotherm up to ca. 0.6% w/w at 70° RH (hygroscopic); desorption profile was unusual and ended beneath unity.

Conclusions

Compound 1 HCl (crystalline, Class 1) was nominated for polymorph screening as Compound 1·HCl exhibited high crystallographic quality.

Compound 1 HCl was freely soluble in SIF buffers at the concentration tested (30 mg/ml). Focusing on its performance in the advanced physicochemical screening, Compound 1 HCl showed no reduction in CP (99.60% area over 10 days) and displayed excellent characteristics related to dynamic vapor sorption, up to ca. 0.2% w/w at 70° RH (slightly hygroscopic isotherm) mono and multilayer sorption >80% RH up to ca. 0.5% w.w; exhibited small water affinity hysteresis.

Experimental Information

Instrumentation

DSC

A Mettler Toledo DSC 3 instrument was used for the thermal analysis operating with STARe™ software. The analysis was conducted in open aluminium pans (40 μl), under nitrogen and sample sizes ranged from 1 to 10 mg. Typical analysis method was 20 to 250° C. at 10° C./minute.

Alternatively, a Mettler Toledo DSC1 with auto-sampler instrument was used for the thermal analysis operating with STARe™ software. The analysis was conducted in open aluminium pans (40 μl), under nitrogen and sample sizes ranged from 1 to 10 mg. Typical analysis method was 25 to 300° C. at 10° C./minute.

DVS

The moisture sorption properties of the feed API were analysed by DVS Intrinsic instrument (Surface Measurement System). Approximately 20 to 50 mg of API was weighed onto an aluminium pan and loaded into the instrument equilibrated at 25° C. The sample was equilibrated under a dry atmosphere (0% relative humidity) for 60 minutes, before increasing the humidity from 0% to 30% at 5% step increment and from 30% to 90% at 10% step increment. A desorption cycle was also applied from 90% to 30% (10% step decrement) and from 30% to 0% (5% step decrement). A rate of change in mass per time unit (dm/dt) of 0.002%/min was set as the equilibrium parameter. Kinetic and isotherm graphs were calculated.

LC-MS

Routine Liquid Chromatography-Mass Spectrometry (LC-MS) data were collected using the Agilent 1260 Infinity II interfaced with 1260 Infinity II DAD HS and Agilent series 1260 Infinity II binary pump.

The instrument used a single quadrupole InfinityLab MSD. The instrument was calibrated up to 2000 Da.

LC-MS Method Parameters:

Inj. vol: 5 μl
Detection: UV @ 254 nm
Mobile Phase A: Acetonitrile±0.1% TFA/$H_2O$ 95:5
Mobile Phase B: Acetonitrile±0.05% TFA/$H_2O$ 5:95

TABLE 98

| LC-MS method parameters | | |
|---|---|---|
| Time (mins) | % A | % B |
| 0.0 | 100 | 0 |
| 1 | 100 | 10 |
| 10.00 | 0 | 100 |
| 10.01 | 100 | 0 |
| 12.00 | 100 | 10 |

Flow Rate: 1 ml/min
Column temperature: 30° C.
Run time 12 minutes.

FT-IR

FT-IR Spectra were acquired using a PerkinElmer Frontier FT-IR spectrometer. Samples were analysed directly using a universal ATR attachment in the mid and far frequency ranges; 4000 to 30 $cm^{-1}$. Spectra were processed using Spectrum software. Standard KBr windows are used for mid-IR applications; polyethylene and polyethylene/diamond windows are used for operation in the far-IR. Further capabilities of the instrument include a liquid flow cell with ZnSe windows used for rapid monitoring of reactions. This couples with time-based software which allows time-resolved measurements to be taken.

$^1$H-NMR $^1$H NMR spectra were acquired using a Bruker 400 MHz spectrometer and data was processed using Topspin. Samples were prepared in DMSO-$d_6$ at typical concentrations of 10 to 20 mg/ml and up to 50 mg/ml for $^1$H NMR w/w assay and calibrated to the corresponding non-deuterated solvent residual at 2.50 ppm.

$^1$H-NMR Assay

Assays (w/w) of API by $^1$H NMR spectroscopy were measured by the project chemist using Topspin. Internal standard 2,3,5,6-terachloronitrobenzene (TCNB, ca. 20 mg, F.W. 260.89) were dissolved in DMSO-$d_6$ (2.0 ml) and the $^1$H NMR spectrum was acquired using an extended relaxation method.

TGA

A Mettler Toledo TGA-2 instrument was used to measure the weight loss as a function of temperature from 25 to 500° C. The scan rate was typically 5 or 10° C. per minute. Experiments and analysis were carried out using the STARe™ software. The analysis was conducted in 100 μl open aluminum pans, under nitrogen and sample sizes ranged from 1 to 10 mg.

XRPD

X-ray powder diffraction (XRPD) analysis was carried out using a Bruker D2 Phaser powder diffractometer equipped with a LynxEye detector. The specimens underwent minimum preparation but, if necessary, were lightly milled in a pestle and mortar before acquisition. The specimens were located at the centre of a silicon sample holder within a 5 mm pocket (ca. 5 to 10 mg). The samples were continuously spun during data collection and scanned using a step size of 0.02°2-theta (2θ) between the range of 4° to 40°2-theta or 5° to 60°2-theta. Data were acquired using either 3 minute or 10-minute acquisition methods. Bruker Diffrac.Suite was used to process the data

HPLC (MET/CR/2616)

HPLC data was acquired using an Agilent HPLC instrument. Samples were diluted to 1 mg/mL concentration in $H_2O$/MeCN (1/1, v/v).

Method Parameters:
  Column: Halo C18, 150×4.6 mm, 2.7 µm
  Inj. volume: 5 µL
  Detection: UV @ 212 nm
  Mobile Phase A: 0.1% TFA in water/acetonitrile 95/5 v/v
  Mobile Phase B: 0.05% TFA in water/acetonitrile 5/95 v/v

TABLE 99

HPLC Parameters

| Time | % A | % B |
|---|---|---|
| 0.0 | 100 | 0 |
| 2.0 | 100 | 0 |
| 25.0 | 50 | 50 |
| 30.0 | 0 | 100 |
| 32.0 | 0 | 100 |
| 32.1 | 100 | 0 |
| 37.0 | 100 | 0 |

Flow rate: 1 mL/min
  Column temperature: 30° C.
  Run time: 37 minutes
  Integration time: 32 minutes
  Wash vial or syringe wash: Sample diluent General Procedures Heat-Up Cool-Down Crystallization Salt Screen Procedure Compound 1 free base (1.0 equiv.) and the corresponding acid (1.1 equiv) were dissolved in 2.0 vol of ethanol at 80° C. The solution was left to cool down to ambient before storing at sub-ambient for ca 18 h. The products were isolated by centrifugation and was oven-dried under reduced pressure over 20 h at 40° C.

Scale Up of Nominated Salts Procedure

Compound 1 free base (1.0 equiv.) and the corresponding acid (1.1 equiv) were dissolved in 2.0 vol of ethanol at 80° C. The solutions were left to cool down to ambient before storing at sub-ambient for ca 18 h. The contents of the vial were filtered over a sintered funnel and was dried under vacuum and nitrogen flow for ca 48 h. The outputs were characterised by DSC, TGA, $^1$H NMR and XRPD.

Scale Up of Compound 1 HCl Salt to 5 g Procedure

Amorphous compound 1 (5.0 g, 1.0 wt) and HCl (2.2 ml, 35% aq., 1.1 eq.) were dissolved in ethanol (2.0 vol) at 80° C., the reddish solution was left to cool to 20° C. (solid was observed) and the suspension was further cooled to sub-ambient temperature (ca. 5° C.) and maintained under these conditions for ca. 6 days. The product was isolated by suction filtration, pulled free of surplus solvents, and dried under sustained nitrogen flux for ca. 3 h; the filter cake (5.16 g) was off-loaded, trayed-up and dried under reduced pressure at 40° C. for ca. 18 h. The product was crystalline compound 1 HCl (FIG. 182) (5.16 g, 88% uncorr.).

Equilibrium Humidity Stability 100 mg portions of compound 1 salts (for inputs see table below) were placed in the relevant open vials. The powders were finely divided and distributed evenly over the base of the vial, such that equal material coverage across the panel was observed. These samples were then maintained 40° C. under 75% RH. The samples were sub-sampled at intervals of 5 and 10 days and analysed by by $^1$H NMR, HPLC, XRPD, DSC, TGA and PLM, for evidence of phase change or chemical degradation (FIG. 269-297).

TABLE 100

Summary of Salts

| Experimental reference | Input (mg) |
|---|---|
| Crystalline compound 1 fumarate form A | 100.2 |
| Crystalline compound 1 HCl salt | 100.7 |
| Crystalline compound 1 maleate salt | 100.3 |
| Crystalline compound 1 benzoate salt | 100.1 |

Calibration Curve of Non-Ionized Compound 1 in Acetonitrile/Water (1/1 v/v)

Separate portions of compound 1 were weighed out into aluminum boats and were charged to the relevant volumetric flasks. Solutions were made to volume with 1 to 1 (v/v) acetonitrile/purified water to give calibrants of known API concentrations and analyzed by HPLC, suitable to determine the concentration of compound 1 free base in the SIF buffer solubility study.

Signal areas of the calibrants were plotted against concentration to generate the corresponding calibration curve with slope 27622 and $R^2$ 0.9917. At the calculated concentrations the measured value exhibited positive agreement with the predicted value.

Solubility Determinations in SIF Buffers Procedure

Each sample (150 mg) was suspended in the relevant SIF buffer (5.0 ml), to give a concentration of 30 mg/ml and maintain at 37° C. for 24 h. The pH was adjusted using 1 M HCl or 1 M NaOH, to ensure that the suspension remains in range.

Sample (1 ml) of the well-stirred representative suspensions was obtained at 1 h, 3 h, 6 h and 24 h and the pH was recorded. The pH of the bulk suspension was re-adjusted when necessary. The obtained sample from each vial was centrifuged, and the supernatant was analysed by HPLC (note, the analyte was diluted, when outside of the calibration range); XRPD analysis was performed on the wet sample pellet for evidence of form change, as well as on the oven-dried pellet (undervacuum at 40° C.).

Example 10. Salt Screen (R)-1-(5-methoxy-1H-indol-1-yl)-N,N-dimethylpropan-2-amine is characterized to evaluate its physical properties. The evaluation is performed by X-ray powder diffraction (XRPD), polarized light microscopy (PLM), differential scanning calorimetry (DSC), thermogravimetry (TG), dynamic vapor sorption/desorption (DVS), and/or solubility testing in organic solvents, water, and mixed solvent systems. XRPD data are used to assess crystallinity. PLM data are used to evaluate crystallinity and particle size/morphology. DSC data are used to evaluate melting point, thermal stability, and crystalline form conversion. TG data are used to evaluate if the free base is a solvate or hydrate, and to evaluate thermal stability. DVS data are used to evaluate hygroscopicity of the free base and if hydrates can be formed at high relative humidity. About 10 to 15 solvents are selected from the list below, based on their properties (polarity, dielectric constant and dipole moment).

TABLE 101

Solvents

| | |
|---|---|
| acetic acid | n-heptane |
| Acetone | n-hexane |
| Acetonitrile | 1,1,1,3,3,3-hexafluoro-2-propanol |
| benzyl alcohol | isobutanol (2-methyl-1-propanol) |
| 1-butanol | isopentanol (3-methyl-1-butanol) |
| 2-butanol | isopropyl alcohol (2-propanol) |
| butyl acetate | isopropylbenzene (cumene) |
| t-butyl methyl ether | Methanol |
| Chlorobenzene | methoxybenzene (anisole) |
| Chloroform | methyl acetate |
| di(ethylene glycol) | methyl ethyl ketone (2-butanone) |
| Dichloromethane | methyl isobutyl ketone |
| diethyl ether | Nitromethane |
| Diethylamine | N-methyl-2-pyrrolidone (NMP) |
| Dimethylacetamide (DMA) | 1-octanol |
| diisopropyl ether | 1-pentanol |
| N,N-dimethyl-formamide (DMF) | 1-propanol |
| dimethyl sulfoxide | Perfluorohexane |
| 1,4-dioxane | propyl acetate |
| 1,2-ethanediol (ethylene glycol) | 1,1,2,2-tetrachloroethane |
| Ethanol | Tetrahydrofuran |
| Ethanolamine | Toluene |
| 2-ethoxyethanol (Cellusolve) | 1,1, 1-trichloroethane |
| ethyl acetate | 2,2,2-trifluoroethanol |
| ethyl formate | Water |
| formic acid | o-xylene (1,2-dimethylbenzene) |
| Glycerol | p-xylene (1,4-dimethylbenzene) |

The information obtained is used for designing the subsequent salt screen. The salt screen is performed by reacting the free base with pharmaceutically acceptable acids under various conditions in attempts to generate crystalline salts. Pharmaceutically acceptable acids that may be used are listed below. Specific acids are selected based on the pKa of the free base, and typically 15 to 20 acids are selected. Experiments are performed using 0.5 molar equivalent, 1 molar equivalent and/or 2 molar equivalents of the acid.

TABLE 102

Exemplary Acids

| | |
|---|---|
| naphthalene-1,5-disulfonic acid | citric acid |
| sulfuric acid | d-glucuronic acid |
| ethane-1,2-disulfonic acid | lactobionic acid |
| p-toluenesulfonic acid | D-glucoheptonic acid |
| thiocyanic acid | (−)-L-pyroglutamic acid |
| methanesulfonic acid | L-malic acid |
| dodecylsulfuric acid | hippuric acid |
| naphthalene-2-sulfonic acid | D-gluconic acid |
| benzenesulfonic acid | D,L-lactic acid |
| oxalic acid | oleic acid |
| glycerophosphoric acid | succinic acid |
| ethanesulfonic acid, 2-hydroxy | glutaric acid |
| L-aspartic acid | cinnamic acid |
| maleic acid | adipic acid |
| phosphoric acid | sebacic acid |
| ethanesulfonic acid | (+)-camphoric acid |
| glutamic acid | acetic acid |
| pamoic (embonic) acid | nicotinic acid |
| glutaric acid, 2-oxo- | isobutyric acid |
| 2-naphthoic acid, 1-hydroxy | propionic acid |
| malonic acid | lauric acid |
| gentisic acid | stearic acid |
| L-tartaric acid | orotic acid |
| fumaric acid | carbonic acid |
| galactaric (mucic) acid | |

Solvent systems for the salt crystallization experiments are selected based on the solubility of the free base and the selected acid. Solvents are used as a single solvent or as solvent mixtures, some containing water. The techniques that are used for salt crystallization are chosen based on the solvent selected and properties of the free base. The following techniques (or combination of techniques) may be used for salt crystallization:

Free base and acid are dissolved in a solvent or mixture of solvents, and the solvents are evaporated at different rates (slow evaporation or fast evaporation) and at different temperatures (ambient or elevated).

Free base and acid are dissolved in a solvent or mixture of solvents (at ambient temperature or an elevated temperature), and the final solution is cooled to a sub-ambient temperature (between −78° C. to 15° C.). The cooling method can be a fast cooling (by plunging the sample into an ice bath or a dry ice/acetone bath), or slow cooling. The solids formed will be recovered by filtration and dried (air dried or vacuum dried).

Free base and acid are dissolved in a solvent or mixture of solvents, and an antisolvent is added to precipitate the salt. The solids formed will be recovered by filtration and dried (air dried or vacuum dried).

Free base and acid are added to a solvent or mixture of solvents, where one or both components are not fully dissolved. The slurry is agitated at different temperatures for a number of days. The solids formed will be recovered by filtration and dried (air dried or vacuum dried). The same experiment is also performed in solvent systems where the solvents are not miscible.

Free base and acid are milled together (by mechanical milling or by mortar and pestle), with a drop of solvent, or without any solvent.

Free base and acid were melted together and cooled to various temperatures using various cooling rates.

If an amorphous form of a salt was obtained, the amorphous salt was exposed to elevated humidity, or elevated temperature (or combination of both), or solvent vapors at various temperatures to form crystalline salts.

The stoichiometric ratio of acid to amine, (R)-1-(5-methoxy-1H-indol-1-yl)-N,N-dimethylpropan-2-amine, is confirmed by $^1$H NMR, HPLC, or both as is known to those of ordinary skill in the art.

The salts obtained are analyzed by XRPD to determine if they are crystalline and, if so, by DSC to see the melting point and by TG to see if they are hydrated/solvated, and by 1H NMR spectroscopy to ensure chemical integrity. KF water titration is performed on salts that are hydrated. DVS analysis is performed to evaluate hygroscopicity of the salt and if hydrated form is present.

Consistent with the methods above, the (R)-1-(5-methoxy-1H-indol-1-yl)-N,N-dimethylpropan-2-amine salts listed in Table 103 were prepared and characterized. The symbol "--" means that data were not collected for that entry.

TABLE 103

| Salt | XRPD | Stoichiometry API to salt | Melting Point | $^1$H NMR Consistent with Structure? |
|---|---|---|---|---|
| HCl | FIG. 167 | — | 204° C. | Yes |
| Malcate | FIG. 168 | 1.0 to 1.0 | 144° C. | Yes |
| Benzoate | FIG. 169 | 1.0 to 1.0 | 100° C. | Yes |
| Tosylate | FIG. 170 | 1.0 to 1.0 | 127° C. | Yes |
| Tartrate | FIG. 171 | 1.0 to 1.0 | 107° C. | Yes |

TABLE 103-continued

| Salt | XRPD | Stoichiometry API to salt | Melting Point | $^1$H NMR Consistent with Structure? |
|---|---|---|---|---|
| HBr | FIG. 172 | — | Bimodal 115° C. and 186° C. | Yes |
| Galactarate | FIG. 173 | 1.0 to 1.0 | 163° C. | Yes |
| Succinate | FIG. 174 | 1.0 to 1.7 | 81° C. and 205° C. | Yes |
| Sulfate | — | — | 157° C. | — |
| Ethane sulfonate (esylate) | — | — | — | — |
| Methane sulfonate (mesylate) | — | | | |
| Phosphate | — | — | — | — |
| Citrate | — | — | 181-184° C. | — |
| Glucuronate | — | — | 143° C. | — |
| Malate | — | — | 193° C. | — |
| Gluconate | — | — | — | — |
| Ascorbate | — | — | 188-192° C. | — |
| Edisylate | — | — | — | — |
| Adipate | — | — | — | — |

Example 11: Polymorph Evaluation

The active pharmaceutical ingredient (API), (R)-1-(5-methoxy-1H-indol-1-yl)-N,N-dimethylpropan-2-amine, which may be a free base or a salt, is characterized to evaluate its physical properties. The evaluation is performed by X-ray powder diffraction (XRPD), polarized light microscopy (PLM), differential scanning calorimetry (DSC), thermogravimetry (TG), dynamic vapor sorption/desorption (DVS), and/or solubility testing in organic solvents, water, and mixed solvent systems. XRPD data are used to assess crystallinity. PLM data are used to evaluate crystallinity and particle size/morphology. DSC data are used to evaluate melting point, thermal stability, and crystalline form conversion. TG data are used to evaluate if the API is a solvate or hydrate, and to evaluate thermal stability. DVS data are used to evaluate hygroscopicity of the API and if hydrates can be formed at high relative humidity. About 10 to 15 solvents may be selected from the list below, based on their properties (polarity, dielectric constant and dipole moment).

TABLE 104

| Solvents | |
|---|---|
| acetic acid | n-heptane |
| acetone | n-hexane |
| acetonitrile | 1, 1, 1,3,3,3-hexafluoro-2-propanol |
| benzyl alcohol | isobutanol (2-methyl-1-propanol) |
| 1-butanol | isopentanol (3-methyl-1-butanol) |
| 2-butanol | isopropyl alcohol (2-propanol) |
| butyl acetate | isopropylbenzene (cumene) |
| t-butyl methyl ether | methanol |
| chlorobenzene | methoxybenzene (anisole) |
| chloroform | methyl acetate |
| di(ethylene glycol) | methyl ethyl ketone (2-butanone ) |
| dichloromethane | methyl isobutyl ketone |
| diethyl ether | nitromethane |
| diethylamine | N-methyl-2-pyrrolidone (NMP) |
| Dimethylacetamide (DMA) | 1-octanol |
| diisopropyl ether | 1-pentanol |
| N,N-dimethyl-formamide (DMF) | 1-propanol |
| dimethyl sulfoxide | perfluorohexane |

TABLE 104-continued

| Solvents | |
|---|---|
| 1,4-dioxane | propyl acetate |
| 1,2-ethanediol (ethylene glycol) | 1, 1,2,2-tetrachloroethane |
| ethanol | tetrahydrofuran |
| ethanolamine | toluene |
| 2-ethoxyethanol (Cellusolve) | 1,1, 1-trichloroethane |
| ethyl acetate | 2,2,2-trifluoroethanol |
| ethyl formate | water |
| formic acid | o-xylene (1,2-dimethylbenzene) |
| glycerol | p-xylene (1,4-dimethylbenzene) |

The information obtained is used for designing the subsequent polymorph screen. Solvents are used as a single solvent or as solvent mixtures, some containing water. The techniques used for the polymorph screen are chosen based on the solvent selected and properties of the API. The following techniques (or a combination of techniques) may be used for the polymorph screening:

API is dissolved in a solvent or mixture of solvents, and the solvents are evaporated at different rates (slow evaporation or fast evaporation) and at different temperatures (ambient or elevated).

API is dissolved in a solvent or mixture of solvents (at ambient temperature or an elevated temperature), and the final solution is cooled (between −78° C. to 20° C.). The cooling method can be a fast cooling (by plunging the sample to an ice bath or a dry ice/acetone bath), or slow cooling. The solids formed will be recovered by filtration and dried (air dried or vacuum dried).

API is dissolved in a solvent or mixture of solvents, and an antisolvent is added to precipitate the salt. The solids formed will be recovered by filtration and dried (air dried or vacuum dried).

API is added to a solvent or mixture of solvents, where the API is not fully dissolved. The slurry will be agitated at different temperatures for a number of days. The solids formed will be recovered by filtration and (air dried or vacuum dried).

API is milled (by mechanical milling or by mortar and pestle), with a drop of solvent, or without any solvent.

API is melted and cooled (at different cooling rates, fast and slow, and cooled to different temperatures) to obtain solids.

API is suspended in a solvent or mixture of solvents, and the slurry is placed in a heating/cooling cycle for multiple cycles. The remaining solids after the final cooling cycle will be filtered and (air dried or vacuum dried).

API is processed to obtain an amorphous form (by melting, milling, solvent evaporation, spray drying or lyophilization). The amorphous form will then be exposed to elevated humidity (or elevated temperature, or combination thereof), or to solvent vapors for extended period of days.

API is exposed to elevated humidity (or elevated temperature, or combination thereof), or to solvent vapors for extended period of days.

Two or more polymorphs of the API are mixed in a solvent or solvent systems (some solvent mixtures containing variable amount of water) to obtain a slurry, and the slurry will be agitated (at various temperatures) for an extended period of time (days). The solvent system used can be pre-saturated with the API. The final solids will be filtered and dried (air dried or vacuum dried).

API is heated to a specific temperature and cooled (at ambient conditions or in a dry box).

The solids obtained are analyzed by XRPD to determine if they are crystalline and, if so, by DSC to see the melting point and by TG to see if they are hydrated/solvated, and by $^1$H NMR spectroscopy to ensure chemical integrity. KF water titration is performed on forms that are hydrated. DVS analysis is performed to evaluate hygroscopicity of the form and if hydrated form is present. In particular variable temperature analyses, including variable temperature XRPD, are performed to assess the stability of each physical form as well as its crystallinity.

Differential scanning calorimetry (DSC) thermograms are obtained using a DSC Q 100 (TA Instruments, New Castle, DE). The temperature axis and cell constant of the DSC cell are calibrated with indium (10 mg, 99.9% pure, melting point 156.6° C., heat of fusion 28.4 J/g). Samples (2.0-5.0 mg) are weighed in aluminum pans on an analytical balance. Aluminum pans without lids are used for the analysis. The samples are equilibrated at 25° C. and heated to 250-300° C. at a heating rate of 10° C./min under continuous nitrogen flow. TG analysis of the samples is performed with a Q 50 (TA Instruments, New Castle, DE). Samples (2.0-5.0 mg) are analyzed in open aluminum pans under a nitrogen flow (50 mL/min) at 25° C. to 210° C. with a heating rate of 10° C./min.

The sample for moisture analysis is allowed to dry at 25° C. for up to 4 hours under a stream of dry nitrogen. The relative humidity is then increased stepwise from 10 to 90% relative humidity (adsorption scan) allowing the sample to equilibrate for a maximum of four hours before weighing and moving on to the next step. The desorption scan is measured from 85 to 0% relative humidity with the same equilibration time. The sample is then dried under a stream of dry nitrogen at 80° C. for 2 hours or until no weight loss is observed.

X-ray powder diffraction data are collected using a Miniflex Tabletop XRD system (Rigaku/MSC, The Woodlands, TX) from 5° to 45°2θ with steps of 0.1°, and the measuring time is 1.0 second/step. All samples are ground to similar size before exposure to radiation. The powder samples are illuminated using CuKα radiation (λ=1.54056 Å) at 30 kV and 15 mA.

Variable temperature XRPD data are collected using a Huber Imaging Plate Guinier Camera 670 employing Ni-filtered CuKα$_1$ radiation (λ=1.5405981 Å) produced at 40 kV and 20 mA by a Philips PW1120/00 generator fitted with a Huber long fine-focus tube PW2273/20 and a Huber Guinier Monochromator Series 611/15. The original powder is packed into a Lindemann capillary (Hilgenberg, Germany) with an internal diameter of 1 mm and a wall thickness of 0.01 mm. The sample is heated at an average rate of 5 Kmin$^{-1}$ using a Huber High Temperature Controller HTC 9634 unit with the capillary rotation device 670.2. The temperature is held constant at selected intervals for 10 min while the sample is exposed to X-rays and multiple scans were recorded. A 2θ-range of 4.00-100.0° is used with a step size of 0.005°2θ.

In certain embodiments wherein the solid form is a solvate, such as a hydrate, the DSC thermogram reveals endothermic transitions. In accordance with the observed DSC transitions, TGA analysis indicates stages of weight change corresponding to desolvation or dehydration and/or melting of the sample. In the case of hydrates, these results are in harmony with Karl Fisher titration data which indicate the water content of the sample.

The moisture sorption profile of a sample can be generated to assess the stability of a solid form is stable over a range of relative humidities. In certain embodiments, the change in moisture content over 10.0 to 95.0% relative humidity is small. In other embodiments the change in moisture content over 10.0 to 95.0% relative humidity is reversible.

In certain embodiments, the XRPD pattern of a sample of solid form indicates that the sample has a well-defined crystal structure and a high degree of crystallinity.

Example 12: Crystalline Compound 1 HCl Polymorph Screen

List of Abbreviations and Definition Used in Example 12

$\varphi_i$ Water activity coefficient
$a_w$ Water activity
ASD Amorphous solid dispersion
ca. circa (Latin: approximately)
cf Confer/conferatur (Latin: to confer, to compare)
° C. degree Celsius
CP Chemical Purity
CP-MAS Cross Polarised Magic Angle Spinning ($^{13}$C NMR solid state technique)
Da Dalton
DSC Differential Scanning Calorimetry (measures changes in heat capacity)
DTA Differential Thermal Analyses (measures changes in temperature)
DVS Dynamic Vapour Sorption (used interchangeably with GVS)
e.g. Exempli gratia (Latin: for example)
etc. Et cetera (Latin: 'and others' or 'and so on')
FT-IR Fourier Transformed, InfraRed spectroscopy (prefixed mid and far)
g Gram (s)
GRAS Generally Recognised As Safe
GVS Gravimetric Vapour Sorption
h Hour (s)
HPLC High Performance Liquid Chromatography
HSM Hot Stage Microscopy (thermal microscopy)
HUCD Heat-up/cool-down crystallisation
i.e. Id Est (Latin: that is)
IPC In-Process check
IR InfraRed Spectroscopy
J Joule
Kelvin Kelvin. SI unit of temperature, used interchangeably with ° C. to express increment/decrement of temperature set point (e.g. ramp rate on DSC thermogram 10 K/min); note K sign not prefixed by.
KF Karl Fischer (determination of the water content by coulometric titration)
kg Kilogram (s)
LAG Liquid Assisted Grinding
LOD Loss On Drying
mag magnification
mAu milli-Absorption units (chromatographic unit of peak height)
mAu*s milli-Absorption units multiplied by second (chromatographic unit of peak area)
MET/CR Aptuit chromatography method reference
min Minute (s)
mg Milligram (s)
ml Millilitre (s)
mol mole, amount of substance N/A Not Applicable
n.a. not analysed
n.d. not detected
nm nanometre
NMR Nuclear Magnetic Resonance
oab on anhydrous basis
osfb on solvent free basis
oasfb on anhydrous solvent free basis
pH $-\log [H^+]$ or pH$=-\log a_{H}^+$
$pK_a-\log (K_a)$, acid dissociation constant
pI isoelectric point, quoted in unit pH
PLM Polarised Light Microscopy
ReiRT Relative Retention Time (not be confused RT)
REP/ Aptuit report (REP) reference
RFA Request For Analysis (unique reference number)
RH Relative Humidity ($a_w$*100)
RT Room Temperature (ambient, typically: 18 to 23° C.)
s Second (s)
SC-XRD Single Crystal X-Ray Determination
SIF Simulated Intestinal fluid
SMPT Solvent mediated phase transition
STA Simulated Thermal Analysis (STA=TGA+DTA)
t time in seconds, minutes, hour, days etc. (interval specified in parentheses); alias in common use tonne (t)
t Tonne, metric unit of mass (1000 kg; 1 Mg), (compaction force in kg, suffixed in parentheses)
T Temperature recorded in degrees Celsius (° C.); alias in common use, SI unit of magnetic flux density, also denoted T
MTBE Methyl tert-butyl ether
TCNB 2,3,5,6-Tetrachloronitrobenzene ($C_6HCl_4NO_2$, F.W. 260.89 $gmol^{-1}$)
TFE Trifluoroethanol (solvent used for solvent drop grinding)
TGA Thermogravimetric Analysis
th. theoretical
UV Ultra Violet
vol. Volume or relative volume
vs. versus
v/v volume/volume
W Watt
w/w weight/weight
XRPD X-Ray Powder Diffraction
Isostructural Crystals are said to be isostructural if they have the same crystal structure but not necessarily the same cell dimensions nor the same chemical composition (Kálmán, A., Párkányi, L. & Argay, G. (1993) Acta Cryst. B49, 1039-1049.)
Isomorphic two crystalline solids are isomorphous if both have the same unit-cell dimensions and space group (source, vide supra).
Isomorphic desolvate via solvent release from an isostructural solvate.
Native Refers to an API in its native or non-ionised form.
Normal light Light oscillating in all directions perpendicular to the axis to which it travels.
Particle size Expressed as a volume distribution, the range x10>PSD<x90 captures the sizes of 80% of the particles.
Plane polarised light Light passed through a polaroid filter which allows only light oscillating in one plane to be transmitted.
Polymorphism Crystalline solid able to exhibit different crystalline phases.
Photomicrograph Imaged captured of a small object under magnification through an optical microscope.
Pseudopolymorphism Different crystal structure attributed to the incorporation of molecular water or solvent.
Solvates Contains a molecule of solvent in the crystal lattice.
Thermogram Differential scanning calorimetry trace: heat flow on y-ordinate (mW), time (minutes)/temperature (° C.) on x-ordinate.

Summary

Compound 1·HCl polymorph screen was completed.

Form A, the stable form is fully characterized by $^1H$ NMR, Q $^1H$ NMR, DSC, TGA, DVS, PLM, SC-XRD and SIF buffer solubility and stability at 40° C./75% RH and 20° C./90%).[5]

[5] SIF buffer solubility and RH stability is reported in REP/PD/1190

Pattern #1 was the other form observed and was generated from heat-up/cool-down crystallization from acetonitrile/water and reverted to Form A upon drying;

Crystals of Pattern #1 were grown and were with the crystallographer at the time of writing this report, DSC analyses were attempted however, the onset coincided with Form A;

Full characterization of the scaled-up batch, including Q $^1H$ NMR, XRPD, TGA, DSC and PLM;

Qualitative solubility panel against 22 solvents (selected from Classes 1 and 2 ICH Q3C (R8) Residual solvents) was performed, showing that the API is soluble in polar and aqueous solvents at temperature;

Suspension equilibration panels in selected solvents at 20° C. and 40° C. delivered all outputs (wet and dry) as Form A;

Heat-up/cool-down crystallisation panel was completed, and XRPD analysis showed that Form A was mainly generated, apart from one hit (see above) that exhibited a metastable form (Pattern #1);

Preparation of Pattern #1 was repeated via controlled heat-up/cool-down crystallization from acetonitrile/water. XRPD analysis resembled Pattern #1 and contained Form A as the minor component;

The products retrieved from mechanochemical pulverization (LAG) were analyzed by XRPD and the phase of the products was consistent with the input (Form A), i.e., no polymorphic changes were observed under these conditions;

Form A was exposed at 20° C./95% RH conditions in both an open-capped and double bagged vials to assess its stability during a 10-day period. TG analyses did not show any water uptake;

DVS data of the stable form (Form A) were collected, indicating that the API is slightly hygroscopic, as it held on to a little water at 0 RH, however, the powder pattern of residue after DVS treatment was congruent with Form A;

Single crystal structure determination of Form A was successful.

Tables of Characterization

TABLE 119

Crystalline Compound 1 HCl Form A
Crystalline compound 1 HCl Form A

Molecular weight: 268.79 gmol$^{-1}$
Exact molecular weight: 268.1342
Molecular formula: $C_{14}H_3N_2O \bullet HCl$
Unary / mono chloride: 13.6% w/w th., hydrochloride (i.e., 1.0 mol of API to 1.0 mol of hydrochloride) The simulated powder pattern obtained from the single crystal structure was in good agreement with Form A, experimentally observed powder pattern of the bulk phase. Hence Form A counterion stoichiometry is the unary / mono hydrochloride salt in the orthorhombic space group $P2_12_12_1$.
Nature of hydrogen bonding: Intermolecular interactions in the form of hydrogen bonding were present in the structure, API and counterion, 2.190 Å (H2-C11) 3.055 Å ( N2-C11);
Crystal system 100(2) K: orthorhombic
Space group 100(2) K: $P2_12_12_1$
Unit cell 100(2) K: a = 6.86590(10) Å, b = 7.34760(10) Å, c = 27.5044(2) Å, a = b = g = 90°, V = 1387.54(3) Å$^3$
Asymmetric unit: contained one molecule of API and one molecule of hydrochloride (Z' = 1, crystal bonded).
XRPD: 12.4°, 12.8°, 13.6°, 17.6°, 17.9°, 18.1°, 18.7°, 20.0°, 20.5°, 21.8°, 23.1°, 24.9°, 25.5°, 25.9°, 27.4°, 29.0°, 30.4 (2θ, 1 d.p),
DSC: onset 200.03° C. (-156.82 Jg$^{-1}$, endotherm,melt ); suspected to exhibit peritectic dehydration by thermal microscopy.
TGA: onset 243.12° C. (-78.08% w/w, ablation).
DVS 0 to 90 to 0% RH (dm/dt <0.002%): 0.0 (0.0011%), 5.0 (0.0078%), 10.0 (0.0161%), 15.0 (0.0248%), 20.0 (0.0329%), 25.0, (0.0379%), 30.0 (0.0462%), 40.0 (0.0659%), 50.0 (0.0961%), 60,0 (0.1388%), 70.0 (0.1902%), 80.0 (0.2647%), 90.0 (0.4599%), 80.0 (0.2935%), 70.0 (0.2211%), 60.0 (0.1671%), 50.0 (0.1367%), 40.0 (0.0968%), 30.0 (0.0860%), 25.0 (0.0714%), 20.0 (0.0648%), 15.0 (0.0547%), 10.0 (0.0455%), 5.0 (0.0344%), 0.0 (0.0239%)
UV chromatographic purity: 99.60% area (254 nm)
$^1$H NMR: (DMSO-d6, 400 MHZ); δ 11.2 (s, 1H), 7.6 (d, J = 8.9 Hz, 1 H), 7.4 (d, J = 3.1 Hz, 1H), 7.1 (d, J = 2.4 Hz, 1H), 6.8 (dd, J = 8.9, 2.4 Hz, 1H), 6.4 (dd, J = 3.1, 0.6 Hz, 1H), 4.7 (dd, J = 13.7, 4.2 Hz, 1H), 4.3 (dd, J = 14.1, 9.8 Hz, 1H), 3.7 (s, 4H), 2.7 (dd, J = 19.2, 4.9 Hz, 6H), 1.1 (d, J = 6.6 Hz, 3H); ppm; conforms to the molecular structure (Σ21H).
Q $^1$H NMR: 99.5% w/w
Appearance: Refer to
Solubility in SIF buffers: Soluble in all SIF buffers at 37° C. during 24 h.

TABLE 120

Crystalline Compound 1 HCl Form B
Crystalline Compound 1 HCl Form B

Molecular weight: 268.79 gmol$^{-1}$
Exact molecular weight: 268.1342
Molecular formula: $C_{14}H_{20}N_2O \bullet HCl$
XRPD: 6.7°, 12.5°, 12.6°, 13.0°, 13.9°, 18.0°, 18.3°, 18.9°, 22.0°, 25.0°, 25.1°, 26.0°, 26.1°, 27.6°, 29.2°, 30.6°, 32.5°, 39.2° (2θ, 1 d.p)
DSC: onset 203.4° C. (-137.4 Jg$^{-1}$, endotherm, melt)
$^1$H NMR: (DMSO-d6, 400 MHZ); 11.1 (s, 1H), 7.6 (d, J = 8.9 Hz, 1 H), 7.4 (d, J = 3.1 Hz, 1H), 7.1 (d, ] = 2.4 Hz, 1H), 6.8 (dd, J = 8.9, 2.4 Hz, 1H), 6.4 (dd, J = 3.1, 0.6 Hz, 1H), 4.7 (dd, J = 13.7, 4.2 Hz, 1H), 4.3 (dd, J = 14.1, 9.8 Hz, 1H), 3.7 (s, 4H), 2.7 (dd, J = 19.2, 4.9 Hz, 6H), 1.1 (d, J = 6.6 Hz, 3H); ppm; conforms to the molecular structure (Σ21H)

Qualitative Solubility Screen:

Note: For this experiment a scale up of the compound 1 HCl salt was performed. The product (5.16 g, 88% corr. yield) was analysed by DSC, TGA, $^1$H NMR and XRPD.

The qualitative solubility screen was carried out to determine the range of solvents incorporated into future suspension equilibration panels.

Products that crystallized were centrifuged and analyzed as wet pellet by XRPD, dried under reduced pressure and re-analyzed by XRPD, with selected samples further analyzed by TGA and $^1$H NMR spectroscopy.

Compound 1 HCl was readily soluble in polar solvents and solvents with high water activity (refer to Table 122, ~25 mg of starting salt was used).

TABLE 122

Solubility Screen of Compound 1 HCl

| Solvent | ICH Class | 5 vol | | | | 10 vol | | | | 15 vol | | | | 20 vol | | | | XRPD (moist pellet) | XRPD (dried pellet) |
|---|---|---|---|---|---|---|---|---|---|---|---|---|---|---|---|---|---|---|---|
| | | Solution at | | reflux | Solid on cooling | Solution at | | reflux | Solid on cooling? | Solution at | | reflux | Solid on cooling | Solution at | | reflux | Solid on cooling | | |
| | | 20° C. | 40° C. | | | 20° C. | 40° C. | | | 20° C. | 40° C. | | | 20° C. | 40° C. | | | | |
| Acetone | 3 | x | x | x | — | x | x | x | — | x | x | x | — | x | x | x | — | Form A | Form A |
| MeCN | 2 | x | x | x | — | x | x | x | — | x | x | P | ✓ | x | x | P | ✓ | Form A | Insuff. mat. |
| TBME | 3 | x | x | x | — | x | x | x | — | x | x | x | — | x | x | x | — | Form A | Insuff. mat. |
| Chlorobenzene | 2 | x | x | x | — | x | x | x | — | x | x | x | — | x | x | x | — | Paste | Form A |
| DCM | 2 | x | x | x | — | x | x | x | — | x | x | x | — | x | x | x | — | Form A | Insuff. mat. |
| EtOH | 3 | x | x | x | — | x | x | x | — | x | x | P | ✓ | x | x | P | ✓ | Form A | Form A |
| EtOAc | 3 | x | x | x | — | x | x | x | — | x | x | x | — | x | x | x | — | Form A | Insuff. mat. |
| Ethyl formate | 3 | x | x | x | — | x | x | x | — | x | x | x | — | x | x | x | — | Form A | Insuff. mat. |
| Heptane | 3 | x | x | x | — | x | x | x | — | x | x | x | — | x | x | x | — | Form A | Insuff. mat. |
| Isopropyl acetate | 3 | x | x | x | — | x | x | x | — | — | — | — | — | — | — | — | — | | Insuff. mat. |
| MeOH | 2 | x | x | x | — | x | P | ✓ | — | — | — | — | — | — | — | — | — | Solution | Insuff. mat. |
| Methyl acetate | 3 | x | x | x | — | x | x | x | — | x | x | x | — | x | x | x | — | Paste | Form A |
| MEK | 3 | x | x | x | — | x | x | x | — | x | x | x | — | x | x | x | — | Paste | Form A |
| MeTHF | # | x | x | x | — | x | x | x | — | x | x | ✓ | — | x | x | x | — | Paste | Form A |
| Nitromethane | 2 | x | x | x | — | x | P | P | ✓ | x | P | P | — | — | — | — | — | Paste | Form A |
| 2-Propanol | 3 | x | x | x | — | x | P | ✓ | ✓ | P | ✓ | ✓ | — | — | — | — | — | Paste | Form A |
| THF | 2 | x | x | x | — | x | x | x | — | x | x | x | — | x | x | x | — | Paste | Insuff. mat. |
| Toluene | 2 | x | x | x | — | x | x | x | — | x | x | x | — | x | x | x | — | Paste | Form A |
| Water | # | ✓ | — | — | ✓ | — | — | — | — | — | — | — | — | — | — | — | — | Solution | Insuff. mat. |
| Acetone/Water (5% v/v, 0.5 aw) | 2 | x | x | P | ✓ | x | P | ✓ | — | — | — | — | — | — | — | — | — | Solution | Insuff. mat. |
| Ethanol/Water (15% v/v, 0.5 aw) | 2 | x | x | ✓ | ✓ | ✓ | — | ✓ | — | — | — | — | — | — | — | — | — | | Insuff. mat. |
| Isopropanol/Water (12%, v/v, 0.5 aw) | 2 | x | x | P | ✓ | x | x | ✓ | — | — | — | — | — | — | — | — | — | Solution | Insuff. mat. |

Suspension Equilibration at 20 and 40° C.

Suspension equilibration is a thermodynamic dwelling technique, designed to promote the evolution of the API into a more stable phase. The purpose of this panel was to determine if Form A evolves into a supra-ordinate form, the companion panel at 40° C. set-point was in place to detect enantiotropic behavior via different relative proportions in different solvents.

All isolated products, both wet and dry were consistent with Form A at both temperatures. The experimental details are summarized in Tables 106 and 107.

TABLE 106

Stable form suspension equilibration panel—Compound 1 HCl salt was the input salt at the indicated weight.

| Input Weight (mg) | Solvent (5.0 vol) | XRPD (Input) | Observations (t = 0 @ 20° C.) | Observations (t = 1 d @ 20° C.) | Observations (t = 10 d @ 20° C.) | XRPD (IPC, 6 d, wet) | XRPD (post oven dried, 40° C. 20 h) |
|---|---|---|---|---|---|---|---|
| 50.4 | Acetone | Form A | Suspension | Suspension | White Paste | Form A | Form A |
| 50.3 | MeCN | Form A | Suspension | Suspension | White Paste | Form A | Form A |
| 50.3 | TBME | Form A | Suspension | Suspension | White Paste | Form A | Form A |
| 50.4 | Chlorobenzene | Form A | Suspension | Suspension | White Suspension | Form A | Form A |
| 49.9 | DCM | Form A | Suspension | Suspension | Pink paste | Form A | Form A |
| 50.0 | EtOH | Form A | Suspension | Suspension | Pink paste | Form A | Form A |
| 49.7 | EtOAc | Form A | Suspension | Suspension | White paste | Form A | Form A |
| 50.0 | Ethyl formate | Form A | Suspension | Suspension | White suspension | Form A | Form A |
| 49.2 | Heptane | Form A | Suspension | Suspension | White suspension | Form A | Form A |
| 50.0 | Isopropyl acetate | Form A | Suspension | Suspension | White suspension | Form A | Form A |
| 50.4 | MeOH | Form A | Suspension | Suspension | Orange suspension | Form A | Form A |
| 49.7 | Methyl acetate | Form A | Suspension | Suspension | White suspension | Form A | Form A |
| 49.8 | MEK | Form A | Suspension | Suspension | Pink suspension | Form A | Form A |
| 49.9 | MeTHF | Form A | Suspension | Feint Suspension | White suspension | Form A | Form A |
| 49.1 | Nitromethane | Form A | Suspension | Feint Suspension | Pink suspension | Form A | Form A |
| 49.3 | 2-Propanol | Form A | Suspension | Feint Suspension | White suspension | Form A | Form A |
| 49.2 | THF | Form A | Suspension | Feint Suspension | Pink suspension | Form A | Form A |
| 50.4 | Toluene | Form A | Suspension | Feint Suspension | White suspension | Form A | Form A |
| 49.6 | Water | Form A | Solution | Solution | Yellow suspension | Form A | Form A |
| 50.2 | Acetone/Water (5% v/v, 0.5 aw) | Form A | Suspension | Suspension | Pink paste | Form A | Form A |
| 50 | Ethanol/Water (15% v/v, 0.5 aw) | Form A | Suspension | Orange Partial | Pink suspension | Form A | Form A |
| 50.2 | Isopropanol/Water (12% v/v, 0.5 aw) | Form A | Suspension | Partial | Pink suspension | Form A | Form A |

TABLE 107 stable form suspension equilibration panel at 40° C.

| Input Weight (mg) | Solvent (5.0 vol) | XRPD (Input) | Observations (t = 0 @ 20° C.) | Observations (t = 1 d @ 20° C.) | Observations (t = 10 d @ 20° C.) | XRPD (IPC, 6 d, wet) | XRPD (post oven dried, 40° C., 20 h) |
|---|---|---|---|---|---|---|---|
| 50.2 | Acetone | Form A | Suspension | Suspension | Yellow susp. | Form A | Form A |

TABLE 107-continued stable form suspension equilibration panel at 40° C.

| Input Weight (mg) | Solvent (5.0 vol) | XRPD (Input) | Observations (t = 0 @ 20° C.) | Observations (t = 1 d @ 20° C. | Observations (t = 10 d @ 20° C.) | XRPD (IPC, 6 d, wet) | XRPD (post oven dried, 40° C., 20 h) |
|---|---|---|---|---|---|---|---|
| 50.2 | Acetonitrile | Form A | Suspension | Suspension | Pink suspension | Form A | Form A |
| 50.0 | tBME | Form A | Suspension | Suspension | White suspension | Form A | Form A |
| 49.9 | Chlorobenzene | Form A | Suspension | Suspension | White suspension | Form A | Form A |
| 49.8 | DCM | Form A | Suspension | Suspension | White suspension | Form A | Form A |
| 50.4 | Ethanol | Form A | Suspension | Suspension | Pink suspension | Form A | Form A |
| 49.7 | Ethyl acetate | Form A | Suspension | Suspension | White suspension | Form A | Form A |
| 49.8 | Ethyl formate | Form A | Suspension | Suspension | White suspension | Form A | Form A |
| 49.6 | Heptane | Form A | Suspension | Suspension | White suspension | Form A | Form A |
| 50.1 | Isopropyl acetate | Form A | Suspension | Suspension | White suspension | Form A | Form A |
| 50.0 | Methanol | Form A | Suspension | Suspension | Orange suspension | Form A | Form A |
| 50.0 | Methyl acetate | Form A | Suspension | Suspension | Pink suspension | Form A | Form A |
| 49.9 | MEK | Form A | Suspension | Suspension | Pink suspension | Form A | Form A |
| 49.8 | MeTHF | Form A | Suspension | Suspension | White suspension | Form A | Form A |
| 50.1 | Nitromethane | Form A | Suspension | Suspension | White suspension | Form A | Form A |
| 50.0 | 2-Propanol | Form A | Suspension | Suspension | White suspension | Form A | Form A |
| 50.1 | THF | Form A | Suspension | Suspension | Pink suspension | Form A | Form A |
| 50.0 | Toluene | | Suspension | Suspension | Pink suspension | Form A | Form A |
| 49.8 | Water | Form A | Solution | Darkened solution | Orange susp. | Form A | Insuff mat |
| 49.5 | Acetone/Water (5% v/v, 0.5 aw) | Form A | Suspension | Feint suspension | Orange suspension | — | Form A |
| 49.8 | Ethanol/Water (15% v/v, 0.5 aw) | Form A | Feint suspension | Feint suspension | Orange suspension | Form A | Form A |
| 50.2 | Isopropanol/Water (12% v/v, 0.5 aw) | Form A | Suspension | Feint suspension | Yellow suspension | Form A | Form A |

Heal-up/Cool-Down Crystallization Screen

A heat up/cool down crystallization screen was performed. An compound 1 HCl Form A was used as input material.

The experiment was repeated to prepare Pattern #1 at larger quantities to obtain thermal data before conversion into Form A occurred. To achieve that, prolonged filtration was performed instead of oven-drying.

The experimental details are summarized in Table 108.

TABLE 108

Heat up/cool-down crystallization screen

| Input Weights (mg) | Solvent A (3.0 vol) | Solvent B | Co-solvents (volumes added, μl) | Key chemical functional groups | b.p. (° C.) | ICH Classes | Observations (t = -, T = 70° C.) | XRPD (Moist pellet) | XRPD (oven dried) |
|---|---|---|---|---|---|---|---|---|---|
| 74.7 | Acetone | Water | 50 | Symmetrical ketone | 56 | 3 | Pink solution | Form A | Form A |
| 75.2 | MeCN | Water | 25 | Simple dipolar-aprotic nitrile | 82 | 2 | Pink solution | Pattern #1 | Form A |
| 75.8 | TBME | MeOH | 425 | Branched aliphatic methoxyether | 55 | 3 | Pink solution | Form A | Form A |

TABLE 108-continued

Heat up/cool-down crystallization screen

| Input Weights (mg) | Solvent A (3.0 vol) | Solvent B | Co-solvents (volumes added, μl) | Key chemical functional groups | b.p. (° C.) | ICH Classes | Observations (t = -, T = 70° C.) | XRPD (Moist pellet) | XRPD (oven dried) |
|---|---|---|---|---|---|---|---|---|---|
| 75.3 | Chlorobenzene | MeOH | 175 | Aromatic halide | 131 | 2 | Pink solution | Form A | Form A |
| 75.5 | DCM | MeOH | 125 | Chlorinated hydrocarbon | 40 | 2 | Pink solution | Form A | Form A |
| 74.4 | EtOH | Water | 50 | Linear aliphatic alcohol | 78 | 3 | Pink solution | Form A | Form A |
| 74.8 | EtOAc | EtOH | 1375 | Aliphatic ester | 75 | 3 | Pink solution | Form A | Form A |
| 74.4 | Ethyl formate | MeOH | 225 | Aliphatic ester | 54 | 3 | Pink solution | Form A | Form A |
| 74.8 | Isopropyl acetate | IPA | 3725 | Branched aliphatic ester | 89 | 3 | Suspension | Form A | Form A |
| 75.4 | MeOH | water | 25 | Simple aliphatic alcohol | 65 | 2 | Pink solution | Form A | Form A |
| 75.4 | Methyl acetate | Water | 75 | Aliphatic ester | 57 | 3 | Pink solution | Insuff. material | Insuff. material |
| 75.3 | MEK | Water | 50 | Asymmetric dialkyl ketone | 80 | 3 | Pink solution | Form A | Form A |
| 75.5 | MeTHF | MeOH | 425 | Asummetric cyclic ether | 80 | | Pink solution | Form A | Form A |
| 75.4 | Nitromethane | MeOH | 50 | Dipolar aprotic nitro | 100 | 2 | Pink solution | Form A | Form A |
| 74.5 | 2-Propanol | Water | 75 | Branched aliphatic alcohol | 83 | 3 | Pink solution | Form A | Form A |
| 75.5 | THE | Water | 50 | Symmetric cyclic ether | 66 | 2 | Pink solution | Form A | Form A |
| 75.5 | Toluene | MeOH | 200 | Alkyl aromatic hydrocarbon | 111 | 2 | Pink solution | Form A | Form A |
| 75.5 | Water | — | — | Water | 100 | # | Pink solution | Insuff. material | Insuff. material |

Wet pellets were analysed by XRPD, a different diffraction pattern was obtained from acetonitrile/water (Pattern #1), that corresponded to a metastable form and reverted to Form A during oven drying. (FIG. 299).

First Attempt: Re-Preparation of Pattern 41

Attempts were made to re-prepare pattern 1 using the methods from Table 108 that initially resulted in pattern 1. The experiment was performed on 75 mg scale. The isolation and drying were carried-out using a Hirsch funnel, and gave insufficient recovered material to perform full analysis.

Therefore, the preparation was repeated, under the same conditions, with isolation via centrifuge, followed by drying under steady $N_2$ flux, with IPC on the wet pellet performed after 30 min (Congruent with Form A).

Drying continued 2 h and yielded enough material to perform full characterisation. This experiment was not successful in giving Pattern #1 because the product reverted to Form A, this serves to highlight the metastability of Pattern #1. Companion analytical data are reported in FIG. 357.

Second Attempt: Re-Preparation of Pattern #1

HUCD crystallization from acetonitrile/water was repeated to generate Pattern #1.

Initial attempt gave Form A.

Third Attempt: Re-preparation of Pattern #1

Preparation was repeated via controlled heat-up/cool-down performed on the crystalline batch, which successfully delivered Pattern #, Form B (see FIG. 303). The procedure heated the sample 20-70° C. at 0.5° C. per minute which was held for 30 minutes and was cooled 70-10° C. at 0.1° C./min O/N.

Experimental Details:

Crystalline compound 1 HCl Form A (ca 50.4 mg, 1.0 wt) was charged to a vial. The acetonitrile (0.150 ml, 3.0 vol) was added to the appropriate vial and the suspension were stirred and heated to 70° C. Water was added in aliquots of 10 μL to complete dissolution (total: 20 μL). 30 The solution was stirred at 70° C. for 30 min to ensure full dissolution. Once dissolved, the solution was left to cool down to ambient and then placed in the fridge overnight.

Specimen quality was determined by PLM and SC-XRD is judged achievable. The DSC profile was measured (FIG. 303). DSC (203.4° C., −137.4 $Jg^{-1}$), was similar to Form A (200.0° C., −156.8 $Jg^{-1}$), currently, an explanation would be conversion to Form A during sample preparation (FIGS. 304-305).

Binary Solvent Evaporation Crystallization

A binary solvent evaporation crystallization panel was performed. Separate portions of Compound 1 HCl 50 mg) were dissolved in a primary solvent of water (500 μl per sample) and a secondary solvent—one of either acetone (250 μl, A), acetonitrile (250 μl, B), THF (250 μl, C) and methanol (250 μl, D).

Each vial was capped with aluminium foil, pieced and allowed to stand undisturbed until the evaporation was completed. Experimental details are included in Table 109.

TABLE 109

Binary Solvent Evaporation Crystallization

| | Input Weights (mg) | Solvent A (10.0 vol) | Co-solvent B | Co-solvents (vol. μL) | b.p. (° C.) | ICH classes | Observations (t = 7 days @ ambient) | Observations (t = 14 days @ ambient) | Yield % | $^1$H NMR (Mol. Struc.) | XRPD |
|---|---|---|---|---|---|---|---|---|---|---|---|
| A | 50.3 | Water | Acetone | 250 | 56 | 3 | Concentrated solution | Solid | 82.5% | concordant | Form A |
| B | 50.4 | Water | Acetonitrile | 250 | 81 | 2 | Concentrated solution | Solid | 78.8% | concordant | Form A |
| C | 50.1 | Water | THF | 250 | 65 | 2 | Concentrated solution | Solid | 99.4% | concordant | Form A |
| D | 49.9 | Water | Methanol | 250 | 65 | 1 | Concentrated solution | Solid | 84.2% | concordant | Form A |

Companion analytical data are reported in FIGS. 306-321.

Equilibrium Humidity Evaluation of Crystalline Compound 1 HCl Form A

The stability of crystalline compound 1 HCl Form A was evaluated. Absorbent compound 1·Cl (Form A), (100 mg) was maintained, open-capped at 95% RH/20° C. and monitored at t=0, t=5 d and t=10 d, time points.

While absorbent Compound 1 HCl Form A), (100 mg) was placed open-capped inside double, cable-tied, electrostatic polythene bags (to mimic a typical packaging configuration) and placed inside the same humidity chamber at 95% RH at 20° C. and monitored at t=0, t=5 d and t=10 d time points. Companion analytical data is reported in FIGS. 322-330. Stability of compound 1·HCl (Form A) at 40° C./75% RH was examined as part of the salt screen, and was stable over 10 d.

TABLE 110

Equilibrium humidity stability t = 0 to 5 days, 95% RH @ 20° C.

T = 0 to 5 days, 95% RH @ 20 ° C.

| Experimental Reference | Input (mg) | XRPD (t = 0) | XRPD (t = 5 d) | XRPD (t = 10 d) |
|---|---|---|---|---|
| Open vial | 102.1 | Form A | Form A | Form A |
| Double polyethylene bagged, open vial | 102.5 | Form A | Form A | Form A | t = 10 days, 95 % RH @ 20° C.

| Experimental Reference | $^1$H NMR methanol (% w/w) | TGA 20 to 200 ° C. (° C., -% w/w) | XRPD | DSC onset, $\Delta H_{fus}$ (° C., Jg-1) |
|---|---|---|---|---|
| Open vial | n.d. | Flat base line, anhydrous | Form A | 204.4 °° C. (131.85) |
| Double polyethylene bagged, open vial | n.d. | Flat base line, anhydrous | Form A | 203.7 °° C. (-132.92) |

TABLE 111

Purify data for crystalline compound 1 HCl Form A after 10 days in an open-capped vial inside double bags at 95% RH/20

| RRT—HPLC analysis (MET/CR/0000) | Area (mAu*) for reference | | | | | | | |
|---|---|---|---|---|---|---|---|---|
| | | 11.29 | 11.41 | 12.41 | 14.32 | 15.05 | 15.41 | 15.78 | 16,50 |
| | RRT = 1.00 | 0.93 | 0.94 | 1.00 | 1.18 | 1.24 | 1.27 | 1.30 | 1.36 |
| Compound 1 HCl (t = 0) | 46522.72 | | 0.07 | 99.65 | 0.03 | 0.05 | 0.07 | 0.04 | 0.08 |
| Compound 1 HCl (t = 10 d) | 20556.47 | 0.06 | 0.02 | 99.79 | 0.03 | 0.04 | 0.02 | | |

TABLE 112

Purify data for crystalline compound 1 HCl Form A after 10 days in an open-capped vial inside double bags at 95% RH/20

| RRT—HPLC analysis (MET/CR/0000) | Area (mAu*) for reference RRT = 1.00 | 11.41 0.94 | 12.01 0.99 | 12.14 1.00 | 14.32 1.18 | 14.68 1.21 | 15.05 1.24 | 15.41 1.27 | 15.78 1.30 | 16.50 1.36 |
|---|---|---|---|---|---|---|---|---|---|---|
| Compound 1 HCl (t = 0) | 46522.72 | 0.07 | 0.02 | 99.65 | 0.03 | | 0.05 | 0.07 | 0.04 | 0.08 |
| Compound 1 HCl (t = 10 d) | 19289.46 | 0.06 | 0.02 | 99.78 | 0.03 | 0.03 | 0.05 | 0.01 | 0.02 | |

Liquid Assisted Grinding and Neat Pulverization

Liquid assisted grinding and neat pulverization experiments were performed.

Separate portions of crystalline compound 1 HCl Form A (50 mg) were pulverized in the presence in water (25 μl, η=0.5), trifluoroethanol (25 μl, η=0.5) as well as under neat-grind conditions.

A single 7 mm steel bead was added to each reactor, after which they were sealed, and oscillated for 30 minutes at 8.0 Hz (ca. 500 rpm).

The products were retrieved and analysed by XRPD, the phase of the products was consistent with the input (Form A), i.e., no polymorphic changes were observed under these conditions.

Since the oscillations input a large amount of kinetic and mechanical energy and are designed to promote chemical and physical change, the products were also analyzed by $^1$H NMR spectroscopy (refer to FIG. 358), no significant chemical changes were observed.

LAG Grinding at 500 rpm was carried out under neat and liquid assisted grinding conditions.

DSC analyses of the product that employed trifluoroethanol as the liquid assist, exhibited a probable crystallisation event (FIG. 359), the analyses was repeated at the later time point and the first endotherm was absent (probably crystallisation of amorphous phase, see FIG. 360), and the fusion temperature remained consistent with Form A.

DVS Analysis

DVS analysis dm/dt 0.0002%/min of crystalline compound 1 HCl Form A was performed. Mass equilibration was enabled in between % RH stepped increments and decrements. Slightly hygroscopic, held on to a little water at 0% RH, powder pattern of residue after DVS treatment was congruent with Form A (FIGS. 331, 332, and 361).

Single Crystal Structure Determination Form A

Single crystals of the API were grown by evaporation of a DCM solution (initial 100 vol). The simulated powder pattern from single crystal structure was in good agreement with Form A powder pattern and explained the powder pattern observed in the bulk phase (FIGS. 362-363).

The information obtained from the SC-XRD data (refer to FIGS. 335-337) were the following:

The final refinement yielded the structure of the unary hydrochloride salt in the orthorhombic space group $P2_12_12_1$.

Z'=1 (asymmetric unit), one molecule of API and one molecule of hydrochloride.

With Z=4 molecules of API within the unit cell; there were no other molecules present in the structure (no solvent).

Intermolecular interactions in the form of hydrogen bonding were present in the structure, API and counterion, 2.190 Å (H2-Cl1) 3.055 Å(N2-Cl1).

No significant π-π stacking interactions were present in the structure.

Void analysis of the structure indicated a maximum probe radius of 0.7 Å that was too small for solvent molecules to occupy: meaning channel and pocket hydrates are less likely to occur.

The final refinement yielded the structure of the unary fumarate salt in the orthorhombic space group $P2_12_12_1$. Z'=1 (asymmetric unit), one molecule of API and one molecule of fumarate. With Z=4 molecules of API within the unit cell; there were no other molecules present in the structure (no solvent). Intermolecular interactions in the form of hydrogen bonding were present in the structure, API and counterion, 2.656 Å (N2-O2) and 2.590 Å (O3-O5); giving the chain-like structure observed in the image. No significant π-π stacking interactions were present in the structure. Void analysis, indicated a maximum probe radius of 0.93 Å, that was too small for solvent molecules to occupy; meaning channel and pocket hydrates are less likely to occur.

Single Crystal Structure Determination—Form B

A sample of Form B was submitted to the UK National Crystallography Service to collect SC-XRD data for Form B, Pattern #1. The simulated powder diffraction pattern resembled Form A (refer to FIG. 364). This signifies the metastability of Form B, as the sample was converted to stable Form A during transit.

Example 13. Attempted Formation of a Crystalline Compound 1 Fumarate Salt by Way of Dissolution in Chloroform and Dropwise Addition to Fumaric Acid in THF A previously published method that allegedly formed a solid compound 1 fumarate salt was reproduced and did not yield a crystalline compound 1 fumarate salt. By contrast, new methods disclosed herein did produce a crystalline compound 1 fumarate salt.

Previously Published Method:

[(2R)-1-(5-Methoxy-1H-indol-1-yl)propan-2-yl]dimethylamine (7.61 g, 32.8 mmol) was dissolved in chloroform (50 mL). This solution was added dropwise to a boiling solution of fumaric acid (3.80 g, 32.8 mmol) in THF (150 mL). The resulting solution was allowed to cool to rt and then concentrated in vacuo. Upon prolonged rotary evaporation (water bath temperature 50° C.) a brittle brown foam formed in the flask. This foam was crushed with a spatula to afford the title compound (11.8 g) as a pale brown solid. Retention time 1.094 min; Purity by UV (225 nm+/−50) =98.8%; Calculated for $[C14H20N2O]^+$ 233.3; found 233.2; $^1$H NMR (400 MHz, DMSO-d$_6$) δ 7.37 (d, J=8.9 Hz, 1H), 7.29 (d, J=3.0 Hz, 1H), 7.04 (d, J=2.4 Hz, 1H), 6.77 (dd, J=8.9, 2.5 Hz, 1H), 6.60 (s, 2H), 6.33 (dd, J=3.1, 0.8 Hz, 1H), 4.26 (dd, J=14.2, 6.2 Hz, 1H), 4.02 (dd, J=14.2, 7.9 Hz, 1H), 3.75 (s, 3H), 3.12 (dp, J=7.9, 6.5 Hz, 1H), 2.31 (s, 6H), 0.85 (d, J=6.6 Hz, 3H). XRPD analysis showed this material was amorphous (FIG. 350).

New Method Disclosed Herein:

A solution of [(2R)-1-(5-methoxy-1H-indol-1-yl)propan-2-yl]dimethylamine (7.14 g, 30.7 mmol) in chloroform (50 mL) was added to a boiling solution of fumaric acid (3.57 g, 30.7 mmol) in THF (150 mL). The solution was then concentrated in vacuo to a viscous brown oil. This material was dissolved in methyl ethyl ketone, also known as 2-butanone (MEK; 25 mL), with sonication, and to the stirring solution was added crystals (ca. 10 mg) of [(2R)-1-(5-methoxy-1H-indol-1-yl)propan-2-yl]dimethylamine fumarate salt (polymorph form A). A fine precipitate was observed after 10 min. The suspension was stirred for 24 hours at rt. The solid was isolated by filtration and the filter cake was washed with MEK (ca. 5 mL). The salt was air dried on the filter for 20 min and then dried in a vacuum oven over a weekend at 40° C. The title compound was obtained as an off-white solid (8.1 g, 75%). Retention time 1.141 minutes; Purity by UV (225 nm+/−50)=98%; Calculated for $[C_{14}H_{20}N_2O]^+$ 233.3; found 233.2; $^1$H NMR (400 MHz, DMSO-$d_6$) δ 7.35 (d, J=8.8 Hz, 1H), 7.29 (d, J=3.0 Hz, 1H), 7.03 (d, 1=2.4 Hz, 1H), 6.76 (dd, J=8.9, 2.5 Hz, 1H), 6.60 (s, 2H), 6.32 (dd, J=3.1, 0.8 Hz, 1H), 4.23 (dd, J=14.2, 6.4 Hz, 1H), 4.00 (dd, J=14.2, 7.7 Hz, 1H), 3.75 (s, 3H), 3.07 (dt, J=7.6, 6.4 Hz, 1H), 2.27 (s, 6H), 0.84 (d, J=6.6 Hz, 3H). XRPD analysis showed that this material was crystalline compound 1 fumarate Form A (FIGS. 351—sample 1, and FIG. 352—sample 2), as the XRPD profile corresponded to the representative XRPD pattern for compound 1 fumarate Form A that is characterized in FIG. 8, and Table 6. The XRPD signals observed for the profiles shown in FIGS. 351 and 352 are provided below.

TABLE 116

Crystalline Compound 1 Fumarate XRPD signals (±0.2 °2θ; ±0.1 °2θ; or ±0.0 °2θ; Cu Kα1 radiation) observed for sample #1 produced by a method disclosed herein.

| Signal No. | Position. [°2θ] | d-spacing [Å] | Relative Intensity [%] |
|---|---|---|---|
| 1 | 10.2118 | 8.65535 | 18.19 |
| 2 | 13.4987 | 6.55428 | 43.98 |
| 3 | 14.1419 | 6.25761 | 55.37 |
| 4 | 15.6865 | 5.64474 | 21.11 |
| 5 | 16.0097 | 5.5315 | 67.09 |
| 6 | 18.5332 | 4.78363 | 19.71 |
| 7 | 19.0629 | 4.65188 | 21.73 |
| 8 | 19.526 | 4.54259 | 41.34 |
| 9 | 20.9831 | 4.2303 | 27.12 |
| 10 | 21.3971 | 4.14939 | 29.15 |
| 11 | 21.6587 | 4.09986 | 36.3 |
| 12 | 22.4904 | 3.95009 | 100 |
| 13 | 23.2901 | 3.81622 | 12.15 |
| 14 | 24.5427 | 3.62422 | 10.23 |
| 15 | 25.1714 | 3.53511 | 10.3 |
| 16 | 28.2412 | 3.15743 | 15.82 |
| 17 | 29.1829 | 3.05765 | 13.51 |

TABLE 117

Crystalline Compound 1 Fumarate XRPD signals (±0.2 °2θ; ±0.1 °2θ; or ±0.0 °2θ; Cu Kα1 radiation) observed for sample #2 produced by a method disclosed herein.

| Signal No. | Position [°2θ] | d-spacing [Å] | Relative Intensity [%] |
|---|---|---|---|
| 1 | 10.2121 | 8.65507 | 17.73 |
| 2 | 13.5021 | 6.55265 | 41.1 |
| 3 | 14.1435 | 6.25689 | 50.24 |
| 4 | 15.7017 | 5.63931 | 20.51 |
| 5 | 16.0141 | 5.52998 | 64.28 |
| 6 | 18.5312 | 4.78413 | 19.76 |
| 7 | 19.0784 | 4.64812 | 22.95 |
| 8 | 19.5294 | 4.54179 | 35.8 |
| 9 | 20.9861 | 4.22971 | 27.92 |
| 10 | 21.4019 | 4.14847 | 29.07 |
| 11 | 21.6681 | 4.09811 | 33.8 |
| 12 | 22.4888 | 3.95036 | 100 |
| 13 | 23.2878 | 3.81661 | 13.57 |
| 14 | 24.5339 | 3.6255 | 10.59 |
| 15 | 25.1566 | 3.53715 | 13.37 |
| 16 | 28.2376 | 3.15782 | 16.44 |
| 17 | 29.1788 | 3.05808 | 14.71 |

Example 14: Preparation and Characterization of Amorphous Forms of Compound 1 Fumarate and Compound 1 HCl Abbreviations $\varphi_i$ Water activity coefficient
$a_w$ Water activity
ASD Amorphous solid dispersion
ca circa (Latin: approximately)
cf. Confer/conferatur (Latin: to confer, to compare)
° C. degree Celsius
CP Chemical Purity
CP-MAS Cross Polarised Magic Angle Spinning ($^{13}C$ NMR solid state technique)
Da Dalton
DSC Differential Scanning Calorinmetry (measures changes in heat capacity)
DTA Differential Thermal Analyses (measures changes in temperature)
DVS Dynamic Vapour Sorption (used interchangeably with GVS)
e.g. Exempli gratia (Latin: for example)
etc. Et cetera (Latin: 'and others' or 'and so on')
FT-IR Fourier Transformed, InfraRed spectroscopy (prefixed mid and far)
g Gram (s)
GRAS Generally Recognised As Safe
GVS Gravimetric Vapour Sorption
h Hour (s)
HFIPA Hexafluoroisopropanol
HPLC High Performance Liquid Chromatography
HSM Hot Stage Microscopy (thermal microscopy)
HUCD Heat-up/cool-down crystallisation
i.e. Id Est (Latin: that is)
IR InfraRed Spectroscopy
J Joule
Kelvin Kelvin. SI unit of temperature, used interchangeably with ° C. to express increment/decrement of temperature set point (e.g. ramp rate on DSC thermogram 10 K/min): note K sign not prefixed by.
KF Karl Fischer (determination of the water content by coulometric titration)
kg Kilogram (s)
LOD Loss On Drying
mag magnification
mAu milli·Absorption units (chronatographic unit of peak height)
mAu*s milli·Absorption units multiplied by second (chromatographic unit of peak area)
MET/CR Aptuit chromatography method reference
min Minute (s)
mg Milligram (s)
ml Millilitre (s)
mol mole, amount of substance
N/A Not Applicable
n.a. not analysed
n.d. not detected
nm nanometre
NMR Nuclear Magnetic Resonance
oab on anhydrous basis
osfb on solvent free basis
oasfb on anhydrous solvent free basis
pH $-\log [H^+]$ or pH=$-\log a_H^+$
$pK_a$ $-\log (K_a)$, acid dissociation constant
pI isoelectric point. quoted in unit pH
PLM Polarised Light Microscopy
RelRT Relative Retention Time (not be confused RT)
REP/ Aptuit report (REP) reference
RFA Request For Analysis (unique reference number)
RH Relative Humidity ($a_w$*100)
RT Room Temperature (ambient, typically: 15 to 25° C.)
s Second (s)
SCXD Single Crystal X-Ray Determination
SMPT Solvent mediated phase tmnsition
STA Simulated Thermal Analysis (STA=TGA+DTA)
t time in seconds, minutes, hour, days etc. (interval specified in parentheses); alias in common use tonne (t)
t Tonne, metric unit of mass (1000 kg; 1 Mg), (compaction force in kg, suffixed in parentheses)
T Temperature recorded in degrees Celsius (° C.); alias in common use, SI unit of magnetic flux density, also denoted T
MTBE Methyl tert-butyl ether
TCNB 2,3,5,6-Tetrachloronitrobenzene ($C_6HCl_4NO_2$. F.W. 260.89 $gmol^{-1}$)
TFE Trifluoroethanol (solvent used for solvent drop grinding)
Tg Glass temperature
TGA Thermogravimetric Analysis
th. theoretical
UV Ultra Violet
vol. Volume or relative volume
vs. versus
v/v volume/volume
W Watt
w/w weight/weight
XRPD X-Ray Powder Diffraction Definitions Isostructural Crystals are said to be isostrctural if they have the same crystal structure but not necessarily the same cell dimensions nor the same chemical composition (Kálman, A., Párkányi, L. & Argay. G. (1993) Acta Cryst. B49, 1039-1049.)
Isomorphic two crystalline solids are isomorphotus if both have the same unit-cell dimensions and space group (source, vide supra).
Isomorphic desolvate via solvent release from an isostructural solvate.
Native Refers to an API in its native or non-ionised form.
Normal light Light oscillating in all directions perpendicular to the axis to which the it travels.
Particle size Expressed as a volume distribution, the range ×10>PSD<×90 captures the sizes of 80% of the particles.
Plane polarised light Light passed through a polaroid filter which allows only light oscillating in ore plane to be transmitted.
Polymorphism Crystalline solid able to exhibit different crystalline phases.
Photomicrograph Imaged captured of a small object under magnification through an optical microscope.
Pseudopolymorphism Different crystal structure attributed to the incorporation of molecular water or solvent.
Solvates Contains a molecule of solvent in the crystal lattice.
Themrogram Differential scanning calorimetry trace: heat flow on y-ordinate (nmW), time (minutes)/temperature (° C.) on x-ordinate.

Experimental

DSC:

A Mettler Toledo DSC 3 instrument was used for the thermal analysis operating with STARe™ software. The analysis was conducted in open aluminium pans (40 µl), under nitrogen and sample sizes ranged from 1 to 10 mg. Typical analysis method was 20 to 250° C. at 10° C./minute.

Alternatively, a Mettler Toledo DSC1 with auto-sampler instrument was used for the thermal analysis operating with STARe™ software. The analysis was conducted in open aluminium pans (40 µl), under nitrogen and sample sizes ranged from 1 to 10 mg. Typical analysis method was 25 to 300° C. at 10° C./minute.

LC-MS

Routine Liquid Chromatography-Mass Spectrometry (LC-MS) data were collected using the Agilent 1260 Infinity II interfaced with 1260 Infinity II DAD HS and Agilent series 1260 Infinity II binary pump.

The instrument used a single quadrupole InfinityLab MSD. The instrument was calibrated up to 2000 Da.

LC-MS method parameters:
Inj.vol: 5 µl
Detection: UV @ 254 nm
Mobile Phase A: Acetonitrile±0.1% TFA/$H_2O$ 95:5
Mobile Phase B: Acetonitrile±0.05% TFA/$H_2O$ 5:95

TABLE 127

LC/MS methods

| Time (mins) | % A | % B |
|---|---|---|
| 0.0 | 100 | 0 |
| 1 | 100 | 0 |
| 10.00 | 0 | 100 |
| 10.01 | 100 | 0 |
| 12.00 | 100 | 0 |

Flow Rate: 1 ml/min
Column temperature: 30° C.
Run time 12 minutes.

$^1$H NMR $^1$H NMR spectra were acquired using a Bruker 400 MHz spectrometer and data was processed using Topspin. Samples were prepared in DMSO-$d_6$ at typical concentrations of 10 to 20 mg/ml and up to 50 mg/ml for $^1$H NMR w/w assay and calibrated to the corresponding non-deuterated solvent residual at 2.50 ppm.

$^1$H NMR Assay

Assays (w/w) of API by $^1$H NMR spectroscopy were measured by the project chemist using Topspin. Internal standard 2,3,5,6-terachloronitrobenzene (TCNB, ca. 20 mg, F.W. 260.89) were dissolved in DMSO-$d_6$ (1.0 ml) and the $^1$H NMR spectrum was acquired using an extended relaxation method.

TGA

A Mettler Toledo TGA-2 instrument was used to measure the weight loss as a function of 25 temperature from 25 to 500° C. The scan rate was typically 5 or 10° C. per minute. Experiments and analysis were carried out using the STARe™ software. The analysis was conducted in 100 µl open aluminium pans, under nitrogen and sample sizes ranged from 1 to 10 mg.

XRPD

X-ray powder diffraction (XRPD) analysis was carried out using a Bruker D2 Phaser powder diffractometer equipped with a LynxEye detector. The specimens underwent minimum preparation but, if necessary, were lightly milled in a pestle and mortar before acquisition. The specimens were located at the centre of a silicon, low background, sample holder within a 5 mm pocket (ca. 5 to 10 mg). The samples were continuously spun during data collection and scanned using a step size of 0.02°2-theta (2θ) between the range of 4° to 40°2-theta or 5° to 60°2-theta. Data were acquired using either 3 minute or 10-minute acquisition methods. Bruker Diffrac.Suite was used to process the data.

Freeze Drying

Each salt was charged into a 7 ml vial (50 mg, 1 wt). Vials were charged with 10 vol water to fully dissolve the sample. Vials were placed on freeze drier overnight, and powders were recovered in each case. Analysis of samples by XRPD was performed, and each sample remained crystalline.

Evaporation

Compound 1 HCl (50.6 mg, 1 wt) charged to a 7 ml vial followed by HFIPA (50 µl, 1 vol), sample reached full dissolution. Solution transferred to XRPD plate, left in ambient conditions to evaporate overnight, product analysed by XRPD.

Rotary Evaporation

Compound 1 monofumarate (50 mg, 1 wt) charged to 7 ml vial followed by methanol (1 ml, 20 vol), forming a solution. Sample was dried by rotary evaporation, yielding an oil, left to stand overnight, material stuck to side of flask unable to be manipulated.

Binary Solvent

Compound 1 monofumarate (50 mg, 1 wt) charged to 7 ml vial, followed by methanol (600 µl, 12 vol). Solution was passed through a syringe filter into a 7 ml vial containing diethyl ether (1 ml, 20 vol). The solution was dried under $N_2$ flux and analysed by XRPD.

DSC

Two DSC pan were charged with the appropriate salts, the first DSC pan was not sealed (Open Pan DSC), the second pan had its lid crimped to the pan (hermetic sealed DSC). The open pan DSC was thermocycled from 20° C. to just after the melt event for each salt, cooled to −20° C. and left to stand under ambient conditions over night. The open pan DSC was reheated to just before the degradation event.

The hermetic sealed DSC was heated from 20° C. to just after the melt event, cooled to −20° C. then reheated to just before the degradation event.

TGA

A TGA crucible was charged with the appropriate salt and thermocycled from 20° C. to past the melt event and then cooled to −20° C., followed by immediately heating to just before the degradation event to measure the Tg.

Hot Plate Melt

A XRPD silicone plate was loaded with the appropriate salt, heated on the hot plate until melted, cooled, and analyzed by XRPD to ensure the phase was amorphous.

An XRPD silicone sample plate was loaded with the appropriate salt, heated on the hot stage microscope block until melted, cooled and analysed by XRPD to ensure that the phase was amorphous. Once amorphous material was obtained, samples of this, were analysed by LC-MS spectrometry and $^1$H NMR spectroscopy to ensure that no change in chemical composition had occurred.

Results

Samples of compound 1 HCl and compound 1 monofumarate were exposed to a variety of techniques in attempts to generate the amorphous forms, including freeze drying, evaporation, antisolvent addition. These techniques were not successful for compound 1 HCl.

The amorphous form of compound 1 monofumarate was obtained from the evaporation of a binary solvent mixture of methanol and diethyl ether. Samples were analyzed by XRPD to determine the crystallinity (Table 128). Amorphous compound 1 monofumarate XRPD is shown in FIG. 379 and FIG. 390.

of amorphous compound 1 monofumarate are shown in FIGS. 381-384 and 385-388, respectively.

A hot stage microscope heating block was used to generate the amorphous in-situ to allow analysis by XRPD. A low background, silicon XRPD sample-plate holder was loaded with the appropriate salt. The plate was heated past the melt event, removed from the hot stage microscope, cooled, to ambient temperature in air and analyzed by XRPD, to ensure that the amorphous form was generated. The amorphous material was then analyzed by $^1$H NMR spectroscopy and LC-MS spectrometry to ensure there was no change in the chemical composition. Each sample was analysed, to confirm the amorphous form, and thermal characterization was performed. $^1$H NMR spectroscopy and LC-MS spectrometry, confirmed that there was no change in the chemical composition of the samples aftertreatment. H NMR and LC profiles of amorphous compound 1 HCl are shown in FIG. 368 and FIG. 378, respectively. $^1$H NMR and LC profiles of amorphous compound 1 monofumarate are shown in FIG. 380 and FIG. 389, respectively.

TABLE 128

Amorphous Study of Compound 1 monofumarate and Compound 1 HCl

| Salt form | Scale investigation | Amorphisation activity | Outcome | Form by XRPD |
|---|---|---|---|---|
| Compound 1 HCl | 50 mg | Freeze dry | Crystalline | Form A |
| Compound 1 HCl | 50 mg | Antisolvent/N$_2$ flow | Crystalline | Form A |
| Compound 1 HCl | 50 mg | HFIPA Evaporation | Crystalline | Form A |
| Compound 1 HCl | 50 mg | HFIPA Evaporation o/n | Crystalline | Form A |
| Compound 1 Monofumarate | 50 mg | Freeze dry | Crystalline | Form A |
| Compound 1 Monofumarate | 50 mg | Rotary Vac (Methanol) | Gum | — |
| Compound 1 Monofumarate | 50 mg | Antisolvent/N$_2$ flow | Gum (Amorphous) | Amorphous |

Initial experiments to produce the amorphous phase were unsuccessful for Compound 1 HCl, although the amorphous phase was generated for Compound 1 monofumarate. Therefore, thermal techniques were used to access the amorphous phase in-situ and complete measurement of the glass temperature (Tg).

Each salt was analysed by DSC and TGA to determine the Tg of the amorphous form. Amorphous forms were generated by thermocycling the salts past their melt temperatures, cooling the specimens, and once cooled the specimens were reheated. Open pan and sealed pan DSC were utilized, open pan DSC were heated past the melt event, cooled, and left to stand under ambient conditions overnight. Sealed pans were immediately cycled with no time left to stand.

TGA (open pan) samples were analysed by thermocycle, with no time for the sample to stand under ambient conditions.

The amorphous forms were generated in these studies and characterized with their Tg being recorded. DSC and TGA profiles of amorphous compound 1 HCl are shown in FIGS. 370-373 and 374-377, respectively. DSC and TGA profiles Thermal Study of Compound 1 Monofumarate and Compound 1 HCl

| Salt form | Experiment | Temperature range (° C.) | Outcome |
|---|---|---|---|
| Compound 1 HCl | Open Pan DSC | 20 to 220 to −20, O/N 20 to 250 | Amorphous |
| Compound 1 HCl | Sealed DSC | 20 to 220 to −20 to 250 | Amorphous |
| Compound 1 HCl | TGA | 20 to 220 to −20 to 250 | Amorphous |
| Compound 1 HCl | Hot plate heat-up | 20 to 236 | Form A |
| Compound 1 HCl | Hot stage plate heat-up | 20 to 260 | Amorphous |
| Compound 1 HCl | Hot stage plate heat-up | 20 to 260 | Form A with PO* |
| Compound 1 HCl | Hot stage plate heat-up | 20 to 275 | Amorphous |
| Compound 1 Monofumarate | Open Pan DSC | 20 to 145 to −20, O/N 20 to 230 | Amorphous |
| Compound 1 Monofumarate | Sealed DSC | 20 to 145 to −20 to 230 | Amorphous |
| Compound 1 Monofumarate | TGA | 20 to 145 to −20 to 230 | Amorphous |

-continued

| Salt form | Experiment | Temperature range (° C.) | Outcome |
|---|---|---|---|
| Compound 1 Monofumarate | Hot plate heat-up | 20 to 165 | Amorphous |
| Compound 1 Monofumarate | Hot stage plate heat-up | 20 to 165 | Amorphous |

*PO- preferred orientation The characterization of the amorphous material was successful with the Tg being determined for each compound (refer to Table 130). Material was characterized by $^1$H NMR and LC-MS to confirm the sample was not degraded during treatment.

| Salt | Glass temperatures (Tg) |
|---|---|
| Compound 1 HCl | 37° C. |
| Compound 1 Monofumarate | 24° C. |

Provenances of reference batches

| | Amorphous Compound 1 HCl |
|---|---|
| Heated up past the melt event on a hot stage microscope | Molecular weight: 268.790 gmol$^{-1}$<br>Exact molecular weight: 268.135<br>Molecular formula: $C_{14}H_{21}ClN_2O$<br>XRPD: Amorphous (FIG. 369)<br>$^1$H NMR: (DMSO-d$_6$, 400 MHz); δ 11.2 (s, 1H), 7.6 (d, 1 H), 7.4 (d, 1H), 7.1 (d, 1H), 6.8 (dd, 1H), 6.4 (d, 1H), 4.7 (d, 1H), 4.3 (dd, 1H), 3.8 (s, 4H), 2.7 (m, 6H), 1.1 (d, 3H); ppm; conforms to the molecular structure (Σ21H). |
| | Amorphous compound 1 fumarate |
| Heated up past the melt event on a hot stage microscope | Molecular weight: 348.399 gmol$^{-1}$<br>Exact molecular weight: 348.169<br>Molecular formula: $C_{18}H_{24}N_2O_3$<br>XRPD: Amorphous (FIG. 379, FIG. 390)<br>$^1$H NMR: (DMSO-d$_6$, 400 MHz); δ 7.4 (d, 1 H), 7.3 (s, 1 H), 7.0 (s, 1 H), 6.8 (dt, 1 H), 6.6 (s, 2 H), 6.3 (td, 1 H), 4.3 (dd, 1 H), 4.0 (dd, 1 H), 3.8 (s, 3 H), 3.1 (p, 1 H), 2.3 (s, 6 H), 0.8 (dd, 3 H) conforms to the molecular structure (Σ22H). |

| | | DSC | | TGA | | $^1$H NMR | $^1$H NMR | |
|---|---|---|---|---|---|---|---|---|
| Designation | Event | Thermal measurements | | % Δwt. | Comment | (stoich.) | (solvent) | Form Assignment |
| Amorphous Compound 1 HCl | Tg, Crystallisation, Melt | Integral<br>Onset<br>Peak<br>Endset | −2.2 Jg$^{-1}$<br>37.07° C.<br>43.00° C.<br>48.35° C. | −18.2%,<br>206.7° C. | De-solvation | 1 to 1 (API to HCl) | — | Amorphous |
| Amorphous Compound 1 monofumarate | Tg | Integral<br>Onset<br>Peak<br>Endset | −1.73 Jg$^{-1}$<br>21.14° C.<br>29.67° C.<br>34.30° C. | — | No events observed. | 1 to 1 (API to fumarate) | — | Amorphous |

Listing of Numbered Embodiments

1. A (R)-1-(5-methoxy-1H-indol-1-yl)-N,N-dimethylpropan-2-amine, compound 1) salt.
2. The compound 1 salt of embodiment 1, wherein the salt is crystalline.
3. The compound 1 salt of embodiment 1, wherein the salt is amorphous.
4. The compound 1 salt of embodiment any one of claims 1 to 3, wherein the salt is a fumarate, monofumarate salt or hemi-fumarate salt.
5. The compound 1 salt of embodiment 1, 2, or 4, wherein the compound 1 salt is a compound 1 monofumarate salt that is a crystalline polymorphic form characterized by XRPD signals at two signals or more, or three signals selected from the group consisting of 22.4°2θ, 15.9°2θ, and 19.5°2θ, 19.3 (0.2°2θ; ±0.1°2θ; or ±0.0°2θ; Cu Kα1 radiation).
6. The compound 1 monofumarate salt of embodiment 4 or 5, wherein the compound 1 monofumarate salt is a crystalline polymorphic form characterized by XRPD signals at 22.4°2θ, 15.9°2θ, and 19.5°2θ.
7. The compound 1 monofumarate salt of any one of embodiments 4-6, wherein the compound 1 monofumarate salt is a crystalline polymorphic form characterized by an XRPD pattern substantially similar to that shown in FIG. 157.
8. The compound 1 monofumarate salt of any one of embodiments 4-7, wherein the compound 1 monofumarate salt is a crystalline polymorphic form characterized by a DSC diagram having a melting signal at about 118.2° C.

9. The compound 1 monofumarate salt of embodiment 8, wherein the compound 1 monofumarate salt is a crystalline polymorphic form characterized by a DSC profile substantially similar to that shown in FIG. 159.

10. The compound 1 monofumarate salt of any one of embodiments 4-9, wherein the compound 1 monofumarate salt is a crystalline polymorph characterized by a TGA diagram having an onset at about 207.9° C.

11. The compound 1 monofumarate salt of any one of embodiments 4-9, wherein the compound 1 monofumarate salt is a crystalline polymorph characterized by a TGA diagram substantially similar to that shown in FIG. 158.

12. The compound 1 monofumarate salt of any one of embodiments 1, 2, or 4, wherein the compound 1 monofumarate salt is a crystalline polymorph characterized by XRPD signals at two signals or more, or three signals selected from the group consisting of 17.6°2θ, 19.4°2θ, and 23.5°2θ (±0.2°2θ; ±0.1°2θ; or ±0.0°2θ; Cu Kα1 radiation).

13. The compound 1 monofumarate salt of embodiment 12, wherein the compound 1 monofumarate salt is a crystalline polymorph characterized by XRPD signals at 17.6°2θ, 19.4°2θ, and 23.5°2θ (±0.2°2θ; ±0.1°2θ; or ±0.0°2θ; Cu Kα1 radiation).

14. The compound 1 monofumarate salt of embodiment 12 or 13, wherein the compound 1 monofumarate salt is a crystalline polymorph characterized by XRPD signals at 16.7°2θ, 17.6°2θ, 19.4°2θ, 23.5°2θ, and 24.7°2θ (±0.2°2θ; ±0.1°2θ; or ±0.0°2θ; Cu Kα1 radiation).

15. The compound 1 monofumarate salt of any one of embodiments 12 to 14, wherein the compound 1 monofumarate salt is a crystalline polymorph characterized by any combination of the XRPD signals contained in Table 32.

16. The compound 1 monofumarate salt of any one of embodiments 12 to 15, wherein the compound 1 monofumarate salt is a crystalline polymorph characterized by an XRPD pattern substantially similar to that shown in FIG. 67.

17. The compound 1 monofumarate salt of any one of embodiments 12 to 16, wherein the compound 1 monofumarate salt is a crystalline polymorph characterized by a DSC diagram having an melting signal at about 66.2° C.

18. The compound 1 monofumarate salt of any one of embodiments 12 to 17, wherein the compound 1 monofumarate salt is a crystalline polymorph characterized by a TGA diagram having an onset at about 208.4° C.

19. The compound 1 fumarate salt of any one of embodiments 1, 2, or 4, wherein the compound 1 fumarate salt is a crystalline polymorph characterized by XRPD signals at two signals or more, or three signals selected from 24.0°2θ, 19.8°2θ, and 18.1°2θ (±0.2°2θ; ±0.1°2θ; or ±0.0°2θ; Cu Kα1 radiation).

20. The compound 1 fumarate salt of embodiment 4 or 19, wherein the compound 1 fumarate salt is a crystalline polymorph characterized by XRPD signals at 24.0°2θ, 19.8°2θ, and 18.1°2θ (±0.2°2θ; ±0.1°2θ; or ±0.0°2θ; Cu Kα1 radiation).

21. The compound 1 fumarate salt of embodiments 19 or 20, wherein the compound 1 fumarate salt is a crystalline polymorph characterized by XRPD signals at 18.1°2θ, 19.8°2θ, 19.9°2θ, 23.6°2θ, and 24.0°2θ (±0.2°2θ; ±0.1°2θ; or ±0.0°2θ; Cu Kα1 radiation).

22. The compound 1 fumarate salt of any one of embodiments 19 to 21, wherein the compound 1 fumarate salt is a crystalline polymorph characterized by XRPD signals at 9.5°2θ, 11.9°2θ, 14.1°2θ, 15.1°2θ, 16.8°2θ, 17.6°2θ, 18.1°2θ, 19.0°2θ, 19.8°2θ, 19.9°2θ, 23.6°2θ, 24.0°2θ, 25.7°2θ, 28.3°2θ, 30.0°2θ, and 31.7°2θ (±0.2°2θ; 0.1°2θ; or ±0.0°2θ; Cu Kα1 radiation).

23. The compound 1 fumarate salt of any one of embodiments 19 to 22, wherein the compound 1 fumarate salt is a crystalline polymorph characterized by any combination of the XRPD signals contained in Table 36.

24. The compound 1 fumarate salt of any one of embodiments 4, or 19 to 23, wherein the compound 1 fumarate salt is a crystalline polymorph characterized by an XRPD pattern substantially similar to that shown in FIG. 70.

25. The compound 1 hemi-fumarate salt of any one of embodiments, 1, 2, or 4, wherein the compound 1 hemi-fumarate salt is a crystalline polymorph characterized by XRPD signals at two signals or more, or three signals selected from the group consisting of 15.8°2θ, 20.9°2θ, and 26.9°2θ (±0.2°2θ; ±0.1°2θ; or ±0.0°2θ; Cu Kα1 radiation).

26. The compound 1 hemi-fumarate salt of embodiment 4 or 25, wherein the compound 1 hemi-fumarate salt is a crystalline polymorph characterized by XRPD signals at 15.8°2θ, 20.9°2θ, and 26.9°2θ (±0.2°2θ; ±0.1°2θ; or ±0.0°2θ; Cu Kα1 radiation).

27. The compound 1 hemi-fumarate salt of embodiment 25 or 26, wherein the compound 1 hemi-fumarate salt is a crystalline polymorph characterized by XRPD signals at 15.1°2θ, 15.8°2θ, 19.2°2θ, 20.9°2θ, and 26.9°2θ (±0.2°2θ; ±0.1°2θ; or ±0.0°2θ; Cu Kα1 radiation).

28. The compound 1 hemi-fumarate salt of any one of embodiments 25 to 27, wherein the hemi-fumarate salt is a crystalline polymorph characterized by XRPD signals at 11.5°2θ, 13.3°2θ, 13.5°2θ, 15.1°2θ, 15.8°2θ, 18.8°2θ, 19.2°2θ, 20.9°2θ, 21.4°2θ, 22.4°2θ, 23.1°2θ, 24.0°2θ, 24.7°2θ, 26.9°2θ, 28.2°2θ, (±0.2°2θ; ±0.1°2θ; or ±0.0°2θ; Cu Kα1 radiation).

29. The compound 1 hemi-fumarate salt of any one of embodiments 25 to 28, wherein the hemi-fumarate salt is a crystalline polymorph characterized by any combination of the XRPD signals contained in Table 35.

30. The compound 1 hemi-fumarate salt of any one of embodiments 4 or 25 to 29 wherein the compound 1 hemi-fumarate salt is a crystalline polymorph characterized by an XRPD pattern substantially similar to that shown in FIG. 7.

31. The compound 1 hemi-fumarate salt of any one of embodiments 4, or 25 to 30, wherein the compound 1 hemi-fumarate salt is a crystalline polymorph characterized by DSC having a melting signal at about 97.2° C.

32. The compound 1 hemi-fumarate salt of any one of embodiments 4, or 25 to 31, wherein the compound 1 hemi-fumarate salt is a crystalline polymorph characterized by DSC profile substantially similar to that shown in FIG. 60.

33. The compound 1 hemi-fumarate salt of any one of embodiments 4 or 25 to 32, wherein the compound 1 hemi-fumarate salt is a crystalline polymorph characterized by a TGA diagram having an onset at about 246.4° C.

34. The compound 1 hemi-fumarate salt of any one of embodiments 4 or 25 to 33, or 20-24, wherein the compound 1 hemi-fumarate salt is a crystalline polymorph characterized by a TGA diagram substantially similar to that shown in FIG. 59.

35. The compound 1 hemi-fumarate salt of any one of embodiments, 1, 2, or 4, wherein the compound 1 hemi-fumarate salt is a crystalline polymorph characterized by XRPD signals at two signals or more, or three signals selected from the group consisting of 15.9°2θ, 21.0°2θ, and 19.4°2θ (±0.2°2θ; ±0.1°2θ; or ±0.0°2θ; Cu Kα1 radiation).

36. The compound 1 hemi-fumarate salt of embodiments 4 or 35, wherein the compound 1 hemi-fumarate salt is a crystalline polymorph characterized by XRPD signals at 15.9°2θ, 21.0°2θ, and 19.4°2θ (±0.2°2θ; ±0.1°2θ; or ±0.0°2θ; Cu Kα1 radiation).

37. The compound 1 hemi-fumarate salt of embodiment 35 or 36, wherein the compound 1 hemi-fumarate salt is a crystalline polymorph characterized by XRPD signals at 15.2°2θ, 15.9°2θ, 19.4°2θ, 21.0 20, and 27.1°2θ (±0.2°2θ; ±0.1°2θ; or ±0.0°2θ; Cu Kα1 radiation).

38. The compound 1 hemi-fumarate salt of any one of embodiments 35 to 37, wherein the compound 1 hemi-fumarate salt is a crystalline polymorph characterized by XRPD signals at 11.7°2θ, 13.4°2θ, 13.7°2θ, 15.2°2θ, 15.9°2θ, 18.9°2θ, 19.4°2θ, 21.0°2θ, 21.6°2θ, 22.5°2θ, 23.2°2θ, and 27.1°2θ (±0.2°2θ; ±0.1°2θ; or ±0.0°2θ; Cu Kα1 radiation).

39. The compound 1 hemi-fumarate salt of any one of embodiments 35 to 38, wherein the hemi-fumarate salt is a crystalline polymorph characterized by any combination of the XRPD signals contained in Table 33.

40. The compound 1 hemi-fumarate salt of any one of embodiments 4 or 35 to 39 wherein the compound 1 hemi-fumarate salt is a crystalline polymorph characterized by DSC having a melting signal at about 91.5° C.

41. The compound 1 hemi-fumarate salt of any one of embodiments 4 or 35 to 40, or 27-29, wherein the compound 1 hemi-fumarate salt is a crystalline polymorph characterized A TGA diagram having an onset at about 246.4° C.

42. The compound 1 fumarate salt of any one of embodiments 1, 2, or 4, wherein the compound 1 fumarate salt is a crystalline polymorph characterized by XRPD signals at two signals or more, or three signals selected from the group consisting of 7.9°2θ, 21.6°2θ, and 20.2°2θ (±0.2°2θ; ±0.1°2θ; or ±0.0°2θ; Cu Kα1 radiation).

43. The compound 1 fumarate salt of any one of embodiments 1, 2, 4, or 42 wherein the compound 1 fumarate salt is a crystalline polymorph characterized by XRPD signals at 7.9°2θ, 21.6°2θ, and 20.2°2θ (±0.2°2θ; ±0.1°2θ; or ±0.0°2θ; Cu Kα1 radiation).

44. The compound 1 fumarate salt of any one of embodiments 42 or 43 wherein the compound 1 fumarate salt is a crystalline polymorph characterized by XRPD signals at 7.9°2θ, 15.7°2θ, 20.2°2θ, 21.6°2θ, and 23.7°2θ (±0.2°2θ; ±0.1°2θ; or ±0.0°2θ; Cu Kα1 radiation).

45. The compound 1 fumarate salt of any one of embodiments 42 to 44 wherein the compound 1 fumarate salt is a crystalline polymorph characterized by any combination of the XRPD signals contained in Table 38.

46. The compound 1 fumarate salt of any one of embodiments, 1, 2, 4, or 42 to 45 wherein the compound 1 fumarate salt is a crystalline polymorph characterized by an XRPD pattern substantially similar to that shown in FIG. 1.

47. The compound 1 fumarate salt of any one of embodiments, 1, 2, or 4, wherein the compound 1 fumarate salt is a crystalline polymorph characterized by XRPD signals at two signals or more, or three signals selected from the group consisting of 19.3°2θ, 8.2°2θ, and 20.2°2θ (±0.2°2θ; ±0.1°2θ; or ±0.0°2θ; Cu Kα1 radiation).

48. The compound 1 fumarate salt of any one of embodiments, 1, 2, 4, or 47, wherein the compound 1 fumarate salt is a crystalline polymorph characterized by XRPD signals at 19.3°2θ, 8.2°2θ, and 20.2°2θ (±0.2°2θ; ±0.1°2θ; or ±0.0°2θ; Cu Kα1 radiation).

49. The compound 1 fumarate salt of any one of embodiments, 47 or 48, wherein the compound 1 fumarate salt is a crystalline polymorph characterized by XRPD signals at 8.2°2θ, 19.3°2θ, 20.2°2θ, 21.7°2θ, and 23.2°2θ (±0.2°2θ; ±0.1°2θ; or ±0.0°2θ; Cu Kα1 radiation).

50. The compound 1 fumarate salt of any one of embodiments, 47 to 49, wherein the compound 1 fumarate salt is a crystalline polymorph characterized by XRPD signals at 8.2°2θ, 12.3°2θ, 13.4°2θ, 13.9°2θ, 14.9°2θ, 16.7°2θ, 17.2°2θ, 18.4°2θ, 19.3°2θ, 20.2°2θ, 20.9°2θ, 21.7°2θ, 22.4°2θ, 23.2°2θ, 23.8°2θ, 24.4°2θ, 25.1°2θ, 26.1°2θ, 27.6°2θ, 29.1°2θ, and 29.8°2θ (±0.2°2θ; ±0.1°2θ; or 0.0°2θ; Cu Kα1 radiation).

51. The compound 1 fumarate salt of any one of embodiments 47 to 50 wherein the compound 1 fumarate salt is a crystalline polymorph characterized by any combination of the XRPD signals contained in Table 39.

52. The compound 1 fumarate salt of any one of embodiments 47 to 51 wherein the compound 1 fumarate salt is a crystalline polymorph characterized by an XRPD pattern substantially similar to that shown in FIG. 71.

53. The compound 1 salt of embodiment 1 or 2, wherein the salt is a HCl salt.

54. The compound 1 HCl salt of any one of embodiments 1, 2, or 53, wherein the compound 1 HCl salt is a crystalline polymorph characterized by XRPD signals at two signals or more, or three signals selected from the group consisting of 18.1°2θ, 24.9°2θ, and 21.7°2θ (±0.2°2θ; ±0.1°2θ; or ±0.0°2θ; Cu Kα1 radiation).

55. The compound 1 HCl salt of embodiment 53 or 54, wherein the compound 1 HCl salt is a crystalline polymorph characterized by XRPD signals at 18.1°2θ, 24.9°2θ, and 21.7°2θ (±0.2°2θ; ±0.1°2θ; or ±0.0°2θ; Cu Kα1 radiation).

56. The compound 1 HCl salt of any one of embodiments 53 to 55, wherein the compound 1 HCl salt is a crystalline polymorph characterized by XRPD signals at 17.8°2θ, 18.1°2θ, 21.7°2θ, 24.9°2θ, and 29.0°2θ (±0.2°2θ; ±0.1°2θ; or ±0.0°2θ; Cu Kα1 radiation).

57. The compound 1 HCl salt of any one of embodiments 53 to 57, wherein the compound 1 HCl salt is a crystalline polymorph characterized by XRPD signals at 6.4°2θ, 12.4°2θ, 13.6°2θ, 15.3°2θ, 17.6°2θ, 17.8°2θ, 18.1°2θ, 18.7°2θ, 20.0°2θ, 20.5°2θ, 21.7°2θ, 23.1°2θ, 24.9°2θ, 25.5°2θ, 25.9°2θ, 27.4°2θ, 29.0°2θ, 30.1°2θ, and 30.3°2θ (±0.2°2θ; ±0.1°2θ; or ±0.0°2θ; Cu Kα1 radiation).

58. The compound 1 HCl salt of any one of embodiments 53 to 57, wherein the compound 1 HCl salt is a crystalline polymorph characterized by any combination of the XRPD signals contained in Table 4.

59. The compound 1 HCl salt of any one of embodiments 53 to 58, wherein compound 1 HCl salt is a crystalline polymorph characterized by an XRPD pattern that is substantially similar to that shown in FIG. 167.

60. The compound 1 HCl salt of any one of embodiments 53 to 59, wherein the compound 1 HCl salt is a crystalline polymorph characterized by a DSC curve having a melting signal at about 229.8° C.

61. The compound 1 HCl salt of any one of embodiments 53 to 60, wherein the compound 1 HCl salt is a crystalline polymorph characterized by a DSC curve that is substantially similar to that shown in FIG. 190.

62. The compound 1 HCl salt of any one of embodiments 53 to 61, wherein the compound 1 HCl salt is a crystalline polymorph characterized by a TGA diagram having an onset at about 243.3° C.

63. The compound 1 HCl salt of any one of embodiments 53 to 62, wherein the compound 1 HCl salt is a crystalline polymorph characterized by a TGA diagram that is substantially similar to that shown in FIG. 195.

64. The compound 1 salt of embodiment 1 or 2, wherein the salt is a maleate salt.

65. The compound 1 salt of embodiment 1, 2, or 64, wherein the compound 1 maleate salt is a crystalline polymorph characterized by XRPD signals at two signals or more, or three signals selected from the group consisting of 23.7°2θ, 21.6°2θ, and 26.0°2θ (±0.2°2θ; ±0.1°2θ; or ±0.0°2θ; Cu Kα1 radiation).

66. The compound 1 maleate salt of embodiment 64 or 65, wherein the compound 1 maleate salt is a crystalline polymorph characterized by XRPD signals at 23.7°2θ, 21.6°2θ, and 26.0°2θ (±0.2°2θ; ±0.1°2θ; or ±0.0°2θ; Cu Kα1 radiation).

67. The compound 1 maleate salt of any one of embodiments 64 to 66, wherein the compound 1 maleate salt is a crystalline polymorph characterized by XRPD signals at 19.2°2θ, 21.6°2θ, 23.7°2θ, 26.0°2θ, and 26.5°2θ (±0.2°2θ; ±0.1°2θ; or ±0.0°2θ; Cu Kα1 radiation).

68. The compound 1 maleate salt of embodiment 64 to 67, wherein the compound 1 maleate salt is a crystalline polymorph characterized by XRPD signals at 9.4°2θ, 10.9°2θ, 11.8°2θ, 16.9°2θ, 18.6°2θ, 19.2°2θ, 20.9°2θ, 21.6°2θ, 22.2°2θ, 23.7°2θ, 25.0°2θ, 26.0°2θ, and 26.5°2θ (±0.2°2θ; ±0.1°2θ; or ±0.0°2θ; Cu Kα1 radiation).

69. The compound 1 maleate salt of any one of embodiments 64 to 68, wherein the compound 1 maleate salt is a crystalline polymorph characterized by any combination of the XRPD signals contained in Table 43.

70. The compound 1 maleate salt of any one of embodiments 64 to 69, wherein compound 1 maleate salt is a crystalline polymorph characterized by an XRPD pattern that is substantially similar to that shown in FIG. 205.

71. The compound 1 maleate salt of any one of embodiments 64 to 70, wherein compound 1 maleate salt is a crystalline polymorph characterized by a DSC curve having a melting signal at about 60.2° C.

72. The compound 1 maleate salt of any one of embodiments 69 to 71, wherein the compound 1 maleate salt is a crystalline polymorph characterized by a DSC that is substantially similar to FIG. 199.

73. The compound 1 maleate salt of any one of embodiments 69 to 72, wherein compound 1 maleate salt is a crystalline polymorph characterized by a TGA curve having an onset at about 200.0° C.

74. The compound 1 maleate salt of any one of embodiments 69 to 73, wherein compound 1 maleate salt is a crystalline polymorph characterized by a TGA curve that is substantially similar to that shown in FIG. 227.

75. The compound 1 salt of embodiment 1 or 2, wherein the compound 1 salt is a benzoate salt.

76. The compound 1 benzoate salt of embodiment 75, wherein the compound 1 benzoate salt is a crystalline polymorph characterized by XRPD signals at two signals or more, or three signals selected from the group consisting of 17.5°2θ, 14.5°2θ, and 18.6°2θ (±0.2°2θ; ±0.1°2θ; or ±0.0°2θ; Cu Kα1 radiation).

77. The compound 1 benzoate salt of embodiment 75 or 76, wherein the compound 1 benzoate salt is a crystalline polymorph characterized by XRPD signals at 17.5°2θ, 14.5°2θ, and 18.6°2θ (±0.2°2θ; ±0.1°2θ; or ±0.0°2θ; Cu Kα1 radiation).

78. The compound 1 benzoate salt of any one of embodiments 75 to 77, wherein the compound 1 benzoate salt is a crystalline polymorph characterized by XRPD signals at 13.8°2θ, 14.5°2θ, 17.5°2θ, 18.6°2θ, and 19.2°2θ (±0.2°2θ; ±0.1°2θ; or ±0.0°2θ; Cu Kα1 radiation).

79. The compound 1 benzoate salt of embodiment 75 or 78, wherein the compound 1 benzoate salt is a crystalline polymorph characterized by XRPD signals at 7.8°2θ, 12.5°2θ, 13.8°2θ, 14.5°2θ, 15.5°2θ, 17.5°2θ, 18.6°2θ, 19.2°2θ, 19.7°2θ, 20.6°2θ, 23.7°2θ, 25.2°2θ, and 25.3°2θ (±0.2°2θ; ±0.1°2θ; or ±0.0°2θ; Cu Kα1 radiation).

80. The compound 1 benzoate salt of any one of embodiments 75 to 79, wherein the compound 1 benzoate salt is a crystalline polymorph characterized by any combination of the XRPD signals contained in Table 45.

81. The compound 1 benzoate salt of any one of embodiments 75 to 80, wherein compound 1 benzoate salt is a crystalline polymorph characterized by an XRPD pattern that is substantially similar to that shown in FIG. 214.

82. The compound 1 benzoate salt of any one of embodiments 75 to 81, wherein compound 1 benzoate salt is a crystalline polymorph characterized by a DSC curve having a melting signal at about 101.0° C.

83. The compound 1 benzoate salt of any one of embodiments 75 to 82, wherein the compound 1 benzoate salt is a crystalline polymorph characterized by a DSC that is substantially similar to FIG. 208.

84. The compound 1 benzoate salt of any one of embodiments 75 to 83, wherein compound 1 benzoate salt is a crystalline polymorph characterized by a TGA curve having an onset at about 102.2° C.

85. The compound 1 benzoate salt of any one of embodiments 75 to 84, wherein compound 1 benzoate salt is a crystalline polymorph characterized by a TGA curve that is substantially similar to that shown in FIG. 213.

86. The compound 1 salt of embodiment 1 or 2, wherein the compound 1 salt is a tosylate salt.

87. The compound 1 tosylate salt of embodiment 86, wherein the compound 1 tosylate salt is a crystalline polymorph characterized by XRPD signals at two signals or more, or three signals selected from the group consisting of 19.8°2θ, 19.5°2θ, and 25.5°2θ (±0.2°2θ; ±0.1°2θ; or ±0.0°2θ; Cu Kα1 radiation).

88. The compound 1 tosylate salt of embodiment 86 or 87, wherein the compound 1 tosylate salt is a crystalline polymorph characterized by XRPD signals at 19.8°2θ, 19.5°2θ, and 25.5°2θ (±0.2°2θ; ±0.1°2θ; or ±0.0°2θ; Cu Kα1 radiation).

89. The compound 1 tosylate salt of any one of embodiments 86 to 88, wherein the compound 1 tosylate salt is a crystalline polymorph characterized by XRPD signals at 14.5°2θ, 15.3°2θ, 19.5°2θ, 19.8°2θ, and 25.5°2θ (±0.2°2θ; ±0.1°2θ; or 0.0°2θ; Cu Kα1 radiation).

90. The compound 1 tosylate salt of any one of embodiments 86 to 89, wherein the compound 1 tosylate salt is a crystalline polymorph characterized by XRPD signals at 10.3°2θ, 14.5°2θ, 15.3°2θ, 16.3°2θ, 16.5°2θ, 18.2°2θ, 19.5°2θ, 19.8°2θ, 20.6°2θ, 20.7°2θ, 22.9°2θ, 23.3°2θ, 25.5°2θ, 26.0°2θ, 26.2°2θ, 26.6°2θ, 29.4°2θ, and 30.3°2θ 20 (±0.2°2θ; ±0.1°2θ; or ±0.0°2θ; Cu Kα1 radiation).

91. The compound 1 tosylate salt of any one of embodiments 86 to 90, wherein the compound 1 tosylate salt is a crystalline polymorph characterized by any combination of the XRPD signals contained in Table 113.

92. The compound 1 tosylate salt of any one of embodiments 86 to 91, wherein compound 1 tosylate salt is a crystalline polymorph characterized by an XRPD pattern that is substantially similar to that shown in FIG. 170.

93. The compound 1 tosylate salt of any one of embodiments 86 to 92, wherein compound 1 tosylate salt is a crystalline polymorph characterized by a DSC curve having a melting signal at about 137.7° C.

94. The compound 1 tosylate salt of any one of embodiments 86 to 93, wherein the compound 1 tosylate salt is a crystalline polymorph characterized by a DSC that is substantially similar to FIG. 234.

95. The compound 1 tosylate salt of any one of embodiments 86 to 94, wherein compound 1 tosylate salt is a crystalline polymorph characterized by a TGA curve having a TGA curve that is substantially similar to that shown in FIG. 235.

96. The compound 1 tosylate salt of any one of embodiments 86 to 95, wherein compound 1 tosylate salt is a crystalline polymorph characterized by a TGA curve as shown in FIG. 235.

97. The compound 1 salt of embodiment 1 or 2, wherein the compound 1 salt is a tartrate salt.

98. The compound 1 tartrate salt of embodiment 97, wherein the compound 1 tartrate salt is a crystalline polymorph characterized by XRPD signals at two signals or more, or three signals selected from the group consisting of 4.3°2θ, 17.5°2θ, and 19.3°2θ (±0.2°2θ; ±0.1°2θ; or ±0.0°2θ; Cu Kα1 radiation).

99. The compound 1 tartrate salt of embodiment 97 or 98, wherein the compound 1 tartrate salt is a crystalline polymorph characterized by XRPD signals at 4.3°2θ, 17.5°2θ, and 19.3°2θ (±0.2°2θ; ±0.1°2θ; or ±0.0°2θ; Cu Kα1 radiation).

100. The compound 1 tartrate salt of any one of embodiments 97 to 99, wherein the compound 1 tartrate salt is a crystalline polymorph characterized by XRPD signals at 4.3°2θ, 14.5°2θ, 17.5°2θ, 19.3°2θ, and 20.1°2θ (±0.2°2θ; ±0.1°2θ; or ±0.0°2θ; Cu Kα1 radiation).

101. The compound 1 tartrate salt of any one of embodiments 97 to 100, wherein the compound 1 tartrate salt is a crystalline polymorph characterized by XRPD signals at 4.3°2θ, 8.7°2θ, 13.1°2θ, 14.5°2θ, 16.2°2θ, 16.9°2θ, 17.5°2θ, 18.7°2θ, 19.3°2θ, 20.1°2θ, 21.0°2θ, 21.8°2θ, 23.3°2θ, 23.7°2θ, 24.8°2θ, 26.2°2θ, 27.5°2θ, 28.0°2θ, 29.1°2θ, 29.2°2θ, 29.7°2θ, 30.8°2θ, 31.8°2θ, 33.3°2θ, 35.0°2θ, 36.1°2θ, 37.6°2θ, and 38.9°2θ (±0.2°2θ; ±0.1°2θ; or ±0.0°2θ; Cu Kα1 radiation).

102. The compound 1 tartrate salt of any one of embodiments 97 to 101, wherein the compound 1 tartrate salt is a crystalline polymorph characterized by any combination of the XRPD signals contained in Table 47.

103. The compound 1 tartrate salt of any one of embodiments 97 to 102, wherein compound 1 tartrate salt is a crystalline polymorph characterized by an XRPD pattern that is substantially similar to that shown in FIG. 171.

104. The compound 1 tartrate salt of any one of embodiments 97 to 103, wherein compound 1 tartrate salt is a crystalline polymorph characterized by a DSC curve having a melting signal at about 115.5° C.

105. The compound 1 tartrate salt of any one of embodiments 97 to 104, wherein the compound 1 tartrate salt is a crystalline polymorph characterized by a DSC that is substantially similar to FIG. 238.

106. The compound 1 tartrate salt of any one of embodiments 97 to 105, wherein compound 1 tartrate salt is a crystalline polymorph characterized by a TGA curve that is substantially similar to that shown in FIG. 239.

107. The compound 1 tartrate salt of any one of embodiments 97 to 106, wherein compound 1 tartrate salt is a crystalline polymorph characterized by a TGA curve as shown in FIG. 239.

108. The compound 1 salt of embodiment 1 or 2, wherein the compound 1 salt is an HBr salt.

109. The compound 1 HBr salt of embodiment 108, wherein the compound 1 HBr salt is a crystalline polymorph characterized by XRPD signals at two signals or more, or three signals selected from the group consisting of 21.6°2θ, 18.1°2θ, and 12.2°2θ (±0.2°2θ; ±0.1°2θ; or ±0.0°2θ; Cu Kα1 radiation).

110. The compound 1 HBr salt of embodiment 108 or 109, wherein the compound 1 HBr salt is a crystalline polymorph characterized by XRPD signals at 21.6°2θ, 18.1°2θ, and 12.2°2θ (±0.2°2θ; ±0.1°2θ; or ±0.0°2θ; Cu Kα1 radiation).

111. The compound 1 HBr salt of any one of embodiments 108 to 110, wherein the compound 1 HBr salt is a crystalline polymorph characterized by XRPD signals at 12.2°2θ, 18.1°2θ, 21.6°2θ, 24.4°2θ, and 28.5°2θ (±0.2°2θ; ±0.1°2θ; or ±0.0°2θ; Cu Kα1 radiation).

112. The compound 1 HBr salt of any one of embodiments 108 to 111, wherein the compound 1 HBr salt is a crystalline polymorph characterized by XRPD signals at 6.5°2θ, 12.2°2θ, 13.0°2θ, 14.2°2θ, 17.5°2θ, 18.1°2θ, 18.4°2θ, 19.8°2θ, 20.6°2θ, 21.6°2θ, 22.9°2θ, 23.3°2θ, 23.7°2θ, 24.4°2θ, 25.5°2θ, 26.1°2θ, 26.8°2θ, 27.0°2θ, 27.5°2θ, 28.4°2θ, 28.5°2θ, 29.6°2θ, 30.1°2θ, 33.3°2θ, and 34.9°2θ (±0.2°2θ; ±0.1°2θ; or ±0.0°2θ; Cu Kα1 radiation).

113. The compound 1 HBr salt of any one of embodiments 108 to 112, wherein the compound 1 HBr salt is a crystalline polymorph characterized by any combination of the XRPD signals contained in Table 48.

114. The compound 1 HBr salt of any one of embodiments 108 to 113, wherein compound 1 HBr salt is a crystalline polymorph characterized by an XRPD pattern that is substantially similar to that shown in FIG. 172.

115. The compound 1 HBr salt of any one of embodiments 108 to 114, wherein compound 1 HBr salt is a crystalline polymorph characterized by a DSC curve having a melting signal at about 194.8° C.

116. The compound 1 HBr salt of any one of embodiments 108 to 115, wherein the compound 1 HBr salt is a crystalline polymorph characterized by a DSC that is substantially similar to FIG. 241.

117. The compound 1 HBr salt of any one of embodiments 108 to 116, wherein compound 1 HBr salt is a crystalline polymorph characterized by a TGA curve having an onset at about 253.7.

118. The compound 1 HBr salt of any one of embodiments 108 to 117, wherein compound 1 HBr salt is a crystalline polymorph characterized by a TGA curve that is substantially similar to that shown in FIG. 242.

119. The compound 1 salt of embodiment 1 or 2, wherein the compound 1 salt is a galactarate salt.

120. The compound 1 galactarate salt of embodiment 119, wherein the compound 1 galactarate salt is a crystalline polymorph characterized by XRPD signals at two signals or more, or three signals selected from the group consisting of 19.6°2θ, 5.2°2θ, and 15.9°2θ (±0.2°2θ; ±0.1°2θ; or ±0.0°2θ; Cu Kα1 radiation).

121. The compound 1 galactarate salt of embodiment 119 or 120, wherein the compound 1 galactarate salt is a crystalline polymorph characterized by XRPD signals at 19.6°2θ, 5.2°2θ, and 15.9°2θ (±0.2°2θ; ±0.1°2θ; or ±0.0°2θ; Cu Kα1 radiation).

122. The compound 1 galactarate salt of any one of embodiments 119 to 121, wherein the compound 1 galactarate salt is a crystalline polymorph characterized by XRPD signals at 5.2°2θ, 15.9°2θ, 17.9°2θ, 19.6°2θ, and 30.7°2θ (±0.2°2θ; ±0.1°2θ; or ±0.0°2θ; Cu Kα1 radiation).

123. The compound 1 galactarate salt of any one of embodiments 119 to 122, wherein the compound 1 galactarate salt is a crystalline polymorph characterized by XRPD signals at 5.2°2θ, 12.1°2θ, 13.0°2θ, 15.9°2θ, 16.4°2θ, 17.9°2θ, 19.6°2θ, 20.4°2θ, 21.5°2θ, 22.4°2θ, 24.9°2θ, 25.2°2θ, 26.7°2θ, 30.7°2θ, 34.4°2θ, 34.8°2θ, and 37.6°2θ (±0.2°2θ; ±0.1°2θ; or ±0.0°2θ; Cu Kα1 radiation).

124. The compound 1 galactarate salt of any one of embodiments 119 to 123, wherein the compound 1 galactarate salt is a crystalline polymorph characterized by any combination of the XRPD signals contained in Table 49.

125. The compound 1 galactarate salt of any one of embodiments 119 to 124, wherein compound 1 galactarate salt is a crystalline polymorph characterized by an XRPD pattern that is substantially similar to that shown in FIG. 173.

126. The compound 1 galactarate salt of any one of embodiments 119 to 125, wherein compound 1 galactarate salt is a crystalline polymorph characterized by a DSC curve having a melting signal at about 167.5° C.

127. The compound 1 galactarate salt of any one of embodiments 119 to 126, wherein the compound 1 galactarate salt is a crystalline polymorph characterized by a DSC that is substantially similar to FIG. 245.

128. The compound 1 salt of embodiment 1 or 2, wherein the compound 1 salt is a succinate salt.

129. The compound 1 succinate salt of embodiment 128 wherein the compound 1 succinate salt is a crystalline polymorph characterized by XRPD signals at two signals or more, or three signals selected from the group consisting of 18.2°2θ, 19.3°2θ, and 22.0°2θ (±0.2°2θ; ±0.1°2θ; or ±0.0°2θ; Cu Kα1 radiation).

130. The compound 1 succinate salt of embodiment 128 or 129, wherein the compound 1 succinate salt is a crystalline polymorph characterized by XRPD signals at 18.2°2θ, 19.3°2θ, and 22.0°2θ (±0.2°2θ; ±0.1°2θ; or ±0.0°2θ; Cu Kα1 radiation).

131. The compound 1 succinate salt of any one of embodiments 128 to 130, wherein the compound 1 succinate salt is a crystalline polymorph characterized by XRPD signals at 18.2°2θ, 19.3°2θ, 20.0°2θ, 22.0°2θ, and 26.1°2θ (±0.2°2θ; ±0.1°2θ; or ±0.0°2θ; Cu Kα1 radiation).

132. The compound 1 succinate salt of any one of embodiments 128 to 131, wherein the compound 1 succinate salt is a crystalline polymorph characterized by XRPD signals at 12.7°2θ, 13.9°2θ, 17.3°2θ, 17.7°2θ, 18.2°2θ, 19.3°2θ, 20.0°2θ, 21.2°2θ, 21.3°2θ, 22.0°2θ, 23.7°2θ, 24.1°2θ, 24.7°2θ, 25.5°2θ, 26.1°2θ, 27.5°2θ, 28.2°2θ, and 31.4°2θ (±0.2°2θ; ±0.1°2θ; or ±0.0°2θ; Cu Kα1 radiation).

133. The compound 1 succinate salt of any one of embodiments 128 to 132, wherein the compound 1 succinate salt is a crystalline polymorph characterized by any combination of the XRPD signals contained in Table 50.

134. The compound 1 succinate salt of any one of embodiments 128 to 133, wherein compound 1 succinate salt is a crystalline polymorph characterized by an XRPD pattern that is substantially similar to that shown in FIG. 174.

135. The compound 1 succinate salt of any one of embodiments 128 to 134, wherein compound 1 succinate salt is a crystalline polymorph characterized by a DSC curve having a melting signal at about 89.8° C.

136. The compound 1 succinate salt of any one of embodiments 128 to 135, wherein the compound 1 succinate salt is a crystalline polymorph characterized by a DSC that is substantially similar to FIG. 248.

137. The compound 1 salt of embodiment 1 or 2, wherein the compound 1 salt is a citrate salt.

138. The compound 1 citrate salt of embodiment 137 wherein the compound 1 citrate salt is a crystalline polymorph characterized by XRPD signals at two signals or more, or three signals selected from the group consisting of 23.9°2θ, 18.2°2θ, and 26.2°2θ (±0.2°2θ; ±0.1°2θ; or ±0.0°2θ; Cu Kα1 radiation).

139. The compound 1 citrate salt of embodiment 137 or 138, wherein the compound 1 citrate salt is a crystalline polymorph characterized by XRPD signals at 23.9°2θ, 18.2°2θ, and 26.2°2θ (±0.2°2θ; ±0.1°2θ; or ±0.0°2θ; Cu Kα1 radiation).

140. The compound 1 citrate salt of any one of embodiments 137 to 139, wherein the compound 1 citrate salt is a crystalline polymorph characterized by XRPD signals at 18.0°2θ, 18.2°2θ, 19.6°2θ, 23.9°2θ, and 26.2°2θ (±0.2°2θ; ±0.1°2θ; or ±0.0°2θ; Cu Kα1 radiation).

141. The compound 1 citrate salt of any one of embodiments 137 to 140, wherein the compound 1 citrate salt is a crystalline polymorph characterized by XRPD signals at 14.2°2θ, 14.4°2θ, 18.0°2θ, 18.2°2θ, 19.6°2θ, 23.9°2θ, 26.1°2θ, 26.2°2θ, 27.6°2θ, 28.9°2θ, 31.1°2θ, 31.4°2θ, 33.7°2θ, 36.2°2θ, 37.0°2θ, and 37.6°2θ (±0.2°2θ; ±0.1°2θ; or ±0.0°2θ; Cu Kα1 radiation).

142. The compound 1 citrate salt of any one of embodiments 137 to 141, wherein the compound 1 citrate salt is a crystalline polymorph characterized by any combination of the XRPD signals contained in Table 51.

143. The compound 1 citrate salt of any one of embodiments 137 to 142, wherein compound 1 citrate salt is a crystalline polymorph characterized by an XRPD pattern that is substantially similar to that shown in FIG. 257.

144. The compound 1 citrate salt of any one of embodiments 137 to 143, wherein compound 1 citrate salt is a crystalline polymorph characterized by a DSC curve having a melting signal at about 182.8° C.

145. The compound 1 citrate salt of any one of embodiments 137 to 144, wherein the compound 1 citrate salt is a crystalline polymorph characterized by a DSC that is substantially similar to FIG. 258.

146. The compound 1 salt of embodiment 1 or 2, wherein the compound 1 salt is a malate salt.

147. The compound 1 malate salt of embodiment 146 wherein the compound 1 malate salt is a crystalline polymorph characterized by XRPD signals at two signals or more, or three signals selected from the group consisting of 19.3°2θ, 24.4°2θ, and 29.4°2θ (±0.2°2θ; ±0.1°2θ; or ±0.0°2θ; Cu Kα1 radiation).

148. The compound 1 malate salt of embodiment 146 or 147, wherein the compound 1 malate salt is a crystalline polymorph characterized by XRPD signals at 19.3°2θ, 24.4°2θ, and 29.4°2θ (±0.2°2θ; ±0.1°2θ; or ±0.0°2θ; Cu Kα1 radiation).

149. The compound 1 malate salt of any one of embodiments 146 to 148, wherein the compound 1 malate salt is a crystalline polymorph characterized by XRPD signals at 19.3°2θ, 21.0°2θ, 24.4°2θ, 29.4°2θ, and 37.7°2θ (±0.2°2θ; ±0.1°2θ; or 0.0°2θ; Cu Kα1 radiation).

150. The compound 1 malate salt of any one of embodiments 146 to 149, wherein the compound 1 malate salt is a crystalline polymorph characterized by XRPD signals at 7.5°2θ, 19.3°2θ, 20.9°2θ, 21.0°2θ, 22.3°2θ, 24.4°2θ, 27.7°2θ, 29.4°2θ, 29.7°2θ, 30.2°2θ, 34.1°2θ, 37.0°2θ, and 37.7°2θ (±0.2°2θ; ±0.1°2θ; or ±0.0°2θ; Cu Kα1 radiation).

151. The compound 1 malate salt of any one of embodiments 146 to 150, wherein the compound 1 malate salt is a crystalline polymorph characterized by any combination of the XRPD signals contained in Table 52.

152. The compound 1 malate salt of any one of embodiments 146 to 151, wherein compound 1 malate salt is a crystalline polymorph characterized by an XRPD pattern that is substantially similar to that shown in FIG. 261.

153. The compound 1 malate salt of any one of embodiments 146 to 152, wherein the compound 1 malate salt is a crystalline polymorph characterized by a DSC curve having a melting signal at about 193.5° C.

154. The compound 1 malate salt of any one of embodiments 146 to 153, wherein the compound 1 malate salt is a crystalline polymorph characterized by a DSC that is substantially similar to FIG. 262.

155. The compound 1 salt of embodiment 1 or 2, wherein the compound 1 salt is a glucuronate salt.

156. The compound 1 glucuronate salt of embodiment 155 wherein the compound 1 glucuronate salt is a crystalline polymorph characterized by XRPD signals at two signals or more, or three signals selected from the group consisting of 20.0°2θ, 20.5°2θ, and 22.5°2θ (±0.2°2θ; ±0.1°2θ; or 0.0°2θ; Cu Kα1 radiation).

157. The compound 1 glucuronate salt of embodiment 155 or 156, wherein the compound 1 glucuronate salt is a crystalline polymorph characterized by XRPD signals at 20.0°2θ, 20.5°2θ, and 22.5°2θ (±0.2°2θ; ±0.1°2θ; or ±0.0°2θ; Cu Kα1 radiation).

158. The compound 1 glucuronate salt of any one of embodiments 155 to 157, wherein the compound 1 glucuronate salt is a crystalline polymorph characterized by XRPD signals at 17.7°2θ, 20.0°2θ, 20.5°2θ, 22.5°2θ, and 24.4°2θ (±0.2°2θ; ±0.1°2θ; or ±0.0°2θ; Cu Kα1 radiation).

159. The compound 1 glucuronate salt of any one of embodiments 155 to 158, wherein the compound 1 glucuronate salt is a crystalline polymorph characterized by XRPD signals at 15.1°2θ, 17.7°2θ, 20.0°2θ, 20.5°2θ, 22.5°2θ, 24.4°2θ, 25.5°2θ, 26.1°2θ, 30.6°2θ, and 35.5°2θ (±0.2°2θ; ±0.1°2θ; or ±0.0°2θ; Cu Kα1 radiation).

160. The compound 1 glucuronate salt of any one of embodiments 155 to 159, wherein the compound 1 glucuronate salt is a crystalline polymorph characterized by any combination of the XRPD signals contained in Table 53.

161. The compound 1 glucuronate salt of any one of embodiments 155 to 160, wherein compound 1 glucuronate salt is a crystalline polymorph characterized by an XRPD pattern that is substantially similar to that shown in FIG. 259.

162. The compound 1 glucuronate salt of any one of embodiments 155 to 161, wherein compound 1 glucuronate salt is a crystalline polymorph characterized by a DSC curve having a melting signal at about 131.83° C.

163. The compound 1 glucuronate salt of any one of embodiments 155 to 162, wherein the compound 1 glucuronate salt is a crystalline polymorph characterized by a DSC that is substantially similar to FIG. 260.

164. The compound 1 salt of embodiment 1 or 2, wherein the compound 1 salt is an ascorbate salt.

165. The compound 1 ascorbate salt of embodiment 164 wherein the compound 1 ascorbate salt is a crystalline polymorph characterized by XRPD signals at two signals or more, or three signals selected from the group consisting of 19.3°2θ, 24.4°2θ, and 29.4°2θ (±0.2°2θ; ±0.1°2θ; or ±0.0°2θ; Cu Kα1 radiation).

166. The compound 1 ascorbate salt of embodiment 164 or 165, wherein the compound 1 ascorbate salt is a crystalline polymorph characterized by XRPD signals at 34.8°2θ, 10.5°2θ, and 19.9°2θ (±0.2°2θ; ±0.1°2θ; or ±0.0°2θ; Cu Kα1 radiation).

167. The compound 1 ascorbate salt of any one of embodiments 164 to 166, wherein the compound 1 ascorbate salt is a crystalline polymorph characterized by XRPD signals at 10.5°2θ, 19.9°2θ, 28.1°2θ, 30.1°2θ, and 34.8°2θ (±0.2°2θ; ±0.1°2θ; or ±0.0°2θ; Cu Kα1 radiation).

168. The compound 1 ascorbate salt of any one of embodiments 164 to 167, wherein the 10 compound 1 ascorbate salt is a crystalline polymorph characterized by XRPD signals at 10.5°2θ, 16.1°2θ, 17.5°2θ, 19.9°2θ, 21.1°2θ, 25.3°2θ, 28.1°2θ, 30.1°2θ, and 34.8°2θ (±0.2°2θ; ±0.1°2θ; or ±0.0°2θ; Cu Kα1 radiation).

169. The compound 1 ascorbate salt of any one of embodiments 164 to 168, wherein the compound 1 ascorbate salt is a crystalline polymorph characterized by any combination of the XRPD signals contained in Table 54.

170. The compound 1 ascorbate salt of any one of embodiments 164 to 169, wherein compound 1 ascorbate salt is a crystalline polymorph characterized by an XRPD pattern that is substantially similar to that shown in FIG. 265.
171. The compound 1 ascorbate salt of any one of embodiments 164 to 170, wherein compound 1 ascorbate salt is a crystalline polymorph characterized by a DSC curve having a melting signal at about 157° C.
172. The compound 1 ascorbate salt of any one of embodiments 164 to 171, wherein the compound 1 ascorbate salt is a crystalline polymorph characterized by a DSC that is substantially similar to FIG. 266.
173. The compound 1 salt of embodiment 1 or 2, wherein the compound 1 salt is a sulfate salt.
174. The compound 1 salt of embodiment 1 or 2, wherein the compound 1 salt is a mesylate salt.
175. The compound 1 salt of embodiment 1 or 2, wherein the compound 1 salt is an esylate salt.
176. The compound 1 salt of embodiment 1 or 2, wherein the compound 1 salt is a phosphate salt.
177. The compound 1 salt of embodiment 1 or 2, wherein the compound 1 salt is a phosphate salt.
178. The compound 1 salt of embodiment 1 or 2, wherein the compound 1 salt is an edisylate salt.
179. The compound 1 salt of embodiment 1 or 2, wherein the compound 1 salt is an adipate salt.
180. The compound 1 monofumarate salt of any one of embodiments 1, 2, or 4, wherein the compound 1 salt is a compound 1 monofumarate salt that is a crystalline polymorphic form characterized by XRPD signals at two signals or more, or three signals selected from the group consisting of 14.0°2θ, 15.9°2θ, and 22.3°2θ (±0.2°2θ; ±0.1°2θ; or ±0.0°2θ; Cu Kα1 radiation).
181. The compound 1 monofumarate salt of embodiment 180, wherein the compound 1 monofumarate salt is a crystalline polymorphic form characterized by XRPD signals at 14.0°2θ, 15.9°2θ, and 22.3°2θ (±0.2°2θ; ±0.1°2θ; or ±0.0°2θ; Cu Kα1 radiation).
182. The compound 1 monofumarate salt of embodiment 180 or 181, wherein the compound 1 monofumarate salt is a crystalline polymorphic form characterized by XRPD signals at 14.0°2θ, 15.9°2θ, 19.4°2θ, 21.3°2θ, and 22.3°2θ (±0.2°2θ; ±0.1°2θ; or ±0.0°2θ; Cu Kα1 radiation).
183. The compound 1 monofumarate salt of any one of embodiments 180 to 182, wherein the compound 1 monofumarate salt is a crystalline polymorphic form characterized by XRPD signals at 13.4°2θ, 14.0°2θ, 15.9°2θ, 18.9°2θ, 19.2°2θ, 19.4°2θ, 20.8°2θ, 21.3°2θ, 21.5°2θ, and 22.3°2θ (±0.2°2θ; ±0.1°2θ; or ±0.0°2θ; Cu Kα1 radiation).
184. The compound 1 monofumarate salt of any one of embodiments 180 to 183, wherein the compound 1 fumarate salt is a crystalline polymorphic form characterized by XRPD signals at 10.1°2θ, 13.4°2θ, 14.0°2θ, 15.6°2θ, 15.9°2θ, 18.4°2θ, 18.9°2θ, 19.2°2θ, 19.4°2θ, 20.8°2θ, 21.3°2θ, 21.5°2θ, 22.3°2θ, 23.2°2θ, 24.4°2θ, 25.0°2θ, 28.1°2θ, and 29.1°2θ (±0.2°2θ; ±0.1°2θ; or ±0.0°2θ; Cu Kα1 radiation).
185. The compound 1 monofumarate salt of any one of embodiments 180 to 184, wherein the compound 1 monofumarate salt is a crystalline polymorphic form characterized by any combination of the XRPD signals in Table 6.
186. The compound 1 monofumarate salt of any one of embodiments 180 to 185, wherein the compound 1 monofumarate salt is a crystalline polymorphic form characterized by the XRPD signals in Table 6 (±0.2°2θ; ±0.1°2θ; or ±0.0°2θ; Cu Kα1 radiation).
187. The compound 1 monofumarate salt of any one of embodiments 180 to 186, wherein the compound 1 monofumarate salt is a crystalline polymorphic form characterized by an XRPD pattern substantially similar to that shown in FIG. 8.
188. The compound 1 monofumarate salt of any one of embodiments 180 to 187, wherein the compound 1 monofumarate salt is a crystalline polymorphic form characterized by a DSC diagram having melting signals at about 116.8° C. and 241.3° C.
189. The compound 1 monofumarate salt of any one of embodiments 180 to 188, wherein the compound 1 monofumarate salt is a crystalline polymorphic form characterized by a DSC profile substantially similar to that shown in FIG. 86.
190. The compound 1 monofumarate salt of any one of embodiments 180 to 189, wherein the compound 1 monofumarate salt is a crystalline polymorph characterized by a TGA diagram having an onset at about 210.71° C.
191. The compound 1 monofumarate salt of any one of embodiments 180 to 190, wherein the compound 1 monofumarate salt is a crystalline polymorph characterized by a TGA diagram substantially similar to that shown in FIG. 81.
192. The compound 1 HCl salt of any one of embodiments 1, 2, or 53, wherein the compound 1 HCl salt is a crystalline polymorph characterized by XRPD signals at two signals or more, or three signals selected from the group consisting of 18.2°2θ, 25.0°2θ, and 26.0°2θ (±0.2°2θ; ±0.1°2θ; or ±0.0°2θ; Cu Kα1 radiation).
193. The compound 1 HCl salt of embodiment 192, wherein the compound 1 HCl salt is a crystalline polymorph characterized by XRPD signals at 18.2°2θ, 25.0°2θ, and 26.0°2θ (±0.2°2θ; ±0.1°2θ; or 0.0°2θ; Cu Kα1 radiation).
194. The compound 1 HCl salt of any one of embodiments 192 or 193, wherein the compound 1 HCl salt is a crystalline polymorph characterized by XRPD signals at 12.9°2θ, 18.2°2θ, 21.9°2θ, 25.0°2θ, and 26.0°2θ (±0.2°2θ; ±0.1°2θ; or ±0.0°2θ; Cu Kα1 radiation).
195. The compound 1 HCl salt of any one of embodiments 192 to 194, wherein the compound 1 HCl salt is a crystalline polymorph characterized by XRPD signals at 6.4°2θ, 6.5°2θ, 12.5°2θ, 12.9°2θ, 17.8°2θ, 18.0°2θ, 18.2°2θ, 18.8°2θ, 20.1°2θ, 20.6°2θ, 21.9°2θ, 23.2°2θ, 25.0°2θ, 25.6°2θ, 26.0°2θ, 27.6°2θ, 28.6°2θ, 29.1°2θ, 32.4°2θ, 34.6°2θ, and 37.8 (±0.2°2θ; ±0.1°2θ; or ±0.0°2θ; Cu Kα1 radiation).
196. The compound 1 HCl salt of any one of embodiments 192 to 195, wherein the compound 1 HCl salt is a crystalline polymorph characterized by any combination of the XRPD signals contained in Table 124.
197. The compound 1 HCl salt of any one of embodiments 192 to 196, wherein compound 1 HCl salt is a crystalline polymorph characterized by an XRPD pattern that is substantially similar to that shown in FIG. 365.
198. The compound 1 salt of any one of embodiments 1, 2, or 4, wherein the compound 1 salt is an amorphous compound 1 fumarate salt characterized by a glass temperature (Tg) of about 24° C.
199. The compound 1 salt of embodiment 198, wherein the amorphous compound 1 fumarate salt is characterized by a XRPD pattern that is substantially similar to that shown in FIG. 379 or 390.

200. The compound 1 salt of embodiment 198 or 199, wherein the amorphous compound 1 fumarate salt is characterized by a DSC profile that is substantially similar to that shown in any one of FIGS. 381 to 384.

201. The compound 1 salt of any one of embodiments 198 to 200, wherein the amorphous compound 1 fumarate salt is characterized by a TGA profile that is substantially similar to that shown in any one of FIGS. 385 to 388.

202. The compound 1 salt of any one of embodiments, 198 to 201, wherein the amorphous compound 1 fumarate salt is characterized by a $^1$H NMR spectrum that is substantially similar to that shown in FIG. 380.

203. The compound 1 salt of any one of embodiments 1, 2, or 53, wherein the compound 1 salt is an amorphous compound 1 HCl salt characterized by a Tg of about 37° C.

204. The compound 1 salt of embodiment 203, wherein the amorphous compound 1 HCl salt is characterized by a XRPD pattern that is substantially similar to that shown in FIG. 369.

205. The compound 1 salt of embodiment 203 or 204, wherein the amorphous compound 1 HCl salt is characterized by a DSC profile that is substantially similar to that shown in any one of FIGS. 370 to 373.

206. The compound 1 salt of any one of embodiments 203 to 205, wherein the amorphous compound 1 HCl salt is characterized by a TGA profile that is substantially similar to that shown in any one of FIGS. 374 to 377.

207. The compound 1 salt of any one of embodiments 203 to 206, wherein the amorphous compound 1 HCl salt is characterized by a $^1$H NMR spectrum that is substantially similar to that shown in FIG. 368.

208. A pharmaceutical composition comprising the compound 1 salt of any one of embodiments 1-208 and a pharmaceutically acceptable excipient.

209. A method of treating a brain disorder, a neurological disorder and/or a psychiatric disorder in a subject in need, comprising administering to the subject a salt of any one of embodiments 1 to 208. or the pharmaceutical composition of embodiment 208.

210. Use of the compound 1 salt of any one of embodiments 1-208 in the preparation of a medicament for the treatment of a brain disorder, a neurological disorder and/or a psychiatric disorder in a subject in need thereof.

211. A compound of any one of embodiments 1-208 for use in the treatment of a brain disorder, a neurological disorder and/or a psychiatric disorder in a subject in need thereof.

What is claimed is:

1. A (R)-1-(5-methoxy-1H-indol-1-yl)-N,N-dimethylpropan-2-amine (compound 1) monofumarate salt, wherein the compound 1 monofumarate salt is a crystalline polymorphic form characterized by XRPD signals at two signals or more, or three signals, selected from the group consisting of 14.0°2θ, 15.9°2θ, and 22.3°2θ (±0.2°2θ; ±0.1°2θ; or ±0.0°2θ; Cu Kα1 radiation).

2. The compound 1 monofumarate salt of claim 1, wherein the compound 1 monofumarate salt is a crystalline polymorphic form characterized by XRPD signals at 14.0°2θ, 15.9°2θ, and 22.3°2θ (±0.2°2θ; ±0.1°2θ; or ±0.0°2θ; Cu Kα1 radiation).

3. The compound 1 monofumarate salt of claim 1, wherein the compound 1 monofumarate salt is a crystalline polymorphic form characterized by XRPD signals at 14.0°2θ, 15.9°2θ, 19.4°2θ, 21.3°2θ, and 22.3°2θ (±0.2°2θ; ±0.1°2θ; or ±0.0°2θ; Cu Kα1 radiation).

4. The compound 1 monofumarate salt of claim 1, wherein the compound 1 monofumarate salt is a crystalline polymorphic form characterized by XRPD signals at 13.4°2θ, 14.0°2θ, 15.9°2θ, 18.9°2θ, 19.2°2θ, 19.4°2θ, 20.8°2θ, 21.3°2θ, 21.5°2θ, and 22.3°2θ (±0.2°2θ; ±0.1°2θ; or ±0.0°2θ; Cu Kα1 radiation).

5. The compound 1 monofumarate salt of claim 1, wherein the compound 1 monofumarate salt is a crystalline polymorphic form characterized by XRPD signals at 14.0°2θ, 15.9°2θ, 18.8°2θ, 19.3°2θ, 20.7°2θ, 21.2°2θ, 21.4°2θ, 22.3°2θ, 28.0°2θ, and 28.9°2θ (±0.2°2θ; ±0.1°2θ; or ±0.0°2θ; Cu Kα1 radiation).

6. The compound 1 monofumarate salt of claim 1, wherein the compound 1 monofumarate salt is a crystalline polymorphic form characterized by XRPD signals at 13.3°2θ, 14.0°2θ, 15.5°2θ, 15.9°2θ, 18.3°2θ, 18.8°2θ, 19.3°2θ, 20.7°2θ, 21.2°2θ, 21.4°2θ, 22.3°2θ, 23.0°2θ, 24.3°2θ, 24.9°2θ, 28.0°2θ, 28.9°2θ, 31.8°2θ, 34.0°2θ, and 37.2°2θ (±0.2°2θ; ±0.1°2θ; or ±0.0°2θ; Cu Kα1 radiation).

7. The compound 1 monofumarate salt of claim 1, wherein the compound 1 monofumarate salt is a crystalline polymorphic form characterized by XRPD signals at 10.1°2θ, 13.4°2θ, 14.0°2θ, 15.6°2θ, 15.9°2θ, 18.4°2θ, 18.9°2θ, 19.2°2θ, 19.4°2θ, 20.8°2θ, 21.3°2θ, 21.5°2θ, 22.3°2θ, 23.2°2θ, 24.4°2θ, 25.0°2θ, 28.1°2θ, and 29.1°2θ (±0.2°2θ; ±0.1°2θ; or ±0.0°2θ; Cu Kα1 radiation).

8. The compound 1 monofumarate salt of claim 1, wherein the compound 1 monofumarate salt is a crystalline polymorphic form characterized by any combination of the XRPD signals in Table 5 or Table 6 (±0.2°2θ; ±0.1°2θ; or ±0.0°2θ; Cu Kα1 radiation).

9. The compound 1 monofumarate salt of claim 1, wherein the compound 1 monofumarate salt is a crystalline polymorphic form characterized by:
   (i) an XRPD pattern substantially similar to that shown in FIG. 8 or FIG. 6;
   (ii) a DSC diagram having melting signals at about 116.8° C. and 241.3° C.;
   (iii) a DSC diagram substantially similar to that shown in FIG. 86;
   (iv) a TGA diagram having an onset at about 210.7° C.; and/or
   (v) a TGA diagram substantially similar to that shown in FIG. 81.

10. A pharmaceutical composition comprising the compound 1 monofumarate salt of claim 1, and a pharmaceutically acceptable excipient.

11. A method of treating a brain disorder, a neurological disorder and/or a psychiatric disorder in a subject in need thereof, comprising administering to the subject the compound 1 monofumarate salt of claim 1.

12. A (R)-1-(5-methoxy-1H-indol-1-yl)-N,N-dimethylpropan-2-amine (compound 1) monofumarate salt, wherein the compound 1 monofumarate salt is a crystalline polymorphic form characterized by XRPD signals at two signals or more, or three signals, selected from the group consisting of 22.6°2θ, 16.1°2θ, and 21.6°2θ (±0.2°2θ; ±0.1°2θ; or ±0.0°2θ; Cu Kα1 radiation).

13. The compound 1 monofumarate salt of claim 12, wherein the compound 1 monofumarate salt is a crystalline polymorphic form characterized by XRPD signals at 22.6°2θ, 16.1°2θ, and 21.6°2θ (±0.2°2θ; ±0.1°2θ; or ±0.0°2θ; Cu Kα1 radiation).

14. The compound 1 monofumarate salt of claim 12, wherein the compound 1 monofumarate salt is a crystalline polymorphic form characterized by XRPD signals at 22.6°2θ, 16.1°2θ, 21.6°2θ, 19.2°2θ, and 15.9°2θ (±0.2°2θ; ±0.1°2θ; or ±0.0°2θ; Cu Kα1 radiation).

15. The compound 1 monofumarate salt of claim 12, wherein the compound 1 monofumarate salt is a crystalline polymorphic form characterized by XRPD signals at 22.6°2θ, 16.1°2θ, 21.6°2θ, 19.2°2θ, 15.9°2θ, 19.5°2θ, 29.2°2θ, 28.3°2θ, 21.3°2θ, 14.2°2θ, 21.2°2θ, 25.2°2θ, 17.0°2θ, 18.7°2θ, 25.5°2θ, 13.6°2θ, 10.3°2θ, and 34.3°2θ (±0.2°2θ; ±0.1°2θ; or ±0.0°2θ; Cu Kα1 radiation).

16. The compound 1 monofumarate salt of claim 12, wherein the compound 1 monofumarate salt is a crystalline polymorphic form characterized by XRPD signals at 22.6°2θ, 16.1°2θ, 21.6°2θ, 14.2°2θ, and 19.5°2θ (±0.2°2θ; ±0.1°2θ; or ±0.0°2θ; Cu Kα1 radiation).

17. The compound 1 monofumarate salt of claim 12, wherein the compound 1 monofumarate salt is a crystalline polymorphic form characterized by XRPD signals at 22.6°2θ, 16.1°2θ, 21.6°2θ, 14.2°2θ, 19.5°2θ, 13.6°2θ, 21.2°2θ, 19.3°2θ, 29.6°2θ, 28.7°2θ, 15.7°2θ, 23.4°2θ, 24.8°2θ, 18.8°2θ, 10.3°2θ, and 25.3°2θ (±0.2°2θ; ±0.1°2θ; or ±0.0°2θ; Cu Kα1 radiation).

18. The compound 1 monofumarate salt of claim 12, wherein the compound 1 monofumarate salt is a crystalline polymorphic form characterized by XRPD signals at 22.6°2θ, 16.1°2θ, 21.6°2θ, 18.5°2θ, 19.6°2θ, and 19.3°2θ (±0.2°2θ; ±0.1°2θ; or ±0.0°2θ; Cu Kα1 radiation).

19. The compound 1 monofumarate salt of claim 12, wherein the compound 1 monofumarate salt is a crystalline polymorphic form characterized by XRPD signals at 22.6°2θ, 16.1°2θ, 21.6°2θ, 19.6°2θ, 19.3°2θ, 18.5°2θ, 21.7°2θ, 23.6°2θ, 25.2°2θ, 23.9°2θ, 17.8°2θ, 14.2°2θ, 21.1°2θ, 16.2°2θ, 28.3°2θ, 13.6°2θ, 10.3°2θ, 29.9°2θ, 16.9°2θ, 29.8°2θ, 29.3°2θ, and 36.7°2θ (±0.2°2θ; ±0.1°2θ; or ±0.0°2θ; Cu Kα1 radiation).

20. The compound 1 monofumarate salt of claim 12, wherein the compound 1 monofumarate salt is a crystalline polymorphic form characterized by the XRPD signals in any one of Table 7, Table 21, and/or Table 115 (±0.2°2θ; ±0.1°2θ; or ±0.0°2θ; Cu Kα1 radiation).

21. The compound 1 monofumarate salt of claim 12, wherein the compound 1 monofumarate salt is a crystalline polymorphic form characterized by any combination of the XRPD signals in Tables 7, 21, and 115 (±0.2°2θ; ±0.1°2θ; or ±0.0°2θ; Cu Kα1 radiation).

22. The compound 1 monofumarate salt of claim 12, wherein the compound 1 monofumarate salt is a crystalline polymorphic form characterized by:
(i) a DSC diagram having melting signals at about 116.2° C. and 242.5° C.;
(ii) a TGA diagram having an onset at about 208.6° C.;
(iii) a DSC diagram substantially similar to that shown in FIG. 85;
(iv) a TGA diagram substantially similar to that shown in FIG. 80; and/or
(v) an XRPD pattern substantially similar to that shown in any one of FIG. 72, FIG. 109, and FIG. 355.

23. A pharmaceutical composition comprising the compound 1 monofumarate salt of claim 12, and a pharmaceutically acceptable excipient.

24. A method of treating a brain disorder, a neurological disorder and/or a psychiatric disorder in a subject in need thereof, comprising administering to the subject the compound 1 monofumarate salt of claim 12.

25. A (R)-1-(5-methoxy-1H-indol-1-yl)-N,N-dimethylpropan-2-amine (compound 1) monofumarate salt, wherein the compound 1 monofumarate salt is a crystalline polymorphic form characterized by XRPD signals at two signals or more, or three signals, selected from the group consisting of 15.9°2θ, 19.3°2θ, and 22.5°2θ (±0.2°2θ; ±0.1°2θ; or ±0.0°2θ; Cu Kα1 radiation).

26. The compound 1 monofumarate salt of claim 25, wherein the compound 1 monofumarate salt is a crystalline polymorphic form characterized by XRPD signals at 14.0°2θ, 15.9°2θ, 19.3°2θ, 21.5°2θ, and 22.5°2θ (±0.2°2θ; ±0.1°2θ; or ±0.0°2θ; Cu Kα1 radiation).

27. The compound 1 monofumarate salt of claim 25, wherein the compound 1 monofumarate salt is a crystalline polymorphic form characterized by any combination of the XRPD signals in Tables 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, and 115 (±0.2°2θ; ±0.1°2θ; or ±0.0°2θ; Cu Kα1 radiation).

28. The compound 1 monofumarate salt of claim 25, wherein the compound 1 monofumarate salt is a crystalline polymorphic form characterized by:
(i) a DSC diagram substantially similar to that shown in any one of FIGS. 84, 85, 86, 87, 99, 100, 101, 102, and 112;
(ii) a TGA diagram substantially similar to that shown in any one of FIGS. 79, 80, 81, 82, 96, 97, 98, 367, 111, 134, 135, 136, 137, 138, 139, and 140; and/or
(iii) an XRPD pattern substantially similar to that shown in any one of FIGS. 6, 8, 52, 54, 61, 69, 72, 73, 74, 75, 76, 77, 92, 93, 94, 95, 103, 104, 105, 109, 126, 127, 128, 129, 130, 131, 132, 133, 152, 157, and 355.

29. A pharmaceutical composition comprising the compound 1 monofumarate salt of claim 25, and a pharmaceutically acceptable excipient.

30. A method of treating a brain disorder, a neurological disorder and/or a psychiatric disorder in a subject in need thereof, comprising administering to the subject the compound 1 monofumarate salt of claim 25.

* * * * *